United States Patent
Aggen et al.

(10) Patent No.: US 11,739,074 B2
(45) Date of Patent: Aug. 29, 2023

(54) RAS INHIBITORS

(71) Applicant: Revolution Medicines, Inc., Redwood City, CA (US)

(72) Inventors: James Aggen, Burlingame, CA (US); G. Leslie Burnett, Redwood City, CA (US); Jennifer Pitzen, Fremont, CA (US); Adrian L. Gill, Atherton, CA (US); Elena S. Koltun, Foster City, CA (US); James Cregg, Belmont, CA (US); Andreas Buckl, San Francisco, CA (US); Anne V. Edwards, San Mateo, CA (US); John E. Knox, Emerald Hills, CA (US)

(73) Assignee: Revolution Medicines, Inc., Redwood City, CA (US)

( * ) Notice: Subject to any disclaimer, the term of this patent is extended or adjusted under 35 U.S.C. 154(b) by 46 days.

(21) Appl. No.: 17/088,848

(22) Filed: Nov. 4, 2020

(65) Prior Publication Data
US 2021/0130326 A1    May 6, 2021

Related U.S. Application Data

(60) Provisional application No. 63/043,523, filed on Jun. 24, 2020, provisional application No. 63/000,355, filed on Mar. 26, 2020, provisional application No. 62/951,562, filed on Dec. 20, 2019, provisional application No. 62/930,406, filed on Nov. 4, 2019.

(51) Int. Cl.
| | |
|---|---|
| C07D 487/04 | (2006.01) |
| C07D 487/10 | (2006.01) |
| C07D 513/14 | (2006.01) |
| C07D 401/14 | (2006.01) |
| A61P 35/00 | (2006.01) |

(52) U.S. Cl.
CPC ............ *C07D 401/14* (2013.01); *A61P 35/00* (2018.01); *C07D 487/04* (2013.01); *C07D 487/10* (2013.01); *C07D 513/14* (2013.01)

(58) Field of Classification Search
CPC ... C07D 487/04; C07D 487/10; C07D 513/14
See application file for complete search history.

(56) References Cited

U.S. PATENT DOCUMENTS

| | | | |
|---|---|---|---|
| 6,183,965 B1 | 2/2001 | Verdine et al. | |
| 6,372,712 B1 | 4/2002 | Briesewitz et al. | |
| 6,686,454 B1 | 2/2004 | Yatscoff et al. | |
| 6,713,607 B2 | 3/2004 | Caggiano et al. | |
| 7,220,552 B1 | 5/2007 | Crabtree et al. | |
| 7,396,660 B2 | 7/2008 | Huang et al. | |
| 7,851,183 B2 | 12/2010 | Zotchev et al. | |
| 8,664,186 B2 | 3/2014 | Aigle et al. | |
| 9,250,237 B2 | 2/2016 | Liu et al. | |
| 9,260,484 B2 | 2/2016 | Briesewitz et al. | |
| 9,428,845 B1 | 8/2016 | Verdine et al. | |
| 9,989,535 B2 | 6/2018 | Verdine et al. | |
| 10,039,839 B2 | 8/2018 | Verdine et al. | |
| 10,203,323 B2 | 2/2019 | Verdine et al. | |
| 10,466,249 B2 | 11/2019 | Verdine et al. | |
| 10,533,016 B2 | 1/2020 | Verdine et al. | |
| 10,948,495 B2 | 3/2021 | Verdine et al. | |
| 10,989,710 B2 | 4/2021 | Verdine et al. | |
| 11,059,830 B2 | 7/2021 | Verdine et al. | |
| 2002/0110874 A1 | 8/2002 | Khosla et al. | |
| 2002/0147133 A1 | 10/2002 | Briesewitz et al. | |
| 2003/0153053 A1 | 8/2003 | Reid | |

(Continued)

FOREIGN PATENT DOCUMENTS

| | | |
|---|---|---|
| EP | 0194972 A2 | 9/1986 |
| EP | 0393934 A1 | 10/1990 |

(Continued)

OTHER PUBLICATIONS

"Registration No. 333-235968: Amendment No. 2 to Form S-1 Registration Statement Under The Securities Act of 1933 for Revolution Medicines, Inc.," United States Securities and Exchange Commission, Washington, D.C., 20549, dated Feb. 11, 2020 (354 pages).
"SMART™ Drugs: Engineering Nature's Solution to the Undruggable Target Challenge," WarpDrive Bio, 2016, available <http://www.warpdrivebio.com/docs/Warp%20Drive%20Bio_SMART%20Drugs%20Platform_2016.pdf> (31 pages).
"Streptomyces iranensis regulatory protein LuxR," EBI Database Accession No. CDR13506 (2014) (2 pages).
"Streptomyces rapamycinicus NRRL 5491 hypothetical protein," EBI Database Accession No. AGP59507 (2014) (2 pages).

(Continued)

*Primary Examiner* — Brian E McDowell
(74) *Attorney, Agent, or Firm* — Clark & Elbing LLP

(57) ABSTRACT

The disclosure features macrocyclic compounds, and pharmaceutical compositions and protein complexes thereof, capable of inhibiting Ras proteins, and their uses in the treatment of cancers. Exemplary Ras inhibitors include compounds of Formula I:

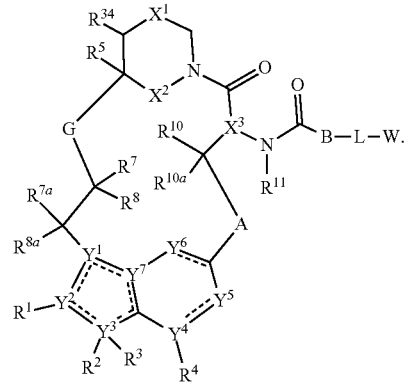

Formula I

2 Claims, 1 Drawing Sheet

(56) References Cited

U.S. PATENT DOCUMENTS

| | | |
|---|---|---|
| 2003/0175901 A1 | 9/2003 | Reeves et al. |
| 2004/0087496 A1 | 5/2004 | Kim et al. |
| 2004/0157768 A1 | 8/2004 | Or et al. |
| 2005/0233431 A1 | 10/2005 | Ashley et al. |
| 2007/0203168 A1 | 8/2007 | Zhao |
| 2007/0218502 A1 | 9/2007 | Hahn et al. |
| 2007/0265333 A1 | 11/2007 | Fu et al. |
| 2011/0117606 A1 | 5/2011 | Jorgensen et al. |
| 2012/0208720 A1 | 8/2012 | Kashiwagi et al. |
| 2012/0270800 A1 | 10/2012 | Verdine et al. |
| 2013/0072439 A1 | 3/2013 | Nash et al. |
| 2014/0073581 A1 | 3/2014 | Liu et al. |
| 2014/0316104 A1 | 10/2014 | Fischer et al. |
| 2015/0250896 A1 | 9/2015 | Zhao |
| 2015/0307855 A1 | 10/2015 | Yuzawa et al. |
| 2016/0199506 A1 | 7/2016 | Verdine et al. |
| 2016/0296528 A1 | 10/2016 | Pastor Fernandez et al. |
| 2016/0341719 A1 | 11/2016 | Verdine et al. |
| 2017/0190734 A1 | 7/2017 | Aciro et al. |
| 2018/0318434 A1 | 11/2018 | Verdine et al. |
| 2020/0197391 A1 | 6/2020 | Jin et al. |
| 2020/0199102 A1 | 6/2020 | Mulvihill et al. |
| 2021/0130303 A1 | 5/2021 | Koltun et al. |
| 2021/0130326 A1 | 5/2021 | Aggen et al. |
| 2021/0130369 A1 | 5/2021 | Koltun et al. |
| 2021/0285955 A1 | 9/2021 | Mulvihill et al. |
| 2021/0405060 A1 | 12/2021 | Verdine et al. |
| 2022/0082556 A1 | 3/2022 | Verdine et al. |
| 2022/0105185 A1 | 4/2022 | Aay et al. |
| 2022/0143202 A1 | 5/2022 | Verdine et al. |
| 2022/0144849 A1 | 5/2022 | Verdine et al. |

FOREIGN PATENT DOCUMENTS

| | | |
|---|---|---|
| EP | 0562853 A1 | 9/1993 |
| EP | 1079859 B1 | 7/2010 |
| KR | 10-2009-0041971 A | 4/2009 |
| WO | WO-86/02080 A1 | 4/1986 |
| WO | WO-95/32294 A1 | 11/1995 |
| WO | WO-96/20216 A1 | 7/1996 |
| WO | WO-98/01546 A2 | 1/1998 |
| WO | WO-98/07743 A1 | 2/1998 |
| WO | WO-98/12217 A1 | 3/1998 |
| WO | WO-99/61055 A1 | 12/1999 |
| WO | WO-00/47724 A2 | 8/2000 |
| WO | WO-01/36460 A2 | 5/2001 |
| WO | WO-01/36612 A1 | 5/2001 |
| WO | WO-01/90070 A2 | 11/2001 |
| WO | WO-03/033010 A1 | 4/2003 |
| WO | WO-2008/069824 A2 | 6/2008 |
| WO | WO-2010/031185 A1 | 3/2010 |
| WO | WO-2010/034243 A1 | 4/2010 |
| WO | WO-2010/088573 A1 | 8/2010 |
| WO | WO-2012/075048 A2 | 6/2012 |
| WO | WO-2012/078915 A1 | 6/2012 |
| WO | WO-2012/174489 A2 | 12/2012 |
| WO | WO-2013/022818 A1 | 2/2013 |
| WO | WO-2013/185090 A1 | 12/2013 |
| WO | WO-2013/185093 A1 | 12/2013 |
| WO | WO-2013/185103 A1 | 12/2013 |
| WO | WO-2014/009774 A1 | 1/2014 |
| WO | WO-2014/187959 A2 | 11/2014 |
| WO | WO-2015/132784 A1 | 9/2015 |
| WO | WO-2016/112279 A1 | 7/2016 |
| WO | WO-2016/112295 A1 | 7/2016 |
| WO | WO-2016/160362 A1 | 10/2016 |
| WO | WO-2017/059207 A1 | 4/2017 |
| WO | WO-2018/081592 A2 | 5/2018 |
| WO | WO-2018/091634 A1 | 5/2018 |
| WO | WO-2018/187401 A1 | 10/2018 |
| WO | WO-2018/187423 A1 | 10/2018 |
| WO | WO-2018/217651 A1 | 11/2018 |
| WO | WO-2020/101736 A1 | 5/2020 |
| WO | WO-2020/132597 A1 | 6/2020 |
| WO | WO-2021/091956 A1 | 5/2021 |
| WO | WO-2021/091967 A1 | 5/2021 |
| WO | WO-2021/091982 A1 | 5/2021 |
| WO | WO-2022/060583 A1 | 3/2022 |
| WO | WO-2022/060836 A1 | 3/2022 |

OTHER PUBLICATIONS

"Substructure Search Report on Specifically Substituted Macrocycles—Substances Only," prepared by Science IP, dated Dec. 17, 2014 (6177 pages).

"Translating Frontier Oncology Targets to Outsmart Cancer™," Corporate Overview Q3-2020, Revolution Medicines, Aug. 20, 2020 (35 pages).

Aebi et al., "Synthesis, Conformation, and Immunosuppressive Activities of Three Analogues of Cyclosporin A Modified in the 1-Position," J Med Chem. 33(3):999-1009 (1990).

Allain et al., "Cyclophilin B mediates cyclosporin A incorporation in human blood T-lymphocytes through the specific binding of complexed drug to the cell surface," Biochem J. 317 (Pt 2):565-70 (1996).

Andrei et al., "Stabilization of protein-protein interactions in drug discovery," Expert Opin Drug Discov. 12(9):925-40 (2017) (17 pages).

Antunes et al., "A mutational analysis defines Vibrio fischeri LuxR binding sites," J Bacteriol. 190(13):4392-7 (2008).

Archibald et al., "Discovery and Evaluation of Potent, Cysteine-based alpha4beta1 Integrin Antagonists," Bioorg Med Chem Lett. 10(9):993-995 (2000).

Baillie, "Targeted Covalent Inhibitors for Drug Design," Covalent Inhibitor Drug Discovery & Development Symposium PBSS, Feb. 7, Foster City, California. (2019) (16 pages).

Banaszynski et al., "Characterization of the FKBP.rapamycin.FRB ternary complex," J Am Chem Soc. 127(13):4715-21 (2005).

Baranasic et al., "Draft Genome Sequence of *Streptomyces rapamycinicus* Strain NRRL 5491, the Producer of the Immunosuppressant Rapamycin," Genome Announc. 1(4):e00581-13 (2013) (2 pages).

Bayle et al., "Rapamycin analogs with differential binding specificity permit orthogonal control of protein activity," Chem Biol. 13(1):99-107 (2006).

Bender et al., "Periodate Oxidation of alpha-Keto gamma-Lactams. Enol Oxidation and beta-Lactam Formation. Mechanism of Periodate Hydroxylation Reactions," J Org Chem. 43(17):3354-3362 (1978).

Benjamin et al., "Rapamycin passes the torch: a new generation of mTOR inhibitors," Nat Rev Drug Discov. 10(11):868-80 (2011).

Bhuyan et al., "Antioxidant activity of peptide-based angiotensin converting enzyme inhibitors," Org Biomol Chem. 10(11):2237-47 (2012).

Blodgett et al., "Unusual transformations in the biosynthesis of the antibiotic phosphinothricin tripeptide," Nat Chem Biol. 3(8):480-5 (2007).

Briesewitz et al., "Affinity modulation of small-molecule ligands by borrowing endogenous protein surfaces," Proc Natl Acad Sci U.S.A. 96(5):1953-8 (1999).

Bruce, "In vivo protein complex topologies: sights through a cross-linking lens," Proteomics. 12(10):1565-75 (2012).

Burgess et al., "Controlled translocation of palladium(II) within a 22 ring atom macrocyclic ligand," Dalton Trans. 43(45):17006-16 (2014) (12 pages).

Chaurasia et al., "Molecular insights into the stabilization of protein-protein interactions with small molecule: The FKBP12-rapamycin-FRB case study," Chem Phys Lett. 587:68-74 (2013).

Che et al., "Inducing protein-protein interactions with molecular glues," Bioorg Med Chem Lett. 28(15):2585-92 (2018) (18 pages).

Chevalier et al., "Straightforward synthesis of bioconjugatable azo dyes. Part 1: Black Hole Quencher-1 (BHQ-1) scaffold," Tetrahedron Lett. 55(50):6759-63 (2014).

Ding et al., "Insights into Bacterial 6-Methylsalicylic Acid Synthase and Its Engineering to Orsellinic Acid Synthase for Spirotetronate Generation," Chem Biol. 17(5):495-503 (2010).

Eberle et al., "Preparation of Functionalized Ethers of Cyclosporin A," Tetrahedron Lett. 35(35):6477-6480 (1994).

(56) References Cited

OTHER PUBLICATIONS

Findlay et al., "The structure of demethoxyrapamycin," Can J Chem. 60:2046-7 (1982).
Garg et al., "Elucidation of the Cryptic Epimerase Activity of Redox-Inactive Ketoreductase Domains from Modular Polyketide Synthases by Tandem Equilibrium Isotope Exchange," J Am Chem Soc. 136(29):10190-10193 (2014).
Gill, "Discovery of Small Molecule Inhibitors of Oncogenic Mutants of RAS," Revolution Medicines, ACS, Apr. 2, Orlando (2019) (23 pages).
Gordon et al., "A SARS-CoV-2 Protein Interaction Map Reveals Targets for Drug Repurposing," Nature. 583(7816):459-68 (Apr. 2020).
Guerra et al., "LAL regulators SCO0877 and SCO7173 as pleiotropic modulators of phosphate starvation response and actinorhodin biosynthesis in Streptomyces coelicolor," PLoS One. 7(2):e31475 (2012) (11 pages).
Hansson et al., "Bioengineering and Semisynthesis of an Optimized Cyclophilin Inhibitor for Treatment of Chronic Viral Infection," Chem Biol. 22(2):285-92 (2015) (24 pages).
He et al., "The LuxR family members GdmRI and GdmRII are positive regulators of geldanamycin biosynthesis in Streptomyces hygroscopicus 17997," Arch Microbiol. 189(5):501-10 (2008).
Hong et al., "Evidence for an iterative module in chain elongation on the azalomycin polyketide synthase," Beilstein J Org Chem. 12:2164-2172 (2016).
Horn et al., "Draft Genome Sequence of Streptomyces iranensis," Genome Announc. 2(4):e00616-14 (2014) (2 Pages).
Horton et al., "Engineering hybrid genes without the use of restriction enzymes: gene splicing by overlap extension," Gene. 77(1):61-8 (1989).
Hosted et al., "Use of rpsL for dominance selection and gene replacement in *Streptomyces roseosporus*," J Bacteriol. 179(1):180-6 (1997).
Huang et al., "Conjugation to Albumin-Binding Molecule Tags as a Strategy to Improve Both Efficacy and Pharmacokinetic Properties of the Complement Inhibitor Compstatin," ChemMedChem. 9(10):2223-6 (2014).
Huang et al., "Enhanced rapamycin production in *Streptomyces hygroscopicus* by integrative expression of aveR, a LAL family transcriptional regulator," World J Microbiol Biotechnol. 27:2103-9 (2011).
Hubler et al., "Synthetic routes to NEtXaa4-cyclosporin A derivatives as potential anti-HIV I drugs," Tetrahedron Lett. 41:7193-6 (2000).
International Search Report and Written Opinion for International Application No. PCT/US2020/058817, dated Jan. 11, 2021 (15 pages).
Ishizawa et al., "Trap display: a high-speed selection method for the generation of functional polypeptides," J Am Chem. 135(14):5433-40 (2013).
Jarvis, "Have drug hunters finally cracked KRas?—After decades of failures, researchers see promise in fresh approaches to developing drugs that block cancer's toughest target," Chemical & Engineering News. 94(23):28-33. <https://cen.acs.org/articles/94/i23/drug-hunters-finally-cracked-KRas.html>, retrieved on Oct. 14, 2018 (2016) (9 pages).
Kawakami et al., "In vitro selection of multiple libraries created by genetic code reprogramming to discover macrocyclic peptides that antagonize VEGFR2 activity in living cells," ACS Chem Biol. 8(6):1205-14 (2013).
Kelsey, "Approaches to Inhibiting RAS-Driven Tumors Beyond KRAS$^{G12C}$," RAS Targeted Drug Development, Revolution Medicines, Sep. 16, 2020 (24 pages).
Kendrew et al., "Recombinant strains for the enhanced production of bioengineered rapalogs," Metab Eng. 15:167-73 (2013).
Kuhn et al., "Synthesis of Functional Ras Lipoproteins and Fluorescent Derivatives," J Am Chem Soc. 123(6):1023-35 (2001).

Kuramochi et al., "Identification of Small Molecule Binding Molecules by Affinity Purification Using a Specific Ligand Immobilized on PEGA Resin," Bioconjug Chem. 19(12):2417-26 (2008).
Laureti et al., "Identification of a bioactive 51-membered macrolide complex by activation of a silent polyketide synthase in Streptomyces ambofaciens," Proc Natl Acad Sci USA. 108(15):6258-63 (2011).
Laureti et al., Supporting Material for "Identification of a bioactive 51-membered macrolide complex by activation of a silent polyketide synthase in Streptomyces ambofaciens," Proc Natl Acad Sci U.S.A. 108(15):6258-63 (2011), accessed via <https://www.pnas.org/content/suppl/2011/03/24/1019077108.DCSupplemental> (41 pages).
Lee et al., "Current implications of cyclophilins in human cancers," J Exp Clin Cancer Res. 29(1):97 (2010) (6 pages).
Leskiw et al., "TTA codons in some genes prevent their expression in a class of developmental, antibiotic-negative, *Streptomyces* mutants," Proc Natl Acad Sci USA. 88(6):2461-5 (1991).
Li et al., "A simple and efficient route to the FKBP-binding domain from rapamycin," available in PMC Sep. 28, 2012, published in final edited form as: Tetrahedron Lett. 52(39):5070-2 (2011) (7 pages).
Luengo et al., "Structure-activity studies of rapamycin analogs: evidence that the C-7 methoxy group is part of the effector domain and positioned at the FKBP12-FRAP interface," Chem Biol. 2(7):471-81 (1995).
Mackman et al., "Discovery of a Potent and Orally Bioavailable Cyclophilin Inhibitor Derived from the Sanglifehrin Macrocycle," J Med Chem. 61(21):9473-9499 (2018).
Majumder et al. "Interaction of aryl hydrocarbon receptor-interacting protein-like 1 with the farnesyl moiety," J Biol Chem. 288(29):21320-21328 (2013).
McGregor et al., "Expanding the Scope of Electrophiles Capable of Targeting K-Ras Oncogenes," Biochemistry. 56(25):3178-3183 (2017).
Meyer et al., "Selective palladation of a large (32 ring atom) macrocyclic ligand at a bis(N-heterocyclic carbene) coordination pocket through transmetallation of the corresponding mercury(II) derivative," Dalton Trans. 41(46):14059-67 (2012) (10 pages).
Mo et al., "Interspecies Complementation of the LuxR Family Pathway-Specific Regulator Involved in Macrolide Biosynthesis," J Microbiol Biotechnol. 26(1):66-71 (2016).
Moore et al., "RAS-targeted therapies: is the undruggable drugged?" Nat Rev Drug Discov. 19(8):533-52 (Aug. 2020).
Mullard, "Cracking KRAS," Nat Rev Drug Discov. 18(12):887-91 (Nov. 2019) (14 pages).
Murphy et al., "Isolation and characterisation of amphotericin B analogues and truncated polyketide intermediates produced by genetic engineering of *Streptomyces nodosus*" Org Biomol Chem. 8(16):3758-70 (2010).
Ochi et al., "New strategies for drug discovery: activation of silent or weakly expressed microbial gene clusters," Appl Microbiol Biotechnol. 97(1):87-98 (2013).
Ostrem et al., "Direct small-molecule inhibitors of KRAS: from structural insights to mechanism-based design," Nat Rev Drug Discov. 15(11):771-785 (2016).
Ostrem et al., "K-Ras(G12C) inhibitors allosterically control GTP affinity and effector interactions," Nature. 503(7477):548-51 (2013) (14 pages).
Papageorgiou et al., "Improved binding affinity for cyclophilin A by a cyclosporin derivative singly modified at its effector domain," J Med Chem. 37(22):3674-6 (1994).
Pfeifer et al., "Biosynthesis of complex polyketides in a metabolically engineered strain of *E. coli*," Science. 291(5509):1790-2 (2001) (4 pages).
Power et al., "Engineered Synthesis of 7-Oxo- and 15-Deoxy-15-Oxo-Amphotericins: Insights into Structure-Activity Relationships in Polyene Antibiotics," Chem Biol. 15(1):78-86 (2008).
PubChem CID 130196149, <https://pubchem.ncbi.nlm.nih.gov/compound/130196149>, retrieved on Apr. 1, 2020 (10 pages).
Quesniaux et al., "Cyclophilin binds to the region of cyclosporine involved in its immunosuppressive activity," Eur J Immunol. 17(9):1359-65 (1987).
Quesniaux et al., "Study of the conformation of cyclosporine in aqueous medium by means of monoclonal antibodies," Int J Pept Protein Res. 31(2):173-85 (1988).

(56) References Cited

OTHER PUBLICATIONS

Ranganathan et al., "Knowledge-based design of bimodular and trimodular polyketide synthases based on domain and module swaps: a route to simple statin analogues," Chem Biol. 6(10):731-41 (1999).

Ray et al., "New Electrophiles and Strategies for Mechanism-Based and Targeted Covalent Inhibitor Design," Biochemistry. 58: 5234-5244 (Dec. 2019).

Reid et al. "A model of structure and catalysis for ketoreductase domains in modular polyketide synthases," Biochemistry. 42(1):72-79 (2003).

Revill et al., "Genetically engineered analogs of ascomycin for nerve regeneration," J Pharmacol Exp Ther. 302(3):1278-85 (2002).

Revolution Medicines, "Translating Frontier Oncology Targets to Outsmart Cancer™: Corporate Overview Q4-2020," dated Nov. 12, 2020 (30 pages).

Ruan et al., "Binding of rapamycin analogs to calcium channels and FKBP52 contributes to their neuroprotective activities," Proc Natl Acad Sci U S A. 105(1):33-8 (2008).

Rudolph, "Covalent Modification In Drug Discovery—A Chemist's Perspective," Pharmaceutical & BioScience Society. Dated Feb. 7, 2019 (39 pages).

Schutt, "Safety Considerations for Covalent Inhibitors," Pharmaceutical & BioScience Society. Dated Feb. 7, 2019 (36 pages).

Schwecke et al., "The biosynthetic gene cluster for the polyketide immunosuppressant rapamycin," Proc Natl Acad Sci U S A. 92(17):7839-43 (1995).

Sebastiano et al., "Impact of Dynamically Exposed Polarity on Permeability and Solubility of Chameleonic Drugs Beyond the Rule of 5," J Med Chem. 61:4189-4202 (2018).

Shigdel et al., "Genomic discovery of an evolutionarily programmed modality for small-molecule targeting of an intractable protein surface," Proc Natl Acad Sci U S A. 117(29):17195-203 (Jul. 2020).

Sieber et al., "Novel inhibitors of the calcineurin/NFATc hub—alternatives to CsA and FK506?" Cell Commun Signal. 7:25 (2009) (19 pages).

Simanshu et al., "RAS Proteins and Their Regulators in Human Disease," available in PMC Jun. 29, 2018, published in final edited form as: Cell. 170(1):17-33 (2017) (34 pages).

Smith, "Translating Frontier Oncology Targets to Outsmart Cancer," RAS-Targeted Drug Discovery Summit, Revolution Medicines, Sep. 19, 2019 (29 pages).

Smulik et al., "Synthesis of cyclosporin A-derived affinity reagents by olefin metathesis," Org Lett. 4(12):2051-4 (2002).

Steadman et al., "Discovery of Potent Cyclophilin Inhibitors Based on the Structural Simplification of Sanglifehrin A," J Med Chem. 60:1000-1017 (2017).

Stewart et al., "Development of Inhibitors of the Activated Form of KRAS$^{G12C}$," AACR Targeting RAS-Driven Cancers, Dec. 9-12, San Diego, California. Poster B37 (2018).

STN record of WO 2014/009774, available online Jan. 16, 2014 (4 pages).

STN record of WO 98/12217, available online Mar. 26, 1998 (6 pages).

Sun et al. "Design and structure-based study of new potential FKBP12 inhibitors," Biophys J. 85(5):3194-3201 (2003).

Sweeney et al., "From chemical tools to clinical medicines: non-immunosuppressive cyclophilin inhibitors derived from the cyclosporin and sanglifehrin scaffolds," J Med Chem. 57(17):7145-59 (2014) (63 pages).

Sànchez-Tilló et al., "Cyclophilin A is required for M-CSF-dependent macrophage proliferation," Eur J Immunol. 36(9):2515-24 (2006).

Takakusagi et al., "Efficient one-cycle affinity selection of binding proteins or peptides specific for a small-molecule using a T7 phage display pool," Bioorg Med Chem. 16(22):9837-46 (2008).

Tanaka et al., "Clinical Acquired Resistance to KRAS$^{G12C}$ Inhibition through a Novel KRAS Switch-II Pocket Mutation and Polyclonal Alterations Converging on RAS-MAPK Reactivation," Cancer Discov. 11(8):1913-1922 (2021).

Tang et al., "Generation of New Epothilones by Genetic Engineering of a Polyketide Synthase in Myxococcus xanthus," J Antibiot (Tokyo). 58(3):178-184 (2005).

UniProtKB Accession No. A0A061A6I8, Sep. 3, 2014, available <http://www.uniprot.org/uniprot/A0A061A6I8>, (12 pages).

UniProtKB Accession No. Q54296, "Polyketide synthase," <https://www.uniprot.org/uniprot/A0A61A6I8.txt?version=14>, retrieved May 29, 2020 (12 pages).

UniProtKB Accession No. Q54296, Nov. 1, 1996, available <http://www.uniprot.org/uniprot/Q54296>, (12 pages).

UniProtKB Accession No. Q54297, Nov. 1, 1996, available <https://www.uniprot.org/uniprot/Q54297.txt>, (3 pages).

Upadhyaya et al., "Direct Ras Inhibitors Identified From a Structurally Rigidified Bicyclic Peptide Library," available in PMC Oct. 21, 2015, published in final edited form as: Tetrahedron. 70(42)7714-7720 (2014) (15 pages).

Vakiti et al., "Stereoselective synthesis of C17-C34 fragment of antascomicin A," Tetrahedron Lett. 55(47):6438-40 (2014).

Vignot et al., "mTOR-targeted therapy of cancer with rapamycin derivatives," Ann Oncol. 16(4):525-37 (2005).

Wagner et al., "New naturally occurring amino acids," Angew Chem Int Ed Engl. 22(11):816-28 (1983).

Wang et al., "Thermodynamic analysis of cyclosporin a binding to cyclophilin a in a lung tumor tissue lysate," Anal Chem. 76(15):4343-8 (2004).

Weissman et al., "Combinatorial biosynthesis of reduced polyketides," Nat Rev Microbiol. 3(12):925-36 (2005).

Weissman, "Genetic engineering of modular PKSs: from combinatorial biosynthesis to synthetic biology," Nat Prod Rep. 33(2):203-230 (2016).

Wilson et al., "Comparative X-ray structures of the major binding protein for the immunosuppressant FK506 (tacrolimus) in unliganded form and in complex with FK506 and rapamycin," Acta Cryst. D51:511-21 (1995).

Wright et al., "Multivalent binding in the design of bioactive compounds," Curr Org Chem. 5(11):1107-31 (2001).

Wu et al., "Creating diverse target-binding surfaces on FKBP12: synthesis and evaluation of a rapamycin analogue library," available in PMC Sep. 12, 2012, published in final edited form as: ACS Comb Sci. 13(5):486-95 (2011) (22 pages).

Wu et al., "Inhibition of ras-effector interactions by cyclic peptides," Med Chem Commun. 4(2):378-82 (2013).

Wu et al., "Synthesis of Ketone Analogues of Prolyl and Pipecolyl Ester FKBP12 Ligands," J Med Chem. 45(16):3558-3568 (2002).

Zhang et al., "Bifunctional Small-Molecule Ligands of K-Ras Induce Its Association with Immunophilin Proteins," Angew Chem Int Ed Engl. 131:16460-5 (Nov. 2019).

Zhou et al., "Biophysical and biochemical characterization of KRAS$^{G12C}$ inhibition through a novel modality," AACR Targeting RAS-Driven Cancers, Dec. 9-12, San Diego, California. Poster A06 (2018).

Guo et al., "Rapamycin-inspired macrocycles with new target specificity," Nat Chem. 11(3):254-263 (Mar. 2019) (13 pages).

RAS INHIBITORS

CROSS-REFERENCE TO RELATED APPLICATIONS

The present application claims the benefit of priority to U.S. Application No. 62/930,406, filed on Nov. 4, 2019; U.S. Application No. 62/951,562, filed on Dec. 20, 2019; U.S. Application No. 63/000,355, filed on Mar. 26, 2020; and U.S. Application No. 63/043,523, filed on Jun. 24, 2020, all of which are hereby incorporated by reference in their entirety.

BACKGROUND

The vast majority of small molecule drugs act by binding a functionally important pocket on a target protein, thereby modulating the activity of that protein. For example, cholesterol-lowering drugs known as statins bind the enzyme active site of HMG-CoA reductase, thus preventing the enzyme from engaging with its substrates. The fact that many such drug/target interacting pairs are known may have misled some into believing that a small molecule modulator could be discovered for most, if not all, proteins provided a reasonable amount of time, effort, and resources. This is far from the case. Current estimates are that only about 10% of all human proteins are targetable by small molecules. Bojadzic and Buchwald, CurrTop Med Chem 18: 674-699 (2019). The other 90% are currently considered refractory or intractable toward above-mentioned small molecule drug discovery. Such targets are commonly referred to as "undruggable." These undruggable targets include a vast and largely untapped reservoir of medically important human proteins. Thus, there exists a great deal of interest in discovering new molecular modalities capable of modulating the function of such undruggable targets.

It has been well established in literature that Ras proteins (K-Ras, H-Ras and N-Ras) play an essential role in various human cancers and are therefore appropriate targets for anticancer therapy. Indeed, mutations in Ras proteins account for approximately 30% of all human cancers in the United States, many of which are fatal. Dysregulation of Ras proteins by activating mutations, overexpression or upstream activation is common in human tumors, and activating mutations in Ras are frequently found in human cancer. For example, activating mutations at codon 12 in Ras proteins function by inhibiting both GTPase-activating protein (GAP)-dependent and intrinsic hydrolysis rates of GTP, significantly skewing the population of Ras mutant proteins to the "on" (GTP-bound) state (Ras(ON)), leading to oncogenic MAPK signaling. Notably, Ras exhibits a picomolar affinity for GTP, enabling Ras to be activated even in the presence of low concentrations of this nucleotide. Mutations at codons 13 (e.g., G13D) and 61 (e.g., Q61K) of Ras are also responsible for oncogenic activity in some cancers.

Despite extensive drug discovery efforts against Ras during the last several decades, a drug directly targeting Ras is still not approved. Additional efforts are needed to uncover additional medicines for cancers driven by the various Ras mutations.

SUMMARY

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF and PI3K, which are required for propagating the oncogenic signal.

As such, in some embodiments, the disclosure features a compound, or pharmaceutically acceptable salt thereof, of structural Formula I:

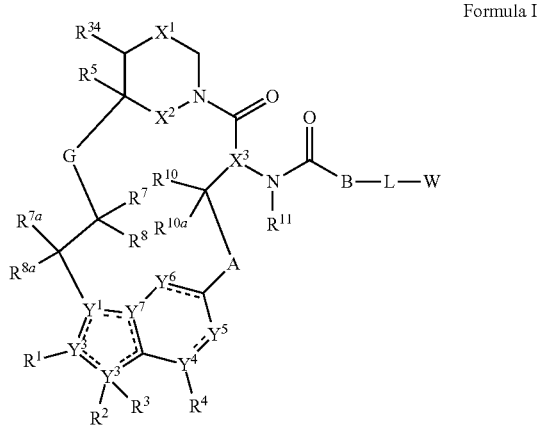

Formula I wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is —CH(R$^9$)— or >C=CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted C$_1$-C$_4$ alkylene, optionally substituted C$_1$-C$_4$ alkenylene, optionally substituted C$_1$-C$_4$ heteroalkylene, —C(O)O—CH(R$^6$)— where C is bound to —C(R$^7$R$^8$)—, —C(O)NH—CH(R$^6$)— where C is bound to —C(R$^7$R$^8$)—, optionally substituted C$_1$-C$_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

X$^1$ is optionally substituted C$_1$-C$_2$ alkylene, NR, O, or S(O)$_n$;

$X^2$ is O or NH;
$X^3$ is N or CH;
n is 0, 1, or 2;
R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;
each $R^1$ is, independently, H or optionally substituted $C_1$-$C_4$ alkyl;
$Y^1$ is C, CH, or N;
$Y^2$, $Y^3$, $Y^4$, and $Y^7$ are, independently, C or N;
$Y^5$ is CH, CH$_2$, or N;
$Y^6$ is C(O), CH, CH$_2$, or N;
$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or
$R^1$ and $R^2$ combine with the atoms to which they are attached to form an optionally substituted 3 to 14-membered heterocycloalkyl;
$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or
$R^2$ and $R^3$ combine with the atom to which they are attached to form an optionally substituted 3 to 8-membered cycloalkyl or optionally substituted 3 to 14-membered heterocycloalkyl;
$R^4$ is absent, hydrogen, halogen, cyano, or methyl optionally substituted with 1 to 3 halogens;
$R^5$ is hydrogen, $C_1$-$C_4$ alkyl optionally substituted with halogen, cyano, hydroxy, or $C_1$-$C_4$ alkoxy, cyclopropyl, or cyclobutyl;
$R^6$ is hydrogen or methyl; $R^7$ is hydrogen, halogen, or optionally substituted $C_1$-$C_3$ alkyl, or
$R^6$ and $R^7$ combine with the carbon atoms to which they are attached to form an optionally substituted 3 to 6-membered cycloalkyl or optionally substituted 3 to 7-membered heterocycloalkyl;
$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or
$R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;
$R^{7a}$ and $R^{8a}$ are, independently, hydrogen, halo, optionally substituted $C_1$-$C_3$ alkyl, or combine with the carbon to which they are attached to form a carbonyl;
$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or
$R^{7'}$ and $R^{8'}$ combine with the carbon atom to which they are attached to form optionally substituted 3 to 6-membered cycloalkyl or optionally substituted 3 to 7-membered heterocycloalkyl;
$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or
$R^9$ and L combine with the atoms to which they are attached to form an optionally substituted 3 to 14-membered heterocycloalkyl;
$R^{9'}$ is hydrogen or optionally substituted $C_1$-$C_6$ alkyl;
$R^{10}$ is hydrogen, halo, hydroxy, $C_1$-$C_3$ alkoxy, or $C_1$-$C_3$ alkyl;
$R^{10a}$ is hydrogen or halo;
$R^{11}$ is hydrogen or $C_1$-$C_3$ alkyl; and
$R^{34}$ is hydrogen or $C_1$-$C_3$ alkyl (e.g., methyl).
Also provided are pharmaceutical compositions comprising a compound of Formula I, or a pharmaceutically acceptable salt thereof, and a pharmaceutically acceptable excipient.
Further provided is a conjugate, or salt thereof, comprising the structure of Formula IV:

M-L-P            Formula IV wherein L is a linker;
P is a monovalent organic moiety; and
M has the structure of Formula V:

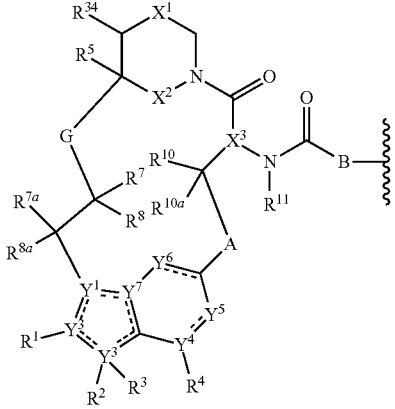

Formula V wherein the dotted lines represent zero, one, two, three, or four non-adjacent double bonds;
A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;
B is —CH(R$^9$)— or >C=CR$^9$R$^{9'}$ where the carbon is bound to the carbonyl carbon of —N(R$^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;
G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, CH$_2$, or N;

$Y^6$ is C(O), CH, CH$_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{34}$ is hydrogen or $C_1$-$C_3$ alkyl (e.g., methyl).

Also provided is a method of treating cancer in a subject in need thereof, the method comprising administering to the subject a therapeutically effective amount of a compound of the present invention, or a pharmaceutically acceptable salt thereof.

In some embodiments, a method is provided of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

DEFINITIONS AND CHEMICAL TERMS

Figure 1A:
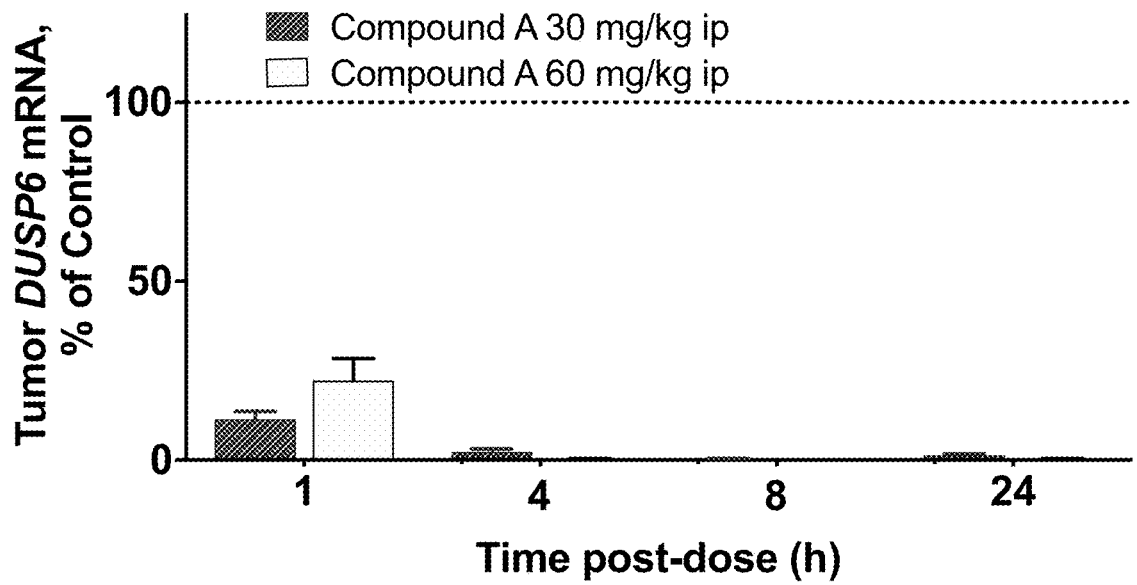
FIG. 1A: A compound of the present invention, Compound A, deeply and durably inhibits oncogenic signals in a pancreatic CDX model (HPAC CDX model, PDAC, KRAS G12D/WT). Single dose experiment, n=3/time point, all dose levels well tolerated.
Figure 1B:
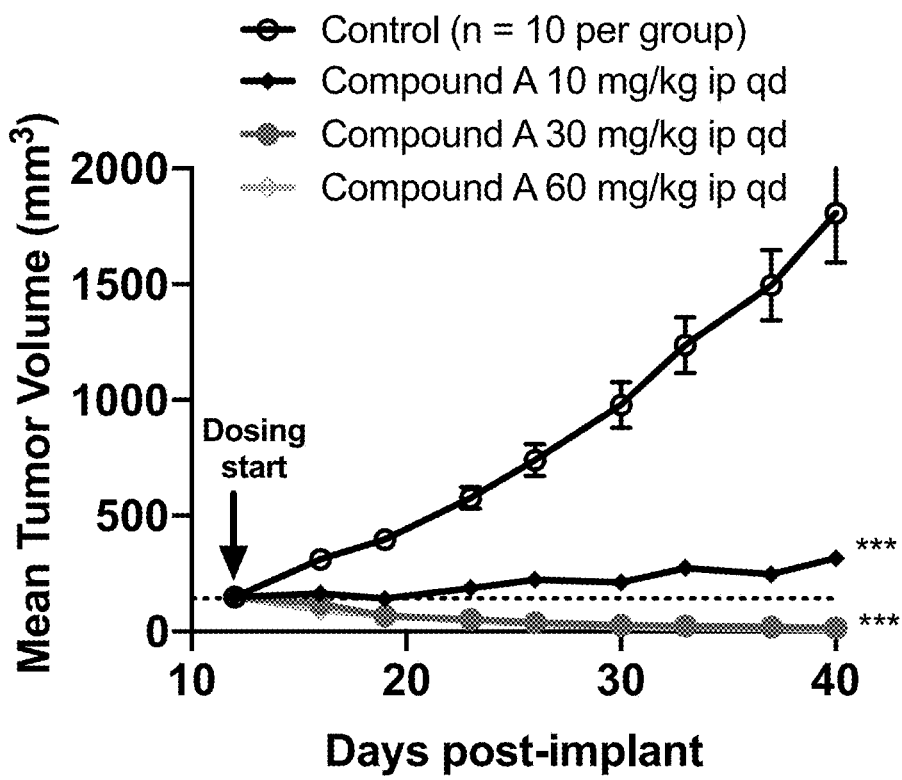
FIG. 1B: Treatment of KRAS G12D tumors in vivo with a compound of the present invention, Compound A, drives tumor regressions in a pancreatic CDX model (HPAC CDX model, PDAC, KRAS G12D/WT). n=10/group, ***p<0.001. All dose levels well tolerated.

In this application, unless otherwise clear from context, (i) the term "a" means "one or more"; (ii) the term "or" is used to mean "and/or" unless explicitly indicated to refer to alternatives only or the alternative are mutually exclusive, although the disclosure supports a definition that refers to only alternatives and "and/or"; (iii) the terms "comprising"

and "including" are understood to encompass itemized components or steps whether presented by themselves or together with one or more additional components or steps; and (iv) where ranges are provided, endpoints are included.

As used herein, the term "about" is used to indicate that a value includes the standard deviation of error for the device or method being employed to determine the value. In certain embodiments, the term "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of a stated value, unless otherwise stated or otherwise evident from the context (e.g., where such number would exceed 100% of a possible value).

As used herein, the term "adjacent" in the context of describing adjacent atoms refers to bivalent atoms that are directly connected by a covalent bond.

A "compound of the present invention" and similar terms as used herein, whether explicitly noted or not, refers to Ras inhibitors described herein, including compounds of Formula I and subformula thereof, and compounds of Table 1 and Table 2, as well as salts (e.g., pharmaceutically acceptable salts), solvates, hydrates, stereoisomers (including atropisomers), and tautomers thereof.

The term "wild-type" refers to an entity having a structure or activity as found in nature in a "normal" (as contrasted with mutant, diseased, altered, etc) state or context. Those of ordinary skill in the art will appreciate that wild-type genes and polypeptides often exist in multiple different forms (e.g., alleles).

Those skilled in the art will appreciate that certain compounds described herein can exist in one or more different isomeric (e.g., stereoisomers, geometric isomers, atropisomers, tautomers) or isotopic (e.g., in which one or more atoms has been substituted with a different isotope of the atom, such as hydrogen substituted for deuterium) forms. Unless otherwise indicated or clear from context, a depicted structure can be understood to represent any such isomeric or isotopic form, individually or in combination.

Compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, one or more compounds depicted herein may exist in different tautomeric forms. As will be clear from context, unless explicitly excluded, references to such compounds encompass all such tautomeric forms. In some embodiments, tautomeric forms result from the swapping of a single bond with an adjacent double bond and the concomitant migration of a proton. In certain embodiments, a tautomeric form may be a prototropic tautomer, which is an isomeric protonation states having the same empirical formula and total charge as a reference form. Examples of moieties with prototropic tautomeric forms are ketone—enol pairs, amide—imidic acid pairs, lactam—lactim pairs, amide—imidic acid pairs, enamine—imine pairs, and annular forms where a proton can occupy two or more positions of a heterocyclic system, such as, 1H- and 3H-imidazole, 1H-, 2H- and 4H-1,2,4-triazole, 1H- and 2H-isoindole, and 1H- and 2H-pyrazole. In some embodiments, tautomeric forms can be in equilibrium or sterically locked into one form by appropriate substitution. In certain embodiments, tautomeric forms result from acetal interconversion.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^3H$ and $^{14}C$) can be useful in compound or substrate tissue distribution assays. Tritiated (i.e., $^3H$) and carbon-14 (i.e., $^{14}C$) isotopes can be useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements). In some embodiments, one or more hydrogen atoms are replaced by $^2H$ or $^3H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

As is known in the art, many chemical entities can adopt a variety of different solid forms such as, for example, amorphous forms or crystalline forms (e.g., polymorphs, hydrates, solvate). In some embodiments, compounds of the present invention may be utilized in any such form, including in any solid form. In some embodiments, compounds described or depicted herein may be provided or utilized in hydrate or solvate form.

At various places in the present specification, substituents of compounds of the present disclosure are disclosed in groups or in ranges. It is specifically intended that the present disclosure include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. Furthermore, where a compound includes a plurality of positions at which substituents are disclosed in groups or in ranges, unless otherwise indicated, the present disclosure is intended to cover individual compounds and groups of compounds (e.g., genera and subgenera) containing each and every individual subcombination of members at each position.

The term "optionally substituted X" (e.g., "optionally substituted alkyl") is intended to be equivalent to "X, wherein X is optionally substituted" (e.g., "alkyl, wherein said alkyl is optionally substituted"). It is not intended to mean that the feature "X" (e.g., alkyl) per se is optional. As described herein, certain compounds of interest may contain one or more "optionally substituted" moieties. In general, the term "substituted", whether preceded by the term "optionally" or not, means that one or more hydrogens of the designated moiety are replaced with a suitable substituent, e.g., any of the substituents or groups described herein. Unless otherwise indicated, an "optionally substituted" group may have a suitable substituent at each substitutable position of the group, and when more than one position in any given structure may be substituted with more than one substituent selected from a specified group, the substituent may be either the same or different at every position. For example, in the term "optionally substituted $C_1$-$C_6$ alkyl-$C_2$-$C_9$ heteroaryl," the alkyl portion, the heteroaryl portion, or both, may be optionally substituted. Combinations of substituents envisioned by the present disclosure are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group may be, independently, deuterium; halogen; —$(CH_2)_{0-4}R^\circ$; —$(CH_2)_{0-4}OR^\circ$; —$O(CH_2)_{0-4}R^\circ$; —$O$—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$(CH_2)_{0-4}O(CH_2)_{0-1}$-pyridyl which may be substituted with $R^\circ$; 4 to 8-membered saturated or unsaturated heterocycloalkyl (e.g., pyridyl); 3 to 8-membered saturated or unsaturated cycloalkyl (e.g., cyclopropyl, cyclobutyl, or cyclopentyl); —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}$—$C(O)$—$N(R^\circ)_2$; —$(CH_2)_{0-4}$—$C(O)$—$N(R^\circ)$—$S(O)_2$—$R^\circ$; —$C(NCN)NR^\circ_2$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR^\circ$; —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NOR^\circ)NR^\circ_2$; —$C(NH)NR^\circ_2$; —$P(O)_2R^\circ$; —$P(O)R^\circ_2$; —$P(O)(OR^\circ)_2$; —$OP(O)R^\circ_2$; —$OP(O)(OR^\circ)_2$; —$OP(O)(OR^\circ)R^\circ$, —$SiR^\circ_3$; —$(C_1$-$C_4$ straight or branched alkylene)$O$—$N(R^\circ)_2$; or —$(C_1$-$C_4$ straight or branched alkylene)$C(O)O$—$N(R^\circ)_2$, wherein each $R^\circ$ may be substituted as defined below and is independently hydrogen, —$C_1$-$C_6$ aliphatic, —$CH_2Ph$, —$O(CH_2)_{0-1}Ph$, —$CH_2$-(5 to 6 membered heteroaryl ring), or a 3 to 6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3 to 12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), may be, independently, halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\bullet)_2$; —$O(haloR^\bullet)$, —$CN$, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$—$(C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_1$-$C_4$ aliphatic, —$CH_2Ph$, —$O(CH_2)_{0-1}Ph$, or a 5 to 6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, —$O(C(R^*_2))_{2-3}O$—, or —$S(C(R^*_2))_{2-3}S$—, wherein each independent occurrence of $R^*$ is selected from hydrogen, $C_1$-$C_6$ aliphatic which may be substituted as defined below, or an unsubstituted 5 to 6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_1$-$C_6$ aliphatic which may be substituted as defined below, or an unsubstituted 5 to 6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(haloR$^\bullet$), —$OH$, —$OR^\bullet$, —$O(haloR^\bullet)$, —$CN$, —$C(O)OH$, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_1$-$C_4$ aliphatic, —$CH_2Ph$, —$O(CH_2)_{0-1}Ph$, or a 5 to 6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_1$-$C_6$ aliphatic which may be substituted as defined below, unsubstituted —$OPh$, or an unsubstituted 3 to 6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3 to 12-membered saturated, partially unsaturated, or aryl mono- or bicyclic ring having 0-4 heteroatoms independently selected from nitrogen, oxygen, or sulfur.

Suitable substituents on an aliphatic group of $R^\backslash$ are independently halogen, —$R^\bullet$, -(haloR$^\bullet$), —$OH$, —$OR^\bullet$, —$O(haloR^\bullet)$, —$CN$, —$C(O)OH$, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_1$-$C_4$ aliphatic, —$CH_2Ph$, —$O(CH_2)_{0-1}Ph$, or a 5 to 6-membered saturated, partially unsaturated, or aryl ring having 0-4 heteroatoms independently selected from nitrogen, oxygen, or sulfur. Suitable divalent substituents on a saturated carbon atom of $R^\dagger$ include $=O$ and $=S$.

The term "acetyl," as used herein, refers to the group —$C(O)CH_3$.

The term "alkoxy," as used herein, refers to a —O—$C_1$-$C_{20}$ alkyl group, wherein the alkoxy group is attached to the remainder of the compound through an oxygen atom.

The term "alkyl," as used herein, refers to a saturated, straight or branched monovalent hydrocarbon group containing from 1 to 20 (e.g., from 1 to 10 or from 1 to 6) carbons. In some embodiments, an alkyl group is unbranched (i.e., is linear); in some embodiments, an alkyl group is branched. Alkyl groups are exemplified by, but not limited to, methyl, ethyl, n- and iso-propyl, n-, sec-, iso- and tert-butyl, and neopentyl.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like. The term "$C_x$-$C_y$ alkylene" represents alkylene groups having between x and y carbons. Exemplary values for x are 1, 2, 3, 4, 5, and 6, and exemplary values for y are 2, 3, 4, 5, 6, 7, 8, 9, 10, 12, 14, 16, 18, or 20 (e.g., $C_1$-$C_6$, $C_1$-$C_{10}$, $C_2$-$C_{20}$, $C_2$-$C_6$, $C_2$-$C_{10}$, or $C_2$-$C_{20}$ alkylene). In some embodiments, the alkylene can be further substituted with 1, 2, 3, or 4 substituent groups as defined herein.

The term "alkenyl," as used herein, represents monovalent straight or branched chain groups of, unless otherwise specified, from 2 to 20 carbons (e.g., from 2 to 6 or from 2 to 10 carbons) containing one or more carbon-carbon double bonds and is exemplified by ethenyl, 1-propenyl, 2-propenyl, 2-methyl-1-propenyl, 1-butenyl, and 2-butenyl. Alkenyls include both cis and trans isomers. The term "alkenylene," as used herein, represents a divalent straight or branched chain groups of, unless otherwise specified, from 2 to 20 carbons (e.g., from 2 to 6 or from 2 to 10 carbons) containing one or more carbon-carbon double bonds.

The term "alkynyl," as used herein, represents monovalent straight or branched chain groups from 2 to 20 carbon atoms (e.g., from 2 to 4, from 2 to 6, or from 2 to 10 carbons) containing a carbon-carbon triple bond and is exemplified by ethynyl, and 1-propynyl.

The term "alkynyl sulfone," as used herein, represents a group comprising the structure

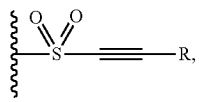

wherein R is any chemically feasible substituent described herein.

The term "amino," as used herein, represents —N($R^†$)$_2$, e.g., —$NH_2$ and —N($CH_3$)$_2$.

The term "aminoalkyl," as used herein, represents an alkyl moiety substituted on one or more carbon atoms with one or more amino moieties.

The term "amino acid," as described herein, refers to a molecule having a side chain, an amino group, and an acid group (e.g., —$CO_2H$ or —$SO_3H$), wherein the amino acid is attached to the parent molecular group by the side chain, amino group, or acid group (e.g., the side chain). As used herein, the term "amino acid" in its broadest sense, refers to any compound or substance that can be incorporated into a polypeptide chain, e.g., through formation of one or more peptide bonds. In some embodiments, an amino acid has the general structure $H_2N$—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. Exemplary amino acids include alanine, arginine, asparagine, aspartic acid, cysteine, glutamic acid, glutamine, glycine, histidine, optionally substituted hydroxylnorvaline, isoleucine, leucine, lysine, methionine, norvaline, ornithine, phenylalanine, proline, pyrrolysine, selenocysteine, serine, taurine, threonine, tryptophan, tyrosine, and valine.

The term "aryl," as used herein, represents a monovalent monocyclic, bicyclic, or multicyclic ring system formed by carbon atoms, wherein the ring attached to the pendant group is aromatic. Examples of aryl groups are phenyl, naphthyl, phenanthrenyl, and anthracenyl. An aryl ring can be attached to its pendant group at any heteroatom or carbon ring atom that results in a stable structure and any of the ring atoms can be optionally substituted unless otherwise specified.

The term "$C_0$," as used herein, represents a bond. For example, part of the term —N(C(O))—($C_0$-$C_5$ alkylene-H)— includes —N(C(O))—($C_0$ alkylene-H)—, which is also represented by —N(C(O)—H)—.

The terms "carbocyclic" and "carbocyclyl," as used herein, refer to a monovalent, optionally substituted 3 to 12-membered monocyclic, bicyclic, or tricyclic ring structure, which may be bridged, fused or spirocyclic, in which all the rings are formed by carbon atoms and at least one ring is non-aromatic. Carbocyclic structures include cycloalkyl, cycloalkenyl, and cycloalkynyl groups. Examples of carbocyclyl groups are cyclohexyl, cyclohexenyl, cyclooctynyl, 1,2-dihydronaphthyl, 1,2,3,4-tetrahydronaphthyl, fluorenyl, indenyl, indanyl, decalinyl, and the like. A carbocyclic ring can be attached to its pendant group at any ring atom that results in a stable structure and any of the ring atoms can be optionally substituted unless otherwise specified.

The term "carbonyl," as used herein, represents a C(O) group, which can also be represented as C=O.

The term "carboxyl," as used herein, means —$CO_2H$, (C=O)(OH), COOH, or C(O)OH or the unprotonated counterparts.

The term "cyano," as used herein, represents a —CN group.

The term "cycloalkyl," as used herein, represents a monovalent saturated cyclic hydrocarbon group, which may be bridged, fused, or spirocyclic having from three to eight ring carbons, unless otherwise specified, and is exemplified by cyclopropyl, cyclobutyl, cyclopentyl, cyclohexyl, cycloheptyl, and cycloheptyl.

The term "cycloalkenyl," as used herein, represents a monovalent, non-aromatic, saturated cyclic hydrocarbon group, which may be bridged, fused, or spirocyclic having from three to eight ring carbons, unless otherwise specified, and containing one or more carbon-carbon double bonds.

The term "diastereomer," as used herein, means stereoisomers that are not mirror images of one another and are non-superimposable on one another.

The term "enantiomer," as used herein, means each individual optically active form of a compound of the invention, having an optical purity or enantiomeric excess (as determined by methods standard in the art) of at least 80% (i.e., at least 90% of one enantiomer and at most 10% of the other enantiomer), preferably at least 90% and more preferably at least 98%.

The term "guanidinyl," refers to a group having the structure:

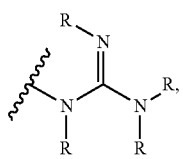

wherein each R is, independently, any any chemically feasible substituent described herein.

The term "guanidinoalkyl alkyl," as used herein, represents an alkyl moiety substituted on one or more carbon atoms with one or more guanidinyl moieties.

The term "haloacetyl," as used herein, refers to an acetyl group wherein at least one of the hydrogens has been replaced by a halogen.

The term "haloalkyl," as used herein, represents an alkyl moiety substituted on one or more carbon atoms with one or more of the same of different halogen moieties.

The term "halogen," as used herein, represents a halogen selected from bromine, chlorine, iodine, or fluorine.

The term "heteroalkyl," as used herein, refers to SET "alkyl" group, as defined herein, in which at least one carbon atom has been replaced with a heteroatom (e.g., an O, N, or S atom). The heteroatom may appear in the middle or at the end of the radical.

The term "heteroaryl," as used herein, represents a monovalent, monocyclic or polycyclic ring structure that contains at least one fully aromatic ring: i.e., they contain 4n+2 pi electrons within the monocyclic or polycyclic ring system and contains at least one ring heteroatom selected from N, O, or S in that aromatic ring. Exemplary unsubstituted heteroaryl groups are of 1 to 12 (e.g., 1 to 11, 1 to 10, 1 to 9, 2 to 12, 2 to 11, 2 to 10, or 2 to 9) carbons. The term "heteroaryl" includes bicyclic, tricyclic, and tetracyclic groups in which any of the above heteroaromatic rings is fused to one or more, aryl or carbocyclic rings, e.g., a phenyl ring, or a cyclohexane ring. Examples of heteroaryl groups include, but are not limited to, pyridyl, pyrazolyl, benzoxazolyl, benzoimidazolyl, benzothiazolyl, imidazolyl, thiazolyl, quinolinyl, tetrahydroquinolinyl, and 4-azaindolyl. A heteroaryl ring can be attached to its pendant group at any ring atom that results in a stable structure and any of the ring atoms can be optionally substituted unless otherwise specified. In some embodiment, the heteroaryl is substituted with 1, 2, 3, or 4 substituents groups.

The term "heterocycloalkyl," as used herein, represents a monovalent, monocyclic, bicyclic or polycyclic ring system, which may be bridged, fused, or spirocyclic, wherein at least one ring is non-aromatic and wherein the non-aromatic ring contains one, two, three, or four heteroatoms independently selected from the group consisting of nitrogen, oxygen, and sulfur. The 5-membered ring has zero to two double bonds, and the 6- and 7-membered rings have zero to three double bonds. Exemplary unsubstituted heterocycloalkyl groups are of 1 to 12 (e.g., 1 to 11, 1 to 10, 1 to 9, 2 to 12, 2 to 11, 2 to 10, or 2 to 9) carbons. The term "heterocycloalkyl" also represents a heterocyclic compound having a bridged multicyclic structure in which one or more carbons or heteroatoms bridges two non-adjacent members of a monocyclic ring, e.g., a quinuclidinyl group. The term "heterocycloalkyl" includes bicyclic, tricyclic, and tetracyclic groups in which any of the above heterocyclic rings is fused to one or more aromatic, carbocyclic, heteroaromatic, or heterocyclic rings, e.g., an aryl ring, a cyclohexane ring, a cyclohexene ring, a cyclopentane ring, a cyclopentene ring, a pyridine ring, or a pyrrolidine ring. Examples of heterocycloalkyl groups are pyrrolidinyl, piperidinyl, 1,2,3,4-tetrahydroquinolinyl, decahydroquinolinyl, dihydropyrrolopyridine, and decahydronapthyridinyl. A heterocycloalkyl ring can be attached to its pendant group at any ring atom that results in a stable structure and any of the ring atoms can be optionally substituted unless otherwise specified.

The term "hydroxy," as used herein, represents a —OH group.

The term "hydroxyalkyl," as used herein, represents an alkyl moiety substituted on one or more carbon atoms with one or more —OH moieties.

The term "isomer," as used herein, means any tautomer, stereoisomer, atropiosmer, enantiomer, or diastereomer of any compound of the invention. It is recognized that the compounds of the invention can have one or more chiral centers or double bonds and, therefore, exist as stereoisomers, such as double-bond isomers (i.e., geometric E/Z isomers) ordiastereomers (e.g., enantiomers (i.e., (+) or (−)) or cis/trans isomers). According to the invention, the chemical structures depicted herein, and therefore the compounds of the invention, encompass all the corresponding stereoisomers, that is, both the stereomerically pure form (e.g., geometrically pure, enantiomerically pure, ordiastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

As used herein, the term "linker" refers to a divalent organic moiety connecting moiety B to moiety W in a compound of Formula I, such that the resulting compound is capable of achieving an IC50 of 2 uM or less in the Ras-RAF disruption assay protocol provided in the Examples below, and provided here:

The purpose of this biochemical assay is to measure the ability of test compounds to facilitate ternary complex formation between a nucleotide-loaded Ras isoform and cyclophilin A; the resulting ternary complex disrupts binding to a BRAF$^{RBD}$ construct, inhibiting Ras signaling through a RAF effector.

In assay buffer containing 25 mM HEPES pH 7.3, 0.002% Tween20, 0.1% BSA, 100 mM NaCl and 5 mM MgCl$_2$, tagless Cyclophilin A, His6-K-Ras-GMPPNP (or other Ras variant), and GST-BRAF$^{RBD}$ are combined in a 384-well assay plate at final concentrations of 25 μM, 12.5 nM and 50 nM, respectively. Compound is present in plate wells as a 10-point 3-fold dilution series starting at a final concentration of 30 μM. After incubation at 25° C. for 3 hours, a mixture of Anti-His Eu-W1024 and anti-GST allophycocyanin is then added to assay sample wells at final concentrations of 10 nM and 50 nM, respectively, and the reaction incubated for an additional 1.5 hours. TR-FRET signal is read on a microplate reader (Ex 320 nm, Em 665/615 nm). Compounds that facilitate disruption of a Ras:RAF complex are identified as those eliciting a decrease in the TR-FRET ratio relative to DMSO control wells.

In some embodiments, the linker comprises 20 or fewer linear atoms. In some embodiments, the linker comprises 15 or fewer linear atoms. In some embodiments, the linker comprises 10 or fewer linear atoms. In some embodiments, the linker has a molecular weight of under 500 g/mol. In some embodiments, the linker has a molecular weight of under 400 g/mol. In some embodiments, the linker has a molecular weight of under 300 g/mol. In some embodiments, the linker has a molecular weight of under 200 g/mol. In some embodiments, the linker has a molecular weight of under 100 g/mol. In some embodiments, the linker has a molecular weight of under 50 g/mol.

As used herein, a "monovalent organic moiety" is less than 500 kDa. In some embodiments, a "monovalent organic moiety" is less than 400 kDa. In some embodiments, a "monovalent organic moiety" is less than 300 kDa. In some embodiments, a "monovalent organic moiety" is less than 200 kDa. In some embodiments, a "monovalent organic moiety" is less than 100 kDa. In some embodiments, a "monovalent organic moiety" is less than 50 kDa. In some embodiments, a "monovalent organic moiety" is less than 25 kDa. In some embodiments, a "monovalent organic moiety" is less than 20 kDa. In some embodiments, a "monovalent organic moiety" is less than 15 kDa. In some embodiments, a "monovalent organic moiety" is less than 10 kDa. In some embodiments, a "monovalent organic moiety" is less than 1 kDa. In some embodiments, a "monovalent organic moiety" is less than 500 g/mol. In some embodiments, a "monovalent organic moiety" ranges between 500 g/mol and 500 kDa.

The term "stereoisomer," as used herein, refers to all possible different isomeric as well as conformational forms which a compound may possess (e.g., a compound of any formula described herein), in particular all possible stereochemically and conformationally isomeric forms, all diastereomers, enantiomers or conformers of the basic molecular structure, including atropisomers. Some compounds of the present invention may exist in different tautomeric forms, all of the latter being included within the scope of the present invention.

The term "sulfonyl," as used herein, represents an —S(O)$_2$— group.

The term "thiocarbonyl," as used herein, refers to a —C(S)— group.

The term "vinyl ketone," as used herein, refers to a group comprising a carbonyl group directly connected to a carbon-carbon double bond.

The term "vinyl sulfone," as used herein, refers to a group comprising a sulfonyl group directed connected to a carbon-carbon double bond.

The term "ynone," as used herein, refers to a group comprising the structure

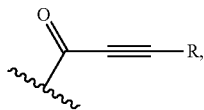

wherein R is any any chemically feasible substituent described herein.

Those of ordinary skill in the art, reading the present disclosure, will appreciate that certain compounds described herein may be provided or utilized in any of a variety of forms such as, for example, salt forms, protected forms, pro-drug forms, ester forms, isomeric forms (e.g., optical or structural isomers), isotopic forms, etc. In some embodiments, reference to a particular compound may relate to a specific form of that compound. In some embodiments, reference to a particular compound may relate to that compound in any form. In some embodiments, for example, a preparation of a single stereoisomer of a compound may be considered to be a different form of the compound than a racemic mixture of the compound; a particular salt of a compound may be considered to be a different form from another salt form of the compound; a preparation containing one conformational isomer ((Z) or (E)) of a double bond may be considered to be a different form from one containing the other conformational isomer ((E) or (Z)) of the double bond; a preparation in which one or more atoms is a different isotope than is present in a reference preparation may be considered to be a different form.

DETAILED DESCRIPTION

Compounds

Provided herein are Ras inhibitors. The approach described herein entails formation of a high affinity three-component complex, or conjugate, between a synthetic ligand and two intracellular proteins which do not interact under normal physiological conditions: the target protein of interest (e.g., Ras), and a widely expressed cytosolic chaperone (presenter protein) in the cell (e.g., cyclophilin A). More specifically, in some embodiments, the inhibitors of Ras described herein induce a new binding pocket in Ras by driving formation of a high affinity tri-complex, or conjugate, between the Ras protein and the widely expressed cytosolic chaperone, cyclophilin A (CYPA). Without being bound by theory, the inventors believe that one way the inhibitory effect on Ras is effected by compounds of the invention and the complexes, or conjugates, they form is by steric occlusion of the interaction site between Ras and downstream effector molecules, such as RAF, which are required for propagating the oncogenic signal.

Without being bound by theory, the inventors postulate that both covalent and non-covalent interactions of a compound of the present invention with Ras and the chaperone protein (e.g., cyclophilin A) may contribute to the inhibition of Ras activity. In some embodiments, a compound of the present invention forms a covalent adduct with a side chain of a Ras protein (e.g., the —CH$_2$—COOH or —CH$_2$—COO-side chain of the aspartic acid at position 12 or 13 of a mutant Ras protein). Covalent adducts may also be formed with other side chains of Ras. In addition or alternatively, non-covalent interactions may be at play: for example, van der Waals, hydrophobic, hydrophilic, and hydrogen bond interactions, and combinations thereof, may contribute to the ability of the compounds of the present invention to form complexes and act as Ras inhibitors. Accordingly, a variety of Ras proteins may be inhibited by compounds of the present invention (e.g., K-Ras, N-Ras, H-Ras, and mutants thereof at positions 12, 13 and 61, such as G12C, G12D, G12V, G12S, G13C, G13D, and Q61L, and others described herein).

Methods of determining covalent adduct formation are known in the art. One method of determining covalent adduct formation is to perform a "cross-linking" assay, such as described in the Examples, and below:

Note—the following protocol describes a procedure for monitoring cross-linking of K-Ras G12C (GMP-PNP) to a compound of the invention. This protocol may also be executed substituting other Ras proteins or nucleotides, such as K-Ras G12D.

The purpose of this biochemical assay is to measure the ability of test compounds to covalently label nucleotide-loaded K-Ras isoforms. In assay buffer containing 12.5 mM HEPES pH 7.4, 75 mM NaCl, 1 mM MgCl$_2$, 1 mM BME, 5 μM Cyclophilin A and 2 μM test compound, a 5 μM stock of GMP-PNP-loaded K-Ras (1-169) G12C is diluted 10-fold to yield a final concentration of 0.5 μM; with final sample volume being 100 μL.

The sample is incubated at 25° C. for a time period of up to 24 hours prior to quenching by the addition of 10 μL of 5% Formic Acid. Quenched samples are centrifuged at 15000 rpm for 15 minutes in a benchtop centrifuge before injecting a 10 μL aliquot onto a reverse phase C4 column and eluting into the mass spectrometer with an increasing acetonitrile gradient in the mobile phase. Analysis of raw data may be carried out using Waters MassLynx MS software, with % bound calculated from the deconvoluted protein peaks for labeled and unlabeled K-Ras.

Accordingly, provided herein is a compound, or pharmaceutically acceptable salt thereof, having the structure of Formula I:

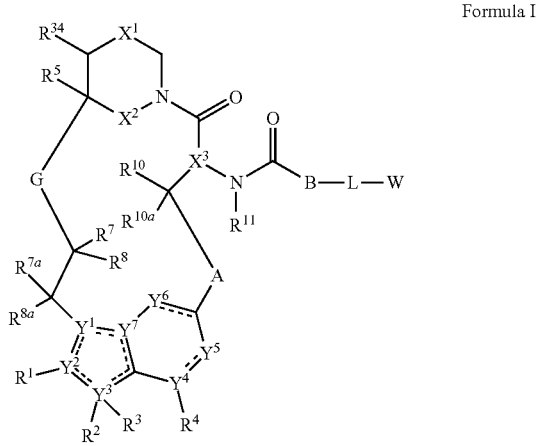

Formula I wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is —CH($R^9$)— or >C=$CR^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl; $R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo; and $R^{11}$ is hydrogen or $C_1$-$C_3$ alkyl; and $R^{34}$ is hydrogen or $C_1$-$C_3$ alkyl (e.g., methyl).

In some embodiments, $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments, $R^{34}$ is hydrogen.

In some embodiments of compounds of the present invention, G is optionally substituted $C_1$-$C_4$ heteroalkylene.

In some embodiments, a compound of the present invention has the structure of Formula Ia, or a pharmaceutically acceptable salt thereof:

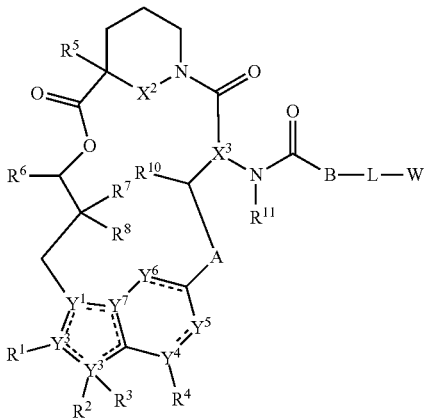

Formula Ia wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments of compounds of the present invention, $X^2$ is NH. In some embodiments, $X^3$ is CH.

In some embodiments of compounds of the present invention, $R^{11}$ is hydrogen. In some embodiments, $R^{11}$ is $C_1$-$C_3$ alkyl, such as methyl.

In some embodiments, a compound of the present invention has the structure of Formula Ib, or a pharmaceutically acceptable salt thereof:

Formula Ib

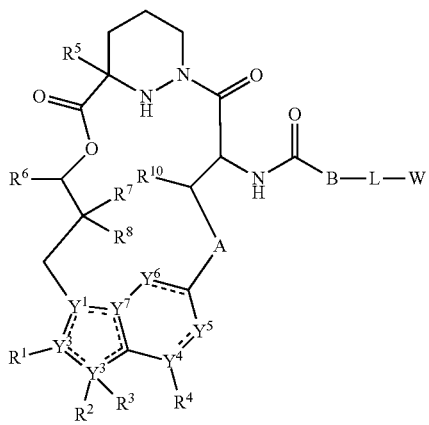

wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R$^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—C$_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

In some embodiments of compounds of the present invention, $X^1$ is optionally substituted $C_1$-$C_2$ alkylene. In some embodiments, $X^1$ is methylene.

In some embodiments of compounds of the present invention, $R^4$ is hydrogen.

In some embodiments of compounds of the present invention, $R^5$ is hydrogen. In some embodiments, $R^5$ is $C_1$-$C_4$ alkyl optionally substituted with halogen. In some embodiments, $R^5$ is methyl.

In some embodiments of compounds of the present invention, $Y^4$ is C. In some embodiments, $R^4$ is hydrogen. In some embodiments, $Y^5$ is CH. In some embodiments, $Y^6$ is CH. In some embodiments, $Y^1$ is C. In some embodiments, $Y^2$ is C. In some embodiments, $Y^3$ is N. In some embodiments, $R^3$ is absent. In some embodiments, $Y^7$ is C.

In some embodiments, a compound of the present invention has the structure of Formula Ic, or a pharmaceutically acceptable salt thereof:

Formula Ic

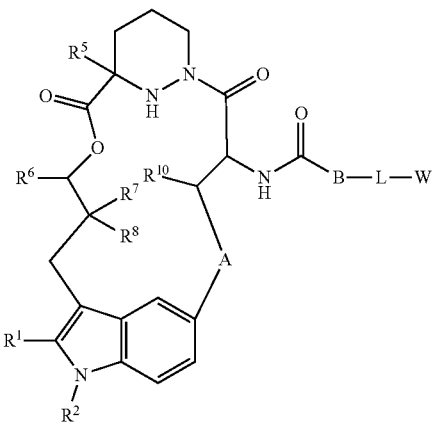

wherein A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

In some embodiments of compounds of the present invention, $R^6$ is hydrogen.

In some embodiments of compounds of the present invention, $R^2$ is hydrogen, cyano, optionally substituted $C_1$-$C_6$ alkyl, optionally substituted 3 to 6-membered cycloalkyl, or optionally substituted 3 to 6-membered heterocycloalkyl. In some embodiments, $R^2$ is optionally substituted $C_1$-$C_6$ alkyl, such as ethyl.

In some embodiments of compounds of the present invention, $R^7$ is optionally substituted $C_1$-$C_3$ alkyl. In some embodiments, $R^7$ is $C_1$-$C_3$ alkyl.

In some embodiments of compounds of the present invention, $R^8$ is optionally substituted $C_1$-$C_3$ alkyl. In some embodiments, $R^8$ is $C_1$-$C_3$ alkyl.

In some embodiments, a compound of the present invention has the structure of Formula Id, or a pharmaceutically acceptable salt thereof:

Formula Id

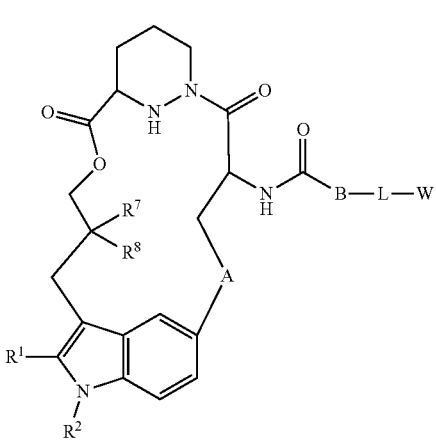

wherein A is —N(H or CH₃)C(O)—(CH₂)— where the amino nitrogen is bound to the carbon atom of —CH (R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

R¹ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

R² is $C_1$-$C_6$ alkyl or 3 to 6-membered cycloalkyl;

R⁷ is $C_1$-$C_3$ alkyl;

R⁸ is $C_1$-$C_3$ alkyl; and

R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments of compounds of the present invention, R¹ is 5 to 10-membered heteroaryl. In some embodiments, R¹ is optionally substituted 6-membered aryl or optionally substituted 6-membered heteroaryl.

In some embodiments, a compound of the present invention has the structure of Formula Ie, or a pharmaceutically acceptable salt thereof:

Formula Ie

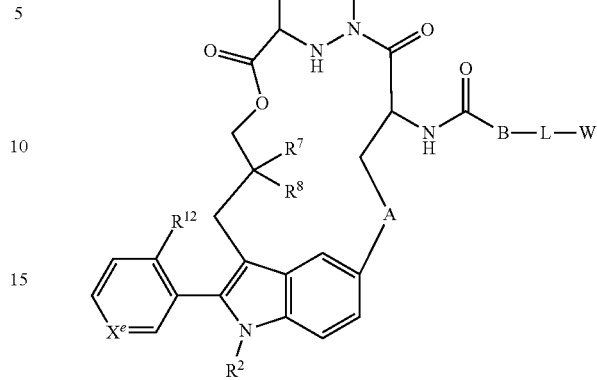

wherein A is —N(H or CH₃)C(O)—(CH₂)— where the amino nitrogen is bound to the carbon atom of —CH (R¹⁰)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH(R⁹)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

R² is $C_1$-$C_6$ alkyl or 3 to 6-membered cycloalkyl;

R⁷ is $C_1$-$C_3$ alkyl;

R⁸ is $C_1$-$C_3$ alkyl; and

R⁹ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl Xᵉ is N or CH; and R¹² is optionally substituted $C_1$-$C_6$ alkyl or optionally substituted $C_1$-$C_6$ heteroalkyl.

In some embodiments of compounds of the present invention, Xᵉ is N. In some embodiments, Xᵉ is CH.

In some embodiments of compounds of the present invention, R¹² is optionally substituted $C_1$-$C_6$ heteroalkyl. In some embodiments, R¹² is

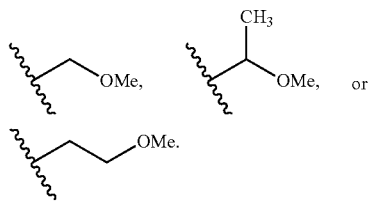

In some embodiments, $R^{12}$ is

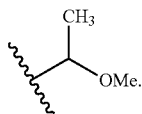 [SMILES: *C(C)OC]

In some embodiments, a compound of the present invention has the structure of Formula If, or a pharmaceutically acceptable salt thereof:

Formula If

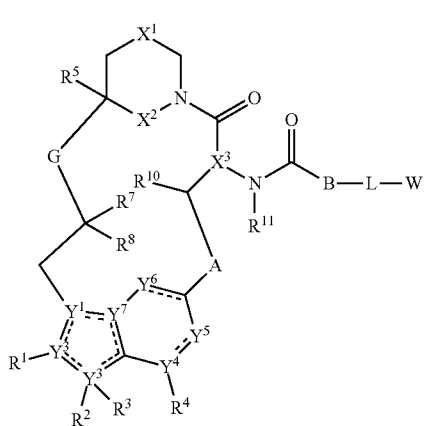

wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments, a compound of the present invention has the structure of Formula VI, or a pharmaceutically acceptable salt thereof:

Formula VI

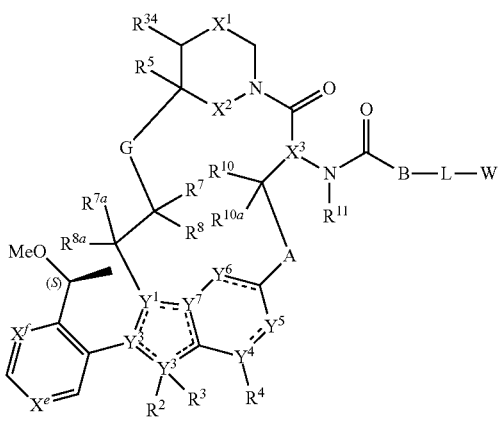

wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene (e.g., phenyl or phenol), or optionally substituted 5 to 10-membered heteroarylene;

B is —CH($R^9$)— or >C=C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl;

$R^{34}$ is hydrogen or $C_1$-$C_3$ alkyl; and $X^e$ and $X^f$ are, independently, N or CH.

In some embodiments, a compound of the present invention has the structure of Formula Via, or a pharmaceutically acceptable salt thereof:

Formula VIa

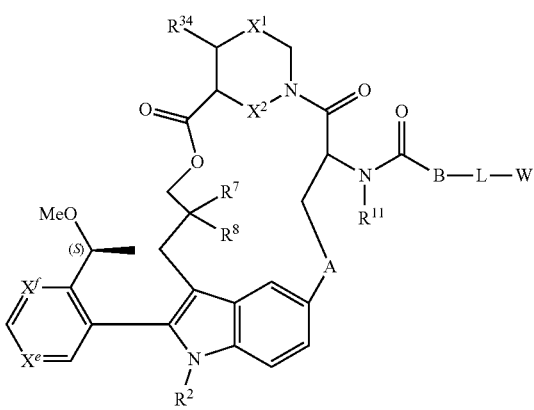

wherein A is optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or $S(O)_n$;

$X^2$ is O or NH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', $S(O)_2$ R', or $S(O)_2N(R')_2$; each R' is, independently, H or optionally substituted $C_1$-$C_4$ alkyl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$X^e$ and $X^f$ are, independently, N or CH;

$R^{11}$ is hydrogen or $C_1$-$C_3$ alkyl; and $R^{21}$ is hydrogen or $C_1$-$C_3$ alkyl.

In some embodiments of a compound of the present invention, $X^e$ is N and $X^f$ is CH. In some embodiments, $X^e$ is CH and $X^f$ is N.

In some embodiments, a compound of the present invention has the structure of Formula VIb, or a pharmaceutically acceptable salt thereof:

Formula VIb

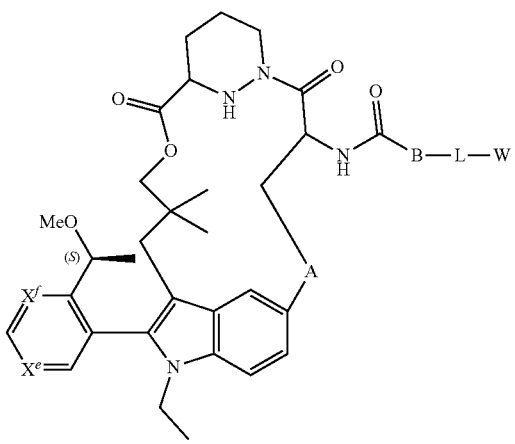

wherein A optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $X^e$ and $X^f$ are, independently, N or CH.

In some embodiments of a compound of the present invention, $X^e$ is N and $X^f$ is CH. In some embodiments, $X^e$ is CH and $X^f$ is N.

In some embodiments, a compound of the present invention has the structure of Formula VII, or a pharmaceutically acceptable salt thereof:

Formula VII

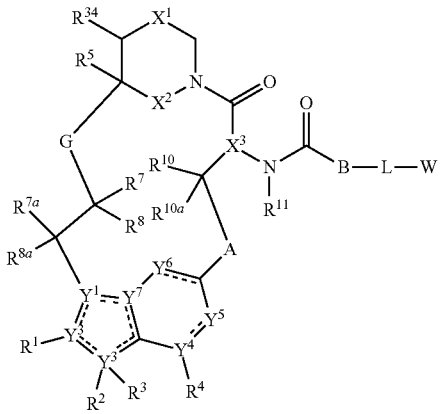

wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is —CH($R^9$)— or >C=C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is

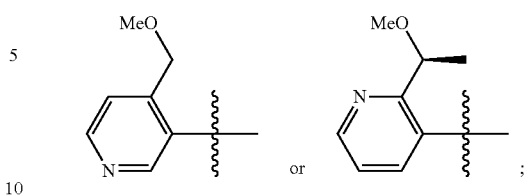

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{34}$ is hydrogen or $C_1$-$C_3$ alkyl (e.g., methyl).

In some embodiments of compounds of the present invention, A is optionally substituted 6-membered arylene. In some embodiments, A has the structure:

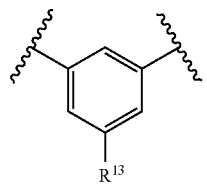

wherein $R^{13}$ is hydrogen, hydroxy, amino, optionally substituted $C_1$-$C_6$ alkyl, or optionally substituted $C_1$-$C_6$ heteroalkyl. In some embodiments, $R^{13}$ is hydrogen. In some embodiments, $R^{13}$ is hydroxy.

In some embodiments of compounds of the present invention, B is —CHR$^9$—. In some embodiments, $R^9$ is optionally substituted $C_1$-$C_6$ alkyl or optionally substituted 3 to 6-membered cycloalkyl. In some embodiments, $R^9$ is:

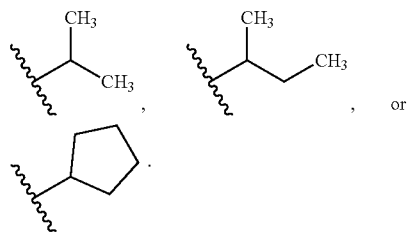

In some embodiments, $R^9$ is:

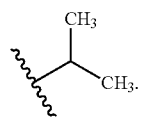

In some embodiments, $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

In some embodiments, B is optionally substituted 6-membered arylene. In some embodiments, B is 6-membered arylene. In some embodiments, B is:

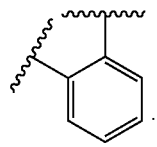 [SMILES: *c1ccccc1*]

In some embodiments of compounds of the present invention, $R^7$ is methyl.

In some embodiments of compounds of the present invention, $R^8$ is methyl.

In some embodiments, $R^{34}$ is hydrogen.

In some embodiments of compounds of the present invention, the linker is the structure of Formula II:

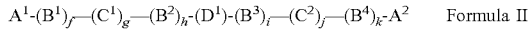

$A^1$-$(B^1)_f$—$(C^1)_g$—$(B^2)_h$-$(D^1)$-$(B^3)_i$—$(C^2)_j$—$(B^4)_k$-$A^2$    Formula II where $A^1$ is a bond between the linker and B; $A^2$ is a bond between W and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and NR$^N$; $R^N$ is hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$— to —$(B^3)_i$—$(C^2)_j$—$(B^4)_k$-$A^2$. In some embodiments, the linker is acyclic. In some embodiments, the linker has the structure of Formula IIa:

Formula IIa wherein $X^a$ is absent or N;

$R^{14}$ is absent, hydrogen or optionally substituted $C_1$-$C_6$ alkyl; and $L^2$ is absent, —SO$_2$—, optionally substituted $C_1$-$C_4$ alkylene or optionally substituted $C_1$-$C_4$ heteroalkylene, wherein at least one of $X^a$, $R^{14}$, or $L^2$ is present. In some embodiments, the linker has the structure:

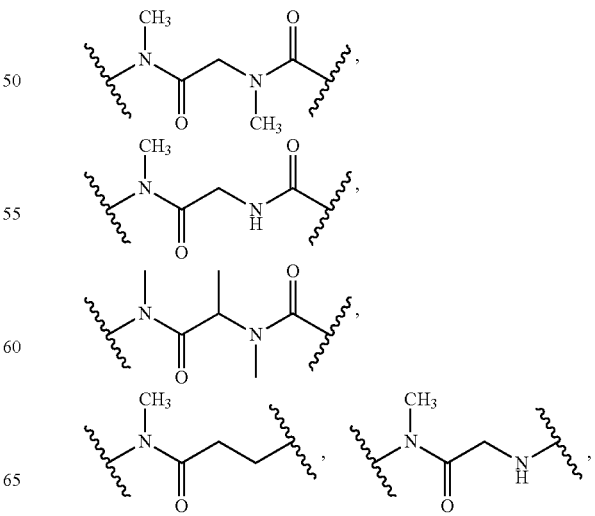

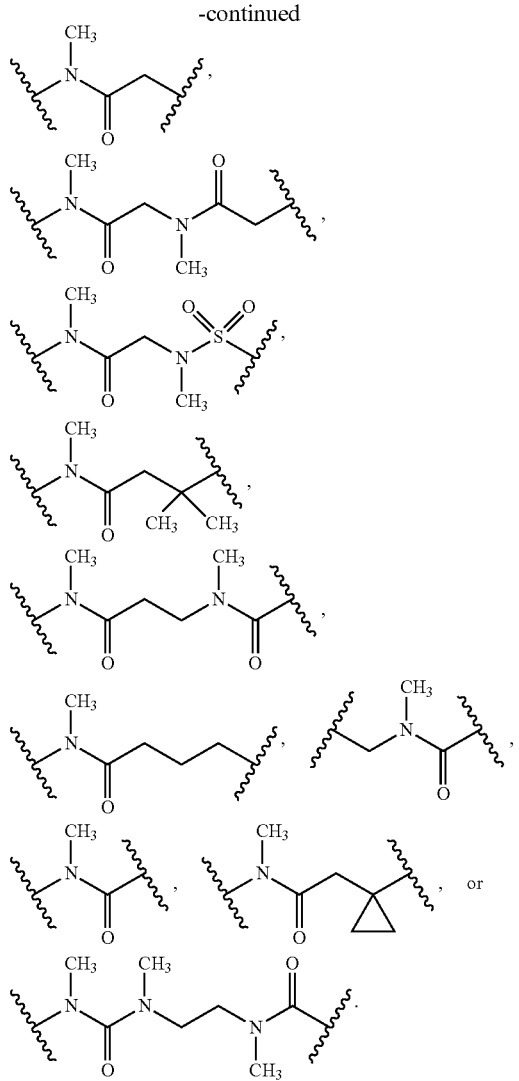

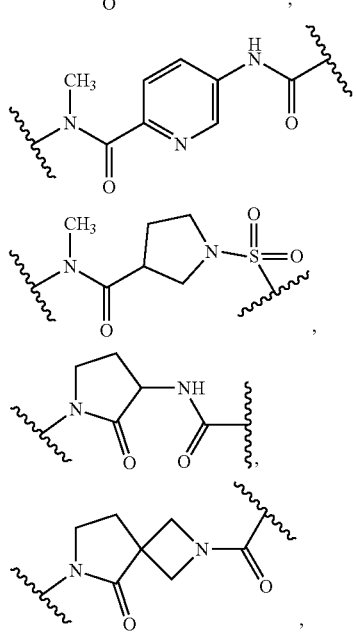

In some embodiments, the linker is or a comprises a cyclic group. In some embodiments, the linker has the structure of Formula IIb:

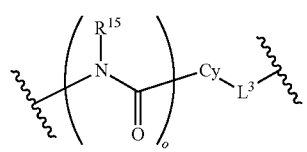

Formula IIb wherein o is 0 or 1;

$R^{15}$ is hydrogen or optionally substituted $C_1$-$C_6$ alkyl;

Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and $L^3$ is absent, —$SO_2$—, optionally substituted $C_1$-$C_4$ alkylene or optionally substituted $C_1$-$C_4$ heteroalkylene. In some embodiments, the linker has the structure:

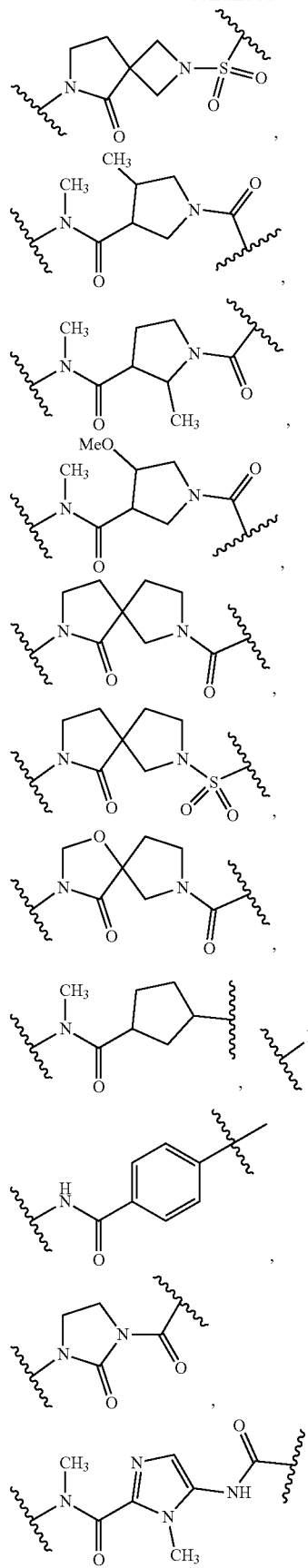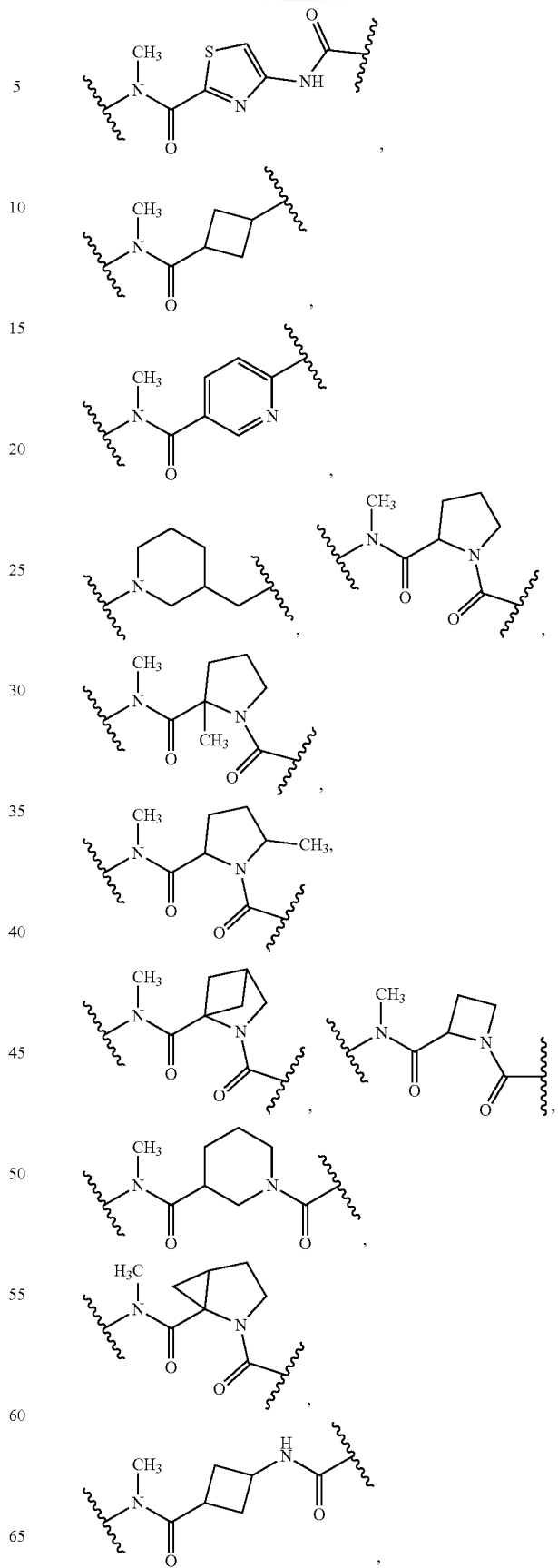

41
-continued
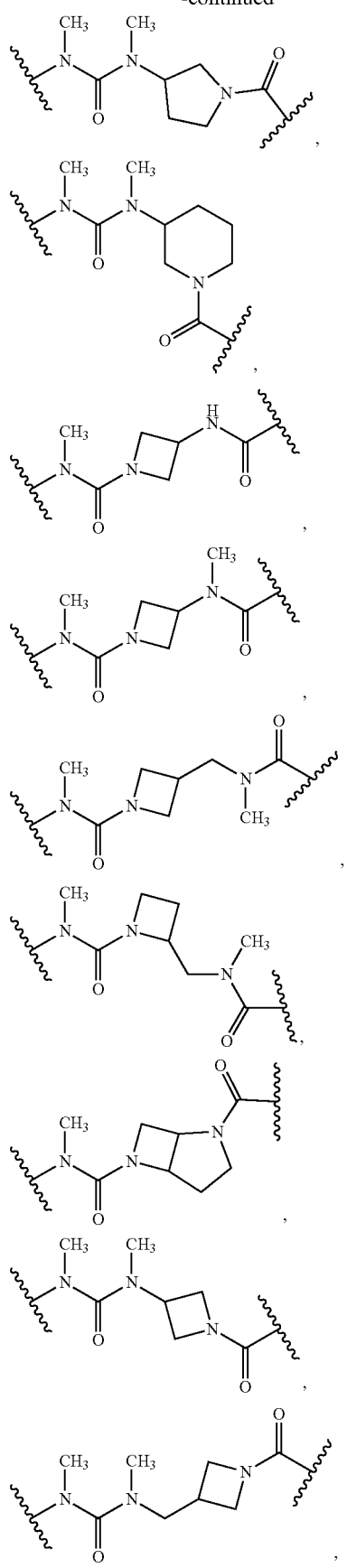
42
-continued
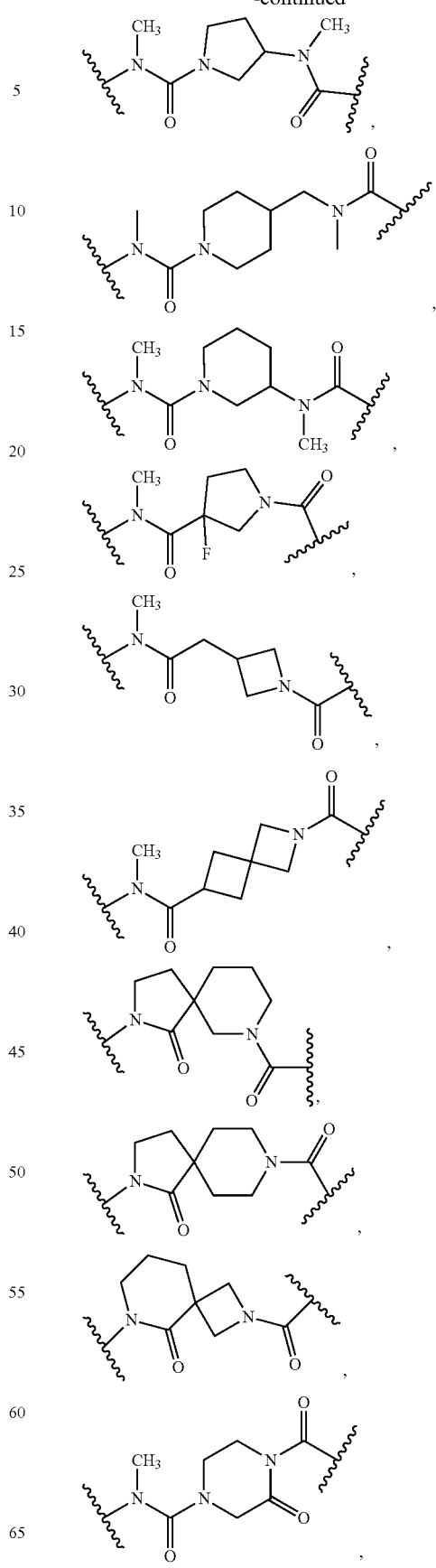

-continued

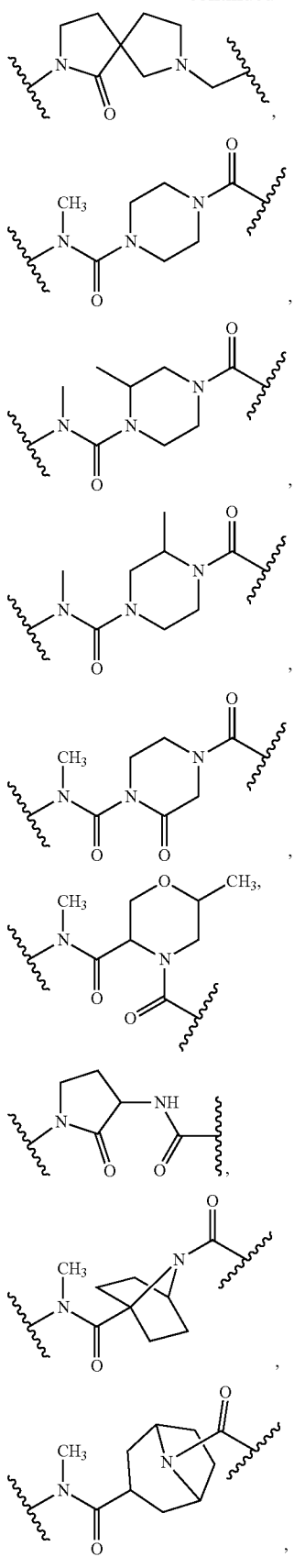

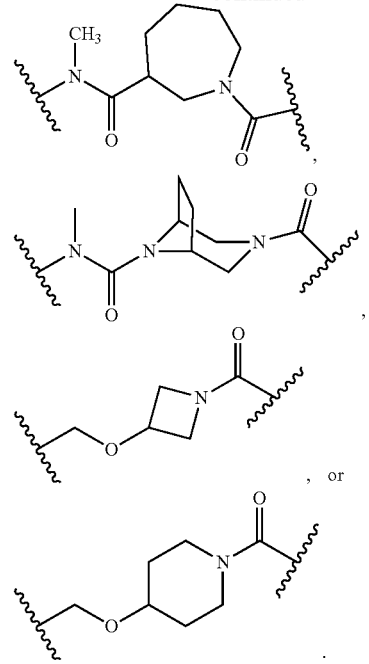

In some embodiments, a linker of Formula II is selected from the group consisting of

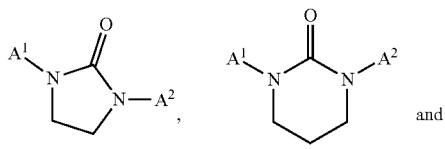

and

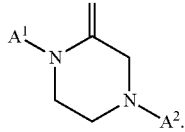

In some embodiments of compounds of the present invention, W comprises a carbodiimide. In some embodiments, W has the structure of Formula IIIa:

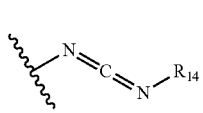

Formula IIIa wherein $R^{14}$ is optionally substituted $C_1$-$C_6$ alkyl, optionally substituted $C_1$-$C_6$ heteroalkyl, optionally substituted 3 to 8-membered cycloalkyl, optionally substituted 6 to 10-membered aryl, optionally substituted 3 to 14-membered heterocycloalkyl, or optionally substituted 5 to 10-membered heteroaryl. In some embodiments, W has the structure:

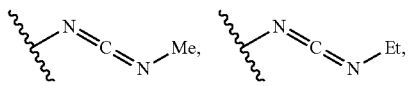

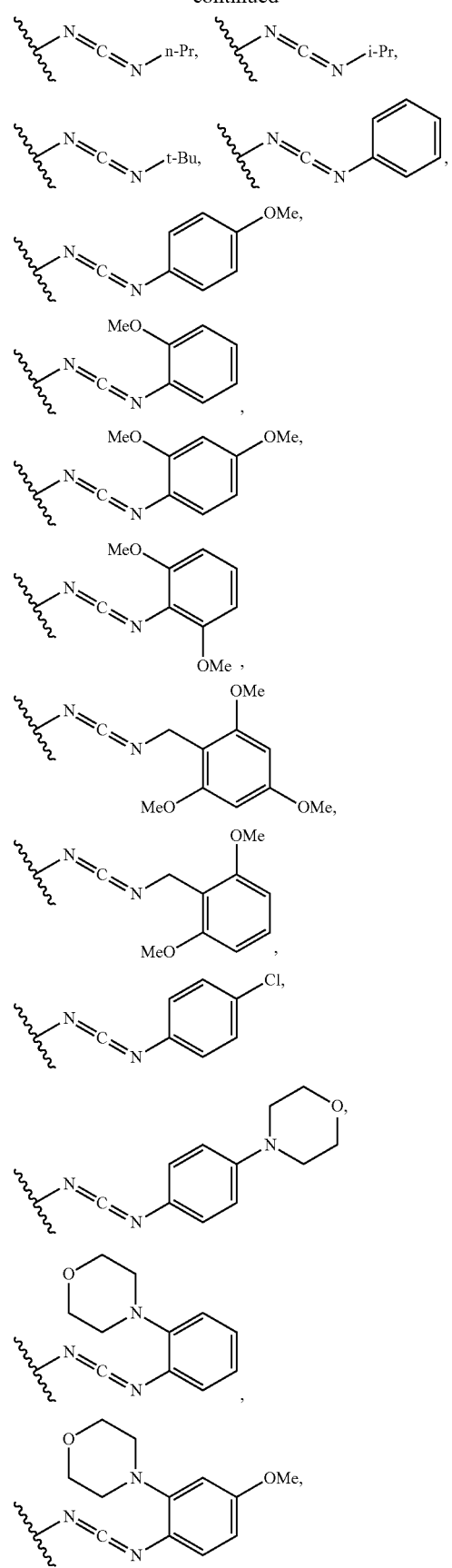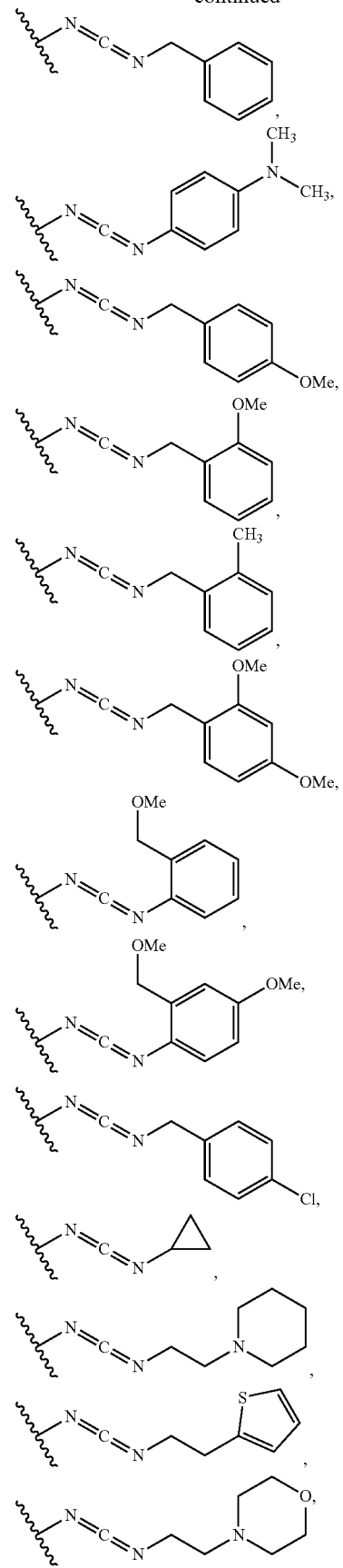

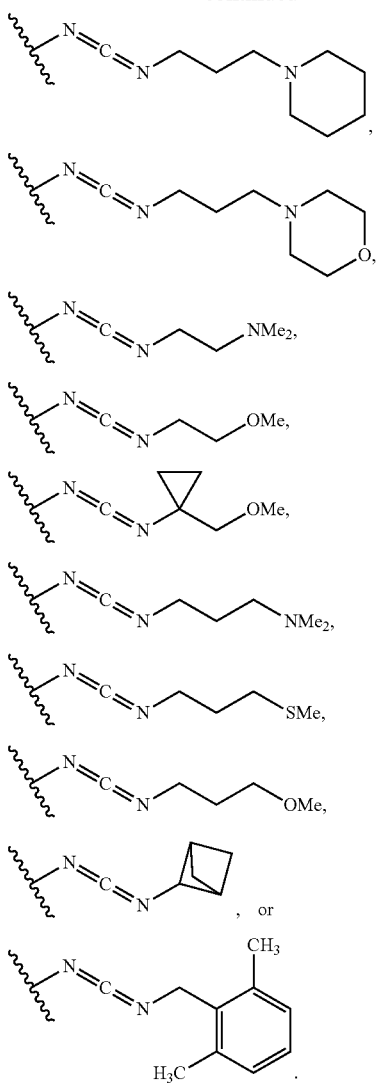

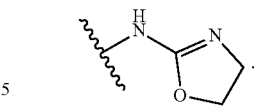

In some embodiments, W comprises a chloroethyl urea, a chloroethyl thiourea, a chloroethyl carbamate, or a chloroethyl thiocarbamate. In some embodiments, W has the structure of Formula IIIc:

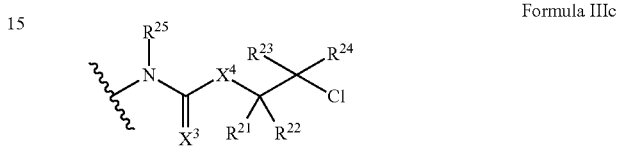

Formula IIIc wherein $X^3$ is O or S;

$X^4$ is O, S, $NR^{26}$;

$R^{21}$, $R^{22}$, $R^{23}$, $R^{24}$, and $R^{26}$ are, independently, hydrogen or optionally substituted $C_1$-$C_6$ alkyl; and $R^{25}$ is hydrogen, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl. In some embodiments, W is In some embodiments, W comprises an oxazoline or thiazoline. In some embodiments, W has the structure of Formula IIIb:

Formula IIb wherein $X^1$ is O or S;

$X^2$ is absent or $NR^{19}$;

$R^{15}$, $R^{16}$, $R^{17}$, and $R^{18}$ are, independently, hydrogen or optionally substituted $C_1$-$C_6$ alkyl; and $R^{19}$ is hydrogen, C(O)(optionally substituted $C_1$-$C_6$ alkyl), optionally substituted $C_1$-$C_6$ alkyl, optionally substituted 6 to 10-membered aryl, optionally substituted 3 to 14-membered heterocycloalkyl, or optionally substituted 5 to 10-membered heteroaryl. In some embodiments, W is In some embodiments, W comprises an aziridine. In some embodiments, W has the structure of Formula IIId1, Formula IIId2, Formula IIId3, or Formula IIId4:

Formula IIId1

Formula IIId2

Formula IIId3

-continued

Formula IIId4

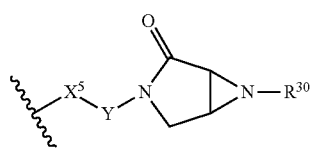

wherein $X^5$ is absent or $NR^{30}$;

Y is absent or C(O), C(S), S(O), $SO_2$, or optionally substituted $C_1$-$C_3$ alkylene;

$R^{27}$ is hydrogen, —C(O)$R^{32}$, —C(O)O$R^{32}$, —SO$R^{33}$, —$SO_2R^{33}$, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl;

$R^{28}$ and $R^{29}$ are, independently, hydrogen, CN, C(O)$R^{31}$, $CO_2R^{31}$, C(O)$R^{31}R^{31}$ optionally substituted $C_1$-$C_6$ alkyl, optionally substituted 3 to 10-membered cycloalkyl, optionally substituted 6 to 10-membered aryl, optionally substituted 3 to 14-membered heterocycloalkyl, or optionally substituted 5 to 10-membered heteroaryl;

each $R^{31}$ is, independently, hydrogen, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl;

$R^{30}$ is hydrogen or optionally substituted $C_1$-$C_6$ alkyl; and $R^{32}$ and $R^{33}$ are, independently, hydrogen, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl. In some embodiments, W is:

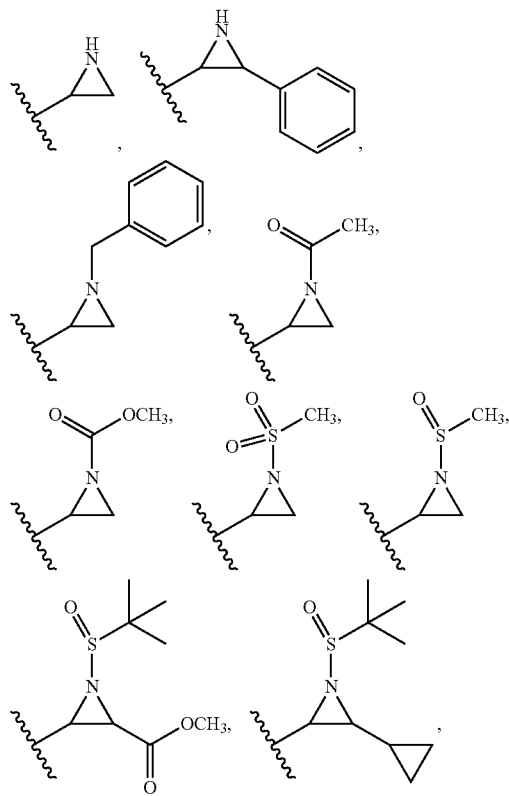

-continued

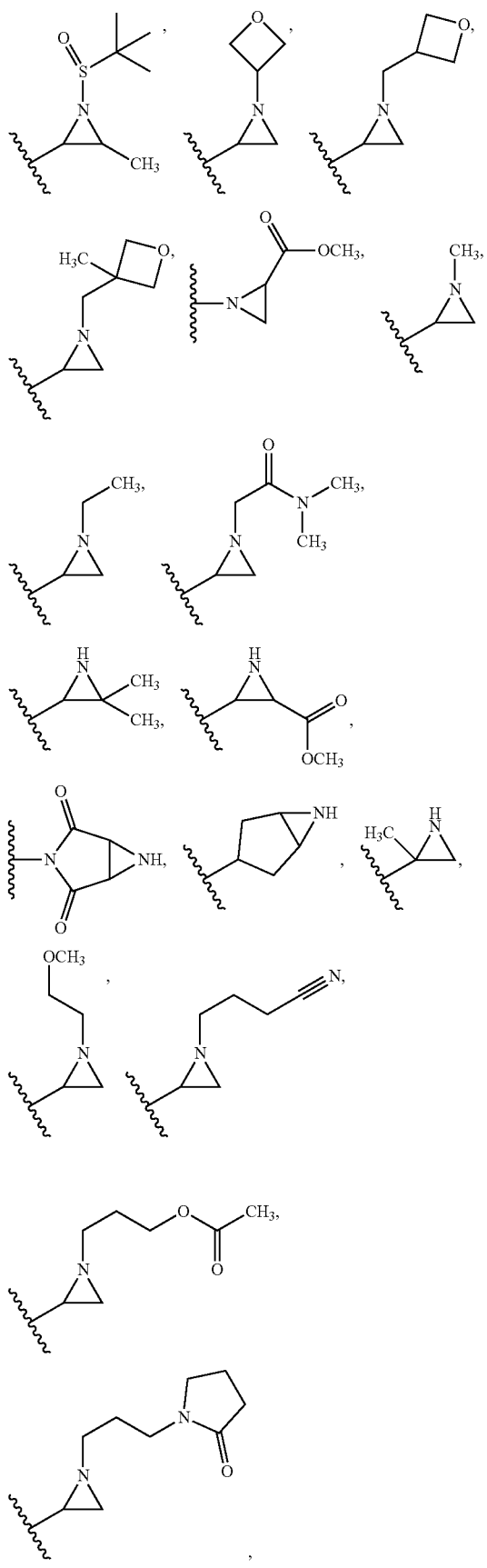

-continued

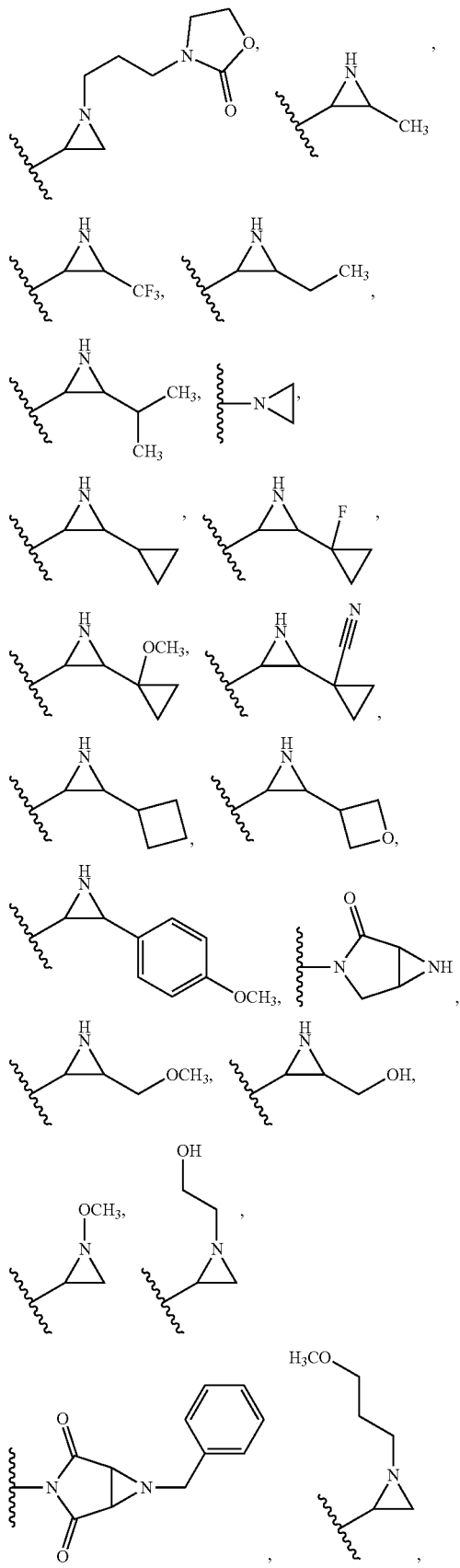

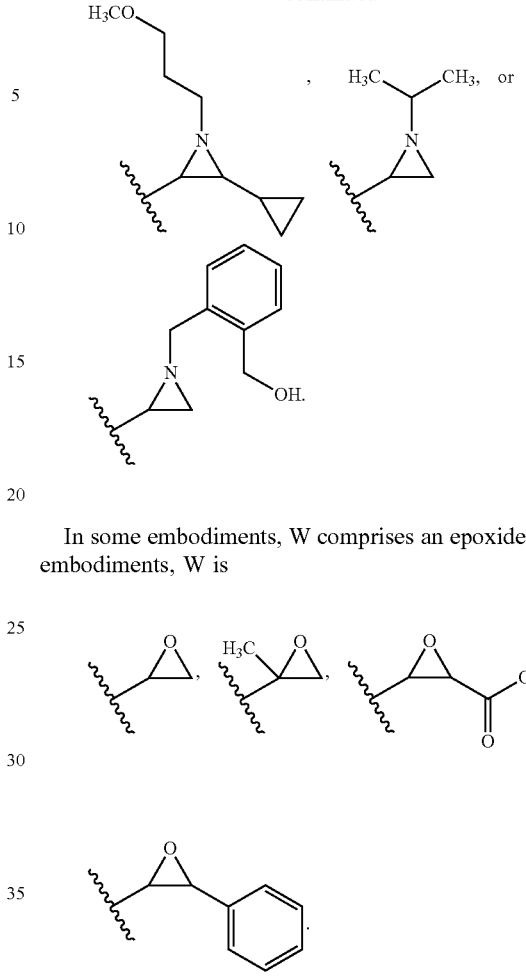

In some embodiments, W comprises an epoxide. In some embodiments, W is

In some embodiments, W is a cross-linking group bound to an organic moiety that is a Ras binding moiety, i.e., RBM-W, wherein upon contact of an RBM-W compound with a Ras protein, the RBM-W binds to the Ras protein to form a conjugate. For example, the W moiety of an RBM-W compound may bind, e.g., cross-link, with an amino acid of the Ras protein to form the conjugate. In some embodiments, the Ras binding moiety is a K-Ras binding moiety. In some embodiments, the K-Ras binding moiety binds to a residue of a K-Ras Switch-II binding pocket of the K-Ras protein. In some embodiments, the Ras binding moiety is an H-Ras binding moiety that binds to a residue of an H-Ras Switch-II binding pocket of an H-Ras protein. In some embodiments, the Ras binding moiety is an N-Ras binding moiety that binds to a residue of an N-Ras Switch-II binding pocket of an N-Ras protein. The W of an RBM-W compound may comprise any W described herein. The Ras binding moiety typically has a molecular weight of under 1200 Da. See, e.g., see, e.g., Johnson et al., 292:12981-12993 (2017) for a description of Ras protein domains, incorporated herein by reference.

In some embodiments, a compound of the present invention is selected from Table 1, or a pharmaceutically acceptable salt or stereoisomer thereof. In some embodiments, a compound of the present invention is selected from Table 1, or a pharmaceutically acceptable salt or atropisomer thereof.

TABLE 1

Certain Compounds of the Present Invention

| Ex# | Structure |
|---|---|
| 1 | 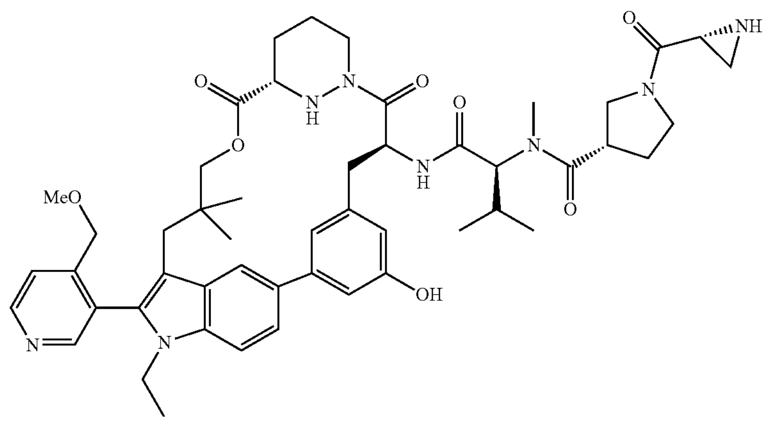 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(C(=O)[C@H]3CN3)C1)C(=O)N1CCC[C@H](N1)C(=O)OCC(C)(C)C2] |
| 2 | 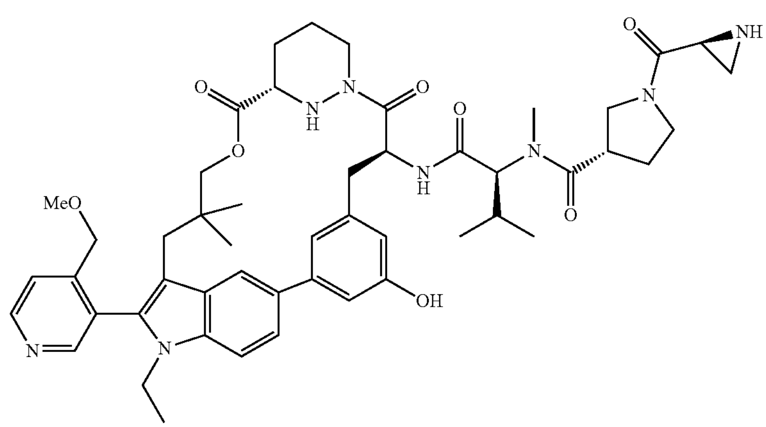 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(C(=O)[C@@H]3CN3)C1)C(=O)N1CCC[C@H](N1)C(=O)OCC(C)(C)C2] |
| 3 | 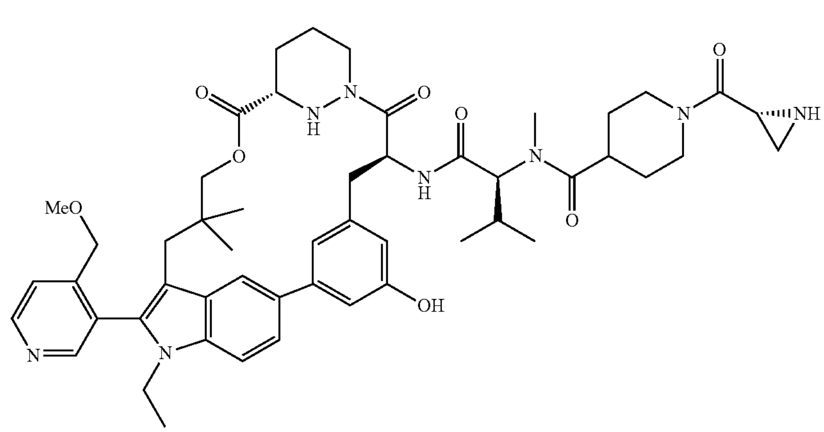 [SMILES: CCn1c(-c2cnccc2COC)c2c3cc(ccc31)-c1cc(O)cc(c1)C[C@H](NC(=O)[C@H](C(C)C)N(C)C(=O)C1CCN(C(=O)[C@H]3CN3)CC1)C(=O)N1CCC[C@H](N1)C(=O)OCC(C)(C)C2] |

TABLE 1-continued

Certain Compounds of the Present Invention

| Ex# | Structure |
|---|---|
| 4 | 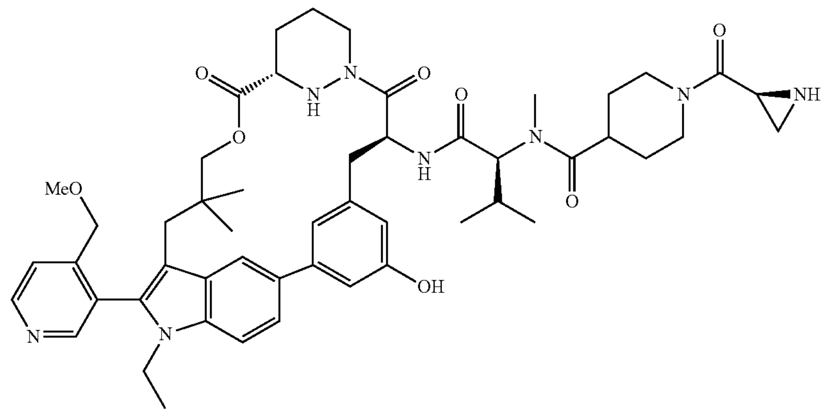 [SMILES: CCn1c(-c2cnccc2COC)c2c3cc(ccc31)-c1cc(O)cc(c1)C[C@H](NC(=O)[C@H](C(C)C)N(C)C(=O)C1CCN(C(=O)[C@@H]3CN3)CC1)C(=O)N1CCC[C@H](N1)C(=O)OCC(C)(C)C2] |
| 5 | 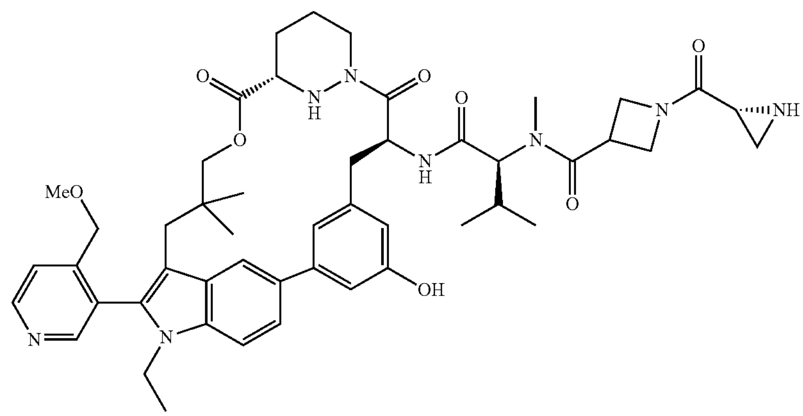 [SMILES: CCn1c(-c2cnccc2COC)c2c3cc(ccc31)-c1cc(O)cc(c1)C[C@H](NC(=O)[C@H](C(C)C)N(C)C(=O)C1CN(C(=O)[C@H]3CN3)C1)C(=O)N1CCC[C@H](N1)C(=O)OCC(C)(C)C2] |
| 6 | 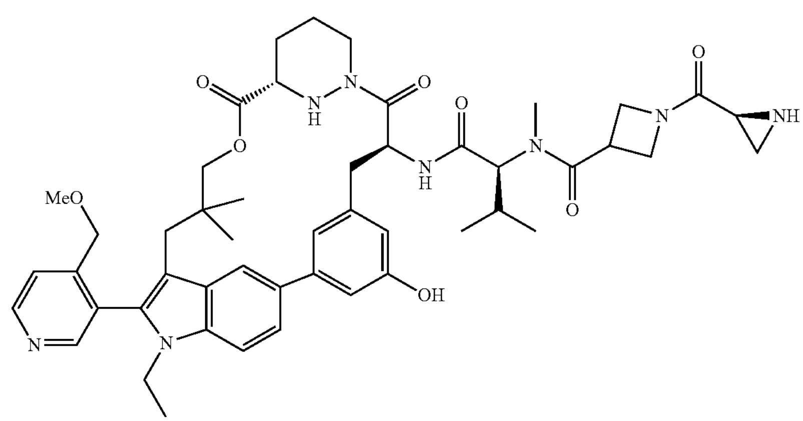 [SMILES: CCn1c(-c2cnccc2COC)c2c3cc(ccc31)-c1cc(O)cc(c1)C[C@H](NC(=O)[C@H](C(C)C)N(C)C(=O)C1CN(C(=O)[C@@H]3CN3)C1)C(=O)N1CCC[C@H](N1)C(=O)OCC(C)(C)C2] |

TABLE 1-continued

Certain Compounds of the Present Invention

| Ex# | Structure |
|---|---|
| 7 | 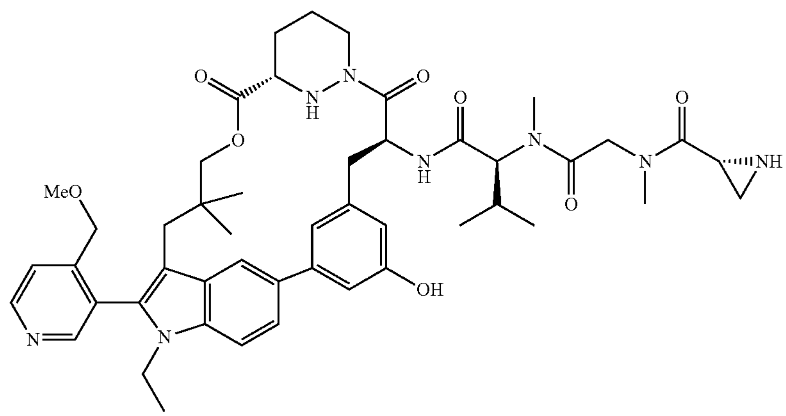 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1CN1)C(=O)N1CCC[C@H](N1)C(=O)OCC(C)(C)C2] |
| 8 | 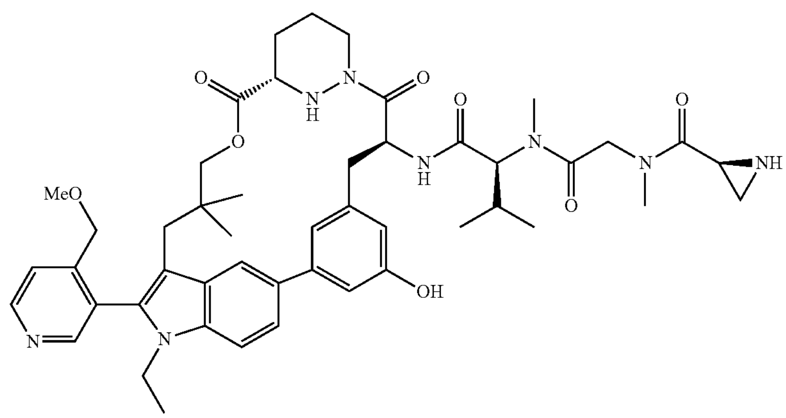 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1CN1)C(=O)N1CCC[C@H](N1)C(=O)OCC(C)(C)C2] |
| 9 | 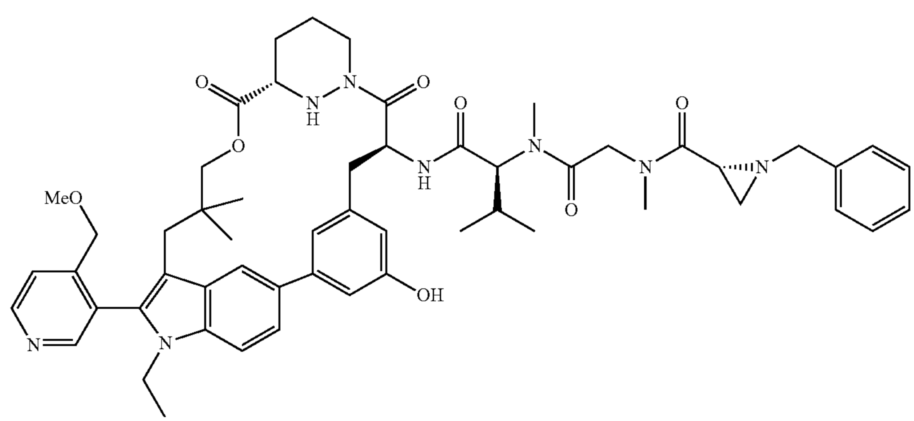 |

TABLE 1-continued

Certain Compounds of the Present Invention

| Ex# | Structure |
| --- | --- |
| 10 | 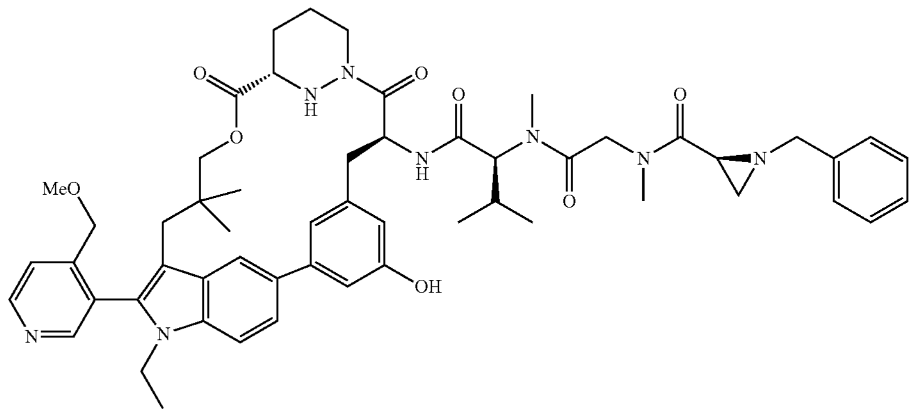 |
| 11 | 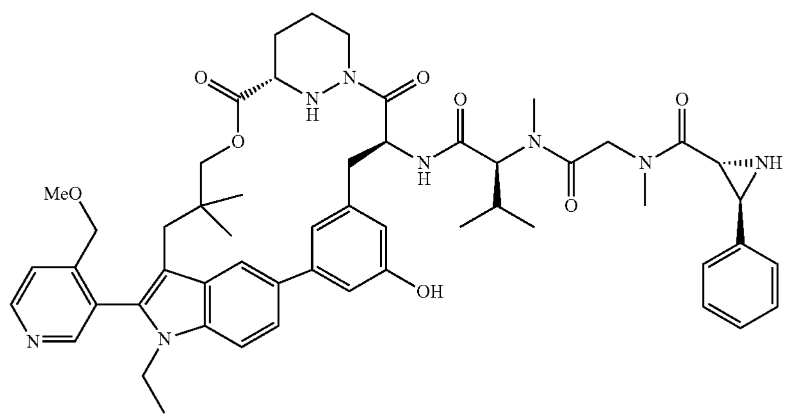 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@H]1c1ccccc1)C(=O)N1CCC[C@H](N1)C(=O)OCC(C)(C)C2] |
| 12 | 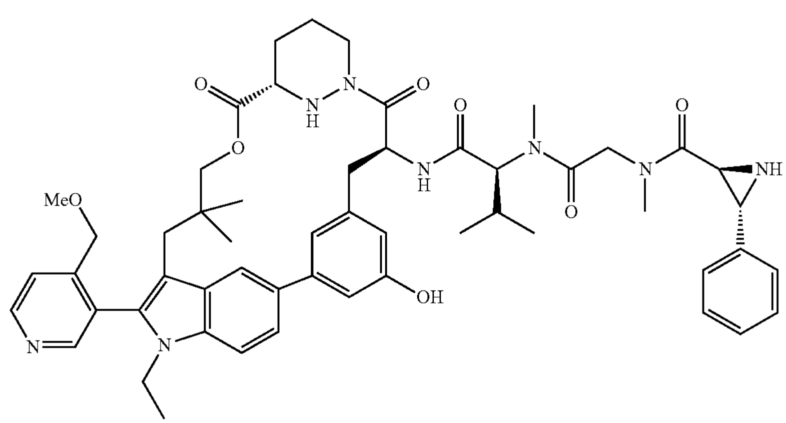 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@@H]1c1ccccc1)C(=O)N1CCC[C@H](N1)C(=O)OCC(C)(C)C2] |

TABLE 1-continued

Certain Compounds of the Present Invention

| Ex# | Structure |
|---|---|
| 13 | 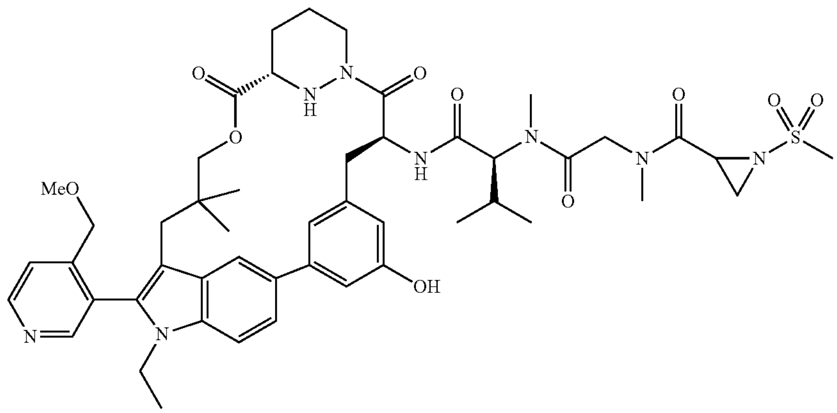 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)C1CN1S(C)(=O)=O)C(=O)N1CCC[C@H](N1)C(=O)OCC(C)(C)C2] |
| 14 | 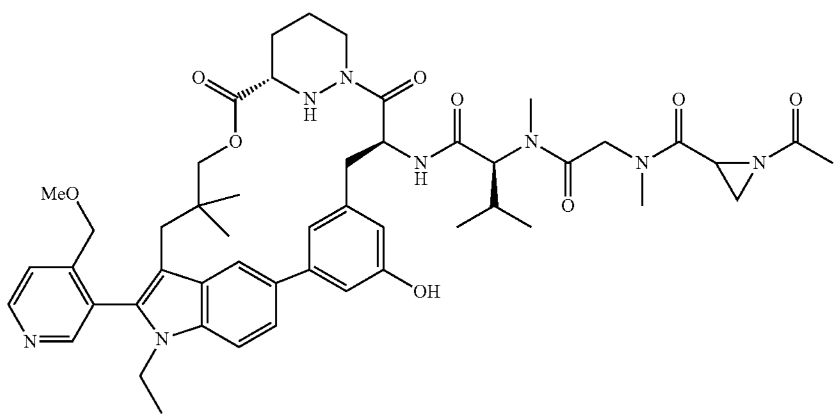 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)C1CN1C(C)=O)C(=O)N1CCC[C@H](N1)C(=O)OCC(C)(C)C2] |
| 15 A and B | 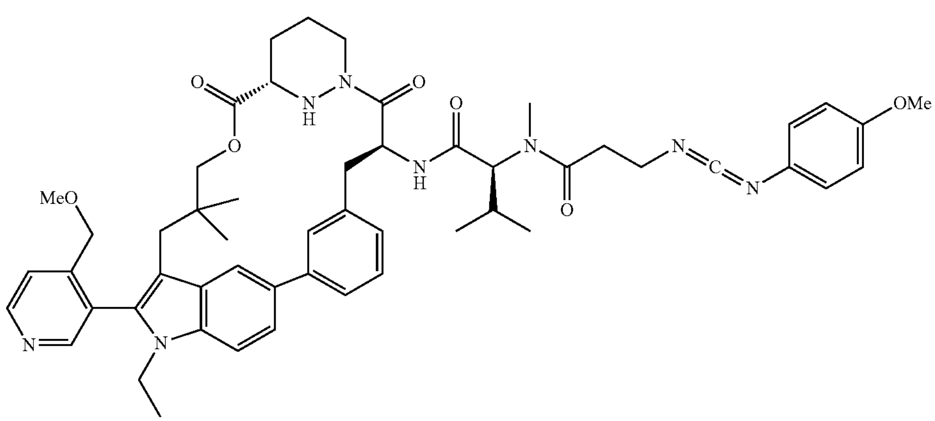 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccc(OC)cc1)C(=O)N1CCC[C@H](N1)C(=O)OCC(C)(C)C2] |

TABLE 1-continued

Certain Compounds of the Present Invention

| Ex# | Structure |
|---|---|
| 16 A and B | 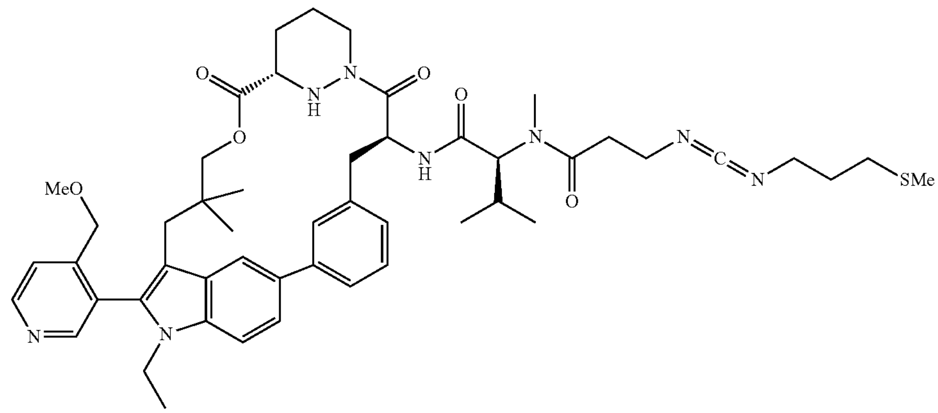 [SMILES: CCn1c(-c2cnccc2COC)c2c3cc(ccc31)-c1cccc(c1)C[C@H](NC(=O)[C@H](C(C)C)N(C)C(=O)CCN=C=NCCCSC)C(=O)N1CCC[C@H](N1)C(=O)OCC(C)(C)C2] |
| 17 A and B | 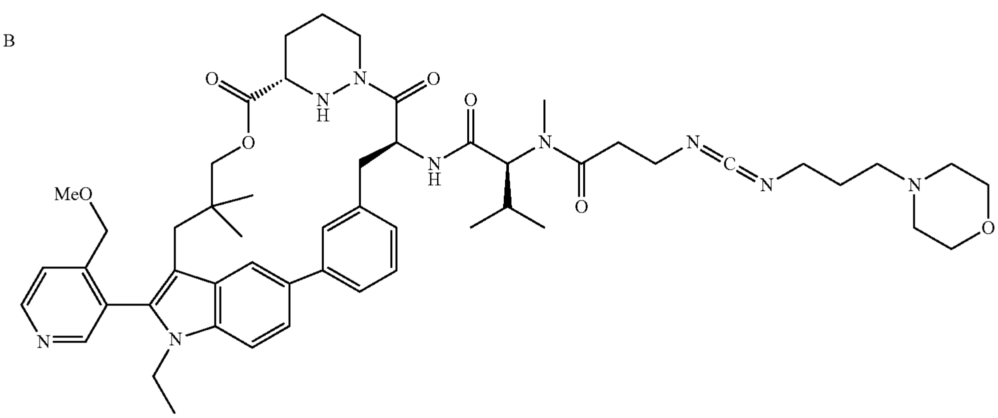 |
| 18 A and B | 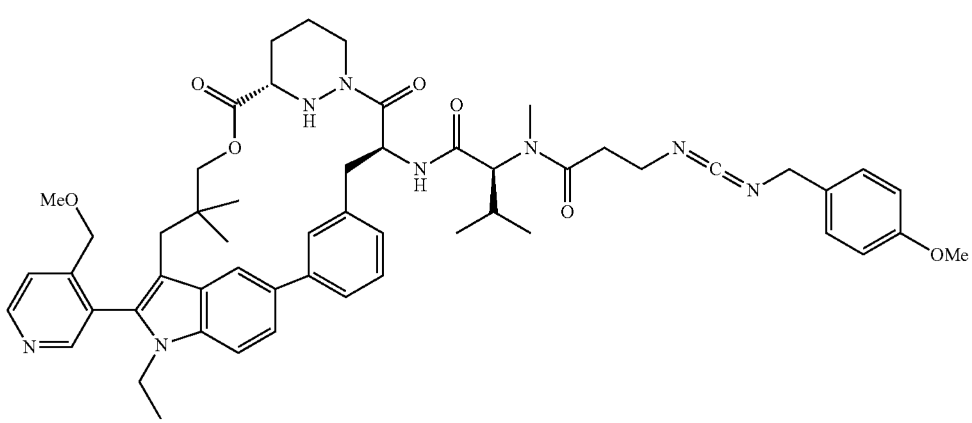 [SMILES: CCn1c(-c2cnccc2COC)c2c3cc(ccc31)-c1cccc(c1)C[C@H](NC(=O)[C@H](C(C)C)N(C)C(=O)CCN=C=NCc1ccc(OC)cc1)C(=O)N1CCC[C@H](N1)C(=O)OCC(C)(C)C2] |

TABLE 1-continued
Certain Compounds of the Present Invention
| Ex# | Structure |
|---|---|
| 19 A and B | 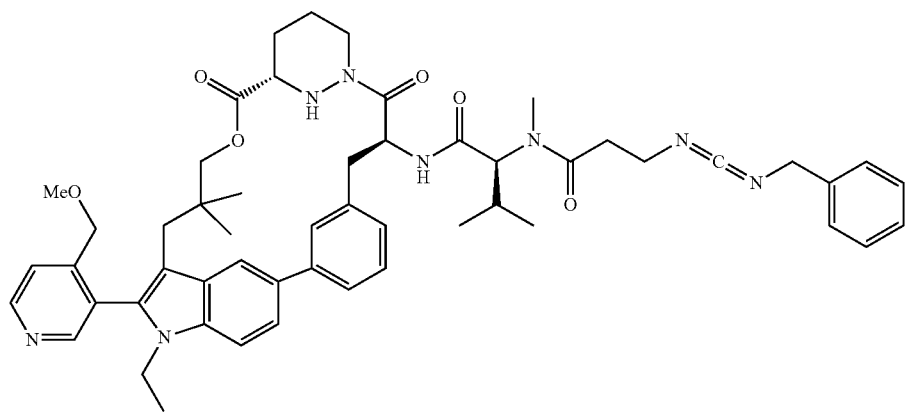 [SMILES: CCn1c(-c2cnccc2COC)c2c3cc(ccc31)-c1cccc(c1)C[C@H](NC(=O)[C@H](C(C)C)N(C)C(=O)CCN=C=NCc1ccccc1)C(=O)N1CCC[C@H](N1)C(=O)OCC(C)(C)C2] |
| 20 A and B | 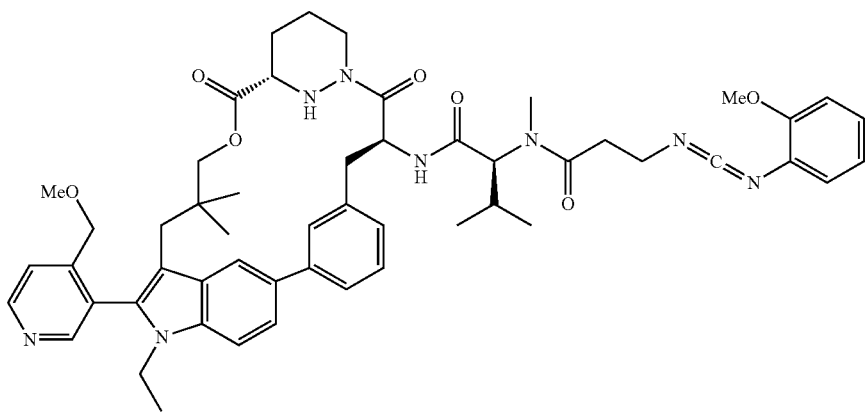 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccccc1OC)C(=O)N1CCC[C@H](N1)C(=O)OCC(C)(C)C2] |
| 21 A and B | 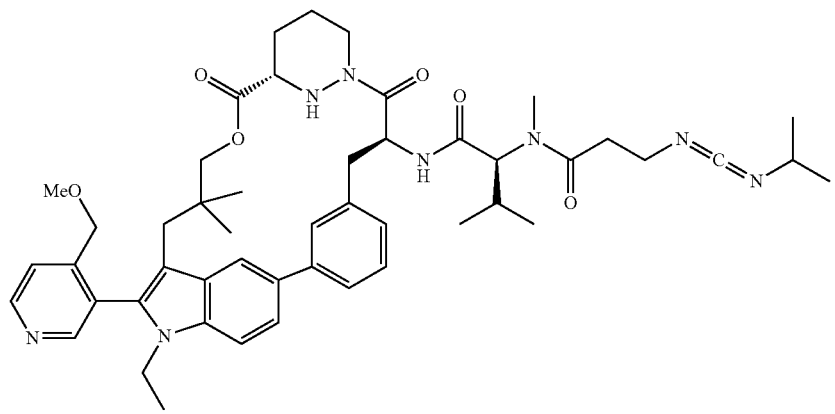 [SMILES: CCn1c(-c2cnccc2COC)c2c3cc(ccc31)-c1cccc(c1)C[C@H](NC(=O)[C@H](C(C)C)N(C)C(=O)CCN=C=NC(C)C)C(=O)N1CCC[C@H](N1)C(=O)OCC(C)(C)C2] |

TABLE 1-continued

Certain Compounds of the Present Invention

| Ex# | Structure |
| --- | --- |
| 22 A and B | |
| 23 A and B | |
| 24 A and B | |

TABLE 1-continued

Certain Compounds of the Present Invention

| Ex# | Structure |
|---|---|
| 25 | 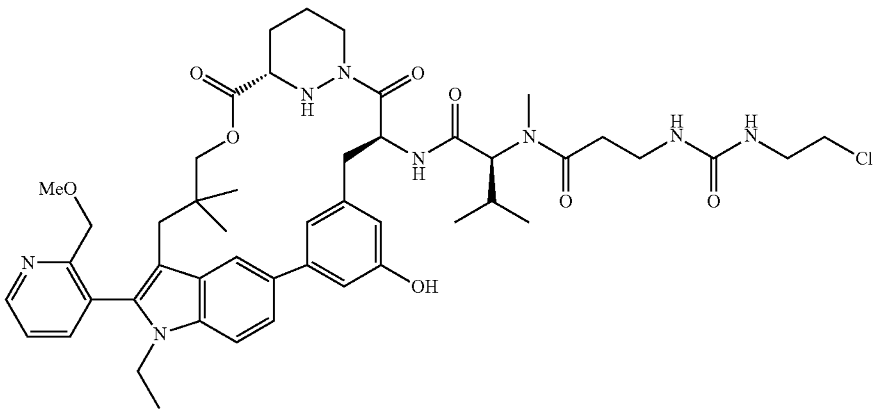 [SMILES: CCn1c(-c2cccnc2COC)c2c3cc(ccc31)-c1cc(O)cc(c1)C[C@H](NC(=O)[C@H](C(C)C)N(C)C(=O)CCNC(=O)NCCCl)C(=O)N1CCC[C@H](N1)C(=O)OCC(C)(C)C2] |
| 26 | 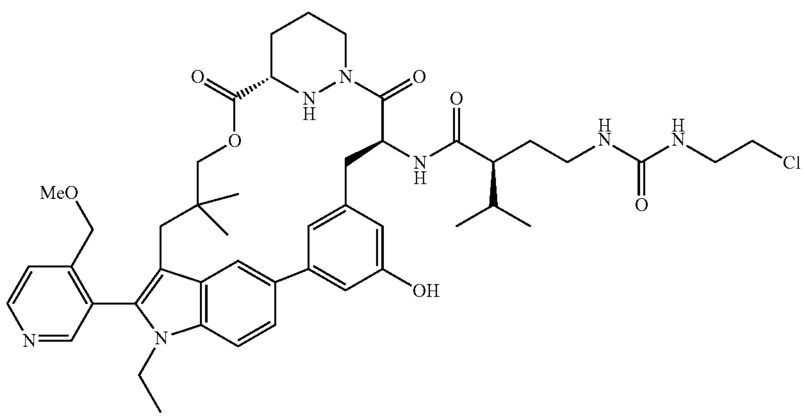 [SMILES: CCn1c(-c2cnccc2COC)c2c3cc(ccc31)-c1cc(O)cc(c1)C[C@H](NC(=O)[C@@H](CCNC(=O)NCCCl)C(C)C)C(=O)N1CCC[C@H](N1)C(=O)OCC(C)(C)C2] |
| 27 | 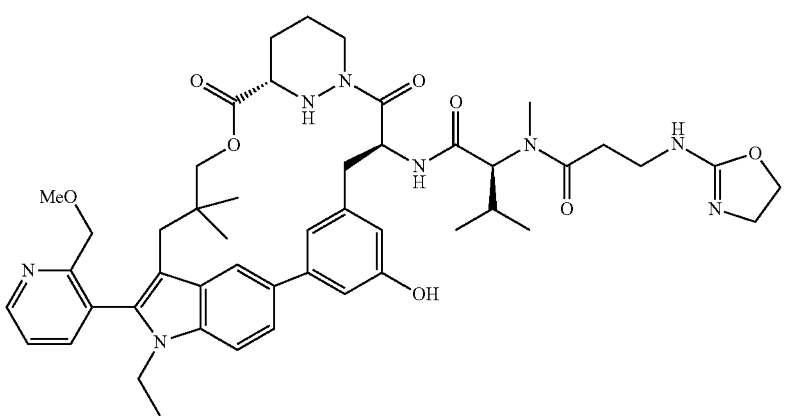 [SMILES: CCn1c(-c2cccnc2COC)c2c3cc(ccc31)-c1cc(O)cc(c1)C[C@H](NC(=O)[C@H](C(C)C)N(C)C(=O)CCNC1=NCCO1)C(=O)N1CCC[C@H](N1)C(=O)OCC(C)(C)C2] |

TABLE 1-continued

Certain Compounds of the Present Invention

| Ex# | Structure |
|---|---|
| 28 | 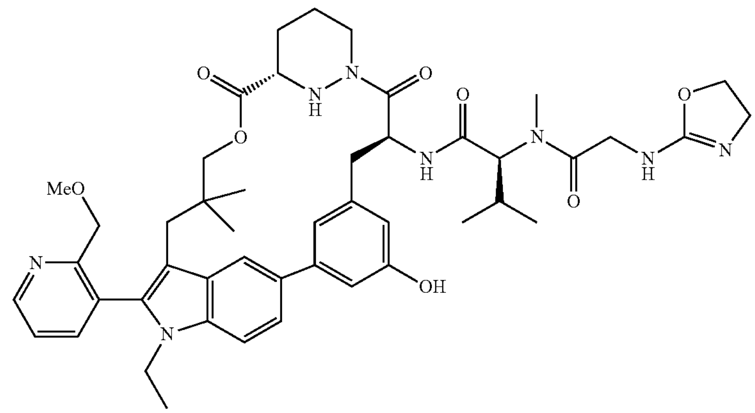 [SMILES: CCn1c(-c2cccnc2COC)c2c3cc(ccc31)-c1cc(O)cc(c1)C[C@H](NC(=O)[C@H](C(C)C)N(C)C(=O)CNC1=NCCO1)C(=O)N1CCC[C@H](N1)C(=O)OCC(C)(C)C2] |
| 29 | 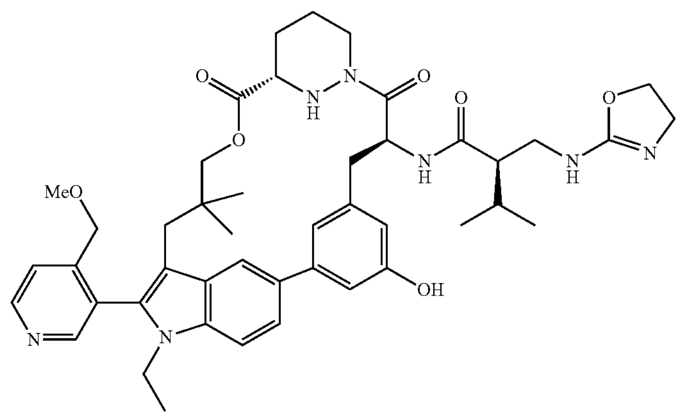 [SMILES: CCn1c(-c2cnccc2COC)c2c3cc(ccc31)-c1cc(O)cc(c1)C[C@H](NC(=O)[C@@H](CNC1=NCCO1)C(C)C)C(=O)N1CCC[C@H](N1)C(=O)OCC(C)(C)C2] |
| 30 | 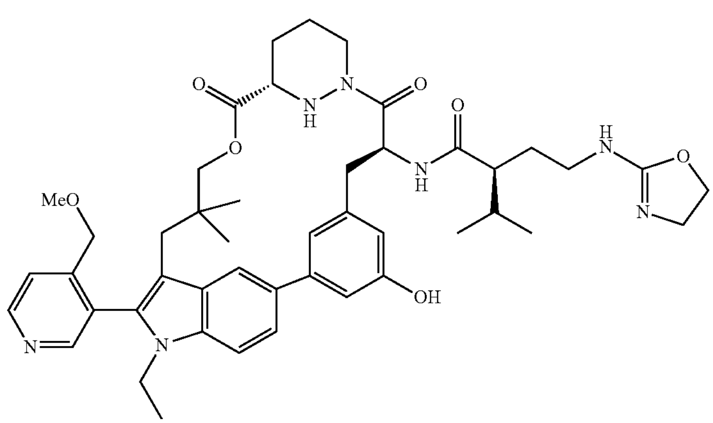 [SMILES: CCn1c(-c2cnccc2COC)c2c3cc(ccc31)-c1cc(O)cc(c1)C[C@H](NC(=O)[C@@H](CCNC1=NCCO1)C(C)C)C(=O)N1CCC[C@H](N1)C(=O)OCC(C)(C)C2] |

TABLE 1-continued

Certain Compounds of the Present Invention

| Ex# | Structure |
| --- | --- |
| 31 | 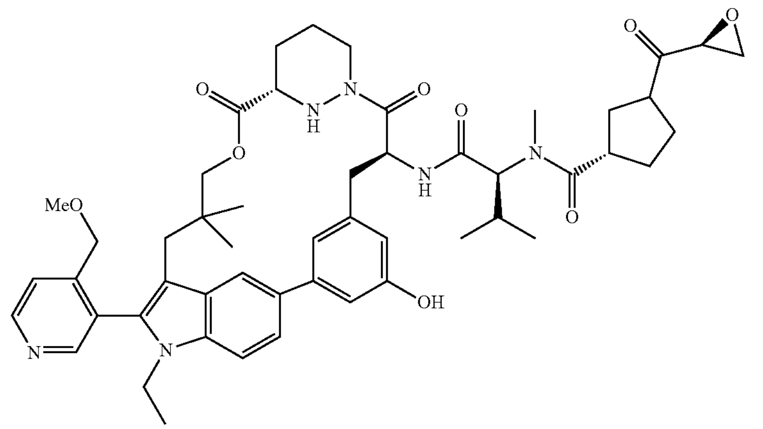 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCC(C(=O)[C@@H]3CO3)C1)C(=O)N1CCC[C@H](N1)C(=O)OCC(C)(C)C2] |
| 32 A and B | 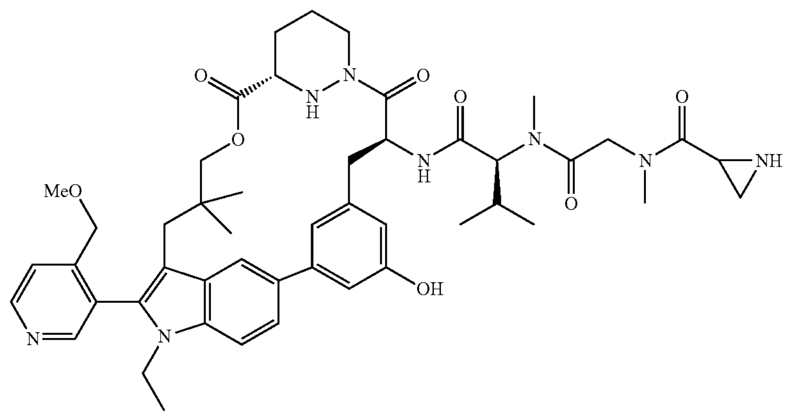 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)C1CN1)C(=O)N1CCC[C@H](N1)C(=O)OCC(C)(C)C2] |
| 33 | 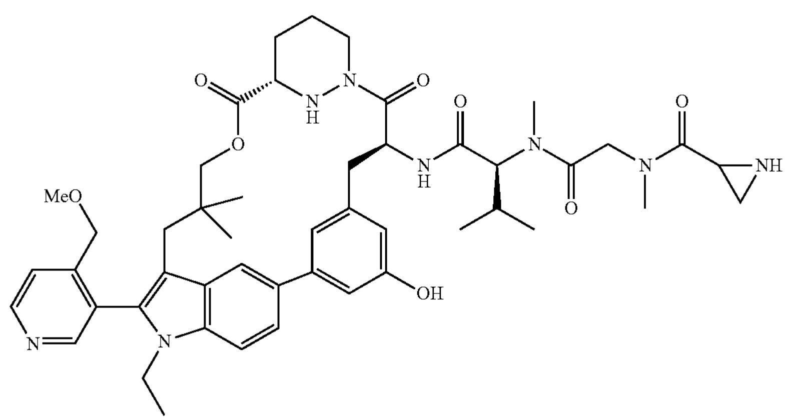 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)C1CN1)C(=O)N1CCC[C@H](N1)C(=O)OCC(C)(C)C2] |

TABLE 1-continued

Certain Compounds of the Present Invention

| Ex# | Structure |
|---|---|
| 34 | 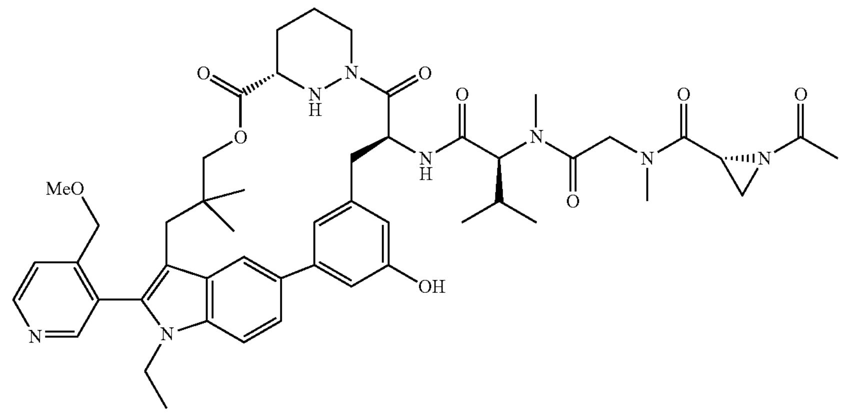 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1CN1C(C)=O)C(=O)N1CCC[C@H](N1)C(=O)OCC(C)(C)C2] |
| 35 | 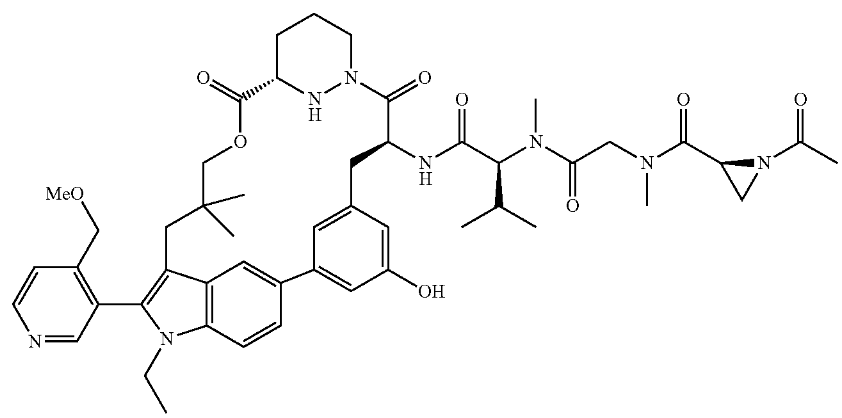 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1CN1C(C)=O)C(=O)N1CCC[C@H](N1)C(=O)OCC(C)(C)C2] |
| 36 | 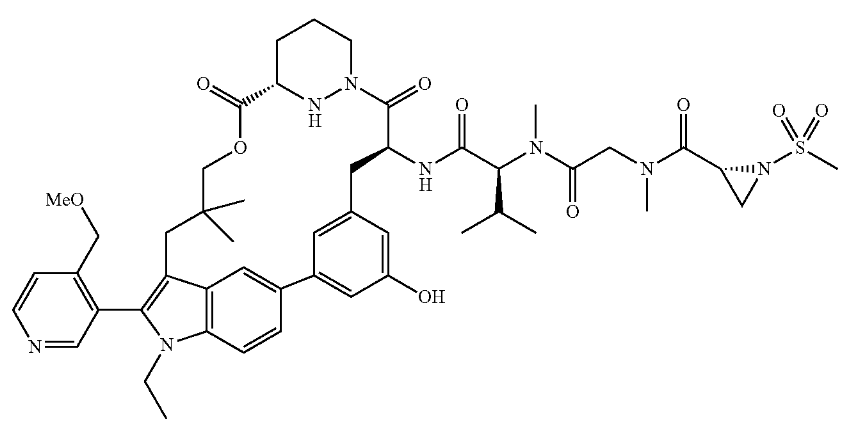 |

TABLE 1-continued
Certain Compounds of the Present Invention
| Ex# | Structure |
|---|---|
| 37 | 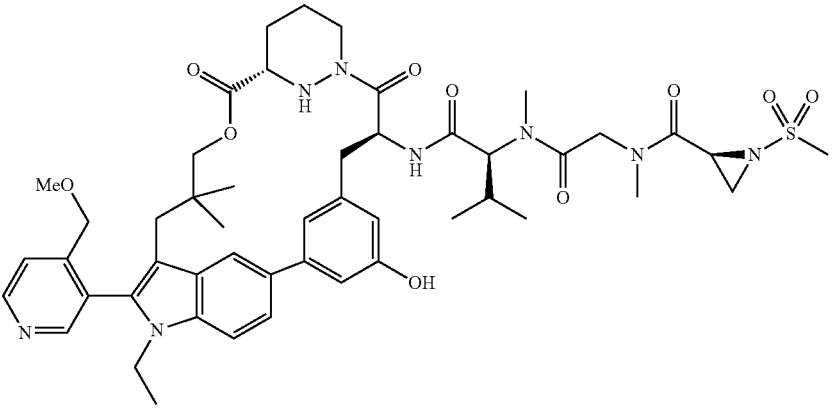 |
| 38 | 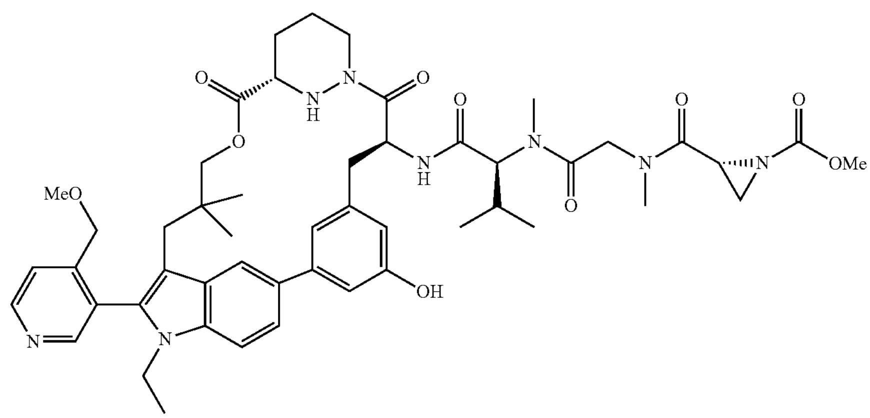 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1CN1C(=O)OC)C(=O)N1CCC[C@H](N1)C(=O)OCC(C)(C)C2] |
| 39 | 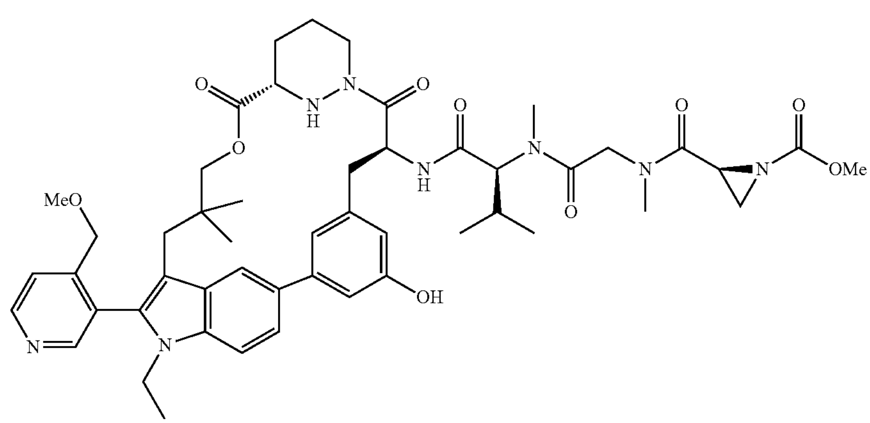 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1CN1C(=O)OC)C(=O)N1CCC[C@H](N1)C(=O)OCC(C)(C)C2] |

TABLE 1-continued
Certain Compounds of the Present Invention
| Ex# | Structure |
|---|---|
| 40 | 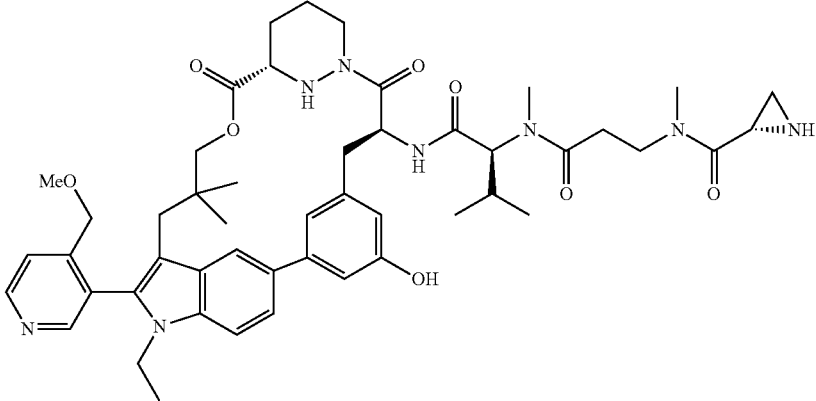 [SMILES: CCn1c(-c2cnccc2COC)c2c3cc(ccc31)-c1cc(O)cc(c1)C[C@H](NC(=O)[C@H](C(C)C)N(C)C(=O)CCN(C)C(=O)[C@@H]1CN1)C(=O)N1CCC[C@H](N1)C(=O)OCC(C)(C)C2] |
| 41 | 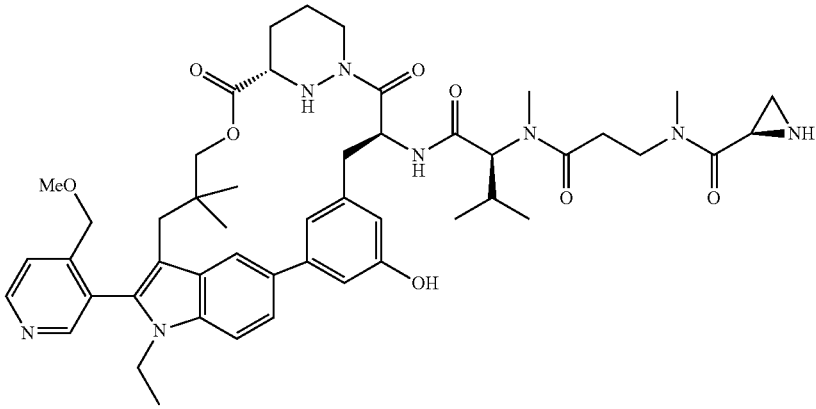 [SMILES: CCn1c(-c2cnccc2COC)c2c3cc(ccc31)-c1cc(O)cc(c1)C[C@H](NC(=O)[C@H](C(C)C)N(C)C(=O)CCN(C)C(=O)[C@H]1CN1)C(=O)N1CCC[C@H](N1)C(=O)OCC(C)(C)C2] |
| 42A | 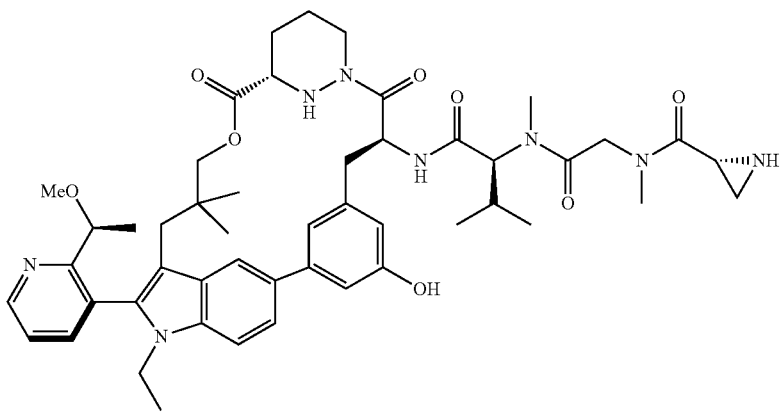 |

TABLE 1-continued

Certain Compounds of the Present Invention

| Ex# | Structure |
|---|---|
| 42B | 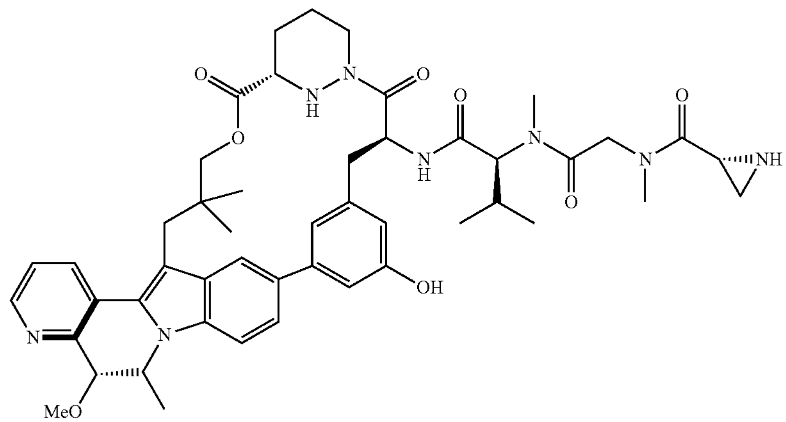 |
| 43A | 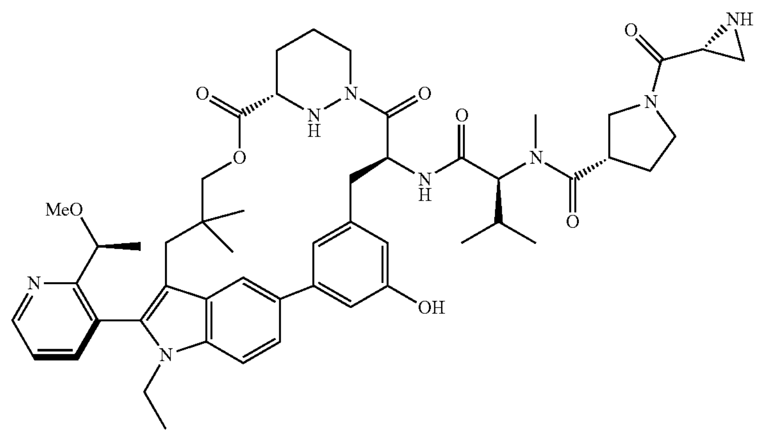 |
| 43B | 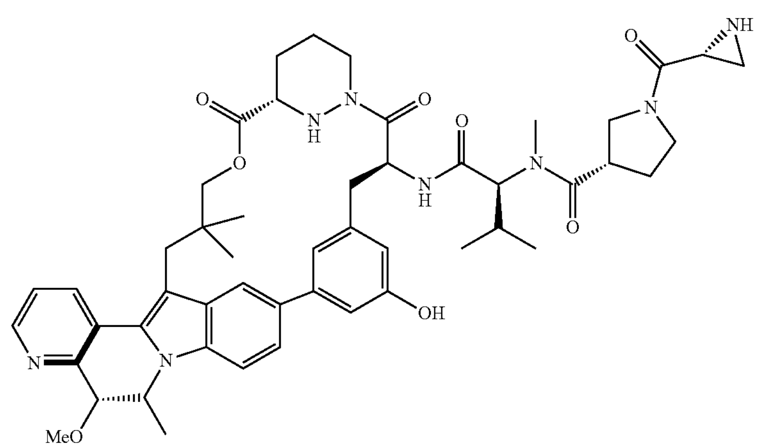 |

TABLE 1-continued
Certain Compounds of the Present Invention
| Ex# | Structure |
|---|---|
| 44 | 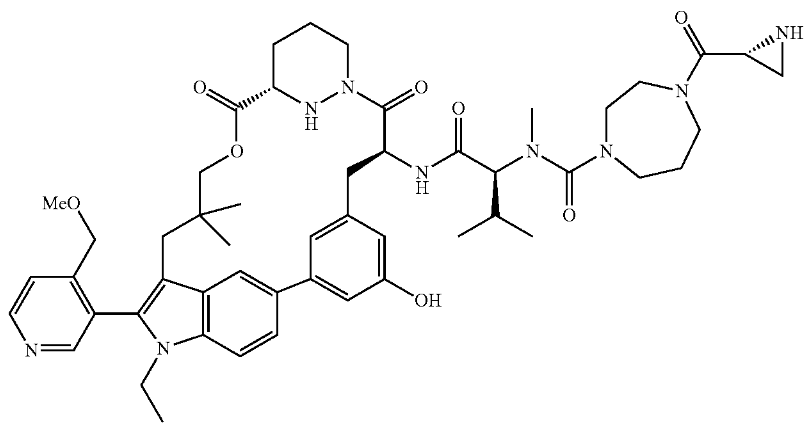 [SMILES: CCn1c(-c2cnccc2COC)c2c3cc(ccc31)-c1cc(O)cc(c1)C[C@H](NC(=O)[C@H](C(C)C)N(C)C(=O)N1CCCN(C(=O)[C@H]3CN3)CC1)C(=O)N1CCC[C@H](N1)C(=O)OCC(C)(C)C2] |
| 45 | 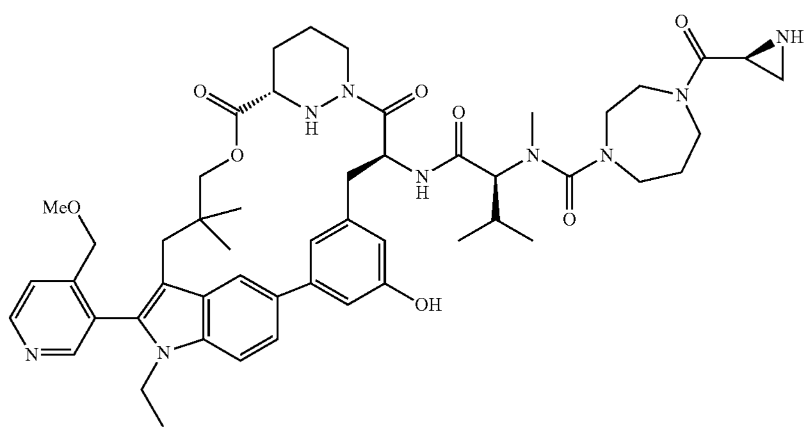 [SMILES: CCn1c(-c2cnccc2COC)c2c3cc(ccc31)-c1cc(O)cc(c1)C[C@H](NC(=O)[C@H](C(C)C)N(C)C(=O)N1CCCN(C(=O)[C@@H]3CN3)CC1)C(=O)N1CCC[C@H](N1)C(=O)OCC(C)(C)C2] |
| 46 | 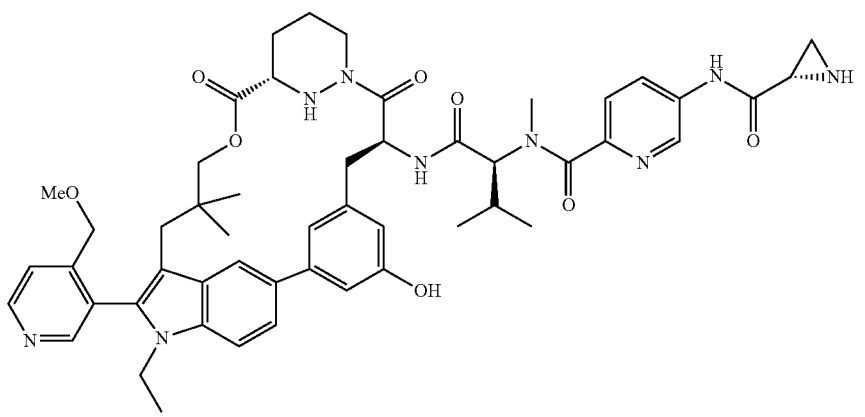 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC(=O)[C@@H]3CN3)cn1)C(=O)N1CCC[C@H](N1)C(=O)OCC(C)(C)C2] |

TABLE 1-continued
Certain Compounds of the Present Invention
| Ex# | Structure |
|---|---|
| 47 A and B | 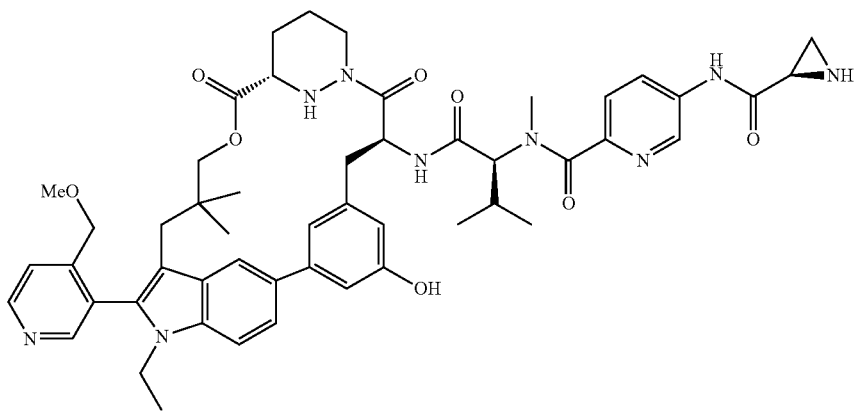 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC(=O)[C@H]3CN3)cn1)C(=O)N1CCC[C@H](N1)C(=O)OCC(C)(C)C2] |
| 48 | 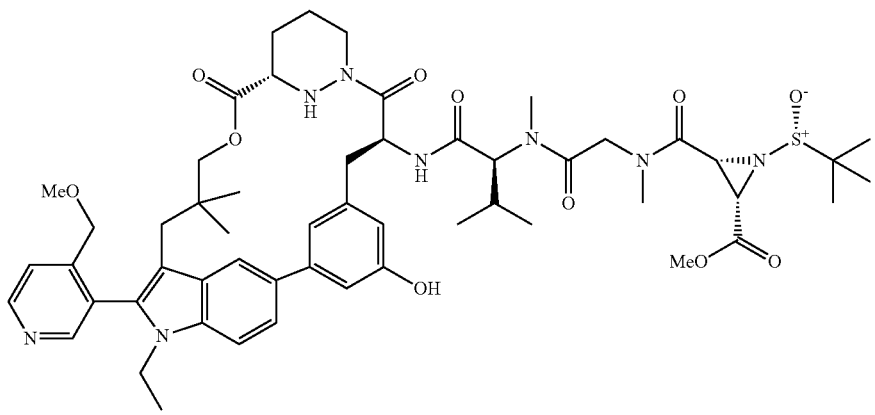 |
| 49 | 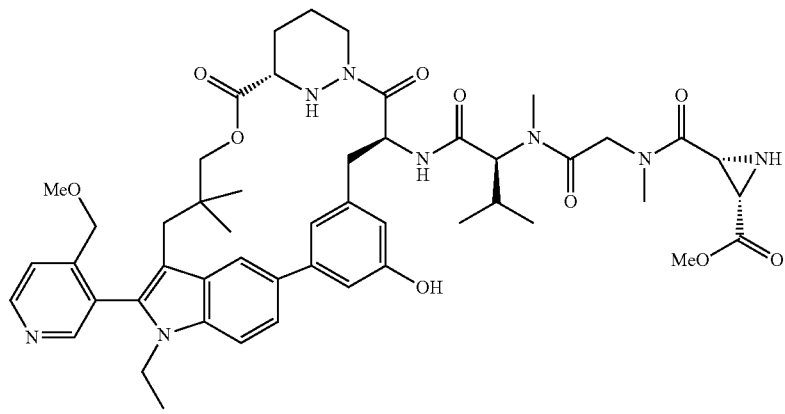 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1C(=O)OC)C(=O)N1CCC[C@H](N1)C(=O)OCC(C)(C)C2] |

TABLE 1-continued

Certain Compounds of the Present Invention

| Ex# | Structure |
| --- | --- |
| 50 | 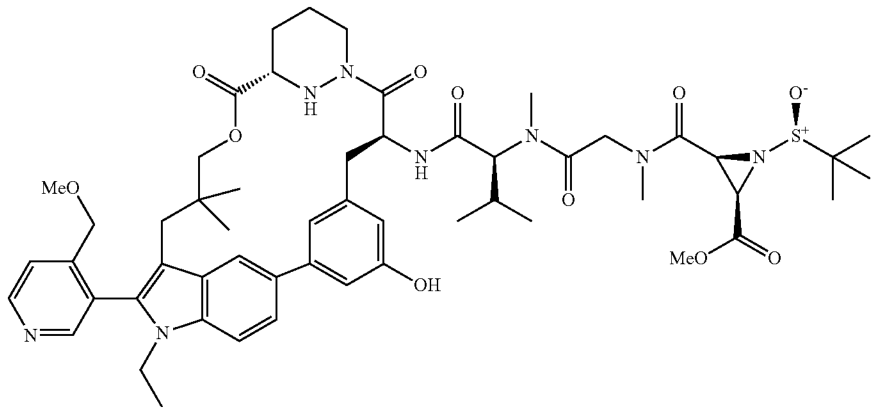 |
| 51 | 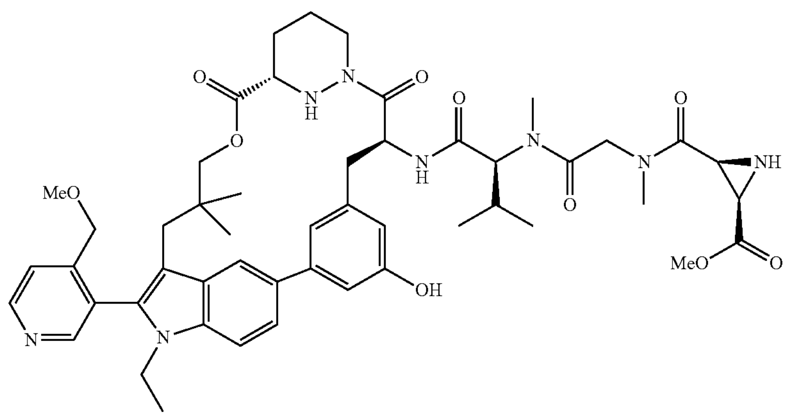 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@H]1C(=O)OC)C(=O)N1CCC[C@H](N1)C(=O)OCC(C)(C)C2] |
| 52 | 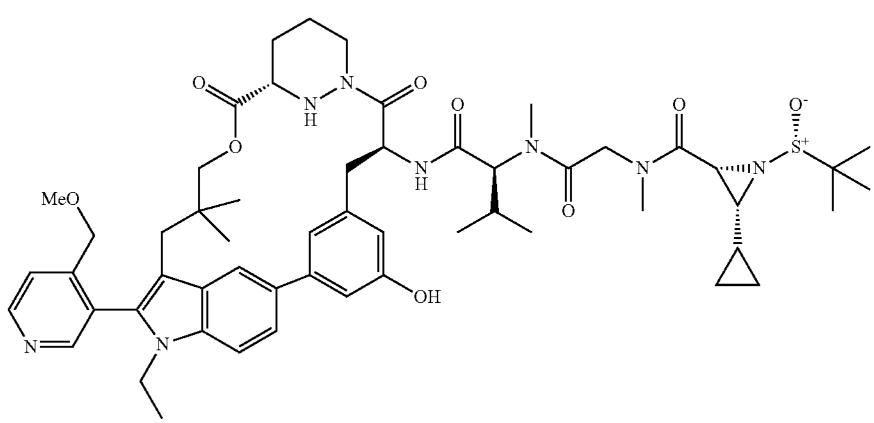 |

TABLE 1-continued
Certain Compounds of the Present Invention
| Ex# | Structure |
|---|---|
| 53 | 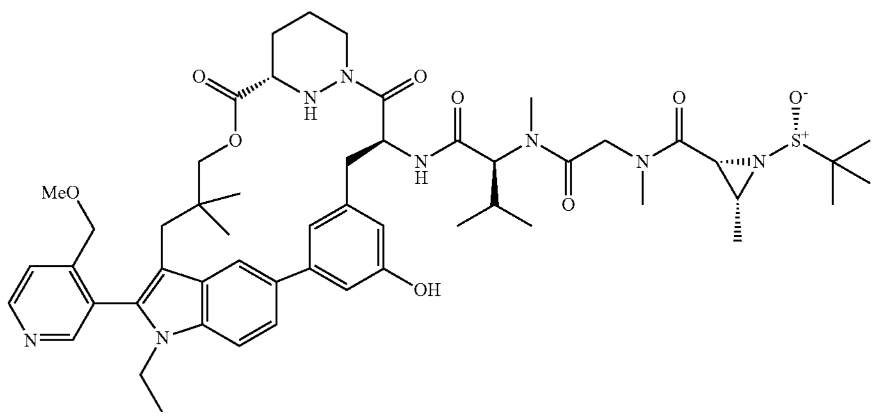 |
| 54 | 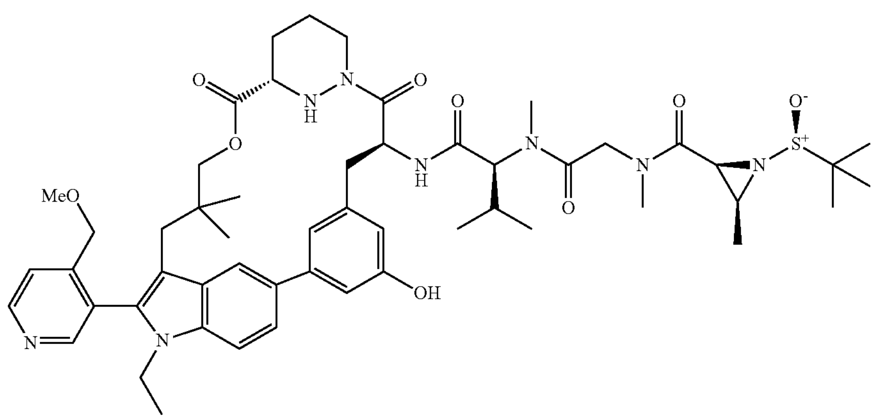 |
| 55 | 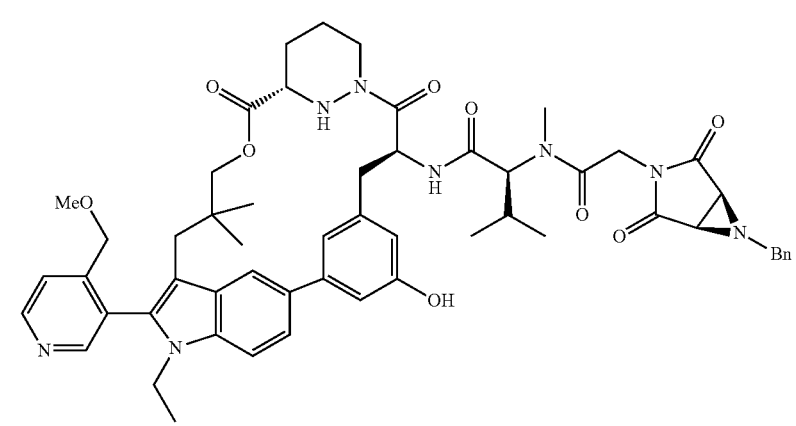 |

TABLE 1-continued

Certain Compounds of the Present Invention

| Ex# | Structure |
|---|---|
| 56* | 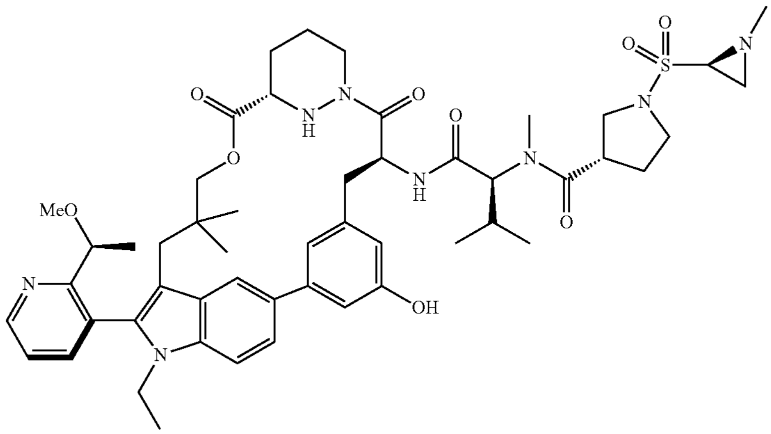 |
| 57* | 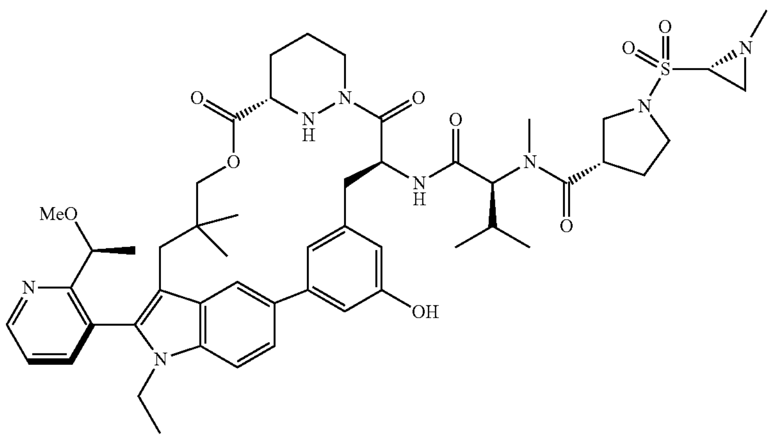 |
| 58 | 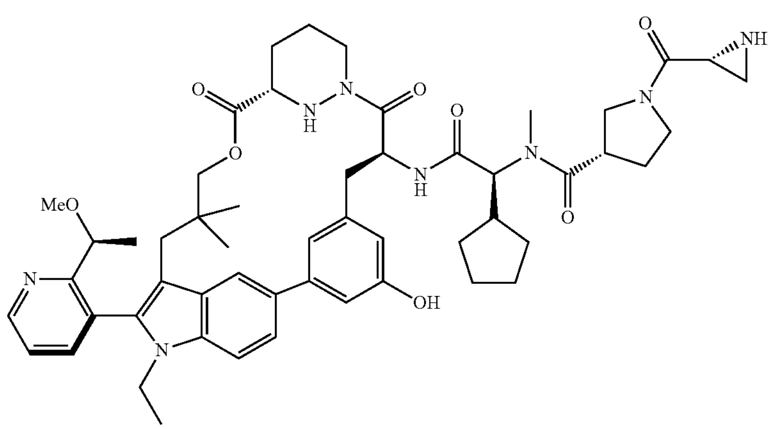 |

TABLE 1-continued

Certain Compounds of the Present Invention

| Ex# | Structure |
|---|---|
| 59 | 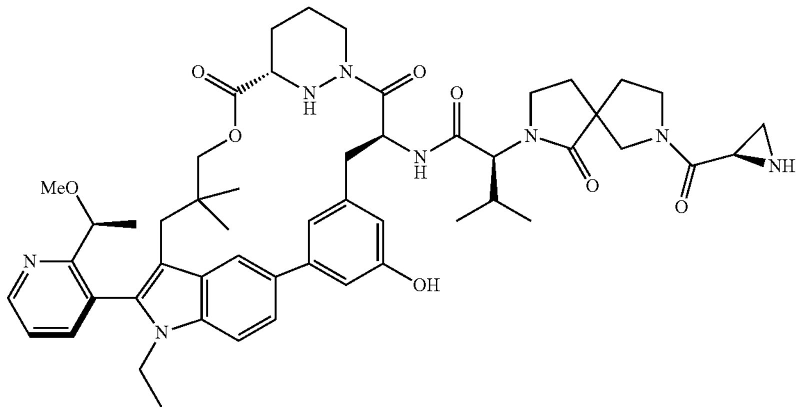 |
| 60 | 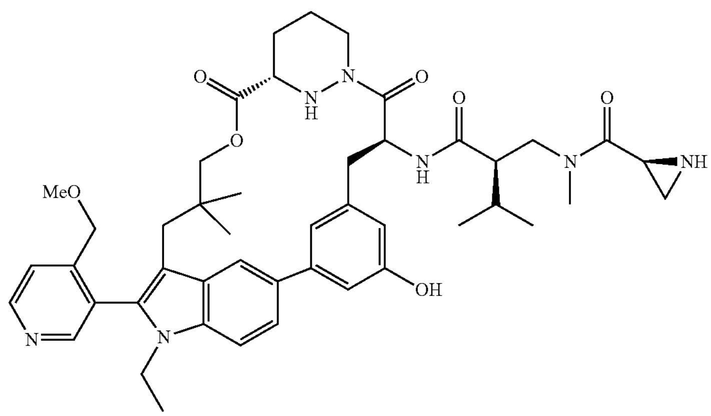 [SMILES: CCn1c(-c2cnccc2COC)c2c3cc(ccc31)-c1cc(O)cc(c1)C[C@H](NC(=O)[C@@H](CN(C)C(=O)[C@@H]1CN1)C(C)C)C(=O)N1CCC[C@H](N1)C(=O)OCC(C)(C)C2] |
| 61 A and B | |

TABLE 1-continued

Certain Compounds of the Present Invention

| Ex# | Structure |
| --- | --- |
| 62 A and B | 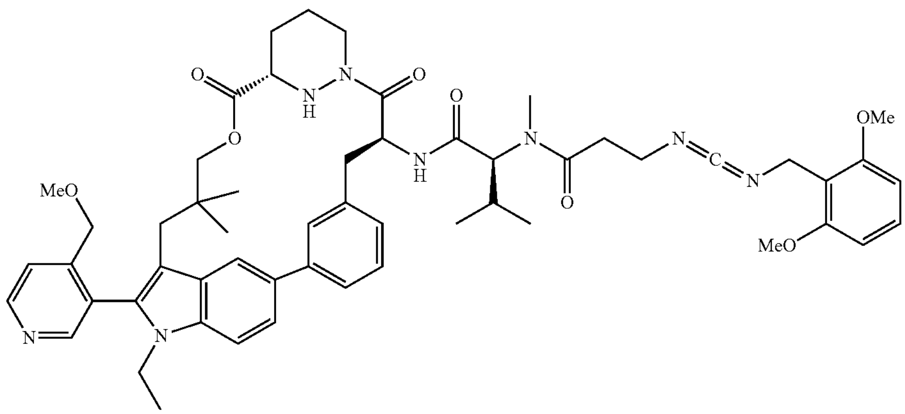 [SMILES: CCn1c(-c2cnccc2COC)c2c3cc(ccc31)-c1cccc(c1)C[C@H](NC(=O)[C@H](C(C)C)N(C)C(=O)CCN=C=NCc1c(OC)cccc1OC)C(=O)N1CCC[C@H](N1)C(=O)OCC(C)(C)C2] |
| 63 | 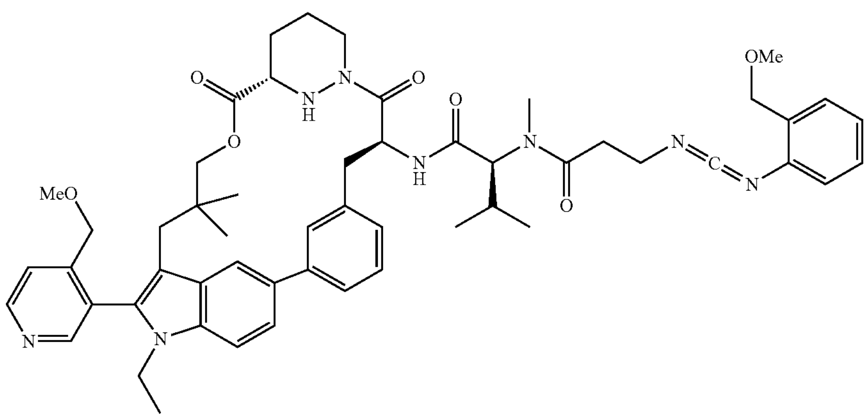 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccccc1COC)C(=O)N1CCC[C@H](N1)C(=O)OCC(C)(C)C2] |
| 64 A and B | 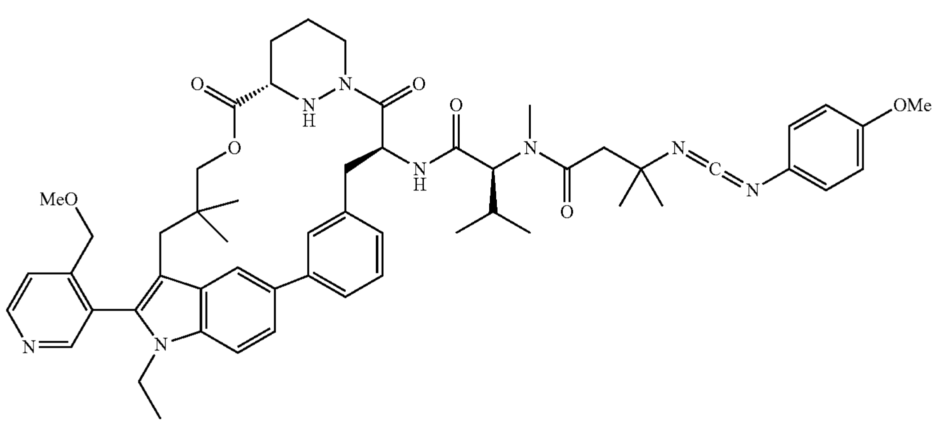 [SMILES: CCn1c(-c2cnccc2COC)c2c3cc(ccc31)-c1cccc(c1)C[C@H](NC(=O)[C@H](C(C)C)N(C)C(=O)CC(C)(C)N=C=Nc1ccc(OC)cc1)C(=O)N1CCC[C@H](N1)C(=O)OCC(C)(C)C2] |

TABLE 1-continued

Certain Compounds of the Present Invention

| Ex# | Structure |
|---|---|
| 65 A and B | 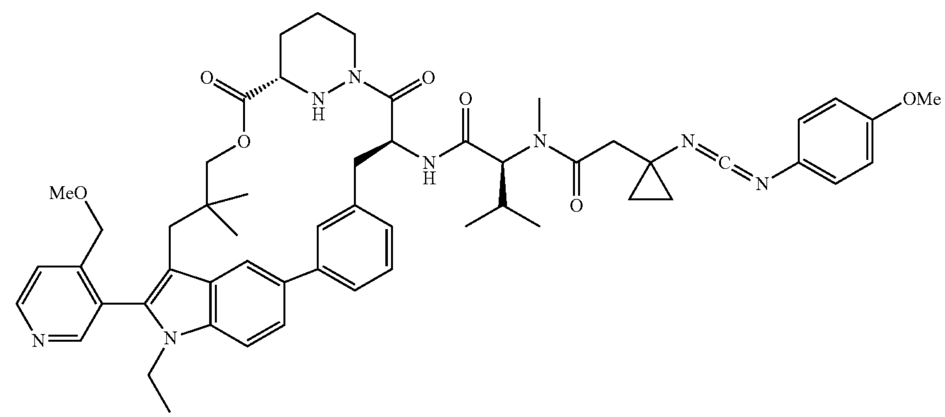 [SMILES: CCn1c(-c2cnccc2COC)c2c3cc(ccc31)-c1cccc(c1)C[C@H](NC(=O)[C@H](C(C)C)N(C)C(=O)CC1(N=C=Nc3ccc(OC)cc3)CC1)C(=O)N1CCC[C@H](N1)C(=O)OCC(C)(C)C2] |
| 66 | 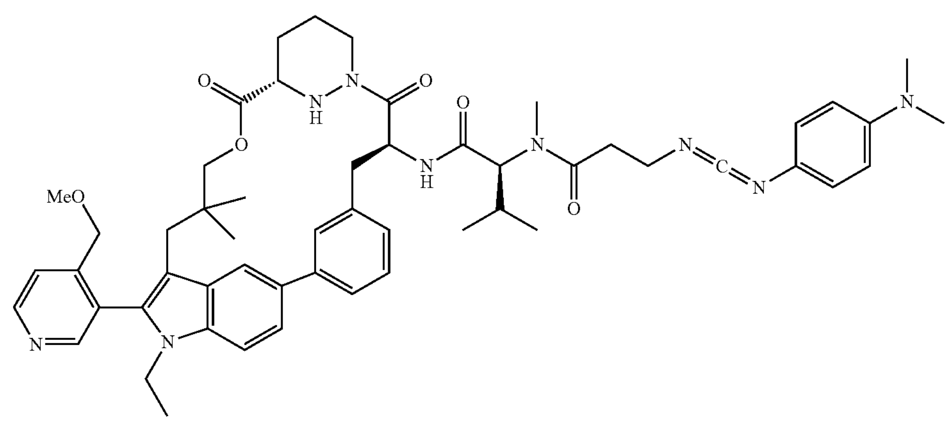 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccc(N(C)C)cc1)C(=O)N1CCC[C@H](N1)C(=O)OCC(C)(C)C2] |
| 67 | 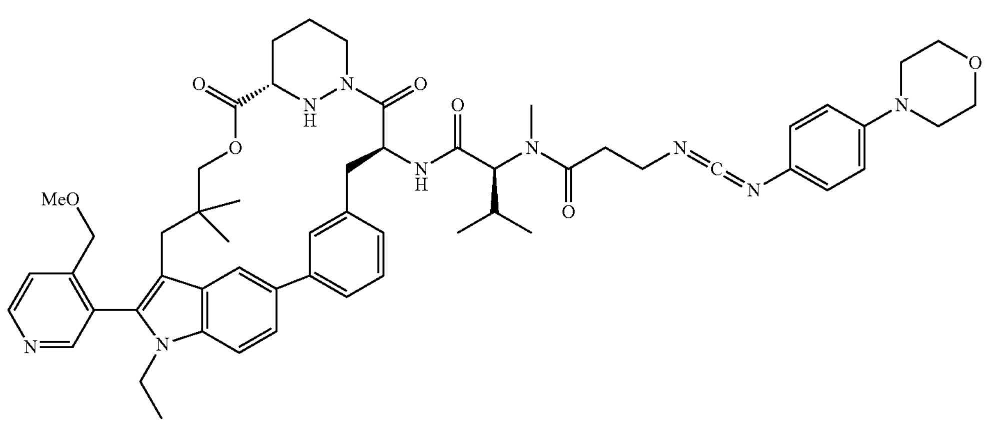 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccc(N3CCOCC3)cc1)C(=O)N1CCC[C@H](N1)C(=O)OCC(C)(C)C2] |

TABLE 1-continued
Certain Compounds of the Present Invention
| Ex# | Structure |
|---|---|
| 68 A and B | 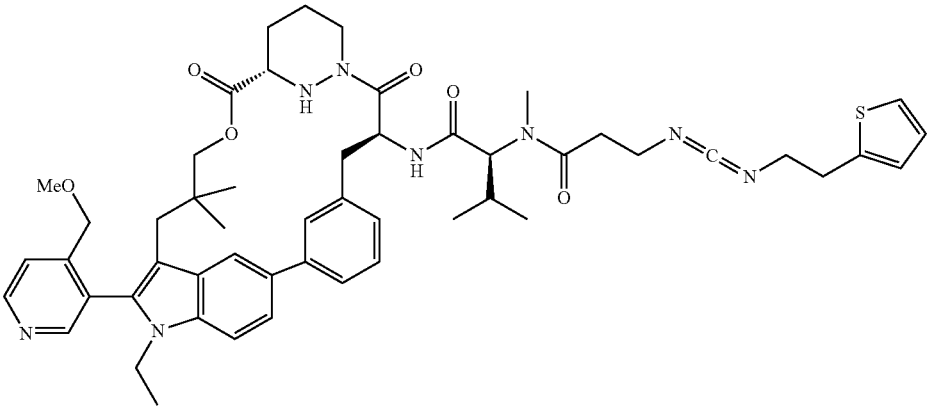 [SMILES: CCn1c(-c2cnccc2COC)c2c3cc(ccc31)-c1cccc(c1)C[C@H](NC(=O)[C@H](C(C)C)N(C)C(=O)CCN=C=NCCc1cccs1)C(=O)N1CCC[C@H](N1)C(=O)OCC(C)(C)C2] |
| 69 A and B | 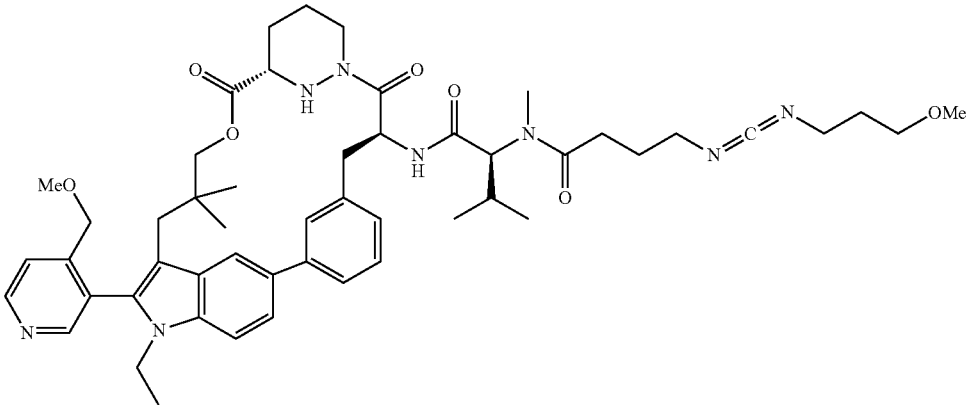 [SMILES: CCn1c(-c2cnccc2COC)c2c3cc(ccc31)-c1cccc(c1)C[C@H](NC(=O)[C@H](C(C)C)N(C)C(=O)CCCN=C=NCCCOC)C(=O)N1CCC[C@H](N1)C(=O)OCC(C)(C)C2] |
| 70 A and B | 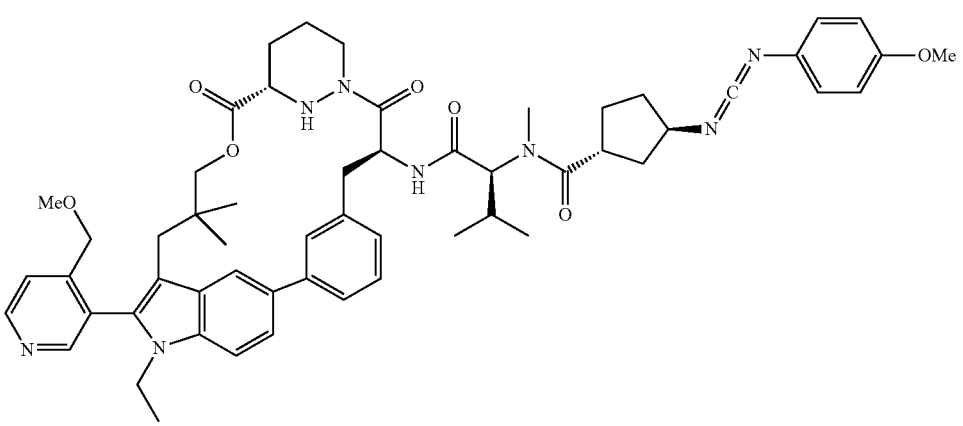 [SMILES: CCn1c(-c2cnccc2COC)c2c3cc(ccc31)-c1cccc(c1)C[C@H](NC(=O)[C@H](C(C)C)N(C)C(=O)[C@@H]1CC[C@@H](N=C=Nc3ccc(OC)cc3)C1)C(=O)N1CCC[C@H](N1)C(=O)OCC(C)(C)C2] |

TABLE 1-continued

Certain Compounds of the Present Invention

| Ex# | Structure |
| --- | --- |
| 71 A and B | 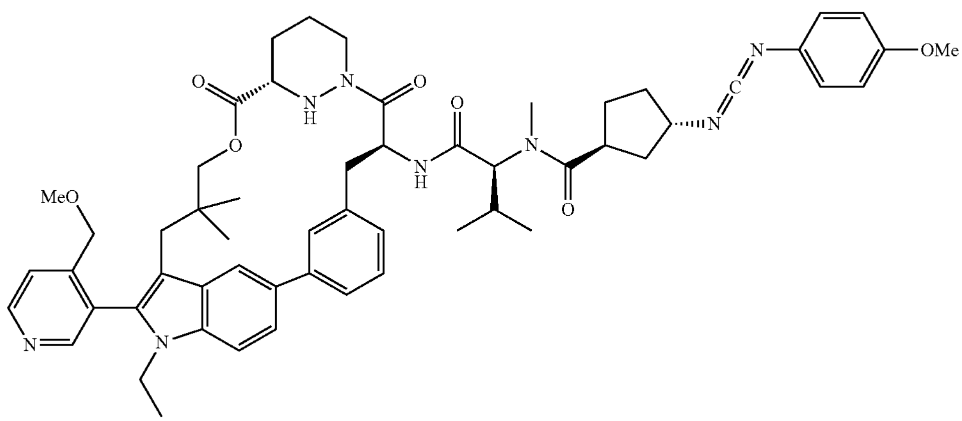 [SMILES: CCn1c(-c2cnccc2COC)c2c3cc(ccc31)-c1cccc(c1)C[C@H](NC(=O)[C@H](C(C)C)N(C)C(=O)[C@H]1CC[C@H](N=C=Nc3ccc(OC)cc3)C1)C(=O)N1CCC[C@H](N1)C(=O)OCC(C)(C)C2] |
| 72 A and B | 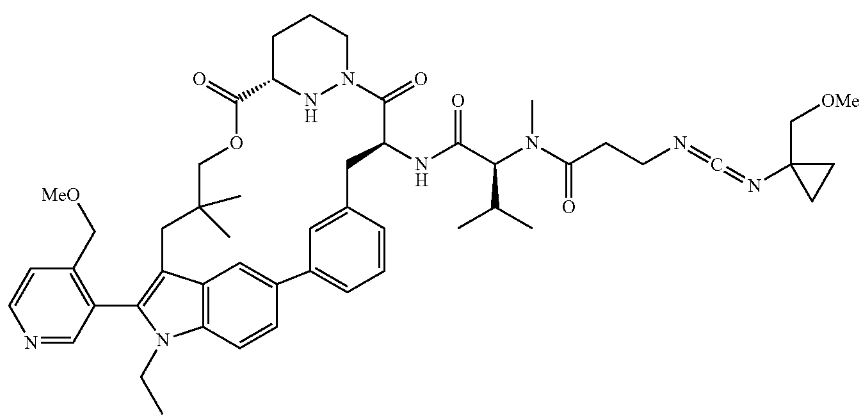 [SMILES: CCn1c(-c2cnccc2COC)c2c3cc(ccc31)-c1cccc(c1)C[C@H](NC(=O)[C@H](C(C)C)N(C)C(=O)CCN=C=NC1(COC)CC1)C(=O)N1CCC[C@H](N1)C(=O)OCC(C)(C)C2] |
| 73 | 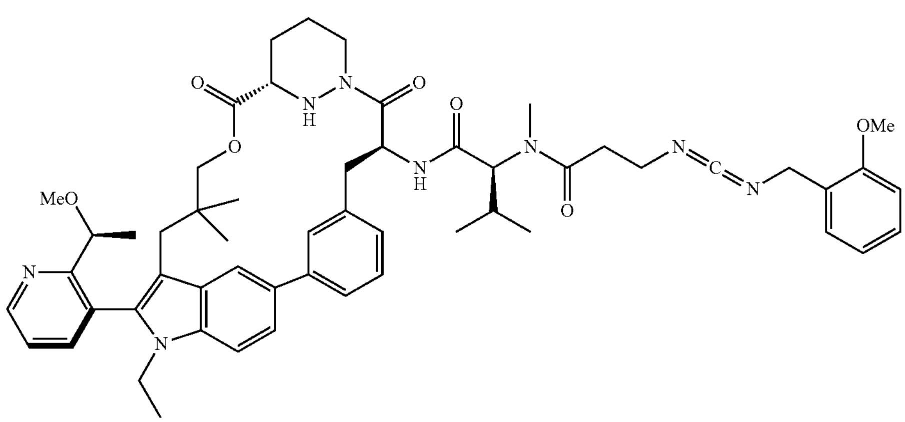 |

TABLE 1-continued

Certain Compounds of the Present Invention

| Ex# | Structure |
|---|---|
| 74 | 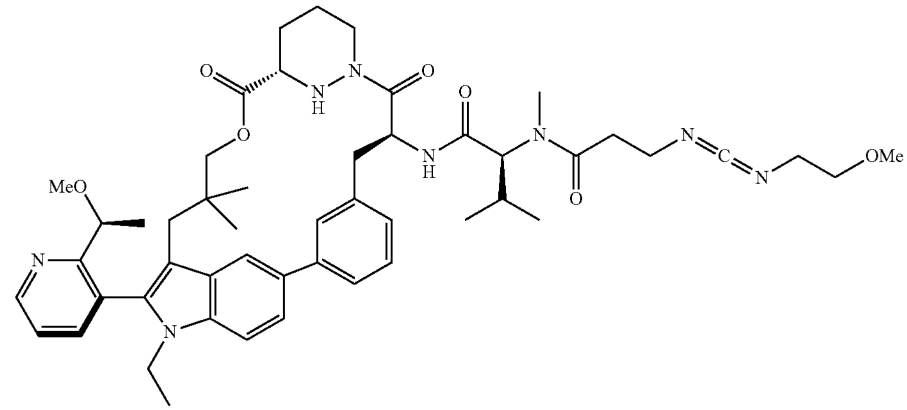 |
| 75 | 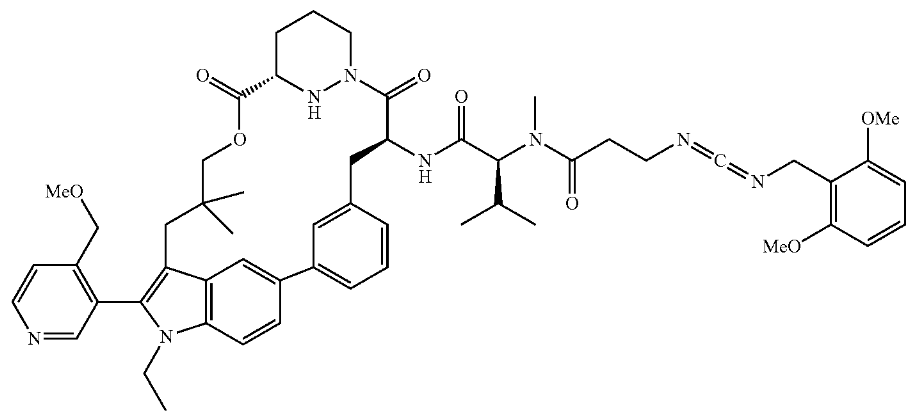 [SMILES: CCn1c(-c2cnccc2COC)c2c3cc(ccc31)-c1cccc(c1)C[C@H](NC(=O)[C@H](C(C)C)N(C)C(=O)CCN=C=NCc1c(OC)cccc1OC)C(=O)N1CCC[C@H](N1)C(=O)OCC(C)(C)C2] |
| 76 | 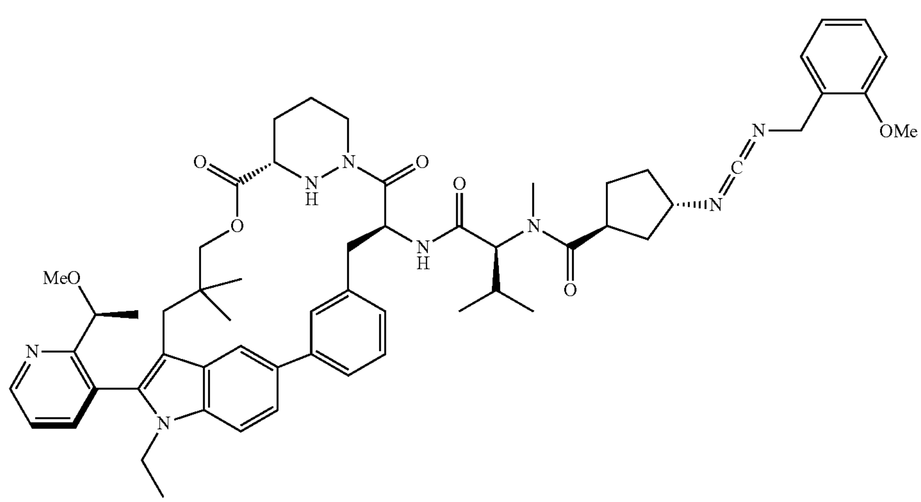 |

TABLE 1-continued
Certain Compounds of the Present Invention
| Ex# | Structure |
|---|---|
| 77 | 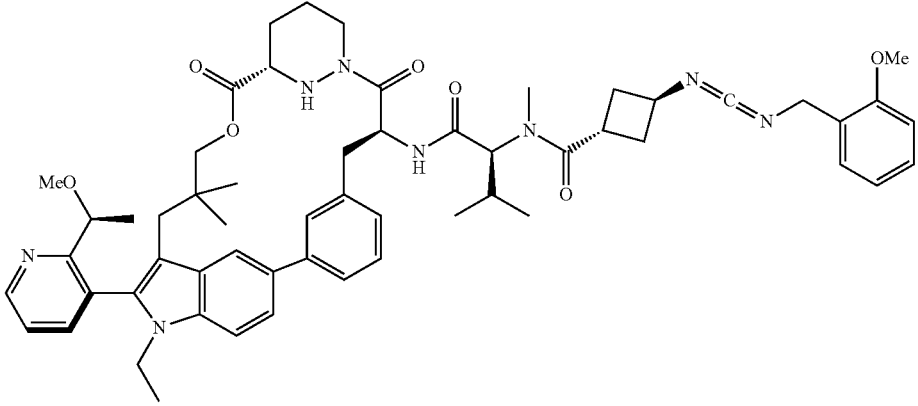 |
| 78 | 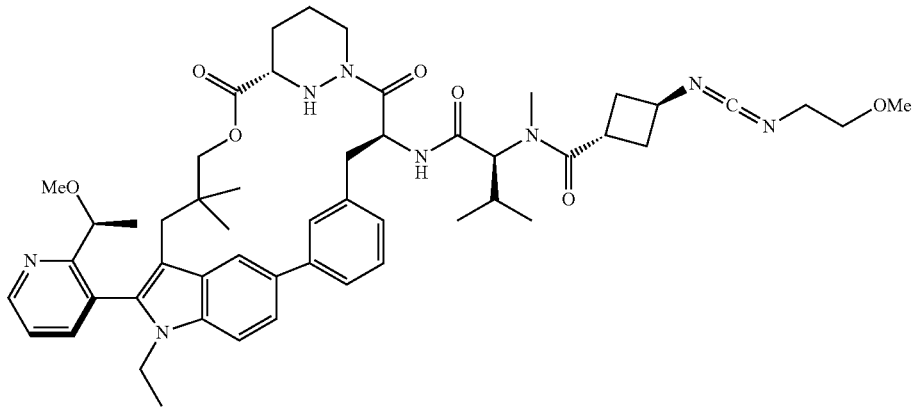 |
| 79 A and B | 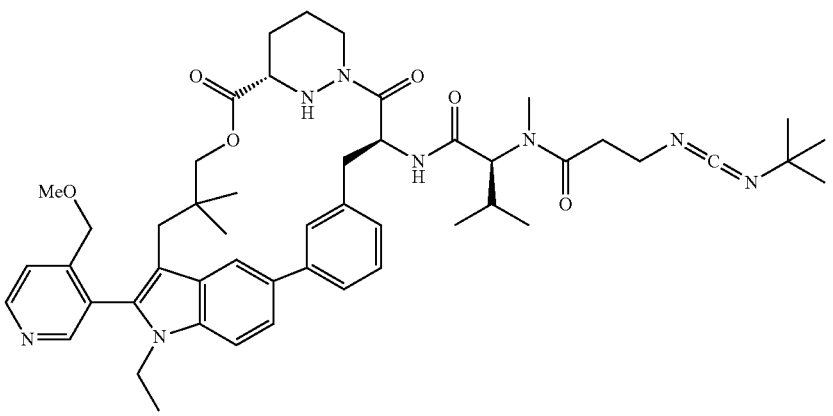 [SMILES: CCn1c(-c2cnccc2COC)c2c3cc(ccc31)-c1cccc(c1)C[C@H](NC(=O)[C@H](C(C)C)N(C)C(=O)CCN=C=NC(C)(C)C)C(=O)N1CCC[C@H](N1)C(=O)OCC(C)(C)C2] |

TABLE 1-continued
Certain Compounds of the Present Invention
| Ex# | Structure |
|---|---|
| 80 | 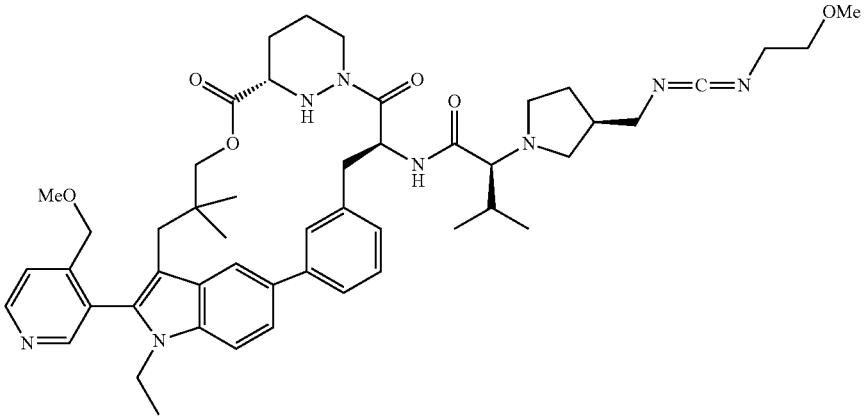 [SMILES: CCn1c(-c2cnccc2COC)c2c3cc(ccc31)-c1cccc(c1)C[C@H](NC(=O)[C@H](C(C)C)N1CC[C@@H](CN=C=NCCOC)C1)C(=O)N1CCC[C@H](N1)C(=O)OCC(C)(C)C2] |
| 81 | 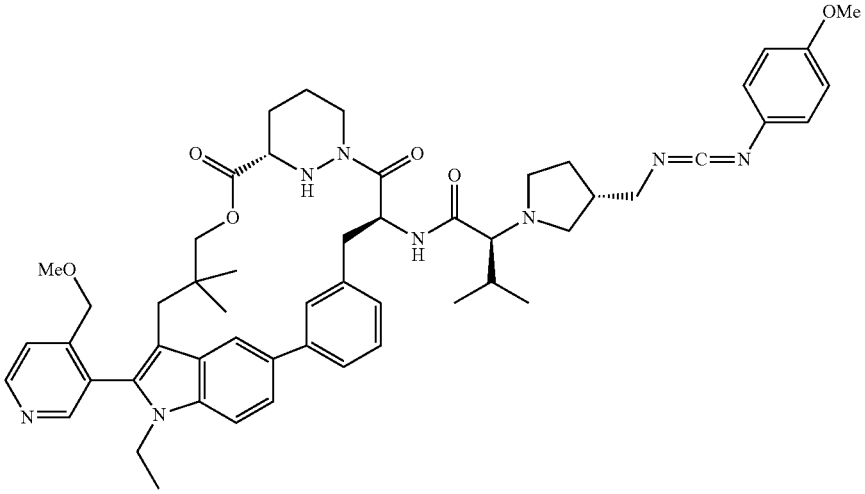 [SMILES: CCn1c(-c2cnccc2COC)c2c3cc(ccc31)-c1cccc(c1)C[C@H](NC(=O)[C@H](C(C)C)N1CC[C@H](CN=C=Nc3ccc(OC)cc3)C1)C(=O)N1CCC[C@H](N1)C(=O)OCC(C)(C)C2] |
| 82 A and B | 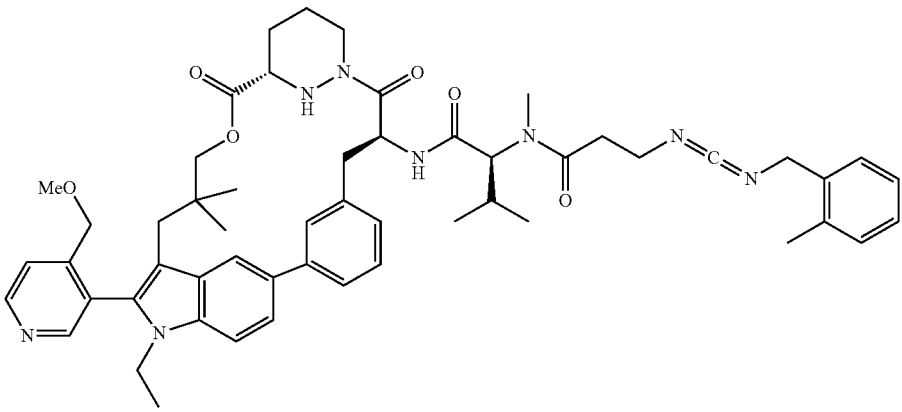 [SMILES: CCn1c(-c2cnccc2COC)c2c3cc(ccc31)-c1cccc(c1)C[C@H](NC(=O)[C@H](C(C)C)N(C)C(=O)CCN=C=NCc1ccccc1C)C(=O)N1CCC[C@H](N1)C(=O)OCC(C)(C)C2] |

US 11,739,074 B2
109                                                                                                                              110
TABLE 1-continued
Certain Compounds of the Present Invention
| Ex# | Structure |
|---|---|
| 83 | 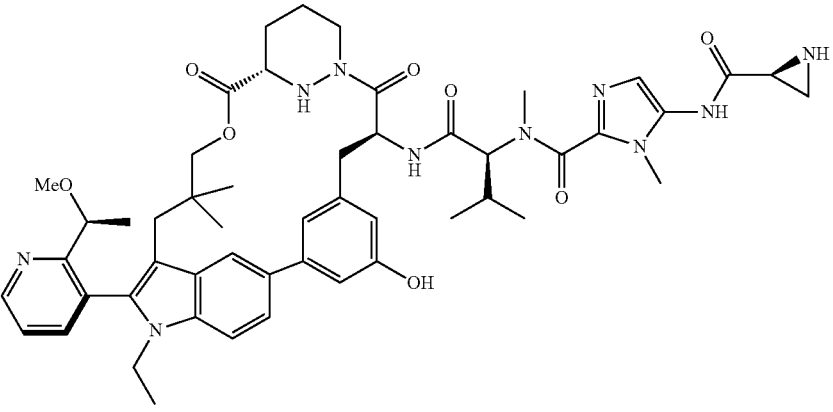 |
| 84 | 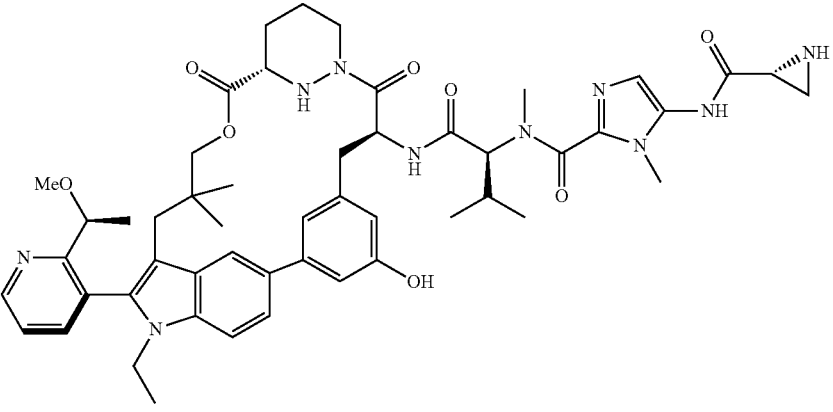 |
| 85 | 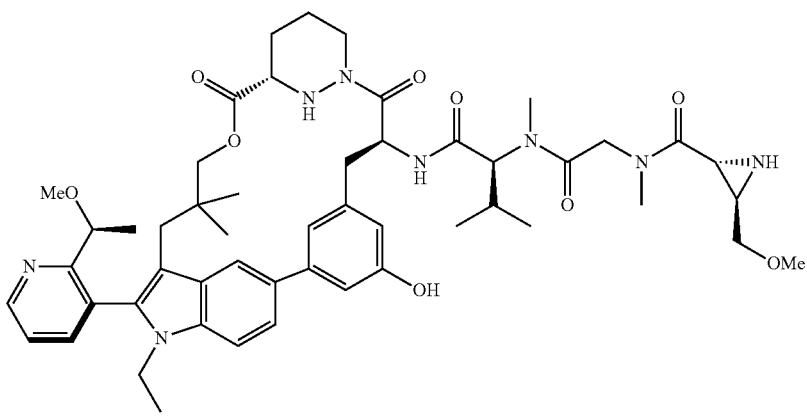 |

TABLE 1-continued

Certain Compounds of the Present Invention

| Ex# | Structure |
| --- | --- |
| 86 | 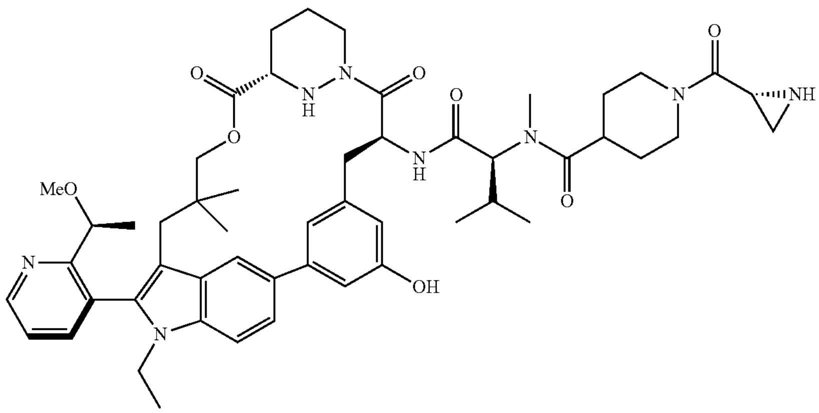 |
| 87 | 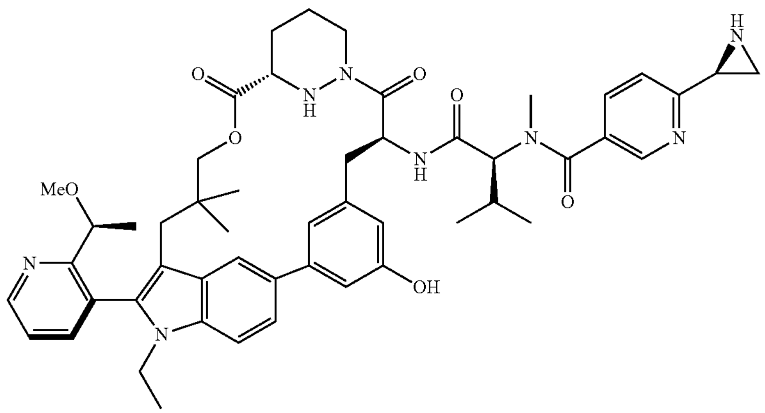 |
| 88 | 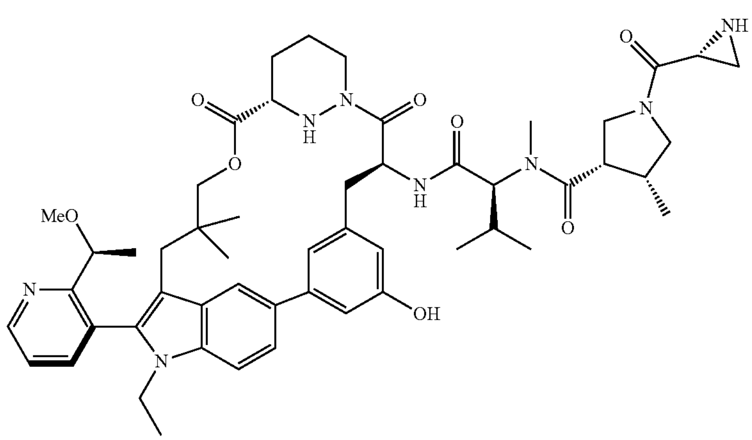 |

US 11,739,074 B2
113                                                                 114
TABLE 1-continued
Certain Compounds of the Present Invention
| Ex# | Structure |
|---|---|
| 89 | 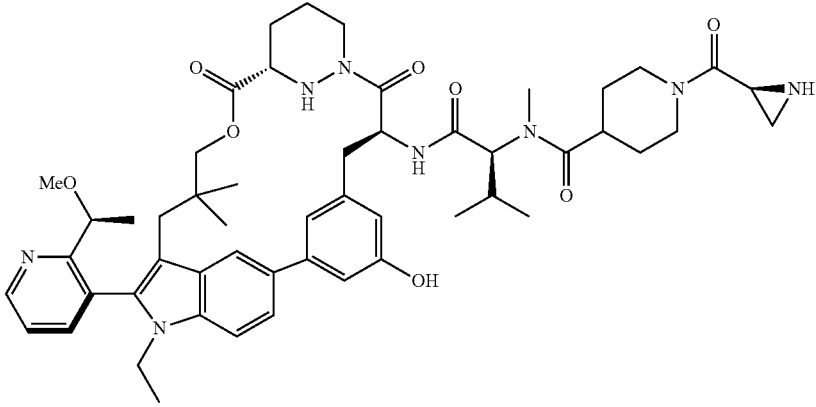 |
| 90 | 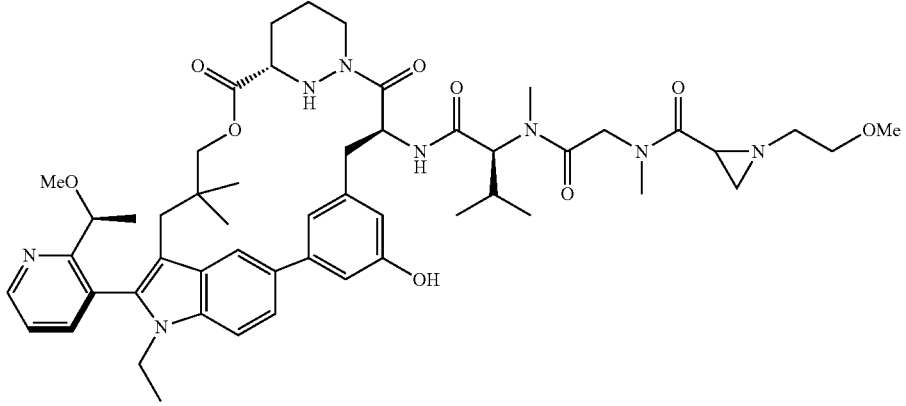 |
| 91* | 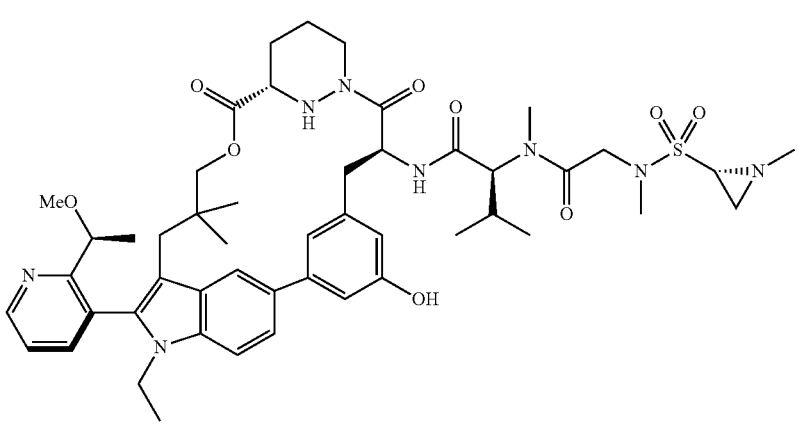 |

TABLE 1-continued

Certain Compounds of the Present Invention

| Ex# | Structure |
|---|---|
| 92* | 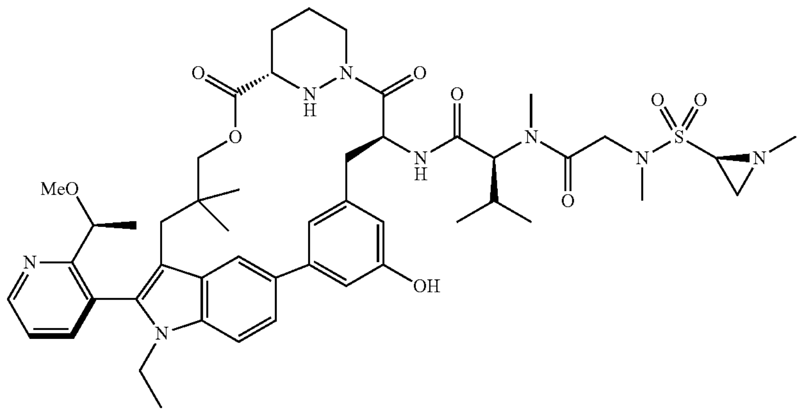 |
| 93 | 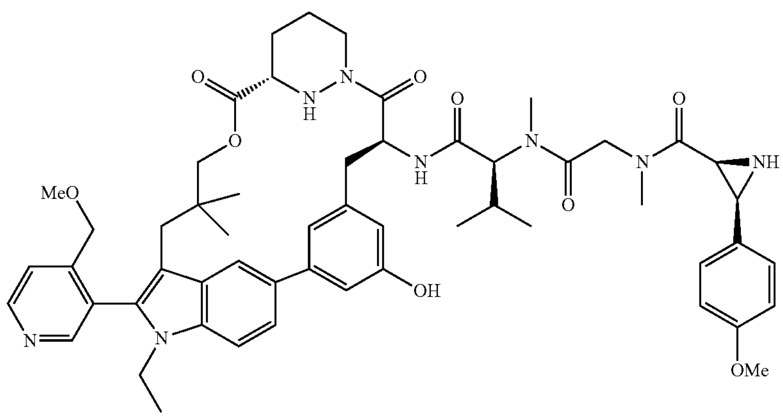 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@H]1c1ccc(OC)cc1)C(=O)N1CCC[C@H](N1)C(=O)OCC(C)(C)C2] |
| 94 | 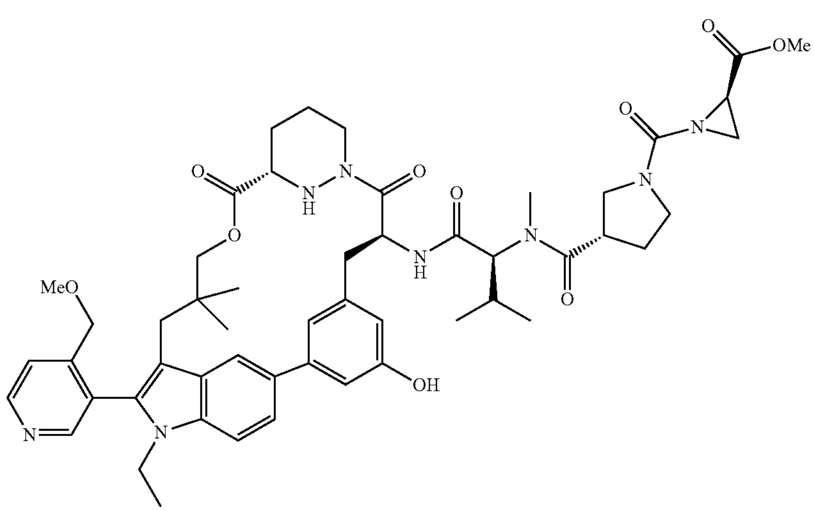 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(C(=O)N3C[C@@H]3C(=O)OC)C1)C(=O)N1CCC[C@H](N1)C(=O)OCC(C)(C)C2] |

TABLE 1-continued

Certain Compounds of the Present Invention

| Ex# | Structure |
|---|---|
| 95 | 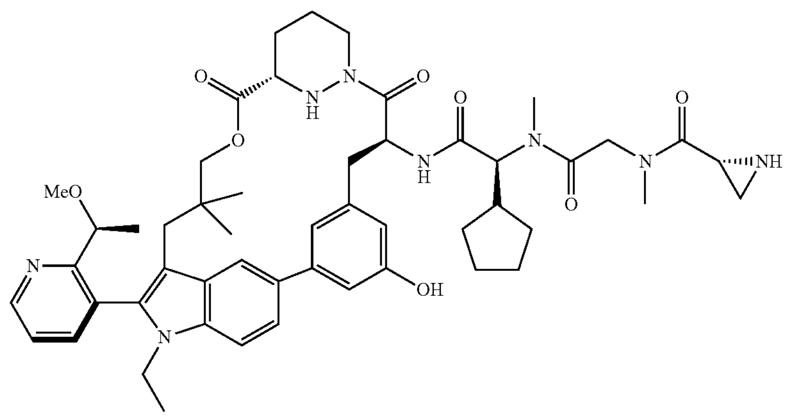 |
| 96 | 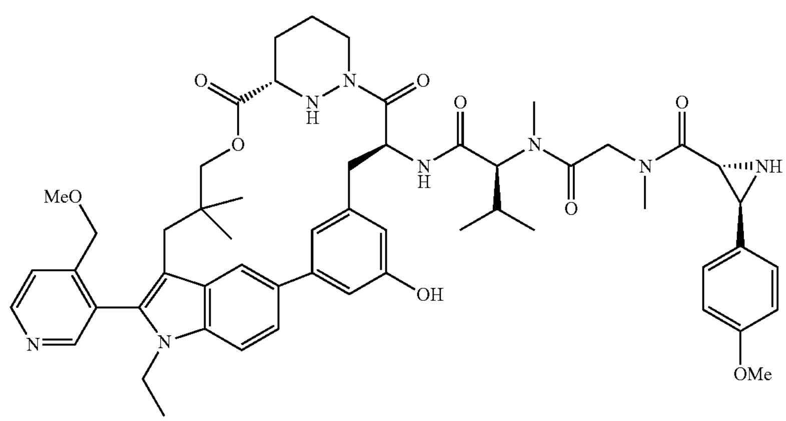 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@H]1c1ccc(OC)cc1)C(=O)N1CCC[C@H](N1)C(=O)OCC(C)(C)C2] |
| 97 | 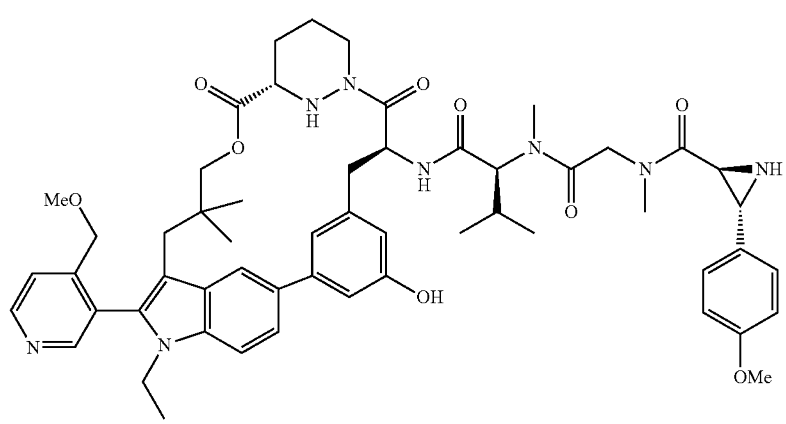 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@@H]1c1ccc(OC)cc1)C(=O)N1CCC[C@H](N1)C(=O)OCC(C)(C)C2] |

TABLE 1-continued

Certain Compounds of the Present Invention

| Ex# | Structure |
|-----|-----------|
| 98  | 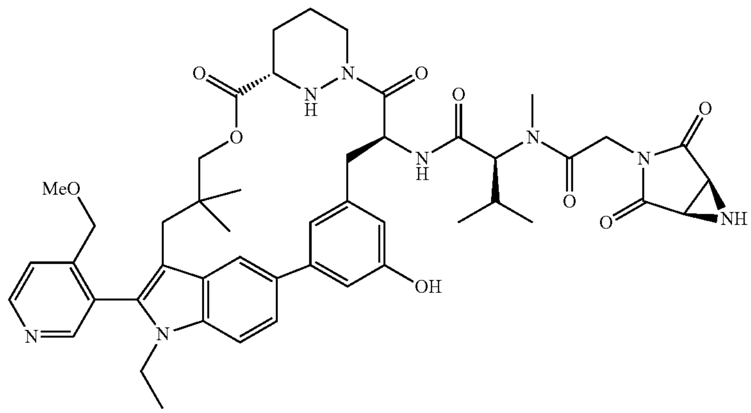 [SMILES: CCn1c(-c2cnccc2COC)c2c3cc(ccc31)-c1cc(O)cc(c1)C[C@H](NC(=O)[C@H](C(C)C)N(C)C(=O)CN1C(=O)[C@H]3N[C@H]3C1=O)C(=O)N1CCC[C@H](N1)C(=O)OCC(C)(C)C2]          |
| 99  | 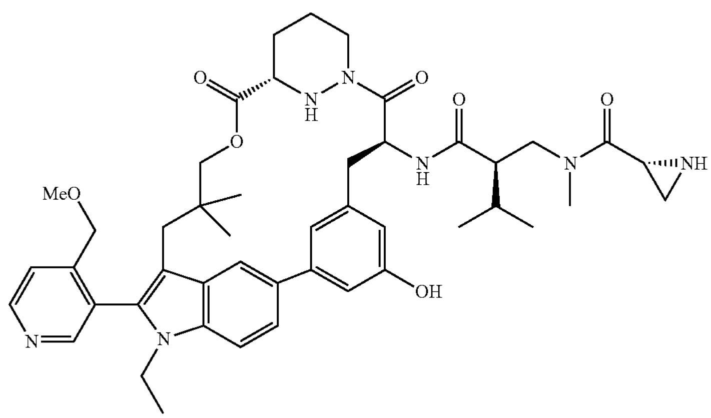 [SMILES: CCn1c(-c2cnccc2COC)c2c3cc(ccc31)-c1cc(O)cc(c1)C[C@H](NC(=O)[C@@H](CN(C)C(=O)[C@H]1CN1)C(C)C)C(=O)N1CCC[C@H](N1)C(=O)OCC(C)(C)C2]          |
| 100 | 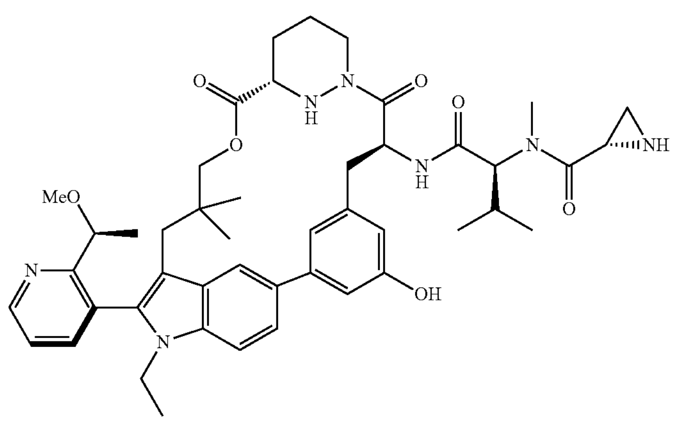          |

TABLE 1-continued

Certain Compounds of the Present Invention

| Ex# | Structure |
|---|---|
| 101 | 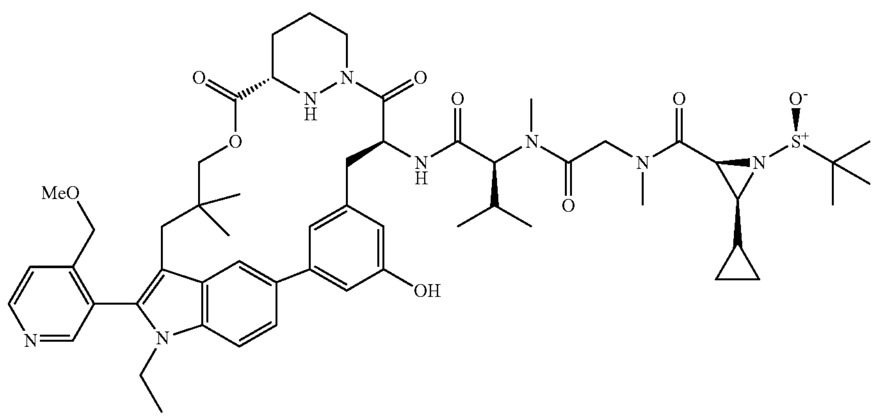 |
| 102 | 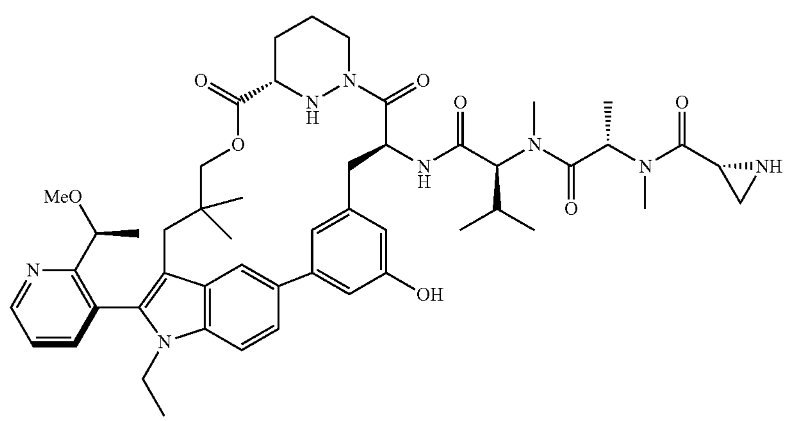 |
| 103 | 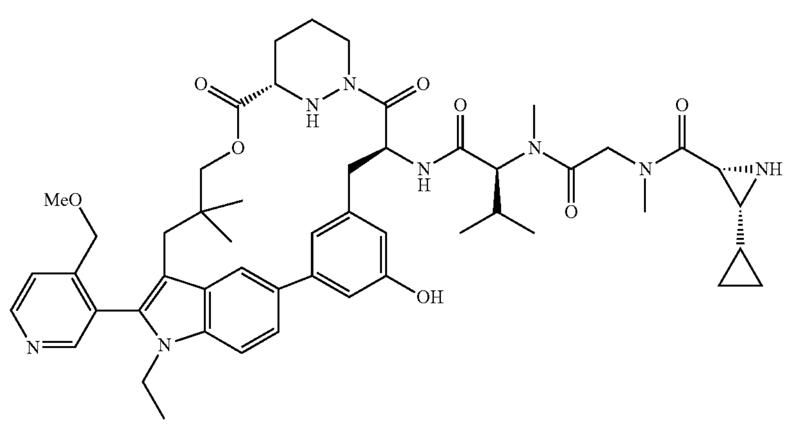 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1C1CC1)C(=O)N1CCC[C@H](N1)C(=O)OCC(C)(C)C2] |

TABLE 1-continued

Certain Compounds of the Present Invention

| Ex# | Structure |
|---|---|
| 104 | 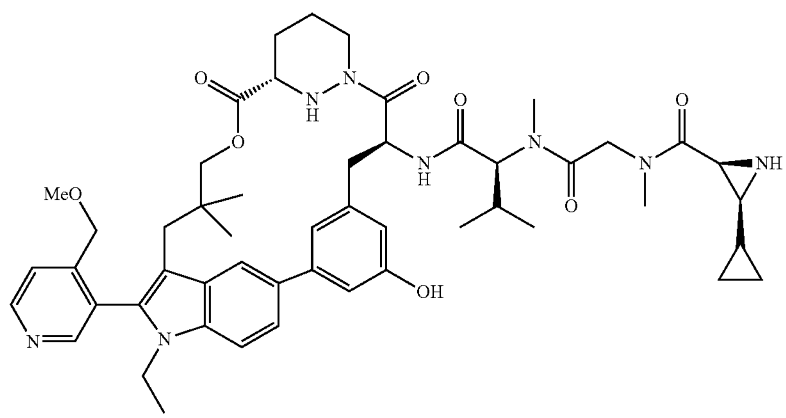 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@H]1C1CC1)C(=O)N1CCC[C@H](N1)C(=O)OCC(C)(C)C2] |
| 105 | 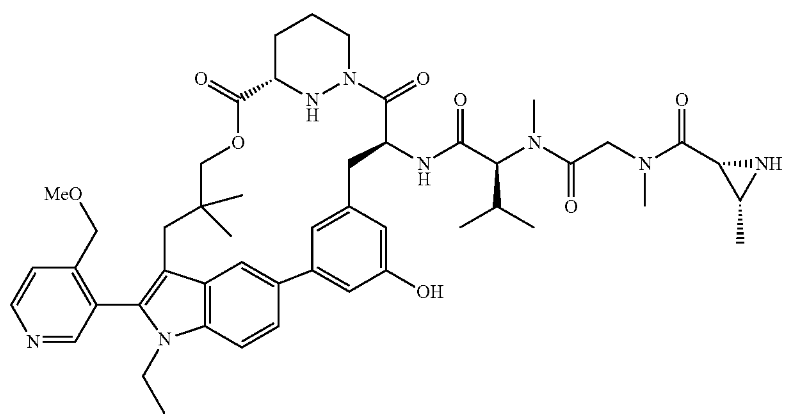 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1C)C(=O)N1CCC[C@H](N1)C(=O)OCC(C)(C)C2] |
| 106 | 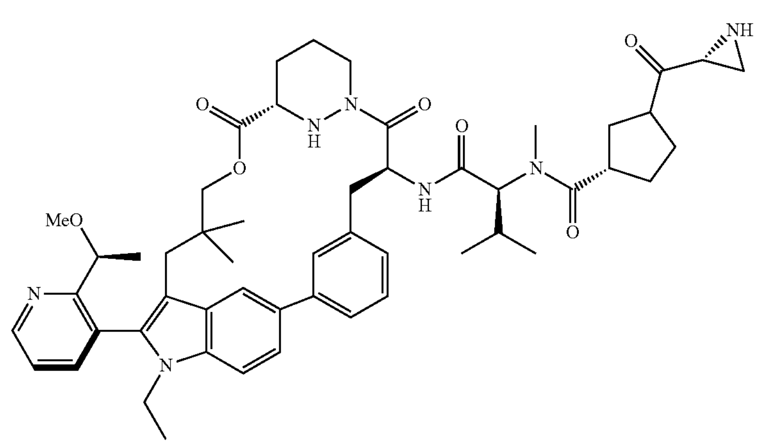 |

TABLE 1-continued

Certain Compounds of the Present Invention

| Ex# | Structure |
|---|---|
| 107 | 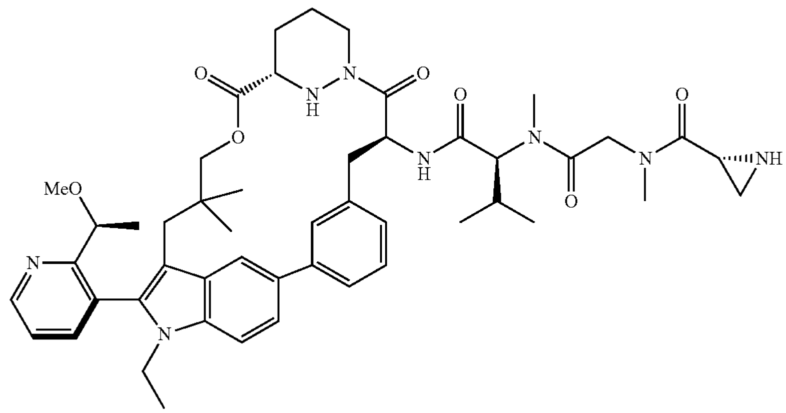 |
| 108* | 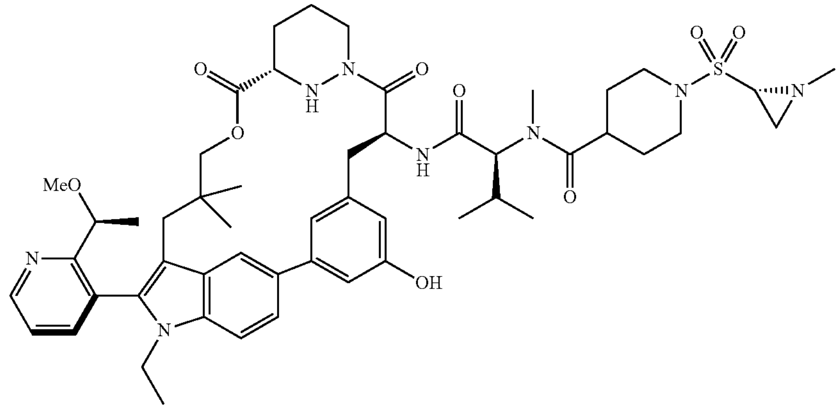 |
| 109 | 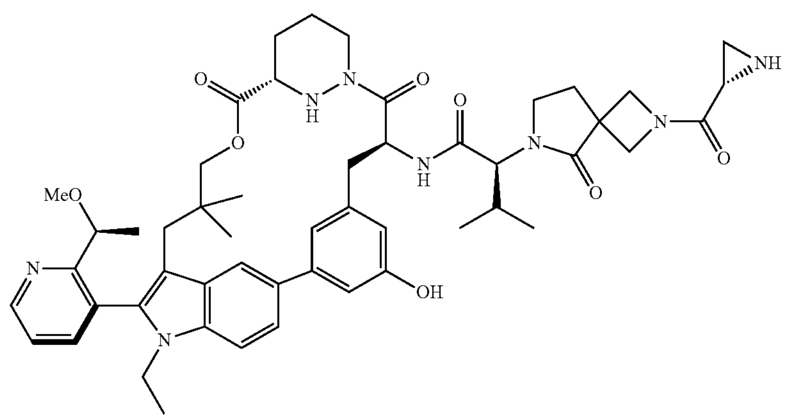 |

TABLE 1-continued

Certain Compounds of the Present Invention

| Ex# | Structure |
|---|---|
| 110 | 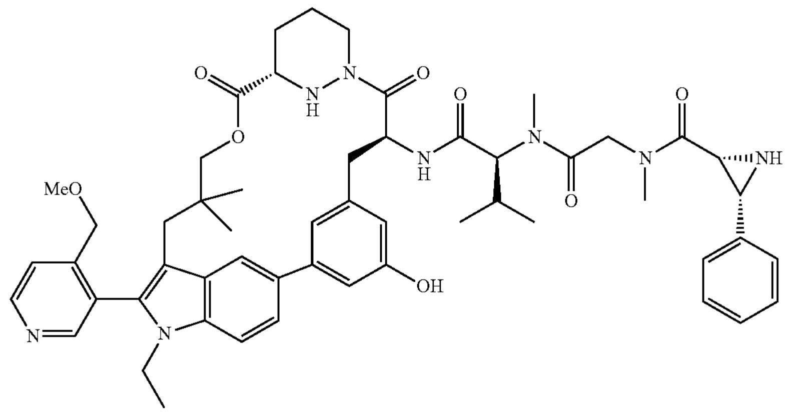 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1c1ccccc1)C(=O)N1CCC[C@H](N1)C(=O)OCC(C)(C)C2] |
| 111 | 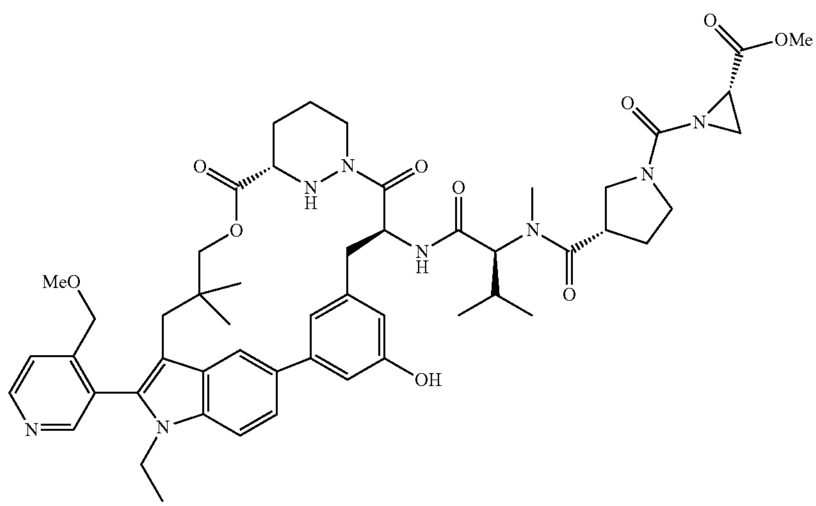 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(C(=O)N3C[C@H]3C(=O)OC)C1)C(=O)N1CCC[C@H](N1)C(=O)OCC(C)(C)C2] |
| 112 | 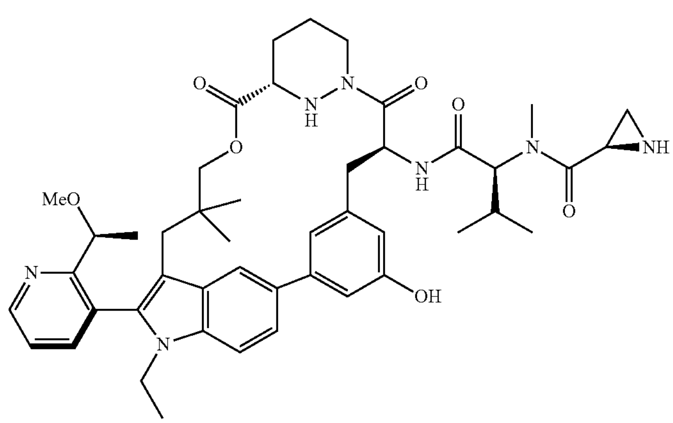 |

US 11,739,074 B2
129                                                                                 130
TABLE 1-continued
Certain Compounds of the Present Invention
| Ex# | Structure |
|---|---|
| 113 | 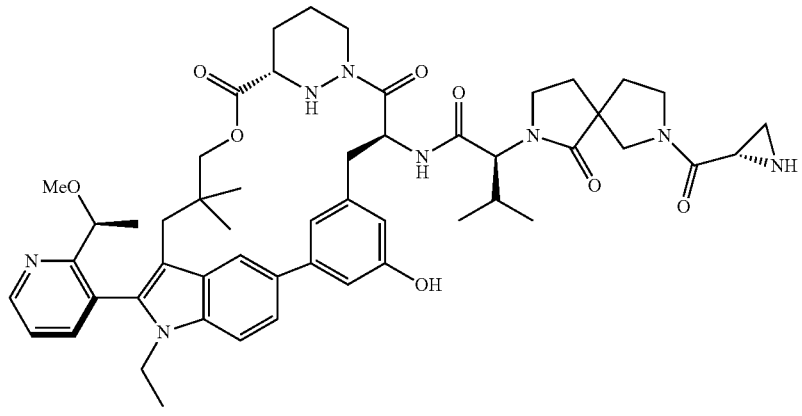 |
| 114 | 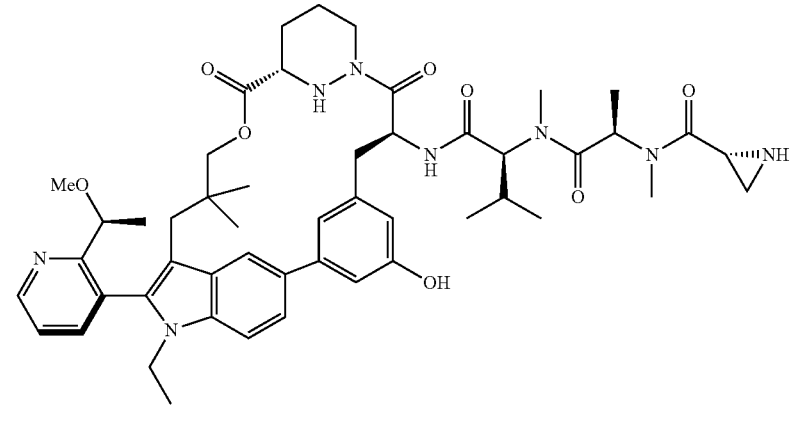 |
| 115 | 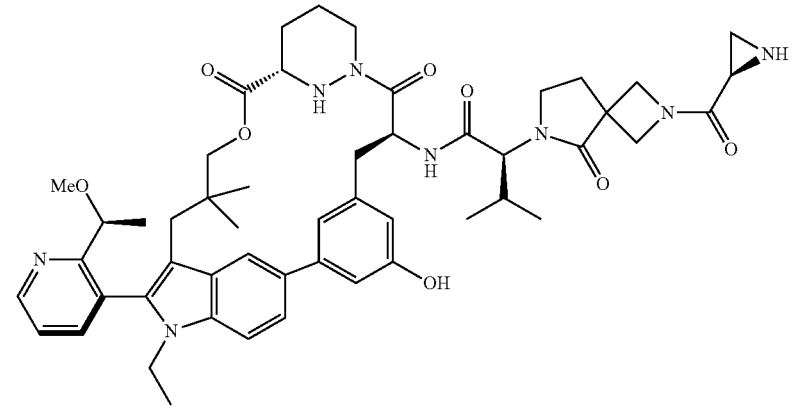 |

TABLE 1-continued

Certain Compounds of the Present Invention

| Ex# | Structure |
|---|---|
| 116 | 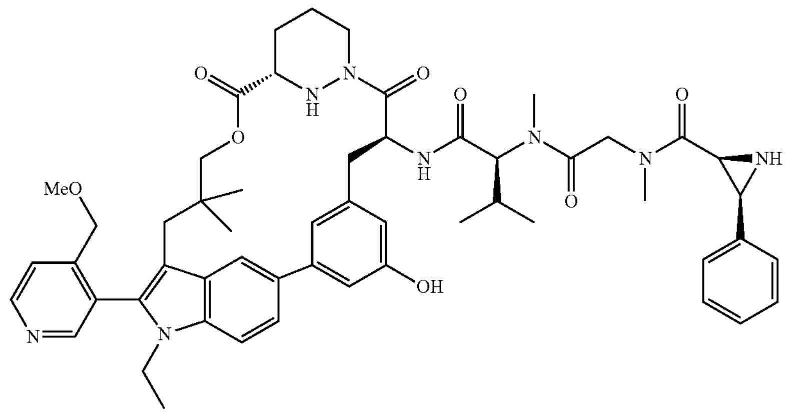 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@H]1c1ccccc1)C(=O)N1CCC[C@H](N1)C(=O)OCC(C)(C)C2] |
| 117* | 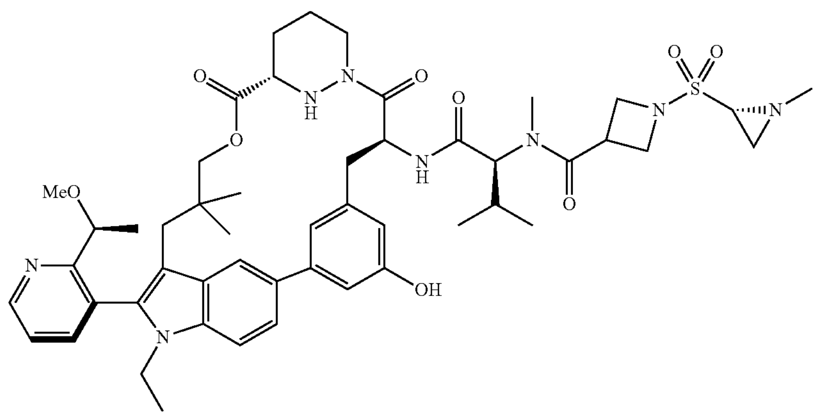 |
| 118* | 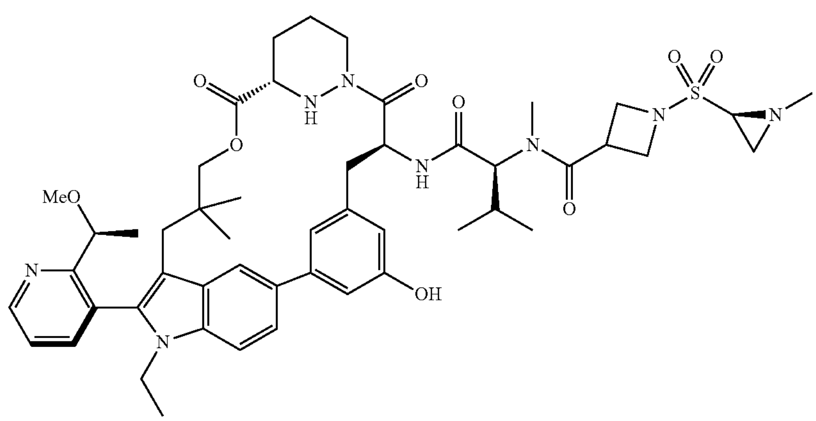 |

TABLE 1-continued

Certain Compounds of the Present Invention

| Ex# | Structure |
| --- | --- |
| 119* | 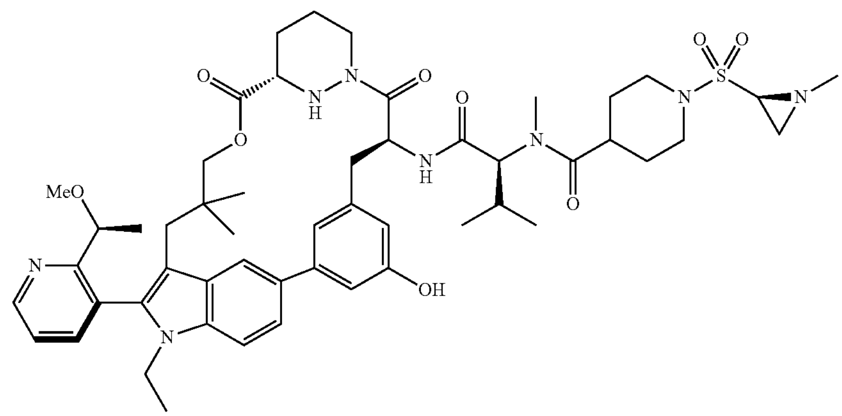 |
| 120 | 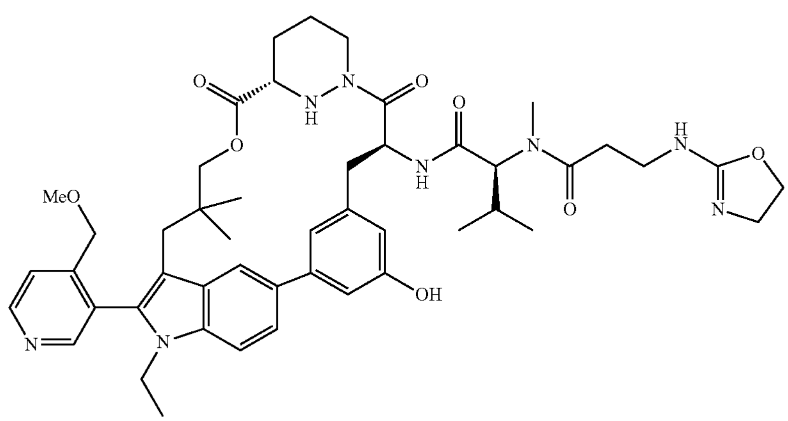 [SMILES: CCn1c(-c2cnccc2COC)c2c3cc(ccc31)-c1cc(O)cc(c1)C[C@H](NC(=O)[C@H](C(C)C)N(C)C(=O)CCNC1=NCCO1)C(=O)N1CCC[C@H](N1)C(=O)OCC(C)(C)C2] |
| 121 | 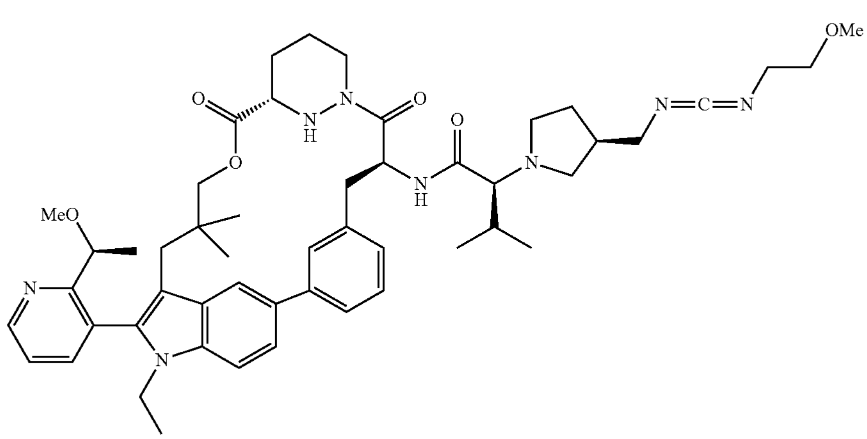 [SMILES: CCn1c(-c2cccnc2[C@H](C)OC)c2c3cc(ccc31)-c1cccc(c1)C[C@H](NC(=O)[C@H](C(C)C)N1CC[C@@H](CN=C=NCCOC)C1)C(=O)N1CCC[C@H](N1)C(=O)OCC(C)(C)C2] |

TABLE 1-continued

Certain Compounds of the Present Invention

| Ex# | Structure |
| --- | --- |
| 122 | 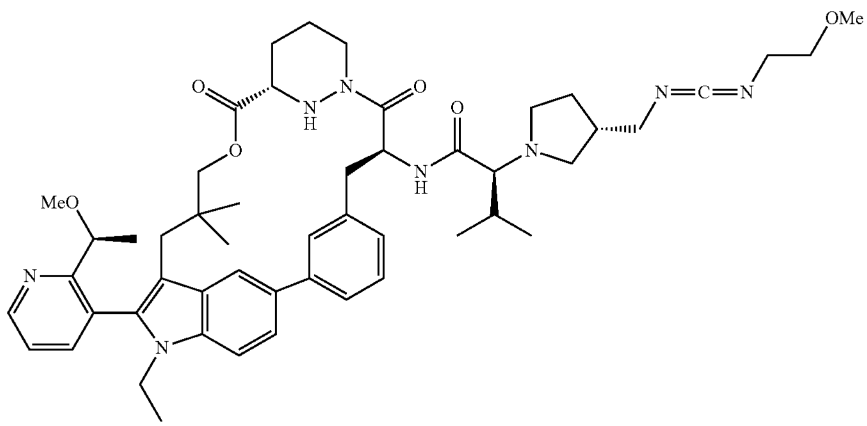 [SMILES: CCn1c(-c2cccnc2[C@H](C)OC)c2c3cc(ccc31)-c1cccc(c1)C[C@H](NC(=O)[C@H](C(C)C)N1CC[C@H](CN=C=NCCOC)C1)C(=O)N1CCC[C@H](N1)C(=O)OCC(C)(C)C2] |
| 123 | 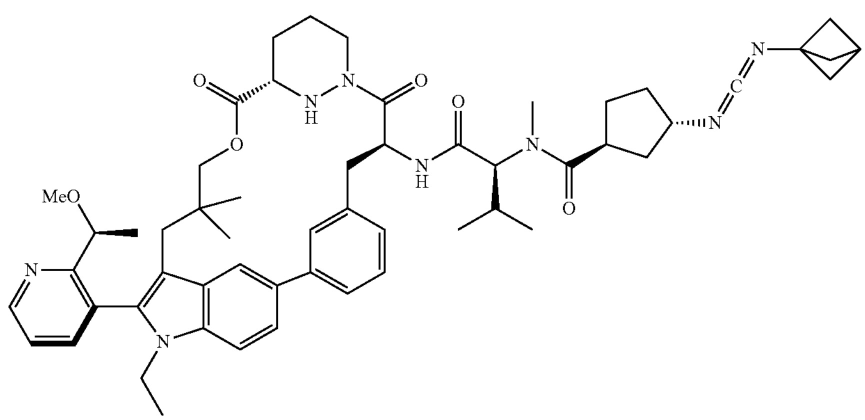 |
| 124 | 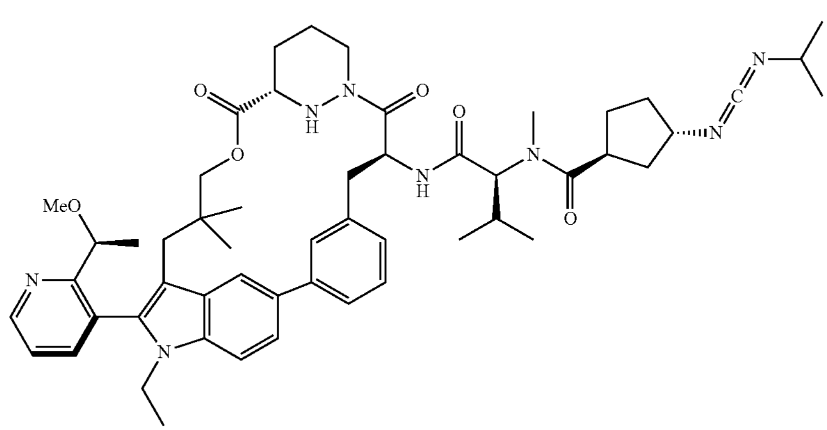 |

TABLE 1-continued

Certain Compounds of the Present Invention

| Ex# | Structure |
|---|---|
| 125 | 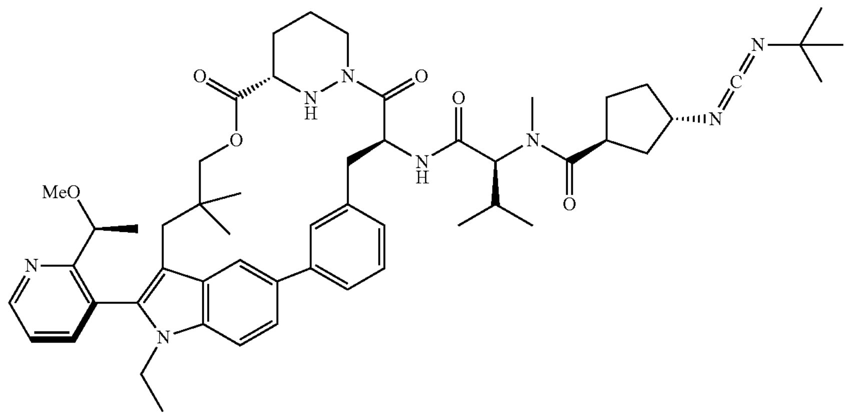 |
| 126 | 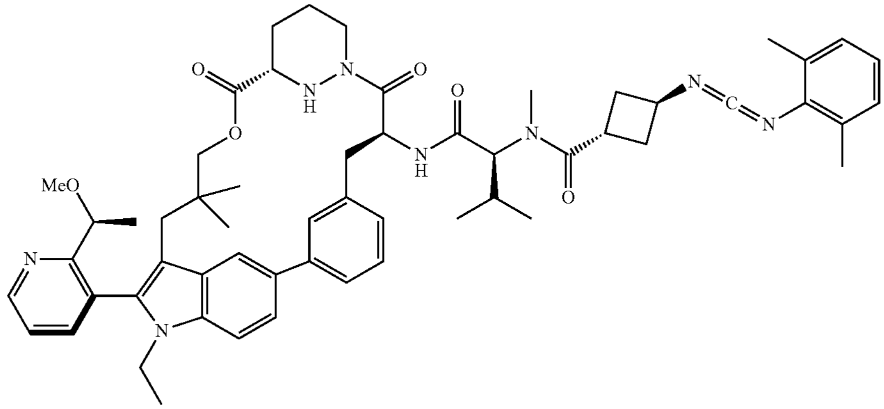 |
| 127 | 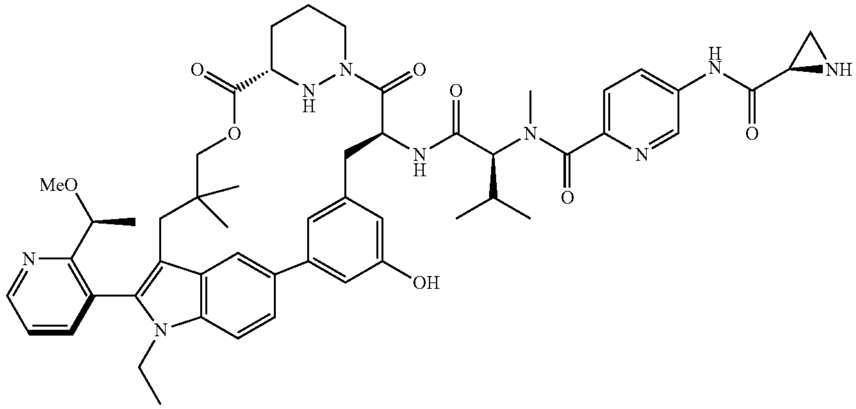 |

TABLE 1-continued
Certain Compounds of the Present Invention
| Ex# | Structure |
|---|---|
| 128 | 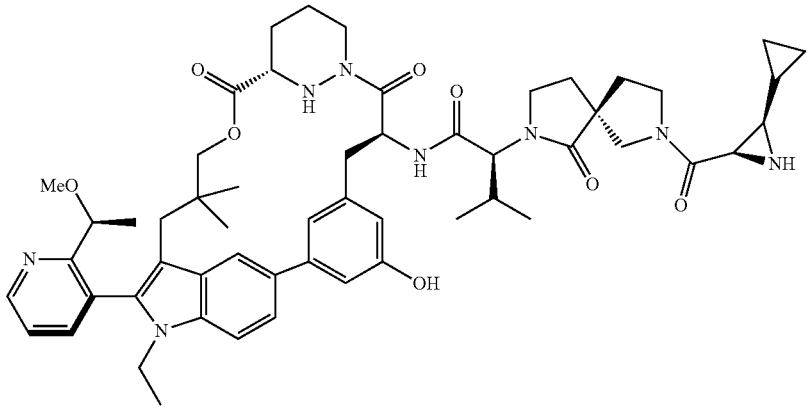 |
| 129 | 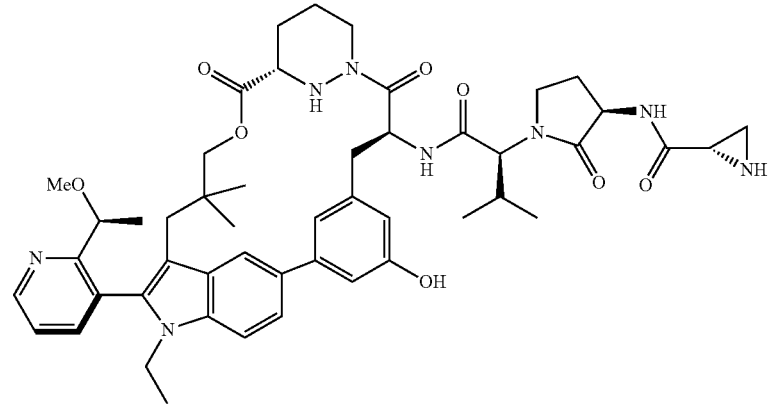 |
| 130 | 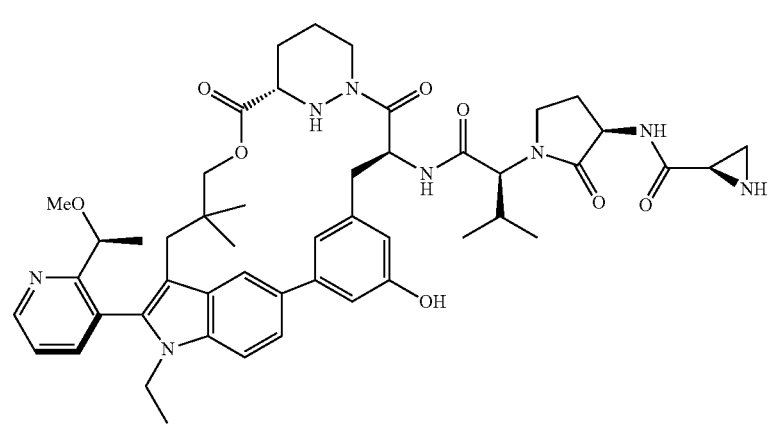 |

TABLE 1-continued

Certain Compounds of the Present Invention

| Ex# | Structure |
|---|---|
| 131 | 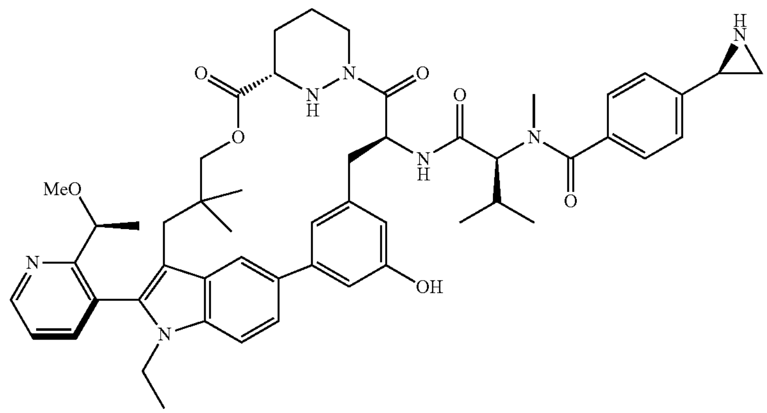 |
| 132 | 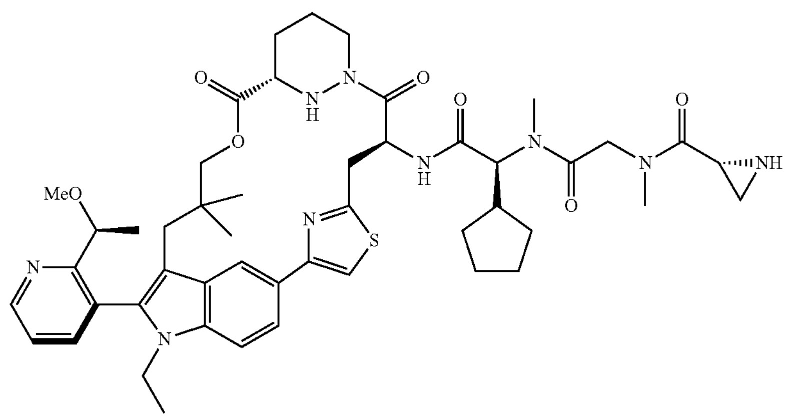 |
| 133 | 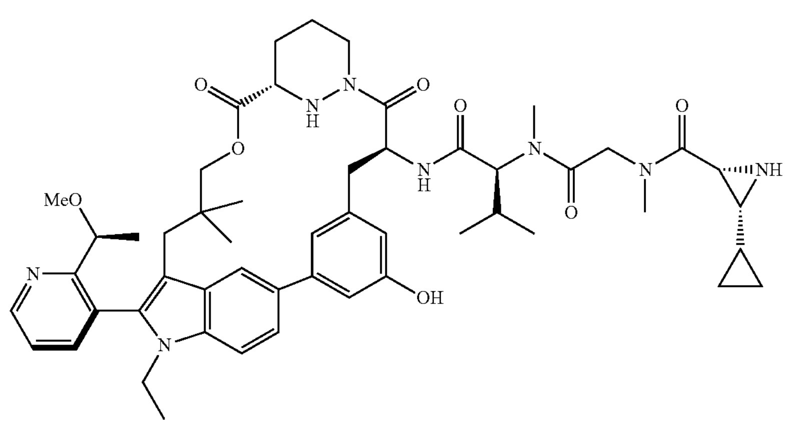 |

TABLE 1-continued

Certain Compounds of the Present Invention

| Ex# | Structure |
|---|---|
| 134 | 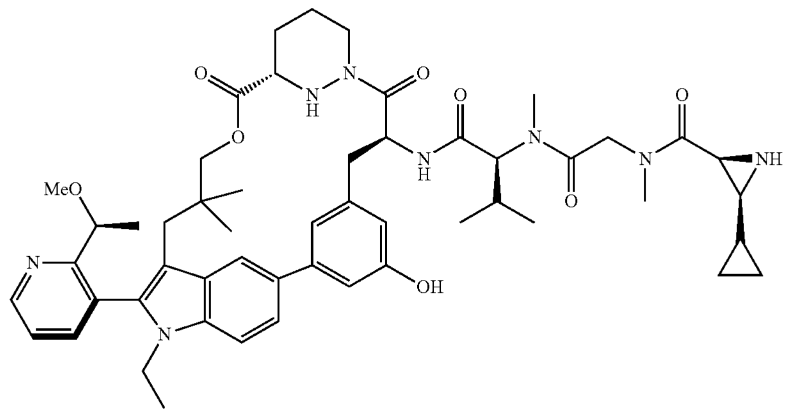 |
| 135 | 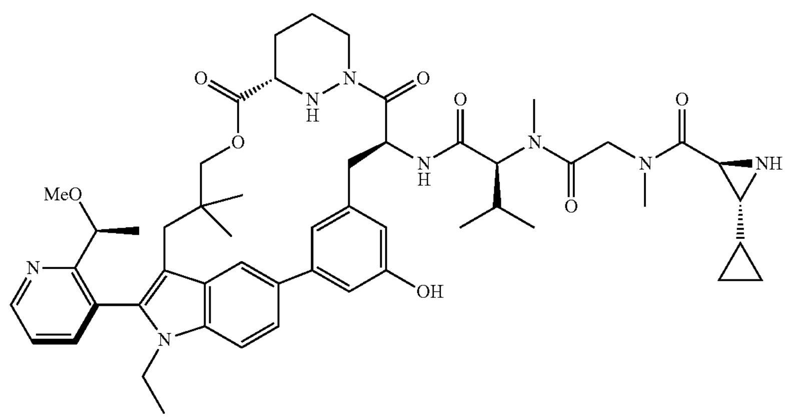 |
| 136 | 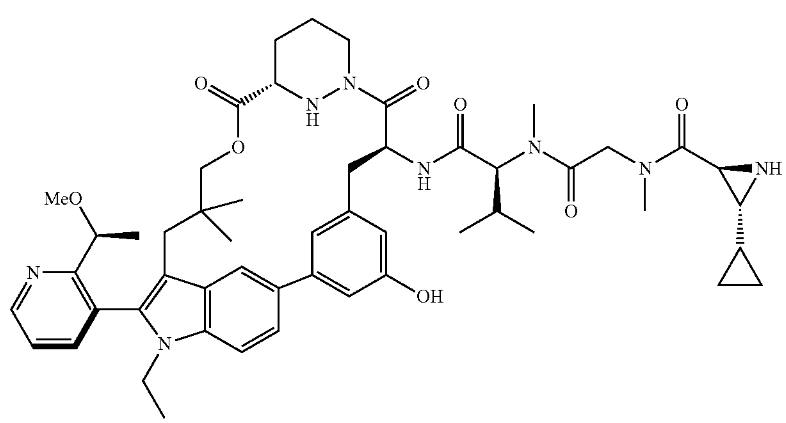 |

TABLE 1-continued

Certain Compounds of the Present Invention

| Ex# | Structure |
|---|---|
| 137 | 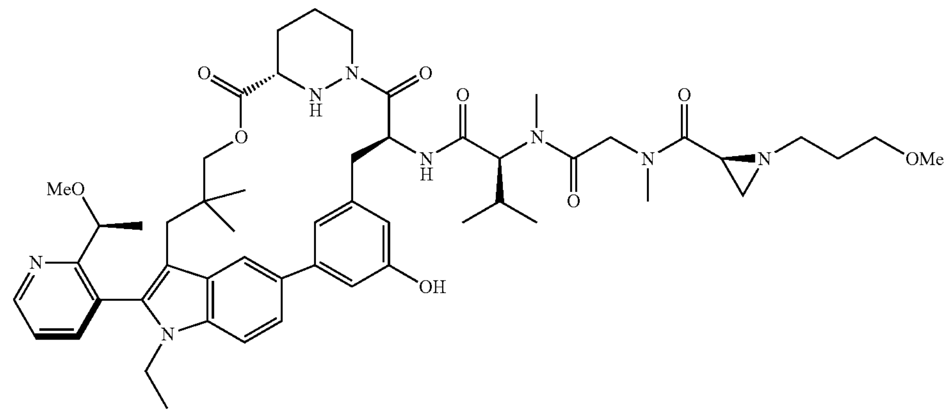 |
| 138 | 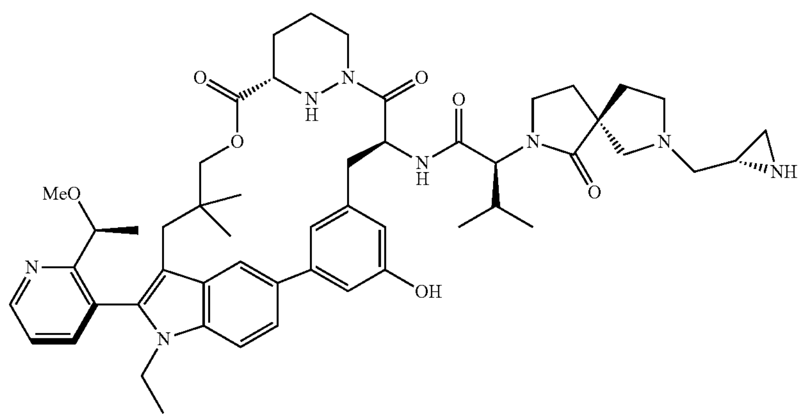 |
| 139 | 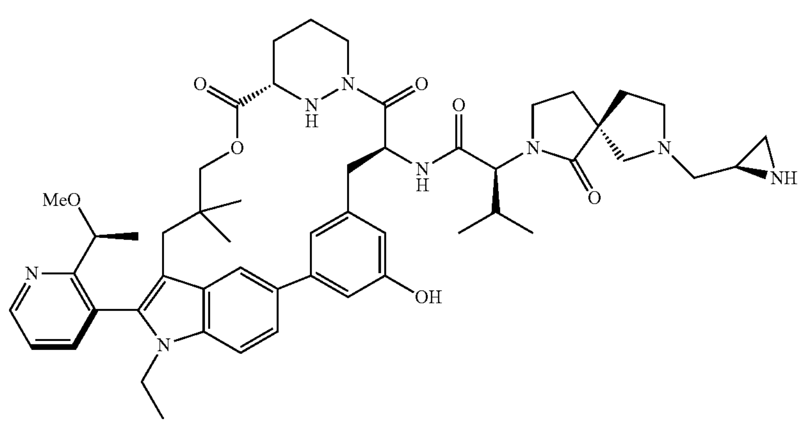 |

TABLE 1-continued

Certain Compounds of the Present Invention

| Ex# | Structure |
|---|---|
| 140 | 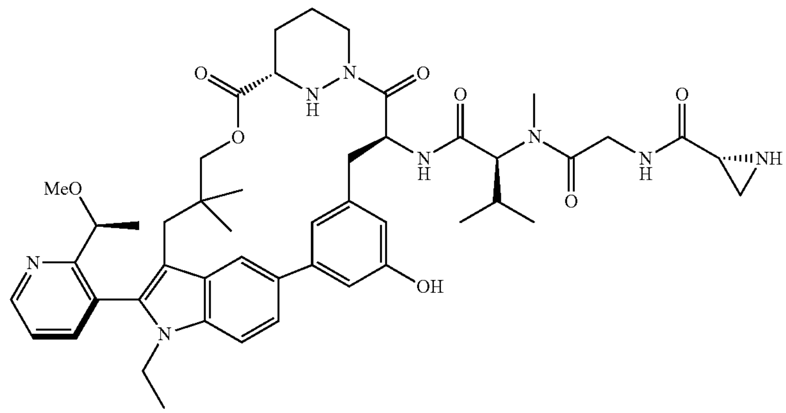 |
| 141 | 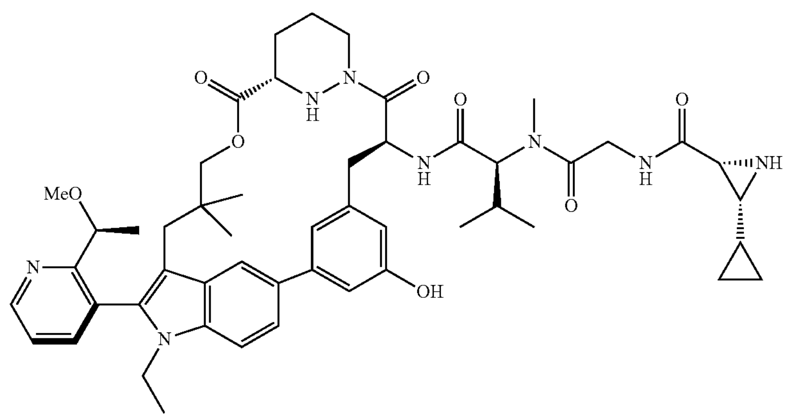 |
| 142 | 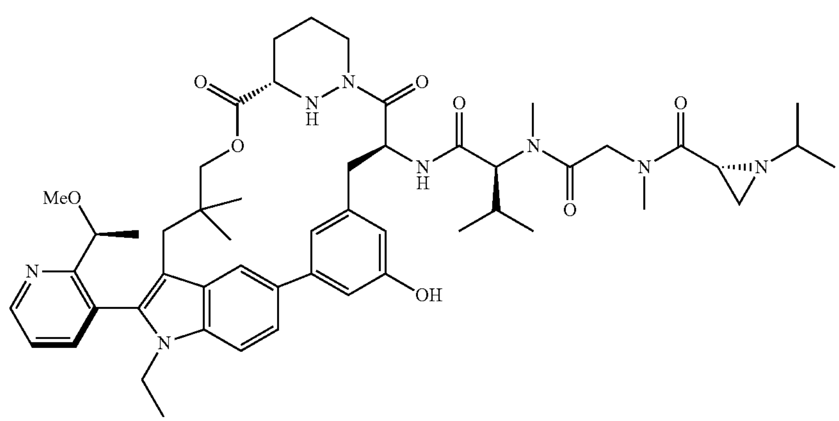 |

TABLE 1-continued

Certain Compounds of the Present Invention

| Ex# | Structure |
|---|---|
| 143 | 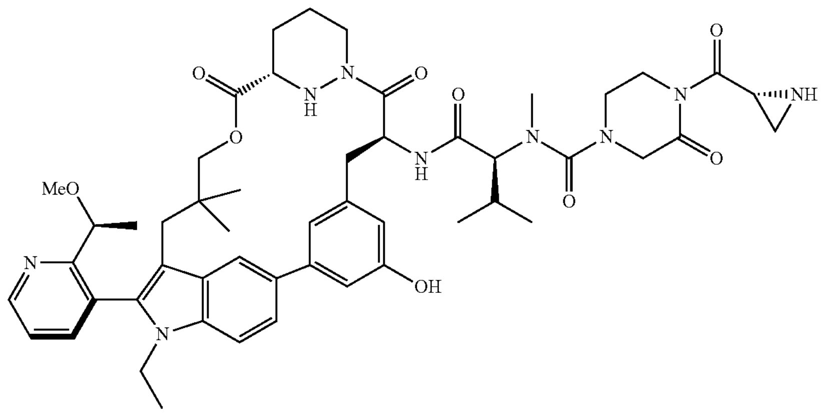 |
| 144 | 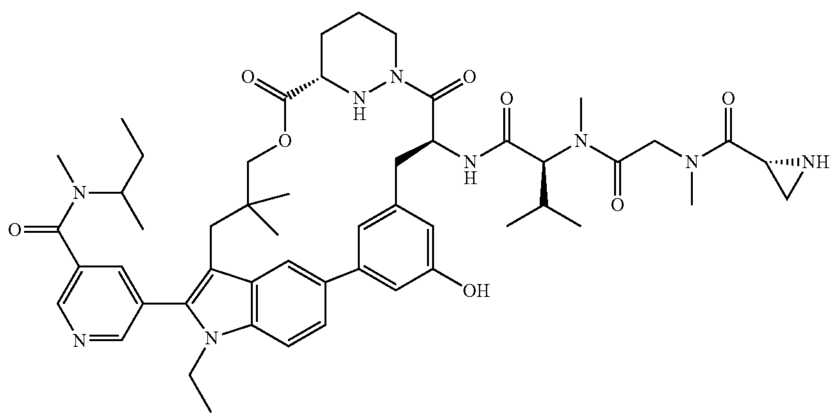 [SMILES: CCC(C)N(C)C(=O)c1cncc(-c2c3c4cc(ccc4n2CC)-c2cc(O)cc(c2)C[C@H](NC(=O)[C@H](C(C)C)N(C)C(=O)CN(C)C(=O)[C@H]2CN2)C(=O)N2CCC[C@H](N2)C(=O)OCC(C)(C)C3)c1] |
| 145 | 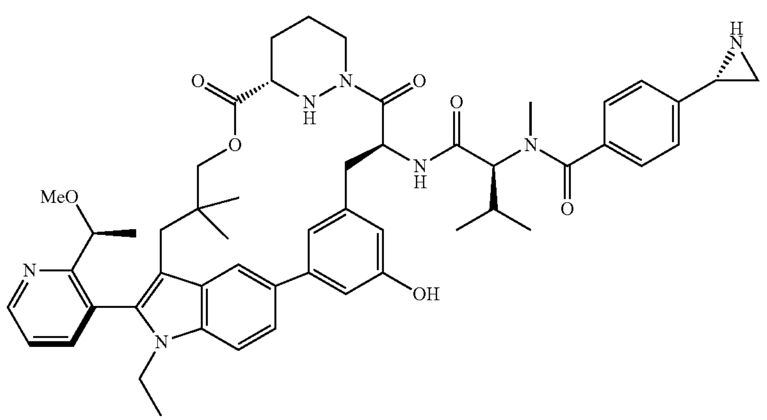 |

TABLE 1-continued

Certain Compounds of the Present Invention

| Ex# | Structure |
|---|---|
| 146 | 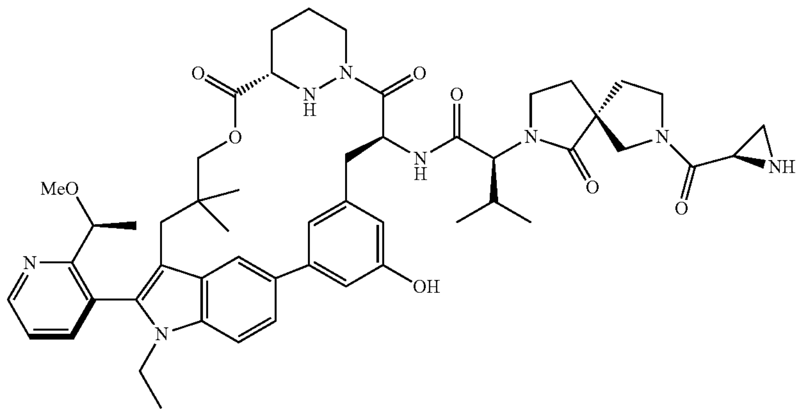 |
| 147 | 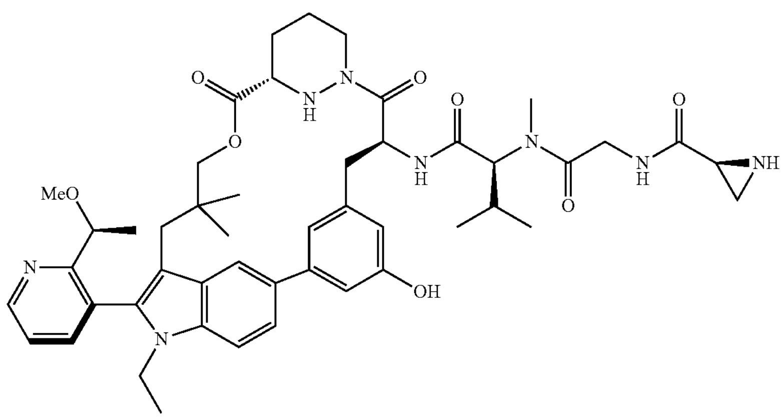 |
| 148 | 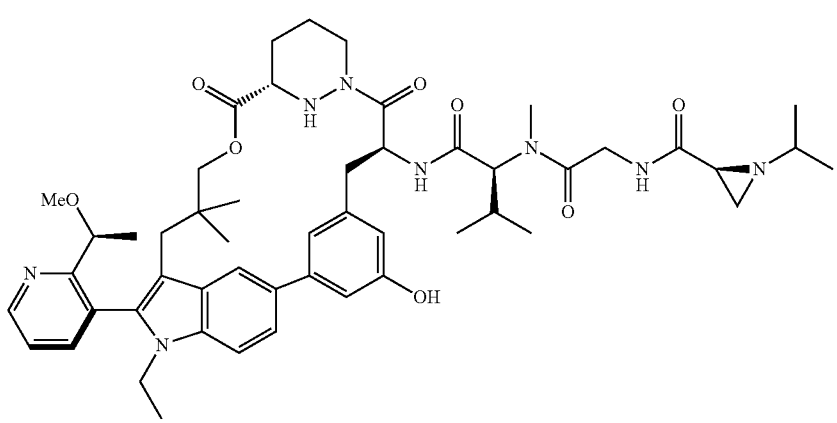 |

TABLE 1-continued

Certain Compounds of the Present Invention

| Ex# | Structure |
|---|---|
| 149 | 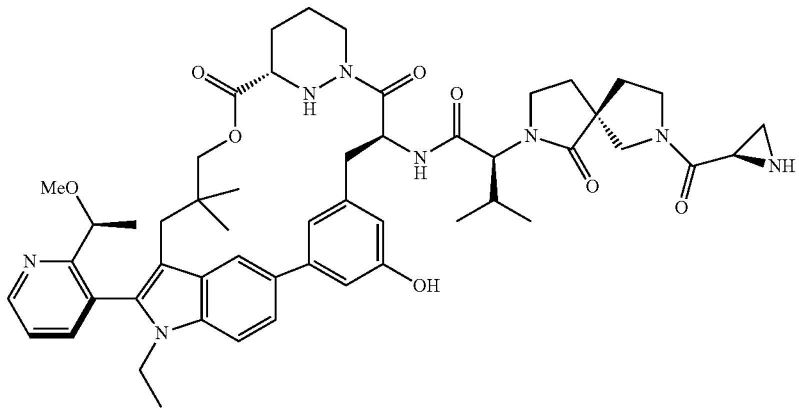 |
| 150 | 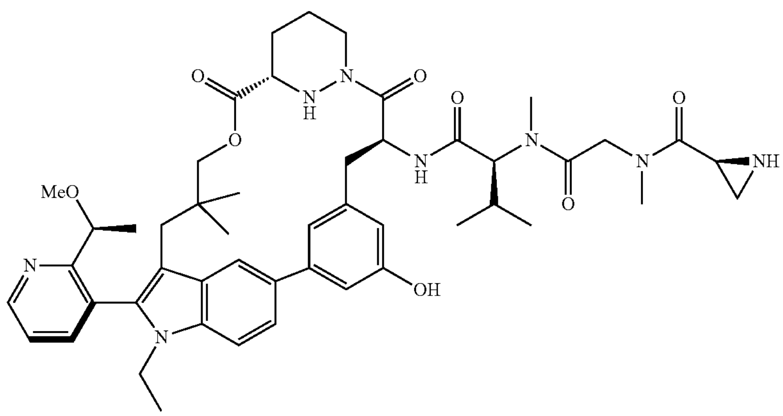 |
| 151 | 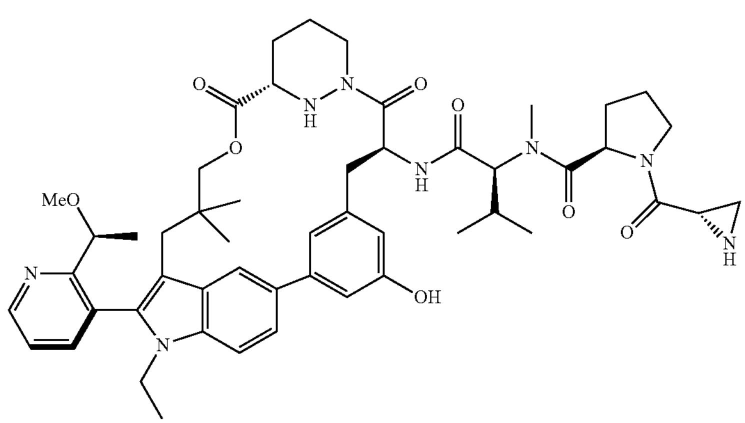 |

TABLE 1-continued

Certain Compounds of the Present Invention

| Ex# | Structure |
|---|---|
| 152 | 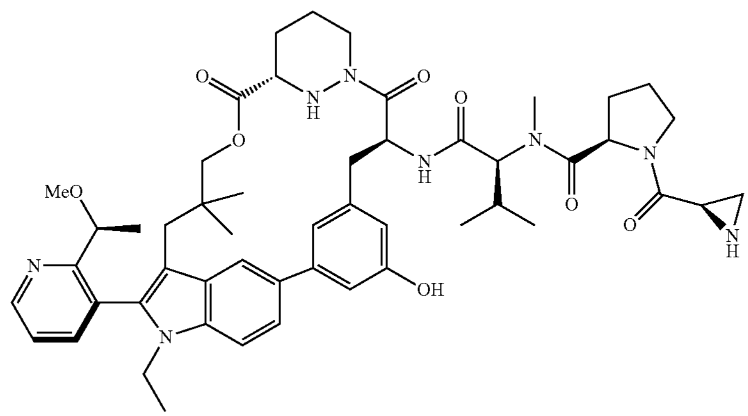 |
| 153 | 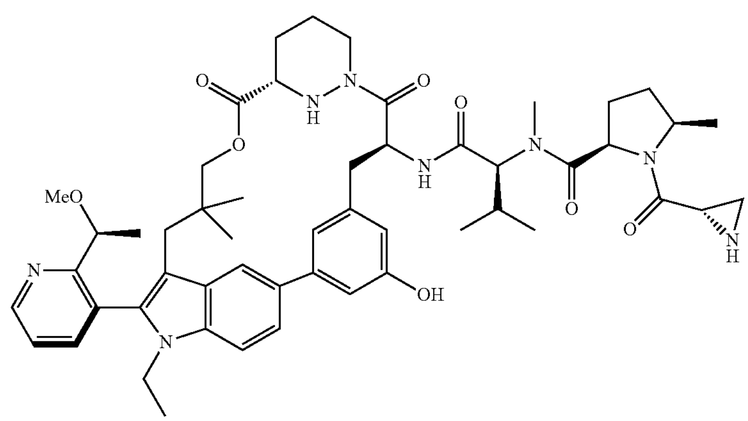 |
| 154 | 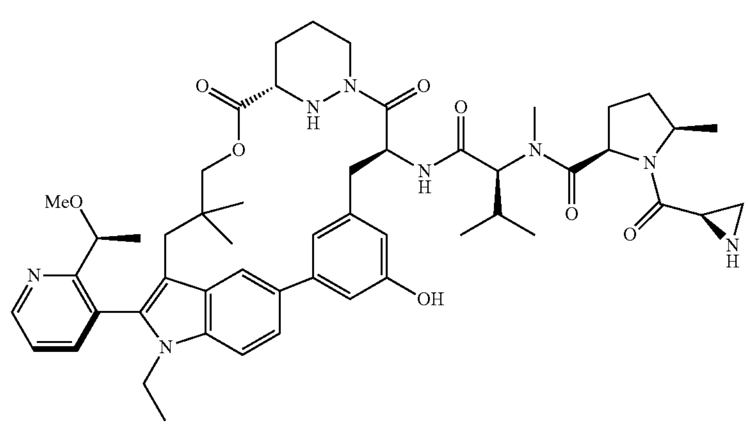 |

TABLE 1-continued

Certain Compounds of the Present Invention

| Ex# | Structure |
|---|---|
| 155 | 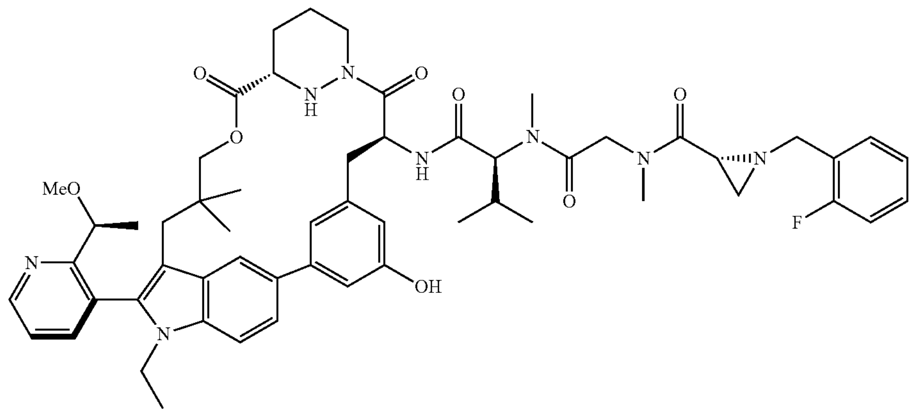 |
| 156 | 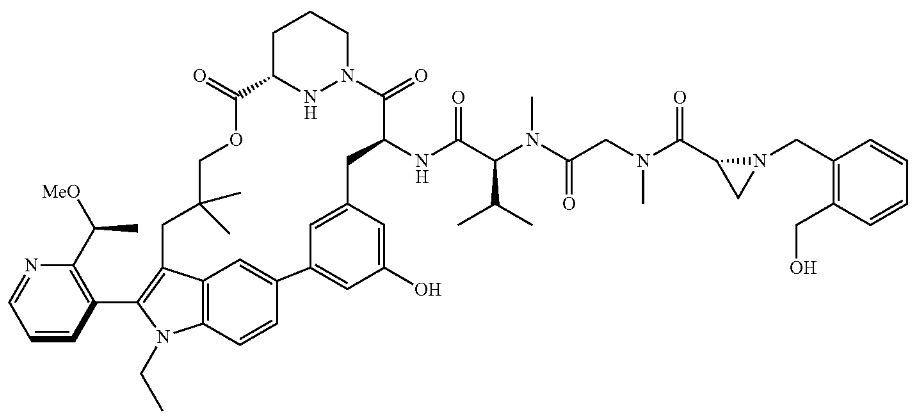 |
| 157 | 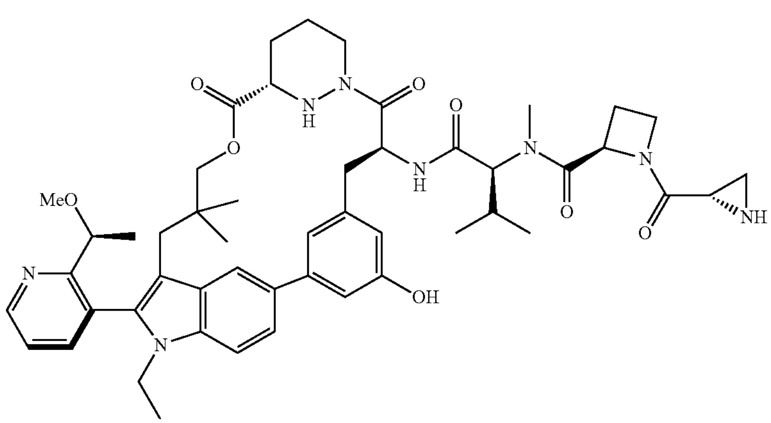 |

TABLE 1-continued

Certain Compounds of the Present Invention

| Ex# | Structure |
|---|---|
| 158 | 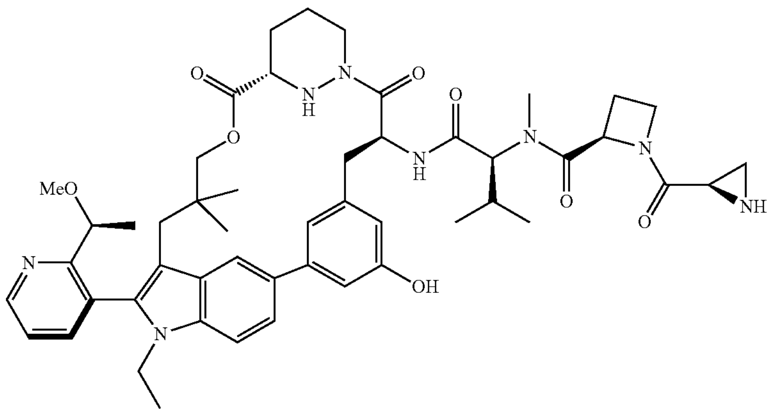 |
| 159 | 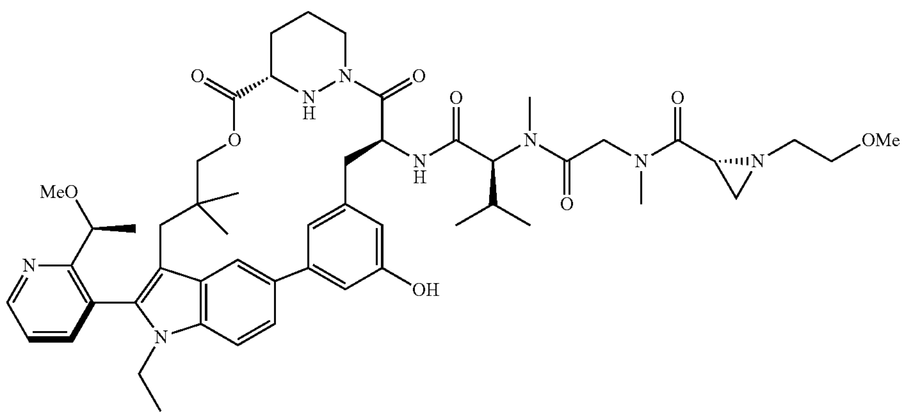 |
| 160 | 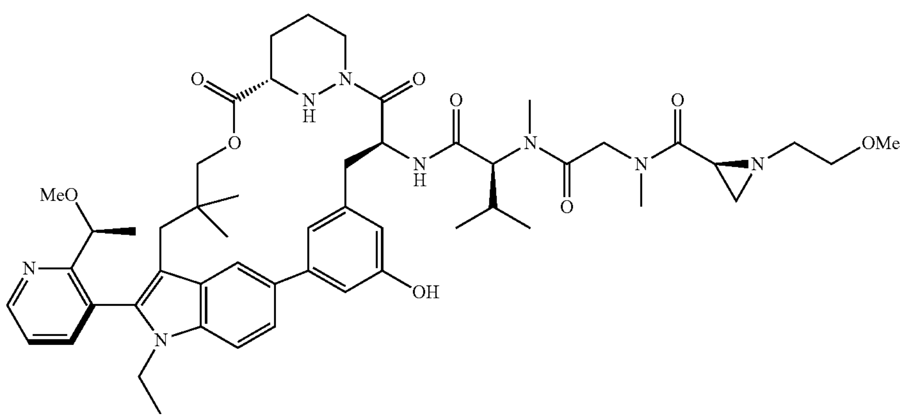 |

TABLE 1-continued

Certain Compounds of the Present Invention

| Ex# | Structure |
|---|---|
| 161 | 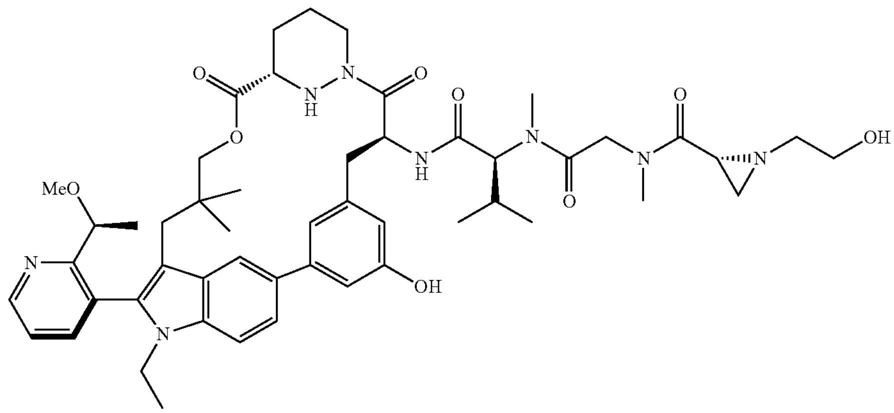 |
| 162 | 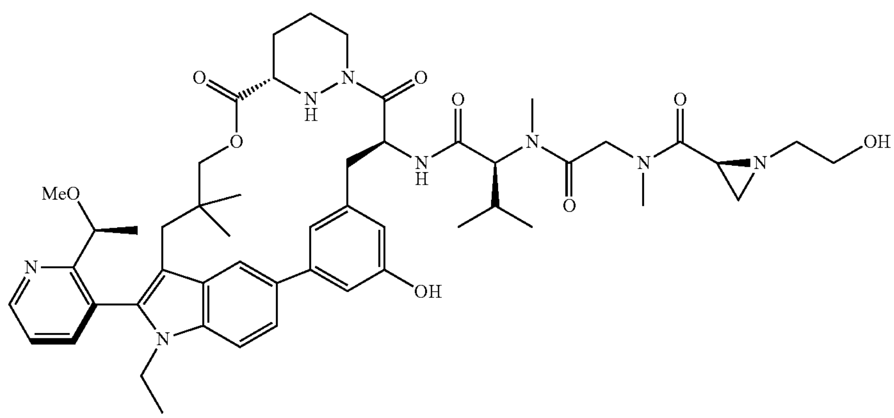 |
| 163 | 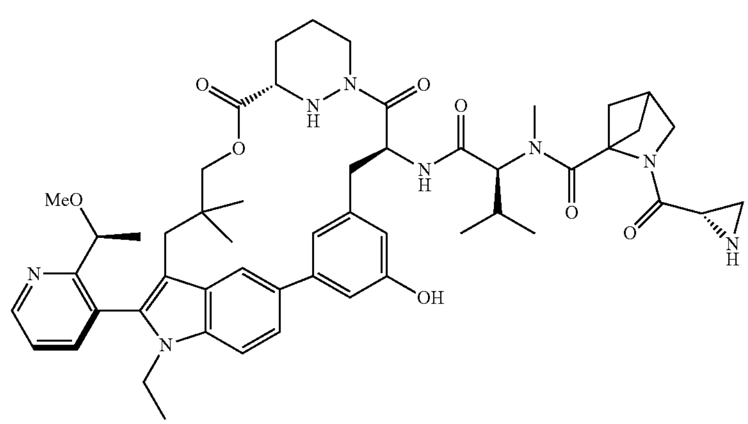 |

TABLE 1-continued
Certain Compounds of the Present Invention
| Ex# | Structure |
|---|---|
| 164 | 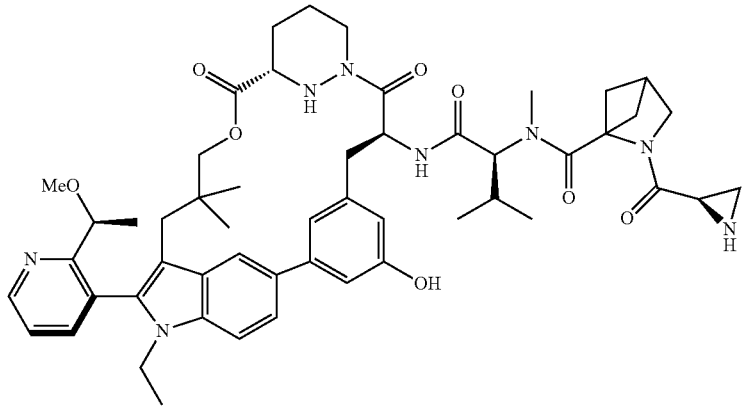 |
| 165 | 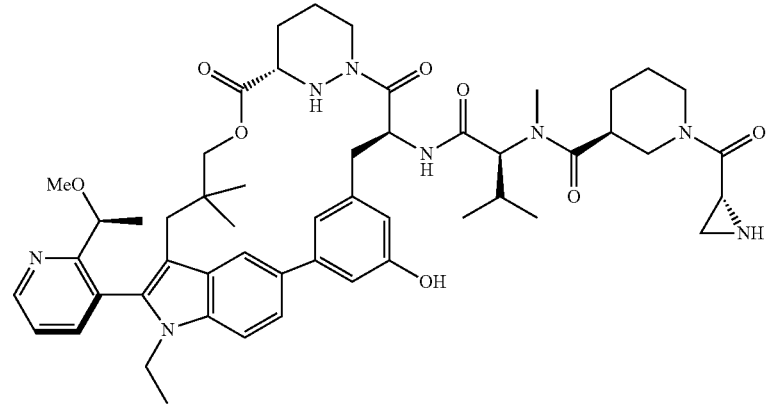 |
| 166 | 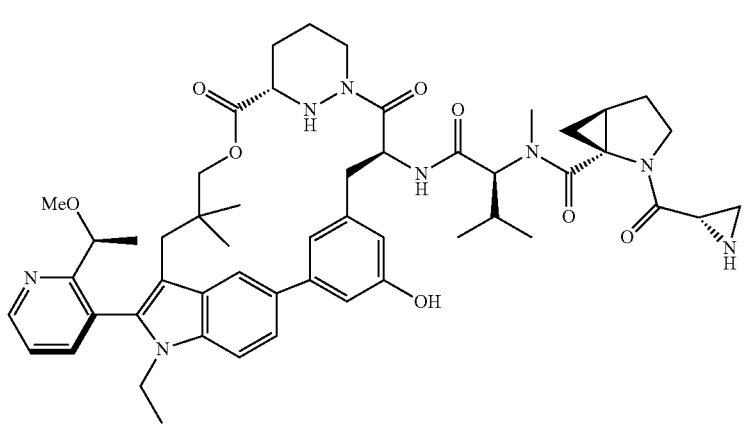 |

TABLE 1-continued

Certain Compounds of the Present Invention

| Ex# | Structure |
|---|---|
| 167 | 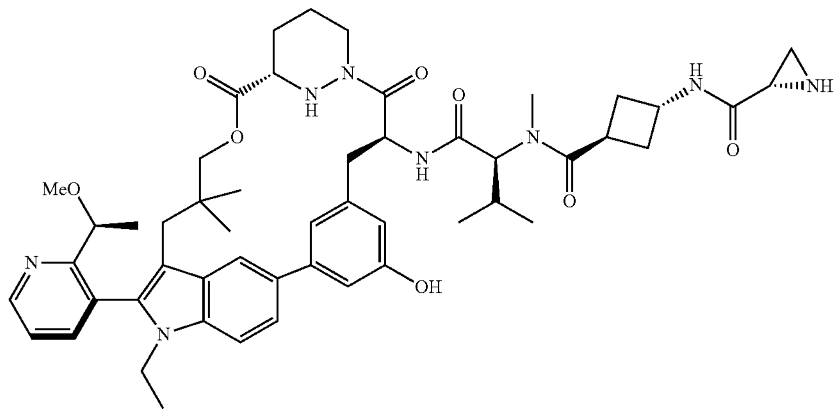 |
| 168 | 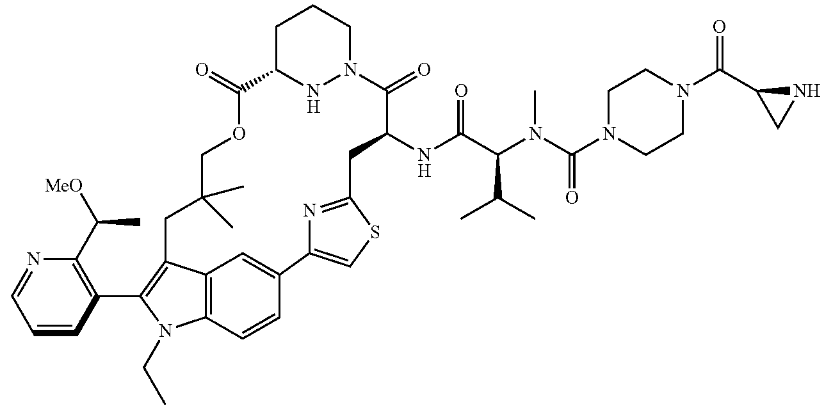 |
| 169 | 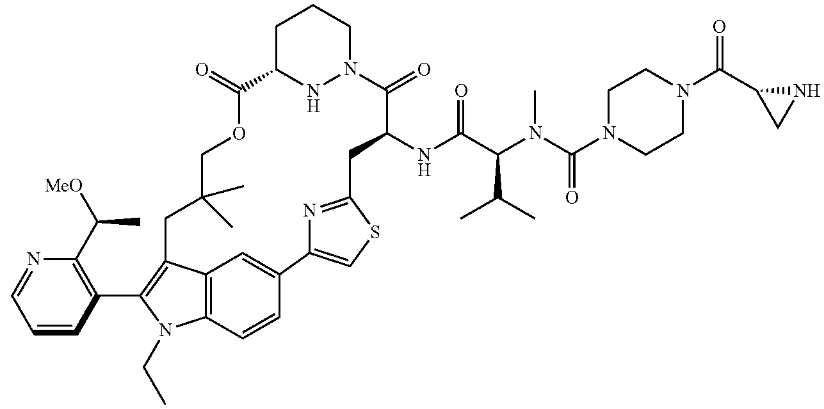 |

TABLE 1-continued

Certain Compounds of the Present Invention

| Ex# | Structure |
|---|---|
| 170 | 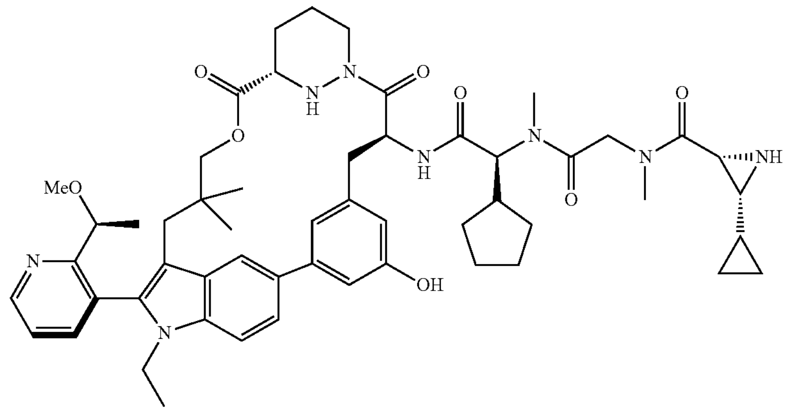 |
| 171 | 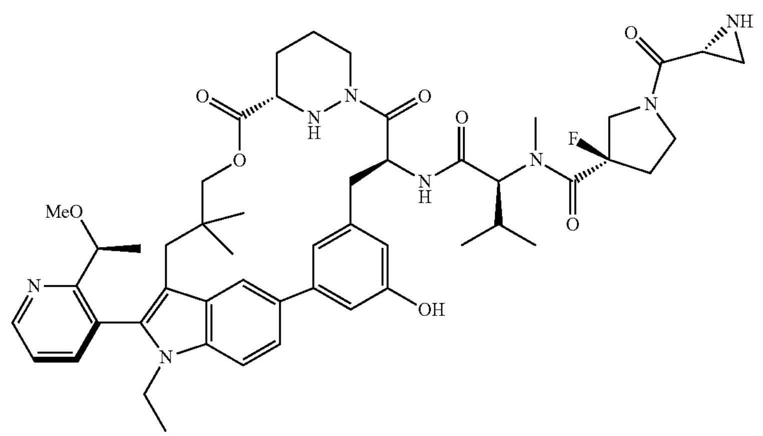 |
| 172 | 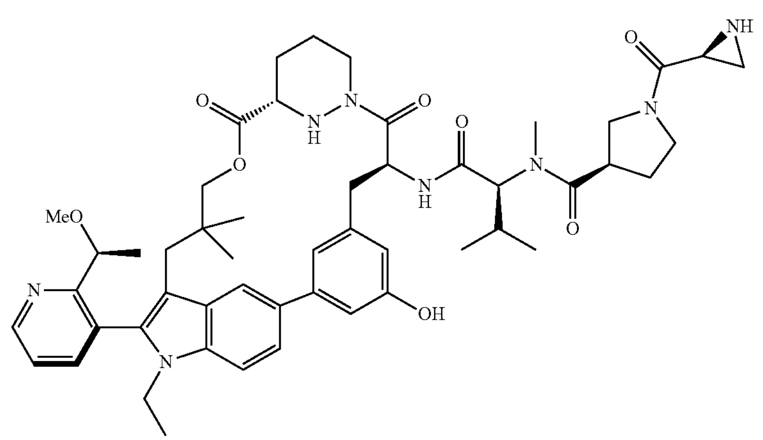 |

TABLE 1-continued
Certain Compounds of the Present Invention
| Ex# | Structure |
|---|---|
| 173 | 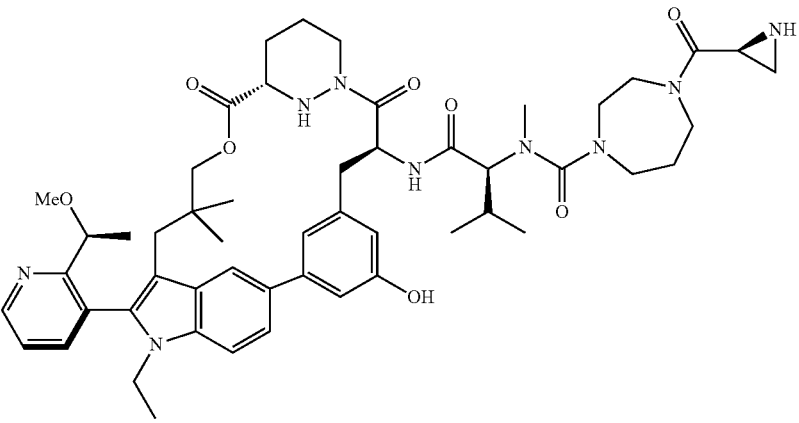 |
| 174 | 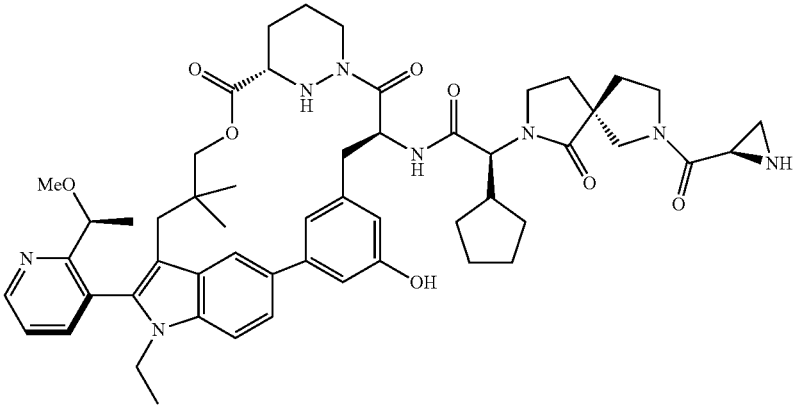 |
| 175 | 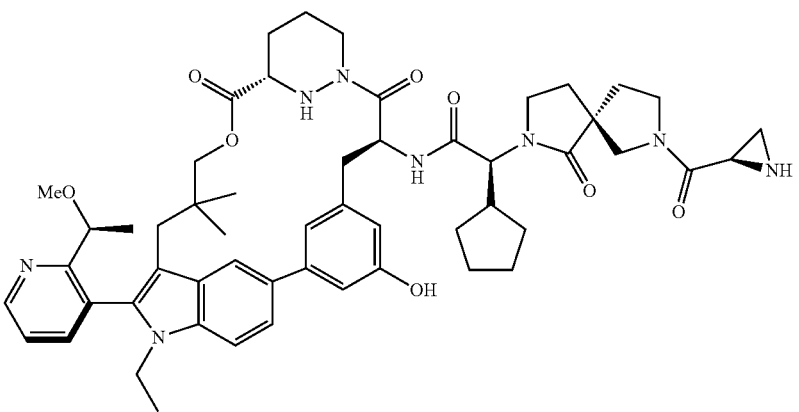 |

TABLE 1-continued

Certain Compounds of the Present Invention

| Ex# | Structure |
|---|---|
| 176 | 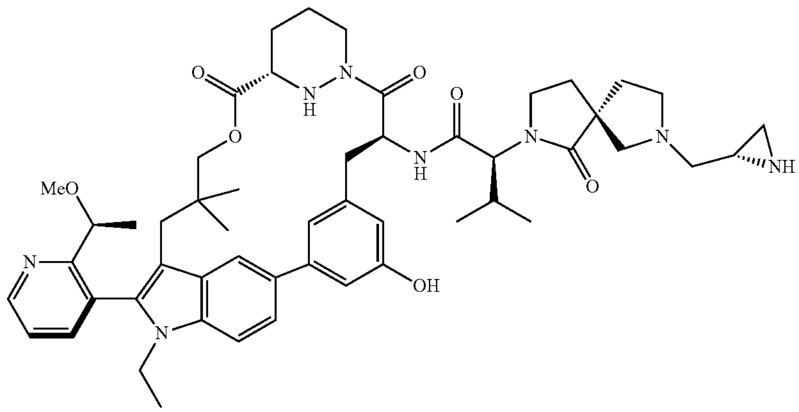 |
| 177 | 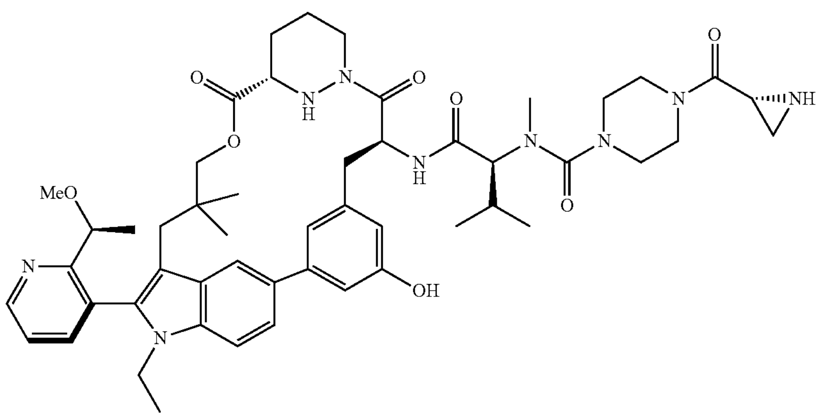 |
| 178 | 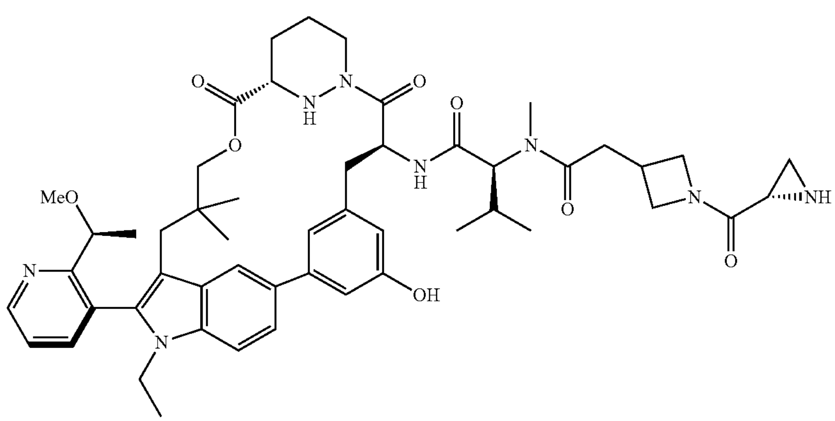 |

TABLE 1-continued

Certain Compounds of the Present Invention

| Ex# | Structure |
|---|---|
| 179 | 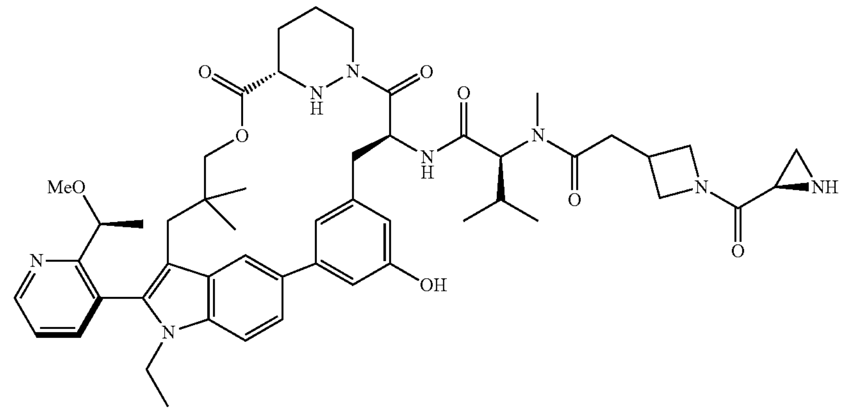 |
| 180 | 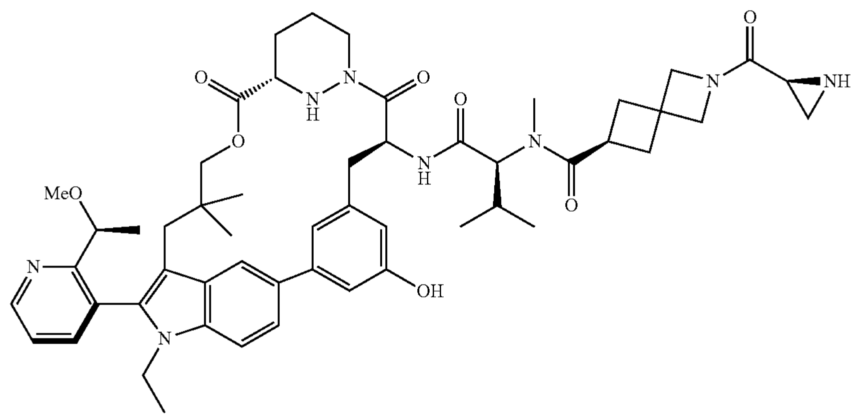 |
| 181 | 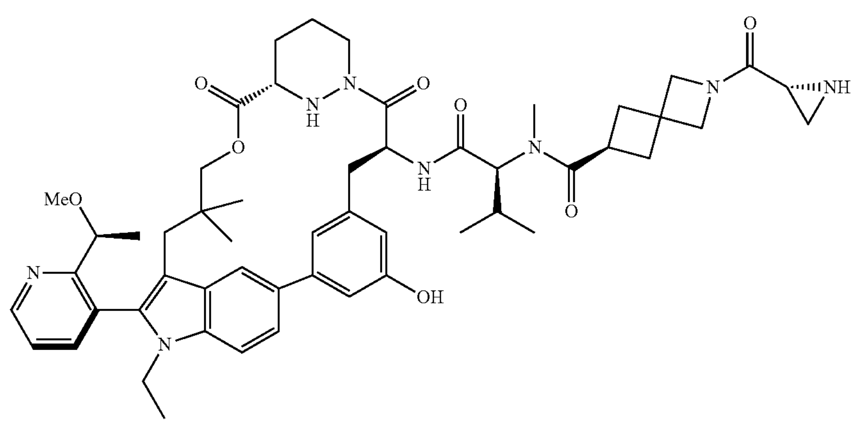 |

TABLE 1-continued
Certain Compounds of the Present Invention
| Ex# | Structure |
|---|---|
| 182 | 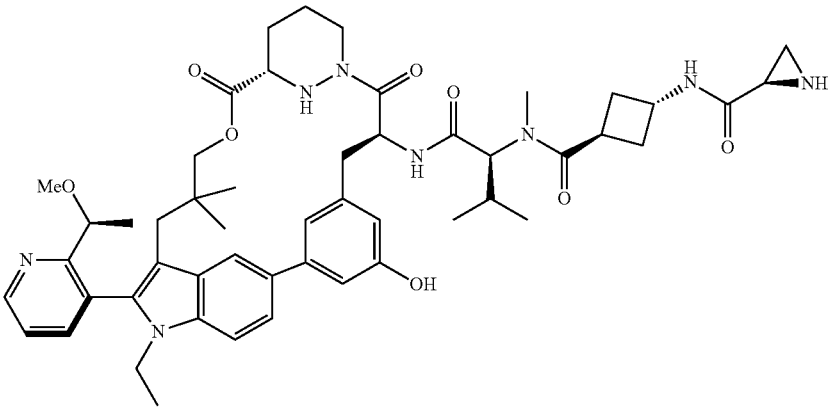 |
| 183 | 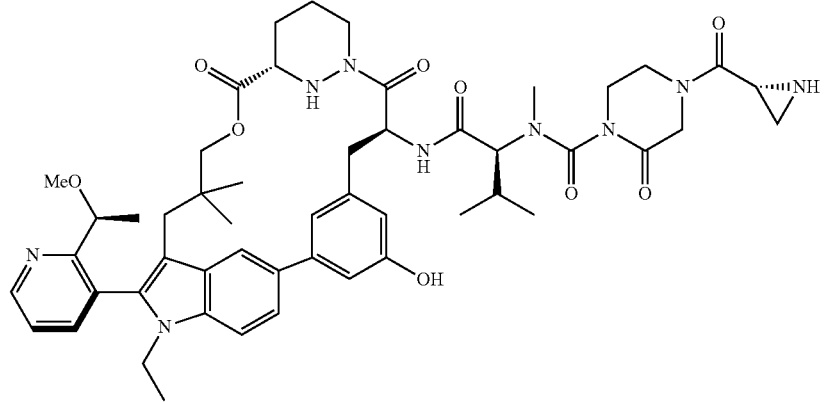 |
| 184 | 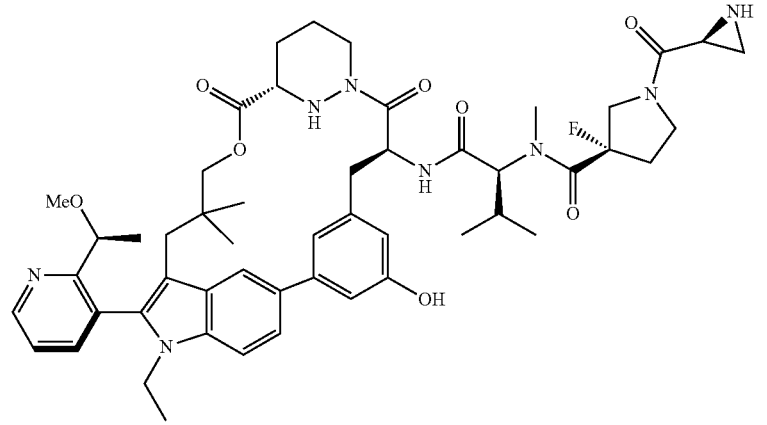 |

TABLE 1-continued

Certain Compounds of the Present Invention

| Ex# | Structure |
|---|---|
| 185 | 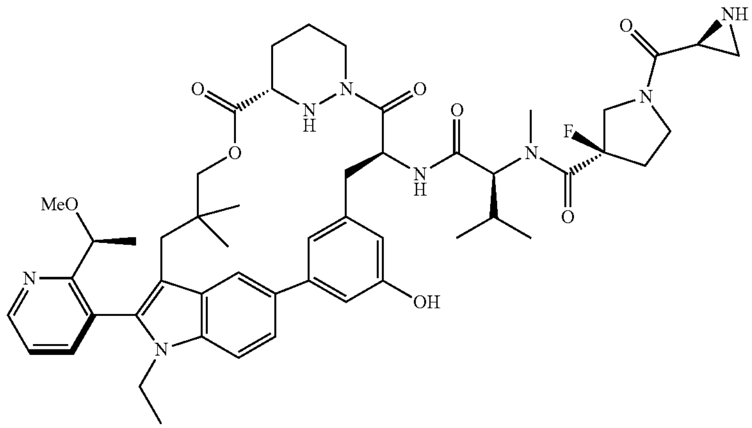 |
| 186 | 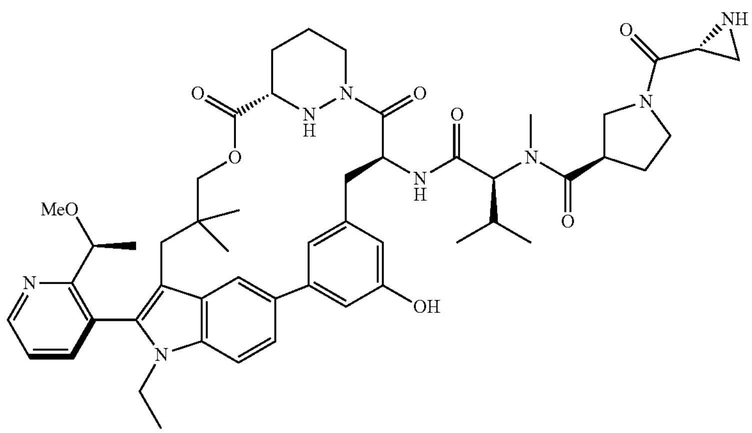 |
| 187 | 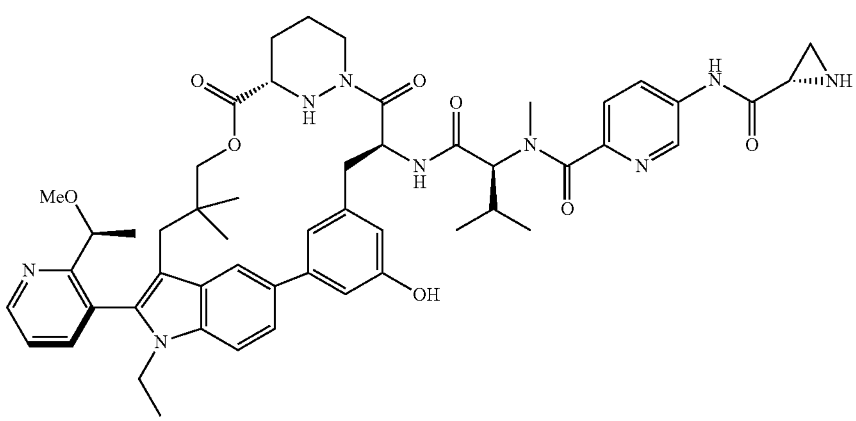 |

TABLE 1-continued

Certain Compounds of the Present Invention

| Ex# | Structure |
|-----|-----------|
| 188 | 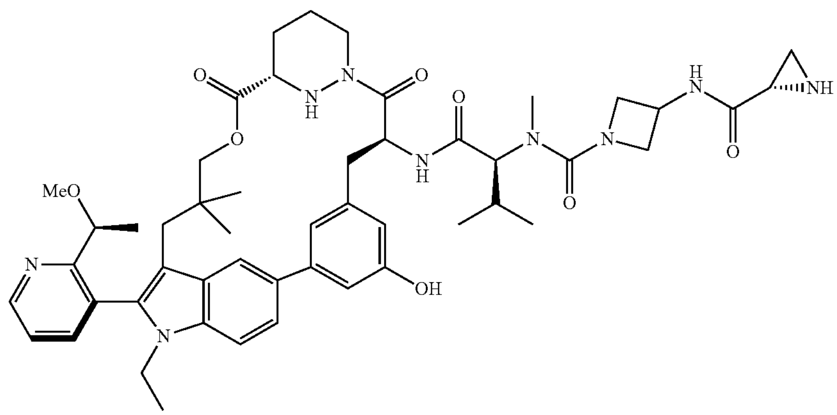 |
| 189 | 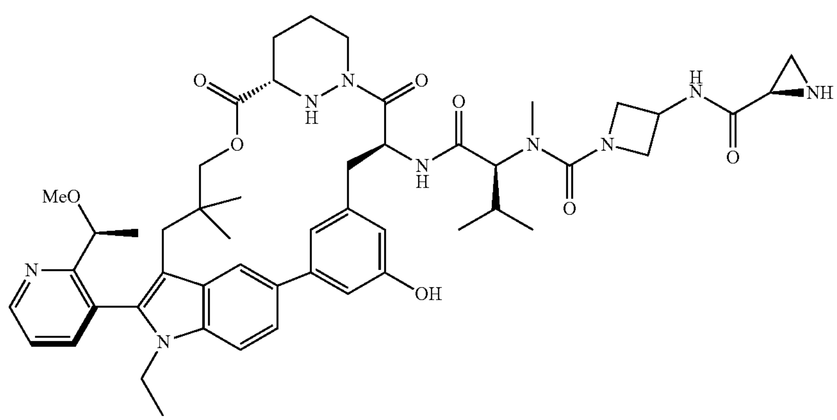 |
| 190 | 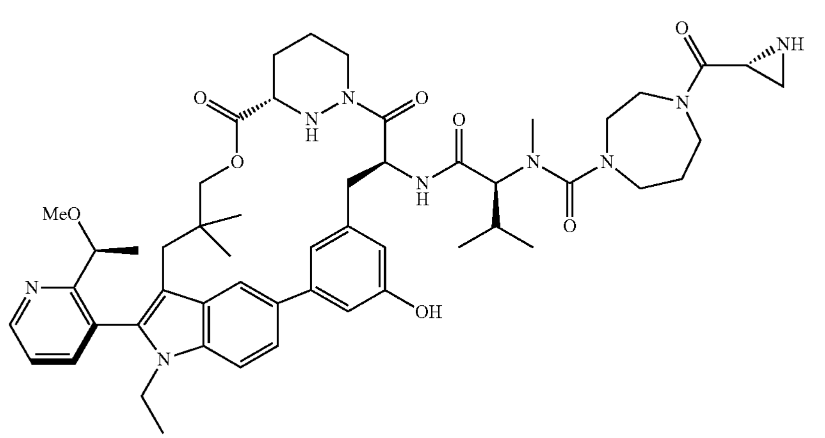 |

TABLE 1-continued
Certain Compounds of the Present Invention
| Ex# | Structure |
|---|---|
| 191 | 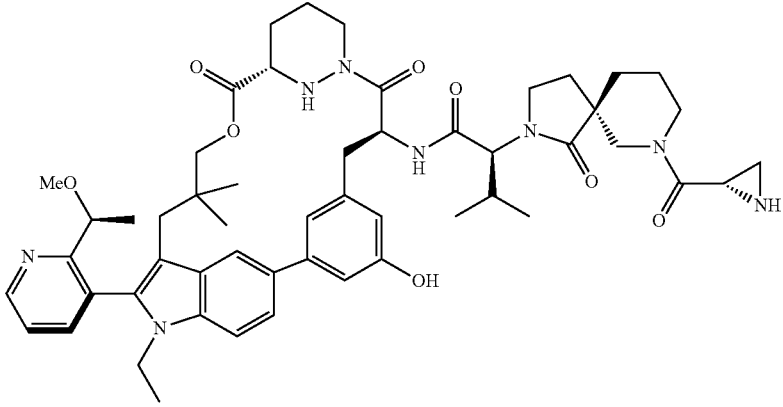 |
| 192 | 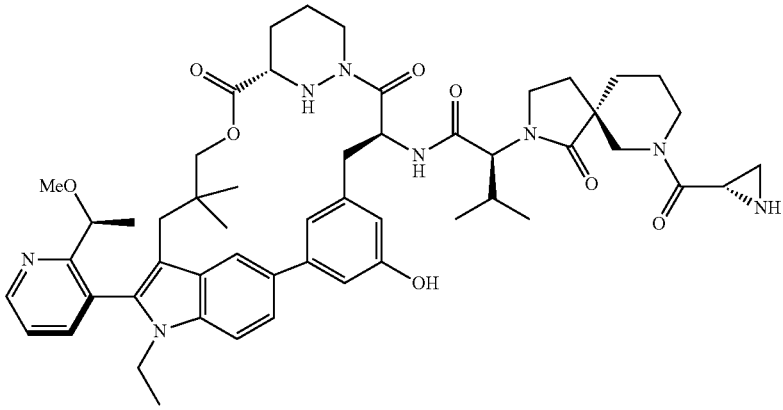 |
| 193 | 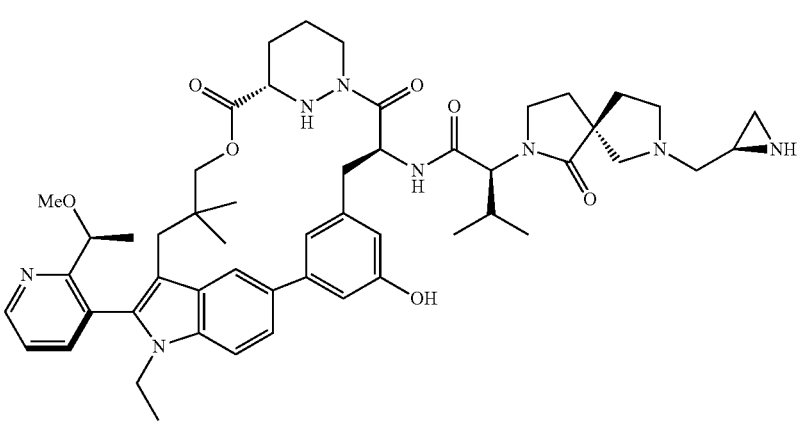 |

TABLE 1-continued
Certain Compounds of the Present Invention
| Ex# | Structure |
|---|---|
| 194 | 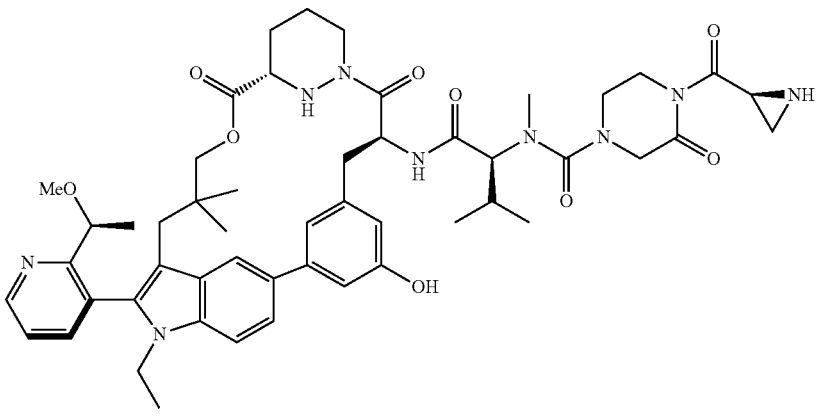 |
| 195 | 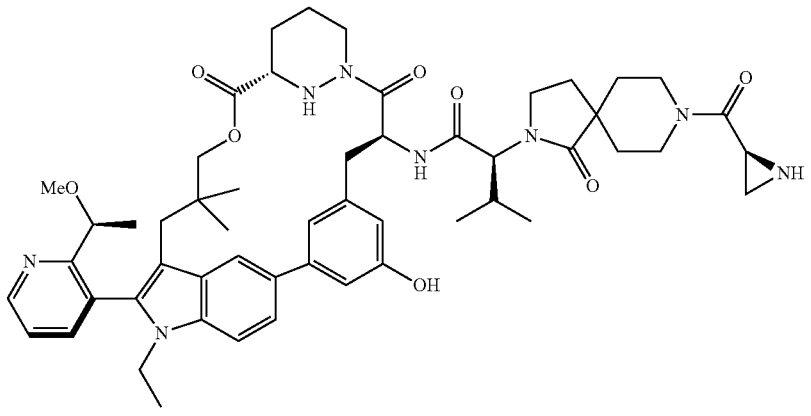 |
| 196 | 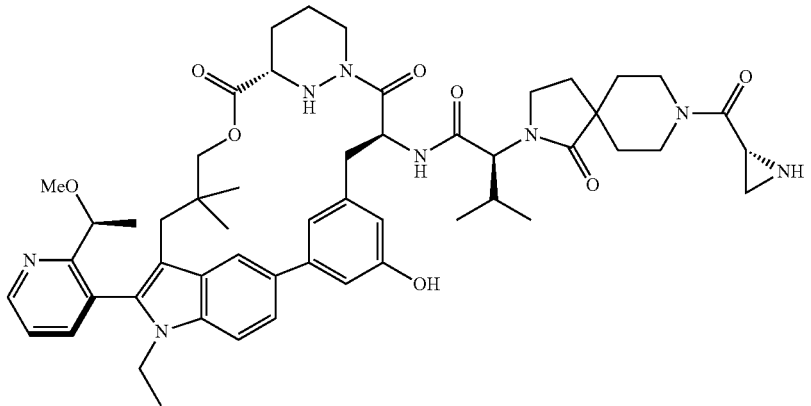 |

TABLE 1-continued
Certain Compounds of the Present Invention
| Ex# | Structure |
|---|---|
| 197 | 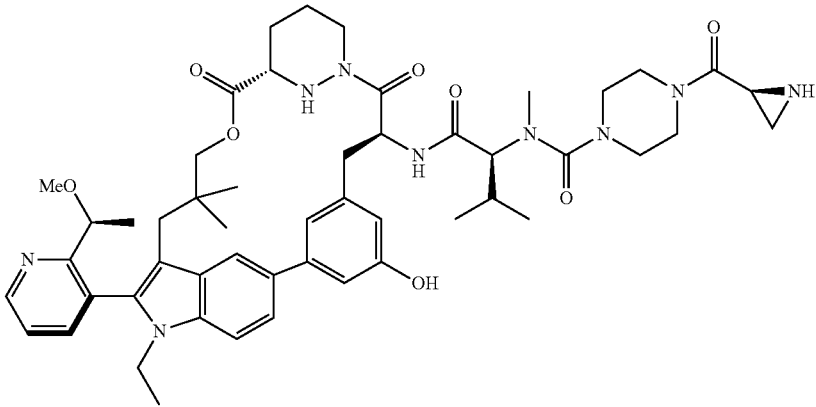 |
| 198 | 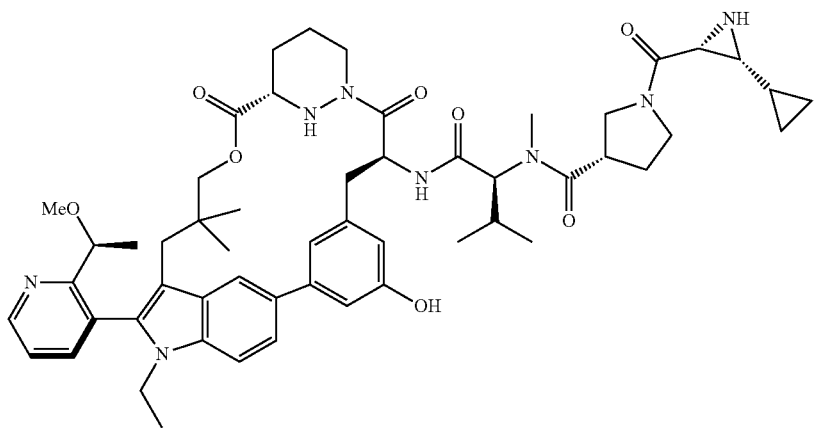 |
| 199 | 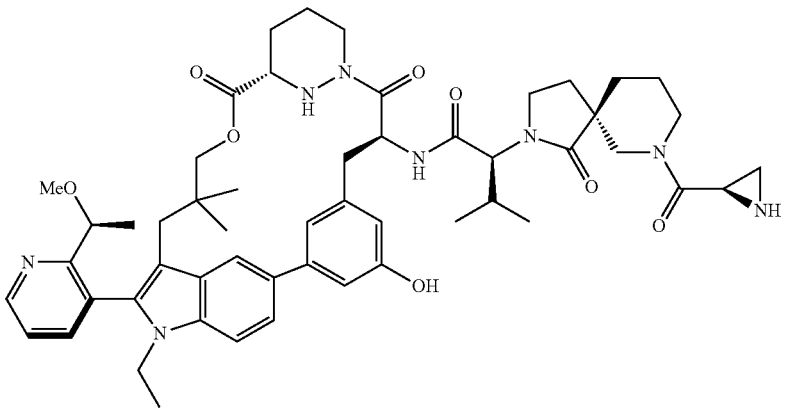 |

TABLE 1-continued

Certain Compounds of the Present Invention

| Ex# | Structure |
|---|---|
| 200 | 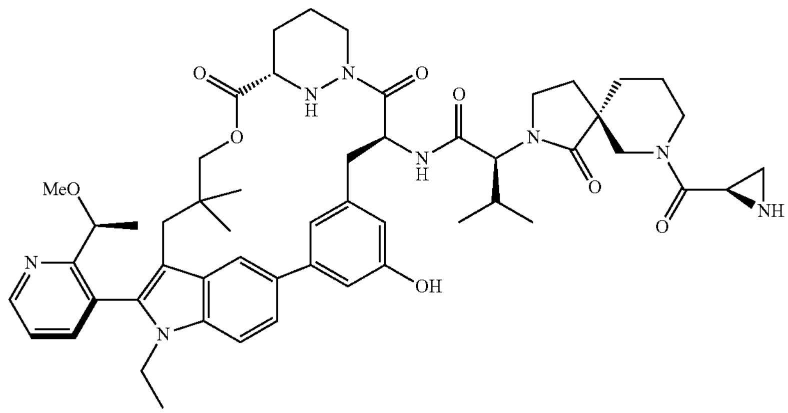 |
| 201 | 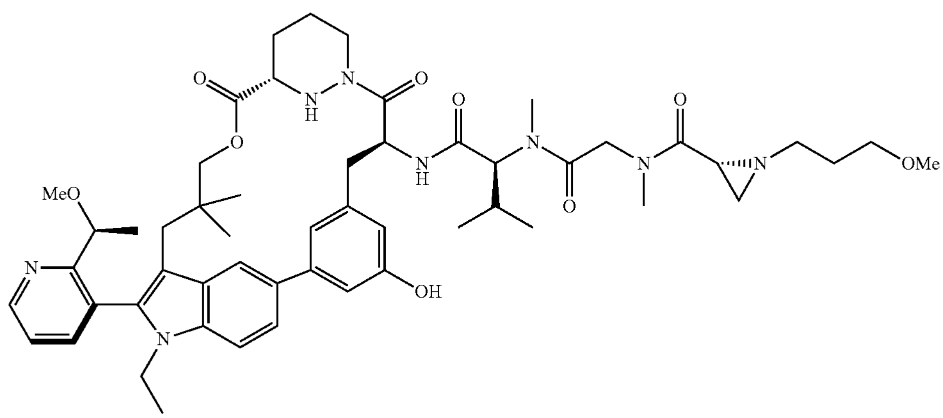 |
| 202 | 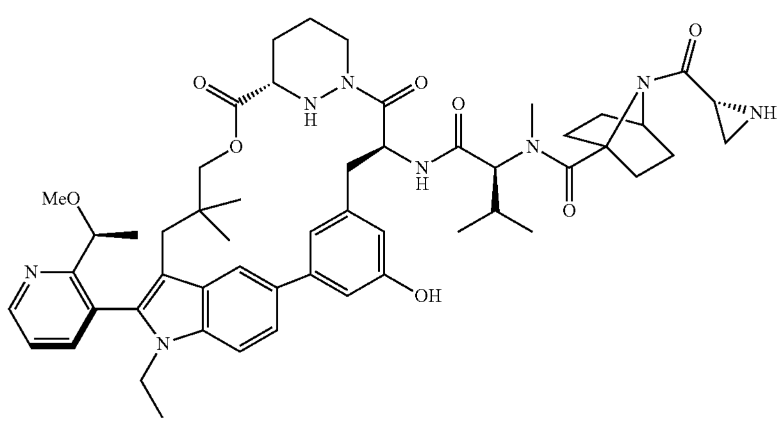 |

TABLE 1-continued

Certain Compounds of the Present Invention

| Ex# | Structure |
|---|---|
| 203 | 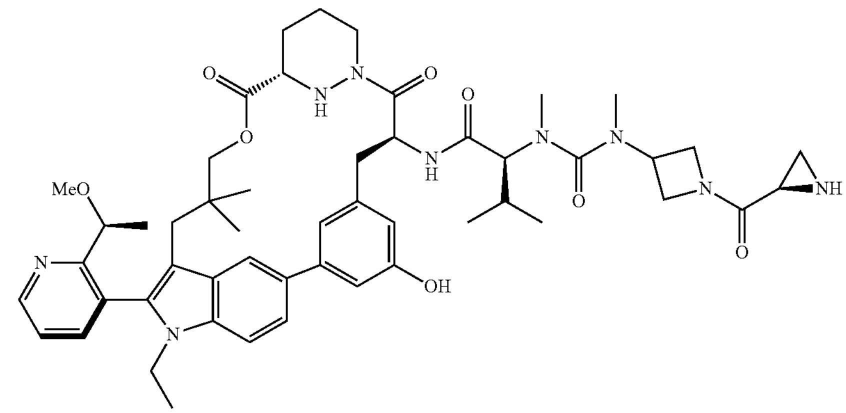 |
| 204 | 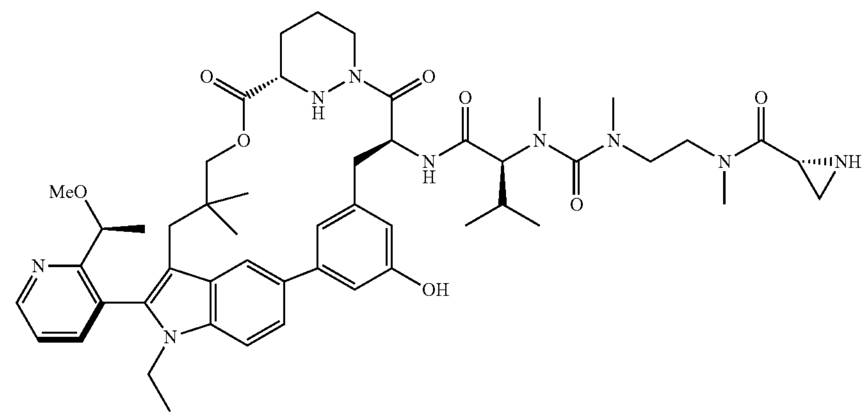 |
| 205 | 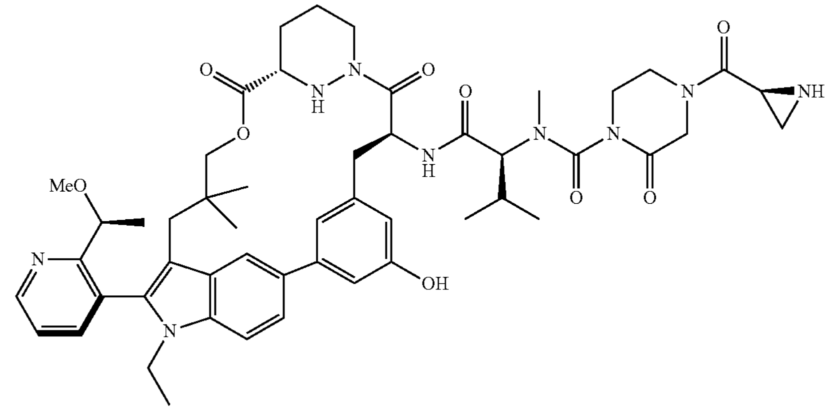 |

TABLE 1-continued

Certain Compounds of the Present Invention

| Ex# | Structure |
|---|---|
| 206 | 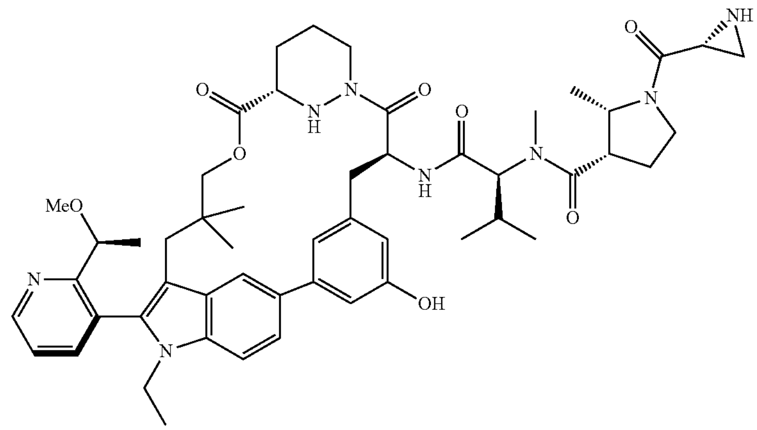 |
| 207 | 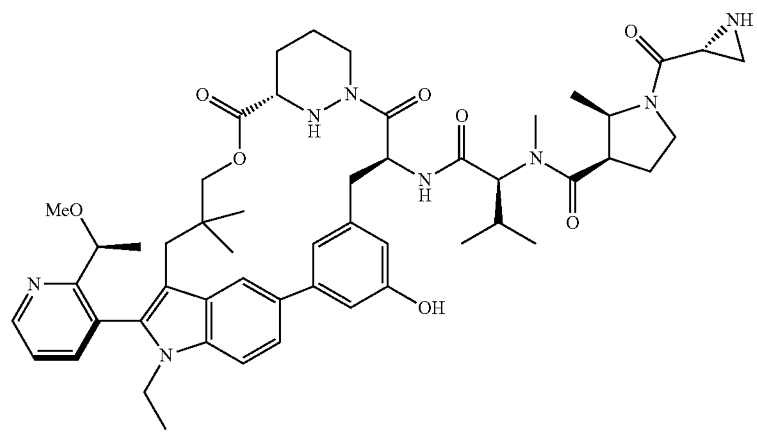 |
| 208 | 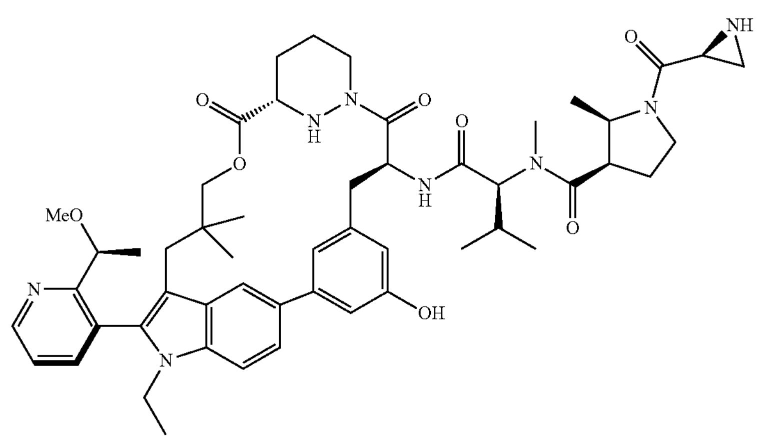 |

TABLE 1-continued

Certain Compounds of the Present Invention

| Ex# | Structure |
|---|---|
| 209 | 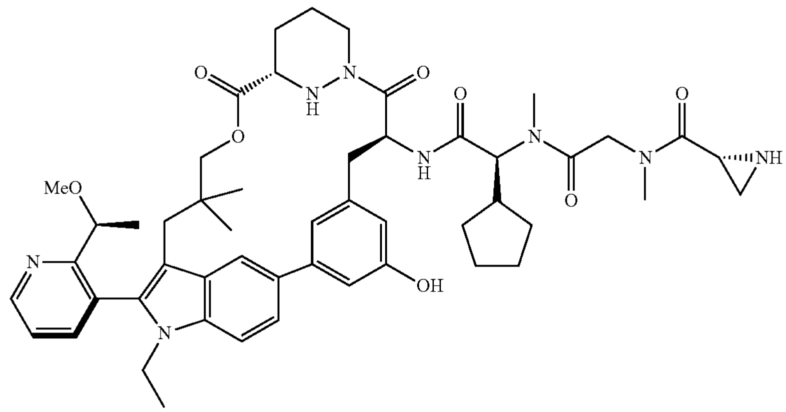 |
| 210 | 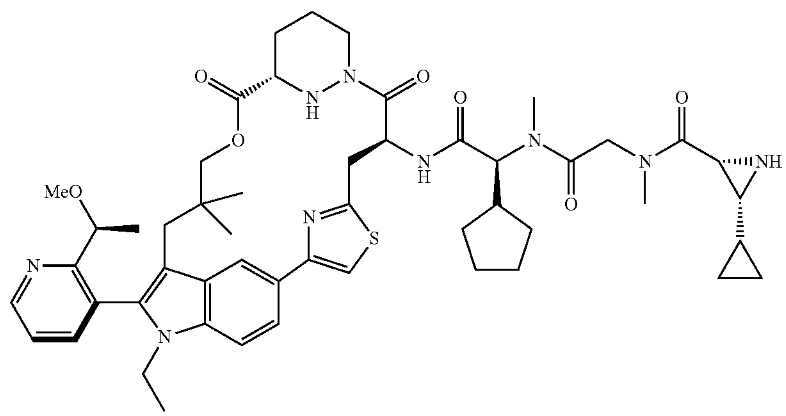 |
| 211 | 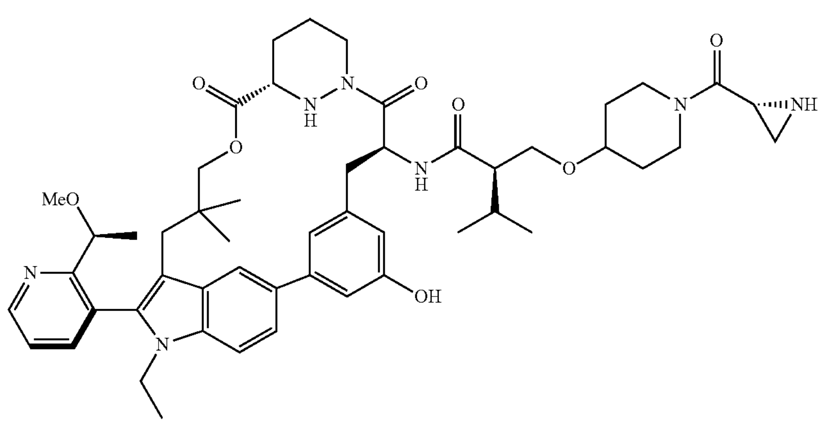 |

TABLE 1-continued
Certain Compounds of the Present Invention
| Ex# | Structure |
|---|---|
| 212 | 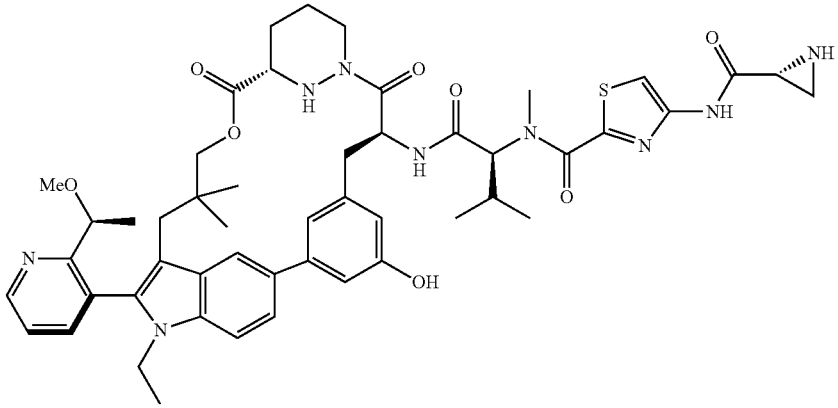 |
| 213 | 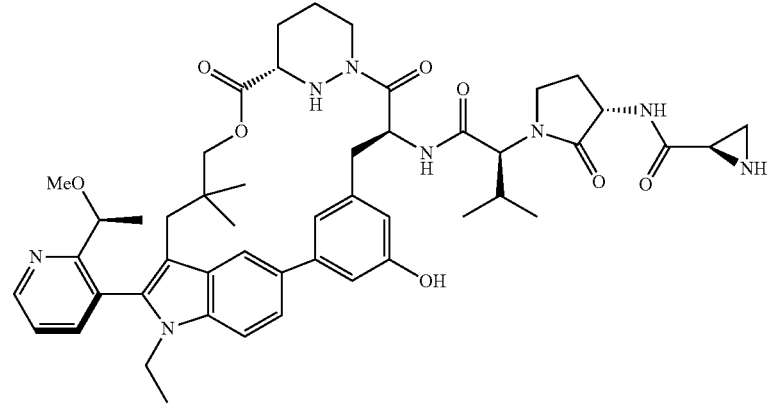 |
| 214 | 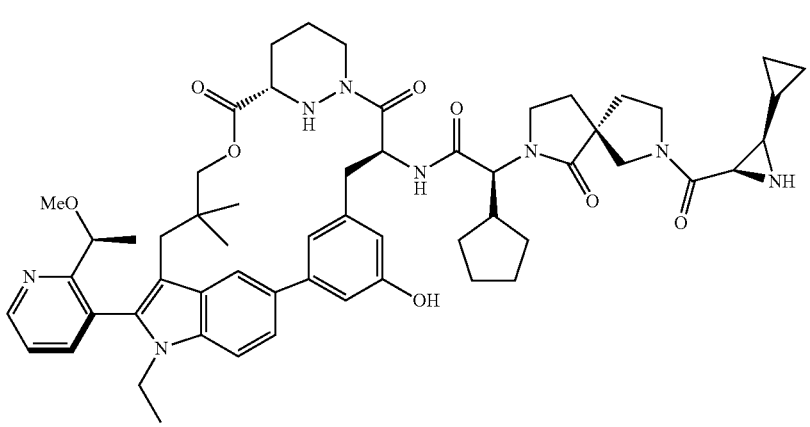 |

US 11,739,074 B2
197                                                                    198
TABLE 1-continued
Certain Compounds of the Present Invention
| Ex# | Structure |
|---|---|
| 215 | 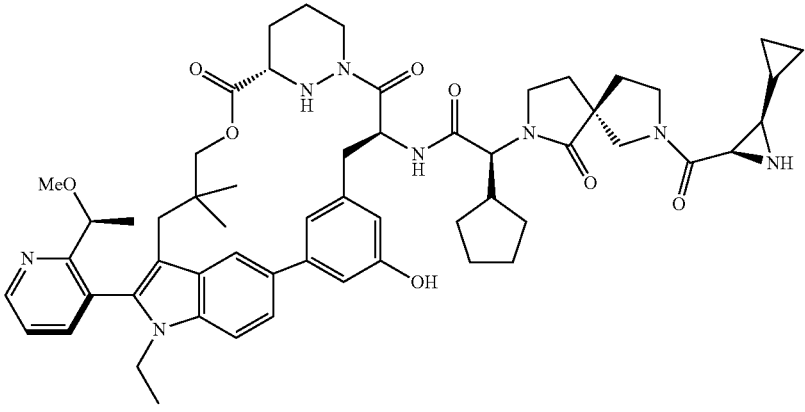 |
| 216 | 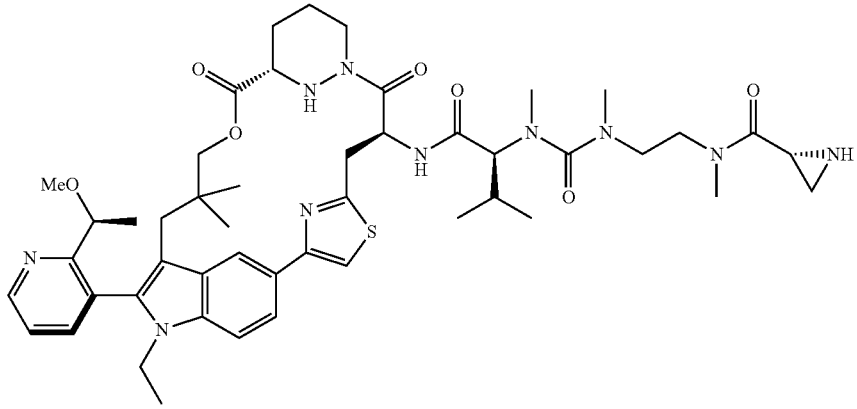 |
| 217 | 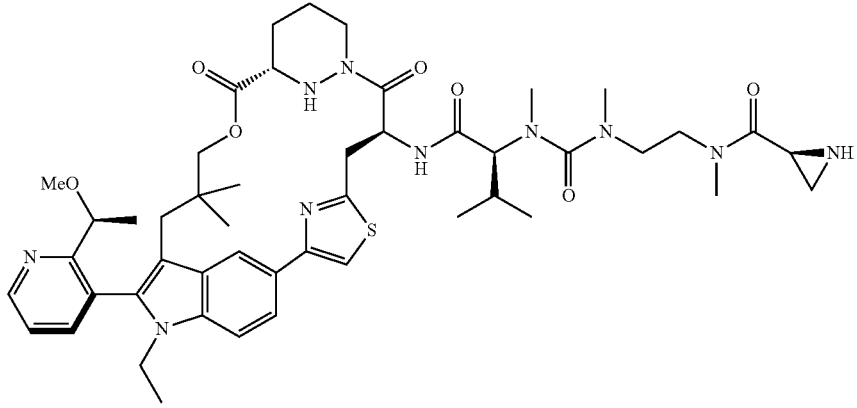 |

TABLE 1-continued

Certain Compounds of the Present Invention

| Ex# | Structure |
|---|---|
| 218 | 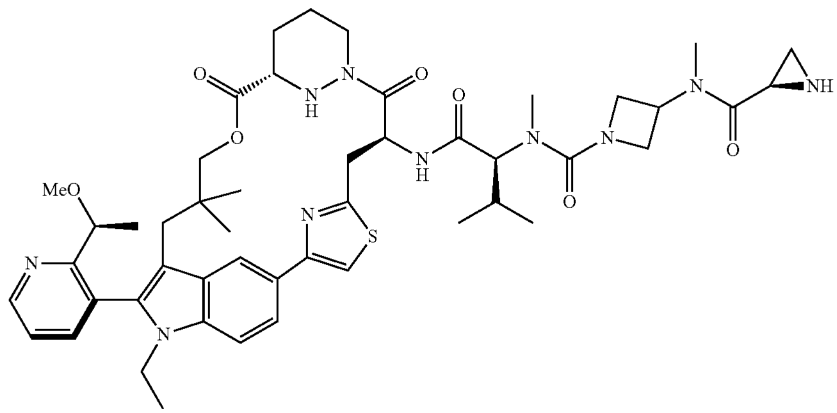 |
| 219 | 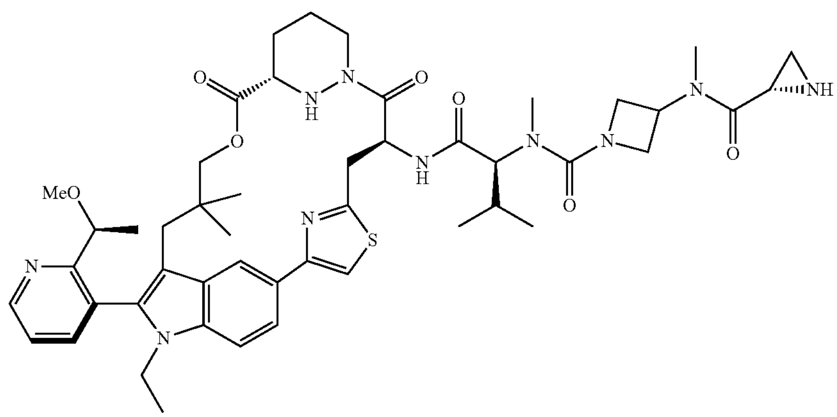 |
| 220 | 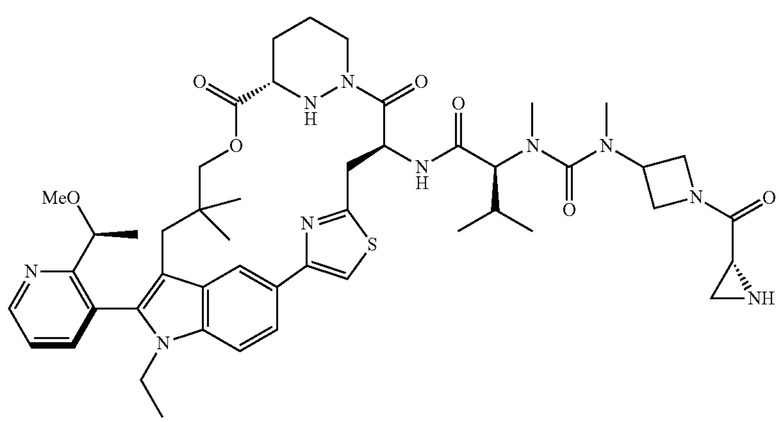 |

TABLE 1-continued

Certain Compounds of the Present Invention

| Ex# | Structure |
| --- | --- |
| 221 | 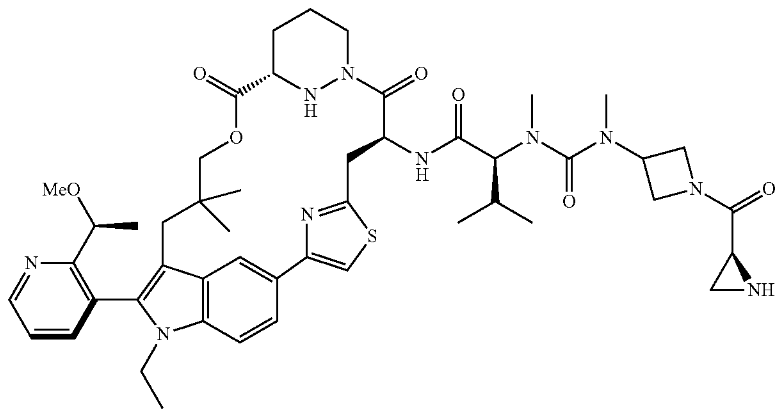 |
| 222 | 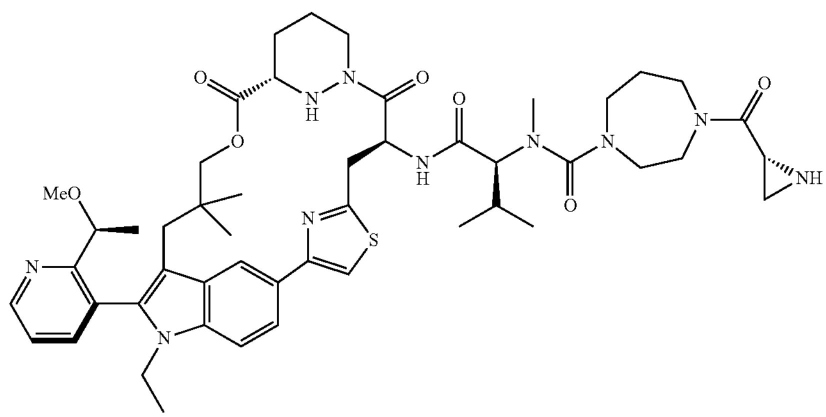 |
| 223 | 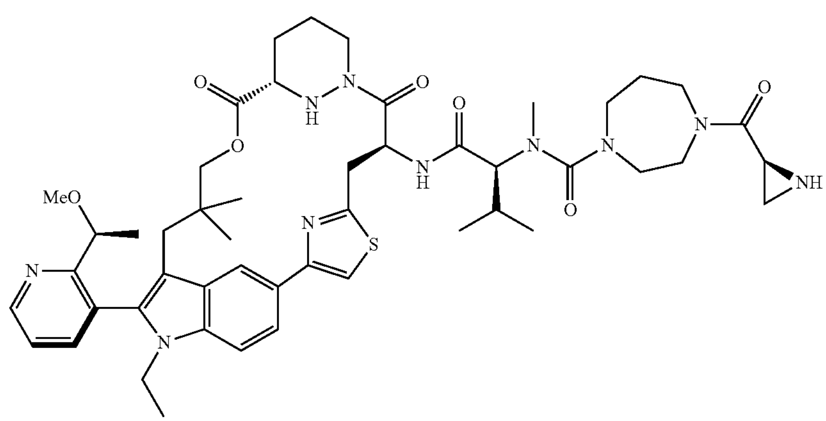 |

TABLE 1-continued
Certain Compounds of the Present Invention
| Ex# | Structure |
|---|---|
| 224 | 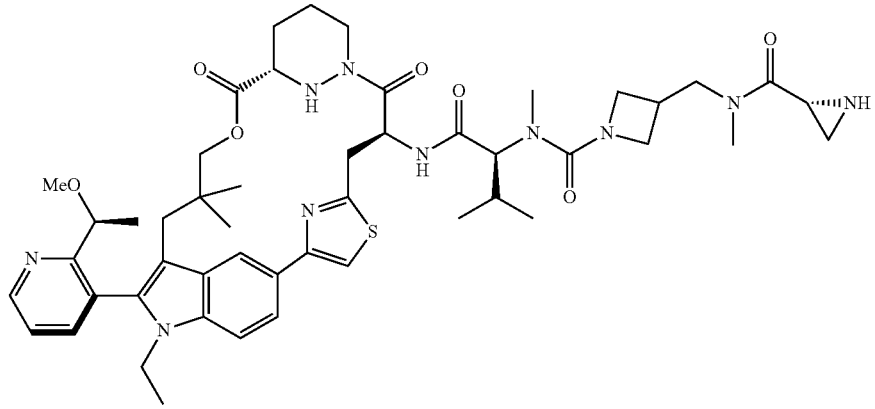 |
| 225 | 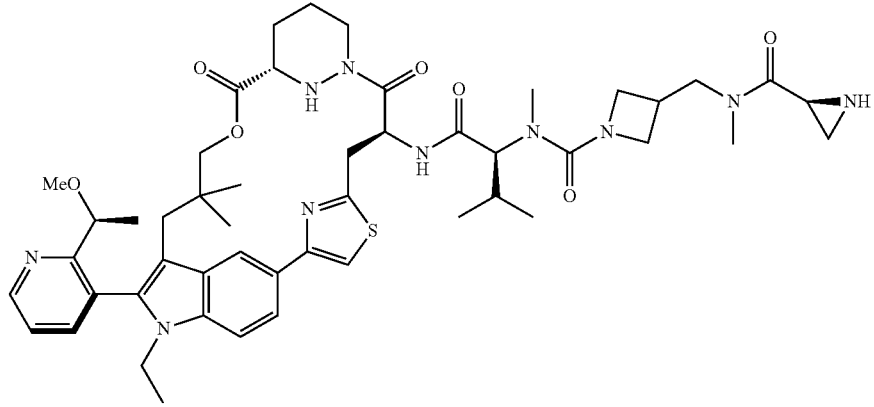 |
| 226 | 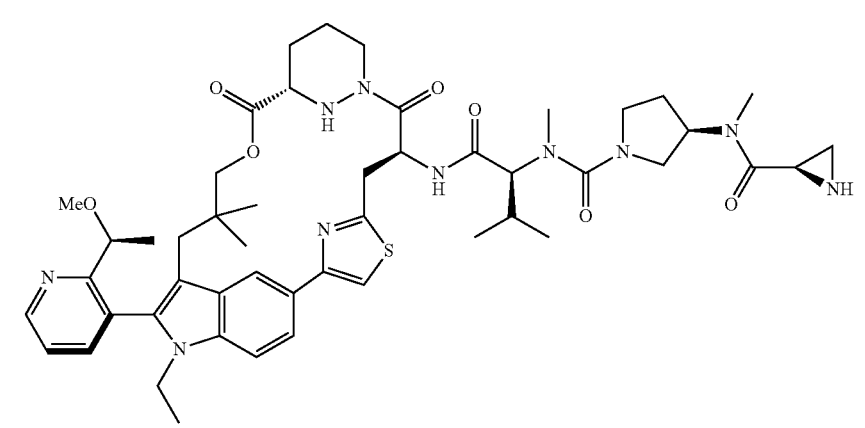 |

TABLE 1-continued

Certain Compounds of the Present Invention

| Ex# | Structure |
|---|---|
| 227 | 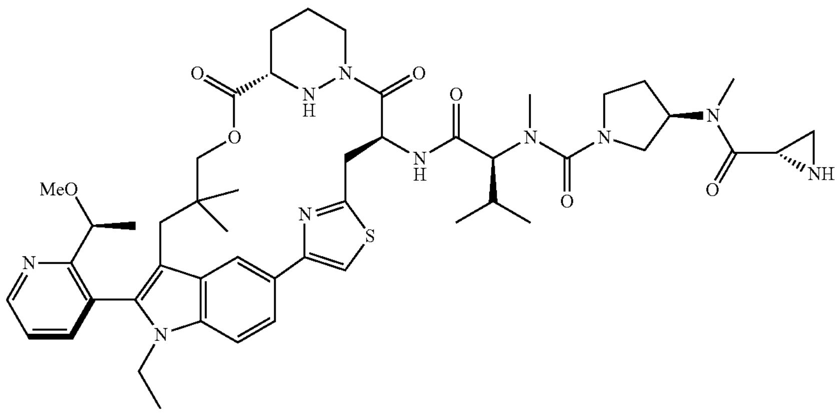 |
| 228 | 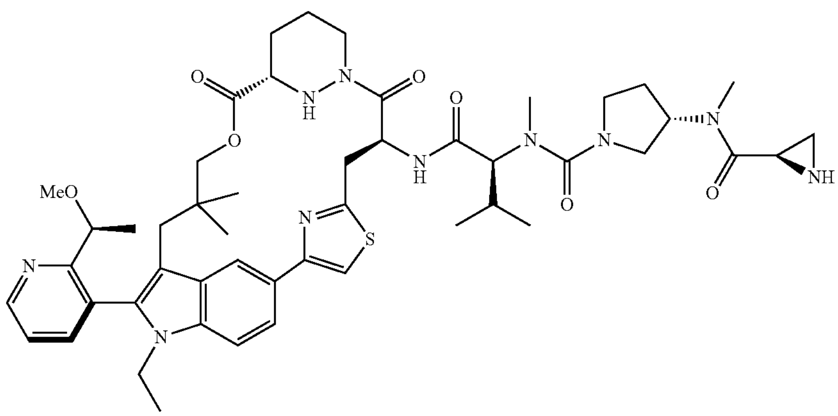 |
| 229 | 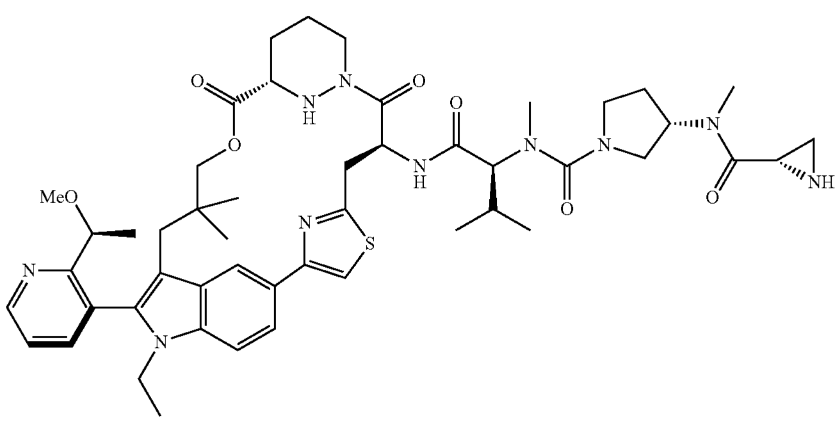 |

TABLE 1-continued

Certain Compounds of the Present Invention

| Ex# | Structure |
|---|---|
| 230 | 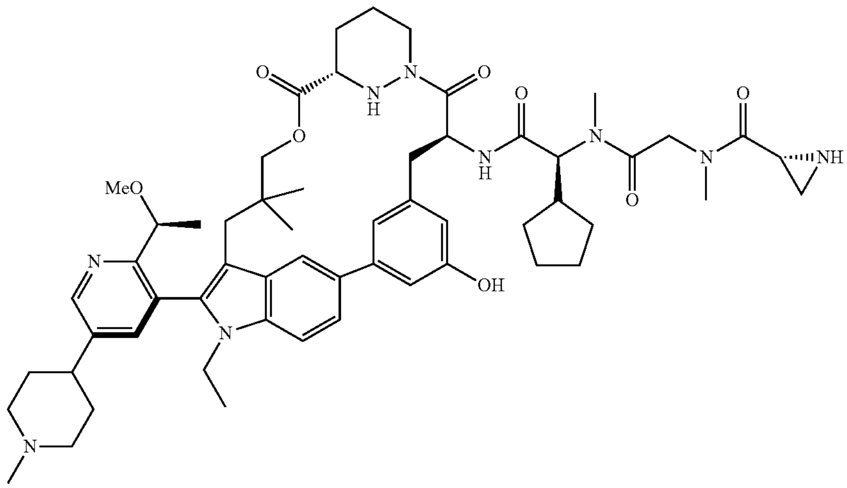 |
| 231 | 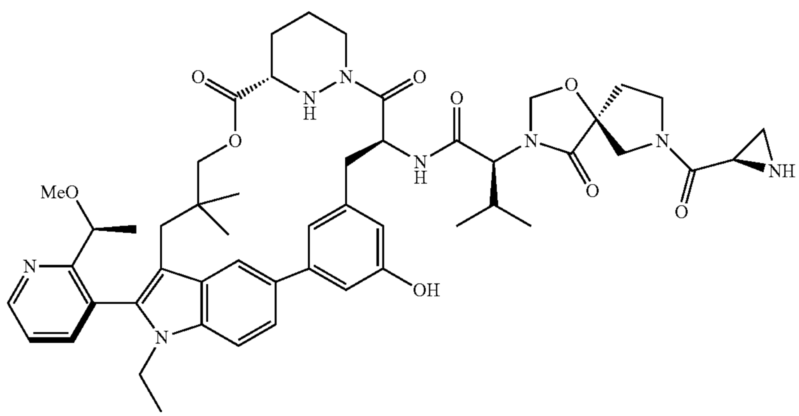 |
| 232 | 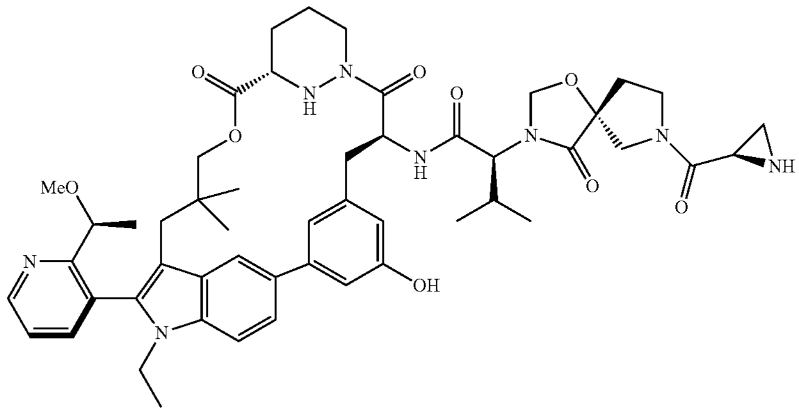 |

TABLE 1-continued

Certain Compounds of the Present Invention

| Ex# | Structure |
|---|---|
| 233 | 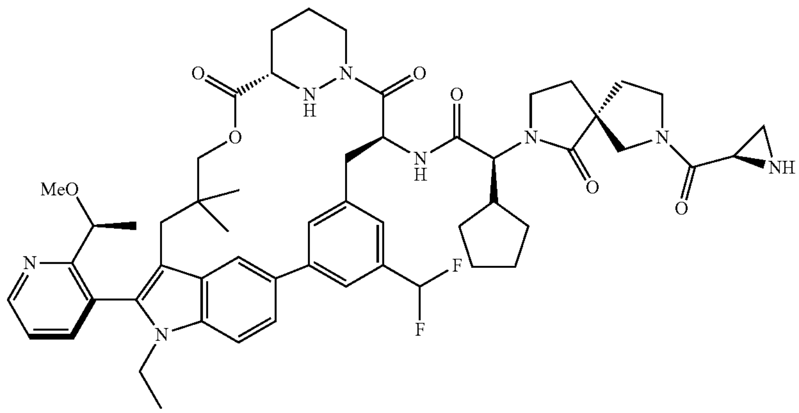 |
| 234 | 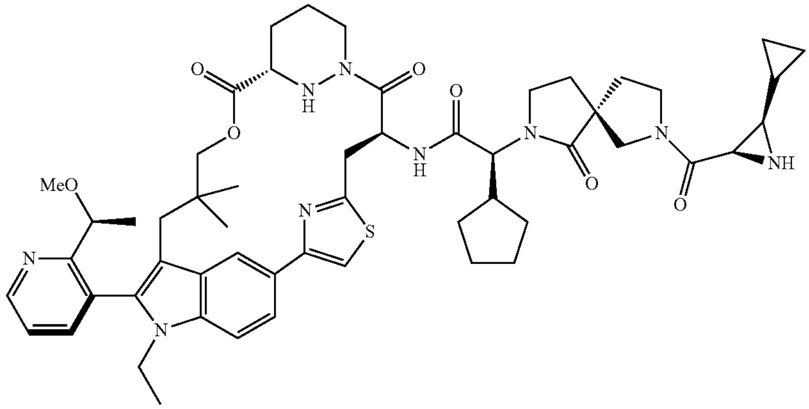 |
| 235 | 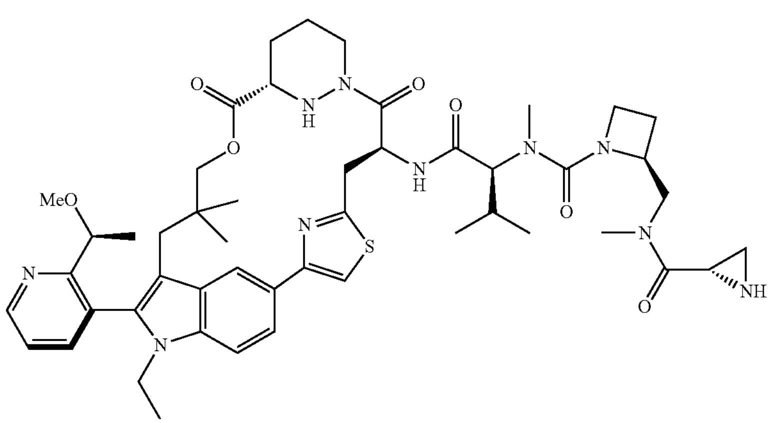 |

TABLE 1-continued

Certain Compounds of the Present Invention

| Ex# | Structure |
|---|---|
| 236 | 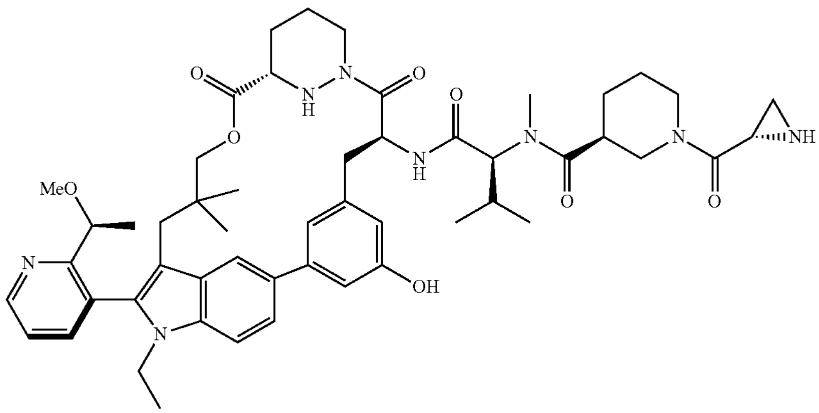 |
| 237 | 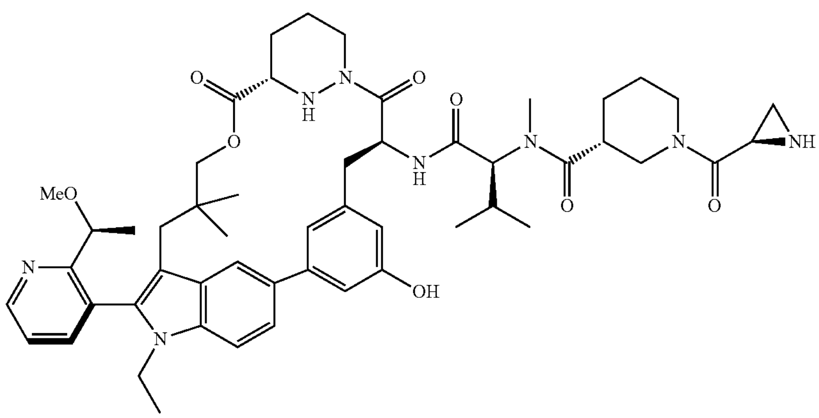 |
| 238 | 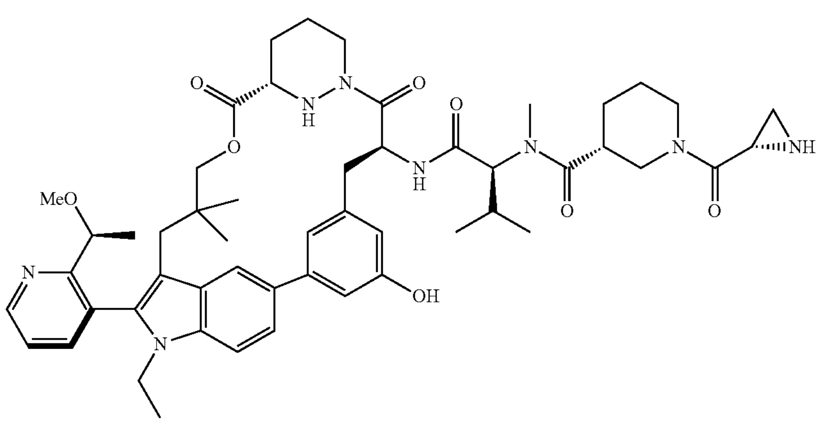 |

TABLE 1-continued
Certain Compounds of the Present Invention
| Ex# | Structure |
|-----|-----------|
| 239 | 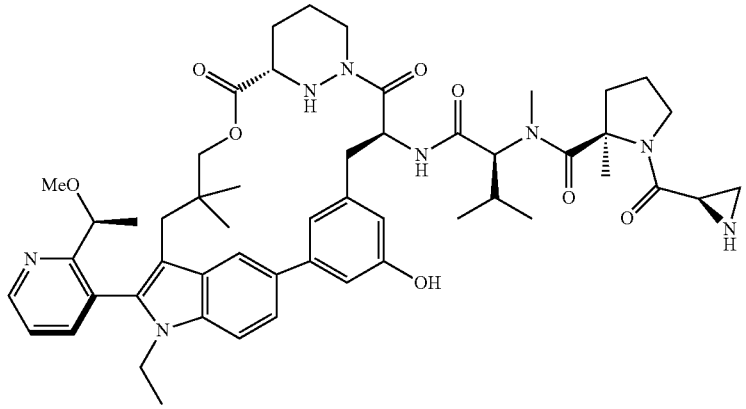 |
| 240 | 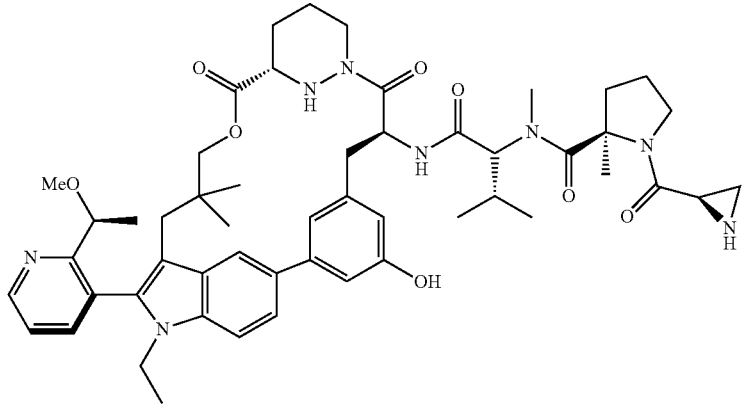 |
| 241 | 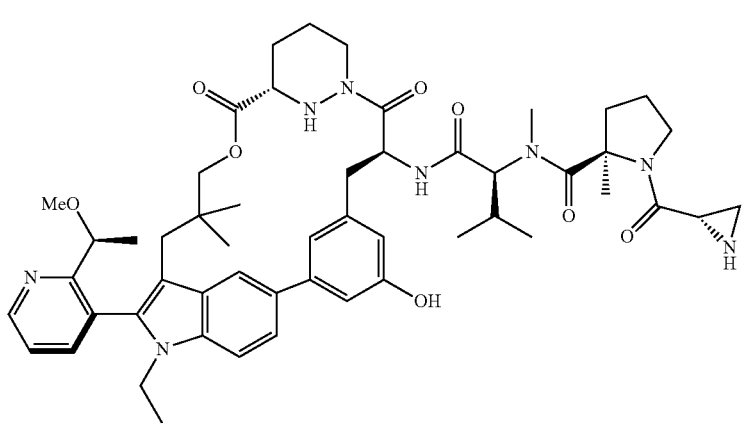 |

TABLE 1-continued
Certain Compounds of the Present Invention
| Ex# | Structure |
|---|---|
| 242 | 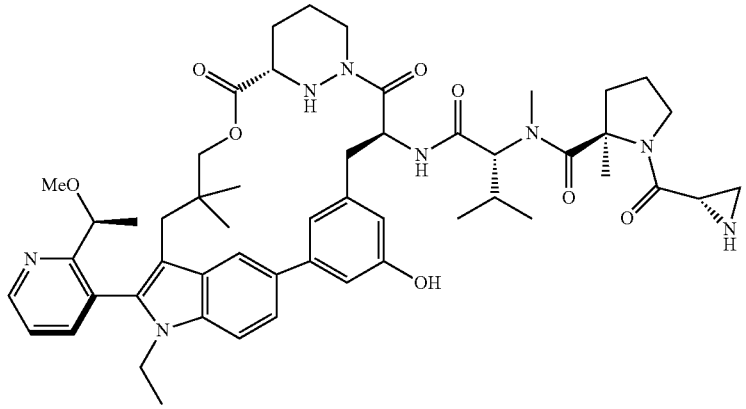 |
| 243 | 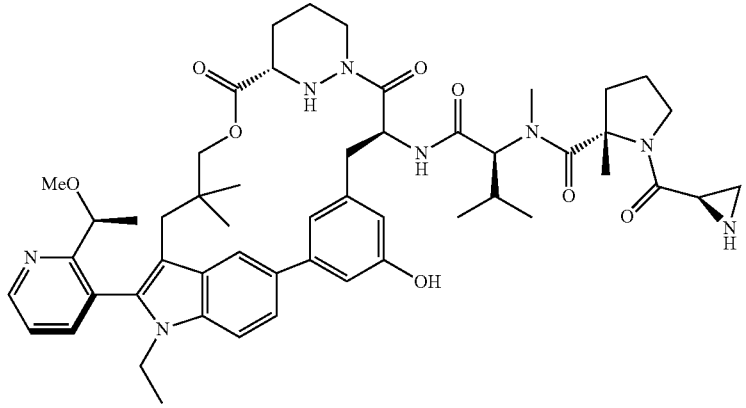 |
| 244 | 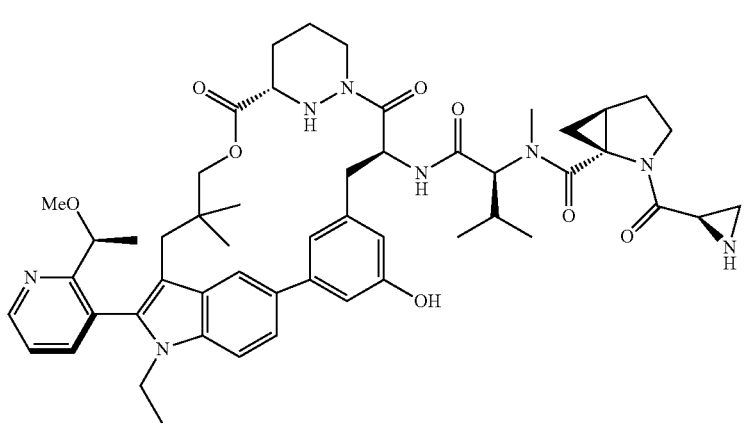 |

TABLE 1-continued

Certain Compounds of the Present Invention

| Ex# | Structure |
|---|---|
| 245 | 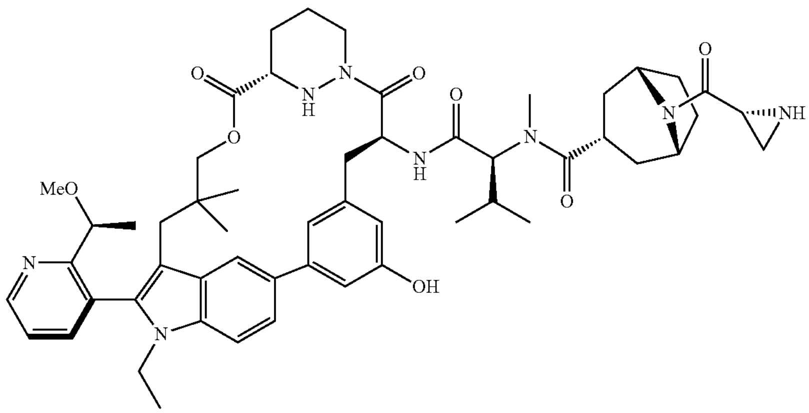 |
| 246 | 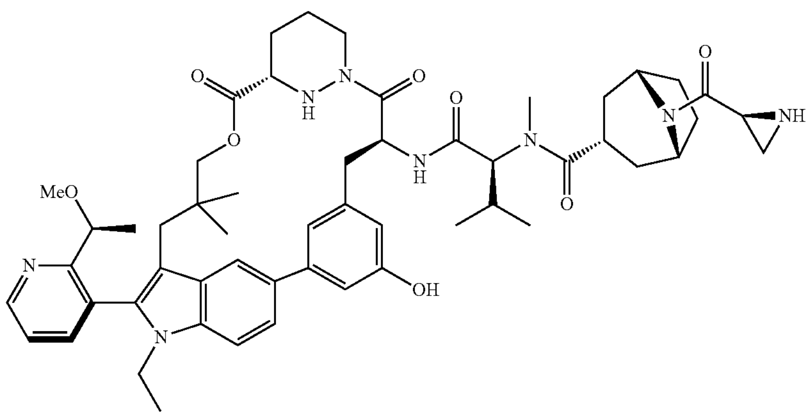 |
| 247 | 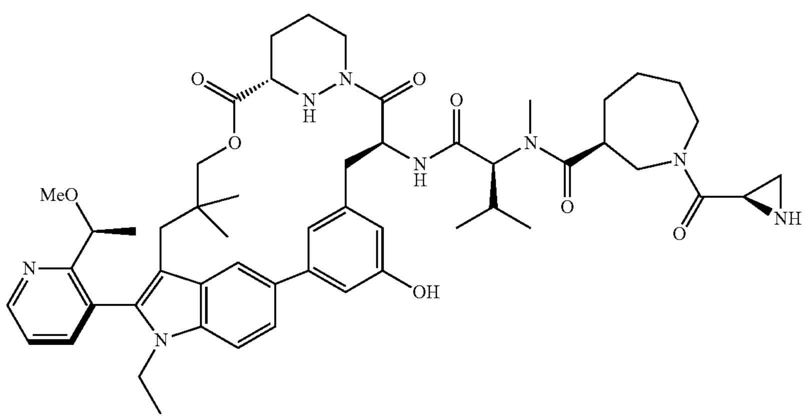 |

TABLE 1-continued

Certain Compounds of the Present Invention

| Ex# | Structure |
|---|---|
| 248 | 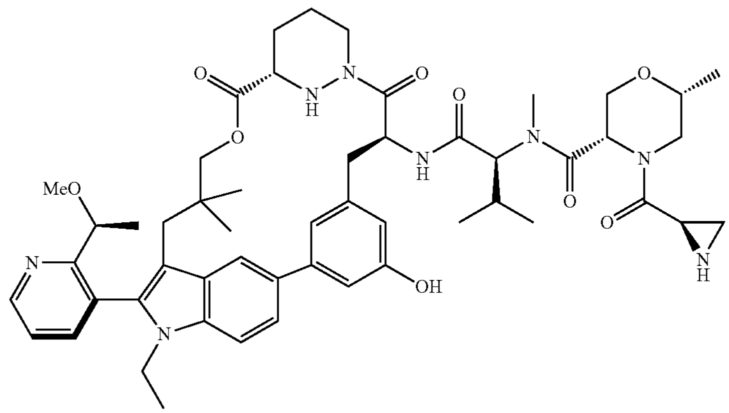 |
| 249 | 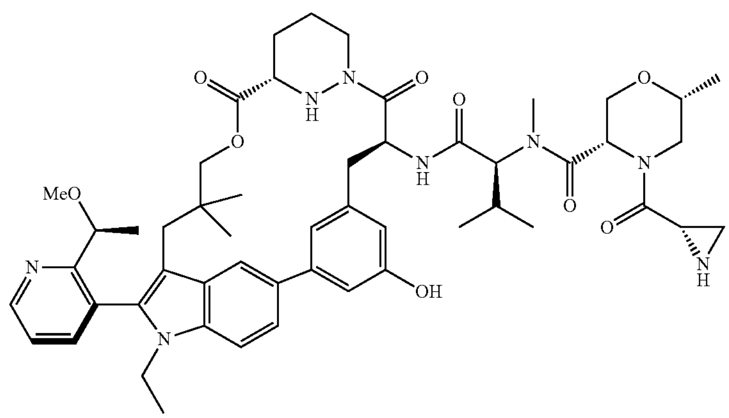 |
| 250 | 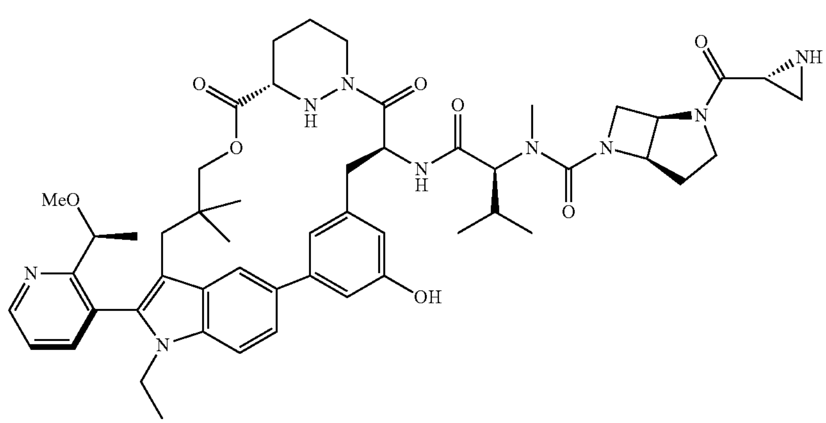 |

TABLE 1-continued

Certain Compounds of the Present Invention

| Ex# | Structure |
|---|---|
| 251 | 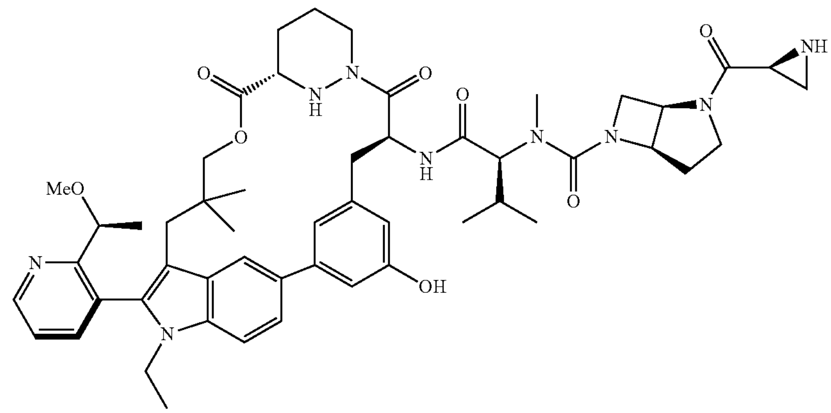 |
| 252 | 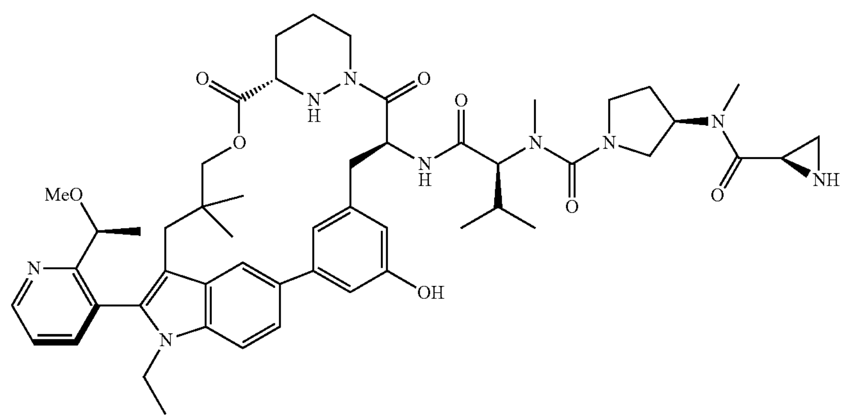 |
| 253 | 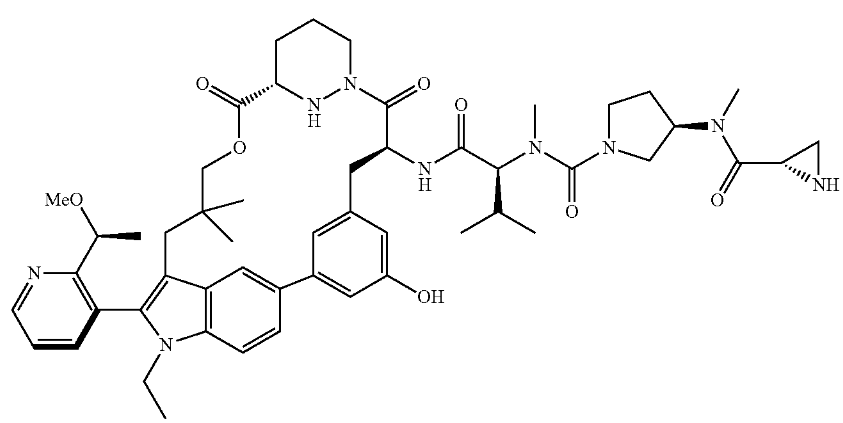 |

TABLE 1-continued

Certain Compounds of the Present Invention

| Ex# | Structure |
|---|---|
| 254 | 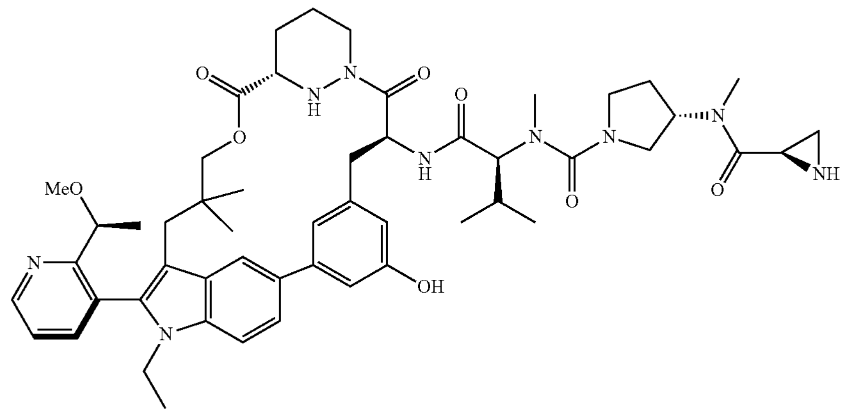 |
| 255 | 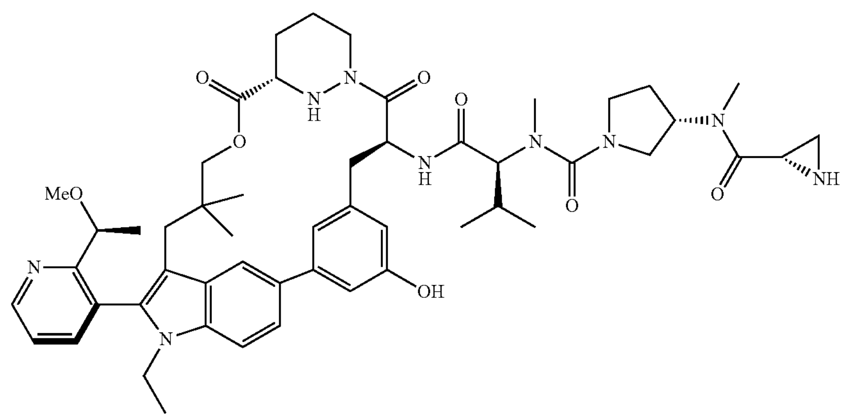 |
| 256 | 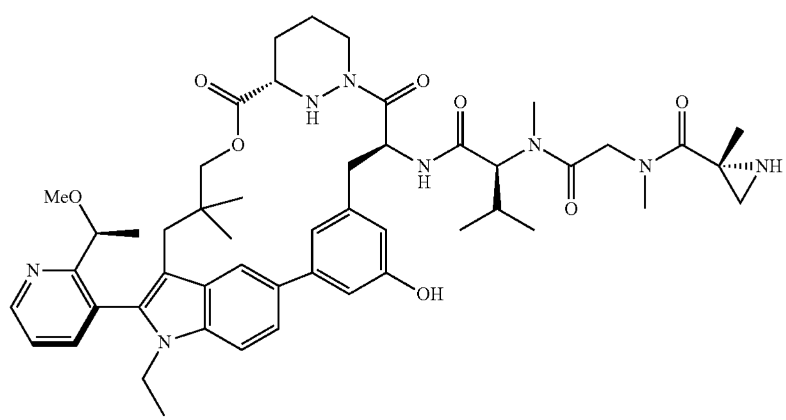 |

TABLE 1-continued

Certain Compounds of the Present Invention

| Ex# | Structure |
|---|---|
| 257 | 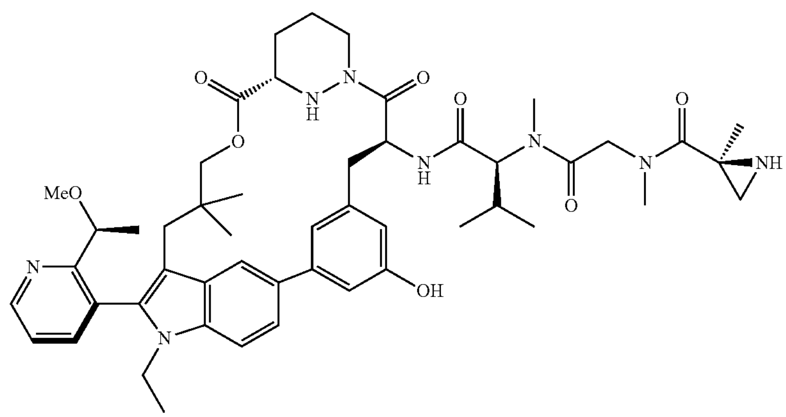 |
| 258* | 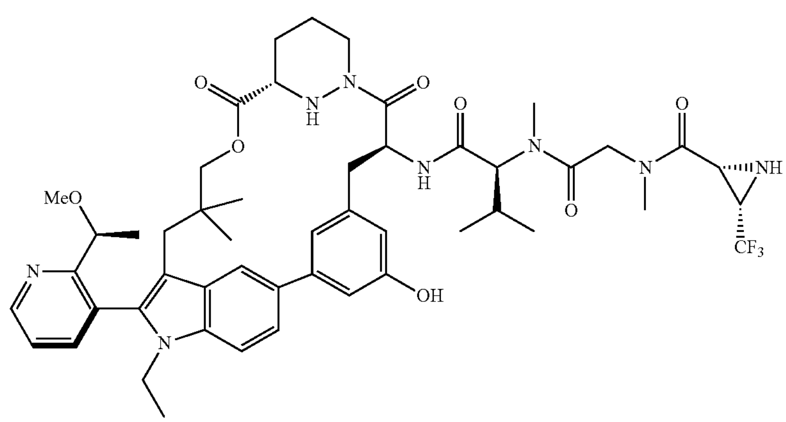 |
| 259* | 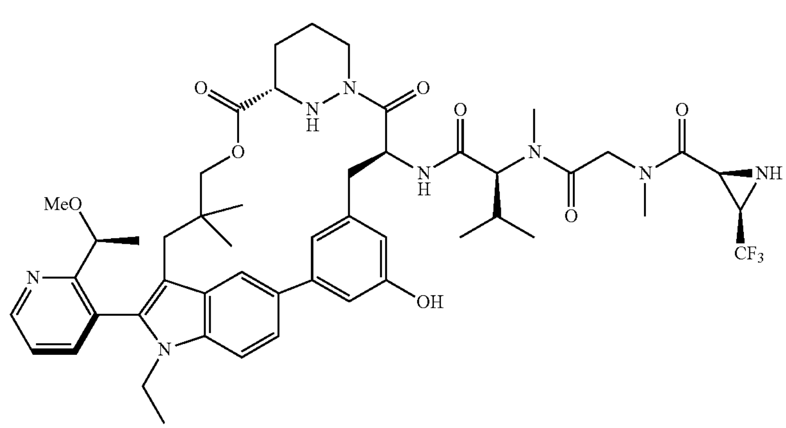 |

US 11,739,074 B2
227                                                                                     228
TABLE 1-continued
Certain Compounds of the Present Invention
| Ex# | Structure |
|---|---|
| 260* | 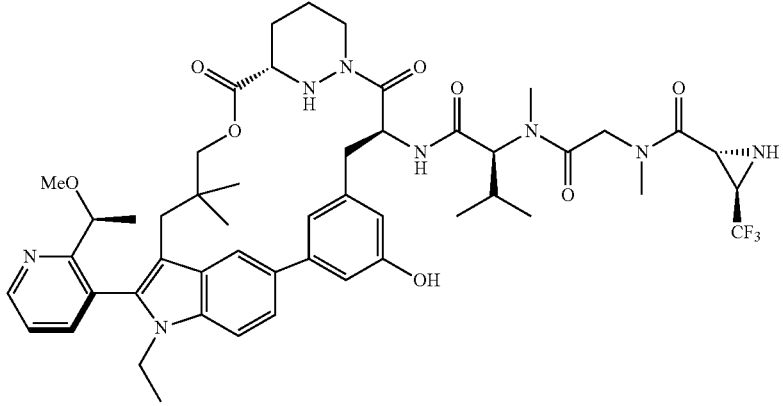 |
| 261* | 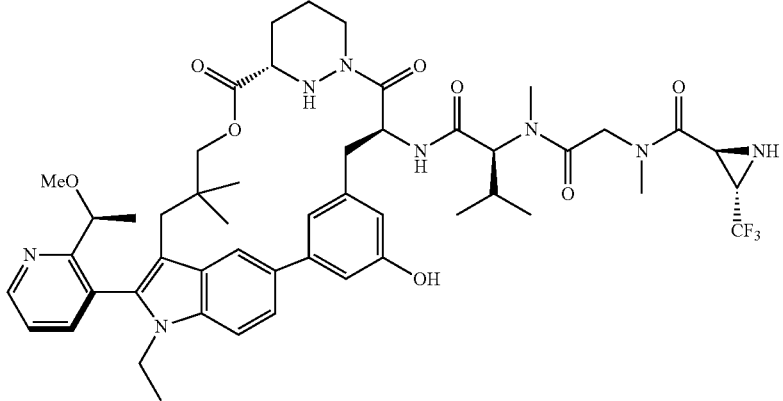 |
| 262 | 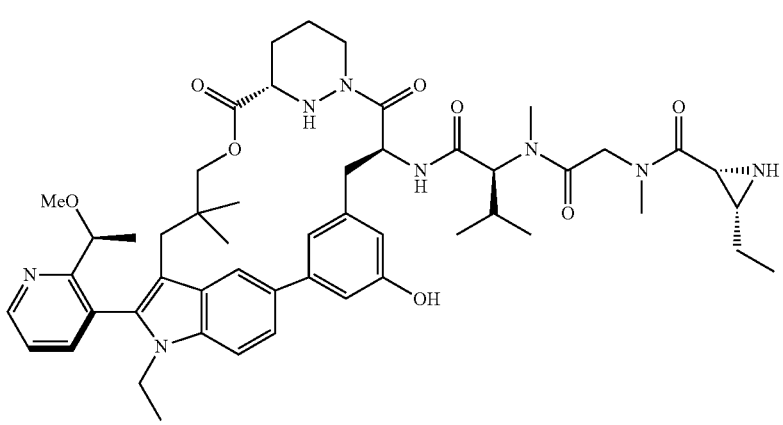 |

TABLE 1-continued

Certain Compounds of the Present Invention

| Ex# | Structure |
|---|---|
| 263 | 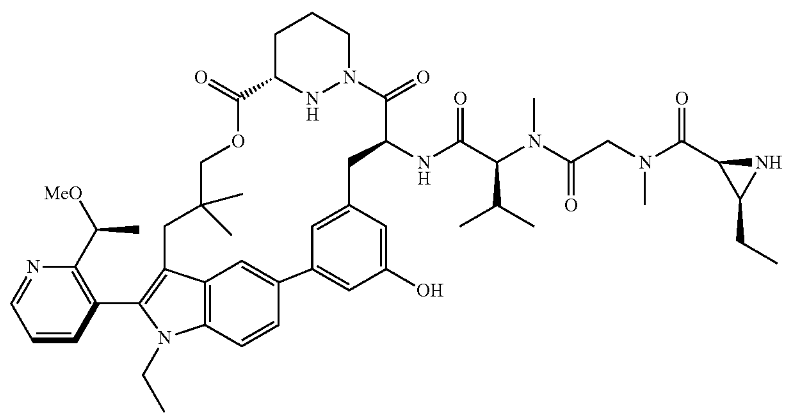 |
| 264 | 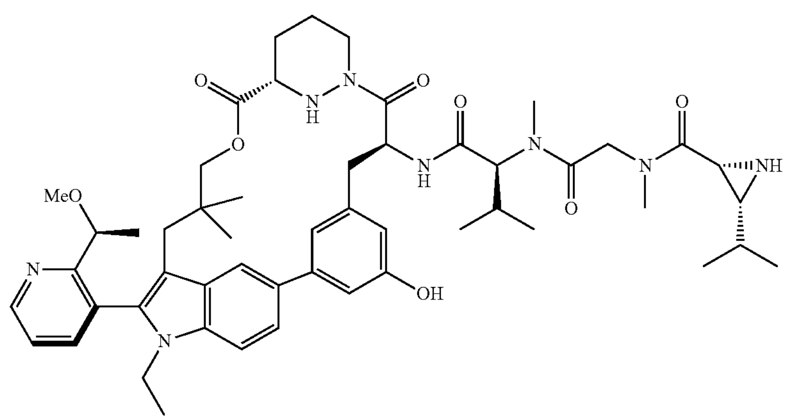 |
| 265 | 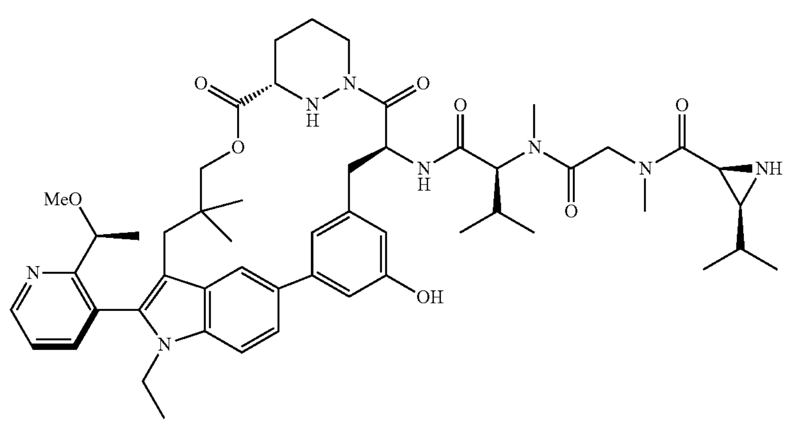 |

TABLE 1-continued

Certain Compounds of the Present Invention

| Ex# | Structure |
|---|---|
| 266 | 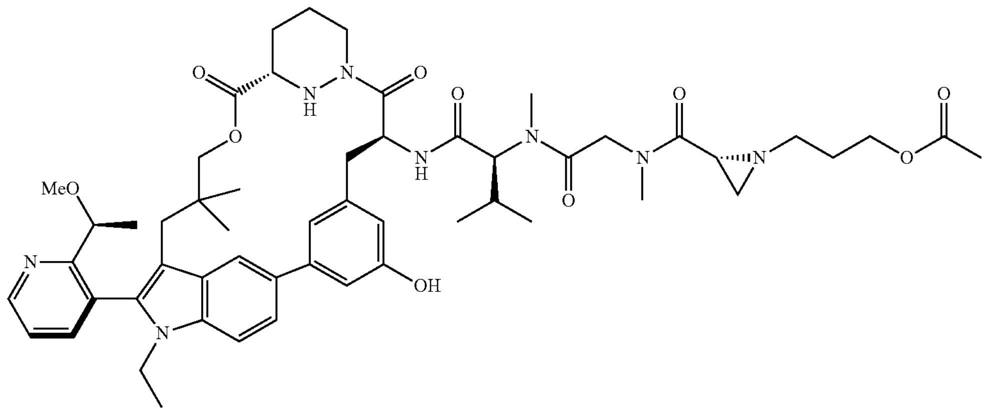 |
| 267 | 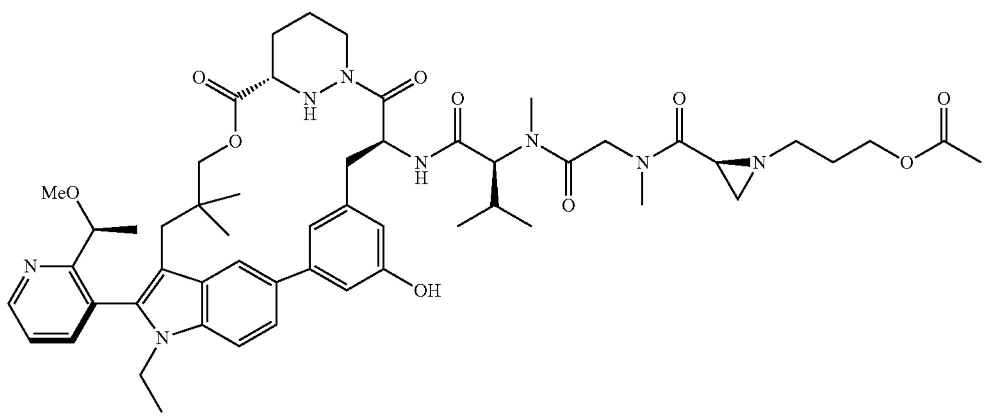 |
| 268 | 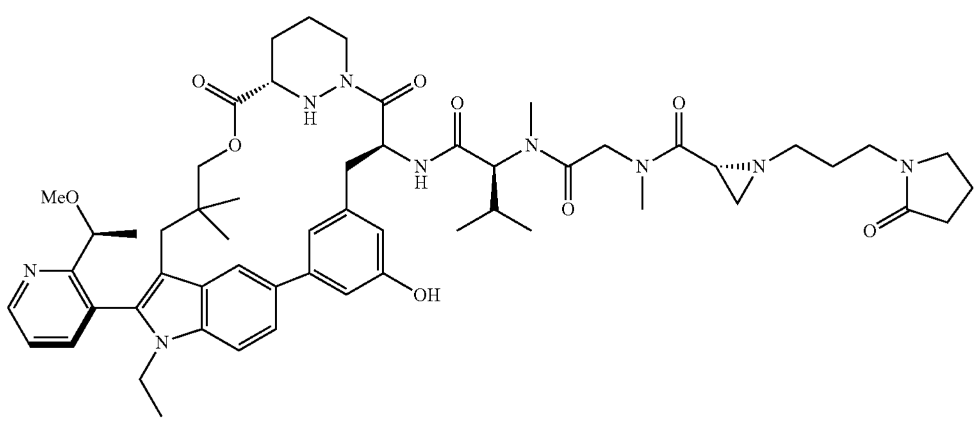 |

US 11,739,074 B2
233                                                                                               234
TABLE 1-continued
Certain Compounds of the Present Invention
| Ex# | Structure |
|---|---|
| 269 | 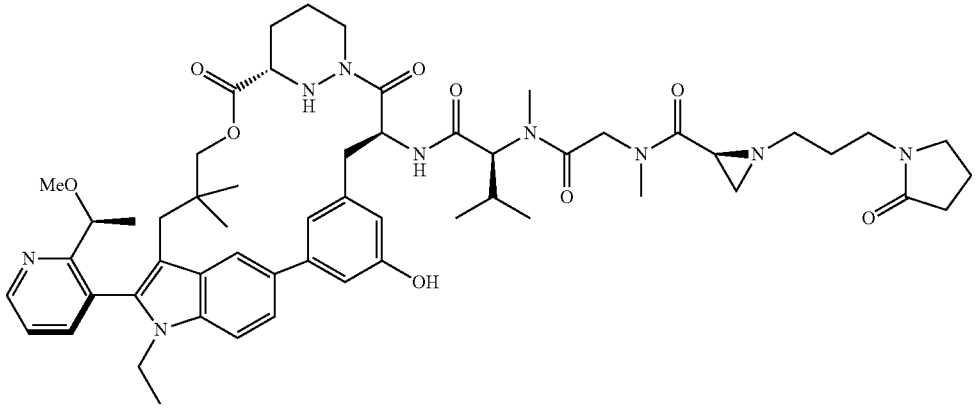 |
| 270 | 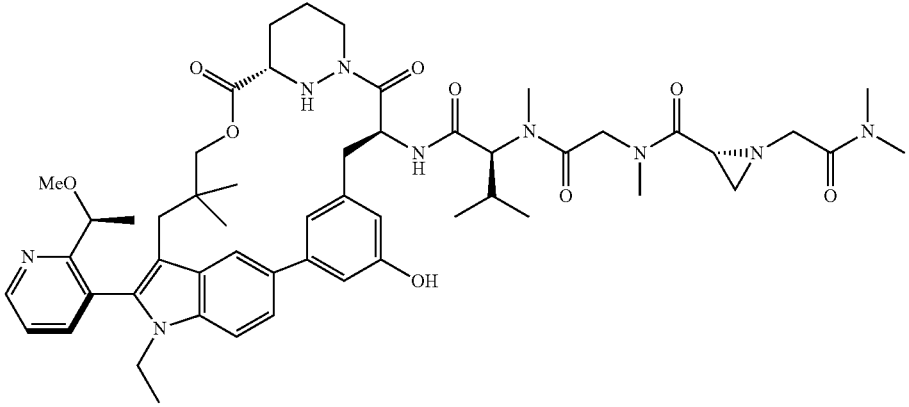 |
| 271 | 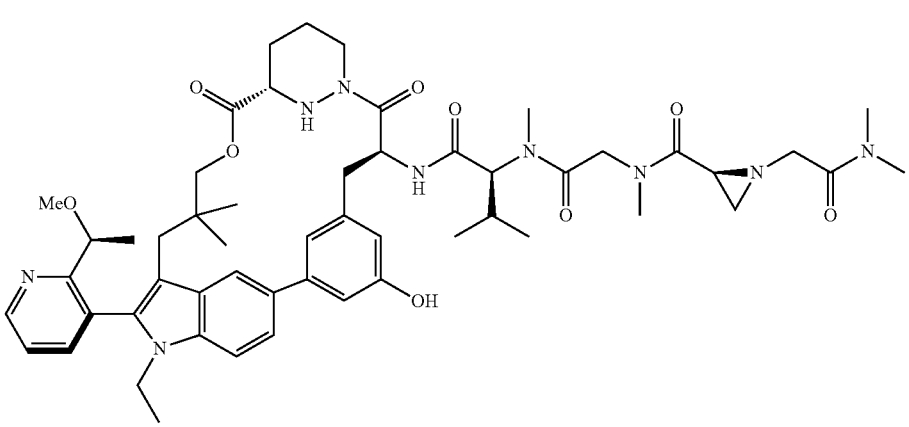 |

TABLE 1-continued

Certain Compounds of the Present Invention

| Ex# | Structure |
| --- | --- |
| 272 | 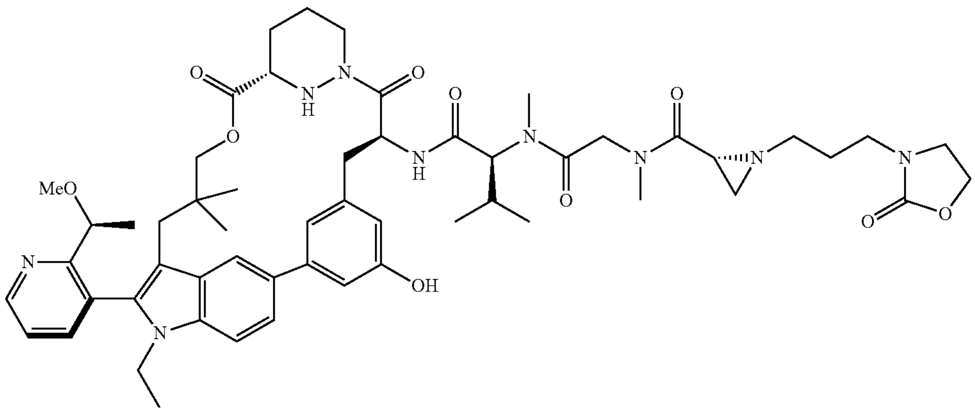 |
| 273 | 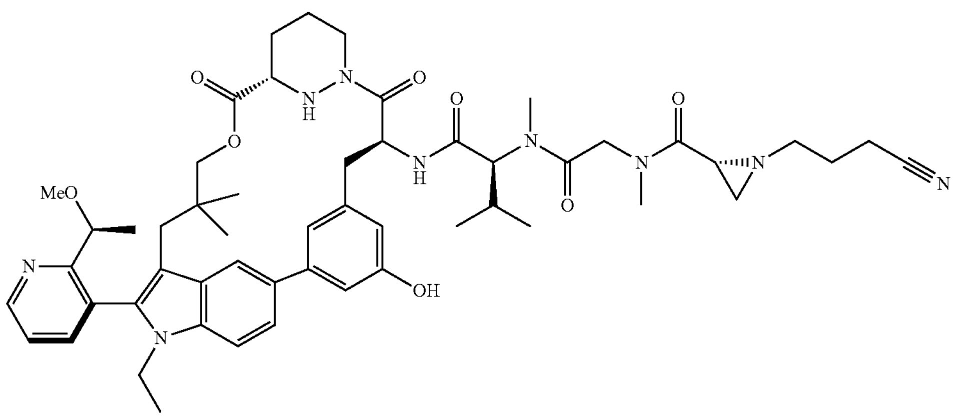 |
| 274 | 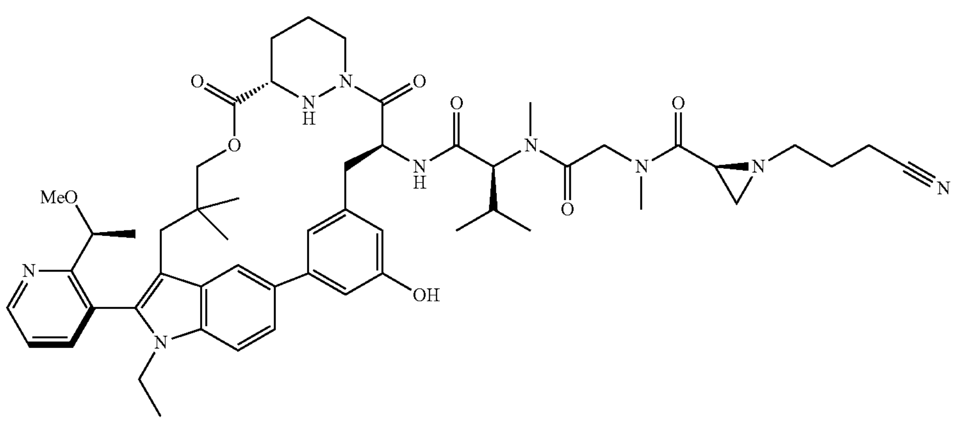 |

TABLE 1-continued
Certain Compounds of the Present Invention
| Ex# | Structure |
|---|---|
| 275 | 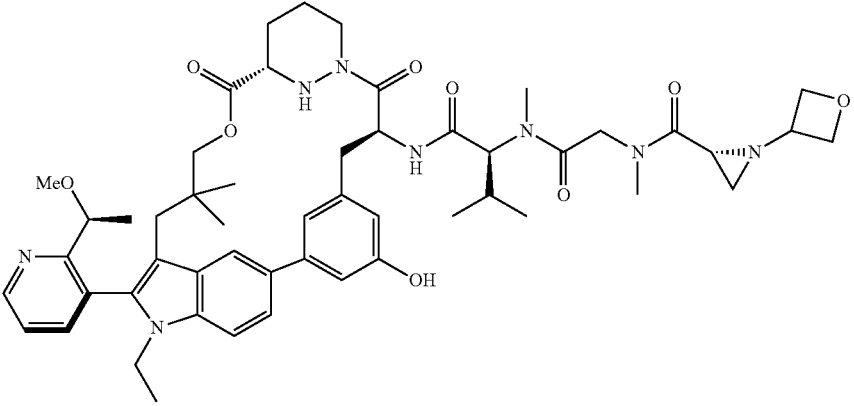 |
| 276 | 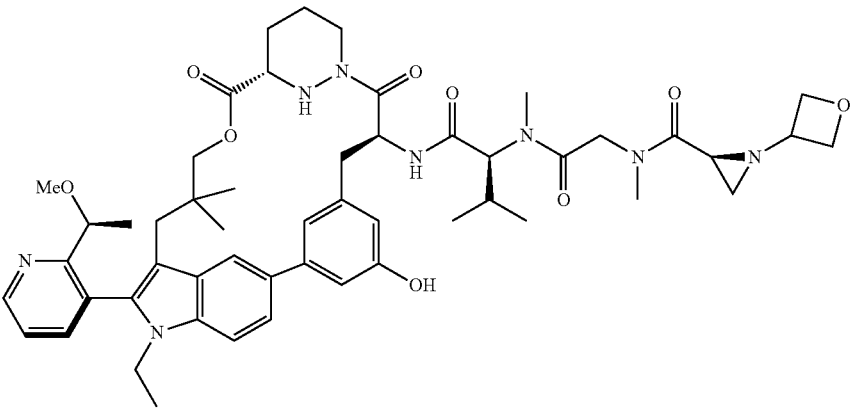 |
| 277 | 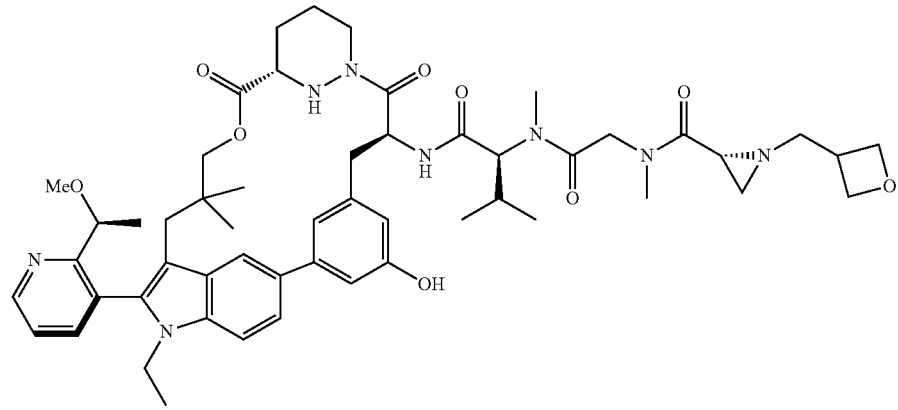 |

TABLE 1-continued
Certain Compounds of the Present Invention
| Ex# | Structure |
|---|---|
| 278 | 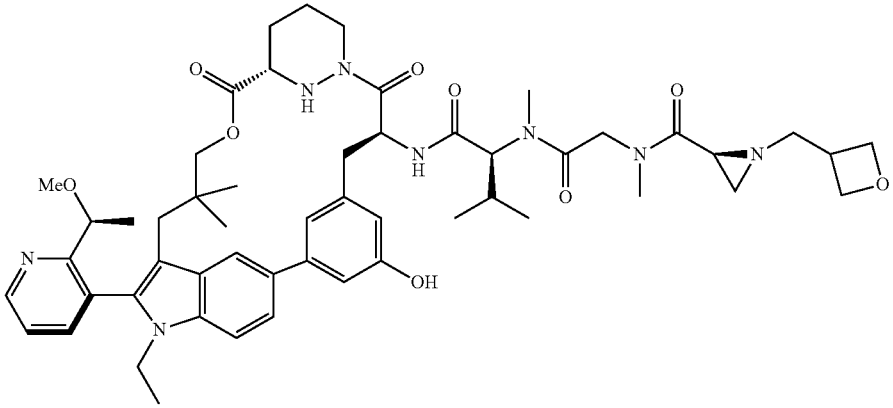 |
| 279 | 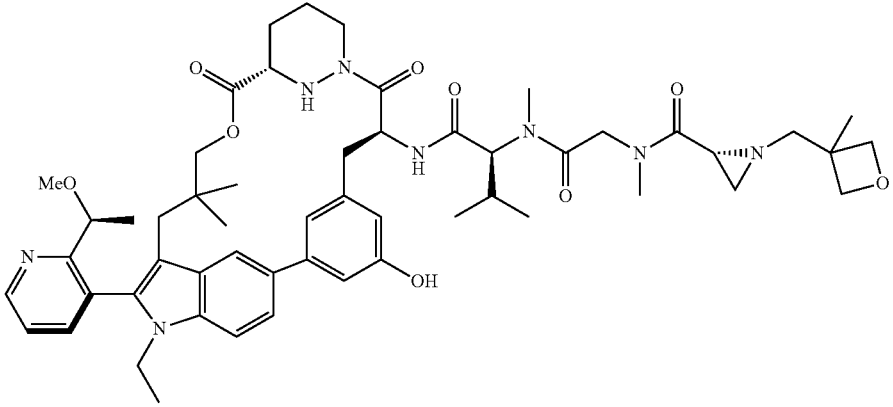 |
| 280 | 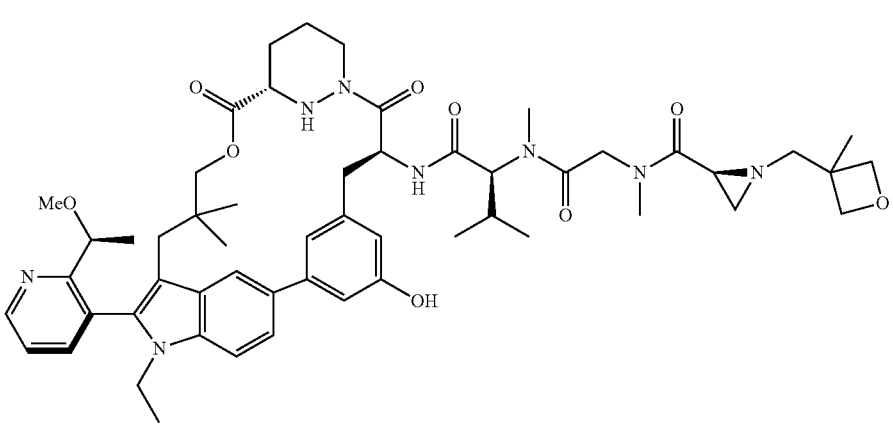 |

TABLE 1-continued

Certain Compounds of the Present Invention

| Ex# | Structure |
|---|---|
| 281* | 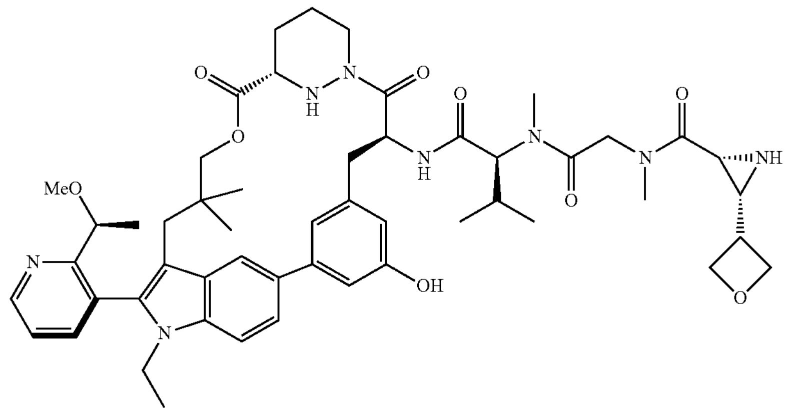 |
| 282* | 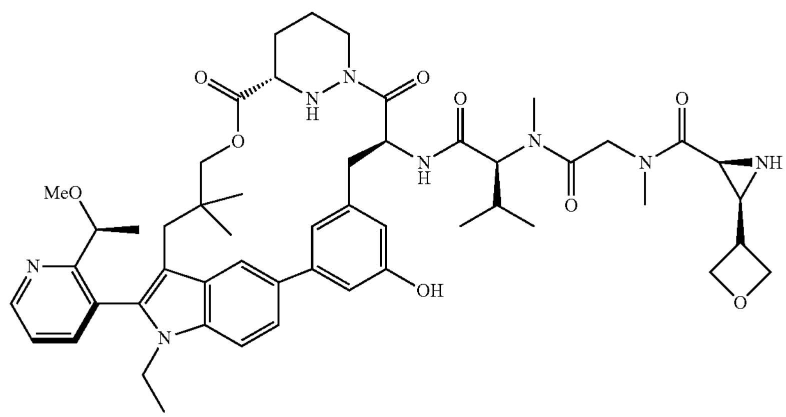 |
| 283* | 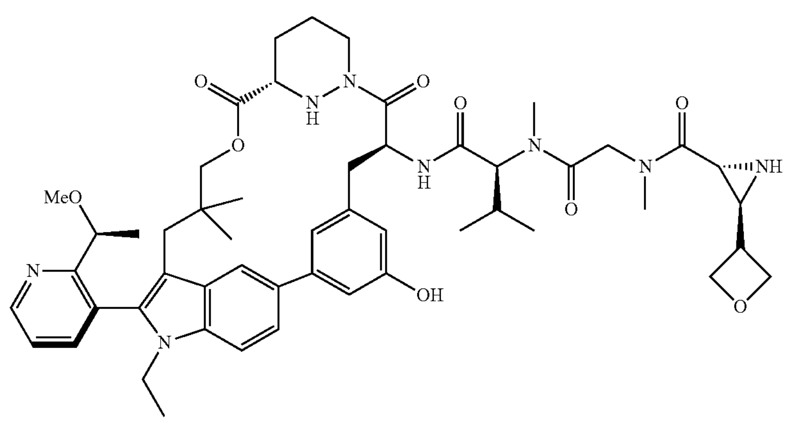 |

TABLE 1-continued

Certain Compounds of the Present Invention

| Ex# | Structure |
|---|---|
| 284* | 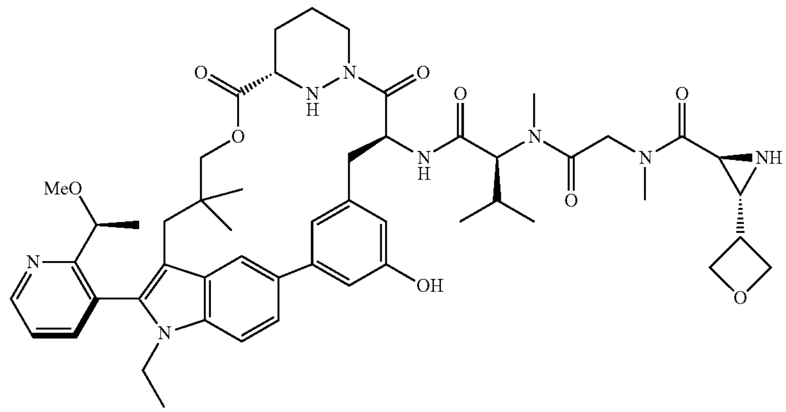 |
| 285 | 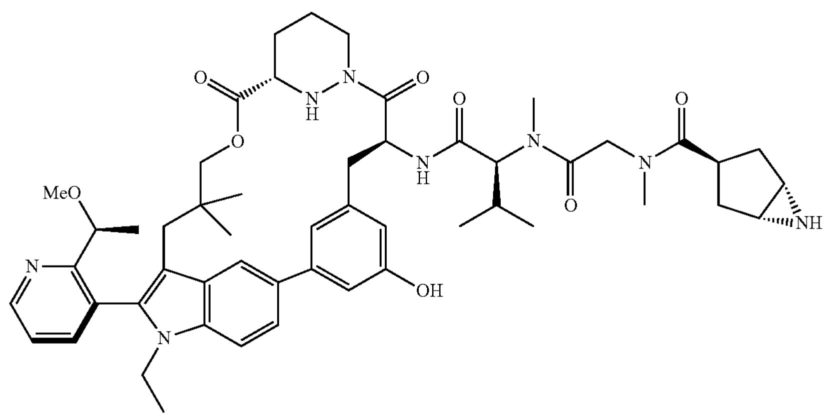 |
| 286 | 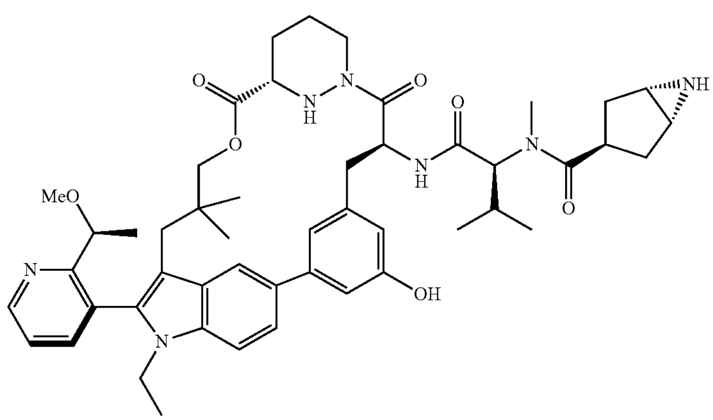 |

| Ex# | Structure |
|---|---|
| 287 | 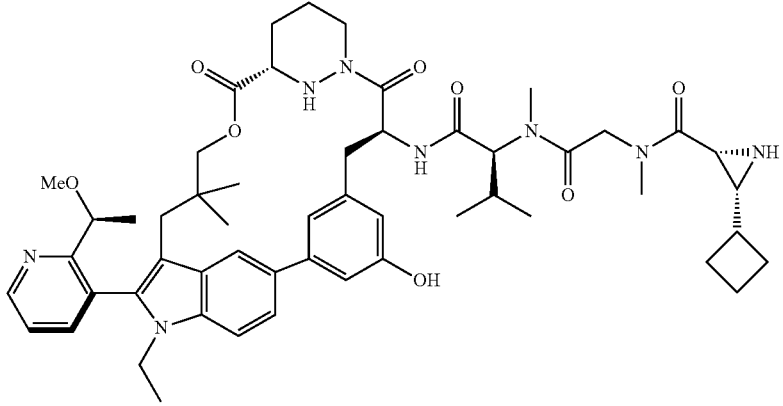 |
| 288 | 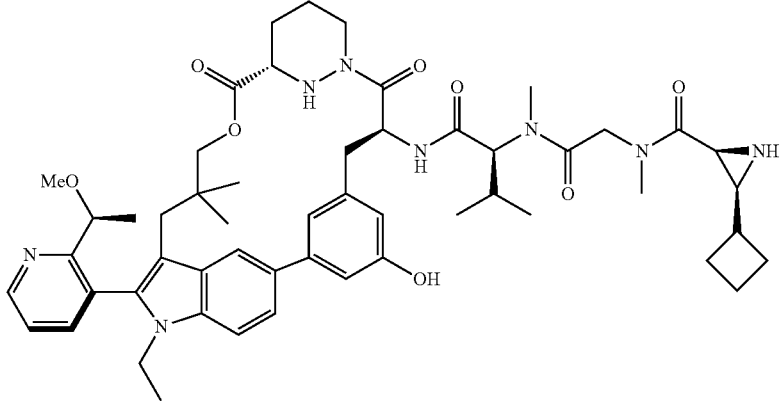 |
| 289 | 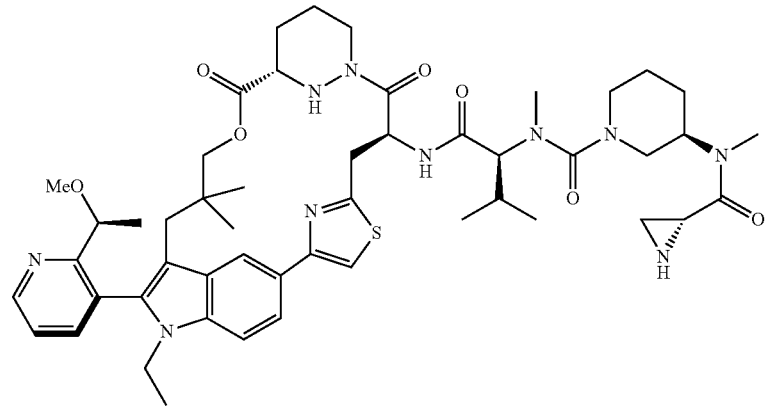 |

TABLE 1-continued
Certain Compounds of the Present Invention
| Ex# | Structure |
|---|---|
| 290 | 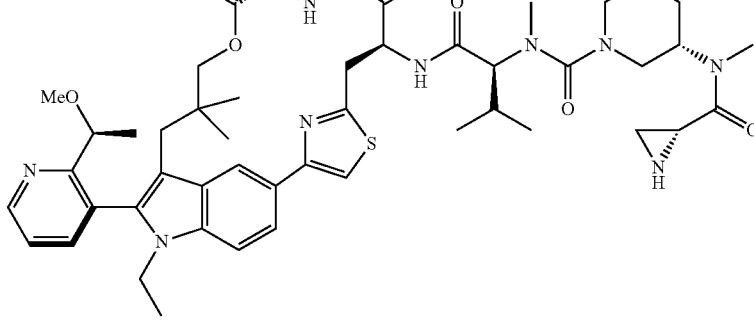 |
| 291 | 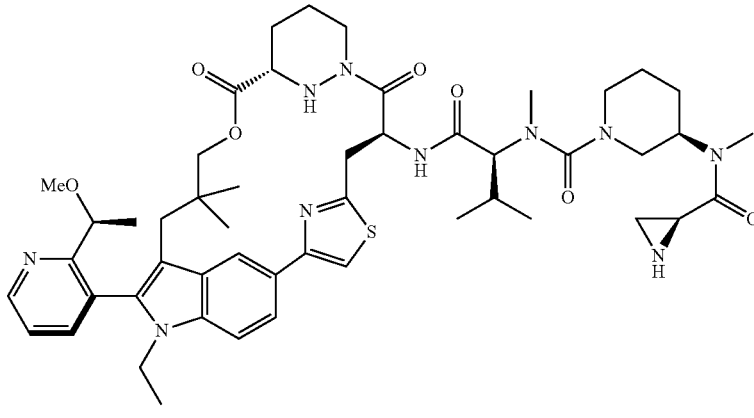 |
| 292 | 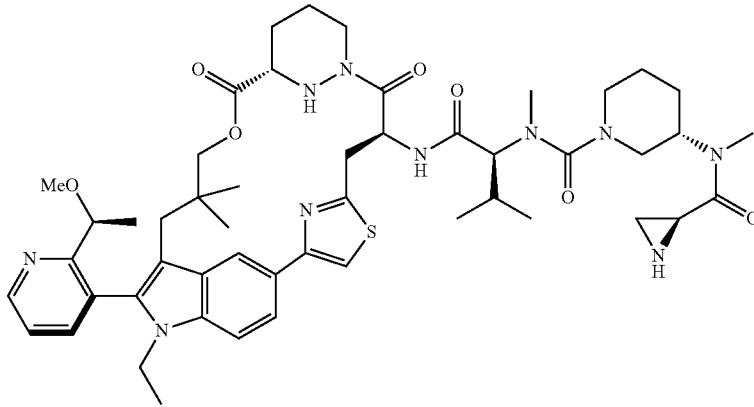 |

TABLE 1-continued
Certain Compounds of the Present Invention
| Ex# | Structure |
|---|---|
| 293 | 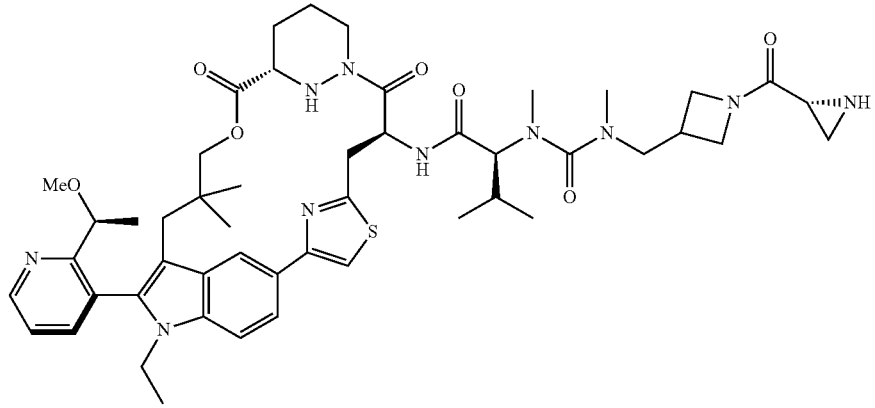 |
| 294 | 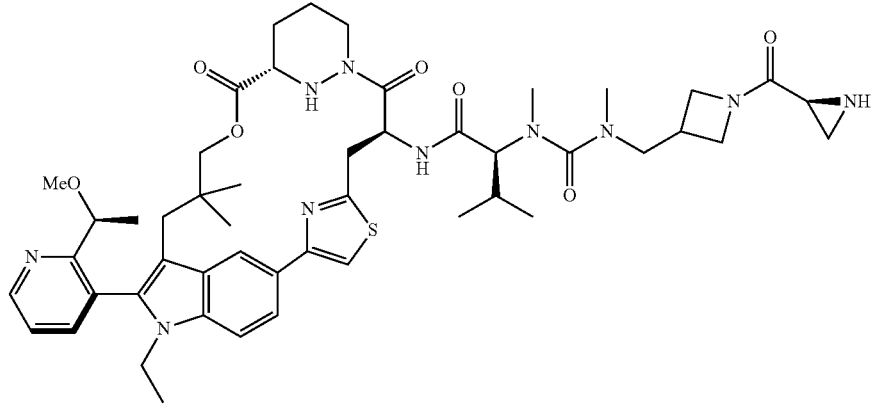 |
| 295 | 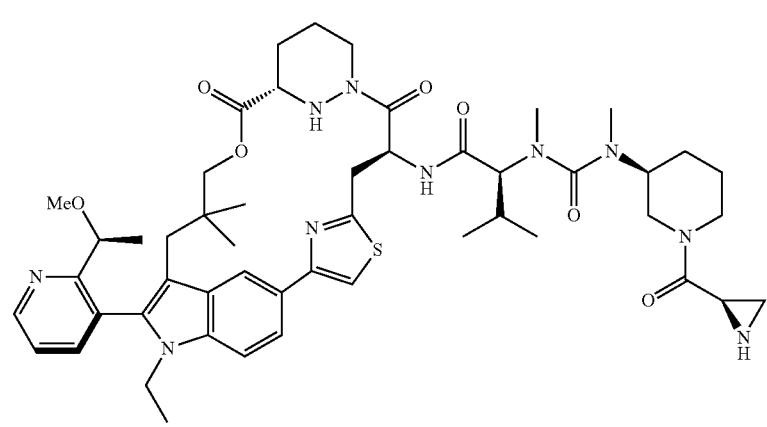 |

TABLE 1-continued

Certain Compounds of the Present Invention

| Ex# | Structure |
|---|---|
| 296 | 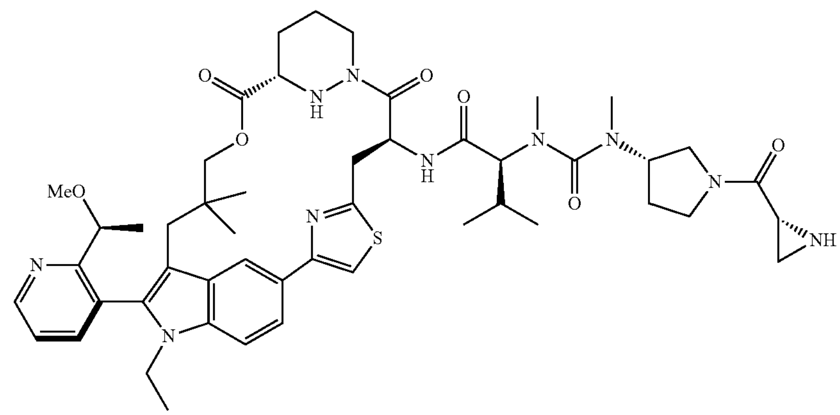 |
| 297 | 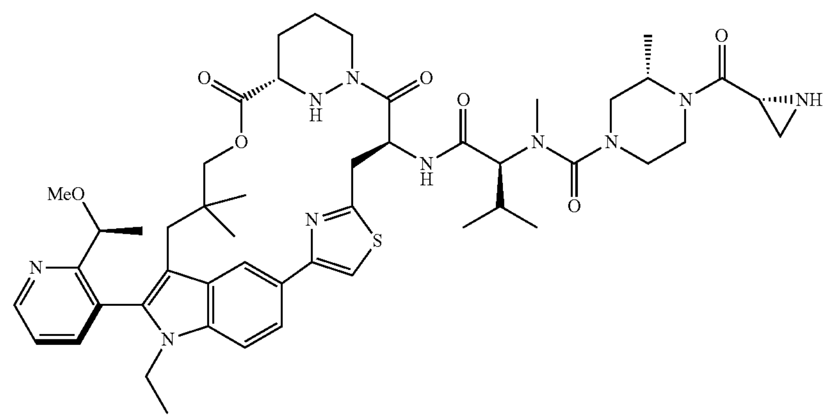 |
| 298 | 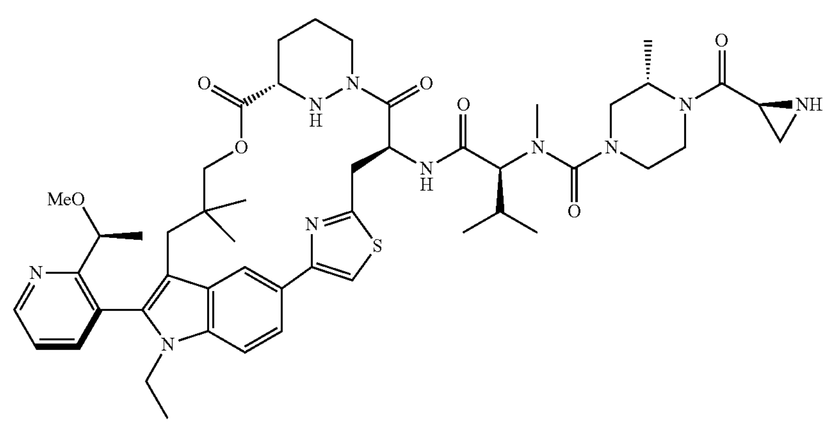 |

TABLE 1-continued

Certain Compounds of the Present Invention

| Ex# | Structure |
|---|---|
| 299 | 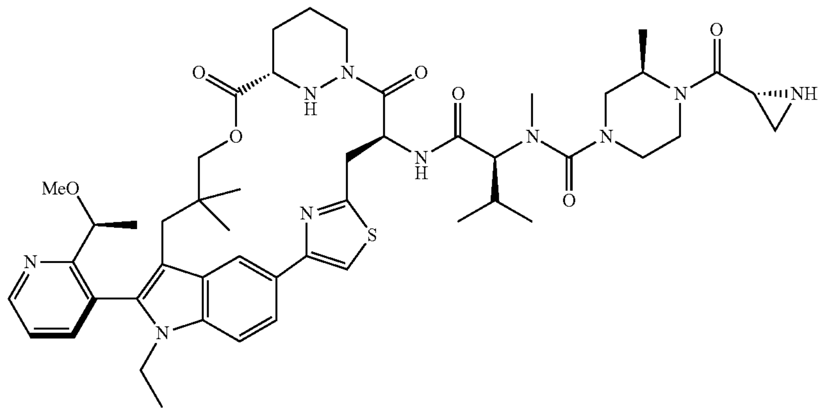 |
| 300 | 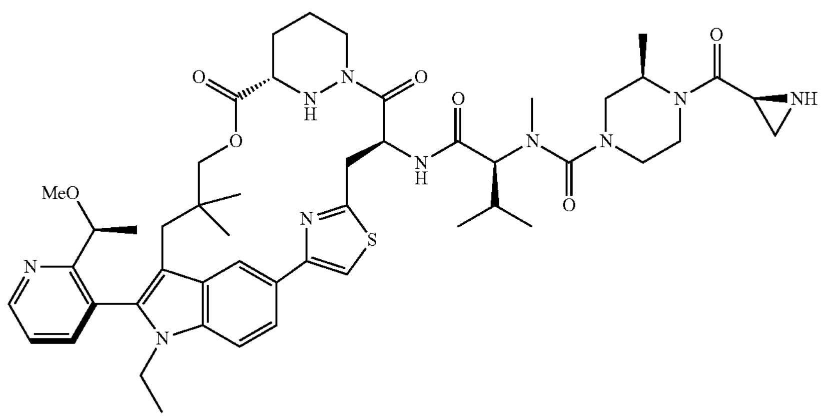 |
| 301 | 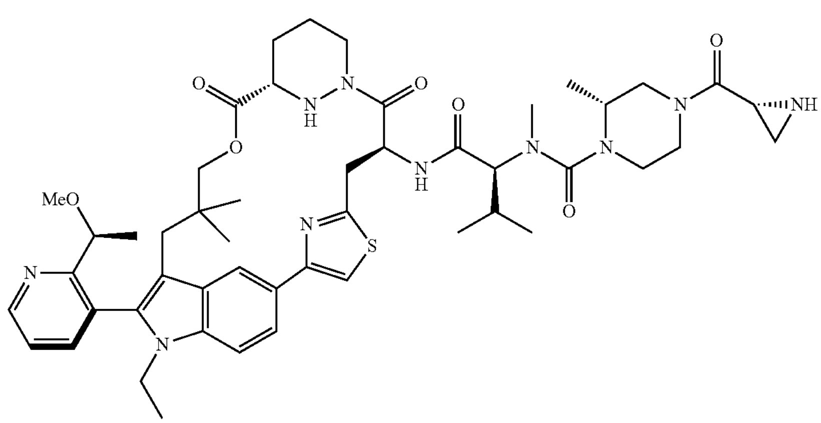 |

TABLE 1-continued

Certain Compounds of the Present Invention

| Ex# | Structure |
|---|---|
| 302 | 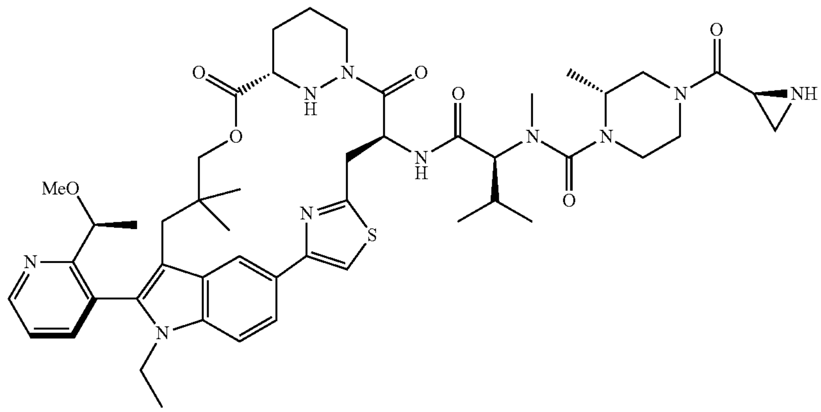 |
| 303 | 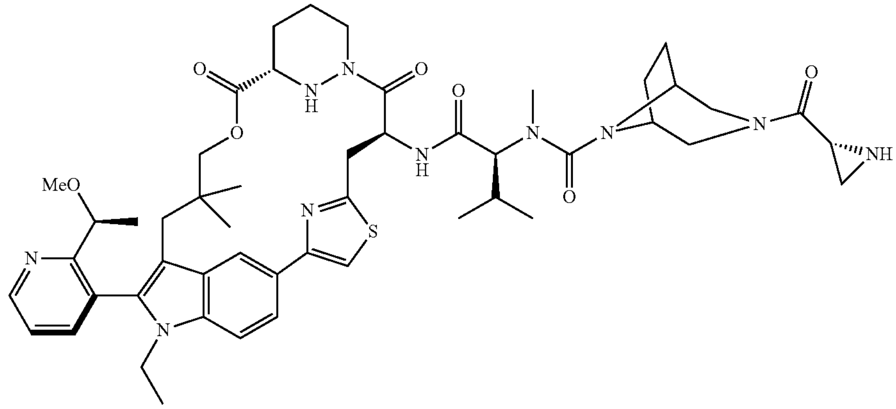 |
| 304 | 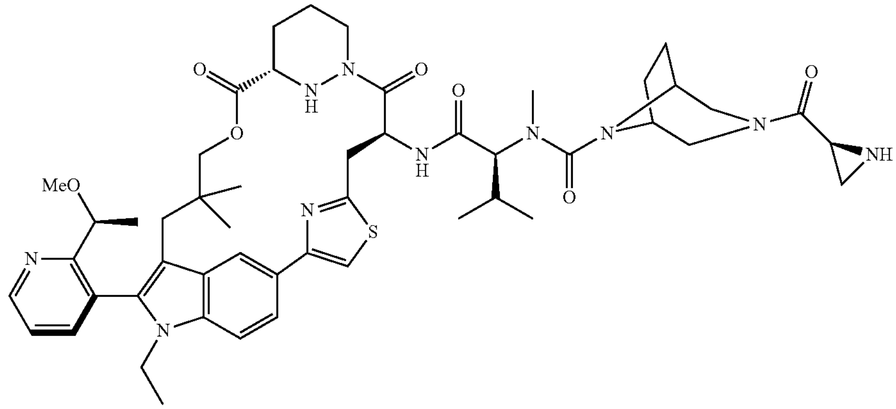 |

TABLE 1-continued

Certain Compounds of the Present Invention

| Ex# | Structure |
|---|---|
| 305 | 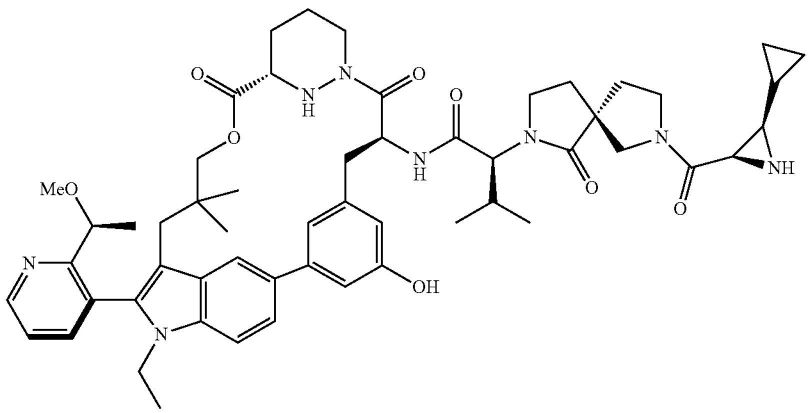 |
| 306 | 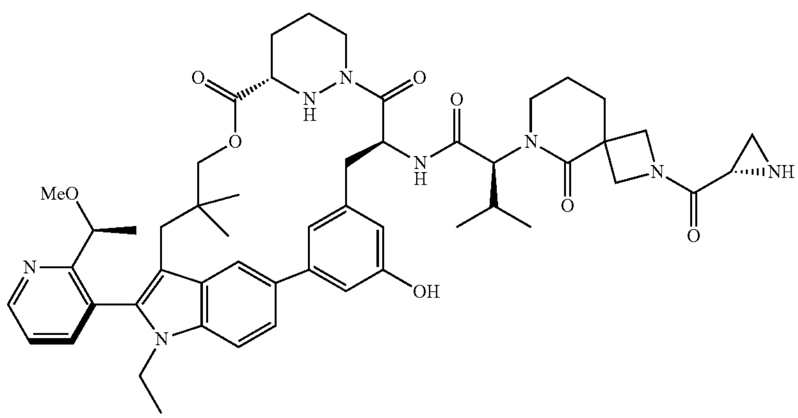 |
| 307 | 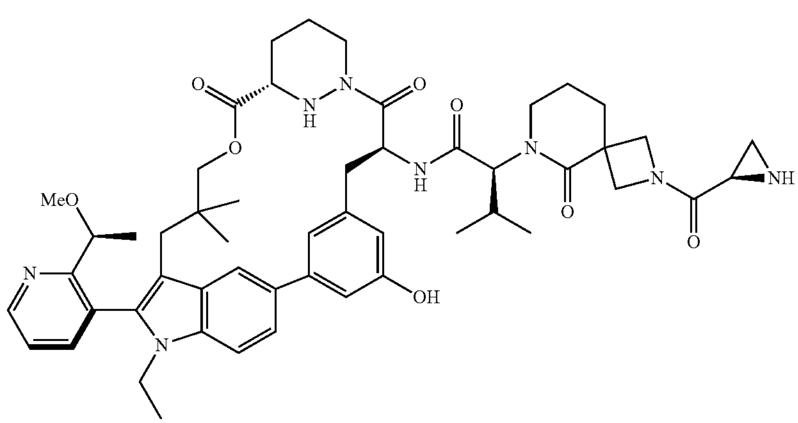 |

TABLE 1-continued

Certain Compounds of the Present Invention

| Ex# | Structure |
|---|---|
| 308* | 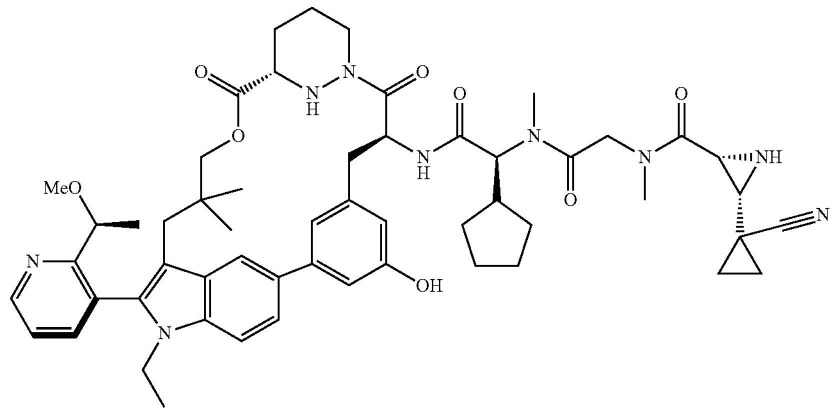 |
| 309 | 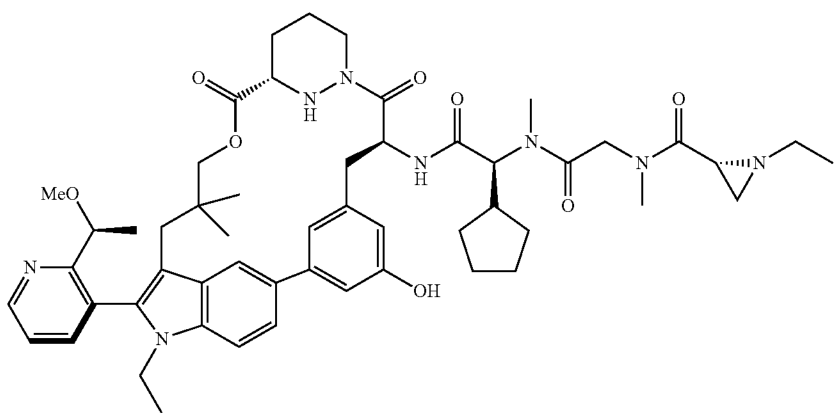 |
| 310 | 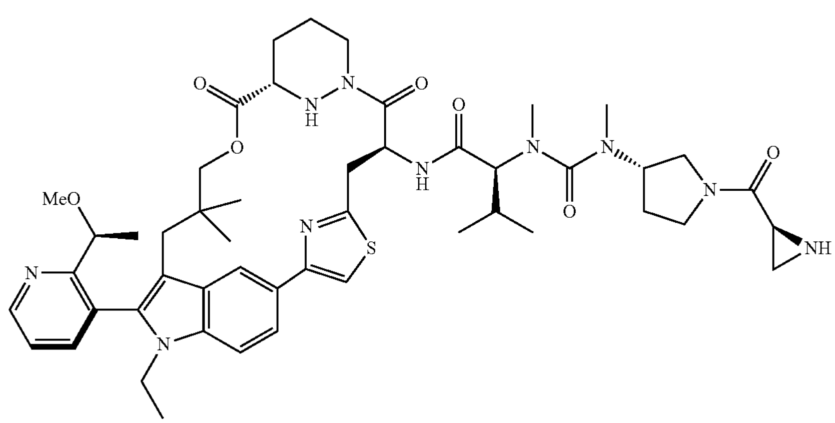 |

TABLE 1-continued

Certain Compounds of the Present Invention

| Ex# | Structure |
|---|---|
| 311 | 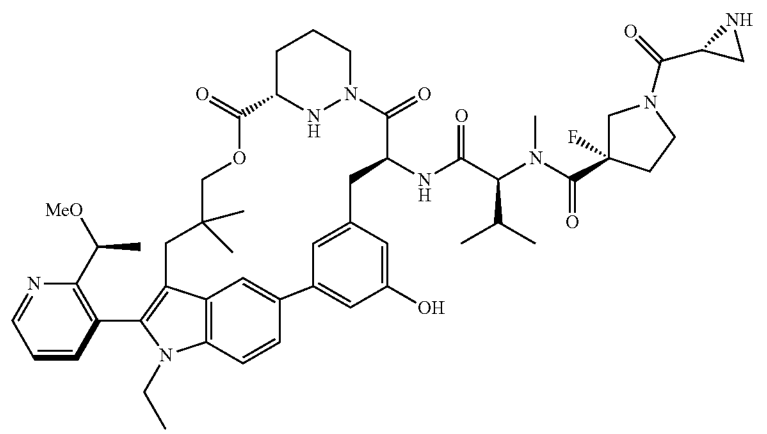 |
| 312 | 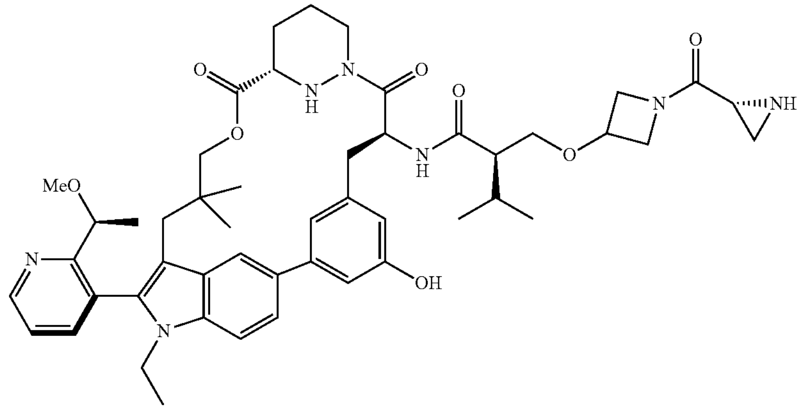 |
| 313 | 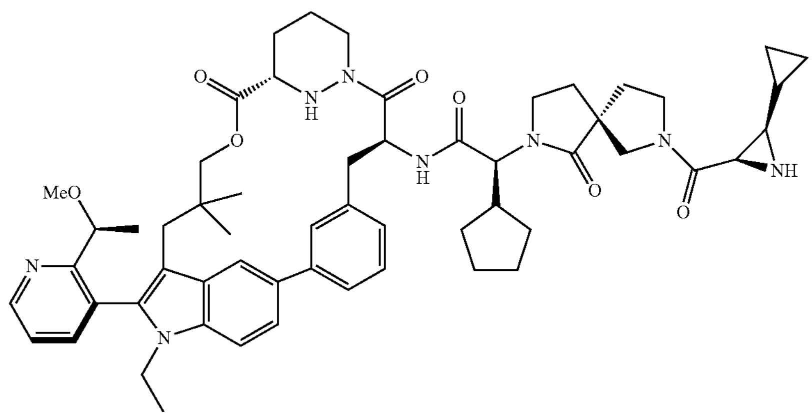 |

TABLE 1-continued

Certain Compounds of the Present Invention

| Ex# | Structure |
|---|---|
| 314* | 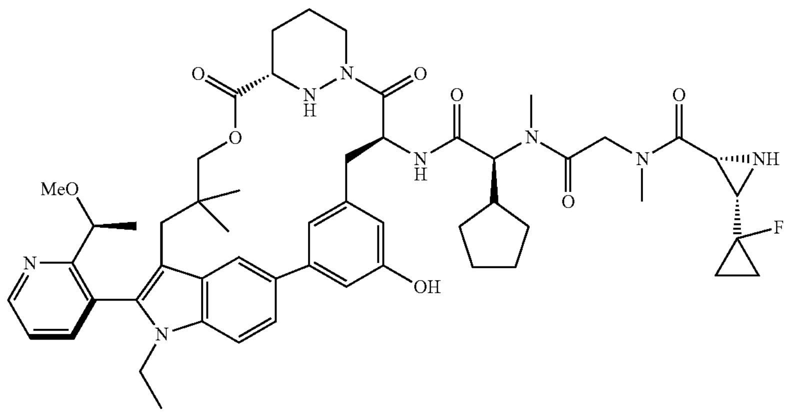 |
| 315* | 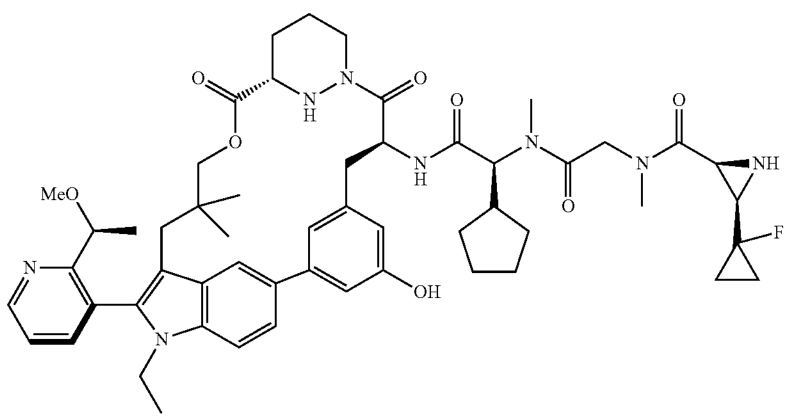 |
| 316* | 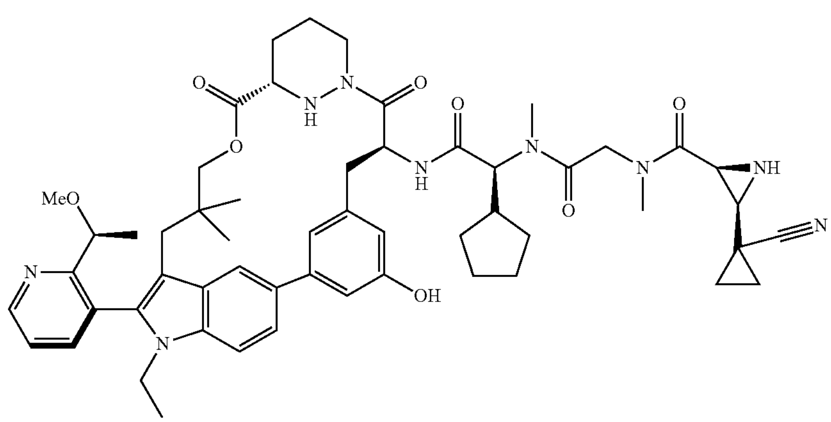 |

TABLE 1-continued
Certain Compounds of the Present Invention
| Ex# | Structure |
|---|---|
| 317 | 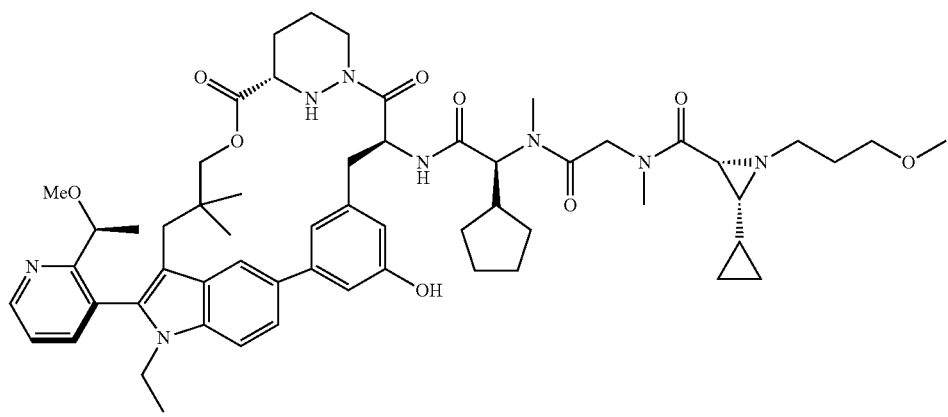 |
| 318 | 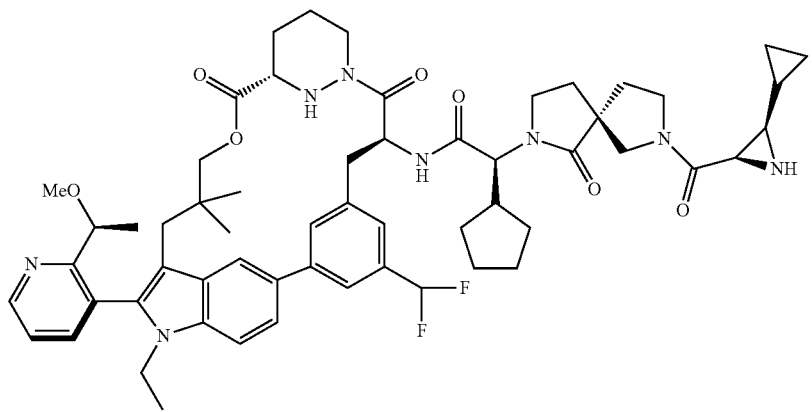 |
| 319 | 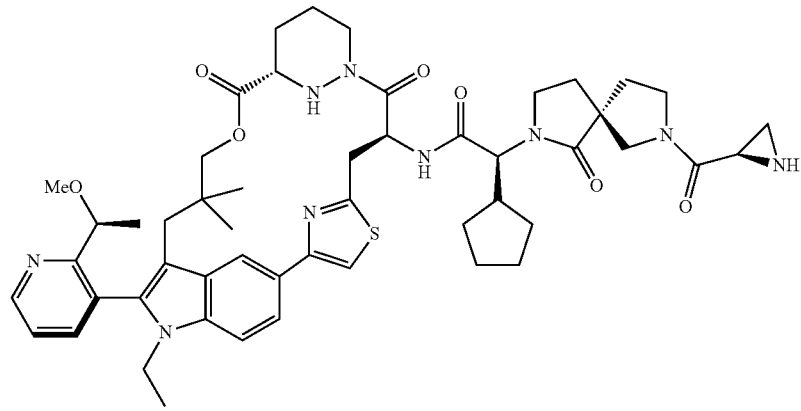 |

TABLE 1-continued

Certain Compounds of the Present Invention

| Ex# | Structure |
|---|---|
| 320 | 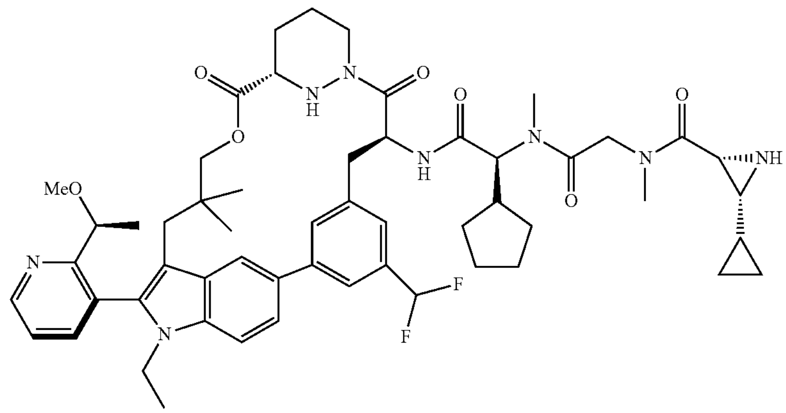 |
| 321 | 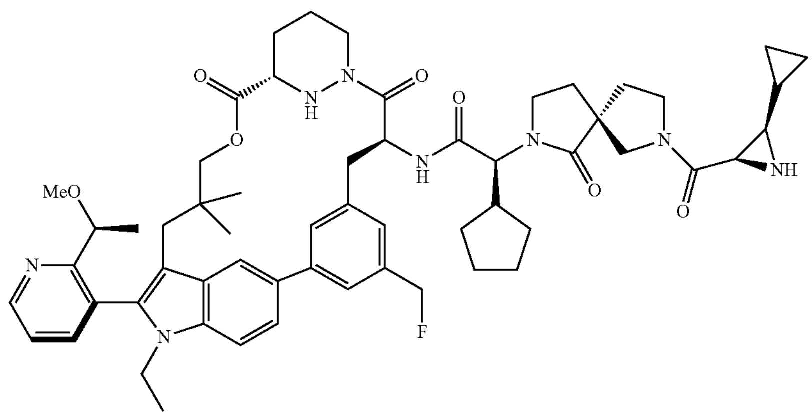 |
| 322* | 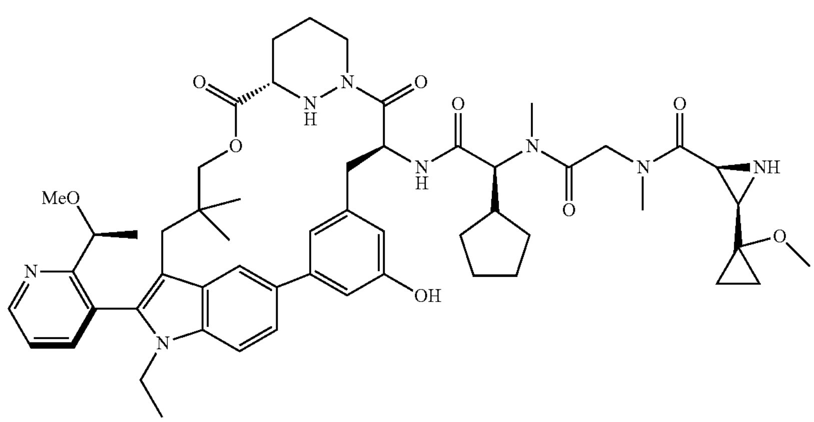 |

TABLE 1-continued

Certain Compounds of the Present Invention

| Ex# | Structure |
|---|---|
| 323* | 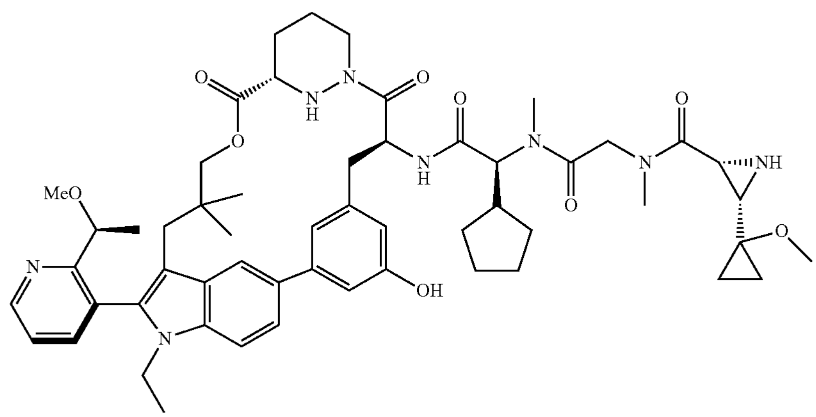 |
| 324 | 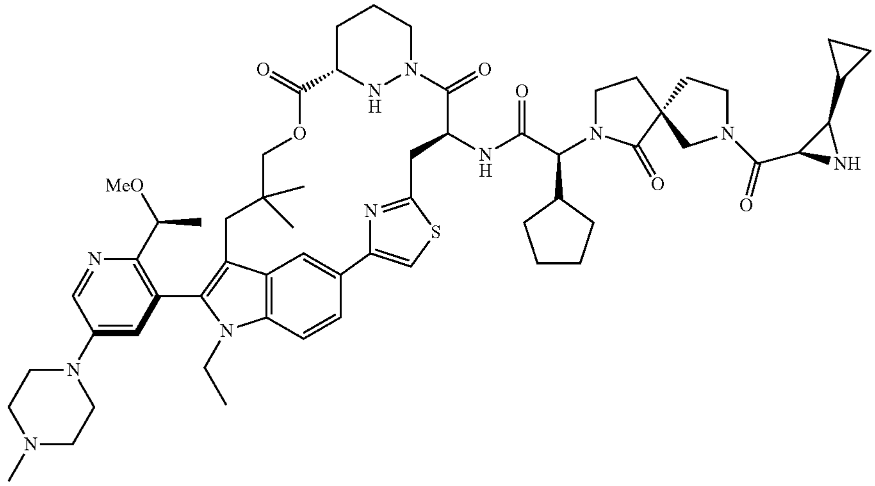 |
| 325 | 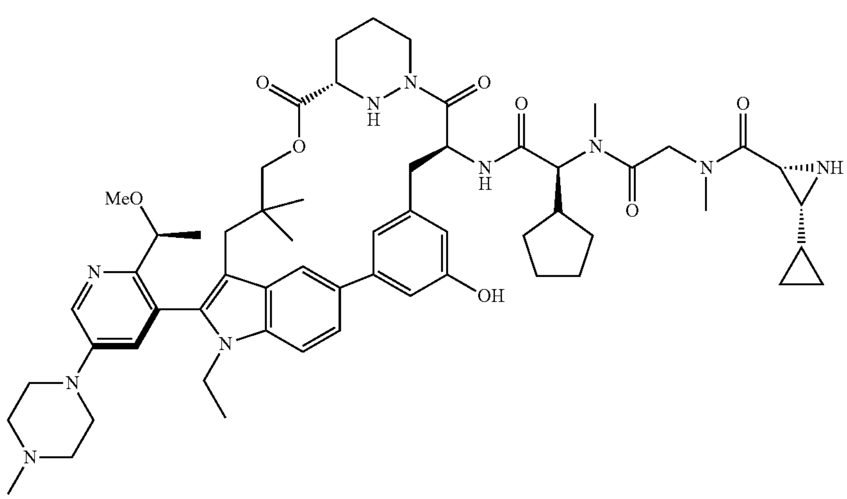 |

US 11,739,074 B2
271 272
TABLE 1-continued
Certain Compounds of the Present Invention
| Ex# | Structure |
|---|---|
| 326 | 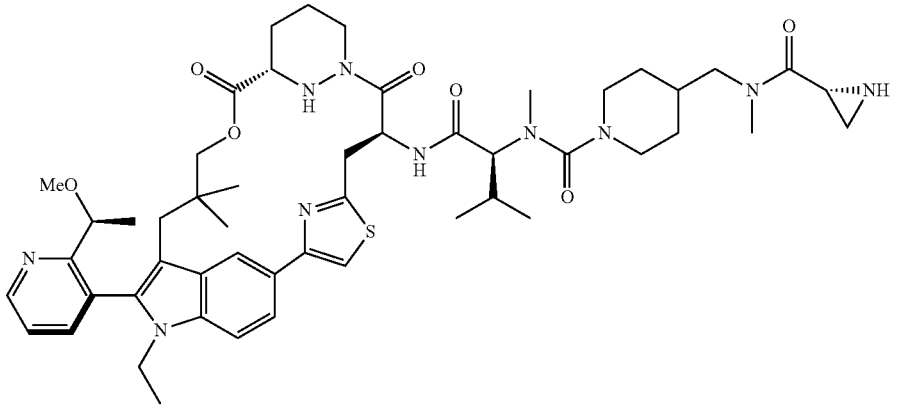 |
| 327 | 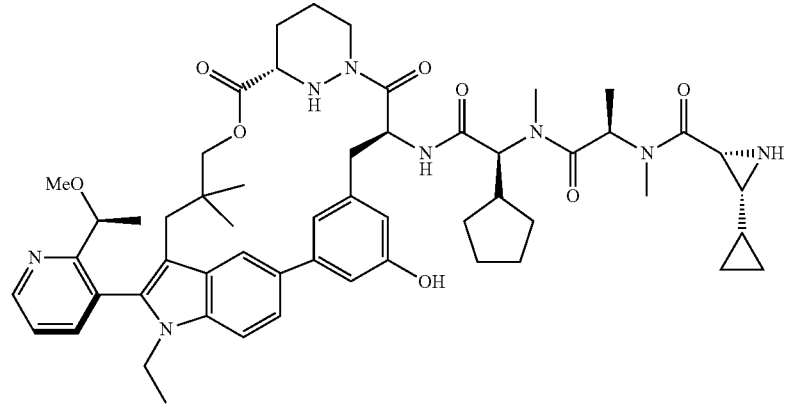 |
| 328 | 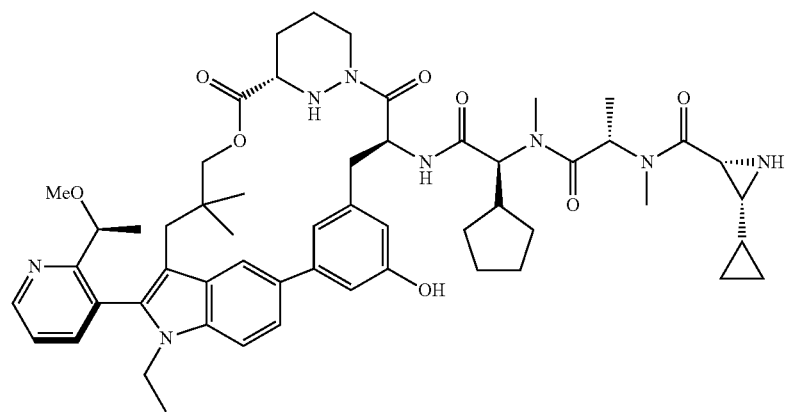 |

TABLE 1-continued

Certain Compounds of the Present Invention

| Ex# | Structure |
|---|---|
| 329 | 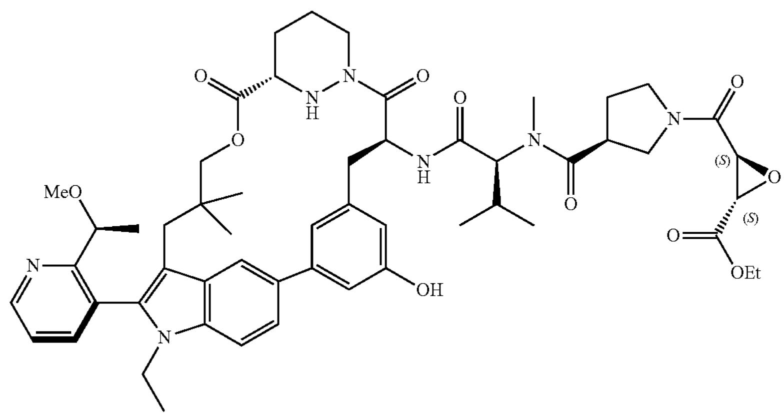 |
| 330 | 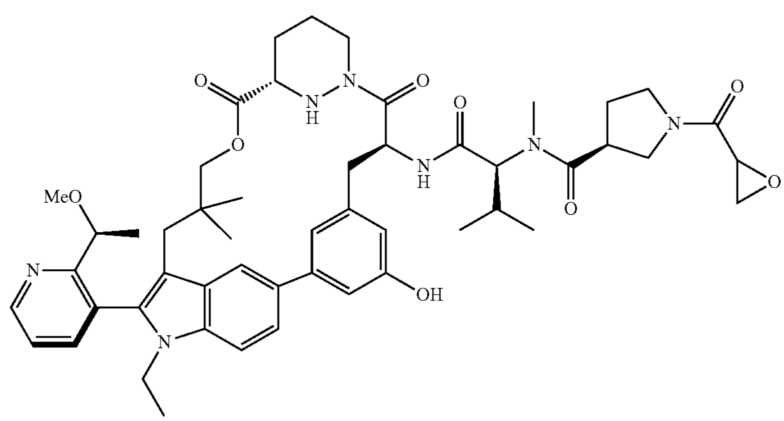 |
| 331 | 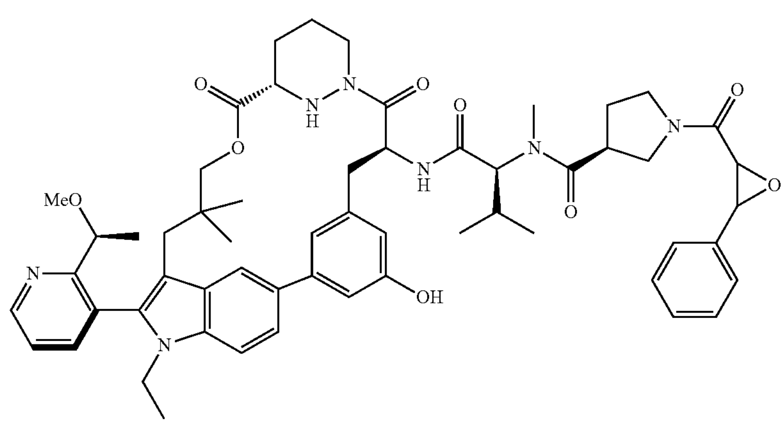 |

TABLE 1-continued

Certain Compounds of the Present Invention

| Ex# | Structure |
|---|---|
| 332 | 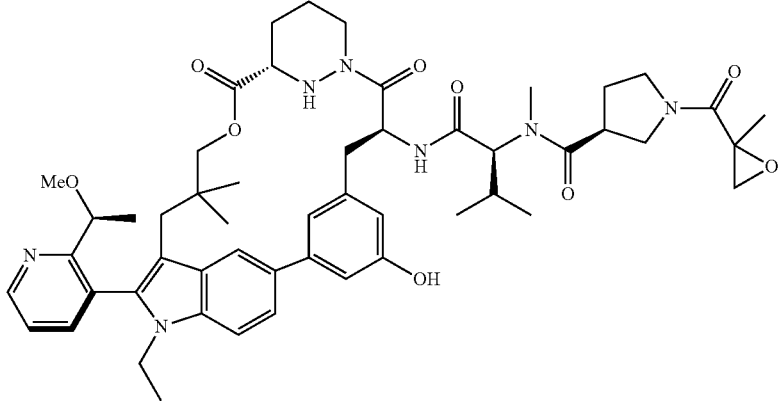 |

*Stereochemistry of the aziridine carbon is assumed.

Note that some comounds are shown with bonds as flat or wedged. In some instances, the relative stereochemistry of stereoisomers has been determined; in some instances, the absolute stereochemistry has been determined. In some instances, a single Example number corresponds to a mixture of stereoisomers. All stereoisomers of the compounds of the foregoing table are contemplated by the pressent invention. In particular embodiments, an atropisomer of a compound of the foregoing table is contemplated.

In some embodiments, a compound of Table 2 is provided, or a pharmaceutically acceptable salt thereof. In some embodiments, a compound of the present invention is selected from Table 2, or a pharmaceutically acceptable salt or atropisomer thereof.

TABLE 2

Certain Compounds of the Present Invention

| Ex # | Structure |
|---|---|
| B5 | 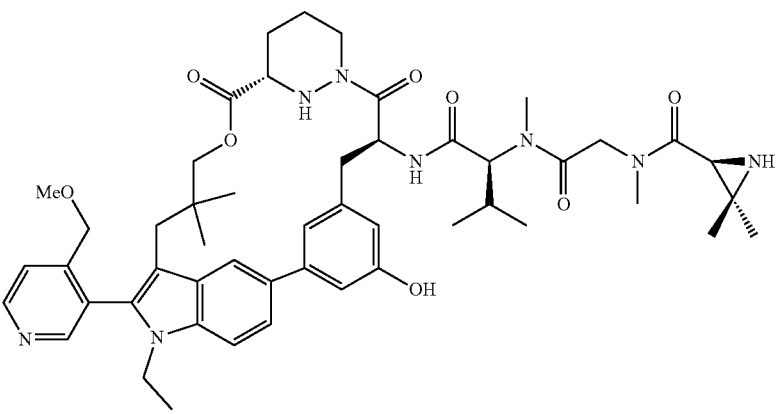 |

TABLE 2-continued
Certain Compounds of the Present Invention
| Ex # | Structure |
|---|---|
| B6 | 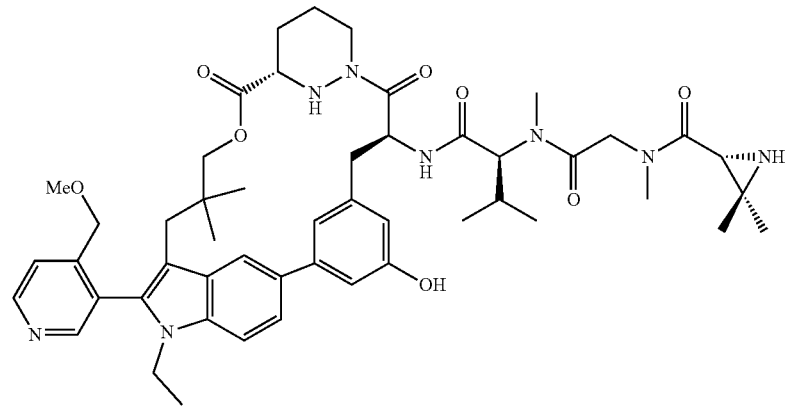 |
| B8 | 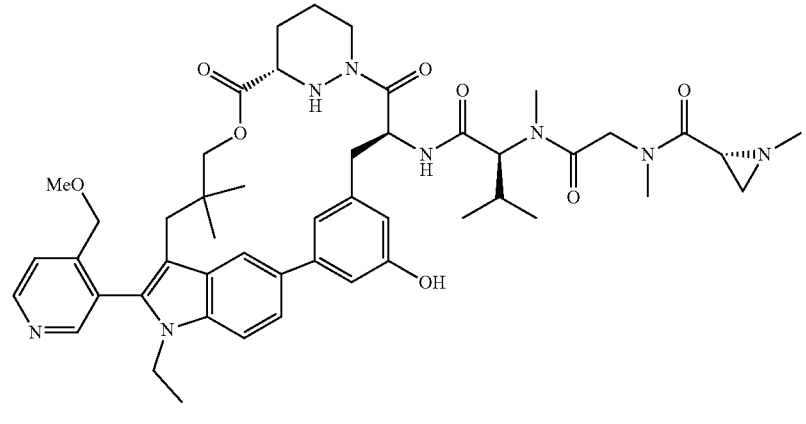 |
| B9 | 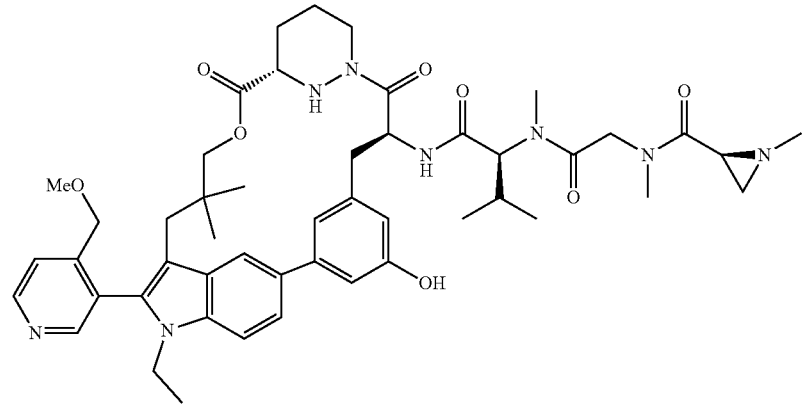 |

TABLE 2-continued
Certain Compounds of the Present Invention
| Ex # | Structure |
|------|-----------|
| B16 | 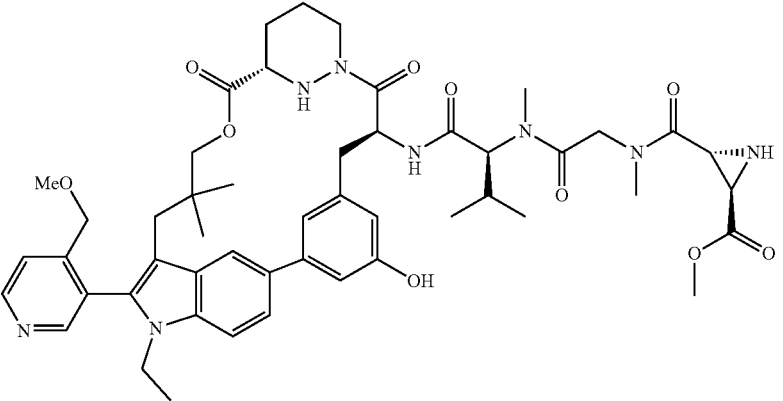 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@H]1C(=O)OC)C(=O)N1CCC[C@H](N1)C(=O)OCC(C)(C)C2] |
| B19 | 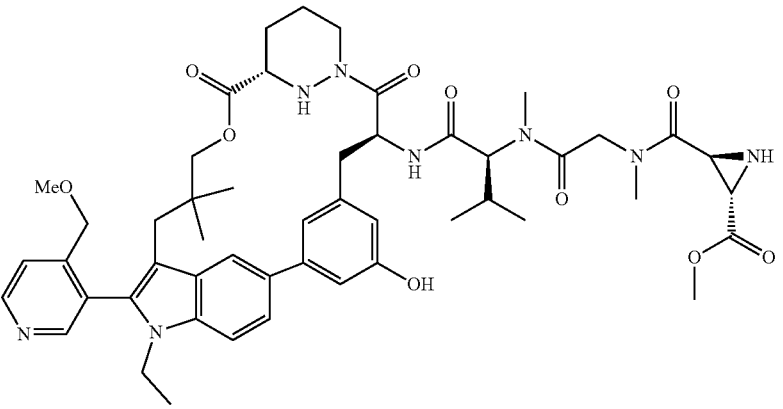 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@@H]1C(=O)OC)C(=O)N1CCC[C@H](N1)C(=O)OCC(C)(C)C2] |
| B29 | 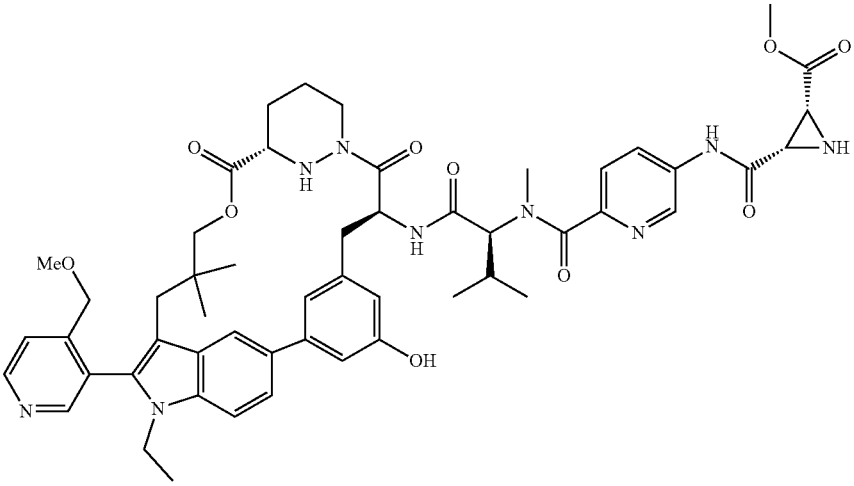 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC(=O)[C@H]3N[C@H]3C(=O)OC)cn1)C(=O)N1CCC[C@H](N1)C(=O)OCC(C)(C)C2] |

TABLE 2-continued

Certain Compounds of the Present Invention

| Ex # | Structure |
|------|-----------|
| B30  | 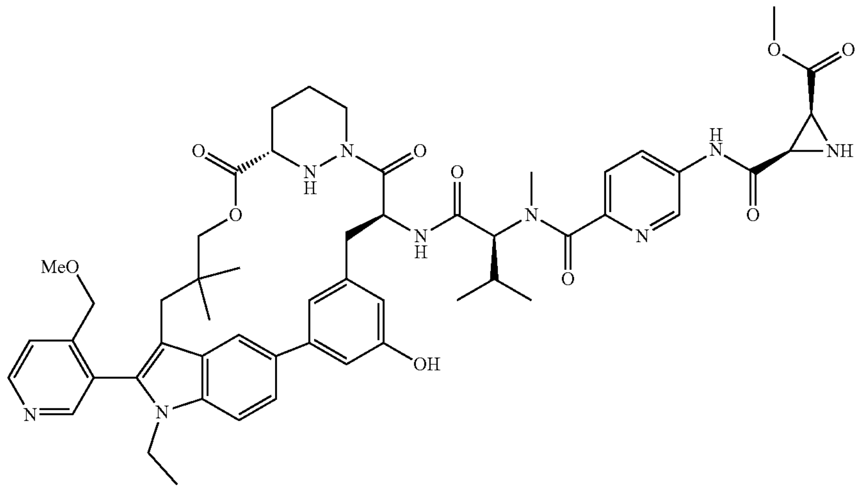 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC(=O)[C@@H]3N[C@@H]3C(=O)OC)cn1)C(=O)N1CCC[C@H](N1)C(=O)OCC(C)(C)C2]          |
| B31  | 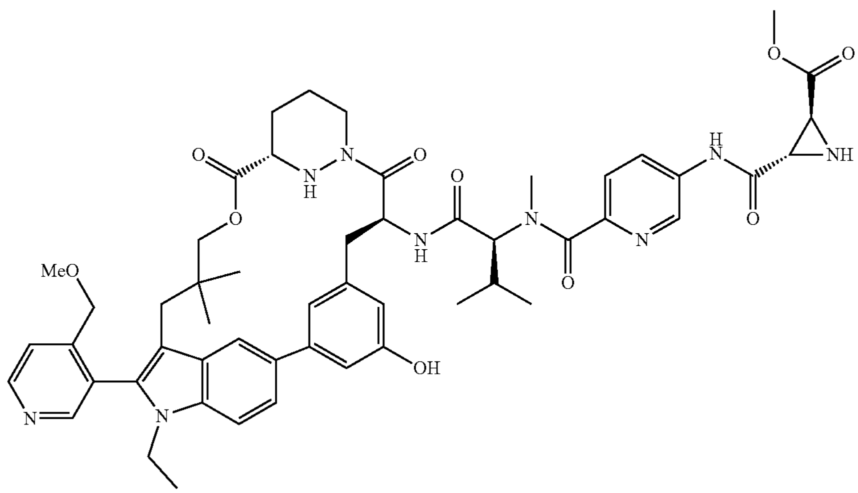 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC(=O)[C@H]3N[C@@H]3C(=O)OC)cn1)C(=O)N1CCC[C@H](N1)C(=O)OCC(C)(C)C2]          |
| B32  | 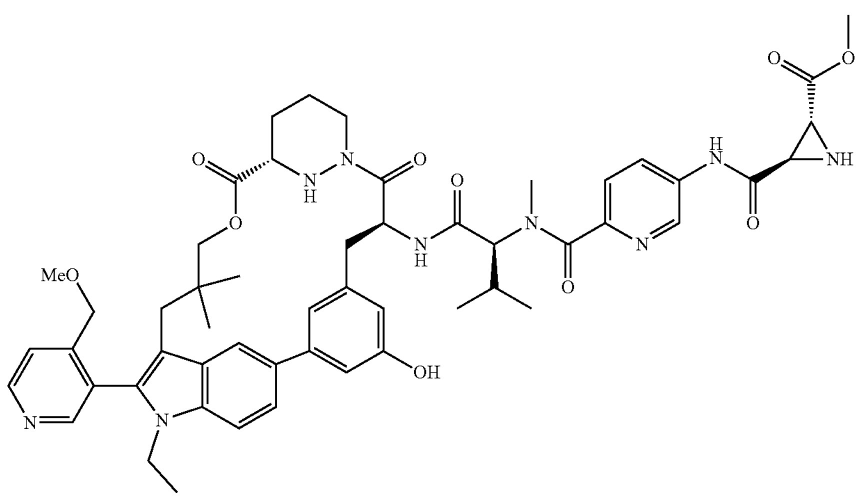 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC(=O)[C@@H]3N[C@H]3C(=O)OC)cn1)C(=O)N1CCC[C@H](N1)C(=O)OCC(C)(C)C2]          |

TABLE 2-continued
Certain Compounds of the Present Invention
| Ex # | Structure |
|---|---|
| B35 | 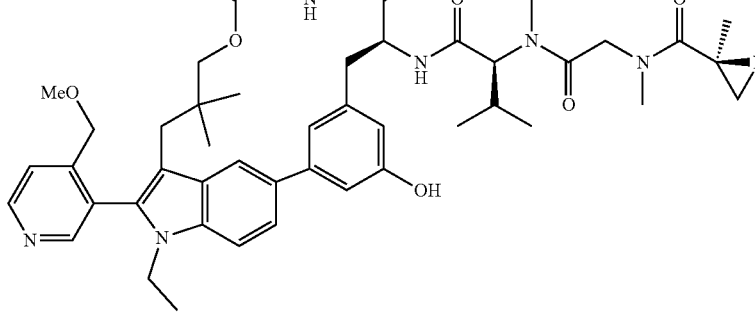 |
| B36 | 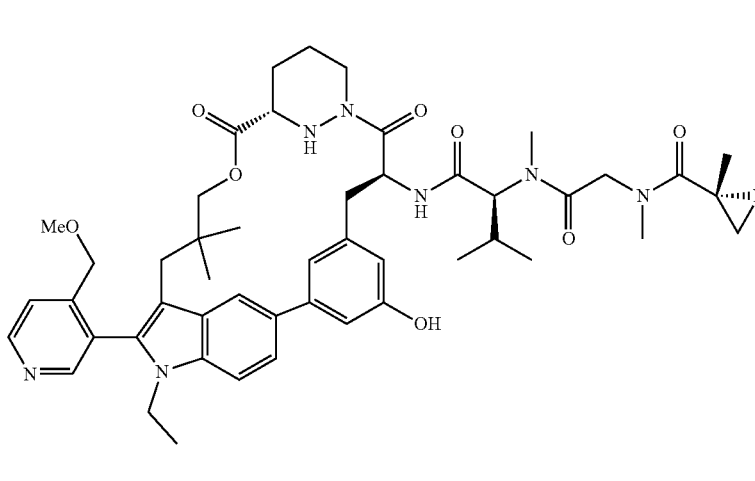 |
| B37 | 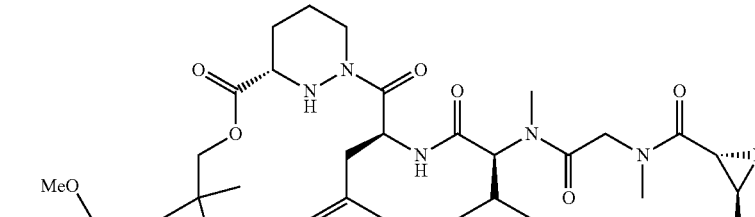 |

TABLE 2-continued

Certain Compounds of the Present Invention

| Ex # | Structure |
|---|---|
| B38 | 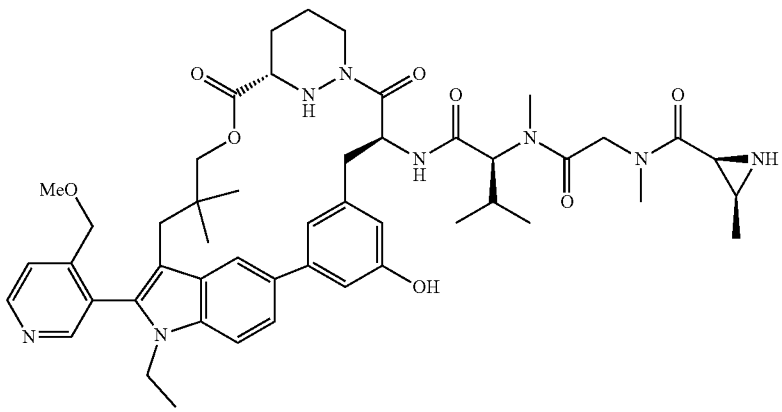 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@H]1C)C(=O)N1CCC[C@H](N1)C(=O)OCC(C)(C)C2] |
| B40 | 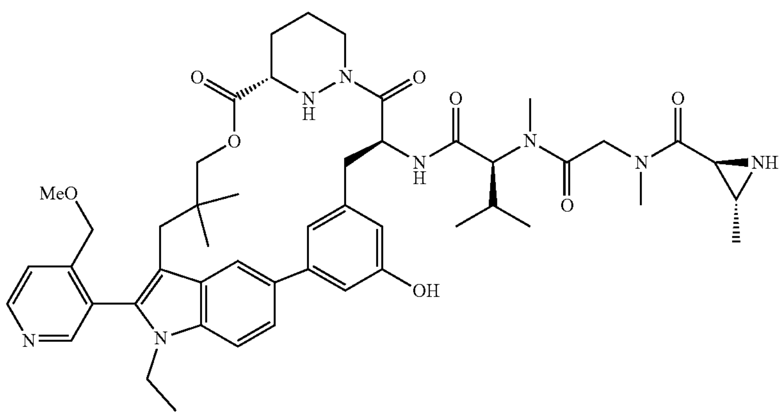 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@@H]1C)C(=O)N1CCC[C@H](N1)C(=O)OCC(C)(C)C2] |
| B41 | 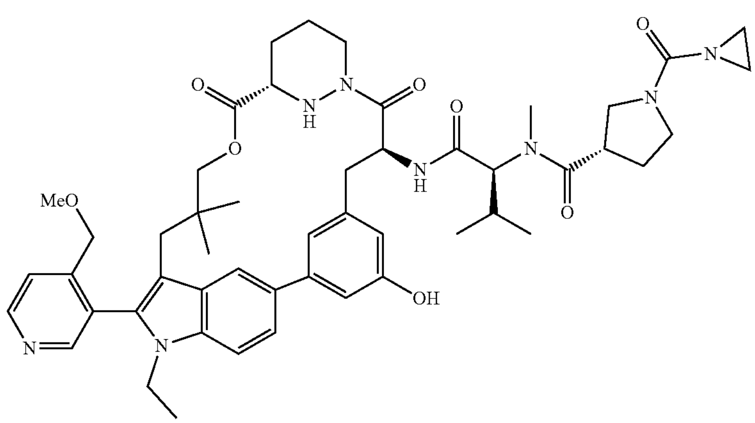 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(C(=O)N3CC3)C1)C(=O)N1CCC[C@H](N1)C(=O)OCC(C)(C)C2] |

TABLE 2-continued

Certain Compounds of the Present Invention

| Ex # | Structure |
|---|---|
| B42 | 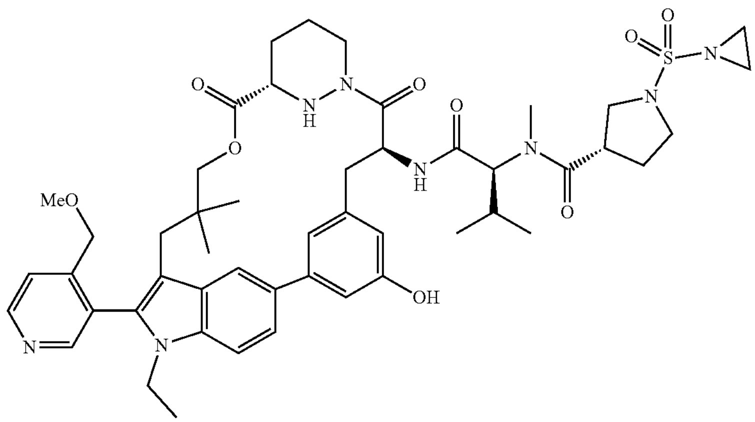 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(S(=O)(=O)N3CC3)C1)C(=O)N1CCC[C@H](N1)C(=O)OCC(C)(C)C2] |
| B43 | 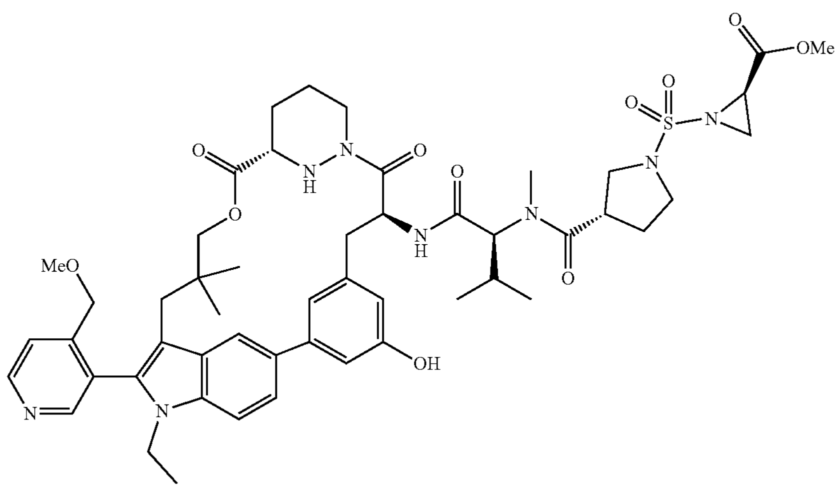 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(S(=O)(=O)N3C[C@@H]3C(=O)OC)C1)C(=O)N1CCC[C@H](N1)C(=O)OCC(C)(C)C2] |
| B44 | 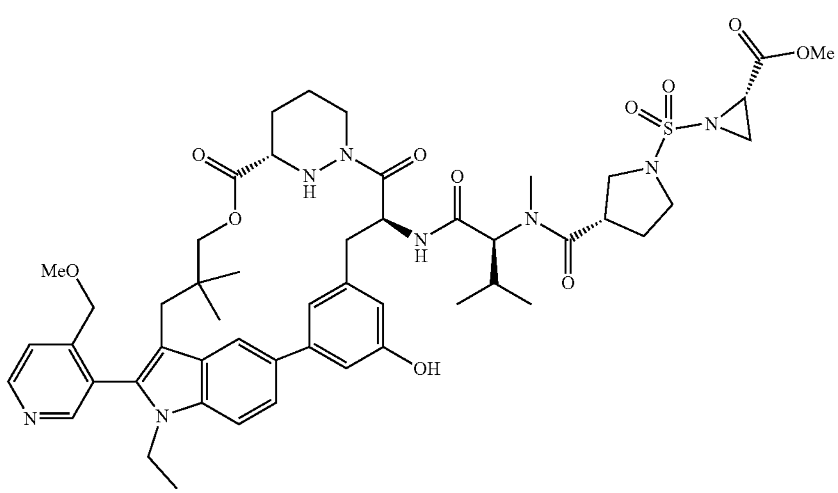 [SMILES: CCn1c(-c2cnccc2COC)c2c3cc(ccc31)-c1cc(O)cc(c1)C[C@H](NC(=O)[C@H](C(C)C)N(C)C(=O)[C@H]1CCN(S(=O)(=O)N3C[C@H]3C(=O)OC)C1)C(=O)N1CCC[C@H](N1)C(=O)OCC(C)(C)C2] |

TABLE 2-continued
Certain Compounds of the Present Invention
| Ex # | Structure |
|------|-----------|
| B46 | 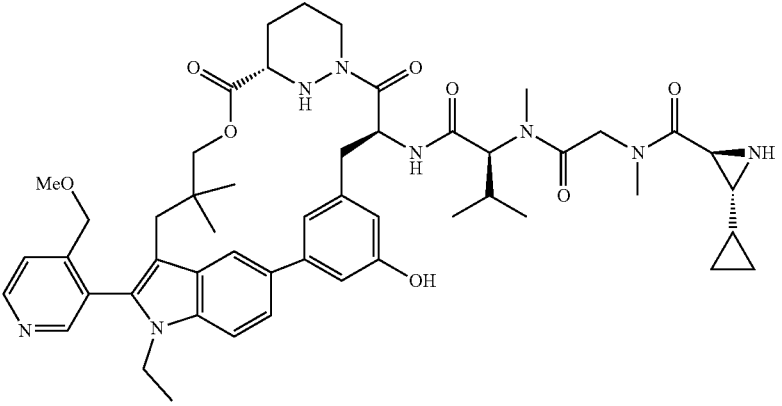 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1N[C@@H]1C1CC1)C(=O)N1CCC[C@H](N1)C(=O)OCC(C)(C)C2] |
| B48 | 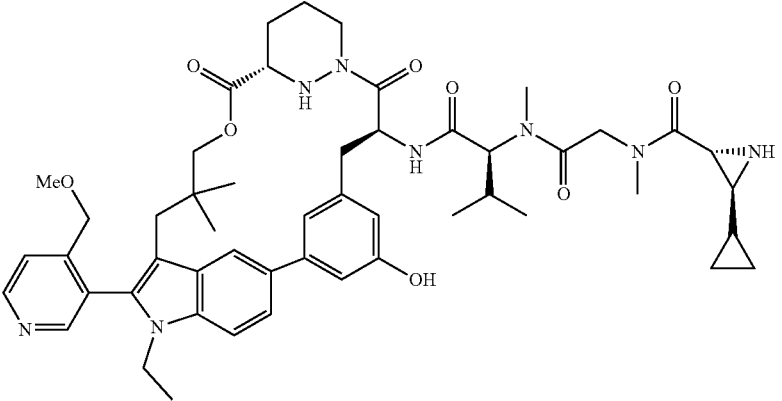 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@H]1C1CC1)C(=O)N1CCC[C@H](N1)C(=O)OCC(C)(C)C2] |
| B51 | 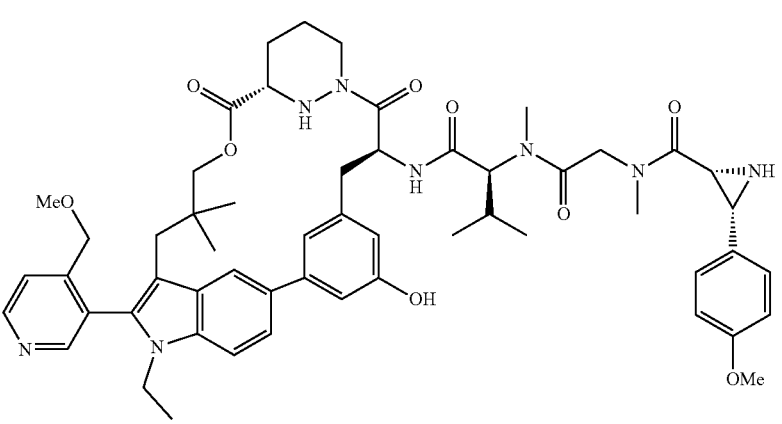 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1c1ccc(OC)cc1)C(=O)N1CCC[C@H](N1)C(=O)OCC(C)(C)C2] |

TABLE 2-continued

Certain Compounds of the Present Invention

| Ex # | Structure |
|---|---|
| B53 | 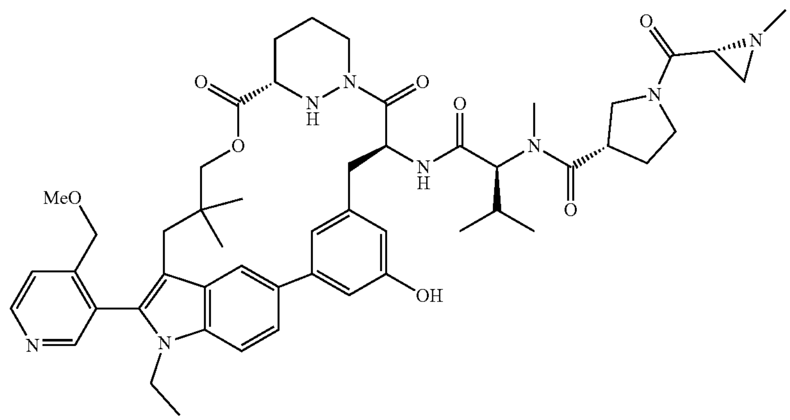 |
| B54 | 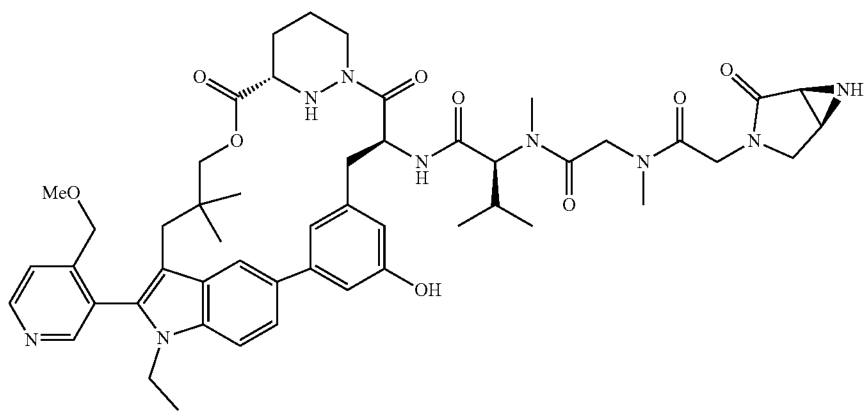 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)CN1C[C@@H]3N[C@@H]3C1=O)C(=O)N1CCC[C@H](N1)C(=O)OCC(C)(C)C2] |
| B55 | 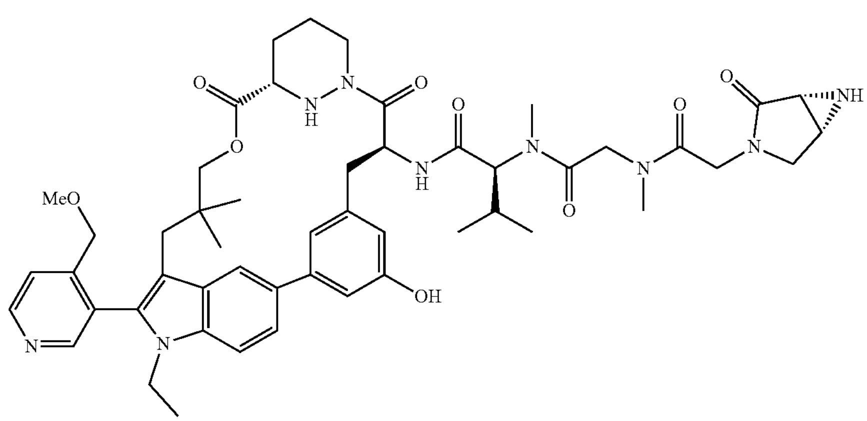 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)CN1C[C@H]3N[C@H]3C1=O)C(=O)N1CCC[C@H](N1)C(=O)OCC(C)(C)C2] |

TABLE 2-continued

Certain Compounds of the Present Invention

| Ex # | Structure |
|---|---|
| B56 | 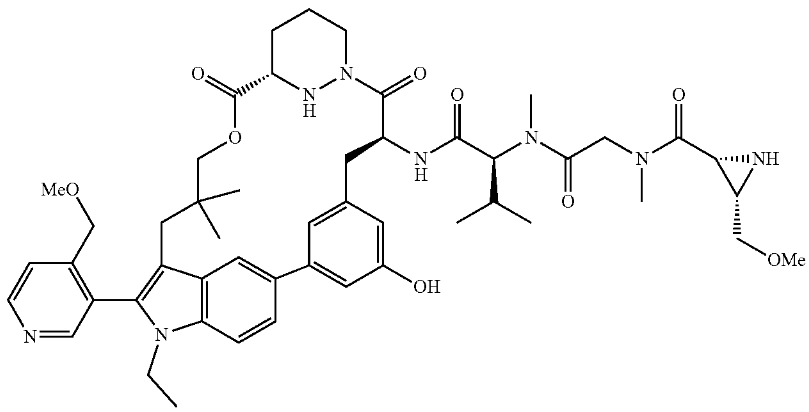 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1COC)C(=O)N1CCC[C@H](N1)C(=O)OCC(C)(C)C2] |
| B57 | 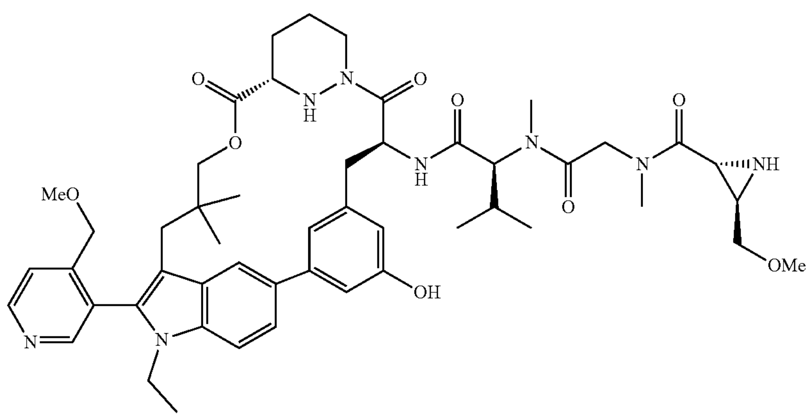 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@H]1COC)C(=O)N1CCC[C@H](N1)C(=O)OCC(C)(C)C2] |
| B58 | 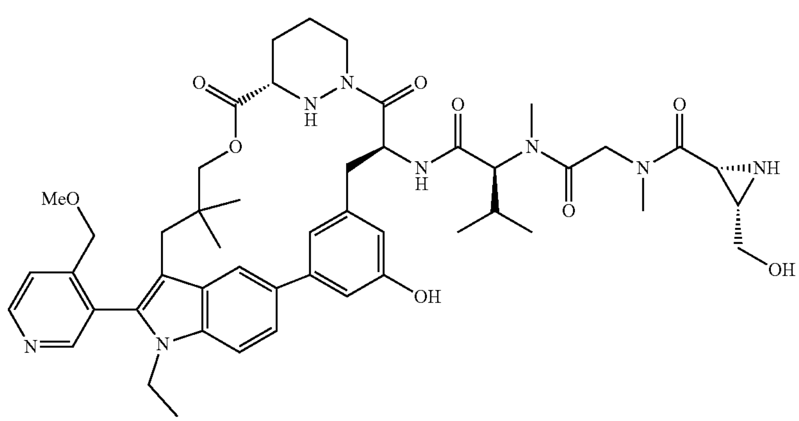 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@@H]1CO)C(=O)N1CCC[C@H](N1)C(=O)OCC(C)(C)C2] |

TABLE 2-continued

Certain Compounds of the Present Invention

| Ex # | Structure |
|---|---|
| B59 | 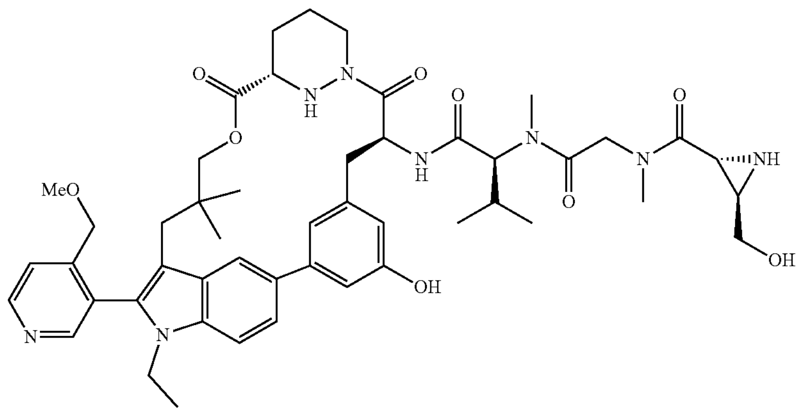 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@@H]1N[C@H]1CO)C(=O)N1CCC[C@H](N1)C(=O)OCC(C)(C)C2] |
| B60 | 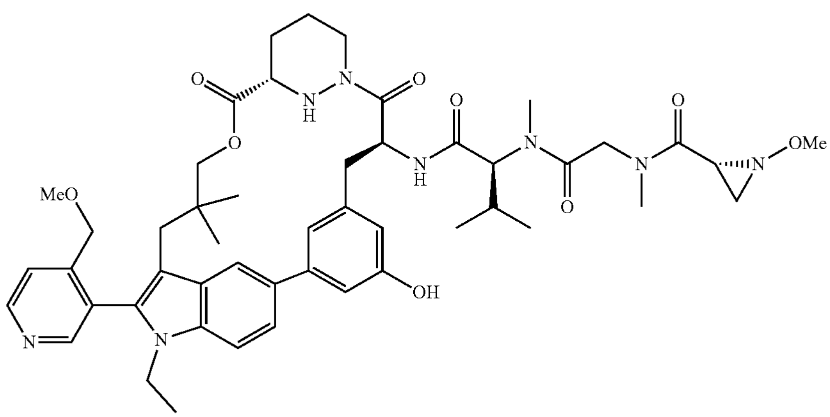 |
| B61 | 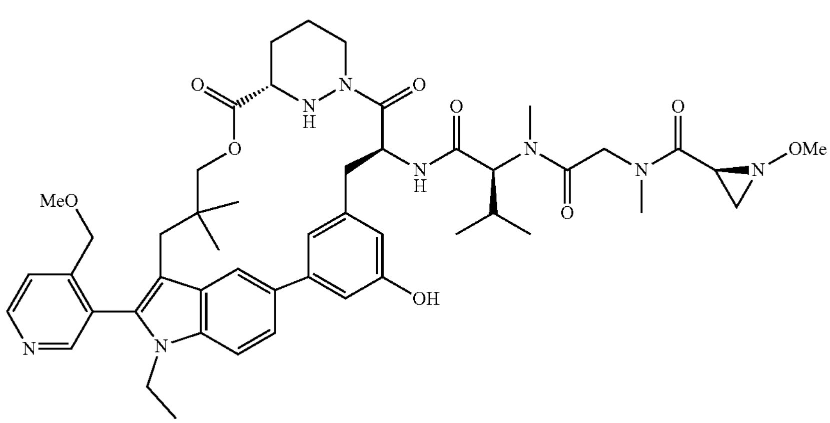 |

TABLE 2-continued
Certain Compounds of the Present Invention
| Ex # | Structure |
|------|-----------|
| B62 | 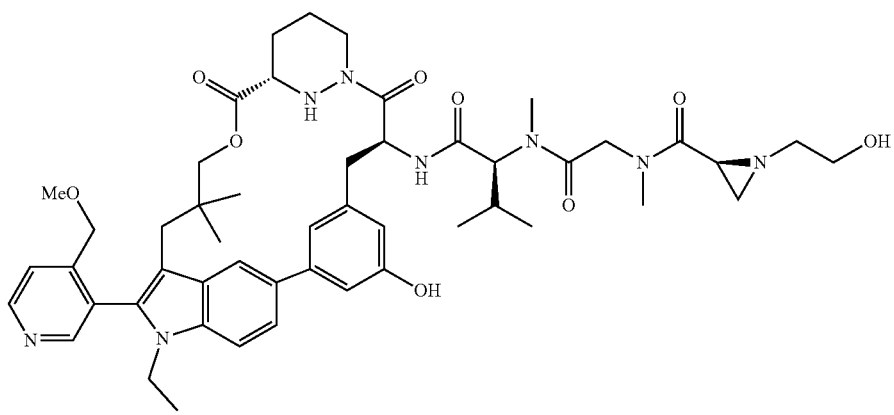 |
| B63 | 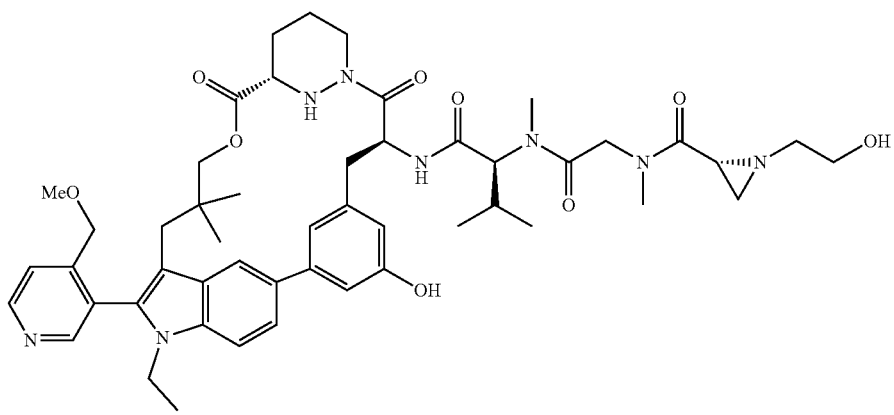 |
| B73 | 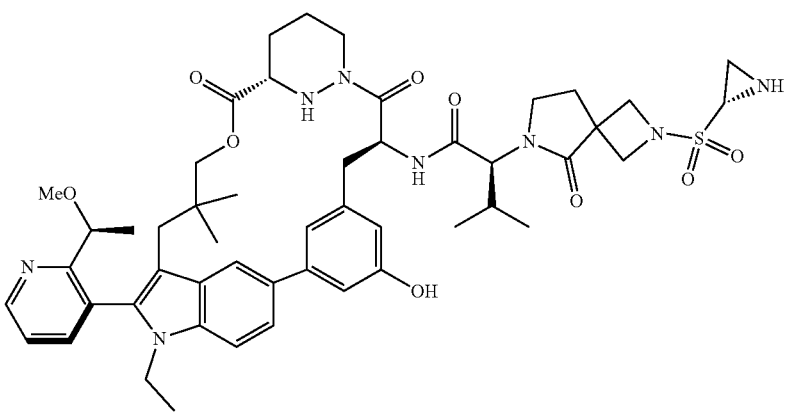 |

TABLE 2-continued

Certain Compounds of the Present Invention

| Ex # | Structure |
| --- | --- |
| B74 | 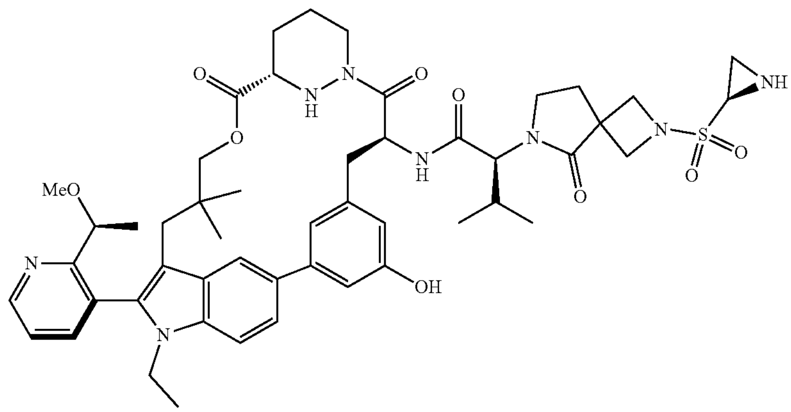 |
| B76 | 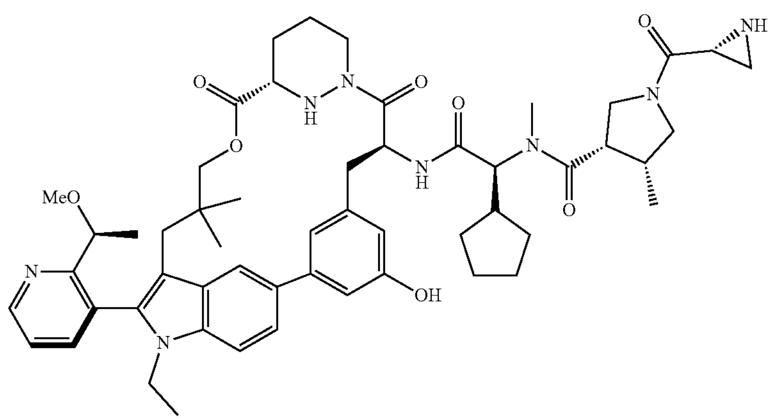 |
| B78 | 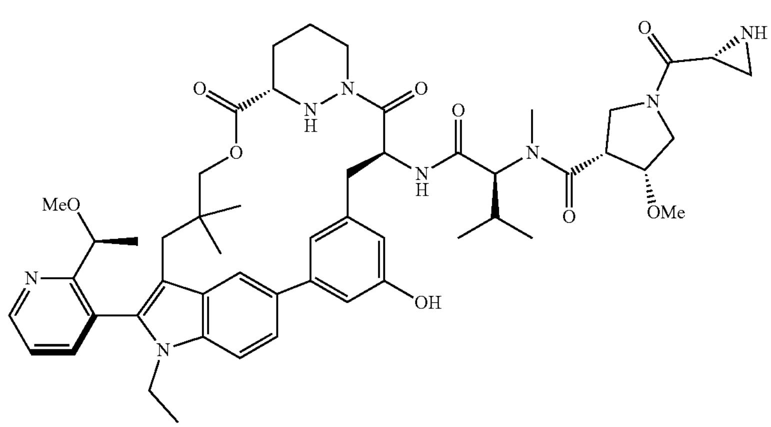 |

TABLE 2-continued

Certain Compounds of the Present Invention

| Ex # | Structure |
|---|---|
| B79 | 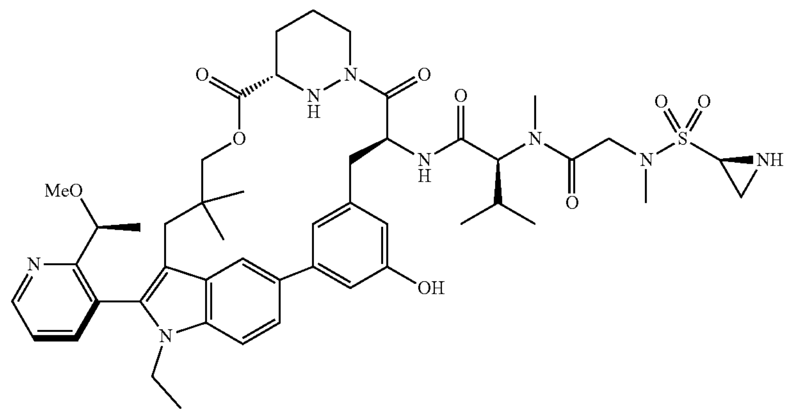 |
| B80 | 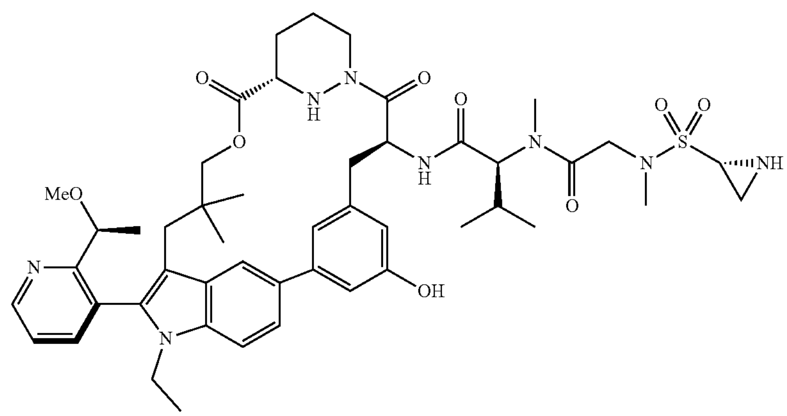 |
| B83 | 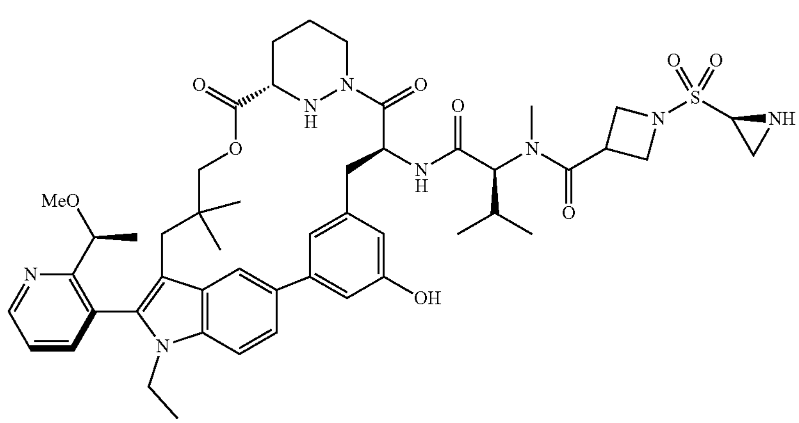 |

TABLE 2-continued
Certain Compounds of the Present Invention
| Ex # | Structure |
|---|---|
| B84 | 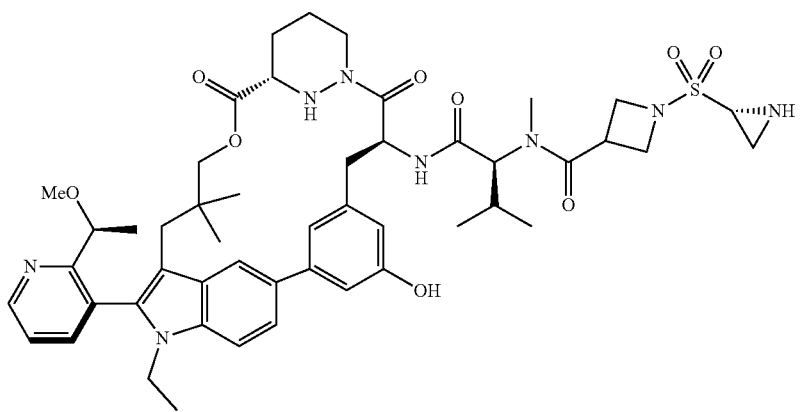 |
| B87 | 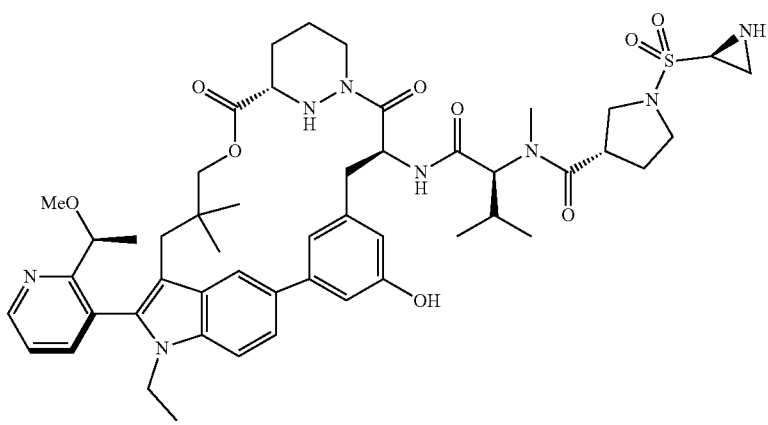 |
| B88 | 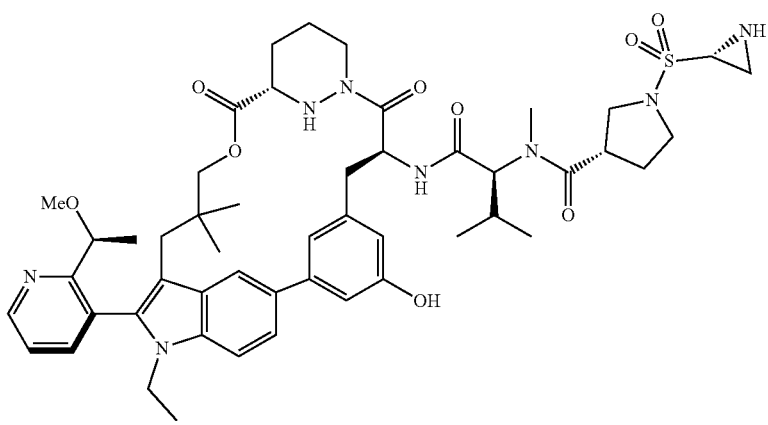 |

TABLE 2-continued

Certain Compounds of the Present Invention

| Ex # | Structure |
|---|---|
| B91 | 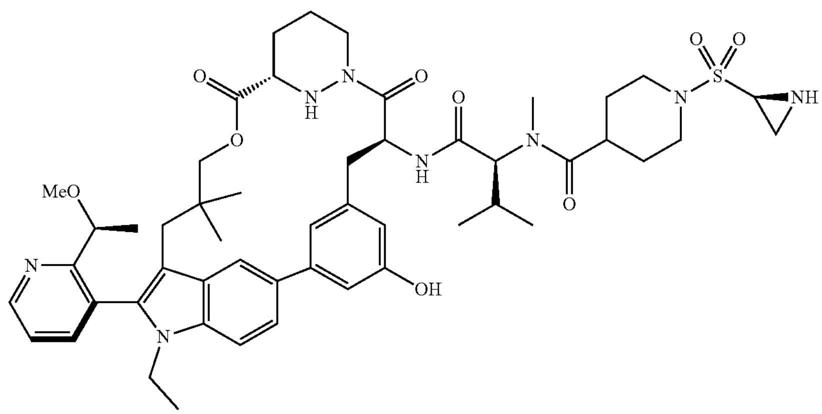 |
| B92 | 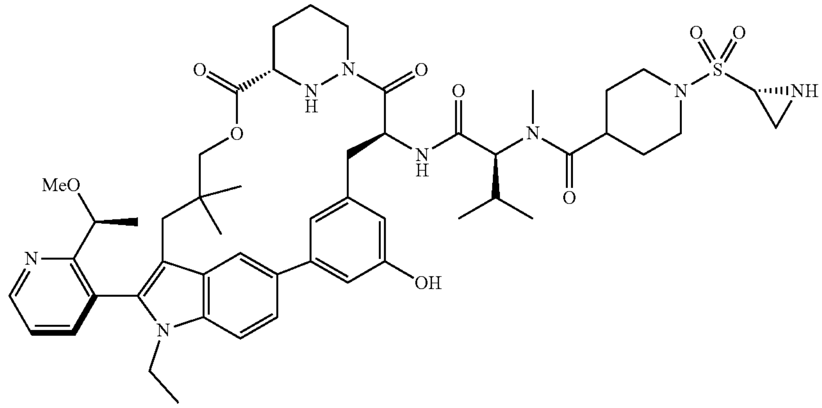 |
| B97 | 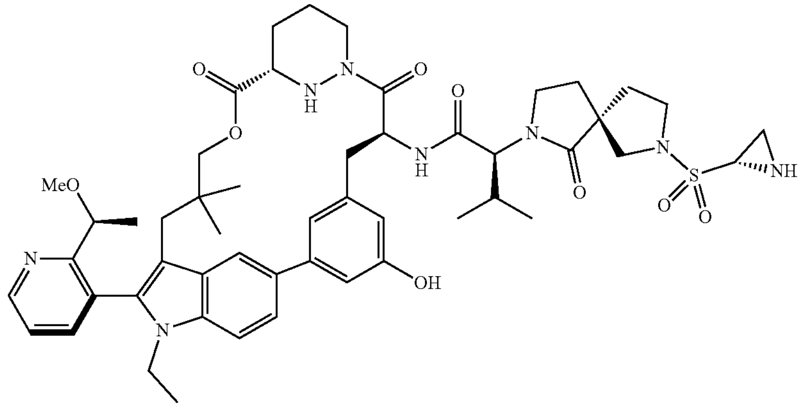 |

TABLE 2-continued

Certain Compounds of the Present Invention

| Ex # | Structure |
|---|---|
| B98 | 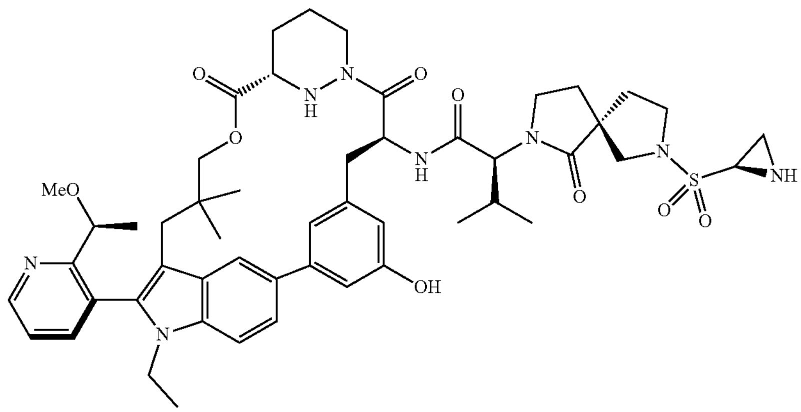 |
| B101 | 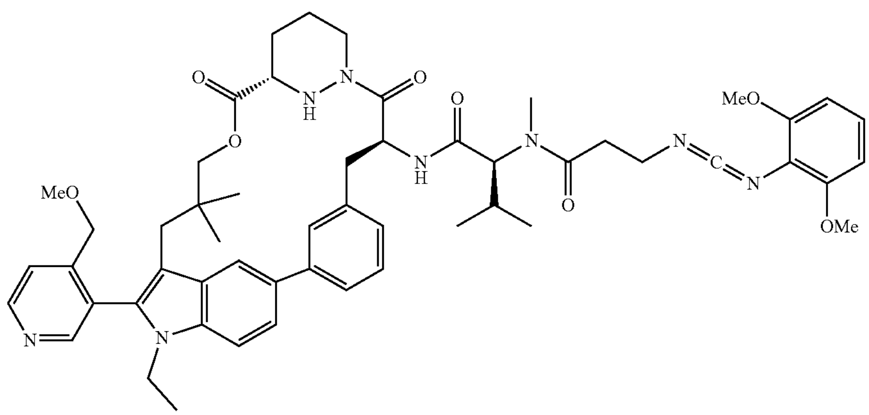 [SMILES: CCn1c(-c2cnccc2COC)c2c3cc(ccc31)-c1cccc(c1)C[C@H](NC(=O)[C@H](C(C)C)N(C)C(=O)CCN=C=Nc1c(OC)cccc1OC)C(=O)N1CCC[C@H](N1)C(=O)OCC(C)(C)C2] |
| B108 | 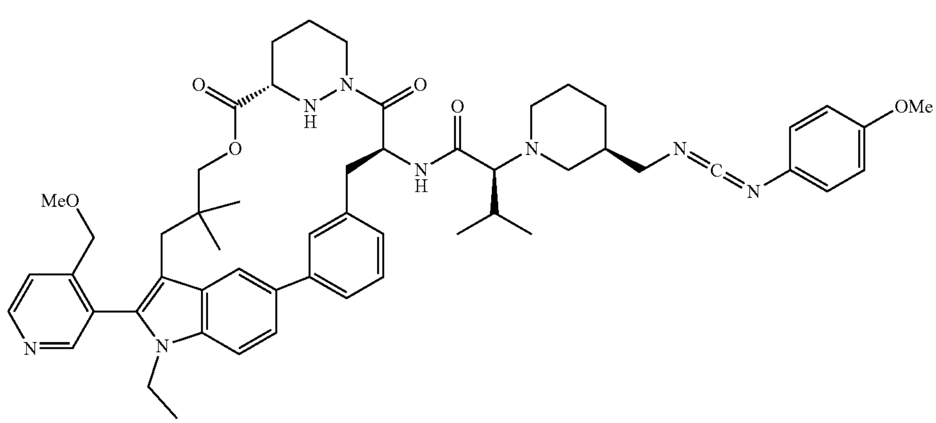 [SMILES: CCn1c(-c2cnccc2COC)c2c3cc(ccc31)-c1cccc(c1)C[C@H](NC(=O)[C@H](C(C)C)N1CCC[C@@H](CN=C=Nc3ccc(OC)cc3)C1)C(=O)N1CCC[C@H](N1)C(=O)OCC(C)(C)C2] |

TABLE 2-continued

Certain Compounds of the Present Invention

| Ex # | Structure |
|---|---|
| B109 | 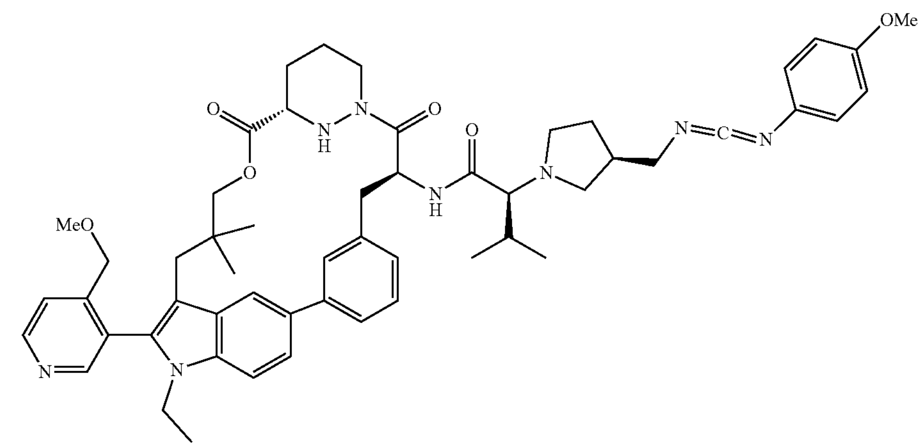 [SMILES: CCn1c(-c2cnccc2COC)c2c3cc(ccc31)-c1cccc(c1)C[C@H](NC(=O)[C@H](C(C)C)N1CC[C@@H](CN=C=Nc3ccc(OC)cc3)C1)C(=O)N1CCC[C@H](N1)C(=O)OCC(C)(C)C2] |
| B113 | 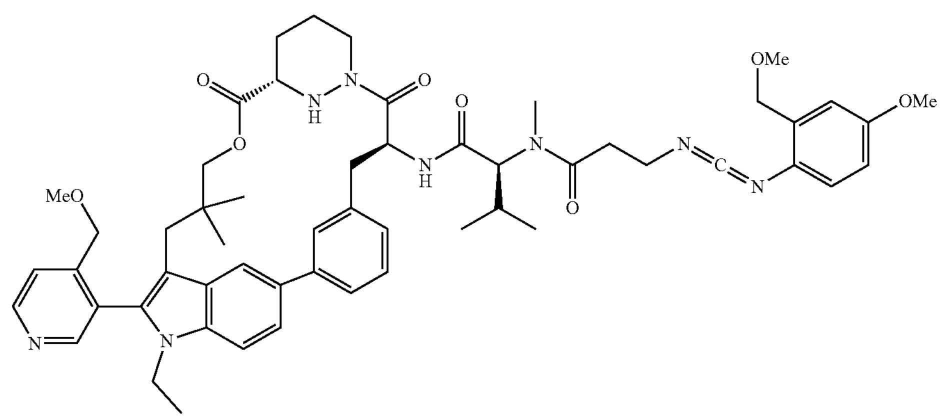 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccc(OC)cc1COC)C(=O)N1CCC[C@H](N1)C(=O)OCC(C)(C)C2] |
| B116 | 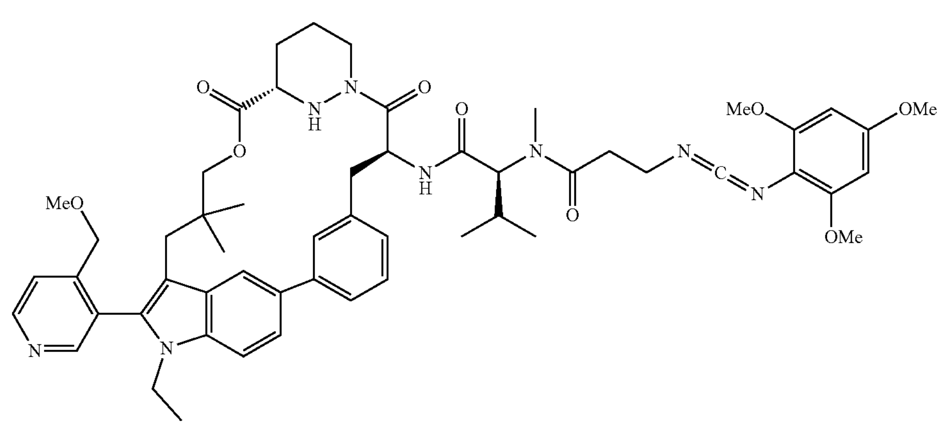 [SMILES: CCn1c(-c2cnccc2COC)c2c3cc(ccc31)-c1cccc(c1)C[C@H](NC(=O)[C@H](C(C)C)N(C)C(=O)CCN=C=Nc1c(OC)cc(OC)cc1OC)C(=O)N1CCC[C@H](N1)C(=O)OCC(C)(C)C2] |

TABLE 2-continued

Certain Compounds of the Present Invention

| Ex # | Structure |
|------|-----------|
| B117 | 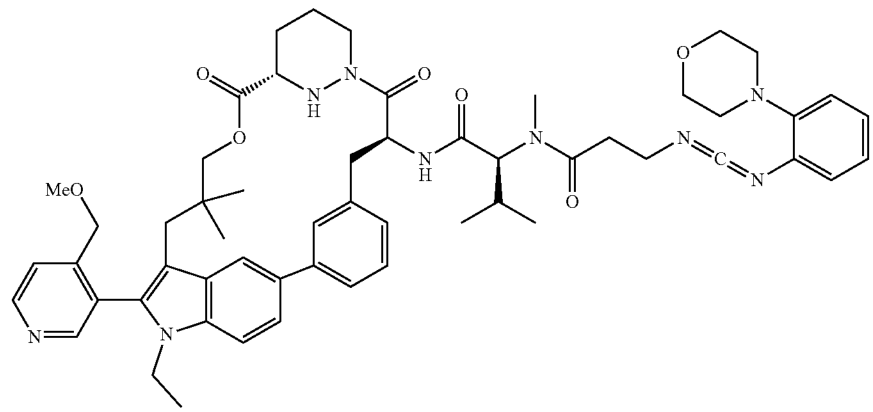 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccccc1N1CCOCC1)C(=O)N1CCC[C@H](N1)C(=O)OCC(C)(C)C2] |
| B118 | 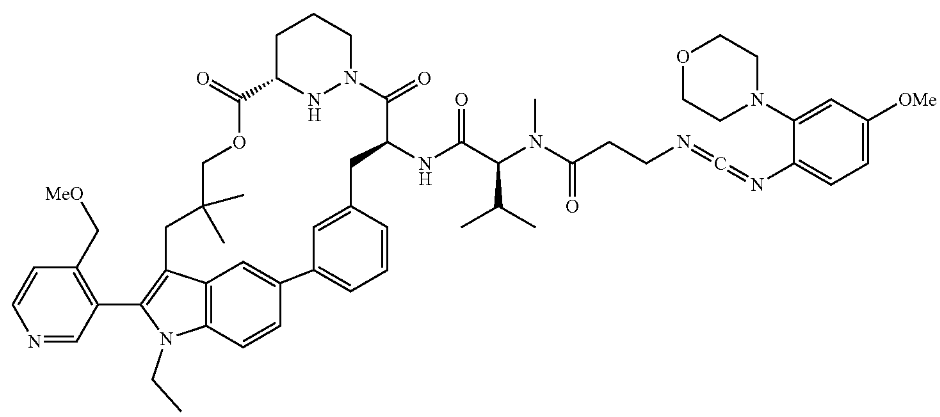 [SMILES: CCn1c(-c2cnccc2COC)c2c3cc(ccc31)-c1cccc(c1)C[C@H](NC(=O)[C@H](C(C)C)N(C)C(=O)CCN=C=Nc1ccc(OC)cc1N1CCOCC1)C(=O)N1CCC[C@H](N1)C(=O)OCC(C)(C)C2] |
| B119 | 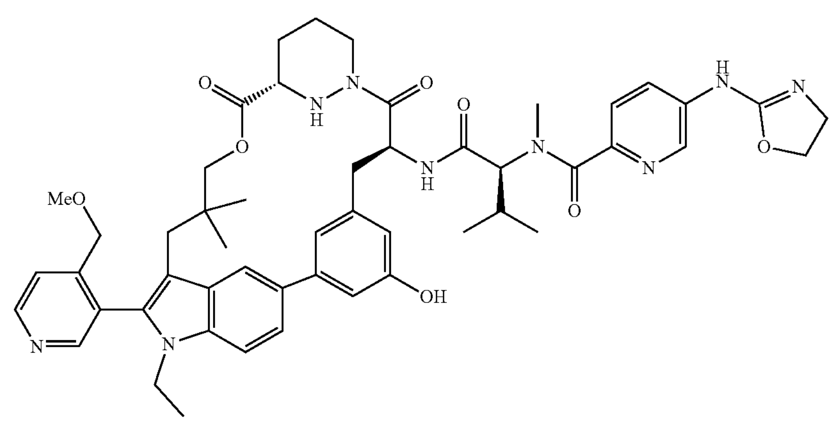 [SMILES: CCn1c(-c2cnccc2COC)c2c3cc(ccc31)-c1cc(O)cc(c1)C[C@H](NC(=O)[C@H](C(C)C)N(C)C(=O)c1ccc(NC3=NCCO3)cn1)C(=O)N1CCC[C@H](N1)C(=O)OCC(C)(C)C2] |

TABLE 2-continued

Certain Compounds of the Present Invention

| Ex # | Structure |
|---|---|
| B120 | 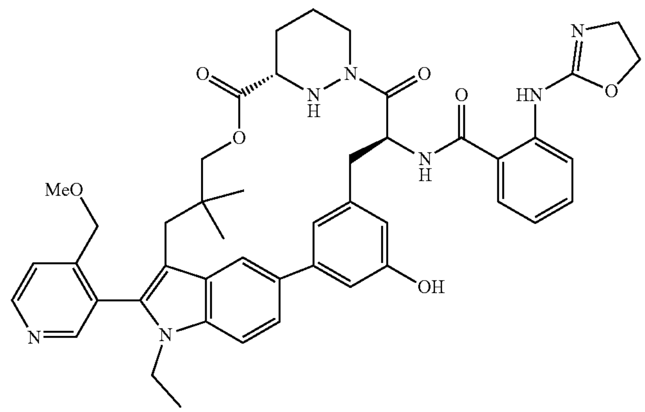 [SMILES: CCn1c(-c2cnccc2COC)c2c3cc(ccc31)-c1cc(O)cc(c1)C[C@H](NC(=O)c1ccccc1NC1=NCCO1)C(=O)N1CCC[C@H](N1)C(=O)OCC(C)(C)C2] |
| B122 | 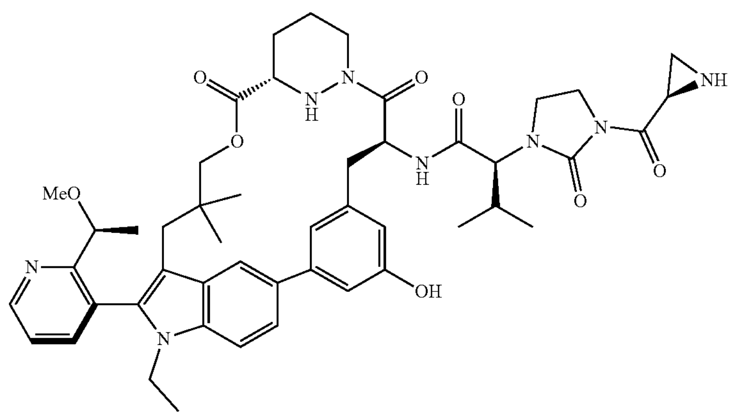 |
| B123 | 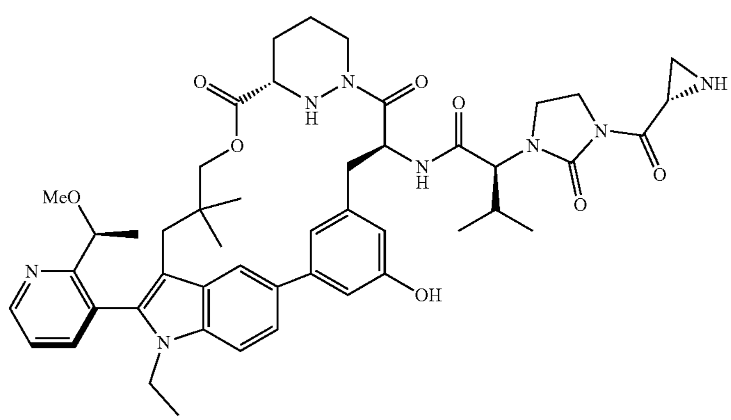 |

Note that some compounds are shown with bonds as flat or wedged. In some instances, the relative stereochemistry of stereoisomers has been determined; in some instances, the absolute stereochemistry has been determined. All stereoisomers of the compuonds of the foregoing table are contemplated by the present invention. In particular embodiments, an atropisomer of a compound of the foregoing table is contemplated.

In some embodiments, a compound of the present invention is or acts as a prodrug, such as with respect to administration to a cell or to a subject in need thereof.

Also provided are pharmaceutical compositions comprising a compound of the present invention, or a pharmaceutically acceptable salt thereof, and a pharmaceutically acceptable excipient.

Further provided is a conjugate, or salt thereof, comprising the structure of Formula IV:

M-L-P      Formula IV wherein L is a linker;
P is a monovalent organic moiety; and
M has the structure of Formula Va:

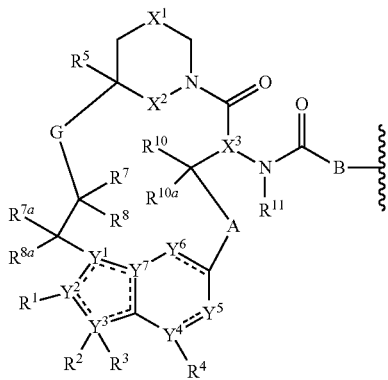

Formula Va wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— or >C=C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', $S(O)_2$ R', or $S(O)_2N(R')_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo; and $R^{11}$ is hydrogen or $C_1$-$C_3$ alkyl.

In some embodiments, the conjugate has the structure of Formula IV:

M-L-P      Formula IV wherein L is a linker;

P is a monovalent organic moiety; and

M has the structure of Formula Vb:

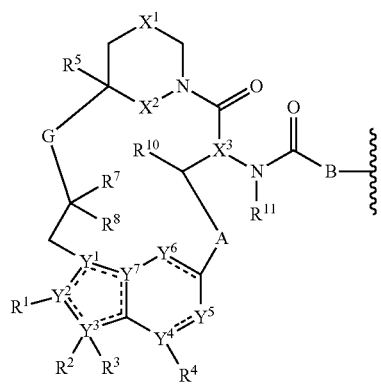

Formula Vb wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', $S(O)_2$ R', or $S(O)_2N(R')_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

In some embodiments, the conjugate has the structure of Formula IV:

M-L-P      Formula IV wherein L is a linker;

P is a monovalent organic moiety; and

M has the structure of Formula Vc:

Formula Vc wherein A is optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

$X^1$ is optionally substituted $C_1$-$C_2$ alkylene, NR, O, or S(O)$_n$;

$X^2$ is O or NH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$X^e$ and $X^f$ are, independently, N or CH;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{11}$ is hydrogen or $C_1$-$C_3$ alkyl; and $R^{34}$ is hydrogen or $C_1$-$C_3$ alkyl.

In some embodiments of a compound of the present invention, $X^e$ is N and $X^f$ is CH. In some embodiments, $X^e$ is CH and $X^f$ is N.

In some embodiments, the conjugate has the structure of Formula IV:

M-L-P     Formula IV wherein L is a linker;

P is a monovalent organic moiety; and

M has the structure of Formula Vd:

Formula Vd wherein A optionally substituted 3 to 6-membered cycloalkylene, optionally substituted 3 to 6-membered heterocycloalkylene, optionally substituted 6-membered arylene (e.g., phenyl or phenol), or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $X^e$ and $X^f$ are, independently, N or CH.

In some embodiments of a compound of the present invention, $X^e$ is N and $X^f$ is CH. In some embodiments, $X^e$ is CH and $X^f$ is N.

In some embodiments of conjugates of the present invention, the linker has the structure of Formula II:

$A^1$-($B^1$)$_f$—($C^1$)$_g$—($B^2$)$_h$-($D^1$)-($B^3$)$_i$—($C^2$)$_j$—($B^4$)$_k$-$A^2$     Formula II where $A^1$ is a bond between the linker and B; $A^2$ is a bond between P and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and NR$^N$; R$^N$ is hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$—$(C^1)_g$—$(B^2)_h$— to —$(B^3)_i$—$(C^2)_j$—$(B^4)_k$-$A^2$. In some embodiments of conjugates of the present invention, the linker is bound to the monovalent organic moiety through a bond to a carboxyl group of an amino acid residue of the monovalent organic moiety.

In some embodiments of conjugates of the present invention, the monovalent organic moiety is a protein. In some embodiments, the protein is a Ras protein. In some embodiments, the Ras protein is K-Ras G12D or K-Ras G13D.

Further provided is a method of treating cancer in a subject in need thereof, the method comprising administering to the subject a therapeutically effective amount of a compound of the present invention, or a pharmaceutically acceptable salt thereof. The cancer may, for example, be pancreatic cancer, colorectal cancer, non-small cell lung cancer, acute myeloid leukemia, multiple myeloma, thyroid gland adenocarcinoma, a myelodysplastic syndrome, or squamous cell lung carcinoma. In some embodiments, the cancer comprises a Ras mutation, such as K-Ras G12D or K-Ras G13D. Other Ras mutations are described herein.

Further provided is a method of treating a Ras protein-related disorder in a subject in need thereof, the method comprising administering to the subject a therapeutically effective amount of a compound of the present invention, or a pharmaceutically acceptable salt thereof.

Further provided is a method of inhibiting a Ras protein in a cell, the method comprising contacting the cell with an effective amount of a compound of the present invention, or a pharmaceutically acceptable salt thereof. For example, the Ras protein is K-Ras G12D or K-Ras G13D. Other Ras proteins are described herein. The cell may be a cancer cell, such as a pancreatic cancer cell, a colorectal cancer cell, a non-small cell lung cancer cell, an acute myeloid leukemia cell, a multiple myeloma cell, a thyroid gland adenocarcinoma cell, a myelodysplastic syndrome cell, or a squamous cell lung carcinoma cell. Other cancer types are described herein. The cell may be in vivo or in vitro.

With respect to compounds of the present invention, one stereoisomer may exhibit better inhibition than another stereoisomer. For example, one atropisomer may exhibit inhibition, whereas the other atropisomer may exhibit little or no inhibition.

In some embodiments, a method or use described herein further comprises administering an additional anti-cancer therapy. In some embodiments, the additional anti-cancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof. In some embodiments, the additional anticancer therapy is a SHP2 inhibitor. Other additional anti-cancer therapies are described herein.

Methods of Synthesis

The compounds described herein may be made from commercially available starting materials or synthesized using known organic, inorganic, or enzymatic processes.

The compounds of the present invention can be prepared in a number of ways well known to those skilled in the art of organic synthesis. By way of example, compounds of the present invention can be synthesized using the methods described in the Schemes below, together with synthetic methods known in the art of synthetic organic chemistry, or variations thereon as appreciated by those skilled in the art. These methods include but are not limited to those methods described in the Schemes below.

Compounds of Table 1 herein were prepared using methods disclosed herein or were prepared using methods disclosed herein combined with the knowledge of one of skill in the art. Compounds of Table 2 may be prepared using methods disclosed herein or may be prepared using methods disclosed herein combined with the knowledge of one of skill in the art.

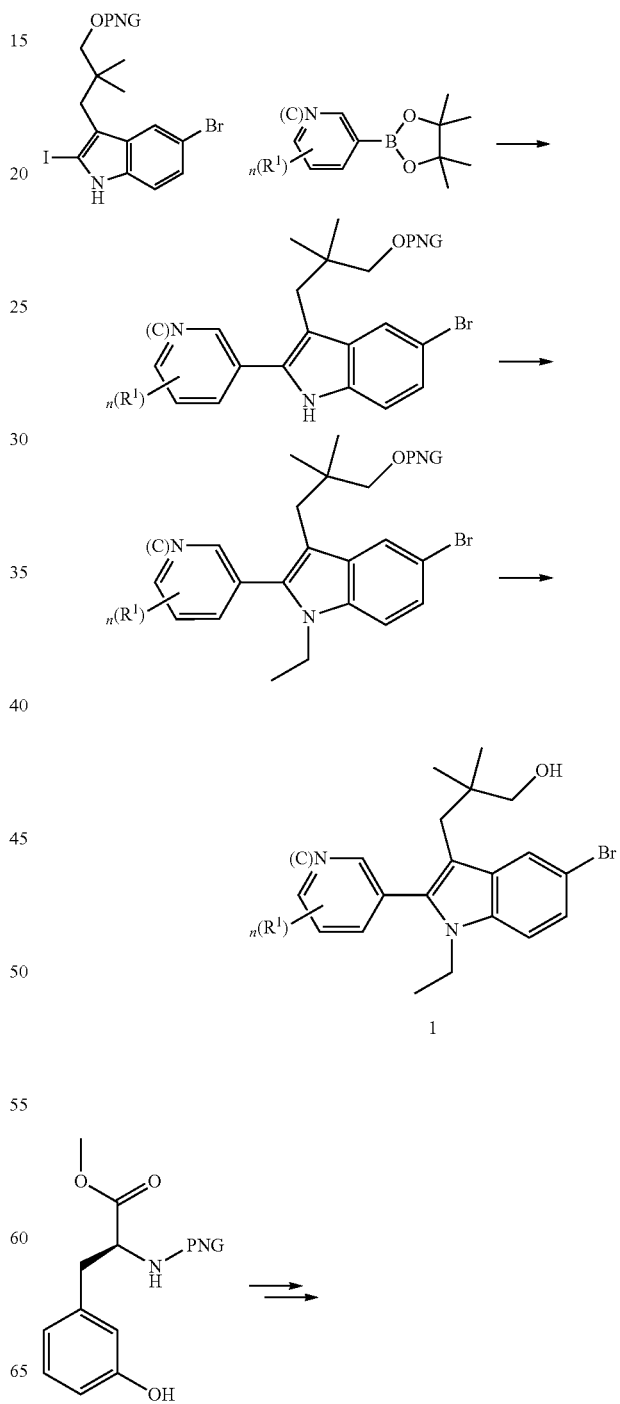

Scheme 1. General synthesis of macrocyclic esters

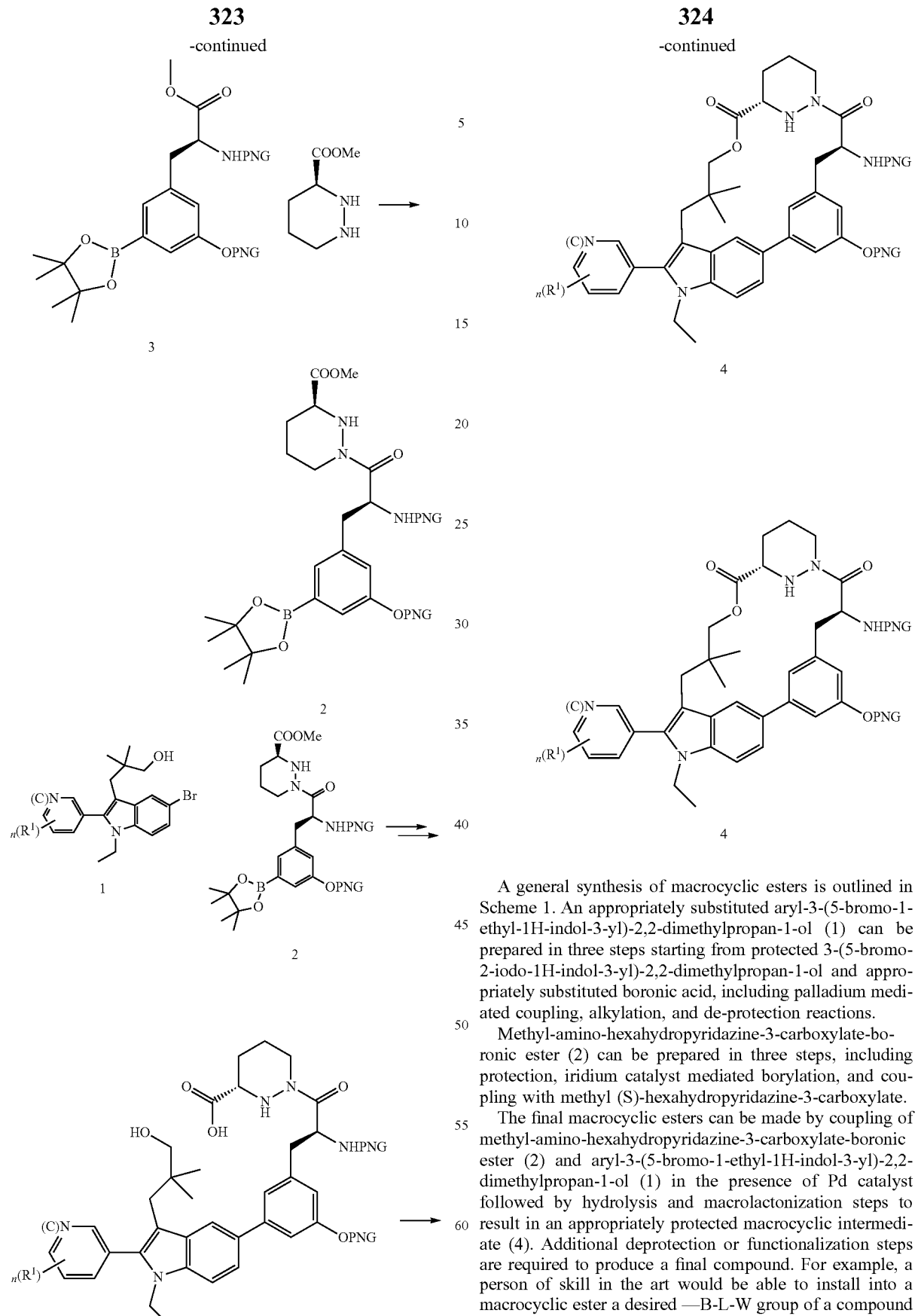

A general synthesis of macrocyclic esters is outlined in Scheme 1. An appropriately substituted aryl-3-(5-bromo-1-ethyl-1H-indol-3-yl)-2,2-dimethylpropan-1-ol (1) can be prepared in three steps starting from protected 3-(5-bromo-2-iodo-1H-indol-3-yl)-2,2-dimethylpropan-1-ol and appropriately substituted boronic acid, including palladium mediated coupling, alkylation, and de-protection reactions.

Methyl-amino-hexahydropyridazine-3-carboxylate-boronic ester (2) can be prepared in three steps, including protection, iridium catalyst mediated borylation, and coupling with methyl (S)-hexahydropyridazine-3-carboxylate.

The final macrocyclic esters can be made by coupling of methyl-amino-hexahydropyridazine-3-carboxylate-boronic ester (2) and aryl-3-(5-bromo-1-ethyl-1H-indol-3-yl)-2,2-dimethylpropan-1-ol (1) in the presence of Pd catalyst followed by hydrolysis and macrolactonization steps to result in an appropriately protected macrocyclic intermediate (4). Additional deprotection or functionalization steps are required to produce a final compound. For example, a person of skill in the art would be able to install into a macrocyclic ester a desired —B-L-W group of a compound of Formula (I), where B, L and W are defined herein, including by using methods exemplified in certain Schemes below and in the Example section herein.

Scheme 2. Alternative general synthesis of macrocyclic esters

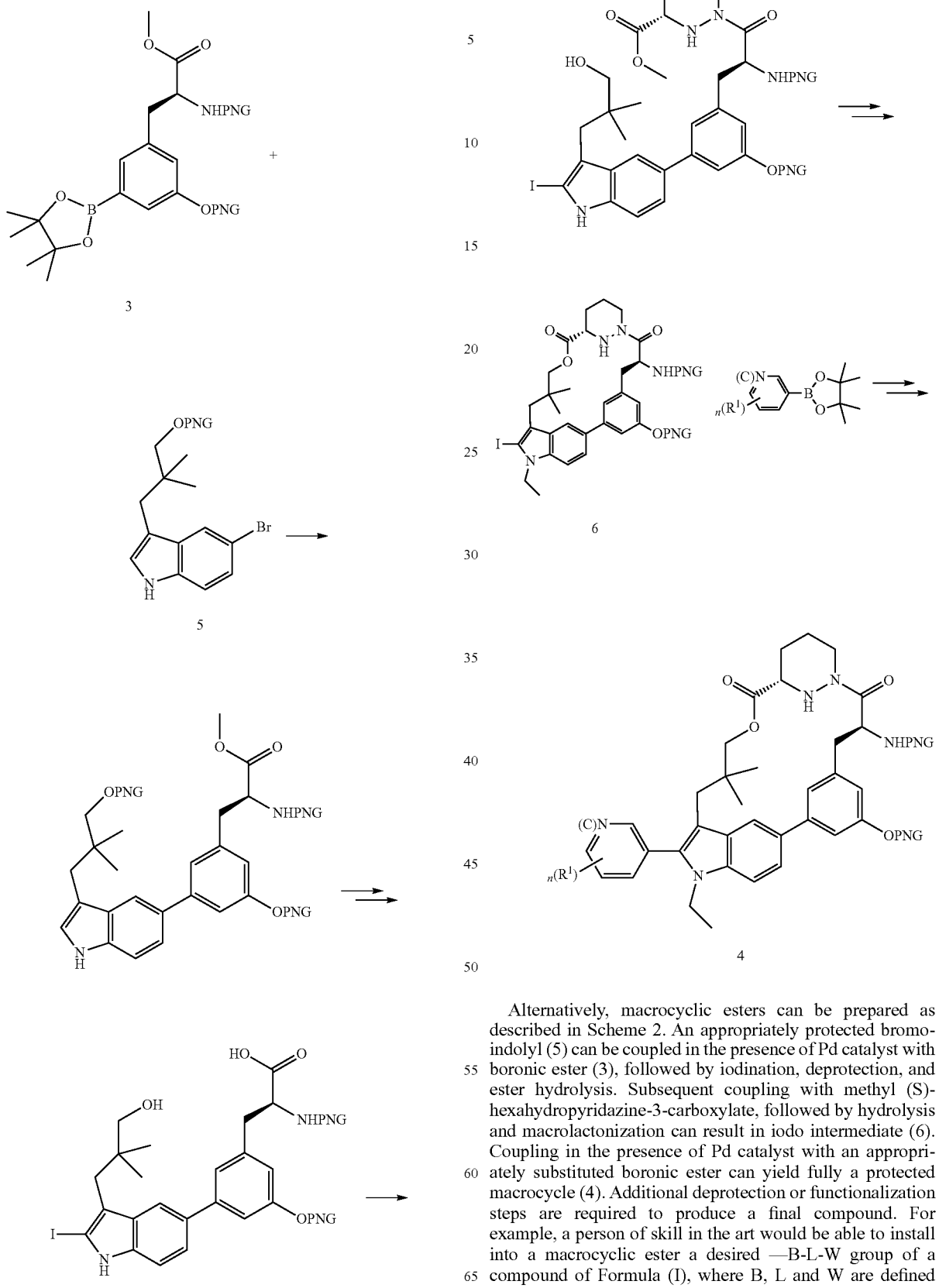

Alternatively, macrocyclic esters can be prepared as described in Scheme 2. An appropriately protected bromo-indolyl (5) can be coupled in the presence of Pd catalyst with boronic ester (3), followed by iodination, deprotection, and ester hydrolysis. Subsequent coupling with methyl (S)-hexahydropyridazine-3-carboxylate, followed by hydrolysis and macrolactonization can result in iodo intermediate (6). Coupling in the presence of Pd catalyst with an appropriately substituted boronic ester can yield fully a protected macrocycle (4). Additional deprotection or functionalization steps are required to produce a final compound. For example, a person of skill in the art would be able to install into a macrocyclic ester a desired —B-L-W group of a compound of Formula (I), where B, L and W are defined herein, including by using methods exemplified in certain Schemes below and in the Example section herein.

Scheme 3. General synthesis of aziridine containing macrocycles

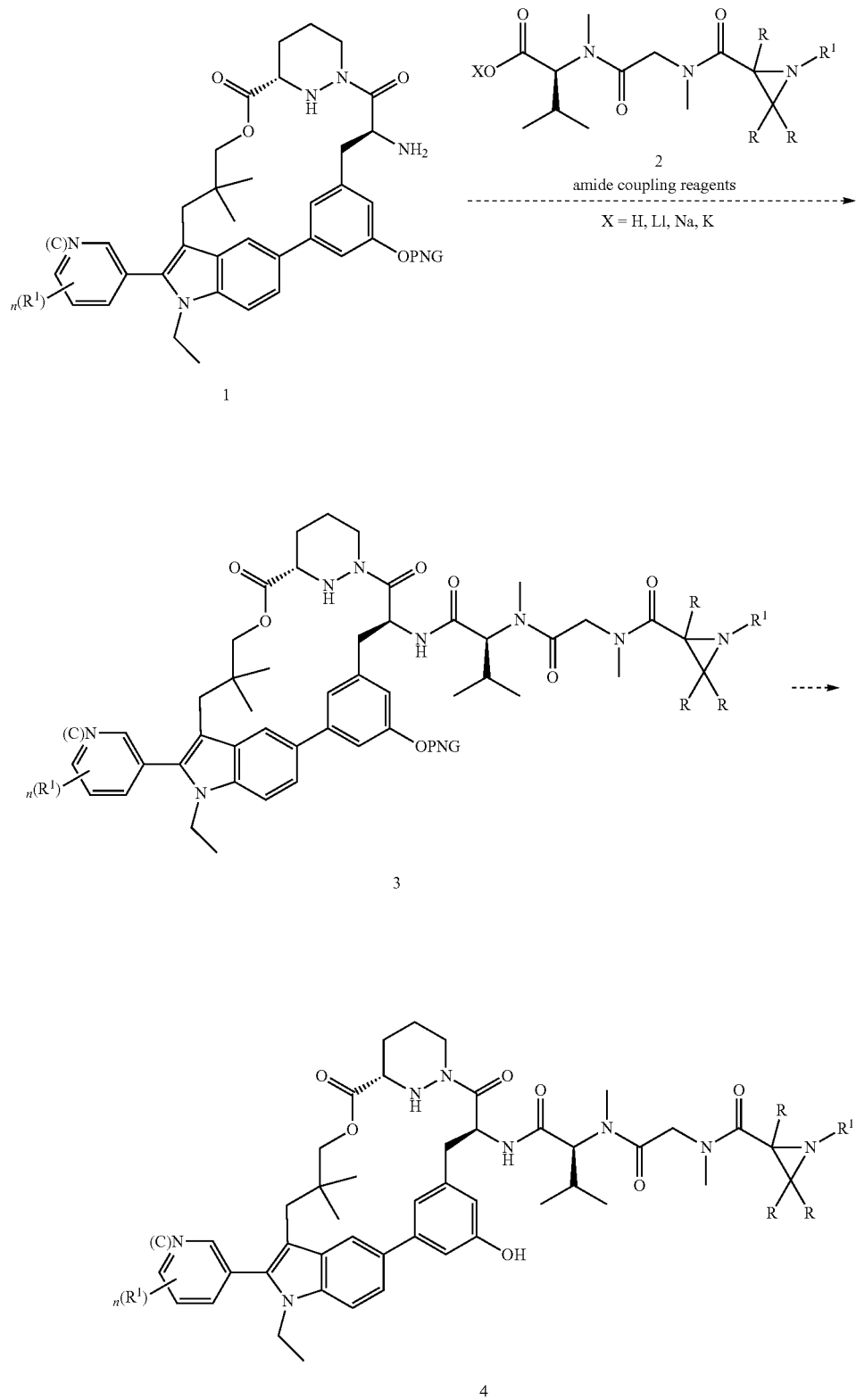

As shown in Scheme 3, compounds of this type may be prepared by the reaction of an appropriate amine (1) with an aziridine containing carboxylic acid (2) in the presence of standard amide coupling reagents, followed by deprotection of the aziridine, if $R^1$ is a protecting group, and deprotection of the phenol, if required, to produce the final compound (4).

Scheme 4. General synthesis of carbodiimide containing macrocycles

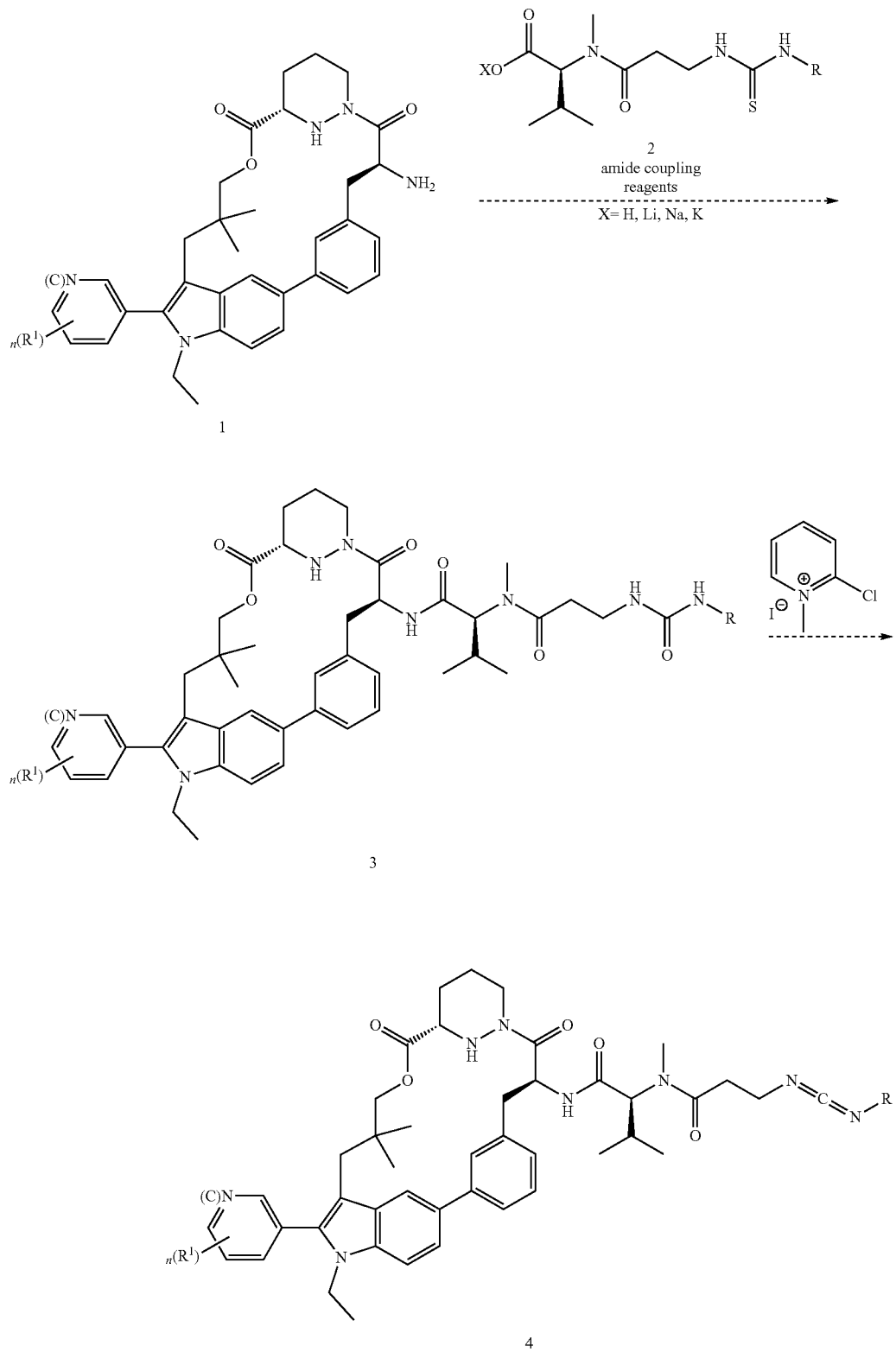

As shown in Scheme 4, compounds of this type may be prepared by the reaction of an appropriate amine (1) with a thiourea containing carboxylic acid (2) in the presence of standard amide coupling reagents, followed by conversion of the thiourea (3) to a carbodiimide (4) in the presence of 2-chloro-1-methylpyridin-1-ium iodide.

Scheme 5. General synthesis of chloroethyl urea containing macrocycles
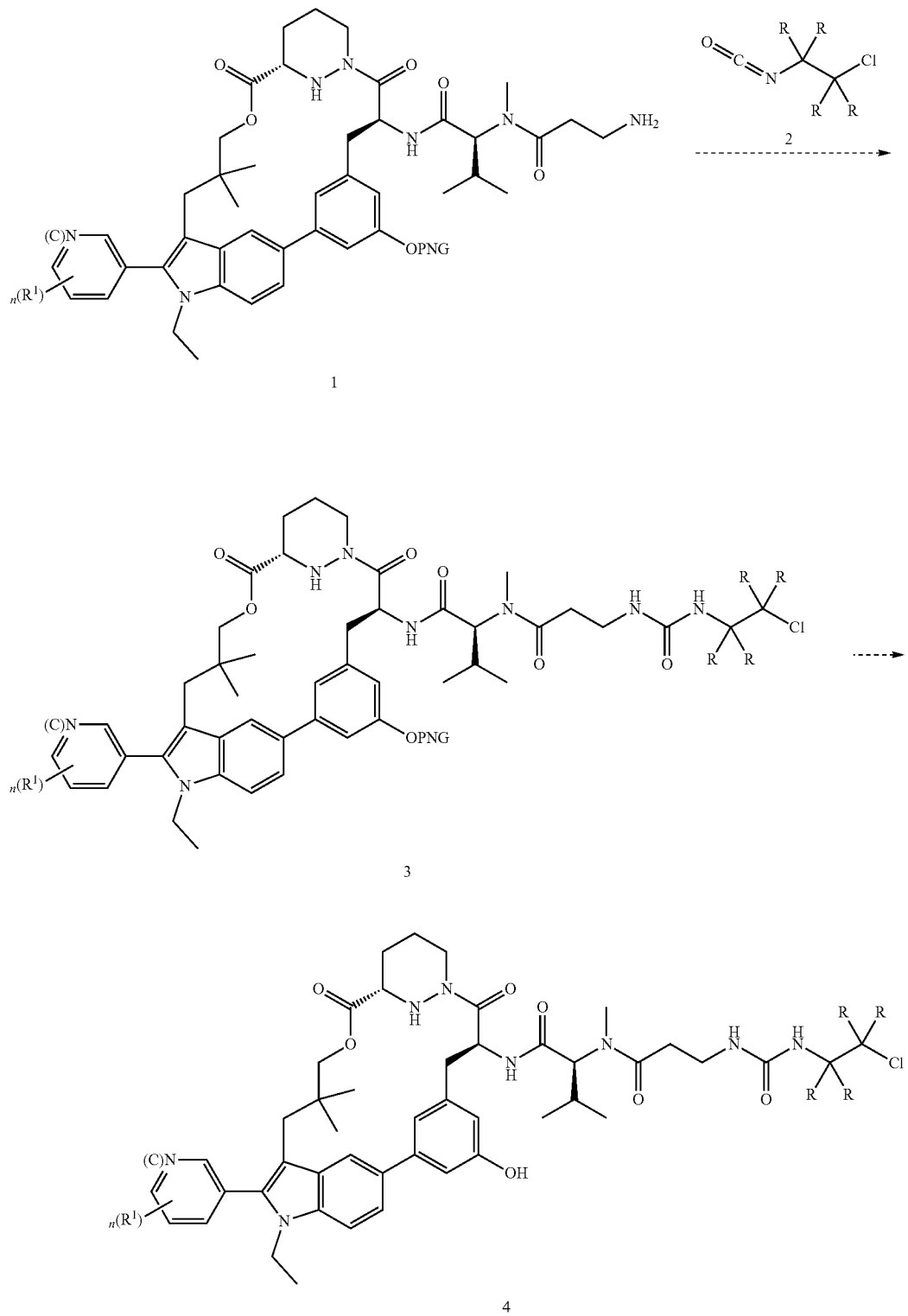
As shown in Scheme 5, compounds of this type may be prepared by the reaction of an appropriate amine (1) with an isocyanate (2) under basic conditions, followed by deprotection of the phenol, if required, to produce the final compound (4).

Scheme 6. General synthesis of amino oxazoline containing macrocycles
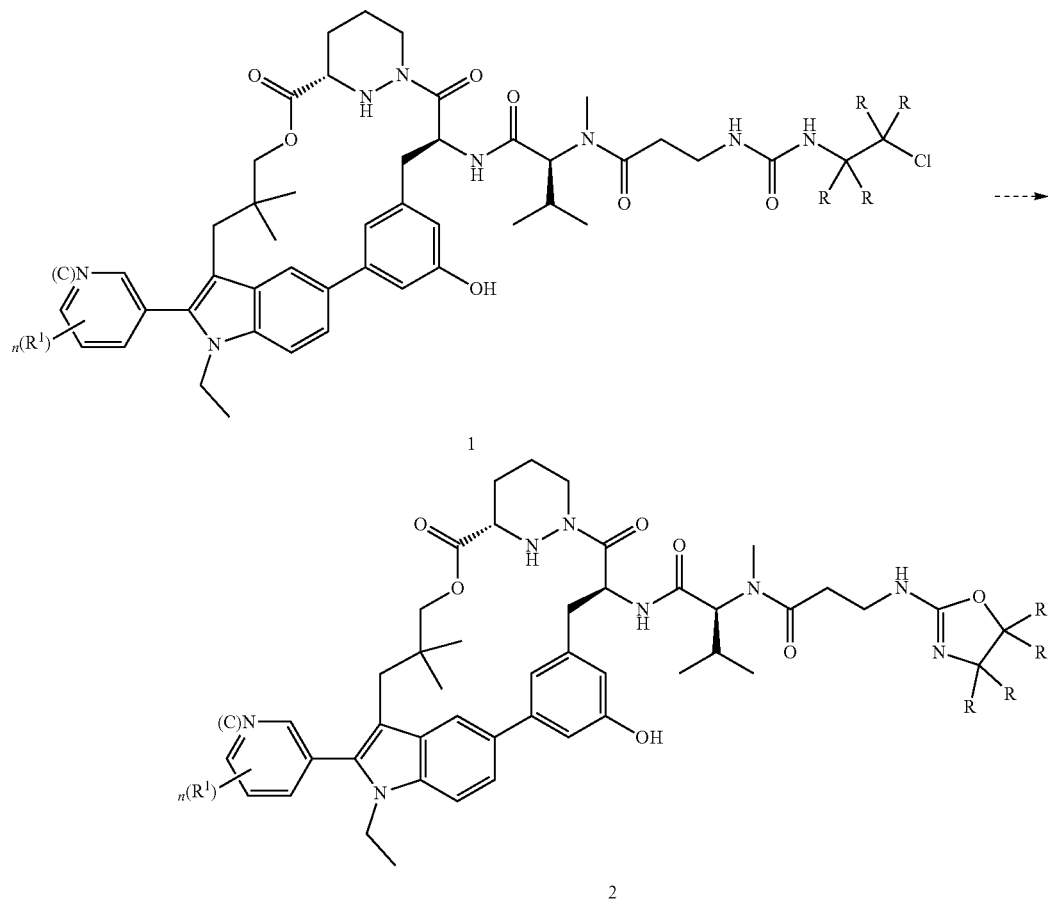
As shown in Scheme 6, compounds of this type may be prepared by cyclization of an appropriate chloroethyl urea (1) under elevated temperatures to produce the final compound (2).
Scheme 7. General synthesis of epoxide containing macrocycles
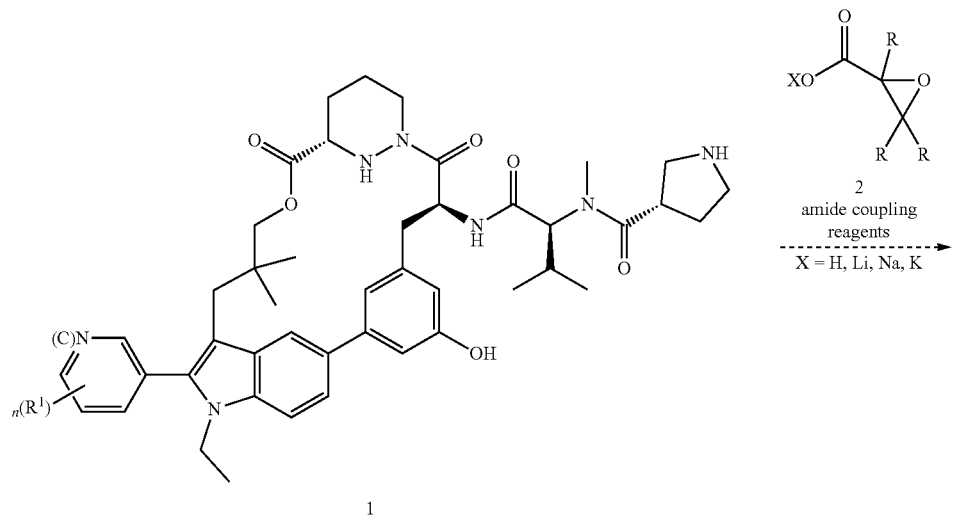

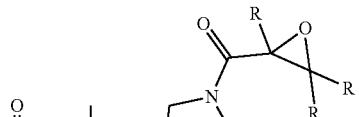

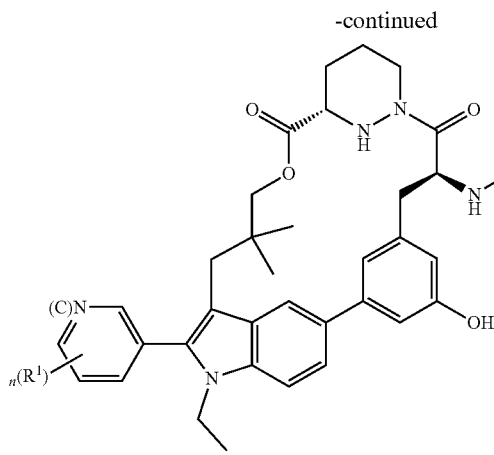

3

As shown in Scheme 7, compounds of this type may be prepared by the reaction of an appropriate amine (1) with an epoxide containing carboxylic acid (2) in the presence of standard amide coupling reagents to produce the final compound (3).

In addition, compounds of the disclosure can be synthesized using the methods described in the Examples below, together with synthetic methods known in the art of synthetic organic chemistry, or variations thereon as appreciated by those skilled in the art. These methods include but are not limited to those methods described in the Examples below. For example, a person of skill in the art would be able to install into a macrocyclic ester a desired —B-L-W group of a compound of Formula (I), where B, L and W are defined herein, including by using methods exemplified in certain Schemes above and in the Example section herein.

Pharmaceutical Compositions and Methods of Use
Pharmaceutical Compositions and Methods of Administration The compounds with which the invention is concerned are Ras inhibitors, and are useful in the treatment of cancer. Accordingly, one embodiment of the present invention provides pharmaceutical compositions containing a compound of the invention or a pharmaceutically acceptable salt thereof, and a pharmaceutically acceptable excipient, as well as methods of using the compounds of the invention to prepare such compositions.

As used herein, the term "pharmaceutical composition" refers to a compound, such as a compound of the present invention, or a pharmaceutically acceptable salt thereof, formulated together with a pharmaceutically acceptable excipient.

In some embodiments, a compound is present in a pharmaceutical composition in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

A "pharmaceutically acceptable excipient," as used herein, refers any inactive ingredient (for example, a vehicle capable of suspending or dissolving the active compound) having the properties of being nontoxic and non-inflammatory in a subject. Typical excipients include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Excipients include, but are not limited to: butylated optionally substituted hydroxyltoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, optionally substituted hydroxylpropyl cellulose, optionally substituted hydroxyl propyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Those of ordinary skill in the art are familiar with a variety of agents and materials useful as excipients. See, e.g., e.g., Ansel, et al., Ansel's Pharmaceutical Dosage Forms and Drug Delivery Systems. Philadelphia: Lippincott, Williams & Wilkins, 2004; Gennaro, et al., Remington: The Science and Practice of Pharmacy. Philadelphia: Lippincott, Williams & Wilkins, 2000; and Rowe, Handbook of Pharmaceutical Excipients. Chicago, Pharmaceutical Press, 2005. In some embodiments, a composition includes at least two different pharmaceutically acceptable excipients. Compounds described herein, whether expressly stated or not, may be provided or utilized in salt form, e.g., a pharmaceutically acceptable salt form, unless expressly stated to the contrary. The term "pharmaceutically acceptable salt," as use herein, refers to those salts of the compounds described herein that are, within the scope of sound medical judgment, suitable for use in contact with the tissues of humans and other animals without undue toxicity, irritation, allergic response and the like, and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention, be prepared from inorganic or organic bases. In some embodiments, the compounds are prepared or used as pharmaceutically acceptable salts prepared as addition products of pharmaceutically acceptable acids or bases. Suitable pharmaceutically acceptable acids and bases are well-known in the art, such as hydrochloric, sulfuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

As used herein, the term "subject" refers to any member of the animal kingdom. In some embodiments, "subject" refers to humans, at any stage of development. In some embodiments, "subject" refers to a human patient. In some embodiments, "subject" refers to non-human animals. In some embodiments, the non-human animal is a mammal (e.g., a rodent, a mouse, a rat, a rabbit, a monkey, a dog, a cat, a sheep, cattle, a primate, or a pig). In some embodiments, subjects include, but are not limited to, mammals, birds, reptiles, amphibians, fish, or worms. In some embodiments, a subject may be a transgenic animal, genetically-engineered animal, or a clone.

As used herein, the term "dosage form" refers to a physically discrete unit of a compound (e.g., a compound of the present invention) for administration to a subject. Each unit contains a predetermined quantity of compound. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or compound administered to a particular subject is determined by one or more attending physicians and may involve administration of multiple dosage forms.

As used herein, the term "dosing regimen" refers to a set of unit doses (typically more than one) that are administered individually to a subject, typically separated by periods of time. In some embodiments, a given therapeutic compound (e.g., a compound of the present invention) has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

A "therapeutic regimen" refers to a dosing regimen whose administration across a relevant population is correlated with a desired or beneficial therapeutic outcome.

The term "treatment" (also "treat" or "treating"), in its broadest sense, refers to any administration of a substance (e.g., a compound of the present invention) that partially or completely alleviates, ameliorates, relieves, inhibits, delays onset of, reduces severity of, or reduces incidence of one or more symptoms, features, or causes of a particular disease, disorder, or condition. In some embodiments, such treatment may be administered to a subject who does not exhibit signs of the relevant disease, disorder or condition, or of a subject who exhibits only early signs of the disease, disorder, or condition. Alternatively, or additionally, in some embodiments, treatment may be administered to a subject who exhibits one or more established signs of the relevant disease, disorder, or condition. In some embodiments, treatment may be of a subject who has been diagnosed as suffering from the relevant disease, disorder, or condition. In some embodiments, treatment may be of a subject known to have one or more susceptibility factors that are statistically correlated with increased risk of development of the relevant disease, disorder, or condition.

The term "therapeutically effective amount" means an amount that is sufficient, when administered to a population suffering from or susceptible to a disease, disorder, or condition in accordance with a therapeutic dosing regimen, to treat the disease, disorder, or condition. In some embodiments, a therapeutically effective amount is one that reduces the incidence or severity of, or delays onset of, one or more symptoms of the disease, disorder, or condition. Those of ordinary skill in the art will appreciate that the term "therapeutically effective amount" does not in fact require successful treatment be achieved in a particular individual.

Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine). Those of ordinary skill in the art will appreciate that, in some embodiments, a therapeutically effective amount may be formulated or administered in a single dose. In some embodiments, a therapeutically effective amount may be formulated or administered in a plurality of doses, for example, as part of a dosing regimen.

For use as treatment of subjects, the compounds of the invention, or a pharmaceutically acceptable salt thereof, can be formulated as pharmaceutical or veterinary compositions. Depending on the subject to be treated, the mode of administration, and the type of treatment desired, e.g., prevention, prophylaxis, or therapy, the compounds, or a pharmaceutically acceptable salt thereof, are formulated in ways consonant with these parameters. A summary of such techniques may be found in *Remington: The Science and Practice of Pharmacy*, 21$^{st}$ *Edition*, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

Compositions can be prepared according to conventional mixing, granulating, or coating methods, respectively, and the present pharmaceutical compositions can contain from about 0.1% to about 99%, from about 5% to about 90%, or from about 1% to about 20% of a compound of the present invention, or pharmaceutically acceptable salt thereof, by weight or volume. In some embodiments, compounds, or a pharmaceutically acceptable salt thereof, described herein may be present in amounts totaling 1-95% by weight of the total weight of a composition, such as a pharmaceutical composition.

The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, reproductive, or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

As used herein, the term "administration" refers to the administration of a composition (e.g., a compound, or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, orvitreal.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. A formulation will generally include a diluent as well as, in some cases, adjuvants, buffers, preservatives and the like. Compounds, or a pharmaceutically acceptable salt thereof, can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol, and the like. Such compositions may also contain amounts of nontoxic auxiliary substances such as wetting or emulsifying agents, pH buffering agents, and the like, such as, for example, sodium acetate, sorbitan monolaurate, and so forth.

Various sustained release systems for drugs have also been devised. See, for example, U.S. Pat. No. 5,624,677.

Systemic administration may also include relatively noninvasive methods such as the use of suppositories, transdermal patches, transmucosal delivery, and intranasal administration. Oral administration is also suitable for compounds of the invention, or pharmaceutically acceptable salts thereof. Suitable forms include syrups, capsules, and tablets, as is understood in the art.

Each compound, or a pharmaceutically acceptable salt thereof, as described herein, may be formulated in a variety of ways that are known in the art. For example, the first and second agents of the combination therapy may be formulated together or separately. Other modalities of combination therapy are described herein.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to subjects, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one subject, multiple uses for a particular subject (at a constant dose or in which the individual compounds, or a pharmaceutically acceptable salt thereof, may vary in potency as therapy progresses); or the kit may contain multiple doses suitable for administration to multiple subjects ("bulk packaging"). The kit components may be assembled in cartons, blister packs, bottles, tubes, and the like.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, oralginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, optionally substituted hydroxylpropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion-controlled release can be achieved by appropriate coating of a tablet, capsule, pellet, or granulate formulation of compounds, or by incorporating the compound, or a pharmaceutically acceptable salt thereof, into an appropriate matrix. A controlled release coating may include one or more of the coating substances mentioned above or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-optionally substituted hydroxylmethacrylate, methacrylate hydrogels, 1,3 butylene glycol, ethylene glycol methacrylate, or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, or halogenated fluorocarbon.

The liquid forms in which the compounds, or a pharmaceutically acceptable salt thereof, and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the invention, or a pharmaceutically acceptable salt thereof, will depend on the nature of the compound, and can readily be determined by one skilled in the art. A dosage may be, for example, about 0.001 mg to about 2000 mg per day, about 1 mg to about 1000 mg per day, about 5 mg to about 500 mg per day, about 100 mg to about 1500 mg per day, about 500 mg to about 1500 mg per day, about 500 mg to about 2000 mg per day, or any range derivable therein.

In some embodiments, the pharmaceutical composition may further comprise an additional compound having antiproliferative activity. Depending on the mode of administration, compounds, ora pharmaceutically acceptable salt thereof, will be formulated into suitable compositions to permit facile delivery. Each compound, or a pharmaceutically acceptable salt thereof, of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

It will be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics or procedures and the desired therapeutic effect to be achieved. It will also be appreciated that the therapies employed may achieve a desired effect for the same disorder, or they may achieve different effects (e.g., control of any adverse effects).

Administration of each drug in a combination therapy, as described herein, can, independently, be one to four times daily for one day to one year, and may even be for the life of the subject. Chronic, long-term administration may be indicated.

Methods of Use

In some embodiments, the invention discloses a method of treating a disease or disorder that is characterized by aberrant Ras activity due to a Ras mutant. In some embodiments, the disease or disorder is a cancer.

Accordingly, also provided is a method of treating cancer in a subject in need thereof, the method comprising administering to the subject a therapeutically effective amount of a compound of the present invention, or a pharmaceutically acceptable salt thereof, or a pharmaceutical composition comprising such a compound or salt. In some embodiments, the cancer is colorectal cancer, non-small cell lung cancer, small-cell lung cancer, pancreatic cancer, appendiceal cancer, melanoma, acute myeloid leukemia, small bowel cancer, ampullary cancer, germ cell cancer, cervical cancer, cancer of unknown primary origin, endometrial cancer, esophagogastric cancer, GI neuroendocrine cancer, ovarian cancer, sex cord stromal tumor cancer, hepatobiliary cancer, or bladder cancer. In some embodiments, the cancer is appendiceal, endometrial or melanoma. Also provided is a method of treating a Ras protein-related disorder in a subject in need thereof, the method comprising administering to the subject a therapeutically effective amount of a compound of the present invention, or a pharmaceutically acceptable salt thereof, or a pharmaceutical composition comprising such a compound or salt.

In some embodiments, the compounds of the present invention or pharmaceutically acceptable salts thereof, pharmaceutical compositions comprising such compounds or salts, and methods provided herein may be used for the treatment of a wide variety of cancers including tumors such as lung, prostate, breast, brain, skin, cervical carcinomas, testicular carcinomas, etc. More particularly, cancers that may be treated by the compounds or salts thereof, pharmaceutical compositions comprising such compounds or salts, and methods of the invention include, but are not limited to, tumor types such as astrocytic, breast, cervical, colorectal, endometrial, esophageal, gastric, head and neck, hepatocellular, laryngeal, lung, oral, ovarian, prostate, and thyroid carcinomas and sarcomas. Other cancers include, for example:

Cardiac, for example: sarcoma (angiosarcoma, fibrosarcoma, rhabdomyosarcoma, liposarcoma), myxoma, rhabdomyoma, fibroma, lipoma, and teratoma;

Lung, for example: bronchogenic carcinoma (squamous cell, undifferentiated small cell, undifferentiated large ceil, adenocarcinoma), alveolar (bronchiolar) carcinoma, bronchial adenoma, sarcoma, lymphoma, chondromatous hamartoma, mesothelioma;

Gastrointestinal, for example: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract, for example: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver, for example: hepatoma (hepatocellular carcinoma), cholangiocarcinoma, hepatoblastoma, angiosarcoma, hepatocellular adenoma, hemangioma;

Biliary tract, for example: gall bladder carcinoma, ampullary carcinoma, cholangiocarcinoma;

Bone, for example: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors;

Nervous system, for example: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, neurofibromatosis type 1, meningioma, glioma, sarcoma);

Gynecological, for example: uterus (endometrial carcinoma, uterine carcinoma, uterine corpus endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granuiosa-thecal cell tumors, Sertoli-Leydig ceil tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic, for example: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma);

Skin, for example: malignant melanoma, basal cell carcinoma, squamous ceil carcinoma, Kaposi's sarcoma, moles dysplastic nevi, lipoma, angioma, dermatofibroma, keloids, psoriasis; and Adrenal glands, for example: neuroblastoma.

In some embodiments, the Ras protein is wild-type ($Ras^{WT}$). Accordingly, in some embodiments, a compound of the present invention is employed in a method of treating a patient having a cancer comprising a $Ras^{WT}$ (e.g., K-$Ras^{WT}$, H-$Ras^{WT}$ or N-$Ras^{WT}$). In some embodiments, the Ras protein is Ras amplification (e.g., K-$Ras^{amp}$). Accordingly, in some embodiments, a compound of the present invention is employed in a method of treating a patient having a cancer comprising a $Ras^{amp}$ (K-$Ras^{amp}$, H-$Ras^{amp}$ or N-$Ras^{amp}$). In some embodiments, the cancer comprises a Ras mutation, such as a Ras mutation described herein. In some embodiments, a mutation is selected from:

(a) the following K-Ras mutants: G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V, and combinations thereof;

(b) the following H-Ras mutants: Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R, and combinations thereof; and (c) the following N-Ras mutants: Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T, and combinations thereof;

or a combination of any of the foregoing. In some embodiments, the cancer comprises a K-Ras mutation selected from the group consisting of G12C, G12D, G13C, G12V, G13D, G12R, G12S, Q61H, Q61K and Q61L. In some embodiments, the cancer comprises an N-Ras mutation selected from the group consisting of G12C, Q61H, Q61K, Q61L, Q61P and Q61R. In some embodiments, the cancer comprises an H-Ras mutation selected from the group consisting of Q61H and Q61L. In some embodiments, the cancer comprises a Ras mutation selected from the group consisting of G12C, G13C, G12A, G12D, G13D, G12S, G13S, G12V and G13V. In some embodiments, the cancer comprises at least two Ras mutations selected from the group consisting of G12C, G13C, G12A, G12D, G13D, G12S, G13S, G12V and G13V. In some embodiments, a compound of the present invention inhibits more than one Ras mutant. For example, a compound may inhibit both K-Ras G12C and K-Ras G13C. A compound may inhibit both N-Ras G12C and K-Ras G12C. A compound may inhibit both N-Ras G12C and K-Ras G12C. In some embodiments, a compound may inhibit both K-Ras G12C and K-Ras G12D. In some embodiments, a compound may inhibit both K-Ras G12V and K-Ras G12C. In some embodiments, a compound may inhibit both K-Ras G12V and K-Ras G12S. In some embodiments, a compound of the present invention inhibits $Ras^{WT}$ in addition to one or more additional Ras mutations (e.g., K, H or N-$Ras^{WT}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K, H or N-$Ras^{WT}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K, H or N-Ras$^{WT}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T). In some embodiments, a compound of the present invention inhibits Ras$^{amp}$ in addition to one or more additional Ras mutations (e.g., K-, H- or N-Ras$^{amp}$ and K-Ras G12D, G12V, G12C, G13D, G12R, G12A, Q61H, G12S, A146T, G13C, Q61L, Q61R, K117N, A146V, G12F, Q61K, L19F, Q22K, V14I, A59T, A146P, G13R, G12L, or G13V; K-, H- or N-Ras$^{amp}$ and H-Ras Q61R, G13R, Q61K, G12S, Q61L, G12D, G13V, G13D, G12C, K117N, A59T, G12V, G13C, Q61H, G13S, A18V, D119N, G13N, A146T, A66T, G12A, A146V, G12N, or G12R; or K-, H- or N-Ras$^{amp}$ and N-Ras Q61R, Q61K, G12D, Q61L, Q61H, G13R, G13D, G12S, G12C, G12V, G12A, G13V, G12R, P185S, G13C, A146T, G60E, Q61P, A59D, E132K, E49K, T50I, A146V, or A59T).

Methods of detecting Ras mutations are known in the art. Such means include, but are not limited to direct sequencing, and utilization of a high-sensitivity diagnostic assay (with CE-IVD mark), e.g., as described in Domagala, et al., Pol J Pathol 3: 145-164 (2012), incorporated herein by reference in its entirety, including TheraScreen PCR; AmoyDx; PNA-CIamp; RealQuality; EntroGen; LightMix; StripAssay; Hybcell plexA; Devyser; Surveyor; Cobas; and TheraScreen Pyro. See, also, e.g., WO 2020/106640.

In some embodiments, the cancer is non-small cell lung cancer and the Ras mutation comprises a K-Ras mutation, such as K-Ras G12C, K-Ras G12V or K-Ras G12D. In some embodiments, the cancer is colorectal cancer and the Ras mutation comprises a K-Ras mutation, such as K-Ras G12C, K-Ras G12V or K-Ras G12D. In some embodiments, the cancer is pancreatic cancer and the Ras mutation comprises an K-Ras mutation, such as K-Ras G12D or K-Ras G12V. In some embodiments, the cancer is pancreatic cancer and the Ras mutation comprises an N-Ras mutation, such as N-Ras G12D. In some embodiments, the cancer is melanoma and the Ras mutation comprises an N-Ras mutation, such as N-Ras Q61R or N-Ras Q61K. In some embodiments, the cancer is non-small cell lung cancer and the Ras protein is K-Ras$^{amp}$. In any of the foregoing if not already specified, a compound may inhibit Ras$^{WT}$ (e.g., K-, H- or N-Ras$^{WT}$) or Ras$^{amp}$ (e.g., K-, H- or N-Ras$^{amp}$) as well.

In some embodiments, a cancer comprises a Ras mutation and an STK11$^{LOF}$, a KEAP1, an EPHA5 or an NF1 mutation. In some embodiments, the cancer is non-small cell lung cancer and comprises a K-Ras G12C mutation. In some embodiments, the cancer is non-small cell lung cancer and comprises a K-Ras G12C mutation and an STK11$^{LOF}$ mutation. In some embodiments, the cancer is non-small cell lung cancer and comprises a K-Ras G12C mutation and an STK11$^{LOF}$ mutation. In some embodiments, a cancer comprises a K-Ras G13C Ras mutation and an STK11$^{LOF}$, a KEAP1, an EPHA5 or an NF1 mutation. In some embodiments, the cancer is non-small cell lung cancer and comprises a K-Ras G12D mutation. In some embodiments, the cancer is non-small cell lung cancer and comprises a K-Ras G12V mutation. In some embodiments, the cancer is colorectal cancer and comprises a K-Ras G12C mutation. In some embodiments, the cancer is pancreatic cancer and comprises a K-Ras G12D mutation. In some embodiments, the cancer is pancreatic cancer and comprises a K-Ras G12V mutation. In some embodiments, the cancer is endometrial cancer and comprises a K-Ras G12C mutation. In some embodiments, the cancer is gastric cancer and comprises a K-Ras G12C mutation. In any of the foregoing, a compound may inhibit Ras$^{WT}$ (e.g., K-, H- or N-Ras$^{WT}$) or Ras$^{amp}$ (e.g., K-, H- or N-Ras$^{amp}$) as well.

Also provided is a method of inhibiting a Ras protein in a cell, the method comprising contacting the cell with an effective amount of a compound of the present invention, or a pharmaceutically acceptable salt thereof. A method of inhibiting RAF-Ras binding, the method comprising contacting the cell with an effective amount of a compound of the present invention, or a pharmaceutically acceptable salt thereof, is also provided. The cell may be a cancer cell. The cancer cell may be of any type of cancer described herein. The cell may be in vivo or in vitro.

Combination Therapy

The methods of the invention may include a compound of the invention used alone or in combination with one or more additional therapies (e.g., non-drug treatments or therapeutic agents). The dosages of one or more of the additional therapies (e.g., non-drug treatments or therapeutic agents) may be reduced from standard dosages when administered alone. For example, doses may be determined empirically from drug combinations and permutations or may be deduced by isobolographic analysis (e.g., Black et al., *Neurology* 65:S3-S6 (2005)).

A compound of the present invention may be administered before, after, or concurrently with one or more of such additional therapies. When combined, dosages of a compound of the invention and dosages of the one or more additional therapies (e.g., non-drug treatment or therapeutic agent) provide a therapeutic effect (e.g., synergistic or additive therapeutic effect). A compound of the present invention and an additional therapy, such as an anti-cancer agent, may be administered together, such as in a unitary pharmaceutical composition, or separately and, when administered separately, this may occur simultaneously or sequentially. Such sequential administration may be close or remote in time.

In some embodiments, the additional therapy is the administration of side-effect limiting agents (e.g., agents intended to lessen the occurrence or severity of side effects of treatment). For example, in some embodiments, the compounds of the present invention can also be used in combination with a therapeutic agent that treats nausea. Examples of agents that can be used to treat nausea include: dronabinol, granisetron, metoclopramide, ondansetron, and prochlorperazine, or pharmaceutically acceptable salts thereof.

In some embodiments, the one or more additional therapies includes a non-drug treatment (e.g., surgery or radiation therapy). In some embodiments, the one or more additional therapies includes a therapeutic agent (e.g., a compound or biologic that is an anti-angiogenic agent, signal transduction inhibitor, antiproliferative agent, glycolysis inhibitor, or autophagy inhibitor). In some embodiments, the one or more additional therapies includes a non-drug treatment (e.g., surgery or radiation therapy) and a therapeutic agent (e.g., a compound or biologic that is an anti-angiogenic agent, signal transduction inhibitor, antiproliferative agent, glycolysis inhibitor, or autophagy inhibitor). In other embodiments, the one or more additional therapies includes two therapeutic agents. In still other embodiments, the one or more additional therapies includes three therapeutic agents. In some embodiments, the one or more additional therapies includes four or more therapeutic agents.

In this Combination Therapy section, all references are incorporated by reference for the agents described, whether explicitly stated as such or not.

Non-Drug Therapies

Examples of non-drug treatments include, but are not limited to, radiation therapy, cryotherapy, hyperthermia, surgery (e.g., surgical excision of tumor tissue), and T cell adoptive transfer (ACT) therapy. In some embodiments, the compounds of the invention may be used as an adjuvant therapy after surgery. In some embodiments, the compounds of the invention may be used as a neo-adjuvant therapy prior to surgery.

Radiation therapy may be used for inhibiting abnormal cell growth or treating a hyperproliferative disorder, such as cancer, in a subject (e.g., mammal (e.g., human)). Techniques for administering radiation therapy are known in the art. Radiation therapy can be administered through one of several methods, or a combination of methods, including, without limitation, external-beam therapy, internal radiation therapy, implant radiation, stereotactic radiosurgery, systemic radiation therapy, radiotherapy, and permanent or temporary interstitial brachy therapy. The term "brachy therapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a ceil conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, or Y-90. Moreover, the radionuclide(s) can be embodied in a gel or radioactive micro spheres.

In some embodiments, the compounds of the present invention can render abnormal cells more sensitive to treatment with radiation for purposes of killing or inhibiting the growth of such ceils. Accordingly, this invention further relates to a method for sensitizing abnormal cells in a mammal to treatment with radiation which comprises administering to the mammal an amount of a compound of the present invention, which amount is effective to sensitize abnormal ceils to treatment with radiation. The amount of the compound in this method can be determined according to the means for ascertaining effective amounts of such compounds described herein. In some embodiments, the compounds of the present invention may be used as an adjuvant therapy after radiation therapy or as a neo-adjuvant therapy prior to radiation therapy.

In some embodiments, the non-drug treatment is a T cell adoptive transfer (ACT) therapy. In some embodiments, the T cell is an activated T cell. The T cell may be modified to express a chimeric antigen receptor (CAR). CAR modified T (CAR-T) cells can be generated by any method known in the art. For example, the CAR-T cells can be generated by introducing a suitable expression vector encoding the CAR to a T cell. Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art may be used. In some embodiments, the T cell is an autologous T cell. Whether prior to or after genetic modification of the T cells to express a desirable protein (e.g., a CAR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 7,572,631; 5,883,223; 6,905,874; 6,797,514; and 6,867,041.

Therapeutic Agents

A therapeutic agent may be a compound used in the treatment of cancer or symptoms associated therewith.

For example, a therapeutic agent may be a steroid. Accordingly, in some embodiments, the one or more additional therapies includes a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, fiucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts or derivatives thereof.

Further examples of therapeutic agents that may be used in combination therapy with a compound of the present invention include compounds described in the following patents: U.S. Pat. Nos. 6,258,812, 6,630,500, 6,515,004, 6,713,485, 5,521,184, 5,770,599, 5,747,498, 5,990,141, 6,235,764, and 8,623,885, and International Patent Applications WO01/37820, WO01/32651, WO02/68406, WO02/66470, WO02/55501, WO04/05279, WO04/07481, WO04/07458, WO04/09784, WO02/59110, WO99/45009, WO00/59509, WO99/61422, WO00/12089, and WO00/02871.

A therapeutic agent may be a biologic (e.g., cytokine (e.g., interferon or an interleukin such as IL-2)) used in treatment of cancer or symptoms associated therewith. In some embodiments, the biologic is an immunoglobulin-based biologic, e.g., a monoclonal antibody (e.g., a humanized antibody, a fully human antibody, an Fc fusion protein, or a functional fragment thereof) that agonizes a target to stimulate an anti-cancer response or antagonizes an antigen important for cancer. Also included are antibody-drug conjugates.

A therapeutic agent may be a T-cell checkpoint inhibitor. In one embodiment, the checkpoint inhibitor is an inhibitory antibody (e.g., a monospecific antibody such as a monoclonal antibody). The antibody may be, e.g., humanized or fully human. In some embodiments, the checkpoint inhibitor is a fusion protein, e.g., an Fc-receptor fusion protein. In some embodiments, the checkpoint inhibitor is an agent, such as an antibody, that interacts with a checkpoint protein. In some embodiments, the checkpoint inhibitor is an agent, such as an antibody, that interacts with the ligand of a checkpoint protein. In some embodiments, the checkpoint inhibitor is an inhibitor (e.g., an inhibitory antibody or small molecule inhibitor) of CTLA-4 (e.g., an anti-CTLA-4 antibody or fusion a protein). In some embodiments, the checkpoint inhibitor is an inhibitor or antagonist (e.g., an inhibitory antibody or small molecule inhibitor) of PD-1. In some embodiments, the checkpoint inhibitor is an inhibitor or antagonist (e.g., an inhibitory antibody or small molecule inhibitor) of PDL-1. In some embodiments, the checkpoint inhibitor is an inhibitor or antagonist (e.g., an inhibitory antibody or Fc fusion or small molecule inhibitor) of PDL-2 (e.g., a PDL-2/Ig fusion protein). In some embodiments, the checkpoint inhibitor is an inhibitor or antagonist (e.g., an inhibitory antibody or small molecule inhibitor) of B7-H3, B7-H4, BTLA, HVEM, TIM3, GAL9, LAG3, VISTA, KIR, 2B4, CD160, CGEN-15049, CHK 1, CHK2, A2aR, B-7 family ligands, or a combination thereof. In some embodiments, the checkpoint inhibitor is pembrolizumab, nivolumab, PDR001 (NVS), REGN2810 (Sanofi/Regeneron), a PD-L1 antibody such as, e.g., avelumab, durvalumab, atezolizumab, pidilizumab, JNJ-63723283 (JNJ), BGB-A317 (BeiGene & Celgene), or a checkpoint inhibitor disclosed in Preusser, M. et al. (2015) Nat. Rev. Neurol., including, without limitation, ipilimumab, tremelimumab, nivolumab, pembrolizumab, AMP224, AMP514/MEDI0680, BMS936559, MEDI4736, MPDL3280A, MSB0010718C, BMS986016, IMP321, lirilumab, IPH2101, 1-7F9, and KW-6002.

A therapeutic agent may be an anti-TIGIT antibody, such as MBSA43, BMS-986207, MK-7684, COM902, AB154, MTIG7192A, or OMP-313M32 (etigilimab).

A therapeutic agent may be an agent that treats cancer or symptoms associated therewith (e.g., a cytotoxic agent, non-peptide small molecules, or other compound useful in the treatment of cancer or symptoms associated therewith, collectively, an "anti-cancer agent"). Anti-cancer agents can be, e.g., chemotherapeutics or targeted therapy agents.

Anti-cancer agents include mitotic inhibitors, intercalating antibiotics, growth factor inhibitors, ceil cycle inhibitors, enzymes, topoisomerase inhibitors, bioiogical response modifiers, alkylating agents, antimetabolites, folic acid analogs, pyrimidine analogs, purine analogs and related inhibitors, *vinca* alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Further anti-cancer agents include leucovorin (LV), irenotecan, oxaliplatin, capecitabine, paclitaxel, and doxetaxel. In some embodiments, the one or more additional therapies includes two or more anti-cancer agents. The two or more anti-cancer agents can be used in a cocktail to be administered in combination or administered separately. Suitable dosing regimens of combination anti-cancer agents are known in the art and described in, for example, Saltz et al., *Proc. Am. Soc. Clin. Oncol.* 18:233a (1999), and Douillard et al., Lancet 355(9209):1041-1047 (2000).

Other non-limiting examples of anti-cancer agents include Gleevec© (Imatinib Mesylate); Kyprolis® (carfilzomib); Velcade® (bortezomsb); Casodex (bicalutamide); Iressa® (gefitinib); alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; sarcodictyin A; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimustine; antibiotics such as the enediyne antibiotics (e.g., calicheamicin, such as calicheamicin gammaII and calicheamicin omegaII (see, e.g., *Agnew, Chem. Inti. Ed Engl.* 33:183-186 (1994)); dynemicin such as dynemicin A; bisphosphonates such as clodronate; an esperamicin; neocarzinostatin chromophore and related chromoprotein enediyne antiobiotic chromophores, aclacinomysins, actinomycin, authramycin, azaserine, bleomycins, cactinomycin, calicheamicin, carabicin, caminomycin, carminomycin, carzinophilin, chromomycins, dactinomycin, daunorubicin, detorubicin, 6-diazo-5-oxo-L-norleucine, adriamycin (doxorubicin), morpholino-doxorubicin, cyanomorpholino-doxorubicin, 2-pyrrolino-doxorubicin, deoxydoxorubicin, epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenishers such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone such as epothilone B; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes such as T-2 toxin, verracurin A, roridin A and anguidine; urethane; vindesine; dacarbazine; mannomustine; mitobronitol; mitolactol; pipobroman; gacytosine; arabinoside ("Ara-C"); cyclophosphamide; thiotepa; taxoids, e.g., Taxol® (paclitaxel), Abraxane® (cremophor-free, albumin-engineered nanoparticle formulation of paclitaxel), and Taxotere® (doxetaxel); chloranbucil; tamoxifen (Nolvadex™); raloxifene; aromatase inhibiting 4(5)-imidazoies; 4-hydroxytamoxifen; trioxifene; keoxifene; LY 117018; onapristone; toremifene (Fareston®); futamide, nilutamide, bicalutamide, leuprolide, goserelin; chlorambucil; Gemzar® gemcitabine; 6-thioguanine; mercaptopurine; platinum coordination complexes such as cisplatin, oxaliplatin and carboplatin; vinblastine; platinum; etoposide (VP-16); ifosfamide; mitoxantrone; vincristine; Navelbine® (vinorelbine); novantrone; teniposide; edatrexate; daunomycin; aminopterin; ibandronate; irinotecan (e.g., CPT-11); topoisomerase inhibitor RFS 2000; difluoromethylornithine (DMFO); retinoids such as retinoic acid; esperamicins; capecitabine (e.g., Xeloda®); and pharmaceutically acceptable salts of any of the above.

Additional non-limiting examples of anti-cancer agents include trastuzumab (Herceptin®), bevacizumab (Avastin®), cetuximab (Erbitux®), rituximab (Rituxan®), Taxol®, Arimidex®, ABVD, avicine, abagovomab, acridine carboxamide, adecatumumab, 17-N-allylamino-17-demethoxygeldanamycin, alpharadin, alvocidib, 3-amino-pyridine-2-carboxaldehyde thiosemicarbazone, amonafide, anthracenedione, anti-CD22 immunotoxins, antineoplastics (e.g., cell-cycle nonspecific antineoplastic agents, and other antineoplastics described herein), antitumorigenic herbs, apaziquone, atiprimod, azathioprine, belotecan, bendamustine, BIBW2992, biricodar, brostallicin, bryostatin, buthionine sulfoximine, CBV (chemotherapy), calyculin, dichloroacetic acid, discodermolide, elsamitrucin, enocitabine, eribulin, exatecan, exisulind, ferruginol, forodesine, fosfestrol, ICE chemotherapy regimen, IT-101, imexon, imiquimod, indolocarbazole, irofulven, laniquidar, larotaxel, lenalidomide, lucanthone, lurtotecan, mafosfamide, mitozolomide, nafoxidine, nedaplatin, olaparib, ortataxel, PAC-1, pawpaw, pixantrone, proteasome inhibitors, rebeccamycin, resiquimod, rubitecan, SN-38, salinosporamide A, sapacitabine, Stanford V, swainsonine, talaporfin, tariquidar, tegafur-uracil, temodar, tesetaxel, triplatin tetranitrate, tris(2-chloroethyl)amine, troxacitabine, uramustine, vadimezan, vinflunine, ZD6126, and zosuquidar.

Further non-limiting examples of anti-cancer agents include natural products such as *vinca* alkaloids (e.g., vinblastine, vincristine, and vinorelbine), epidipodophyllotoxins (e.g., etoposide and teniposide), antibiotics (e.g., dactinomycin (actinomycin D), daunorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethamine, cyclophosphamide and analogs, melphalan, and chlorambucil), ethylenimines and methylmelamines (e.g., hexaamethylmelaamine and thiotepa), CDK inhibitors (e.g., a CDK4/6 inhibitor such as abemaciclib, ribociclib, palbociclib; seliciclib, UCN-01, P1446A-05, PD-0332991, dinaciclib, P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs, pyrimidine analogs (e.g., fluorouracil, floxuridine, and cytarabine), purine analogs and related inhibitors (e.g., mercaptopurine, thioguanine, pentostatin, and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTOR inhibitors (e.g., vistusertib, temsirolimus, everolimus, ridaforolimus, and sirolimus), KSP(Eg5) inhibitors (e.g., Array 520), DNA binding agents (e.g., Zalypsis®), PI3K inhibitors such as PI3K delta inhibitor (e.g., GS-1101 and TGR-1202), PI3K delta and gamma inhibitor (e.g., CAL-130), copanlisib, alpelisib and idelalisib; multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HU-MAX-CD38), anti-CSI (e.g., elotuzumab), HSP90 inhibitors (e.g., 17 AAG and KOS 953), PI3K/Akt inhibitors (e.g., perifosine), Akt inhibitors (e.g., GSK-2141795), PKC inhibitors (e.g., enzastaurin), FTIs (e.g., Zarnestra™), anti-CD138 (e.g., BT062), Torcl/2 specific kinase inhibitors (e.g., INK128), ER/UPR targeting agents (e.g., MKC-3946), cFMS inhibitors (e.g., ARRY-382), JAK1/2 inhibitors (e.g., CYT387), PARP inhibitors (e.g., olaparib and veliparib (ABT-888)), and BCL-2 antagonists.

In some embodiments, an anti-cancer agent is selected from mechlorethamine, camptothecin, ifosfamide, tamoxifen, raloxifene, gemcitabine, Navelbine®, sorafenib, or any analog or derivative variant of the foregoing.

In some embodiments, the anti-cancer agent is a HER2 inhibitor. Non-limiting examples of HER2 inhibitors include monoclonal antibodies such as trastuzumab (Herceptin®) and pertuzumab (Perjeta®); small molecule tyrosine kinase inhibitors such as gefitinib (Iressa®), erlotinib (Tarceva®), pilitinib, CP-654577, CP-724714, canertinib (CI 1033), HKI-272, lapatinib (GW-572016; Tykerb®), PKI-166, AEE788, BMS-599626, HKI-357, BIBW 2992, ARRY-334543, JNJ-26483327, and JNJ-26483327.

In some embodiments, an anti-cancer agent is an ALK inhibitor. Non-limiting examples of ALK inhibitors include ceritinib, TAE-684 (NVP-TAE694), PF02341066 (crizotinib or 1066), alectinib; brigatinib; entrectinib; ensartinib (X-396); lorlatinib; ASP3026; CEP-37440; 4SC-203; TL-398; PLB1003; TSR-011; CT-707; TPX-0005, and AP26113. Additional examples of ALK kinase inhibitors are described in examples 3-39 of WO05016894.

In some embodiments, an anti-cancer agent is an inhibitor of a member downstream of a Receptor Tyrosine Kinase (RTK)/Growth Factor Receptor (e.g., a SHP2 inhibitor (e.g., SHP099, TNO155, RMC-4550, RMC-4630, JAB-3068, RLY-1971), a SOS1 inhibitor (e.g., BI-1701963, BI-3406), a Raf inhibitor, a MEK inhibitor, an ERK inhibitor, a PI3K inhibitor, a PTEN inhibitor, an AKT inhibitor, or an mTOR inhibitor (e.g., mTORC1 inhibitor or mTORC2 inhibitor). In some embodiments, the anti-cancer agent is JAB-3312. In some embodiments, an anti-cancer agent is an additional Ras inhibitor (e.g., AMG 510, MRTX1257, MRTX849, ARS-853, ARS-1620, ARS-3248 (or JNJ-74699157), LY3499446), or a Ras vaccine, or another therapeutic modality designed to directly or indirectly decrease the oncogenic activity of Ras. Other examples of Ras inhibitors that may be combined with a Ras inhibitor of the present invention are provided in the following, incorporated herein by reference in their entireties: WO 2020050890, WO 2020047192, WO 2020035031, WO 2020028706, WO 2019241157, WO 2019232419, WO 2019217691, WO 2019217307, WO 2019215203, WO 2019213526, WO 2019213516, WO 2019155399, WO 2019150305, WO 2019110751, WO 2019099524, WO 2019051291, WO 2018218070, WO 2018217651, WO 2018218071, WO 2018218069, WO 2018206539, WO 2018143315, WO 2018140600, WO 2018140599, WO 2018140598, WO 2018140514, WO 2018140513, WO 2018140512, WO 2018119183, WO 2018112420, WO 2018068017, WO 2018064510, WO 2017201161, WO 2017172979, WO 2017100546, WO 2017087528, WO 2017058807, WO 2017058805, WO 2017058728, WO 2017058902, WO 2017058792, WO 2017058768, WO 2017058915, WO 2017015562, WO 2016168540, WO 2016164675, WO 2016049568, WO 2016049524, WO 2015054572, WO 2014152588, WO 2014143659 and WO 2013155223.

In some embodiments, a therapeutic agent that may be combined with a compound of the present invention is an inhibitor of the MAP kinase (MAPK) pathway (or "MAPK inhibitor"). MAPK inhibitors include, but are not limited to, one or more MAPK inhibitor described in Cancers (Basel) 2015 September; 7(3): 1758-1784. For example, the MAPK inhibitor may be selected from one or more of trametinib, binimetinib, selumetinib, cobimetinib, LErafAON (Neo-Pharm), ISIS 5132; vemurafenib, pimasertib, TAK733, RO4987655 (CH4987655); CI-1040; PD-0325901; CH5126766; MAP855; AZD6244; refametinib (RDEA 119/BAY 86-9766); GDC-0973/XL581; AZD3330 (ARRY-424704/ARRY-704); RO5126766 (Roche, described in PLoS One. 2014 Nov. 25; 9(11)); and GSK1120212 (or JTP-74057, described in Clin Cancer Res. 2011 Mar. 1; 17(5):989-1000). The MAPK inhibitor may be PLX8394, LXH254, GDC-5573, or LY3009120.

In some embodiments, an anti-cancer agent is a disrupter or inhibitor of the RAS-RAF-ERK or PI3K-AKT-TOR or PI3K-AKT signaling pathways. The PI3K/AKT inhibitor may include, but is not limited to, one or more PI3K/AKT inhibitor described in Cancers (Basel) 2015 September; 7(3): 1758-1784. For example, the PI3K/AKT inhibitor may be selected from one or more of NVP-BEZ235; BGT226; XL765/SAR245409; SF1126; GDC-0980; PI-103; PF-04691502; PKI-587; GSK2126458.

In some embodiments, an anti-cancer agent is a PD-1 or PD-L1 antagonist.

In some embodiments, additional therapeutic agents include ALK inhibitors, HER2 inhibitors, EGFR inhibitors, IGF-1R inhibitors, MEK inhibitors, PI3K inhibitors, AKT inhibitors, TOR inhibitors, MCL-1 inhibitors, BCL-2 inhibitors, SHP2 inhibitors, proteasome inhibitors, and immune therapies. In some embodiments, a therapeutic agent may be a pan-RTK inhibitor, such as afatinib.

IGF-1R inhibitors include linsitinib, or a pharmaceutically acceptable salt thereof.

EGFR inhibitors include, but are not limited to, small molecule antagonists, antibody inhibitors, or specific antisense nucleotide or siRNA. Useful antibody inhibitors of EGFR include cetuximab (Erbitux®), panitumumab (Vectibix®), zalutumumab, nimotuzumab, and matuzumab. Further antibody-based EGFR inhibitors include any anti-EGFR antibody or antibody fragment that can partially or completely block EGFR activation by its natural ligand. Non-limiting examples of antibody-based EGFR inhibitors include those described in Modjtahedi et al., Br. J. Cancer 1993, 67:247-253; Teramoto et al., Cancer 1996, 77:639-645; Goldstein et al., Clin. Cancer Res. 1995, 1:1311-1318; Huang et al., 1999, Cancer Res. 15:59(8):1935-40; and Yang et al., Cancer Res. 1999, 59:1236-1243. The EGFR inhibitor can be monoclonal antibody Mab E7.6.3 (Yang, 1999 supra), or Mab C225 (ATCC Accession No. HB-8508), or an antibody or antibody fragment having the binding specificity thereof.

Small molecule antagonists of EGFR include gefitinib (Iressa®), erlotinib (Tarceva®), and lapatinib (TykerB®). See, e.g., Yan et al., Pharmacogenetics and Pharmacogenomics In Oncology Therapeutic Antibody Development, BioTechniques 2005, 39(4):565-8; and Paez et al., EGFR Mutations In Lung Cancer Correlation With Clinical Response To Gefitinib Therapy, Science 2004, 304(5676): 1497-500. In some embodiments, the EGFR inhibitor is osimertinib (Tagrisso®). Further non-limiting examples of small molecule EGFR inhibitors include any of the EGFR inhibitors described in the following patent publications, and all pharmaceutically acceptable salts of such EGFR inhibitors: EP 0520722; EP 0566226; WO96/33980; U.S. Pat. No. 5,747,498; WO96/30347; EP 0787772; WO97/30034; WO97/30044; WO97/38994; WO97/49688; EP 837063; WO98/02434; WO97/38983; WO95/19774; WO95/19970; WO97/13771; WO98/02437; WO98/02438; WO97/32881; DE 19629652; WO98/33798; WO97/32880; WO97/32880; EP 682027; WO97/02266; WO97/27199; WO98/07726; WO97/34895; WO96/31510; WO98/14449; WO98/14450; WO98/14451; WO95/09847; WO97/19065; WO98/17662; U.S. Pat. Nos. 5,789,427; 5,650,415; 5,656,643; WO99/35146; WO99/35132; WO99/07701; and WO92/20642. Additional non-limiting examples of small molecule EGFR inhibitors include any of the EGFR inhibitors described in Traxler et al., Exp. Opin. Ther. Patents 1998, 8(12):1599-1625. In some embodiments, an EGFR inhibitor is an ERBB inhibitor. In humans, the ERBB family contains HER1 (EGFR, ERBB1), HER2 (NEU, ERBB2), HER3 (ERBB3), and HER (ERBB4).

MEK inhibitors include, but are not limited to, pimasertib, selumetinib, cobimetinib (Cotellic®), trametinib (Mekinist®), and binimetinib (Mektovi®). In some embodiments, a MEK inhibitor targets a MEK mutation that is a Class I MEK1 mutation selected from D67N; P124L; P124S; and L177V. In some embodiments, the MEK mutation is a Class II MEK1 mutation selected from ΔE51-Q58; ΔF53-Q58; E203K; L177M; C121S; F53L; K57E; Q56P; and K57N.

PI3K inhibitors include, but are not limited to, wortmannin; 17-hydroxywortmannin analogs described in WO06/044453; 4-[2-(1H-Indazol-4-yl)-6-[[4-(methylsulfonyl)piperazin-1-yl]methyl]thieno[3,2-d]pyrimidin-4-yl]morpholine (also known as pictilisib or GDC-0941 and described in WO09/036082 and WO09/055730); 2-methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in WO06/122806); (S)—1-(4-((2-(2-aminopyrimidin-5-yl)-7-methyl-4-morpholinothieno[3,2-d]pyrimidin-6-yl)methyl)piperazin-1-yl)-2-hydroxypropan-1-one (described in WO08/070740); LY294002 (2-(4-morpholinyl)-8-phenyl-4H-1-benzopyran-4-one (available from Axon Medchem); PI 103 hydrochloride (3-[4-(4-morpholinylpyrido-[3',2':4,5]furo[3,2-d]pyrimidin-2-yl] phenol hydrochloride (available from Axon Medchem); PIK 75 (2-methyl-5-nitro-2-[(6-bromoimidazo[1,2-a]pyridin-3-yl)methylene]-1-methylhydrazide-benzenesulfonic acid, monohydrochloride) (available from Axon Medchem); PIK 90 (N-(7,8-dimethoxy-2,3-dihydro-imidazo[1,2-c]quinazolin-5-yl)-nicotinamide (available from Axon Medchem); AS-252424 (5-[I-[5-(4-fluoro-2-hydroxy-phenyl)-furan-2-yl]-meth-(Z)-ylidene]-thiazolidine-2,4-dione (available from Axon Medchem); TGX-221 (7-methyl-2-(4-morpholinyl)-9-[1-(phenylamino)ethyl]-4H-pyrido-[1,2-a]pyrimidin-4-one (available from Axon Medchem); XL-765; and XL-147. Other PI3K inhibitors include demethoxyviridin, perifosine, CAL101, PX-866, BEZ235, SF1126, INK1117, IPI-145, BKM120, XL147, XL765, Palomid 529, GSK1059615, ZSTK474, PWT33597, IC87114, TGI 00-115, CAL263, PI-103, GNE-477, CUDC-907, and AEZS-136.

AKT inhibitors include, but are not limited to, Akt-1-1 (inhibits AktI) (Barnett et al., Biochem. J. 2005, 385(Pt. 2): 399-408); Akt-1-1,2 (inhibits AkI and 2) (Barnett et al., Biochem. J. 2005, 385(Pt. 2): 399-408); API-59CJ-Ome (e.g., Jin et al., Br. J. Cancer 2004, 91:1808-12); 1-H-imidazo[4,5-c]pyridinyl compounds (e.g., WO 05/011700); indole-3-carbinol and derivatives thereof (e.g., U.S. Pat. No. 6,656,963; Sarkar and Li J Nutr. 2004, 134(12 Suppl): 3493S-3498S); perifosine (e.g., interferes with Akt membrane localization; Dasmahapatra et al. Clin. Cancer Res. 2004, 10(15):5242-52); phosphatidylinositol ether lipid analogues (e.g., Gills and Dennis Expert. Opin. Investig. Drugs 2004, 13:787-97); and triciribine (TCN or API-2 or NCI identifier: NSC 154020; Yang et al., Cancer Res. 2004, 64:4394-9).

mTOR inhibitors include, but are not limited to, ATP-competitive mTORC1/mTORC2 inhibitors, e.g., PI-103, PP242, PP30; Torin 1; FKBP12 enhancers; 4H-1-benzopyran-4-one derivatives; and rapamycin (also known as sirolimus) and derivatives thereof, including: temsirolimus (Torisel®); everolimus (Afinitor®; WO94/09010); ridaforolimus (also known as deforolimus or AP23573); rapalogs, e.g., as disclosed in WO98/02441 and WO01/14387, e.g. AP23464 and AP23841; 40-(2-hydroxyethyl) rapamycin; 40-[3-hydroxy(hydroxymethyl)methylpropanoate]-rapamycin (also known as CC1779); 40-epi-(tetrazolyt)-rapamycin (also called ABT578); 32-deoxorapamycin; 16-pentynyloxy-32(S)-dihydrorapamycin; derivatives disclosed in WO05/005434; derivatives disclosed in U.S. Pat. Nos. 5,258,389, 5,118,677, 5,118,678, 5,100,883, 5,151,413, 5,120,842, and 5,256,790, and in WO94/090101, WO92/05179, WO93/111130, WO94/02136, WO94/02485, WO95/14023, WO94/02136, WO95/16691, WO96/41807, WO96/41807, and WO2018204416; and phosphorus-containing rapamycin derivatives (e.g., WO05/016252). In some embodiments, the mTOR inhibitor is a bisteric inhibitor (see, e.g., WO2018204416, WO2019212990 and WO2019212991), such as RMC-5552.

BRAF inhibitors that may be used in combination with compounds of the invention include, for example, vemurafenib, dabrafenib, and encorafenib. A BRAF may comprise a Class 3 BRAF mutation. In some embodiments, the Class 3 BRAF mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R; and A762E.

MCL-1 inhibitors include, but are not limited to, AMG-176, MIK665, and S63845. The myeloid cell leukemia-1 (MCL-1) protein is one of the key anti-apoptotic members of the B-cell lymphoma-2 (BCL-2) protein family. Over-expression of MCL-1 has been closely related to tumor progression as well as to resistance, not only to traditional chemotherapies but also to targeted therapeutics including BCL-2 inhibitors such as ABT-263.

In some embodiments, the additional therapeutic agent is a SHP2 inhibitor. SHP2 is a non-receptor protein tyrosine phosphatase encoded by the PTPN11 gene that contributes to multiple cellular functions including proliferation, differentiation, cell cycle maintenance and migration. SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors acting through receptor tyrosine kinases (RTKs) leads to exposure of the catalytic site resulting in enzymatic activation of SHP2.

SHP2 is involved in signaling through the RAS-mitogen-activated protein kinase (MAPK), the JAK-STAT or the phosphoinositol 3-kinase-AKT pathways. Mutations in the PTPN11 gene and subsequently in SHP2 have been identified in several human developmental diseases, such as Noonan Syndrome and Leopard Syndrome, as well as human cancers, such as juvenile myelomonocytic leukemia, neuroblastoma, melanoma, acute myeloid leukemia and cancers of the breast, lung and colon. Some of these mutations destabilize the auto-inhibited conformation of SHP2 and promote autoactivation or enhanced growth factor driven activation of SHP2. SHP2, therefore, represents a highly attractive target for the development of novel therapies for the treatment of various diseases including cancer. A SHP2 inhibitor (e.g., RMC-4550 or SHP099) in combination with a RAS pathway inhibitor (e.g., a MEK inhibitor) have been shown to inhibit the proliferation of multiple cancer cell lines in vitro (e.g., pancreas, lung, ovarian, and breast cancer). Thus, combination therapy involving a SHP2 inhibitor with a RAS pathway inhibitor could be a general strategy for preventing tumor resistance in a wide range of malignancies.

Non-limiting examples of such SHP2 inhibitors that are known in the art, include: Chen et al. *Mol Pharmacol.* 2006, 70, 562; Sarver et al., *J. Med. Chem.* 2017, 62, 1793; Xie et al., *J. Med. Chem.* 2017, 60, 113734; and Igbe et al., *Oncotarget,* 2017, 8, 113734; and PCT applications: WO2015107493; WO2015107494; WO201507495; WO2016203404; WO2016203405; WO2016203406; WO2011022440; WO2017156397; WO2017079723; WO2017211303; WO2012041524; WO2017211303; WO2019051084; WO2017211303; US20160030594; US20110281942; WO2010011666; WO2014113584; WO2014176488; WO2017100279; WO2019051469; U.S. Pat. No. 8,637,684; WO2007117699; WO2015003094; WO2005094314; WO2008124815; WO2009049098; WO2009135000; WO2016191328; WO2016196591; WO2017078499; WO2017210134; WO2018013597; WO2018129402; WO2018130928; WO20181309928; WO2018136264; WO2018136265; WO2018160731; WO2018172984; and WO2010121212, each of which is incorporated herein by reference.

In some embodiments, a SHP2 inhibitor binds in the active site. In some embodiments, a SHP2 inhibitor is a mixed-type irreversible inhibitor. In some embodiments, a SHP2 inhibitor binds an allosteric site e.g., a non-covalent allosteric inhibitor. In some embodiments, a SHP2 inhibitor is a covalent SHP2 inhibitor, such as an inhibitor that targets the cysteine residue (C333) that lies outside the phosphatase's active site. In some embodiments a SHP2 inhibitor is a reversible inhibitor. In some embodiments, a SHP2 inhibitor is an irreversible inhibitor. In some embodiments, the SHP2 inhibitor is SHP099. In some embodiments, the SHP2 inhibitor is TN0155. In some embodiments, the SHP2 inhibitor is RMC-4550. In some embodiments, the SHP2 inhibitor is RMC-4630. In some embodiments, the SHP2 inhibitor is JAB-3068. In some embodiments, the SHP2 inhibitor is RLY-1971.

In some embodiments, the additional therapeutic agent is selected from the group consisting of a MEK inhibitor, a HER2 inhibitor, a SHP2 inhibitor, a CDK4/6 inhibitor, an mTOR inhibitor, a SOS1 inhibitor, and a PD-L1 inhibitor. In some embodiments, the additional therapeutic agent is selected from the group consisting of a MEK inhibitor, a SHP2 inhibitor, and a PD-L1 inhibitor. See, e.g., Hallin et al., Cancer Discovery, DOI: 10.1158/2159-8290 (Oct. 28, 2019) and Canon et al., Nature, 575:217 (2019). In some embodiments, a Ras inhibitor of the present invention is used in combination with a MEK inhibitor and a SOS1 inhibitor. In some embodiments, a Ras inhibitor of the present invention is used in combination with a PDL-1 inhibitor and a SOS1 inhibitor. In some embodiments, a Ras inhibitor of the present invention is used in combination with a PDL-1 inhibitor and a SHP2 inhibitor. In some embodiments, a Ras inhibitor of the present invention is used in combination with a MEK inhibitor and a SHP2 inhibitor. In some embodiments, the cancer is colorectal cancer and the treatment comprises administration of a Ras inhibitor of the present invention in combination with a second or third therapeutic agent.

Proteasome inhibitors include, but are not limited to, carfilzomib (Kyprolis®), bortezomib (Velcade®), and oprozomib.

Immune therapies include, but are not limited to, monoclonal antibodies, immunomodulatory imides (IMiDs), GITR agonists, genetically engineered T-cells (e.g., CAR-T cells), bispecific antibodies (e.g., BiTEs), and anti-PD-1, anti-PDL-1, anti-CTLA4, anti-LAGI, and anti-OX40 agents).

Immunomodulatory agents (IMiDs) are a class of immunomodulatory drugs (drugs that adjust immune responses) containing an imide group. The IMiD class includes thalidomide and its analogues (lenalidomide, pomalidomide, and apremilast).

Exemplary anti-PD-1 antibodies and methods for their use are described by Goldberg et al., Blood 2007, 110(1):186-192; Thompson et al., Clin. Cancer Res. 2007, 13(6):1757-1761; and WO06/121168 A1), as well as described elsewhere herein.

GITR agonists include, but are not limited to, GITR fusion proteins and anti-GITR antibodies (e.g., bivalent anti-GITR antibodies), such as, a GITR fusion protein described in U.S. Pat. Nos. 6,111,090, 8,586,023, WO2010/003118 and WO2011/090754; or an anti-GITR antibody described, e.g., in U.S. Pat. No. 7,025,962, EP 1947183, U.S. Pat. Nos. 7,812,135, 8,388,967, 8,591,886, 7,618,632, EP 1866339, and WO2011/028683, WO2013/039954, WO05/007190, WO07/133822, WO05/055808, WO99/40196, WO01/03720, WO99/20758, WO06/083289, WO05/115451, and WO2011/051726.

Another example of a therapeutic agent that may be used in combination with the compounds of the invention is an anti-angiogenic agent. Anti-angiogenic agents are inclusive of, but not limited to, in vitro synthetically prepared chemical compositions, antibodies, antigen binding regions, radionuclides, and combinations and conjugates thereof. An anti-angiogenic agent can be an agonist, antagonist, allosteric modulator, toxin or, more generally, may act to inhibit or stimulate its target (e.g., receptor or enzyme activation or inhibition), and thereby promote cell death or arrest cell growth. In some embodiments, the one or more additional therapies include an anti-angiogenic agent.

Anti-angiogenic agents can be MMP-2 (matrix-metalloproteinase 2) inhibitors, MMP-9 (matrix-metalloprotienase 9) inhibitors, and COX-II (cyclooxygenase 11) inhibitors. Non-limiting examples of anti-angiogenic agents include rapamycin, temsirolimus (CCI-779), everolimus (RAD001), sorafenib, sunitinib, and bevacizumab. Examples of useful COX-II inhibitors include alecoxib, valdecoxib, and rofecoxib. Examples of useful matrix metalloproteinase inhibitors are described in WO96/33172, WO96/27583, WO98/07697, WO98/03516, WO98/34918, WO98/34915, WO98/33768, WO98/30566, WO90/05719, WO99/52910, WO99/52889, WO99/29667, WO99007675, EP0606046, EP0780386, EP1786785, EP1181017, EP0818442, EP1004578, and US20090012085, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Further exemplary anti-angiogenic agents include KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF (e.g., bevacizumab), or soluble VEGF receptors or a ligand binding region thereof) such as VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as Vectibix® (panitumumab), erlotinib (Tarceva®), anti-AngI and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). Other anti-angiogenic agents include Campath, IL-8, B-FGF, Tek antagonists (US2003/0162712; U.S. Pat. No. 6,413,932), anti-TWEAK agents (e.g., specifically binding antibodies or antigen binding regions, or soluble TWEAK receptor antagonists; see U.S. Pat. No. 6,727,225), ADAM distintegrin domain to antagonize the binding of integrin to its ligands (US 2002/0042368), specifically binding anti-eph receptor or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto). Additional anti-angiogenic agents include: SD-7784 (Pfizer, USA); cilengitide (Merck KGaA, Germany, EPO 0770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands), DACantiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 0970070); ARGENT technology (Ariad, USA); YIGSR-Stealth (Johnson & Johnson, USA); fibrinogen-E fragment (BioActa, UK); angiogenic inhibitor (Trigen, UK); TBC-1635 (Encysive Pharmaceuticals, USA); SC-236 (Pfizer, USA); ABT-567 (Abbott, USA); Metastatin (EntreMed, USA); maspin (Sosei, Japan); 2-methoxyestradiol (Oncology Sciences Corporation, USA); ER-68203-00 (IV AX, USA); BeneFin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); bevacizumab (pINN) (Genentech, USA); angiogenic inhibitors (SUGEN, USA);

XL 784 (Exelixis, USA); XL 647 (Exelixis, USA); MAb, alpha5beta3 integrin, second generation (Applied Molecular Evolution, USA and Medlmmune, USA); enzastaurin hydrochloride (Lilly, USA); CEP 7055 (Cephalon, USA and Sanofi-Synthelabo, France); BC 1 (Genoa Institute of Cancer Research, Italy); rBPI 21 and BPI-derived antiangiogenic (XOMA, USA); PI 88 (Progen, Australia); cilengitide (Merck KGaA, German; Munich Technical University, Germany, Scripps Clinic and Research Foundation, USA); AVE 8062 (Ajinomoto, Japan); AS 1404 (Cancer Research Laboratory, New Zealand); SG 292, (Telios, USA); Endostatin (Boston Childrens Hospital, USA); ATN 161 (Attenuon, USA); 2-methoxyestradiol (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenic, (EntreMed, USA); urokinase plasminogen activator inhibitor, (Dendreon, USA); oglufanide (pINN), (Melmotte, USA); HIF-lalfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol; anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors; SU 11248 (Pfizer, USA and SUGEN USA); ABT 518, (Abbott, USA); YH16 (Yantai Rongchang, China); S-3APG (Boston Childrens Hospital, USA and EntreMed, USA); MAb, KDR (ImClone Systems, USA); MAb, alpha5 beta (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA) CV 247 (Ivy Medical, UK); CKD 732 (Chong Kun Dang, South Korea); irsogladine, (Nippon Shinyaku, Japan); RG 13577 (Aventis, France); WX 360 (Wilex, Germany); squalamine, (Genaera, USA); RPI 4610 (Sirna, USA); heparanase inhibitors (InSight, Israel); KL 3106 (Kolon, South Korea); Honokiol (Emory University, USA); ZK CDK (Schering AG, Germany); ZK Angio (Schering AG, Germany); ZK 229561 (Novartis, Switzerland, and Schering AG, Germany); XMP 300 (XOMA, USA); VGA 1102 (Taisho, Japan); VE-cadherin-2 antagonists (ImClone Systems, USA); Vasostatin (National Institutes of Health, USA); Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Further examples of therapeutic agents that may be used in combination with compounds of the invention include agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor, c-Met.

Another example of a therapeutic agent that may be used in combination with compounds of the invention is an autophagy inhibitor. Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used. In some embodiments, the one or more additional therapies include an autophagy inhibitor.

Another example of a therapeutic agent that may be used in combination with compounds of the invention is an anti-neoplastic agent. In some embodiments, the one or more additional therapies include an anti-neoplastic agent. Non-limiting examples of anti-neoplastic agents include acemannan, aclarubicin, aldesleukin, alemtuzumab, alitretinoin, altretamine, amifostine, aminolevulinic acid, amrubicin, amsacrine, anagrelide, anastrozole, ancer, ancestim, arglabin, arsenic trioxide, BAM-002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon-1, interferon alpha, natural, interferon beta, interferon beta-Ia, interferon beta-Ib, interferon gamma, natural interferon gamma-Ia, interferon gamma-Ib, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, virulizin, zinostatin stimalamer, orzoledronic acid; abarelix; AE 941 (Aeterna), ambamustine, antisense oligonucleotide, bcl-2 (Genta), APC 8015 (Dendreon), decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techni clone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Additional examples of therapeutic agents that may be used in combination with compounds of the invention include ipilimumab (Yervoy®); tremelimumab; galiximab; nivolumab, also known as BMS-936558 (Opdivo®); pembrolizumab (Keytruda®); avelumab (Bavencio®); AMP224; BMS-936559; MPDL3280A, also known as RG7446; MEDI-570; AMG557; MGA271; IMP321; BMS-663513; PF-05082566; CDX-1127; anti-OX40 (Providence Health Services); huMAbOX40L; atacicept; CP-870893; lucatumumab; dacetuzumab; muromonab-CD3; ipilumumab; MEDI4736 (Imfinzi®); MSB0010718C; AMP 224; adalimumab (Humira®); ado-trastuzumab emtansine (Kadcyla®); aflibercept (Eylea®); alemtuzumab (Campath®); basiliximab (Simulect®); belimumab (Benlysta®); basiliximab (Simulect®); belimumab (Benlysta®); brentuximab vedotin (Adcetris®); canakinumab (Haris®); certolizumab pegol (Cimzia®); daclizumab (Zenapax®); daratumumab (Darzalex®); denosumab (Prolia®); eculizumab (Soliris®); efalizumab (Raptiva®); gemtuzumab ozogamicin (Mylotarg®); golimumab (Simponi®); ibritumomab tiuxetan (Zevalin®); infliximab (Remicade®); motavizumab (Numax®); natalizumab (Tysabri®); obinutuzumab (Gazyva®); ofatumumab (Arzerra®); omalizumab (Xolair®); palivizumab (Synagis®); pertuzumab (Perjeta®); pertuzumab (Perjeta®); ranibizumab (Lucentis®); raxibacumab (Abthrax®); tocilizumab (Actemra®); tositumomab; tositumomab-i-131; tositumomab and tositumomab-i-131 (Bexxar®); ustekinumab (Stelara®); AMG 102; AMG 386; AMG 479; AMG 655; AMG 706; AMG 745; and AMG 951.

The compounds described herein can be used in combination with the agents disclosed herein or other suitable agents, depending on the condition being treated. Hence, in some embodiments the one or more compounds of the disclosure will be co-administered with other therapies as described herein. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described herein can be formulated together in the same dosage form and administered simultaneously. Alternatively, a compound of the invention and any of the therapies described herein can be simultaneously administered, wherein both the agents are present in separate formulations. In another alternative, a compound of the present disclosure can be administered and followed by any of the therapies described herein, or vice versa. In some embodiments of the separate administration protocol, a compound of the invention and any of the therapies described herein are administered a few minutes apart, or a few hours apart, or a few days apart.

In some embodiments of any of the methods described herein, the first therapy (e.g., a compound of the invention) and one or more additional therapies are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours, up to 24 hours, or up to 1-7, 1-14, 1-21 or 1-30 days before or after the one or more additional therapies.

The invention also features kits including (a) a pharmaceutical composition including an agent (e.g., a compound of the invention) described herein, and (b) a package insert with instructions to perform any of the methods described herein. In some embodiments, the kit includes (a) a pharmaceutical composition including an agent (e.g., a compound of the invention) described herein, (b) one or more additional therapies (e.g., non-drug treatment or therapeutic agent), and (c) a package insert with instructions to perform any of the methods described herein.

As one aspect of the present invention contemplates the treatment of the disease or symptoms associated therewith with a combination of pharmaceutically active compounds that may be administered separately, the invention further relates to combining separate pharmaceutical compositions in kit form. The kit may comprise two separate pharmaceutical compositions: a compound of the present invention, and one or more additional therapies. The kit may comprise a container for containing the separate compositions such as a divided bottle or a divided foil packet. Additional examples of containers include syringes, boxes, and bags. In some embodiments, the kit may comprise directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

NUMBERED EMBODIMENTS

[1] A compound, or pharmaceutically acceptable salt thereof, having the structure of Formula I:

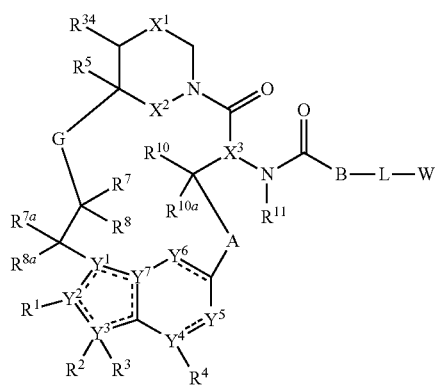

Formula I wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 10-membered heteroarylene;

B is —CH($R^9$)— or >C=C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$ or N;

$Y^6$ is C(O), CH, $CH_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl; and $R^{34}$ is hydrogen or $C_1$-$C_3$ alkyl.

[2] The compound, or pharmaceutically acceptable salt thereof, of paragraph [1], wherein G is optionally substituted $C_1$-$C_4$ heteroalkylene.

[3] The compound, or pharmaceutically acceptable salt thereof, of paragraph [1] or [2], wherein the compound has the structure of Formula Ia:

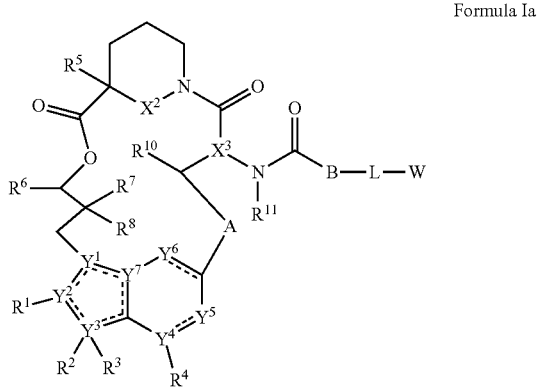

Formula Ia wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{10}$ is hydrogen, hydroxy, $C_1$-$C_3$ alkoxy, or $C_1$-$C_3$ alkyl; and $R^{11}$ is hydrogen or $C_1$-$C_3$ alkyl.

[4] The compound, or pharmaceutically acceptable salt thereof, of any one of paragraphs [1] to [3], wherein $X^2$ is NH.

[5] The compound, or pharmaceutically acceptable salt thereof, of any one of paragraphs [1] to [4], wherein $X^3$ is CH.

[6] The compound, or pharmaceutically acceptable salt thereof, of any one of paragraphs [1] to [5], wherein $R^{11}$ is hydrogen.

[7] The compound, or pharmaceutically acceptable salt thereof, of any one of paragraphs [1] to [5], wherein $R^{11}$ is $C_1$-$C_3$ alkyl.

[8] The compound, or pharmaceutically acceptable salt thereof, of paragraph [7], wherein $R^{11}$ is methyl.

[9] The compound, or pharmaceutically acceptable salt thereof, of any one of paragraphs [1] to [6], wherein the compound has the structure of Formula Ib:

Formula Ib wherein the dotted lines represent zero, one, two, three, or four non-adjacent double bonds;

A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ and $Y^6$ are, independently, CH or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

[10] The compound, or pharmaceutically acceptable salt thereof, of any one of paragraphs [1] to [9] wherein $X^1$ is optionally substituted $C_1$-$C_2$ alkylene.

[11] The compound, or pharmaceutically acceptable salt thereof, of paragraph [10], wherein $X^1$ is methylene.

[12] The compound, or pharmaceutically acceptable salt thereof, of any one of paragraphs [1] to [11], wherein $R^5$ is hydrogen.

[13] The compound, or pharmaceutically acceptable salt thereof, of any one of paragraphs [1] to [11], wherein $R^5$ is $C_1$-$C_4$ alkyl optionally substituted with halogen.

[14] The compound, or pharmaceutically acceptable salt thereof, of paragraph [13], wherein $R^5$ is methyl.

[15] The compound, or pharmaceutically acceptable salt thereof, of any one of paragraphs [1] to [14], wherein $Y^4$ is C.

[16] The compound, or pharmaceutically acceptable salt thereof, of any one of paragraphs [1] to [15], wherein $R^4$ is hydrogen.

[17] The compound, or pharmaceutically acceptable salt thereof, of any one of paragraphs [1] to [16], wherein $Y^5$ is CH.

[18] The compound, or pharmaceutically acceptable salt thereof, of any one of paragraphs [1] to [17], wherein $Y^6$ is CH.

[19] The compound, or pharmaceutically acceptable salt thereof, of any one of paragraphs [1] to [18], wherein $Y^1$ is C.

[20] The compound, or pharmaceutically acceptable salt thereof, of any one of paragraphs [1] to [19], wherein $Y^2$ is C.

[21] The compound, or pharmaceutically acceptable salt thereof, of any one of paragraphs [1] to [20], wherein $Y^3$ is N.

[22] The compound, or pharmaceutically acceptable salt thereof, of any one of paragraphs [1] to [21], wherein $R^3$ is absent.

[23] The compound, or pharmaceutically acceptable salt thereof, of any one of paragraphs [1] to [22], wherein $Y^7$ is C.

[24] The compound, or pharmaceutically acceptable salt thereof, of any one of paragraphs [1] to [6] or [9] to [23], wherein the compound has the structure of Formula Ic:

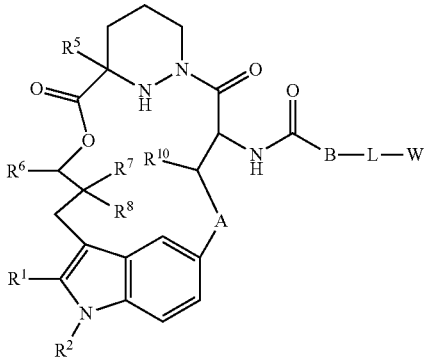

Formula Ic wherein A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is hydrogen, optionally substituted $C_1$-$C_6$ alkyl, optionally substituted $C_2$-$C_6$ alkenyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=$CR^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $R^{10}$ is hydrogen, hydroxy, $C_1$-$C_3$ alkoxy, or $C_1$-$C_3$ alkyl.

[25] The compound, or pharmaceutically acceptable salt thereof, of any one of paragraphs [1] to [24], wherein $R^6$ is hydrogen.

[26] The compound, or pharmaceutically acceptable salt thereof, of any one of paragraphs [1] to [25], wherein $R^2$ is hydrogen, cyano, optionally substituted $C_1$-$C_6$ alkyl, optionally substituted 3 to 6-membered cycloalkyl, or optionally substituted 3 to 6-membered heterocycloalkyl.

[27] The compound, or pharmaceutically acceptable salt thereof, of paragraph [26], wherein $R^2$ is optionally substituted $C_1$-$C_6$ alkyl.

[28] The compound, or pharmaceutically acceptable salt thereof, of paragraph [27], wherein $R^2$ is ethyl.

[29] The compound, or pharmaceutically acceptable salt thereof, of any one of paragraphs [1] to [28], wherein $R^7$ is optionally substituted $C_1$-$C_3$ alkyl.

[30] The compound, or pharmaceutically acceptable salt thereof, of paragraph [29], wherein $R^7$ is $C_1$-$C_3$ alkyl.

[31] The compound, or pharmaceutically acceptable salt thereof, of any one of paragraphs [1] to [30], wherein $R^8$ is optionally substituted $C_1$-$C_3$ alkyl.

[32] The compound, or pharmaceutically acceptable salt thereof, of paragraph [31], wherein $R^8$ is $C_1$-$C_3$ alkyl.

[33] The compound, or pharmaceutically acceptable salt thereof, of any one of paragraphs [1] to [32], wherein the compound has the structure of Formula Id:

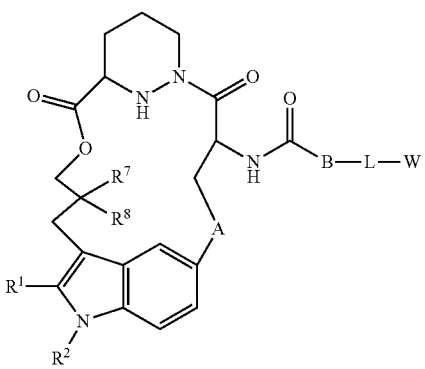

Formula Id wherein A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl.

[34] The compound, or pharmaceutically acceptable salt thereof, of any one of paragraphs [1] to [33], wherein $R^1$ is 5 to 10-membered heteroaryl.

[35] The compound, or pharmaceutically acceptable salt thereof, of paragraph [34], wherein $R^1$ is optionally substituted 6-membered aryl or optionally substituted 6-membered heteroaryl.

[36] The compound, or pharmaceutically acceptable salt thereof, of any one of paragraphs [1] to [35], wherein the compound has the structure of Formula Ie:

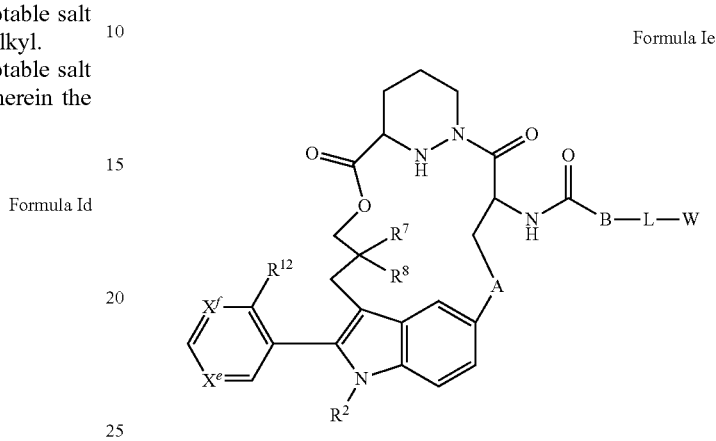

Formula Ie wherein A is —N(H or $CH_3$)C(O)—($CH_2$)— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl $X^e$ and $X^f$ are, independently, N or CH; and $R^{12}$ is optionally substituted $C_1$-$C_6$ alkyl or optionally substituted $C_1$-$C_6$ heteroalkyl, or optionally substituted 3 to 7-membered heterocycloalkyl.

[37] The compound, or pharmaceutically acceptable salt thereof, of paragraph [36], wherein $X^e$ is N and $X^f$ is CH.

[38] The compound, or pharmaceutically acceptable salt thereof, of paragraph [36], wherein $X^e$ is CH and $X^f$ is N.

[39] The compound, or pharmaceutically acceptable salt thereof, of any one of paragraphs [36] to [38], wherein $R^{12}$ is optionally substituted $C_1$-$C_6$ heteroalkyl.

[40] The compound, or pharmaceutically acceptable salt thereof, of any one of paragraphs [36] to [39], wherein $R^{12}$ is

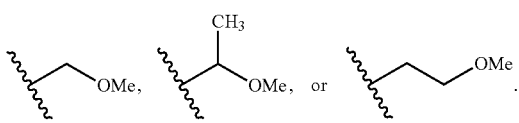

[41] The compound, or pharmaceutically acceptable salt thereof, of paragraph [1] or [2], wherein the compound has the structure of Formula VI:

Formula VI

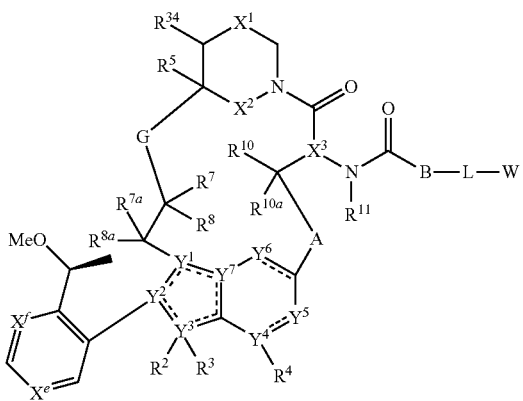

wherein the dotted lines represent zero, one, two, three, or four non-adjacent double bonds;

A is —N(H or $CH_3$)C(O)—$(CH_2)$— where the amino nitrogen is bound to the carbon atom of —CH($R^{10}$)—, optionally substituted 3 to 6-membered cycloalkylene, optionally substituted 3 to 6-membered heterocycloalkylene, optionally substituted 6-membered arylene, or optionally substituted 5 to IQ-membered heteroarylene;

B is —CH($R^9$)— or >C=C$R^9R^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or $S(O)_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, $CH_2$, or N;

$Y^6$ is C(O), CH, $CH_2$, or N;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=C$R^{7'}R^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10}$ is hydrogen, halo, hydroxy, $C_1$-$C_3$ alkoxy, or $C_1$-$C_3$ alkyl;

$R^{10a}$ is hydrogen or halo;

$R^{11}$ is hydrogen or $C_1$-$C_3$ alkyl;

$R^{34}$ is hydrogen or $C_1$-$C_3$ alkyl; and
$X^e$ and $X^f$ are, independently, N or CH.

[42] The compound, or pharmaceutically acceptable salt thereof, of paragraph [41], wherein the compound has the structure of Formula VIa:

Formula VIa wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$X^1$ is optionally substituted $C_1$-$C_2$ alkylene, NR, O, or S(O)$_n$;

$X^2$ is O or NH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$X^e$ and $X^f$ are, independently, N or CH;

$R^{11}$ is hydrogen or $C_1$-$C_3$ alkyl; and $R^{21}$ is hydrogen or $C_1$-$C_3$ alkyl.

[43] The compound, or pharmaceutically acceptable salt thereof, of paragraph [41] or [42], wherein the compound has the structure of Formula VIb:

Formula VIb wherein A optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $X^e$ and $X^f$ are, independently, N or CH.

[44] The compound, or pharmaceutically acceptable salt thereof, of any one of paragraphs [1] to [43], wherein A is optionally substituted 6-membered arylene.

[45] The compound, or pharmaceutically acceptable salt thereof, of paragraph [44], wherein A has the structure:

wherein $R^{13}$ is hydrogen, hydroxy, amino, optionally substituted $C_1$-$C_6$ alkyl, or optionally substituted $C_1$-$C_6$ heteroalkyl.

[46] The compound, or pharmaceutically acceptable salt thereof, of paragraph [45], wherein $R^{13}$ is hydrogen.

[47] The compound, or pharmaceutically acceptable salt thereof, of paragraph [45], wherein $R^{13}$ is hydroxy.

[48] The compound, or pharmaceutically acceptable salt thereof, of any one of paragraphs [1] to [47], wherein B is —CHR$^9$—.

[49] The compound, or pharmaceutically acceptable salt thereof, of paragraph [48], wherein R$^9$ is optionally substituted C$_1$-C$_6$ alkyl or optionally substituted 3 to 6-membered cycloalkyl.

[50] The compound, or pharmaceutically acceptable salt thereof, of paragraph [49], wherein R$^9$ is:

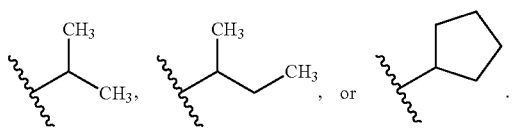

[51] The compound, or pharmaceutically acceptable salt thereof, of paragraph [50], wherein R$^9$ is

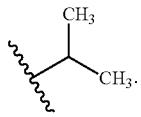

[52] The compound, or pharmaceutically acceptable salt thereof, of any one of paragraphs [1] to [47], wherein B is optionally substituted 6-membered arylene.

[53] The compound, or pharmaceutically acceptable salt thereof, of paragraph [52], wherein B is 6-membered arylene.

[54] The compound, or pharmaceutically acceptable salt thereof, of paragraph [53], wherein B is:

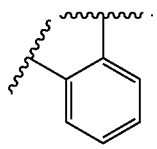 [SMILES: *c1ccccc1*]

[55] The compound, or pharmaceutically acceptable salt thereof, of any one of paragraphs [1] to [54], wherein R$^7$ is methyl.

[56] The compound, or pharmaceutically acceptable salt thereof, of any one of paragraphs [1] to [55], wherein R$^8$ is methyl.

[57] The compound, or pharmaceutically acceptable salt thereof, of any one of paragraphs [1] to [56], wherein the linker is the structure of Formula II:

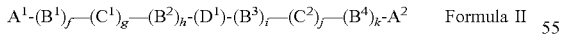  Formula II where A$^1$ is a bond between the linker and B; A$^2$ is a bond between W and the linker; B$^1$, B$^2$, B$^3$, and B$^4$ each, independently, is selected from optionally substituted C$_1$-C$_2$ alkylene, optionally substituted C$_1$-C$_3$ heteroalkylene, O, S, and NR$^N$; R$^N$ is hydrogen, optionally substituted C$_1$-C$_4$ alkyl, optionally substituted C$_2$-C$_4$ alkenyl, optionally substituted C$_2$-C$_4$ alkynyl, optionally substituted 3 to 14-membered heterocycloalkyl, optionally substituted 6 to 10-membered aryl, or optionally substituted C$_1$-C$_7$ heteroalkyl; C$^1$ and C$^2$ are each, independently, selected from carbonyl, thiocarbonyl, sulphonyl, or phosphoryl; f, g, h, i, j, and k are each, independently, 0 or 1; and D$^1$ is optionally substituted C$_1$-C$_{10}$ alkylene, optionally substituted C$_2$-C$_{10}$ alkenylene, optionally substituted C$_2$-C$_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted C$_2$-C$_{10}$ polyethylene glycolene, or optionally substituted C$_1$-C$_{10}$ heteroalkylene, or a chemical bond linking A$^1$-(B$^1$)$_f$—(C$^1$)$_g$—(B$^2$)$_h$— to —(B$^3$)$_i$—(C$^2$)$_j$—(B$^4$)$_k$-A$^2$.

[58] The compound, or a pharmaceutically acceptable salt thereof, of any one of paragraphs [1] to [57], wherein the linker is acyclic.

[59] The compound, or a pharmaceutically acceptable salt thereof, of paragraph [58], wherein the linker has the structure of Formula IIa:

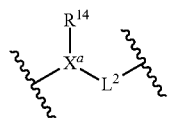  Formula IIa wherein X$^a$ is absent or N;

R$^{14}$ is absent, hydrogen or optionally substituted C$_1$-C$_6$ alkyl; and

L$^2$ is absent, —SO$_2$—, optionally substituted C$_1$-C$_4$ alkylene or optionally substituted C$_1$-C$_4$ heteroalkylene, wherein at least one of X$^a$, R$^{14}$, or L$^2$ is present.

[60] The compound, or a pharmaceutically acceptable salt thereof, of paragraph [59], wherein the linker has the structure:

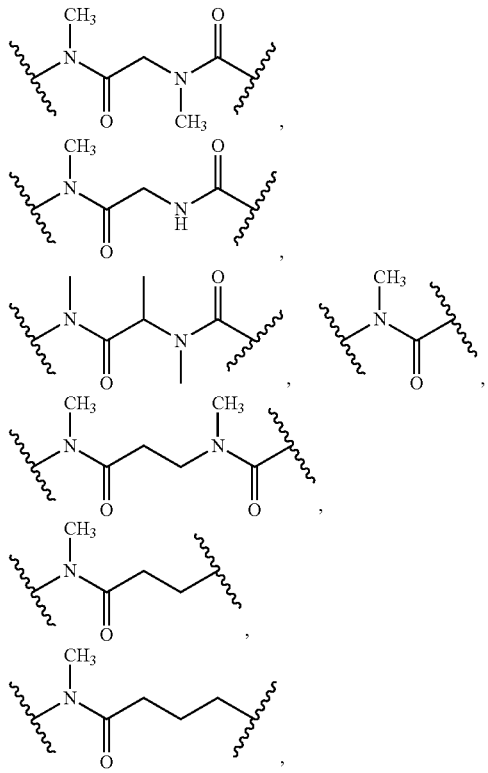

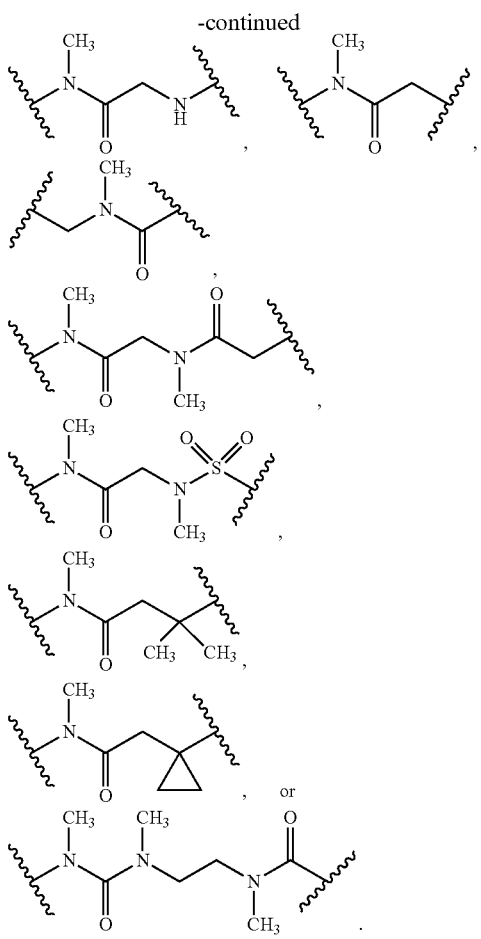

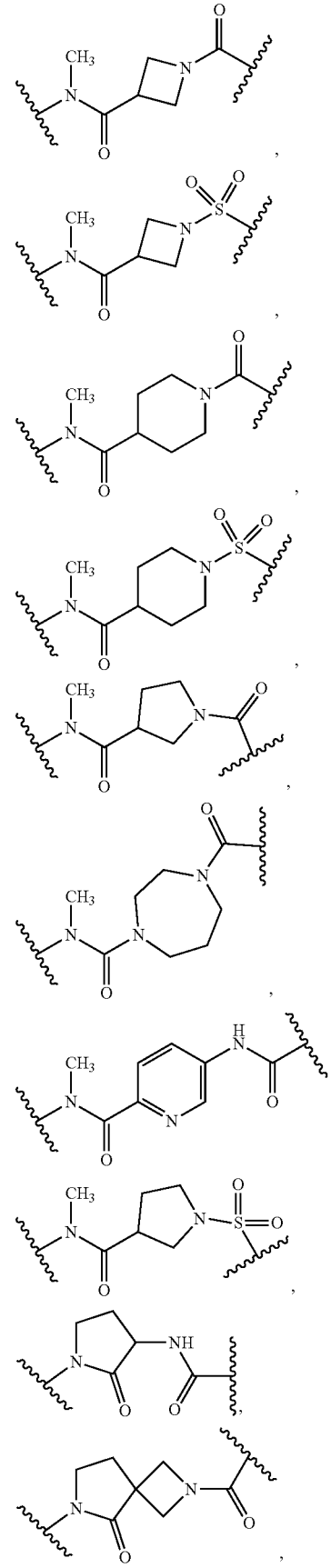

[61] The compound, or a pharmaceutically acceptable salt thereof, of any one of paragraphs [1] to [57], wherein the linker is or a comprises a cyclic group.

[62] The compound, or a pharmaceutically acceptable salt thereof, of any one of paragraphs [1] to [57] or [61], wherein the linker has the structure of Formula IIb:

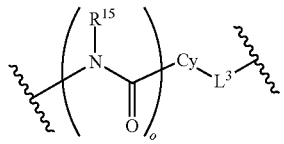

Formula IIb wherein o is 0 or 1;

$R^{15}$ is hydrogen or optionally substituted $C_1$-$C_6$ alkyl;

Cy is optionally substituted 3 to 8-membered cycloalkylene, optionally substituted 3 to 8-membered heterocycloalkylene, optionally substituted 6-10 membered arylene, or optionally substituted 5 to 10-membered heteroarylene; and $L^3$ is absent, —$SO_2$—, optionally substituted $C_1$-$C_4$ alkylene or optionally substituted $C_1$-$C_4$ heteroalkylene.

[63] The compound, or a pharmaceutically acceptable salt thereof, of paragraph [62], wherein the linker has the structure:

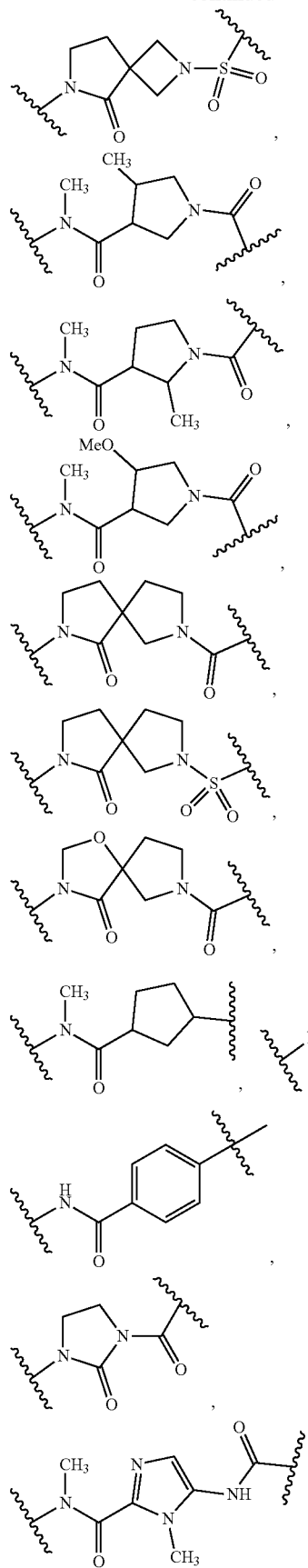
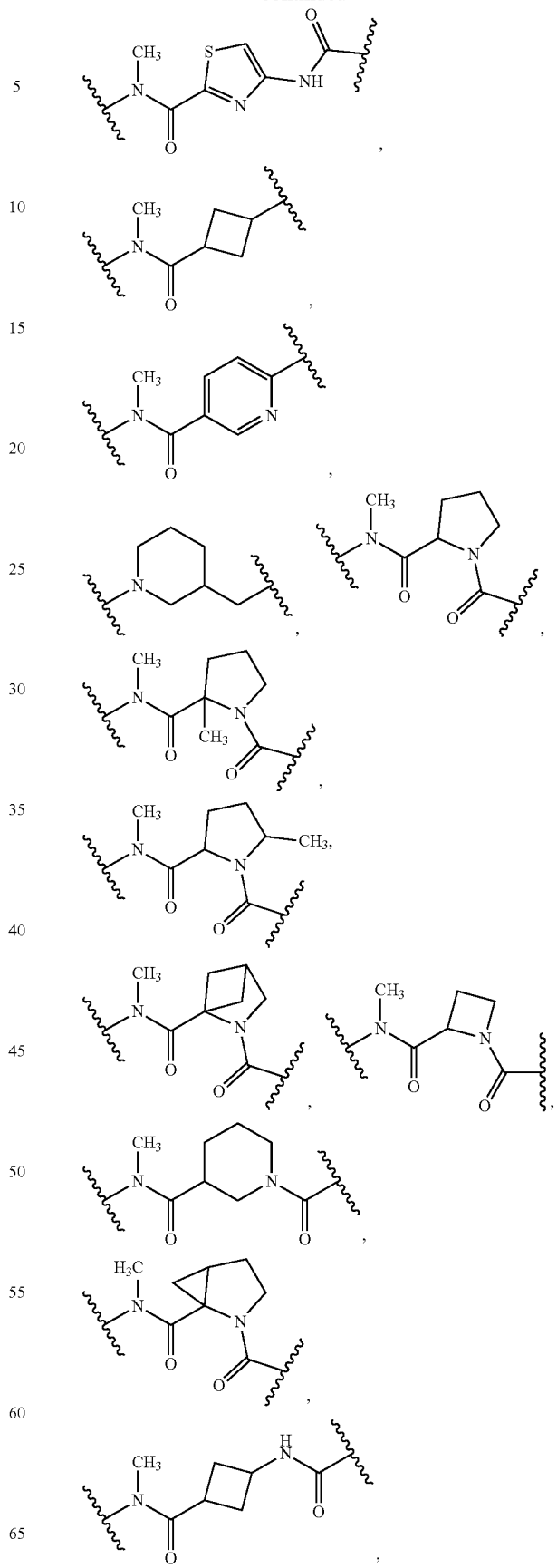

383
-continued
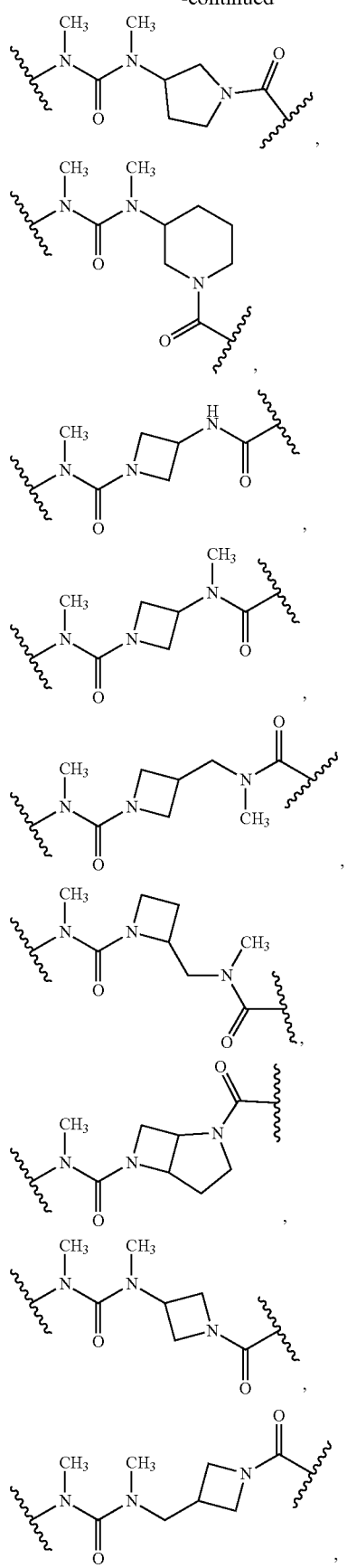
384
-continued
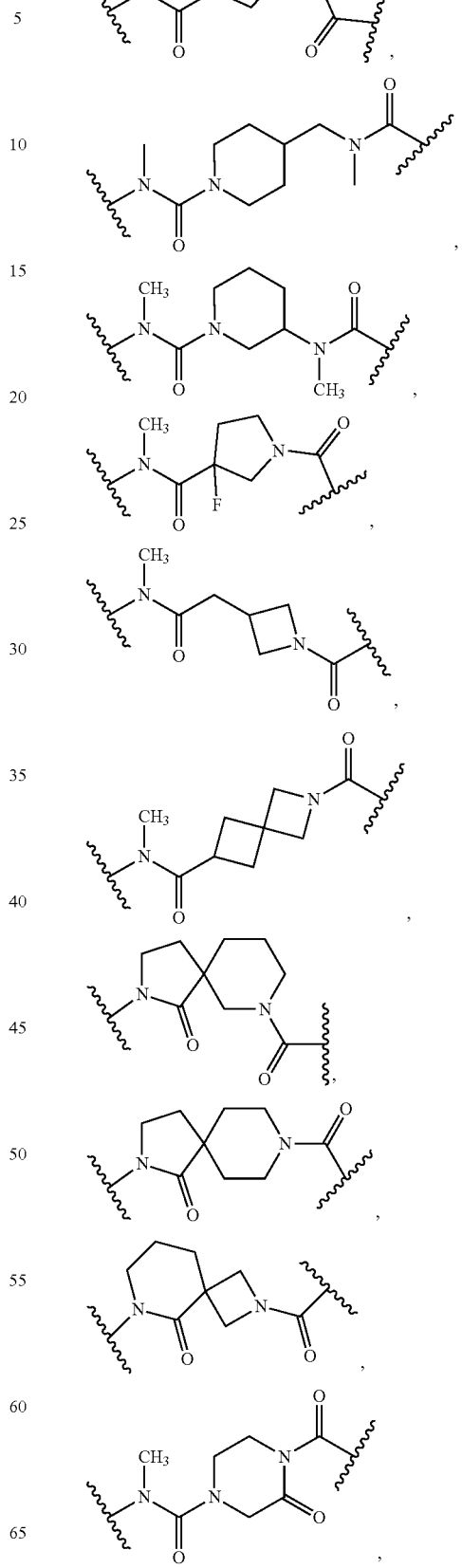

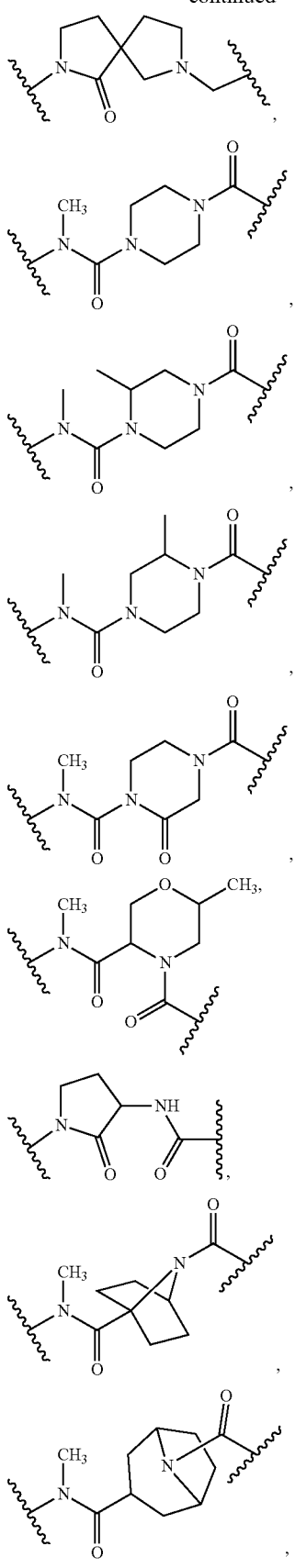

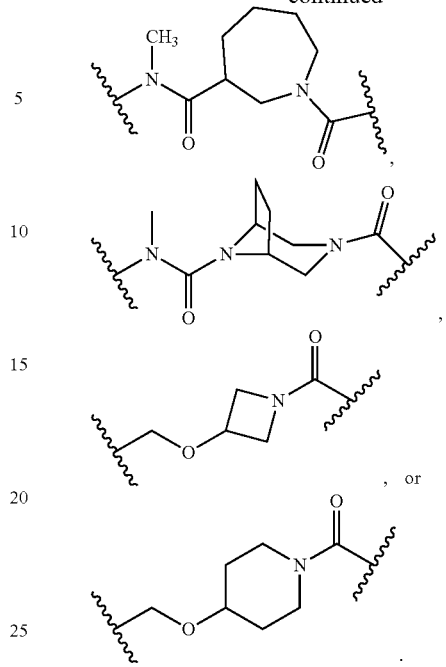

[64] The compound, or a pharmaceutically acceptable salt thereof, of any one of paragraphs [1] to [63], wherein W comprises a carbodiimide.

[65] The compound, or a pharmaceutically acceptable salt thereof, of paragraph [64], wherein W has the structure of Formula IIIa:

Formula IIIa

wherein $R^{14}$ is optionally substituted $C_1$-$C_6$ alkyl, optionally substituted $C_1$-$C_6$ heteroalkyl, optionally substituted 3 to 8-membered cycloalkyl, optionally substituted 6 to 10-membered aryl, optionally substituted 3 to 14-membered heterocycloalkyl, or optionally substituted 5 to 10-membered heteroaryl.

[66] The compound, or a pharmaceutically acceptable salt thereof, of paragraph [65], wherein W has the structure:

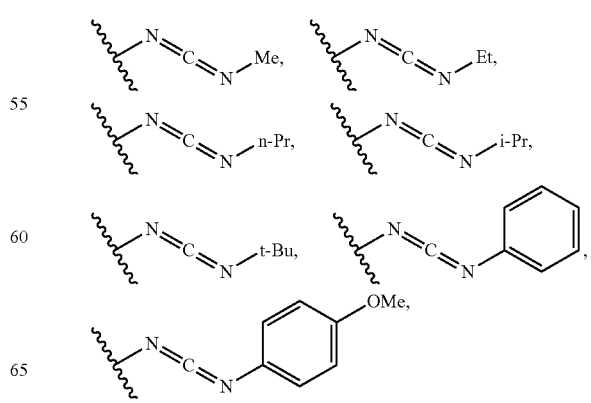

387
-continued
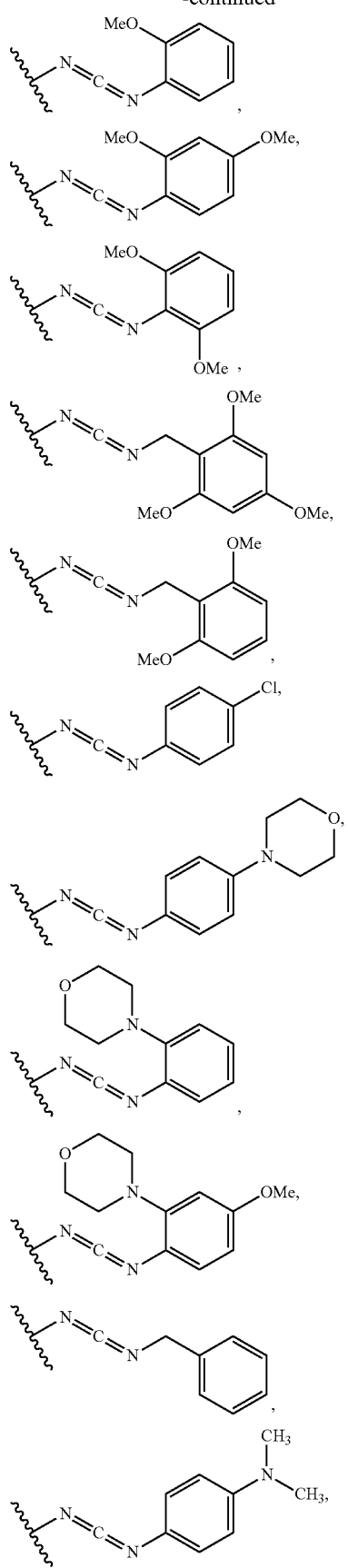
388
-continued
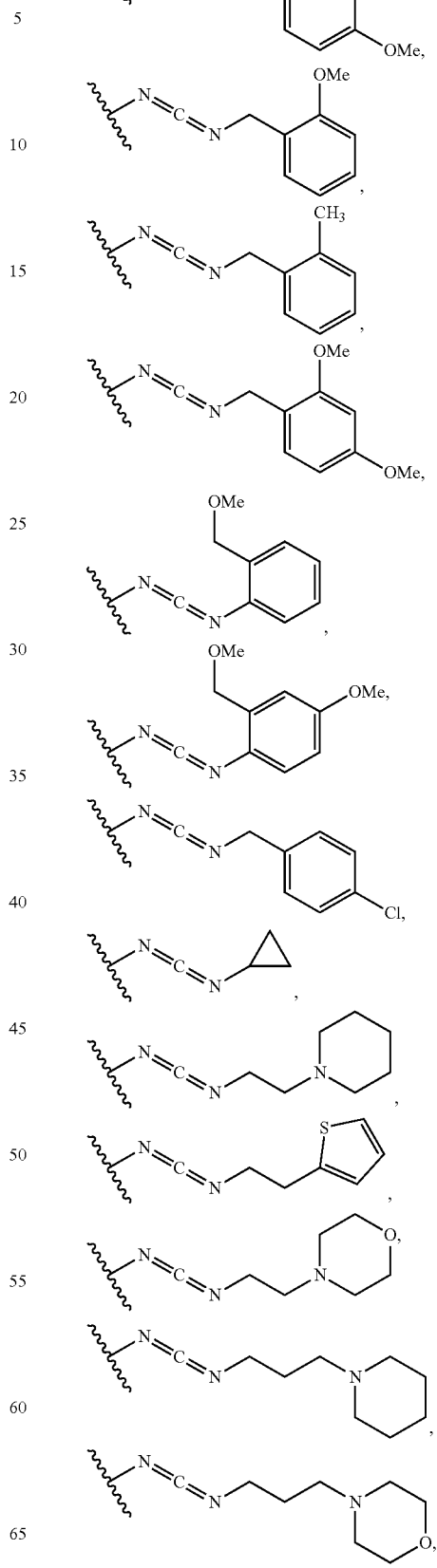

-continued

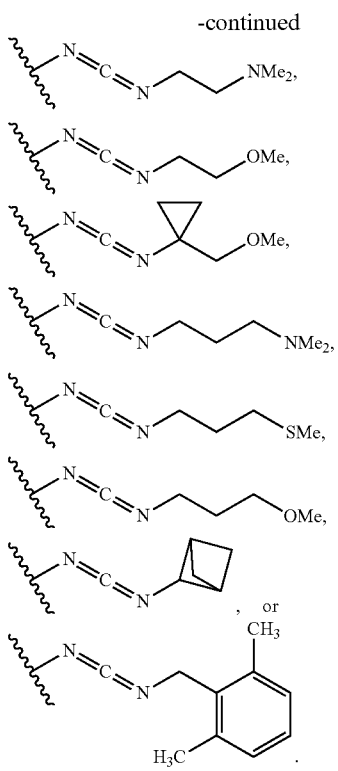

[67] The compound, or a pharmaceutically acceptable salt thereof, of any one of paragraphs [1] to [63], wherein W comprises an oxazoline or thiazoline.

[68] The compound, or a pharmaceutically acceptable salt thereof, of paragraph [67], wherein W has the structure of Formula IIIb:

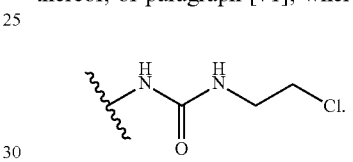

Formula IIb wherein $X^1$ is O or S;
$X^2$ is absent or $NR^{19}$;
$R^{15}$, $R^{16}$, $R^{17}$, and $R^{18}$ are, independently, hydrogen or optionally substituted $C_1$-$C_6$ alkyl; and
$R^{19}$ is hydrogen, C(O)(optionally substituted $C_1$-$C_6$ alkyl), optionally substituted $C_1$-$C_6$ alkyl, optionally substituted 6 to 10-membered aryl, optionally substituted 3 to 14-membered heterocycloalkyl, or optionally substituted 5 to 10-membered heteroaryl.

[69] The compound, or a pharmaceutically acceptable salt thereof, of paragraph [68], wherein W is:

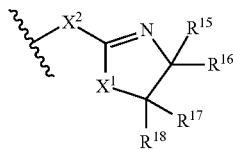

[70] The compound, or a pharmaceutically acceptable salt thereof, of any one of paragraphs [1] to [63], wherein W comprises a chloroethyl urea, a chloroethyl thiourea, a chloroethyl carbamate, or a chloroethyl thiocarbamate.

[71] The compound, or a pharmaceutically acceptable salt thereof, of paragraph [70], wherein W has the structure of Formula IIIc:

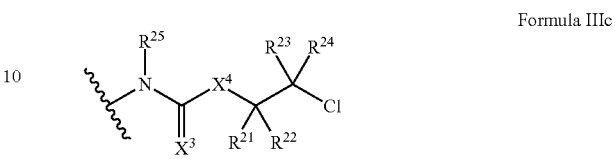

Formula IIIc wherein $X^3$ is O or S;
$X^4$ is O, S, $NR^{26}$;
$R^{21}$, $R^{22}$, $R^{23}$, $R^{24}$, and $R^{26}$ are, independently, hydrogen or optionally substituted $C_1$-$C_6$ alkyl; and
$R^{25}$ is hydrogen, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl.

[72] The compound, or a pharmaceutically acceptable salt thereof, of paragraph [71], wherein W is

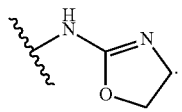

[73] The compound, or a pharmaceutically acceptable salt thereof, of any one of paragraphs [1] to [63], wherein W comprises an aziridine.

[74] The compound, or a pharmaceutically acceptable salt thereof, of paragraph [73], wherein W has the structure of Formula IIId1, Formula IIId2, Formula IIId3, or Formula IIId4:

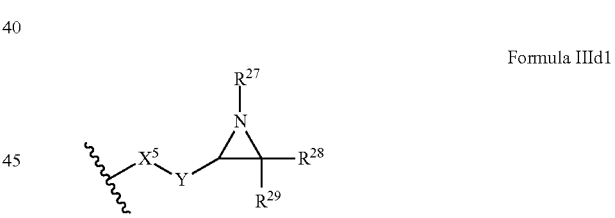

Formula IIId1

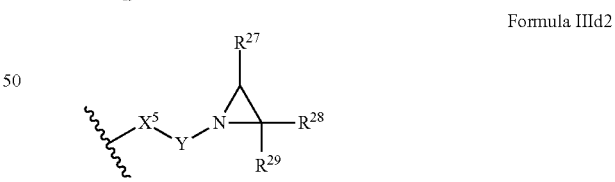

Formula IIId2

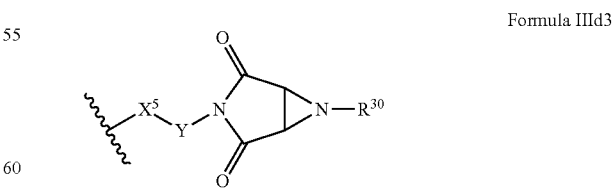

Formula IIId3

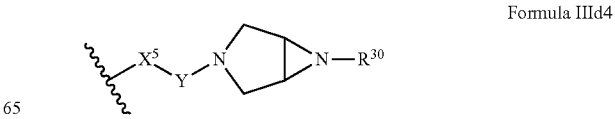

Formula IIId4 wherein $X^5$ is absent or $NR^{30}$;

Y is absent or C(O), C(S), S(O), $SO_2$, or optionally substituted $C_1$-$C_3$ alkylene;

$R^{27}$ is hydrogen, —C(O)$R^{32}$, —C(O)O$R^{32}$, —$SO_2R^{33}$, —$SOR^{33}$, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl;

$R^{28}$ and $R^{29}$ are, independently, hydrogen, CN, C(O)$R^{31}$, $CO_2R^{31}$, C(O)$R^{31}R^{31}$ optionally substituted $C_1$-$C_6$ alkyl, optionally substituted 3 to 10-membered cycloalkyl, optionally substituted 6 to 10-membered aryl, optionally substituted 3 to 14-membered heterocycloalkyl, or optionally substituted 5 to 10-membered heteroaryl;

each $R^{31}$ is, independently, hydrogen, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl;

$R^{30}$ is hydrogen or optionally substituted $C_1$-$C_6$ alkyl; and $R^{32}$ and $R^{33}$ are, independently, hydrogen, optionally substituted $C_1$-$C_6$ alkyl, optionally substituted 6 to 10-membered aryl, optionally substituted 3 to 14-membered heterocycloalkyl, or optionally substituted 5 to 10-membered heteroaryl.

[75] The compound, or a pharmaceutically acceptable salt thereof, of paragraph [73] or [74], wherein W is:

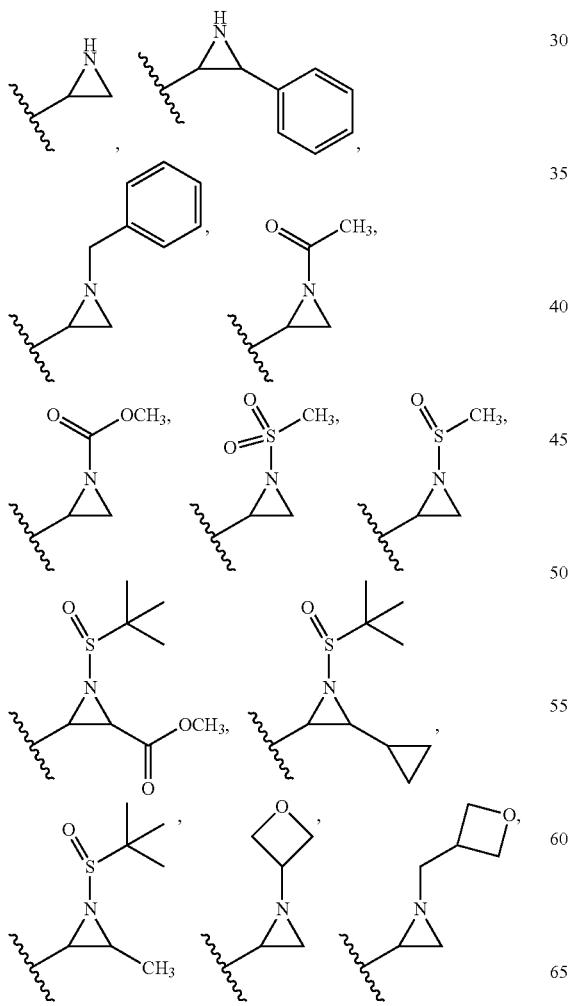

-continued

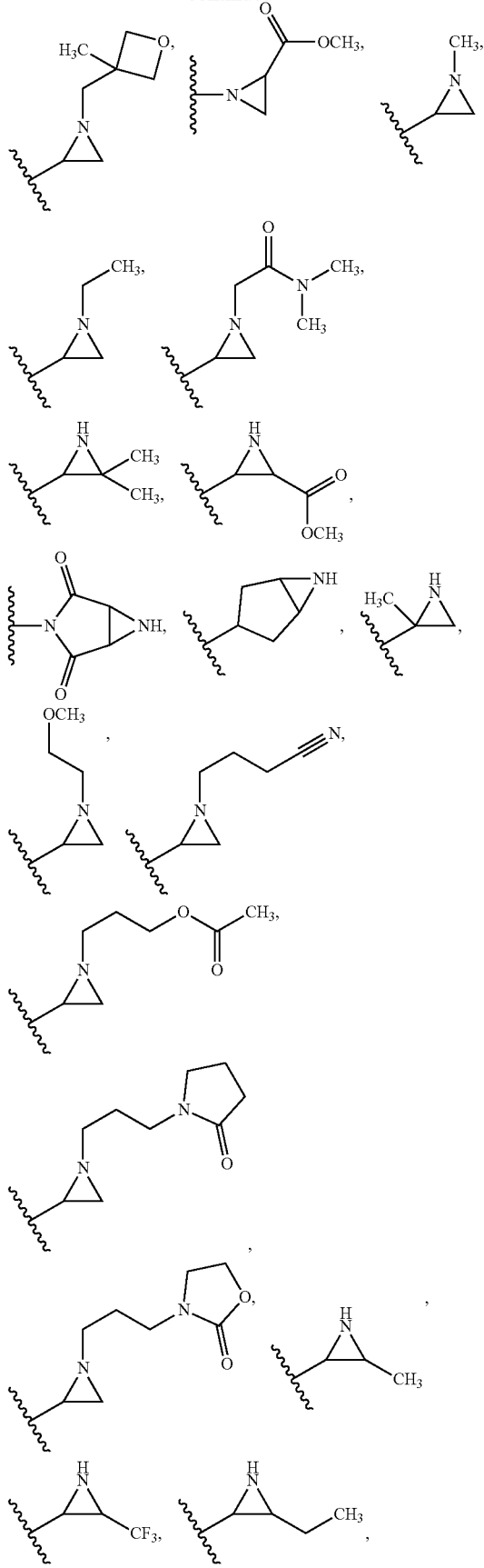

393
-continued

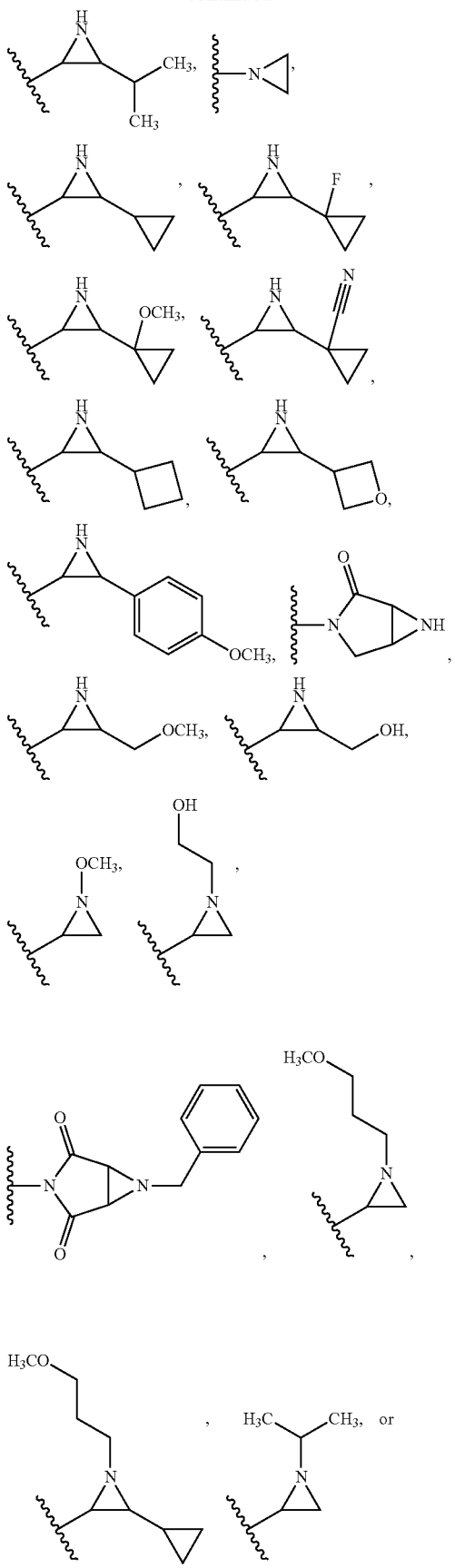

394
-continued

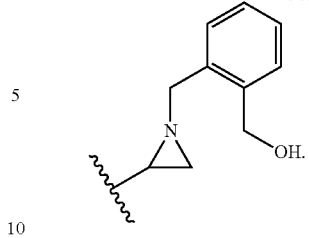

[76] The compound, or a pharmaceutically acceptable salt thereof, of any one of paragraphs [1] to [63], wherein W comprises an epoxide.

[77] The compound, or a pharmaceutically acceptable salt thereof, of paragraph [76], wherein W is

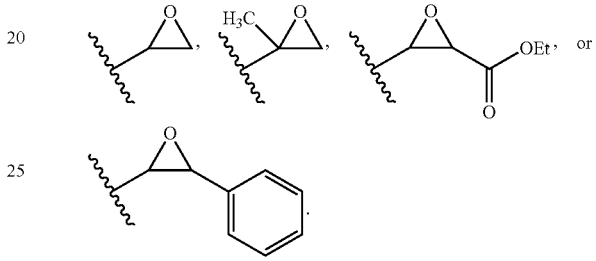

[78] A compound, or a pharmaceutically acceptable salt thereof, of Table 1 or Table 2.

[79] A pharmaceutical composition comprising a compound, or a pharmaceutically acceptable salt thereof, of any one of paragraphs [1] to [78] and a pharmaceutically acceptable excipient.

[80] A conjugate, or salt thereof, comprising the structure of Formula IV:

$$M\text{-}L\text{-}P \qquad \text{Formula IV}$$

wherein L is a linker;
P is a monovalent organic moiety; and
M has the structure of Formula V:

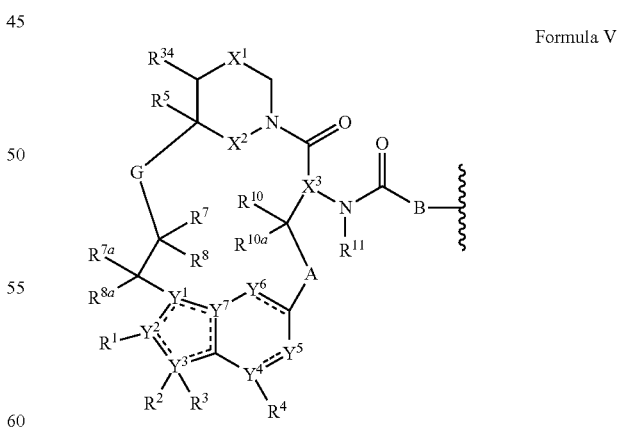

Formula V wherein the dotted lines represent zero, one, two, three, or four non-adjacent double bonds;

A is —N(H or CH$_3$)C(O)—(CH$_2$)— where the amino nitrogen is bound to the carbon atom of —CH(R$^{10}$)—, optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— or >C=CR$^9$R$^{9'}$ where the carbon is bound to the carbonyl carbon of —N($R^{11}$)C(O)—, optionally substituted 3 to 6-membered cycloalkylene, optionally substituted 3 to 6-membered heterocycloalkylene, optionally substituted 6-membered arylene, or 5 to 6-membered heteroarylene;

G is optionally substituted $C_1$-$C_4$ alkylene, optionally substituted $C_1$-$C_4$ alkenylene, optionally substituted $C_1$-$C_4$ heteroalkylene, —C(O)O—CH($R^6$)— where C is bound to —C($R^7R^8$)—, —C(O)NH—CH($R^6$)— where C is bound to —C($R^7R^8$)—, optionally substituted $C_1$-$C_4$ heteroalkylene, or 3 to 8-membered heteroarylene;

$X^1$ is optionally substituted $C_1$-$C_2$ alkylene, NR, O, or S(O)$_n$;

$X^2$ is O or NH;

$X^3$ is N or CH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$R', or S(O)$_2$N(R')$_2$;

each R' is, independently, H or optionally substituted $C_1$-$C_4$ alkyl;

$Y^1$ is C, CH, or N;

$Y^2$, $Y^3$, $Y^4$, and $Y^7$ are, independently, C or N;

$Y^5$ is CH, CH$_2$, or N;

$Y^6$ is C(O), CH, CH$_2$, or N;

$R^1$ is cyano, optionally substituted $C_1$-$C_6$ alkyl, optionally substituted $C_1$-$C_6$ heteroalkyl, optionally substituted 3 to 6-membered cycloalkyl, optionally substituted 3 to 6-membered cycloalkenyl, optionally substituted 3 to 6-membered heterocycloalkyl, optionally substituted 6 to 10-membered aryl, or optionally substituted 5 to 10-membered heteroaryl, or $R^1$ and $R^2$ combine with the atoms to which they are attached to form an optionally substituted 3 to 14-membered heterocycloalkyl;

$R^2$ is absent, hydrogen, optionally substituted $C_1$-$C_6$ alkyl, optionally substituted $C_2$-$C_6$ alkenyl, optionally substituted $C_2$-$C_6$ alkynyl, optionally substituted 3 to 6-membered cycloalkyl, optionally substituted 3 to 7-membered heterocycloalkyl, optionally substituted 6-membered aryl, optionally substituted 5 or 6-membered heteroaryl; $R^3$ is absent, or $R^2$ and $R^3$ combine with the atom to which they are attached to form an optionally substituted 3 to 8-membered cycloalkyl or optionally substituted 3 to 14-membered heterocycloalkyl;

$R^4$ is absent, hydrogen, halogen, cyano, or methyl optionally substituted with 1 to 3 halogens;

$R^5$ is hydrogen, $C_1$-$C_4$ alkyl optionally substituted with halogen, cyano, hydroxy, or $C_1$-$C_4$ alkoxy, cyclopropyl, or cyclobutyl;

$R^6$ is hydrogen or methyl; $R^7$ is hydrogen, halogen, or optionally substituted $C_1$-$C_3$ alkyl, or $R^6$ and $R^7$ combine with the carbon atoms to which they are attached to form an optionally substituted 3 to 6-membered cycloalkyl or optionally substituted 3 to 7-membered heterocycloalkyl;

$R^8$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^7$ and $R^8$ combine with the carbon atom to which they are attached to form C=CR$^{7'}$R$^{8'}$; C=N(OH), C=N(O—$C_1$-$C_3$ alkyl), C=O, C=S, C=NH, optionally substituted 3 to 6-membered cycloalkyl, or optionally substituted 3 to 7-membered heterocycloalkyl;

$R^{7a}$ and $R^{8a}$ are, independently, hydrogen, halo, optionally substituted $C_1$-$C_3$ alkyl, or combine with the carbon to which they are attached to form a carbonyl;

$R^{7'}$ is hydrogen, halogen, or optionally substituted $C_1$-$C_3$ alkyl; $R^{8'}$ is hydrogen, halogen, hydroxy, cyano, optionally substituted $C_1$-$C_3$ alkoxyl, optionally substituted $C_1$-$C_3$ alkyl, optionally substituted $C_2$-$C_6$ alkenyl, optionally substituted $C_2$-$C_6$ alkynyl, optionally substituted 3 to 8-membered cycloalkyl, optionally substituted 3 to 14-membered heterocycloalkyl, optionally substituted 5 to 10-membered heteroaryl, or optionally substituted 6 to 10-membered aryl, or $R^{7'}$ and $R^{8'}$ combine with the carbon atom to which they are attached to form optionally substituted 3 to 6-membered cycloalkyl or optionally substituted 3 to 7-membered heterocycloalkyl;

$R^9$ is hydrogen, F, optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl, or $R^9$ and L combine with the atoms to which they are attached to form an optionally substituted 3 to 14-membered heterocycloalkyl;

$R^{9'}$ is hydrogen or optionally substituted $C_1$-$C_6$ alkyl;

$R^{10a}$ is hydrogen or halo;

$R^{11}$ is hydrogen or $C_1$-$C_3$ alkyl; and $R^{34}$ is hydrogen or $C_1$-$C_3$ alkyl.

[81] A conjugate, or salt thereof, of paragraph [80], wherein M has the structure of Formula Vc:

Formula Vc wherein A is optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

$X^1$ is optionally substituted $C_1$-$C_2$ alkylene, NR, O, or S(O)$_n$;

$X^2$ is O or NH;

n is 0, 1, or 2;

R is hydrogen, cyano, optionally substituted $C_1$-$C_4$ alkyl, optionally substituted $C_2$-$C_4$ alkenyl, optionally substituted $C_2$-$C_4$ alkynyl, C(O)R', C(O)OR', C(O)N(R')$_2$, S(O)R', S(O)$_2$ R', or S(O)$_2$N(R')$_2$;

each R' is, independently, H or optionally substituted $C_1$-$C_4$ alkyl;

$X^e$ and $X^f$ are, independently, N or CH;

$R^2$ is $C_1$-$C_6$ alkyl or 3 to 6-membered cycloalkyl;

$R^7$ is $C_1$-$C_3$ alkyl;

$R^8$ is $C_1$-$C_3$ alkyl; and $R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl;

$R^{11}$ is hydrogen or $C_1$-$C_3$ alkyl; and $R^{34}$ is hydrogen or $C_1$-$C_3$ alkyl. In some embodiments of a compound of the present invention, $X^e$ is N and $X^f$ is CH. In some embodiments, $X^e$ is CH and $X^f$ is N.

[82] The conjugate, or salt thereof, of paragraph [80] or [81], wherein M has the structure of Formula Vd:

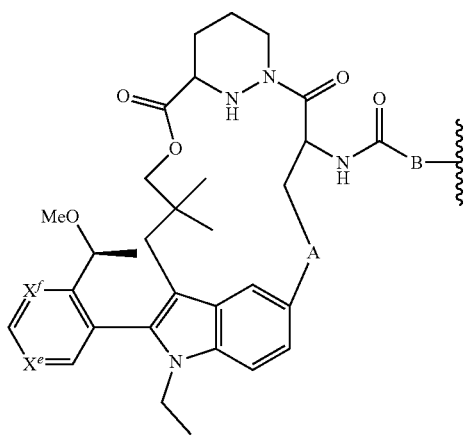

Formula Vd wherein A optionally substituted 3 to 6-membered cycloalkylene, optionally substituted 3 to 6-membered heterocycloalkylene, optionally substituted 6-membered arylene, or optionally substituted 5 to 6-membered heteroarylene;

B is —CH($R^9$)— where the carbon is bound to the carbonyl carbon of —NHC(O)—, optionally substituted 3 to 6-membered cycloalkylene, optionally substituted 3 to 6-membered heterocycloalkylene, optionally substituted 6-membered arylene, or 5 to 6-membered heteroarylene;

L is absent or a linker;

W is a cross-linking group comprising a carbodiimide, an oxazoline, a thiazoline, a chloroethyl urea, a chloroethyl thiourea, a chloroethyl carbamate, a chloroethyl thiocarbamate, an aziridine, a trifluoromethyl ketone, a boronic acid, a boronic ester, an N-ethoxycarbonyl-2-ethoxy-1,2-dihydroquinoline (EEDQ), an iso-EEDQ or other EEDQ derivative, an epoxide, an oxazolium, or a glycal;

$R^9$ is optionally substituted $C_1$-$C_6$ alkyl, optionally substituted $C_1$-$C_6$ heteroalkyl, optionally substituted 3 to 6-membered cycloalkyl, or optionally substituted 3 to 7-membered heterocycloalkyl; and $X^e$ and $X^f$ are, independently, N or CH.

[83] The conjugate, or salt thereof, of any one of paragraphs [80] to [82], wherein the linker has the structure of Formula II:

$$A^1\text{-}(B^1)_f\text{---}(C^1)_g\text{---}(B^2)_h\text{-}(D^1)\text{-}(B^3)_i\text{---}(C^2)_j\text{---}(B^4)_k\text{-}A^2 \quad \text{Formula II}$$

where $A^1$ is a bond between the linker and B; $A^2$ is a bond between P and the linker; $B^1$, $B^2$, $B^3$, and $B^4$ each, independently, is selected from optionally substituted $C_1$-$C_2$ alkylene, optionally substituted $C_1$-$C_3$ heteroalkylene, O, S, and NR$^N$; R$^N$ is hydrogen, optionally substituted $C_1$-$C_4$ alkyl, optionally substituted $C_2$-$C_4$ alkenyl, optionally substituted $C_2$-$C_4$ alkynyl, optionally substituted 3 to 14-membered heterocycloalkyl, optionally substituted 6 to 10-membered aryl, or optionally substituted $C_1$-$C_7$ heteroalkyl; $C^1$ and $C^2$ are each, independently, selected from carbonyl, thiocarbonyl, sulphonyl, or phosphoryl; f, g, h, i, j, and k are each, independently, 0 or 1; and $D^1$ is optionally substituted $C_1$-$C_{10}$ alkylene, optionally substituted $C_2$-$C_{10}$ alkenylene, optionally substituted $C_2$-$C_{10}$ alkynylene, optionally substituted 3 to 14-membered heterocycloalkylene, optionally substituted 5 to 10-membered heteroarylene, optionally substituted 3 to 8-membered cycloalkylene, optionally substituted 6 to 10-membered arylene, optionally substituted $C_2$-$C_{10}$ polyethylene glycolene, or optionally substituted $C_1$-$C_{10}$ heteroalkylene, or a chemical bond linking $A^1$-$(B^1)_f$ —$(C^1)_g$—$(B^2)_h$— to —$(B^3)_i$—$(C^2)_j$—$(B^4)_k$-$A^2$.

[84] The conjugate, or salt thereof, of any one of paragraphs [80] to [83], wherein the monovalent organic moiety is a protein.

[85] The conjugate, or salt thereof, of paragraph [84], wherein the protein is a Ras protein.

[86] The conjugate, or salt thereof, of paragraph [85], wherein the Ras protein is K-Ras G12D or K-Ras G13D.

[87] The conjugate, or salt thereof, of any one of paragraphs [80] to [86], wherein the linker is bound to the monovalent organic moiety through a bond to a carboxyl group of an amino acid residue of the monovalent organic moiety.

[88] A method of treating cancer in a subject in need thereof, the method comprising administering to the subject a therapeutically effective amount of a compound, or a pharmaceutically acceptable salt thereof, of any one of paragraphs [1] to [78] or a pharmaceutical composition of paragraph [79],

[89] The method of paragraph [88], wherein the cancer is pancreatic cancer, non-small cell lung cancer, colorectal cancer or endometrial cancer.

[90] The method of paragraph [88] or [89], wherein the cancer comprises a Ras mutation.

[91] The method of paragraph [90], wherein the Ras mutation is K-Ras G12D or K-Ras G13D.

[92] A method of treating a Ras protein-related disorder in a subject in need thereof, the method comprising administering to the subject a therapeutically effective amount of a compound, or a pharmaceutically acceptable salt thereof, of any one of paragraphs [1] to [78] or a pharmaceutical composition of paragraph [79],

[93] A method of inhibiting a Ras protein in a cell, the method comprising contacting the cell with an effective amount of a compound, or a pharmaceutically acceptable salt thereof, of any one of paragraphs [1] to [78] or a pharmaceutical composition of paragraph [79],

[94] The method of paragraph [92] or [93], wherein the Ras protein is K-Ras G12D or K-Ras G13D.

[95] The method of paragraph [93] or [94], wherein the cell is a cancer cell.

399

[96] The method of paragraph [95], wherein the cancer cell is a pancreatic cancer cell, a non-small cell lung cancer cell, a colorectal cancer cell, or an endometrial cell.

[97] The method or use of any one of paragraphs [88] to [96], wherein the method further comprises administering an additional anticancer therapy.

[98] The method of paragraph [97], wherein the additional anticancer therapy is an EGFR inhibitor, a second Ras inhibitor, a SHP2 inhibitor, a SOS1 inhibitor, a Raf inhibitor, a MEK inhibitor, an ERK inhibitor, a PI3K inhibitor, a PTEN inhibitor, an AKT inhibitor, an mTORC1 inhibitor, a BRAF inhibitor, a PD-L1 inhibitor, a PD-1 inhibitor, a CDK4/6 inhibitor, a HER2 inhibitor, or a combination thereof.

[99] The method of paragraph [97] or [98], wherein the additional anticancer therapy is a SHP2 inhibitor.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure or scope of the appended claims.

Chemical Syntheses

Definitions used in the following examples and elsewhere herein are:

CH$_2$Cl$_2$, DCM Methylene chloride, Dichloromethane
CH$_3$CN, MeCN Acetonitrile
CuI Copper (I) iodide
DIPEA Diisopropylethyl amine
DMF N,N-Dimethylformamide
EtOAc Ethyl acetate
h hour
H$_2$O Water
HCl Hydrochloric acid
K$_3$PO$_4$ Potassium phosphate (tribasic)
MeOH Methanol
Na$_2$SO$_4$ Sodium sulfate
NMP N-methyl pyrrolidone
Pd(dppf)Cl$_2$ [1,1'-Bis(diphenylphosphino)ferrocene]dichloropalladium(II)

Instrumentation

Mass spectrometry data collection took place with a Shimadzu LCMS-2020 or Waters Acquity UPLC with either a QDa detector or SQ Detector 2. Samples were injected in their liquid phase onto a C-18 reverse phase column to remove assay buffer and prepare the samples for the mass spectrometer. The compounds were eluted from the column using an acetonitrile gradient and fed into the mass analyzer. Initial data analysis took place with either Shimadzu LabSolutions or Waters MassLynx. NMR data was collected with either a Bruker AVANCE III HD 400 MHz or a Bruker Ascend 500 MHz instrument and the raw data was analyzed with either TopSpin or Mestrelab Mnova.

Synthesis of Intermediates

Intermediate 1. Synthesis of 3-(5-bromo-1-ethyl-2-[2-[(1S)-1-methoxyethyl]pyridin-3-yl]indol-3-yl)-2,2-dimethylpropan-1-ol

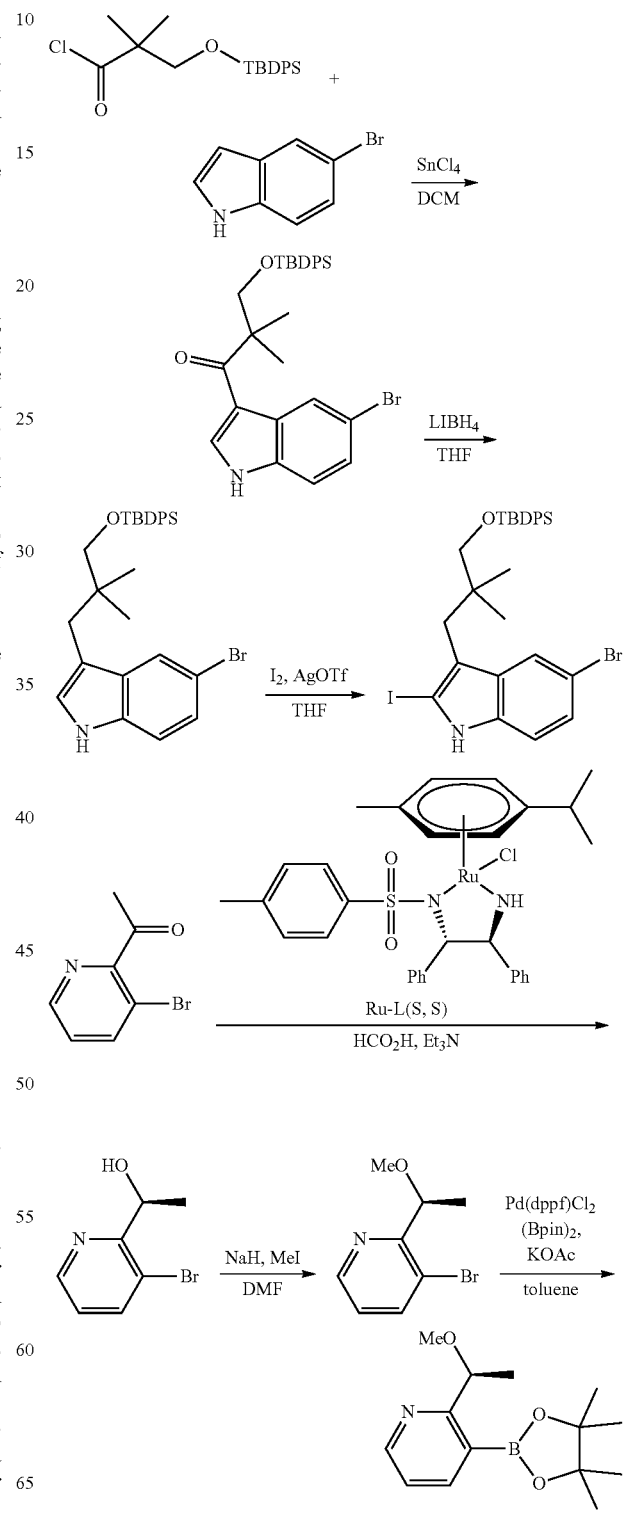

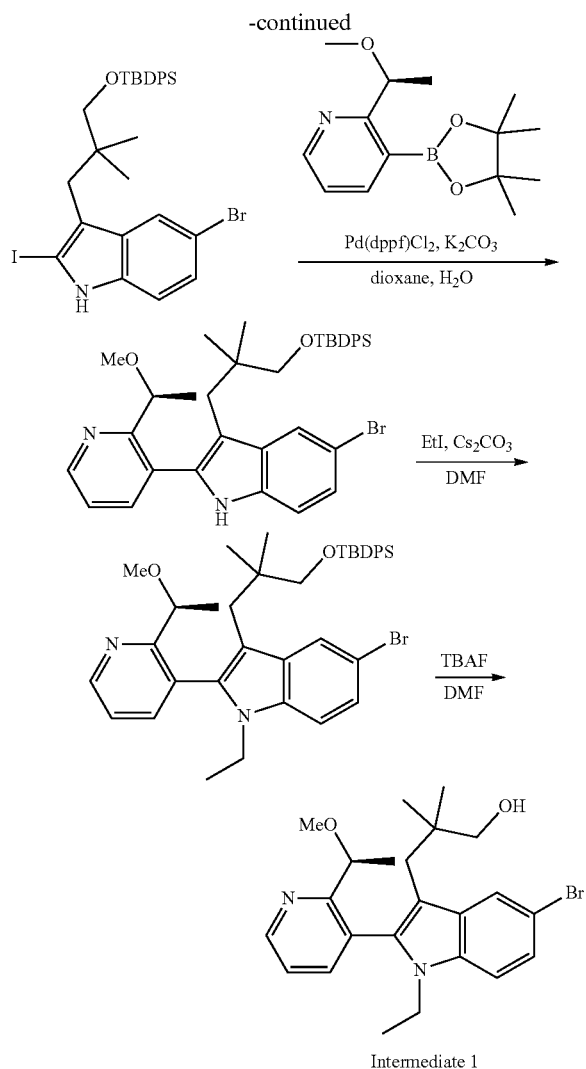

Intermediate 1

Step 1: Synthesis of 1-(5-bromo-1H-indol-3-yl)-3-((tert-butyldiphenylsilyl)oxy)-2,2-dimethylpropan-1-one To a mixture of 3-((tert-butyldiphenylsilyl)oxy)-2,2-dimethylpropanoyl chloride (65 g, 137 mmol, crude) in DCM (120 mL) at 0° C. under an atmosphere of $N_2$ was added 1M $SnCl_4$ in DCM (137 mL, 137 mmol) slowly. The mixture was stirred at 0° C. for 30 min, then a solution of 5-bromo-1H-indole (26.8 g, 137 mmol) in DCM (40 mL) was added dropwise. The mixture was stirred at 0° C. for 45 min, then diluted with EtOAc (300 mL), washed with brine (4×100 mL), dried over $Na_2SO_4$ and filtered. The filtrate was concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (55 g, 75% yield). LCMS (ESI) m/z: [M+Na] calcd for $C_{29}H_{32}BrNO_2SiNa$ 556.1; found 556.3.

Step 2: Synthesis of 1-(5-bromo-1H-indol-3-yl)-3-((tert-butyldiphenylsilyl)oxy)-2,2-dimethylpropan-1-one To a mixture of 1-(5-bromo-1H-indol-3-yl)-3-((tert-butyldiphenylsilyl)oxy)-2,2-dimethylpropan-1-one (50 g, 93.6 mmol) in THF (100 mL) at 0° C. under an atmosphere of $N_2$ was added $LiBH_4$ (6.1 g, 281 mmol). The mixture was heated to 60° C. and stirred for 20 h, then MeOH (10 mL) and EtOAc (100 mL) were added and the mixture washed with brine (50 mL), dried over $Na_2SO_4$, filtered and the filtrate concentrated under reduced pressure. The residue was diluted with DCM (50 mL), cooled to 10° C. and diludine (9.5 g, 37.4 mmol) and $TsOH.H_2O$ (890 mg, 4.7 mmol) were added. The mixture was stirred at 10° C. for 2 h, filtered, the filtrate concentrated under reduced pressure and the residue was purified by silica gel column chromatography to give 1-(5-bromo-1H-indol-3-yl)-3-((tert-butyldiphenylsilyl)oxy)-2,2-dimethylpropan-1-one (41 g, 84% yield). LCMS (ESI) m/z: [M+H] calcd for $C_{29}H_{34}BrNOSi$: 519.2; found 520.1; $^1H$ NMR (400 MHz, $CDCl_3$) δ 7.96 (s, 1H), 7.75-7.68 (m, 5H), 7.46-7.35 (m, 6H), 7.23-7.19 (m, 2H), 6.87 (d, J=2.1 Hz, 1H), 3.40 (s, 2H), 2.72 (s, 2H), 1.14 (s, 9H), 0.89 (s, 6H).

Step 3: Synthesis of 5-bromo-3-(3-((tert-butyldiphenylsilyl)oxy)-2,2-dimethylpropyl)-2-iodo-1H-indole To a mixture of 1-(5-bromo-1H-indol-3-yl)-3-((tert-butyldiphenylsilyl)oxy)-2,2-dimethylpropan-1-one (1.5 g, 2.9 mmol) and $I_2$ (731 mg, 2.9 mmol) in THF (15 mL) at room temperature was added AgOTf (888 mg, 3.5 mmol). The mixture was stirred at room temperature for 2 h, then diluted with EtOAc (200 mL) and washed with saturated $Na_2S_2O_3$ (100 mL), dried over anhydrous $Na_2SO_4$ and filtered. The filtrate was concentrated under reduced pressure and the residue was purified by silica gel column chromatography to give 5-bromo-3-(3-((tert-butyldiphenylsilyl)oxy)-2,2-dimethylpropyl)-2-iodo-1H-indole (900 mg, 72% yield) as a solid. $^1H$ NMR (400 MHz, DMSO-$d_6$) δ 11.70 (s, 1H), 7.68 (d, J=1.3 Hz, 1H), 7.64-7.62 (m, 4H), 7.46-7.43 (m, 6H), 7.24-7.22 (d, 1H), 7.14-7.12 (dd, J=8.6, 1.6 Hz, 1H), 3.48 (s, 2H), 2.63 (s, 2H), 1.08 (s, 9H), 0.88 (s, 6H).

Step 4: Synthesis of (1S)-1-(3-bromopyridin-2-yl)ethanol

To a stirred mixture of HCOOH (66.3 g, 1.44 mol) in $Et_3N$ (1002 mL, 7.2 mol) at 0° C. under an atmosphere of Ar was added (4S,5S)-2-chloro-2-methyl-1-(4-methylbenzenesulfonyl)-4,5-diphenyl-1,3-diaza-2-ruthenacyclopentane cymene (3.9 g, 6.0 mmol) portion-wise. The mixture was heated to 40° C. and stirred for 15 min, then cooled to room temperature and 1-(3-bromopyridin-2-yl)ethanone (120 g, 600 mmol) added in portions. The mixture was heated to 40° C. and stirred for an additional 2 h, then the solvent was concentrated under reduced pressure. Brine (2 L) was added to the residue, the mixture was extracted with EtOAc (4×700 mL), dried over anhydrous $Na_2SO_4$ and filtered. The filtrate was concentrated under reduced pressure and the residue was purified by silica gel column chromatography to give (1S)-1-(3-bromopyridin-2-yl)ethanol (100 g, 74% yield) a an oil. LCMS (ESI) m/z: [M+H] calcd for $C_7H_8BrNO$: 201.98; found 201.9.

Step 5: Synthesis of 3-bromo-2-[(1S)-1-methoxyethyl]pyridine

To a stirred mixture of (1S)-1-(3-bromopyridin-2-yl)ethanol (100 g, 495 mmol) in DMF (1 L) at 0° C. was added NaH, 60% dispersion in oil (14.25 g, 594 mmol) in portions. The mixture was stirred at 0° C. for 1 h. MeI (140.5 g, 990 mmol) was added dropwise at 0° C. and the mixture was allowed to warm to room temperature and stirred for 2 h. The mixture was cooled to 0° C. and saturated NH₂Cl (5 L) was added. The mixture was extracted with EtOAc (3×1.5 L), dried over anhydrous Na₂SO₄ and filtered. The filtrate was concentrated under reduced pressure and the residue was purified by silica gel column chromatography to give 3-bromo-2-[(1S)-1-methoxyethyl]pyridine (90 g, 75% yield) as an oil. LCMS (ESI) m/z: [M+H] calcd for $C_8H_{10}BrNO$: 215.99; found 215.9.

Step 6: Synthesis of 2-[(1S)-1-methoxyethyl]-3-(4, 4,5,5-tetramethyl-1,3,2-dioxaborolan-2-yl)pyridine To a stirred mixture of 3-bromo-2-[(1S)-1-methoxyethyl] pyridine (90 g, 417 mmol) in toluene (900 mL) at room temperature under an atmosphere of Ar was added bis(pinacolato)diboron (127 g, 500 mmol) and KOAc (81.8 g, 833 mmol) and Pd(dppf)Cl₂ (30.5 g, 41.7 mmol). The mixture was heated to 100° C. and stirred for 3 h. The filtrate was concentrated under reduced pressure and the residue was purified by Al₂O₃ column chromatography to give 2-[(1S)-1-methoxyethyl]-3-(4,4,5,5-tetramethyl-1,3,2-dioxaborolan-2-yl)pyridine (100 g, 63% yield) as a semi-solid. LCMS (ESI) m/z: [M+H] calcd for $C_{14}H_{22}BNO_3$: 264.17; found 264.1.

Step 7: Synthesis of 5-bromo-3-[3-[(tert-butyldiphenylsilyl)oxy]-2,2-dimethylpropyl]-2-[2-[(1S)-1-methoxyethyl]pyridin-3-yl]-1H-indole To a stirred mixture of 5-bromo-3-[3-[(tert-butyldiphenylsilyl)oxy]-2,2-dimethylpropyl]-2-iodo-1H-indole (140 g, 217 mmol) and 2-[(1S)-1-methoxyethyl]-3-(4,4,5,5-tetramethyl-1,3,2-dioxaborolan-2-yl)pyridine (100 g, 380 mmol) in 1,4-dioxane (1.4 L) at room temperature under an atmosphere of Ar was added K₂CO₃ (74.8 g, 541 mmol), Pd(dppf)Cl₂ (15.9 g, 21.7 mmol) and H₂O (280 mL) in portions. The mixture was heated to 85° C. and stirred for 4 h, then cooled, H₂O (5 L) added and the mixture extracted with EtOAc (3×2 L). The combined organic layers were washed with brine (2×1 L), dried over anhydrous Na₂SO₄ and filtered. The filtrate was concentrated under reduced pressure and the residue was purified by silica gel column chromatography to give 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 45% yield) as a solid. LCMS (ESI) m/z: [M+H] calcd for $C_{37}H_{43}BrN_2O_2Si$: 655.23; found 655.1.

Step 8: Synthesis of 5-bromo-3-[3-[(tert-butyldiphenylsilyl)oxy]-2,2-dimethylpropyl]-1-ethyl-2-[2-[(1S)-1-methoxyethyl]pyridin-3-yl]indole To a stirred mixture of 5-bromo-3-[3-[(tert-butyldiphenylsilyl)oxy]-2,2-dimethylpropyl]-2-[2-[(1S)-1-methoxyethyl]pyridin-3-yl]-1H-indole (71 g, 108 mmol) in DMF (0.8 L) at 0° C. under an atmosphere of N₂ was added Cs₂CO₃ (70.6 g, 217 mmol) and EtI (33.8 g, 217 mmol) in portions. The mixture was warmed to room temperature and stirred for 16 h then H₂O (4 L) added and the mixture extracted with EtOAc (3×1.5 L). The combined organic layers were washed with brine (2×1 L), dried over anhydrous Na₂SO₄ and filtered. The filtrate was concentrated under reduced pressure and the residue was purified by silica gel column chromatography to give 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 80% yield) as an oil. LCMS (ESI) m/z: [M+H] calcd for $C_{39}H_{47}BrN_2O_2Si$: 683.26; found 683.3.

Step 9: Synthesis of 3-(5-bromo-1-ethyl-2-[2-[(1S)-1-methoxyethyl]pyridin-3-yl]indol-3-yl)-2,2-dimethylpropan-1-ol To a stirred mixture of TBAF (172.6 g, 660 mmol) in THF (660 mL) at room temperature under an atmosphere of N₂ was added 5-bromo-3-[3-[(tert-butyldiphenylsilyl)oxy]-2,2-dimethylpropyl]-1-ethyl-2-[2-[(1S)-1-methoxyethyl]pyridin-3-yl]indole (66 g, 97 mmol) in portions. The mixture was heated to 50° C. and stirred for 16 h, cooled, diluted with H₂O (5 L) and extracted with EtOAc (3×1.5 L). The combined organic layers were washed with brine (2×1 L), dried over anhydrous Na₂SO₄ and filtered. After filtration, the filtrate was concentrated under reduced pressure. The filtrate was concentrated under reduced pressure and the residue was purified by silica gel column chromatography to give 3-(5-bromo-1-ethyl-2-[2-[(1S)-1-methoxyethyl]pyridin-3-yl]indol-3-yl)-2,2-dimethylpropan-1-ol (30 g, 62% yield) as a solid. LCMS (ESI) m/z: [M+H] calcd for $C_{23}H_{29}BrN_2O_2$: 445.14; found 445.1.

Intermediate 1. Alternative Synthesis Through Fisher Indole Route

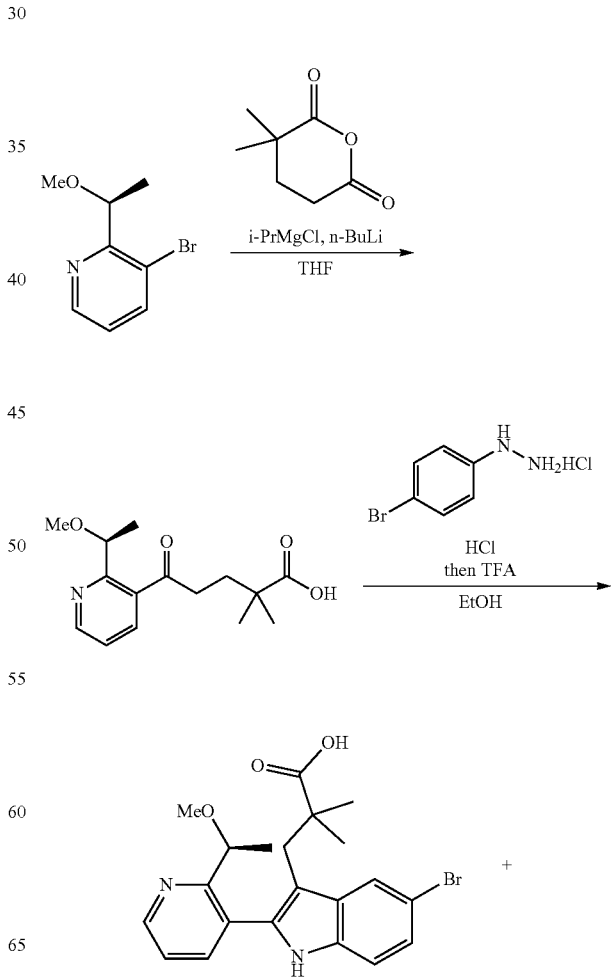

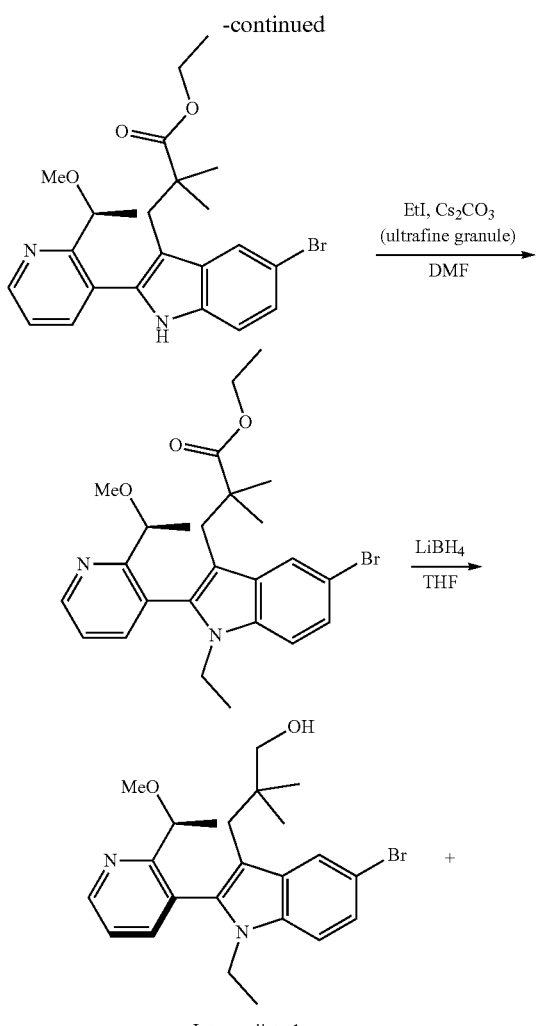

Intermediate 1

Step 1: Synthesis of 5-[2-[(1S)-1-methoxyethyl]pyridin-3-yl]-2,2-dimethyl-5-oxopentanoic Acid To a mixture of i-PrMgCl (2M in in THF, 0.5 L) at −10° C. under an atmosphere of N₂ was added n-BuLi, 2.5 M in hexane (333 mL, 833 mmol) dropwise over 15 min. The mixture was stirred for 30 min at −10° C. then 3-bromo-2-[(1S)-1-methoxyethyl]pyridine (180 g, 833 mmol) in THF (0.5 L) added dropwise over 30 min at −10° C. The resulting mixture was warmed to −5° C. and stirred for 1 h, then 3,3-dimethyloxane-2,6-dione (118 g, 833 mmol) in THF (1.2 L) was added dropwise over 30 min at −5° C. The mixture was warmed to 0° C. and stirred for 1.5 h, then quenched with the addition of pre-cooled 4M HCl in 1,4-dioxane (0.6 L) at 0° C. to adjust pH ~5. The mixture was diluted with H₂O (3 L) at 0° C. and extracted with EtOAc (3×2.5 L). The combined organic layers were dried over anhydrous Na₂SO₄, filtered, the filtrate was concentrated under reduced pressure and the residue was purified by silica gel column chromatography to give 5-[2-[(1S)-1-methoxyethyl]pyridin-3-yl]-2,2-dimethyl-5-oxopentanoic acid (87 g, 34% yield) as a solid. LCMS (ESI) m/z: [M+H] calcd for $C_{15}H_{21}NO_4$: 280.15; found 280.1.

Step 2: Synthesis of 3-(5-bromo-2-[2-[(1S)-1-methoxyethyl]pyridin-3-yl]-1H-indol-3-yl)-2,2-dimethylpropanoic Acid and Ethyl (S)-3-(5-bromo-2-(2-(1-methoxyethyl)pyridin-3-yl)-1H-indol-3-yl)-2,2-dimethylpropanoate To a mixture of 5-[2-[(1S)-1-methoxyethyl]pyridin-3-yl]-2,2-dimethyl-5-oxopentanoic acid (78 g, 279 mmol) in EtOH (0.78 L) at room temperature under an atmosphere of N₂ was added (4-bromophenyl)hydrazine HCl salt (68.7 g, 307 mmol) in portions. The mixture was heated to 85° C. and stirred for 2 h, cooled to room temperature, then 4M HCl in 1,4-dioxane (69.8 mL, 279 mmol) added dropwise. The mixture was heated to 85° C. and stirred for an additional 3 h, then concentrated under reduced pressure and the residue was dissolved in TFA (0.78 L). The mixture was heated to 60° C. and stirred for 1.5 h, concentrated under reduced pressure and the residue adjusted to pH ~5 with saturated NaHCO₃, then extracted with EtOAc (3×1.5 L). The combined organic layers were dried over anhydrous Na₂SO₄, filtered, the filtrate concentrated under reduced pressure and the residue was purified by silica gel column chromatography to give 3-(5-bromo-2-[2-[(1S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (78 g, crude). LCMS (ESI) m/z: [M+H] calcd for $C_{21}H_{23}BrN_2O_3$: 430.1 and $C_{23}H_{27}BrN_2O_3$: 459.12; found 431.1 (carboxylic acid) and 459.1.

Step 3: Synthesis of ethyl 3-(5-bromo-1-ethyl-2-[2-[(1S)-1-methoxyethyl]pyridin-3-yl]indol-3-yl)-2,2-dimethylpropanoate To a mixture of 3-(5-bromo-2-[2-[(1S)-1-methoxyethyl]pyridin-3-yl]-1H-indol-3-yl)-2,2-dimethylpropanoic acid and ethyl (S)-3-(5-bromo-2-(2-(1-methoxyethyl)pyridin-3-yl)-1H-indol-3-yl)-2,2-dimethylpropanoate (198 g, 459 mmol) in DMF (1.8 L) at 0° C. under an atmosphere of N₂ was added Cs₂CO₃ (449 g, 1.38 mol) in portions. EtI (215 g, 1.38 mmol) in DMF (200 mL) was then added dropwise at 0° C. The mixture was warmed to room temperature and stirred for 4 h then diluted with brine (5 L) and extracted with EtOAc (3×2.5 L). The combined organic layers were washed with brine (2×1.5 L), dried over anhydrous Na₂SO₄ and filtered. The filtrate was concentrated under reduced pressure and the residue was purified by silica gel column chromatography to give ethyl 3-(5-bromo-1-ethyl-2-[2-[(1S)-1-methoxyethyl]pyridin-3-yl]indol-3-yl)-2,2-dimethylpropanoate (160 g, 57% yield) as a solid. LCMS (ESI) m/z: [M+H] calcd for $C_{25}H_{31}BrN_2O_3$: 487.17; found 487.2.

Step 4: Synthesis of 3-(5-bromo-1-ethyl-2-(2-((S)-1-methoxyethyl)pyridin-3-yl)-1H-indol-3-yl)-2,2-dimethylpropan-1-ol To a mixture of ethyl 3-(5-bromo-1-ethyl-2-[2-[(1S)-1-methoxyethyl]pyridin-3-yl]indol-3-yl)-2,2-dimethylpropanoate (160 g, 328 mmol) in THF (1.6 L) at 0° C. under an atmosphere of N₂ was added LiBH₄ (28.6 g, 1.3 mol). The mixture was heated to 60° C. for 16 h, cooled, and quenched with pre-cooled (0° C.) aqueous NH₄Cl (5 L). The mixture was extracted with EtOAc (3×2 L) and the combined organic layers were washed with brine (2×1 L), dried over anhydrous Na₂SO₄ and filtered. The filtrate was concentrated under reduced pressure and the residue was purified by silica gel column chromatography to give to two atropisomers of 3-(5-bromo-1-ethyl-2-(2-((S)-1-methoxyethyl)pyridin-3-yl)-1H-indol-3-yl)-2,2-dimethylpropan-1-ol (as single atropisomers) (60 g, 38% yield) and (40 g, 26% yield) both as solids. LCMS (ESI) m/z: [M+H] calcd for $C_{23}H_{29}BrN_2O_2$: 445.14; found 445.2.

Intermediate 2 and Intermediate 4. Synthesis of (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate

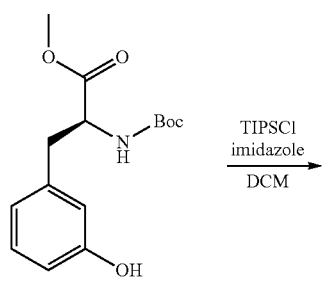

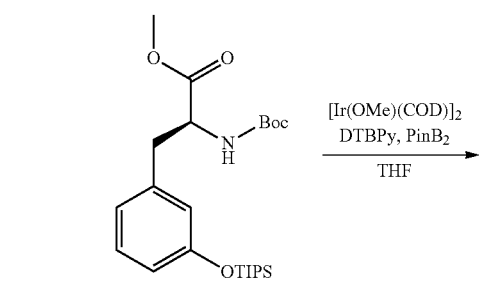

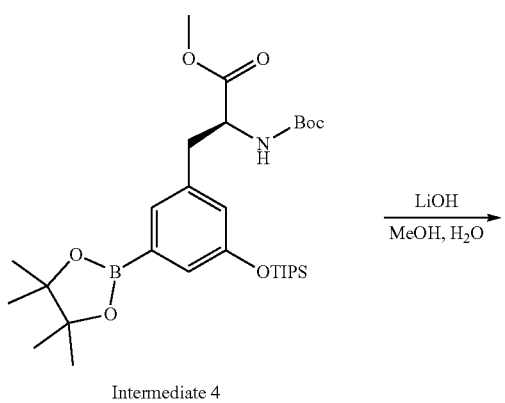

Intermediate 4

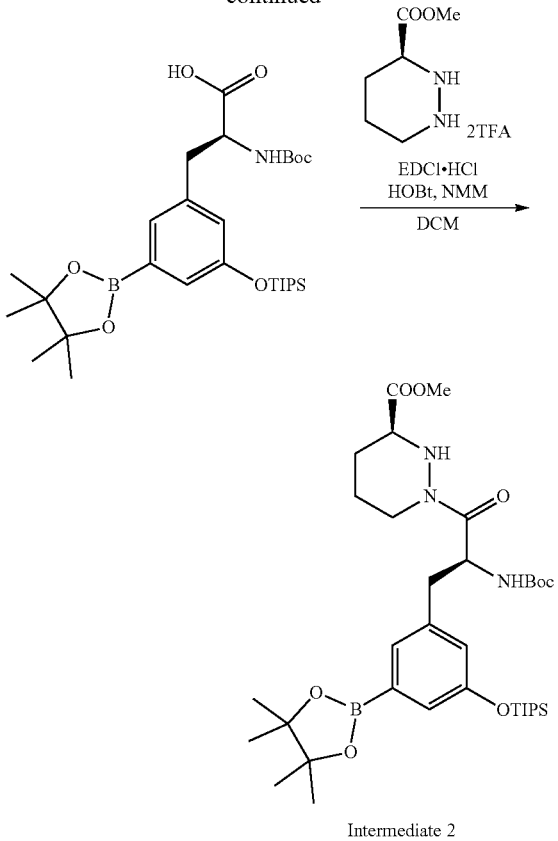

Intermediate 2

Step 1: Synthesis of (S)-methyl 2-(tert-butoxycarbonylamino)-3-(3-(triisopropylsilyloxy)phenyl)-propanoate To a mixture of (S)-methyl 2-(tert-butoxycarbonylamino)-3-(3-hydroxyphenyl)propanoate (10.0 g, 33.9 mmol) in DCM (100 mL) was added imidazole (4.6 g, 67.8 mmol) and TIPSCl (7.8 g, 40.7 mmol). The mixture was stirred at room temperature overnight then diluted with DCM (200 mL) and washed with H₂O (3×150 mL). The organic layer was dried over anhydrous Na₂SO₄, filtered, concentrated under reduced pressure and the residue was purified by silica gel column chromatography to give (S)-methyl 2-(tert-butoxycarbonylamino)-3-(3-(triisopropylsilyloxy)phenyl)-propanoate (15.0 g, 98% yield) as an oil. LCMS (ESI) m/z: [M+Na] calcd for $C_{24}H_{41}NO_5SiNa$: 474.22; found 474.2.

Step 2: Synthesis of (S)-methyl 2-(tert-butoxycarbonylamino)-3-(3-(4,4,5,5-tetramethyl-1,3,2-dioxaborolan-2-yl)-5-(triisopropylsilyloxy)phenyl)-propanoate A mixture of (S)-methyl 2-(tert-butoxycarbonylamino)-3-(3-(triisopropylsilyloxy)phenyl)-propanoate (7.5 g, 16.6 mmol), PinB₂ (6.3 g, 24.9 mmol), [Ir(OMe)(COD)]₂ (1.1 g, 1.7 mmol) and 4-tert-butyl-2-(4-tert-butyl-2-pyridyl)pyridine (1.3 g, 5.0 mmol) was purged with Ar, then THF (75 mL) was added and the mixture placed under an atmosphere of Ar and sealed. The mixture was heated to 80° C. and stirred for 16 h, concentrated under reduced pressure, and the residue was purified by silica gel column chromatography to give (S)-methyl 2-(tert-butoxycarbonylamino)-3-(3-(4,4,5,5-tetramethyl-1,3,2-dioxaborolan-2-yl)-5-(triisopropylsilyloxy)phenyl)-propanoate (7.5 g, 78% yield) as a solid. LCMS (ESI) m/z: [M+Na] calcd for $C_{30}H_{52}BNO_7SiNa$: 600.35; found 600.4; $^1H$ NMR (300 MHz, $CD_3OD$) δ 7.18 (s, 1H), 7.11 (s, 1H), 6.85 (s, 1H), 4.34 (m, 1H), 3.68 (s, 3H), 3.08 (m, 1H), 2.86 (m, 1H), 1.41-1.20 (m, 26H), 1.20-1.01 (m, 22H), 0.98-0.79 (m, 4H).

Step 3: Synthesis of (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic Acid To a mixture of triisopropylsilyl (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoate (4.95 g, 6.9 mmol) in MeOH (53 mL) at 0° C. was added LiOH (840 mg, 34.4 mmol) in $H_2O$ (35 mL). The mixture was stirred at 0° C. for 2 h, then acidified to pH ~5 with 1M HCl and extracted with EtOAc (2×250 mL). The combined organic layers were washed with brine (3×100 mL), dried over anhydrous $Na_2SO_4$, filtered and the filtrate concentrated under reduced pressure to give (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic acid (3.7 g, 95% yield), which was used directly in the next step without further purification. LCMS (ESI) m/z: [M+NH$_4$] calcd for $C_{29}H_{50}BNO_7SiNH_4$: 581.38; found 581.4.

Step 4: Synthesis of methyl (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate To a mixture of methyl (S)-hexahydropyridazine-3-carboxylate (6.48 g, 45.0 mmol) in DCM (200 mL) at 0° C. was added NMM (41.0 g, 405 mmol), (S)-2-((tert-butoxycarbonyl)amino)-3-(3-(4,4,5,5-tetramethyl-1,3,2-dioxaborolan-2-yl)-5-((triisopropylsilyl)oxy)phenyl)propanoic acid (24 g, 42.6 mmol) in DCM (50 mL) then HOBt (1.21 g, 9.0 mmol) and EDCl HCl salt (12.9 g, 67.6 mmol). The mixture was warmed to room temperature and stirred for 16 h, then diluted with DCM (200 mL) and washed with $H_2O$ (3×150 mL). The organic layer was dried over anhydrous $Na_2SO_4$, filtered, the filtrate concentrated under reduced pressure and the residue was purified by silica gel column chromatography to give methyl (S)-1-((S)-2-((tert-butoxycarbonyl)amino)-3-(3-(4,4,5,5-tetramethyl-1,3,2-dioxaborolan-2-yl)-5-((triisopropylsilyl)oxy)phenyl)propanoyl)hexahydropyridazine-3-carboxylate (22 g, 71% yield) as an oil. LCMS (ESI) m/z: [M+H] calcd for $C_{35}H_{60}BN_3O_8Si$: 690.42; found 690.5.

Intermediate 3. Synthesis of (S)-tert-butyl 3-methyl-2-((S)—N-methylpyrrolidine-3-carboxamido)butanoate

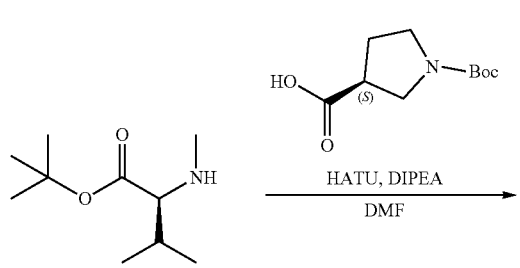

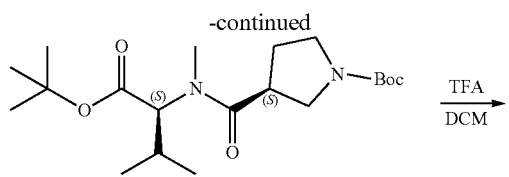

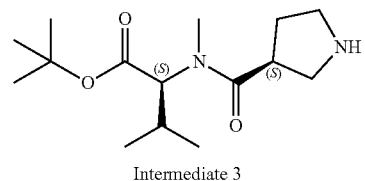

Intermediate 3

Step 1: Synthesis of (S)-tert-butyl 3-(((S)-1-(tert-butoxy)-3-methyl-1-oxobutan-2-yl)(methyl)carbamoyl)pyrrolidine-1-carboxylate To a mixture of (S)-1-(tert-butoxycarbonyl)pyrrolidine-3-carboxylic acid (2.2 g, 10.2 mmol) in DMF (10 mL) at room temperature was added HATU (7.8 g, 20.4 mmol) and DIPEA (5 mL). After stirring at room temperature for 10 min, tert-butyl methyl-L-valinate (3.8 g, 20.4 mmol) in DMF (10 mL) was added. The mixture was stirred at room temperature for 3 h, then diluted with DCM (40 mL) and $H_2O$ (30 mL). The aqueous and organic layers were separated, and the organic layer was washed with $H_2O$ (3×30 mL), brine (30 mL), dried over anhydrous $Na_2SO_4$ and filtered. The filtrate was concentrated under reduced pressure and the residue was purified by silica gel column chromatography to give (S)-tert-butyl 3-(((S)-1-(tert-butoxy)-3-methyl-1-oxobutan-2-yl)(methyl)carbamoyl)pyrrolidine-1-carboxylate (3.2 g, 82% yield) as an oil. LCMS (ESI) m/z: [M+Na] calcd for $C_{20}H_{36}N_2O_5Na$: 407.25; found 407.2.

Step 2: Synthesis of (S)-tert-butyl 3-methyl-2-((S)—N-methylpyrrolidine-3-carboxamido)butanoate A mixture of (S)-tert-butyl 3-(((S)-1-(tert-butoxy)-3-methyl-1-oxobutan-2-yl)(methyl)carbamoyl)pyrrolidine-1-carboxylate (3.2 g, 8.4 mmol) in DCM (13 mL) and TFA (1.05 g, 9.2 mmol) was stirred at room temperature for 5 h. The mixture was concentrated under reduced pressure to give (S)-tert-butyl 3-methyl-2-((S)—N-methylpyrrolidine-3-carboxamido)butanoate (2.0 g, 84% yield) as an oil. LCMS (ESI) m/z: [M+H] calcd for $C_{15}H_{28}N_2O_3$: 285.21; found 285.2.

411

Intermediate 5. Synthesis of tert-butyl ((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate

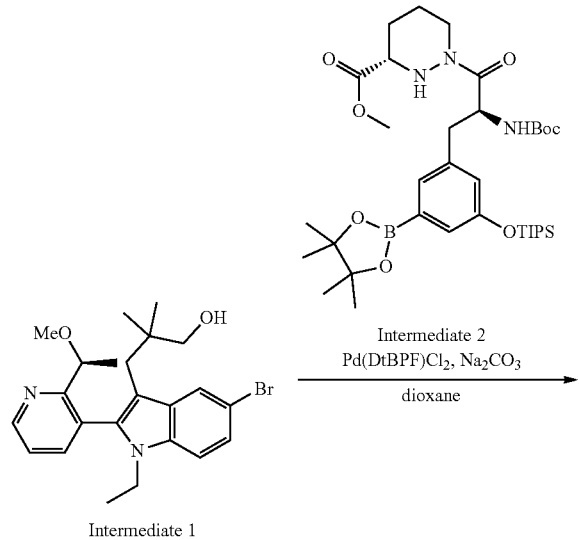

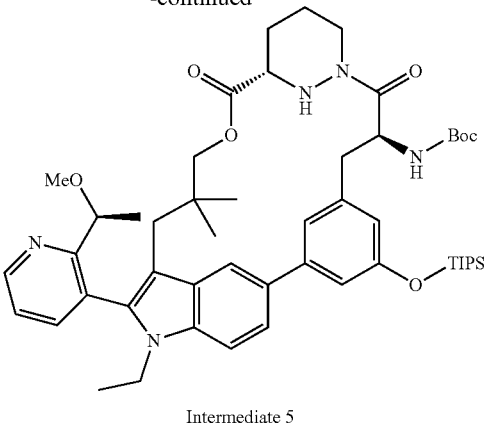

Intermediate 5

Step 1: Synthesis of methyl (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylate To a stirred mixture of 3-(5-bromo-1-ethyl-2-[2-[(1S)-1-methoxyethyl]pyridin-3-yl]indol-3-yl)-2,2-dimethylpropan-1-ol (30 g, 67 mmol) and methyl (3S)-1-[(2S)-2-[(tert-butoxycarbonyl)amino]-3-[3-(4,4,5,5-tetramethyl-1,3,2-dioxaborolan-2-yl)-5-[(triisopropylsilyl)oxy]phenyl]propanoyl]-1,2-diazinane-3-carboxylate (55.8 g, 80.8 mmol) in 1,4-dioxane (750 mL) at room temperature under an atmosphere of Ar was added Na$_2$CO$_3$ (17.9 g, 168.4 mmol), Pd(DtBPF)Cl$_2$ (4.39 g, 6.7 mmol), and H$_2$O (150 mL) in portions. The mixture was heated to 85° C. and stirred for 3 h, cooled, diluted with H$_2$O (2 L), and extracted with EtOAc (3×1 L). The combined organic layers were washed with brine (2×500 mL), dried over anhydrous Na$_2$SO$_4$, and filtered. The filtrate was concentrated under reduced pressure and the residue was purified by silica gel column chromatography to give methyl (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylate (50 g, 72% yield) as a solid. LCMS (ESI) m/z: [M+H] calcd for C$_{52}$H$_{77}$N$_5$O$_8$Si: 928.56; found 928.8.

Step 2: Synthesis of (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylic Acid To a stirred mixture of methyl (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylate (50 g, 54 mmol) in DCE (500 mL) at room temperature was added trimethyltin hydroxide (48.7 g, 269 mmol) in portions. The mixture was heated to 65° C. and stirred for 16 h, then filtered and the filter cake washed with DCM (3×150 mL). The filtrate was concentrated under reduced pressure to give (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-

[(triisopropylsilyl)oxy]phenyl]propanoyl]-1,2-diazinane-3-carboxylic acid (70 g, crude), which was used directly in the next step without further purification. LCMS (ESI) m/z: [M+H] calcd for $C_{51}H_{75}N_5O_8Si$: 914.55; found 914.6.

Step 3: Synthesis of tert-butyl (($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a stirred mixture of (3S)-1-[(2S)-2-[(tert-butoxycarbonyl)amino]-3-[3-[1-ethyl-3-(3-hydroxy-2,2-dimethylpropyl)-2-[2-[(1S)-1-methoxyethyl]pyridin-3-yl]indol-5-yl]-5-[(triisopropylsilyl)oxy]phenyl]propanoyl]-1,2-diazinane-3-carboxylic acid (70 g) in DCM (5 L) at 0° C. under an atmosphere of $N_2$ was added DIPEA (400 mL, 2.3 mol), HOBT (51.7 g, 383 mmol) and EDCl (411 g, 2.1 mol) in portions. The mixture was warmed to room temperature and stirred for 16 h, then diluted with DCM (1 L), washed with brine (3×1 L), dried over anhydrous $Na_2SO_4$, and filtered. The filtrate was concentrated under reduced pressure and the residue was purified by silica gel column chromatography to give tert-butyl (($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (36 g, 42% yield) as a solid. LCMS (ESI) m/z: [M+H] calcd for $C_{51}H_{73}N_5O_7Si$: 896.54; found 896.5.

Intermediate 6. Synthesis of tert-butyl (($6^3$S,4S)-$1^2$-iodo-10,10-dimethyl-5,7-dioxo-$2^5$-((triisopropylsilyl)oxy)-$6^1$,$6^2$,$6^3$,$6^4$,$6^5$,$6^6$-hexahydro-$1^1$-H-8-oxa-1(5,3)-indola-6(1,3)-pyridazina-2(1,3)-benzenacycloundecaphane-4-yl)carbamate

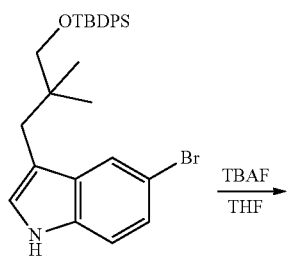

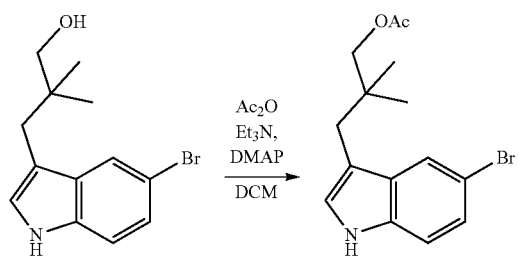

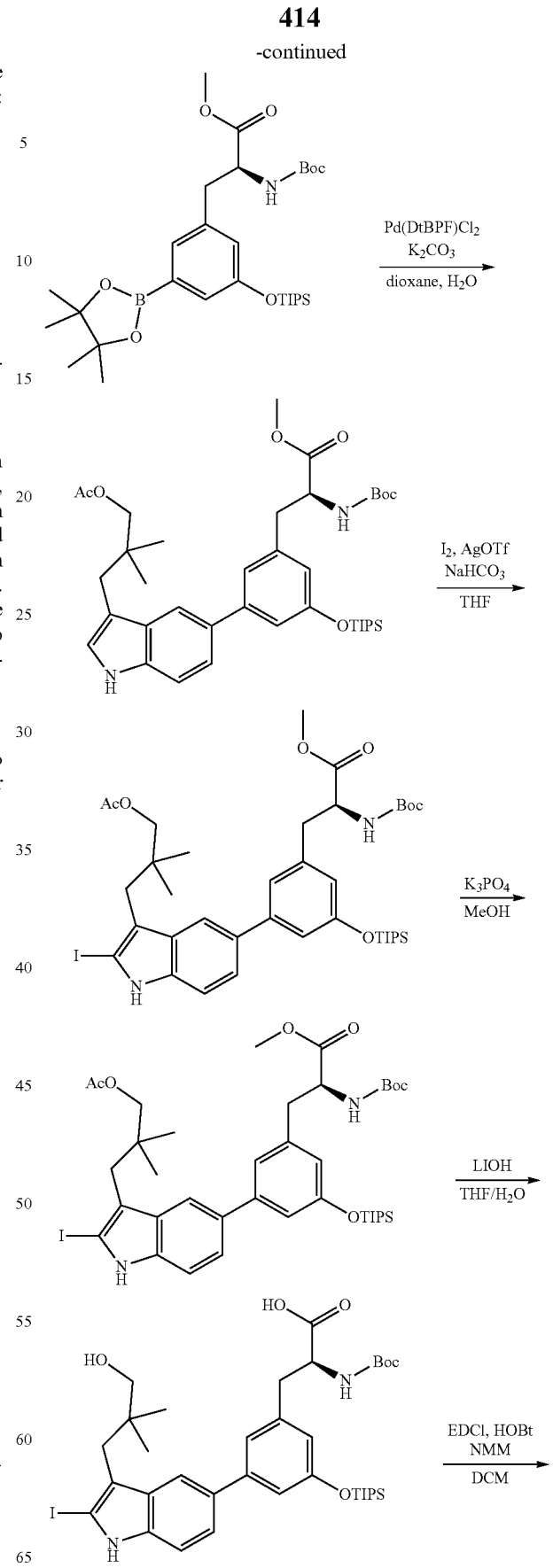

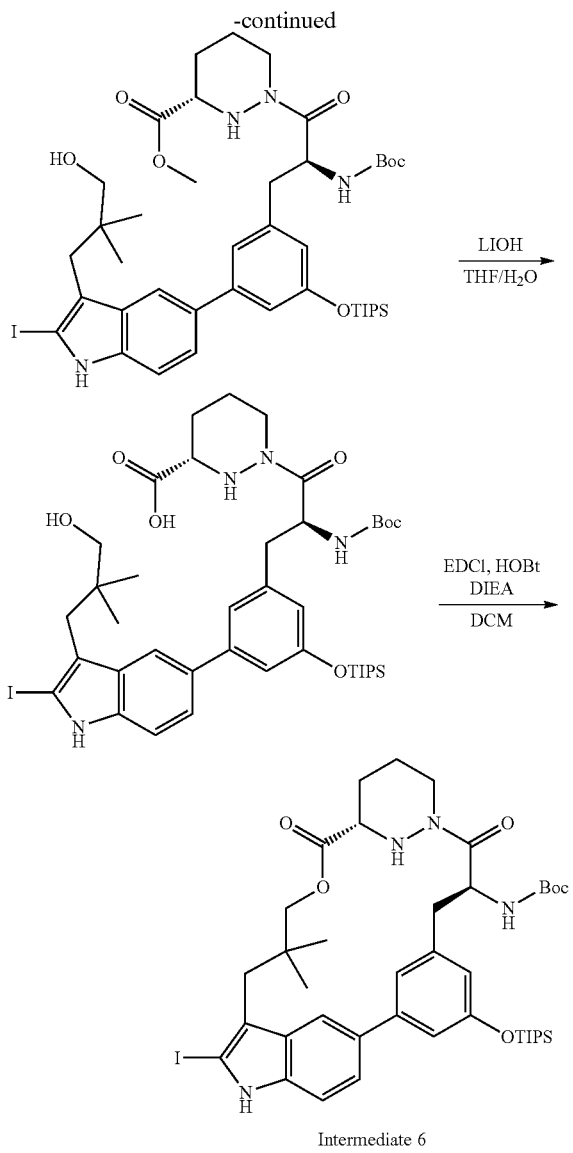

Intermediate 6

Step 1: Synthesis of 3-(5-bromo-1H-indol-3-yl)-2,2-dimethylpropan-1-ol

This reaction was undertaken on five batches in parallel on the scale illustrated below. Into a 2 L round-bottom flask were added 5-bromo-3-[3-[(tert-butyldiphenylsilyl)oxy]-2,2-dimethylpropyl]-1H-indole (100 g, 192 mmol) and TBAF (301.4 g, 1.15 mol) in THF (1.15 L) at room temperature. The resulting mixture was heated to 50° C. and stirred for 16 h, then the mixture was concentrated under reduced pressure.

At this stage the residues from all five batches were combined, diluted with H$_2$O (5 L), and extracted with EtOAc (3×2 L). The combined organic layers were washed with brine (2×1.5 L), dried over anhydrous Na$_2$SO$_4$, and filtered. The filtrate was concentrated under reduced pressure and the residue was purified by silica gel column chromatography to give 3-(5-bromo-1H-indol-3-yl)-2,2-dimethylpropan-1-ol (310 g, crude) as a solid. LCMS (ESI) m/z: [M+H] calcd for C$_{13}$H$_{16}$BrNO: 282.05 and 284.05; found 282.1 and 284.1.

Step 2: Synthesis of 3-(5-bromo-1H-indol-3-yl)-2,2-dimethylpropyl Acetate

This reaction was undertaken on two batches in parallel in accordance with the procedure below. To a stirred mixture of 3-(5-bromo-1H-indol-3-yl)-2,2-dimethylpropan-1-ol (135 g, 478 mmol) and Et$_3$N (200 mL, 1.44 mol) in DCM (1.3 L) at 0° C. under an atmosphere of N$_2$ was added Ac$_2$O (73.3 g, 718 mmol) and DMAP (4.68 g, 38.3 mmol) in portions. The resulting mixture was stirred for 10 min at 0° C., then washed with H$_2$O (3×2 L).

At this stage, the organic layers from both batches were combined and washed with brine (2×1 L), dried over anhydrous Na$_2$SO$_4$, and filtered. The filtrate was concentrated under reduced pressure and the residue was purified by column chromatography to give 3-(5-bromo-1H-indol-3-yl)-2,2-dimethylpropyl acetate (304 g, 88% yield) as a solid. $^1$H NMR (400 MHz, DMSO-d$_6$) δ 11.16-11.11 (m, 1H), 7.69 (d, J=2.0 Hz, 1H), 7.32 (d, J=8.6 Hz, 1H), 7.19-7.12 (m, 2H), 3.69 (s, 2H), 2.64 (s, 2H), 2.09 (s, 3H), 0.90 (s, 6H).

Step 3: Synthesis of methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate This reaction was undertaken on four batches in parallel in accordance with the procedure below. Into a 2 L round-bottom flasks were added methyl (2S)-2-[(tert-butoxycarbonyl)amino]-3-[3-(4,4,5,5-tetramethyl-1,3,2-dioxaborolan-2-yl)-5-[(triisopropylsilyl)oxy]phenyl]propanoate (125 g, 216 mmol), 1,4-dioxane (1 L), H$_2$O (200 mL), 3-(5-bromo-1H-indol-3-yl)-2,2-dimethylpropyl acetate (73.7 g, 227 mmol), K$_2$CO$_3$ (59.8 g, 433 mmol), and Pd(DtBPF)Cl$_2$ (7.05 g, 10.8 mmol) at room temperature under an atmosphere of Ar. The resulting mixture was heated to 65° C. and stirred for 2 h, then diluted with H$_2$O (10 L) and extracted with EtOAc (3×3 L). The combined organic layers were washed with brine (2×2 L), dried over anhydrous Na$_2$SO$_4$, and filtered. The filtrate was concentrated under reduced pressure.

At this point the residue from all four batches was combined and purified by column chromatography to give methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate (500 g, 74% yield) as an oil. LCMS (ESI) m/z: [M+Na] calcd for C$_{39}$H$_{58}$N$_2$O$_7$SiNa: 717.39; found 717.3.

Step 4: Synthesis of methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate This reaction was undertaken on three batches in parallel in accordance with the procedure below. To a stirred mixture of methyl (2S)-3-(3-[3-[3-(acetyloxy)-2,2-dimethylpropyl]-1H-indol-5-yl]-5-[(triisopropylsilyl)oxy]phenyl)-2-[(tert-butoxycarbonyl)amino]propanoate (150 g, 216 mmol) and NaHCO$_3$ (21.76 g, 259 mmol) in THF (1.5 L) was added AgOTf (66.5 g, 259 mmol) in THF dropwise at 0° C. under an atmosphere of nitrogen. 12 (49.3 g, 194 mmol) in THF was added dropwise over 1 h at 0° C. and the resulting mixture was stirred for an additional 10 min at 0° C. The combined experiments were diluted with aqueous Na$_2$S$_2$O$_3$ (5 L) and extracted with EtOAc (3×3 L). The combined organic layers were washed with brine (2×1.5 L), dried over anhydrous Na$_2$SO$_4$, filtered, and concentrated under reduced pressure to a residue.

At this stage, the residue from all three batches was combined and purified by column chromatography to give methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate (420 g, 71% yield) as an oil. LCMS (ESI) m/z: [M+Na] calcd for C$_{39}$H$_{57}$IN$_2$O$_7$SiNa: 843.29; found 842.9.

Step 5: Synthesis of methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate This reaction was undertaken on three batches in parallel in accordance with the procedure below. To a 2 L round-bottom flask were added methyl (2S)-3-(3-[3-[3-(acetyloxy)-2,2-dimethylpropyl]-2-iodo-1H-indol-5-yl]-5-[(triisopropylsilyl)oxy]phenyl)-2-[(tert-butoxycarbonyl)amino]propanoate (140 g, 171 mmol), MeOH (1.4 L), and K$_3$PO$_4$ (108.6 g, 512 mmol) at 0° C. The mixture was warmed to room temperature and stirred for 1 h, then the combined experiments were diluted with H$_2$O (9 L) and extracted with EtOAc (3×3 L). The combined organic layers were washed with brine (2×2 L), dried over anhydrous Na$_2$SO$_4$, filtered, and the filtrate was concentrated under reduced pressure.

At this stage the residue from all three batches was combined to give methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate (438 g, crude) as a solid. LCMS (ESI) m/z: [M+Na] calcd for C$_{37}$H$_{55}$IN$_2$O$_6$SiNa: 801.28; found 801.6.

Step 6: Synthesis of (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic Acid This reaction was undertaken on three batches in parallel in accordance with the procedure below. To a stirred mixture of methyl (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoate (146 g, 188 mmol) in THF (1.46 L) was added LiOH (22.45 g, 937 mmol) in H$_2$O (937 mL) dropwise at 0° C. The resulting mixture was warmed to room temperature and stirred for 1.5 h [note: LCMS showed 15% de-TIPS product]. The mixture was acidified to pH 5 with 1M HCl (1M) and the combined experiments were extracted with EtOAc (3×3 L). The combined organic layers were washed with brine (2×2 L), dried over anhydrous Na$_2$SO$_4$, filtered, and the filtrate was concentrated under reduced pressure.

At this stage the residue from all three batches was combined to give (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic acid (402 g, crude) as a solid. LCMS (ESI) m/z: [M+Na] calcd for C$_{36}$H$_{53}$IN$_2$O$_6$SiNa: 787.26; found 787.6.

Step 7: Synthesis of methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate To a stirred mixture of (2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoic acid (340 g, 445 mmol) and methyl (3S)-1,2-diazinane-3-carboxylate (96.1 g, 667 mmol) in DCM (3.5 L) was added NMM (225 g, 2.2 mol), EDCl (170 g, 889 mmol), and HOBt (12.0 g, 88.9 mmol) portionwise at 0° C. The mixture was warmed to room temperature and stirred for 16 h, then washed with H$_2$O (3×2.5 L), brine (2×1 L), dried over anhydrous Na$_2$SO$_4$, and filtered. The filtrate was concentrated under reduced pressure and the residue was purified by column chromatography to give methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate (310 g, 62% yield) as an oil. LCMS (ESI) m/z: [M+H] calcd for C$_{42}$H$_{63}$IN$_4$O$_7$Si: 891.36; found 890.8.

Step 8: Synthesis of (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic Acid This reaction was undertaken on three batches in parallel in accordance with the procedure below. To a stirred mixture of methyl (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylate (85.0 g, 95.4 mmol) in THF (850 mL) was added LiOH (6.85 g, 286 mmol) in H$_2$O (410 mL) dropwise at 0° C. under an atmosphere of N$_2$. The mixture was stirred at 0° C. for 1.5 h [note: LCMS showed 15% de-TIPS product], then acidified to pH 5 with 1M HCl At this stage the mixtures from all three batches was combined and extracted with EtOAc (3×2 L). The combined organic layers were washed with brine (2×1.5 L), dried over anhydrous Na$_2$SO$_4$, filtered, and the filtrate was concentrated under reduced pressure to give (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid (240 g, crude) as a solid. LCMS (ESI) m/z: [M+H] calcd for C$_{41}$H$_{61}$IN$_4$O$_7$Si: 877.35; found 877.6.

Step 9: Synthesis of tert-butyl ((6$^3$S,4S)-1$^2$-iodo-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane-4-yl)carbamate This reaction was undertaken on two batches in parallel in accordance with the procedure below. To a stirred mixture of (3S)-1-[(2S)-2-[(tert-butoxycarbonyl)amino]-3-[3-[3-(3-hydroxy-2,2-dimethylpropyl)-2-iodo-1H-indol-5-yl]-5-[(triisopropylsilyl)oxy]phenyl]propanoyl]-1,2-diazinane-3-carboxylic acid (120 g, 137 mmol) in DCM (6 L) was added DIPEA (357 mL, 2.05 mol), EDCl (394 g, 2.05 mol), and HOBT (37 g, 274 mmol) in portions at 0° C. under an atmosphere of N$_2$. The mixture was warmed to room temperature and stirred overnight.

At this stage the solutions from both batches were combined and washed with H$_2$O (3×6 L), brine (2×6 L), dried over anhydrous Na$_2$SO$_4$, and filtered. The filtrate was concentrated under reduced pressure and the residue was purified by column chromatography to give tert-butyl ((6$^3$S,4S)-1$^2$-iodo-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane- 4-yl)carbamate (140 g, 50% yield) as a solid. LCMS (ESI) m/z: [M+H] calcd for $C_{41}H_{59}IN_4O_6Si$: 859.33; found 858.3.

Intermediate 7. Synthesis of $(6^3S,4S)$-4-amino-$1^1$-ethyl-$2^5$-hydroxy-$1^2$-(4-(methoxymethyl)pyridin-3-yl)-10,10-dimethyl-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione

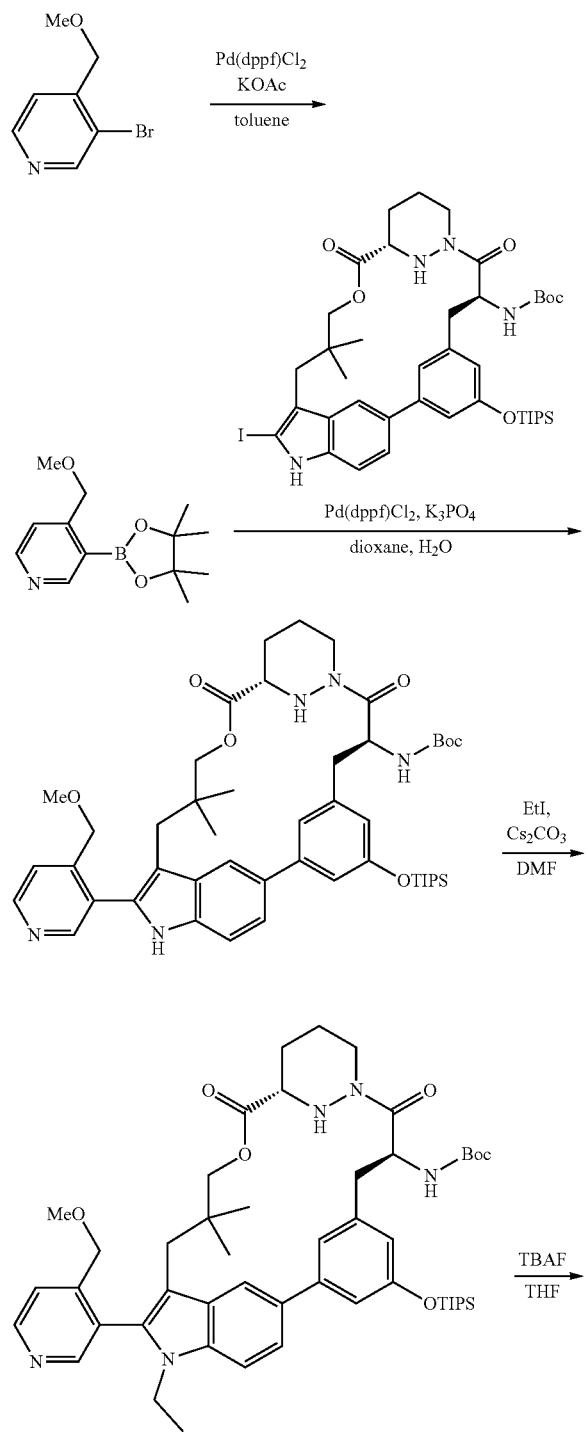

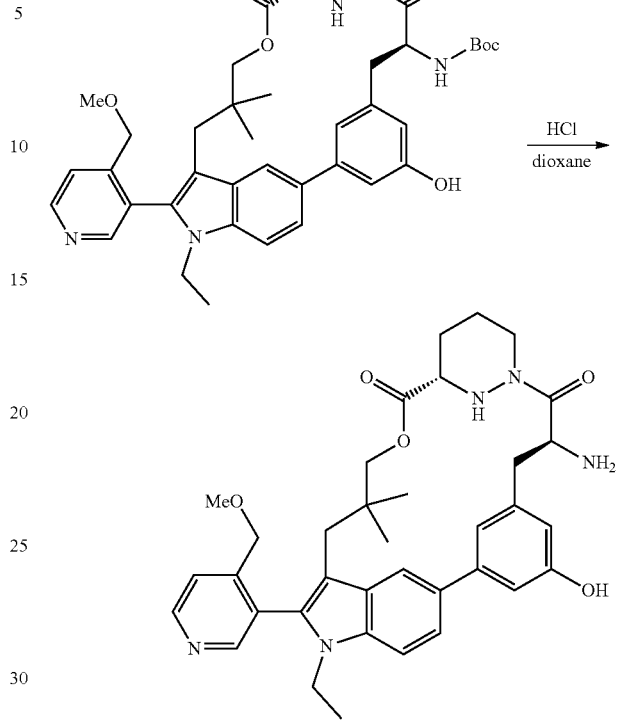

Step 1: Synthesis of 4-(methoxymethyl)-3-(4,4,5,5-tetramethyl-1,3,2-dioxaborolan-2-yl)pyridine To a mixture of 3-bromo-4-(methoxymethyl)pyridine (1.0 g, 5.0 mmol), 4,4,5,5-tetramethyl-2-(tetramethyl-1,3,2-dioxaborolan-2-yl)-1,3,2-dioxaborolane (1.51 g, 5.9 mmol) and KOAc (1.21 g, 12.3 mmol) in toluene (10 mL) at room temperature under an atmosphere of Ar was added Pd(dppf)Cl$_2$ (362 mg, 0.5 mmol). The mixture was heated to 110° C. and stirred overnight, then concentrated under reduced pressure to give 4-(methoxymethyl)-3-(4,4,5,5-tetramethyl-1,3,2-dioxaborolan-2-yl)pyridine, which was used directly in the next step directly without further purification. LCMS (ESI) m/z: [M+H] calcd for $C_{13}H_{20}BNO_3$: 250.16; found 250.3.

Step 2: Synthesis of give tert-butyl $((6^3S,4S)$-$1^2$-(4-(methoxymethyl)pyridin-3-yl)-10,10-dimethyl-5,7-dioxo-$2^5$-((triisopropylsilyl)oxy)-$6^1,6^2,6^3,6^4,6^5,6^6$-hexahydro-$1^1$-H-8-oxa-1(5,3)-indola-6(1,3)-pyridazina-2(1,3)-benzenacycloundecaphane-4-yl) carbamate To a mixture of 4-(methoxymethyl)-3-(4,4,5,5-tetramethyl-1,3,2-dioxaborolan-2-yl)pyridine (290 mg, 1.16 mmol), K$_3$PO$_4$ (371 mg, 1.75 mmol) and tert-butyl $((6^3S, 4S)$-$1^2$-iodo-10,10-dimethyl-5,7-dioxo-$2^5$-((triisopropylsilyl)oxy)-$6^1,6^2,6^3,6^4,6^5,6^6$-hexahydro-$1^1$-H-8-oxa-1(5,3)-indola-6(1,3)-pyridazina-2(1,3)-benzenacycloundecaphane-4-yl)carbamate (500 mg, 0.58 mmol) in 1,4-dioxane (5 mL) and H$_2$O (1 mL) at room temperature under an atmosphere of Ar was added Pd(dppf)Cl$_2$ (43 mg, 0.06 mmol). The mixture was heated to 70° C. and stirred for 2 h, then H$_2$O was added and the mixture extracted with EtOAc (2×10 mL). The combined organic layers were washed with brine (10 mL), dried over anhydrous $Na_2SO_4$, and filtered. The filtrate was concentrated under reduced pressure and the residue was purified by silica gel column chromatography to give tert-butyl ((6$^3$S,4S)-1$^2$-(4-(methoxymethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane-4-yl)carbamate (370 mg, 74% yield) as a foam. LCMS (ESI) m/z: [M+H] calcd for $C_{48}H_{67}N_5O_7Si$: 854.49; found 854.6.

Step 3: Synthesis of tert-butyl ((6$^3$S,4S)-1$^1$-ethyl-1$^2$-(4-(methoxymethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane-4-yl)carbamate A mixture of tert-butyl ((6$^3$S,4S)-1$^2$-(4-(methoxymethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane-4-yl)carbamate (350 mg, 0.41 mmol), $Cs_2CO_3$ (267 mg, 0.82 mmol), and EtI (128 mg, 0.82 mmol) in DMF (4 mL) was stirred at 35° C. overnight. $H_2O$ was added and the mixture was extracted with EtOAc (2×15 mL). The combined organic layers were washed with brine (15 mL), dried over anhydrous $Na_2SO_4$, and filtered. The filtrate was concentrated under reduced pressure and the residue was purified by silica gel column chromatography to give tert-butyl ((6$^3$S,4S)-1$^1$-ethyl-1$^2$-(4-(methoxymethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane-4-yl)carbamate (350 mg, 97% yield) as an oil. LCMS (ESI) m/z: [M+H] calcd for $C_{50}H_{71}N_5O_7Si$: 882.52; found 882.6.

Step 4: Synthesis of tert-butyl ((6$^3$S,4S)-1$^1$-ethyl-2$^5$-hydroxy-1$^2$-(4-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate A mixture of tert-butyl ((6$^3$S,4S)-1$^1$-ethyl-1$^2$-(4-(methoxymethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$-H-8-oxa-1(5,3)-indola-6(1,3)-pyridazina-2(1,3)-benzenacycloundecaphane-4-yl)carbamate (350 mg, 0.4 mmol) and 1M TBAF in THF (0.48 mL, 0.480 mmol) in THF (3 mL) at 0° C. under an atmosphere of Ar was stirred for 1 h. The mixture was concentrated under reduced pressure and the residue was purified by silica gel column chromatography to give tert-butyl ((6$^3$S,4S)-1$^1$-ethyl-2$^5$-hydroxy-1$^2$-(4-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (230 mg, 80% yield) as an oil. LCMS (ESI) m/z: [M+H] calcd for $C_{41}H_{51}H_5O_7$: 726.39; found 726.6.

Step 5: Synthesis of (6$^3$S,4S)-4-amino-1$^1$-ethyl-2$^5$-hydroxy-1$^2$-(4-(methoxymethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione To a mixture of tert-butyl N-[(8S,14S)-22-ethyl-4-hydroxy-21-[4-(methoxymethyl)pyridin-3-yl]-18,18-dimethyl-9,15-dioxo-16-oxa-10,22,28-triazapentacyclo[18.5.2.1^[2,6].1^[10,14].0^[23,27]]nonacosa-1(26),2,4,6(29),20,23(27),24-heptaen-8-yl]carbamate (200 mg, 0.28 mmol) in 1,4-dioxane (2 mL) at 0° C. under an atmosphere of Ar was added 4M HCl in 1,4-dioxane (2 mL, 8 mmol). The mixture was allowed to warm to room temperature and was stirred overnight, then concentrated under reduced pressure to give (6$^3$S,4S)-4-amino-1$^1$-ethyl-2$^5$-hydroxy-1$^2$-(4-(methoxymethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione (200 mg). LCMS (ESI) m/z: [M+H] calcd for $C_{36}H_{43}N_5O_5$: 626.34; found 626.5.

Intermediate 8. Synthesis of (6$^3$S,4S)-4-amino-1$^1$-ethyl-1$^2$-(4-(methoxymethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione

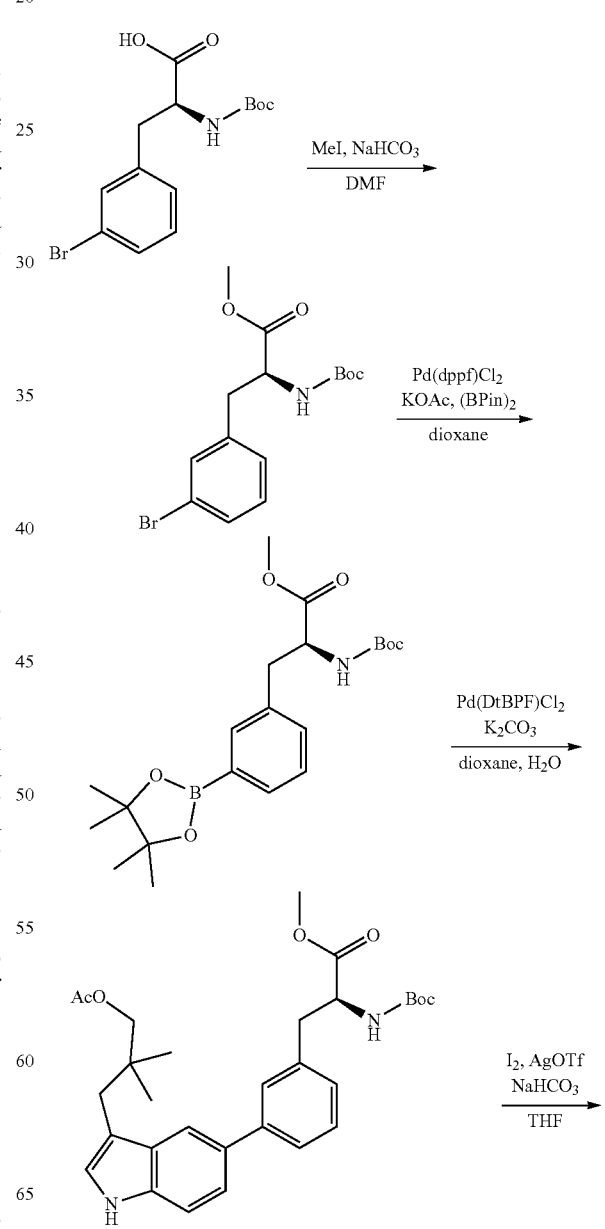

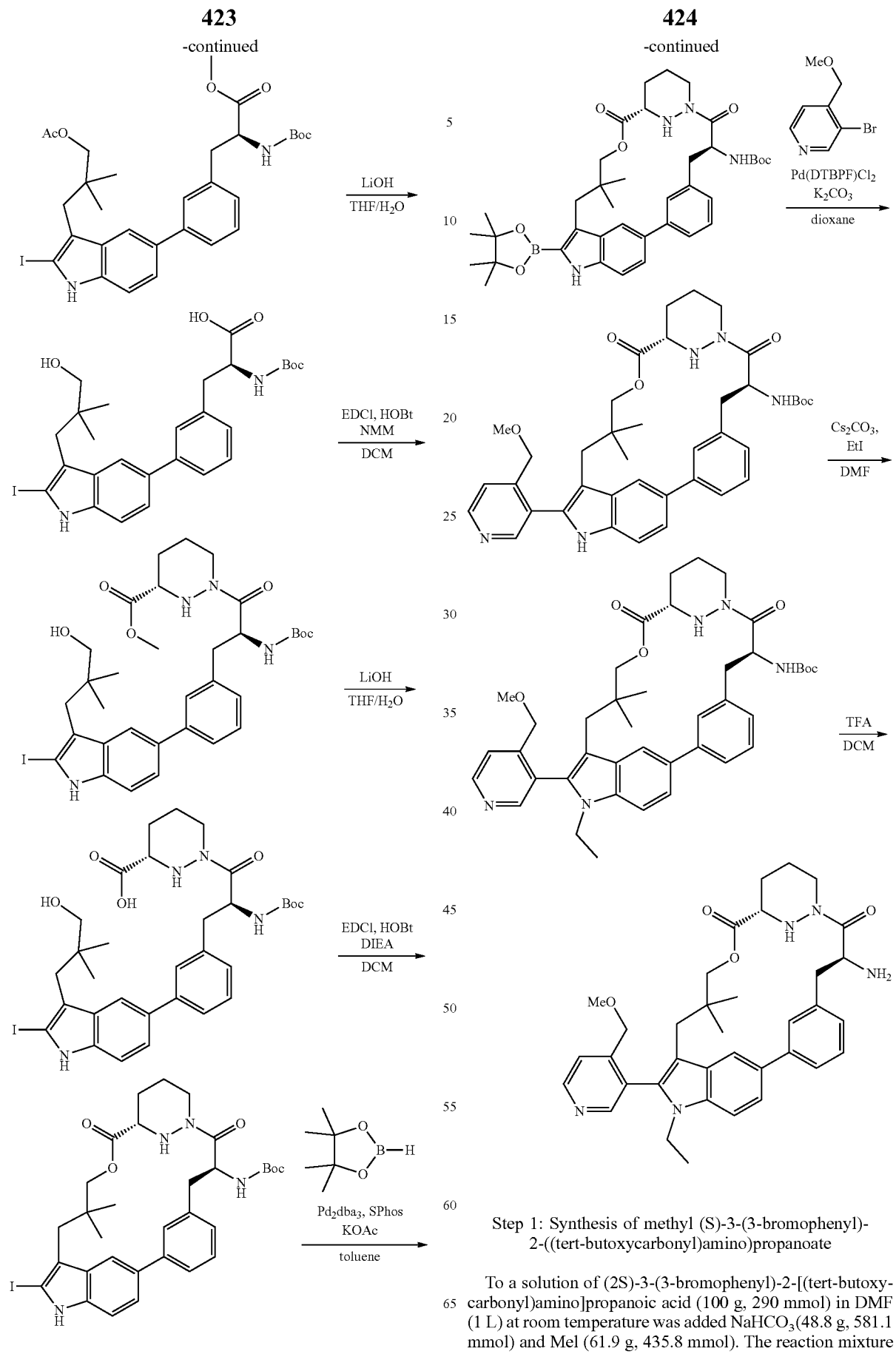
Step 1: Synthesis of methyl (S)-3-(3-bromophenyl)-2-((tert-butoxycarbonyl)amino)propanoate
To a solution of (2S)-3-(3-bromophenyl)-2-[(tert-butoxycarbonyl)amino]propanoic acid (100 g, 290 mmol) in DMF (1 L) at room temperature was added NaHCO$_3$ (48.8 g, 581.1 mmol) and MeI (61.9 g, 435.8 mmol). The reaction mixture was stirred for 16 h and was then quenched with H₂O (1 L) and extracted with EtOAc (3×1 L). The combined organic layers were washed with brine (3×500 mL), dried over Na₂SO₄, filtered, and concentrated under reduced pressure. The residue was purified by silica gel chromatography (13% EtOAc/pet. ether) to afford the desired product (109 g, crude). LCMS (ESI) m/z: [M+Na] calcd for $C_{15}H_{20}BrNO_4$: 380.05; found 380.0.

Step 2: Synthesis of methyl (S)-2-((tert-butoxycarbonyl)amino)-3-(3-(4,4,5,5-tetramethyl-1,3,2-dioxaborolan-2-yl)phenyl)propanoate To a stirred solution of methyl (2S)-3-(3-bromophenyl)-2-[(tert-butoxycarbonyl)amino]propanoate (108 g, 301.5 mmol) and bis(pinacolato)diboron (99.53 g, 391.93 mmol) in 1,4-dioxane (3.2 L) was added KOAc (73.97 g, 753.70 mmol) and Pd(dppf)Cl₂ (22.06 g, 30.15 mmol). The reaction mixture was heated to 90° C. for 3 h and was then cooled to room temperature and extracted with EtOAc (2×3 L). The combined organic layers were washed with brine (3×800 mL), dried over Na₂SO₄, filtered, and concentrated under reduced pressure. The residue was purified by silica gel chromatography (5% EtOAc/pet. ether) to afford the desired product (96 g, 78.6% yield). LCMS (ESI) m/z: [M+Na] calcd for $C_{21}H_{32}BNO_6$: 428.22; found 428.1.

Step 3: Synthesis of methyl (S)-3-(3-(3-(3-acetoxy-2,2-dimethylpropyl)-1H-indol-5-yl)phenyl)-2-((tert-butoxycarbonyl)amino)propanoate To a mixture of methyl (2S)-2-[(tert-butoxycarbonyl)amino]-3-[3-(4,4,5,5-tetramethyl-1,3,2-dioxaborolan-2-yl)phenyl]propanoate (94 g, 231.9 mmol) and 3-(5-bromo-1H-indol-3-yl)-2,2-dimethylpropyl acetate (75.19 g, 231.93 mmol) in 1,4-dioxane (1.5 L) and H₂O (300 mL) was added K₂CO₃ (64.11 g, 463.85 mmol) and Pd(DtBPF)Cl₂ (15.12 g, 23.19 mmol). The reaction mixture was heated to 70° C. and stirred for 4 h. The reaction mixture was extracted with EtOAc (2×2 L) and the combined organic layers were washed with brine (3×600 mL), dried over Na₂SO₄, filtered, and concentrated under reduced pressure. The residue was purified by silica gel chromatography (20% EtOAc/pet. ether) to afford the desired product (130 g, crude). LCMS (ESI) m/z: [M+H] calcd for $C_{30}H_{38}N_2O_6$: 523.28; found 523.1.

Step 4: Synthesis of methyl (S)-3-(3-(3-(3-acetoxy-2,2-dimethylpropyl)-2-iodo-1H-indol-5-yl)phenyl)-2-((tert-butoxycarbonyl)amino)propanoate To a solution of methyl (2S)-3-(3-[3-[3-(acetyloxy)-2,2-dimethylpropyl]-1H-indol-5-yl]phenyl)-2-[(tert-butoxycarbonyl)amino]propanoate (95.0 g, 181.8 mmol) and iodine (36.91 g, 145.41 mmol) in THF (1 L) at −10° C. was added AgOTf (70.0 g, 272.7 mmol) and NaHCO₃ (22.9 g, 272.65 mmol). The reaction mixture was stirred for 30 min and was then quenched by the addition of sat. Na₂S₂O₃ (100 mL) at 0° C. The resulting mixture was extracted with EtOAc (3×1 L) and the combined organic layers were washed with brine (3×500 mL), dried over Na₂SO₄, filtered, and concentrated under reduced pressure. The residue was purified by silica gel chromatography (50% EtOAc/pet. ether) to afford the desired product (49.3 g, 41.8% yield). LCMS (ESI) m/z: [M+H] calcd for $C_{30}H_{37}IN_2O_6$: 649.18; found 649.1.

Step 5: Synthesis of (S)-2-((tert-butoxycarbonyl)amino)-3-(3-(3-(3-hydroxy-2,2-dimethylpropyl)-2-iodo-1H-indol-5-yl)phenyl)propanoic Acid To a solution of methyl (2S)-3-(3-[3-[3-(acetyloxy)-2,2-dimethylpropyl]-2-iodo-1H-indol-5-yl]phenyl)-2-[(tert-butoxycarbonyl)amino]propanoate (60 g, 92.5 mmol) in THF (600 mL) was added a solution of LiOH.H₂O (19.41 g, 462.5 mmol) in H₂O (460 mL). The resulting solution was stirred overnight and then the pH was adjusted to 6 with HCl (1 M). The resulting solution was extracted with EtOAc (2×500 mL) and the combined organic layers was washed with sat. brine (2×500 mL), dried over Na₂SO₄, filtered, and concentrated under reduced pressure to afford the desired product (45 g, 82.1% yield). LCMS (ESI) m/z: [M+Na] calcd for $C_{27}H_{33}IN_2O_5$: 615.13; found 615.1.

Step 6: Synthesis of methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate To a solution of (2S)-2-[(tert-butoxycarbonyl)amino]-3-[3-[3-(3-hydroxy-2,2-dimethylpropyl)-2-iodo-1H-indol-5-yl]phenyl]propanoic acid (30 g, 50.6 mmol) and methyl (3S)-1,2-diazinane-3-carboxylate (10.9 g, 75.9 mmol) in DCM (400 mL) was added NMM (40.97 g, 405.08 mmol), HOBT (2.05 g, 15.19 mmol), and EDCI (19.41 g, 101.27 mmol). The reaction mixture was stirred overnight and then the mixture was washed with sat. NH₄Cl (2×200 mL) and sat. brine (2×200 mL), and the mixture was dried over Na₂SO₄, filtered, and concentrated under reduced pressure to afford the desired product (14 g, 38.5% yield). LCMS (ESI) m/z: [M+H] calcd for $C_{33}H_{43}IN_4O_6$: 718.23; found 719.4.

Step 7: Synthesis of (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylic Acid To a solution of methyl (S)-1-((S)-2-((tert-butoxycarbonyl)amino)-3-(3-(3-(3-hydroxy-2,2-dimethylpropyl)-2-iodo-1H-indol-5-yl)phenyl)propanoyl)hexahydropyridazine-3-carboxylate (92 g, 128.0 mmol) in THF (920 mL) at 0° C. was added a solution of LiOH.H₂O (26.86 g, 640.10 mmol) in H₂O (640 mL). The reaction mixture was stirred for 2 h and was then concentrated under reduced pressure to afford the desired product (90 g, crude). LCMS (ESI) m/z: [M+H] calcd for $C_{32}H_{41}IN_4O_6$: 705.22; found 705.1).

Step 8: Synthesis of tert-butyl ((6³S,4S)-1²-iodo-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate To a solution of of (3S)-1-[(2S)-2-[(tert-butoxycarbonyl)amino]-3-[3-[3-(3-hydroxy-2,2-dimethylpropyl)-2-iodo-1H-indol-5-yl]phenyl]propanoyl]-1,2-diazinane-3-carboxylic acid (90 g, 127.73 mmol) in DCM (10 L) at 0° C. was added HOBt (34.52 g, 255.46 mmol), DIPEA (330.17 g, 2554.62 mmol) and EDCl (367.29 g, 1915.96 mmol). The reaction mixture was stirred for 16 h and was then concentrated under reduced pressure. The mixture was extracted with DCM (2×2 L) and the combined organic layers were washed with brine (3×1 L), dried over Na₂SO₄, filtered, and concentrated under reduced pressure. The residue was purified by silica gel chromatography (50% EtOAc/pet. ether) to afford the desired product (70 g, 79.8% yield). LCMS (ESI) m/z: [M+H] calcd for $C_{32}H_{39}IN_4O_5$: 687.21; found 687.1.

Step 9: Synthesis of tert-butyl ((6³S,4S)-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate To a solution of tert-butyl ((6³S,4S)-1²-iodo-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (22.0 g, 32.0 mmol) in toluene (300.0 mL) was added $Pd_2(dba)_3$ (3.52 g, 3.85 mmol), S-Phos (3.95 g, 9.61 mmol), and KOAc (9.43 g, 96.13 mmol) followed by 4,4,5,5-tetramethyl-1,3,2-dioxaborolane (26.66 g, 208.3 mmol), dropwise. The resulting solution was heated to 60° C. and stirred for 3 h. The reaction mixture was then cooled to room temperature, filtered, the filter cake was washed with EtOAc, and the filtrate was concentrated under reduced pressure. The residue was purified by normal phase chromatography to afford the desired product (22 g, 90% yield) as a solid. LCMS (ESI) m/z: [M+H] calcd for $C_{38}H_{51}BN_4O_7$: 687.39; found 687.3.

Step 10: Synthesis of tert-butyl ((6³S,4S)-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate To a mixture of tert-butyl ((6³S,4S)-10,10-dimethyl-5,7-dioxo-12-(4,4,5,5-tetramethyl-1,3,2-dioxaborolan-2-yl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) carbamate (3.0 g, 4.37 mmol) and 3-bromo-4-(methoxymethyl)pyridine (1.766 g, 8.74 mmol) in dioxane/$H_2O$ (5/1) at 60° C. was added $K_2CO_3$ (2.415 g, 17.48 mmol) and Pd(DTBPF)Cl₂ (0.5695 g, 0.874 mmol). The reaction mixture was stirred for 4 h. The reaction mixture was cooled to room temperature and was extracted with EtOAc (300 mL). The solution was washed with brine (3×100 mL), dried over $Na_2SO_4$, filtered, and concentrated under reduced pressure. The residue was purified by normal phase chromatography (50% EtOAc/pet. ether) to afford the desired product (1.96 g, 65.8% yield) as a solid. LCMS (ESI) m/z: [M+H] calcd for $C_{39}H_{47}N_5O_6$: 682.36; found 682.7.

Step 11: Synthesis of tert-butyl ((6³S,4S)-1¹-ethyl-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate To a solution of tert-butyl ((6³S,4S)-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (1.96 g, 2.88 mmol) and ethyl iodide (0.347 mL, 4.31 mmol) in DMF (20.0 mL) was added $Cs_2CO_3$ (2.342 g, 7.19 mmol). The resulting mixture was stirred at room temperature for 5 h and then diluted with EtOAc (200 mL). The mixture was washed with $H_2O$ (3×100 mL), dried over $Na_2SO_4$, filtered, and concentrated under reduced pressure. The residue was purified by normal phase chromatography (50% EtOAc/pet. ether) to afford the desired product (1.24 g, 61% yield) as a solid. LCMS (ESI) m/z: [M+H] calcd for $C_{41}H_{51}N_5O_6$: 710.39; found 710.7.

Step 12: Synthesis of (6³S,4S)-4-amino-1¹-ethyl-1²-(4-(methoxymethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione To a solution of tert-butyl ((6³S,4S)-1¹-ethyl-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) carbamate (1.09 g, 1.54 mmol) in DCM (1.5 mL) at 0° C. was added TFA (1.50 mL). The reaction mixture was stirred for 1 h, concentrated under reduced pressure, and then azeotroped with toluene (3×20 mL) to afford the desired crude product (1.09 g) as a solid. LCMS (ESI) m/z: [M+H] calcd for $C_{36}H_{43}N_5O_4$: 610.34; found 610.4.

Intermediate 9. Synthesis of tert-butyl ((6³S,4S)-1¹-ethyl-1²-(2-((S)-1-methoxyethyl) pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) carbamate

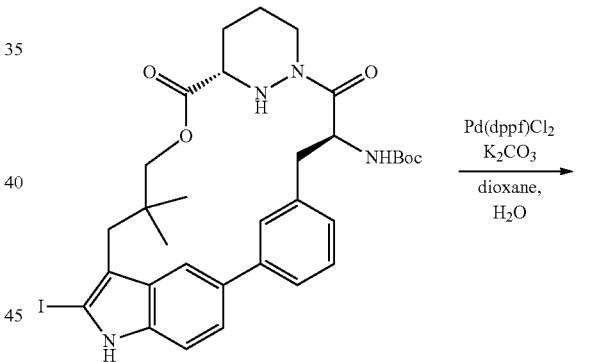

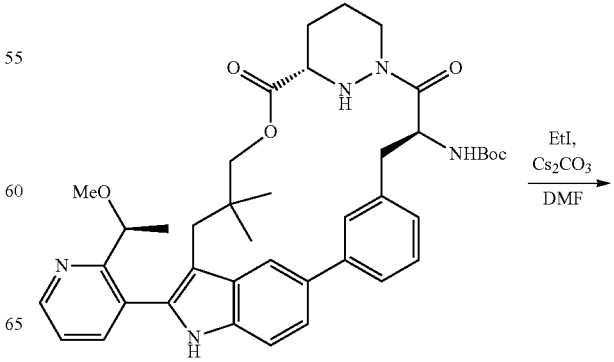

-continued

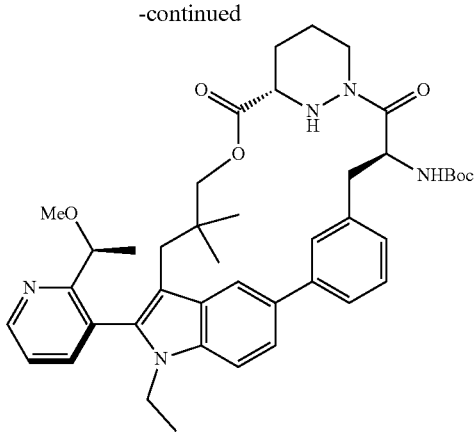

Step 1: Synthesis of tert-butyl (($6^3$S,4S)-$1^2$-(2-((S)-1-methoxyethyl) pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate To a solution of tert-butyl (($6^3$S,4S)-$1^2$-iodo-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (13 g, 18.93 mmol) and 2-[(1S)-1-methoxyethyl]-3-(4,4,5,5-tetramethyl-1,3,2-dioxaborolan-2-yl)pyridine (14.95 g, 56.8 mmol) in dioxane (130 mL) and $H_2O$ (26 mL) was added $K_2CO_3$ (5.23 g, 37.9 mmol) and Pd(dppf)$Cl_2$ (1.39 g, 1.89 mmol). The reaction mixture was stirred for 4 h at 70° C. The mixture was cooled to room temperature, filtered, and washed with EtOAc (3×100 mL). The filtrate was washed with brine (2×100 mL), dried over $Na_2SO_4$, filtered, and concentrated under reduced pressure. The residue was purified by prep-TLC (10% MeOH/DCM) to afford the desired product (21 g, 85.3% yield). LCMS (ESI) m/z: [M+H] calcd for $C_{40}H_{49}N_5O_6$: 696.38; found 696.4.

Step 2: Synthesis of tert-butyl (($6^3$S,4S)-$1^1$-ethyl-$1^2$-(2-((S)-1-methoxyethyl) pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate To a solution of tert-butyl (($6^3$S,4S)-$1^2$-(2-((S)-1-methoxyethyl) pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl) carbamate (20 g, 28.7 mmol) and $Cs_2CO_3$ (18.7 g, 57.5 mmol) in DMF (150 mL) at 0° C. was added a solution of ethyl iodide (13.45 g, 86.22 mmol) in DMF (50 mL). The resulting mixture was stirred overnight at 35° C. and was then diluted with $H_2O$ (500 mL). The mixture was extracted with EtOAc (2×300 mL) and the combined organic layers were washed with brine (3×100 mL), dried over $Na_2SO_4$, filtered, and concentrated under reduced pressure. The residue was purified by silica gel chromatography (10%→50% EtOAc/pet. ether) to afford the desired product (4.23 g, 18.8% yield) and the atropisomer (5.78 g, 25.7% yield). LCMS (ESI) m/z: [M+H] calcd for $C_{42}H_{53}N_5O_6$: 724.41; found 724.4.

Intermediate 10. Synthesis of (2S)—N-(($6^3$S,4S)-$1^1$-ethyl-$1^2$-(4-(methoxymethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-3-methyl-2-(methylamino)butanamide

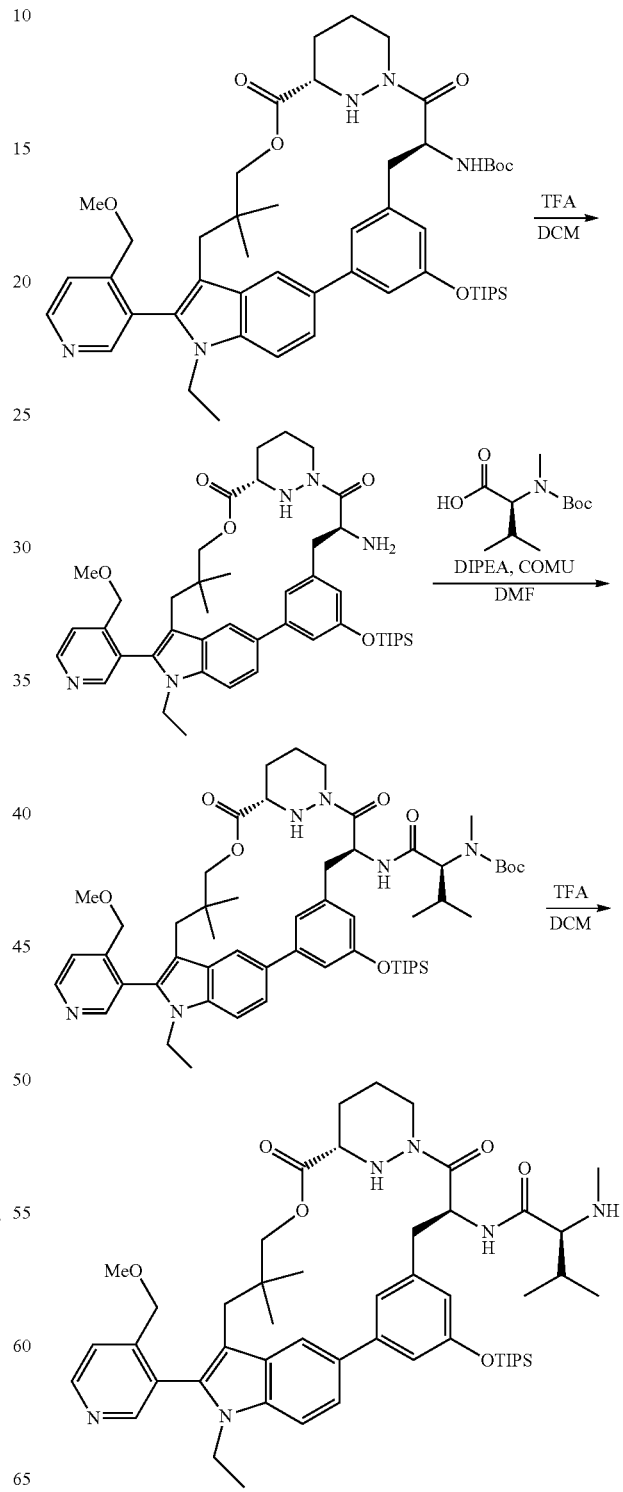

Step 1: Synthesis of (6³S,4S)-4-amino-1¹-ethyl-1²-(4-(methoxymethyl)pyridin-3-yl)-10,10-dimethyl-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione A mixture of tert-butyl ((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (880 mg, 1.2 mmol), DCM (10 mL), and TFA (5 mL) was stirred at 0° C. for 30 min. The mixture was concentrated under reduced pressure to afford the desired product, which was used directly in the next step without further purification. LCMS (ESI) m/z: [M+H] calcd for $C_{45}H_{63}N_5O_5Si$: 782.47; found 782.7.

Step 2: Synthesis of tert-butyl ((2S)-1-(((6³S,4S)-1¹-ethyl-1²-(4-(methoxymethyl)pyridin-3-yl)-10,10-dimethyl-5,7-dioxo-25-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate To a mixture of (6³S,4S)-4-amino-1¹-ethyl-1²-(4-(methoxymethyl)pyridin-3-yl)-10,10-dimethyl-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (880 mg, 1.13 mmol) and N-(tert-butoxycarbonyl)-N-methyl-L-valine (521 mg, 2.3 mmol) in DMF (8.8 mL) at 0° C. was added DIPEA (1.95 mL, 11.3 mmol) and COMU (88 mg, 0.21 mmol). The mixture was stirred at 0° C. for 30 min, then diluted with H₂O (100 mL) and extracted with EtOAc (3×100 mL). The combined organic layers were washed with brine (3×100 mL), dried over anhydrous Na₂SO₄, and filtered. The filtrate was concentrated under reduced pressure and the residue was purified by prep-TLC to afford the desired product (1 g, 89% yield) as a solid. LCMS (ESI) m/z: [M+H] calcd for $C_{56}H_{82}N_6O_8Si$: 995.61; found 995.5.

Step 3: Synthesis of (2S)—N-((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide A mixture of tert-butyl ((2S)-1-(((6³S,4S)-1¹-ethyl-1²-(4-(methoxymethyl)pyridin-3-yl)-10,10-dimethyl-5,7-dioxo-25-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate (1.0 g, 1.0 mmol), DCM (10 mL) and TFA (5 mL) was stirred for 30 min. The mixture was concentrated under reduced pressure and the residue was basified to pH ~8 with sat. NaHCO₃, then extracted with EtOAc (3×10 mL). The combined organic layers were washed with brine (3×10 mL), dried over Na₂SO₄, filtered, and the filtrate concentrated under reduced pressure to afford the desired product (880 mg, 98% yield) as a solid. LCMS (ESI) m/z: [M+H] calcd for $C_{51}H_{74}N_6O_6Si$: 895.55; found 895.5.

Intermediate 11. Synthesis of (2S)—N-((63S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(N-methyl-2-(methylamino)acetamido)butanamide

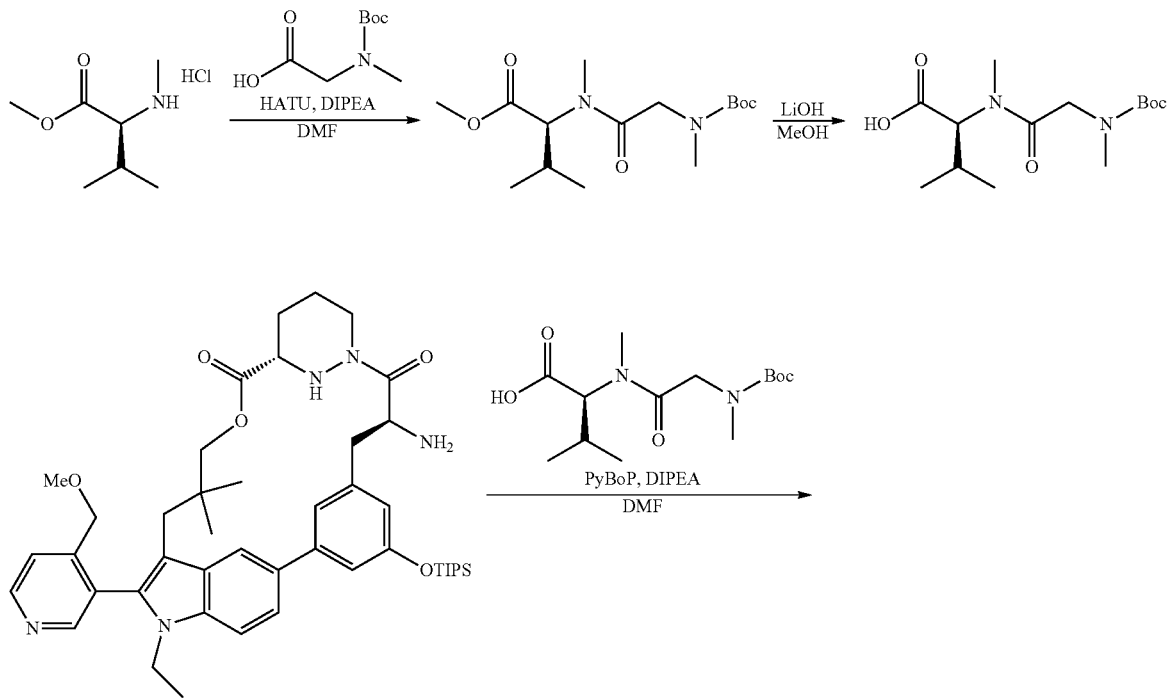

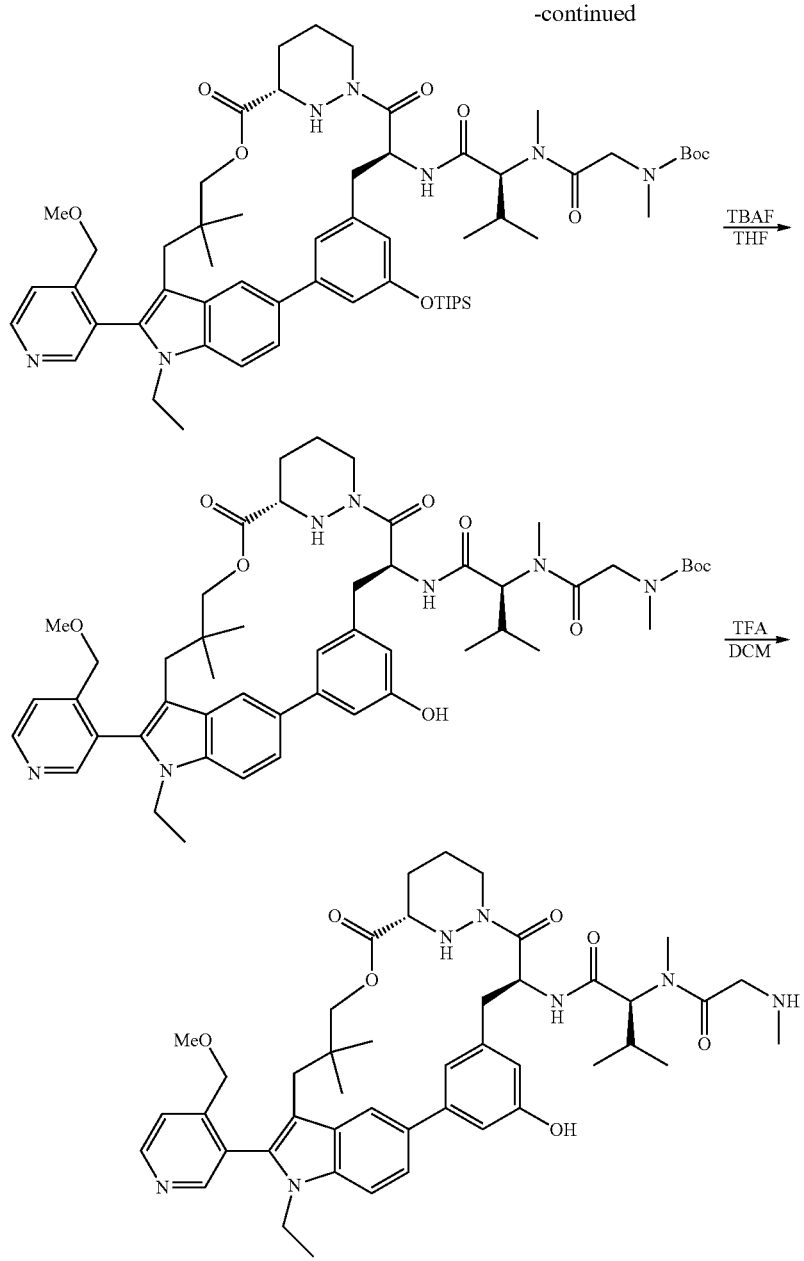

Step 1: Synthesis of methyl N—(N-(tert-butoxycarbonyl)-N-methylglycyl)-N-methyl-L-valinate To a solution of methyl methyl-L-valinate hydrochloride (2.0 g, 11.01 mmol) and N-(tert-butoxycarbonyl)-N-methylglycine (3.12 g, 16.51 mmol) in DMF (60.0 mL) at 0° C. was added DIPEA (9.58 mL, 55.01 mmol) and HATU (8.37 g, 22.02 mmol). The reaction mixture was stirred overnight and was then quenched with $H_2O$ (100 mL). The mixture was extracted with EtOAc (3×100 mL) and the combined organic layers were washed with brine (100 mL), dried over $Na_2SO_4$, and concentrated under reduced pressure. The residue was purified by reverse phase chromatography (40→60% MeCN/$H_2O$) to afford the desired product (2.9 g, 83% yield) as an oil. LCMS (ESI) m/z: [M+H] calcd for $C_{15}H_{28}N_2O_5$: 317.21; found 317.4.

Step 2: Synthesis of N—(N-(tert-butoxycarbonyl)-N-methylglycyl)-N-methyl-L-valine To a solution of methyl N—(N-(tert-butoxycarbonyl)-N-methylglycyl)-N-methyl-L-valinate (3.70 g, 11.69 mmol) in THF (37.0 mL) was added a solution of $LiOH.H_2O$ (1.96 g, 46.71 mmol) in $H_2O$ (47.0 mL). The reaction mixture was stirred for 4 h, and then 1M HCl was added until the pH was adjusted to 5. The resulting solution was extracted with EtOAc (3×100 mL) and the combined organic layers were washed with brine (3×50 mL), dried over $Na_2SO_4$, and concentrated under reduced pressure. The residue was purified by reverse phase chromatography (60→60% MeCN/$H_2O$) to afford the desired product (1.47 g, 41.6% yield) as a solid. LCMS (ESI) m/z: [M+H] calcd for $C_{14}H_{26}N_2O_5$: 303.19; found 303.4.

Step 3: Synthesis of tert-butyl (2-(((2S)-1-(((6³S, 4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate To a solution of (6³S,4S)-4-amino-1¹-ethyl-1²-(4-(methoxymethyl)pyridin-3-yl)-10,10-dimethyl-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (300.0 mg, 0.384 mmol) and N—(N-(tert-butoxycarbonyl)-N-methylglycyl)-N-methyl-L-valine (173.9 mg, 0.575 mmol) in DMF (3.0 mL) at 0° C. was added DIPEA (0.534 mL, 3.069 mmol) and PyBOP (399.2 mg, 0.767 mmol). The reaction mixture was stirred for 2 h and was then diluted with H₂O (30 mL). The resulting mixture was extracted with EtOAc (3×20 mL) and the combined organic layers were washed with brine (3×20 mL), dried over Na₂SO₄, filtered, and concentrated under reduced pressure. The residue was purified by normal phase chromatography (25% EtOAc/pet. ether) to afford the desired product (300 mg, 73% yield) as a solid. LCMS (ESI) m/z: [M+H] calcd for C₅₉H₈₇N₇O₉Si: 1066.64; found 1067.4.

Step 4: Synthesis of tert-butyl (2-(((2S)-1-(((6³S, 4S)-1¹-ethyl-2⁵-hydroxy-1²-(4-(methoxymethyl)pyridin-3-yl)-10,10-dimethyl-5,7-dioxo-6¹,6²,6³,6⁴, 6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate To a solution of tert-butyl (2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate (355.0 mg) in THF (4.0 mL) at 0° C. was added TBAF (1.0 mL). The reaction mixture was stirred for 1 h and was then concentrated under reduced pressure. The residue was purified by normal phase chromatography (25% EtOAc/pet. ether) to afford the desired product (280 mg, 92% yield) as a solid. LCMS (ESI) m/z: [M+H] calcd for $C_{50}O_{67}N_7O_9$: 910.51; found 911.0.

Step 5: Synthesis of (2S)—N-((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(N-methyl-2-(methylamino)acetamido)butanamide To a solution of tert-butyl (2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate (150.0 mg, 0.165 mmol) in DCM (2.0 mL) at 0° C. was added TFA (0.70 mL). The reaction mixture was stirred for 1 h and was then concentrated under reduced pressure to afford the desired crude product (150 mg) as a solid. LCMS (ESI) m/z: [M+H] calcd for C₄₅H₅₉N₇O₇: 810.46; found 810.4.

Intermediate 12. Synthesis of (3S)—N-((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide

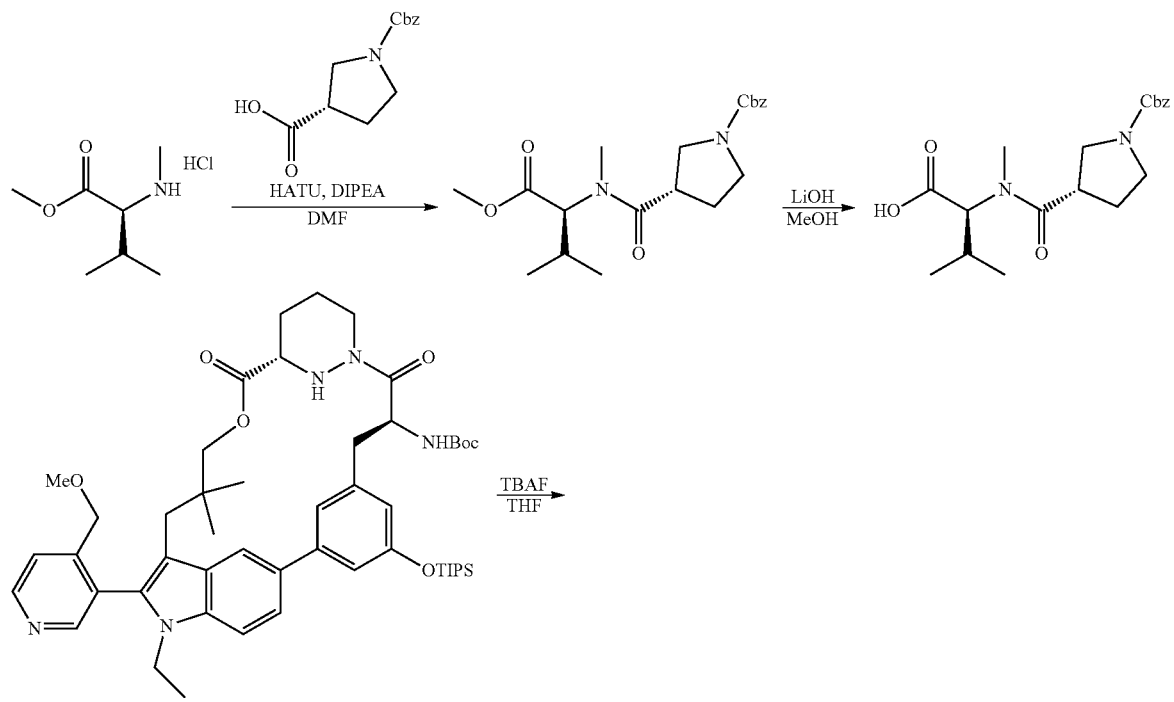

-continued
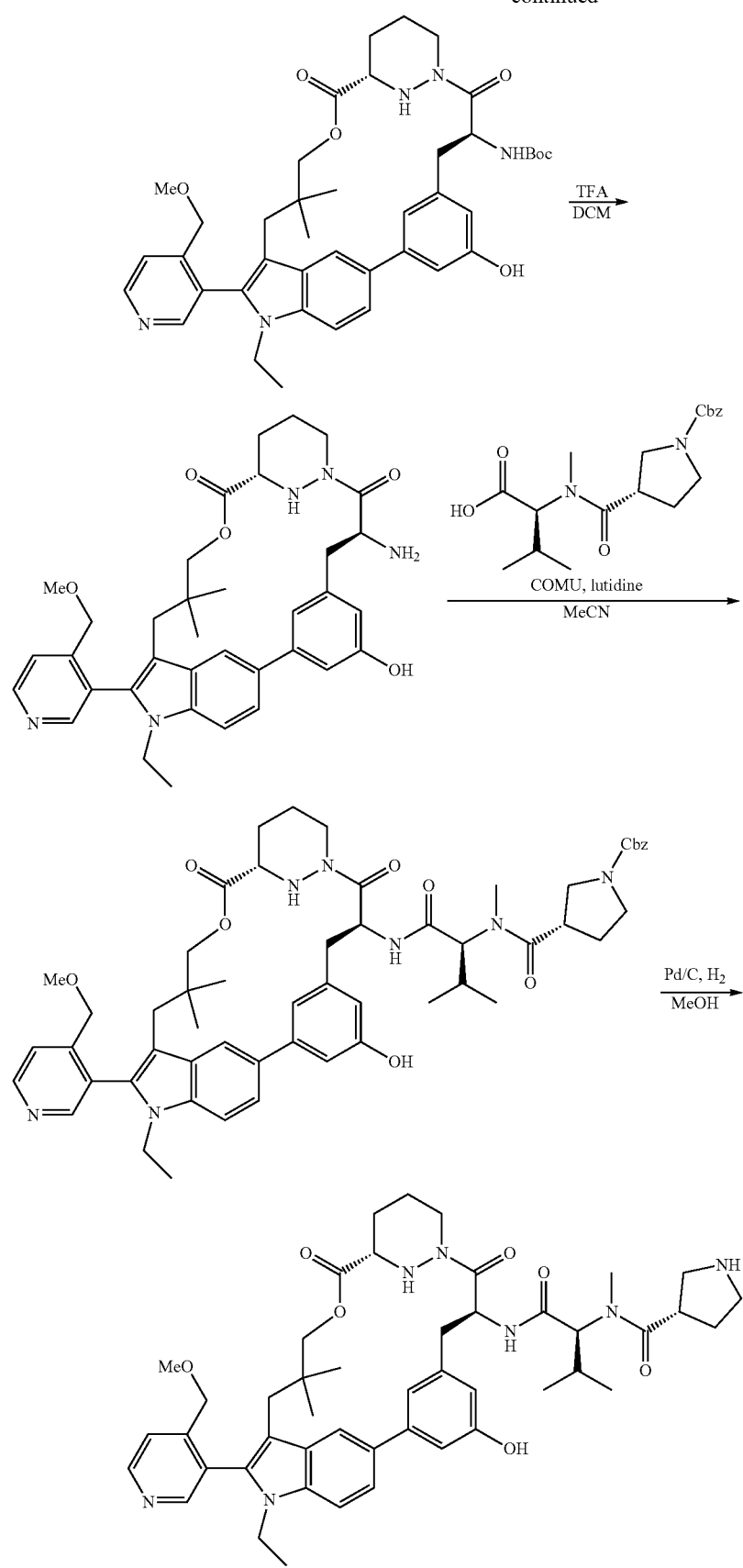

Step 1: Synthesis of benzyl (S)-3-(((S)-1-methoxy-3-methyl-1-oxobutan-2-yl)(methyl)carbamoyl)pyrrolidine-1-carboxylate To a solution of methyl methyl-L-valinate hydrochloride (2.0 g, 13.8 mmol) and (S)-1-((benzyloxy)carbonyl)pyrrolidine-3-carboxylic acid (4.12 mg, 16.5 mmol) in DMF (20.0 mL) at 0° C. was added DIPEA (12 mL, 68.870 mmol). The reaction mixture was stirred for 0.5 h, and then HATU (7.856 mg, 20.66 mmol) was added. The resulting mixture was warmed to room temperature and stirred for 1 h. The reaction mixture was then diluted with EtOAc (800 mL) and was washed with sat. $NH_4Cl$ (500 mL) and brine (3×350 mL). The combined organic layers were dried over $Na_2SO_4$, filtered, and concentrated under reduced pressure. The residue was purified by normal phase chromatography (0→80% EtOAc/pet. ether) to afford the desired product (3.8 g, 73% yield) as an oil. LCMS (ESI) m/z: [M+H] calcd for $C_{20}H_{28}N_2O_5$: 377.21; found 377.2.

Step 2: Synthesis of N—((S)-1-((benzyloxy)carbonyl)pyrrolidine-3-carbonyl)-N-methyl-L-valine To a solution of benzyl (S)-3-(((S)-1-methoxy-3-methyl-1-oxobutan-2-yl)(methyl)carbamoyl)pyrrolidine-1-carboxylate (1.125 g, 2.99 mmol) in MeOH (10.0 mL) was added a solution of LiOH (180.0 mg, 7.52 mmol) in $H_2O$ (2 mL). The reaction mixture was stirred for 4 h and was then quenched with sat. aq. $NH_4Cl$. The mixture with extracted with EtOAc (3×60 mL) and the combined organic layers were concentrated under reduced pressure to afford the desired product. LCMS (ESI) m/z: [M+H] calcd for $C_{19}H_{26}N_2O_5$: 363.19; found 363.2.

Step 3: Synthesis of tert-butyl (($6^3$S,4S)-$1^1$-ethyl-$2^5$-hydroxy-$1^2$-(4-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a solution of tert-butyl (($6^3$S,4S)-$1^1$-ethyl-$1^2$-(4-(methoxymethyl)pyridin-3-yl)-10,10-dimethyl-5,7-dioxo-$2^5$-(((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (1.70 g, 1.93 mmol) in THF (20 mL) at 0° C. was added TBAF (755.7 mg, 2.89 mmol). The reaction mixture was stirred for 2 h and was then quenched with $H_2O$ (200 mL). The resulting mixture was extracted with EtOAc (3×200 mL) and the combined organic layers were washed with brine (3×200 mL), dried over $Na_2SO_4$, filtered, and concentrated under reduced pressure. The residue was purified by normal phase chromatography (17% EtOAc/pet. ether) to afford the desired product (1.1 g, 70% yield) as a solid. LCMS (ESI) m/z: [M+H] calcd for $C_{41}H_{51}N_5O_7$: 726.39; found 726.7.

Step 4: Synthesis of (($6^3$S,4S)-4-amino-$1^1$-ethyl-$2^5$-hydroxy-$1^2$-(4-(methoxymethyl)pyridin-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione To a solution of tert-butyl (($6^3$S,4S)-$1^1$-ethyl-$2^5$-hydroxy-$1^2$-(4-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (500.0 mg, 0.689 mmol) in DCM (10.0 mL) at 0° C. was added TFA (0.527 mL, 6.888 mmol). The resulting mixture was stirred for 1 h and then was concentrated under reduced pressure to afford the desired crude product (500 mg) as a solid. LCMS (ESI) m/z: [M+H] calcd for $C_{36}H_{43}N_5O_5$: 626.34; found 626.4.

Step 5: Synthesis of benzyl (3S)-3-(((2S)-1-((($6^3$S,4S)-$1^1$-ethyl-$2^5$-hydroxy-$1^2$-(4-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)pyrrolidine-1-carboxylate To a solution of N—((S)-1-((benzyloxy)carbonyl)pyrrolidine-3-carbonyl)-N-methyl-L-valine (676.4 mg, 6.31 mmol) in MeCN (10.0 mL) at 0° C. was added COMU (432.5 mg, 1.01 mmol). The reaction mixture was stirred for 5 min followed by the addition of ($6^3$S,4S)-4-amino-$1^1$-ethyl-$2^5$-hydroxy-$1^2$-(4-(methoxymethyl)pyridin-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione (395.0 mg, 0.631 mmol). The reaction mixture was warmed to room temperature and stirred for 20 h. The mixture was then concentrated under reduced pressure, taken up in EtOAc (100 mL), and washed with brine (3×5 mL). The organic layer was dried over $Na_2SO_4$, filtered, and concentrated under reduced pressure. The residue was purified by normal phase chromatography to afford a crude solid (0.81 g), which was then purified by reversed phase chromatography (MeCN/$H_2O$) to afford the desired product (174 mg, 29% yield) as a solid. LCMS (ESI) m/z: [M+H] calcd for $C_{55}H_{67}N_7O_9$: 970.51; found 970.8.

Step 6: Synthesis of (3S)—N-((2S)-1-((($6^3$S,4S)-$1^1$-ethyl-$2^5$-hydroxy-$1^2$-(4-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide To a solution of benzyl (3S)-3-(((2S)-1-((($6^3$S,4S)-$1^1$-ethyl-$2^5$-hydroxy-$1^2$-(4-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)pyrrolidine-1-carboxylate (174.0 mg, 0.179 mmol) in MeOH (20.0 mL) was added Pd/C (87.0 mg, 0.08 mmol) followed by 2% aq. HCl (one drop). The reaction mixture was stirred at room temperature under a $H_2$ atmosphere (1 atm) for 14 h, at which point the reaction mixture was purged with $N_2$, filtered, and concentrated under reduced pressure to afford the crude product (130 mg, 86.7% yield) as a solid. LCMS (ESI) m/z: [M+H] calcd for $C_{47}H_{61}N_7O_7$: 836.47; found 836.5.

Intermediate 13. Synthesis of (2S)-2-(3-amino-N-methylpropanamido)-N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide
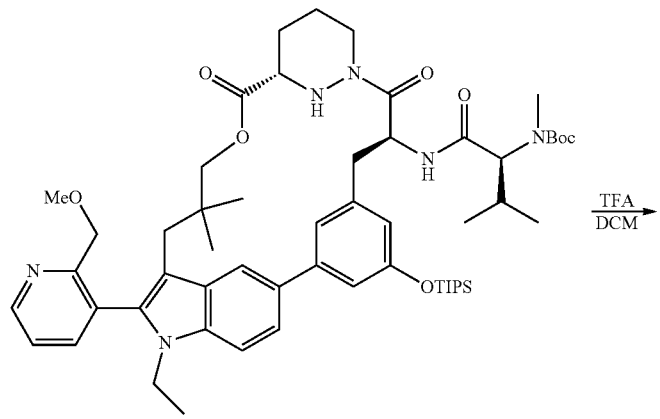
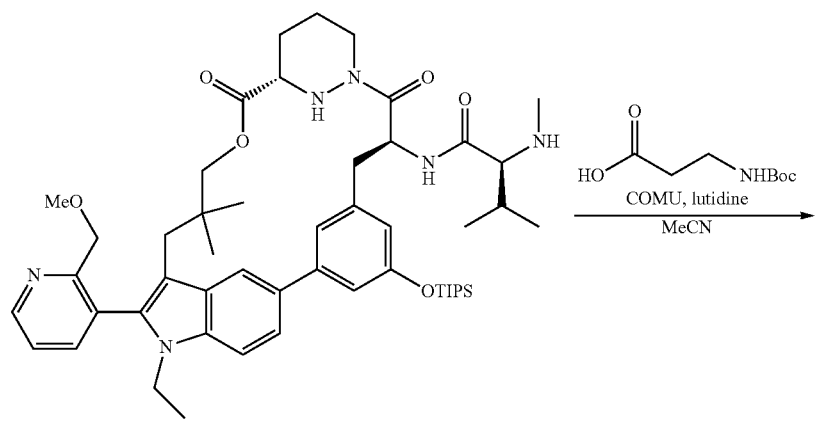
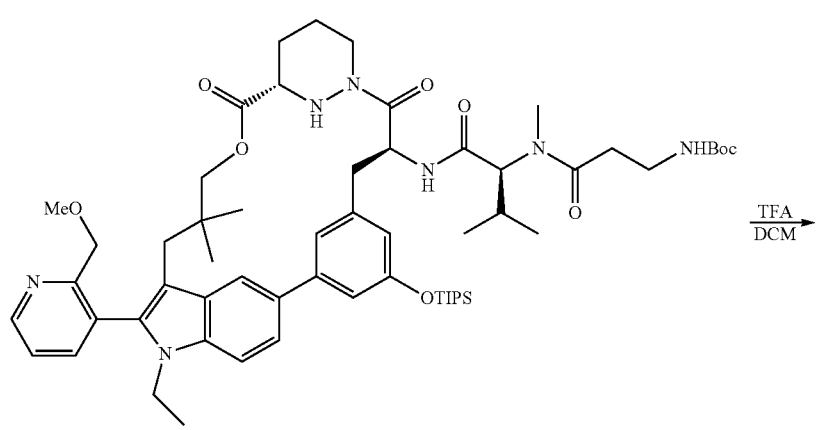

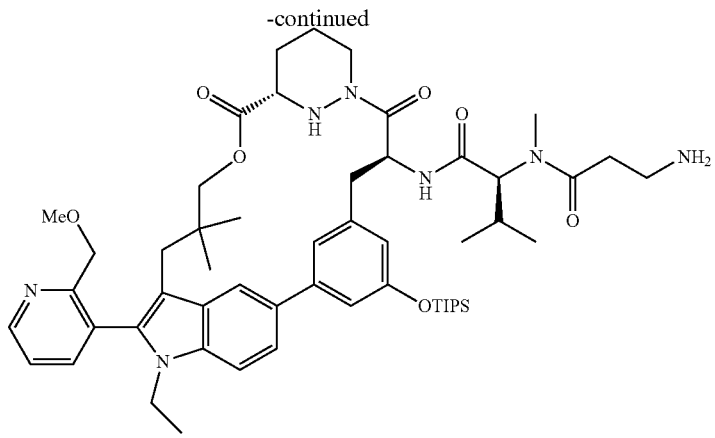

Step 1: Synthesis of (2S)—N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide To a solution of tert-butyl ((2S)-1-(((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate (212.4 mg, 212 µmol) in DCM (500 µL) at 0° C. was added TFA (500 µL, 6.52 mmol). After 2 h, the reaction was diluted with DCM (10 mL) and H₂O (10 mL), and then sat. aq. NaHCO₃ was added until the solution was pH 9. The aqueous layer was extracted with DCM (10 mL) and the combined organic layers were dried over Na₂SO₄, filtered, and concentrated under reduced pressure to afford the crude product (194 mg, 103% yield). LCMS (ESI) m/z: [M+H] calcd for C₅₁H₇₄N₆O₆Si: 895.55; found 895.7.

Step 2: Synthesis of tert-butyl (3-(((2S)-1-(((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-3-oxopropyl)carbamate To a mixture of (2S)—N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide (150 mg, 167 µmol), COMU (88.5 mg, 206 µmol), and 3-((tert-butoxycarbonyl)amino)propanoic acid (39.6 mg, 209 µmol) in MeCN (1.66 mL) was added 2,6-lutidine (77.7 µL, 668 µmol). The reaction was stirred for 18 h at room temperature and then for 1 h at 55° C. The reaction mixture was cooled to room temperature and was concentrated under reduced pressure. The crude residue was purified by reverse phase chromatography (20→60% MeCN/H₂O) to afford the product (132 mg, 67% yield). LCMS (ESI) m/z: [M+H] calcd for C₅₉H₈₇N₇O₉Si: 1066.64; found 1066.7.

Step 3: Synthesis of (2S)-2-(3-amino-N-methylpropanamido)-N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of tert-butyl (3-(((2S)-1-(((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-3-oxopropyl)carbamate (120 mg, 112 µmol) in DCM (560 µL) at 0° C. was added TFA (560 µL, 7.30 mmol). After 40 min, the reaction was diluted with DCM (10 mL) and then sat. aq. NaHCO₃ was added. The organic layer was dried over Na₂SO₄, filtered, and then concentrated under reduced pressure to afford the product (106 mg, 98% yield), which was used in the next step without purification. LCMS (ESI) m/z: [M+H] calcd for C₅₄H₇₉N₇O₇Si: 966.59; found 966.8.

Intermediate 14. Synthesis of (2S)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(methylamino)acetamide

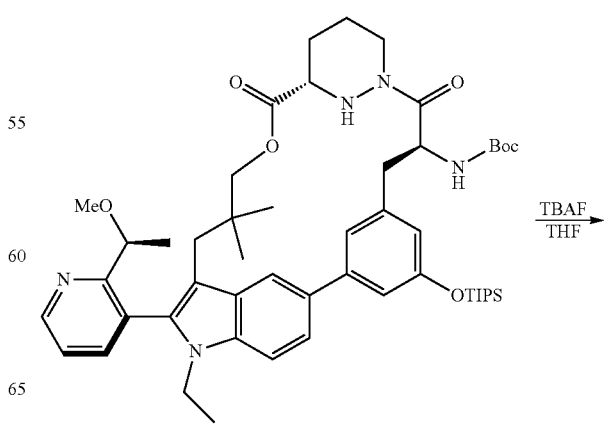

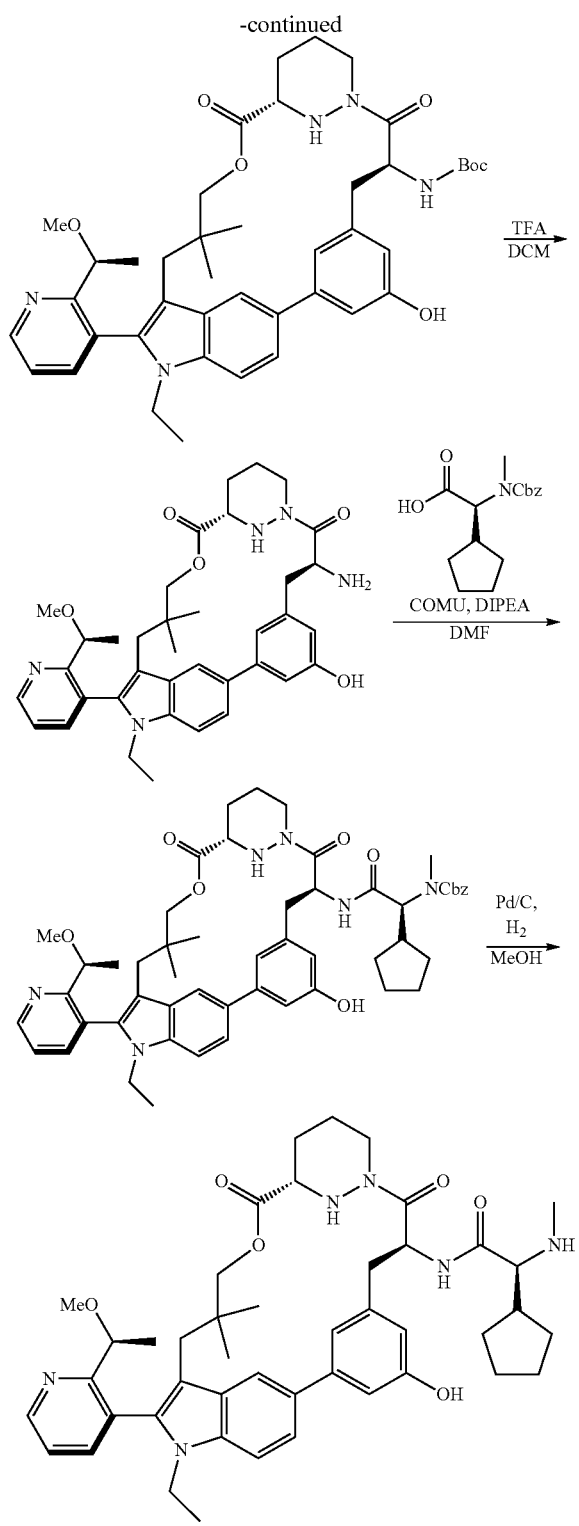

Step 1: Synthesis of tert-butyl (($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2 (1,3)- benzenacycloundecaphane-4-yl)carbamate To a stirred solution of tert-butyl (($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (18.0 g, 20.1 mmol) in THF (180 mL) at 0° C. was added a 1M solution of TBAF in THF (24.1 mL, 24.1 mmol). The mixture was stirred at 0° C. for 1 h, then diluted with brine (1.5 L), and extracted with EtOAc (3×1 L). The combined organic layers were washed with brine (2×500 mL), dried over anhydrous $Na_2SO_4$, filtered, and concentrated under reduced pressure. Purification by normal phase chromatography afforded the desired product (11.5 g, 69% yield). LCMS (ESI) m/z: [M+H] calcd for $C_{42}H_{53}N_5O_7$: 740.40; found 740.4.

Step 2: Synthesis of ($6^3$S,4S)-4-amino-$1^1$-ethyl-$2^5$-hydroxy-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione To a stirred solution of tert-butyl (($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1 (5,3)-indola-6(1,3)-pyridazina-2(1,3)-benzenacycloundecaphane-4-yl)carbamate (11.5 g, 15.5 mmol) in DCM (120 mL) at 0° C. was added TFA (60 mL, 808 mmol). The mixture was stirred at 0° C. for 1 h, then concentrated under reduced pressure and the residue again concentrated under reduced pressure with toluene (3×20 mL) to afford the desired crude product (12 g). LCMS (ESI) m/z: [M+H] calcd for $C_{37}H_{45}N_5O_5$: 640.35; found 640.6.

Step 3: Synthesis of benzyl ((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)(methyl)carbamate To a stirred solution of ($6^3$S,4S)-4-amino-$1^1$-ethyl-$2^5$-hydroxy-$1^2$-(2-((S)-1-methoxyethyl)pyridin-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione (400.0 mg, 0.63 mmol) in DMF (4.0 mL) at 0° C. was added DIPEA (1.09 mL, 6.25 mmol) and (S)-2-(((benzyloxy)carbonyl)(methyl)amino)-2-cyclopentylacetic acid (255.0 mg, 0.88 mmol) followed by COMU (347.8 mg, 0.81 mmol). The resulting mixture was stirred at 0° C. for 1 h and was then diluted with $H_2O$ (40 mL). The aqueous layer was extracted with EtOAc (3×15 mL) and the combined organic layers were washed with brine (2×10 mL), dried over $Na_2SO_4$, filtered, and concentrated under reduced pressure. The residue was purified by prep-TLC (25% EtOAc/pet. ether) to afford the desired product (510 mg, 80% yield). LCMS (ESI) m/z: [M+H] calcd for $C_{53}H_{64}N_6O_8$: 913.49; found 913.6.

Step 4: Synthesis of (2S)-2-cyclopentyl-N-(($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-2-(methylamino)acetamide To a stirred solution of benzyl ((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)

(methyl)carbamate (480.0 mg, 0.53 mmol), in MeOH (25 mL) was added Pd/C (200.0 mg, 1.88 mmol). The resulting mixture was placed under an atmosphere of $H_2$ (1 atm) and stirred for 2 h. The mixture was filtered, the filter cake was washed with MeOH (3×10 mL), and the filtrate was concentrated under reduced pressure to afford the desired crude product (440 mg). LCMS (ESI) m/z: [M+H] calcd for $C_{45}H_{58}N_6O_6$: 779.45; found 779.4.

Intermediate 15. Synthesis of (2S)—N-((6$^3$S,4S)-1$^1$-ethyl-2$^5$-hydroxy-1$^2$-(4-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)-3-methyl-2-(N-methyl-3-(methylamino)propanamido)butanamide

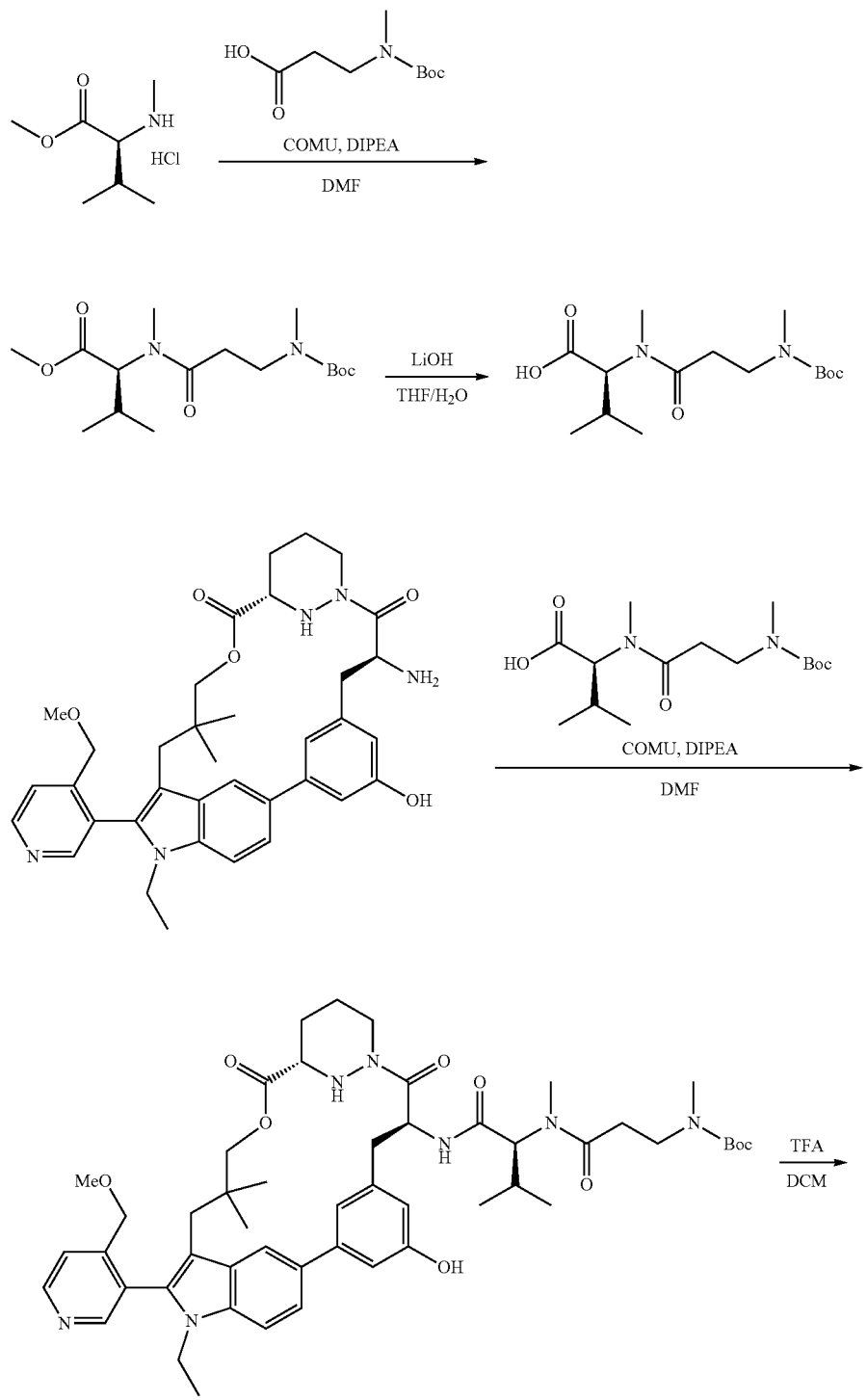

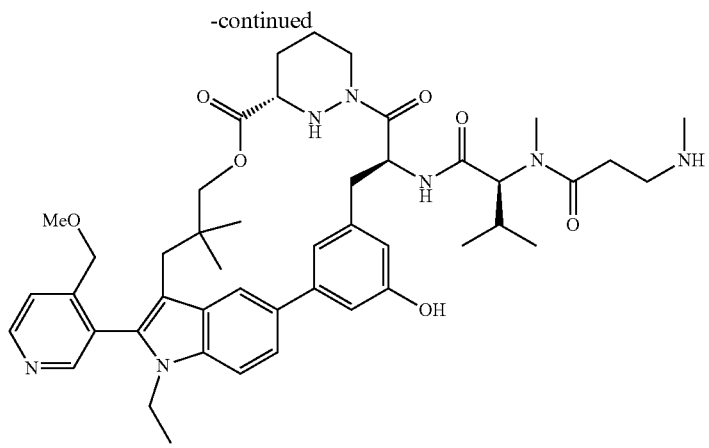

Step 1: Synthesis of Methyl N-(3-((tert-butoxycarbonyl)(methyl)amino)propanoyl)-N-methyl-L-valinate To a solution of methyl methyl-L-valinate hydrochloride (1.0 g, 6.89 mmol) in DMF (20.0 mL) at 0° C. was added DIPEA (5.92 mL, 0.034 mmol), 3-((tert-butoxycarbonyl)(methyl)amino)propanoic acid (2.10 g, 0.010 mmol), and COMU (3.54 g, 8.27 mmol). The resulting mixture was stirred for 30 min and then quenched with $H_2O$ (20 mL). The aqueous layer was extracted with EtOAc (3×20 mL) and the combined organic layers were washed with brine (3×20 mL), dried over $Na_2SO_4$, filtered, and concentrated under reduced pressure. The residue was purified by reverse phase chromatography (0-100% MeCN/$H_2O$) to afford the desired product (2 g, 87.9% yield). LCMS (ESI) m/z: [M+H] calcd for $C_{16}H_{30}N_2O_5$: 331.22; found 331.2.

Step 2: Synthesis of N-(3-((tert-butoxycarbonyl)(methyl)amino)propanoyl)-N-methyl-L-valine To a solution of N-(3-((tert-butoxycarbonyl)(methyl)amino)propanoyl)-N-methyl-L-valinate (1.0 g, 3.03 mmol) in THF (20.0 mL) and $H_2O$ (4.0 mL) was added LiOH (0.14 g, 6.05 mmol). The resulting mixture was stirred for 3 h at room temperature. The mixture was acidified to pH 3 with HCl (1N) and was then extracted with EtOAc (3×20 mL). The combined organic layers were washed with brine (3×20 mL), dried over $Na_2SO_4$, filtered, and concentrated under reduced pressure to afford the desired crude product (800 mg, 83.6% yield). LCMS (ESI) m/z: [M+H] calcd for $C_{15}H_{28}N_2O_5$: 317.21; found 317.2.

Step 3: Synthesis of tert-butyl (3-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-3-oxopropyl)(methyl)carbamate To a solution of (6³S,4S)-4-amino-1¹-ethyl-2⁵-hydroxy-1²-(4-(methoxymethyl)pyridin-3-yl)-10,10-dimethyl-6¹,6², 6³,6⁴,6⁵,6⁶-hexahydro-1¹H-8-oxa-1(5,3)-indola-6(1,3)-pyridazina-2(1,3)-benzenacycloundecaphane-5,7-dione (600.0 mg, 0.96 mmol) in DMF (6.0 mL) at 0° C. was added DIPEA (1.67 mL, 9.59 mmol), N-(3-((tert-butoxycarbonyl)(methyl)amino)propanoyl)-N-methyl-L-valine (455.1 mg, 1.44 mmol), and COMU (492.5 mg, 1.15 mmol). The resulting mixture was stirred for 30 min and was then quenched with $H_2O$ (60 mL). The aqueous layer was extracted with EtOAc (3×60 mL) and the combined organic layers were washed with brine (3×60 mL), dried over $Na_2SO_4$, filtered, and concentrated under reduced pressure. The residue was purified by reverse phase chromatography (0→100% MeCN/$H_2O$) to afford the desired product (650 mg, 73.4% yield). LCMS (ESI) m/z: [M+H] calcd for $C_{51}H_{69}N_7O_9$: 924.52; found 924.6.

Step 4: Synthesis of (2S)—N-((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(N-methyl-3-(methylamino)propanamido)butanamide To a solution of tert-butyl (3-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-3-oxopropyl)(methyl)carbamate (650.0 mg) in DCM (7.0 mL) at 0° C. was added TFA (3.5 mL). The resulting mixture was stirred for 30 min and was then concentrated under reduced pressure. The resulting residue was diluted with toluene (3×10 mL) and concentrated under reduced pressure to afford the desired crude product. LCMS (ESI) m/z: [M+H] calcd for $C_{46}H_{61}N_7O_7$: 824.47; found 824.6.

Intermediate 16. Synthesis of (2S)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(N-methyl-2-(methylamino)acetamido)acetamide
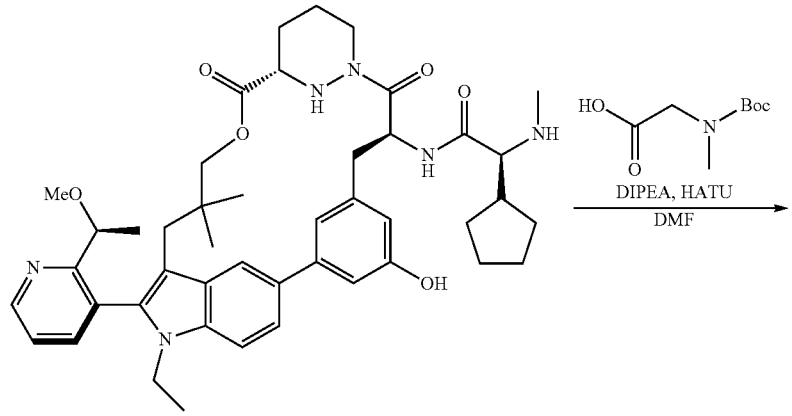
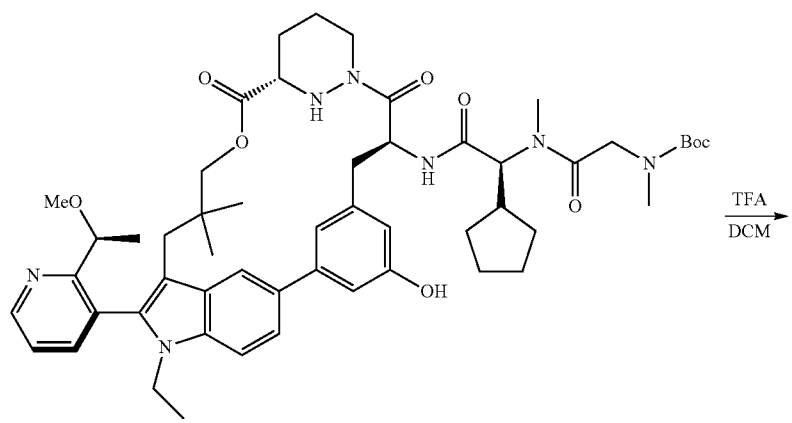
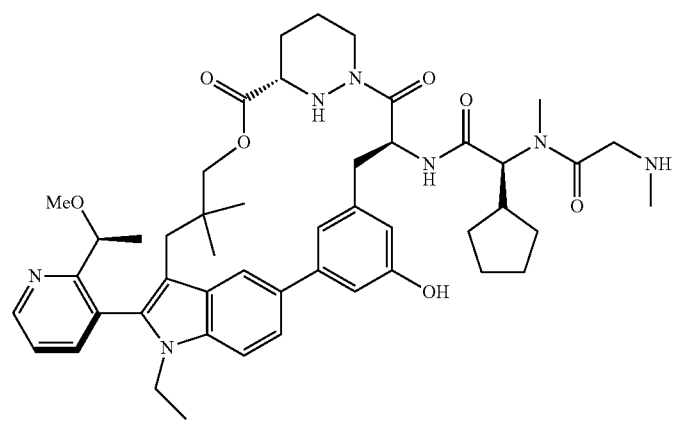 [SMILES: CCn1c(-c2cnccc2COC)c2c3cc(ccc31)-c1cc(O)cc(c1)C[C@H](NC(=O)[C@H](C(C)C)N(C)C(=O)CNC)C(=O)N1CCC[C@H](N1)C(=O)OCC(C)(C)C2]

Step 1: Synthesis of tert-butyl (2-(((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)(methyl)amino)-2-oxoethyl)(methyl)carbamate To a mixture of (2S)-2-cyclopentyl-N-(($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-2-(methylamino)acetamide (300.0 mg, 0.385 mmol), DIPEA (0.657 mL, 3.851 mmol), and N-(tert-butoxycarbonyl)-N-methylglycine (109.30 mg, 0.578) in DMF (3.0 mL) at 0° C. was added HATU (175.72 mg, 0.462 mmol). The resulting mixture was stirred at 0° C. for 30 min and was then diluted with H₂O (30 mL). The resulting mixture was extracted with EtOAc (3×30 mL). The combined organic layers were washed with brine (3×30 mL), dried with Na₂SO₄, filtered, and concentrated under reduced pressure. Purification by prep-TLC (50% EtOAc/pet. ether) to afford the desired product (300 mg, 82.0% yield). LCMS (ESI) m/z: [M+H] calcd for $C_{53}H_{71}N_7O_9$: 950.54; found 950.4.

Step 2: Synthesis of (2S)-2-cyclopentyl-N-(($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-2-(N-methyl-2-(methylamino)acetamido)acetamide To a mixture of tert-butyl (2-(((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)(methyl)amino)-2-oxoethyl)(methyl)carbamate (300.0 mg, 0.316 mmol) in DCM (3.0 mL) at 0° C. was added TFA (1.50 mL). The resulting mixture was stirred at 0° C. for 30 min and was then concentrated under reduced pressure to afford the desired crude product. LCMS (ESI) m/z: [M+H] calcd for $C_{48}H_{63}N_7O_7$: 850.49; found 850.5.

Intermediate 17. Synthesis of (2R,5R)—N-((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N,5-dimethylpyrrolidine-2-carboxamide

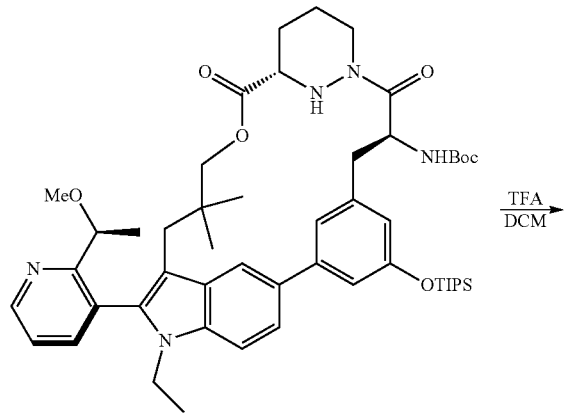

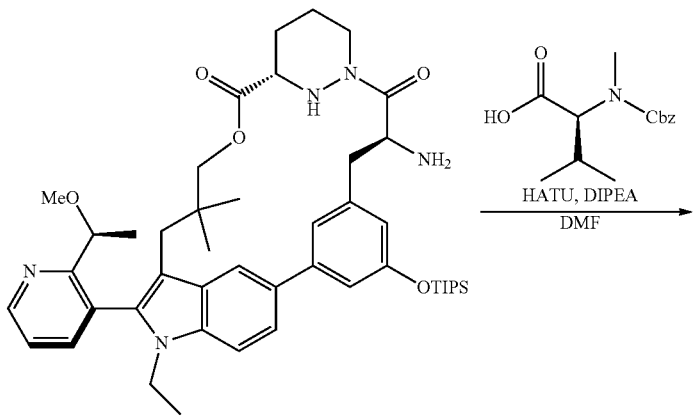

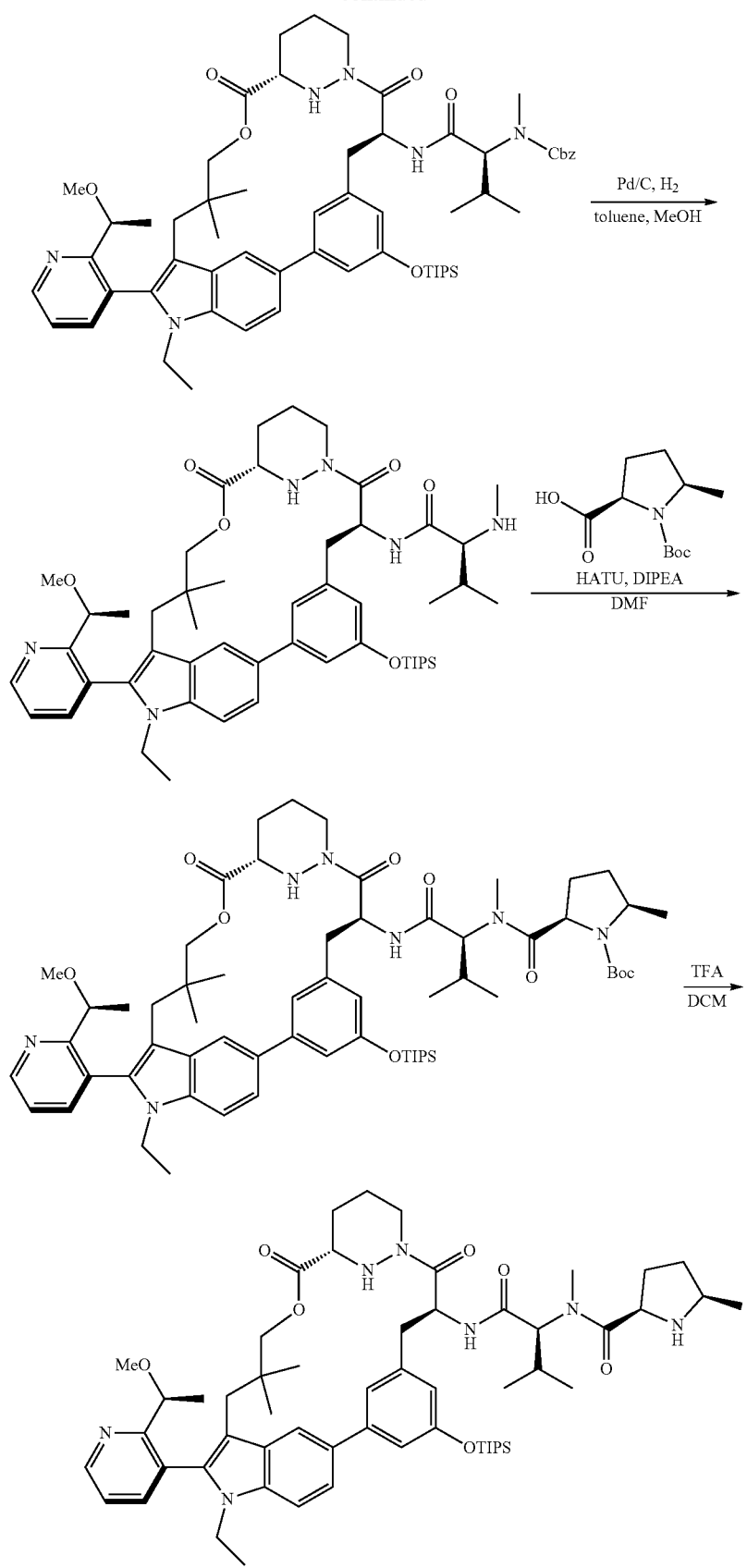

Step 1: Synthesis of (6³S,4S)-4-amino-1¹-ethyl-1²-(2-((S)-1-methoxyethyl)pyridin-3-yl)-10,10-dimethyl-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione To a solution of tert-butyl ((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (20.0 g, 22.315 mmol) in DCM (150.0 mL) at 0° C. was added TFA (50.0 mL). The resulting mixture was warmed to room temperature and stirred for 2 h and then concentrated under reduced pressure. The residue was dissolved in EtOAc (100 mL) and the solution was neutralized to pH 8 with sat. aq. NaHCO₃. The solution was extracted with EtOAc (3×150 mL) and the combined organic layers were washed with brine (100 mL), dried over Na₂SO₄, filtered, and concentrated under reduced pressure to afford the desired product (17.86 g, crude). LCMS (ESI) m/z: [M+H] calcd for $C_{46}H_{65}N_5O_5Si$: 796.49; found 795.5.

Step 2: Synthesis of benzyl ((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate To a solution of (6³S,4S)-4-amino-1¹-ethyl-1²-(2-((S)-1-methoxyethyl)pyridin-3-yl)-10,10-dimethyl-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (17.86 g, 22.433 mmol) and (2S)-2-[[(benzyloxy)carbonyl](methyl)amino]-3-methylbutanoic acid (8.93 g, 33.65 mmol) in DMF (150.0 mL) at 0° C. was added DIPEA (19.5 mL, 112.17 mmol) and HATU (17.06 g, 44.87 mmol). The resulting mixture was warmed to room temperature and stirred for 2 h. The reaction mixture was cooled to 0° C. and was quenched by the addition of H₂O (500 mL). The mixture was extracted with EtOAc (3×150 mL) and the combined organic layers were washed with brine (200 mL), dried over Na₂SO₄, filtered, and concentrated under reduced pressure. The residue was purified by normal phase chromatography (25% EtOAc/pet. ether) to afford the desired product (19.0 g, 81.2% yield). LCMS (ESI) m/z: [M+H] calcd for $C_{60}H_{82}N_6O_8Si$: 1043.61; found 1042.6.

Step 3: Synthesis of (2S)—N-((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide To a solution of benzyl ((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate (1.20 g, 1.150 mmol) in MeOH (1.2 mL) and toluene (1.2 mL) was added Pd/C (10%, 240 mg). The resulting mixture was placed under an atmosphere of H₂ (1 atm) and stirred overnight. The mixture was filtered and concentrated under reduced pressure to afford the desired product (1.05 g, 97.4% yield). LCMS (ESI) m/z: [M+H] calcd for $C_{52}H_{76}N_6O_6Si$: 909.57; found 909.3.

Step 4: Synthesis of tert-butyl (2R,5R)-2-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)-5-methylpyrrolidine-1-carboxylate To a solution of (2S)—N-((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide (500 mg, 0.550 mmol) in DMF (5 mL) at 0° C. was added DIPEA (0.94 mL, 5.499 mmol) and (2R,5R)-1-(tert-butoxycarbonyl)-5-methylpyrrolidine-2-carboxylic acid (504.29 mg, 2.199 mmol) followed by HATU (627.23 mg, 1.650 mmol) in portions. The resulting mixture was warmed to room temperature and stirred for 1 h. Purification by reverse phase chromatography (0→100% MeCN/H₂O) afforded the desired product (147 mg, 22.2% yield). LCMS (ESI) m/z: [M+H] calcd for $C_{63}H_{93}N_7O_9Si$: 1120.69; found 1120.6.

Step 5: Synthesis of (2R,5R)—N-((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N,5-dimethylpyrrolidine-2-carboxamide To a solution of tert-butyl (2R,5R)-2-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)-5-methylpyrrolidine-1-carboxylate (150.0 mg, 0.134 mmol) in DCM at 0° C. was added TFA (1.50 mL, 13.155 mmol) dropwise. The resulting mixture was warmed to room temperature and stirred for 2 h and was then basified to pH 8 with sat. NaHCO₃. The resulting mixture was extracted with EtOAc (3×5 mL) and the combined organic layers were washed with brine (2×5 mL), dried with Na₂SO₄, filtered, and concentrated under reduced pressure to afford the desired product (85 mg, 54.1% yield). LCMS (ESI) m/z: [M+H] calcd for $C_{58}H_{85}N_7O_7Si$: 1020.64; found 1020.4.

Intermediate 18. Synthesis of (2R)—N-((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-i-methylpyrrolidine-2-carboxamide
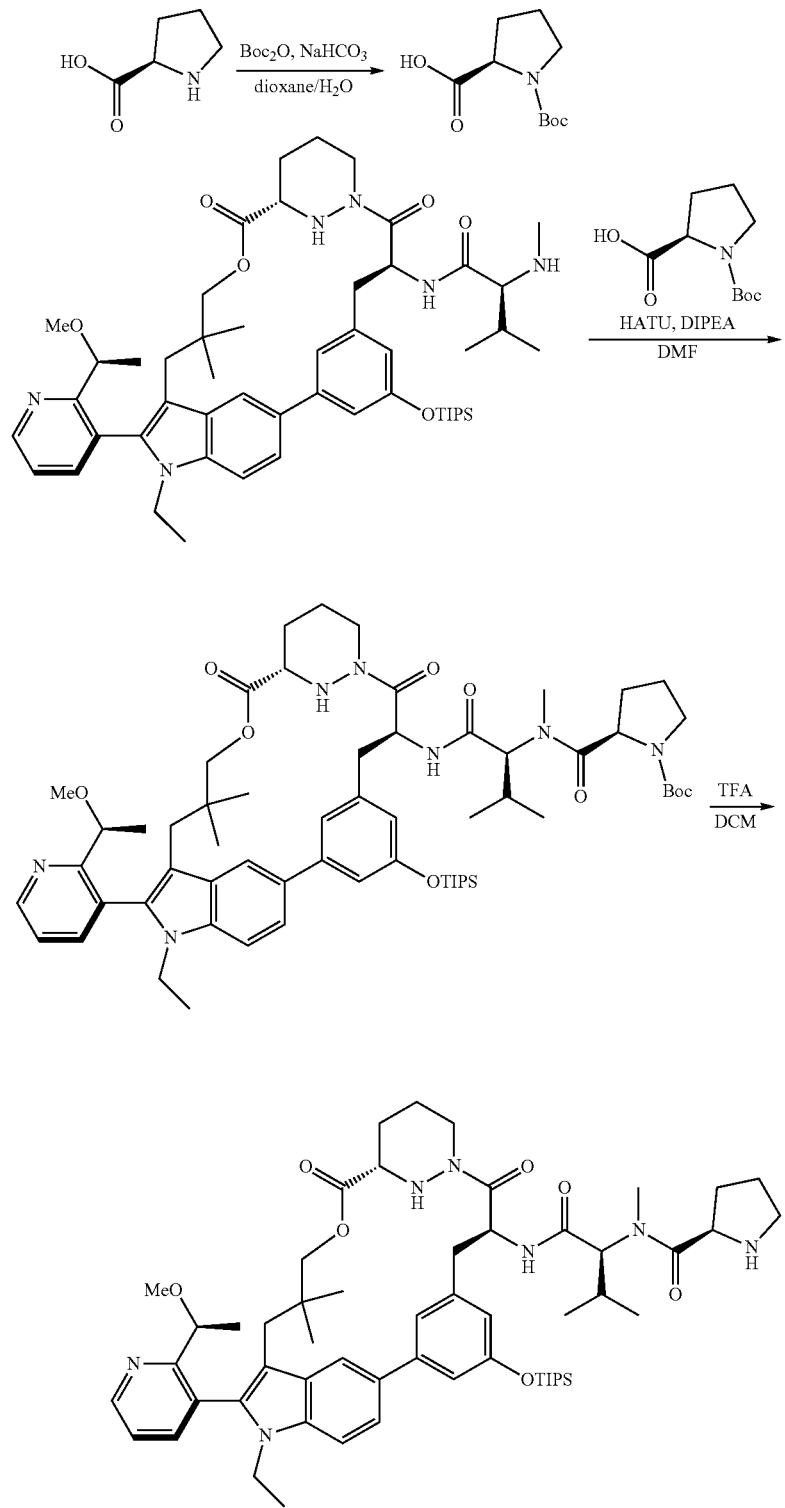

Step 1: Synthesis of (tert-butoxycarbonyl)-D-proline

To a solution of D-proline (5.0 g, 43.43 mmol) in 1,4-dioxane (50 mL) and sat. NaHCO$_3$ (50 mL) at 0° C. was added Boc$_2$O (14.217 g, 65.143 mmol) in portions. The resulting mixture was stirred for 2 h at room temperature and was then extracted with EtOAc (100 mL). The aqueous layer was acidified to pH 6 with HCl and was then extracted into EtOAc (3×100 mL). The combined organic layers were washed with H$_2$O (2×100 mL), dried with Na$_2$SO$_4$, filtered, and concentrated under reduced pressure to afford the desired product which was used without further purification. LCMS (ESI) m/z: [M−H] calcd for C$_{10}$H$_{17}$NO$_4$: 214.11; found 214.0.

Step 2: Synthesis of tert-butyl (2R)-2-(((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)pyrrolidine-1-carboxylate To a solution of (2S)—N-((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)-3-methyl-2-(methylamino)butanamide (142.03 mg, 0.660 mmol) in DMF was added DIPEA (0.710 mL, 5.499 mmol) followed by HATU (250.89 mg, 0.660 mmol) in portions. The resulting mixture was heated to 40° C. and stirred for 2 h. Purification by reverse phase chromatography (0→100% MeCN/H$_2$O) afforded the desired product (350 mg, 54.6% yield). LCMS (ESI) m/z: [M+H] calcd for C$_{62}$H$_{91}$N$_7$O$_9$Si: 1106.67; found 1106.8.

Step 3: Synthesis of (2R)—N-((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-i-methylpyrrolidine-2-carboxamide To a solution of tert-butyl (2R)-2-(((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)pyrrolidine-1-carboxylate (350.0 mg, 0.325 mmol) in DCM (4 mL) at 0° C. was added TFA (2.0 mL). The resulting mixture was stirred for 30 min at 0° C. and then was concentrated under reduced pressure. The residue was dissolved in toluene (5 mL) then concentrated under reduced pressure three times to afford the desired product which was used without further purification. LCMS (ESI) m/z: [M+H] calcd for C$_{57}$H$_{83}$N$_7$O$_7$Si: 1006.62; found 1006.4.

Intermediate 19. Synthesis of (2R)—N-((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N-methylazetidine-2-carboxamide

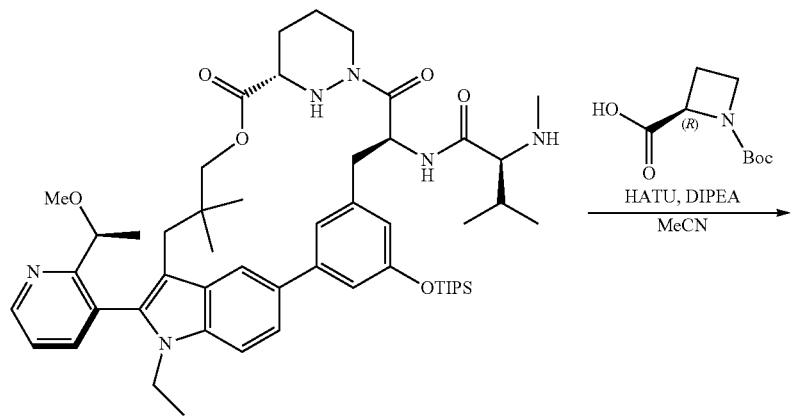

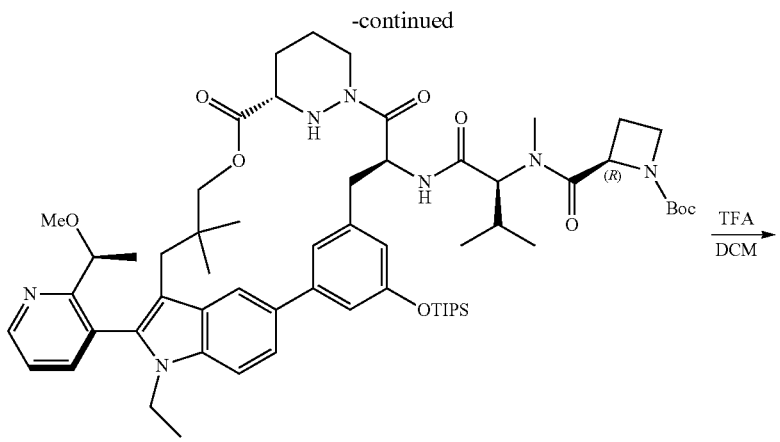

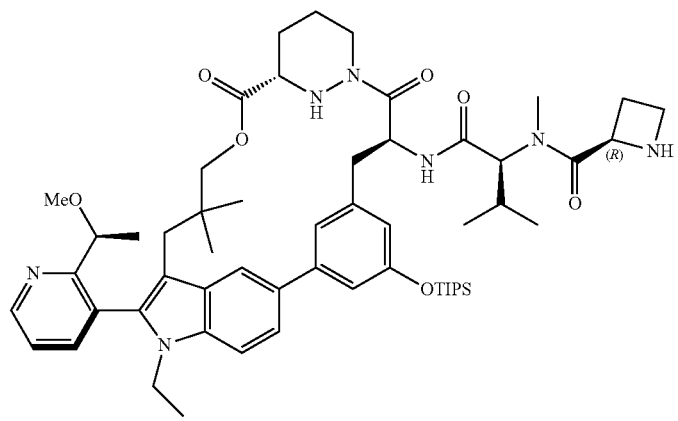

Step 1: Synthesis of tert-butyl (2R)-2-(((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)azetidine-1-carboxylate To a mixture of (2S)—N-(($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-3-methyl-2-(methylamino)butanamide (1.0 g, 1.10 mmol), (R)-1-(tert-butoxycarbonyl)azetidine-2-carboxylic acid (0.33 g, 1.650 mmol) and HATU (1.25 g, 3.299 mmol) in MeCN (20 mL) at 0° C. was added DIPEA (0.94 mL, 5.499 mmol). The resulting mixture was stirred at 0° C. for 3 h and then was concentrated under reduced pressure. Purification by prep-TLC (10% MeOH/DCM) afforded the desired product (800 mg, 59.9% yield). LCMS (ESI) m/z: [M+H] calcd for $C_{61}H_{89}N_7O_9Si$: 1092.65; found 1092.6.

Step 2: Synthesis of (2R)—N-((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methylazetidine-2-carboxamide To a mixture of tert-butyl (2R)-2-(((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1$,$6^2$,$6^3$,$6^4$,$6^5$, $6^6$-hexahydro-$1^1$H-8-oxa-1(5,3)-indola-6(1,3)-pyridazina-2 (1,3)-benzenacycloundecaphane-4-yl)amino)-3-methyl-1-oxobutan-2-yl)(methyl)carbamoyl)azetidine-1-carboxylate (400.0 mg, 0.366 mmol) in DCM (8.0 mL) at 0° C. was added TFA (4.0 mL). When the reaction was complete the mixture was concentrated under reduced pressure to afford the desired product (400 mg, crude). LCMS (ESI) m/z: [M+H] calcd for $C_{56}H_{81}N_7O_7Si$: 992.61; found 992.4.

Intermediate 20. Synthesis of N-(sec-butyl)-5-((6³S, 4S)-1¹-ethyl-2⁵-hydroxy-10,10-dimethyl-4-((S)-3-methyl-2-(N-methyl-2-(methylamino)acetamido)butanamido)-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-N-methylnicotinamide
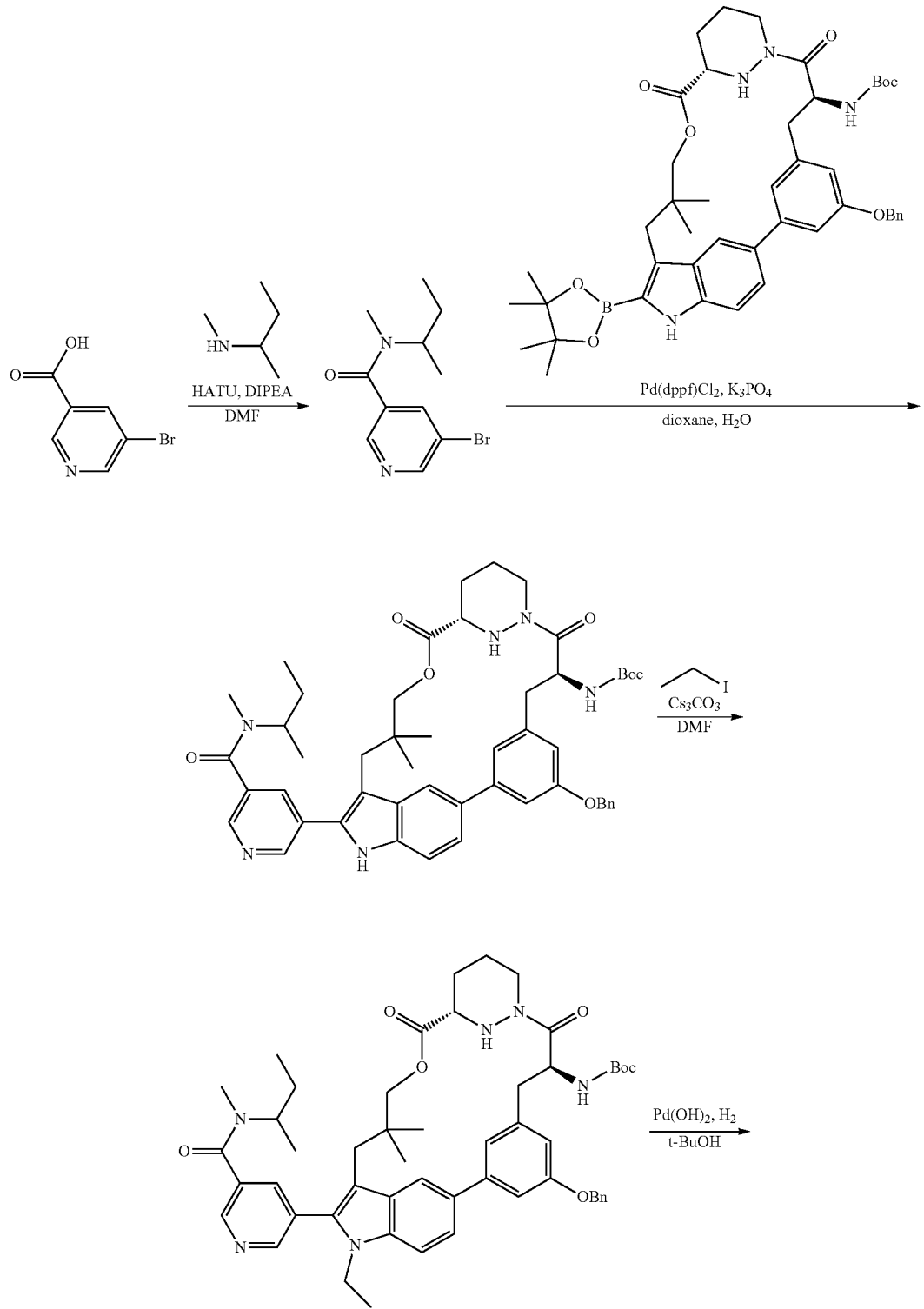

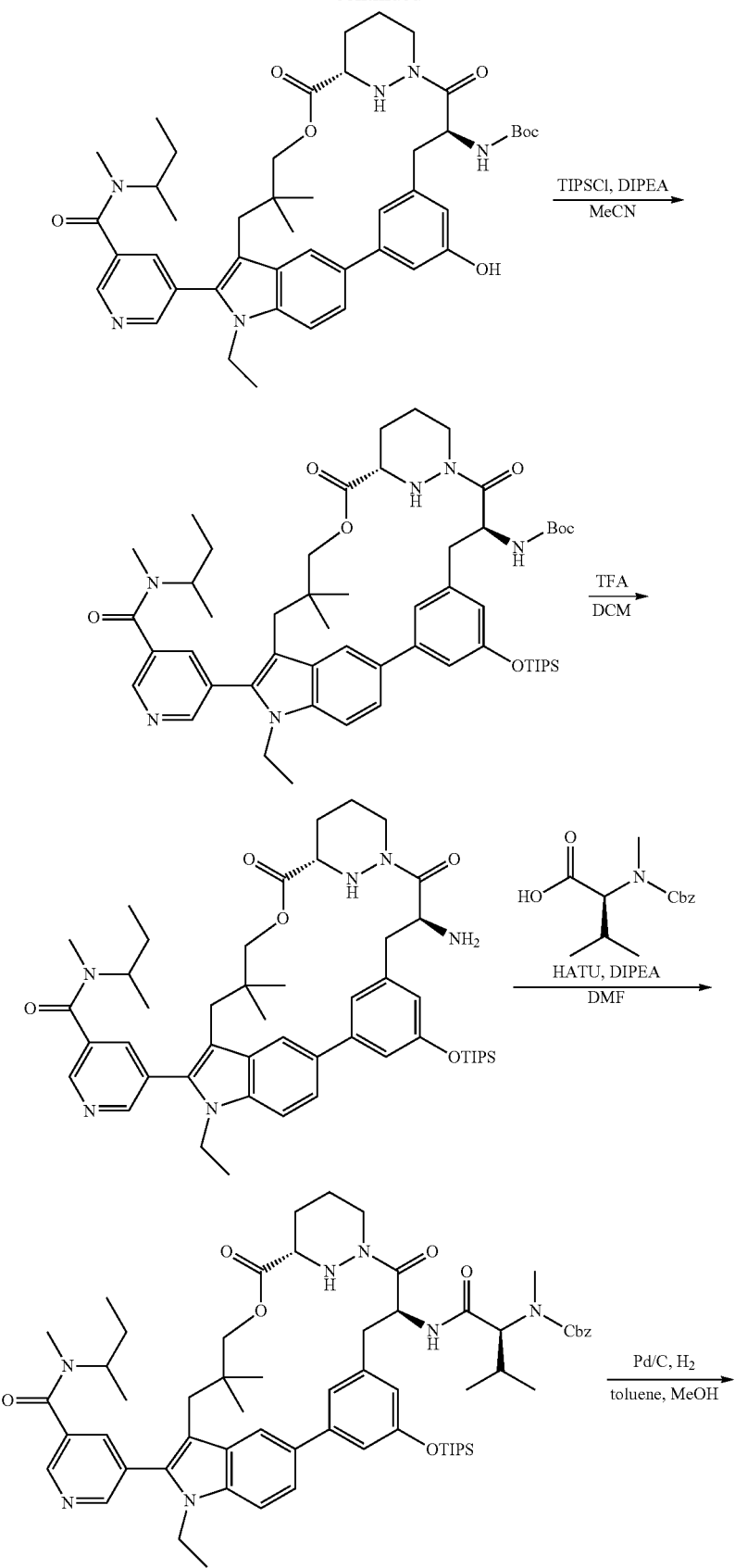

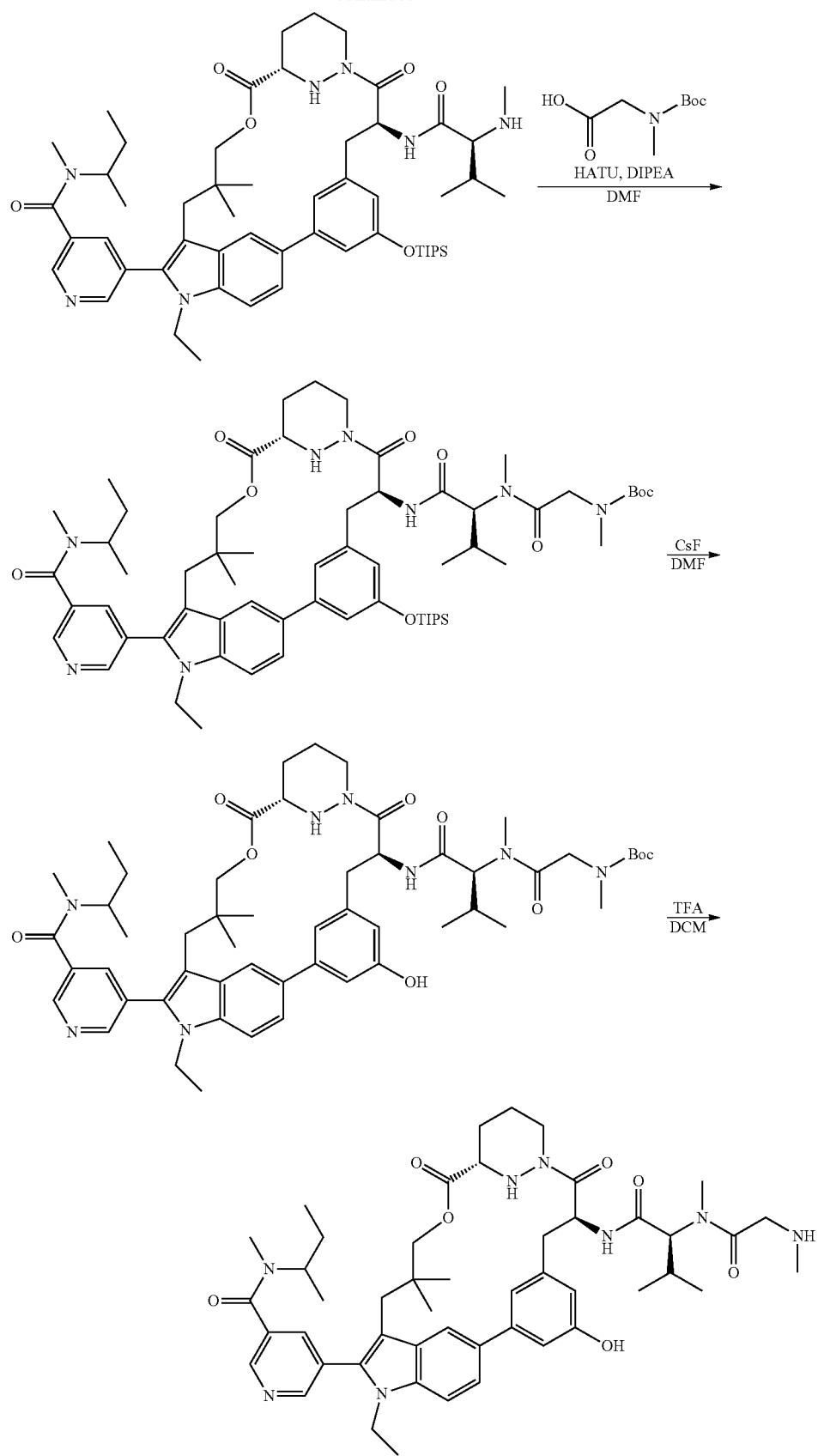

Step 1: Synthesis of 5-bromo-N-(sec-butyl)-N-methylnicotinamide

To a solution of 5-bromonicotinic acid (2.0 g, 9.901 mmol) and HATU (5.65 g, 14.851 mmol) in DMF (40 mL) at 0° C. was added DIPEA (5.2 mL 9.9 mmol). The resulting mixture was stirred for 30 min at 0° C. and then N-methylbutan-2-amine (0.91 g, 10.396 mmol) was added. The resulting mixture was warmed to room temperature and stirred overnight, then diluted with $H_2O$ (40 mL). The mixture was extracted with EtOAc (3×30 mL) and the combined organic layers were washed with brine (50 mL), dried over $Na_2SO_4$, filtered, and concentrated under reduced pressure. The residue was purified by silica gel chromatography (50% EtOAc/pet. ether) to afford the desired product (1.96 g, 73.2% yield). LCMS (ESI) m/z: [M+H] calcd for $C_{11}H_{15}BrN_2O$: 271.04; found 271.1.

Step 2: Synthesis of tert-butyl (($6^3$S,4S)-25-(benzyloxy)-$1^2$-(5-(sec-butyl(methyl)carbamoyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a solution of 5-bromo-N-(sec-butyl)-N-methylnicotinamide (800.0 mg, 2.95 mmol) and $K_3PO_3$ (1.565 g, 7.376 mmol) in 1,4-dioxane (30.0 mL) and $H_2O$ (6.0 mL) was added tert-butyl (($6^3$S,4S)-$2^5$-(benzyloxy)-10,10-dimethyl-5,7-dioxo-$1^2$-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (2.81 g, 3.540 mmol) and Pd(dppf)Cl$_2$ (215.87 mg, 0.295 mmol). The resulting mixture was heated to 85° C. and stirred for 3 h. The mixture was then cooled to room temperature, quenched with $H_2O$, and extracted with EtOAc (3×100 mL). The combined organic layers were washed with $H_2O$ (100 mL), dried over $Na_2SO_4$, filtered, and concentrated. The residue was purified by silica gel chromatography (10% MeOH/DCM) to afford the desired product (2.2 g, crude). LCMS (ESI) m/z: [M+H] calcd for $C_{50}H_{60}N_6O_7$: 857.46; found 857.5.

Step 3: Synthesis of tert-butyl (($6^3$S,4S)-$2^5$-(benzyloxy)-$1^2$-(5-(sec-butyl(methyl)carbamoyl)pyridin-3-yl)-$1^1$-ethyl-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a solution of tert-butyl (($6^3$S,4S)-25-(benzyloxy)-$1^2$-(5-(sec-butyl(methyl)carbamoyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (2.10 g, 2.450 mmol) and $Cs_2CO_3$ (2.39 g, 7.351 mmol) in DMF (20.0 mL) was added ethyl iodide (0.57 g, 3.675 mmol). The resulting mixture was stirred for 3 h at room temperature and was then quenched with $H_2O$ (200 mL). The resulting mixture was extracted with EtOAc (3×100 mL) and the combined organic layers were washed with brine (50 mL), dried over $Na_2SO_4$, filtered, and concentrated under reduced pressure. The residue was purified by silica gel chromatography (10% MeOH/DCM) to afford the desired product (800 mg, 36.9% yield). LCMS (ESI) m/z: [M+H] calcd for $C_{52}H_{64}N_6O_7$: 885.49; found 885.5.

Step 4: Synthesis of tert-butyl (($6^3$S,4S)-$1^2$-(5-(sec-butyl(methyl)carbamoyl)pyridin-3-yl)-$1^1$-ethyl-$2^5$-hydroxy-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a solution of tert-butyl (($6^3$S,4S)-$2^5$-(benzyloxy)-$1^2$-(5-(sec-butyl(methyl)carbamoyl)pyridin-3-yl)-$1^1$-ethyl-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (770.0 mg, 0.870 mmol) in tert-BuOH (20.0 mL) was added Pd(OH)$_2$/C (24.42 mg, 0.174 mmol). The resulting suspension was stirred overnight at 50° C. under a hydrogen atmosphere (1 atm). The mixture was then cooled to room temperature, filtered and the filter cake was washed with MeOH (3×30 mL). The filtrate was concentrated under reduced pressure to afford the desired product (810 mg, crude). LCMS (ESI) m/z: [M+H] calcd for $C_{45}H_{58}N_6O_7$: 795.44; found 795.5.

Step 5: Synthesis of tert-butyl (($6^3$S,4S)-$1^2$-(5-(sec-butyl(methyl)carbamoyl)pyridin-3-yl)-$1^1$-ethyl-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a solution of tert-butyl (($6^3$S,4S)-$1^2$-(5-(sec-butyl(methyl)carbamoyl)pyridin-3-yl)-$1^1$-ethyl-$2^5$-hydroxy-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (800.0 mg, 1.0 mmol) and DIPEA (0.876 mL, 5.031 mmol) in MeCN (10.0 mL) was added chlorotris(propan-2-yl)silane (291.02 mg, 1.509 mmol). The resulting mixture was stirred for 3 h and was then quenched with $H_2O$. The resulting mixture was extracted with EtOAc (3×50 mL) and the combined organic layers were washed with $H_2O$ (3×30 mL), dried over $Na_2SO_4$, filtered, and concentrated under reduced pressure. The residue was purified by silica gel chromatography (10% MeOH/DCM) to afford the desired product (800 mg, 83.6% yield). LCMS (ESI) m/z: [M+H] calcd for $C_{54}H_{78}N_6O_7Si$: 951.58; found 950.8.

Step 6: Synthesis of 5-(($6^3$S,4S)-4-amino-$1^1$-ethyl-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-$1^2$-yl)-N-(sec-butyl)-N-methylnicotinamide To a solution of tert-butyl (($6^3$S,4S)-$1^2$-(5-(sec-butyl(methyl)carbamoyl)pyridin-3-yl)-$1^1$-ethyl-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (720.0 mg, 0.757 mmol) in DCM (10.0 mL) at 0° C. was added TFA (3.0 mL, 40.4 mmol). The resulting mixture was stirred for 2 h and was then concentrated under reduced pressure. The residue was cooled to at 0° C. and neutralized with sat. aq. NaHCO$_3$. The resulting mixture was extracted with EtOAc (3×100 mL) and the combined organic layers were washed with $H_2O$ (3×30 mL), dried over $Na_2SO_4$, filtered, and concentrated under reduced pressure to afford the desired product (540 mg, crude). LCMS (ESI) m/z: [M+H] calcd for $C_{49}H_{70}N_6O_5Si$: 851.53; found 851.8.

Step 7: Synthesis of benzyl ((2S)-1-(((6³S,4S)-1²-(5-(sec-butyl(methyl)carbamoyl)pyridin-3-yl)-1¹-ethyl-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate To a solution of 5-((6³S,4S)-4-amino-1¹-ethyl-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-N-(sec-butyl)-N-methylnicotinamide (530.0 mg, 0.623 mmol) and N-((benzyloxy)carbonyl)-N-methyl-L-valine (198.23 mg, 0.747 mmol) in DMF (10.0 mL) were added HATU (473.49 mg, 1.245 mmol) and DIPEA (0.542 mL, 3.113 mmol). The resulting mixture was stirred for 2 h and was then quenched with $H_2O$ and extracted with EtOAc (3×50 mL). The combined organic layers were washed with $H_2O$ (3×30 mL), dried over $Na_2SO_4$, filtered, and concentrated under reduced pressure. The residue was purified by silica gel chromatography (10% MeOH/DCM) to afford the desired product (720 mg, crude). LCMS (ESI) m/z: [M+H] calcd for $C_{63}H_{87}N_7O_8Si$: 1098.65; found 1098.7.

Step 8: Synthesis of N-(sec-butyl)-5-((6³S,4S)-1¹-ethyl-10,10-dimethyl-4-((S)-3-methyl-2-(methylamino)butanamido)-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-N-methylnicotinamide To a solution of benzyl ((2S)-1-(((6³S,4S)-1²-(5-(sec-butyl(methyl)carbamoyl)pyridin-3-yl)-1¹-ethyl-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamate (670.0 mg, 0.610 mmol) in toluene (10.0 mL) and MeOH (1.0 mL) was added Pd/C (12.98 mg, 0.122 mmol). The suspension was stirred overnight under a hydrogen atmosphere (1 atm) and was then filtered, and the filter cake washed with MeOH (3×50 mL). The filtrate was concentrated under reduced pressure to afford the desired product (600 mg, crude). LCMS (ESI) m/z: [M+H] calcd for $C_{55}H_{81}N_7O_6Si$: 964.61; found 964.8.

Step 9: Synthesis of tert-butyl (2-(((2S)-1-(((6³S,4S)-1²-(5-(sec-butyl(methyl)carbamoyl)pyridin-3-yl)-1¹-ethyl-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate To a solution of N-(sec-butyl)-5-((6³S,4S)-1¹-ethyl-10,10-dimethyl-4-((S)-3-methyl-2-(methylamino)butanamido)-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-N-methylnicotinamide (490.0 mg, 0.508 mmol) and N-(tert-butoxycarbonyl)-N-methylglycine (114.4 mg, 0.610 mmol) in DMF (10.0 mL) was added HATU (386.39 mg, 1.016 mmol) and DIPEA (0.443 mL, 2.540 mmol). The resulting mixture was stirred for 2 h and was then quenched with $H_2O$ and extracted with EtOAc (3×30 mL). The combined organic layers were washed with $H_2O$ (3×30 mL), dried over $Na_2SO_4$, filtered, and concentrated under reduced pressure to afford the desired product (560 mg, 79.3% yield). LCMS (ESI) m/z: [M+H] calcd for $C_{63}H_{94}N_8O_9Si$: 1135.70; found 1136.3.

Step 10: Synthesis of tert-butyl (2-(((2S)-1-(((6³S, 4S)-1²-(5-(sec-butyl(methyl)carbamoyl)pyridin-3-yl)-1¹-ethyl-2⁵-hydroxy-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate To a solution of tert-butyl (2-(((2S)-1-(((6³S,4S)-1²-(5-(sec-butyl(methyl)carbamoyl)pyridin-3-yl)-1¹-ethyl-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate (540.0 mg, 0.476 mmol) in DMF (10.0 mL) was added CsF (288.94 mg, 1.90 mmol). The resulting mixture was stirred for 2 h and was then quenched with $H_2O$ and extracted with EtOAc (3×50 mL). The combined organic layers were washed with $H_2O$ (3×30 mL), dried over $Na_2SO_4$, filtered, and concentrated under reduced pressure. The residue was purified by silica gel chromatography (10% MeOH/DCM) to afford the desired product (430 mg, crude). LCMS (ESI) m/z: [M+H] calcd for $C_{54}H_{74}N_8O_9$: 979.57; found 980.0.

Step 11: Synthesis of N-(sec-butyl)-5-((6³S,4S)-1¹-ethyl-2⁵-hydroxy-10,10-dimethyl-4-((S)-3-methyl-2-(N-methyl-2-(methylamino)acetamido)butanamido)-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-N-methylnicotinamide To a solution of tert-butyl (2-(((2S)-1-(((6³S,4S)-1²-(5-(sec-butyl(methyl)carbamoyl)pyridin-3-yl)-1¹-ethyl-2⁵-hydroxy-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamate (400.0 mg, 0.408 mmol) in DCM (10.0 mL) at 0° C. was added TFA (3.0 mL, 40.4 mmol). The reaction was stirred for 1 h and was then quenched with sat. aq. $NaHCO_3$. The mixture was extracted with EtOAc (3×50 mL) and the combined organic layers were washed with $H_2O$ (3×30 mL), dried over $Na_2SO_4$, filtered, and concentrated under reduced pressure to afford the desired product (380 mg, crude). LCMS (ESI) m/z: [M+H] calcd for $C_{49}H_{66}N_8O_7$: 879.51; found 879.5.

Intermediate 21. Synthesis of (2S)-2-(2-amino-N-methylacetamido)-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide
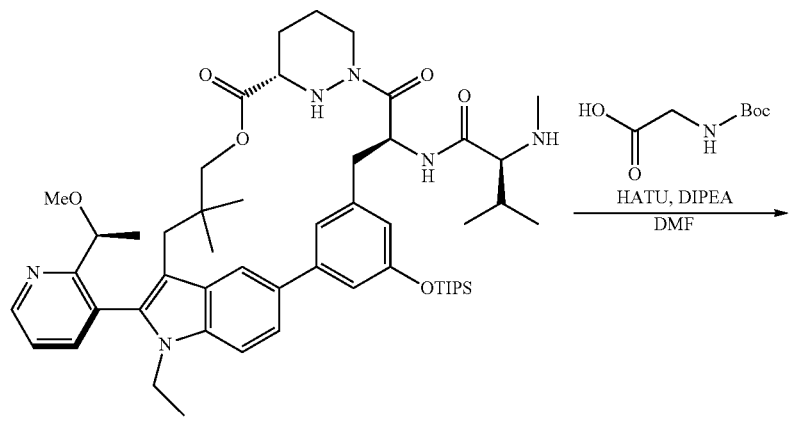
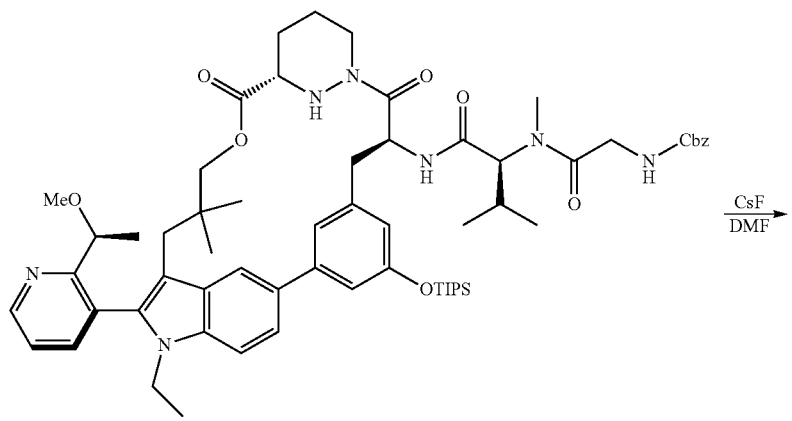
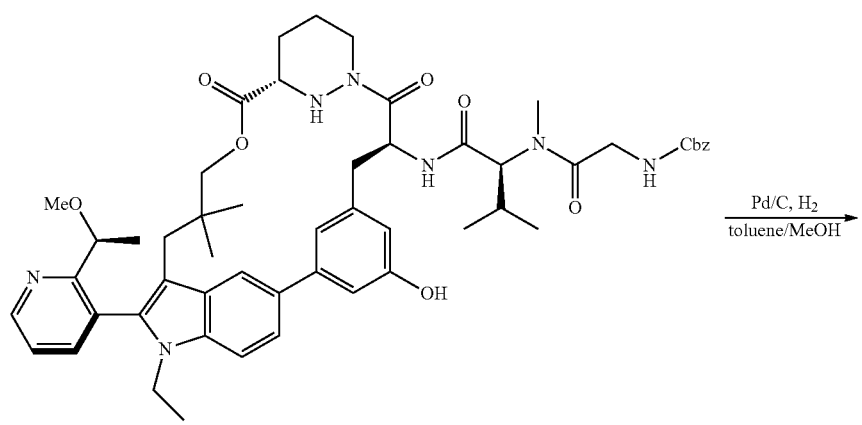

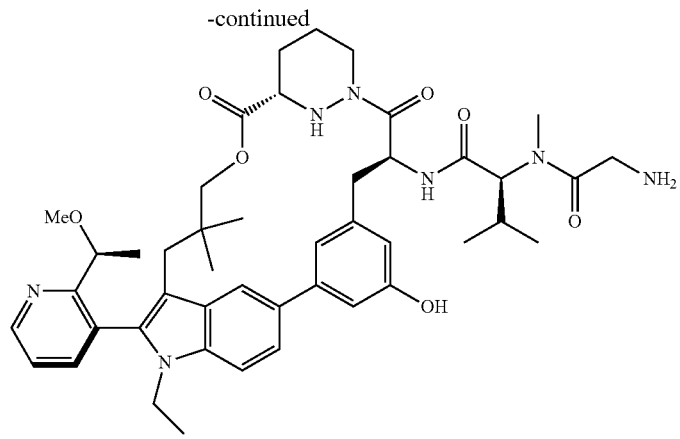

Step 1: Synthesis of benzyl (2-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)carbamate To a solution of (2S)—N-((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide (2.50 g, 2.75 mmol) and ((benzyloxy)carbonyl)glycine (690 mg, 3.30 mmol) in DMF (25 mL) at 0° C. was added HATU (2.10 g, 5.50 mmol) followed by DIPEA (1.5 mL, 8.25 mmol). The reaction mixture was stirred for 2 h and was then quenched with H₂O and extracted with EtOAc (3×50 mL). The combined organic layers were washed with H₂O (3×10 mL), dried with Na₂SO₄, filtered, and concentrated under reduced pressure. Purification by silica gel column chromatography (50% EtOAC/hexanes) afforded desired product (2.0 g, 72% yield). LCMS (ESI) m/z: [M+H] calcd for C₆₂H₈₅N₇O₉Si: 1100.63; found 1100.7.

Step 2: Synthesis of benzyl (2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)carbamate To a solution of benzyl (2-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)carbamate (400 mg, 0.36 mmol) in DMF at 0° C. was added CsF (220 mg, 1.5 mmol). The reaction mixture was stirred for 2 h and was then quenched with H₂O and extracted with EtOAc (3×50 mL). The combined organic layers were washed with H₂O (3×10 mL), dried with Na₂SO₄, filtered, and concentrated under reduced pressure to afford the desired product (300 mg, 87% yield). LCMS (ESI) m/z: [M+H] calcd for C₅₃H₆₅N₇O₉: 944.49; found 944.4.

Step 3: Synthesis of (2S)-2-(2-amino-N-methylacetamido)-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of benzyl (2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)carbamate (300 mg, 0.32 mmol) in toluene (10 mL) and MeOH (1 mL) was added Pd/C (50 mg, 0.47 mmol). The suspension was stirred overnight under an atmosphere of hydrogen (1 atm). The reaction mixture was then was filtered and the filter cake was washed with EtOAc (3×10 mL). The filtrate was concentrated under reduced pressure to afford the desired product (180 mg, 43% yield). LCMS (ESI) m/z: [M+H] calcd for C₄₅H₅₉N₇O₇: 810.46; found 810.5.

Intermediate 22. (3S,4R)—N-((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N,4-dimethylpyrrolidine-3-carboxamide

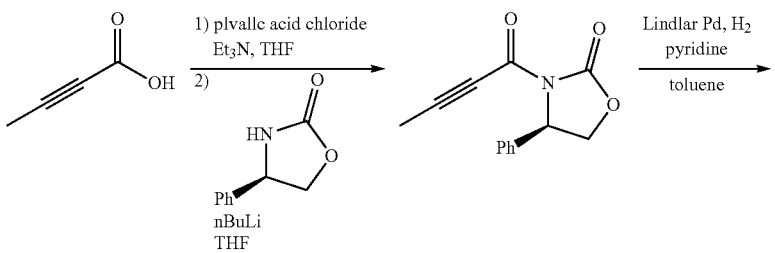

-continued
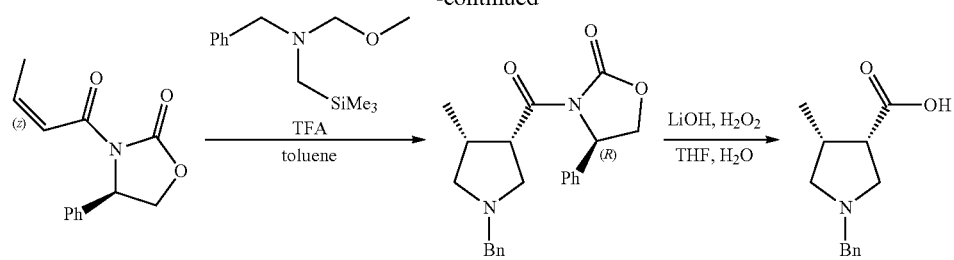
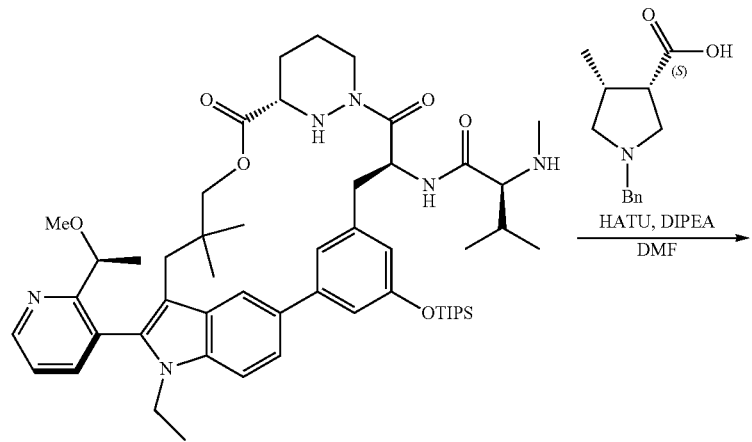
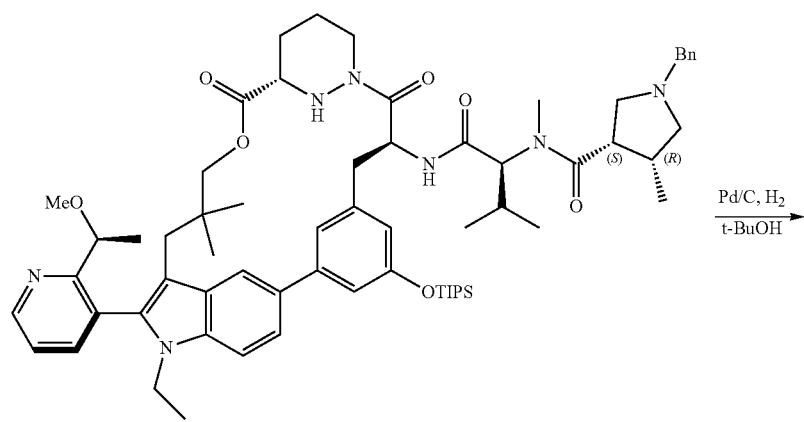
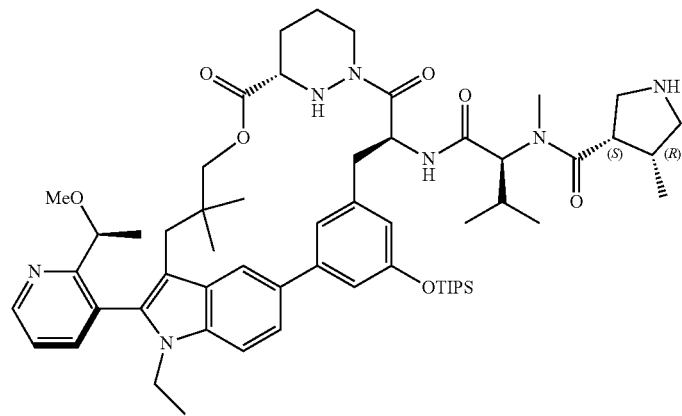

Step 1: Synthesis of (R)-3-(but-2-ynoyl)-4-phenyloxazolidin-2-one

To a solution of 2-butynoic acid (5.0 g, 59.47 mmol) in THF (100 mL) at −78° C. was added pivalic acid chloride (7.39 g, 61.26 mmol) and Et$_3$N (6.2 mL, 61.85 mmol) and then the mixture was stirred for 15 min and then warmed to 0° C. and stirred for 45 min. In a second flask, to a solution of (4R)-4-phenyl-1,3-oxazolidin-2-one (9.70 g, 59.47 mmol) in THF (100 mL) at −78° C. was added n-BuLi (2.5 M in hexane, 25 mL, 62.5 mmol). The mixture was stirred at −78° C. for 15 min and was then added to the initial mixture. The combined solutions were warmed to room temperature and stirred overnight. The reaction solution was quenched with sat. NH$_4$Cl (200 mL) and then the mixture was extracted with EtOAc (3×100 mL). The combined organic layers were washed with brine (200 mL), dried over Na$_2$SO$_4$, filtered, and concentrated under reduced pressure. Purification by normal phase chromatography (20% EtOAc/pet. ether) afforded the desired product (6.0 g, 44.0% yield). LCMS (ESI) m/z: [M+H] calcd for C$_{13}$H$_{11}$NO$_3$: 230.08; found 229.9.

Step 2: Synthesis of (R,Z)-3-(but-2-enoyl)-4-phenyloxazolidin-2-one

To a solution of (R)-3-(but-2-ynoyl)-4-phenyloxazolidin-2-one (6.0 g, 26.17 mmol) in pyridine (6.0 mL) and toluene (60.0 mL) at 0° C. was added Lindlar Pd catalyst (594.57 mg, 2.88 mmol). The resulting mixture was stirred for 30 min at 0° C. under a hydrogen atmosphere (1 atm). The mixture was filtered, and the filter cake was washed with toluene (10.0 mL). The filtrate was concentrated under reduced pressure to afford the desired product (5.5 g, crude). LCMS (ESI) m/z: [M+H] calcd for C$_{13}$H$_{13}$NO$_3$: 232.10; found 231.9.

Step 3: (R)-3-((3S,4R)-1-benzyl-4-methylpyrrolidine-3-carbonyl)-4-phenyloxazolidin-2-one To a solution of (R,Z)-3-(but-2-enoyl)-4-phenyloxazolidin-2-one (3.0 g, 12.97 mmol) and benzyl(methoxymethyl)[(trimethylsilyl)methyl]amine (3.70 g, 15.57 mmol) in toluene (20.0 mL) at 0° C. was added TFA (1.30 mL, 0.87 mmol). The resulting mixture was warmed to room temperature and stirred overnight. The mixture was then concentrated under reduced pressure. The residue was purified by silica gel column chromatography (20% EtOAc/pet. ether) to afford the desired product (2 g, 42.3% yield). LCMS (ESI) m/z: [M+H] calcd for C$_{22}$H$_{24}$N$_2$O$_3$: 365.19; found 365.2.

Step 4: Synthesis of (3S,4R)-1-benzyl-4-methylpyrrolidine-3-carboxylic acid

A solution of LiOH.H$_2$O (0.16 g, 6.860 mmol) and H$_2$O$_2$ (0.13 g, 3.76 mmol) in H$_2$O (5 mL) was added to a solution of (R)-3-((3S,4R)-1-benzyl-4-methylpyrrolidine-3-carbonyl)-4-phenyloxazolidin-2-one (1.0 g, 2.74 mmol) in THF (15.0 mL) at 0° C. The resulting mixture was stirred for 2 h and was then quenched with H$_2$O (30 mL) and sodium sulfite (0.69 g, 5.48 mmol) and the solution was extracted with EtOAc (2×50 mL). The aqueous phase was adjusted to pH 4 with NaH$_2$PO$_4$.H$_2$O and 10% HCl, and the brine was added. The solution was extracted with i-PrOH/DCM (1:3, 5×50 mL) and the combined organic layers were washed with brine (40 mL), dried over Na$_2$SO$_4$, filtered, and concentrated under reduced pressure to afford the desired product (400 mg, crude). LCMS (ESI) m/z: [M+H] calcd for C$_{13}$H$_{17}$NO$_2$: 220.14; found 220.2.

Step 5: Synthesis of (3S,4R)-1-benzyl-N-((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N,4-dimethylpyrrolidine-3-carboxamide To a mixture of (2S)—N-((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)-3-methyl-2-(methylamino)butanamide (414.67 mg, 0.456 mmol) and (3S,4R)-1-benzyl-4-methylpyrrolidine-3-carboxylic acid (200.0 mg, 0.912 mmol) in DMF (5.0 mL) at 0° C. was added HATU (693.58 mg, 1.824 mmol) and DIPEA (0.794 mL, 4.560 mmol). The resulting mixture was warmed to room temperature and stirred for 2 h. The reaction was quenched with the addition of sat. aq. NH$_4$Cl (40 mL) and then extracted with EtOAc (3×30 mL). The combined organic layers were washed with brine (2×20 mL), dried over Na$_2$SO$_4$, filtered, and concentrated under reduced pressure. The residue was purified by prep-TLC (9% MeOH/DCM) to afford the desired product (350 mg, 34.6% yield). LCMS (ESI) m/z: [M+H] calcd for C$_{65}$H$_{91}$N$_7$O$_7$Si: 1110.68; found 1110.9.

Step 6: (3S,4R)—N-((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N,4-dimethylpyrrolidine-3-carboxamide To a solution of (3S,4R)-1-benzyl-N-((2S)-1-(((6$^3$S,4S)-1$^1$-ethyl-1$^2$-(2-((S)-1-methoxyethyl)pyridin-3-yl)-10,10-dimethyl-5,7-dioxo-2$^5$-((triisopropylsilyl)oxy)-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N,4-dimethylpyrrolidine-3-carboxamide (300.0 mg, 0.270 mmol) in t-BuOH (10.0 mL) was added Pd/C (60.08 mg, 0.565 mmol). The resulting suspension was stirred overnight under a hydrogen atmosphere (1 atm). The mixture was then filtered, the filter cake was washed with MeOH (2×5 mL), and the filtrate was concentrated under reduced pressure to afford the desired product (280 mg, crude). LCMS (ESI) m/z: [M+H] calcd for C$_{58}$H$_{85}$N$_7$O$_7$Si: 1020.64; found 1020.8.

Intermediate 23. Synthesis of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)—N-methyl-2-(methylamino)propanamido)butanamide
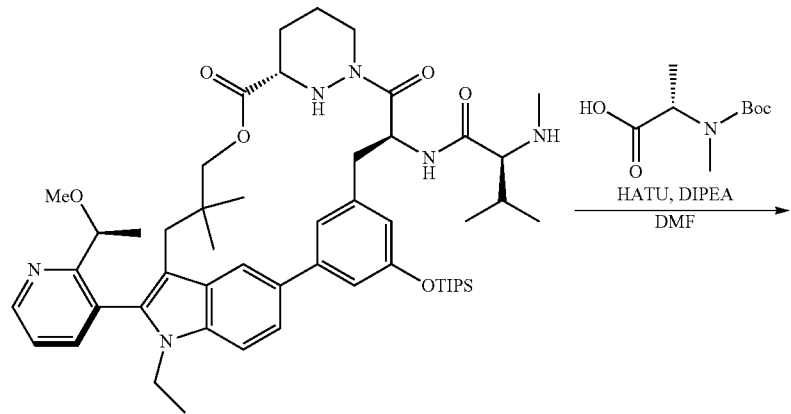
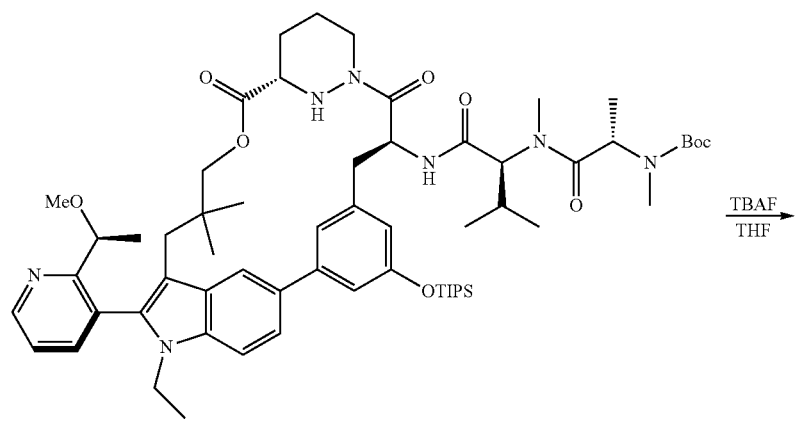
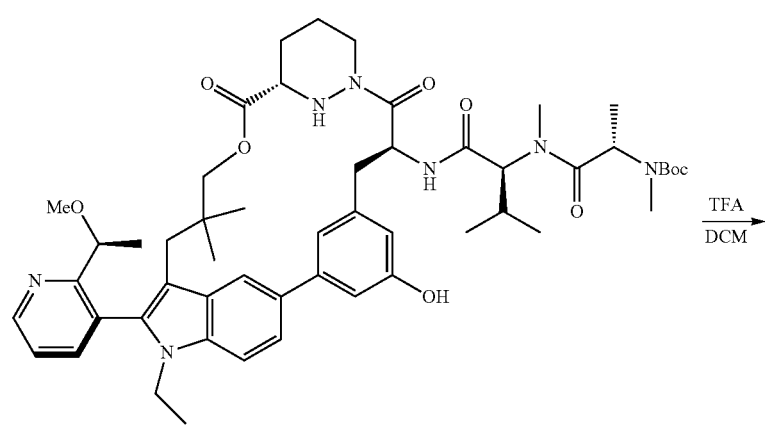

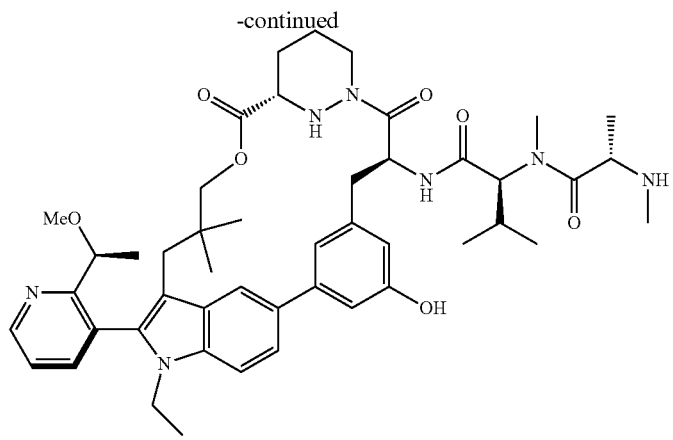

Step 1: Synthesis of tert-butyl ((2S)-1-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-1-oxopropan-2-yl)(methyl)carbamate To a solution of (2S)—N-((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino)butanamide (500.0 mg, 0.55 mmol), DIPEA (480 mL, 2.75 mmol) and (2S)-2-[(tert-butoxycarbonyl)(methyl)amino]propanoic acid (167.63 mg, 0.825 mmol) in DMF (5.0 mL) at 0° C. was added HATU (271.80 mg, 0.715 mmol). The mixture was warmed to room temperature and stirred for 4 h. The reaction was then quenched with $H_2O$ and extracted with EtOAc (2×10 mL). The combined organic layers were washed with brine (5 mL), dried over $Na_2SO_4$, filtered, and concentrated under reduced pressure. The residue was purified by silica gel column chromatography (50% EtOAc/pet. ether) to afford the desired product (550 mg, 91.4% yield). LCMS (ESI) m/z: [M+H] calcd for $C_{61}H_{91}N_7O_9Si$: 1094.67; found 1094.5.

Step 2: Synthesis of tert-butyl ((2S)-1-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-1-oxopropan-2-yl)(methyl)carbamate To a solution of tert-butyl ((2S)-1-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-1-oxopropan-2-yl)(methyl)carbamate (540 mg, 0.493 mmol) in THF (5.0 mL) at 0° C. was added TBAF (1M in THF, 0.59 mL, 0.592 mmol). The mixture was warmed to room temperature and stirred for 30 min. The reaction was quenched with $H_2O$ and was then extracted with EtOAc (2×10 mL). The combined organic layers were washed with brine (10 mL), dried over $Na_2SO_4$, filtered, After filtration, and concentrated under reduced pressure. The residue was purified by silica gel column chromatography (20% EtOAc/pet. ether) to afford the desired product (320 mg, 69.1% yield). LCMS (ESI) m/z: [M+H] calcd for $C_{52}H_{71}N_7O_9$: 938.534; found 938.4.

Step 3: Synthesis of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)—N-methyl-2-(methylamino)propanamido)butanamide To a solution of tert-butyl ((2S)-1-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-1-oxopropan-2-yl)(methyl)carbamate (300.0 mg, 0.320 mmol) in DCM (3.0 mL) at 0° C. and was added TFA (1.0 mL). The mixture was warmed to room temperature and stirred for 2 h. The mixture was concentrated under reduced pressure to afford the desired product (300 mg, crude). LCMS (ESI) m/z: [M+H] calcd for $C_{47}H_{63}N_7O_7$: 838.49; found 838.4.

Intermediate 24. Synthesis of tert-butyl ((6³S,4S,Z)-1¹-ethyl-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)-pyridazinacycloundecaphane-4-yl)carbamate

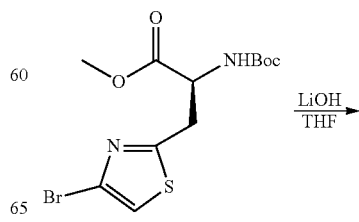

487
-continued

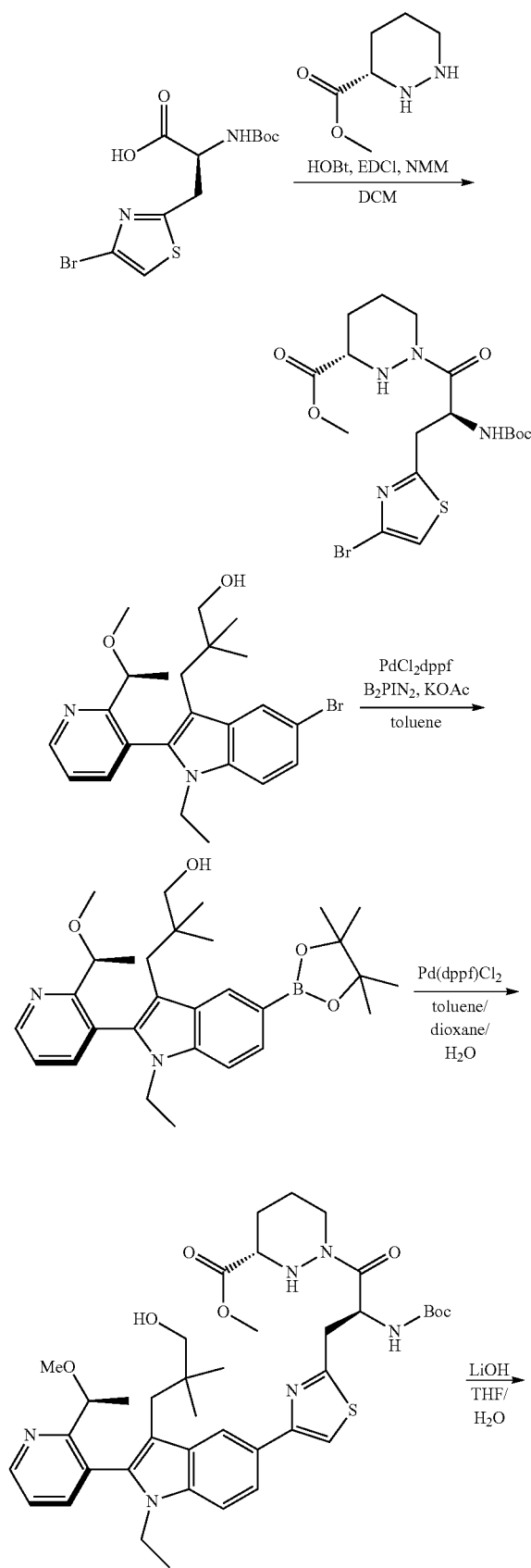

488
-continued

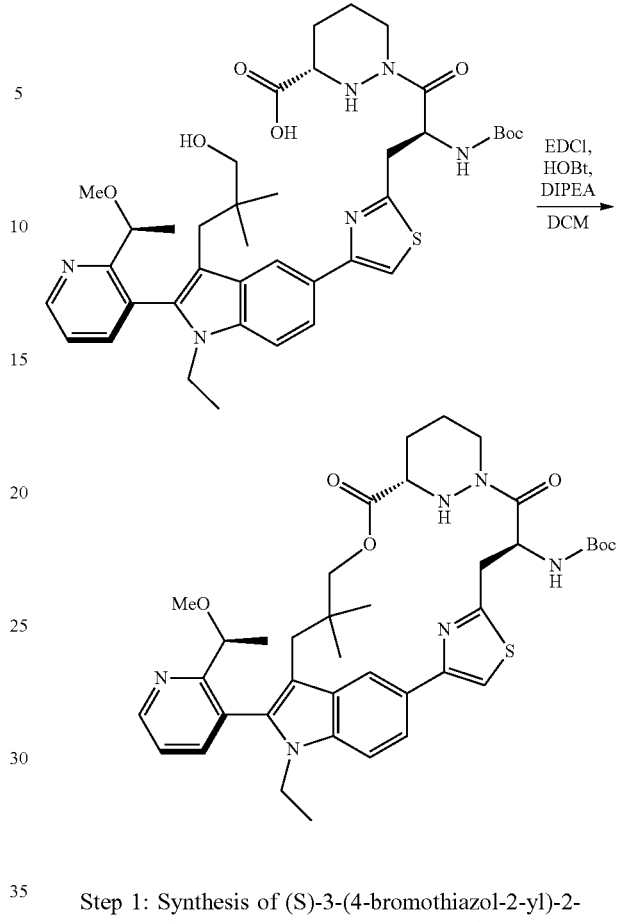

Step 1: Synthesis of (S)-3-(4-bromothiazol-2-yl)-2-((tert-butoxycarbonyl)amino)propanoic Acid To a solution of methyl (2S)-3-(4-bromo-1,3-thiazol-2-yl)-2-[(tert-butoxycarbonyl)amino]propanoate (110 g, 301.2 mmol) in THF (500 mL) and H$_2$O (200 mL) at room temperature was added LiOH (21.64 g, 903.6 mmol). The resulting solution was stirred for 1 h and was then concentrated under reduced pressure. The resulting residue was adjusted to pH 6 with 1 M HCl and then extracted with DCM (3×500 mL). The combined organic layers were, dried over Na$_2$SO$_4$, filtered, and concentrated under reduced pressure to afford the desired product (108 g, crude). LCMS (ESI) m/z: [M+H] calcd for C$_{11}$H$_{15}$BrN$_2$O$_4$S: 351.00; found 351.0.

Step 2: Synthesis of methyl (S)-1-((S)-3-(4-bromothiazol-2-yl)-2-((tert-butoxycarbonyl)amino)propanoyl)hexahydropyridazine-3-carboxylate To a solution of (S)-3-(4-bromothiazol-2-yl)-2-((tert-butoxycarbonyl)amino)propanoic acid (70 g, 199.3 mmol) in DCM (500 mL) at 0° C. was added methyl (3S)-1,2-diazinane-3-carboxylate bis(trifluoroacetic acid) salt (111.28 g, 298.96 mmol), NMM (219.12 mL. 1993.0 mmol), EDCl (76.41 g, 398.6 mmol) and HOBt (5.39 g, 39.89 mmol). The resulting solution was warmed to room temperature and stirred for 1 h. The reaction was then quenched with H$_2$O (500 mL) and was extracted with EtOAc (3×500 mL). The combined organic layers were dried over Na$_2$SO$_4$, filtered, and concentrated under reduced pressured. The residue was purified by silica gel chromatography (0→50% EtOAc/pet.

Step 3: Synthesis of (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethyl-propan-1-ol To a solution of 3-(5-bromo-1-ethyl-2-(2-((S)-1-methoxyethyl)pyridin-3-yl)-1H-indol-3-yl)-2,2-dimethylpropan-1-ol (60 g, 134.7 mmol) in toluene (500 mL) at room temperature was added bis(pinacolato)diboron (51.31 g, 202.1 mmol), Pd(dppf)Cl$_2$ (9.86 g, 13.48 mmol) and KOAc (26.44 g, 269.4 mmol). Then reaction mixture was then heated to 90° C. and stirred for 2 h. The reaction solution was then cooled to room temperature and concentrated under reduced pressure. Purification by silica gel chromatography (0–50% EtOAc/pet. ether) afforded the desired product (60.6 g, 94.0% yield). LCMS (ESI) m/z: [M+H] calcd for C$_{29}$H$_{41}$BN$_2$O$_4$: 493.32; found 493.3.

Step 4: Synthesis of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylate To a solution of (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (30 g, 60.9 mmol) in toluene (600 mL), dioxane (200 mL), and H$_2$O (200 mL) at room temperature was added methyl (S)-1-((S)-3-(4-bromothiazol-2-yl)-2-((tert-butoxycarbonyl)amino)propanoyl)hexahydropyridazine-3-carboxylate (43.62 g, 91.4 mmol), K$_3$PO$_4$ (32.23 g, 152.3 mmol) and Pd(dppf)Cl$_2$ (8.91 g, 12.18 mmol). The resulting solution was heated to 70° C. and stirred overnight. The reaction mixture was then cooled to room temperature and was quenched with H$_2$O (200 mL). The resulting mixture was extracted with EtOAc (3×1000 mL) and the combined organic layers were dried over Na$_2$SO$_4$, filtered, and concentrated under reduced pressure. The residue was purified by silica gel chromatography (0→90% EtOAc/pet. ether) to afford the desired product (39.7 g, 85.4% yield). LCMS (ESI) m/z: [M+H] calcd for C$_{40}$H$_{54}$N$_6$O$_7$S: 763.39; found 763.3.

Step 5: Synthesis of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl) hexahydropyridazine-3-carboxylic Acid To a solution of methyl (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylate (39.7 g, 52.0 mmol) in THF (400 mL) and H$_2$O (100 mL) at room temperature was added LiOH.H$_2$O (3.74 g, 156.2 mmol). The resulting mixture was stirred for 1.5 h and was then concentrated under reduced pressure. The residue was acidified to pH 6 with 1 M HCl and extracted with DCM (3×1000 mL). The combined organic layers were dried over Na$_2$SO$_4$, filtered, and concentrated under reduced pressure to afford the desired product (37.9 g, crude). LCMS (ESI) m/z: [M+H] calcd for C$_{39}$H$_{52}$N$_6$O$_7$S: 749.37; found 749.4.

Step 6: Synthesis of tert-butyl ((6$^3$S,4S,Z)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate To a solution of (S)-1-((S)-2-((tert-butoxycarbonyl)amino)-3-(4-(1-ethyl-3-(3-hydroxy-2,2-dimethylpropyl)-2-(2-((S)-1-methoxyethyl)pyridin-3-yl)-1H-indol-5-yl)thiazol-2-yl)propanoyl)hexahydropyridazine-3-carboxylic acid (37.9 g, 50.6 mmol), HOBt (34.19 g, 253.0 mmol) and DIPEA (264.4 mL, 1518 mmol) in DCM (4 L) at 0° C. was added EDCl (271.63 g, 1416.9 mmol). The resulting mixture was warmed to room temperature and stirred overnight. The reaction mixture was then quenched with H$_2$O and washed with 1 M HCl (4×1 L). The organic layer was separated and concentrated under reduced pressure. The residue was purified by silica gel chromatography (0→70% EtOAc/pet. ether) to afford the desired product (30 g, 81.1% yield). LCMS (ESI) m/z: [M+H] calcd for C$_{39}$H$_{50}$N$_6$O$_6$S: 731.36; found 731.3.

Intermediate 25. Synthesis of (6$^3$S,4S)-4-amino-1$^1$-ethyl-2$^5$-hydroxy-1$^2$-(2-((S)-1-methoxyethyl)-5-(1-methylpiperidin-4-yl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione

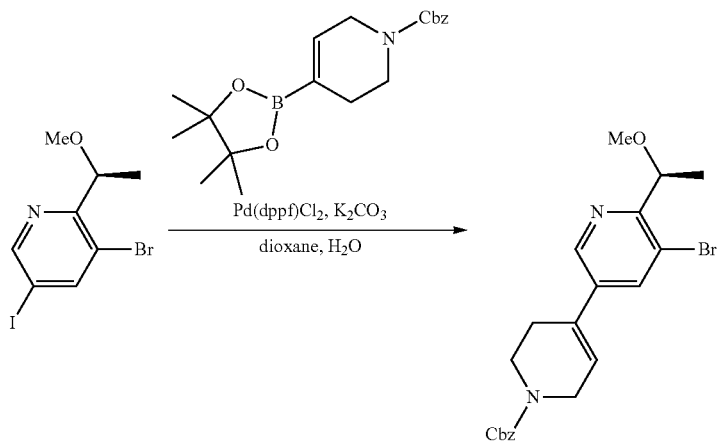

491
-continued
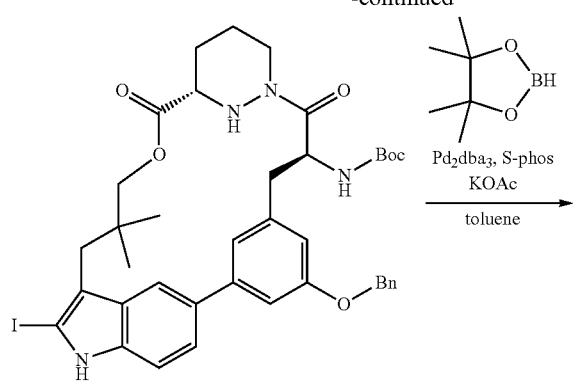
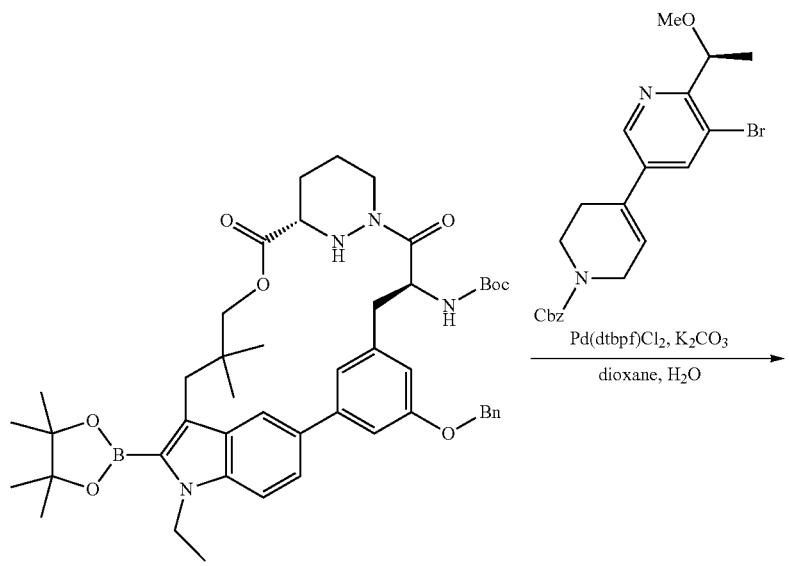
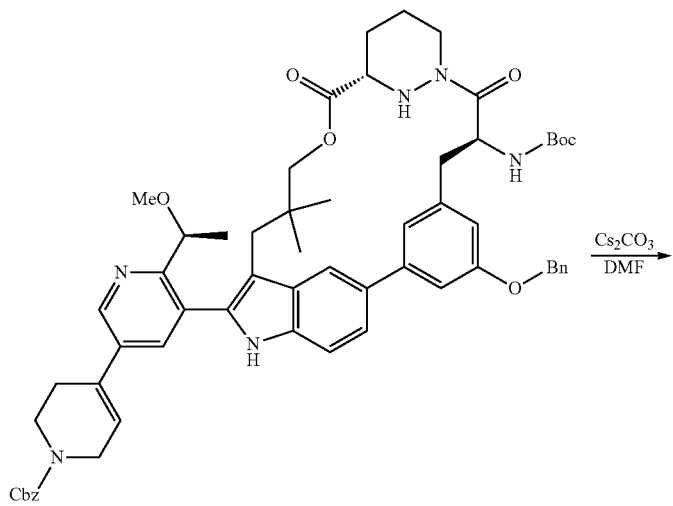

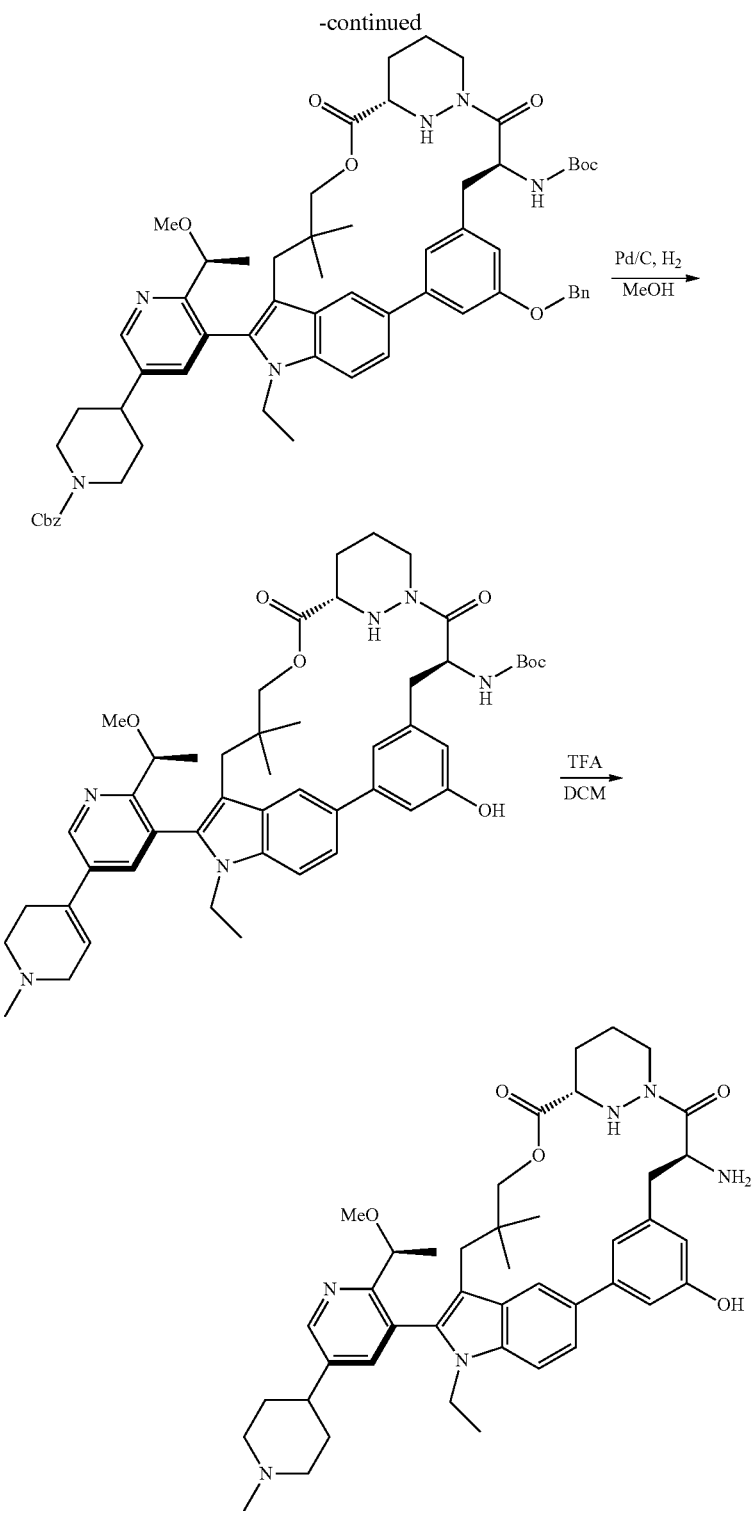

Step 1: Synthesis of benzyl (S)-5-bromo-6-(1-methoxyethyl)-3',6'-dihydro-[3,4'-bipyridine]-1'(2'H)-carboxylate To a solution of (S)-3-bromo-5-iodo-2-(1-methoxyethyl)pyridine (6.0 g, 17.55 mmol) and benzyl 4-(4,4,5,5-tetramethyl-1,3,2-dioxaborolan-2-yl)-3,6-dihydropyridine-1(2H)-carboxylate (7.23 g, 21.05 mmol) in dioxane (70 mL) and H₂O (14 mL) was added K₂CO₃ (6.06 g, 43.86 mmol) and Pd(dppf)Cl₂ (1.28 g, 1.76 mmol). The reaction mixture was heated to 60° C. and stirred for 3 h. The mixture was diluted with H₂O (50 mL) then extracted into EtOAc (3×100 mL). The combined organic layers were washed with brine (3×50 mL), dried over Na₂SO₄, filtered, and concentrated under reduced pressure. Purification by silica gel column chromatography (25% EtOAc/pet. ether) afforded the desired product (7.1 g, 94% yield). LCMS (ESI) m/z: [M+H] calcd for $C_{21}H_{23}BrN_2O_3$: 431.10; found 431.1.

Step 2: Synthesis of tert-butyl ((6³S,4S)-2⁵-(benzyloxy)-10,10-dimethyl-5,7-dioxo-1²-(4,4,5,5-tetramethyl-1,3,2-dioxaborolan-2-yl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate To a solution of tert-butyl ((6³S,4S)-2⁵-(benzyloxy)-1²-iodo-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (5.0 g, 6.31 mmol), $Pd_2(dba)_3$ (690 mg, 757 μmol), S-Phos (0.78 g, 1.89 mmol), and KOAc (2.17 g, 22.08 mmol) in toluene (75 mL) was added 4,4,5,5-tetramethyl-1,3,2-dioxaborolane (5.65 g, 44.15 mmol). The reaction mixture was heated to 60° C. and stirred for 3 h. The reaction was quenched with $H_2O$ at 0° C. then extracted into EtOAc (3×100 mL). The combined organic layers were washed with brine (3×30 mL), dried over $Na_2SO_4$, filtered, and concentrated under reduced pressure. Purification by silica gel column chromatography (50% EtOAc/pet. ether) afforded the desired product (4.5 g, 90% yield). LCMS (ESI) m/z: [M+H] calcd for $C_{75}H_{57}BN_4O_8$: 793.43; found 793.4.

Step 3: Synthesis of benzyl 5-((6³S,4S)-2⁵-(benzyloxy)-4-((tert-butoxycarbonyl)amino)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-6-((S)-1-methoxyethyl)-3',6'-dihydro-[3,4'-bipyridine]-1'(2'H)-carboxylate To a solution of tert-butyl ((6³S,4S)-2⁵-(benzyloxy)-10,10-dimethyl-5,7-dioxo-1²-(4,4,5,5-tetramethyl-1,3,2-dioxaborolan-2-yl)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (4.0 g, 5.05 mmol) and benzyl (S)-5-bromo-6-(1-methoxyethyl)-3',6'-dihydro-[3,4'-bipyridine]-1'(2'H)-carboxylate (2.61 g, 6.06 mmol) in dioxane (50 mL) and $H_2O$ (10 mL) was added $K_2CO_3$ (1.74 g, 12.6 mmol) and $Pd(dtbpf)Cl_2$ (330 mg, 505 μmol). The reaction mixture was heated to 70° C. After 3 h the reaction was diluted with $H_2O$ (40 mL) and extracted into EtOAc (3×100 mL). The combined organic layers were washed with brine (2×50 mL), dried over $Na_2SO_4$, filtered, and concentrated under reduced pressure. Purification by silica gel column chromatography (50% EtOAc/pet. ether) afforded the desired product (4.1 g, 80% yield). LCMS (ESI) m/z: [M+H] calcd for $C_{60}H_{68}N_6O_9$: 1017.51; found 1017.4.

Step 4: Synthesis of benzyl 5-((6³S,4S)-2⁵-(benzyloxy)-4-((tert-butoxycarbonyl)amino)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-6-((S)-1-methoxyethyl)-3',6'-dihydro-[3,4'-bipyridine]-1'(2'H)-carboxylate To a solution of benzyl 5-((6³S,4S)-2⁵-(benzyloxy)-4-((tert-butoxycarbonyl)amino)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-6-((S)-1-methoxyethyl)-3',6'-dihydro-[3,4'-bipyridine]-1'(2'H)-carboxylate (4.0 g, 3.93 mmol) and $Cs_2CO_3$ (3.84 g, 11.80 mmol) in DMF (30 mL) at 0° C. was added iodoethane (2.45 g, 15.73 mmol). The reaction mixture was warmed to room temperature. After 3 h the reaction mixture was diluted with $H_2O$ (100 mL) and extracted into EtOAc (3×200 mL). The combined organic layers were washed with brine (3×100 mL), dried over $Na_2SO_4$, filtered, and concentrated under reduced pressure. Purification by silica gel column chromatography (66% EtOAc/pet. ether) afforded the desired product (1.4 g, 34% yield). LCMS (ESI) m/z: [M+H] calcd for $C_{62}H_{72}N_6O_9$: 1045.54; found 1045.5.

Step 5: Synthesis of tert-butyl ((6³S,4S)-1¹-ethyl-2⁵-hydroxy-1²-(2-((S)-1-methoxyethyl)-5-(1-methylpiperidin-4-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate A solution of benzyl 5-((6³S,4S)-2⁵-(benzyloxy)-4-((tert-butoxycarbonyl)amino)-1¹-ethyl-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-1²-yl)-6-((S)-1-methoxyethyl)-3',6'-dihydro-[3,4'-bipyridine]-1'(2'H)-carboxylate (1.29 g, 1.23 mmol) and Pd/C (700 mg) in MeOH (30 mL) was stirred for 72 h at room temperature under $H_2$ atmosphere. The reaction mixture was then filtered with MeOH (3×50 mL). The filtrate was concentrated under reduced pressure which afforded the desired product (850 mg, crude). LCMS (ESI) m/z: [M+H] calcd for $C_{48}H_{64}N_6O_7$: 837.49; found 837.7.

Step 6: Synthesis of (6³S,4S)-4-amino-1¹-ethyl-2⁵-hydroxy-1²-(2-((S)-1-methoxyethyl)-5-(1-methylpiperidin-4-yl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione To a solution of tert-butyl ((6³S,4S)-1¹-ethyl-2⁵-hydroxy-1²-(2-((S)-1-methoxyethyl)-5-(1-methylpiperidin-4-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)carbamate (840 mg, 1.00 mmol) in DCM (10 mL) at 0° C. was added TFA (3.0 mL, 40.4 mmol). The reaction mixture was warmed to room temperature. After 2 h the reaction was cooled to 0° C., quenched with sat. at. $NaHCO_3$, and extracted into EtOAc (3×50 mL). The combined organic layers were washed with brine (2×30 mL), dried over $Na_2SO_4$, filtered, and concentrated under reduced pressure which afforded product (670 mg, crude). LCMS (ESI) m/z: [M+H] calcd for $C_{43}H_{56}N_6O_5$: 737.44; found 737.3.

Intermediate 26. Synthesis of (6³S, 4S)-4-amino-1¹-ethyl-2⁵-hydroxy-1²-(2-((S)-1-methoxyethyl)-5-(4-methylpiperazin-1-yl)pyridine-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione

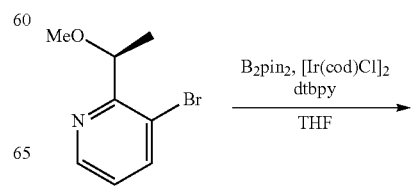

497
-continued

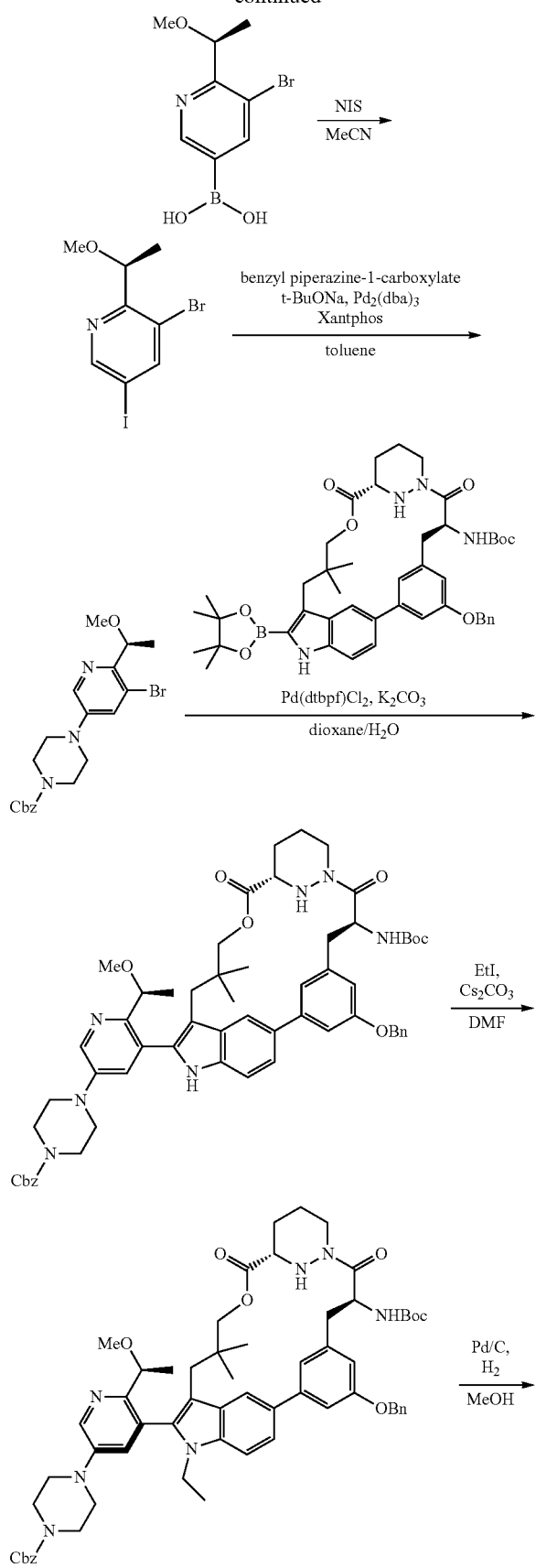

498
-continued

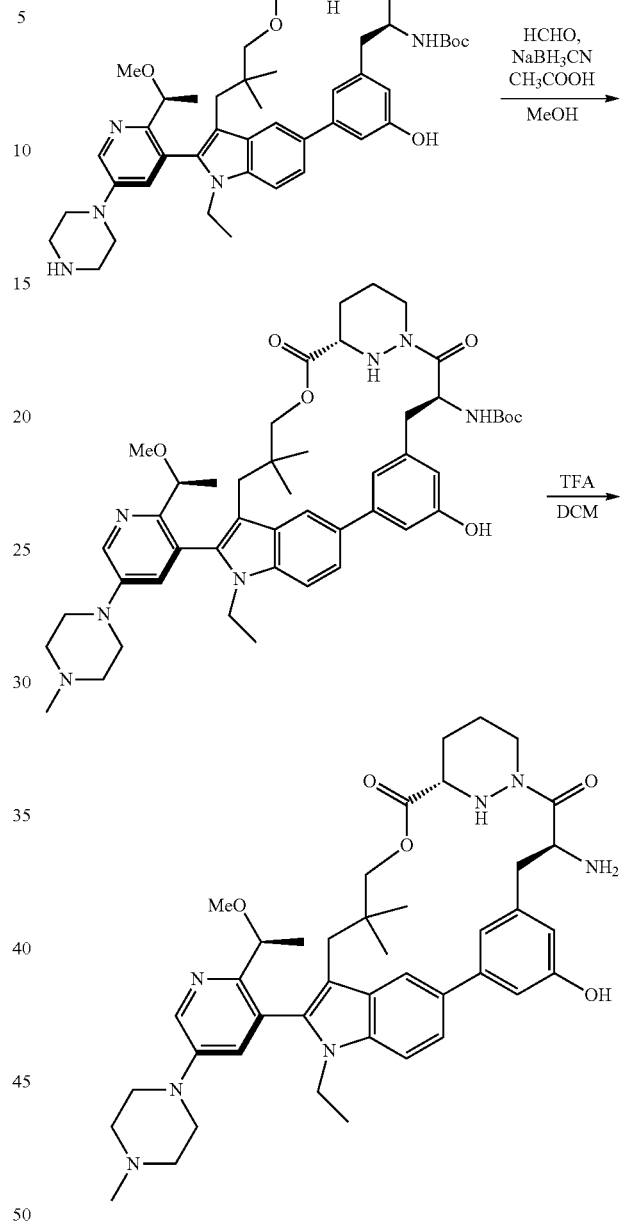

Step 1: Synthesis of (S)-(5-bromo-6-(1-methoxy-ethyl)pyridin-3-yl)boronic Acid To a solution of (S)-3-bromo-2-(1-methoxyethyl)pyridine (40 g, 185 mmol) and bis(pinacolato)diboron (70.5 g, 278 mmol) in THF (1.6 L) at 75° C. was added 4,4'-di-tert-butyl-2,2'-bipyridine (7.45 g, 27.7 mmol) and [Ir(cod)Cl]$_2$ (1.24 mg, 1.85 mmol). After 16 h the mixture was concentrated under reduced pressure and the residue diluted with H$_2$O (1 L). The aqueous layer extracted with DCM/MeOH (2 L, 5:1), dried with Na$_2$SO$_4$, filtered, and concentrated under reduced pressure. Following purification by reverse phase chromatography (10→50% MeCN/H$_2$O, 0.1% HCO$_2$H) the combined product fractions were partially concentrated under reduced pressure. The aqueous layer was extracted with DCM/MeOH (3000 mL, 5:1), dried with $Na_2SO_4$, filtered, and concentrated under reduced pressure to afford the desired product (35.0 g, 65.5% yield). LCMS (ESI) m/z: [M+Na] calcd for $C_8H_{11}BBrNO_3$: 282.00; found 281.1.

Step 2: Synthesis of (S)-3-bromo-5-iodo-2-(1-methoxyethyl)pyridine

To a solution of (S)-(5-bromo-6-(1-methoxyethyl)pyridin-3-yl)boronic acid (35.0 g, 135 mmol) in MeCN (100 mL) was added N-iodosuccinimide (60.6 g, 269 mmol). The resulting reaction mixture was stirred overnight and then concentrated under reduced pressure. Purification by normal phase chromatography (10% EtOAc/pet. ether) afforded the desired product (40.0 g, 78.1% yield). LCMS (ESI) m/z: [M+H] calcd for $C_8H_9BrINO$: 341.90; found 341.8.

Step 3: Synthesis of benzyl (S)-4-(5-bromo-6-(1-methoxyethyl)pyridin-3-yl)piperazine-1-carboxylate To a solution of (S)-3-bromo-5-iodo-2-(1-methoxyethyl)pyridine (7.0 g, 20.5 mmol) and benzyl piperazine-1-carboxylate (9.0 g, 40.8 mmol) in toluene (70 mL) were added $Pd_2(dba)_3$ (375 mg, 0.409 mmol), Xantphos (1.18 g, 2.05 mmol) and sodium tert-butoxide (2.29 g, 24.6 mmol). The resulting mixture was heated to 120° C. and stirred for 16 h then cooled to room temperature and concentrated under reduced pressure. Purification by normal phase chromatography (25% EtOAc/pet. ether) afforded the desired product (5.0 g, 50.6% yield). LCMS (ESI) m/z: [M+H] calcd for $C_{20}H_{24}BrN_3O_3$: 434.11; found 434.0.

Step 4: Synthesis of benzyl 4-(5-(($6^3$S,4S)-$2^5$-(benzyloxy)-4-((tert-butoxycarbonyl)amino)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-$1^2$-yl)-6-((S)-1-methoxyethyl)pyridin-3-yl)piperazine-1-carboxylate To a solution of benzyl (S)-4-(5-bromo-6-(1-methoxyethyl)pyridin-3-yl)piperazine-1-carboxylate (3.29 g, 7.56 mmol) and tert-butyl (($6^3$S,4S)-$2^5$-(benzyloxy)-10,10-dimethyl-5,7-dioxo-$1^2$-(4,4,5,5-tetramethyl-1,3,2-dioxaborolan-2-yl)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (50 g, 6.31 mmol) dioxane (40 mL) and $H_2O$ (10 mL) were added $K_2CO_3$ (1.74 g, 12.614 mmol) and $Pd(dtbpf)Cl_2$ (822 mg, 1.26 mmol) and the resulting mixture was heated to 80° C. for 2 h. The reaction mixture was then concentrated under reduced pressure and diluted with $H_2O$ (1 L). The aqueous layer was extracted with EtOAc (3×200 mL) and the combined organic layers were washed with $H_2O$, dried with $Na_2SO_4$, filtered, and concentrated under reduced pressure. Purification by normal phase chromatography (50% EtOAc/pet. ether) afforded the desired product (5.0 g, 73.8% yield). LCMS (ESI) m/z: [M+H] calcd for $C_{59}H_{69}N_7O_9$: 1020.54; found 1020.6.

Step 5: Synthesis of benzyl 4-(5-(($6^3$S,4S)-$2^5$-(benzyloxy)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-$1^2$-yl)-6-((S)-1-methoxyethyl)pyridin-3-yl)piperazine-1-carboxylate To a stirred solution of benzyl 4-(5-(($6^3$S,4S)-$2^5$-(benzyloxy)-4-((tert-butoxycarbonyl)amino)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-$1^2$-yl)-6-((S)-1-methoxyethyl)pyridin-3-yl)piperazine-1-carboxylate (5.0 g, 5 mmol) in DMF (50 mL) at 0° C. was added $Cs_2CO_3$ (3.19 g, 9.80 mmol) and ethyl iodide (1.53 g, 10 mmol). The resulting mixture was stirred for 2 h at room temperature and then diluted with $H_2O$ (200 mL). The aqueous layer was extracted with EtOAc (3×100 mL) and the combined organic layers were washed with $H_2O$, dried with $Na_2SO_4$, filtered, and concentrated under reduced pressure. Purification by normal phase chromatography (33% EtOAc/pet. ether) afforded the desired product (1.8 g, 35% yield). LCMS (ESI) m/z: [M+H] calcd for $C_{61}H_{73}N_7O_9$: 1048.56; found 1048.4.

Step 6: Synthesis of tert-butyl (($6^3$S, 4S)-$1^1$-ethyl-$2^5$-hydroxy-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a stirred solution of benzyl 4-(5-(($6^3$S, 4S)-$2^5$-(benzyloxy)-4-((tert-butoxycarbonyl)amino)-$1^1$-ethyl-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-$1^2$-yl)-6-((S)-1-methoxyethyl)pyridin-3-yl)piperazine-1-carboxylate (1.80 g, 1.72 mmol) in MeOH (20 mL) was added Pd/C (900 mg). The resulting mixture was stirred for 2 h at room temperature under a hydrogen atmosphere, filtered, and the filter cake washed with MeOH. The filtrate was concentrated under reduced pressure to afford the crude desired product which was used without further purification. LCMS (ESI) m/z: [M+H] calcd for $C_{46}H_{61}N_7O_7$: 824.47; found 824.3.

Step 7: Synthesis of tert-butyl(($6^3$S,4S)-$1^1$-ethyl-$2^5$-hydroxy-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a stirred solution of tert-butyl (($6^3$S, 4S)-$1^1$-ethyl-$2^5$-hydroxy-$1^2$-(2-((S)-1-methoxyethyl)-5-(piperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate carbamate (590 mg, 0.716 mmol) and HCHO (129 mg, 1.43 mmol, 37 wt % in $H_2O$) in MeOH (6 ml) at 0° C. were added $CH_3COOH$ (122 mg, 2.02 mmol) and $NaBH_3CN$ (85.3 mg, 1.35 mmol). The resulting mixture was warmed to room temperature and stirred for 2 h. The reaction mixture was then concentrated under reduced pressure and diluted with $H_2O$ (100 mL). The aqueous layer was extracted with EtOAc (3×100 mL) and the combined organic layers were washed with $H_2O$, dried with $Na_2SO_4$, filtered, concentrated under reduced pressure. pressure to afford the crude desired product which was used without further purification. LCMS (ESI) m/z: [M+H] calcd for $C_{47}H_{63}N_7O_9$: 838.49; found 838.4.

Step 8: Synthesis of ($6^3$S, 4S)-4-amino-$1^1$-ethyl-$2^5$-hydroxy-$1^2$-(2-((S)-1-methoxyethyl)-5-(4-methylpiperazin-1-yl)pyridine-3-yl)-10,10-dimethyl-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-5,7-dione To a stirred solution of tert-butyl(($6^3$S,4S)-$1^1$-ethyl-$2^5$-hydroxy-$1^2$-(2-((S)-1-methoxyethyl)-5-(4-methylpiperazin-1-yl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (590 mg, 0.704 mmol) in DCM (6 mL) at 0° C. was added TFA (3.0 mL). The resulting mixture was stirred for 30 min and then concentrated under reduced pressure to afford the crude desired product which was used without further purification. LCMS (ESI) m/z: [M+H] calcd for $C_{42}H_{55}N_7O_5$: 738.44; found 738.4.

Intermediate 27. Synthesis of $(6^3S,4S,Z)$-4-amino-$1^1$-ethyl-$1^2$-(2-((S)-1-methoxyethyl)-5-(4-methylpiperazin-1-yl)pyridin-3-yl)-10,10-dimethyl-$6^1,6^2,6^3,6^4$, $6^5,6^6$-hexahydro-$1^1$H-8-oxa-2(4,2)-thiazola-1(5,3)-indola-6(1,3)-pyridazinacycloundecaphane-5,7-dione

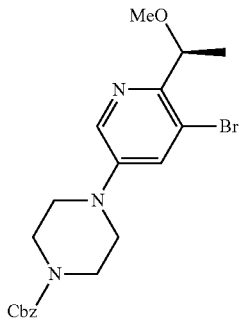 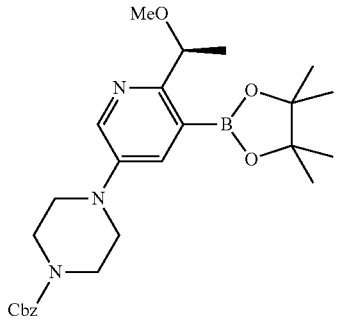 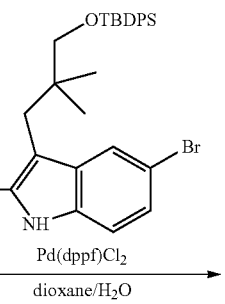

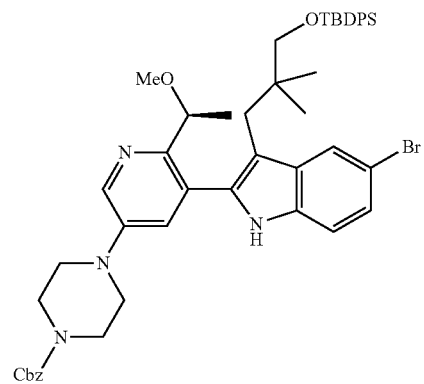 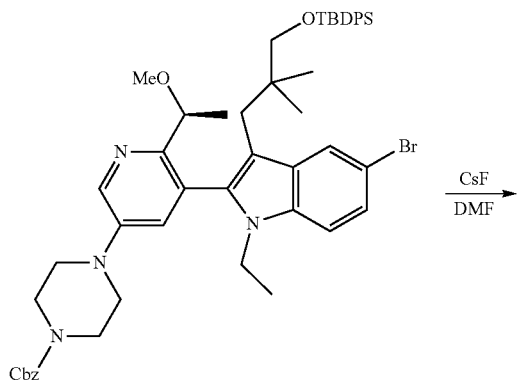

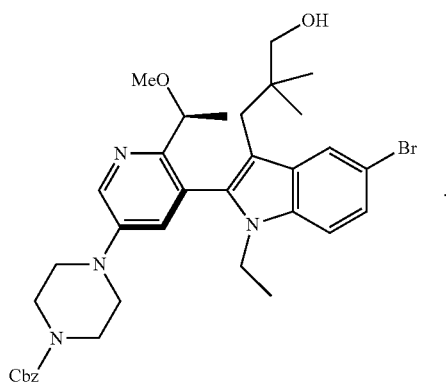

503
504
-continued
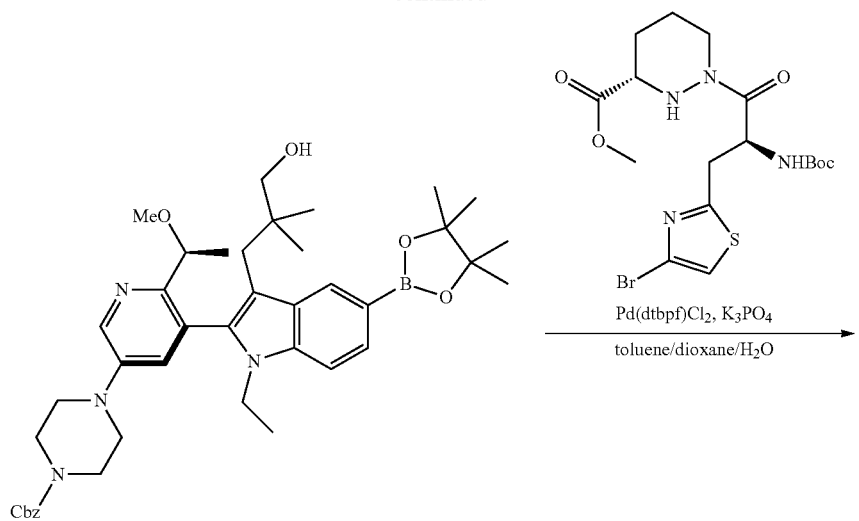
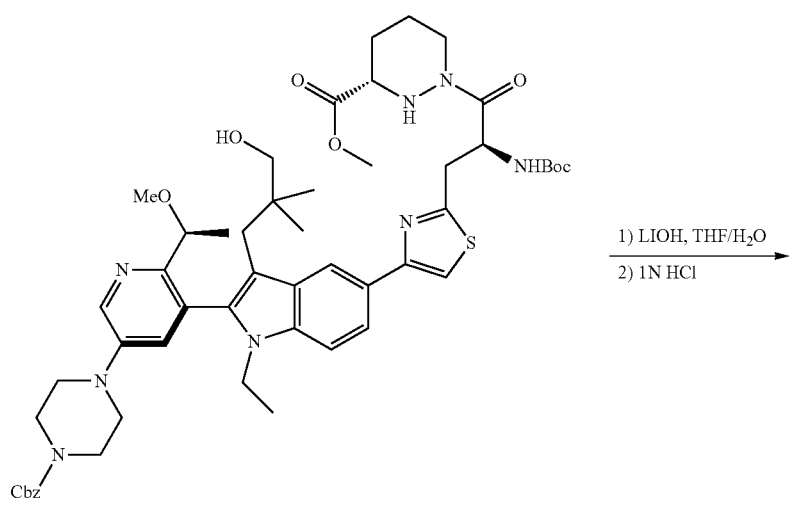
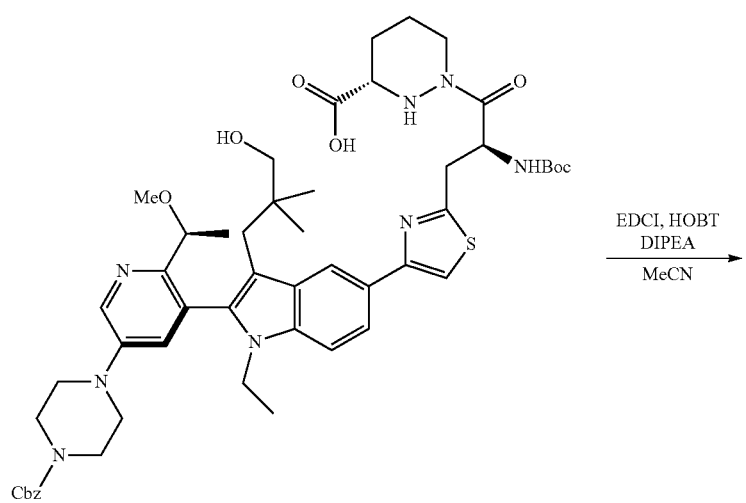

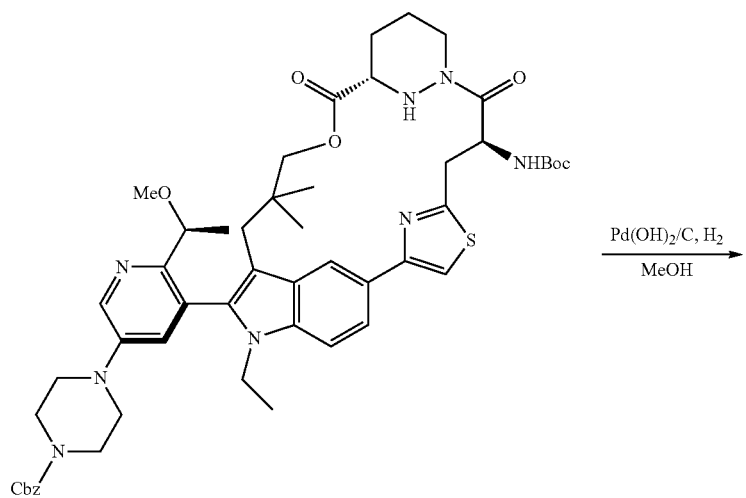
Pd(OH)$_2$/C, H$_2$
MeOH
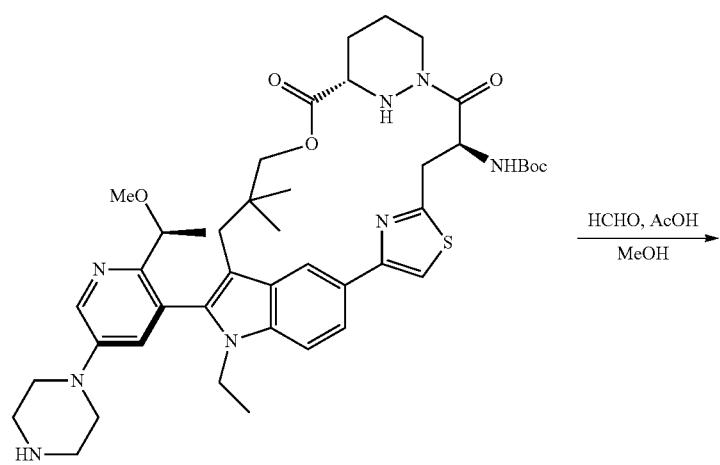
HCHO, AcOH
MeOH
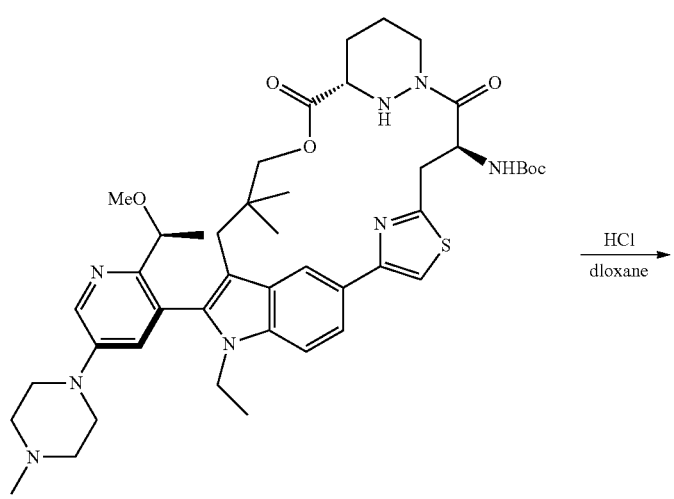
HCl
dioxane

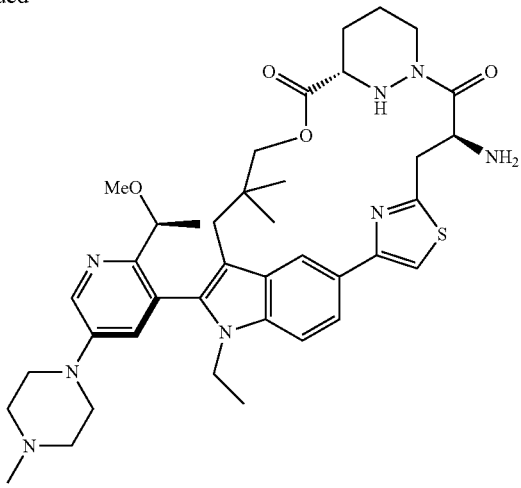

Step 1: Synthesis of benzyl (S)-4-(5-bromo-6-(1-methoxyethyl)pyridin-3-yl)piperazine-1-carboxylate Into a 3-L 3-necked round-bottom flask purged and maintained with an inert atmosphere of argon, was placed benzyl 4-[5-bromo-6-[(1S)-1-methoxyethyl]pyridin-3-yl]piperazine-1-carboxylate (135 g, 310.821 mmol), bis(pinacolato) diboron (86.82 g, 341.903 mmol), Pd(dppf)Cl$_2$ (22.74 g, 31.082 mmol), KOAc (76.26 g, 777.052 mmol), and toluene (1 L). The resulting solution was stirred for 2 days at 90° C. in an oil bath. The reaction mixture was cooled to room temperature. The resulting mixture was concentrated under reduced pressure. The residue was purified by neutral alumina column chromatography (25% EtOAc/hexanes) to afford the desired product (167 g, crude). LCMS (ESI) m/z: [M+H] calcd for $C_{26}H_{36}BN_3O_5$: 481.3; found 482.1.

Step 2: Synthesis of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate Into a 3-L 3-necked round-bottom flask purged and maintained with an inert atmosphere of argon, was placed (S)-4-(6-(1-methoxyethyl)-5-(4,4,5,5-tetramethyl-1,3,2-dioxaborolan-2-yl)pyridin-3-yl)piperazine-1-carboxylate (167 g, 346.905 mmol), 5-bromo-3-[3-[(tert-butyldiphenylsilyl)oxy]-2,2-dimethylpropyl]-2-iodo-1H-indole (224.27 g, 346.905 mmol), Pd(dppf)Cl$_2$ (25.38 g, 34.69 mmol), dioxane (600 mL), H$_2$O (200 mL), K$_3$PO$_4$ (184.09 g, 867.262 mmol), and toluene (200 mL). The resulting solution was stirred for overnight at 70° C. in an oil bath. The reaction mixture was cooled to room temperature after reaction completed. The resulting mixture was concentrated under reduced pressure. The residue was purified by normal phase column chromatography (50% EtOAc/hexanes) to afford the desired product (146 g, 48.2% yield). LCMS (ESI) m/z: [M+H] calcd for $C_{49}H_{57}BrN_4O_4Si$: 872.3; found 873.3.

Step 3: Synthesis of benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate To a stirred mixture of benzyl (S)-4-(5-(5-bromo-3-(3-((tert-butyldiphenylsilyl)oxy)-2,2-dimethylpropyl)-1H-indol-2-yl)-6-(1-methoxyethyl)pyridin-3-yl)piperazine-1-carboxylate (146 g, 167.047 mmol) and Cs$_2$CO$_3$ (163.28 g, 501.14 mmol) in DMF (1200 mL) was added C$_2$H$_5$I (52.11 g, 334.093 mmol) in portions at 0° C. under N$_2$ atmosphere. The final reaction mixture was stirred at room temperature for 12 h. The resulting mixture was diluted with EtOAc (1 L) and washed with brine (3×1.5 L). The organic layers were dried over anhydrous Na$_2$SO$_4$. After filtration, the filtrate was concentrated under reduced pressure to afford the desired product (143 g, crude). LCMS (ESI) m/z: [M+H] calcd for $C_{51}H_{61}BrN_4O_4Si$: 900.4; found 901.4.

Step 4: Synthesis of benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate To a stirred mixture of benzyl (S)-4-(5-(5-bromo-3-(3-((tert-butyldiphenylsilyl)oxy)-2,2-dimethylpropyl)-1-ethyl-1H-indol-2-yl)-6-(1-methoxyethyl)pyridin-3-yl)piperazine-1-carboxylate (143 g, 158.526 mmol) in DMF (1250 mL) was added CsF (72.24 g, 475.578 mmol). The reaction mixture was stirred at 60° C. for 2 days under N$_2$ atmosphere. The resulting mixture was diluted with EtOAc (1 L) and washed with brine (3×1 L). The organic phase was concentrated under reduced pressure and the residue was purified by silica gel column chromatography to afford two atropisomers of benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (38 g, 36% yield, RT=1.677 min in 3 min LCMS (0.1% FA)) and B (34 g, 34% yield, RT=1.578 min in 3 min LCMS (0.1% FA)). LCMS (ESI) m/z: [M+H] calcd for $C_{35}H_{43}BrN_4O_4$: 663.2; found 662.2.

Step 5: Synthesis of benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate Into a 500-mL 3-necked round-bottom flask purged and maintained with an inert atmosphere of nitrogen, was placed benzyl (S)-4-(5-(5-bromo-1-ethyl-3-(3-hydroxy-2,2-dimethylpropyl)-1H-indol-2-yl)-6-(1-methoxyethyl)pyridin-3-yl)piperazine-1-carboxylate A (14 g, 21.095 mmol), bis (pinacolato)diboron (5.89 g, 23.205 mmol), Pd(dppf)Cl$_2$ (1.54 g, 2.11 mmol), KOAc (5.18 g, 52.738 mmol), and toluene (150 mL). The resulting solution was stirred for 5 h at 90° C. in an oil bath. The reaction mixture was then cooled to room temperature. The resulting mixture was concentrated under reduced pressure and the residue was purified by silica gel column chromatography to afford the desired product (12 g, 76.0% yield). LCMS (ESI) m/z: [M+H] calcd for C$_{41}$H$_{55}$BN$_4$O$_6$: 710.4; found 711.3.

Step 6: Synthesis of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl) hexahydropyridazine-3-carboxylate Into a 250-mL round-bottom flask purged and maintained with an inert atmosphere of argon, was placed benzyl (S)-4-(5-(1-ethyl-3-(3-hydroxy-2,2-dimethylpropyl)-5-(4,4,5,5-tetramethyl-1,3,2-dioxaborolan-2-yl)-1H-indol-2-yl)-6-(1-methoxyethyl)pyridin-3-yl)piperazine-1-carboxylate (10.8 g, 15.196 mmol), methyl (3S)-1-[(2S)-3-(4-bromo-1,3-thiazol-2-yl)-2-[(tert-butoxycarbonyl)amino]propanoyl]-1,2-diazinane-3-carboxylate (7.98 g, 16.716 mmol), Pd(dtbpf)Cl$_2$ (0.99 g, 1.52 mmol), K$_3$PO$_4$ (8.06 g, 37.99 mmol), toluene (60 mL), dioxane (20 mL), and H$_2$O (20 mL). The resulting solution was stirred for 3 h at 70° C. in an oil bath. The reaction mixture was then cooled to room temperature. The resulting solution was extracted with EtOAc (2×50 mL) and concentrated under reduced pressure. The residue was purified by normal phase column chromatography to afford the desired product (8 g, 50.9% yield). LCMS (ESI) m/z: [M+H] calcd for C$_{52}$H$_{68}$N$_8$O$_9$S: 980.5; found 980.9.

Step 7: Synthesis of (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl) hexahydropyridazine-3-carboxylic Acid To a stirred mixture of methyl (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylate (12 g, 12.230 mmol) in THF (100 mL) and H$_2$O (100 mL) was added LiOH (2.45 g, 61.148 mmol) under N$_2$ atmosphere and the resulting mixture was stirred for 2 h at room temperature. The resulting mixture was concentrated under reduced pressure and the pH of aqueous phase was acidified to 5 with HCl (1N) at 0° C. The aqueous layer was extracted with DCM (3×100 mL). The organic phase was concentrated under reduced pressure to afford the desired product (10 g, 84.5% yield). LCMS (ESI) m/z: [M+H] calcd for C$_{51}$H$_{66}$N$_8$O$_9$S: 966.5; found 967.0.

Step 8: Synthesis of benzyl 4-(5-((6$^3$S,4S,Z)-4-((tert-butoxycarbonyl)amino)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-1$^2$-yl)-6-((S)-1-methoxyethyl)pyridin-3-yl)piperazine-1-carboxylate Into a 3-L round-bottom flask purged and maintained with an inert atmosphere of nitrogen, was placed (S)-1-((S)-3-(4-(2-(5-(4-((benzyloxy)carbonyl)piperazin-1-yl)-2-((S)-1-methoxyethyl)pyridin-3-yl)-1-ethyl-3-(3-hydroxy-2,2-dimethylpropyl)-1H-indol-5-yl)thiazol-2-yl)-2-((tert-butoxycarbonyl)amino)propanoyl)hexahydropyridazine-3-carboxylic acid (18 g, 18.61 mmol), MeCN (1.8 L), DIPEA (96.21 g, 744.417 mmol), EDCI (107.03 g, 558.313 mmol), HOBT (25.15 g, 186.104 mmol). The resulting solution was stirred for overnight at room temperature. The resulting mixture was concentrated under reduced pressure after reaction completed. The resulting solution was diluted with DCM (1 L) and was washed with HCl (3×1 L, 1N aqueous). The resulting mixture was washed with H$_2$O (3×1 L) and then the organic layer was concentrated. The residue was purified by normal phase column chromatography (50% EtOAc/hexanes) to afford the desired product (10.4 g, 54.9% yield). LCMS (ESI) m/z: [M+H] calcd for C$_{51}$-1641%08S: 948.5; found 949.3.

Step 9: Synthesis of tert-butyl ((6$^3$S,4S,Z)-11-ethyl-1$^2$-(2-((S)-1-methoxyethyl)-5-(piperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl) carbamate Into a 250-mL round-bottom flask purged and maintained with an inert atmosphere of nitrogen, was placed benzyl 4-(5-((6$^3$S,4S,Z)-4-((tert-butoxycarbonyl)amino)-1$^1$-ethyl-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-1$^2$-yl)-6-((S)-1-methoxyethyl)pyridin-3-yl)piperazine-1-carboxylate (10.40 g, 10.957 mmol), Pd(OH)$_2$/C (5 g, 46.984 mmol), and MeOH (100 mL). The resulting solution was stirred for 3 h at room temperature under a 2 atm H$_2$ atmosphere. The solids were filtered out and the filter cake was washed with MeOH (3×100 mL). The combined organic phase was concentrated under reduced pressure to afford the desired product (8.5 g, 90.4% yield). LCMS (ESI) m/z: [M+H] calcd for C$_{43}$H$_{58}$N$_8$O$_6$S: 814.4; found 815.3.

Step 10: Synthesis of tert-butyl ((6$^3$S,4S,Z)-1$^1$-ethyl-1$^2$-(2-((S)-1-methoxyethyl)-5-(4-methylpiperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl)carbamate Into a 1000-mL round-bottom flask purged and maintained with an inert atmosphere of nitrogen, was placed tert-butyl ((6$^3$S,4S,Z)-11-ethyl-1$^2$-(2-((S)-1-methoxyethyl)-5-(piperazin-1-yl)pyridin-3-yl)-10,10-dimethyl-5,7-dioxo-6$^1$,6$^2$,6$^3$,6$^4$,6$^5$,6$^6$-hexahydro-1$^1$H-8-oxa-2(4,2)-thiazola-1(5,3)-indola-6(1,3)-pyridazinacycloundecaphane-4-yl) carbamate (8.5 g, 10.429 mmol), MeOH (100 mL), AcOH (1.88 g, 31.286 mmol) and stirred for 15 min. Then HCHO (1.88 g, 23.15 mmol, 37% aqueous solution) and NaBH$_3$CN (788 mg, 12.5 mmol) was added at room temperature. The resulting solution was stirred for 3 hr. The resulting mixture was quenched with H$_2$O (100 mL) and concentrated under reduced pressure to remove MeOH. The resulting solution was diluted with DCM (300 mL) and was washed with H$_2$O (3×100 mL). The organic phase was concentrated under reduced pressure to afford the desired product (8.2 g, 90.1% yield). LCMS (ESI) m/z: [M+H] calcd for C$_{44}$H$_{60}$N$_8$O$_6$S: 828.4; found 829.3.

511

Step 10: Synthesis of (6³S,4S,Z)-4-amino-1¹-ethyl-1²-(2-((S)-1-methoxyethyl)-5-(4-methylpiperazin-1-yl)pyridin-3-yl)-10,10-dimethyl-6¹,6²,6³,6⁴,6⁵,6⁶-hexahydro-1¹H-8-oxa-2(4,2)-thiazola-1(5,3)-indola-6(1,3)-pyridazinacycloundecaphane-5,7-dione Into a 250-mL round-bottom flask purged and maintained with an inert atmosphere of nitrogen, was placed tert-butyl ((6³S,4S,Z)-1¹-ethyl-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-2(4,2)-thiazola-1(5,3)-indola-6(1,3)- pyridazinacycloundecaphane-4-yl)carbamate (8.20 g, 9.891 mmol) and dioxane (40 mL), followed by the addition of HCl in 1,4-dioxane (4M, 40 mL) at 0° C. The resulting solution was stirred for 1 h at 0° C. The mixture was then concentrated under reduced pressure. The resulting solution was diluted with DCM (600 mL) and sat. aq. NaHCO₃(400 mL). The organic phase was then washed twice with brine (500 mL). The organic phase was concentrated under reduced pressure to afford the desired product (7.2 g, 94.9% yield).

Intermediate 28. Synthesis of (6³S,4S)-4-amino-2⁵-(difluoromethyl)-1¹-ethyl-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione

512

-continued

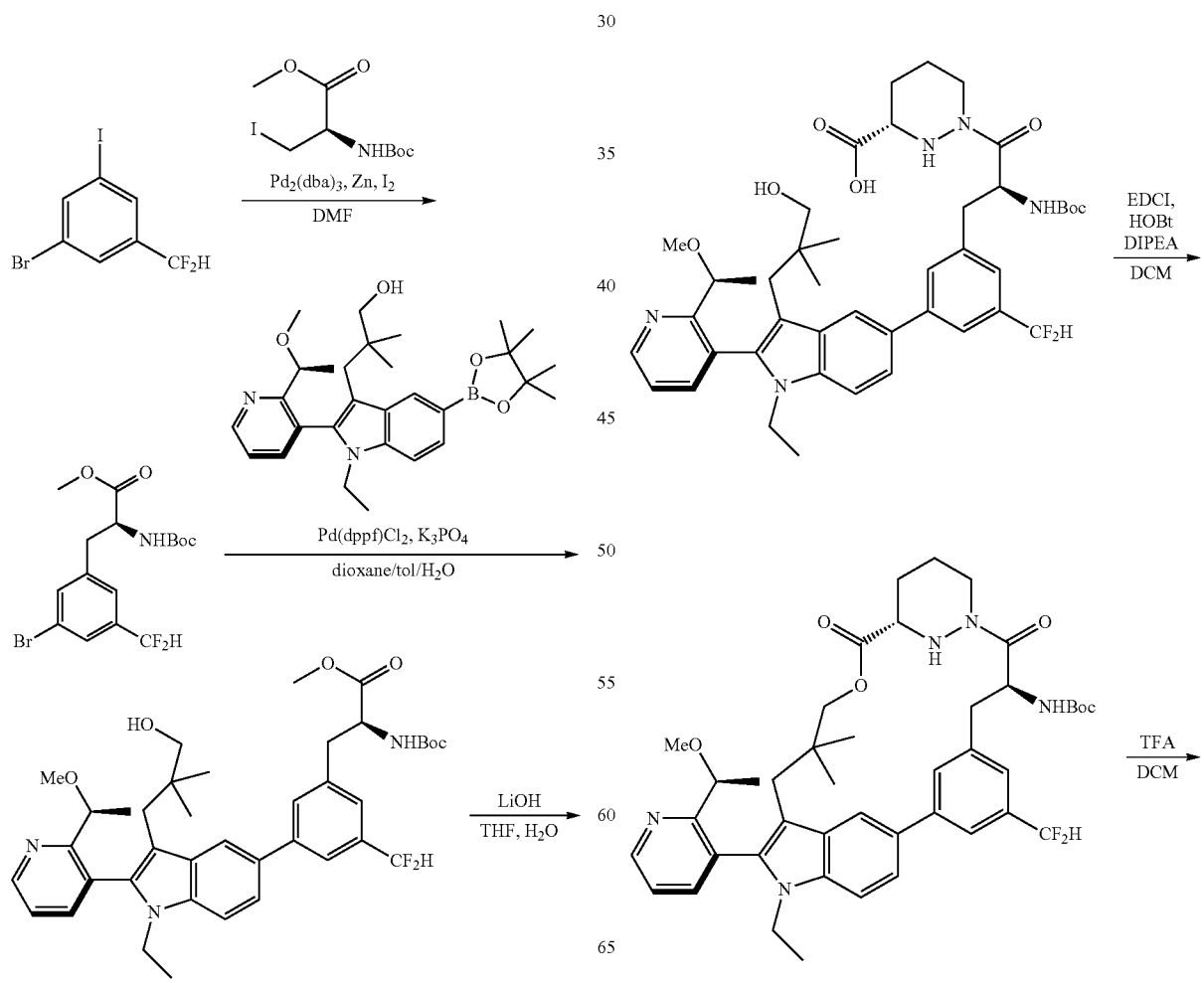

-continued

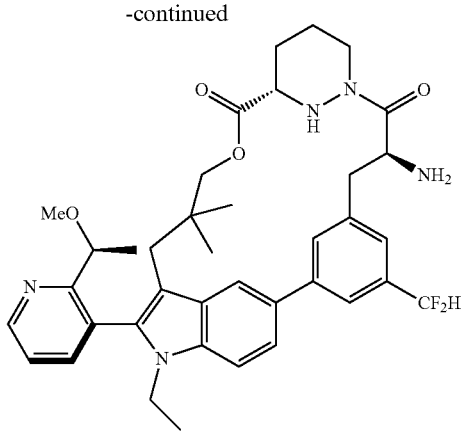

Step 1: Synthesis of methyl (S)-3-(3-bromo-5-(difluoromethyl)phenyl)-2-((tert-butoxycarbonyl)amino)propanoate Into a 1000 mL 3-necked round-bottom flask was added Zn powder (43.42 g, 663.835 mmol) and 12 (1.30 g, 5.106 mmol) in DMF (400 mL) at room temperature. To the above mixture was added a solution of methyl (2R)-2-[(tert-butoxycarbonyl)amino]-3-iodopropanoate (36.42 g, 110.64 mmol) in DMF (10 mL). The mixture was heated to 30° C. for 10 min. To the mixture was then added a solution of methyl (2R)-2-[(tert-butoxycarbonyl)amino]-3-iodopropanoate (72.83 g, 221.28 mmol) in DMF (20 mL) dropwise at room temperature. The resulting mixture was stirred for 30 min. The resulting mixture was filtered and the solution was added to a mixture of 1-bromo-3-(difluoromethyl)-5-iodobenzene (85.0 g, 255.321 mmol), tris(furan-2-yl) phosphane (3.56 g, 15.319 mmol), and $Pd_2(dba)_3$ (4.68 g, 5.106 mmol) in DMF (400 mL) at room temperature under argon atmosphere. The reaction mixture was heated to 60° C. for 10 min and was then removed from the oil bath and was stirred for 1 h until the temperature of the resulting mixture cooled down to 50° C. The reaction was quenched with aq. $NH_4Cl$ (3000 mL) and the aqueous layer was extracted with EtOAc (3×1000 mL). The combined organic layers were washed with brine (2×1000 mL), dried over anhydrous $Na_2SO_4$, filtered, and concentrated under reduced pressure. The residue was purified by silica gel column chromatography (9% EtOAc/pet. ether) to afford the desired product (59 g, 56.6% yield).

Step 2: Synthesis of methyl (S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoate A mixture of methyl (2S)-3-[3-bromo-5-(difluoromethyl)phenyl]-2-[(tert-butoxycarbonyl)amino] propanoate (90.0 g, 220.459 mmol), (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (1.50 g, 3.046 mmol), $Pd(dppf)Cl_2$ (16.13 g, 22.046 mmol) and $K_3PO_4$ (116.99 g, 551.148 mmol) in dioxane (600 mL), $H_2O$ (200 mL), and toluene (200 mL) was stirred for 2 h at 70° C. The resulting mixture was concentrated under reduced pressure and then diluted with $H_2O$ (300 mL). The mixture was extracted with EtOAc (3×500 mL). The combined organic layers were washed with $H_2O$ (3×500 mL), dried over anhydrous $Na_2SO_4$. After filtration, the filtrate was concentrated under reduced pressure and the residue was purified by silica gel column chromatography (50% EtOAc/pet. ether) to afford the desired product (128 g, 83.7% yield). LCMS (ESI) m/z: [M+H] calcd for $C_{39}H_{49}F_2N_3O_6$: 694.37; found 694.2.

Step 3: Synthesis of (S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoic Acid To a stirred solution of methyl (S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoate (125.0 g, 180.159 mmol) in THF (800 mL) was added $LiOH \cdot H_2O$ (11.48 g, 479.403 mmol) in $H_2O$ (200 mL) dropwise at 0° C. The resulting mixture was stirred for 2 h at 0° C. The mixture was acidified to pH 6 with 1 M HCl (aq.) and was then extracted with EtOAc (3×800 mL). The combined organic layers were washed with brine (2×200 mL), dried over anhydrous $Na_2SO_4$. After filtration, the filtrate was concentrated under reduced pressure to afford the desired product (125 g, crude). LCMS (ESI) m/z: [M+H] calcd for $C_{38}H_{47}F_2N_3O_6$: 680.37; found 680.2.

Step 4: Synthesis of methyl (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylate To a stirred solution of methyl (3S)-1,2-diazinane-3-carboxylate (39.77 g, 275.814 mmol) and NMM (185.98 g, 1838.760 mmol) in DCM (1500 mL) was (S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoic acid (125.0 g, 183.876 mmol), HOBt (12.42 g, 91.938 mmol) and EDCI (70.50 g, 367.752 mmol) in portions at 0° C. The resulting mixture was stirred at room temperature for 16 h. The reaction mixture was then washed with 0.5 M HCl (2×1000 mL) and brine (2×800 mL), dried over anhydrous $Na_2SO_4$, filtered, and concentrated under reduced pressure. The residue was purified by silica gel column chromatography (50% EtOAc/pet.ether) to afford the desired product (110 g, 74.2% yield). LCMS (ESI) m/z: [M+H] calcd for $C_{44}H_{57}F_2N_5O_7$: 806.43; found 806.2.

Step 5: Synthesis of (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylic Acid To a stirred solution of methyl (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylate (110.0 g, 136.482 mmol) in THF (800 mL) was added a solution of $LiOH \cdot H_2O$ (17.18 g, 409.446 mmol) in $H_2O$ (200 mL) in portions at 0° C. The resulting mixture was stirred for 2 h at 0° C. and was then neutralized to pH 6 with 0.5 M HCl. The resulting mixture was extracted with EtOAc (3×800 mL) and the combined organic layers were washed with brine (2×600 mL), dried over anhydrous Na$_2$SO$_4$, filtered, and concentrated under reduced pressure to afford the desired product (100 g, crude). LCMS (ESI) m/z: [M+H] calcd for C$_{43}$H$_{55}$F$_2$N$_5$O$_7$: 792.42; found 792.4.

Step 6: Synthesis of tert-butyl ((6$^3$S,4S)-2$^5$-(difluoromethyl)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate To a stirred solution of (S)-1-((S)-2-((tert-butoxycarbonyl)amino)-3-(3-(difluoromethyl)-5-(1-ethyl-3-(3-hydroxy-2,2-dimethylpropyl)-2-(2-((S)-1-methoxyethyl)pyridin-3-yl)-1H-indol-5-yl)phenyl)propanoyl)hexahydropyridazine-3-carboxylic acid (100.0 g, 126.273 mmol) in DCM (6000 mL) was added DIPEA (163.20 g, 1262.730 mmol), HOBt (85.31 g, 631.365 mmol), and EDCl (363.10 g, 1894.095 mmol) dropwise at 0° C. The resulting mixture was stirred overnight at room temperature. The mixture was then washed with 0.5 M HCl (2×2 000 mL) and brine (2×2000 mL), dried over anhydrous Na$_2$SO$_4$, filtered, and concentrated under reduced pressure. The residue was purified by silica gel column chromatography (50% EtOAc/pet. ether) to afford the desired product (70 g, 71.6% yield). LCMS (ESI) m/z: [M+H] calcd for C$_{43}$H$_{53}$F$_2$N$_5$O$_6$: 774.41; found 774.0.

Step 7: Synthesis of (6$^3$S,4S)-4-amino-2$^5$-(difluoromethyl)-1$^1$-ethyl-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione To a stirred solution of tert-butyl ((6$^3$S,4S)-2$^5$-(difluoromethyl)-1$^1$-ethyl-1$^2$-(2-((S)-1-methoxyethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)carbamate (202.0 mg, 0.261 mmol) in DCM (2 mL) was added TFA (1.0 mL) dropwise at 0° C. The resulting mixture was stirred for 1.5 h at 0° C. and was then concentrated under reduced pressure to afford the desired product. LCMS (ESI) m/z: [M+H] calcd for C$_{38}$H$_{45}$F$_2$N$_5$O$_4$: 674.35; found 674.5.

Intermediate 29. Synthesis of (6$^3$S,4S)-4-amino-1$^1$-ethyl-2$^5$-(fluoromethyl)-1$^2$-(2-((S)-1-methoxyethyl)pyridin-3-yl)-10,10-dimethyl-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-5,7-dione

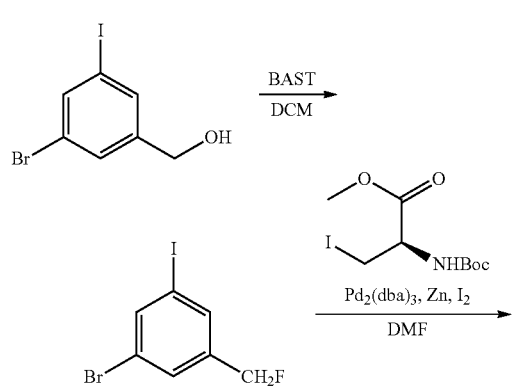

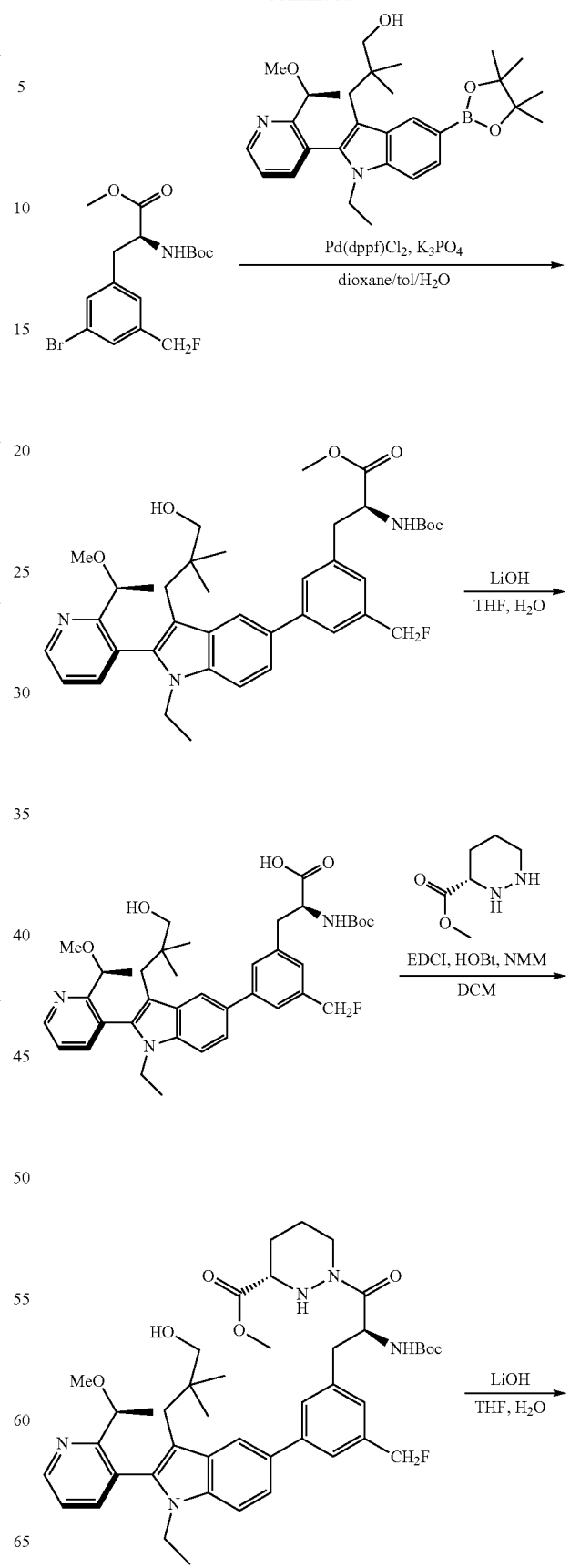

517
-continued

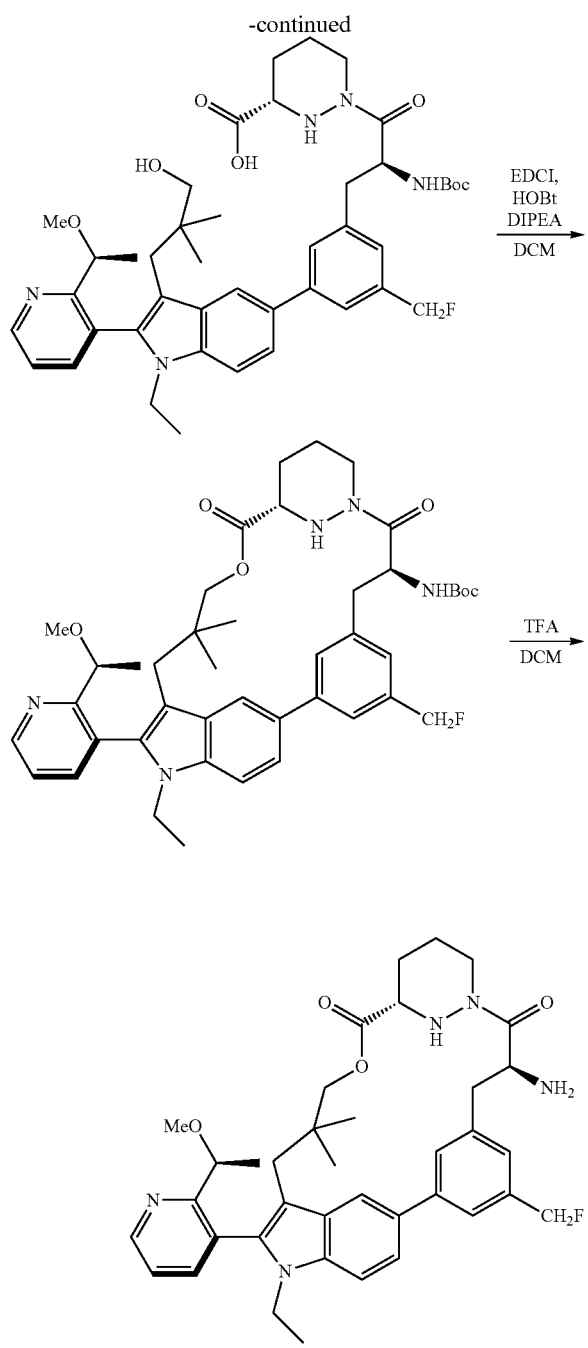

518

Step 2: Synthesis of methyl (2S)-3-[3-bromo-5-(fluoromethyl)phenyl]-2-[(tert-butoxycarbonyl)amino]propanoate Into a 1000 mL 3-necked round-bottom flask was added Zn powder (32.40 g, 495.358 mmol) in DMF (350.0 mL) and $I_2$ (967.12 mg, 3.810 mmol). To the mixture was added a solution of methyl (2R)-2-[(tert-butoxycarbonyl)amino]-3-iodopropanoate (27.0 g, 82.03 mmol) in DMF (10 mL). The mixture was heated to 30° C. for 10 min. To the mixture was then added a solution of methyl (2R)-2-[(tert-butoxycarbonyl)amino]-3-iodopropanoate (54.0 g, 164.07 mmol) in DMF (20 mL). The resulting mixture was stirred for 30 min at room temperature and was filtered. The resulting solution was added to a mixture of 1-bromo-3-(fluoromethyl)-5-iodobenzene (60 g, 190.522 mmol), tris(furan-2-yl)phosphane (2.65 g, 11.431 mmol), and $Pd_2(dba)_3$ (3.49 g, 3.810 mmol) in DMF (400 mL) at room temperature under argon atmosphere and the reaction mixture was heated to 60° C. for 10 min then removed the oil bath. The resulting mixture was stirred for about 1 h until the temperature cooled down to 50° C. The reaction was quenched with aq. $NH_4Cl$ (3000 mL) and the resulting mixture was extracted with EtOAc (3×1000 mL). The combined organic layers were washed with brine (2×1000 mL) and dried over anhydrous $Na_2SO_4$. After filtration, the filtrate was concentrated under reduced pressure. The residue was purified by silica gel column chromatography (9% EtOAc/pet. ether) to afford the desired product (45 g, 60% yield).

Step 3: Synthesis of methyl (S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoate A mixture of methyl (2S)-3-[3-bromo-5-(fluoromethyl)phenyl]-2-[(tert-butoxycarbonyl)amino]propanoate (75.28 g, 192.905 mmol), (S)-3-(1-ethyl-2-(2-(1-methoxyethyl)pyridin-3-yl)-5-(4,4,5,5-tetramethyl-1,3,2-dioxaborolan-2-yl)-1H-indol-3-yl)-2,2-dimethylpropan-1-ol (95 g, 192.905 mmol), $Pd(dppf)Cl_2$ (14.11 g, 19.291 mmol) and $K_2CO_3$ (53.32 g, 385.810 mmol) in dioxane (900 mL) and $H_2O$ (180 mL) was stirred for 2 h at 80° C. The resulting mixture was concentrated under reduced pressure and was then diluted with $H_2O$. The resulting mixture was extracted with EtOAc (3×1200 mL) and the combined organic layers were washed with $H_2O$ (3×500 mL) and dried over anhydrous $Na_2SO_4$. After filtration, the filtrate was concentrated under reduced pressure. The residue was purified by silica gel column chromatography (50% EtOAc/pet. ether) to afford the desired product (105 g, 80% yield). LCMS (ESI) m/z: [M+H] calcd for $C_{39}H_{50}FN_3O_6$: 676.38; found 676.1.

Step 4: Synthesis of (S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoic Acid To a stirred solution of methyl (S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoate (108 g, 159.801 mmol) in THF (500 mL) was added a solution of $LiOH \cdot H_2O$ (11.48 g, 479.403 mmol) in $H_2O$ (500 mL) at 0° C. The resulting mixture was stirred for 2 h at 0° C. and was then acidified to pH 6 with 1 M HCl (aq.). The mixture was extracted with EtOAc (3×800 mL) and the combined Step 1: Synthesis of 1-bromo-3-(fluoromethyl)-5-iodobenzene To a solution of (3-bromo-5-iodophenyl)methanol (175.0 g, 559.227 mmol) in DCM (2 L) was added BAST (247.45 g, 1118.454 mmol) dropwise at 0° C. The resulting mixture was stirred for 16 h at room temperature. The reaction was quenched with sat. aq. $NaHCO_3$ at 0° C. The organic layers were washed with $H_2O$ (3×700 mL) and dried over anhydrous $Na_2SO_4$. After filtration, the filtrate was concentrated under reduced pressure. The residue was purified by silica gel column chromatography (3% EtOAc/pet. ether) to afford the desired product (120 g, 68% yield).

organic layers were washed with brine (2×200 mL) and dried over anhydrous $Na_2SO_4$. After filtration, the filtrate was concentrated under reduced pressure to afford the desired product (101 g, crude). LCMS (ESI) m/z: [M+H] calcd for $C_{38}H_{48}FN_3O_6$: 662.36; found 662.1.

Step 5: Synthesis of methyl (S)-1-((S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoyl)hexahydropyridazine-3-carboxylate To a stirred solution of (S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoic acid (103 g, 155.633 mmol) and NMM (157.42 g, 1556.330 mmol) in DCM (1200 mL) was added methyl (3S)-1,2-diazinane-3-carboxylate (33.66 g, 233.449 mmol), HOBt (10.51 g, 77.816 mmol) and EDCl (59.67 g, 311.265 mmol) in portions at 0° C. The resulting mixture was stirred a t room temperature for 16 h. The organic layers were then washed with 0.5 M HCl (2×1000 mL) and brine (2×800 mL), dried over anhydrous $Na_2SO_4$, filtered, and concentrated under reduced pressure. The residue was purified by silica gel column chromatography (50% EtOAc/pet. ether) to afford the desired product (103 g, 83% yield). LCMS (ESI) m/z: [M+H] calcd for $C_{44}H_{58}FN_5O_7$: 788.44; found 788.1.

Step 6: Synthesis of (S)-1-((S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoyl)hexahydropyridazine-3-carboxylic Acid To a stirred solution of methyl (S)-1-((S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoyl)hexahydropyridazine-3-carboxylate (103 g, 130.715 mmol) in THF (700 mL) was added a solution of $LiOH·H_2O$ (27.43 g, 653.575 mmol) in $H_2O$ (700 mL) at 0° C. The resulting mixture was stirred for 2 h at 0° C. and was then neutralized to pH 6 with 1 M HCl. The resulting mixture was extracted with EtOAc (3×800 mL) and the combined organic layers were washed with brine (2×600 mL), dried over anhydrous $Na_2SO_4$, filtered, and concentrated under reduced pressure to afford the desired product (101 g, crude). LCMS (ESI) m/z: [M+H] calcd for $C_{43}H_{56}FN_5O_7$: 774.43; found 774.1.

Step 7: Synthesis of tert-butyl (($6^3$S,4S)-$1^1$-ethyl-$2^5$-(fluoromethyl)-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate To a stirred solution of (5)-1-((S)-2-((tert-butoxycarbonyl)amino)-3-(3-(1-ethyl-3-(3-hydroxy-2,2-dimethylpropyl)-2-(2-((S)-1-methoxyethyl)pyridin-3-yl)-1H-indol-5-yl)-5-(fluoromethyl)phenyl)propanoyl)hexahydropyridazine-3-carboxylic acid (101 g, 130.50 mmol) in DCM (5500 mL) was added DIPEA (227.31 mL, 1305.0 mmol) and HOBt (88.17 g, 652.499 mmol), and EDCl (375.26 g, 1957.498 mmol) at 0° C. The resulting mixture was stirred at room temperature overnight. The mixture was then washed with 0.5 M HCl (2×2000 mL), brine (2×2000 mL), dried over anhydrous $Na_2SO_4$, filtered, and concentrated under reduced pressure. The residue was purified by silica gel column chromatography (50% EtOAc/pet. ether) to afford the desired product (68 g, 65% yield). LCMS (ESI) m/z: [M+H] calcd for $C_{43}H_{54}FN_5O_6$: 756.42; found 756.4.

Step 8: Synthesis of (2S)—N-(($6^3$S,4S)-$1^1$-ethyl-$2^5$-(fluoromethyl)-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-3-methyl-2-(methylamino)butanamide To a stirred solution of tert-butyl (($6^3$S,4S)-$1^1$-ethyl-$2^5$-(fluoromethyl)-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)carbamate (350 mg, 0.403 mmol) in DCM (4 mL) was added TFA (1.50 mL) at 0° C. The resulting mixture was stirred at room temperature for 1.5 h and was then concentrated under reduced pressure to afford the desired product (600 mg, crude). LCMS (ESI) m/z: [M+H] calcd for $C_{38}H_{46}FN_5O_4$: 656.36; found 656.4.

Intermediate A-1. Synthesis of N-methyl-N—((S)-1-((R)-1-tritylaziridine-2-carbonyl)pyrrolidine-3-carbonyl)-L-valine

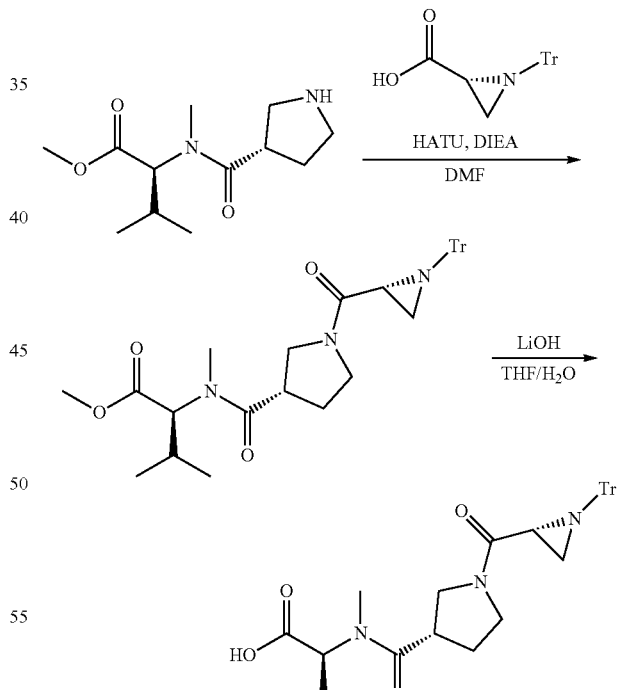

Step 1: Synthesis of methyl N-methyl-N—((S)-1-((R)-1-tritylaziridine-2-carbonyl)pyrrolidine-3-carbonyl)-L-valinate To a mixture of methyl N-methyl-N—((S)-pyrrolidine-3-carbonyl)-L-valinate (0.840 g, 3.47 mmol) and (R)-1-tritylaziridine-2-carboxylic acid (1.713 g, 5.2 mmol) in DMF (20 mL) at 0° C. was added DIPEA (3.0 mL, 17.33 mmol) and HATU (2.636 g, 6.93 mmol). The reaction mixture was stirred for 3 h, at which point the mixture was extracted with EtOAc (200 mL). The EtOAc layer was washed with brine (3×50 mL), dried over Na$_2$SO$_4$, filtered, and concentrated under reduced pressure. The crude residue was purified by reverse phase chromatography (10→50% MeCN/H$_2$O) to afford the desired product (1.02 g, 53% yield) as a solid. LCMS (ESI) m/z: [M+H] calcd for C$_{34}$H$_{39}$N$_3$O$_4$: 554.30; found 554.3.

Step 2: Synthesis of N-methyl-N—((S)-1-((R)-1-tritylaziridine-2-carbonyl)pyrrolidine-3-carbonyl)-L-valine To a solution of methyl N-methyl-N—((S)-1-((R)-1-tritylaziridine-2-carbonyl)pyrrolidine-3-carbonyl)-L-valinate (1.0 g, 1.81 mmol) in THF (10 mL) at 0° C. was added a solution of LiOH.H$_2$O (0.3789 g, 9.03 mmol) in H$_2$O (9.0 mL). After 3 h, the reaction solution was neutralized to pH 7 with sat. aq. NH$_4$Cl. The resulting mixture was extracted with EtOAc (3×50 mL) and the combined organic layers were washed with brine (3×20 mL), dried over Na$_2$SO$_4$, filtered, and concentrated under reduced pressure to afford the crude product (740 mg, 75.9% yield) as a solid. LCMS (ESI) m/z: [M−H] calcd for C$_{33}$H$_{37}$N$_3$O$_4$: 538.27; found 538.2.

Intermediate A-2. Synthesis of N-methyl-N—((S)-1-((S)-1-tritylaziridine-2-carbonyl)pyrrolidine-3-carbonyl)-L-valine Step 1: Synthesis of Methyl N-methyl-N—((S)-1-((S)-1-tritylaziridine-2-carbonyl)pyrrolidine-3-carbonyl)-L-valinate To a mixture of methyl N-methyl-N—((S)-pyrrolidine-3-carbonyl)-L-valinate (0.800 g, 3.30 mmol) and (S)-1-tritylaziridine-2-carboxylic acid (1.305 g, 3.96 mmol) in DMF (16 mL) at 0° C. was added DIPEA (2.9 mL, 16.5 mmol) and HATU (1.88 g, 4.9 mmol). The reaction mixture was warmed to room temperature and stirred for 1 h, at which point the mixture was diluted with EtOAc. The mixture was washed with sat. NH$_4$Cl and the resulting aqueous layer extracted with EtOAc. The combined organic layers were washed with brine, dried over Na$_2$SO$_4$, filtered, and concentrated under reduced pressure. The crude residue was purified by reverse phase chromatography (10→80% MeCN/H$_2$O) to afford the desired product (1.17 g, 64% yield) as a solid. LCMS (ESI) m/z: [M+H] calcd for C$_{34}$H$_{39}$N$_3$O$_4$: 554.30; found 554.3.

Step 2: Synthesis of N-methyl-N—((S)-1-((S)-1-tritylaziridine-2-carbonyl)pyrrolidine-3-carbonyl)-L-valine To a stirred solution of methyl N-methyl-N—((S)-1-tritylaziridine-2-carbonyl)pyrrolidine-3-carbonyl)-L-valinate (1.10 g, 1.99 mmol) in THF (10.0 mL) at 0° C. was added a 1M solution of LiOH (9.93 mL, 9.93 mmol). The reaction mixture was warmed to room temperature and stirred for 16 h. The reaction mixture was cooled to 0° C. and quenched with sat. aq. NH$_4$Cl to pH 6. The resulting mixture was extracted with EtOAc. The combined organic layers were washed with brine, dried over Na$_2$SO$_4$, filtered, and concentrated under reduced pressure to afford the desired crude product (1.2 g). LCMS (ESI) m/z: [M+H] calcd for C$_{33}$H$_{37}$N$_3$O$_4$: 540.29; found 540.3.

Intermediate A-3. Synthesis of N-methyl-N-(1-((R)-1-tritylaziridine-2-carbonyl)piperidine-4-carbonyl)-L-valine

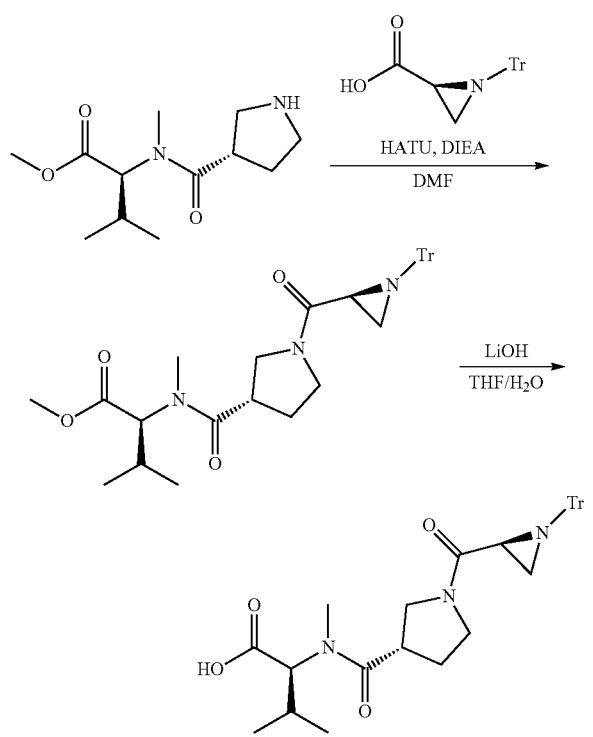

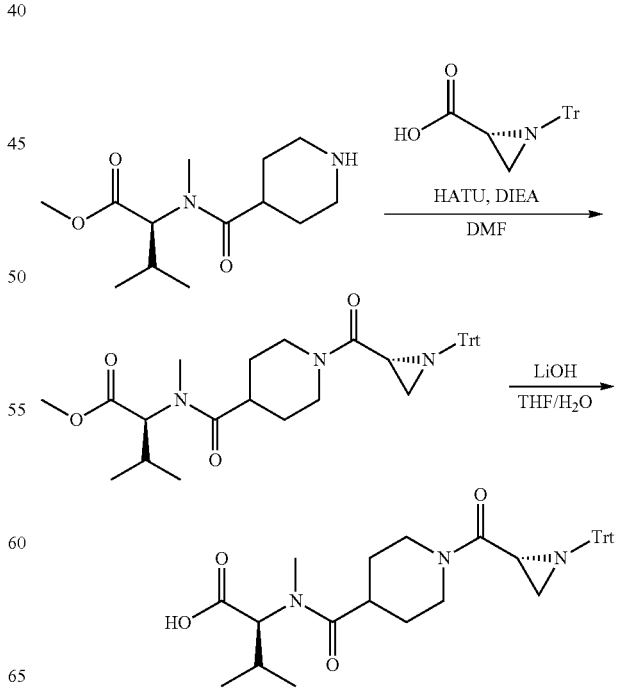

Step 1: Synthesis of methyl N-methyl-N-(1-((R)-1-tritylaziridine-2-carbonyl)piperidine-4-carbonyl)-L-valinate To a solution of (R)-1-tritylaziridine-2-carboxylic acid (1.157 g, 3.51 mmol) and methyl N-methyl-N-(piperidine-4-carbonyl)-L-valinate (0.600 g, 2.34 mmol) in DMF (20 mL) at 0° C. was added DIPEA (0.204 mL, 11.70 mmol) and HATU (1.780 g, 4.68 mmol. After 3 h, the reaction mixture was extracted with EtOAc (200 mL). The combined organic layers were washed with brine (3×50 mL), dried over $Na_2SO_4$, filtered, and concentrated under reduced pressure. The residue was purified by reverse phase chromatography (10→50% MeCN/$H_2O$) to afford the desired product (740 mg, 55.7% yield) as a solid. LCMS (ESI) m/z: [M+H] calcd for $C_{35}H_{41}N_3O_4$: 568.32; found 568.3.

Step 2: Synthesis of N-methyl-N-(1-((R)-1-tritylaziridine-2-carbonyl)piperidine-4-carbonyl)-L-valine To a solution of methyl N-methyl-N-(1-((R)-1-tritylaziridine-2-carbonyl)piperidine-4-carbonyl)-L-valinate (0.700 g, 1.23 mmol) in THF (7.0 mL) at 0° C. was added a solution of $LiOH \cdot H_2O$ (0.259 g, 6.17 mmol) in $H_2O$ (6.0 mL). The resulting solution was warmed to room temperature and stirred for 3 h. The reaction mixture was diluted with EtOAc (100 mL) and was washed with sat. brine (5×50 mL). The organic layer was dried over $Na_2SO_4$, filtered, and concentrated under reduced pressure to afford the crude product (700 mg) as a solid. LCMS (ESI) m/z: [M−H] calcd for $C_{34}H_{39}N_3O_4$: 552.29; found 552.2.

Intermediate A-4. Synthesis of N-methyl-N-(1-((S)-1-tritylaziridine-2-carbonyl)piperidine-4-carbonyl)-L-valine

Step 1: Synthesis of methyl N-methyl-N-(1-((S)-1-tritylaziridine-2-carbonyl)piperidine-4-carbonyl)-L-valinate To a solution of methyl N-methyl-N-(piperidine-4-carbonyl)-L-valinate (0.550 g, 2.15 mmol) and (S)-1-tritylaziridine-2-carboxylic acid (0.848 g, 2.57 mmol) in DMF (10.0 mL) at 0° C. was added DIPEA (1.9 mL, 10.7 mmol) and HATU (1.2 g, 3.2 mmol). The reaction mixture was warmed to room temperature and stirred for 1 h. The reaction mixture was diluted with EtOAc (50 mL) and washed with sat. $NH_4Cl$ (60 mL). The aqueous layer was extracted with EtOAc (3×50 mL). The combined organic layers were washed with brine (200 mL), dried over $Na_2SO_4$, filtered, and concentrated under reduced pressure. The residue was purified by reverse phase chromatography (10→80% MeCN/$H_2O$) to afford the desired product (1.2 g, 98.5% yield) as a solid. LCMS (ESI) m/z: [M+H] calcd for $C_{35}H_{41}N_3O_4$: 568.32; found 568.3.

Step 2: Synthesis of N-methyl-N-(1-((S)-1-tritylaziridine-2-carbonyl)piperidine-4-carbonyl)-L-valine To a solution of methyl N-methyl-N-(1-((S)-1-tritylaziridine-2-carbonyl)piperidine-4-carbonyl)-L-valinate (1.20 g, 2.11 mmol) in THF (11.0 mL) at 0° C. was added 1M LiOH (10.57 mL, 10.57 mmol). The resulting solution was warmed to room temperature and stirred for 16 h. The reaction mixture was cooled to 0° C. and quenched with sat. $NH_4Cl$ until pH 6. The resulting mixture was extracted with EtOAc (3×50 mL) and the combined organic layers were washed with brine (3×50 mL), dried over $Na_2SO_4$, filtered, and concentrated under reduced pressure to afford the crude product (900 mg). LCMS (ESI) m/z: [M−H] calcd for $C_{34}H_{39}N_3O_4$: 554.29; found 554.3.

Intermediate A-5. Synthesis of N-methyl-N-(1-((R)-1-tritylaziridine-2-carbonyl)azetidine-3-carbonyl)-L-valine

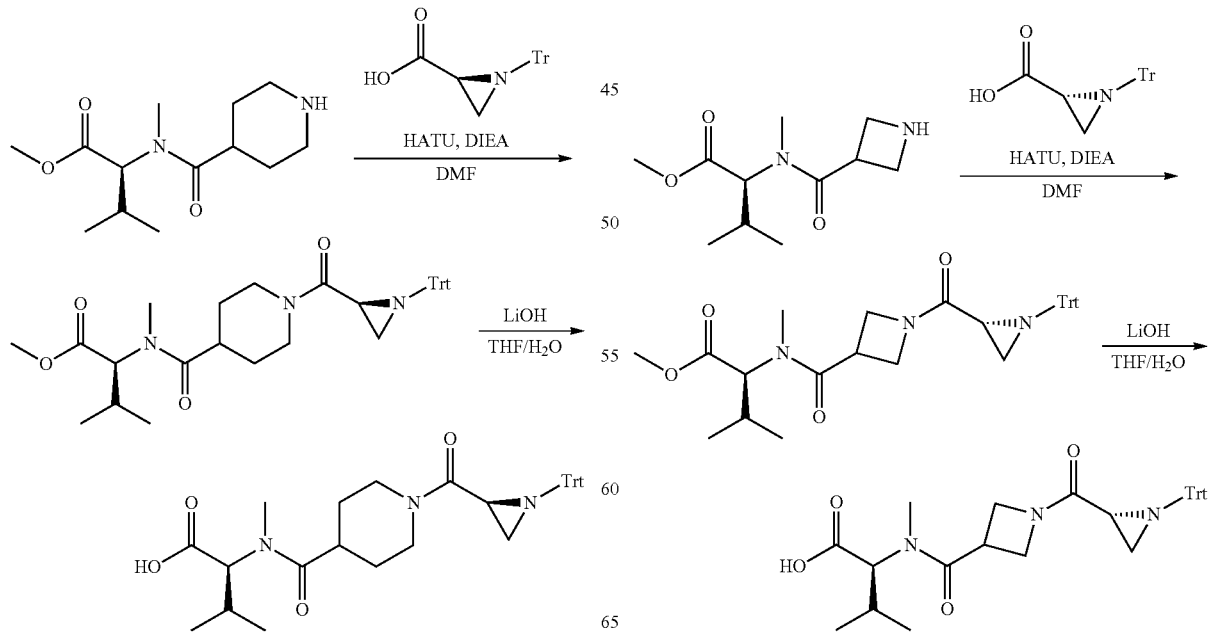

Step 1: Synthesis of methyl N-methyl-N-(1-((R)-1-tritylaziridine-2-carbonyl)azetidine-3-carbonyl)-L-valinate To a solution of methyl N-(azetidine-3-carbonyl)-N-methyl-L-valinate (0.410 g, 1.79 mmol) and (R)-1-tritylaziridine-2-carboxylic acid (0.887 g, 2.69 mmol) in DMF (10 mL) at 0° C. was added DIPEA (1.56 mL, 8.98 mmol) and HATU (1.37 g, 3.59 mmol). The reaction mixture was stirred for 1 h. The resulting mixture was then extracted with EtOAc (3×50 mL) and the combined organic layers were washed with brine (3×20 mL), dried over $Na_2SO_4$, filtered, and concentrated under reduced pressure. The residue was purified by reverse phase chromatography (10→80% $MeCN/H_2O$) to afford the desired product (650 mg, 67% yield) as a solid. LCMS (ESI) m/z: [M+H] calcd for $C_{33}H_{37}N_3O_4$: 540.29; found 540.3.

Step 2: Synthesis of N-methyl-N-(1-((R)-1-tritylaziridine-2-carbonyl)azetidine-3-carbonyl)-L-valine To a solution of methyl N-methyl-N-(1-((R)-1-tritylaziridine-2-carbonyl)azetidine-3-carbonyl)-L-valinate (0.650 mg, 1.20 mmol) in THF (10 mL) at 0° C. was added a 1M solution of $LiOH.H_2O$ (6.03 mL). The reaction mixture was stirred for 3 h. The resulting mixture was then quenched with sat. $NH_4Cl$ until pH 7. The resulting mixture was extracted with EtOAc (3×20 mL) and the combined organic layers were washed with brine (3×20 mL), dried over $Na_2SO_4$, filtered, and concentrated under reduced pressure to afford the desired crude product (588 mg) as a solid. LCMS (ESI) m/z: [M−H] calcd for $C_{32}H_{35}N_3O_4$: 526.27; found 526.3.

Intermediate A-6. Synthesis of N-methyl-N-(1-((S)-1-tritylaziridine-2-carbonyl)azetidine-3-carbonyl)-L-valine

Step 1: Synthesis of methyl N-methyl-N-(1-((S)-1-tritylaziridine-2-carbonyl)azetidine-3-carbonyl)-L-valinate To a solution of methyl N-(azetidine-3-carbonyl)-N-methyl-L-valinate (0.550 g, 2.41 mmol) and (S)-1-tritylaziridine-2-carboxylic acid (0.952 g, 2.89 mmol) in DMF (10 mL) at 0° C. was added DIPEA (2.1 mL, 12.05 mmol) and HATU (1.37 g, 3.61 mmol). The reaction mixture was warmed to room temperature and stirred for 1 h. The resulting mixture was diluted with EtOAc (50 mL) and washed with sat. $NH_4Cl$ (60 mL). The aqueous layer was then extracted with EtOAc (3×50 mL) and the combined organic layers were washed with brine (200 mL), dried over $Na_2SO_4$, filtered, and concentrated under reduced pressure. The residue was purified by reverse phase chromatography (10→80% $MeCN/H_2O$) to afford the desired product (820 mg, 63% yield) as a solid. LCMS (ESI) m/z: [M+H] calcd for $C_{33}H_{37}N_3O_4$: 540.29; found 540.3.

Step 2: Synthesis of N-methyl-N-(1-((S)-1-tritylaziridine-2-carbonyl)azetidine-3-carbonyl)-L-valine To a solution of methyl N-methyl-N-(1-((S)-1-tritylaziridine-2-carbonyl)azetidine-3-carbonyl)-L-valinate (0.800 g, 1.48 mmol) in THF (8.0 mL) at 0° C. was added 1M LiOH (7.41 mL, 7.41 mmol). The reaction mixture was warmed to room temperature and stirred for 16 h and was then cooled to 0° C. and quenched with sat. $NH_4Cl$ until pH 6. The resulting mixture was extracted with EtOAc (3×50 mL) and the combined organic layers were washed with brine (150 mL), dried over $Na_2SO_4$, filtered, and concentrated under reduced pressure. The residue was purified by reverse phase chromatography (10→80% $MeCN/H_2O$+0.5% $NH_4HCO_3$) to afford the desired product (440 mg, 56% yield) as a solid. LCMS (ESI) m/z: [M−H] calcd for $C_{32}H_{35}N_3O_4$: 524.25; found 524.2.

Intermediate A-7. Synthesis of (2R,3S)-3-phenylaziridine-2-carboxylic Acid

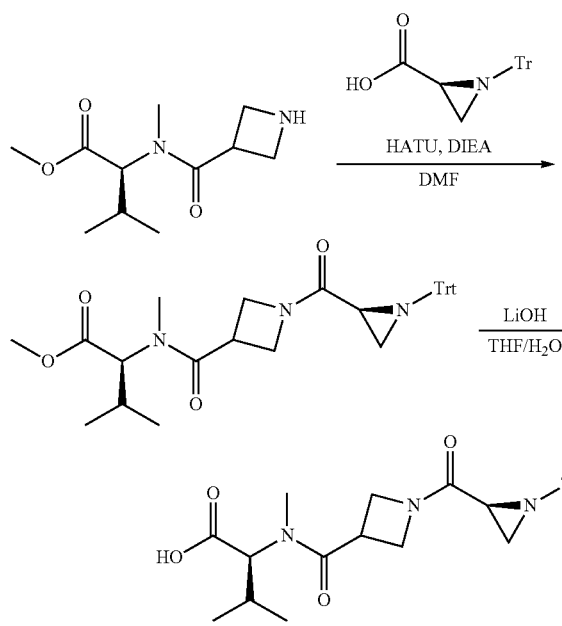

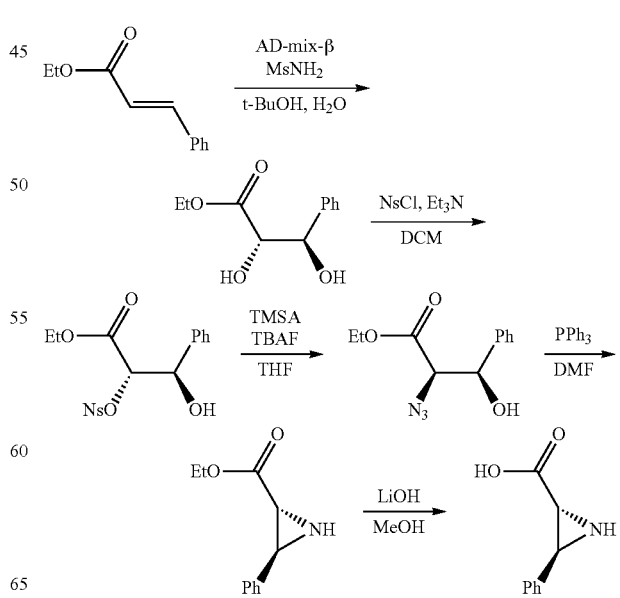

Step 1: Synthesis of ethyl (2S,3R)-2,3-dihydroxy-3-phenylpropanoate

To a solution of ethyl cinnamate (2.0 g, 11.4 mmol) in t-BuOH (35.0 mL) and H$_2$O (35.0 mL) at 0° C. was added AD-mix-β (15.83 g, 20.32 mmol), and methanesulfonamide (1.08 g, 11.3 mmol). The reaction mixture was stirred at room temperature for 16 h. The reaction was cooled to 0° C. and quenched with aq. KHSO$_4$. The resulting mixture was extracted with EtOAc (3×100 mL) and the combined organic layers were washed with brine (2×90 mL), dried over Na$_2$SO$_4$, filtered, and concentrated under reduced pressure. The residue was purified by normal phase chromatography (50% EtOAc/pet. ether) to afford the desired product (2.2 g, 82% yield) as a solid.

Step 2: Synthesis of Ethyl (2S,3R)-3-hydroxy-2-(((4-nitrophenyl)sulfonyl)oxy)-3-phenylpropanoate To a solution of ethyl (2S,3R)-2,3-dihydroxy-3-phenylpropanoate (2.0 g, 9.5 mmol) and Et$_3$N (3.97 mL, 28.5 mmol) in DCM (30.0 mL) at 0° C. was added 4-nitrobenzenesulfonyl chloride (2.11 g, 9.51 mmol). The resulting mixture was stirred for 1 h and was then diluted with H$_2$O (300 mL). The mixture was extracted with DCM (3×100 mL) and the combined organic layers were washed with brine (2×100 mL), dried over Na$_2$SO$_4$, filtered, and concentrated under reduced pressure. The residue was purified by prep-TLC (50% EtOAc/pet. ether) to afford the desired product (2.8 g, 67% yield) as a solid.

Step 3: Synthesis of ethyl (2R,3R)-2-azido-3-hydroxy-3-phenylpropanoate

To a solution of ethyl (2S,3R)-3-hydroxy-2-(((4-nitrophenyl)sulfonyl)oxy)-3-phenylpropanoate (2.80 g, 7.08 mmol) in THF (30 mL) at room temperature was added trimethylsilyl azide (1.63 g, 14.2 mmol) and TBAF (1M in THF, 14.16 mL, 14.16 mmol). The reaction mixture was heated to 60° C. and was stirred for 16 h. The reaction mixture was then cooled to room temperature, diluted with H$_2$O (150 mL), and extracted with EtOAc (3×50 mL). The combined organic layers were washed with brine (2×30 mL), dried over Na$_2$SO$_4$, filtered, and concentrated under reduced pressure. The residue was purified by normal phase chromatography (50% EtOAc/pet. ether) to afford the desired product (1.2 g, 64% yield) as an oil.

Step 4: Synthesis of ethyl (2R,3S)-3-phenylaziridine-2-carboxylate

To a solution of ethyl (2R,3R)-2-azido-3-hydroxy-3-phenylpropanoate (1.20 g, 5.10 mmol) in DMF (15.0 mL) was added PPh$_3$ (1.61 g, 6.12 mmol). The reaction mixture was stirred at room temperature for 30 min and then heated to 80° C. for an additional 16 h. The reaction mixture was then cooled to room temperature, diluted with H$_2$O (100 mL), and extracted with EtOAc (3×40 mL). The combined organic layers were washed with brine (20 mL), dried over Na$_2$SO, filtered, and concentrated under reduced pressure. The residue was purified by normal phase chromatography (16% EtOAc/pet. ether) to afford the desired product (620 mg, 57% yield) as an oil. LCMS (ESI) m/z: [M+H] calcd for C$_{11}$H$_{13}$NO$_2$: 192.10; found 192.0.

Step 5: Synthesis of (2R,3S)-3-phenylaziridine-2-carboxylic Acid

To a solution of ethyl (2R,3S)-3-phenylaziridine-2-carboxylate (0.100 g, 0.523 mmol) in MeOH (0.70 mL) at 0° C. was added a solution of LiOH (18.8 mg, 0.784 mmol) in H$_2$O (0.70 mL). The reaction mixture was stirred for 1 h. The mixture was then diluted with MeCN (10 mL), and the resulting precipitate was collected by filtration and washed with MeCN (2×10 mL) to afford the crude desired product (70 mg) as a solid. LCMS (ESI) m/z: [M+H] calcd for C$_9$H$_9$NO$_2$: 164.07; found 164.0.

Intermediate A-8. Synthesis of (2S,3R)-3-phenylaziridine-2-carboxylic Acid

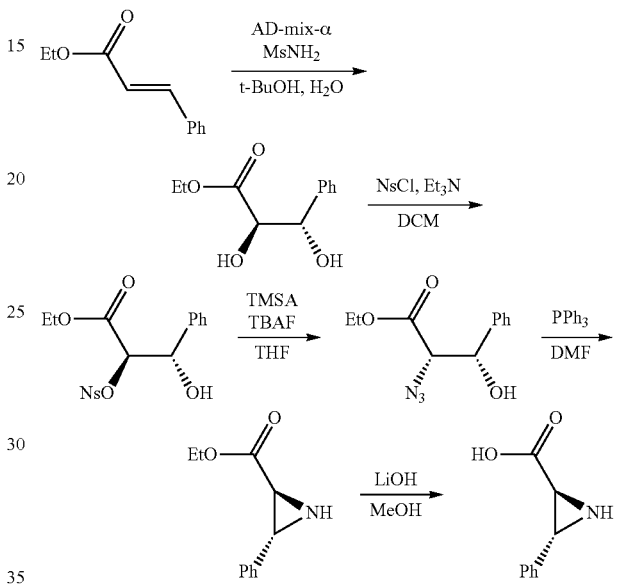

Step 1: Synthesis of ethyl (2R,3S)-2,3-dihydroxy-3-phenylpropanoate

To a solution of ethyl cinnamate (2.0 g, 11.4 mmol) in t-BuOH (35.0 mL) and H$_2$O (35.0 mL) at 0° C. was added AD-mix-α (15.83 g, 20.32 mmol), and methanesulfonamide (1.08 g, 11.3 mmol). The reaction mixture was stirred at room temperature for 16 h. The reaction was cooled to 0° C. and quenched with aq. KHSO$_4$. The resulting mixture was extracted with EtOAc (3×100 mL) and the combined organic layers were washed with brine (2×80 mL), dried over Na$_2$SO$_4$, filtered, and concentrated under reduced pressure. The residue was purified by normal phase chromatography (50% EtOAc/pet. ether) to afford the desired product (2.2 g, 82% yield) as a solid.

Step 2: Synthesis of ethyl (2R,3S)-3-hydroxy-2-(((4-nitrophenyl)sulfonyl)oxy)-3-phenylpropanoate To a solution of ethyl (2R,3S)-2,3-dihydroxy-3-phenylpropanoate (2.10 g, 9.99 mmol) and Et$_3$N (4.18 mL, 29.9 mmol) in DCM (30.0 mL) at 0° C. was added 4-nitrobenzenesulfonyl chloride (2.21 g, 9.99 mmol). The resulting mixture was stirred for 1 h and was then diluted with H$_2$O (200 mL). The mixture was extracted with DCM (3×80 mL) and the combined organic layers were washed with brine (2×80 mL), dried over Na$_2$SO$_4$, filtered, and concentrated under reduced pressure. The residue was purified by prep-TLC (50% EtOAc/pet. ether) to afford the desired product (3.0 g, 68% yield) as a solid.

Step 3: Synthesis of ethyl (2S,3S)-2-azido-3-hydroxy-3-phenylpropanoate

To a solution of ethyl (2R,3S)-3-hydroxy-2-(((4-nitrophenyl)sulfonyl)oxy)-3-phenylpropanoate (3.0 g, 7.59 mmol) in THF (30 mL) at room temperature was added trimethylsilyl azide (1.75 g, 15.2 mmol) and TBAF (1M in THF, 15.18 mL, 15.18 mmol). The reaction mixture was heated to 60° C. and was stirred for 16 h. The reaction mixture was then cooled to room temperature, diluted with H$_2$O (150 mL), and extracted with EtOAc (3×50 mL). The combined organic layers were washed with brine (2×30 mL), dried over Na$_2$SO$_4$, filtered, and concentrated under reduced pressure. The residue was purified by normal phase chromatography (50% EtOAc/pet. ether) to afford the desired product (1.4 g, 70% yield) as an oil.

Step 4: Synthesis of ethyl (2S,3R)-3-phenylaziridine-2-carboxylate

To a solution of ethyl (2S,3S)-2-azido-3-hydroxy-3-phenylpropanoate (1.40 g, 5.95 mmol) in DMF (20.0 mL) was added PPh$_3$ (1.87 g, 7.14 mmol). The reaction mixture was stirred at room temperature for 30 min and then heated to 80° C. for an additional 16 h. The reaction mixture was then cooled to room temperature, diluted with H$_2$O (150 mL), and extracted with EtOAc (3×50 mL). The combined organic layers were washed with brine (40 mL), dried over Na$_2$SO, filtered, and concentrated under reduced pressure. The residue was purified by normal phase chromatography (16% EtOAc/pet. ether) to afford the desired product (720 mg, 56% yield) as an oil. LCMS (ESI) m/z: [M+H] calcd for C$_{11}$H$_{13}$NO$_2$: 192.10; found 192.0.

Step 5: Synthesis of (2S,3R)-3-phenylaziridine-2-carboxylic Acid

To a solution of ethyl (2S,3R)-3-phenylaziridine-2-carboxylate (0.100 g, 0.523 mmol) in MeOH (0.70 mL) at 0° C. was added a solution of LiOH (18.8 mg, 0.784 mmol) in H$_2$O (0.70 mL). The reaction mixture was stirred for 1 h. The mixture was then diluted with MeCN (10 mL), and the resulting precipitate was collected by filtration and washed with MeCN (2×10 mL) to afford the crude desired product (68 mg) as a solid. LCMS (ESI) m/z: [M+H] calcd for C$_9$H$_9$NO$_2$: 164.07; found 164.0.

Intermediate A-9. Synthesis of N—(N—((R)-1-benzylaziridine-2-carbonyl)-N-methylglycyl)-N-methyl-L-valine

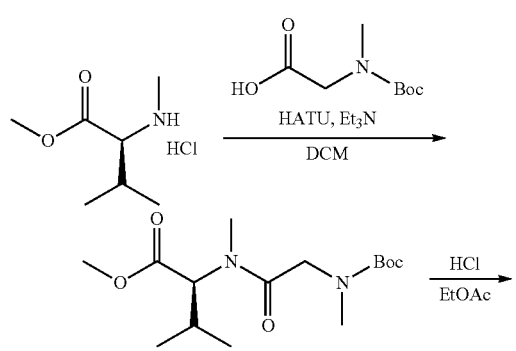

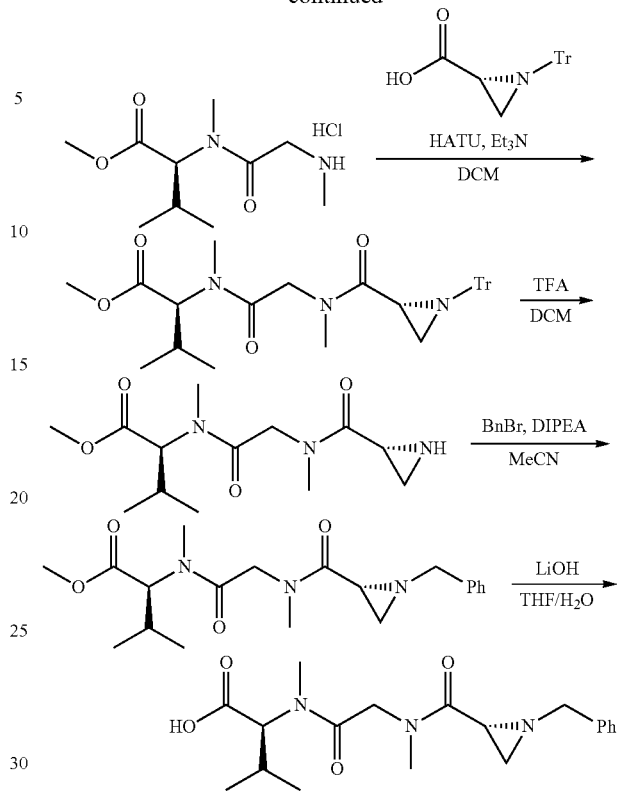

Step 1: Synthesis of methyl N—(N-(tert-butoxycarbonyl)-N-methylglycyl)-N-methyl-L-valinate To a solution of methyl methyl-L-valinate hydrochloride (4.0 g, 22.0 mmol) and N-(tert-butoxycarbonyl)-N-methylglycine (5.0 g, 26.4 mmol) in DCM (100.0 mL) was added Et$_3$N (9.2 mL, 66.1 mmol) and HATU (10.88 g, 28.63 mmol). The reaction mixture was stirred for 4 h. The reaction was then neutralized to pH 7 with sat. aq. NaHCO$_3$. The mixture was extracted with DCM and the combined organic layers were washed with brine, dried over Na$_2$SO$_4$, filtered, and concentrated under reduced pressure. The residue was purified by normal phase chromatography (50% EtOAc/pet. ether) to afford the desired product (6.2 g, 89% yield) as an oil. LCMS (ESI) m/z: [M+H] calcd for C$_{15}$H$_{28}$N$_2$O$_5$: 317.21; found 317.2.

Step 2: Synthesis of methyl N-methyl-N-(methylglycyl)-L-valinate hydrochloride To a solution of methyl N—(N-(tert-butoxycarbonyl)-N-methylglycyl)-N-methyl-L-valinate (4.97 g, 15.7 mmol) in EtOAc (150.0 mL) at 0° C. was added HCl (4M in dioxane, 50.0 mL, 200 mmol). The reaction mixture was stirred for 3 h and then concentrated under reduced pressure to afford the desired crude product (4.26 g, 107% yield) as an oil. LCMS (ESI) m/z: [M+H] calcd for C$_{10}$H$_{20}$N$_2$O$_3$: 217.16; found 217.1.

Step 3: Synthesis of methyl N-methyl-N—(N-methyl-N—((R)-1-tritylaziridine-2-carbonyl)glycyl)-L-valinate To a solution of methyl N-methyl-N-(methylglycyl)-L-valinate hydrochloride (1.0 g, 3.9 mmol) and (R)-1-tritylaziridine-2-carboxylic acid (1.30 g, 3.94 mmol) in DCM (25.0 mL) was added Et$_3$N (2.76 mL, 19.8 mmol) and HATU (1.81 g, 4.76 mmol). The reaction mixture was stirred for 1 h. The reaction was then neutralized to pH 7 with sat. aq. NaHCO$_3$. The mixture was extracted with DCM and the combined organic layers were washed with brine, dried over Na$_2$SO$_4$, filtered, and concentrated under reduced pressure. The residue was purified by normal phase chromatography (50% EtOAc/pet. ether) to afford the desired product (1.1 g, 52.6% yield) as a solid. LCMS (ESI) m/z: [M+H] calcd for C$_{32}$H$_{37}$N$_3$O$_4$: 528.29; found 528.2.

Step 4: Synthesis of methyl N—(N—((R)-aziridine-2-carbonyl)-N-methylglycyl)-N-methyl-L-valinate To a solution methyl N-methyl-N—(N-methyl-N—((R)-1-tritylaziridine-2-carbonyl)glycyl)-L-valinate (1.0 g, 3.9 mmol) in DCM (6 mL) at 0° C. was added TFA (2 mL). The reaction mixture was warmed to room temperature and stirred for 1 h, then concentrated under reduced pressure to afford the desired crude product (250 mg) as an oil. LCMS (ESI) m/z: [M+H] calcd for C$_{13}$H$_{23}$N$_3$O$_4$: 286.18; found 286.1.

Step 5: Synthesis of methyl N—(N—((R)-1-benzylaziridine-2-carbonyl)-N-methylglycyl)-N-methyl-L-valinate To a solution of methyl N—(N—((R)-aziridine-2-carbonyl)-N-methylglycyl)-N-methyl-L-valinate (220.0 mg, 0.771 mmol) in MeCN (2.0 mL) was added DIPEA (537 μL, 3.08 mmol) and benzyl bromide (101 μL, 0.848 mmol). The reaction mixture was stirred for 6 h. The reaction mixture was then concentrated under reduced pressure. The residue was purified by prep-TLC (9% MeOH/DCM) to afford the desired product (261 mg, 90% yield) as an oil. LCMS (ESI) m/z: [M+H] calcd for C$_{20}$H$_{29}$N$_3$O$_4$: 376.22; found 376.2.

Step 6: Synthesis of N—(N—((R)-1-benzylaziridine-2-carbonyl)-N-methylglycyl)-N-methyl-L-valine To a solution of methyl N—(N—((R)-1-benzylaziridine-2-carbonyl)-N-methylglycyl)-N-methyl-L-valinate (261.0 mg, 0.695 mmol) in THF (3.38 mL) was added a solution of LiOH (83.2 mg, 3.48 mmol) in H$_2$O (3.50 mL). The reaction mixture was stirred for 1 h. The reaction was then quenched with sat. aq. NH$_4$Cl. The resulting mixture was extracted with EtOAc and the combined organic layers were washed with brine, dried over Na$_2$SO$_4$, filtered, and concentrated under reduced pressure. The residue was purified by reverse phase chromatography (10→50% MeCN/H$_2$O) to afford the desired product (230 mg, 91% yield) as an oil. LCMS (ESI) m/z: [M+H] calcd for C$_{19}$H$_{27}$N$_3$O$_4$: 362.21; found 362.2.

Intermediate A-10. Synthesis of N—(N—((R)-1-benzylaziridine-2-carbonyl)-N-methylglycyl)-N-methyl-L-valine

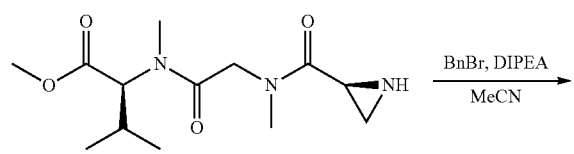

Step 1: Synthesis of methyl N—(N—((S)-1-benzylaziridine-2-carbonyl)-N-methylglycyl)-N-methyl-L-valinate

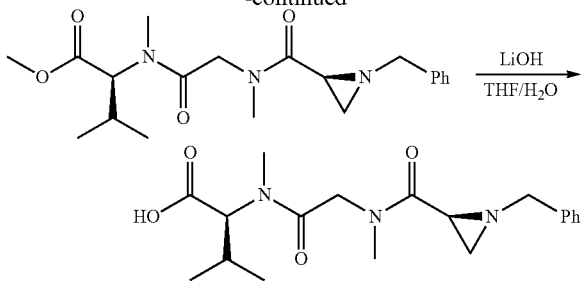

To a solution of methyl N—(N—((S)-aziridine-2-carbonyl)-N-methylglycyl)-N-methyl-L-valinate (362.0 mg, 1.269 mmol) in MeCN (6.0 mL) at 0° C. was added DIPEA (883 μL, 5.08 mmol) and benzyl bromide (165 μL, 1.39 mmol). The reaction mixture was then warmed to room temperature and stirred overnight. The reaction mixture was then concentrated under reduced pressure. The residue was purified by prep-TLC (7% MeOH/DCM) to afford the desired product (287 mg, 60% yield) as an oil. LCMS (ESI) m/z: [M+H] calcd for C$_{20}$H$_{29}$N$_3$O$_4$: 376.22; found 376.2.

Step 2: Synthesis of N$_4$N—((S)-1-benzylaziridine-2-carbonyl)-N-methylglycyl)-N-methyl-L-valine To a solution of methyl N—(N—((S)-1-benzylaziridine-2-carbonyl)-N-methylglycyl)-N-methyl-L-valinate (270.0 mg, 0.719 mmol) in THF (3.6 mL) was added a solution of LiOH (86.1 mg, 3.59 mmol) in H$_2$O (3.60 mL). The reaction mixture was stirred for 30 min. The reaction was then quenched with sat. aq. NH$_4$Cl. The resulting mixture was extracted with EtOAc (3×15 mL) and the combined organic layers were washed with brine, dried over Na$_2$SO$_4$, filtered, and concentrated under reduced pressure to afford the desired crude product (240 mg, 92% yield) as an oil. LCMS (ESI) m/z: [M+H] calcd for C$_{19}$H$_{27}$N$_3$O$_4$: 362.21; found 362.2.

Intermediate A-11. Synthesis of N-methyl-N—(N-methyl-N—((R)-1-tritylaziridine-2-carbonyl)glycyl)-L-valine

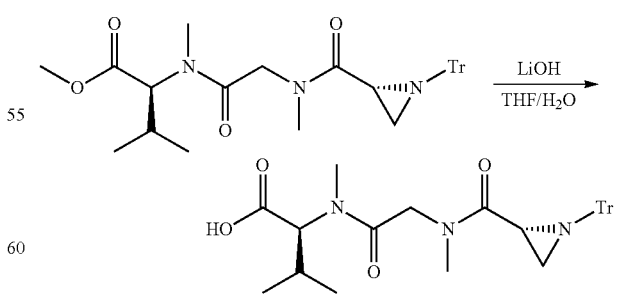

To a solution of methyl N-methyl-N—(N-methyl-N—((R)-1-tritylaziridine-2-carbonyl)glycyl)-L-valinate (1.30 g, 2.46 mmol) in THF (10.0 mL) at 0° C. was added a solution of LiOH (177.0 mg, 7.39 mmol) in H$_2$O (7.40 mL). The resulting mixture was warmed to room temperature, stirred for 3 h, and was then acidified to pH 5 with HCl (aq). The resulting mixture was extracted with EtOAc (3×80 mL) and the combined organic layers were washed with brine (2×50 mL), dried over Na$_2$SO$_4$, filtered, and concentrated under reduced pressure to afford the desired crude product (1 g, 71% yield). LCMS (ESI) m/z: [M+H] calcd for C$_{31}$H$_{35}$N$_3$O$_4$: 514.27; found 514.3.

Intermediate A-12. Synthesis of N-methyl-N-(4-((R)-1-tritylaziridine-2-carbonyl)-1,4-diazepane-1-carbonyl)-L-valine

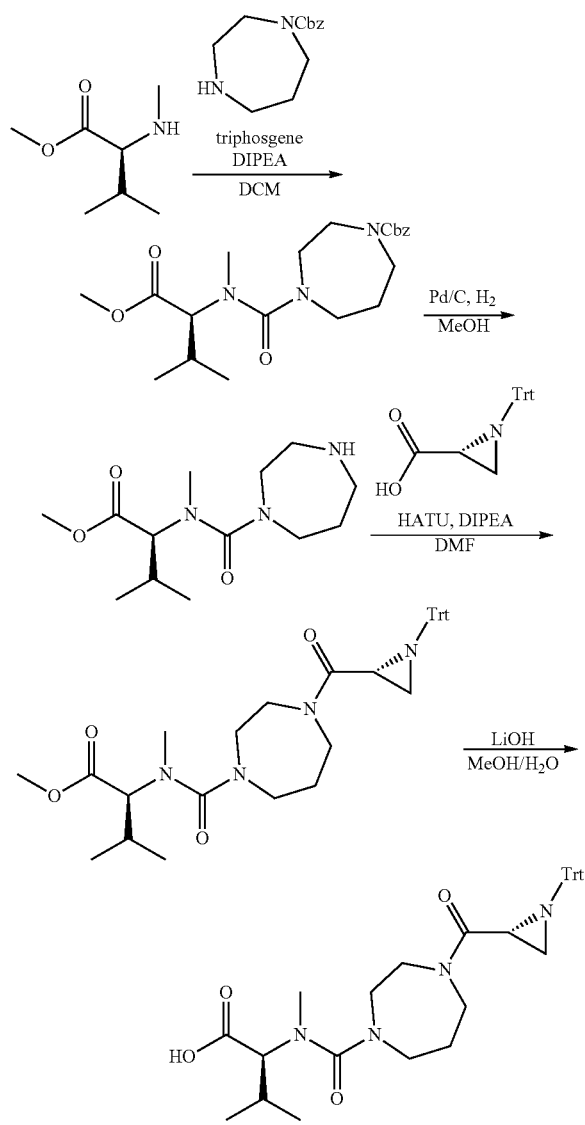

Step 1: Synthesis of benzyl (S)-4-((1-methoxy-3-methyl-1-oxobutan-2-yl)(methyl)carbamoyl)-1,4-diazepane-1-carboxylate To a solution of methyl N-methyl-L-valinate (2.50 g, 17.22 mmol) in DCM at 0° C. was added DIPEA (1.8 mL, 10.33 mmol) followed by triphosgene (2.55 g, 8.61 mmol). The resulting mixture was stirred for 3 h at 0° C. To the mixture was then added benzyl 1,4-diazepane-1-carboxylate (4.03 g, 17.20 mmol). The resulting mixture was warmed to room temperature and stirred overnight. The reaction was cooled to 0° C. and was quenched with NaHCO$_3$. The aqueous layer was extracted with EtOAc (2×30 mL) and the combined organic layers were washed with brine (2×30 mL), dried over Na$_2$SO$_4$, filtered, and concentrated under reduced pressure. The residue was purified by normal phase chromatography (25% EtOAc/pet. ether) to afford the desired product (3.5 g, 50.1% yield). LCMS (ESI) m/z: [M+H] calcd for C$_{21}$H$_{31}$N$_3$O$_5$: 406.23; found 406.5.

Step 2: Synthesis of methyl N-(1,4-diazepane-1-carbonyl)-N-methyl-L-valinate

To a solution of benzyl (S)-4-((1-methoxy-3-methyl-1-oxobutan-2-yl)(methyl)carbamoyl)-1,4-diazepane-1-carboxylate (2.0 g, 4.93 mmol) in MeOH (20 mL) was added Pd/C (10% wt, 1 g). The mixture was placed under a hydrogen atmosphere (1 atm) and stirred for 2 h. The reaction mixture was filtered through a Celite and concentrated under reduced pressure to afford the desired crude product (1.3 g, 97.1% yield). LCMS (ESI) m/z: [M+H] calcd for C$_{13}$H$_{25}$N$_3$O$_3$: 272.20; found 272.3.

Step 3: Synthesis of methyl N-methyl-N-(4-((R)-1-tritylaziridine-2-carbonyl)-1,4-diazepane-1-carbonyl)-L-valinate To a solution of methyl N-(1,4-diazepane-1-carbonyl)-N-methyl-L-valinate (1.0 g, 3.69 mmol) and (R)-1-tritylaziridine-2-carboxylic acid (1.46 g, 4.42 mmol) in DMF at 0° C. was added DIPEA (1.93 mL, 11.06 mmol) followed by HATU (2.10 g, 5.52 mmol). The resulting mixture was warmed to room temperature and stirred for 1 h. The reaction mixture was then diluted with H$_2$O (15 mL) and the aqueous layer was extracted with EtOAc (3×30 mL). The combined organic layers were washed with brine (3×30 mL), dried over Na$_2$SO$_4$, filtered, and concentrated under reduced pressure. The residue was purified by normal phase chromatography (25% EtOAc/pet. ether) to afford the desired product (1.6 g, 74.5% yield). LCMS (ESI) m/z: [M+H] calcd for C$_{35}$H$_{42}$N$_4$O$_4$: 583.33; found 583.5.

Step 4: Synthesis of N-methyl-N-(4-((R)-1-tritylaziridine-2-carbonyl)-1,4-diazepane-1-carbonyl)-L-valine To a solution of methyl N-methyl-N-(4-((R)-1-tritylaziridine-2-carbonyl)-1,4-diazepane-1-carbonyl)-L-valinate (1.60 g, 2.75 mmol) in MeOH (10.0 mL) and H$_2$O (5.0 mL) at 0° C. was added LiOH (0.66 g, 27.56 mmol). The resulting mixture was warmed to room temperature and stirred overnight. The reaction mixture was acidified to pH 5 with HCl (aq) and the aqueous layer was extracted with EtOAc (3×30 mL). The combined organic layers were washed with brine (3×30 mL), dried over Na$_2$SO$_4$, filtered, concentrated under reduced pressure to afford the desired crude product (1.4 g, 95.6% yield). LCMS (ESI) m/z: [M+H] calcd for C$_{34}$H$_{40}$N$_4$O$_4$: 569.31; found 569.5.

Intermediate A-13. Synthesis of N-methyl-N-(4-((S)-1-tritylaziridine-2-carbonyl)-1,4-diazepane-1-carbonyl)-L-valine

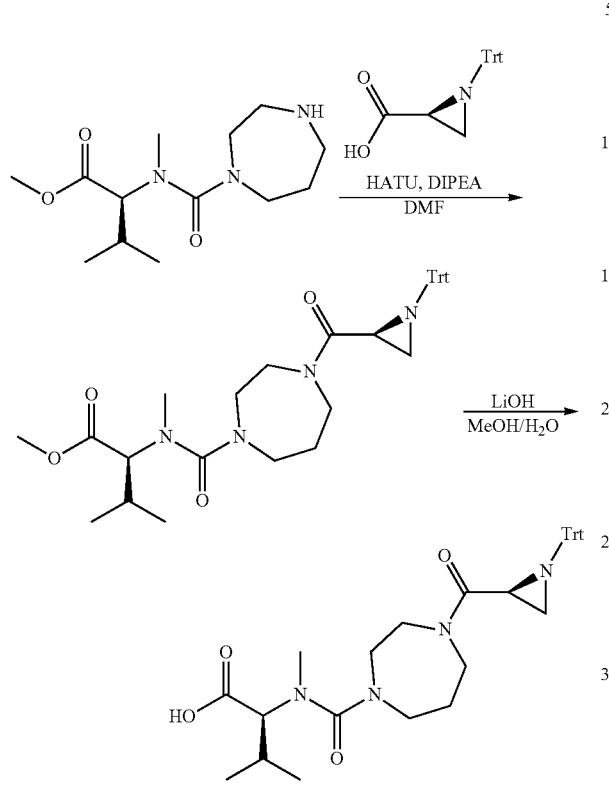

Step 1: Synthesis of methyl N-methyl-N-(4-((S)-1-tritylaziridine-2-carbonyl)-1,4-diazepane-1-carbonyl)-L-valinate To a solution of methyl N-(1,4-diazepane-1-carbonyl)-N-methyl-L-valinate (1.16 g, 4.28 mmol) and (S)-1-tritylaziridine-2-carboxylic acid (1.69 g, 5.13 mmol) in DMF (10 mL) at 0° C. was added DIPEA (2.23 mL, 12.82 mmol) followed by HATU (2.44 g, 6.41 mmol). The resulting mixture was stirred for 1 h at 0° C. The reaction mixture was then diluted with $H_2O$ (15 mL) and the aqueous layer was extracted with EtOAc (3×15 mL). The combined organic layers were washed with brine (3×15 mL), dried over $Na_2SO_4$, filtered, and concentrated under reduced pressure. The residue was purified by normal phase chromatography (17% EtOAc/pet. ether) to afford the desired product (2 g, 80.3% yield). LCMS (ESI) m/z: [M+H] calcd for $C_{35}H_{42}N_4O_4$: 583.33; found 583.5.

Step 2: Synthesis of N-methyl-N-(4-((S)-1-tritylaziridine-2-carbonyl)-1,4-diazepane-1-carbonyl)-L-valine To a solution of methyl N-methyl-N-(4-((S)-1-tritylaziridine-2-carbonyl)-1,4-diazepane-1-carbonyl)-L-valinate (1.0 g, 1.72 mmol) in MeOH (8.0 mL) and $H_2O$ (4.0 mL) at 0° C. was added LiOH (411 mg, 17.16 mmol). The resulting mixture was warmed to room temperature and stirred overnight. The reaction mixture was acidified to pH 5 with HCl (aq) and the aqueous layer was extracted with EtOAc (3×10 mL). The combined organic layers were washed with brine (3×10 mL), dried over $Na_2SO_4$, filtered, concentrated under reduced pressure to afford the desired crude product (0.6 g, 61.5% yield). LCMS (ESI) m/z: [M+H] calcd for $C_{34}H_{40}N_4O_4$: 569.31; found 569.5.

Intermediate A-14. Synthesis of N-methyl-N-(5-((S)-1-tritylaziridine-2-carboxamido)picolinoyl)-L-valine

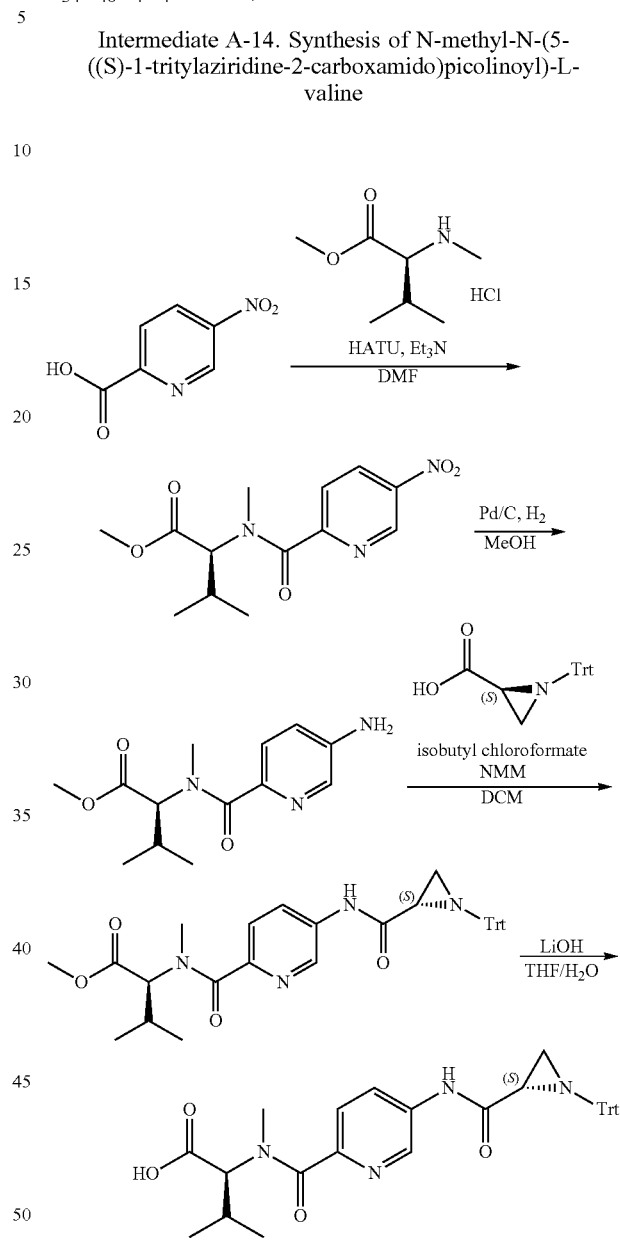

Step 1: Synthesis of methyl N-methyl-N-(5-nitropicolinoyl)-L-valinate

To a solution of methyl N-methyl-L-valinate hydrochloride (190.0 mg, 1.31 mmol) and 5-nitropicolinic acid (200.0 mg, 1.19 mmol) in DMF (2 mL) at 0° C. was added HATU (678.6 mg, 1.79 mmol) and $Et_3N$ (0.332 mL, 2.38 mmol). The resulting mixture was warmed to room temperature and stirred for 2 h. The resulting mixture was then extracted with EtOAc (2×50 mL) and the combined organic layers were washed with $H_2O$ (20 mL) and brine (20 mL), dried over $Na_2SO_4$, filtered, and concentrated under reduced pressure. The residue was purified by normal phase chromatography (33% EtOAc/pet. ether) to afford the desired product (210 mg, 59.8% yield). LCMS (ESI) m/z: [M+H] calcd for $C_{13}H_{17}N_3O_5$: 296.12; found 296.0.

Step 2: Synthesis of methyl N-(5-aminopicolinoyl)-N-methyl-L-valinate

To a solution of methyl N-methyl-N-(5-nitropicolinoyl)-L-valinate (5.0 g, 16.93 mmol) in MeOH (50.0 mL) was added Pd/C (2.50 g). The reaction mixture was placed under a hydrogen atmosphere (1 atm) and was stirred for 2 h. The mixture was filtered, the filter cake was washed with MeOH (2×20 mL), and the filtrate was concentrated under reduced pressure to afford the desired crude product (5.3 g). LCMS (ESI) m/z: [M+H] calcd for $C_{13}H_{19}N_3O_3$: 266.15; found 266.0.

Step 3: Synthesis of methyl N-methyl-N-(5-((S)-1-tritylaziridine-2-carboxamido)picolinoyl)-L-valinate To a solution (S)-1-tritylaziridine-2-carboxylic acid (55.9 mg, 0.17 mmol) in DCM at 0° C. was added isobutyl chloroformate (21.7 µL, 0.23 mmol) and N-methylmorpholine (66.8 µL, 0.61 mmol). The resulting mixture was stirred for 1 h and then methyl N-(5-aminopicolinoyl)-N-methyl-L-valinate (30.0 mg, 0.11 mmol) was added. The resulting mixture was warmed to room temperature and stirred for an additional 5 h. The mixture was extracted with DCM (3×50 mL) and the combined organic layers were washed with sat. $NaHCO_3$ (30 mL) and brine, dried over $Na_2SO_4$, filtered, and concentrated under reduced pressure. The residue was purified by normal phase chromatography (33% EtOAc/pet. ether) to afford the desired product (1.09 g, 66.9% yield). LCMS (ESI) m/z: [M+H] calcd for $C_{35}H_{36}N_4O_4$: 577.28; found 577.1.

Step 4: Synthesis of N-methyl-N-(5-((S)-1-tritylaziridine-2-carboxamido)picolinoyl)-L-valine To a solution methyl N-methyl-N-(5-((S)-1-tritylaziridine-2-carboxamido)picolinoyl)-L-valinate (100.0 mg, 0.17 mmol) in THF (0.5 mL) at 0° C. was added a solution of LiOH (20.76 mg, 0.87 mmol) in $H_2O$ (0.5 mL). The resulting mixture was warmed to room temperature and stirred for 6 h. The mixture was acidified to pH 5 with 1 M citric acid. The resulting mixture was extracted with EtOAc (3×20 mL) and the combined organic layers were washed with brine (5 mL), dried over $Na_2SO_4$, filtered, and concentrated under reduced pressure to afford the desired crude product (76.8 mg, 78.7% yield). LCMS (ESI) m/z: [M+H] calcd for $C_{34}H_{34}N_4O_4$: 563.27; found 563.3.

Intermediate A-15. Synthesis of N-methyl-N-(5-((R)-1-tritylaziridine-2-carboxamido)picolinoyl)-L-valine

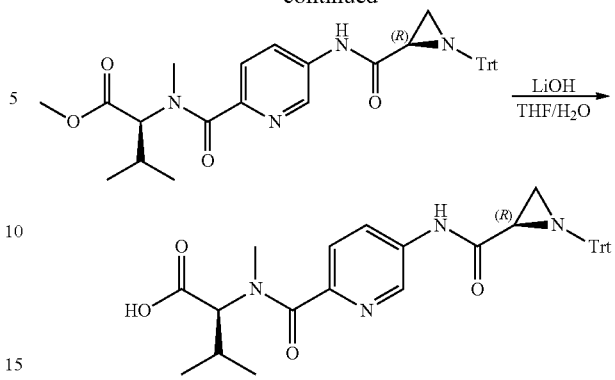

Step 1: Synthesis of methyl N-methyl-N-(5-((R)-1-tritylaziridine-2-carboxamido)picolinoyl)-L-valinate To a solution (R)-1-tritylaziridine-2-carboxylic acid (1396.7 mg, 4.24 mmol) in DCM (8 mL) at 0° C. was added isobutyl chloroformate (440 µL, 3.39 mmol) and N-methylmorpholine (466 µL, 4.24 mmol). The resulting mixture was stirred for 1 h and then methyl N-(5-aminopicolinoyl)-N-methyl-L-valinate (750.0 mg, 2.83 mmol) was added. The resulting mixture was warmed to room temperature and stirred for an additional 5 h. The mixture was quenched by the addition of $NaHCO_3$ and the aqueous layer was extracted with DCM (2×100 mL). The combined organic layers were washed with brine (120 mL), dried over $Na_2SO_4$, filtered, and concentrated under reduced pressure. The residue was purified by normal phase chromatography (50% EtOAc/pet. ether) to afford the desired product (580 mg, 35.6% yield). LCMS (ESI) m/z: [M+H] calcd for $C_{35}H_{36}N_4O_4$: 577.28; found 577.2.

Step 2: Synthesis of N-methyl-N-(5-((R)-1-tritylaziridine-2-carboxamido)picolinoyl)-L-valine To a solution methyl N-methyl-N-(5-((R)-1-tritylaziridine-2-carboxamido)picolinoyl)-L-valinate (558.0 mg, 0.97 mmol) in THF (14 mL) at 0° C. was added a solution of LiOH (115.9 mg, 4.84 mmol) in $H_2O$ (14 mL). The resulting mixture was warmed to room temperature and stirred for 6 h. The mixture was acidified to pH 5 with 1 M citric acid. The resulting mixture was extracted with EtOAc (3×100 mL) and the combined organic layers were washed with brine (30 mL), dried over $Na_2SO_4$, filtered, and concentrated under reduced pressure to afford the desired crude product (580 mg, 78.7% yield). LCMS (ESI) m/z: [M+H] calcd for $C_{34}H_{34}N_4O_4$: 563.27; found 563.2.

Intermediate A-16. Synthesis of (2R,3S)-1-((R)-tert-butylsulfinyl)-3-(methoxycarbonyl)aziridine-2-carboxylic Acid

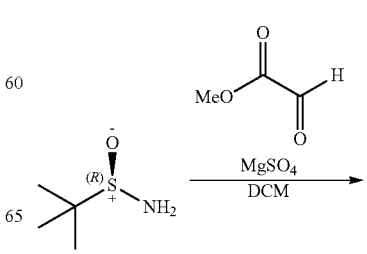

539

-continued

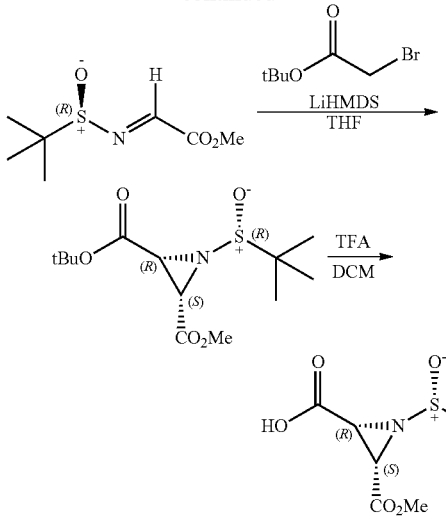

Step 1: Synthesis of methyl (R,E)-2-((tert-butylsulfinyl)imino)acetate

To a solution of (R)-2-methylpropane-2-sulfinamide (13.21 g, 109.01 mmol) and methyl 2-oxoacetate (8.0 g, 90.85 mmol) in DCM (130 mL) at room temperature was added MgSO$_4$ (54.67 g, 454.23 mmol). The resulting mixture was heated to 35° C. and stirred for 16 h. The resulting mixture was filtered, the filter cake washed with EtOAc (3×50 mL), and the filtrate was concentrated under reduced pressure. The residue was purified by normal phase chromatography (25% EtOAc/pet. ether) to afford the desired (5.8 g, 33.4% yield). LCMS (ESI) m/z: [M+H] calcd for C$_7$H$_{13}$NO$_3$S: 192.07; found 191.9.

Step 2: Synthesis of 2-(tert-butyl) 3-methyl (2R,3S)-1-((R)-tert-butylsulfinyl)aziridine-2,3-dicarboxylate To a solution of 1M LiHMDS (61.40 mL, 61.40 mmol) in THF (300.0 mL) at −78° C. was added tert-butyl 2-bromoacetate (11.83 g, 60.65 mmol). The resulting mixture was stirred for 30 min. To the reaction mixture was then added methyl methyl (R,E)-2-((tert-butylsulfinyl)imino)acetate (5.8 g, 30.33 mmol). The resulting mixture was warmed to −60° C. and stirred for 2.5 h. The reaction was warmed to 0° C. and quenched with sat. NH$_4$Cl (aq.). The resulting mixture was extracted with EtOAc (3×200 mL). The combined organic layers were washed with brine (500 mL), dried over Na$_2$SO$_4$, filtered, and concentrated under reduced pressure. The residue was purified by reverse phase chromatography (10→50% MeCN/H$_2$O) to afford the desired product (1.34 g, 4.5% yield). LCMS (ESI) m/z: [M+H] calcd for C$_{13}$H$_{23}$NO$_5$S: 306.14; found 306.2.

Step 3: Synthesis of (2R,3S)-1-((R)-tert-butylsulfinyl)-3-(methoxycarbonyl)aziridine-2-carboxylic Acid To a solution of 2-(tert-butyl) 3-methyl (2R,3S)-1-((R)-tert-butylsulfinyl)aziridine-2,3-dicarboxylate (302.0 mg, 0.99 mmol) in DCM (3.0 mL) at 0° C. was added TFA (1.50 mL). The resulting mixture was stirred for 1 h and then concentrated under reduced pressure to afford the desired crude product (300 mg). LCMS (ESI) m/z: [M+H] calcd for C$_9$H$_{15}$NO$_5$S: 250.07; found 250.1.

Intermediate A-17. Synthesis of (2R,3S)-1-((S)-tert-butylsulfinyl)-3-(methoxycarbonyl)aziridine-2-carboxylic Acid

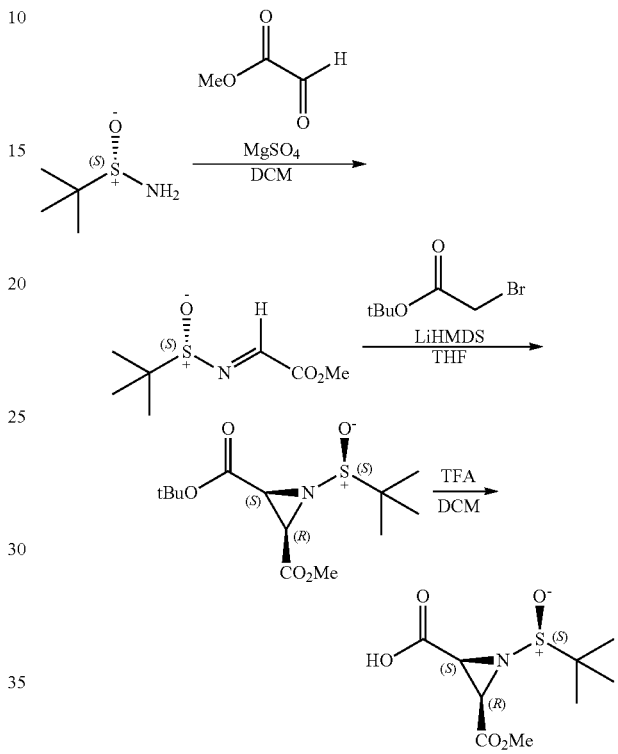

Step 1: Synthesis of methyl (S,E)-2-((tert-butylsulfinyl)imino)acetate

To a solution of (S)-2-methylpropane-2-sulfinamide (9.81 g, 80.94 mmol) and methyl 2-oxoacetate (5.94 g, 67.45 mmol) in DCM (100 mL) at room temperature was added MgSO$_4$ (40.60 g, 337.26 mmol). The resulting mixture was heated to 35° C. and stirred for 16 h. The resulting mixture was filtered, the filter cake washed with EtOAc (3×50 mL), and the filtrate was concentrated under reduced pressure. The residue was purified by normal phase chromatography (25% EtOAc/pet. ether) to afford the desired (5.68 g, 44.0% yield). LCMS (ESI) m/z: [M+H] calcd for C$_7$H$_{13}$NO$_3$S: 192.07; found 191.1.

Step 2: Synthesis of 2-(tert-butyl) 3-methyl (2R,3S)-1-((S)-tert-butylsulfinyl)aziridine-2,3-dicarboxylate To a solution of 1M LiHMDS (59.40 mL, 59.40 mmol) in THF (300.0 mL) at −78° C. was added tert-butyl 2-bromoacetate (11.59 g, 59.40 mmol). The resulting mixture was stirred for 30 min. To the reaction mixture was then added methyl methyl (S,E)-2-((tert-butylsulfinyl)imino)acetate (5.68 g, 29.70 mmol). The resulting mixture was warmed to −60° C. and stirred for 2.5 h. The reaction was warmed to 0° C. and quenched with sat. NH$_4$Cl (aq.). The resulting mixture was extracted with EtOAc (3×200 mL). The combined organic layers were washed with brine (500 mL), dried over $Na_2SO_4$, filtered, and concentrated under reduced pressure. The residue was purified by reverse phase chromatography (10→50% $MeCN/H_2O$) to afford the desired product (1.26 g, 13.9% yield). LCMS (ESI) m/z: [M+H] calcd for $C_{13}H_{23}NO_5S$: 306.14; found 306.1.

Step 3: Synthesis of (2R,3S)-1-((S)-tert-butylsulfinyl)-3-(methoxycarbonyl)aziridine-2-carboxylic Acid To a solution of 2-(tert-butyl) 3-methyl (2R,3S)-1((S)-tert-butylsulfinyl)aziridine-2,3-dicarboxylate (457.0 mg, 1.50 mmol) in DCM (6.0 mL) at 0° C. was added TFA (3.0 mL). The resulting mixture was stirred for 1 h and then concentrated under reduced pressure to afford the desired crude product (450 mg). LCMS (ESI) m/z: [M+H] calcd for $C_9H_{15}NO_5S$: 250.07; found 250.1.

Intermediate A-18. Synthesis of (2R,3R)-1-((R)-tert-butylsulfinyl)-3-cyclopropylaziridine-2-carboxylic Acid

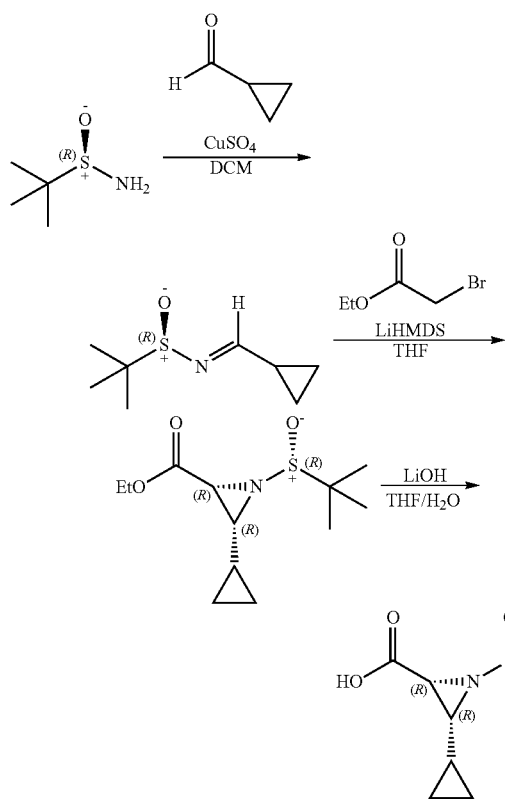

Step 1: Synthesis of (R,E)-N-(cyclopropylmethylene)-2-methylpropane-2-sulfinamide To a solution of (R)-2-methylpropane-2-sulfinamide (1.0 g, 8.25 mmol) and cyclopropanecarbaldehyde (1.16 g, 16.55 mmol) in DCM (50 mL) at room temperature was added $CuSO_4$ (3.95 g, 24.75 mmol). The resulting mixture was stirred overnight. The reaction mixture was then filtered, the filter cake washed with EtOAc, and the filtrate was concentrated under reduced pressure. The residue was purified by prep-TLC (17% EtOAc/pet. ether) to afford the desired product (1.4 g, 97.9% yield). LCMS (ESI) m/z: [M+H] calcd for $C_8H_{15}NOS$: 174.10; found 174.1.

Step 2: Synthesis of ethyl (2R,3R)-1-((R)-tert-butylsulfinyl)-3-cyclopropylaziridine-2-carboxylate To a solution of 1M LiHMDS (23 mL, 23 mmol) in THF (50.0 mL) at −78° C. was added ethyl bromoacetate (3.83 g, 22.95 mmol). The resulting mixture was warmed to −70° C. and stirred for 1 h. To the reaction mixture was then added (R,E)-N-(cyclopropylmethylene)-2-methylpropane-2-sulfinamide (2.0 g, 11.48 mmol). The resulting mixture was stirred for 1 h at −70° C. The reaction mixture was warmed to 0° C. and quenched with $H_2O$. The aqueous layer was extracted with EtOAc (3×100 mL). The combined organic layers were washed with brine, dried over $Na_2SO_4$, filtered, and concentrated under reduced pressure. The residue was purified by prep-TLC (25% EtOAc/pet. ether) to afford the desired product (1.8 g, 60.5% yield). LCMS (ESI) m/z: [M+H] calcd for $C_{12}H_{21}NO_3S$: 306.14; found 260.13.

Step 3: Synthesis of (2R,3R)-1-((R)-tert-butylsulfinyl)-3-cyclopropylaziridine-2-carboxylic Acid To a solution of ethyl (2R,3R)-1-((R)-tert-butylsulfinyl)-3-cyclopropylaziridine-2-carboxylate (900.0 mg, 3.47 mmol) in THF (3.0 mL) and $H_2O$ (3.0 mL) at 0° C. was added $LiOH \cdot H_2O$ (218.4 mg, 5.21 mmol). The resulting mixture was stirred for 1 h and was then quenched by $H_2O$. The aqueous layer was extracted with EtOAc (3×50) and the combined organic layers were washed with brine, dried over $Na_2SO_4$, filtered, and concentrated under reduced pressure to afford the desired crude product (400 mg, 29.9% yield). LCMS (ESI) m/z: [M+H] calcd for $C_{10}H_{17}NO_3S$: 232.10; found 232.1.

Intermediate A-19. Synthesis of (2R,3R)-1-((R)-tert-butylsulfinyl)-3-methylaziridine-2-carboxylic Acid

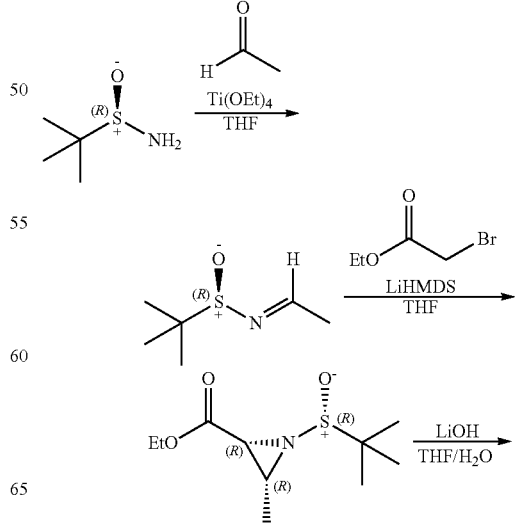

543

-continued

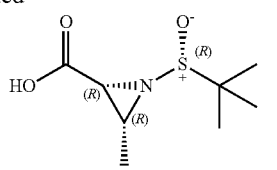

Step 1: Synthesis of (R,E)-N-ethylidene-2-methylpropane-2-sulfinamide

To a solution of (R)-2-methylpropane-2-sulfinamide (3.0 g, 24.75 mmol) and tetraethoxytitanium (1.7 g, 7.43 mmol) in THF (30 mL) at 0° C. was added acetaldehyde (218.1 mg, 4.95 mmol). The resulting mixture was stirred for 20 min and was then quenched with H$_2$O (100 mL). The suspension was filtered, and the filter cake washed with EtOAc (3×100 mL). The aqueous layer was extracted with EtOAc (3×100 mL) and the combined organic layers were washed with brine (3×100 mL), dried over Na$_2$SO$_4$, filtered, and concentrated under reduced pressure. Purification by normal phase chromatography (9% EtOAc/pet. ether) afforded desired product (3 g, 82% yield). LCMS (ESI) m/z: [M+H] calcd for C$_6$H$_{13}$NOS: 148.08; found 148.0.

Step 2: Synthesis of ethyl (2R,3R)-1-((R)-tert-butylsulfinyl)-3-methylaziridine-2-carboxylate To a solution of 1M LiHMDS (40.75 mL, 40.75 mmol) in THF (30.0 mL) at −78° C. was added ethyl bromoacetate (6.80 g, 40.75 mmol). The resulting mixture was stirred for 1 h. To the reaction mixture was then added (R,E)-N-ethylidene-2-methylpropane-2-sulfinamide (3.0 g, 20.38 mmol). The resulting mixture was stirred for 2 h at −78° C. and then quenched with H$_2$O (300 mL). The aqueous layer was extracted with EtOAc (3×300 mL) and the combined organic layers were washed with brine (3×100 mL), dried over Na$_2$SO$_4$, filtered, and concentrated under reduced pressure. The residue was purified by reverse phase chromatography (10→50% MeCN/H$_2$O) to afford the desired product (1.4 g, 29.5% yield). LCMS (ESI) m/z: [M+H] calcd for C$_{10}$H$_{19}$NO$_3$S: 234.12; found 234.1.

Step 3: Synthesis of (2R,3R)-1-((R)-tert-butylsulfinyl)-3-methylaziridine-2-carboxylic Acid To a solution of ethyl (2R,3R)-1-((R)-tert-butylsulfinyl)-3-methylaziridine-2-carboxylate (1.0 g, 4.29 mmol) in THF (6.4 mL) and H$_2$O (6.4 mL) at 0° C. was added LiOH.H$_2$O (539.5 mg, 12.86 mmol). The resulting mixture was warmed to room temperature and stirred for 2 h and was then neutralized to pH 5 with HCl (aq.) and sat. NH$_4$Cl (aq.). The aqueous layer was extracted with EtOAc (3×10 mL) and the combined organic layers were washed with brine, dried over Na$_2$SO$_4$, filtered, and concentrated under reduced pressure to afford the desired crude product (489 mg, 55.6% yield). LCMS (ESI) m/z: [M+H] calcd for C$_8$H$_{15}$NO$_3$S: 206.09; found 206.0.

544

Intermediate A-20. Synthesis of (2S,3S)-1-(S)-tert-butylsulfinyl)-3-methylaziridine-2-carboxylic Acid

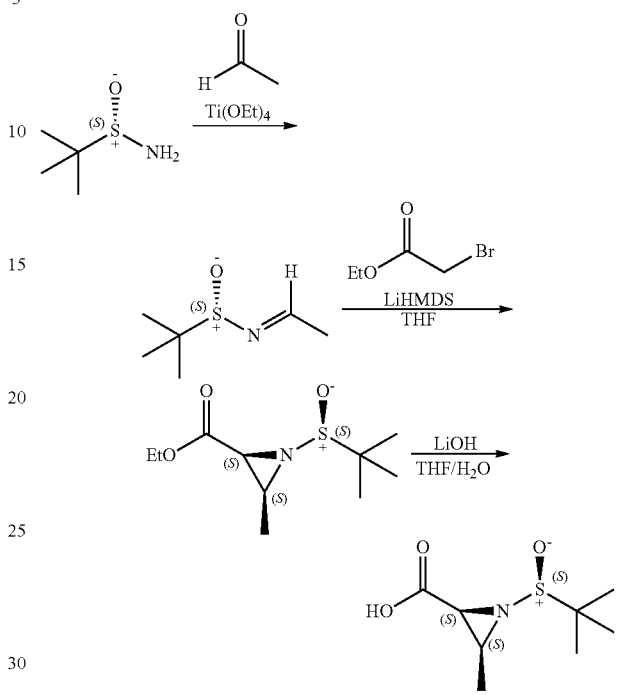

Step 1: Synthesis of (S,E)-N-ethylidene-2-methylpropane-2-sulfinamide

To a mixture of (S)-2-methylpropane-2-sulfinamide (5.0 g, 41.25 mmol) and tetraethoxytitanium (18.82 g, 82.51 mmol) at 0° C. was added acetaldehyde (3.63 g, 82.51 mmol). The resulting mixture was warmed to room temperature and stirred for 30 min and was then quenched with H$_2$O (100 mL). The suspension was filtered, and the filter cake washed with EtOAc (3×100 mL). The aqueous layer was extracted with EtOAc (3×100 mL) and the combined organic layers were washed with brine (3×100 mL), dried over Na$_2$SO$_4$, filtered, and concentrated under reduced pressure to afford desired crude product (3.9 g, 64% yield). LCMS (ESI) m/z: [M+H] calcd for C$_6$H$_{13}$NOS: 148.08; found 148.2.

Step 2: Synthesis of ethyl (2S,3S)-1-((S)-tert-butylsulfinyl)-3-methylaziridine-2-carboxylate To a solution of 1M LiHMDS (40.75 mL, 40.75 mmol) in THF (30.0 mL) at −78° C. was added ethyl bromoacetate (6.80 g, 40.75 mmol). The resulting mixture was stirred for 1 h. To the reaction mixture was then added (S,E)-N-ethylidene-2-methylpropane-2-sulfinamide (3.0 g, 20.38 mmol). The resulting mixture was stirred for 2 h at −78° C. and then quenched with H$_2$O. The aqueous layer was extracted with EtOAc (3×200 mL) and the combined organic layers were washed with brine (3×300 mL), dried over Na$_2$SO$_4$, filtered, and concentrated under reduced pressure. The residue was purified by reverse phase chromatography (10→50% MeCN/H$_2$O) to afford the desired product (2 g, 42% yield). LCMS (ESI) m/z: [M+H] calcd for C$_{10}$H$_{19}$NO$_3$S: 234.12; found 234.0.

Step 3: Synthesis of (2S,3S)-1-((S)-tert-butylsulfinyl)-3-methylaziridine-2-carboxylic Acid To a solution of ethyl (2S,3S)-1-((S)-tert-butylsulfinyl)-3-methylaziridine-2-carboxylate (80.0 mg, 0.34 mmol) in THF (1.0 mL) and H₂O (0.2 mL) at 0° C. was added LiOH.H₂O (32.9 mg, 1.37 mmol). The resulting mixture was warmed to room temperature and stirred for 4 h and was then acidified to pH 3 with HCl (aq.). The aqueous layer was extracted with EtOAc (3×10 mL) and the combined organic layers were washed with brine, dried over Na₂SO₄, filtered, and concentrated under reduced pressure to afford the desired crude product (70 mg, 99% yield). LCMS (ESI) m/z: [M+H] calcd for C₈H₁₅NO₃S: 206.09; found 206.0.

Intermediate A-21 and A-22. Synthesis of N-methyl-N-((S)-1-(((R)-1-methylaziridin-2-yl)sulfonyl)pyrrolidine-3-carbonyl)-L-valine and N-methyl-N-((S)-1-(((S)-1-methylaziridin-2-yl)sulfonyl)pyrrolidine-3-carbonyl)-L-valine

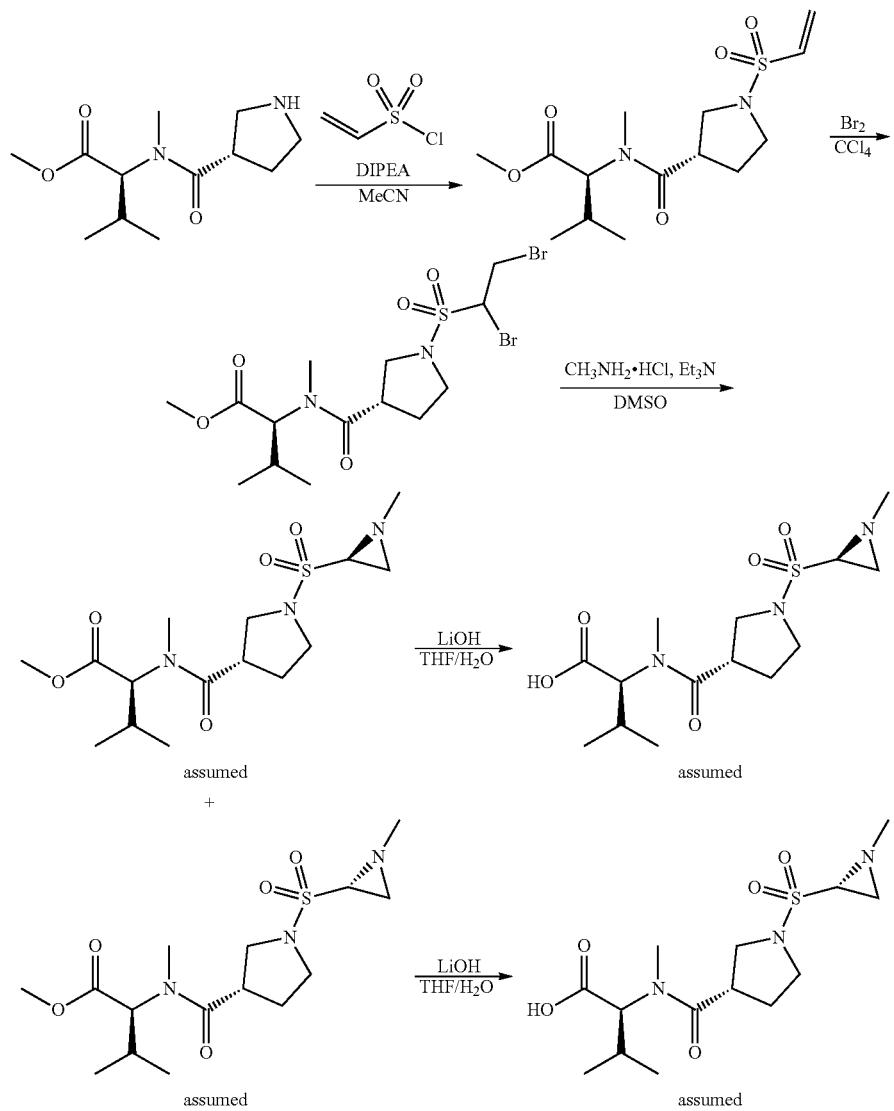

Step 1: Synthesis of methyl N-methyl-N-((S)-1-(vinylsulfonyl)pyrrolidine-3-carbonyl)-L-valinate To a mixture of methyl N-methyl-N-((S)-pyrrolidine-3-carbonyl)-L-valinate (7.0 g, 28.89 mmol) in MeCN (200 mL) at −20° C. was added DIPEA (10.0 mL, 57.78 mmol) followed by ethenesulfonyl chloride (4.0 g, 31.78 mmol). The resulting solution was stirred for 2 h at −20° C. and was then diluted with EtOAc (800 mL). The resulting solution was washed with brine (3×100 mL) and concentrated under reduced pressure. Purification by normal phase chromatography (50% EtOAc/pet. ether) afforded the desired product (4.8 g, 49.9%, yield). LCMS (ESI) m/z: [M+H] calcd for C₁₄H₂₄N₂O₅S: 333.15; found 333.1.

Step 2: Synthesis of methyl N-((3S)-1-((1,2-dibromoethyl)sulfonyl)pyrrolidine-3-carbonyl)-N-methyl-L-valinate To a solution of methyl N-methyl-N-((S)-1-(vinylsulfonyl)pyrrolidine-3-carbonyl)-L-valinate (4.5 g, 13.54 mmol) in CCl₄ (100 mL) at 0° C. was added Br₂ (2.77 mL, 54.15 mmol). The resulting solution was stirred for overnight and was then quenched by the addition of sat. NaHCO$_3$(100 mL). The aqueous layer was extracted with EtOAc (3×200 mL) and the combined organic layers were washed with brine, dried with Na$_2$SO$_4$, filtered, and concentrated under reduced pressure. Purification by normal phase chromatography (25% EtOAc/pet. ether) afforded the desired product (2.6 g, 39.0% yield). LCMS (ESI) m/z: [M+H] calcd for C$_{14}$H$_{24}$Br$_2$N$_2$O$_5$S: 492.99; found 493.0.

Step 3: Synthesis of methyl N-methyl-N—((S)-1-(((R)-1-methylaziridin-2-yl)sulfonyl)pyrrolidine-3-carbonyl)-L-valinate and methyl N-methyl-N—((S)-1-(((S)-1-methylaziridin-2-yl)sulfonyl)pyrrolidine-3-carbonyl)-L-valinate To a solution of methyl N-((3S)-1-((1,2-dibromoethyl)sulfonyl)pyrrolidine-3-carbonyl)-N-methyl-L-valinate (2.6 g, 5.28 mmol) in DMSO (250 mL) was added methanamine hydrochloride (1.07 g, 15.85 mmol) and Et$_3$N (7.37 mL, 52.82 mmol). The reaction mixture was heated to 75° C. and stirred overnight. The mixture was then cooled to room temperature and diluted with EtOAc (1.5 L). The resulting mixture was washed with sat. NH$_4$Cl (2×200 mL) and brine (2×200 mL) and the organic layer was then concentrated under reduced pressure. Purification by reverse phase chromatography (40→60% MeCN/H$_2$O) afforded a mixture of the desired products. The diastereomers were separated by prep-SFC (28% MeOH/CO$_2$) to afford methyl N-methyl-N—((S)-1-(((R)-1-methylaziridin-2-yl)sulfonyl)pyrrolidine-3-carbonyl)-L-valinate (0.46 g, 24% yield) and methyl N-methyl-N—((S)-1-(((S)-1-methylaziridin-2-yl)sulfonyl)pyrrolidine-3-carbonyl)-L-valinate (0.35 g, 18.3% yield). LCMS (ESI) m/z: [M+H] calcd for C$_{15}$H$_{27}$N$_3$O$_5$S: 362.17; found 362.1.

Step 4: Synthesis of N-methyl-N—((S)-1-(((R)-1-methylaziridin-2-yl)sulfonyl)pyrrolidine-3-carbonyl)-L-valine To a solution of methyl N-methyl-N—((S)-1-(((R)-1-methylaziridin-2-yl)sulfonyl)pyrrolidine-3-carbonyl)-L-valinate (200.0 mg, 0.55 mmol) in THF (2.0 mL) and H$_2$O (2.0 mL) at 0° C. was added LiOH (53.0 mg, 2.21 mmol). The resulting solution was stirred for 2 h at 0° C. and then the reaction mixture was acidified to pH 6 with 1M HCl. The aqueous layer was extracted with EtOAc and the combined organic layers were washed with brine, dried with Na$_2$SO$_4$, filtered, and concentrated under reduced pressure. Purification by reverse phase chromatography (5→55% MeCN/H$_2$O) afforded the desired product (110 mg, 57.2%, yield). LCMS (ESI) m/z: [M+H] calcd for C$_{14}$H$_{25}$N$_3$O$_5$S: 348.16; found 348.1.

Step 5: Synthesis of N-methyl-N—((S)-1-(((S)-1-methylaziridin-2-yl)sulfonyl)pyrrolidine-3-carbonyl)-L-valine To a solution of methyl N-methyl-N—((S)-1-(((S)-1-methylaziridin-2-yl)sulfonyl)pyrrolidine-3-carbonyl)-L-valinate (200.0 mg, 0.55 mmol) in THF (2.0 mL) and H$_2$O (2.0 mL) at 0° C. was added LiOH (53.0 mg, 2.21 mmol). The resulting solution was stirred for 2 h at 0° C. and then the reaction mixture was acidified to pH 6 with 1M HCl. The aqueous layer was extracted with EtOAc and the combined organic layers were washed with brine, dried with Na$_2$SO$_4$, filtered, and concentrated under reduced pressure. Purification by reverse phase chromatography (5→55 MeCN/H$_2$O) afforded the desired product (121 mg, 62.9%, yield). LCMS (ESI) m/z: [M+H] calcd for C$_{14}$H$_{25}$N$_3$O$_5$S: 348.16; found 348.1.

Intermediate A-23. Synthesis of (2S)-3-methyl-2-(1-oxo-7-((S)-1-tritylaziridine-2-carbonyl)-2,7-diazaspiro[4.4]nonan-2-yl)butanoic Acid

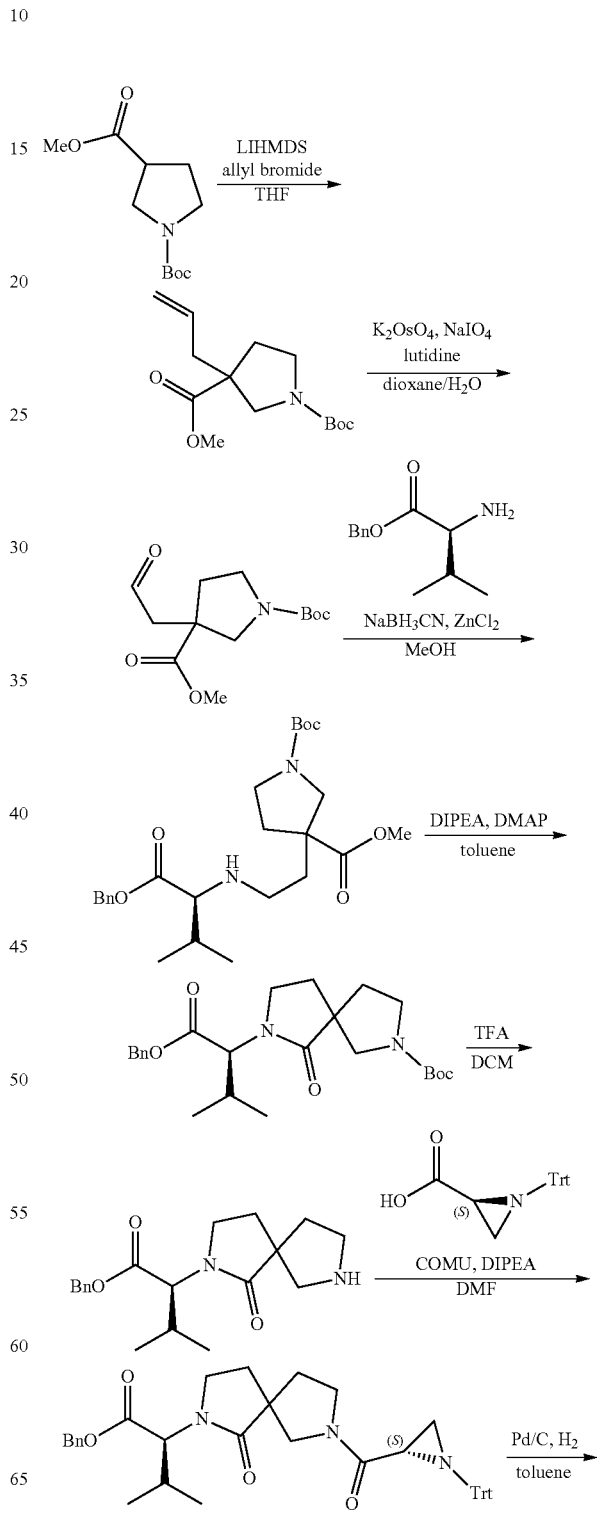

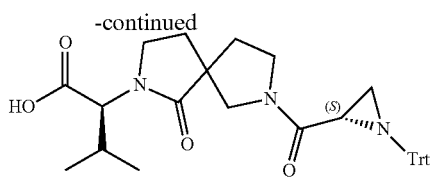

Step 1: Synthesis of 1-(tert-butyl) 3-methyl 3-allylpyrrolidine-1,3-dicarboxylate To a mixture of 1-(tert-butyl) 3-methyl pyrrolidine-1,3-dicarboxylate (10 g, 43.616 mmol) in THF (100 mL) at −78° C. was added 1M LiHMDS (65.42 mL, 65.424 mmol) dropwise. The resulting mixture was stirred at −78° C. for 1 h and then a solution of allyl bromide (7.91 g, 65.423 mmol) in THF was added dropwise over 10 min. The resulting mixture was stirred at −78° C. for an additional 2 h and was then quenched by the addition of sat. NH$_4$Cl at 0° C. The resulting mixture was extracted with EtOAc (3×100 mL) and the combined organic layers were washed with brine (2×80 mL), dried with Na$_2$SO$_4$, filtered, and concentrated under reduced pressure. Purification by silica gel column chromatography (20% EtOAc/pet. ether) afforded the desired product (10 g, 76% yield).

Step 2: Synthesis of 1-(tert-butyl) 3-methyl 3-(2-oxoethyl)pyrrolidine-1,3-dicarboxylate To a mixture of 1-(tert-butyl) 3-methyl 3-allylpyrrolidine-1,3-dicarboxylate (11.0 g, 40.84 mmol) and 2,6-lutidine (8.75 g, 81.68 mmol) in dioxane (190 mL) and H$_2$O (19 mL) at 0° C. was added K$_2$OsO$_4$.2H$_2$O (0.75 g, 2.04 mmol). The resulting mixture was stirred at 0° C. for 15 min and then NaIO$_4$ (34.94 g, 163.36 mmol) was added in portions. The mixture was warmed to room temperature and stirred for an additional 3 h, then was quenched by the addition of sat. Na$_2$S$_2$O$_3$ at 0° C. The resulting mixture was extracted with EtOAc (3×300 mL) and the combined organic layers were washed with brine (200 mL), dried with Na$_2$SO$_4$, filtered, and concentrated under reduced pressure. Purification by reverse phase chromatography (0→40% MeCN/H$_2$O, 0.1% HCO$_2$H) afforded the desired product (6.4 g, 51% yield).

Step 3: Synthesis of 1-(tert-butyl) 3-methyl 3-(2-(((S)-1-(benzyloxy)-3-methyl-1-oxobutan-2-yl)amino)ethyl)pyrrolidine-1,3-dicarboxylate To a mixture of 1-(tert-butyl) 3-methyl 3-(2-oxoethyl)pyrrolidine-1,3-dicarboxylate (6.30 g, 23.220 mmol) and benzyl L-valinate (7.22 g, 34.831 mmol) in MeOH (70 mL) at 0° C. was added ZnCl$_2$ (4.75 g, 34.831 mmol). The resulting mixture was warmed to room temperature and stirred for 30 min, then cooled to 0° C. NaBH$_3$CN (2.92 g, 46.441 mmol) was added in portions then the mixture was warmed to room temperature and stirred for 2 h. The reaction was quenched by the addition of sat. NH$_4$Cl at 0° C. and the resulting mixture was then extracted with EtOAc (3×200 mL). The combined organic layers were washed with brine (150 mL), dried with Na$_2$SO$_4$, filtered, and concentrated under reduced pressure. Purification by silica gel column chromatography (33% EtOAc/pet. ether) afforded the desired product (6.4 g, 53% yield). LCMS (ESI) m/z: [M+H] calcd for C$_{25}$H$_{38}$N$_2$O$_6$: 463.28; found 463.3.

Step 4: Synthesis of tert-butyl 7-((S)-1-(benzyloxy)-3-methyl-1-oxobutan-2-yl)-6-oxo-2,7-diazaspiro[4.4]nonane-2-carboxylate To a mixture of 1-(tert-butyl) 3-methyl 3-(2-(((S)-1-(benzyloxy)-3-methyl-1-oxobutan-2-yl)amino)ethyl)pyrrolidine-1,3-dicarboxylate (4.50 g, 9.728 mmol) and DIPEA (16.6 mL, 97.28 mmol) in toluene (50 mL) was added DMAP (1.19 g, 9.728 mmol) and then mixture was heated to 80° C. After 24 h the reaction was cooled to room temperature and concentrated under reduced pressure. Purification by reverse phase chromatography (15→60% MeCN/H$_2$O, 0.1% HCO$_2$H) afforded the desired product (3 g, 64% yield). LCMS (ESI) m/z: [M+H] calcd for C$_{24}$H$_{34}$O$_5$: 431.26; found 431.2.

Step 5: Synthesis of benzyl (2S)-3-methyl-2-(1-oxo-2,7-diazaspiro[4.4]nonan-2-yl)butanoate To a solution of tert-butyl 7-((S)-1-(benzyloxy)-3-methyl-1-oxobutan-2-yl)-6-oxo-2,7-diazaspiro[4.4]nonane-2-carboxylate (400.0 mg, 0.929 mmol) in DCM (3.0 mL) at 0° C. was added TFA (1.50 mL, 20.195 mmol) dropwise. The resulting mixture was stirred at 0° C. for 1 h and was then concentrated under reduced pressure. The TFA residue was further removed by azeotropic distillation with toluene three times to afford the desired product (400 mg, crude). LCMS (ESI) m/z: [M+H] calcd for C$_{19}$H$_{26}$N$_2$O$_3$: 331.20; found 331.1.

Step 6: Synthesis of benzyl (2S)-3-methyl-2-(1-oxo-7-((S)-1-tritylaziridine-2-carbonyl)-2,7-diazaspiro[4.4]nonan-2-yl)butanoate To a solution of benzyl (2S)-3-methyl-2-(1-oxo-2,7-diazaspiro[4.4]nonan-2-yl)butanoate (400.0 mg, 1.21 mmol) and DIPEA (2.06 mL, 12.11 mmol) in DMF (5 mL) at 0° C. was added (S)-1-tritylaziridine-2-carboxylic acid (558.26 mg, 1.695 mmol) followed by COMU (673.55 mg, 1.574 mmol) in portions. The resulting mixture was stirred at 0° C. for 1 h and was then diluted with H$_2$O (50 mL). The aqueous layer was extracted with EtOAc (3×20 mL) and the combined organic layers were washed with brine (20 mL), dried with Na$_2$SO$_4$, filtered, and concentrated under reduced pressure. Purification by prep-TLC (33% EtOAc/pet. ether) afforded the desired product (510 mg, 59% yield). LCMS (ESI) m/z: [M+H] calcd for C$_{41}$H$_{43}$N$_3$O$_4$: 642.34; found 642.3.

Step 7: Synthesis of (2S)-3-methyl-2-(1-oxo-7-((S)-1-tritylaziridine-2-carbonyl)-2,7-diazaspiro[4.4]nonan-2-yl)butanoic Acid To a mixture of benzyl (2S)-3-methyl-2-(1-oxo-7-((S)-1-tritylaziridine-2-carbonyl)-2,7-diazaspiro[4.4]nonan-2-yl)butanoate (480.0 mg, 0.748 mmol) in toluene (35.0 mL) was added Pd/C 200.0 mg, 1.879 mmol). The resulting mixture was placed under an atmosphere of H$_2$ (1 atm), heated to 50° C. and stirred for 3 h. The mixture was cooled to room temperature, filtered, the filter cake was washed with MeOH (3×10 mL), and the filtrate was concentrated under reduced pressure to afford the desired product (310 mg, 67% yield). LCMS (ESI) m/z: [M−H] calcd for C$_{34}$H$_{37}$N$_3$O$_4$: 550.27; found 550.3.

Intermediate A-24. Synthesis of (2S)-3-methyl-2-(1-oxo-7-((R)-1-tritylaziridine-2-carbonyl)-2,7-diazaspiro[4.4]nonan-2-yl)butanoic Acid

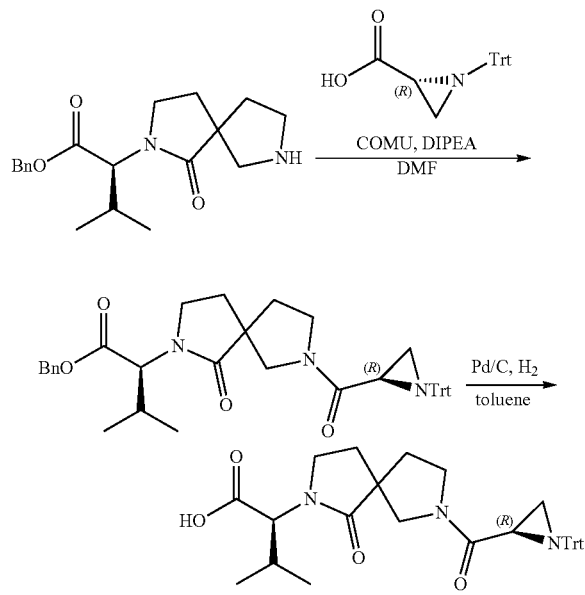

Step 1: Synthesis of benzyl (2S)-3-methyl-2-(1-oxo-7-((R)-1-tritylaziridine-2-carbonyl)-2,7-diazaspiro[4.4]nonan-2-yl)butanoate To a solution of benzyl (2S)-3-methyl-2-(1-oxo-2,7-diazaspiro[4.4]nonan-2-yl)butanoate (400.0 mg, 1.21 mmol) and (R)-1-tritylaziridine-2-carboxylic acid (518.4 mg, 1.57 mmol) in DMF (4.0 mL) at 0° C. was added DIPEA (1.0 mL, 6.05 mmol) followed by COMU (621.7 mg, 1.45 mmol). The resulting mixture was stirred for 1 h and was then diluted with H$_2$O (40 mL). The aqueous layer was extracted with EtOAc (3×15 mL) and the combined organic layers were washed with brine (2×10 mL), dried over Na$_2$SO$_4$, filtered and concentrated under reduced pressure. The residue was purified by prep-TLC (33% EtOAc/pet. ether) to afford the desired product (540 mg, 62% yield). LCMS (ESI) m/z: [M+H] calcd for C$_{41}$H$_{43}$N$_3$O$_4$: 642.33; found 642.4.

Step 2: Synthesis of (2S)-3-methyl-2-(1-oxo-7-((R)-1-tritylaziridine-2-carbonyl)-2,7-diazaspiro[4.4]nonan-2-yl)butanoic Acid To a solution of benzyl (2S)-3-methyl-2-(1-oxo-7-((R)-1-tritylaziridine-2-carbonyl)-2,7-diazaspiro[4.4]nonan-2-yl)butanoate (510.0 mg, 0.80 mmol) in toluene (30 mL) was added Pd/C (250.0 mg, 2.35 mmol). The resulting mixture was placed under a hydrogen atmosphere (1 atm), heated to 50° C., and stirred for 3 h. The reaction was then cooled to room temperature, filtered, the filter cake was washed with MeOH (3×10 mL), and the filtrate was concentrated under reduced pressure to afford the desired crude product (330 mg). LCMS (ESI) m/z: [M+H] calcd for C$_{34}$H$_{37}$N$_3$O$_4$: 552.29; found 552.3.

Intermediate A-25 and A-26. Synthesis of benzyl (S)-3-methyl-2-((S)-1-oxo-2,7-diazaspiro[4.4]nonan-2-yl)butanoate and benzyl (S)-3-methyl-2-((R)-1-oxo-2,7-diazaspiro[4.4]nonan-2-yl)butanoate

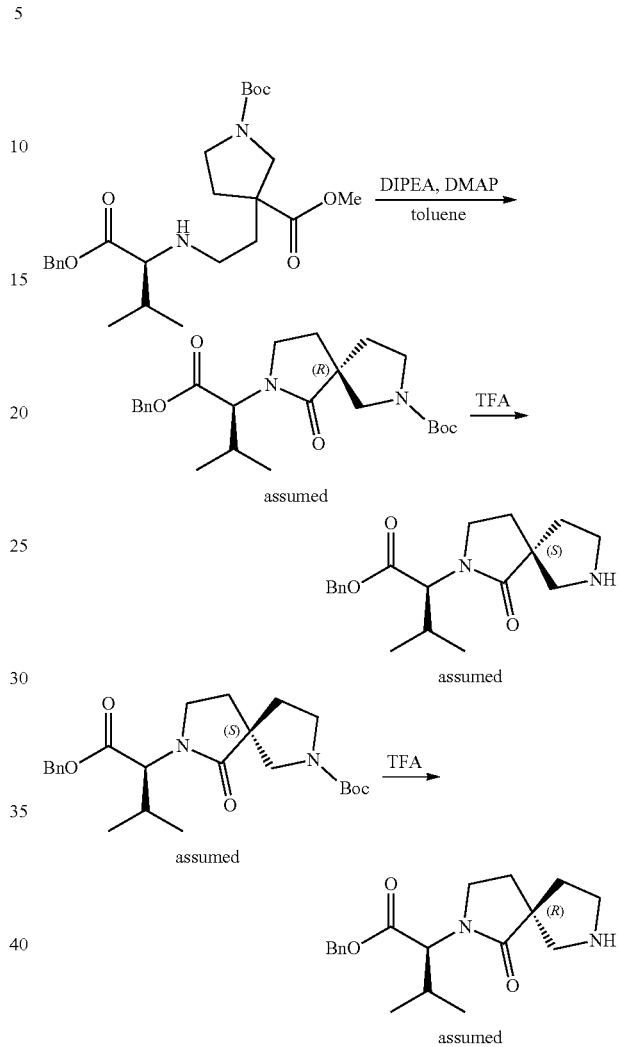

Step 1: Synthesis of tert-butyl (R)-7-((S)-1-(benzyloxy)-3-methyl-1-oxobutan-2-yl)-6-oxo-2,7-diazaspiro[4.4]nonane-2-carboxylate and tert-butyl (S)-7-((S)-1-(benzyloxy)-3-methyl-1-oxobutan-2-yl)-6-oxo-2,7-diazaspiro[4.4]nonane-2-carboxylate To a mixture of 1-(tert-butyl) 3-methyl 3-(2-(((S)-1-(benzyloxy)-3-methyl-1-oxobutan-2-yl)amino)ethyl)pyrrolidine-1,3-dicarboxylate (4.50 g, 9.728 mmol) and DIPEA (16.6 mL, 97.28 mmol) in toluene (50 mL) was added DMAP (1.19 g, 9.728 mmol) and then mixture was heated to 80° C. After 24 h the reaction was cooled to room temperature and concentrated under reduced pressure. Purification by reverse phase chromatography (10→50% MeCN/H$_2$O, 0.1% HCO$_2$H). The diastereomers were then separated by chiral prep-SFC (30% EtOH/CO$_2$) to afford tert-butyl (R)-7-((S)-1-(benzyloxy)-3-methyl-1-oxobutan-2-yl)-6-oxo-2,7-diazaspiro[4.4]nonane-2-carboxylate (1.0 g, 32% yield, LCMS (ESI) m/z: [M+H] calcd for C$_{24}$H$_{34}$N$_2$O$_5$: 431.26; found 431.2) and tert-butyl (S)-7-((S)-1-(benzyloxy)-3-methyl-1-oxobutan-2-yl)-6-oxo-2,7-diazaspiro[4.4]

nonane-2-carboxylate carboxylate (1.0 g, 32% yield, LCMS (ESI) m/z: [M+H] calcd for $C_{24}H_{34}N_2O_5$: 431.26; found 431.2).

Step 2: Synthesis of benzyl (S)-3-methyl-2-((S)-1-oxo-2,7-diazaspiro[4.4]nonan-2-yl)butanoate To a solution of tert-butyl (5R)-7-[(2S)-1-(benzyloxy)-3-methyl-1-oxobutan-2-yl]-6-oxo-2,7-diazaspiro[4.4] nonane-2-carboxylate (1.40 g, 3.25 mmol) in DCM (14 mL) at 0° C. was added TFA (5.0 mL, 67.3 mmol). The resulting mixture was stirred at 0° C. for 1 h and was then concentrated under reduced pressure. The mixture was diluted with $H_2O$ (20 mL) and was basified to pH 8 with sat. $NaHCO_3$(aq.) at 0° C. The resulting mixture was extracted with EtOAc (3×50 mL) and combined organic layers were washed with brine (40 mL), dried over $Na_2SO_4$, filtered, and concentrated under reduced pressure to afford the desired product (1.4 g, crude). LCMS (ESI) m/z: [M+H] calcd for $C_{19}H_{26}N_2O_3$: 331.20; found 331.2).

Step 3: Synthesis of benzyl (S)-3-methyl-2-((R)-1-oxo-2,7-diazaspiro[4.4]nonan-2-yl)butanoate To a solution of tert-butyl (5S)-7-[(2S)-1-(benzyloxy)-3-methyl-1-oxobutan-2-yl]-6-oxo-2,7-diazaspiro[4.4] nonane-2-carboxylate (1.0 g, 2.3 mmol) in DCM (10 mL) at 0° C. was added TFA (4.0 mL, 53.9 mmol). The resulting mixture was stirred at 0° C. for 1 h and was then concentrated under reduced pressure. The mixture was diluted with $H_2O$ (10 mL) and was basified to pH 8 with sat. $NaHCO_3$(aq.) at 0° C. The resulting mixture was extracted with EtOAc (3×20 mL) and combined organic layers were washed with brine (20 mL), dried over $Na_2SO_4$, filtered, and concentrated under reduced pressure to afford the desired product (1.0 g, crude). LCMS (ESI) m/z: [M+H] calcd for $C_{19}H_{26}N_2O_3$: 331.20; found 331.1).

Intermediate A-27. Synthesis of (2S)-3-methyl-2-(1-oxo-7-((R)-1-tritylaziridine-2-carbonyl)-2,7-diazaspiro[4.4]nonan-2-yl)butanoic Acid

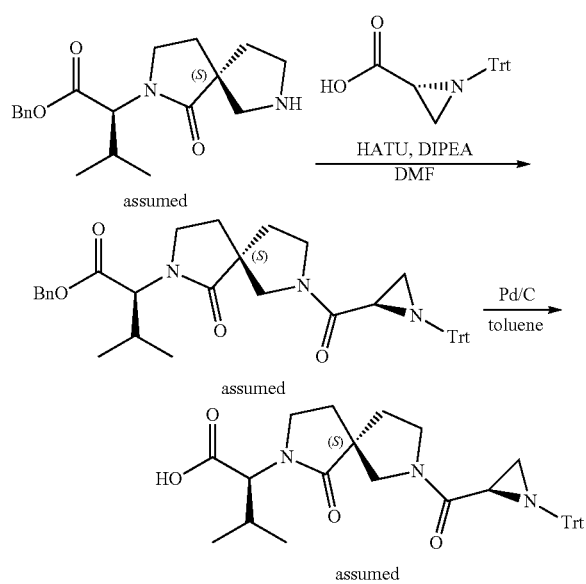

Step 1: Synthesis of benzyl (S)-3-methyl-2-((S)-1-oxo-7-((R)-1-tritylaziridine-2-carbonyl)-2,7-diazaspiro[4.4]nonan-2-yl)butanoate To a solution of benzyl (S)-3-methyl-2-((S)-1-oxo-2,7-diazaspiro[4.4]nonan-2-yl)butanoate (400 mg, 1.2 mmol) and DIPEA (1.1 mL, 6.1 mmol) in DMF (5.0 mL) at 0° C. was added (R)-1-tritylaziridine-2-carboxylic acid (480 mg, 1.5 mmol) and HATU (550 mg, 1.5 mmol). The resulting mixture was stirred for 1 h then purified by reverse phase chromatography (15→80% MeCN/$H_2O$, 0.5% $NH_4HCO_3$) to afford the desired product (500 mg, 57% yield). LCMS (ESI) m/z: [M+H] calcd for $C_{41}H_{43}N_3O_4$: 642.34; found 642.3.

Step 2: Synthesis of (2S)-3-methyl-2-(1-oxo-7-((R)-1-tritylaziridine-2-carbonyl)-2,7-diazaspiro[4.4] nonan-2-yl)butanoic Acid A solution of benzyl (S)-3-methyl-2-((S)-1-oxo-7-((R)-1-tritylaziridine-2-carbonyl)-2,7-diazaspiro[4.4]nonan-2-yl) butanoate (450 mg, 0.70 mmol) and Pd/C (120 mg, 1.13 mmol) in toluene (30 mL) at 50° C. was stirred under a hydrogen atmosphere (1 atm). The mixture was stirred for 3 h and then was filtered, and the filter cake was washed with MeOH (3×30 mL). The filtrate was concentrated under reduced pressure to afford the desired product (430 mg, crude). LCMS (ESI) m/z: [M+H] calcd for $C_{34}H_{37}N_3O_4$: 552.29; found 552.3.

Intermediate 28. Synthesis of (S)-3-methyl-2-((R)-1-oxo-7-((R)-1-tritylaziridine-2-carbonyl)-2,7-diazaspiro[4.4]nonan-2-yl)butanoic Acid

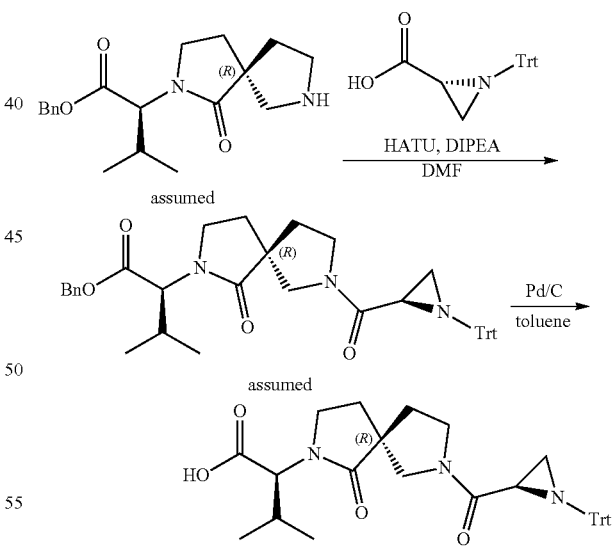

Step 1: Synthesis of benzyl (S)-3-methyl-2-((R)-1-oxo-7-((R)-1-tritylaziridine-2-carbonyl)-2,7-diazaspiro[4.4]nonan-2-yl)butanoate To a solution of benzyl (S)-3-methyl-2-((R)-1-oxo-2,7-diazaspiro[4.4]nonan-2-yl)butanoate (500 mg, 1.5 mmol) and DIPEA (1.3 mL, 7.6 mmol) in DMF (7.0 mL) at 0° C.

was added (R)-1-tritylaziridine-2-carboxylic acid (550 mg, 1.7 mmol) and HATU (630 mg, 1.7 mmol). The resulting mixture was stirred for 1 h then purification by reverse phase chromatography (10→80% MeCN/H$_2$O, 0.5% NH$_4$HCO$_3$) afforded desired product (700 mg, 64% yield) as an off-white solid. LCMS (ESI) m/z: [M+H] calcd for C$_{41}$H$_{43}$N$_3$O$_4$: 642.34; found 642.3.

Step 2: Synthesis of (S)-3-methyl-2-((R)-1-oxo-7-((R)-1-tritylaziridine-2-carbonyl)-2,7-diazaspiro[4.4]nonan-2-yl)butanoic Acid A solution of benzyl (S)-3-methyl-2-((R)-1-oxo-7-((R)-1-tritylaziridine-2-carbonyl)-2,7-diazaspiro[4.4]nonan-2-yl)butanoate (650 mg, 0.70 mmol) and Pd/C (140 mg, 1.3 mmol) in toluene (30 mL) at 50° C. was stirred under a hydrogen atmosphere (1 atm). The mixture was stirred for 3 h and then was filtered, and the filter cake was washed with MeOH (3×30 mL). The filtrate was concentrated under reduced pressure to afford the desired product (550 mg, crude). LCMS (ESI) m/z: [M+H] calcd for C$_{34}$H$_{37}$N$_3$O$_4$: 552.29; found 552.3.

Intermediate A-29. Synthesis of (S)-2-((R)-7-(tert-butoxycarbonyl)-1-oxo-2,7-diazaspiro[4.4]nonan-2-yl)-3-methylbutanoic Acid

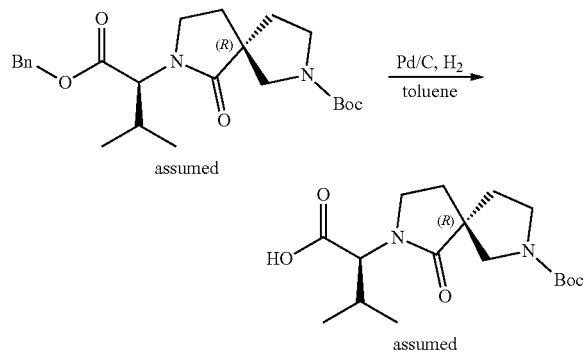

To a solution of tert-butyl (R)-7-((S)-1-(benzyloxy)-3-methyl-1-oxobutan-2-yl)-6-oxo-2,7-diazaspiro[4.4]nonane-2-carboxylate (600 mg, 1.4 mmol) in toluene (20 mL) was added Pd/C (120 mg, 1.1 mmol). The reaction mixture was heated at 50° C. and stirred under a hydrogen atmosphere (1 atm) for 3 h. The mixture was filtered, and the filter cake was washed with MeOH (3×20 mL). The filtrate was concentrated under reduced pressure to afford the desired product (550 mg, crude). LCMS (ESI) m/z: [M–H] calcd for C$_{17}$H$_{28}$N$_2$O$_5$: 339.19; found 339.1.

Intermediate A-30. Synthesis of (S)-2-((S)-7-(tert-butoxycarbonyl)-1-oxo-2,7-diazaspiro[4.4]nonan-2-yl)-3-methylbutanoic Acid

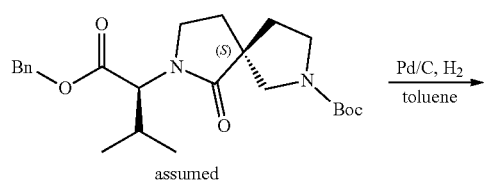

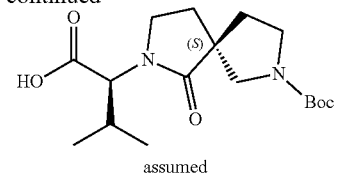

To a solution of tert-butyl (S)-7-((S)-1-(benzyloxy)-3-methyl-1-oxobutan-2-yl)-6-oxo-2,7-diazaspiro[4.4]nonane-2-carboxylate (550 mg, 1.3 mmol) in toluene (30 mL) was added Pd/C (120 mg, 1.1 mmol). The reaction mixture was heated at 50° C. and stirred under a hydrogen atmosphere (1 atm) for 3 h. The mixture was filtered, and the filter cake was washed with MeOH (3×20 mL). The filtrate was concentrated under reduced pressure to afford the desired product (550 mg, crude). LCMS (ESI) m/z: [M–H] calcd for C$_{17}$H$_{28}$N$_2$O$_5$: 339.19; found 339.2.

Intermediate A-31. Synthesis of (R)-3-methyl-2-(((S)—N-methyl-1-tritylaziridine-2-carboxamido)methyl)butanoic Acid

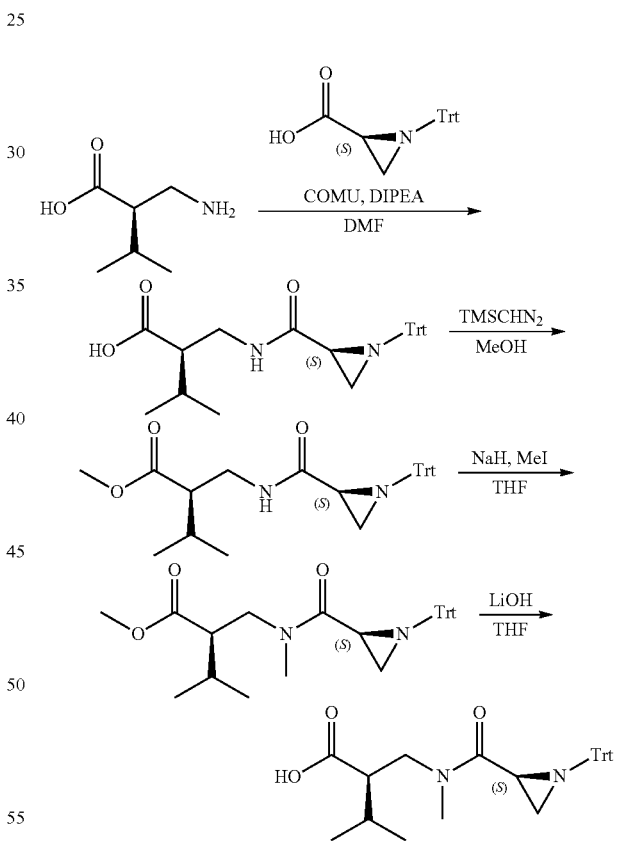

Step 1: Synthesis of (R)-3-methyl-2-(((S)-1-tritylaziridine-2-carboxamido)methyl)butanoic Acid To a solution of (S)-1-tritylaziridine-2-carboxylic acid (1 g, 2.9 mmol) in DMF (10 mL) at 0° C. was added DIPEA (2.5 mL, 14.55 mmol) followed by COMU (1.12 g, 2.62 mmol). The resulting mixture was stirred for 20 min and (R)-2-(aminomethyl)-3-methylbutanoic acid (382.0 mg, 2.91 mmol) was added. The resulting mixture was warmed to room temperature and stirred for an additional 2 h. The reaction mixture was then quenched with H₂O and the aqueous layer was extracted with EtOAc. The combined organic layers were washed with brine, dried over Na₂SO₄, filtered, and concentrated under reduced pressure. The crude residue was purified by reverse phase chromatography (30→70% MeCN/H₂O+0.1% NH₄HCO₃) to afford the desired product (850 mg, 63% yield). LCMS (ESI) m/z: [M−H] calcd for $C_{28}H_{30}N_2O_3$: 441.22; found 441.2.

Step 2: Synthesis of methyl (R)-3-methyl-2-(((S)-1-tritylaziridine-2-carboxamido)methyl)butanoate To a solution of (R)-3-methyl-2-(((S)—N-methyl-1-tritylaziridine-2-carboxamido)methyl)butanoic acid (840.0 mg, 1.90 mmol) in MeOH (5.0 mL) at 0° C. was added TMSCHN₂ (10.0 mL, 0.45 mmol). The resulting mixture was warmed to room temperature and stirred for 2 h, at which point the reaction mixture was concentrated under reduced pressure. The residue was purified by reverse phase chromatography (30→80% MeCN/H₂O+0.1% NH₄HCO₃) to afford the desired product (450 mg, 52% yield). LCMS (ESI) m/z: [M−H] calcd for $C_{29}H_{32}N_2O_3$: 455.23; found 455.1.

Step 3: Synthesis of methyl (R)-3-methyl-2-(((S)—N-methyl-1-tritylaziridine-2-carboxamido)methyl)butanoate To a solution of methyl (R)-3-methyl-2-(((S)-1-tritylaziridine-2-carboxamido)methyl)butanoate (440.0 mg, 0.96 mmol) in THF (5.0 mL) at 0° C. was added NaH (46.25 mg, 1.93 mmol). The resulting mixture was stirred for 30 min and then MeI (1.37 g, 9.65 mmol) was added. The resulting mixture was warmed to room temperature and stirred for an additional 4 h. The reaction mixture was then quenched with H₂O and the aqueous layer was extracted with EtOAc (3×300 mL). The combined organic layers were washed with brine (3×200 mL), dried over Na₂SO₄, filtered, and concentrated under reduced pressure. The residue was purified by reverse phase chromatography (10→90% MeCN/H₂O+0.1% NH₄HCO₃) to afford the desired product (340 mg, 75% yield). LCMS (ESI) m/z: [M+H] calcd for $C_{30}H_{34}N_2O_3$: 471.26; found 471.3.

Step 4: Synthesis of (R)-3-methyl-2-(((S)—N-methyl-1-tritylaziridine-2-carboxamido)methyl)butanoic Acid To a solution of methyl (R)-3-methyl-2-(((S)—N-methyl-1-tritylaziridine-2-carboxamido)methyl)butanoate (340.0 mg, 0.72 mmol) in MeOH (3.0 mL) and H₂O (3.0 mL) was added LiOH.H₂O (242.5 mg, 5.78 mmol). The resulting mixture was stirred for 16 h at room temperature and was then acidified to pH 4 with KHSO₄ (1 N). The resulting mixture was extracted with EtOAc (3×300 mL) and the combined organic layers were washed with brine (3×300 mL), dried over Na₂SO₄, filtered, and concentrated under reduced pressure. The residue was purified by reverse phase chromatography (10→80% MeCN/H₂O+0.1% NH₄HCO₃) to afford the desired product (260 mg). LCMS (ESI) m/z: [M+H] calcd for $C_{29}H_{32}N_2O_3$: 455.23; found 455.1.

Intermediate A-32. Synthesis of N-methyl-N-(1-((R)-1-tritylaziridine-2-carbonyl)piperidine-4-carbonyl)-L-valine

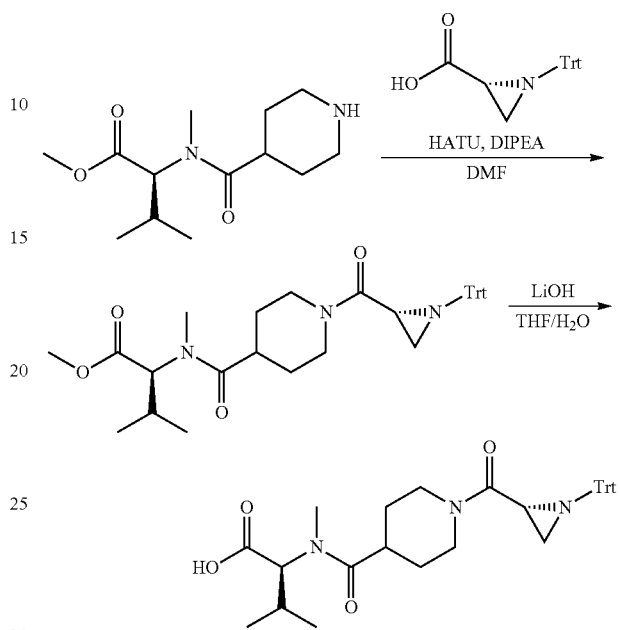

Step 1: Synthesis of methyl N-methyl-N-(1-((R)-1-tritylaziridine-2-carbonyl)piperidine-4-carbonyl)-L-valinate To a mixture of methyl N-methyl-N-(piperidine-4-carbonyl)-L-valinate (750 mg, 2.93 mmol) and (R)-1-tritylaziridine-2-carboxylic acid (1.13 g, 3.43 mmol) in DMF (7 mL) at 0° C. was added DIPEA (2.50 mL, 14.62 mmol) followed by HATU (2.20 g, 5.79 mmol) in portions. The resulting mixture was warmed to room temperature and stirred for 3 h. The reaction mixture was diluted with EtOAc (300 mL) and the mixture was washed with brine (2×150 mL), dried with Na₂SO₄, filtered, and concentrated under reduced pressure. Purification by normal phase chromatography (50% EtOAc/hexanes) afforded the desired product (1.5 g, 90.3% yield). LCMS (ESI) m/z: [M+H] calcd for $C_{35}H_{41}N_3O_4$: 568.32; found 568.3.

Step 2: Synthesis of N-methyl-N-(1-((R)-1-tritylaziridine-2-carbonyl)piperidine-4-carbonyl)-L-valine To a solution of methyl N-methyl-N-(1-((R)-1-tritylaziridine-2-carbonyl)piperidine-4-carbonyl)-L-valinate (500 mg, 0.881 mmol) in THF (5 mL) at 0° C. was added a solution of LiOH (111 mg, 2.64 mmol) in H₂O (2.6 mL). The resulting mixture was warmed to room temperature and stirred for 4 h. The reaction mixture was diluted with H₂O (300 mL) and acidified to pH 5 with 1M HCl. The resulting mixture was extracted with DCM (3×100 mL) and the combined organic layers were washed with brine (2×150 mL), dried with Na₂SO₄, filtered, and concentrated under reduced pressure to afford the desired product (600 mg, crude) which was used without further purification. LCMS (ESI) m/z: [M−H] calcd for $C_{34}H_{39}N_3O_4$: 552.29; found 552.3.

Intermediate A-33. Synthesis of N-methyl-N-(1-((S)-1-tritylaziridine-2-carbonyl)piperidine-4-carbonyl)-L-valine

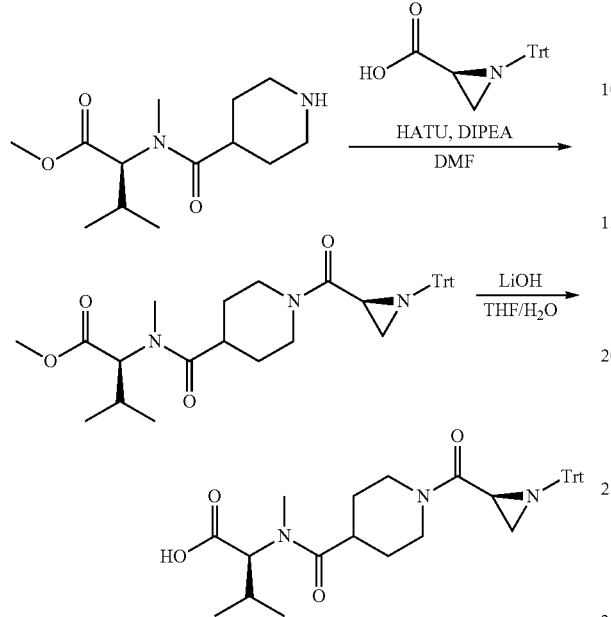

Step 1: Synthesis of methyl N-methyl-N-(1-((S)-1-tritylaziridine-2-carbonyl)piperidine-4-carbonyl)-L-valinate To a mixture of methyl N-methyl-N-(piperidine-4-carbonyl)-L-valinate (0.90 g, 3.511 mmol) and (S)-1-tritylaziridine-2-carboxylic acid (2.31 g, 7.022 mmol) in DMF (10 mL) at 0° C. was added DIPEA (3.06 mL, 17.57 mmol) and HATU (2.67 g, 7.022 mmol). The resulting mixture was warmed to room temperature and stirred for 2 h. The reaction mixture was diluted with EtOAc (50 mL) and the mixture was washed with $H_2O$, brine (100 mL), dried with $Na_2SO_4$, filtered, and concentrated under reduced pressure. Purification by normal phase chromatography (100% EtOAc) afforded the desired product (1.47 g, 73.7% yield). LCMS (ESI) m/z: [M+H] calcd for $C_{35}H_{41}N_3O_4$: 568.32; found 568.3.

Step 2: Synthesis of N-methyl-N-(1-((S)-1-tritylaziridine-2-carbonyl)piperidine-4-carbonyl)-L-valine To a solution of methyl N-methyl-N-(1-((S)-1-tritylaziridine-2-carbonyl)piperidine-4-carbonyl)-L-valinate (1.0 g, 1.76 mmol) in THF (15 mL) at 0° C. was added a solution of LiOH (370 mg, 8.80 mmol) in $H_2O$ (15 mL). The resulting mixture was warmed to room temperature and stirred for 3 h. The reaction mixture was acidified to pH 6 with 1M HCl. The aqueous layer was extracted with EtOAc (2×50 mL) and the combined organic layers were dried with $Na_2SO_4$, filtered, and concentrated under reduced pressure to adfford the desired product (1.33 g, crude) which was used without further purification. LCMS (ESI) m/z: [M+H] calcd for $C_{34}H_{39}N_3O_4$: 554.30; found 554.3.

Intermediate A-34. Synthesis of sodium (R)-1-methyl-5-(1-tritylaziridine-2-carboxamido)-1H-imidazole-2-carboxylate

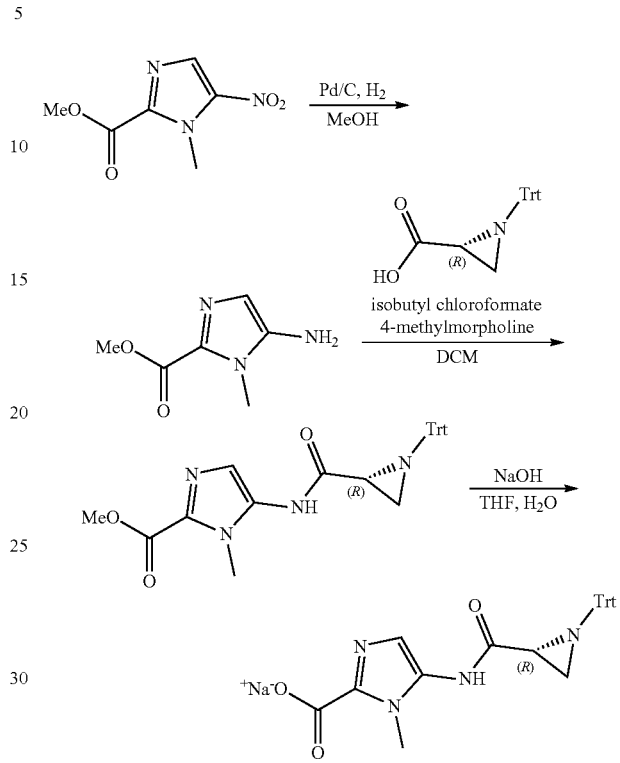

Step 1: Synthesis of methyl 5-amino-1-methyl-1H-imidazole-2-carboxylate

To a mixture of methyl 1-methyl-5-nitro-1H-imidazole-2-carboxylate (1.0 g, 5.401 mmol) in MeOH (15 mL) was added Pd/C (500 mg). The resulting mixture was placed under an atmosphere of $H_2$ (1 atm) and stirred for 3 h. The mixture was filtered, the filter cake was washed with MeOH (3×20 mL), and the filtrate was concentrated under reduced pressure to afford the desired product (1.0 g, crude). LCMS (ESI) m/z: [M+H] calcd for $C_6H_9N_3O_2$: 156.08; found 156.1.

Step 2: Synthesis of methyl (R)-1-methyl-5-(1-tritylaziridine-2-carboxamido)-1H-imidazole-2-carboxylate To a mixture of (R)-1-tritylaziridine-2-carboxylic acid (2.55 g, 7.741 mmol) in DCM (12.0 mL) at 0° C. was added a solution of isobutyl chloroformate (845.06 mg, 6.187 mmol) and N-methylmorpholine (1.04 g, 10.282 mmol) in DCM in portions over 30 min. To the resulting mixture was added methyl 5-amino-1-methyl-1H-imidazole-2-carboxylate (800.0 mg, 5.156 mmol). The mixture was stirred at room temperature overnight then diluted with DCM (300 mL) and washed with $H_2O$ (3×100 mL). The organic layer was washed with brine (2×150 mL), dried with $Na_2SO_4$, filtered, and concentrated under reduced pressure. Purification by silica gel column chromatography (25% EtOAc/hexanes) afforded the desired product (1.2 g, 49.9% yield). LCMS (ESI) m/z: [M+H] calcd for $C_{28}H_{26}N_4O_3$: 467.21; found 467.2.

Step 3: Synthesis of sodium (R)-1-methyl-5-(1-tritylaziridine-2-carboxamido)-1H-imidazole-2-carboxylate To a mixture of methyl (R)-1-methyl-5-(1-tritylaziridine-2-carboxamido)-1H-imidazole-2-carboxylate (300 mg, 0.643 mmol) in THF (3 mL) was added a solution of NaOH (38.58 mg, 0.965 mmol) in H$_2$O. The resulting mixture was stirred for 2 h and then concentrated under reduced pressure to afford the desired product (400 mg, crude). LCMS (ESI) m/z: [M+H] calcd for C$_{27}$H$_{24}$N$_4$O$_3$: 453.19; found 453.2.

Intermediate A-35. Synthesis of (S)-1-methyl-5-(1-tritylaziridine-2-carboxamido)-1H-imidazole-2-carboxylic Acid

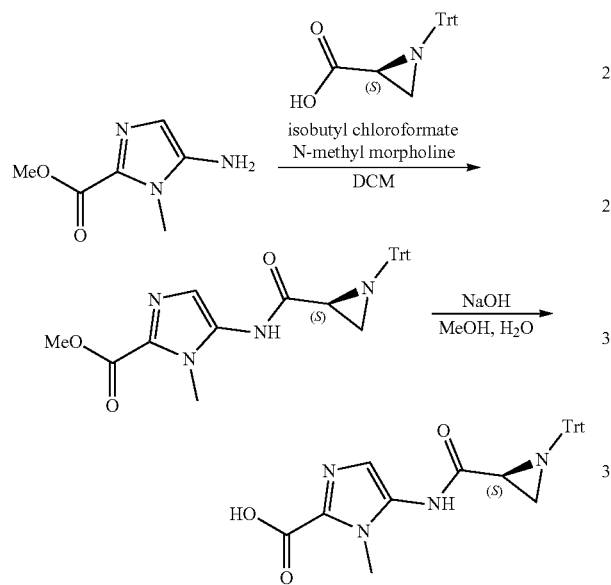

Step 1: Synthesis of methyl (S)-1-methyl-5-(1-tritylaziridine-2-carboxamido)-1H-imidazole-2-carboxylate To a mixture of (S)-1-tritylaziridine-2-carboxylic acid (1.18 g, 3.577 mmol) in DCM (15 mL) at 0° C. was added isobutyl chloroformate (423.41 mg, 3.100 mmol) and N-methylmorpholine (0.39 mL, 3.862 mmol) dropwise. The resulting mixture was stirred at 0° C. for 1 h then methyl 5-amino-1-methyl-1H-imidazole-2-carboxylate (370.0 mg, 2.385 mmol) was added. The mixture was warmed to room temperature and stirred overnight. The reaction was quenched with sat. NaHCO$_3$ at 0° C. and the resulting mixture was extracted with DCM (2×100 mL). The combined organic layers were washed with brine (150 mL), dried with Na$_2$SO$_4$, filtered, and concentrated under reduced pressure. Purification by silica gel column chromatography (100% EtOAc) afforded the desired product (380 mg, 34.2% yield). LCMS (ESI) m/z: [M+H] calcd for C28H26N4O3: 467.21; found 467.3.

Step 2: Synthesis of (S)-1-methyl-5-(1-tritylaziridine-2-carboxamido)-1H-imidazole-2-carboxylic Acid To a mixture of methyl (S)-1-methyl-5-(1-tritylaziridine-2-carboxamido)-1H-imidazole-2-carboxylate (380.0 mg, 0.815 mmol) in MeOH (5 mL) at 0° C. was added NaOH (146.60 mg, 3.665 mmol) in H$_2$O (3.6 mL) dropwise. The resulting mixture was warmed to room temperature and stirred for 6 h then was acidified to pH 6 with 1M HCl. The resulting mixture was extracted with DCM (2×100 mL), and the combined organic layers were washed with brine (150 mL), dried with Na$_2$SO$_4$, filtered, and concentrated under reduced pressure to afford the desired product (350 mg, crude). LCMS (ESI) m/z: [M–H] calcd for C$_{27}$H$_{24}$N$_4$O$_3$: 451.17; found 451.1.

Intermediate A-36 and A-37. Synthesis of (R)—N-methyl-N-((1-methylaziridin-2-yl)sulfonyl)glycine and (S)—N-methyl-N-((1-methylaziridin-2-yl)sulfonyl)glycine

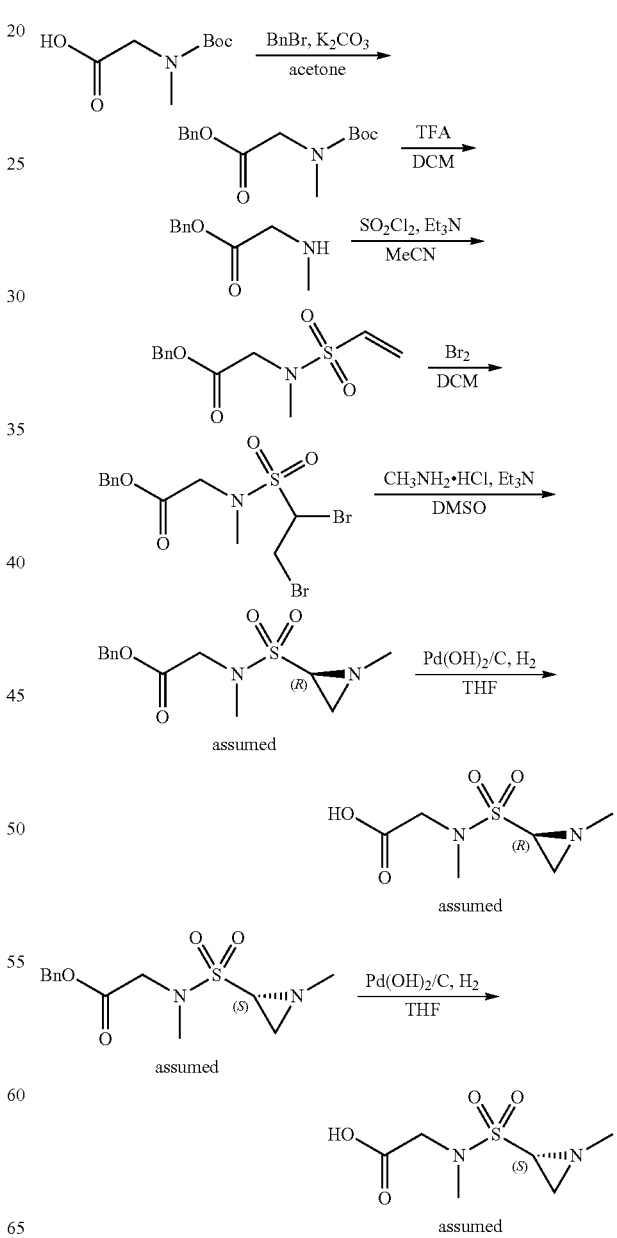

Step 1: Synthesis of benzyl N-(tert-butoxycarbonyl)-N-methylglycinate

To a stirred mixture of [(tert-butoxycarbonyl)(methyl) amino]acetic acid (15. g, 79.28 mmol) in acetone (150 mL) was added BnBr (14.14 mL, 82.70 mmol) and $K_2CO_3$ (21.91 g, 158.55 mmol) in portions at 0° C. The resulting mixture was stirred for 4 h at room temperature. The resulting mixture was filtered, the filter cake was washed with acetone (3×100 mL), and the filtrate was concentrated under reduced pressure. The residue was purified by silica gel column chromatography (33% EtOAc/pet. ether) to afford the desired product (15.2 g, 68.6% yield). LCMS (ESI) m/z: [M+Na] calcd for $C_{15}H_{21}NO_4$: 302.14; found 302.0.

Step 2: Synthesis of Benzyl Methylglycinate

To a stirred solution of benzyl N-(tert-butoxycarbonyl)-N-methylglycinate (10.0 g, 35.80 mmol) in DCM (100 mL) was added TFA (50 mL) dropwise at 0° C. The resulting mixture was stirred for 1 h at 0° C. and then the resulting mixture was concentrated under reduced pressure to afford the desired product (7.80 g, crude). LCMS (ESI) m/z: [M+H] calcd for $C_{10}H_{13}NO_2$: 180.10; found 179.1.

Step 3: Synthesis of Benzyl N-methyl-N-(vinylsulfonyl)glycinate

To a solution of benzyl methylglycinate (15.60 g, 87.04 mmol) and $Et_3N$ (36.4 mL, 261.1 mmol) in MeCN (300 mL) at −70° C. was added a solution of 2-chloroethanesulfonyl chloride (17.03 g, 104.47 mmol) in MeCN (150 mL). The resulting mixture was warmed to room temperature and stirred for 20 min. The reaction mixture was cooled −50° C. and additional $Et_3N$ (36.4 mL, 261.1 mmol) was added to reaction mixture. The reaction mixture was warmed to room temperature and stirred for 1 h. The reaction was then quenched with $H_2O$ at 0° C. The mixture was acidified to pH 6 with 1 M HCl aq and was then extracted with DCM (800 mL), dried over $Na_2SO_4$, filtered, and concentrated under reduced pressure. The residue was purified by silica gel column chromatography (33% EtOAc/pet. ether) to afford the desired product (7.53 g, 32.1% yield). LCMS (ESI) m/z: [M+$H_2O$] calcd for $C_{12}H_{15}NO_4S$: 287.08; found 287.2.

Step 4: Synthesis of benzyl N-((1,2-dibromoethyl)sulfonyl)-N-methylglycinate To a solution of benzyl N-methyl-N-(vinylsulfonyl)glycinate (5.58 g, 20.7 mmol) in DCM (50 mL) at −20° C. was added a solution of $Br_2$ (1.06 mL, 6.64 mmol) in DCM (10 mL). The resulting mixture was warmed to room temperature and stirred overnight. The reaction mixture was then cooled to 0° C. and quenched with sat. aq. $Na_2S_2O_3$ (30 mL). The resulting mixture was washed with sat. aq. $Na_2HCO_3$ and then extracted with DCM (2×200 mL), the combined organic layers dried over $Na_2SO_4$, filtered, and concentrated under reduced pressure. The residue was purified by silica gel column chromatography (33% EtOAc/pet. ether) to afford the desired product (5.1 g, 57.4% yield). LCMS (ESI) m/z: [M+$H_2O$] calcd for $C_{12}H_{15}Br_2NO_4S$: 444.92; found 444.9.

Step 5: Synthesis of benzyl (R)—N-methyl-N-((1-methylaziridin-2-yl)sulfonyl)glycinate and benzyl (S)—N-methyl-N-((1-methylaziridin-2-yl)sulfonyl)glycinate To a stirred solution of benzyl N-((1,2-dibromoethyl) sulfonyl)-N-methylglycinate (7.20 g, 16.78 mmol) and methylamine hydrochloride (3.39 g, 50.2 mmol) in DMSO (750 mL) was added $Et_3N$ (23.32 mL, 230.47 mmol). The resulting mixture was stirred for 2 h at room temperature then heated to 75° C. and stirred overnight. The reaction mixture was cooled to room temperature and extracted with EtOAc (2×1000 mL). The combined organic layers were washed with $H_2O$ (1500 mL) and brine (1500 mL), dried over $Na_2SO_4$, filtered, and concentrated under reduced pressure. The residue was purified by silica gel column chromatography (EtOAc) to afford a mixture of diastereomers. The diastereomers were separated by prep-SFC (10% EtOH/Hex) to afford benzyl (R)—N-methyl-N-((1-methylaziridin-2-yl)sulfonyl)glycinate (500 mg, 31.3% yield) and benzyl (S)—N-methyl-N-((1-methylaziridin-2-yl)sulfonyl)glycinate (600 mg, 37.5% yield). LCMS (ESI) m/z: [M+H] calcd for $C_{13}H_{18}N_2O_4S$: 299.11; found 299.0.

Step 6: Synthesis of (R)—N-methyl-N-((1-methylaziridin-2-yl)sulfonyl)glycine A suspension of benzyl (R)—N-methyl-N-((1-methylaziridin-2-yl)sulfonyl)glycinate (300.0 mg) and $Pd(OH)_2$/C (150.0 mg) in THF at room temperature was stirred under an atmosphere of hydrogen (1 atm) for 3 h. The mixture was filtered, the filter cake was washed with MeOH (3×20 mL), and the filtrate was concentrated under reduced pressure to afford the desired product (206 mg, crude). LCMS (ESI) m/z: [M+H] calcd for $C_6H_{12}N_2O_4S$: 209.06; found 209.0.

Step 7: Synthesis of (S)—N-methyl-N-((1-methylaziridin-2-yl)sulfonyl)glycine A suspension of benzyl (R)—N-methyl-N-((1-methylaziridin-2-yl)sulfonyl)glycinate (300.0 mg, 1.01 mmol) and $Pd(OH)_2$/C (150.0 mg) in THF at room temperature was stirred under an atmosphere of hydrogen (1 atm) for 3 h. The mixture was filtered, the filter cake was washed with MeOH (3×20 mL), and the filtrate was concentrated under reduced pressure to afford the desired product (216 mg, crude). LCMS (ESI) m/z: [M+H] calcd for $C_6H_{12}N_2O_4S$: 209.06; found 209.1.

Intermediate A-38. Synthesis of (2S,3S)-1-(tert-butylsulfinyl)-3-cyclopropylaziridine-2-carboxylic Acid

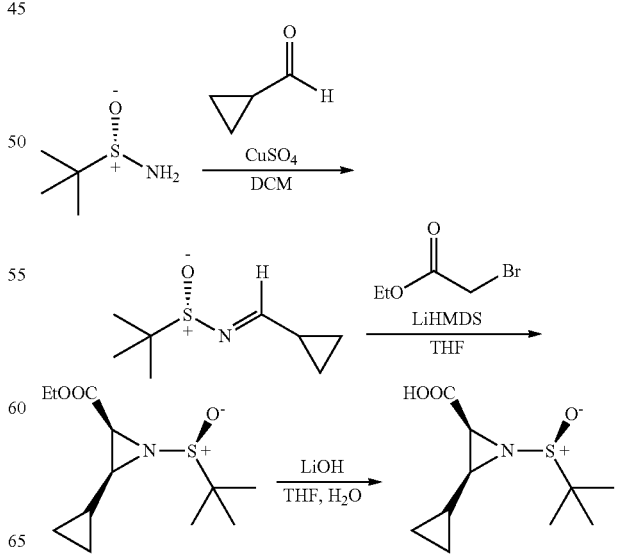

Step 1: Synthesis of (E)-N-(cyclopropylmethylene)-2-methylpropane-2-sulfinamide To a suspension of (S)-2-methylpropane-2-sulfinamide (4.0 g, 33.0 mmol) and CuSO$_4$ (15.80 g, 99.01 mmol) in DCM (200.0 mL) was added cyclopropanecarbaldehyde (4.63 g, 66.0 mmol). The resulting mixture was stirred overnight and was then filtered, the filter cake was washed with DCM (3×100 mL), and the filtrate was concentrated under reduced pressure to afford the desired product (3.5 g, 61.2% yield). LCMS (ESI) m/z: [M+H] calcd for C$_8$H$_{15}$NOS: 174.10; found 174.1.

Step 2: Synthesis of ethyl (2S,3S)-1-(tert-butylsulfinyl)-3-cyclopropylaziridine-2-carboxylate To a solution of ethyl bromoacetate (481.91 mg, 2.886 mmol) in THF (5.0 mL) at −78° C. was added LiHMDS (2.90 mL, 2.90 mmol). The resulting mixture was stirred for 2 h at −78° C. and then a solution of (E)-N-(cyclopropylmethylene)-2-methylpropane-2-sulfinamide (250.0 mg, 1.443 mmol) was added. The resulting mixture was stirred for 2 h at −78° C. and was then was then quenched with H$_2$O at 0° C. The aqueous layer was extracted with EtOAc (3×50 mL), and the combined organic layers were dried over Na$_2$SO$_4$, filtered, and concentrated under reduced pressure. The residue was purified by prep-TLC (17% EtOAc/pet. ether) to afford the desired product (250 mg, 66.8% yield). LCMS (ESI) m/z: [M+H] calcd for C$_{12}$H$_{21}$NO$_3$S: 260.13; found 260.1.

Step 3: Synthesis of (2S,3S)-1-(tert-butylsulfinyl)-3-cyclopropylaziridine-2-carboxylic Acid A solution of ethyl (2S,3S)-1-(tert-butylsulfinyl)-3-cyclopropylaziridine-2-carboxylate (500.0 mg, 1.928 mmol) in THF (2.0 mL) and H$_2$O (2.0 mL) at 0° C. was added LiOH.H$_2$O (121.34 mg, 2.89 mmol). The reaction mixture was stirred for 1 h and was then acidified to pH 6 with 1 M HCl (aq.). The resulting mixture was extracted with EtOAc (2×10 mL) and the combined organic layers were washed with brine (10 mL), dried over Na$_2$SO$_4$, filtered, and the filtrate was concentrated under reduced pressure to afford the desired product (400 mg, 89.7% yield). LCMS (ESI) m/z: [M+H] calcd for C$_{10}$H$_{17}$NO$_3$S: 232.10; found 232.0.

Intermediate A-39. Synthesis of (2R,3R)-3-(methoxymethyl)-1-tritylaziridine-2-carboxylic Acid

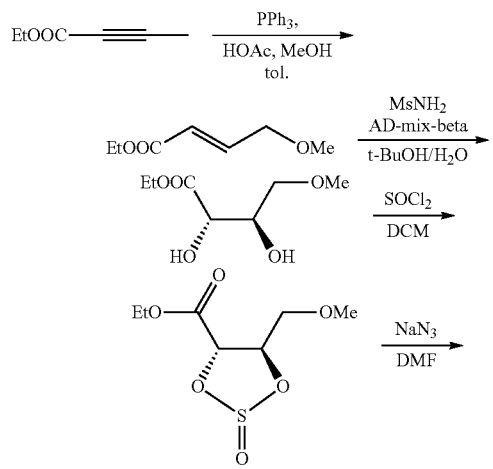

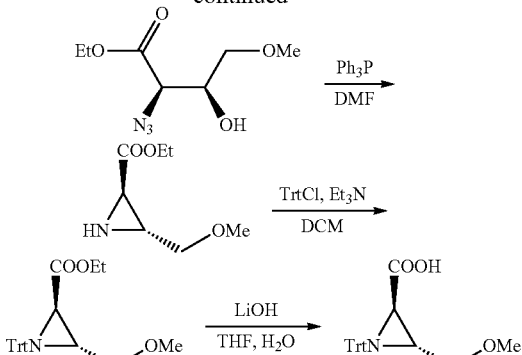

Step 1: Synthesis of ethyl (E)-4-methoxybut-2-enoate

To a solution of ethyl but-2-ynoate (10.0 g, 89.18 mmol) in MeOH (8.80 mL, 118.594 mmol) and HOAc (1.05 mL, 18.3 mmol) was added a solution of PPh$_3$ (1.20 g, 4.58 mmol) in toluene (60.0 mL). The resulting solution heated to 110° C. and stirred overnight. The reaction mixture was cooled to room temperature and was then diluted with H$_2$O (60 mL). The resulting solution was extracted with EtOAc (2×60), and the combined organic layers were washed with brine (2×20 mL), dried over Na$_2$SO$_4$, filtered, and concentrated under reduced pressure. The residue was purified by silica gel column chromatography (9% EtOAc/pet. ether) to afford the desired product (4.9 g, 38.1% yield). LCMS (ESI) m/z: [M+H] calcd for C$_7$H$_{12}$O$_3$: 145.09; found 144.9.

Step 2: Synthesis of ethyl (2S,3R)-2,3-dihydroxy-4-methoxybutanoate

To a solution of ethyl (E)-4-methoxybut-2-enoate (5.0 g, 34.68 mmol), and methanesulfonamide (3.30 g, 34.68 mmol) in t-BuOH (150.0 mL) and H$_2$O (100.0 mL) was added AD-mix-β (48.63 g, 62.43 mmol). The resulting solution was heated to 30° C. and stirred overnight. The solution was then cooled to room temperature and adjusted to pH 2 with KHSO$_4$. The resulting solution was extracted with EtOAc (2×100 mL) and the combined organic layers were dried over Na$_2$SO$_4$, filtered, and concentrated under reduced pressure to afford the desired product (1.28 g, crude). LCMS (ESI) m/z: [M+H] calcd for C$_7$H$_{14}$O$_5$: 179.09; found 179.0.

Step 3: Synthesis of ethyl (4S,5R)-5-(methoxymethyl)-1,3,2-dioxathiolane-4-carboxylate 2-oxide To a solution of ethyl (2S,3R)-2,3-dihydroxy-4-methoxybutanoate (4.10 g, 23.01 mmol) in DCM (20.0 mL) at 0° C. was added SOCl$_2$ (5.47 g, 45.9 mmol). The resulting mixture was heated to 50° C. and stirred for 3 h. The reaction mixture was then cooled to room temperature and concentrated under reduced pressure to afford the desired product (4.0 g, crude).

Step 4: Synthesis of ethyl (2R,3S)-2-azido-3-hydroxy-4-methoxybutanoate

To a solution of ethyl (4S,5R)-5-(methoxymethyl)-1,3,2-dioxathiolane-4-carboxylate 2-oxide (4.0 g crude, 17.84 mmol) in DMF (20.0 mL) at 0° C. was added NaN$_3$ (5.80 g, 89.22 mmol). The resulting mixture was heated to 35° C. and stirred overnight. The reaction mixture was then diluted with H$_2$O (200 mL) and was extracted with EtOAc (3×50 mL). The combined organic layers were washed with brine (3×50 mL), dried over Na$_2$SO$_4$, filtered, and concentrated under reduced pressure. The residue was purified by silica gel column chromatography (17% EtOAc/pet. ether) to afford the desired product (1.0 g, 27.6% yield). LCMS (ESI) m/z: [M+H] calcd for C$_7$H$_{13}$N$_3$O$_4$: 204.10; found 204.0.

Step 5: Synthesis of ethyl (2R,3R)-3-(methoxymethyl)aziridine-2-carboxylate

To a solution of ethyl (2R,3S)-2-azido-3-hydroxy-4-methoxybutanoate (1.0 g, 4.92 mmol) in DMF (10 mL) at 0° C. was added PPh$_3$ (1.29 g, 4.92 mmol) in portions over 30 min. The reaction solution was then warmed to room temperature and stirred for 30 min. The reaction mixture was then heated to 85° C. and stirred until the reaction was complete. The reaction mixture was then concentrated under reduced pressure and purified by prep-TLC (33% EtOAc/pet. ether) to afford the desired product (480 mg, 61.3% yield). LCMS (ESI) m/z: [M+H] calcd for C$_7$H$_{13}$NO$_3$: 160.10; found 160.1.

Step 6: Synthesis of ethyl (2R,3R)-3-(methoxymethyl)-1-tritylaziridine-2-carboxylate To a solution of ethyl (2R,3R)-3-(methoxymethyl)aziridine-2-carboxylate (480.0 mg, 3.02 mmol) and Et$_3$N (2.1 mL, 15.0 mmol) in DCM (10 mL) at 0° C. was added Trt-Cl (1.681 g, 6.031 mmol). The resulting mixture was warmed to room temperature and stirred for 2 h. The mixture was concentrated then concentrated under reduced pressure and the residue was purified by prep-TLC (5% EtOAc/pet. ether) to afford the desired product (700 mg, crude).

Step 7: Synthesis of (2R,3R)-3-(methoxymethyl)-1-tritylaziridine-2-carboxylic Acid To a solution of ethyl (2R,3R)-3-(methoxymethyl)-1-(triphenylmethyl)aziridine-2-carboxylate (200.0 mg, 0.498 mmol) in THF (5.0 mL) and H$_2$O (5 mL) was added LiOH.H$_2$O (41.81 mg, 0.996 mmol). The resulting solution was stirred at room temperature for 24 h. The mixture was then diluted with H$_2$O (10 mL) and extracted with EtOAc (20 mL). The aqueous layer was then acidified to pH 7 with sat. aq. NH$_4$Cl and extracted with EtOAc (2×10 mL). The combined organic layers were dried over Na$_2$SO$_4$, filtered, and concentrated under reduced pressure to afford the desired product (60 mg, 32.3% yield). LCMS (ESI) m/z: [M−H] calcd for C$_{24}$H$_{23}$NO$_3$: 372.16; found 372.1.

Intermediate A-40. Synthesis of (2S,3S)-1-(tert-butylsulfinyl)-3-(4-methoxyphenyl)aziridine-2-carboxylic Acid

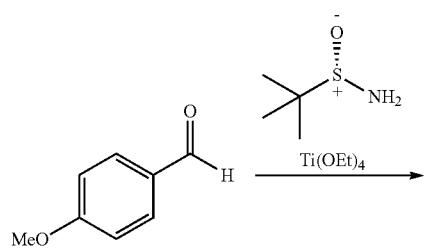

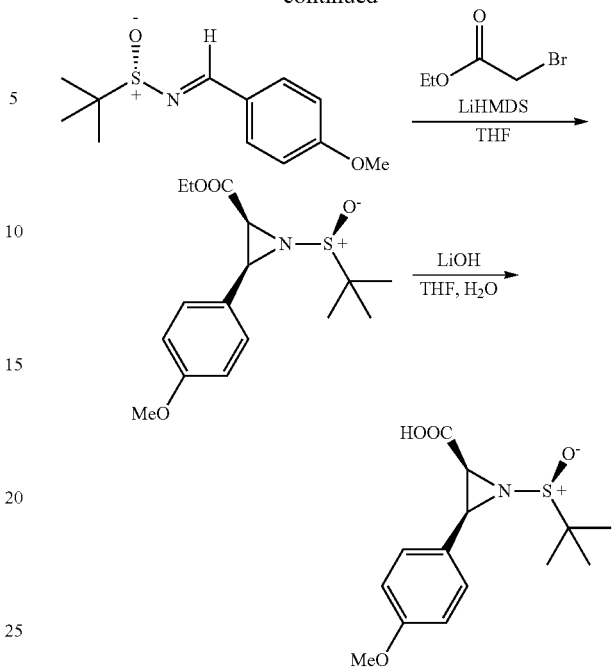

Step 1: (E)-N-(4-methoxybenzylidene)-2-methylpropane-2-sulfinamide

A solution of (S)-2-methylpropane-2-sulfinamide (2.50 g) and anisaldehyde (2.81 g) in Ti(OEt)$_4$ (20.0 mL) was stirred at 70° C. for 1 h. The resulting mixture was cooled to room temperature, diluted with EtOAc (60 mL), and then poured into H$_2$O. The mixture was filtered, and the filter cake was washed with EtOAc (3×50 mL). The resulting mixture was extracted with EtOAc (3×50 mL) and the combined organic layers were washed with brine (50 mL), dried over Na$_2$SO$_4$, filtered, and concentrated under reduced pressure. The residue was purified by silica gel column chromatography (25% EtOAc/pet. ether) to afford the desired product (4 g, 81.0% yield). LCMS (ESI) m/z: [M+H] calcd for C$_{12}$H$_{17}$NO$_2$S: 240.11; found 240.1.

Step 2: Synthesis of ethyl (2S,3S)-1-(tert-butylsulfinyl)-3-(4-methoxyphenyl)aziridine-2-carboxylate To a solution of ethyl 2-bromoacetate (5.60 g, 33.5 mmol) in THF (100 mL) at −78° C. was added LiHMDS (1M in THF, 34 mL, 33.473 mmol). After 30 min a solution of (E)-N-(4-methoxybenzylidene)-2-methylpropane-2-sulfinamide (4 g, 16.74 mmol) in THF (20 mL) was added. The resulting mixture was stirred at −78° C. for additional 3 h. The reaction was then quenched with sat. aq. NH$_4$Cl. The mixture was extracted with EtOAc (3×100 mL) and the combined organic layers were washed with brine (50 mL), dried over Na$_2$SO$_4$, filtered, and concentrated under reduced pressure. The residue was purified by silica gel chromatography (25% EtOAc/pet. ether) to afford the desired product (2.7 g, 49.6% yield). LCMS (ESI) m/z: [M+H] calcd for C$_{16}$H$_{23}$NO$_4$S: 326.14; found 326.1.

Step 3: Synthesis of (2S,3S)-1-(tert-butylsulfinyl)-3-(4-methoxyphenyl)aziridine-2-carboxylic Acid To a solution of ethyl (2S,3S)-1-(tert-butylsulfinyl)-3-(4-methoxyphenyl)aziridine-2-carboxylate (80 0.0 mg, 2.68 mmol) in THF (2.0 mL) at 0° C. was added a solution of LiOH.H₂O (309.46 mg, 7.38 mmol) in H₂O (3.0 mL). The resulting mixture was warmed to room temperature and stirred for 4 h. The mixture was then acidified to pH 6 with sat. aq. NH₄Cl and then extracted with EtOAc (3×50 mL). The combined organic layers were dried over Na₂SO₄, filtered, and concentrated under reduced pressure to afford the desired product (690 mg, 94.4% yield). LCMS (ESI) m/z: [M−H] calcd for $C_{14}H_{19}NO_4S$: 296.10; found 296.2.

Intermediate A-41. Synthesis of (2S,3R)-3-(4-methoxyphenyl)aziridine-2-carboxylic Acid

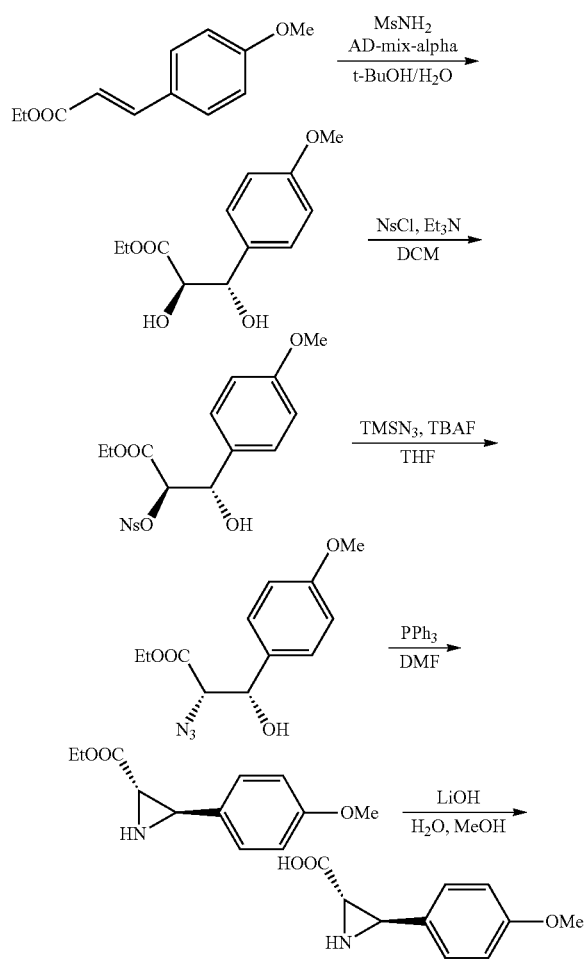

Step 1: Synthesis of ethyl (2R,3S)-2,3-dihydroxy-3-(4-methoxyphenyl)propanoate

To a solution of ethyl p-methoxycinnamate (5.0 g, 24.24 mmol) in tBuOH (70.0 mL) and H₂O (70.0 mL) at 0° C. was added AD-mix-α (33.80 g, 43.39 mmol) and methanesulfonamide (2.31 mg, 0.024 mmol). The resulting mixture was warmed to room temperature and stirred overnight. The reaction was then cooled to 0° C. and quenched with KHSO₄ (aq.). The mixture was extracted with EtOAc (3×100 mL) and the combined organic layers were washed with brine (2×90 mL), dried over Na₂SO₄, filtered, and concentrated under reduced pressure. The residue was purified by silica gel chromatography (50% EtOAc/pet. ether) to afford the desired product (5.7 g, 88.1% yield).

Step 2: Synthesis of ethyl (2R,3S)-3-hydroxy-3-(4-methoxyphenyl)-2-(((4-nitrophenyl)sulfonyl)oxy)propanoate To a solution of ethyl (2R,3S)-2,3-dihydroxy-3-(4-methoxyphenyl)propanoate (3.0 g, 12.49 mmol) and Et₃N (0.174 mL, 1.249 mmol) in DCM (30.0 mL) at 0° C. was added 4-nitrobenzenesulfonyl chloride (2.76 g, 12.49 mmol). The resulting mixture was stirred for 1 h and was then diluted with H₂O. The mixture was extracted with DCM (3×100 mL) and the combined organic layers were washed with brine (2×100 mL), dried over Na₂SO₄, filtered, and concentrated under reduced pressure. The residue was purified by prep-TLC (50% EtOAc/pet. ether) to afford the desired product (3.8 g, 68.0% yield). LCMS (ESI) m/z: [M+Na] calcd for $C_{18}H_{19}NO_9S$: 448.07; found 448.2.

Step 3: Synthesis of ethyl (2S,3S)-2-azido-3-hydroxy-3-(4-methoxyphenyl)propanoate To a solution of ethyl (2R,3S)-3-hydroxy-3-(4-methoxyphenyl)-2-(((4-nitrophenyl)sulfonyl)oxy)propanoate (1.20 g, 2.82 mmol) in THF at 0° C. was added TBAF (1M in THF, 5.64 mL, 5.64 mmol) and TMSN₃ (648.79 mg, 5.64 mmol). The resulting mixture was heated to at 60° C. and stirred for 16 h. The reaction was then cooled to at 0° C. and quenched with sat. aq. NH₄Cl. The mixture was extracted with EtOAc (3×100 mL) and the combined organic layers were washed with H₂O (2×100 mL), dried over Na₂SO₄, filtered, and concentrated under reduced pressure. The residue was purified by prep-TLC (33% EtOAc/pet. ether) to afford the desired product (540 mg, 70.7% yield).

Step 4: Synthesis of ethyl (2S,3R)-3-(4-methoxyphenyl)aziridine-2-carboxylate

To a solution of ethyl (2S,3S)-2-azido-3-hydroxy-3-(4-methoxyphenyl)propanoate (440.0 mg, 1.659 mmol) in DMF was added PPh₃ (522.06 mg, 1.99 mmol). The resulting mixture was stirred at room temperature for 30 min and was then heated to 80° C. and stirred overnight. The mixture was then extracted with EtOAc (3×100 mL), and the combined organic layers were washed with H₂O (2×100 mL), dried over anhydrous Na₂SO₄, filtered, and concentrated under reduced pressure. The residue was purified by prep-TLC (25% EtOAc/pet. ether) to afford the desired product (200 mg, 51.8% yield). LCMS (ESI) m/z: [M+H] calcd for $C_{12}H_{15}NO_3$: 222.12; found 222.1.

Step 5: Synthesis of (2S,3R)-3-(4-methoxyphenyl)aziridine-2-carboxylic Acid

To a solution of ethyl (2S,3R)-3-(4-methoxyphenyl)aziridine-2-carboxylate (200.0 mg, 0.904 mmol) in MeOH and H₂O at 0° C. was added LiOH.H₂O (86.6 mg, 3.62 mmol). The resulting mixture was stirred for 1 h and was then neutralized to pH 7 with HCl (aq.). The mixture was extracted with EtOAc (3×100 mL) and the combined organic layers were washed with H₂O (2×100 mL), dried over Na₂SO₄, filtered, and concentrated under reduced pressure to afford the desired product (180 mg, 97.9% yield). LCMS (ESI) m/z: [M−H] calcd for $C_{10}H_{11}NO_3$: 192.07; found 192.0.

Intermediate A-42. Synthesis of (2R,3S)-3-(4-methoxyphenyl)aziridine-2-carboxylic Acid

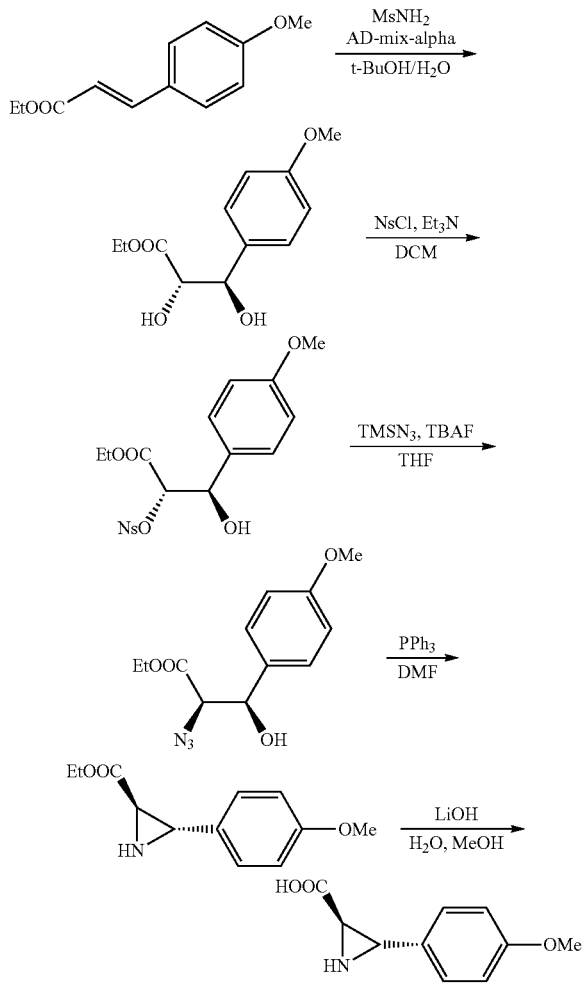

Step 1: Synthesis of ethyl (2S,3R)-2,3-dihydroxy-3-(4-methoxyphenyl)propanoate To a solution of ethyl p-methoxycinnamate (5.0 g, 24.24 mmol) in tBuOH (70.0 mL) and $H_2O$ (70.0 mL) at 0° C. was added AD-mix-R (33.80 g, 43.39 mmol) and methanesulfonamide (2.31 mg, 0.024 mmol). The resulting mixture was warmed to room temperature and stirred overnight. The reaction was then cooled to 0° C. and quenched with $KHSO_4$ (aq.). The mixture was extracted with EtOAc (3×100 mL) and the combined organic layers were washed with brine (2×90 mL), dried over $Na_2SO_4$, filtered, and concentrated under reduced pressure. The residue was purified by silica gel chromatography (50% EtOAc/pet. ether) to afford the desired product (5.7 g, 88.1% yield).

Step 2: Synthesis of ethyl (2S,3R)-3-hydroxy-3-(4-methoxyphenyl)-2-(((4-nitrophenyl)sulfonyl)oxy)propanoate To a solution of ethyl (2S,3R)-2,3-dihydroxy-3-(4-methoxyphenyl)propanoate (5.80 g, 24.14 mmol) and $Et_3N$ (10.1 mL, 72.42 mmol) in DCM (30.0 mL) at 0° C. was added 4-nitrobenzenesulfonyl chloride (5.34 g, 24.1 mmol). The resulting mixture was stirred for 1 h and was then diluted with $H_2O$. The mixture was extracted with DCM (3×100 mL) and the combined organic layers were washed with brine (2×100 mL), dried over $Na_2SO_4$, filtered, and concentrated under reduced pressure. The residue was purified by prep-TLC (50% EtOAc/pet. ether) to afford the desired product (7.2 g, 67.0% yield). LCMS (ESI) m/z: [M+H] calcd for $C_{18}H_{19}NO_9S$: 426.09; found 426.2.

Step 3: Synthesis of ethyl (2R,3R)-2-azido-3-hydroxy-3-(4-methoxyphenyl)propanoate To a solution of ethyl (2S,3R)-3-hydroxy-3-(4-methoxyphenyl)-2-(((4-nitrophenyl)sulfonyl)oxy)propanoate (5.0 g, 11.75 mmol) in THF at 0° C. was added TBAF (1M in THF, 23.5 mL, 23.51 mmol) and $TMSN_3$ (2.7 g, 23.5 mmol). The resulting mixture was heated to at 60° C. and stirred for 16 h. The reaction was then cooled to at 0° C. and quenched with sat. aq. $NH_4Cl$. The mixture was extracted with EtOAc (3×100 mL) and the combined organic layers were washed with $H_2O$ (2×100 mL), dried over $Na_2SO_4$, filtered, and concentrated under reduced pressure. The residue was purified by prep-TLC (33% EtOAc/pet. ether) to afford the desired product (2.3 g, 70.1% yield).

Step 4: Synthesis of ethyl (2R,3S)-3-(4-methoxyphenyl)aziridine-2-carboxylate To a solution of ethyl (2R,3R)-2-azido-3-hydroxy-3-(4-methoxyphenyl)propanoate (2.30 g, 8.67 mmol) in DMF was added $PPh_3$ (2.73 g, 10.4 mmol). The resulting mixture was stirred at room temperature for 30 min and was then heated to 80° C. and stirred overnight. The mixture was then extracted with EtOAc (3×100 mL), and the combined organic layers were washed with $H_2O$ (2×100 mL), dried over anhydrous $Na_2SO_4$, filtered, and concentrated under reduced pressure. The residue was purified by prep-TLC (25% EtOAc/pet. ether) to afford the desired product (1.6 g, 79.2% yield). LCMS (ESI) m/z: [M+H] calcd for $C_{12}H_{15}NO_3$: 222.12; found 222.1.

Step 5: Synthesis of (2R,3S)-3-(4-methoxyphenyl)aziridine-2-carboxylic Acid

To a solution of ethyl (2S,3R)-3-(4-methoxyphenyl)aziridine-2-carboxylate (200.0 mg, 0.904 mmol) in MeOH and $H_2O$ at 0° C. was added $LiOH·H_2O$ (86.6 mg, 3.62 mmol). The resulting mixture was stirred for 1 h and was then neutralized to pH 7 with HCl (aq.). The mixture was extracted with EtOAc (3×100 mL) and the combined organic layers were washed with $H_2O$ (2×100 mL), dried over $Na_2SO_4$, filtered, and concentrated under reduced pressure to afford the desired product (180 mg, 97.9% yield). LCMS (ESI) m/z: [M−H] calcd for $C_{10}H_{11}NO_3$: 192.07; found 192.0.

Intermediate A-43. Synthesis of (2S,3S)-1-((S)-tert-butylsulfinyl)-3-phenylaziridine-2-carboxylic Acid

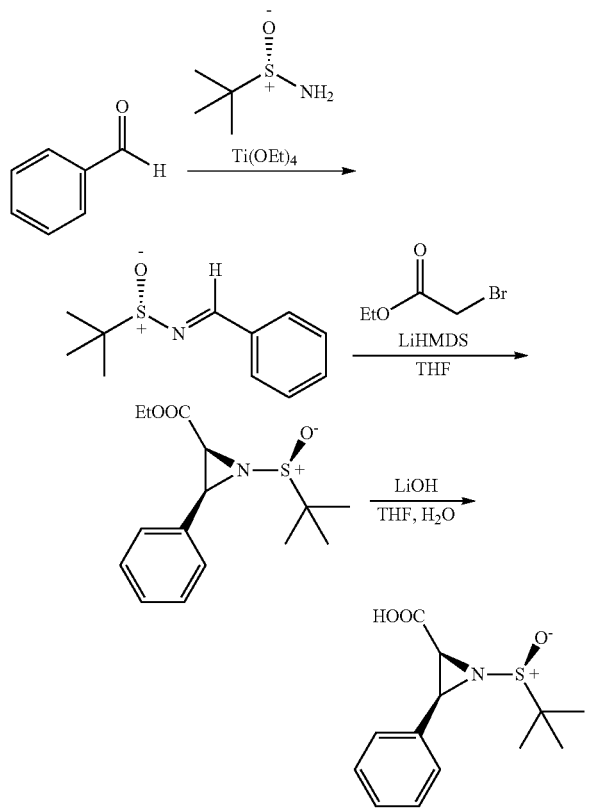

Step 1: Synthesis of (S,E)-N-benzylidene-2-methylpropane-2-sulfinamide

A solution of (S)-2-methylpropane-2-sulfinamide (2.50 g, 20.6 mmol), titanium ethoxide (9.41 g, 41.25 mmol) and benzaldehyde (2.19 g, 20.7 mmol) was heated at 70° C. for 1 h, cooled, and diluted with H$_2$O (250 mL). The aqueous layer was extracted with EtOAc (3×80 mL) and the combined organic layers were washed with brine (2×100 mL), dried with Na$_2$SO$_4$, filtered and concentrated under reduced pressure to afford the desired product (4.3 g, crude) which was used without further purification. LCMS (ESI) m/z: [M+H] calcd for C$_{11}$H$_{15}$NOS: 210.10; found 210.2.

Step 2: Synthesis of ethyl (2S,3S)-1-((S)-tert-butylsulfinyl)-3-phenylaziridine-2-carboxylate To a solution of ethyl bromoacetate (798 mg, 4.78 mmol) in THF (15 mL) at −78° C. was added LiHMDS (1M in THF, 4.78 mL, 4.78 mmol). After 1 h, (S,E)-N-benzylidene-2-methylpropane-2-sulfinamide (500 mg, 2.39 mmol) in THF (5 mL) was added in portions over 20 min. The reaction mixture was stirred at −78° C. for 2 h and then quenched by the addition of sat. NH$_4$Cl. The aqueous layer was extracted with EtOAc (3×40 mL) and the combined organic layers were washed with brine (2×30 mL), dried with Na$_2$SO$_4$, filtered, and concentrated under reduced pressure. Purification by reverse phase chromatography (30→60% MeCN/H$_2$O, 0.1% HCO$_2$H) afforded the desired product (480 mg, 61% yield). LCMS (ESI) m/z: [M+H] calcd for C$_{15}$H$_{21}$NO$_3$S: 296.13; found 296.2.

Step 3: Synthesis (2S,3S)-1-((S)-tert-butylsulfinyl)-3-phenylaziridine-2-carboxylic Acid To a solution of ethyl (2S,3S)-1-((S)-tert-butylsulfinyl)-3-phenylaziridine-2-carboxylate (600 mg, 2.03 mmol) in THF (4.0 mL) at 0° C. was added a solution of LiOH (97.2 mg, 4.06 mmol) in H$_2$O (4.0 mL). The resulting mixture was stirred for 2 h at 0° C. and then acidified to pH 5 with 1 M HCl. The aqueous layer was extracted with EtOAc (3×40 mL) and the combined organic layers were washed with brine (2×20 mL), dried with Na$_2$SO$_4$, filtered, and concentrated under reduced pressure to afford the desired compound (450 mg, crude) which was used without further purification. LCMS (ESI) m/z: [M+H] calcd for C$_{13}$H$_{17}$NO$_3$S: 268.10; found 268.1.

Intermediate A-44. Synthesis of (2R,3R)-1-((R)-tert-butylsulfinyl)-3-phenylaziridine-2-carboxylic Acid

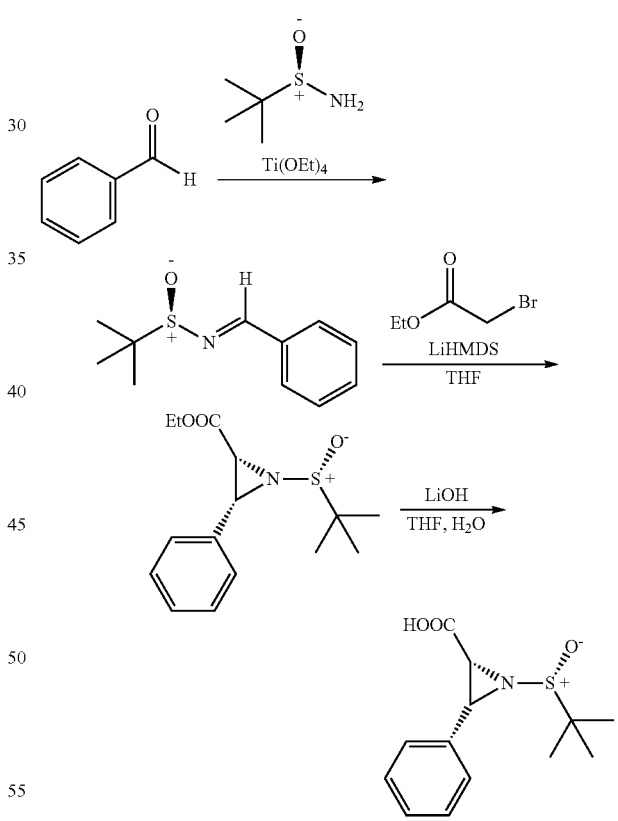

Step 1: Synthesis (R,E)-N-benzylidene-2-methylpropane-2-sulfinamide

A solution (R)-2-methylpropane-2-sulfinamide (2.50 g, 20.6 mmol), titanium tetraethoxide (9.41 g, 41.3 mmol) and benzaldehyde (2.19 g, 20.6 mmol) was heated 70° C. for 1 h, cooled, and diluted with H$_2$O (250 mL). The aqueous layer was extracted with EtOAc (3×90 mL) and the combined organic layers were washed with brine (2×100 mL), dried with Na$_2$SO$_4$, filtered and concentrated under reduced pressure to afford the desired product (4.2 g, crude) which was used without further purification. LCMS (ESI) m/z: [M+H] calcd for C$_{11}$H$_{15}$NOS: 210.10; found 210.1.

Step 2: Synthesis of ethyl (2R,3R)-1-((R)-tert-butylsulfinyl)-3-phenylaziridine-2-carboxylate To a solution of ethyl bromoacetate (6.38 g, 38.2 mmol) in THF (150 mL) at −78° C. was added LiHMDS (1M in THF, 7.19 mL, 42.9 mmol). After 1 h, (R,E)-N-benzylidene-2-methylpropane-2-sulfinamide (4.0 g, 19.1 mmol) in THF (50 mL) was added in portions over 20 min. The reaction mixture was stirred at −78° C. for 2 h and then quenched by the addition of sat. NH$_4$Cl. The aqueous layer was extracted with EtOAc (3×80 mL) and the combined organic layers were washed with brine (2×60 mL), dried with Na$_2$SO$_4$, filtered and concentrated under reduced pressure. Purification by reverse phase chromatography (30→60% MeCN/H$_2$O, 0.1% HCO$_2$H) afforded the desired product (3.9 g, 62% yield). LCMS (ESI) m/z: [M+H] calcd for C$_{15}$H$_{21}$NO$_3$S: 296.13; found 296.2.

Step 3: Synthesis (2R,3R)-1-((R)-tert-butylsulfinyl)-3-phenylaziridine-2-carboxylic Acid To a solution of ethyl (2R,3R)-1-((R)-tert-butylsulfinyl)-3-phenylaziridine-2-carboxylate (200 mg, 0.677 mmol) in THF (1.5 mL) at 0° C. was added a solution of LiOH (32.4 mg, 1.35 mmol) in H$_2$O (1.3 mL). The resulting mixture was stirred for 2 h at 0° C. and then acidified to pH 5 with 1M HCl. The aqueous layer was extracted with EtOAc (3×20 mL) and the combined organic layers were washed with brine (2×10 mL), dried with Na$_2$SO$_4$, filtered, and concentrated under reduced pressure to afford the desired compound (220 mg, crude) which was used without further purification. LCMS (ESI) m/z: [M+H] calcd for C$_{13}$H$_{17}$NO$_3$S: 268.10; found 268.4.

Intermediate A-45 and A-46. Synthesis of and (S)—N-(1-(2-methoxyethyl)aziridine-2-carbonyl)-N-methylglycine and (R)—N-(1-(2-methoxyethyl)aziridine-2-carbonyl)-N-methylglycine

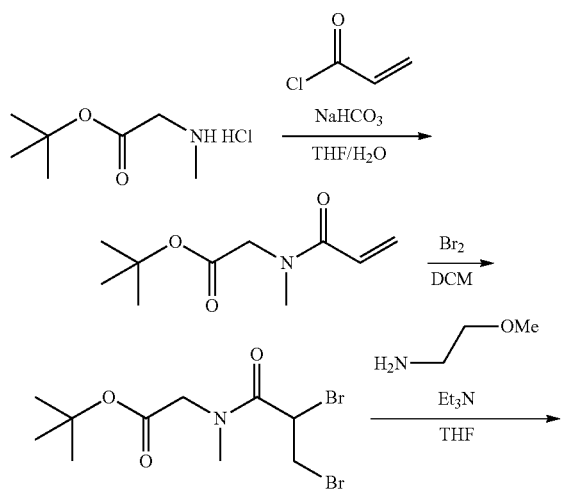

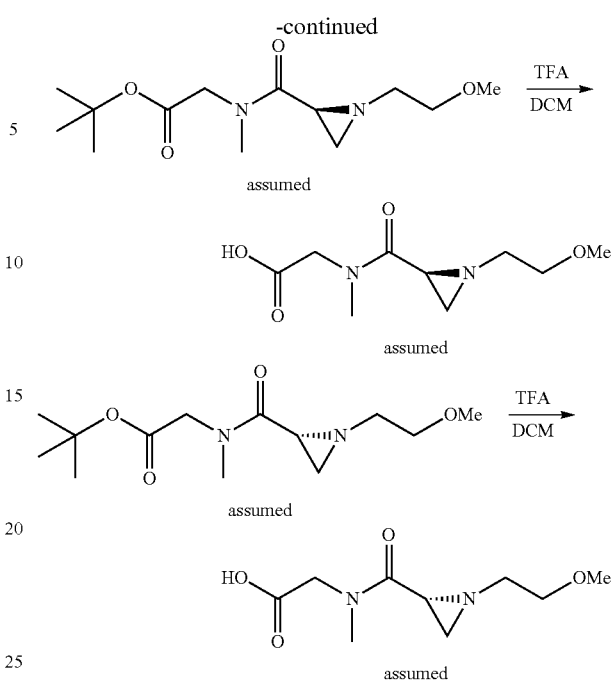

Step 1: Synthesis of tert-butyl N-acryloyl-N-methylglycinate

To a mixture of tert-butyl methylglycinate hydrochloride (1.0 g, 5.5 mmol) and NaHCO$_3$ (1.39 g, 16.5 mmol) in THF (10 mL) and H$_2$O (5.0 mL) at 0° C. was added acryloyl chloride (750 mg, 8.26 mmol). The resulting solution was stirred for 2 h at room temperature and the reaction was then quenched by the addition H$_2$O (50 mL). The aqueous layer was extracted with EtOAc (2×50 mL) and the combined organic layers were washed with brine, dried with Na$_2$SO$_4$, filtered, and concentrated under reduced pressure. Purification by normal phase chromatography (10→33% EtOAc/pet. ether) afforded the desired product (900 mg, 73.8% yield). LCMS (ESI) m/z: [M+H] calcd for C$_{10}$H$_{17}$NO$_3$: 200.13; found 200.2.

Step 2: Synthesis of tert-butyl N-(2,3-dibromopropanoyl)-N-methylglycinate

To a solution of tert-butyl N-acryloyl-N-methylglycinate (2.0 g, 10.1 mmol) in DCM (40 mL) at −20° C. was added Br$_2$ (3.21 g, 20.1 mmol). The resulting mixture was stirred for 2 h at −20° C. and then quenched by the addition of Na$_2$S$_2$O$_3$ (100 mL). The aqueous layer was extracted with DCM (2×100 mL) and the combined organic layers were washed with brine, dried with Na$_2$SO$_4$, and concentrated under reduced pressure to afford the desired product (2.4 g, crude) which was used without further purification. LCMS (ESI) m/z: [M+Na] calcd for C$_{10}$H$_{17}$Br$_2$NO$_3$: 381.96; found 381.8.

Step 3: Synthesis of tert-butyl (S)—N-(1-(2-methoxyethyl)aziridine-2-carbonyl)-N-methylglycinate and tert-butyl (R)—N-(1-(2-methoxyethyl)aziridine-2-carbonyl)-N-methylglycinate To a solution of tert-butyl N-(2,3-dibromopropanoyl)-N-methylglycinate (4.0 g, 11.1 mmol) and 2-methoxyethan-1- amine (4.18 g, 55.7 mmol) in THF (40 mL) was added Et₃N (4.66 mL, 33.4 mmol). The resulting solution was stirred at 35° C. overnight was then quenched by the addition of H₂O. The aqueous layer was extracted with DCM (2×100 mL) and the combined organic layers were washed with brine, dried with Na₂SO₄, filtered, and concentrated under reduced pressure. Purification by reverse phase chromatography (30→50% MeCN/H₂O) afforded a mixture of the desired products. The enantiomers were separated by chiral preparative normal phase chromatography (hexane, 10 mM NH₃-MeOH/EtOH) to afford tert-butyl (S)—N-(1-(2-methoxyethyl)aziridine-2-carbonyl)-N-methylglycinate (400 mg, 33.3% yield) and tert-butyl (R)—N-(1-(2-methoxyethyl)aziridine-2-carbonyl)-N-methylglycinate (360 mg, 30% yield). LCMS (ESI) m/z: [M+H] calcd for C₁₃H₂₄N₂O₄: 273.18; found 273.0.

Step 4: Synthesis of (S)—N-(1-(2-methoxyethyl)aziridine-2-carbonyl)-N-methylglycine To a solution of tert-butyl (S)—N-(1-(2-methoxyethyl)aziridine-2-carbonyl)-N-methylglycinate (250 mg, 0.918 mmol) in DCM (6.0 mL) at 0° C. was added TFA (3.0 mL). The resulting mixture was stirred at 2 h at 0° C. and then concentrated under reduced pressure to afford the desired product (250 mg, crude) which was used without further purification. LCMS (ESI) m/z: [M+H] calcd for C₉H₁₆N₂O₄: 217.12; found 217.1.

Step 5: Synthesis of (R)—N-(1-(2-methoxyethyl)aziridine-2-carbonyl)-N-methylglycine To a solution tert-butyl (R)—N-(1-(2-methoxyethyl)aziridine-2-carbonyl)-N-methylglycinate (180 mg, 0.661 mmol) in DCM (6.0 mL) at 0° C. was added TFA (3.0 mL). The resulting mixture was stirred at 2 h at 0° C. and then concentrated under reduced pressure to afford the desired product (150 mg, crude) which was used without further purification. LCMS (ESI) m/z: [M+H] calcd for C₉H₁₆N₂O₄: 217.12; found 217.1.

Intermediate A-47 and A-48. Synthesis of N-methyl-N-(1-(((R)-1-methylaziridin-2-yl)sulfonyl)piperidine-4-carbonyl)-L-valine and N-methyl-N-(1-(((S)-1-methylaziridin-2-yl)sulfonyl)piperidine-4-carbonyl)-L-valine

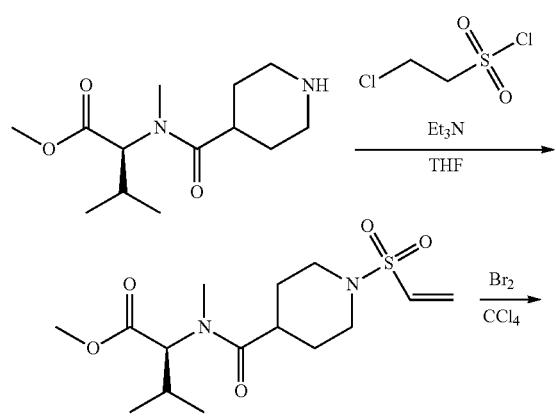

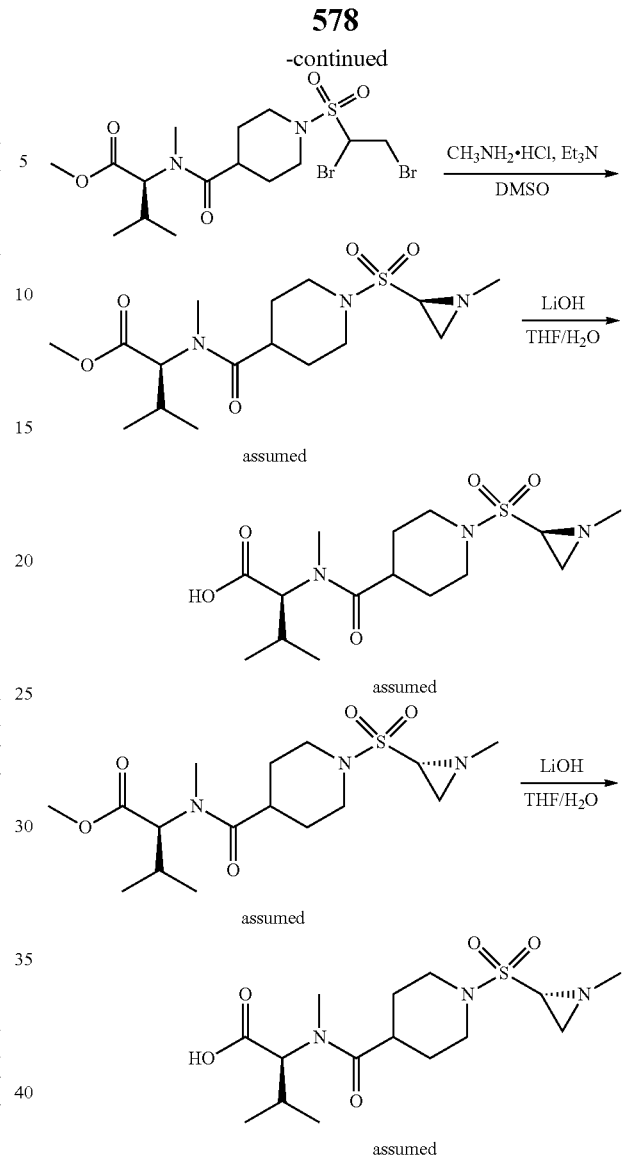

Step 1: Synthesis of methyl N-methyl-N-(1-(vinylsulfonyl)piperidine-4-carbonyl)-L-valinate To a solution of 2-chloroethanesulfonyl chloride (1.91 g, 11.7 mmol) in THF (20 mL) at −70° C. was added methyl N-methyl-N-(piperidine-4-carbonyl)-L-valinate (2.0 g, 7.8 mmol) followed by Et₃N (790 □L, 780 □mol). After warming to −50° C. additional Et₃N (790 □L, 780 □mol) was added and the reaction mixture warmed to room temperature. After 1 h the reaction was quenched at 0° C. by the addition of H₂O (30 mL), acidified to pH 6 with 1M HCl, and extracted with CHCl₃ (3×30 mL). The combined organic layers were dried with MgSO₄, filtered, and concentrated under reduced pressure. Purification by normal phase chromatography (50% EtOAc/pet. ether) afforded the desired product (560 mg, 20.7% yield). LCMS (ESI) m/z: [M+H] calcd for C₁₅H₂₆N₂O₅S: 347.17; found 347.2.

Step 2: Synthesis of methyl N-(1-((1,2-dibromoethyl)sulfonyl)piperidine-4-carbonyl)-N-methyl-L-valinate To a solution of methyl N-methyl-N-(1-(vinylsulfonyl)piperidine-4-carbonyl)-L-valinate (580 mg, 1.67 mmol) in CCl$_4$ (28 mL) at room temperature was added Br$_2$ (580 mg, 1.67 mmol) The resulting mixture was stirred overnight at room temperature and then quenched by the addition of sat. NaHCO$_3$(30 mL). The aqueous layer was extracted with DCM (3×30 mL) and the combined organic layers were dried with Na$_2$SO$_4$, filtered and concentrated under reduced pressure to afford the desired product which was used without further purification. LCMS (ESI) m/z: [M+H] calcd for C$_{15}$H$_{26}$Br$_2$N$_2$O$_5$S: 506.99; found 506.9.

Step 3: Synthesis of methyl N-methyl-N-(1-(((R)-1-methylaziridin-2-yl)sulfonyl)piperidine-4-carbonyl)-L-valinate and methyl N-methyl-N-(1-(((S)-1-methylaziridin-2-yl)sulfonyl)piperidine-4-carbonyl)-L-valinate To a solution of methyl N-(1-((1,2-dibromoethyl)sulfonyl)piperidine-4-carbonyl)-N-methyl-L-valinate (4.80 g, 9.481 mmol) in DMSO (48 mL) was added methanamine hydrochloride (1.92 g, 28.436 mmol) and Et$_3$N (13.2 mL, 94.8 mmol). The reaction mixture was heated to 75° C. and stirred overnight. The mixture was then cooled to 0° C., diluted NH$_4$Cl, and extracted with EtOAc (600 mL). The organic layer was washed with brine, dried with Na$_2$SO$_4$, filtered, concentrated under reduced pressure. Purification with normal phase chromatography (86% EtOAc/hexane) afforded a mixture of the desired products. The diastereomers were separated by prep-SFC chromatography (20% IPA/CO$_2$) to afford methyl N-methyl-N-(1-(((R)-1-methylaziridin-2-yl)sulfonyl)piperidine-4-carbonyl)-L-valinate (700 mg, 38.9% yield) and methyl N-methyl-N-(1-(((S)-1-methylaziridin-2-yl)sulfonyl)piperidine-4-carbonyl)-L-valinate (790 mg, 43.9% yield). LCMS (ESI) m/z: [M+H] calcd for C$_{16}$H$_{29}$N$_3$O$_5$S: 376.19; found 376.1.

Step 4: Synthesis of N-methyl-N-(1-(((R)-1-methylaziridin-2-yl)sulfonyl)piperidine-4-carbonyl)-L-valine To a solution of methyl N-methyl-N-(1-(((R)-1-methylaziridin-2-yl)sulfonyl)piperidine-4-carbonyl)-L-valinate (200 mg, 0.533 mmol) in THF (2.0 mL) at 0° C. was added 1M LiOH (1 mL) The resulting mixture was stirred for 3 h at room temperature and then acidified to pH 6 with 1M HCl. The aqueous layer was extracted with EtOAc (3×10 mL) and the combined organic layers were dried with Na$_2$SO$_4$, filtered, and concentrated under reduced pressure to afford the desired product which was used without further purification. LCMS (ESI) m/z: [M+H] calcd for C$_{15}$H$_{27}$N$_3$O$_5$S: 362.18; found 362.2.

Step 5: Synthesis of N-methyl-N-(1-(((S)-1-methylaziridin-2-yl)sulfonyl)piperidine-4-carbonyl)-L-valine To a solution methyl N-methyl-N-(1-(((S)-1-methylaziridin-2-yl)sulfonyl)piperidine-4-carbonyl)-L-valinate (300 mg, 0.799 mmol) in THF (3.0 mL) at 0° C. was added 1M LiOH (3.0 mL). The resulting mixture was stirred for 3 h at room temperature and then acidified to pH 6 with 1M HCl. The aqueous layer was extracted with EtOAc (3×10 mL) and the combined organic layers dried with Na$_2$SO$_4$, filtered and concentrated under reduced pressure to afford the desired product which was used without further purification. LCMS (ESI) m/z: [M+H] calcd for C$_{15}$H$_{27}$N$_3$O$_5$S: 362.18; found 362.2.

Intermediate A-49 and A-50. Synthesis of N-methyl-N-(1-(((R)-1-methylaziridin-2-yl)sulfonyl)azetidine-3-carbonyl)-L-valine and N-methyl-N-(1-(((S)-1-methylaziridin-2-yl)sulfonyl)azetidine-3-carbonyl)-L-valine

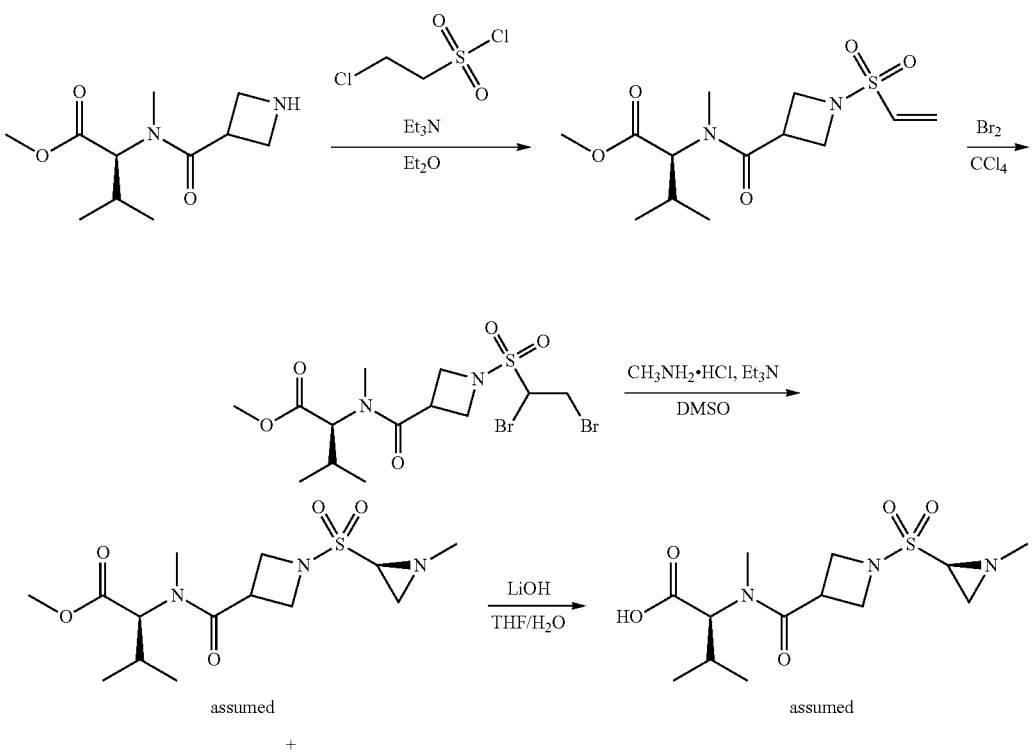

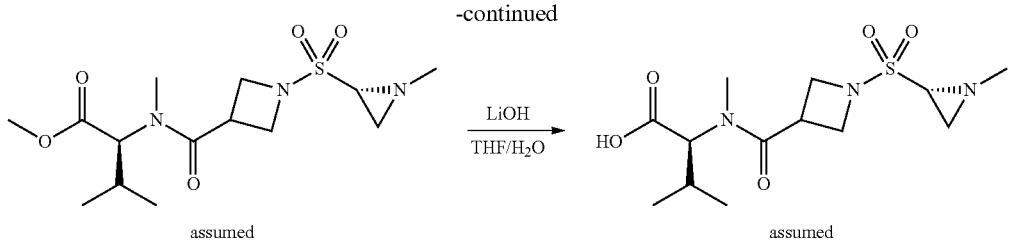

assumed            assumed

Step 1: Synthesis of methyl N-methyl-N-(1-(vinylsulfonyl)azetidine-3-carbonyl)-L-valinate To a solution of 2-chloroethanesulfonyl chloride (357 mg, 2.19 mmol) in $Et_2O$ (4.0 mL) at −70° C. was added an $Et_2O$ (4.0 mL) solution of methyl N-(azetidine-3-carbonyl)-N-methyl-L-valinate (500 mg, 2.19 mmol) followed by $Et_3N$ (0.304 mL, 2.19 mmol). The resulting mixture was stirred for 30 min at −50° C. at which time $Et_3N$ (0.304 mL, 2.19 mmol) was added. The resulting mixture was stirred for 1 h at room temperature and then quenched with $H_2O$ at 0° C. The mixture was acidified to pH 6 with 1M HCl and extracted with $CHCl_3$ (3×10 mL). The combined organic layers were washed with brine, dried with $Na_2SO_4$, filtered, and concentrated under reduced pressure. Purification by normal phase chromatography (50% EtOAc/pet. ether) afforded the desired product (180 mg, 25.8% yield). LCMS (ESI) m/z: [M+H] calcd for $C_{13}H_{22}N_2O_5S$: 319.13; found 319.1.

Step 2: Synthesis of methyl N-(1-((1,2-dibromoethyl)sulfonyl)azetidine-3-carbonyl)-N-methyl-L-valinate To a solution of methyl N-methyl-N-(1-(vinylsulfonyl)azetidine-3-carbonyl)-L-valinate (460 mg, 1.45 mmol) in $CCl_4$ (6.0 mL) at room temperature was added a $CCl_4$ (2.0 mL) solution of $Br_2$ (346 mg, 2.17 mmol). The resulting mixture was stirred overnight and then quenched at 0° C. by the addition of sat. $NaHCO_3$ and $Na_2S_2O_3$. The aqueous layer was extracted with DCM (3×10 mL) and the combined organic layers were washed with brine, dried with $Na_2SO_4$, and concentrated under reduced pressure to afford the desired product (500 mg) which was used without further purification. LCMS (ESI) m/z: [M+H] calcd for $C_{13}H_{22}Br_2N_2O_5S$: 478.97; found 478.0.

Step 3: Synthesis of methyl N-methyl-N-(1-(((R)-1-methylaziridin-2-yl)sulfonyl)azetidine-3-carbonyl)-L-valinate and methyl N-methyl-N-(1-(((S)-1-methylaziridin-2-yl)sulfonyl)azetidine-3-carbonyl)-L-valinate To a solution of methyl N-(1-((1,2-dibromoethyl)sulfonyl)azetidine-3-carbonyl)-N-methyl-L-valinate (260 mg, 0.54 mmol) in DMSO (4.0 mL) was added methanamine hydrochloride (110.0 mg, 1.63 mmol) and $Et_3N$ (0.758 mL, 5.44 mmol). The resulting mixture was heated to 75° C. and stirred overnight. The mixture was then cooled to room temperature, diluted with $H_2O$ (10 mL), and extracted with EtOAc (3×5 mL). The combined organic layers were washed with brine, dried with $Na_2SO_4$, filtered and concentrated under reduced pressure. Purification by normal phase chromatography (50% EtOAc/pet. ether) afforded a mixture of the desired products. The diastereomers were separated by chiral prep normal phase chromatography (hexane, 10 mM $NH_3$-MeOH/IPA) to afford methyl N-methyl-N-(1-(((R)-1-methylaziridin-2-yl)sulfonyl)azetidine-3-carbonyl)-L-valinate (0.59 g, 35% yield) and methyl N-methyl-N-(1-(((S)-1-methylaziridin-2-yl)sulfonyl)azetidine-3-carbonyl)-L-valinate (0.56 g, 33% yield). LCMS (ESI) m/z: [M+H] calcd for $C_{14}H_{25}N_3O_5S$: 348.16; found 348.2.

Step 4: Synthesis of N-methyl-N-(1-(((R)-1-methylaziridin-2-yl)sulfonyl)azetidine-3-carbonyl)-L-valine To a solution of methyl N-methyl-N-(1-(((R)-1-methylaziridin-2-yl)sulfonyl)azetidine-3-carbonyl)-L-valinate (225.0 mg, 0.65 mmol) in THF (1.5 mL) at 0° C. was added LiOH (77.0 mg, 3.23 mmol) dissolved in $H_2O$ (1.5 mL). The resulting mixture was stirred for 2 h at room temperature and then acidified to pH 6 with 1M HCl. The aqueous layer was extracted with EtOAc and the combined organic layers were washed with brine, dried with $Na_2SO_4$, filtered, and concentrated under reduced pressure to afford the desired product (270 mg) which was used without further purification. LCMS (ESI) m/z: [M+H] calcd for $C_{13}H_{23}N_3O_5S$: 334.15; found 334.0.

Step 5: Synthesis of N-methyl-N-(1-(((S)-1-methylaziridin-2-yl)sulfonyl)azetidine-3-carbonyl)-L-valine To a solution of methyl N-methyl-N-(1-(((S)-1-methylaziridin-2-yl)sulfonyl)azetidine-3-carbonyl)-L-valinate (365.0 mg, 1.05 mmol) in THF (2.0 mL) and $H_2O$ (2.0 mL) at 0° C. was added LiOH hydrate (132.0 mg, 3.15 mmol). The resulting mixture was stirred for 2 h at room temperature then acidified to pH 6 with 1M HCl and diluted with $H_2O$ (20 mL). The aqueous layer was extracted with EtOAc and the combined organic layers were washed with brine, dried with $Na_2SO_4$, filtered, and concentrated under reduced pressure to afford the desired product (257 mg, crude) which was used without further purification. LCMS (ESI) m/z: [M+H] calcd for $C_{13}H_{23}N_3O_5S$: 334.15; found 334.3.

Intermediate A-51. Synthesis of 2-((1R,5S)-2,4-dioxo-6-trityl-3,6-diazabicyclo[3.1.0]hexan-3-yl) acetic Acid

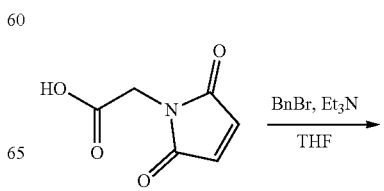

583
-continued

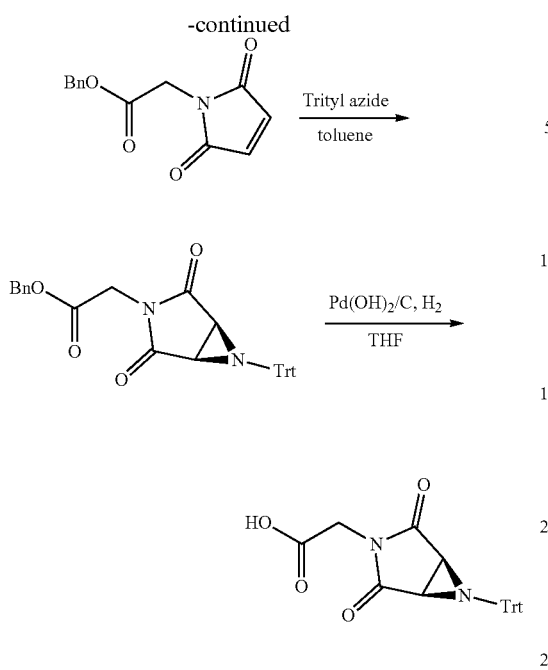

Step 1: Synthesis of benzyl 2-(2,5-dioxo-2,5-dihydro-1H-pyrrol-1-yl)acetate

To a solution of 2-(2,5-dioxo-2,5-dihydro-1H-pyrrol-1-yl) acetic acid (5.0 g, 32.2 mmol) and Et$_3$N (13.5 mL, 96.7 mmol) in THF (80 mL) at 0° C. was added benzyl bromide (11.03 g, 64.5 mmol). The resulting mixture was stirred overnight at room temperature and then filtered. The filter cake was washed with THF (3×40 mL) and the filtrate was concentrated under reduced pressure. Purification by silica gel chromatography (16% EtOAc/hexanes) afforded the desired product (4.4 g, 55.7% yield) LCMS (ESI) m/z: [2M+Na] calcd for C$_{13}$H$_{11}$NO$_4$: 513.14; found 513.2.

Step 2: Synthesis of benzyl 2-((1R,5S)-2,4-dioxo-6-trityl-3,6-diazabicyclo[3.1.0]hexan-3-yl)acetate To a solution of benzyl 2-(2,5-dioxo-2,5-dihydro-1H-pyrrol-1-yl)acetate of (1.0 g, 4.0 mmol) in toluene (10 mL) was added trityl azide (1.36 g, 4.89 mmol). The resulting mixture was stirred overnight at 120° C. and then concentrated under reduced pressure. Purification by reverse flash chromatography (50→80% MeCN/H$_2$O) afforded the desired product (400 mg, 19.5% yield). LCMS (ESI) m/z: [M+Na] calcd for C$_{32}$H$_{26}$N$_2$O$_4$: 525.19; found 525.2.

Step 3: Synthesis of 2-((1R,5S)-2,4-dioxo-6-trityl-3,6-diazabicyclo[3.1.0]hexan-3-yl)acetic Acid To a solution of benzyl 2-((1R,5S)-2,4-dioxo-6-trityl-3,6-diazabicyclo[3.1.0]hexan-3-yl)acetate (220 mg, 0.438 mmol) in THF (8.0 mL) was added Pd(OH)$_2$/C (60 mg). The resulting solution was placed under a hydrogen atmosphere for 3 h using a H$_2$ balloon, filtered through Celite, and concentrated under reduced pressure to afford the desired product (160 mg, crude) which was used without further purification. LCMS (ESI) m/z: [M−H] calcd for C$_{25}$H$_{20}$N$_2$O$_4$: 411.13; found 411.2.

584

Intermediate A-52. Synthesis of (S)-3-methyl-2-(5-oxo-2-((S)-1-tritylaziridine-2-carbonyl)-2,6-diazaspiro[3.4]octan-6-yl)butanoic Acid

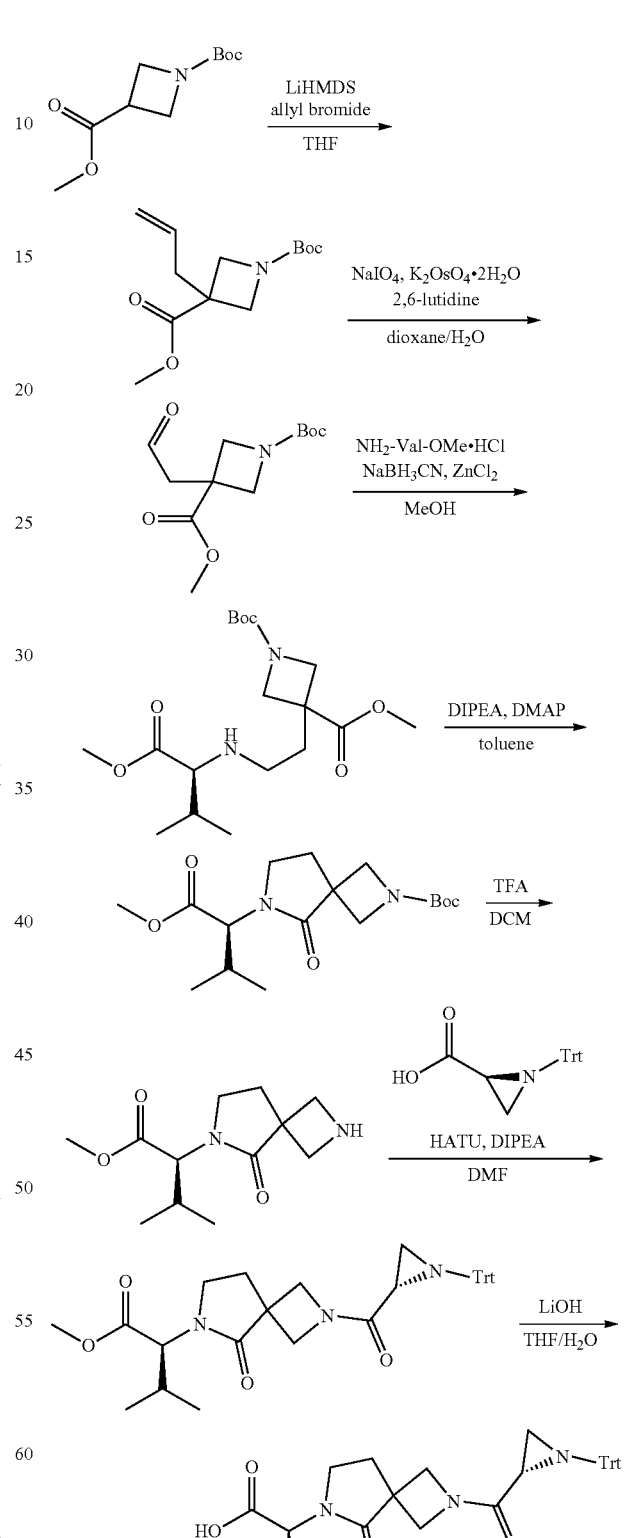

Step 1: Synthesis of 1-(tert-butyl) 3-methyl 3-allylazetidine-1,3-dicarboxylate To a solution of 1-(tert-butyl) 3-methyl azetidine-1,3-dicarboxylate (20.0 g, 92.9 mmol) and LiHMDS (140 mL, 1M in THF, 139 mmol) in THF (200 mL) at −78° C. was added allyl bromide (16.9 g, 139 mmol). The resulting solution was stirred overnight at room temperature and then quenched with the addition of sat. NH$_4$Cl (100 mL) and diluted with EtOAc (800 mL). The organic layer was washed with brine (3×300 mL), dried with Na$_2$SO$_4$, filtered and concentrated under reduced pressure. Purification by silica gel column chromatography (17% EtOAc/pet. ether) afforded the desired product (15.0 g, 63.2% yield). LCMS (ESI) m/z: [M+H−tBu] calcd for C$_{13}$H$_{21}$NO$_4$: 200.10; found 200.0.

Step 2: Synthesis of 1-(tert-butyl) 3-methyl 3-(2-oxoethyl)azetidine-1,3-dicarboxylate To a solution of 1-(tert-butyl) 3-methyl 3-allylazetidine-1,3-dicarboxylate (6.0 g, 23 mmol) and 2,6-lutidine (504 mg, 47.0 mmol) in dioxane (60 mL) and H$_2$O (60 mL) at 0° C. was added K$_2$OsO$_4$.2H$_2$O (433 mg, 1.18 mmol). The resulting mixture was stirred at room temperature for 15 min then NaIO$_4$ (20.1 g, 94.0 mmol) was added at 0° C. The reaction was stirred for 3 h at room temperature and then quenched with sat. Na$_2$S$_2$O$_3$ at 0° C. The aqueous layer was extracted with EtOAc (2×400 mL) and the combined organic layers were washed with 1 M HCl (2×80 mL), brine (2×100 mL), dried with Na$_2$SO$_4$, filtered and concentrated under reduced pressure to afford the desired product (2.84 g, crude) which was used without further purification. LCMS (ESI) m/z: [M−H] calcd for C$_{12}$H$_{19}$NO$_5$: 256.12; found 256.0.

Step 3: Synthesis of 1-(tert-butyl) 3-methyl (S)-3-(2-((1-methoxy-3-methyl-1-oxobutan-2-yl)amino)ethyl)azetidine-1,3-dicarboxylate To a solution of 1-(tert-butyl) 3-methyl 3-(2-oxoethyl)azetidine-1,3-dicarboxylate (13.0 g, 50.5 mmol) and methyl L-valinate hydrochloride (7.29 g, 55.6 mmol) in MeOH (130 mL) at 0° C. were added ZnCl$_2$ (7.57 g, 55.6 mmol) and NaBH$_3$CN (6.35 g, 101 mmol). The resulting mixture was stirred at room temperature overnight, partially concentrated under reduced pressure and diluted with EtOAc (500 mL). The resulting solution was washed with brine (3×200 mL), dried with Na$_2$SO$_4$, filtered, and concentrated under reduced pressure. Purification by normal phase chromatography (10→66% EtOAc/pet. ether) afforded the desired product (7.72 g, 41.0% yield). LCMS (ESI) m/z: [M+H] calcd for C$_{18}$H$_{32}$N$_2$O$_6$: 373.24; found 373.1.

Step 4: Synthesis of tert-butyl (S)-6-(1-methoxy-3-methyl-1-oxobutan-2-yl)-5-oxo-2,6-diazaspiro[3.4]octane-2-carboxylate To a solution of 1-(tert-butyl) 3-methyl (S)-3-(2-((1-methoxy-3-methyl-1-oxobutan-2-yl)amino)ethyl)azetidine-1,3-dicarboxylate (6.0 g, 16 mmol) and DIPEA (28.0 mL, 161 mmol) in toluene (60 mL) at room temperature was added DMAP (197 mg, 1.61 mmol). The resulting mixture was stirred at 80° C. overnight, diluted with EtOAc (50 mL), washed with H$_2$O (50 mL), brine (3×50 mL) dried with Na$_2$SO$_4$, and filtered, and concentrated under reduced pressure. Purification by reverse phase chromatography 45→80% MeCN/H$_2$O) afforded the desired product (4.3 g, 78.4% yield). LCMS (ESI) m/z: [M+H−tBu] calcd for C$_{17}$H$_{28}$N$_2$O$_5$: 285.15; found 285.0.

Step 5: Synthesis of methyl (S)-3-methyl-2-(5-oxo-2,6-diazaspiro[3.4]octan-6-yl)butanoate To a solution of tert-butyl (S)-6-(1-methoxy-3-methyl-1-oxobutan-2-yl)-5-oxo-2,6-diazaspiro[3.4]octane-2-carboxylate (2.7 g, 7.9 mmol) in DCM (27 mL) at room temperature was added TFA (8.10 mL, 71.0 mmol). The resulting mixture was stirred for 1 h and then concentrated under reduced pressure to afford the desired product, (1.70 g, crude) which was used without further purification. LCMS (ESI) m/z: [M+H] calcd for C$_{12}$H$_{20}$N$_2$O$_3$: 241.16; found 240.1.

Step 6: Synthesis of methyl (S)-3-methyl-2-(5-oxo-2-((S)-1-tritylaziridine-2-carbonyl)-2,6-diazaspiro[3.4]octan-6-yl)butanoate To a solution methyl (S)-3-methyl-2-(5-oxo-2,6-diazaspiro[3.4]octan-6-yl)butanoate (700 mg, 2.91 mmol) and (S)-1-tritylaziridine-2-carboxylic acid (1.15 g, 3.50 mmol) in DMF (7.0 mL) at 0° C. was added DIPEA (2.5 mL, 14.6 mmol). After 30 min HATU (1.66 g, 4.37 mmol) was added and the resulting mixture was stirred at room temperature for 1 h. The reaction was then diluted with EtOAc (20 mL) and the organic layer was washed with sat. NH$_4$Cl (50 mL), brine (3×50 mL), dried with Na$_2$SO$_4$, filtered, and concentrated under reduced pressure. Purification by normal phase chromatography (0→80% EtOAc/pet. ether) afforded the desired product (300 mg, 18.7% yield). LCMS (ESI) m/z: [M+H] calcd for C$_{34}$H$_{37}$N$_3$O$_4$: 552.29; found 552.2.

Step 7: Synthesis of (S)-3-methyl-2-(5-oxo-2-((S)-1-tritylaziridine-2-carbonyl)-2,6-diazaspiro[3.4]octan-6-yl)butanoic Acid To a solution of methyl (S)-3-methyl-2-(5-oxo-2-((S)-1-tritylaziridine-2-carbonyl)-2,6-diazaspiro[3.4]octan-6-yl)butanoate (700 mg, 1.27 mmol) in THF (10 mL) and H$_2$O (2.0 mL) at 0° C. was added LiOH (152 mg, 6.34 mmol). After 30 min the reaction mixture was warmed to room temperature for 1 h and then acidified to pH 6 with 1M HCl. The aqueous layer was extracted with EtOAc (3×50 mL) and the combined organic layers were washed with brine, dried with Na$_2$SO$_4$, filtered, and concentrated under reduced pressure to afford the desired product (300 mg, 18.7% yield) which was used without further purification. LCMS (ESI) m/z: [M+H] calcd for C$_{33}$H$_{35}$N$_3$O$_4$: 538.27; found 538.2.

Intermediate A-53. Synthesis of (S)-3-methyl-2-(5-oxo-2-((R)-1-tritylaziridine-2-carbonyl)-2,6-diazaspiro[3.4]octan-6-yl)butanoic Acid

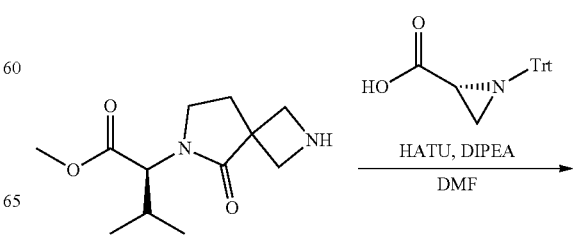

587

-continued

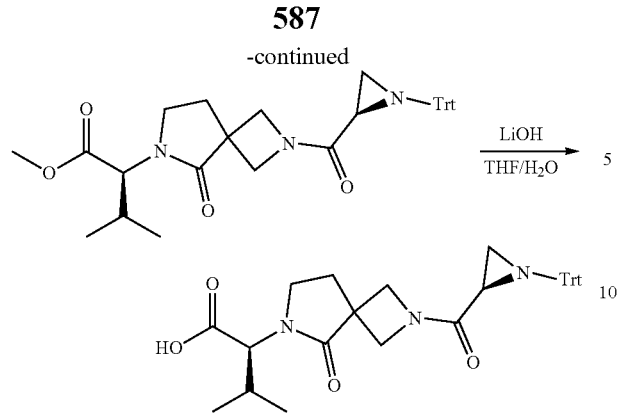

Step 1: Synthesis of methyl (S)-3-methyl-2-(5-oxo-2-((R)-1-tritylaziridine-2-carbonyl)-2,6-diazaspiro[3.4]octan-6-yl)butanoate To a solution (R)-1-tritylaziridine-2-carboxylic acid (1.0 g, 3.0 mmol) and methyl (S)-3-methyl-2-(5-oxo-2,6-diazaspiro[3.4]octan-6-yl)butanoate (875 mg, 3.64 mmol) in DMF (10 mL) at 0° C. was added DIPEA (2.64 mL, 15.2 mmol). After 30 min HATU (1.73 g, 4.554 mmol) was added and the resulting mixture was stirred for 1 h at room temperature. The reaction was then diluted with EtOAc (20 mL) and the organic layer was washed with sat. NH$_4$Cl (50 mL), brine (3×50 mL), dried with Na$_2$SO$_4$, filtered, and concentrated under reduced pressure. Purification by silica gel chromatography (0→80% EtOAc/pet. ether) afforded the desired product (789 mg, 47% yield). LCMS (ESI) m/z: [M+H] calcd for C$_{34}$H$_{37}$N$_3$O$_4$: 552.29; found 552.3.

Step 2: Synthesis of (S)-3-methyl-2-(5-oxo-2-((R)-1-tritylaziridine-2-carbonyl)-2,6-diazaspiro[3.4]octan-6-yl)butanoic Acid To a stirred solution of methyl (S)-3-methyl-2-(5-oxo-2-((R)-1-tritylaziridine-2-carbonyl)-2,6-diazaspiro[3.4]octan-6-yl)butanoate (900 mg, 1.63 mmol) in THF (10 mL) and H$_2$O (2.5 mL) at 0° C. was added LiOH (156 mg, 6.53 mmol). After 30 min the reaction mixture was warmed to room temperature for 1 h and then acidified to pH 6 with 1M HCl. The aqueous layer was extracted with EtOAc (3×50 mL) and the combined organic layers were washed with brine, dried with Na$_2$SO$_4$, filtered, and concentrated under reduced pressure to afford the desired product (240 mg, 27.4% yield). LCMS (ESI) m/z: [M+H] calcd for C$_{33}$H$_{35}$N$_3$O$_4$: 538.27; found 538.2.

Intermediate A-54. Synthesis of (S)-1-((R)-2-(methoxycarbonyl)aziridine-1-carbonyl)pyrrolidine-3-carboxylic Acid

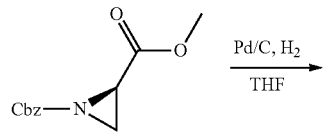

588

-continued

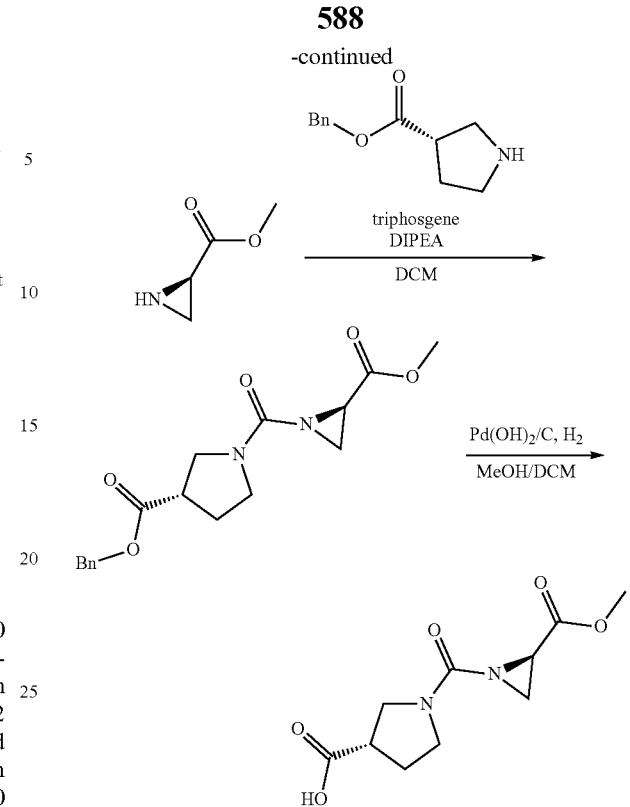

Step 1: Synthesis of methyl (R)-aziridine-2-carboxylate

A suspension of 1-benzyl 2-methyl (R)-aziridine-1,2-dicarboxylate (1.50 g, 6.4 mmol) and Pd/C (300 mg, 2.8 mmol) in THF (15 mL) under an atmosphere of hydrogen (1 atm) was stirred for 3 h before the solids were removed by filtration. The crude solution was concentrated under reduced pressure which afforded desired product (600 mg, crude). LCMS (ESI) m/z: [M+H] calcd for C$_4$H$_7$NO$_2$: 102.06; found 102.3.

Step 2: Synthesis of benzyl (S)-1-((R)-2-(methoxycarbonyl)aziridine-1-carbonyl)pyrrolidine-3-carboxylate To solution of methyl (R)-aziridine-2-carboxylate (1.0 g, 9.90 mmol) and benzyl (S)-pyrrolidine-3-carboxylate (2.63 g, 10.9 mmol, HCl salt) in DCM (30.0 mL) at −10° C. was added DIPEA (10.3 mL, 59.3 mmol) followed by triphosgene (880 mg, 2.97 mmol). The resulting solution was stirred for 30 min and was then quenched by the addition of H$_2$O (50 mL). The aqueous layer was extracted with DCM (2×100 mL), washed with brine (2×50 mL), dried over Na$_2$SO$_4$, and concentrated under reduced pressure. Purification by prep-TLC (50% EtOAc/pet. ether) afforded desired product (1.30 g, 28% yield). LCMS (ESI) m/z: [M+H] calcd for C$_{17}$H$_{20}$N$_2$O$_5$: 333.15; found 333.2.

Step 3: Synthesis of (S)-1-((R)-2-(methoxycarbonyl)aziridine-1-carbonyl)pyrrolidine-3-carboxylic Acid To a solution of benzyl (S)-1-((R)-2-(methoxycarbonyl)aziridine-1-carbonyl)pyrrolidine-3-carboxylate (200 mg, 600 μmol) in MeOH (5 mL) and DCM (5 mL) under $H_2$ was added Pd(OH)$_2$/C (130 mg, 90 μmol). The resulting mixture was stirred for 30 min at room temperature and then the mixture was filtered. The filter cake was washed with MeOH (2×10 mL) and the filtrate was concentrated under reduced pressure which afforded desired product (140 mg, 96% yield) as an off-white solid. LCMS (ESI) m/z: [M+H] calcd for $C_{10}H_{14}N_2O_5$: 243.10; found 243.3.

Intermediate A-55. Synthesis of (S)-1-((S)-2-(methoxycarbonyl)aziridine-1-carbonyl)pyrrolidine-3-carboxylic Acid

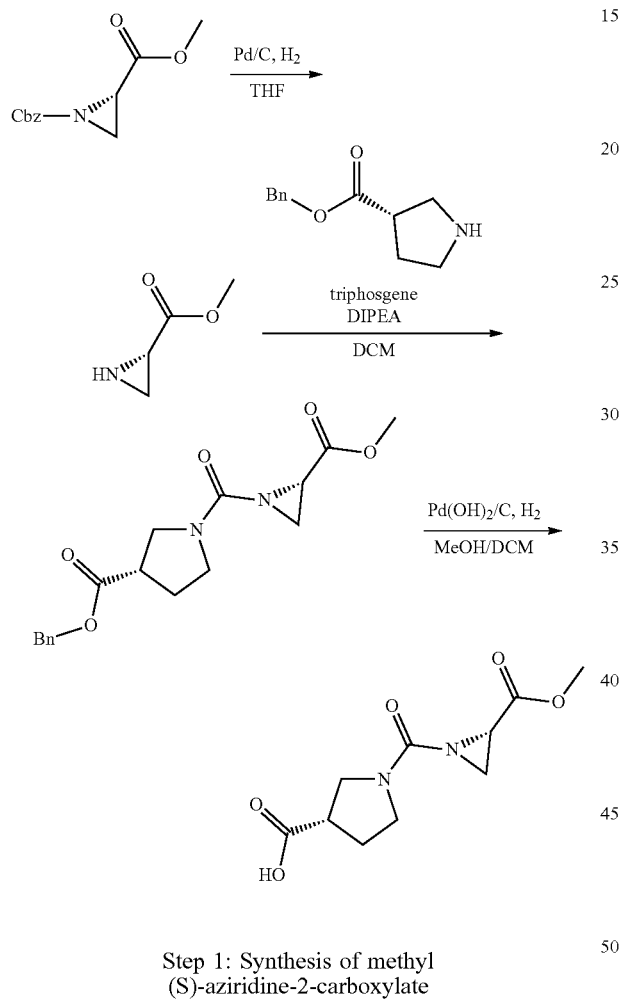

Step 1: Synthesis of methyl (S)-aziridine-2-carboxylate

A suspension of 1-benzyl 2-methyl (S)-aziridine-1,2-dicarboxylate (200 mg, 850 μmol) and Pd/C (20 mg, 38 μmol) in THF (4.0 mL) under an atmosphere of hydrogen (1 atm) was stirred for 2 h before the solids were removed by filtration. The crude solution was concentrated under reduced pressure which afforded desired product (92 mg, crude). LCMS (ESI) m/z: [M+H] calcd for $C_4H_{17}NO_2$: 102.06; found 102.3.

Step 2: Synthesis of benzyl (S)-1-((S)-2-(methoxycarbonyl)aziridine-1-carbonyl)pyrrolidine-3-carboxylate To a solution of methyl (S)-aziridine-2-carboxylate (900 mg, 8.9 mmol) and benzyl (S)-pyrrolidine-3-carboxylate (2.37 g, 9.80 mmol, HCl salt) in DCM (30 mL) at −10° C. was added DIPEA (9.30 mL, 53.4 mmol) followed by triphosgene (790 mg, 2.67 mmol). The resulting solution was stirred for 30 min and was then quenched by the addition of $H_2O$ (50 mL). The aqueous layer was extracted with DCM (2×100 mL), washed with brine (2×50 mL), dried over $Na_2SO_4$, filtered, and concentrated under reduced pressure. Purification by prep-TLC (50% EtOAc/pet. ether) afforded desired product (360 mg, 8.5% yield) as an off-white oil. LCMS (ESI) m/z: [M+H] calcd for $C_{17}H_{20}N_2O_5$: 333.15; found 333.2.

Step 3: Synthesis of (S)-1-((S)-2-(methoxycarbonyl)aziridine-1-carbonyl)pyrrolidine-3-carboxylic Acid To a solution of benzyl (S)-1-((S)-2-(methoxycarbonyl)aziridine-1-carbonyl)pyrrolidine-3-carboxylate (130 mg, 390 μmol) in MeOH (3 mL) and DCM (3 mL) under $H_2$ was added Pd(OH)$_2$/C (55 mg, 39 μmol). The resulting solution was stirred for 30 min at room temperature and then the reaction mixture was filtered. The filter cake was washed with MeOH (2×10 mL) and the filtrate was concentrated under reduced pressure which afforded desired product (90 mg, 95% yield) as an off-white solid. LCMS (ESI) m/z: [M+H] calcd for $C_{10}H_{14}N_2O_5$: 243.10; found 243.3.

Intermediate A-56. Synthesis of (2R,3S)-3-cyclopropylaziridine-2-carboxylic Acid

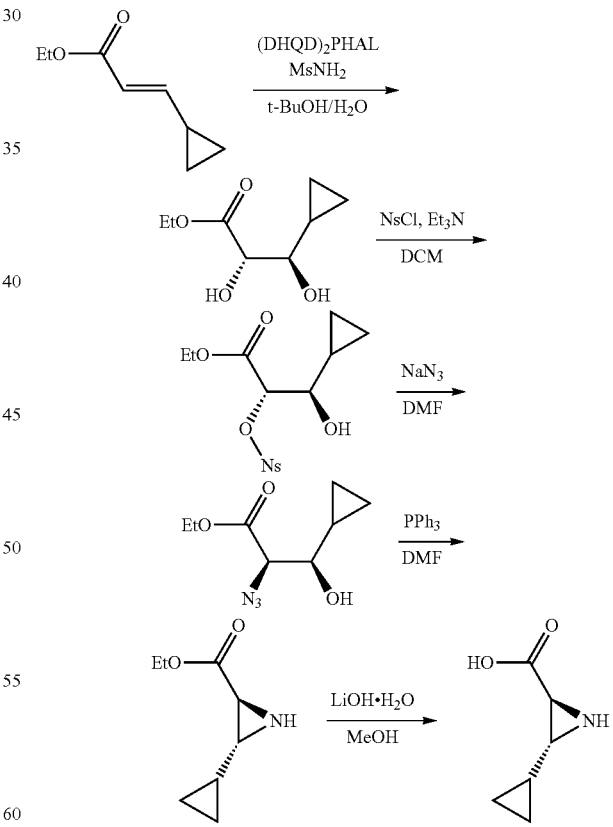

Step 1: Synthesis of ethyl (2S,3R)-3-cyclopropyl-2,3-dihydroxypropanoate

A solution of ethyl (E)-3-cyclopropylacrylate (10.4 mL, 71 mmol) in tert-BuOH (270 mL) and $H_2O$ (270 mL) was stirred at 0° C. After 5 min MsNH$_2$ (6.8 g, 71 mmol) and (DHQD)$_2$PHAL (100 g, 130 mmol) were added and the reaction mixture was warmed to room temperature. After stirring overnight, sat. Na$_2$SO$_3$ was added and the mixture was stirred for 30 min. The mixture was acidified to pH 6 with KH$_2$PO$_4$. Purification by silica gel column chromatography (33% EtOAc/pet. ether) afforded desired product (5.5 g, 44% yield).

Step 2: Synthesis of ethyl (2S,3R)-3-cyclopropyl-3-hydroxy-2-(((4-nitrophenyl)sulfonyl)oxy)propanoate A solution of ethyl (2S,3R)-3-cyclopropyl-2,3-dihydroxy-propanoate (5.40 g, 31.0 mmol) and Et$_3$N (13.0 mL, 93.0 mmol) in DCM (20 mL) was stirred at 0° C. and a solution of 4-nitrobenzenesulfonyl chloride (6.53 g, 29.5 mmol) in DCM (10 mL) was added. The reaction mixture was stirred for 1.5 h and was then extracted with DCM (3×200 mL). The combined organic layers were washed with brine (100 mL), dried with Na$_2$SO$_4$, filtered, and concentrated under reduced pressure. Purification by silica gel column chromatography (33% EtOAc/pet. ether) afforded desired product (6.9 g, 62% yield).

Step 3: Synthesis of ethyl (2R,3R)-2-azido-3-cyclopropyl-3-hydroxypropanoate

A mixture of ethyl (2S,3R)-3-cyclopropyl-3-hydroxy-2-(((4-nitrophenyl)sulfonyl)oxy)propanoate (6.90 g, 19.2 mmol) and NaN$_3$ (6.24 g, 96.0 mmol) in DMF (70.0 mL) was heated to 50° C. The reaction mixture was stirred for 5 h and then extracted with EtOAc (3×200 mL). The combined organic layers were washed with brine (100 mL), dried with Na$_2$SO$_4$, filtered, and concentrated under reduced pressure. Purification by silica gel column chromatography (20% EtOAc/pet. ether) afforded desired product (2.8 g, 73% yield).

Step 4: Synthesis of ethyl (2R,3S)-3-cyclopropylaziridine-2-carboxylate

A mixture of triphenylphosphine (1.84 g, 7.02 mmol) in DMF (5 mL) was stirred at 0° C. After 5 min ethyl (2R,3R)-2-azido-3-cyclopropyl-3-hydroxypropanoate (1.40 g, 7.03 mmol) was added and the reaction was warmed to room temperature. The reaction mixture was heated to 80° C. and stirred for 1 h. The mixture was then cooled to room temperature and extracted with EtOAc (3×50 mL). The combined organic layers were washed with brine (50 mL), dried with Na$_2$SO$_4$, filtered, and concentrated under reduced pressure. Purification by silica gel column chromatography (20% EtOAc/pet. ether) afforded the desired product (230 mg, 46% yield). LCMS (ESI) m/z: [M+H] calcd for C$_8$H$_{13}$NO$_2$: 156.10; found 156.2.

Step 5: Synthesis of lithium (2R,3S)-3-cyclopropylaziridine-2-carboxylate

To a mixture of ethyl (2R,3S)-3-cyclopropylaziridine-2-carboxylate (230 mg, 1.5 mmol) in MeOH (3.0 mL) was added LiOH.H$_2$O (125 mg, 3.0 mmol). The reaction was stirred for 3 h and then filtered. The filtrate was concentrated under reduced pressure which afforded the desired product (150 mg, crude). LCMS (ESI) m/z: [M+H] calcd for C$_6$H$_9$NO$_2$: 128.07; found 128.2.

Intermediate A-57. Synthesis of (2R,3S)-3-cyclopropylaziridine-2-carboxylic Acid

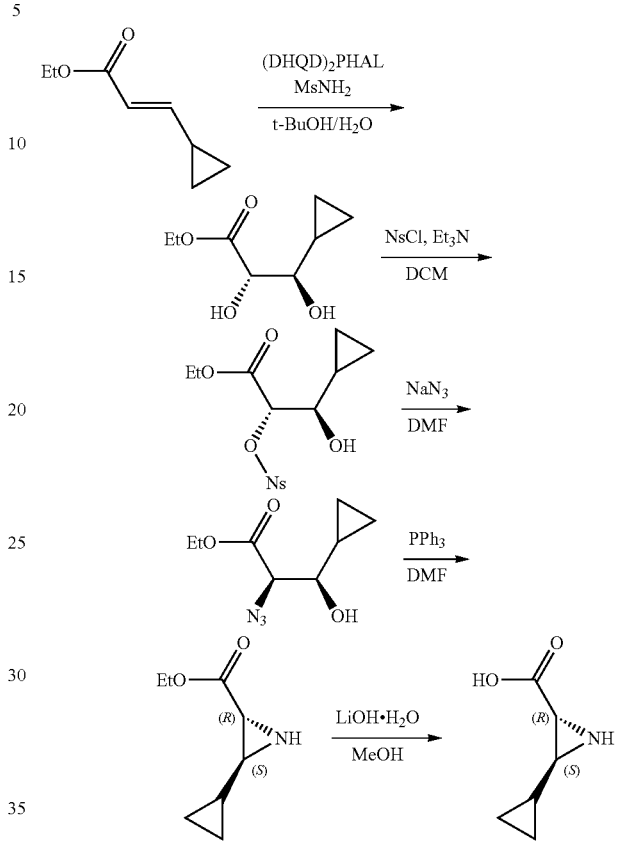

Step 1: Synthesis of ethyl (2S,3R)-3-cyclopropyl-2,3-dihydroxypropanoate

A solution of ethyl (E)-3-cyclopropylacrylate (10.4 mL, 71 mmol) in tert-BuOH (270 mL) and H$_2$O (270 mL) was stirred at 0° C. After 5 min MsNH$_2$ (6.8 g, 71 mmol) and (DHQD)$_2$PHAL (100 g, 130 mmol) were added and the reaction mixture was warmed to room temperature. After stirring overnight, sat. Na$_2$SO$_3$ was added and the mixture was stirred for 30 min. The mixture was acidified to pH 6 with KH$_2$PO$_4$. Purification by silica gel column chromatography (33% EtOAC/pet. ether) afforded desired product (5.5 g, 44% yield).

Step 2: Synthesis of ethyl (2S,3R)-3-cyclopropyl-3-hydroxy-2-(((4-nitrophenyl)sulfonyl)oxy)propanoate A solution of ethyl (2S,3R)-3-cyclopropyl-2,3-dihydroxy-propanoate (5.40 g, 31.0 mmol) and Et$_3$N (13.0 mL, 93.0 mmol) in DCM (20 mL) was stirred at 0° C. and a solution of 4-nitrobenzenesulfonyl chloride (6.53 g, 29.5 mmol) in DCM (10 mL) was added. The reaction mixture was stirred for 1.5 h and was then extracted with DCM (3×200 mL). The combined organic layers were washed with brine (100 mL), dried with Na$_2$SO$_4$, filtered, and concentrated under reduced pressure. Purification by silica gel column chromatography (33% EtOAc/pet. ether) afforded desired product (6.9 g, 62% yield).

Step 3: Synthesis of ethyl (2R,3R)-2-azido-3-cyclopropyl-3-hydroxypropanoate A mixture of ethyl (2S,3R)-3-cyclopropyl-3-hydroxy-2-(((4-nitrophenyl)sulfonyl)oxy)propanoate (6.90 g, 19.2 mmol) and NaN$_3$ (6.24 g, 96.0 mmol) in DMF (70.0 mL) was heated to 50° C. The reaction mixture was stirred for 5 h and then extracted with EtOAc (3×200 mL). The combined organic layers were washed with brine (100 mL), dried with Na$_2$SO$_4$, filtered, and concentrated under reduced pressure. Purification by silica gel column chromatography (20% EtOAc/pet. ether) afforded desired product (2.8 g, 73% yield).

Step 4: Synthesis of ethyl (2R,3S)-3-cyclopropylaziridine-2-carboxylate

A mixture of triphenylphosphine (1.84 g, 7.02 mmol) in DMF (5 mL) was stirred at 0° C. After 5 min ethyl (2R,3R)-2-azido-3-cyclopropyl-3-hydroxypropanoate (1.40 g, 7.03 mmol) was added and the reaction was warmed to room temperature. The reaction mixture was heated to 80° C. and stirred for 1 h. The mixture was then cooled to room temperature and extracted with EtOAc (3×50 mL). The combined organic layers were washed with brine (50 mL), dried with Na$_2$SO$_4$, filtered, and concentrated under reduced pressure. Purification by silica gel column chromatography (20% EtOAc/pet. ether) afforded the desired product (230 mg, 46% yield). LCMS (ESI) m/z: [M+H] calcd for C$_8$H$_{13}$NO$_2$: 156.10; found 156.2.

Step 5: Synthesis of lithium (2R,3S)-3-cyclopropylaziridine-2-carboxylate

To a mixture of ethyl (2R,3S)-3-cyclopropylaziridine-2-carboxylate (230 mg, 1.5 mmol) in MeOH (3.0 mL) was added LiOH·H$_2$O (125 mg, 3.0 mmol). The reaction was stirred for 3 h and then filtered. The filtrate was concentrated under reduced pressure which afforded the desired product (150 mg, crude). LCMS (ESI) m/z: [M+H] calcd for C$_6$H$_9$NO$_2$: 128.07; found 128.2.

Intermediate A-58. Synthesis of (2S,3R)-3-cyclopropylaziridine-2-carboxylic Acid

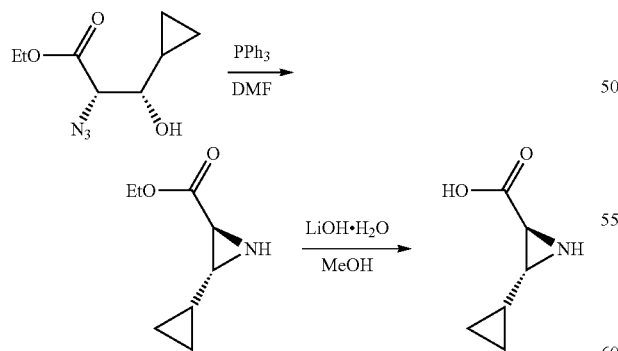

Step 1: Synthesis of ethyl (2S,3R)-3-cyclopropylaziridine-2-carboxylate

A mixture of PPh$_3$ (1.4 g, 5.4 mmol) in DMF (15.0 mL) was stirred at 0° C. After 30 min, ethyl (2S,3S)-2-azido-3-cyclopropyl-3-hydroxypropanoate (980 mg, 4.92 mmol) was added. The reaction mixture was heated to 80° C. After 2 h the reaction was quenched by the addition of H$_2$O (20 mL) and was extracted with EtOAc (3×30 mL). Purification by silica gel column chromatography (17% EtOAc/pet. ether) afforded desired product (500 mg, 65% yield).

Step 2: Synthesis of lithium (2S,3R)-3-cyclopropylaziridine-2-carboxylate

To a solution of ethyl (2S,3R)-3-cyclopropylaziridine-2-carboxylate (450 mg, 2.9 mmol) in THF (6.0 mL) and H$_2$O (2.0 mL) was added LiOH (90 mg, 3.8 mmol). The reaction was stirred for 2 h and then filtered. The filtrate was concentrated under reduced pressure which afforded the desired product (300 mg, crude).

Intermediate A-59. Synthesis of (R)-3-methyl-2-(((R)—N-methyl-1-tritylaziridine-2-carboxamido)methyl)butanoic Acid

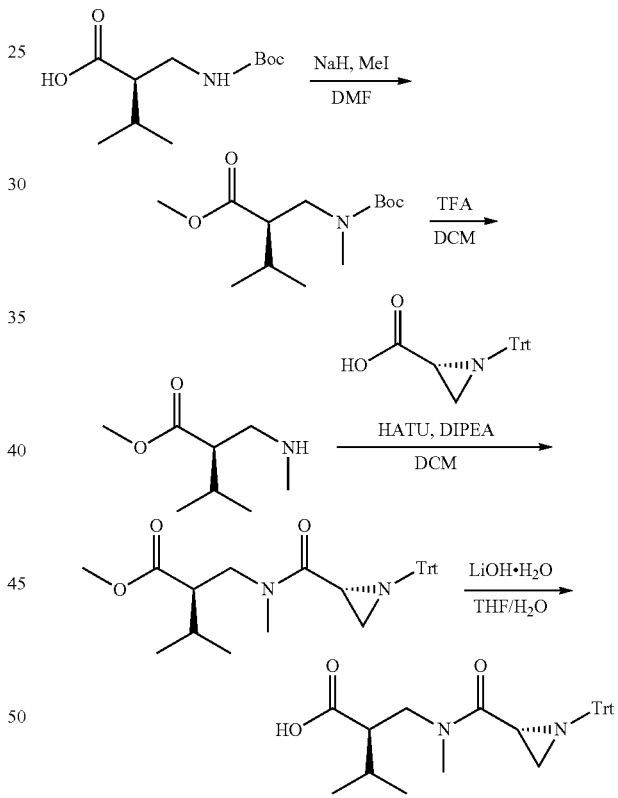

Step 1: Synthesis of methyl (R)-2-(((tert-butoxycarbonyl)(methyl)amino)methyl)-3-methylbutanoate To a solution of (R)-2-(((tert-butoxycarbonyl)amino)methyl)-3-methylbutanoic acid (500 mg, 2.16 mmol) in DMF (10.0 mL) at 0° C. was added NaH (130 mg, 5.40 mmol). After 30 min, MeI (540 μL, 8.65 mmol) was added and the reaction was warmed to room temperature. After 2 h the reaction was cooled to 0° C. and quenched by the addition of sat. aq. NH$_4$Cl (10 mL). The resulting mixture was extracted with EtOAc (3×20 mL) and the combined organic layers were washed with brine (40 mL), dried with Na$_2$SO$_4$, and concentrated under reduced pressure. Purification by prep-TLC (9% EtOAc/pet. ether) afforded the desired product (500 mg, 89.2% yield). LCMS (ESI) m/z: [M+H] calcd for C$_{13}$H$_{25}$NO$_4$: 260.19; found 260.2.

Step 2: Synthesis of methyl (R)-3-methyl-2-((methylamino)methyl)butanoate

To a solution of methyl (R)-2-(((tert-butoxycarbonyl)(methyl)amino)methyl)-3-methylbutanoate (500 mg, 1.93 mmol) in DCM (5.0 mL) at 0° C. was added TFA (2.50 mL) dropwise. The resulting mixture was warmed to room temperature. After 2 h the reaction mixture was concentrated under reduced pressure to afford desired product (600 mg, crude) as a yellow solid.

Step 3: Synthesis of methyl (R)-3-methyl-2-(((R)—N-methyl-1-tritylaziridine-2-carboxamido)methyl)butanoate To a solution of methyl (R)-3-methyl-2-((methylamino)methyl)butanoate (550 mg, 3.45 mmol) and (R)-1-tritylaziridine-2-carboxylic acid (1.25 g, 3.80 mmol) in DCM (5.0 mL) at 0° C. was added DIPEA (1.81 mL, 10.4 mmol) followed by HATU (1.58 g, 4.15 mmol). The resulting mixture was warmed to room temperature. After 2 h the reaction was quenched with H$_2$O (30 mL) and extracted with EtOAc (3×30 mL). The combined organic layers were washed with brine (50 mL), dried with Na$_2$SO$_4$, and concentrated under reduced pressure. Purification by silica gel column chromatography (9% EtOAc/pet. ether) afforded the desired product (300 mg, 19% yield) as a yellow oil. LCMS (ESI) m/z: [M+H] calcd for C$_{30}$H$_{34}$N$_2$O$_3$: 471.27; found 471.3.

Step 4: Synthesis of (R)-3-methyl-2-(((R)—N-methyl-1-tritylaziridine-2-carboxamido)methyl)butanoic Acid To a solution of methyl (R)-3-methyl-2-(((R)—N-methyl-1-tritylaziridine-2-carboxamido)methyl)butanoate (200 mg, 0.425 mmol) in THF (2.0 mL) at 0° C. was added LiOH.H$_2$O (89 mg, 2.13 mmol) in H$_2$O (2.0 mL) dropwise. The resulting mixture was warmed to room temperature. After 5 h the mixture was neutralized to pH 7 with 1M HCl. The reaction was extracted with EtOAc (3×20 mL). The combined organic layers were washed with brine (30 mL), dried with Na$_2$SO$_4$, and concentrated under reduced pressure to afford product (200 mg, crude) as an off-white solid. The crude product was used in the next step directly without further purification. LCMS (ESI) m/z: [M+H] calcd for C$_{29}$H$_{32}$N$_2$O$_3$: 457.25; found 457.2.

Intermediate A-60. Synthesis of sodium (R)-1-methyl-5-(1-tritylaziridine-2-carboxamido)-1H-imidazole-2-carboxylate

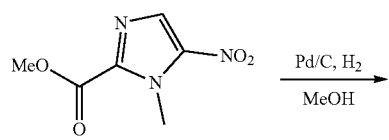

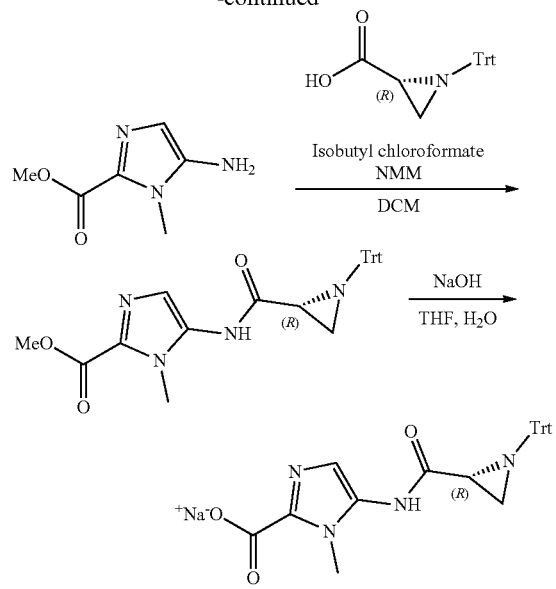

Step 1: Synthesis of methyl 5-amino-1-methyl-1H-imidazole-2-carboxylate

A mixture of methyl 1-methyl-5-nitro-1H-imidazole-2-carboxylate (1.0 g, 5.401 mmol) and Pd/C (500.0 mg) in MeOH (15 mL) at room temperature was stirred under an atmosphere of hydrogen (1 atm) for 3 h. The mixture was filtered and the filter cake was washed with MeOH (3×20 mL). The filtrate was concentrated under reduced pressure to afford the desired product (1.0 g, crude). LCMS (ESI) m/z: [M+Na] calcd for C$_6$H$_{19}$N$_3$O$_2$: 156.08; found 156.1.

Step 2: Synthesis of methyl (R)-1-methyl-5-(1-tritylaziridine-2-carboxamido)-1-imidazole-2-carboxylate A solution of (R)-1-tritylaziridine-2-carboxylic acid (2.55 g, 7.741 mmol) in DCM (12.0 mL) at 0° C. was added in portions over 30 min to a solution of isobutyl chloroformate (845.1 mg, 6.187 mmol) and N-methylmorpholine (1.04 g, 10.282 mmol) in DCM. To the mixture was then added methyl 5-amino-1-methyl-1H-imidazole-2-carboxylate (800.0 mg, 5.156 mmol) at 0° C. The resulting mixture was warmed to room temperature and stirred overnight. The mixture was diluted with DCM (300 mL) and washed with H$_2$O (3×100 mL), washed with brine (2×150 mL), dried over Na$_2$SO$_4$, filtered, and concentrated under reduced pressure. The residue was purified by silica gel chromatography (25% EtOAc/hexanes) to afford the final product (1.2 g, 49.9% yield). LCMS (ESI) m/z: [M+H] calcd for C$_{28}$H$_{26}$N$_4$O$_3$: 467.21; found 467.2.

Step 3: Synthesis of sodium (R)-1-methyl-5-(1-tritylaziridine-2-carboxamido)-1H-imidazole-2-carboxylate To a solution of methyl (R)-1-methyl-5-(1-tritylaziridine-2-carboxamido)-1-imidazole-2-carboxylate (300.0 mg, 0.643 mmol) in THF (3 mL) at room temperature was added NaOH.H$_2$O (38.6 mg, 0.965 mmol). The resulting solution was warmed to room temperature and stirred for 2 h. The solution was concentrated under reduced pressure to afford the desired product (400 mg, crude). LCMS (ESI) m/z: [M+H] calcd for $C_{27}H_{24}N_4O_3$: 453.19; found 453.2.

Intermediate A-61. Synthesis of (S)-1-methyl-5-(1-tritylaziridine-2-carboxamido)-1H-imidazole-2-carboxylic Acid

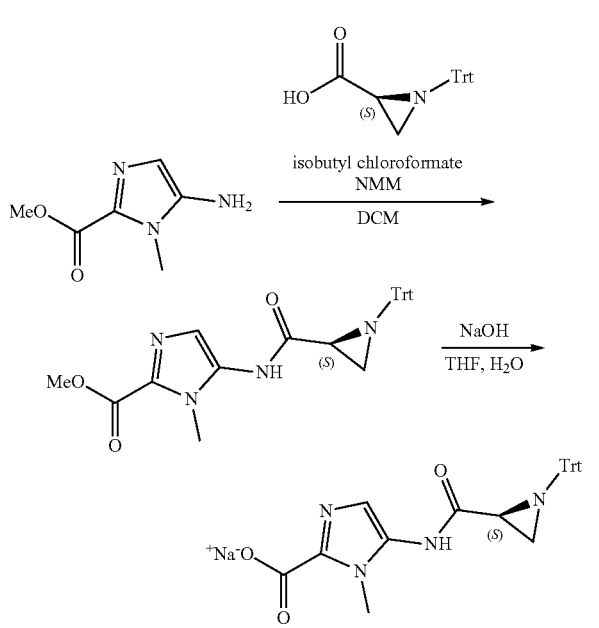

Step 1: Synthesis of methyl (S)-1-methyl-5-(1-tritylaziridine-2-carboxamido)-1H-imidazole-2-carboxylate To a solution of (S)-1-tritylaziridine-2-carboxylic acid (1.18 g, 3.577 mmol) in DCM (15 mL) at 0° C. was added isobutyl chloroformate (423.4 mg, 3.100 mmol) and N-methylmorpholine (0.39 mL) 3.862 mmol). The resulting mixture was stirred for 1 h at 0° C. and then methyl 5-amino-1-methyl-1H-imidazole-2-carboxylate (370.0 mg, 2.385 mmol) was added and the resulting mixture was warmed to at room temperature and stirred overnight. The reaction mixture was quenched with sat. aq. $NaHCO_3$ at 0° C. before being extracted with DCM (2×100 mL). The combined organic layers were washed with brine (150 mL), dried over $Na_2SO_4$, filtered, and concentrated under reduced pressure. The resulting residue was purified by silica gel chromatography (100% EtOAc) to afford the final product (380 mg, 34.2% yield) as a yellow solid. LCMS (ESI) m/z: [M+Na] calcd for $C_{28}H_{26}N_4O_3$: 467.21; found 467.3.

Step 2: Synthesis of (S)-1-methyl-5-(1-tritylaziridine-2-carboxamido)-1H-imidazole-2-carboxylic To a solution of NaOH (146.6 mg, 3.665 mmol) in $H_2O$ (3.6 mL) at 0° C. was added a solution of methyl (S)-1-methyl-5-(1-tritylaziridine-2-carboxamido)-1H-imidazole-2-carboxylate (380.0 mg, 0.815 mmol) in MeOH (5 mL). The resulting solution was warmed to room temperature and stirred for 6 h. The mixture was acidified to pH 6 with aq. 1 M HCl before being extracted with DCM (2×100 mL). The combined organic layers were washed with brine (150 mL), dried over $Na_2SO_4$, filtered, and concentrated under reduced pressure to afford the desired product (350 mg, crude). LCMS (ESI) m/z: [M+H] calcd for $C_{27}H_{24}N_4O_3$: 451.18; found 451.1.

Intermediate A-62. Synthesis of 4-((2S)-1-(tert-butylsulfinyl)aziridin-2-yl)benzoic Acid

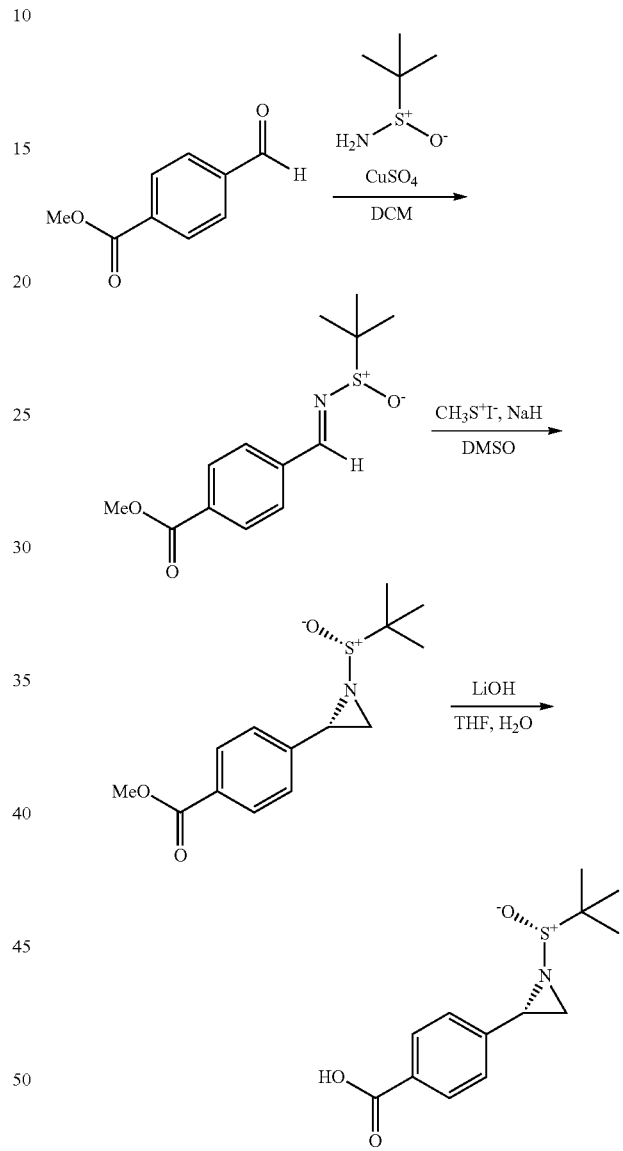

Step 1: Synthesis of methyl (E)-4-(((tert-butylsulfinyl)imino)methyl)benzoate

To a solution of methyl 4-formylbenzoate (100.0 mg, 0.609 mmol) and 2-methylpropane-2-sulfinamide (76.0 mg, 0.627 mmol) in DCM (2.0 mL) was added $CuSO_4$ (291.7 mg, 1.827 mmol). The resulting solution was stirred overnight at room temperature and was then filtered. The filter cake was washed with EtOAc (3×200 mL) and the filtrate was concentrated under reduced pressure. The resulting residue was purified by silica gel column chromatography (67% EtOAc/pet. ether) to afford the desired product (2 g, 61.4% yield). LCMS (ESI) m/z: [M+H] calcd for $C_{13}H_{17}NO_3S$: 268.10; found 268.0.

Step 2: Synthesis of methyl 4-((2S)-1-(tert-butylsulfinyl)aziridin-2-yl)benzoate Methyl (E)-4-((((tert-butylsulfinyl)imino)methyl)benzoate (500.0 mg, 1.863 mmol), $Me_3S^+I^-$ (1.14 g, 5.590 mmol), and 60% NaH (134.15 mg, 5.590 mmol) were dissolved in DMSO (10.0 mL) at room temperature. The resulting mixture was stirred for 2 h and then the reaction was quenched by the addition of sat. aq. $NH_4Cl$ (10 mL). The resulting mixture was extracted with EtOAc (3×50 mL) and the combined organic layers were washed with brine (2×100 mL), dried over $Na_2SO_4$, filtered, and concentrated under reduced pressure. The resulting residue was purified by silica gel chromatography (10% EtOAc/pet. ether) to afford the desired product (300 mg, 57.0% yield). LCMS (ESI) m/z: [M+H] calcd for $C_{14}H_{19}NO_3S$: 282.12; found 282.1.

Step 3: Synthesis of 4-((2S)-1-(tert-butylsulfinyl) aziridin-2-yl)benzoic Acid

To a solution of methyl 4-((2S)-1-(tert-butylsulfinyl)aziridin-2-yl)benzoate (400.0 mg, 1.422 mmol) in THF (5.0 mL) and $H_2O$ (1.0 mL) was added LiOH (103.0 mg, 4.301 mmol). The resulting mixture was stirred overnight at room temperature and was then acidified to pH ~3 with 1 M HCl. The mixture was extracted with EtOAc (3×200 mL), dried over $Na_2SO_4$, filtered, and concentrated under reduced pressure. The resulting residue was purified by prep-TLC (10% MeOH/DCM) to afford the desired product (130 mg, 91.2% yield). LCMS (ESI) m/z: [M−H] calcd for $C_{13}H_{17}NO_3S$: 266.09; found 266.0.

Intermediate A-63. Synthesis of (S)-3-methyl-2-((R)-2-oxo-3-((R)-1-tritylaziridine-2-carboxamido) pyrrolidin-1-yl)butanoic Acid

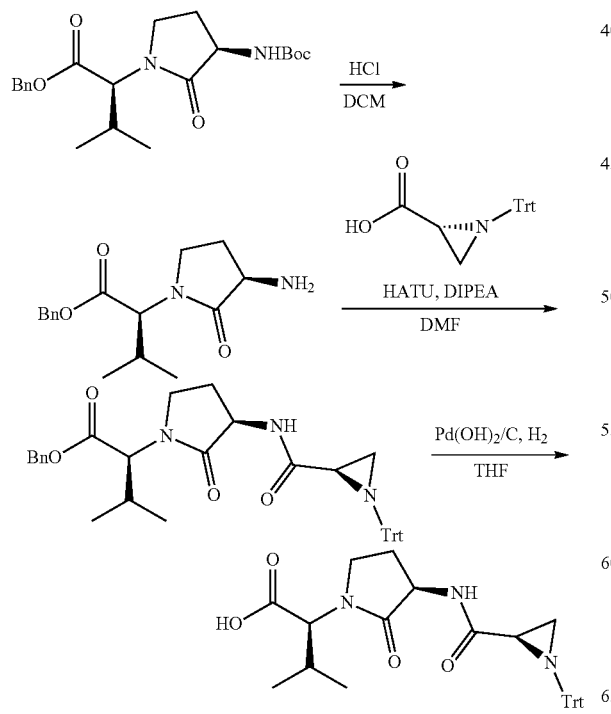

Step 1: Synthesis of benzyl (S)-2-((R)-3-amino-2-oxopyrrolidin-1-yl)-3-methylbutanoate To a solution of benzyl (S)-2-((R)-3-((tert-butoxycarbonyl)amino)-2-oxopyrrolidin-1-yl)-3-methylbutanoate (1.0 g, 2.561 mmol) in DCM (10.0 mL) was added 4M HCl in 1,4-dioxane (5.0 mL) at 0° C. The resulting mixture was stirred for 2 h at room temperature under an argon atmosphere. The resulting mixture was concentrated under reduced pressure to afford the desired crude product (890 mg, crude) as a yellow solid. LCMS (ESI) m/z: [M+H] calcd for $C_{16}H_{22}N_2O_3$: 291.17; found 291.1.

Step 2: Synthesis of benzyl (S)-3-methyl-2-((R)-2-oxo-3-((R)-1-tritylaziridine-2-carboxamido)pyrrolidin-1-yl)butanoate To a solution of benzyl (S)-2-((R)-3-amino-2-oxopyrrolidin-1-yl)-3-methylbutanoate (450.0 mg, 1.550 mmol) and (R)-1-tritylaziridine-2-carboxylic acid (765.8 mg, 2.325 mmol) in DMF were added HATU (1.179 g, 3.100 mmol) and DIPEA (1.35 mL, 7.75 mmol) dropwise at 0° C. The resulting mixture was stirred for 2 h at room temperature and was then extracted with EtOAc (2×100 mL). The combined organic layers were washed with $H_2O$, brine (20 mL), dried over $Na_2SO_4$, filtered, and concentrated under reduced pressure. The resulting residue was purified by silica gel chromatography (50% EtOAc/pet. ether) to afford the desired product (470 mg, 50.4% yield). LCMS (ESI) m/z: [M+H] calcd for $C_{38}H_{39}N_3O_4$: 602.31; found 602.3.

Step 3: Synthesis of (S)-3-methyl-2-((R)-2-oxo-3-((R)-1-tritylaziridine-2-carboxamido)pyrrolidin-1-yl) butanoic Acid A suspension of benzyl (S)-3-methyl-2-((R)-2-oxo-3-((R)-1-tritylaziridine-2-carboxamido)pyrrolidin-1-yl)butanoate (430.0 mg, 0.715 mmol) and $Pd(OH)_2/C$ (230.0 mg, 1.638 mmol) were in THF (5 mL) was stirred for 3 h under and atmosphere of hydrogen (1 atm). The resulting mixture was filtered and the filter cake was washed with MeOH (2×50 mL). The filtrate was concentrated under reduced pressure to afford the crude final product (16 mg, crude) as a white solid. LCMS (ESI) m/z: [M+H] calcd for $C_{31}H_{33}N_3O_4$: 510.24; found 510.1.

Intermediate A-64. Synthesis of potassium (S)-1-isopropylaziridine-2-carboxylate

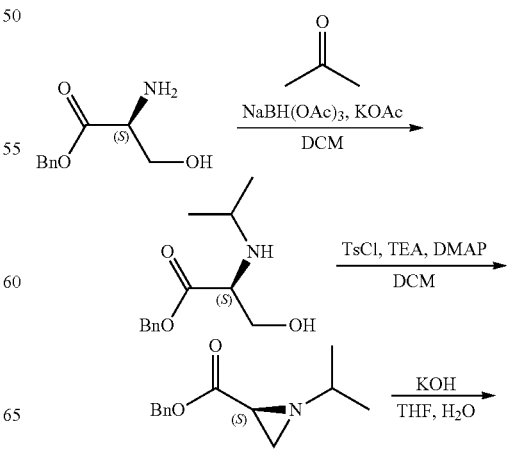

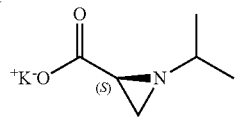

Step 1: Synthesis benzyl isopropyl-L-serinate

To a solution of benzyl L-serinate (3.65 g, 18.69 mmol), KOAc (1.83 g, 18.69 mmol), and acetone (2.5 mL, 33.66 mmol) in DCM (60.0 mL) was added NaBH(AcO)$_3$ (4.76 g, 22.436 mmol) in portions at 0° C. The resulting mixture was stirred overnight at room temperature. The reaction was quenched by the addition of sat. aq. NaHCO$_3$(50 mL) at room temperature. The resulting mixture was extracted with DCM (3×80 mL). The combined organic layers were washed with brine (50 mL), dried over Na$_2$SO$_4$, filtered, and concentrated under reduced pressure. The residue was purified by silica gel chromatography (67% EtOAc/hexanes) to afford the desired product (2.7 g, 60.9% yield) as an off-white solid. LCMS (ESI) m/z: [M+H] calcd for C$_{13}$H$_{19}$NO$_3$: 238.14; found 238.2.

Step 2: Synthesis of benzyl (S)-1-isopropylaziridine-2-carboxylate

To a solution of benzyl isopropyl-L-serinate (2.70 g, 11.378 mmol), Et$_3$N (4.75 mL, 34.134 mmol) and DMAP (2.57 mg, 0.021 mmol) in DCM (50.0 mL) was added a solution of TsCl (2.60 g, 13.65 mmol) in DCM dropwise at 0° C. The resulting mixture was stirred overnight at room temperature and was then stirred for 4 h at 40° C. The reaction mixture was diluted with H$_2$O (80 mL) and was then extracted with DCM (2×50 mL). The combined organic layers were washed with brine (30 mL), dried over Na$_2$SO$_4$, filtered, and concentrated under reduced pressure. The residue was purified by silica gel chromatography (20% EtOAc/hexanes) to afford the desired product (2.3 g, 93.2% yield). LCMS (ESI) m/z: [M+H] calcd for C$_{13}$H$_{17}$NO$_2$: 220.13; found 220.1.

Step 3: Synthesis of potassium (S)-1-isopropylaziridine-2-carboxylate

To a solution of benzyl (S)-1-isopropylaziridine-2-carboxylate (800.0 mg, 3.65 mmol) and H$_2$O (6.0 mL) and THF (8.0 mL) was added a solution of KOH (245.62 mg, 4.378 mmol) in H$_2$O (2.0 mL) dropwise at 0° C. The resulting mixture was stirred for 2 h at room temperature. The mixture was diluted with H$_2$O (10 mL) and the aqueous layer was washed with MTBE (3×8 mL). The aqueous layer was dried by lyophilization to afford the desired product (400 mg, crude). LCMS (ESI) m/z: [M+H] calcd for C$_6$H$_{11}$NO$_2$: 130.09; found 130.0.

Intermediate A-65. Synthesis of potassium (R)-1-isopropylaziridine-2-carboxylate

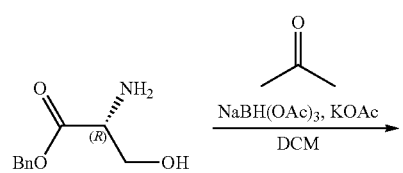

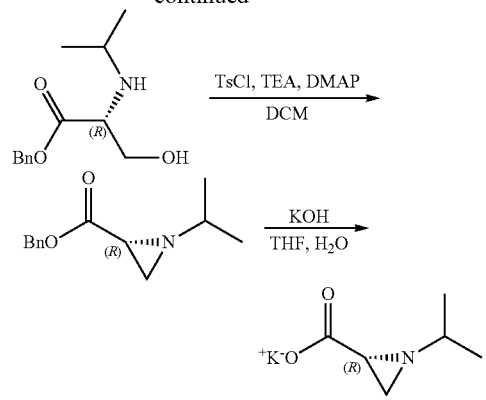

Step 1: Synthesis benzyl isopropyl-D-serinate

To a solution of benzyl D-serinate (2.10 g, 10.757 mmol), KOAc (1.06 g, 10.757 mmol), and acetone (1.2 mL, 16.136 mmol) in DCM (40.0 mL) was added a solution of NaBH (AcO)$_3$ (2.96 g, 13.984 mmol) in portions at 0° C. The resulting mixture was stirred overnight at room temperature. The reaction was quenched by the addition of sat. aq. NaHCO$_3$(50 mL) and the mixture was extracted with DCM (3×50 mL). The combined organic layers were washed with brine (50 mL), dried over Na$_2$SO$_4$, filtered, and concentrated under reduced pressure. The residue was purified by silica gel chromatography (67% EtOAc/hexanes) to afford the desired product (1.7 g, 66.6% yield). LCMS (ESI) m/z: [M+H] calcd for C$_{13}$H$_{19}$NO$_3$: 238.14; found 238.0.

Step 2: Synthesis of benzyl (R)-1-isopropylaziridine-2-carboxylate

To a solution of benzyl isopropyl-D-serinate (1.75 g, 7.375 mmol), Et$_3$N (2.58 mL, 18.437 mmol) and DMAP (90.09 mg, 0.737 mmol) in DCM (30.0 mL) was added a solution of TsCl (1.69 g, 8.850 mmol) in DCM dropwise at 0° C. The resulting mixture was stirred overnight at room temperature before being stirred for 4 h at 40° C. The mixture was diluted with H$_2$O (80 mL) and then extracted with DCM (3×50 mL). The combined organic layers were washed with brine (50 mL), dried over Na$_2$SO$_4$, filtered, and concentrated under reduced pressure. The residue was purified by silica gel chromatography (20% EtOAc/hexanes) to afford the desired product (1.4 g, 86.6% yield). LCMS (ESI) m/z: [M+H] calcd for C$_{13}$H$_{17}$NO$_2$: 220.13; found 219.9.

Step 3: Synthesis of Potassium (R)-1-isopropylaziridine-2-carboxylate

To a solution of benzyl (R)-1-isopropylaziridine-2-carboxylate (600.0 mg, 2.736 mmol) in H$_2$O (3.0 mL) and THF (5.0 mL) was added a solution of KOH (184.22 mg, 3.283 mmol) in H$_2$O (2.0 mL) dropwise at 0° C. The resulting mixture was stirred for 2 h at room temperature. The mixture was then diluted with H$_2$O (10 mL) and the aqueous layer was washed with MTBE (3×8 mL). The aqueous layer was then dried by lyophilization to afford the desired product (260 mg, crude). LCMS (ESI) m/z: [M+H] calcd for C$_6$H$_{11}$NO$_2$: 130.09; found 130.1.

Intermediate A-66. Synthesis of N-methyl-N-(3-oxo-4-((R)-1-tritylaziridine-2-carbonyl)piperazine-1-carbonyl)-L-valine

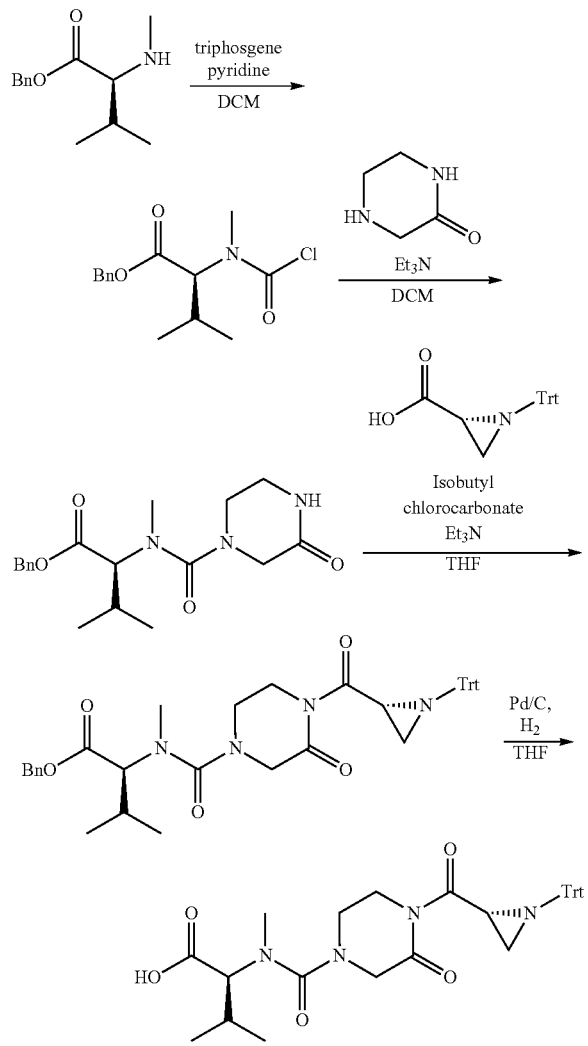

Step 1: Synthesis of benzyl N-(chlorocarbonyl)-N-methyl-L-valinate

To a solution of benzyl methyl-L-valinate (2.0 g, 9.038 mmol) in DCM (20.0 mL) was added a solution of triphosgene (800 mg, 2.711 mmol) and pyridine (2.14 g, 27.113 mmol) in DCM (20.0 mL) dropwise at 0° C. The resulting mixture was stirred for 2 h at room temperature before being diluted with EtOAc. The solution was stirred for 30 min at room temperature and was then filtered. The filtrate was concentrated under reduced pressure to afford the crude product which was used in the next step directly without further purification. LCMS (ESI) m/z: [M+H] calcd for $C_{14}H_{18}ClNO_3$: 284.11; found 283.1.

Step 2: Synthesis of benzyl N-methyl-N-(3-oxopiperazine-1-carbonyl)-L-valinate To a solution of piperazin-2-one (100.0 mg, 0.999 mmol) and Et₃N (0.487 mL, 3.496 mmol) in DCM (5.0 mL) was added a solution of benzyl N-(chlorocarbonyl)-N-methyl-L-valinate (311.75 mg, 1.099 mmol) in DCM (5 mL) dropwise at 0° C. The resulting mixture was stirred for 4 h at room temperature. The mixture was then diluted with H₂O (5 mL), the aqueous layer was extracted with DCM (3×5 mL), and the combined organic layers were concentrated under reduced pressure. The residue was purified by prep-TLC (100% EtOAc) to afford the desired product (200 mg, 57.6% yield). LCMS (ESI) m/z: [M+H] calcd for $C_{18}H_{25}N_3O_4$: 348.19; found 348.1.

Step 3: Synthesis of benzyl N-methyl-N-(3-oxo-4-((R)-1-tritylaziridine-2-carbonyl)piperazine-1-carbonyl)-L-valinate To a solution of (R)-1-tritylaziridine-2-carboxylic acid (711.11 mg, 2.159 mmol) in THF was added Et₃N (0.40 mL, 2.878 mmol) and isobutyl chlorocarbonate (255.53 mg, 1.871 mmol) dropwise at 0° C. under a nitrogen atmosphere. The resulting mixture was stirred for 1 h at room temperature and then benzyl N-methyl-N-(3-oxopiperazine-1-carbonyl)-L-valinate (500.0 mg, 1.439 mmol) was added at room temperature. The resulting mixture was warmed to 70° C. and stirred overnight. The reaction was then cooled to room temperature and concentrated under reduced pressure. The residue was purified by prep-TLC (EtOAc/50% pet. ether) to afford the desired product (200 mg, 21.1% yield). LCMS (ESI) m/z: [M+H] calcd for $C_{40}H_{42}N_4O_5$: 659.32; found 677.4.

Step 4: Synthesis of N-methyl-N-(3-oxo-4-((R)-1-tritylaziridine-2-carbonyl)piperazine-1-carbonyl)-L-valine A suspension of benzyl N-methyl-N-(3-oxo-4-((R)-1-tritylaziridine-2-carbonyl)piperazine-1-carbonyl)-L-valinate (140.0 mg, 0.212 mmol) and Pd/C (50.0 mg) in THF (3 mL) was stirred for 2 h under a hydrogen atmosphere (1 atm). The mixture was then filtered and the filter cake was washed with MeOH (3×15 mL). The filtrate was concentrated under reduced pressure to afford the desired product (100 mg, crude). LCMS (ESI) m/z: [M−H] calcd for $C_{33}H_{36}N_4O_5$: 567.26; found 567.1.

Intermediate A-67. Synthesis of (S)-1-(2-((tert-butyldiphenyl)silyl)oxy)ethyl)aziridine-2-carboxylic Acid

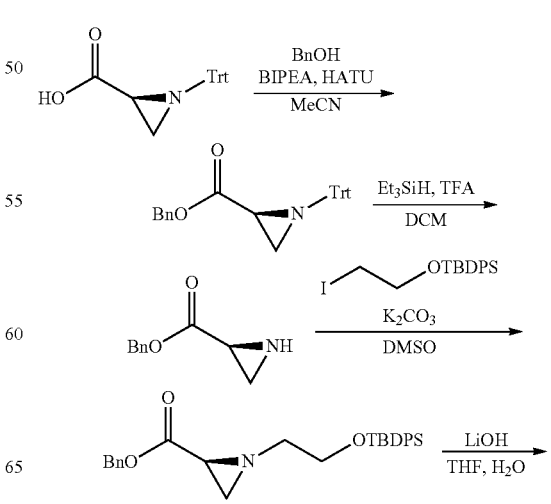

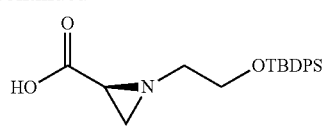

Step 1: Synthesis of benzyl (S)-1-tritylaziridine-2-carboxylate

To a solution of (S)-1-tritylaziridine-2-carboxylic acid (500.0 mg, 1.518 mmol), benzyl alcohol (246.2 mg, 2.277 mmol) and DIPEA (0.793 mL, 4.554 mmol) in MeCN (10.0 mL) was added HATU (1.73 mg, 4.554 mmol). The resulting solution was stirred for 3 h at room temperature and was then concentrated under reduced pressure. The crude residue was purified by prep-TLC (50% EtOAc/pet. ether) to afford the desired product (300 mg, 47.1% yield) as an off-white slid. LCMS (ESI) m/z: [M+Na] calcd for $C_{29}H_{25}NO_2$: 442.18; found 442.3.

Step 2: Synthesis of benzyl (S)-aziridine-2-carboxylate

To a solution of benzyl (S)-1-tritylaziridine-2-carboxylate (300.0 mg, 0.715 mmol) in DCM (5.0 mL) at 0° C. was added TFA (326.2 mg, 2.860 mmol) and $Et_3SiH$ (332.6 mg, 2.860 mmol). The resulting mixture was stirred at 0° C. for 3 h and was then concentrated under reduced pressure. The residue was purified by prep-TLC (10% MeOH/DCM) to afford the desired product (130 mg, 82.1% yield). LCMS (ESI) m/z: [M+H] calcd for $C_{10}H_{11}NO_2$: 178.09; found 178.2.

Step 3: Synthesis of benzyl (S)-1-(2-((tert-butyldiphenylsilyl)oxy)ethyl)aziridine-2-carboxylate To a solution of benzyl (S)-aziridine-2-carboxylate (400.0 mg, 2.257 mmol) and tert-butyl(2-iodoethoxy)diphenylsilane (1.85 g, 4.52 mmol) in DMSO (10.0 mL) was added $K_2CO_3$ (935.9 mg, 6.772 mmol) at room temperature. The mixture was stirred at 60° C. for 5 h. The mixture was diluted with $H_2O$ (30.0 mL) and was extracted with EtOAc (2×30 mL). The combined organic layers were washed with brine (2×50 mL), dried over $Na_2SO_4$, filtered, and concentrated under reduced pressure. The resulting residue was purified by prep-TLC (20% EtOAc/pet. ether) to afford the desired product (200 mg, 15.4% yield). LCMS (ESI) m/z: [M+H] calcd for $C_{28}H_{33}NO_3Si$: 460.23; found 460.0.

Step 4: Synthesis of Lithium (S)-1-(2-((tert-butyldiphenylsilyl)oxy)ethyl)aziridine-2-carboxylate To a solution of benzyl (S)-1-(2-((tert-butyldiphenylsilyl)oxy)ethyl)aziridine-2-carboxylate (200.0 mg, 0.435 mmol) in MeOH (2.0 mL) was added $LiOH \cdot H_2O$ (36.5 mg, 0.870 mmol). The resulting mixture was stirred overnight and was then concentrated under reduced pressure to afford the desired product (200 mg, crude). LCMS (ESI) m/z: [M+H] calcd for $C_{21}H_{27}NO_3Si$: 370.18; found 370.1.

Intermediate A-68. Synthesis of (R)-1-(2-((tert-butyldiphenyl)silyl)oxy)ethyl)aziridine-2-carboxylic Acid

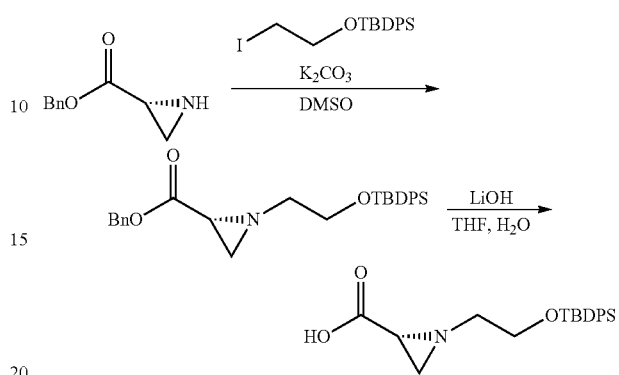

Step 1: Synthesis of Methyl Benzyl (R)-1-(2-((tert-butyldiphenylsilyl)oxy)ethyl)aziridine-2-carboxylate To a solution of benzyl (R)-aziridine-2-carboxylate (600.0 mg, 3.386 mmol) and $K_2CO_3$ (1.87 g, 13.544 mmol) in DMSO (8.0 mL) was added tert-butyl(2-iodoethoxy)diphenylsilane (1.39 g, 3.386 mmol) in portions at room temperature. The resulting mixture was stirred at 80° C. for 16 h. The reaction mixture was then cooled to room temperature and concentrated under reduced pressure. The residue was purified by reverse phase chromatography (60→90% MeCN/$H_2O$) to afford the desired product (150 mg, 9.6% yield) as a colorless solid. LCMS (ESI) m/z: [M+Na] calcd for $C_{28}H_{33}NO_3Si$: 482.21; found 482.3.

Step 2: Synthesis of (R)-1-(2-((tert-butyldiphenylsilyl)oxy)ethyl)aziridine-2-carboxylic Acid To a solution of methyl benzyl (R)-1-(2-((tert-butyldiphenylsilyl)oxy)ethyl)aziridine-2-carboxylate (180.0 mg, 0.392 mmol) in $H_2O$ (2.0 mL) and THF (3.0 mL) at 0° C. was added a solution of $LiOH \cdot H_2O$ (32.87 mg, 0.392 mmol) in $H_2O$ (1.0 mL). The resulting mixture was diluted with $H_2O$ (6.0 mL) and the aqueous layer was washed with MTBE (3×4 mL). The aqueous layer was dried by lyophilization which afforded the desired product (140 mg, crude). LCMS (ESI) m/z: [M+H] calcd for $C_{21}H_{27}NO_3Si$: 370.18; found 370.0.

Intermediate A-69. Synthesis of 6-((2S)-1-(tert-butylsulfinyl)aziridin-2-yl)nicotinic Acid

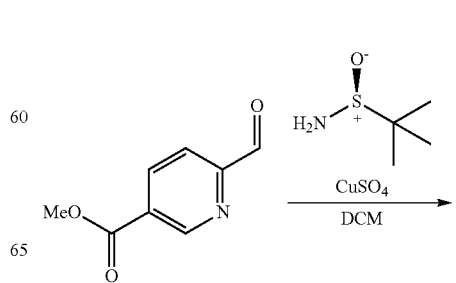

-continued

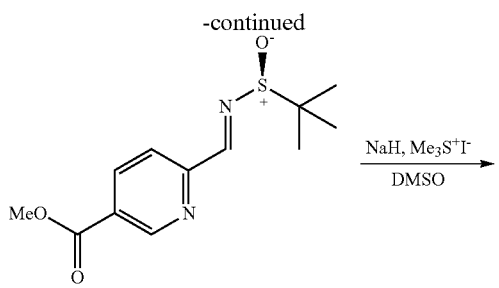

Step 1: Synthesis of methyl (E)-6-(((tert-butylsulfinyl)imino)methyl)nicotinate To a mixture of methyl 6-formylnicotinate (2.0 g, 12.11 mmol) and 2-methylpropane-2-sulfinamide (2.94 g, 24.26 mmol) in DCM (60 mL) was added CuSO$_4$ (5.80 g, 36.34 mmol). The resulting mixture was stirred at room temperature for 18 h. The reaction mixture was filtered, the filter cake was washed with DCM (3×30 mL), and the filtrate was concentrated under reduced pressure. Purification by normal phase chromatography (66% EtOAc/pet. ether) afforded the desired product (2.581 g, 80% yield). LCMS (ESI) m/z: [M+H] calcd for C$_{12}$H$_{16}$N$_2$O$_3$S: 269.10; found 269.1.

Step 2: Synthesis of 6-((2S)-1-(tert-butylsulfinyl)aziridin-2-yl)nicotinic Acid To a suspension of NaH (60%, 179.76 mg, 7.491 mmol) in DMSO (20 mL) at 0° C. was added Me$_3$S$^+$I$^-$ (1.53 g, 7.491 mmol) and the resulting mixture was warmed to room temperature and stirred for 1 h. To the reaction mixture was added a solution of methyl (E)-6-(((tert-butylsulfinyl)imino)methyl)nicotinate (670.0 mg, 2.497 mmol) in DMSO (20 mL) in portions. The mixture was stirred at room temperature for 3 h and was then diluted with EtOAc. The mixture was acidified to pH 4 with 1 M HCl and then the aqueous layer was extracted with EtOAc. The combined organic layers were concentrated under reduced pressure. Purification by reverse phase chromatography (10→15% MeCN/H$_2$O) afforded the desired product (313 mg, 45% yield). LCMS (ESI) m/z: [M+H] calcd for C$_{12}$H$_{16}$N$_2$O$_3$S: 269.10; found 269.1.

Intermediate A-70. Synthesis of N-methyl-N—(N-methyl-N—((R)-1-tritylaziridine-2-carbonyl)-D-alanyl)-L-valine

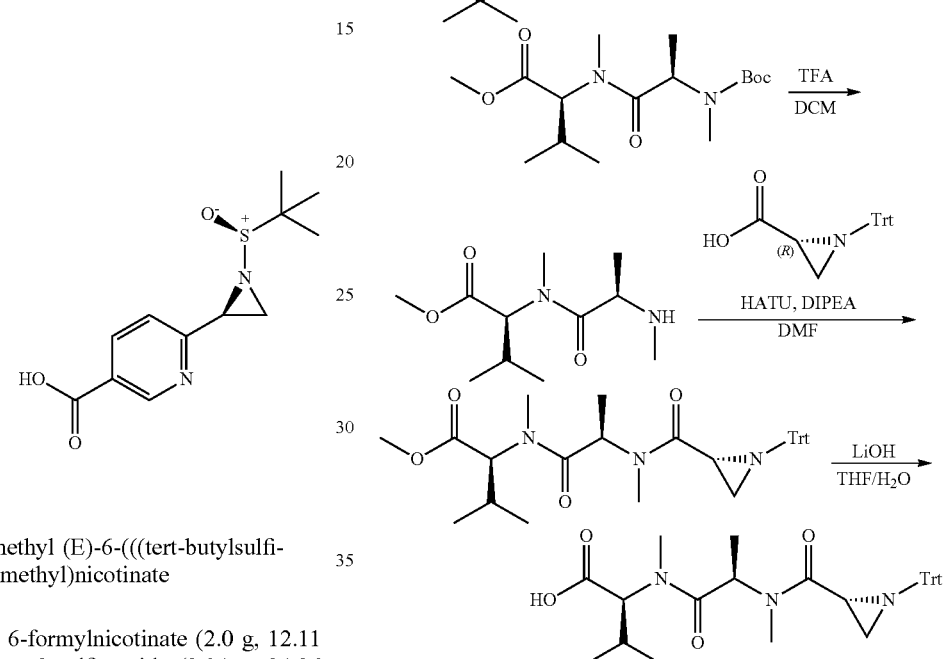

Step 1: Synthesis of methyl N—(N-(tert-butoxycarbonyl)-N-methyl-D-alanyl)-N-methyl-L-valinate To a solution of methyl-L-valinate hydrochloride (1.0 g, 5.51 mmol) and N-(tert-butoxycarbonyl)-N-methyl-D-alanine (1.34 g, 6.59 mmo) in DCM (20.0 mL) at 0° C. was added Et$_3$N (2.3 mL, 16.51 mmol) and HATU (2.72 g, 7.16 mmol). The mixture was warmed to room temperature and stirred for 4 h. The reaction mixture was then diluted with DCM (20 mL) and washed with sat. aq. NH$_4$Cl (2×40 mL) and brine (40 mL), dried over Na$_2$SO$_4$, filtered, and concentrated under reduced pressure. The residue was purified by silica gel column chromatography (20% EtOAc/pet. ether) to afford the desired product (1.5 g, 82.5% yield). LCMS (ESI) m/z: [M+H] calcd for C$_{16}$H$_{30}$N$_2$O$_5$: 331.23; found 331.1.

Step 2: Synthesis of methyl N-methyl-N-(methyl-D-alanyl)-L-valinate

To a solution of methyl N—(N-(tert-butoxycarbonyl)-N-methyl-D-alanyl)-N-methyl-L-valinate (1.50 g, 4.54 mmol) in DCM (9.0 mL) at 0° C. was added TFA (4.5 mL). The resulting mixture was warmed to room temperature and stirred for 1 h. The reaction mixture was concentrated under reduced pressure to afford the desired product (1 g, crude). LCMS (ESI) m/z: [M+H] calcd for $C_{11}H_{22}N_2O_3$: 231.17; found 231.2.

Step 3: Synthesis of Methyl N-methyl-N—(N-methyl-N—((R)-1-tritylaziridine-2-carbonyl)-D-alanyl)-L-valinate To a solution of methyl N-methyl-N-(methyl-D-alanyl)-L-valinate (900.0 mg, 3.91 mmol) and (R)-1-tritylaziridine-2-carboxylic acid (1.544 g, 4.689 mmol) in DMF (20.0 mL) at 0° C. was added DIPEA (3.4 mL, 19.54 mmol) and HATU (2.228 g, 5.86 mmol). The mixture was warmed to room temperature and stirred for 1 h. The reaction mixture was diluted with $H_2O$ (50 mL) and extracted with EtOAc (3×50 mL). The combined organic layers were dried over $Na_2SO_4$, filtered, and concentrated under reduced pressure. The residue was purified by silica gel column chromatography (33% EtOAc/pet. ether) to afford the desired product (1.2 g, 56.7% yield). LCMS (ESI) m/z: [M+H] calcd for $C_{33}H_{39}N_3O_4$: 542.30; found 542.3.

Step 4: Synthesis of N-methyl-N—(N-methyl-N—((R)-1-tritylaziridine-2-carbonyl)-D-alanyl)-L-valine To a solution of methyl N-methyl-N—(N-methyl-N—((R)-1-tritylaziridine-2-carbonyl)-D-alanyl)-L-valinate (200.0 mg, 0.369 mmol) in THF (2.0 mL) at 0° C. was added a solution of $LiOH.H_2O$ (77 mg, 1.84 mmol) in $H_2O$ (1.85 mL). The resulting mixture was warmed to room temperature and stirred overnight. The mixture was adjusted to pH 9 with 1 M HCl and then adjusted to pH 7 with aq. $NH_4Cl$. The aqueous layer was extracted with EtOAc (3×20 mL). The combined organic layers were dried over $Na_2SO_4$, filtered, and concentrated under reduced pressure to afford the desired product (200 mg, crude. LCMS (ESI) m/z: [M+H] calcd for $C_{32}H_{37}N_3O_4$: 528.29; found 528.3.

Intermediate A-71 and A-72. Synthesis of (2R,3S)-1-(4-methoxybenzyl)-3-(trifluoromethyl)aziridine-2-carboxylic acid and (2S,3R)-1-(4-methoxybenzyl)-3-(trifluoromethyl)aziridine-2-carboxylic Acid

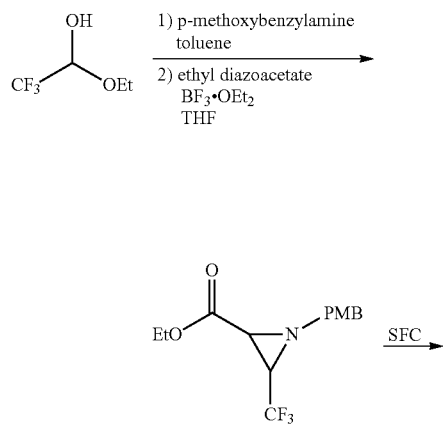

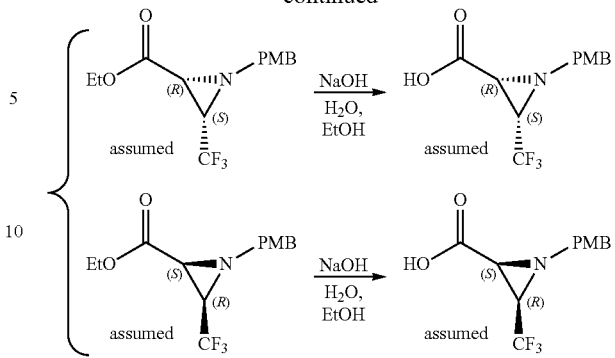

Step 1: Synthesis of ethyl 1-(4-methoxybenzyl)-3-(trifluoromethyl)aziridine-2-carboxylate A solution of 1-ethoxy-2,2,2-trifluoroethan-1-ol (2.17 mL, 18.37 mmol) and p-methoxybenzylamine (1.89 mL, 14.58 mmol) in toluene (46 mL) was refluxed for 16 h under Dean-Stark conditions. The reaction was concentrated under reduced pressure and the resulting residue was dissolved in THF (80 mL) and cooled to −78° C. $BF_3.Et_2O$ (0.360 mL, 2.92 mmol) was added to the solution, followed by dropwise addition of ethyl diazoacetate (1.83 mL, 17.50 mmol). The reaction was stirred for 4 h at room temperature. The reaction mixture was quenched by addition of aq. sat. $NaHCO_3$(5 mL), and the resulting solution was extracted with DCM (3×50 mL). The combined organic layers were washed with $H_2O$ (20 mL) and brine (10 mL). The organic phase was dried over $Na_2SO_4$, filtered, and concentrated under reduced pressure. The residue was purified by silica gel column chromatography (1→10% EtOAc/pet. ether) afford the desired product (2 g, 45.2 yield).

Step 2: Synthesis of ethyl (2R,3S)-1-(4-methoxybenzyl)-3-(trifluoromethyl)aziridine-2-carboxylate and ethyl (2S,3R)-1-(4-methoxybenzyl)-3-(trifluoromethyl)aziridine-2-carboxylate Ethyl 1-(4-methoxybenzyl)-3-(trifluoromethyl)aziridine-2-carboxylate (1 g) was purified by SFC separation (column: REGIS(S,S)WHELK-01(250 mm*25 mm, 10 um); mobile phase: [Neu-IPA]; B %: 13%-13%, min) to afford ethyl (2R,3S)-1-(4-methoxybenzyl)-3-(trifluoromethyl)aziridine-2-carboxylate (530 mg) and ethyl (2S,3R)-1-(4-methoxybenzyl)-3-(trifluoromethyl)aziridine-2-carboxylate (470 mg).

Step 3: Synthesis of (2R,3S)-1-(4-methoxybenzyl)-3-(trifluoromethyl)aziridine-2-carboxylic Acid To a solution of ethyl (2R,3S)-1-(4-methoxybenzyl)-3-(trifluoromethyl)aziridine-2-carboxylate (430 mg, 1.42 mmol) in EtOH (4 mL) and $H_2O$ (6 mL) was added NaOH (113.42 mg, 2.84 mmol). The mixture was stirred at room temperature for 5 h. The mixture was acidified with aq. HCl (2M) to pH=1-2. The reaction mixture was poured into $H_2O$ (3 mL) and the aqueous phase was extracted with EtOAc (3×3 mL). The combined organic phase was washed with brine (5 mL), dried over $Na_2SO_4$, filtered and concentrated under reduced pressure to afford the desired product (350 mg, 89.1% yield). LCMS (ESI) m/z: [M+H] calcd for $C_{12}H_{11}FNO_3$: 274.08; found 274.1.

Step 4: Synthesis of (2S,3R)-1-(4-methoxybenzyl)-3-(trifluoromethyl)aziridine-2-carboxylic Acid To a solution of ethyl (2S,3R)-1-(4-methoxybenzyl)-3-(trifluoromethyl)aziridine-2-carboxylate (370 mg, 1.22 mmol) in H$_2$O (2 mL) and EtOH (4 mL) was added NaOH (97.59 mg, 2.44 mmol). The mixture was stirred at room temperature for 5 h. The mixture was brought to pH=1-2 with the addition of aq. HCl (2 M). The reaction mixture was poured into H$_2$O (3 mL) and the aqueous phase was extracted with EtOAc (3×3 mL). The combined organic phase was washed with brine (5 mL), dried over Na$_2$SO$_4$, filtered, and concentrated under reduced pressure to afford the desired product (300 mg, 89.0% yield). LCMS (ESI) m/z: [M+H] calcd for C$_{12}$H$_{11}$FNO$_3$:234.08; found 234.2.

Intermediate A-73 and A-74. Synthesis of (2S,3S)-1-benzyl-3-(trifluoromethyl)aziridine-2-carboxylic acid and (2R,3R)-1-benzyl-3-(trifluoromethyl)aziridine-2-carboxylic Acid

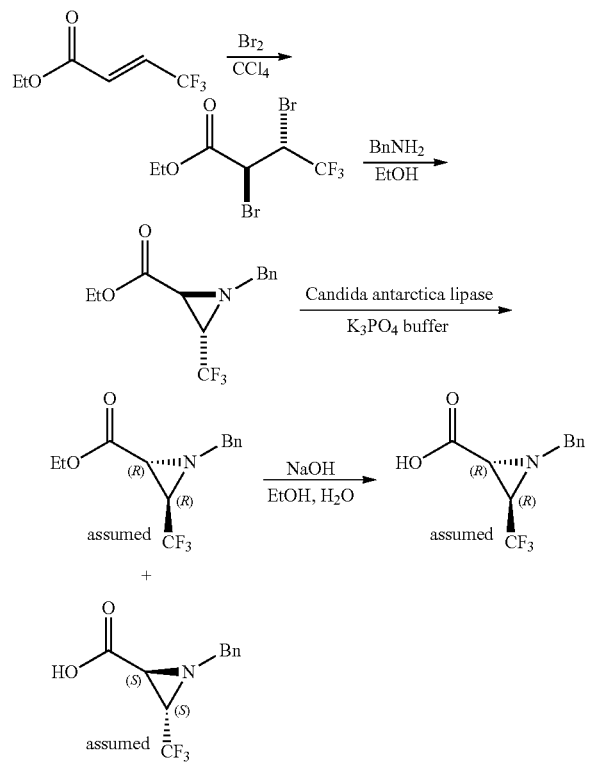

Step 1: Synthesis of ethyl (2S,3R)-2,3-dibromo-4,4,4-trifluorobutanoate

To a solution of ethyl (E)-4,4,4-trifluorobut-2-enoate (5 g, 29.74 mmol, 4.42 mL) in CCl$_4$ (90 mL) was added Br$_2$ (1.69 mL, 32.72 mmol) and the solution was stirred at 75° C. for 5 h. The reaction mixture was concentrated under reduced pressure to give the desired product (10.72 g, crude).

Step 2: Synthesis of ethyl (2S,3S)-1-benzyl-3-(trifluoromethyl)aziridine-2-carboxylate To a solution of ethyl (2S,3R)-2,3-dibromo-4,4,4-trifluorobutanoate (10.72 g, 32.69 mmol) in EtOH (30 mL) was slowly added the solution of BnNH$_2$ (12.47 mL, 114.42 mmol) in EtOH (120 mL) at -5° C. under N$_2$. The mixture was warmed to room temperature and stirred for 15 h. The mixture was concentrated under reduced pressure and EtOAc (120 mL) was added to the residue. The precipitate was filtered off and the filtrate was washed with aqueous HCl (3%, 180 mL) and H$_2$O (100 mL), dried over Na$_2$SO$_4$, filtered and concentrated under reduced pressure. The residue was purified by silica gel chromatography (20% EtOAc/pet. ether) to afford the desired product (6.02 g, 67.4% yield).

Step 3: Synthesis of ethyl (2R,3R)-1-benzyl-3-(trifluoromethyl)aziridine-2-carboxylate and (2S,3S)-1-benzyl-3-(trifluoromethyl)aziridine-2-carboxylic Acid Ethyl (2R,3R)-1-benzyl-3-(trifluoromethyl)aziridine-2-carboxylate and (2S,3S)-1-benzyl-3-(trifluoromethyl)aziridine-2-carboxylic acid were synthesized in Enzyme Screening Platform, based on the procedure in *Tetrahedron Asymmetry* 1999, 10, 2361.

Step 5: Synthesis of (2R,3R)-1-benzyl-3-(trifluoromethyl)aziridine-2-carboxylic Acid To a solution of ethyl (2R,3R)-1-benzyl-3-(trifluoromethyl)aziridine-2-carboxylate (200 mg, 731.93 μmol) in EtOH (5 mL) was added NaOH (2 M, 548.95 μL) and the mixture was stirred at room temperature for 1 h. The reaction mixture was concentrated under reduced pressure to remove EtOH. Then to the mixture was added HCl (1 M) to adjust pH to 1, and extracted with EtOAc (3×5 mL). The combined organic layers were washed with brine (2×10 mL), dried over Na$_2$SO$_4$, filtered and concentrated under reduced pressure to afford the desired product (138 mg, 76.9% yield). LCMS (ESI) m/z: [M+H] calcd for C$_{11}$H$_{10}$F$_3$NO$_2$: 246.07; found 245.9.

Intermediate A-75. Synthesis of 1-(oxetan-3-yl)aziridine-2-carboxylic Acid

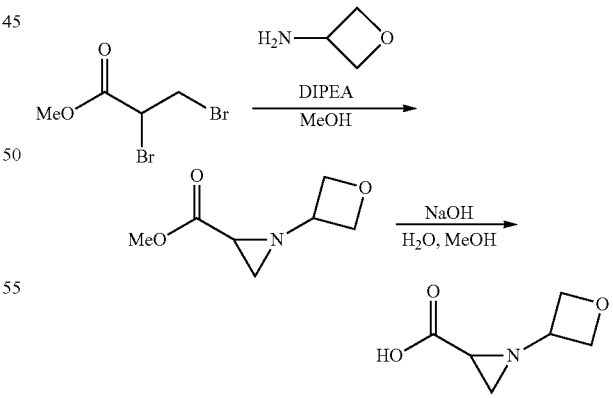

Step 1: Synthesis of methyl 1-(oxetan-3-yl)aziridine-2-carboxylate

To a solution of methyl 2,3-dibromopropanoate (515.46 μL, 4.07 mmol) in MeOH (15 mL) was added DIPEA (3.54 mL, 20.33 mmol). After addition, the mixture was stirred for 15 min, and then oxetan-3-amine (297.25 mg, 4.07 mmol) was added dropwise. The resulting mixture was stirred at room temperature for 12 h. The reaction mixture was poured into H$_2$O (20 mL), the aqueous phase was extracted with DCM (2×25 mL). The combined organic phase was washed with brine (20 mL), dried with Na$_2$SO$_4$, filtered and concentrated under reduced pressure. The residue was purified by silica gel chromatography (10%→30% EtOAc/pet. ether) to afford the desired product (380 mg, 59.5% yield).

Step 2: Synthesis of 1-(oxetan-3-yl)aziridine-2-carboxylic Acid

To a solution of methyl 1-(oxetan-3-yl)aziridine-2-carboxylate (280 mg, 1.78 mmol) in EtOH (3 mL) was added NaOH (2 M, 1.34 mL) at room temperature and the resulting mixture was stirred for 3 h. The reaction mixture was adjusted to pH 8 by the addition of HCl (1 M), and lyophilized to afford the desired product (200 mg, 78.4% yield).

Intermediate A-76. Synthesis of (2S,3S)-1-((S)-tert-butylsulfinyl)-3-cyclobutylaziridine-2-carboxylic Acid

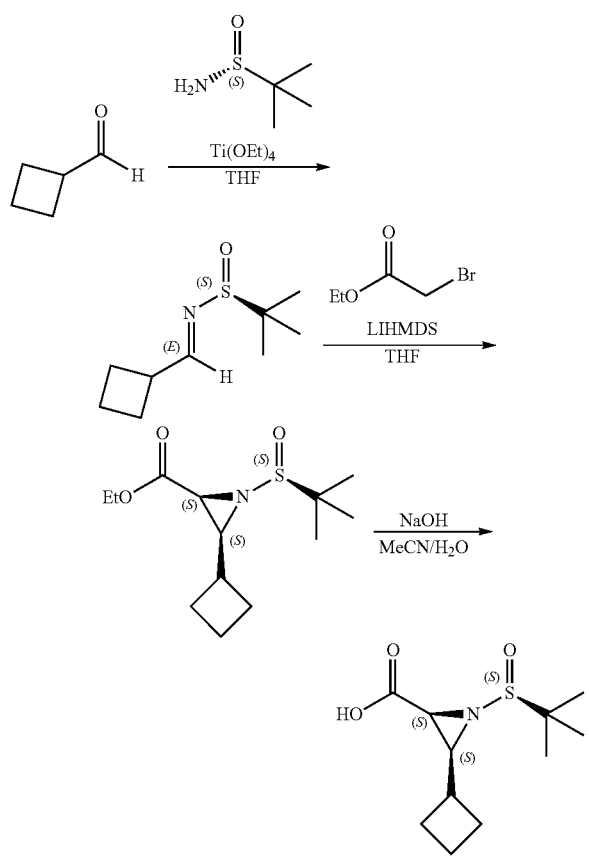

Step 1: Synthesis of (S,E)-N-(cyclobutylmethylene)-2-methylpropane-2-sulfinamide To a solution of cyclobutanecarbaldehyde (0.5 g, 5.94 mmol) in THF (10 mL) was added (S)-2-methylpropane-2-sulfinamide (792.48 mg, 6.54 mmol) and Ti(OEt)$_4$ (2.47 mL, 11.89 mmol). The mixture was stirred at 75° C. for 3 h. The reaction mixture was cooled to room temperature and quenched by addition brine (30 mL), and filtered to remove solids. The mixture was extracted with EtOAc (3×30 mL). The combined organic layers were washed with brine (2×10 mL), dried over Na$_2$SO$_4$, filtered and concentrated under reduced pressure to give a residue. The residue was purified by silica gel chromatography (2%→10% EtOAc/pet. ether) to afford the desired product (907.3 mg, 39.9% yield). LCMS (ESI) m/z: [M+H] calcd for C$_9$H$_{17}$NOS: 188.1; found 188.3.

Step 2: Synthesis of ethyl (2S,3S)-1-((S)-tert-butylsulfinyl)-3-cyclobutylaziridine-2-carboxylate To a solution of ethyl 2-bromoacetate (1.60 g, 9.61 mmol, 1.06 mL) in THF (9 mL) was added LiHMDS (1 M, 9.61 mL) at −78° C., after 2 min, (S,E)-N-(cyclobutylmethylene)-2-methylpropane-2-sulfinamide (0.9 g, 4.81 mmol) was added. The mixture was stirred at −78° C. for 2 h. The reaction mixture was quenched by addition H$_2$O (25 mL) at −78° C. and warmed to room temperature, then the mixture extracted with EtOAc (3×20 mL). The combined organic layers were washed with brine (2×5 mL), dried over Na$_2$SO$_4$, filtered and concentrated under reduced pressure to give a residue, which was purified by silica gel chromatography (10%→20% EtOAc/pet. ether) to afford the desired product (426 mg, crude). LCMS (ESI) m/z: [M+H] calcd for C$_{13}$H$_{23}$NO$_3$S: 274.14; found 274.3.

Step 3: Synthesis of (2S,3S)-1-((S)-tert-butylsulfinyl)-3-cyclobutylaziridine-2-carboxylic Acid To a solution of (2S,3S)-1-((S)-tert-butylsulfinyl)-3-cyclobutylaziridine-2-carboxylate (100 mg, 365.78 μmol) in MeCN (0.5 mL) and H$_2$O (0.5 mL) was added NaOH (21.95 mg, 548.67 μmol) at 0° C., the mixture was warmed to room temperature and stirred for 2 h. The reaction mixture was adjusted to pH 5 by addition aq. 10% citric acid (~10 mL) and was then extracted with EtOAc (3×20 mL). The combined organic layers were washed with brine (2×5 mL), dried over Na$_2$SO$_4$, filtered and concentrated under reduced pressure to afford the desired product (92.6 mg, crude). LCMS (ESI) m/z: [M+H] calcd for C$_{11}$H$_{19}$NO$_3$S: 246.11; found 246.3.

Intermediate A-77. Synthesis of (2R,3R)-1-((R)-tert-butylsulfinyl)-3-cyclobutylaziridine-2-carboxylic Acid

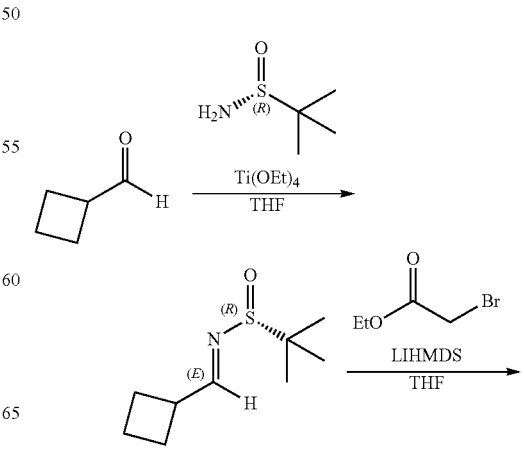

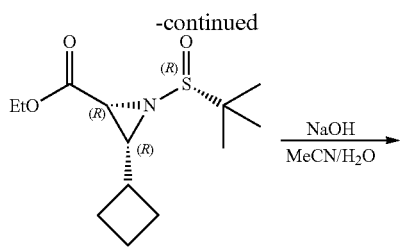

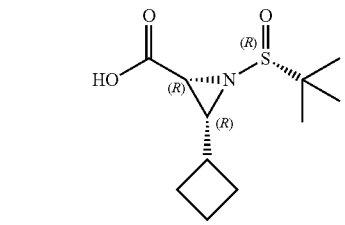

Step 1: Synthesis of (R,E)-N-(cyclobutylmethylene)-2-methylpropane-2-sulfinamide To a solution of cyclobutanecarbaldehyde (0.25 g, 2.97 mmol) in THF (5 mL) was added (R)-2-methylpropane-2-sulfinamide (396.24 mg, 3.27 mmol) and Ti(OEt)$_4$ (1.36 g, 5.94 mmol, 1.23 mL). The mixture was stirred at 75° C. for 3 h in two batches. The two batches were combined and the reaction mixture was quenched by the addition of brine (15 mL). The solution was extracted with EtOAc (3×20 mL) and the combined organic layers were washed with brine (2×5 mL), dried over Na$_2$SO$_4$, filtered and concentrated under reduced pressure to give a residue, which was purified by silica gel chromatography (10%→20% EtOAc/pet. ether) to afford the desired product (786.7 mg, 70.7% yield). LCMS (ESI) m/z: [M+H] calcd for C$_9$H$_{17}$NOS: 188.1; found 188.3.

Step 2: Synthesis of ethyl (2R,3R)-1-((R)-tert-butylsulfinyl)-3-cyclobutylaziridine-2-carboxylate To a solution of ethyl 2-bromoacetate (236.19 µL, 2.14 mmol) in THF (2 mL) was added LiHMDS (1 M, 2.14 mL) at −78° C., after 30 min, (R,E)-N-(cyclobutylmethylene)-2-methylpropane-2-sulfinamide (0.2 g, 1.07 mmol) was added. The mixture was warmed to −40° C. and stirred for 4 h. The reaction mixture was quenched by addition H$_2$O (18 mL) at −40° C. and warmed to room temperature The mixture was extracted with EtOAc (3×15 mL) and the combined organic layers were washed with brine (2×5 mL), dried over Na$_2$SO$_4$, filtered and concentrated under reduced pressure to give a residue, which was purified by prep-TLC (20% EtOAc/pet. ether) to afford the desired product (0.1 g, crude). LCMS (ESI) m/z: [M+H] calcd for C$_{13}$H$_{23}$NO$_3$S: 274.14; found 274.3.

Step 3: Synthesis of (2R,3R)-1-((R)-tert-butylsulfinyl)-3-cyclobutylaziridine-2-carboxylic Acid In two batches, to a solution ethyl (2R,3R)-1-((R)-tert-butylsulfinyl)-3-cyclobutylaziridine-2-carboxylate (25 mg, 91.44 µmol) in MeCN (0.25 mL) and H$_2$O (0.25 mL) was added NaOH (5.49 mg, 137.17 µmol) at 0° C., the mixture was warmed to room temperature and stirred for 5 h. The reaction mixtures were combined, and adjust to pH to 5 with aq. 10% citric acid (10 mL), then extracted with EtOAc (3×20 mL). The combined organic layers were washed with brine (2×5 mL), dried over Na$_2$SO$_4$, filtered and concentrated under reduced pressure to afford the desired product (53 mg, crude). LCMS (ESI) m/z: [M+H] calcd for C$_{11}$H$_{19}$NO$_3$S: 246.11; found 246.2.

Intermediate A-78. Synthesis of N-methyl-N-(methyl((S)-1-((R)-1-tritylaziridine-2-carbonyl)piperidin-3-yl)carbamoyl)-L-valine

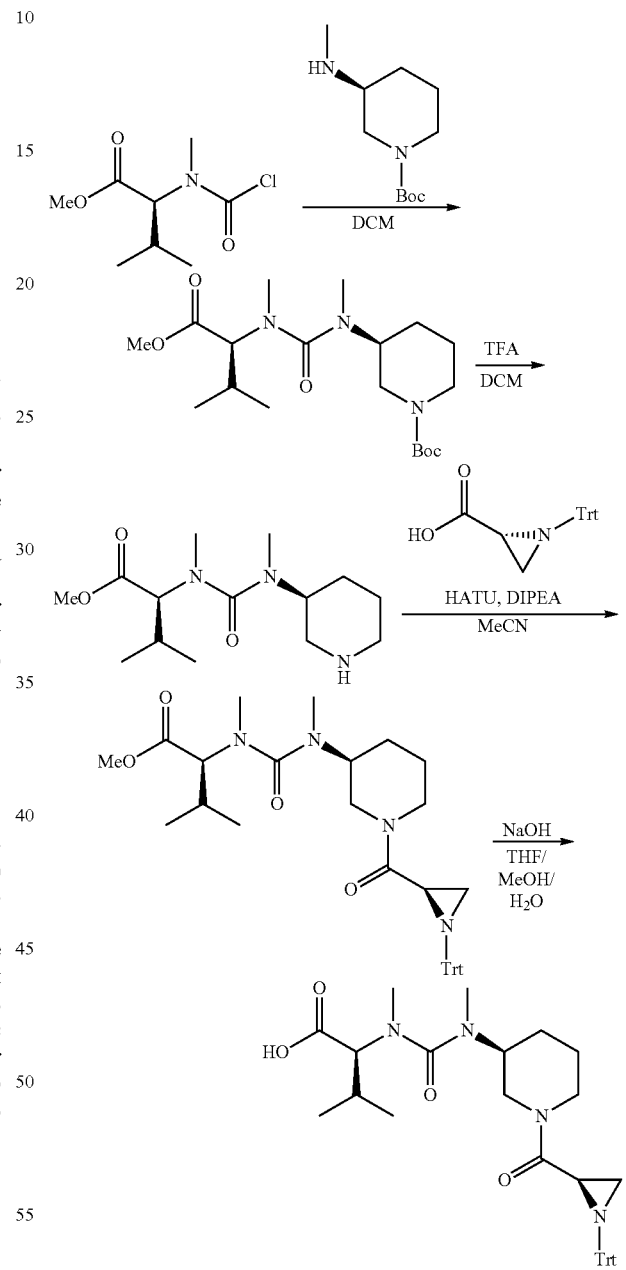

Step 1: Synthesis of tert-butyl (S)-3-(3-((S)-1-methoxy-3-methyl-1-oxobutan-2-yl)-1,3-dimethylureido)piperidine-1-carboxylate A mixture of methyl N-(chlorocarbonyl)-N-methyl-L-valinate (1.94 g, 9.34 mmol) in DCM was added to a solution of (S)-tert-butyl 3-(methylamino)piperidine-1-carboxylate (2.80 g, 13.08 mmol) in DCM (18 mL) at 0° C. The mixture was stirred at 40° C. for 3 h. The mixture was added to saturated aq. NH₄Cl (80 mL), and the aqueous phase was extracted with DCM (3×40 mL). the combined organic phase was washed with brine (50 mL), dried over Na₂SO₄, filtered and concentrated under reduced pressure. The crude product was purified by silica gel chromatography (30%→100% EtOAc/pet. ether) to afford the desired product (1.9 g, 55.3% yield). LCMS (ESI) m/z: [M+H] calculated for C₁₉H₃₅N₃O₅: 386.26; found 386.2.

Step 2: Synthesis of methyl N-methyl-N-(methyl ((S)-piperidin-3-yl)carbamoyl)-L-valinate To a solution of give tert-butyl (S)-3-(3-((S)-1-methoxy-3-methyl-1-oxobutan-2-yl)-1,3-dimethylureido)piperidine-1-carboxylate (1 g, 2.59 mmol) in DCM (10 mL) was added TFA (3.84 mL, 51.88 mmol) at 0° C. The reaction was stirred at room temperature for 1 h. The mixture was added into saturated aq. Na₂CO₃ (100 mL) at 0° C. to adjust to pH 9. The aqueous phase was extracted with DCM (3×50 mL) and the combined organic phases were washed with brine (10 mL), dried with Na₂SO₄, filtered and concentrated under reduced pressure to afford the desired product (710 mg, crude). LCMS (ESI) m/z: [M+H] calculated for C₁₄H₂₇N₃O₃: 286.21; found 286.1.

Step 3: Synthesis of methyl N-methyl-N-(methyl ((S)-1-((R)-1-tritylaziridine-2-carbonyl)piperidin-3-yl)carbamoyl)-L-valinate To a solution of (R)-1-tritylaziridine-2-carboxylic acid (1.24 g, 2.63 mmol, 70% purity) in MeCN (5 mL) at 0° C. was added DIPEA (1.22 mL, 7.01 mmol) and HATU (1.33 g, 3.50 mmol) followed by methyl N-methyl-N-(methyl((S)-piperidin-3-yl)carbamoyl)-L-valinate (500 mg, 1.75 mmol). The reaction mixture was warmed to room temperature and stirred 30 min. The mixture was added to saturated aq. NH₄Cl (100 mL) and the aqueous phase was extracted with DCM (3×50 mL). The combined organic phase was washed with brine (60 mL), dried over Na₂SO₄, filtered and concentrated under reduced pressure. The residue was purified by silica gel chromatography (50%→100% EtOAc/pet. ether) to afford the desired product (650 mg, 49.7% yield). LCMS (ESI) m/z: [M+H] calculated for C₃₆H₄₄N₄O₄: 597.34; found 597.3.

Step 4: Synthesis of N-methyl-N-(methyl((S)-1-((R)-1-tritylaziridine-2-carbonyl)piperidin-3-yl)carbamoyl)-L-valine NaOH (58.34 mg, 1.46 mmol) was added to a solution of methyl N-methyl-N-(methyl((S)-1-((R)-1-tritylaziridine-2-carbonyl)piperidin-3-yl)carbamoyl)-L-valinate (640 mg, 857.97 μmol) in THF (4 mL), MeOH (1.3 mL), and H₂O (1.3 mL). The mixture was stirred at room temperature for 20 h. The reaction solution was directly lyophilized to afford the desired product (700 mg, crude). LCMS (ESI) m/z: [M+H] calculated for C₃₅H₄₂N₄O₄: 583.32; found 583.4.

Intermediate A-79. Synthesis of N-methyl-N-(methyl((S)-1-((R)-1-tritylaziridine-2-carbonyl)pyrrolidin-3-yl)carbamoyl)-L-valine

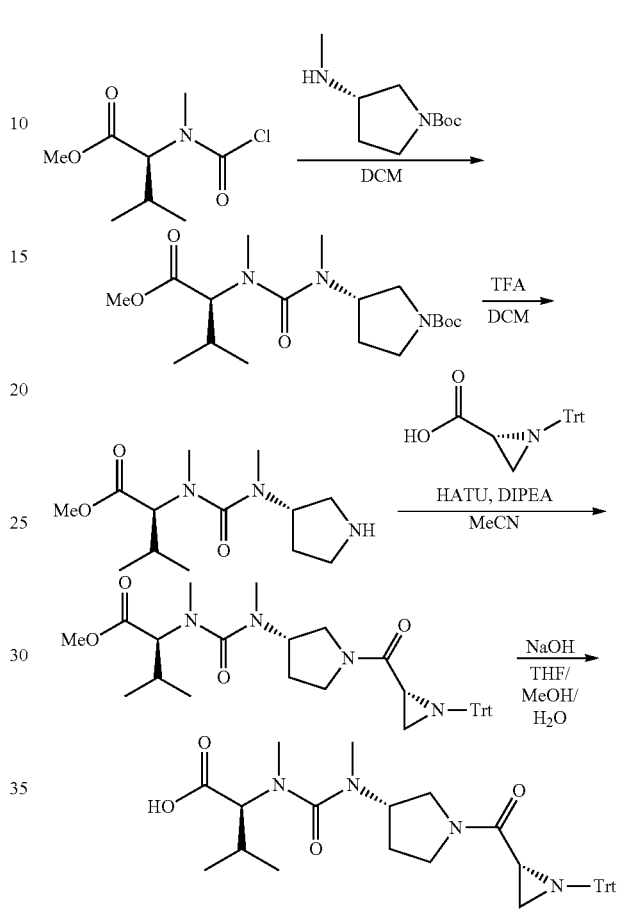

Step 1: Synthesis of tert-butyl (S)-3-(3-((S)-1-methoxy-3-methyl-1-oxobutan-2-yl)-1,3-dimethylureido)pyrrolidine-1-carboxylate A solution of methyl N-(chlorocarbonyl)-N-methyl-L-valinate (1.14 g, 5.49 mmol) in DCM (10 mL) was added to a solution of tert-butyl (S)-3-(methylamino)pyrrolidine-1-carboxylate (1.54 g, 7.69 mmol) in DCM (10 mL) at 0° C. The mixture was warmed to room temperature and stirred for 2 h. The mixture was then added to sat. NH₄Cl (50 mL), and the aqueous phase was extracted with DCM (3×30 mL). The combined organic phase was washed with brine (30 mL), dried over Na₂SO₄, filtered and concentrated under reduced pressure. The crude product was purified by silica gel chromatography (30%→100% EtOAc/pet. ether) to afford the desired product (1.07 g, 52.5% yield).

Step 2: Synthesis of methyl N-methyl-N-(methyl ((S)-pyrrolidin-3-yl)carbamoyl)-L-valinate To a solution of tert-butyl (S)-3-(3-((S)-1-methoxy-3-methyl-1-oxobutan-2-yl)-1,3-dimethylureido)pyrrolidine-1-carboxylate (1.05 g, 2.83 mmol) in DCM (11 mL) at 0° C. was added TFA (4.19 mL, 56.53 mmol). The reaction was then warmed to room temperature and stirred for 1 h. The mixture was added to sat. Na₂CO₃ (200 mL) at 0° C. dropwise to adjust to pH 9. The aqueous phase was extracted with DCM (3×100 mL), and the combined organic phase was washed with brine (100 mL), dried with Na₂SO₄, filtered and concentrated under reduced pressure to afford the desired product (800 mg, crude).

Step 3: Synthesis of methyl N-methyl-N-(methyl ((S)-1-((R)-1-tritylaziridine-2-carbonyl)pyrrolidin-3-yl)carbamoyl)-L-valinate To a solution of (R)-1-tritylaziridine-2-carboxylic acid (1.04 g, 2.21 mmol) in MeCN (4 mL) at 0° C. was added HATU (1.12 g, 2.95 mmol), and DIPEA (1.03 mL, 5.90 mmol) followed by methyl N-methyl-N-(methyl((S)-pyrrolidin-3-yl)carbamoyl)-L-valinate (400 mg, 1.47 mmol). The mixture was warmed to room temperature and stirred for 0.5 h. The mixture was poured into NH₄Cl aq. (50 mL) and extracted with DCM (3×20 mL). The combined organic phases were washed with brine (30 mL), dried with Na₂SO₄, filtered and concentrated under reduced pressure. The crude product was purified by silica gel chromatography (50%→100% EtOAc/pet. ether) to afford the desired product (580 mg, 67.5% yield).

Step 4: Synthesis of N-methyl-N-(methyl((S)-1-((R)-1-tritylaziridine-2-carbonyl)pyrrolidin-3-yl) carbamoyl)-L-valine To a solution of methyl N-methyl-N-(methyl((S)-1-((R)-1-tritylaziridine-2-carbonyl)pyrrolidin-3-yl)carbamoyl)-L-valinate (650 mg, 1.12 mmol) in THF (3.9 mL) and MeOH (1.3 mL) was added a solution of NaOH (89.23 mg, 2.23 mmol) in H₂O (1.3 mL). The mixture was stirred at room temperature for 16 h. The reaction mixture was diluted with H₂O (10 mL) and then lyophilized directly to afford the desired product (700 mg, crude). LCMS (ESI) m/z: [M+H] calcd for $C_{34}H_{40}N_4O_4$: 569.30; found, 569.4.

Intermediate A-80. Synthesis of N-methyl-N—((S)-3-methyl-4-((R)-1-tritylaziridine-2-carbonyl)piperazine-1-carbonyl)-L-valine

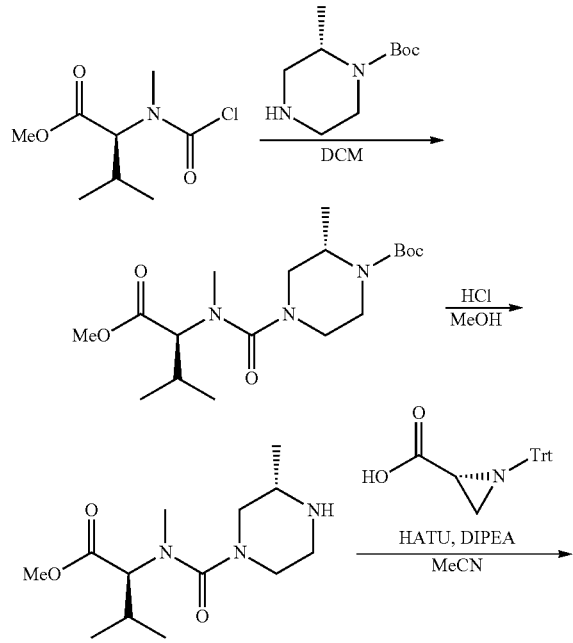

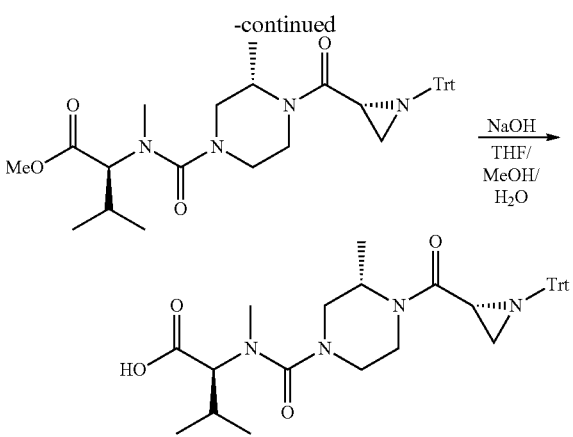

Step 1: Synthesis of tert-butyl (S)-4-(((S)-1-methoxy-3-methyl-1-oxobutan-2-yl)(methyl)carbamoyl)-2-methylpiperazine-1-carboxylate To a solution of methyl tert-butyl (S)-2-methylpiperazine-1-carboxylate (3.31 g, 16.52 mmol) in DCM (30 mL) at 0° C. was added a solution of methyl N-(chlorocarbonyl)-N-methyl-L-valinate in DCM (0.55 M, 30 mL). The mixture was stirred at room temperature for 30 min. The reaction mixture was diluted with H₂O (30 mL) and extracted with DCM (3×20 mL). The combined organic layers were washed with brine (2×15 mL), dried over Na₂SO₄, filtered and concentrated under reduced pressure to give a residue. The residue was purified by silica gel chromatography (20%-50% EtOAc/pet. ether) to afford the desired product (5 g, 81.5% yield). LCMS (ESI) m/z: [M+H] calcd for $C_{18}H_{33}N_3O_5$:372.2; found 372.1.

Step 2: Synthesis of methyl N-methyl-N—((S)-3-methylpiperazine-1-carbonyl)-L-valinate To tert-butyl (S)-4-(((S)-1-methoxy-3-methyl-1-oxobutan-2-yl)(methyl)carbamoyl)-2-methylpiperazine-1-carboxylate (3 g, 8.08 mmol) was added a solution of 4M HCl in MeOH (30 mL). The mixture was stirred at room temperature for 1 h. The reaction mixture was adjusted to pH 8 with saturated aq. NaHCO₃, and was then diluted with H₂O (50 mL) and extracted with DCM (3×30 mL). The combined organic layers were washed with brine (50 mL), dried over Na₂SO₄, filtered and concentrated under reduced pressure to afford the desired product (1.8 g, 82.1% yield).

Step 3: Synthesis of methyl N-methyl-N—((S)-3-methyl-4-((R)-1-tritylaziridine-2-carbonyl)piperazine-1-carbonyl)-L-valinate To a solution of (2R)-1-tritylaziridine-2-carboxylic acid (971.10 mg, 2.95 mmol) in MeCN (10 mL) was added HATU (1.35 g, 3.54 mmol), DIPEA (1.54 mL, 8.84 mmol) and methyl N-methyl-N—((S)-3-methylpiperazine-1-carbonyl)-L-valinate (0.8 g, 2.95 mmol). The mixture was stirred at room temperature for 12 h. The reaction mixture was then diluted with H₂O (20 mL) and extracted with DCM (3×15 mL). The combined organic layers were washed with brine 20 mL (2×10 mL), dried over Na₂SO₄, filtered and concentrated under reduced pressure to give a residue. The residue was purified by silica gel chromatography (30%→50% EtOAc/pet. ether) to afford the desired product (0.35 g, 20.4% yield). LCMS (ESI) m/z: [M+H] calculated for $C_{35}H_{42}N_4O_4$: 583.3; found 583.2.

Step 4: Synthesis of N-methyl-N—((S)-3-methyl-4-((R)-1-tritylaziridine-2-carbonyl)piperazine-1-carbonyl)-L-valine To a solution of methyl N-methyl-N—((S)-3-methyl-4-((R)-1-tritylaziridine-2-carbonyl)piperazine-1-carbonyl)-L-valinate (200 mg, 343.21 μmol) in $H_2O$ (1 mL), THF (1 mL), and MeOH (1 mL) at 0° C. was added LiOH.$H_2O$ (14.40 mg, 343.21 μmol). The mixture was stirred at room temperature for 8 h and was then lyophilized directly to afford the desired product (390 mg, 98.7% yield). LCMS (ESI) m/z: [M+Na] calculated for $C_{34}H_{40}N_4O_4$: 591.3; found 591.2.

Intermediate A-81. Synthesis of N-methyl-N—((S)-3-methyl-4-((S)-1-tritylaziridine-2-carbonyl)piperazine-1-carbonyl)-L-valine

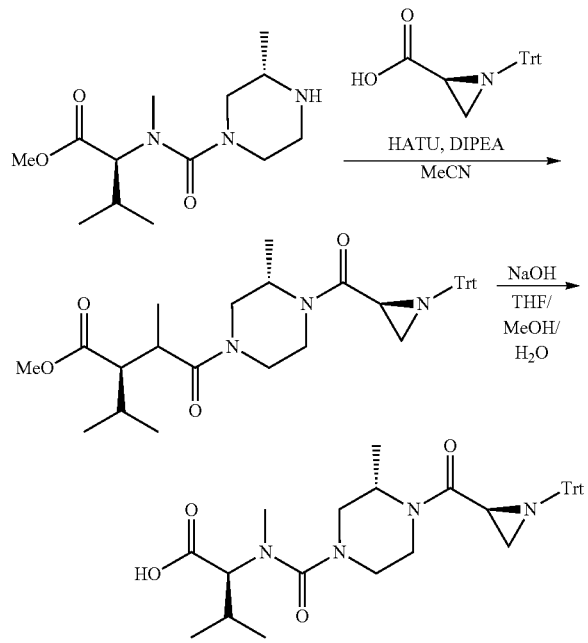

Step 1: Synthesis of methyl N-methyl-N—((S)-3-methyl-4-((S)-1-tritylaziridine-2-carbonyl)piperazine-1-carbonyl)-L-valinate To a solution of methyl N-methyl-N—((S)-3-methylpiperazine-1-carbonyl)-L-valinate (500 mg, 1.84 mmol) in MeCN (5 mL) at 0° C. was added (S)-1-tritylaziridine-2-carboxylic acid (1.30 g, 2.76 mmol, 70% purity), HATU (1.05 g, 2.76 mmol) and DIPEA (962.85 μL, 5.53 mmol). The mixture was stirred at room temperature for 30 min. The reaction mixture was then diluted with $H_2O$ (10 mL) and extracted with DCM (3×5 mL). The combined organic layers were washed with brine (2×5 mL), dried over $Na_2SO_4$, filtered and concentrated under reduced pressure to give a residue. The residue was purified by silica gel chromatography (20%→33% EtOAc/pet. ether) to afford the desired product (0.5 g, 46.6% yield). LCMS (ESI) m/z: [M+Na] calculated for $C_{35}H_{42}O_4N_4$: 605.2; found 605.2.

Step 2: Synthesis of N-methyl-N—((S)-3-methyl-4-((S)-1-tritylaziridine-2-carbonyl)piperazine-1-carbonyl)-L-valine To a solution of methyl N-methyl-N—((S)-3-methyl-4-((S)-1-tritylaziridine-2-carbonyl)piperazine-1-carbonyl)-L-valinate (400 mg, 686.42 μmol) in $H_2O$ (2 mL), THF (2 mL), and MeOH (2 mL) at 0° C. was added LiOH.$H_2O$ (28.80 mg, 686.42 μmol). The mixture was stirred at room temperature for 8 h. The mixture was lyophilized directly to afford then desired product (390 mg, 98.7% yield). LCMS (ESI) m/z: [M+Na] calculated for $C_{34}H_{40}N_4O_4$: 591.3; found 591.2.

Intermediate A-82. Synthesis of N-methyl-N—((R)-3-methyl-4-((R)-1-tritylaziridine-2-carbonyl)piperazine-1-carbonyl)-L-valine

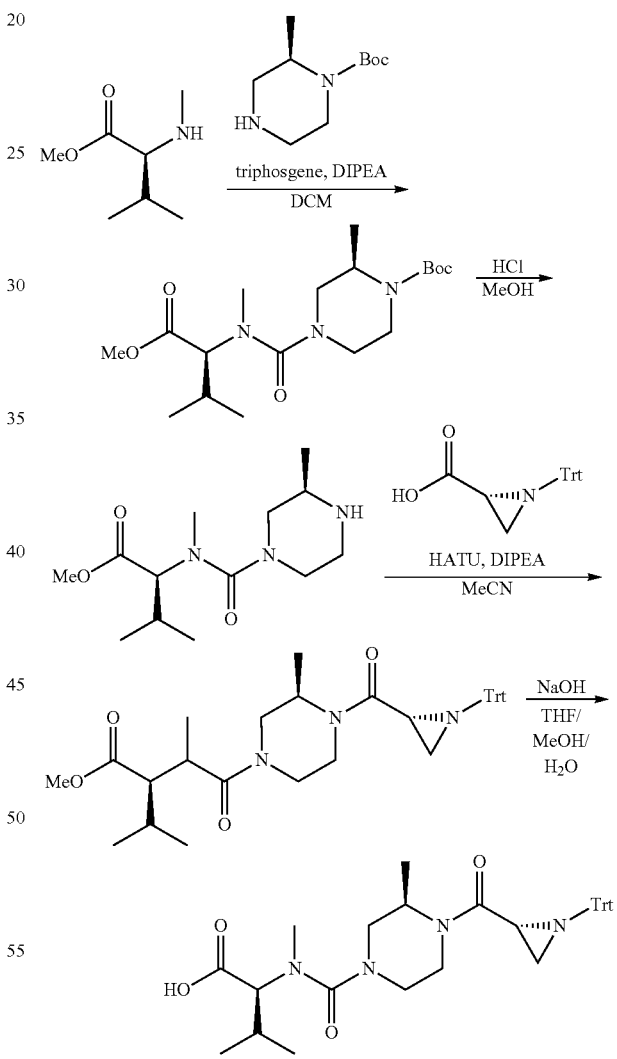

Step 1: Synthesis of tert-butyl (R)-4-(((S)-1-methoxy-3-methyl-1-oxobutan-2-yl)(methyl)carbamoyl)-2-methylpiperazine-1-carboxylate To a mixture of methyl methyl-L-valinate hydrochloride (3 g, 16.51 mmol) and DIPEA (17.26 mL, 99.09 mmol) in DCM (60 mL) at 0° C. was added bis(trichloromethyl)carbonate (2.45 g, 8.26 mmol) in one portion. The mixture was stirred at 0° C. for 30 min, then tert-butyl (R)-2-methylpiperazine-1-carboxylate (3.31 g, 16.51 mmol) was added to the mixture. The mixture was stirred at 0° C. for 1 h, then the pH of the solution was adjusted to 8 with sat. NaHCO₃. The residue was poured into H₂O (20 mL) and stirred for 5 min. The aqueous phase was extracted with EtOAc (2×20 mL), and the combined organic phase was washed with sat. NaHCO₃ (20 mL), dried with Na₂SO₄, filtered and concentrated under reduced pressure. The residue was purified by silica gel chromatography (1%→10% EtOAc/pet. ether) to afford the desired product (3.1 g, 50.5% yield). LCMS (ESI) m/z: [M+H] calculated for $C_{18}H_{33}N_3O_5$: 372.3; found 372.2.

Step 2: Synthesis of methyl N-methyl-N—((R)-3-methylpiperazine-1-carbonyl)-L-valinate To a mixture of tert-butyl (R)-4-(((S)-1-methoxy-3-methyl-1-oxobutan-2-yl)(methyl)carbamoyl)-2-methylpiperazine-1-carboxylate (2.5 g, 6.73 mmol) was added 4M HCl in MeOH (25 mL) at 0° C. The mixture was stirred at room temperature for 1 h. The mixture was then concentrated under reduced pressure to afford the desired product (2 g, 96.5% yield).

Step 3: Synthesis of methyl N-methyl-N—((R)-3-methyl-4-((R)-1-tritylaziridine-2-carbonyl)piperazine-1-carbonyl)-L-valinate To a mixture of (R)-1-tritylaziridine-2-carboxylic acid (1.03 g, 3.12 mmol) and HATU (1.11 g, 2.92 mmol) in MeCN (1 mL) was added DIPEA (1.36 mL, 7.80 mmol) followed by methyl N-methyl-N—((R)-3-methylpiperazine-1-carbonyl)-L-valinate (600 mg, 1.95 mmol). The mixture was stirred at room temperature for 1 h. The mixture was then concentrated under reduced pressure. The residue was purified by silica gel chromatography (1%→50% EtOAc/pet. ether) to afford the desired product (450 mg, 39.62% yield). LCMS (ESI) m/z: [M+H] calculated for $C_{35}H_{42}N_4O_4$: 583.3; found 583.2.

Step 4: Synthesis of N-methyl-N—((R)-3-methyl-4-((R)-1-tritylaziridine-2-carbonyl)piperazine-1-carbonyl)-L-valine To a mixture of methyl N-methyl-N—((R)-3-methyl-4-((R)-1-tritylaziridine-2-carbonyl)piperazine-1-carbonyl)-L-valinate (450 mg, 772.23 µmol) in H₂O (1 mL), MeOH (1 mL), and THF (3 mL) was added LiOH.H₂O (48.60 mg, 1.16 mmol). The mixture was stirred at room temperature for 10 h and was then lyophilized to afford the desired product (410 mg, 92.4% yield). LCMS (ESI) m/z: [M+Na] calculated for $C_{34}H_{40}N_4O_4$: 591.3; found 591.3.

Intermediate A-83. Synthesis of N-methyl-N—((R)-3-methyl-4-((S)-1-tritylaziridine-2-carbonyl)piperazine-1-carbonyl)-L-valine

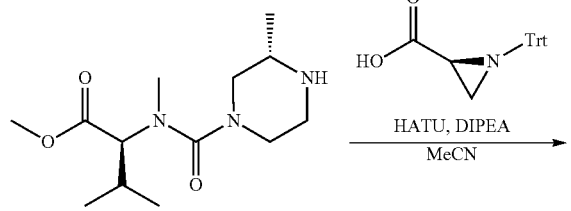

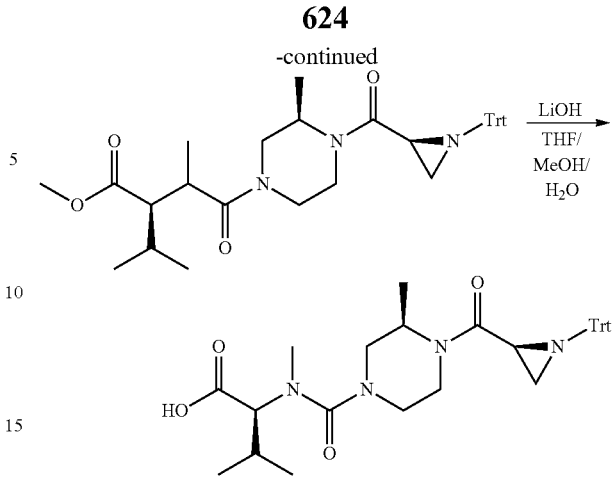

Step 1: Synthesis of methyl N-methyl-N—((R)-3-methyl-4-((S)-1-tritylaziridine-2-carbonyl)piperazine-1-carbonyl)-L-valinate To a mixture of (S)-1-tritylaziridine-2-carboxylic acid (1.03 g, 3.12 mmol) and HATU (1.11 g, 2.92 mmol) in MeCN (1 mL) was added DIPEA (1.36 mL, 7.80 mmol) followed by methyl N-methyl-N—((R)-3-methylpiperazine-1-carbonyl)-L-valinate (600 mg, 1.95 mmol). The mixture was stirred at room temperature for 1 h and was then concentrated under reduced pressure. The residue was purified by silica gel chromatography (0%→50% EtOAc/pet. ether) to afford the desired product (430 mg, 37.8% yield). LCMS (ESI) m/z: [M+H] calculated for $C_{35}H_{42}N_4O_4$: 583.3; found 583.2.

Step 2: Synthesis of N-methyl-N—((R)-3-methyl-4-((S)-1-tritylaziridine-2-carbonyl)piperazine-1-carbonyl)-L-valine To a mixture of methyl N-methyl-N—((R)-3-methyl-4-((S)-1-tritylaziridine-2-carbonyl)piperazine-1-carbonyl)-L-valinate (430 mg, 737.91 µmol) in H₂O (1 mL), MeOH (1 mL), and THF (3 mL) was added LiOH.H₂O (46.44 mg, 1.11 mmol). The mixture was stirred at room temperature for 10 h and was then lyophilized to afford the desired product (370 mg, 87.3% yield). LCMS (ESI) m/z: [M+Na] calculated for $C_{34}H_{40}N_4O_4$: 591.3; found 591.3.

Intermediate A-84. Synthesis of N—((R)-4-(tert-butoxycarbonyl)-2-methylpiperazine-1-carbonyl)-N-methyl-L-valine

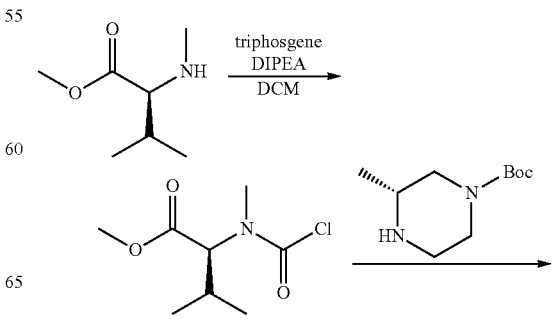

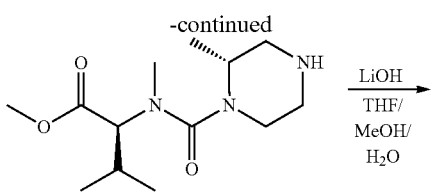

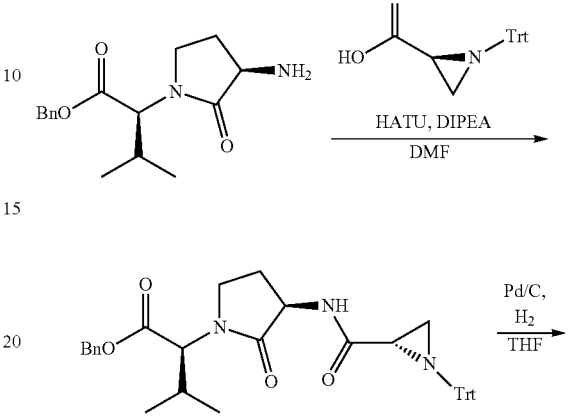

Intermediate A-85. Synthesis of (S)-3-methyl-2-((R)-2-oxo-3-((S)-1-tritylaziridine-2-carboxamido)pyrrolidin-1-yl)butanoic Acid

Step 1: Synthesis of methyl N-(chlorocarbonyl)-N-methyl-L-valinate

To a solution of methyl methyl-L-valinate hydrochloride (1.8 g, 9.91 mmol) in DCM (20 mL) at 0° C. was added DIPEA (5.18 mL, 29.73 mmol) followed by bis(trichloromethyl) carbonate (1.47 g, 4.95 mmol). The mixture was stirred at 0° C. for 20 min. The reaction mixture used for the next step directly without workup.

Step 2: Synthesis of tert-butyl (R)-4-(((S)-1-methoxy-3-methyl-1-oxobutan-2-yl)(methyl)carbamoyl)-3-methylpiperazine-1-carboxylate A solution of methyl N-(chlorocarbonyl)-N-methyl-L-valinate (1.03 g, 4.96 mmol) in DCM (10 mL) was added to a solution of tert-butyl (3R)-3-methylpiperazine-1-carboxylate (993.41 mg, 4.96 mmol) in DCM (1 mL) at 0° C. The mixture was then stirred at 0° C. for 15 min. The mixture was added to aq. NH$_4$Cl (10 mL) and the solution was then extracted with DCM (3×10 mL). The combined organic phase was washed with brine (2 mL), dried over Na$_2$SO$_4$, filtered and concentrated under reduced pressure. The residue was purified by silica gel chromatography (0%→50% EtOAc/pet. ether) to afford the desired product (750 mg, 36.2% yield).

Step 3: Synthesis of N—((R)-4-(tert-butoxycarbonyl)-2-methylpiperazine-1-carbonyl)-N-methyl-L-valine To a solution of tert-butyl (R)-4-(((S)-1-methoxy-3-methyl-1-oxobutan-2-yl)(methyl)carbamoyl)-3-methylpiperazine-1-carboxylate (700 mg, 1.88 mmol) in THF (0.5 mL) and H$_2$O (0.5 mL) at 0° C. was added LiOH.H$_2$O (237.23 mg, 5.65 mmol). The mixture was stirred at room temperature for 3 h. The pH of the reaction mixture was adjusted to 6-7 with 1 N HCl. The mixture was extracted with EtOAc (3×10 mL), dried over Na$_2$SO$_4$, and concentrated under reduced pressure to afford the desired product (600 mg, 85.5% yield).

Step 1: Synthesis of benzyl (S)-3-methyl-2-((R)-2-oxo-3-((S)-1-tritylaziridine-2-carboxamido)pyrrolidin-1-yl)butanoate To a mixture of benzyl (2S)-2-[(3R)-3-amino-2-oxopyrrolidin-1-yl]-3-methylbutanoate (420.0 mg, 1.446 mmol), DIPEA (934.73 mg, 7.232 mmol) and (2S)-1-(triphenylmethyl)aziridine-2-carboxylic acid (619.40 mg, 1.880 mmol) in DMF (5 mL) at 0° C. was added HATU (659.99 mg, 1.736 mmol). The resulting mixture was stirred at room temperature for 2 h. The reaction mixture was quenched with H$_2$O. The resulting mixture was extracted with EtOAc (2×10 mL), and the combined organic layers were washed with brine (10 mL), dried over Na$_2$SO$_4$, filtered, and concentrated under reduced pressure. The residue was purified by silica gel column chromatography (30% EtOAc/pet. ether) to afford the desired product (480 mg, 55.2% yield). LCMS (ESI) m/z: [M−H] calcd for C$_{38}$H$_{38}$N$_3$O$_4$: 600.29; found 600.3.

Step 2: Synthesis of (S)-3-methyl-2-((R)-2-oxo-3-((S)-1-tritylaziridine-2-carboxamido)pyrrolidin-1-yl) butanoic Acid A suspension of benzyl (2S)-3-methyl-2-[(3R)-2-oxo-3-[(2S)-1-(triphenylmethyl)aziridine-2-amido]pyrrolidin-1-yl]butanoate (450.0 mg, 0.748 mmol) and Pd/C (200 mg) in THF (5 mL) at room temperature was stirred for 3 h under a hydrogen atmosphere. The mixture was then filtered and concentrated under reduced pressure to afford the desired product (400 mg, crude). LCMS (ESI) m/z: [M−H] calcd for C$_{31}$H$_{32}$N$_3$O$_4$: 510.24; found 510.2.

Intermediate A-86. Synthesis of (S)-2-(8-(tert-butoxycarbonyl)-1-oxo-2,8-diazaspiro[4.5]decan-2-yl)-3-methylbutanoic Acid

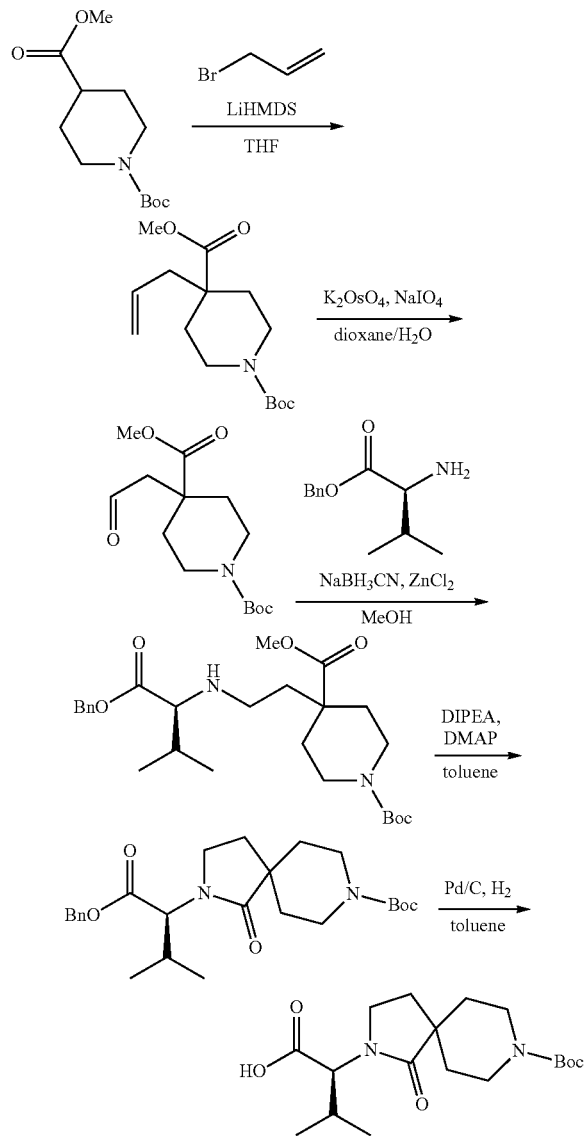

Step 1: Synthesis of 1-(tert-butyl) 4-methyl 4-allylpiperidine-1,4-dicarboxylate To a solution of 1-tert-butyl 4-methyl piperidine-1,4-dicarboxylate (5.0 g, 20.551 mmol) in THF (50 mL) at −78° C. was added LiHMDS (27 mL, 26.714 mmol, 1M in THF) followed by allyl bromide (3.23 g, 26.716 mmol). The resulting mixture was stirred overnight at room temperature. The reaction was quenched with sat. aq. NH$_4$Cl (aq.) and the combined organic layers were washed with brine (3×100 mL), dried over Na$_2$SO$_4$, filtered and concentrated under reduced pressure. The residue was purified by silica gel column chromatography (50% EtOAc/pet. ether) to afford the desired product (4.5 g, 73.4% yield).

Step 2: Synthesis of 1-(tert-butyl) 4-methyl 4-(2-oxoethyl)piperidine-1,4-dicarboxylate To a solution of 1-tert-butyl 4-methyl 4-(prop-2-en-1-yl) piperidine-1,4-dicarboxylate (1.0 g, 3.529 mmol) and K$_2$OsO$_4$·2H$_2$O (1.3 g, 3.529 mmol) in 1,4-dioxane (5 mL) and H$_2$O (5 mL) at 0° C. was added NaIO$_4$ (1.51 g, 7.058 mmol). The resulting mixture was stirred at room temperature for 5 h. The mixture was extracted with EtOAc (3×50 mL) and the combined organic layers were washed with H$_2$O (3×100 mL), dried over Na$_2$SO$_4$, filtered, and concentrated under reduced pressure. The crude product was used in the next step directly without further purification to afford the desired product (800 mg, 75.% yield). LCMS (ESI) m/z: [M−H] calcd for C$_{14}$H$_{23}$NO$_5$: 284.16; found 284.0.

Step 3: Synthesis of 1-(tert-butyl) 4-methyl (S)-4-(2-((1-(benzyloxy)-3-methyl-1-oxobutan-2-yl)amino)ethyl)piperidine-1,4-dicarboxylate To a solution of 1-tert-butyl 4-methyl 4-(2-oxoethyl) piperidine-1,4-dicarboxylate (4.0 g, 14.018 mmol) and benzyl (2S)-2-amino-3-methylbutanoate (3.49 g, 16.822 mmol) in MeOH (40 mL) at 0° C. was added ZnCl$_2$ (2.10 g, 15.420 mmol) and NaBH$_3$CN (1.76 g, 28.037 mmol). The resulting mixture was stirred at room temperature for 2 h. The reaction was quenched with sat. aq. NH$_4$Cl and the combined organic layers were washed with brine (3×100 mL), dried over Na$_2$SO$_4$, filtered, and concentrated under reduced pressure. The residue was purified by silica gel column chromatography (50% EtOAc/pet. ether) to afford the desired product. LCMS (ESI) m/z: [M+H] calcd for C$_{26}$H$_{40}$N$_2$O$_6$: 477.29; found 477.3.

Step 4: Synthesis of tert-butyl (S)-2-(1-(benzyloxy)-3-methyl-1-oxobutan-2-yl)-1-oxo-2,8-diazaspiro[4.5]decane-8-carboxylate To a solution of 1-tert-butyl 4-methyl 4-(prop-2-en-1-yl) piperidine-1,4-dicarboxylate (2.20 g, 4.616 mmol) and DIPEA (5.97 g, 46.159 mmol) in toluene was added DMAP (0.56 g, 4.616 mmol) in portions at 120° C. The resulting mixture was stirred overnight at 120° C. The reaction was cooled to room temperature and quenched with sat. aq. NH$_4$Cl. The combined organic layers were washed with brine (3×100 mL), dried over Na$_2$SO$_4$, filtered, and concentrated under reduced pressure. The residue was purified by Prep-TLC (50% EtOAc/pet. ether) to afford the desired product (1.5 g, 50.2% yield). LCMS (ESI) m/z: [M+H] calcd for C$_{25}$H$_{36}$N$_2$O$_5$: 445.26; found 445.3.

Step 5: Synthesis of (S)-2-(8-(tert-butoxycarbonyl)-1-oxo-2,8-diazaspiro[4.5]decan-2-yl)-3-methylbutanoic Acid To a solution of tert-butyl 2-[(2S)-1-(benzyloxy)-3-methyl-1-oxobutan-2-yl]-1-oxo-2,8-diazaspiro[4.5]decane-8-carboxylate (2.40 g, 5.398 mmol) in toluene (25 mL) at room temperature was added Pd/C (2.40 g, 22.552 mmol). The resulting suspension was stirred overnight at room temperature under an H$_2$ atmosphere. The mixture was concentrated under reduced pressure, filtered, the filter cake washed with EtOAc (3×50 mL), and the filtrate was concentrated under reduced pressure. The residue was purified by silica gel column chromatography (50% EtOAc/pet.

ether) to afford the desired product (2. 2 g, 72.5% yield). LCMS (ESI) m/z: [M−H] calcd for $C_{18}H_{30}N_2O_5$: 353.22; found 353.2.

Intermediate A-87. Synthesis of N-methyl-N-(3-oxo-4-((S)-1-tritylaziridine-2-carbonyl)piperazine-1-carbonyl)-L-valine

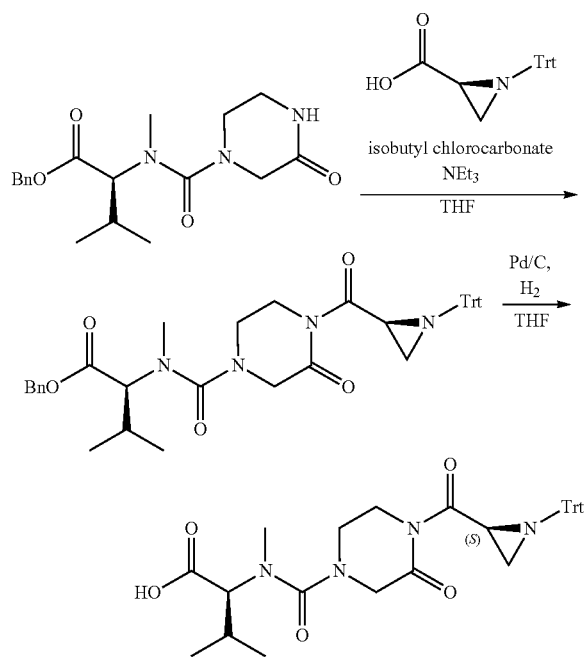

Step 1: Synthesis of benzyl N-methyl-N-(3-oxo-4-((S)-1-tritylaziridine-2-carbonyl)piperazine-1-carbonyl)-L-valinate To a solution of (2S)-1-(triphenylmethyl)aziridine-2-carboxylic acid (2.13 g, 6.466 mmol) in THF (10 mL) at 0° C. was added $Et_3N$ (0.87 g, 8.598 mmol) and isobutyl chlorocarbonate (1.44 g, 10.54 mmol). The resulting mixture was stirred at room temperature for 1 h, and then benzyl (2S)-3-methyl-2-[methyl(3-oxopiperazine-1-carbonyl)amino]butanoate (1.50 g, 4.318 mmol) was added. The resulting mixture was stirred overnight at 70° C. The reaction mixture was then concentrated under reduced pressure. The residue was purified by Prep-TLC (50% EtOAc/pet. ether) to afford the desired product (900 mg, 31.6% yield). LCMS (ESI) m/z: [M−H] calcd for $C_{40}H_{42}N_4O_5$: 657.32; found 657.1.

Step 2: Synthesis of N-methyl-N-(3-oxo-4-((S)-1-tritylaziridine-2-carbonyl)piperazine-1-carbonyl)-L-valine A solution of benzyl N-methyl-N-(3-oxo-4-((S)-1-tritylaziridine-2-carbonyl)piperazine-1-carbonyl)-L-valinate (500 mg) and Pd/C (50 mg) in THF (5 mL) was stirred for 2 h at room temperature under a hydrogen atmosphere. The resulting mixture was filtered, the filter cake was washed with MeOH (3×30 mL), and the filtrate was concentrated under reduced pressure to afford the desired product (460 mg, crude). LCMS (ESI) m/z: [M−H] calcd for $C_{33}H_{36}N_4O_5$: 567.27; found 567.1.

Intermediate A-88. Synthesis of lithium (R)-1-(3-methoxypropyl)aziridine-2-carboxylate

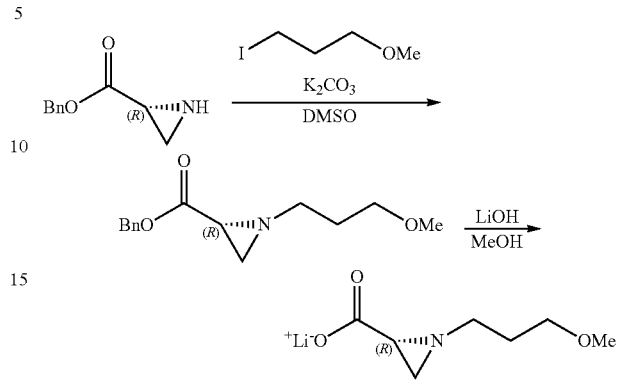

Step 1: Synthesis of benzyl (R)-1-(3-methoxypropyl)aziridine-2-carboxylate

To a mixture of benzyl (R)-aziridine-2-carboxylate (350.0 mg, 1.975 mmol) and $K_2CO_3$ (545.95 mg, 3.950 mmol) in DMSO (4 mL) at 60° C. was added 1-iodo-3-methoxypropane (790.13 mg, 3.950 mmol). The resulting mixture was stirred for 2 h and was then cooled to room temperature, diluted with brine (50 mL), and extracted with EtOAc (3×20 mL). The combined organic layers were concentrated under reduced pressure. The crude product was purified by reverse phase chromatography (30%→38% $MeCN/H_2O$) to afford the desired product (170 mg, 31.1% yield). LCMS (ESI) m/z: [M+H] calcd for $C_{14}H_{19}NO_3$: 250.14; found 250.2.

Step 2: Synthesis of lithium (R)-1-(3-methoxypropyl)aziridine-2-carboxylate A mixture of benzyl (R)-1-(3-methoxypropyl)aziridine-2-carboxylate (170 mg, 0.682 mmol) and LiOH (57.23 mg, 1.364 mmol) in MeOH (2 mL) was stirred at 0° C. for 1 h. The mixture was concentrated under reduced pressure to afford the desired product (200 mg, crude). LCMS (ESI) m/z: [M+H] calcd for $C_7H_{13}NO_3$: 160.09; found 160.3.

Intermediate A-89. Synthesis of lithium (S)-1-(3-methoxypropyl)aziridine-2-carboxylate

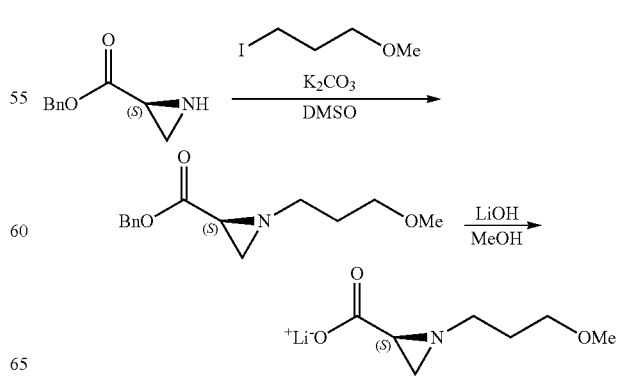

Step 1: Synthesis of benzyl (S)-1-(3-methoxypropyl)aziridine-2-carboxylate

To a mixture of benzyl (S)-aziridine-2-carboxylate (250 mg, 1.411 mmol) and K$_2$CO$_3$ (389.96 mg, 2.822 mmol) in DMSO (4 mL) at 60° C. was added 1-iodo-3-methoxypropane (564.38 mg, 2.822 mmol). The resulting mixture was stirred for 2 h and was then cooled to room temperature, diluted with brine (50 mL), and extracted with EtOAc (3×20 mL). The combined organic layers were concentrated under reduced pressure. The crude product was purified by reverse phase chromatography (25%→40% H$_2$O/MeCN) to afford the desired product (234 mg, 63.2% yield). LCMS (ESI) m/z: [M+H] calcd for C$_{14}$H$_{19}$NO$_3$: 250.14; found 250.2.

Step 2: Synthesis of lithium (S)-1-(3-methoxypropyl)aziridine-2-carboxylate

A mixture of benzyl (S)-1-(3-methoxypropyl) aziridine-2-carboxylate (230 mg, 0.923 mmol) and LiOH.H$_2$O (77.43 mg, 1.845 mmol) in MeOH (3 mL) was stirred for 1 h at 0° C. The resulting mixture was concentrated under reduced pressure to afford the desired product (320 mg, crude). LCMS (ESI) m/z: [M+H] calcd for C$_7$H$_{13}$NO$_3$: 160.09; found 160.1.

Intermediate A-90. Synthesis of tert-butyl (S)-2-((S)-1-(benzyloxy)-3-methyl-1-oxobutan-2-yl)-1-oxo-2,7-diazaspiro[4.5]decane-7-carboxylate and tert-butyl (R)-2-((S)-1-(benzyloxy)-3-methyl-1-oxobutan-2-yl)-1-oxo-2,7-diazaspiro[4.5]decane-7-carboxylate

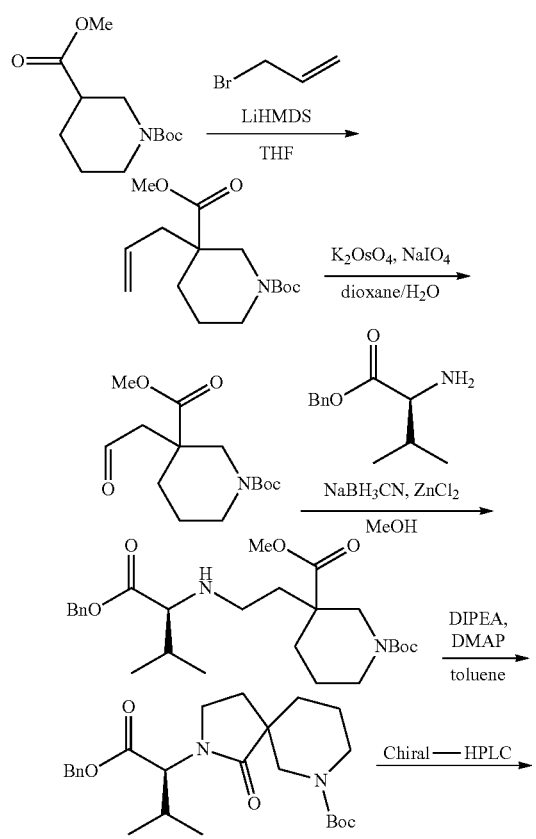

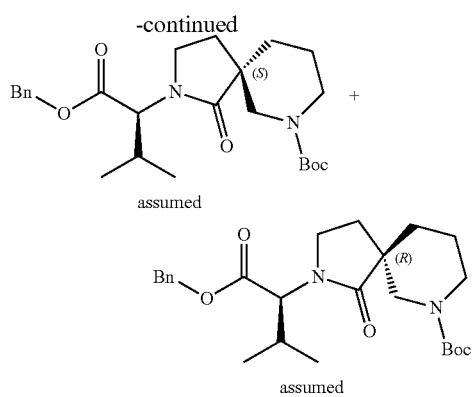

Step 1: Synthesis of 1-(tert-butyl) 3-methyl 3-allylpiperidine-1,3-dicarboxylate To a solution of 1-tert-butyl 3-methyl piperidine-1,3-dicarboxylate (10.0 g, 41.101 mmol) and LiHMDS (82 mL, 82.202 mmol, 1M in THF) in THF (100 mL) at −78° C. was added allyl bromide (9.94 g, 82.202 mmol). The reaction was warmed to room temperature and stirred overnight. The solution was then quenched with sat. aq. NH$_4$Cl and diluted with EtOAc (500 mL). The organic layer was washed with brine (3×150 mL), dried over Na$_2$SO$_4$, filtered and concentrated under reduced pressure. The residue was purified by silica gel column chromatography to afford the desired product (9.9 g, 85% yield). LCMS (ESI) m/z: [M+H] calcd for C$_{15}$H$_{25}$NO$_4$: 284.18; found 284.0.

Step 2: Synthesis of 1-(tert-butyl) 3-methyl 3-(2-oxoethyl)piperidine-1,3-dicarboxylate To a solution of 1-(tert-butyl) 3-methyl 3-allylpiperidine-1,3-dicarboxylate1-(tert-butyl) 3-methyl 3-allylpiperidine-1,3-dicarboxylate (9.1 g, 32.114 mmol) and 2,6-lutidine (6.88 g, 64.227 mmol) in dioxane (180 mL) and H$_2$O (180 mL) at 0° C. was added K$_2$OsO$_4$.2H$_2$O (591.61 mg, 1.606 mmol). The resulting mixture was stirred for 15 min at room temperature and was then cooled to at 0° C. and NaIO$_4$ (27.47 g, 128.455 mmol) was added in portions. The resulting mixture was stirred for 3 h at room temperature. And thee reaction was then quenched with sat. aq. Na$_2$S$_2$O$_3$ at 0° C. The resulting mixture was extracted with EtOAc (2×500 mL), and thee combined organic layers were washed with 1M HCl (2×200 mL), brine (2×200 mL), dried over Na$_2$SO$_4$, filtered, and concentrated under reduced pressure to afford the desired product (7.5 g, 81.9% yield). LCMS (ESI) m/z: [M+H] calcd for C$_{14}$H$_{23}$NO$_5$: 286.16; found 286.1.

Step 3: Synthesis of 1-(tert-butyl) 3-methyl 3-(2-(((R)-1-(benzyloxy)-3-methyl-1-oxobutan-2-yl)amino)ethyl)piperidine-1,3-dicarboxylate To a solution of 1-(tert-butyl) 3-methyl 3-(2-oxoethyl) piperidine-1,3-dicarboxylate (9.0 g, 31.541 mmol) and benzyl (2S)-2-amino-3-methylbutanoate (7.19 g, 34.695 mmol) in MeOH (90 mL) at 0° C. was added ZnCl$_2$ (4.73 g, 34.695 mmol) and NaBH$_3$CN (3.96 g, 63.083 mmol). The resulting mixture was stirred overnight at room temperature. Desired product could be detected by LCMS, and it was concentrated under reduced pressure and extracted with EtOAc (1200 mL). The organic layer was washed with brine (3×150 mL), dried over Na$_2$SO$_4$, filtered, and concentrated under reduced pressure. Purification by reverse phase chromatography afforded the desired product (9.9 g, 65.9% yield). LCMS (ESI) m/z: [M+H] calcd for C$_{26}$H$_{40}$N$_2$O$_6$: 477.29; found 477.2.

Step 4: Synthesis of tert-butyl (S)-2-((S)-1-(benzyloxy)-3-methyl-1-oxobutan-2-yl)-1-oxo-2,7-diazaspiro[4.5]decane-7-carboxylate and tert-butyl (R)-2-((S)-1-(benzyloxy)-3-methyl-1-oxobutan-2-yl)-1-oxo-2,7-diazaspiro[4.5]decane-7-carboxylate To a solution of 1-(tert-butyl) 3-methyl 3-(2-(((R)-1-(benzyloxy)-3-methyl-1-oxobutan-2-yl)amino)ethyl)piperidine-1,3-dicarboxylate (9.9 g, 20.772 mmol) and DIPEA (26.84 g, 207.715 mmol) in toluene (100 mL) was added DMAP (5.07 g, 41.543 mmol). The resulting mixture was stirred at 80° C. for 50 h. The resulting mixture was concentrated under reduced pressure and the residue was taken up in EtOAc (1000 mL). The organic layer was washed with brine (3×150 mL), dried over Na$_2$SO$_4$, filtered, and concentrated under reduced pressure. The crude product was purified by CHIRAL-HPLC (50% EtOH/Hex) to afford tert-butyl (S)-2-((S)-1-(benzyloxy)-3-methyl-1-oxobutan-2-yl)-1-oxo-2,7-diazaspiro[4.5]decane-7-carboxylate (1.75 g) and tert-butyl (R)-2-((S)-1-(benzyloxy)-3-methyl-1-oxobutan-2-yl)-1-oxo-2,7-diazaspiro[4.5]decane-7-carboxylate (1.98 g). LCMS (ESI) m/z: [M+H] calcd for C$_{25}$H$_{36}$N$_2$O$_5$: 445.26; found 445.2.

Intermediates A-91 and A-92. Synthesis of (S)-2-((S)-7-(tert-butoxycarbonyl)-4-oxo-1-oxa-3,7-diazaspiro[4.4]nonan-3-yl)-3-methylbutanoic acid and (S)-2-((R)-7-(tert-butoxycarbonyl)-4-oxo-1-oxa-3,7-diazaspiro[4.4]nonan-3-yl)-3-methylbutanoic Acid Step 1: Synthesis of tert-butyl 3-hydroxy-3-(((S)-1-methoxy-3-methyl-1-oxobutan-2-yl)carbamoyl)pyrrolidine-1-carboxylate To a solution of 1-(tert-butoxycarbonyl)-3-hydroxypyrrolidine-3-carboxylic acid (800 mg, 3.46 mmol) and DIPEA (3.01 mL, 17.3 mmol) in DMF (10 mL) at 0° C. was added methyl L-valinate (681 mg, 5.19 mmol) and HATU (1.71 g, 4.497 mmol). The resulting mixture was warmed to room temperature and stirred for 2 h then diluted with H$_2$O (20 mL) and extracted into EtOAc (3×20 mL). The combined organic layers were washed with brine (2×20 mL), dried over Na$_2$SO$_4$, filtered, and concentrated under reduced pressure. Purification by reverse phase chromatography (30→55% MeCN/H$_2$O, 0.1% NH$_4$HCO$_3$) afforded the desired product (1 g, 76% yield). LCMS (ESI) m/z: [M+Na] calcd for C$_{16}$H$_{28}$N$_2$O$_6$: 367.18; found 366.9.

Step 2: Synthesis of (S)-2-((S)-7-(tert-butoxycarbonyl)-4-oxo-1-oxa-3,7-diazaspiro[4.4]nonan-3-yl)-3-methylbutanoic acid and (S)-2-((R)-7-(tert-butoxycarbonyl)-4-oxo-1-oxa-3,7-diazaspiro[4.4]nonan-3-yl)-3-methylbutanoic Acid To a solution of tert-butyl 3-hydroxy-3-(((S)-1-methoxy-3-methyl-1-oxobutan-2-yl)carbamoyl)pyrrolidine-1-carboxylate (1.0 g, 2.90 mmol) and Cs$_2$CO$_3$ (1.89 g, 5.81 mmol) in MeCN (15 mL) at 0° C. was added paraformaldehyde (436 mg, 14.5 mmol). The resulting mixture was heated to 80° C. and stirred overnight. Purification by reverse phase chromatography (10-40% MeCN/H$_2$O, 0.1% NH$_4$HCO$_3$) afforded a mixture of the desired products. The diastereomers were separated by prep-SFC (30% EtOH/hexanes, 0.3% TFA) to afford (S)-2-((S)-7-(tert-butoxycarbonyl)-4-oxo-1-oxa-3,7-diazaspiro[4.4]nonan-3-yl)-3-methylbutanoic acid (250 mg, 24% yield) and (S)-2-((R)-7-(tert-butoxycarbonyl)-4-oxo-1-oxa-3,7-diazaspiro[4.4]nonan-3-yl)-3-methylbutanoic acid (200 mg, 19% yield). LCMS (ESI) m/z: [M+Na] calcd for C$_{16}$H$_{26}$N$_2$O$_6$: 365.17; found 365.0.

Intermediate A-93. Synthesis of (S)-1-((3-methyloxetan-3-yl)methyl)aziridine-2-carboxylic Acid

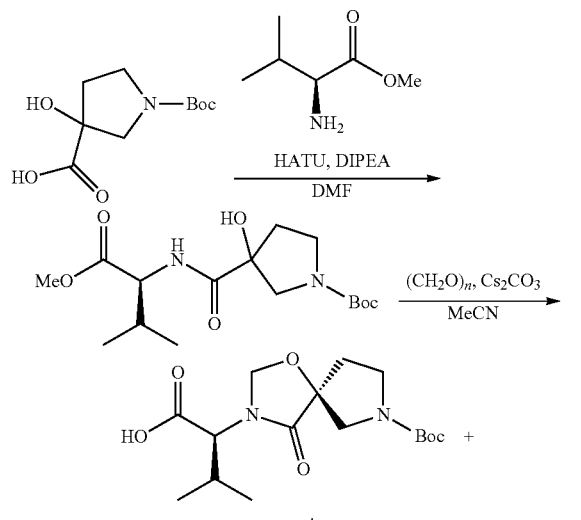

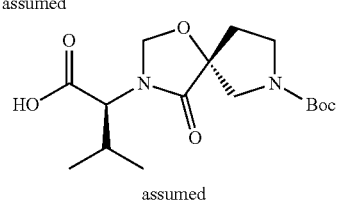

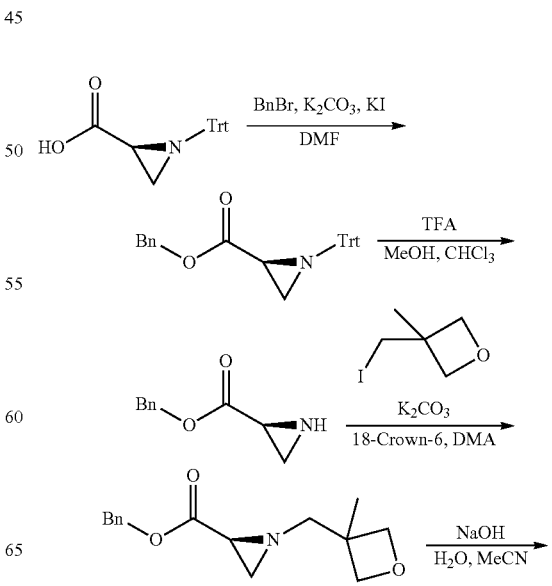

-continued

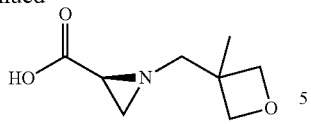

Step 1: Synthesis of benzyl (S)-1-tritylaziridine-2-carboxylate

To a mixture of (S)-1-tritylaziridine-2-carboxylic acid (3.0 g, 9.11 mmol) and benzyl bromide (2.16 mL, 18.22 mmol) in DMF (30 mL) was added $K_2CO_3$ (2.25 g, 18.22 mmol) and KI (76 mg, 455 µmol). The reaction mixture was heated to 50° C. and stirred for 30 min then was cooled to room temperature and diluted with $H_2O$ (30 mL) and EtOAc (30 mL). The aqueous layer was extracted with EtOAc (3×40 mL), and the combined organic layers were washed with brine (5×70 mL), dried over $Na_2SO_4$, filtered, and concentrated under reduced pressure to afford the desired product (4.7 g, crude).

Step 2: Synthesis of benzyl (S)-aziridine-2-carboxylate

To a mixture of benzyl (S)-1-tritylaziridine-2-carboxylate (3.4 g, 8.10 mmol) in MeOH (17.5 mL) and $CHCl_3$ (17.5 mL) at 0° C. was added TFA (9.0 mL, 122 mmol). The reaction mixture was stirred for 30 min then was poured into sat. aq. $NaHCO_3$ (50 mL), extracted into DCM (4×35 mL), dried over $Na_2SO_4$, filtered, and concentrated under reduced pressure. Purification by silica gel column chromatography (6→100% EtOAc/pet. ether) afforded the desired product (445 mg, 31% yield).

Step 3: Synthesis of benzyl (S)-1-((3-methyloxetan-3-yl)methyl)aziridine-2-carboxylate To a mixture of benzyl (S)-aziridine-2-carboxylate (440 mg, 2.48 mmol) and 3-(iodomethyl)-3-methyloxetane (2.11 g, 9.93 mmol) in DMA (5 mL) was added $K_2CO_3$ (1.72 g, 12.42 mmol) and 18-crown-6 (32.8 mg, 124 µmol). The reaction mixture was heated to 80° C. and stirred for 12 h, and was then diluted with $H_2O$ (25 mL) and EtOAc (25 mL). The aqueous layer was extracted with EtOAc (3×20 mL), and the combined organic layers were washed with brine (5×45 mL), dried over $Na_2SO_4$, filtered, and concentrated under reduced pressure. Purification by prep-TLC (50% EtOAc/pet. ether) afforded the desired product (367 mg, 57% yield). LCMS (ESI) m/z: [M+H] calcd for $C_{15}H_{19}NO_3$: 262.14; found 262.0.

Step 4: Synthesis of (S)-1-((3-methyloxetan-3-yl)methyl)aziridine-2-carboxylic Acid To a mixture of benzyl (S)-1-((3-methyloxetan-3-yl)methyl)aziridine-2-carboxylate (100 mg, 383 µmol) in MeCN (500 µL) and $H_2O$ (500 µL) at 0° C. was added NaOH (23 mg, 574 µmol). The reaction mixture was stirred at 0° C. for 1 h then was concentrated under reduced pressure to afford the desired product (100 mg, crude). LCMS (ESI) m/z: [M+H] calcd for $C_8H_{13}NO_3$: 172.10; found 172.0.

Intermediate A-94. Synthesis of (2R,3R)-1-(tert-butylsulfinyl)-3-ethylaziridine-2-carboxylic Acid

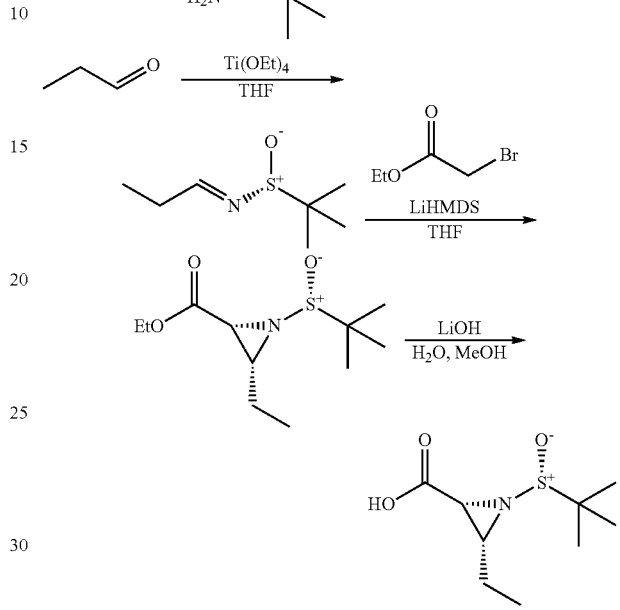

Step 1: Synthesis of (R,E)-2-methyl-N-propylidenepropane-2-sulfinamide

To a solution of propionaldehyde (6.27 mL, 86.1 mmol) in THF (200 mL) was added (R)-2-methylpropane-2-sulfinamide (10.4 g, 86.1 mmol) and titanium ethoxide (51 mL, 170 mmol). The reaction mixture was heated to 70° C. for 3 h then cooled to room temperature and quenched with $H_2O$ (50 mL), filtered, and extracted into EtOAc (3×30 mL). The combined organic layers were washed with brine (30 mL), dried over $Na_2SO_4$, filtered, and concentrated under reduced pressure. Purification by silica gel column chromatography (9→17% EtOAc/pet. ether) afforded the desired product (4.0 g, 29% yield).

Step 2: Synthesis of ethyl (2R,3R)-1-(tert-butylsulfinyl)-3-ethylaziridine-2-carboxylate To a solution of ethyl 2-bromoacetate (2.74 mL, 24.8 mmol) in THF (40 mL) at −78° C. was added LiHMDS (24.80 mL, 1 M in THF). After 30 min (R,E)-2-methyl-N-propylidenepropane-2-sulfinamide (2.0 g, 12.4 mmol) in THF (20 mL) was added to the reaction mixture. The mixture was stirred for 1 h then warmed to room temperature, quenched with $H_2O$ (50 mL), and extracted into EtOAc (3×50 mL). The combined organic layers were washed with brine (2×50 mL), dried over $Na_2SO_4$, filtered, and concentrated under reduced pressure. Purification by silica gel column chromatography (17→25% EtOAc/pet. ether) afforded product (1.34 g, 44% yield). LCMS (ESI) m/z: [M+H] calcd for $C_{11}H_{21}NO_3S$: 248.13; found 248.1.

Step 3: Synthesis of (2R,3R)-1-(tert-butylsulfinyl)-3-ethylaziridine-2-carboxylic Acid To a solution of ethyl (2R,3R)-1-(tert-butylsulfinyl)-3-ethylaziridine-2-carboxylate (600 mg, 2.4 mmol) in MeOH (3 mL) and H$_2$O (3 mL) was added LiOH (70 mg, 2.9 mmol). The resulting mixture was stirred for 16 h then diluted with H$_2$O (20 mL) and washed with DCM (3×10 mL). Lyophilization of the aqueous layer afforded product (600 mg, crude). LCMS (ESI) m/z: [M+H] calcd for C$_9$H$_{17}$NO$_3$S: 220.10; found 220.3.

Intermediate A-95. Synthesis of (2S,3S)-1-(tert-butylsulfinyl)-3-ethylaziridine-2-carboxylic Acid

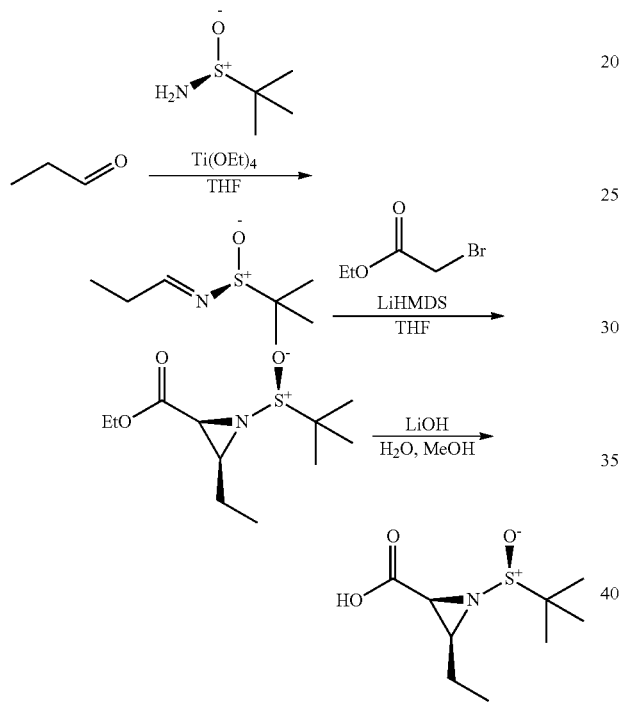

Step 1: Synthesis of (S,E)-2-methyl-N-propylidenepropane-2-sulfinamide

To a solution of propionaldehyde (6.27 mL, 86.1 mmol) in THF (50 mL) was added (S)-2-methylpropane-2-sulfinamide (10.4 g, 86.1 mmol) and titanium ethoxide (51 mL, 170 mmol). The reaction mixture was heated to 70° C. for 3 h then cooled to room temperature and quenched with H$_2$O (30 mL), filtered, and extracted into DCM (3×100 mL). The combined organic layers were washed with brine (10 mL), dried over Na$_2$SO$_4$, filtered, and concentrated under reduced pressure. Purification by silica gel column chromatography (25% EtOAc/pet. ether) afforded product (4.6 g, 33% yield).

Step 2: Synthesis of ethyl (2S,3S)-1-(tert-butylsulfinyl)-3-ethylaziridine-2-carboxylate To a solution of ethyl 2-bromoacetate (2.74 mL, 24.8 mmol) in THF (40 mL) at −78° C. was added LiHMDS (24.80 mL, 1M in THF). After 30 min (S,E)-2-methyl-N-propylidenepropane-2-sulfinamide (2.0 g, 12.4 mmol) in THF (20 mL) was added to the reaction mixture. The mixture was stirred for 1 h then warmed to room temperature, quenched with H$_2$O (20 mL), and extracted into EtOAc (3×20 mL). The combined organic layers were washed with brine (2×25 mL), dried over Na$_2$SO$_4$, filtered, and concentrated under reduced pressure. Purification by reverse phase chromatography (31→51% MeCN/H$_2$O, 10 mM NH$_4$HCO$_3$) afforded product (600 mg, 20% yield). LCMS (ESI) m/z: [M+H] calcd for C$_{11}$H$_{21}$NO$_3$S: 248.13; found 248.1.

Step 3: Synthesis of (2S,3S)-1-(tert-butylsulfinyl)-3-ethylaziridine-2-carboxylic Acid To a solution of ethyl (2S,3S)-1-(tert-butylsulfinyl)-3-ethylaziridine-2-carboxylate (600 mg, 2.4 mmol) in MeOH (300 µL) and H$_2$O (300 µL) was added LiOH (87 mg, 3.6 mmol). The resulting mixture was stirred for 12 h then diluted with H$_2$O (20 mL) and washed with DCM (3×10 mL). Lyophilization of the aqueous layer afforded product (600 mg, crude). LCMS (ESI) m/z: [M+H] calcd for C$_9$H$_{17}$NO$_3$S: 220.10; found 220.2.

Intermediate A-96. Synthesis of (2R,3R)-3-isopropyl-1-tritylaziridine-2-carboxylic Acid

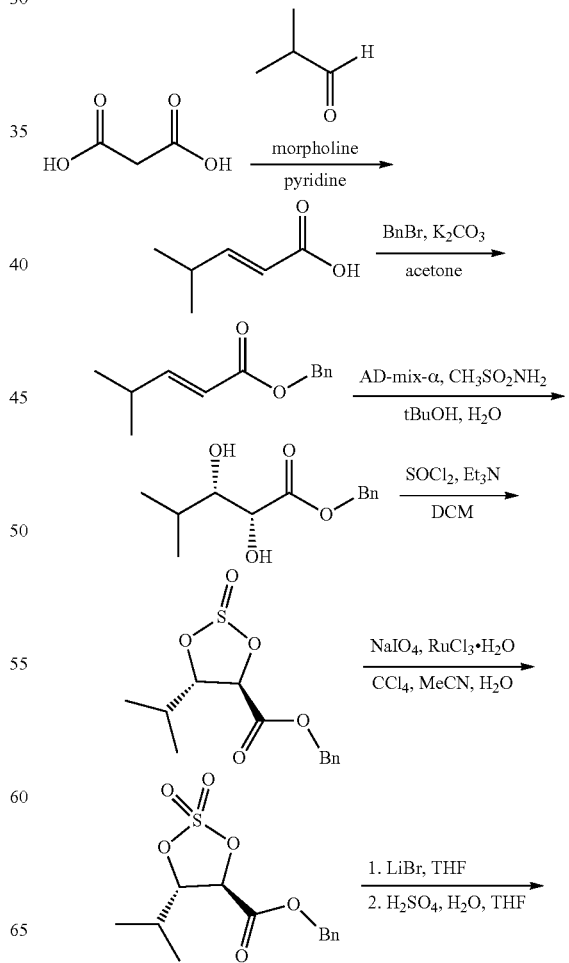

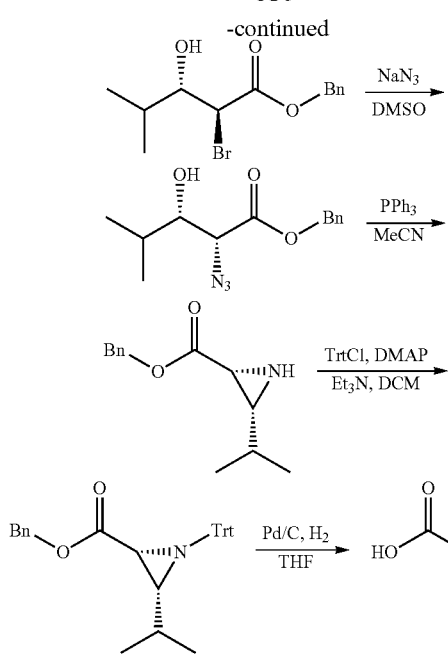

Step 1: Synthesis of (E)-4-methylpent-2-enoic Acid

Two batches of a solution of malonic acid (25.0 mL, 240 mmol), isobutyraldehyde (34.7 mL, 380 mmol) and morpholine (380 µL, 4.32 mmol) in pyridine (75 mL) were stirred for 24 h then were heated to 115° C. and stirred for 12 h. The combined reaction mixtures were poured into $H_2SO_4$ (1M, 800 mL) and extracted into EtOAc (3×300 mL). The combined organic layers were washed with brine (300 mL), dried over $Na_2SO_4$, filtered, and concentrated under reduced pressure. The residue was dissolved in NaOH (1 M, 500 mL), washed with EtOAc (2×200 mL), acidified to pH=4-2 with HCl (4M), and extracted into EtOAc (3×300 mL). The combined organic layers were washed with brine (300 mL), dried over $Na_2SO_4$, filtered, and concentrated under reduced pressure which afforded product (54 g, 98% yield).

Step 2: Synthesis of benzyl (E)-4-methylpent-2-enoate

To two batches of a solution of (E)-4-methylpent-2-enoic acid (6.25 mL, 52.6 mmol) in acetone (90 mL) was added $K_2CO_3$ (13.8 g, 100 mmol) and the mixtures were stirred for 30 min. Then a solution of benzyl bromide (6.31 mL, 53.1 mmol) in acetone (10 mL) was added and the mixtures were heated to 75° C. for 5 h. The reaction mixtures were cooled to room temperature and concentrated under reduced pressure. The residue was dissolved in EtOAc (200 mL) and $H_2O$ (200 mL) then extracted into EtOAc (2×200 mL). The combined organic layers were washed with brine (300 mL), dried over $Na_2SO_4$, filtered, and concentrated under reduced pressure. Purification by silica gel chromatography (0-10% EtOAc/pet. ether) afforded product (9.0 g, 42% yield).

Step 3: Synthesis of benzyl (2R,3S)-2,3-dihydroxy-4-methylpentanoate

To a solution of AD-mix-α (61.7 g) and methanesulfonamide (4.19 g, 44.1 mmol) in tert-BuOH (225 mL) and $H_2O$ (225 mL) was added benzyl (E)-4-methylpent-2-enoate (9 g, 44.1 mmol). The mixture was stirred at room temperature for 12 h then $Na_2SO_3$ (67.5 g) was added and stirred for 30 min. The reaction mixture was diluted with EtOAc (300 mL) and $H_2O$ (300 mL) and extracted into EtOAc (3×300 mL), washed with brine (300 mL), dried over $Na_2SO_4$, filtered, and concentrated under reduced pressure. Purification by silica gel chromatography (0-25% EtOAc/pet. ether) afforded product (8.3 g, 79% yield). LCMS (ESI) m/z: [M+Na] calcd for $C_{13}H_{18}O_4$: 261.11; found 261.0.

Step 4: Synthesis of benzyl (4R,5S)-5-isopropyl-1,3,2-dioxathiolane-4-carboxylate 2-oxide To a solution of benzyl (2R,3S)-2,3-dihydroxy-4-methylpentanoate (10 g, 42.0 mmol) in DCM (100 mL) at 0° C. was added $Et_3N$ (17.5 mL, 126 mmol) and $SOCl_2$ (4.26 mL, 58.8 mmol). The reaction mixture was stirred 30 min then was diluted with DCM (30 mL) and $H_2O$ (100 mL), extracted into DCM (3×50 mL), washed with brine (100 mL), dried over $Na_2SO_4$, filtered, and concentrated under reduced pressure which afforded product (11.0 g, 92% yield).

Step 5: Synthesis of benzyl (4R,5S)-5-isopropyl-1,3,2-dioxathiolane-4-carboxylate 2,2-dioxide To a solution of benzyl (4R,5S)-5-isopropyl-1,3,2-dioxathiolane-4-carboxylate 2-oxide (11 g, 38.7 mmol) in $H_2O$ (250 mL), MeCN (125 mL), and $CCl_4$ (125 mL) was added $NaIO_4$ (3.22 mL, 58.0 mmol) and $RuCl_3 \cdot H_2O$ (872 mg, 3.87 mmol). The mixture was stirred at room temperature for 1 h then was diluted with EtOAc (200 mL) and $H_2O$ (50 mL), filtered, and the filtrate was extracted into EtOAc (3×200 mL). The combined organic layers were washed sequentially with brine (200 mL) and sat. aq. $Na_2CO_3$ (300 mL), dried over $Na_2SO_4$, filtered, and concentrated under reduced pressure. Purification by silica gel chromatography (0→17% EtOAc/pet. ether) afforded product (11 g, 95% yield).

Step 6: Synthesis of benzyl (2S,3S)-2-bromo-3-hydroxy-4-methylpentanoate

To a solution of benzyl (4R,5S)-5-isopropyl-1,3,2-dioxathiolane-4-carboxylate 2,2-dioxide (11 g, 36.6 mmol) in THF (520 mL) was added LiBr (3.49 mL, 139 mmol). The reaction mixture was stirred at room temperature for 5 h and then concentrated under reduced pressure. The residue was diluted in THF (130 mL) and $H_2O$ (65 mL), cooled to 0° C., then $H_2SO_4$ solution (20% aq., 1.3 L) was added and the mixture was warmed to room temperature and stirred for 24 h. The mixture was diluted with EtOAc (1.0 L), extracted into EtOAc (2×300 mL), washed sequentially with $Na_2CO_3$ (sat. aq., 300 mL) and brine (300 mL), then was concentrated under reduced pressure. Purification by silica gel chromatography (0→17% EtOAc/pet. ether) afforded product (10 g, 81% yield).

Step 7: Synthesis of benzyl (2R,3S)-2-azido-3-hydroxy-4-methylpentanoate

To a solution of benzyl (2S,3S)-2-bromo-3-hydroxy-4-methylpentanoate (10 g, 33.2 mmol) in DMSO (100 mL) was added $NaN_3$ (4.32 g, 66.4 mmol). The reaction mixture was stirred at room temperature for 12 h then was diluted with EtOAc (300 mL) and $H_2O$ (200 mL). The aqueous phase was extracted into EtOAc (2×200 mL), washed with brine (200 mL), dried over $Na_2SO_4$, filtered, and concentrated under reduced pressure. Purification by silica gel chromatography (0→17% EtOAc/pet. ether) afforded product (7.5 g, 79% yield).

Step 8: Synthesis of benzyl (2R,3R)-3-isopropylaziridine-2-carboxylate

To a solution of benzyl (2R,3S)-2-azido-3-hydroxy-4-methylpentanoate (7.5 g, 28.5 mmol) in MeCN (150 mL) was added PPh$_3$ (7.70 g, 29.3 mmol). The reaction mixture was stirred at room temperature for 1 h and then heated to 70° C. and stirred for 4 h. The reaction mixture was concentrated under reduced pressure and purification by silica gel chromatography (0→17% EtOAc/pet. ether) afforded product (4.5 g, 66% yield). LCMS (ESI) m/z: [M+H] calcd for $C_{13}H_{17}NO_2$: 220.13; found 220.0.

Step 9: Synthesis of benzyl (2R,3R)-3-isopropyl-1-tritylaziridine-2-carboxylate

To a solution of benzyl (2R,3R)-3-isopropylaziridine-2-carboxylate (2 g, 9.12 mmol) in DCM (30 mL) at 0° C. was added Et$_3$N (3.81 mL, 27.4 mmol) and trityl chloride (3.05 g, 10.9 mmol) followed by DMAP (111 mg, 912 µmol). The reaction mixture was stirred at 0° C. for 1 h and then was diluted with DCM (50 mL) and H$_2$O (50 mL) then extracted into DCM (2×30 mL). The combined organic layers were washed with brine (50 mL), dried over Na$_2$SO$_4$, filtered, and concentrated under reduced pressure. Purification by silica gel chromatography (0→25% DCM/pet. ether) afforded product (3.1 g, 72% yield).

Step 10: Synthesis of (2R,3R)-3-isopropyl-1-tritylaziridine-2-carboxylic Acid

Two solutions of benzyl (2R,3R)-3-isopropyl-1-tritylaziridine-2-carboxylate (200 mg, 430 µmol) and Pd/C (100 mg) in THF (4 mL) were stirred for 1 h at room temperature under H$_2$ atmosphere. The reaction mixtures were combined, filtered, and concentrated under reduced pressure. Purification by silica gel chromatography (0→50% EtOAc/pet. ether) afforded product (160 mg, 51% yield).

Intermediate A-97. Synthesis of (2S,3S)-1-benzyl-3-isopropylaziridine-2-carboxylic Acid

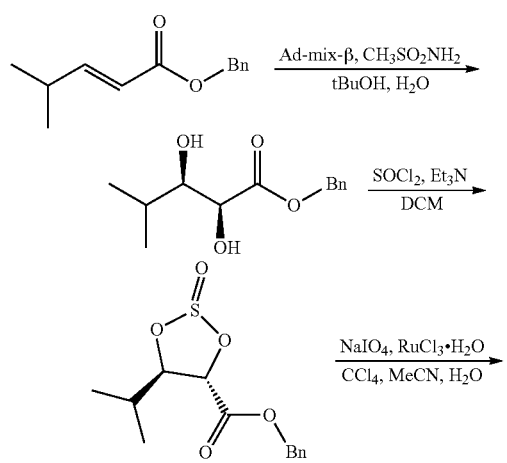

Step 1: Synthesis of benzyl (2S,3R)-2,3-dihydroxy-4-methylpentanoate

To a solution of AD-mix-R (61.7 g) and methanesulfonamide (4.19 g, 44.1 mmol) in tert-BuOH (225 mL) and H$_2$O (225 mL) was added benzyl (E)-4-methylpent-2-enoate (9 g, 44.1 mmol). The mixture was stirred at room temperature for 12 h then Na$_2$SO$_3$ (67.5 g) was added and stirred for 30 min. The reaction mixture was diluted with EtOAc (300 mL) and H$_2$O (300 mL) and extracted into EtOAc (3×300 mL), washed with brine (300 mL), dried over Na$_2$SO$_4$, filtered, and concentrated under reduced pressure. Purification by silica gel chromatography (0-25% EtOAc/pet. ether) afforded product (8.8 g, 84% yield). LCMS (ESI) m/z: [M+Na] calcd for $C_{13}H_{18}O_4$: 261.11; found 261.0.

Step 2: Synthesis of benzyl (4S,5R)-5-isopropyl-1,3,2-dioxathiolane-4-carboxylate 2-oxide To a solution of benzyl (2S,3R)-2,3-dihydroxy-4-methylpentanoate (11.6 g, 48.7 mmol) in DCM (116 mL) at 0° C. was added Et$_3$N (20.3 mL, 146 mmol) and SOCl$_2$ (4.94 mL, 68.2 mmol). The reaction mixture was stirred 30 min then was diluted with DCM (100 mL) and H$_2$O (100 mL), extracted into DCM (3×100 mL), washed with brine (200 mL), dried over Na$_2$SO$_4$, filtered, and concentrated under reduced pressure which afforded product (13.0 g, 94% yield).

Step 3: Synthesis of benzyl (4S,5R)-5-isopropyl-1,3,2-dioxathiolane-4-carboxylate 2,2-dioxide To a solution of benzyl (4S,5R)-5-isopropyl-1,3,2-dioxathiolane-4-carboxylate 2-oxide (13 g, 45.7 mmol) in H$_2$O

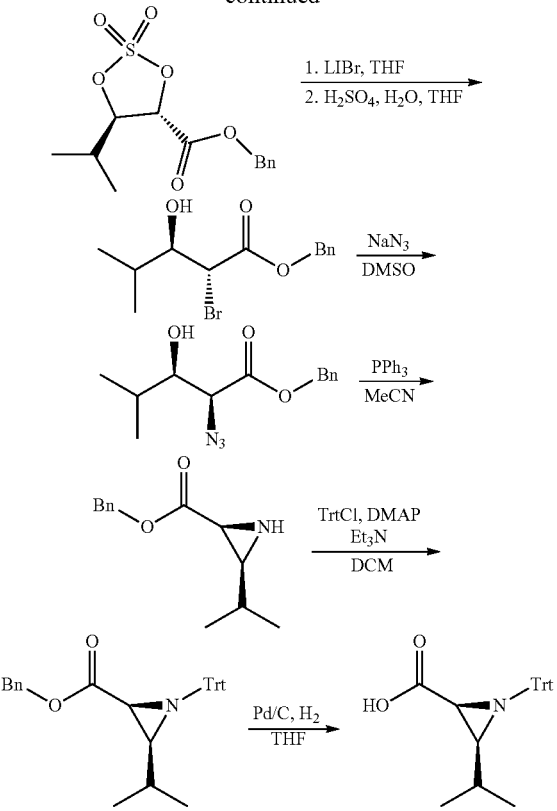

(290 mL), MeCN (145 mL), and CCl$_4$ (145 mL) was added NaIO$_4$ (3.80 mL, 68.6 mmol) and RuCl$_3$.H$_2$O (1.03 g, 4.57 mmol). The mixture was stirred at room temperature for 1 h then was diluted with DCM (500 mL) and H$_2$O (300 mL), filtered, and the filtrate was extracted into DCM (3×200 mL). The combined organic layers were washed sequentially with brine (500 mL) and sat. aq. Na$_2$CO$_3$ (300 mL), dried over Na$_2$SO$_4$, filtered, and concentrated under reduced pressure. Purification by silica gel chromatography (0→17% EtOAc/pet. ether) afforded product (11.5 g, 80% yield).

Step 4: Synthesis of benzyl (2R,3R)-2-bromo-3-hydroxy-4-methylpentanoate

To a solution of benzyl (4S,5R)-5-isopropyl-1,3,2-dioxathiolane-4-carboxylate 2,2-dioxide (11.5 g, 38.3 mmol) in THF (520 mL) was added LiBr (3.65 mL, 146 mmol). The reaction mixture was stirred at room temperature for 5 h and then concentrated under reduced pressure. The residue was diluted in THF (130 mL) and H$_2$O (65 mL), cooled to 0° C., then H$_2$SO$_4$ solution (20% aq., 1.3 L) was added and the mixture was warmed to room temperature and stirred for 24 h. The mixture was diluted with EtOAc (1.0 L), washed with Na$_2$CO$_3$ (sat. aq., 300 mL), then was concentrated under reduced pressure. Purification by silica gel chromatography (0→17% EtOAc/pet. ether) afforded product (10 g, 83% yield).

Step 5: Synthesis of benzyl (2S,3R)-2-azido-3-hydroxy-4-methylpentanoate

To a solution of benzyl (2R,3R)-2-bromo-3-hydroxy-4-methylpentanoate (10 g, 33.2 mmol) in DMSO (100 mL) was added NaN$_3$ (4.33 g, 66.6 mmol). The reaction mixture was stirred at room temperature for 12 h then was diluted with EtOAc (300 mL) and H$_2$O (200 mL). The mixture was extracted into EtOAc (2×200 mL), dried over Na$_2$SO$_4$, filtered, and concentrated under reduced pressure. Purification by silica gel chromatography (0→17% EtOAc/pet. ether) afforded product (7.5 g, 76% yield).

Step 6: Synthesis of benzyl (2S,3S)-3-isopropylaziridine-2-carboxylate

To a solution of benzyl (2S,3R)-2-azido-3-hydroxy-4-methylpentanoate (7.5 g, 28.5 mmol) in MeCN (150 mL) was added PPh$_3$ (7.70 g, 29.3 mmol). The reaction mixture was stirred at room temperature for 1 h and then heated to 70° C. and stirred for 3 h. The reaction mixture was concentrated under reduced pressure and purification by silica gel chromatography (0→17% EtOAc/pet. ether) afforded product (4.5 g, 64% yield). LCMS (ESI) m/z: [M+H] calcd for C$_{13}$H$_{17}$NO$_2$: 220.13; found 220.1.

Step 7: Synthesis of benzyl (2S,3S)-1-benzyl-3-isopropylaziridine-2-carboxylate

To a solution of benzyl (2S,3S)-3-isopropylaziridine-2-carboxylate (1 g, 4.56 mmol) in MeCN (10 mL) was added K$_2$CO$_3$ (3.15 g, 22.8 mmol) and benzyl bromide (812 μL, 6.84 mmol). The reaction mixture was stirred at room temperature for 6 h then was diluted with EtOAc (30 mL) and H$_2$O (30 mL), extracted into EtOAc (2×30 mL), washed with brine (50 mL), dried over Na$_2$SO$_4$, filtered, and concentrated under reduced pressure. Purification by silica gel chromatography (0→17% EtOAc/pet. ether) afforded product (1.3 g, 89% yield). LCMS (ESI) m/z: [M+H] calcd for C$_{20}$H$_{23}$NO$_2$: 310.18; found 310.1.

Step 8: Synthesis of (2S,3S)-1-benzyl-3-isopropylaziridine-2-carboxylic Acid

To a solution of benzyl (2S,3S)-1-benzyl-3-isopropylaziridine-2-carboxylate (600 mg, 1.94 mmol) in THF (6 mL), MeCN (3 mL), and H$_2$O (6 mL) at 0° C. was added LiOH.H$_2$O (163 mg, 3.88 mmol). The reaction mixture was stirred at room temperature for 1 h and was adjusted to pH=7-8 with HCl (0.5M). Lyophilization afforded product (750 mg, crude). LCMS (ESI) m/z: [M+H] calcd for C$_{13}$H$_{17}$NO$_2$: 220.13; found 220.1.

Intermediate A-98, A-99, A-100, and A-101. Synthesis of ethyl (2R,3R)-1-benzhydryl-3-(oxetan-3-yl)aziridine-2-carboxylate, ethyl (2S,3S)-1-benzhydryl-3-(oxetan-3-yl)aziridine-2-carboxylate, ethyl (2R,3S)-1-benzhydryl-3-(oxetan-3-yl)aziridine-2-carboxylate, and ethyl (2S,3R)-1-benzhydryl-3-(oxetan-3-yl)aziridine-2-carboxylate

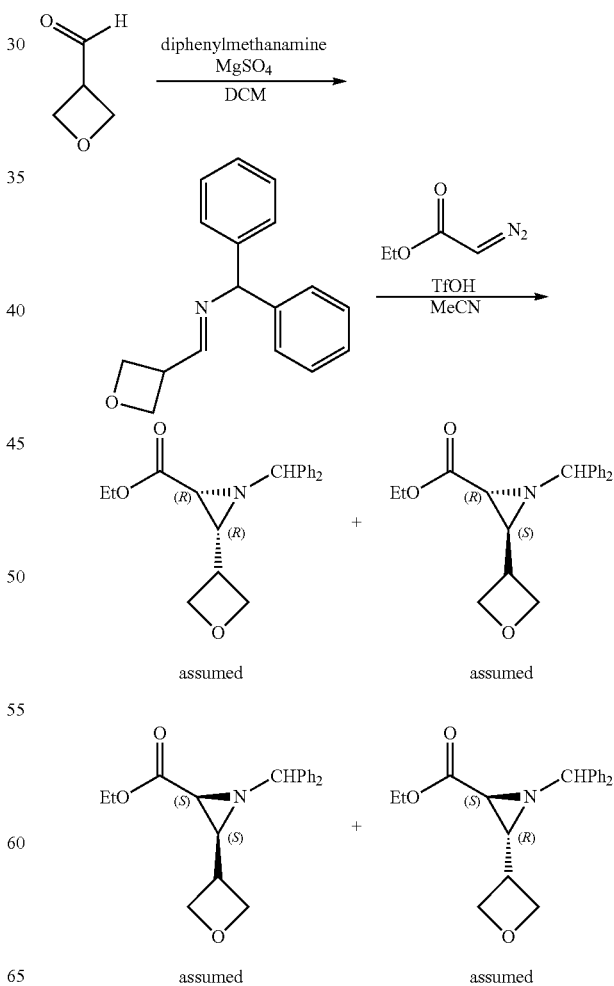

Step 1: Synthesis of N-benzhydryl-1-(oxetan-3-yl)methanimine

To a solution oxetane-3-carbaldehyde (5.0 g, 58 mmol) and MgSO₄ (6.99 g, 58.1 mmol) in DCM (120 mL) at 0° C. was added diphenylmethanamine (12.1 mL, 69.7 mmol). The mixture was stirred for 12 h at room temperature then filtered and concentrated under reduced pressure to afford the desired compound (14 g, 95.9% yield) which was used without further purification.

Step 2: Synthesis of ethyl cis-1-benzhydryl-3-(oxetan-3-yl)aziridine-2-carboxylate and ethyl trans-1-benzhydryl-3-(oxetan-3-yl)aziridine-2-carboxylate To a solution of N-benzhydryl-1-(oxetan-3-yl)methanimine (10 g, 39.79 mmol) in MeCN (150 mL) was added TfOH (878 mL, 9.95 mmol) and after 5 min ethyl diazoacetate (5.0 mL, 47.8 mmol) was added. The reaction mixture was stirred for 12 h at room temperature then cooled to 0° C. and quenched by the addition of saturated NaHCO₃ (300 mL). The aqueous layer was extracted with EtOAc (3×200 mL) and the combined organic layers were washed with brine, dried with Na₂SO₄, filtered, and concentrated under reduced pressure. Purification by reverse phase chromatography (50→65% MeCN/H₂O, 10 mM NH₄HCO₃) afforded racemic ethyl cis-1-benzhydryl-3-(oxetan-3-yl)aziridine-2-carboxylate (1.1 g, 8.2% yield) and racemic ethyl trans-1-benzhydryl-3-(oxetan-3-yl)aziridine-2-carboxylate (780 mg, 5.8% yield)

Step 3: Separation of racemic ethyl cis-1-benzhydryl-3-(oxetan-3-yl)aziridine-2-carboxylate: ethyl (2R,3R)-1-benzhydryl-3-(oxetan-3-yl)aziridine-2-carboxylate and ethyl (2S,3S)-1-benzhydryl-3-(oxetan-3-yl)aziridine-2-carboxylate Racemic ethyl cis-1-benzhydryl-3-(oxetan-3-yl)aziridine-2-carboxylate (800 mg, 2.37 mmol) was separated by chiral prep-SFC (25% MeOH/CO₂) to afford ethyl (2R,3R)-1-benzhydryl-3-(oxetan-3-yl) aziridine-2-carboxylate (320 mg, 40% yield) and ethyl (2S,3S)-1-benzhydryl-3-(oxetan-3-yl)aziridine-2-carboxylate (320 mg, 40% yield).

Step 4: Separation of racemic ethyl trans-1-benzhydryl-3-(oxetan-3-yl)aziridine-2-carboxylate: ethyl (2R,3S)-1-benzhydryl-3-(oxetan-3-yl)aziridine-2-carboxylate and ethyl (2S,3R)-1-benzhydryl-3-(oxetan-3-yl)aziridine-2-carboxylate Racemic ethyl trans1-benzhydryl-3-(oxetan-3-yl)aziridine-2-carboxylate (700 mg, 2.07 mmol) was separated by chiral prep-SFC (25% EtOH, 0.1% NH₄OH/CO₂) to afford ethyl (2R,3S)-1-benzhydryl-3-(oxetan-3-yl) aziridine-2-carboxylate (300 mg, 42% yield) and ethyl (2S,3R)-1-benzhydryl-3-(oxetan-3-yl)aziridine-2-carboxylate (320 mg, 43% yield).

Intermediate A-102 and A-103. Synthesis of (2R,3R)-1-benzhydryl-3-(oxetan-3-yl)aziridine-2-carboxylic acid and (2S,3S)-1-benzhydryl-3-(oxetan-3-yl)aziridine-2-carboxylic Acid

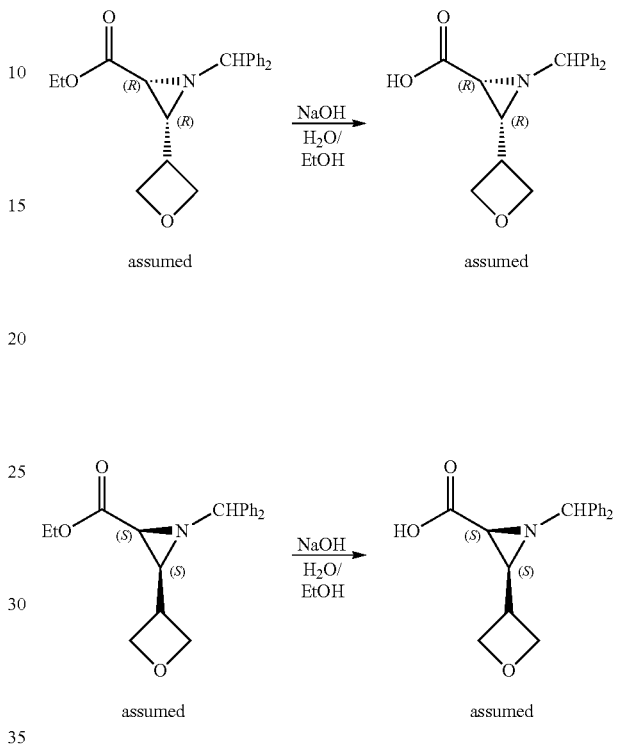

Step 1: Synthesis of (2R,3R)-1-benzhydryl-3-(oxetan-3-yl)aziridine-2-carboxylic Acid To a solution of ethyl (2R,3R)-1-benzhydryl-3-(oxetan-3-yl)aziridine-2-carboxylate (156 mg, 463 mmol) in EtOH (3 mL) was added 2M NaOH (347 mL, 696 mmol). The reaction mixture was stirred for 3 h at room temperature and then concentrated under reduced pressure. The concentrate was acidified to pH 5 with 1M HCl and extracted with DCM (3×5 mL) and the combined organic layers were washed with brine, dried with Na₂SO₄, filtered and concentrated under reduced pressure to afford the desired compound (110 mg, 72.6% yield).

Step 2: Synthesis of (2S,3S)-1-benzhydryl-3-(oxetan-3-yl)aziridine-2-carboxylic Acid To a solution of ethyl (2S,3S)-1-benzhydryl-3-(oxetan-3-yl)aziridine-2-carboxylate (150 mg, 444 mmol) in EtOH (5 mL) was added 2M NaOH (333 mL, 666 mmol). The reaction mixture was stirred for 3 h at room temperature and then acidified to pH 5 with 1M HCl. The aqueous layer extracted with DCM (3×10 mL) and the combined organic layers were washed with brine, dried with Na₂SO₄, filtered, and concentrated under reduced pressure to afford the desired compound (120 mg, 86.1% yield).

Intermediate A-104 and A-105. Synthesis of sodium (2R,3S)-1-benzhydryl-3-(oxetan-3-yl)aziridine-2-carboxylate and sodium (2S,3R)-1-benzhydryl-3-(oxetan-3-yl)aziridine-2-carboxylate

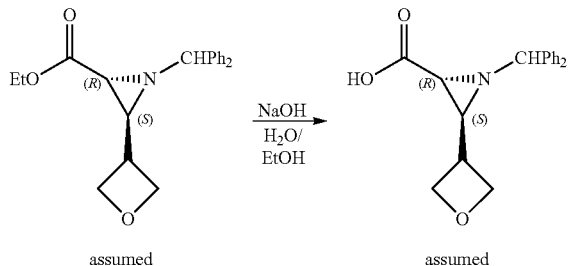

assumed      assumed

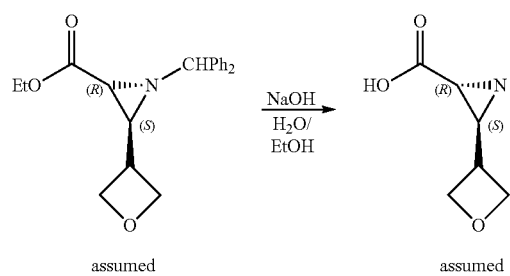

assumed      assumed

Step 1: Synthesis of sodium (2R,3S)-1-benzhydryl-3-(oxetan-3-yl)aziridine-2-carboxylate To a solution of ethyl (2R,3S)-1-benzhydryl-3-(oxetan-3-yl)aziridine-2-carboxylate (150 mg, 444 mmol) in EtOH (3 mL) was added 2M NaOH (333.42 mL, 666 mmol). The reaction mixture was stirred for 3 h at room temperature and then the pH was adjusted to pH 8 with 1M HCl. The resulting solution was lyophilized to afford the desired compound (165 mg, crude) which was used without further purification. LCMS (ESI) m/z: [M] calcd for $C_{19}H_{18}NO_3$: 308.13; found 308.0.

Step 2: Synthesis of sodium (2S,3R)-1-benzhydryl-3-(oxetan-3-yl)aziridine-2-carboxylate To a solution of ethyl (2S,3R)-1-benzhydryl-3-(oxetan-3-yl)aziridine-2-carboxylate (170 mg, 503 mmol) in EtOH (3 mL) was added 2M NaOH (378 mL, 754 mmol). The reaction mixture was stirred for 3 h at room temperature and then the pH was adjusted to pH 8 with 1M HCl. The resulting solution was lyophilized to afford the desired compound (230 mg, crude) which was used without further purification. LCMS (ESI) m/z: [M] calcd for $C_{19}H_{18}NO_3$: 308.13; found 308.0.

Intermediate A-106. Synthesis of (R)-1-((benzyloxy)carbonyl)-2-methylaziridine-2-carboxylic Acid

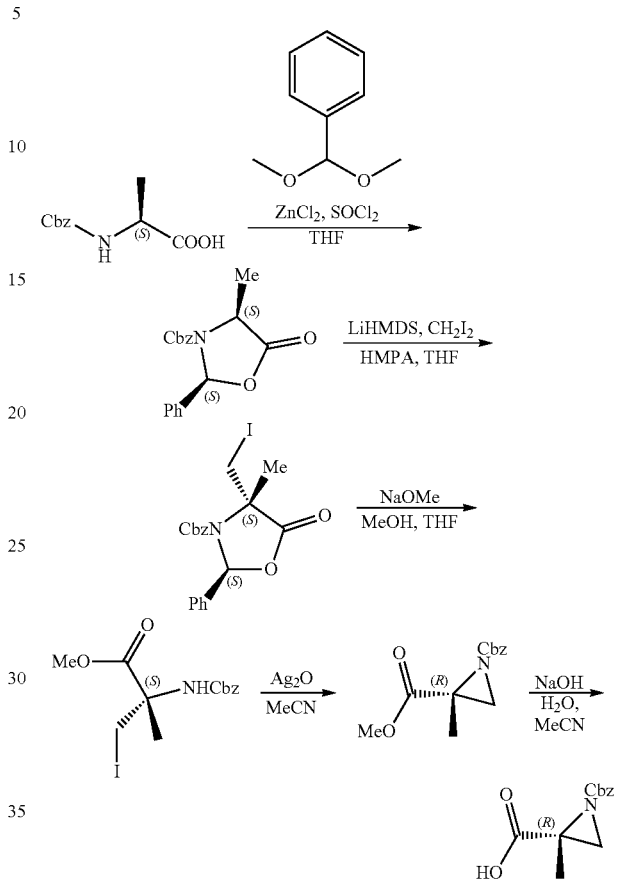

Step 1: Synthesis of benzyl (2S,4S)-4-methyl-5-oxo-2-phenyloxazolidine-3-carboxylate To a mixture of ((benzyloxy)carbonyl)-L-alanine (25 g, 111.99 mmol) and (dimethoxymethyl)benzene (71.38 mL, 115.35 mmol) in THF (180 mL) was added $SOCl_2$ (8.94 g, 123.19 mmol) in one portion at 0° C. The mixture was stirred for 10 min before $ZnCl_2$ (5.77 mL, 123.26 mmol) was added to the solution, then the mixture was stirred at 0° C. for 4 h. The reaction mixture was quenched by dropwise addition of cold $H_2O$ and adjusted to pH=5 with sat. $NaHCO_3$, then extracted with EtOAc (2×100 mL). The organic phase was washed with a aq. sat. $NaHCO_3$ (30 mL) and brine (30 mL), dried over $Na_2SO_4$, and concentrated under reduced pressure. The residue was purified by silica gel column chromatography (1→10% EtOAc/pet. ether) to afford product (15 g, 43% yield).

Step 2: Synthesis of Benzyl (2S,4S)-4-(iodomethyl)-4-methyl-5-oxo-2-phenyloxazolidine-3-carboxylate HMPA (5.22 mL, 29.74 mmol) and LHMDS (1 M, 6.62 mL) were mixed in THF (45 mL) under $N_2$ atmosphere at 20° C. This solution was cooled to −78° C. and a solution of benzyl (2S,4S)-4-methyl-5-oxo-2-phenyloxazolidine-3-carboxylate (2.0 g, 6.42 mmol) in THF (12 mL) was added dropwise with stirring. After stirring an additional 30 min, a solution of CH$_2$I$_2$ (1.55 mL, 19.27 mmol) in THF (6 mL) was added dropwise. The mixture was stirred at −78° C. for 90 min. The mixture was warmed to 0° C. and quenched with sat. aq. NH$_4$Cl (70 mL). The mixture was extracted with EtOAc (2×30 mL), and the combined organic layers was washed with sat. aq. NH$_4$Cl (20 mL), H$_2$O (2×20 mL), and brine (30 mL) dried over Na$_2$SO$_4$, filtered, and concentrated under reduced pressure. The resulting residue was purified by silica gel column chromatography (1→20% EtOAc/pet. ether) to afford product (1.2 g, 41.4% yield).

Step 3: Synthesis of methyl (S)-2-(((benzyloxy) carbonyl)amino)-3-iodo-2-methylpropanoate To a mixture of benzyl (2S,4S)-4-(iodomethyl)-4-methyl-5-oxo-2-phenyloxazolidine-3-carboxylate (1.2 g, 2.66 mmol) in THF (20 mL) was added a solution of NaOMe (957.69 mg, 5.32 mmol, 30% purity) in MeOH (9 mL) dropwise over 10 min at −40° C. under N$_2$. The mixture was stirred at −40° C. for 2 h, then warmed to −20° C. and stirred for 1 h. The reaction was quenched by addition of H$_2$O (20 mL), and the resulting mixture was extracted with EtOAc (3×20 mL). The combined organic layers were washed with brine (20 mL), dried over Na$_2$SO$_4$, filtered, and concentrated under reduced pressure. The residue was purified by silica gel column chromatography (1→20% EtOAc/pet. ether) to afford product (870 mg, 2.24 mmol, 84.4% yield).

Step 4: Synthesis of 1-benzyl 2-methyl (R)-2-methylaziridine-1,2-dicarboxylate

To a mixture of methyl (S)-2-(((benzyloxy)carbonyl) amino)-3-iodo-2-methylpropanoate (0.87 g, 2.31 mmol) in MeCN (125 mL) was added Ag$_2$O (1.60 g, 6.92 mmol) in one portion at room temperature. The mixture was stirred at 90° C. for 30 min. The mixture was filtered and concentrated under reduced pressure to afford product (500 mg, 2.01 mmol, 86.9% yield).

Step 5: Synthesis of 1-benzyl 2-methyl (R)-2-methylaziridine-1,2-dicarboxylate

To a mixture of 1-benzyl 2-methyl (R)-2-methylaziridine-1,2-dicarboxylate (250 mg, 1.0 mmol) in MeCN (2.5 mL) and H$_2$O (2.5 mL) was added NaOH (40.12 mg, 1.0 mmol) in one portion at 0° C. under N$_2$. The mixture was stirred at 0° C. for 30 min. The mixture was concentrated under reduced pressure to afford crude product (256 mg, crude). LCMS (ESI) m/z: [M+H] calcd for C$_{12}$H$_{12}$NO$_4$: 234.1; found 234.1.

Intermediate A-107. Synthesis of (S)-1-((benzyloxy)carbonyl)-2-methylaziridine-2-carboxylic Acid

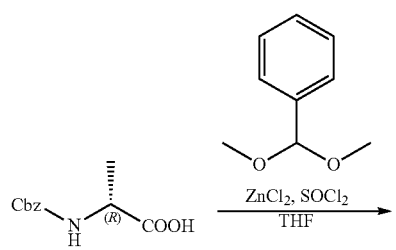

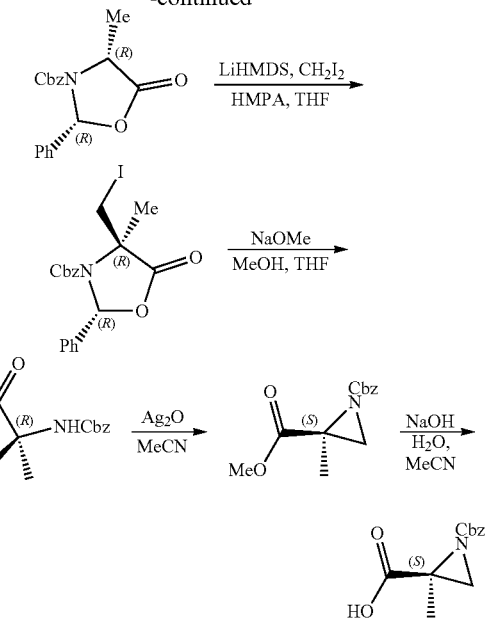

Step 1: Synthesis of benzyl (2R,4R)-4-methyl-5-oxo-2-phenyloxazolidine-3-carboxylate Five batches were completed in parallel. To a mixture of ((benzyloxy)carbonyl)-D-alanine (5 g, 22.40 mmol) and (dimethoxymethyl)benzene (3.71 mL, 24.64 mmol) in THF (35 mL) was added SOCl$_2$ (1.79 mL, 24.64 mmol) in one portion at 0° C. After the mixture was stirred for 10 min, ZnCl$_2$ (1.15 mL, 24.64 mmol) was added to the solution. Then the mixture was stirred at 0° C. for 4 h. The give batches were combined and concentrated under reduced pressure. The residue was purified by silica gel column chromatography (1→10% EtOAc/pet. ether) to afford product (20 g, 57.4% yield).

Step 2: Synthesis of benzyl (2R,4R)-4-(iodomethyl)-4-methyl-5-oxo-2-phenyloxazolidine-3-carboxylate Four batches were completed in parallel. THF (300 mL), HMPA (13.06 mL, 74.34 mmol) and LHMDS (1 M, 16.54 mL) were mixed under N$_2$ atmosphere at 20° C. with stirring. The solution was cooled to −78° C. and a solution of benzyl (2R,4R)-4-methyl-5-oxo-2-phenyloxazolidine-3-carboxylate (5 g, 16.06 mmol) in THF (84 mL) was added dropwise. After stirring an additional 30 min, a solution of CH$_2$I$_2$ (3.89 mL, 48.18 mmol) in THF (33 mL) was added dropwise. The mixture was stirred at −78° C. for 90 min. The four batches were combined and warmed to 0° C. Sat. aq. NH$_4$Cl (100 mL) was added to the combined solution and the resulting mixture was extracted with EtOAc (2×100 mL). The combined EtOAc layers was washed with sat. aq. NH$_4$Cl (50 mL), H$_2$O (2×20 mL), and brine (30 mL), dried over Na$_2$SO$_4$, filtered, and concentrated under reduced pressure. The resulting residue was purified by silica gel column chromatography (1→17% EtOAc/pet. ether) to afford product (16 g, 55.2% yield).

Step 3: Synthesis of methyl (R)-2-(((benzyloxy) carbonyl)amino)-3-iodo-2-methylpropanoate To a mixture of benzyl (2R,4R)-4-(iodomethyl)-4-methyl-5-oxo-2-phenyloxazolidine-3-carboxylate (16 g, 35.46 mmol) in THF (90 mL) was added NaOMe (12.77 g, 70.91 mmol, 30% purity) dropwise over 10 min at −40° C. under N$_2$. The mixture was stirred at −40° C. for 2 h, then warmed to −20° C. and stirred for 1 h. The reaction was quenched by addition of H$_2$O (100 mL), and the resulting mixture was extracted with diethyl ether (3×100 mL). The combined organic layers were washed with brine (50 mL), dried over Na$_2$SO$_4$, filtered, and concentrated under reduced pressure. The resulting residue was purified by silica gel column chromatography (1→17% EtOAc/pet. ether) to afford product (10 g, 74.8% yield.

Step 4: Synthesis of 1-benzyl 2-methyl (S)-2-methylaziridine-1,2-dicarboxylate

Four batches were completed in parallel. To a mixture of methyl (R)-2-(((benzyloxy)carbonyl)amino)-3-iodo-2-methylpropanoate (8 g, 21.20 mmol) in MeCN (800 mL) was added Ag$_2$O (14.76 g, 63.64 mmol) in one portion at 20° C. The mixture was stirred at 90° C. for 30 min. The four batches were combined, filtered, and concentrated under reduced pressure to afford product (5.1 g, 90.9% yield.

Step 5: Synthesis of (S)-1-((benzyloxy)carbonyl)-2-methylaziridine-2-carboxylic Acid To a solution of 1-benzyl 2-methyl (S)-2-methylaziridine-1,2-dicarboxylate (1 g, 4.01 mmol) in MeCN (5 mL) was added a solution of NaOH (240.69 mg, 6.02 mmol) in H$_2$O (5 mL) at 0° C., then the mixture was stirred at 0° C. for 30 min. The mixture was lyophilized directly to afford crude product (1.05 g, crude). LCMS (ESI) m/z: [M+H] calcd for C$_{12}$H$_{12}$N$_4$: 234.08; found 234.2.

Intermediates A-108 and A-109. Synthesis of tert-butyl (R)-7-((S)-2-(benzyloxy)-1-cyclopentyl-2-oxoethyl)-6-oxo-2,7-diazaspiro[4.4]nonane-2-carboxylate and tert-butyl (S)-7-((S)-2-(benzyloxy)-1-cyclopentyl-2-oxoethyl)-6-oxo-2,7-diazaspiro[4.4]nonane-2-carboxylate

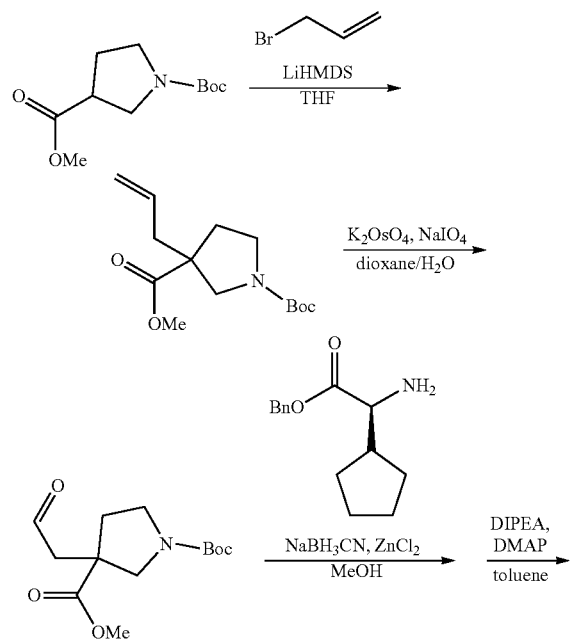

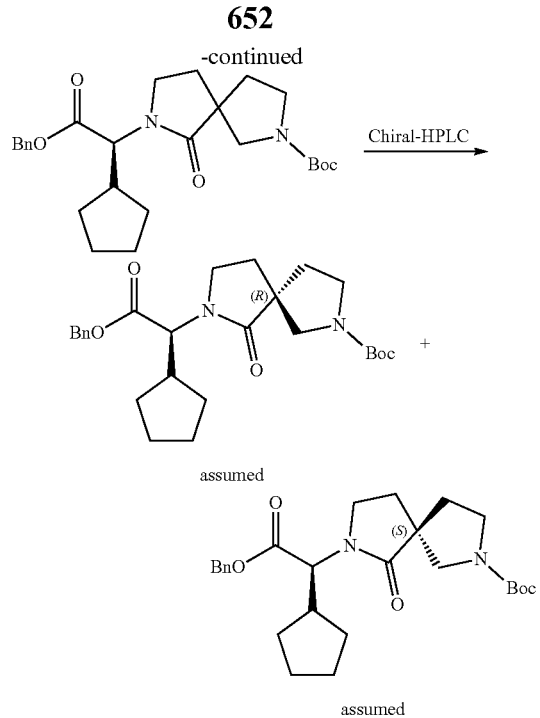

Step 1: Synthesis of 1-(tert-butyl) 3-methyl 3-allylpyrrolidine-1,3-dicarboxylate To a solution of 1-(tert-butyl) 3-methyl pyrrolidine-1,3-dicarboxylate (10.0 g, 43.6 mmol) in THF (100 mL) at −78° C. was added LiHMDS (65.0 mL, 65.4 mmol, 1 M in THF). After 1 h allyl bromide (5.63 mL, 65.4 mmol) was added and the resulting mixture was warmed to room temperature overnight. The reaction was quenched at 0° C. by the addition of NH$_4$Cl (200 mL). The aqueous layer was extracted with EtOAc (3×100 mL) and the combined organic layers were washed with brine, dried with Na$_2$SO$_4$, filtered, and concentrated under reduced pressure. Purification by normal phase chromatography (5% EtOAc/pet. ether) afforded the desired product (10.0 g, 76.6% yield).

Step 3: Synthesis of 1-(tert-butyl) 3-methyl 3-(2-oxoethyl)pyrrolidine-1,3-dicarboxylate To a solution of 1-(tert-butyl) 3-methyl 3-allylpyrrolidine-1,3-dicarboxylate (10.0 g, 37.1 mmol) and 2,6-dimethylpyridine (8.65 mL, 80.7 mmol) in dioxane (571 mL) and H$_2$O (142 mL) at 0° C. was added K$_2$OsO$_4$.2H$_2$O (0.27 g, 0.73 mmol). After 15 min NaIO$_4$ (23.82 g, 111.4 mmol) was added and the resulting mixture was stirred overnight at room temperature and then was diluted with H$_2$O (200 mL). The aqueous layer extracted with EtOAc (3×200 mL) and the combined organic layers were washed with 2 M HCl, dried with Na$_2$SO$_4$, filtered and concentrated under reduced pressure to afford the desired product (9.7 g, crude) which was used without further purification.

Step 4: Synthesis of 1-(tert-butyl) 3-methyl 3-(2-(((S)-2-(benzyloxy)-1-cyclopentyl-2-oxoethyl)amino)ethyl)pyrrolidine-1,3-dicarboxylate To a solution of 1-(tert-butyl) 3-methyl 3-(2-oxoethyl)pyrrolidine-1,3-dicarboxylate (9.60 g, 35.4 mmol) in MeOH (100 mL) at 0° C. was added benzyl (S)-2-amino-2-cyclopentylacetate (12.38 g, 53.075 mmol) and zinc chloride (7.23 g, 53.1 mmol). After 30 min NaBH₃CN (4.45 g, 70.8 mmol) was added and the resulting mixture stirred for 2 h at room temperature, concentrated under reduced pressure and the residue diluted with H₂O (150 mL). The aqueous layer was extracted with EtOAc (3×50 mL) and the combined organic layers were washed with brine, dried with Na₂SO₄, filtered, and then concentrated under reduced pressure. Purification by normal phase chromatography (20% EtOAc/pet. ether) afforded the desired product (11.1 g, 64.2% yield). LCMS (ESI) m/z: [M+H] calcd for $C_{27}H_{40}N_2O_6$: 489.30; found 489.3.

Step 5: Synthesis of tert-butyl (R)-7-((S)-2-(benzyloxy)-1-cyclopentyl-2-oxoethyl)-6-oxo-2,7-diazaspiro[4.4]nonane-2-carboxylate and tert-butyl (S)-7-((S)-2-(benzyloxy)-1-cyclopentyl-2-oxoethyl)-6-oxo-2,7-diazaspiro[4.4]nonane-2-carboxylate To a solution of stirred solution of 1-(tert-butyl) 3-methyl 3-(2-(((S)-2-(benzyloxy)-1-cyclopentyl-2-oxoethyl)amino)ethyl)pyrrolidine-1,3-dicarboxylate (11.1 g, 22.7 mmol) in toluene (120 mL) was added DIPEA (39.6 mL, 227 mmol) and DMAP (2.78 g, 22.7 mmol). The resulting mixture was stirred for 2 days at 80° C. and then concentrated under reduced pressure. Purification by reverse phase chromatography (20→70% MeCN/H₂O, 0.1% HCO₂H) afforded a mixture of desired products. The diastereomers were separated by prep-SFC (30% EtOH/CO₂) to afford tert-butyl (R)-7-((S)-2-(benzyloxy)-1-cyclopentyl-2-oxoethyl)-6-oxo-2,7-diazaspiro[4.4]nonane-2-carboxylate (3.73 g, 44.4% yield) LCMS (ESI) m/z: [M+H] calcd for $C_{26}H_{36}N_2O_5$: 457.27; found 457.3 and tert-butyl (S)-7-((S)-2-(benzyloxy)-1-cyclopentyl-2-oxoethyl)-6-oxo-2,7-diazaspiro[4.4]nonane-2-carboxylate (3.87 g, 46.1% yield)) LCMS (ESI) m/z: [M+H] calcd for $C_{26}H_{36}N_2O_5$: 457.27; found 457.3.

Intermediate B-1. Synthesis of N-(3-(3-(4-methoxyphenyl)thioureido)propanoyl)-N-methyl-L-valine

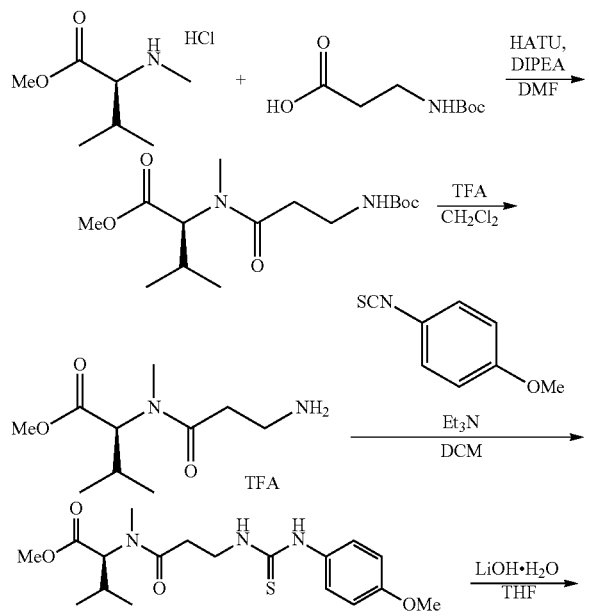

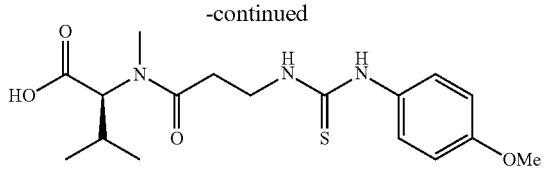

Step 1: Synthesis of methyl N-(3-((tert-butoxycarbonyl)amino)propanoyl)-N-methyl-L-valinate To a solution of 3-((tert-butoxycarbonyl)amino)propanoic acid (1.04 g, 5.50 mmol) in DMF (6 mL) was added DIPEA (2.38 mL, 13.7 mmol) followed by HATU (2.71 g, 7.15 mmol). The reaction mixture was stirred for 5 min and methyl methyl-L-valinate hydrochloride (1 g, 5.50 mmol) was added. The reaction was stirred at room temperature for 3 h and was then quenched with H₂O. The aqueous layer was extracted with EtOAc (3×10 mL) and the combined organic layers were washed with brine, and dried over Na₂SO₄, filtered, and concentrated under reduced pressure to afford the desired crude product.

Step 2: Synthesis of methyl N-(3-aminopropanoyl)-N-methyl-L-valinate Trifluoroacetic Acid To a solution of methyl N-(3-((tert-butoxycarbonyl)amino)propanoyl)-N-methyl-L-valinate (1.74 g, 5.50 mmol) in DCM (3 mL) was added TFA (2.09 mL, 27.4 mmol). The reaction was stirred at room temperature overnight and was then concentrated under reduced pressure to afford a solution of the desired crude product as a 33.5% solution in TFA.

Step 3: Synthesis of methyl N-(3-(3-(4-methoxyphenyl)thioureido)propanoyl)-N-methyl-L-valinate To a 33.5 wt % solution of methyl N-(3-aminopropanoyl)-N-methyl-L-valinate trifluoroacetic acid (800 mg, 0.811 mmol) in TFA was added DCM (5 mL) followed by Et₃N (593 μL, 4.26 mmol) and 4-methoxyphenyl isothiocyanate (117.0 μL, 852 μmol). The reaction was stirred at room temperature for 3 h. The reaction mixture was then washed with H₂O (2×5 mL), aq. NH₄Cl (5 mL), and brine (5 mL). The organic layer was dried over Na₂SO₄ and concentrated under reduced pressure to afford the crude product (290.2 mg 89.2% yield) as an oil, which was taken on without purification. LCMS (ESI) m/z: [M+H] calcd for $C_{18}H_{27}N_3O_4S$: 382.18; found 382.2.

Step 4: Synthesis of N-(3-(3-(4-methoxyphenyl)thioureido)propanoyl)-N-methyl-L-valine To a solution of methyl N-(3-(3-(4-methoxyphenyl)thioureido)propanoyl)-N-methyl-L-valinate (290.2 mg, 0.76 mmol) in THF (1 mL) was added a solution of LiOH.H₂O (41.4 mg, 0.99 mmol) in H₂O (300 μL). The reaction mixture was stirred overnight and was then acidified with HCl (4 M in dioxane, 120 μL, 0.48 mmol). The solution was then concentrated, the residue was dissolved in EtOAc, and the organic layer washed with H₂O (3×5 mL) and brine (5 mL). The organic layer was dried over Na₂SO₄ and concentrated under reduced pressure to afford the crude product (215.1 mg 77.0% yield), which was taken forward without further purification. LCMS (ESI) m/z: [M+H] calcd for $C_{17}H_{25}N_3O_4S$: 368.16; found 368.2.

The following table of compounds were prepared using the methods or variations thereof used to synthesize Intermediate B-1.

TABLE 3

Intermediate B

| Structure | Molecular Formula | Calculated MW | Observed MW |
|---|---|---|---|
| Intermediate B-1 | $C_{17}H_{25}N_3O_4S$ | [M + H] = 368.16 | [M + H] = 368.5 |
| Intermediate B-2 | $C_{18}H_{27}N_3O_3S$ | [M + H] = 366.19 | [M + H] = 366.6 |
| Intermediate B-3 | $C_{18}H_{27}N_3O_4S$ | [M + H] = 382.18 | [M + H] = 382.5 |
| Intermediate B-4 | $C_{19}H_{29}N_3O_5S$ | [M + H] = 412.19 | [M + H] = 412.6 |
| Intermediate B-5 | $C_{15}H_{27}N_3O_4S$ | [M + H] = 346.18 | [M + H] = 346.6 |
| Intermediate B-6 | $C_{19}H_{29}N_3O_4S$ | [M + H] = 396.20 | [M + H] = 396.6 |
| Intermediate B-7 | $C_{19}H_{27}N_3O_4S$ | [M + H] = 394.18 | [M + H] = 394.7 |

TABLE 3-continued
Intermediate B
| Structure | Molecular Formula | Calculated MW | Observed MW |
|---|---|---|---|
| 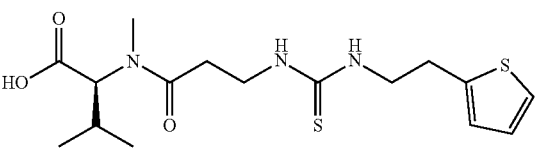 [SMILES: CC(C)[C@@H](C(=O)O)N(C)C(=O)CCNC(=S)NCCc1cccs1]<br>Intermediate B-8 | $C_{16}H_{25}N_3O_3S_2$ | [M + H] = 372.14 | [M + H] = 327.6 |
| 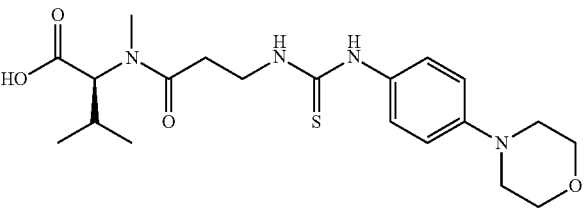 [SMILES: CC(C)[C@@H](C(=O)O)N(C)C(=O)CCNC(=S)Nc1ccc(N2CCOCC2)cc1]<br>Intermediate B-9 | $C_{20}H_{30}N_4O_4S$ | [M + H] = 423.21 | [M + H] = 423.6 |
| 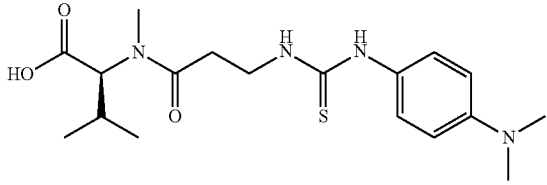 [SMILES: CC(C)[C@@H](C(=O)O)N(C)C(=O)CCNC(=S)Nc1ccc(N(C)C)cc1]<br>Intermediate B-10 | $C_{18}H_{28}N_4O_3S$ | [M + H] = 381.20 | [M + H] = 381.6 |
| 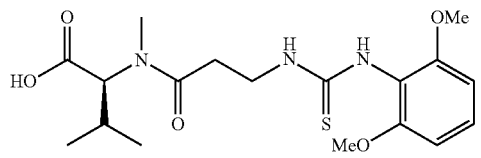 [SMILES: COc1cccc(OC)c1NC(=S)NCCC(=O)N(C)[C@H](C(=O)O)C(C)C]<br>Intermediate B-11 | $C_{18}H_{27}N_3O_5S$ | [M + H] = 398.17 | [M + H] = 398.6 |
| 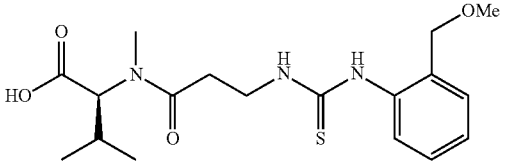 [SMILES: COCc1ccccc1NC(=S)NCCC(=O)N(C)[C@H](C(=O)O)C(C)C]<br>Intermediate B-12 | $C_{18}H_{27}N_3O_4S$ | [M + H] = 382.18 | [M + H] = 382.6 |
| 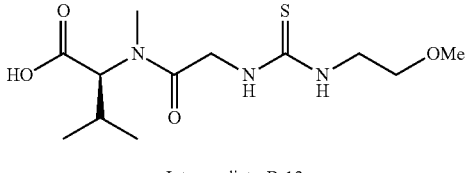<br>Intermediate B-13 | $C_{12}H_{23}N_3O_4S$ | [M + Na] = 328.13 | [M + Na] = 328.5 |
| 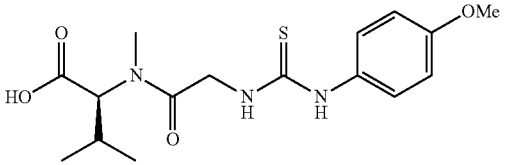 [SMILES: COc1ccc(NC(=S)NCC(=O)N(C)[C@H](C(=O)O)C(C)C)cc1] | $C_{16}H_{23}N_3O_4S$ | [M + H] = 354.15 | [M + H] = 354.5 |

TABLE 3-continued

| Intermediate B | | | |
|---|---|---|---|
| Structure | Molecular Formula | Calculated MW | Observed MW |
| Intermediate B-14 | $C_{14}H_{27}N_3O_4S$ | [M + H] = 334.18 | [M + H] = 334.6 |
| Intermediate B-15 | $C_{18}H_{27}N_3O_4S$ | [M + H] = 382.18 | [M + H] = 382.6 |
| Intermediate B-16 | $C_{17}H_{25}N_3O_3S_2$ | [M + H] = 384.14 | [M + H] = 384.3 |
| Intermediate B-17 | $C_{18}H_{27}N_3O_5S$ | [M + H] = 398.17 | [M + H] = 398.4 |
| Intermediate B-18 | $C_{17}H_{25}N_3O_4S$ | [M + H] = 368.16 | [M + H] = 368.4 |
| Intermediate B-19 | $C_{17}H_{32}N_4O_4S$ | [M + H] = 389.22 | [M + H] = 389.4 |
| Intermediate B-20 | $C_{14}H_{27}N_3O_3S_2$ | [M + H] = 350.16 | [M + H] = 350.4 |
| Intermediate B-21 | | | |

TABLE 3-continued

| Structure | Molecular Formula | Calculated MW | Observed MW |
|---|---|---|---|
| Intermediate B-22 | $C_{18}H_{27}N_3O_4S$ | [M + H] = 382.18 | [M + H] = 382.4 |
| Intermediate B-23 | $C_{18}H_{27}N_3O_4S$ | [M + H] = 382.18 | [M + H] = 382.4 |
| Intermediate B-24 | $C_{13}H_{25}N_3O_4S$ | [M + H] = 320.16 | [M + H] = 320.3 |
| Intermediate B-25 | $C_{13}H_{25}N_3O_3S$ | [M + H] = 304.17 | [M + H] = 304.5 |
| Intermediate B-26 | $C_{13}H_{25}N_3O_3S$ | [M + H] = 304.17 | [M + H] = 304.3 |
| Intermediate B-27 | $C_{17}H_{25}N_3O_3S$ | [M + H] = 352.17 | [M + H] = 352.4 |
| Intermediate B-28 | $C_{21}H_{31}N_3O_4S$ | [M + H] = 422.21 | [M + H] = 422.7 |

TABLE 3-continued
Intermediate B
| Structure | Molecular Formula | Calculated MW | Observed MW |
|---|---|---|---|
| 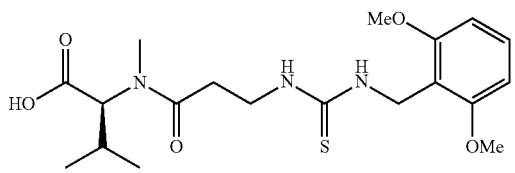 [SMILES: COc1cccc(OC)c1CNC(=S)NCCC(=O)N(C)[C@H](C(=O)O)C(C)C]<br>Intermediate B-29 | $C_{19}H_{29}N_3O_5S$ | [M + H] = 412.19 | [M + H] = 412.2 |
| 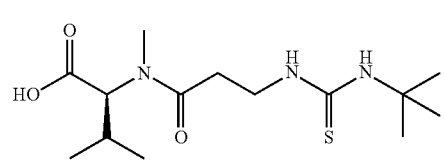 [SMILES: CC(C)[C@@H](C(=O)O)N(C)C(=O)CCNC(=S)NC(C)(C)C]<br>Intermediate B-30 | $C_{14}H_{27}N_3O_3S$ | [M + H] = 318.19 | [M + H] = 318.6 |
| 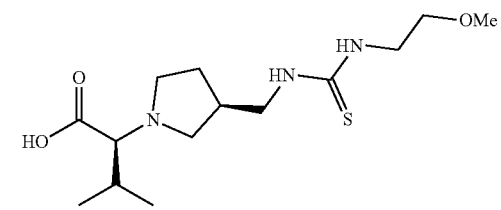 [SMILES: COCCNC(=S)NC[C@@H]1CCN([C@H](C(=O)O)C(C)C)C1]<br>Intermediate B-31 | $C_{14}H_{27}N_3O_3S$ | [M + H] = 318.19 | [M + H] = 318.7 |
| 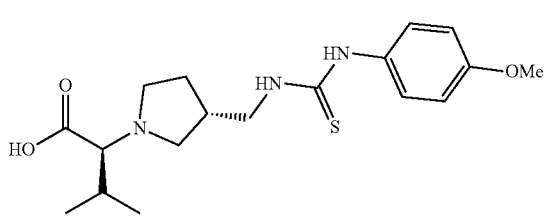 [SMILES: COc1ccc(NC(=S)NC[C@H]2CCN([C@H](C(=O)O)C(C)C)C2)cc1]<br>Intermediate B-32 | $C_{18}H_{27}N_3O_3S$ | [M + H] = 366.19 | [M + H] = 366.7 |
| 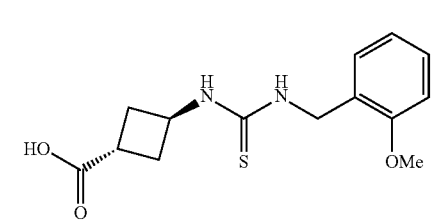 [SMILES: COc1ccccc1CNC(=S)N[C@H]1C[C@H](C(=O)O)C1]<br>Intermediate B-33 | $C_{14}H_{18}N_2O_3S$ | [M + H] = 295.11 | [M + H] = 295.6 |
| 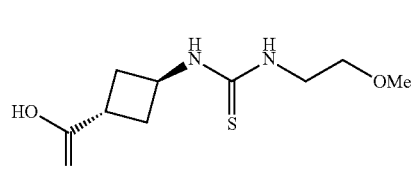<br>Intermediate B-34 | $C_9H_{16}N_2O_3S$ | [M + H] = 233.10 | [M + H] = 233.4 |

Example 1. Synthesis of (3S)-1-((R)-aziridine-2-carbonyl)-N-((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide
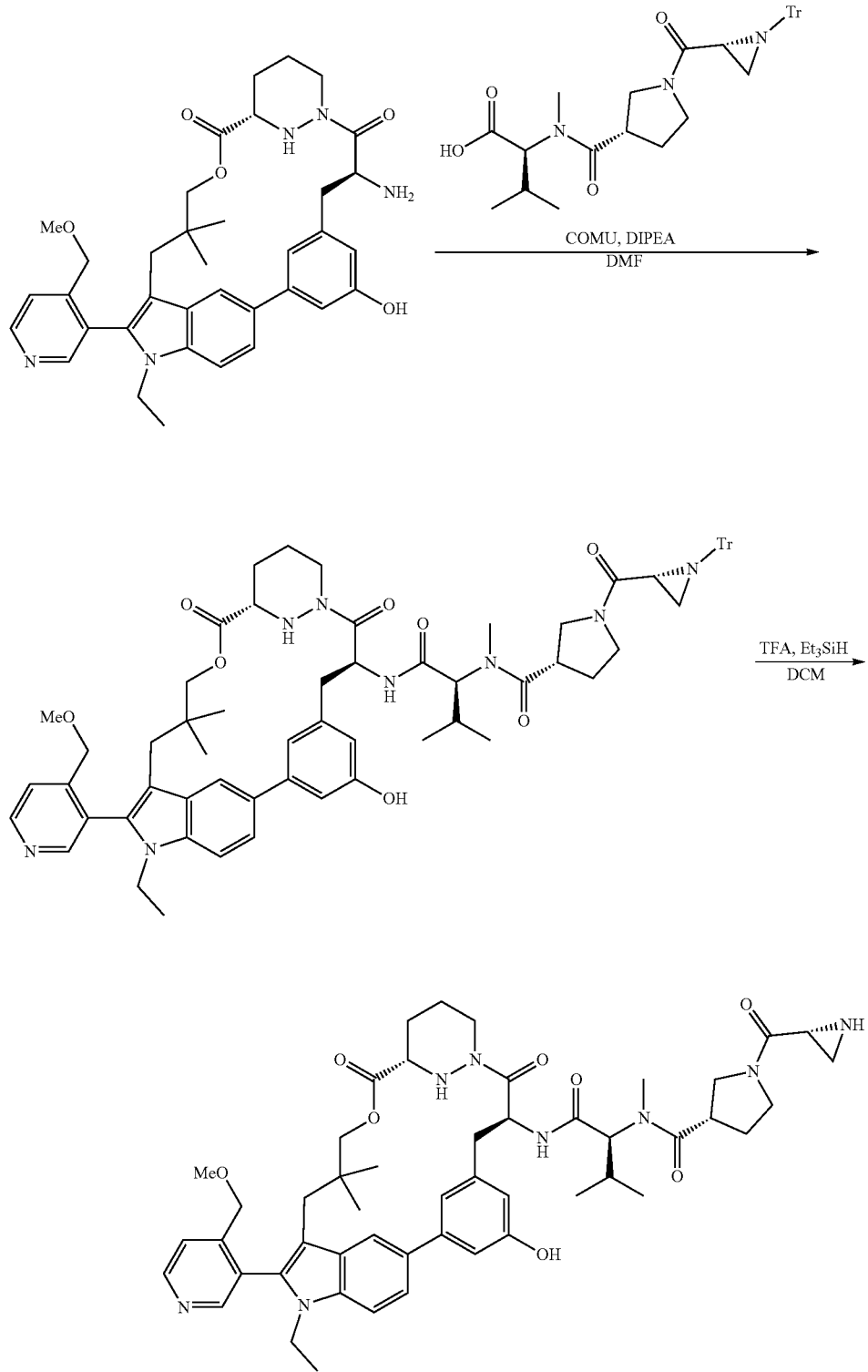

Step 1: Synthesis of (3S)—N-((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methyl-1-((R)-1-tritylaziridine-2-carbonyl)pyrrolidine-3-carboxamide To a solution of (6³S,4S)-4-amino-1¹-ethyl-2⁵-hydroxy-1²-(4-(methoxymethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (520.0 mg, 0.831 mmol) and N-methyl-N—((S)-1-((R)-1-tritylaziridine-2-carbonyl)pyrrolidine-3-carbonyl)-L-valine (0.6727 g, 1.25 mmol) in DMF (10 mL) at 0° C. was added COMU (0.5338 mg, 1.25 mmol) followed by DIPEA (1.16 mL, 6.65 mmol). After 2 h, the reaction mixture was extracted with EtOAc (3×100 mL) and the combined organic layers were washed with brine (3×30 mL), dried over Na₂SO₄, filtered, and concentrated under reduced pressure. The crude residue was purified by reverse phase chromatography (10→50% MeCN/H₂O) to afford the desired product (500 mg, 52.4% yield) as a solid. LCMS (ESI) m/z: [M+H] calcd for C₆₉H₇₈N₈O₈: 1147.60; found 1147.8.

Step 2: Synthesis of (3S)-1-((R)-aziridine-2-carbonyl)-N-((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide To a stirred solution of (3S)—N-((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methyl-1-((R)-1-tritylaziridine-2-carbonyl)pyrrolidine-3-carboxamide (145.0 mg, 0.126 mmol) in DCM (3 mL) at 0° C. was added Et₃SiH (58.8 mg, 0.505 mmol) followed by TFA (57.6 mg, 0.505 mmol). After 1 h, DIPEA was added to the reaction mixture until pH 8. The resulting mixture was concentrated under reduced pressure, and the residue was purified by reverse phase chromatography (10→50% MeCN/H₂O) to afford the desired product (70 mg, 61.2% yield) as a solid. LCMS (ESI) m/z: [M+H] calcd for C₅₀H₆₄N₈O₈: 905.49; found 905.7.

Example 7. Synthesis of (2R)—N-(2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide

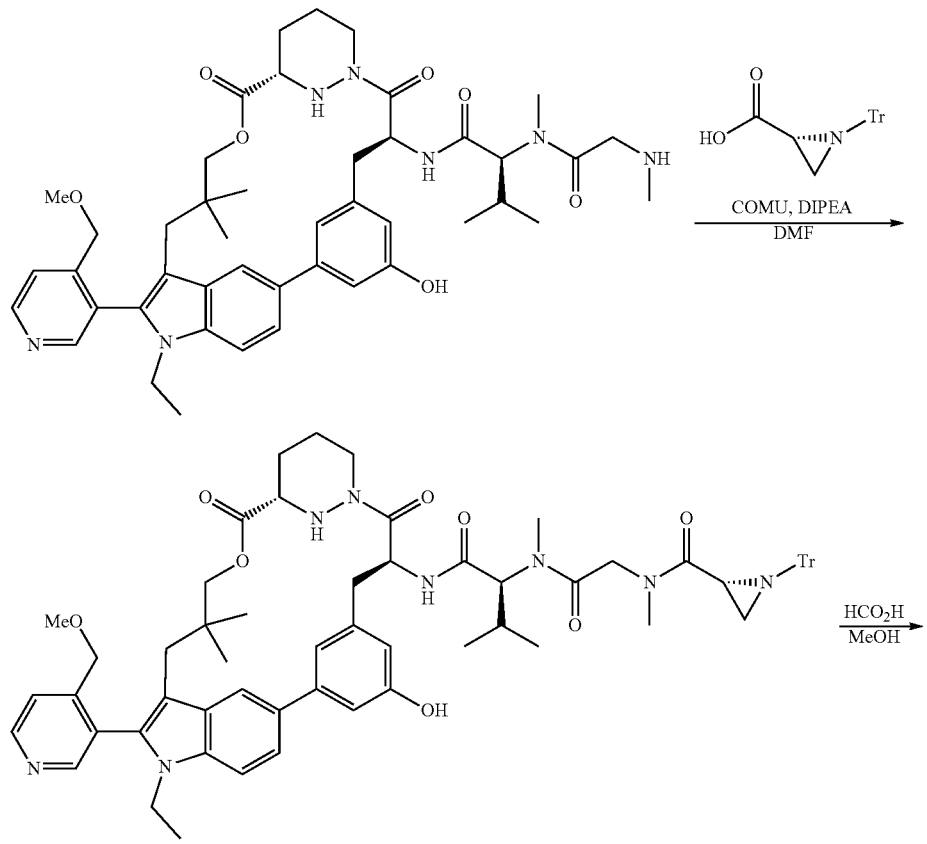

-continued

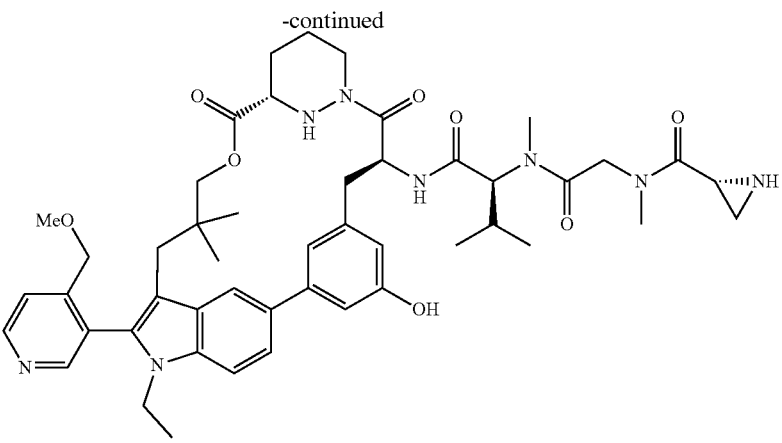

Step 1: Synthesis of (2R)—N-(2-(((2S)-1-(((6³S, 4S)-1¹-ethyl-2⁵-hydroxy-1²-(4-(methoxymethyl) pyridin-3-yl)-10,10-dimethyl-5,7-dioxo-6¹,6²,6³,6⁴, 6⁵,6⁶-hexahydro-1¹H-8-oxa-1(5,3)-indola-6(1,3)-pyridazina-2(1,3)-benzenacycloundecaphane-4-yl) amino)-3-methyl-1-oxobutan-2-yl)(methyl)amino)-2-oxoethyl)-N-methyl-1-tritylaziridine-2-carboxamide To a solution of (2S)—N-((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(N-methyl-2-(methylamino)acetamido) butanamide (285.7 mg, 0.353 mmol) in DMF (3.0 mL) at 0° C. was added (R)-1-tritylaziridine-2-carboxylic acid (232.4 mg, 0.705 mmol) followed by DIPEA (0.61 mL, 4.7 mmol) and COMU (211.4 mg, 0.494 mmol). The resulting mixture was warmed to room temperature and stirred for 1 h. The reaction mixture was diluted with H₂O (15 mL) and the mixture was extracted with EtOAc (3×4 mL). The combined organic layers were washed with brine (10 mL), dried over Na₂SO₄, filtered, and concentrated under reduced pressure. The residue was purified by prep-TLC (12% EtOAc/pet. ether) to afford the desired product (301 mg, 68% yield) as a solid. LCMS (ESI) m/z: [M+H] calcd for $C_{67}H_{76}N_8O_8$: 1121.59; found 1121.8.

Step 2: Synthesis of (2R)—N-(2-(((2S)-1-(((6³S, 4S)-1¹-ethyl-2⁵-hydroxy-1²-(4-(methoxymethyl) pyridin-3-yl)-10,10-dimethyl-5,7-dioxo-6¹,6²,6³,6⁴, 6⁵,6⁶-hexahydro-1¹H-8-oxa-1(5,3)-indola-6(1,3)-pyridazina-2(1,3)-benzenacycloundecaphane-4-yl) amino)-3-methyl-1-oxobutan-2-yl)(methyl)amino)-2-oxoethyl)-N-methylaziridine-2-carboxamide To a solution of (2R)—N-(2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-tritylaziridine-2-carboxamide (301.0 mg, 0.268 mmol) in MeOH (3.0 mL) at 0° C. was added HCO₂H (1.50 mL). The reaction mixture was stirred for 1 h and then neutralized to pH 8 with DIPEA. The resulting mixture was diluted with H₂O (15 mL) and extracted with EtOAc (3×4 mL). The combined organic layers were dried over Na₂SO₄, filtered, and concentrated under reduced pressure. The residue was purified by reverse phase chromatography (30→60% MeCN/H₂O) to afford the desired product (89.9 mg, 38% yield) as a solid. LCMS (ESI) m/z: [M+H] calcd for $C_{48}H_{62}N_8O_8$: 879.48; found 879.7.

Example 15. Synthesis of two Isomers, 15A and 15B, of (2S)—N-((6³S,4S)-1¹-ethyl-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5, 3)-indola-6(1,3)-pyridazina-2(1,3)-benzenacycloundecaphane-4-yl)-2-(3-((((4-methoxyphenyl)imino)methylene)amino)-N-methylpropanamido)-3-methylbutanamide

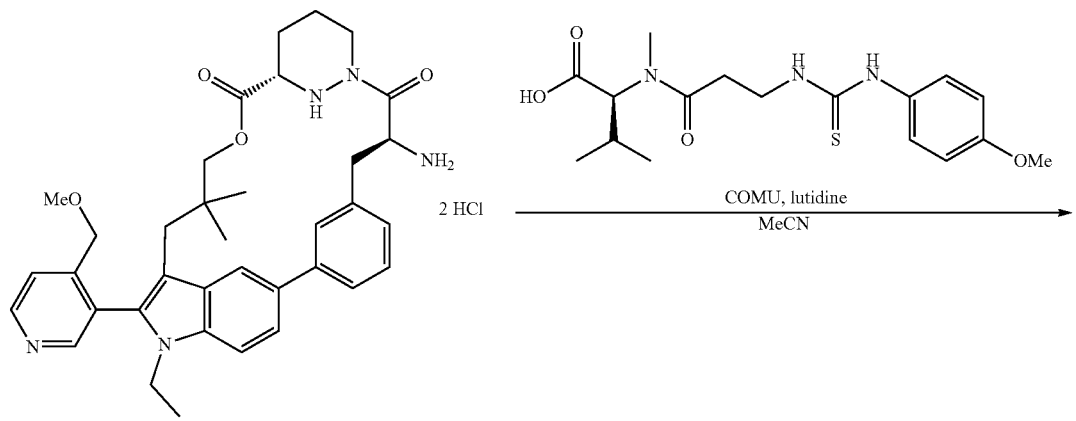

-continued

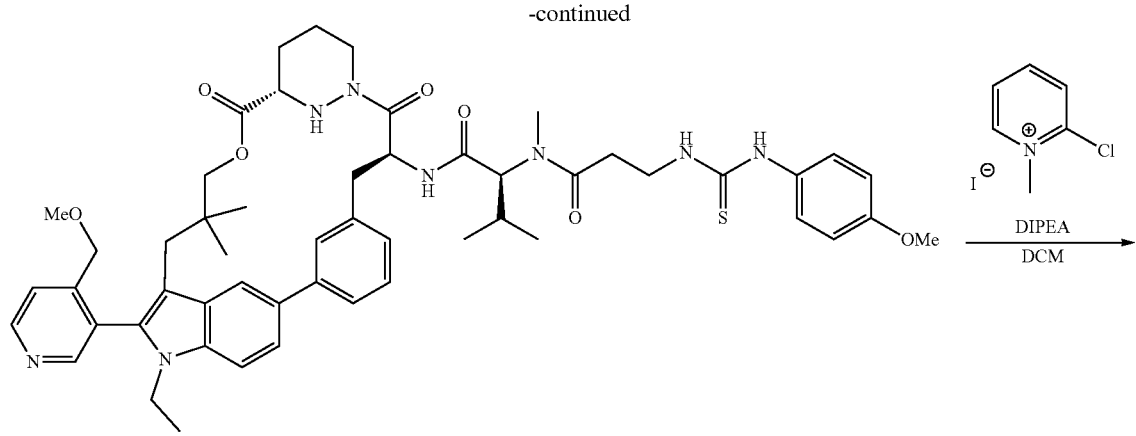

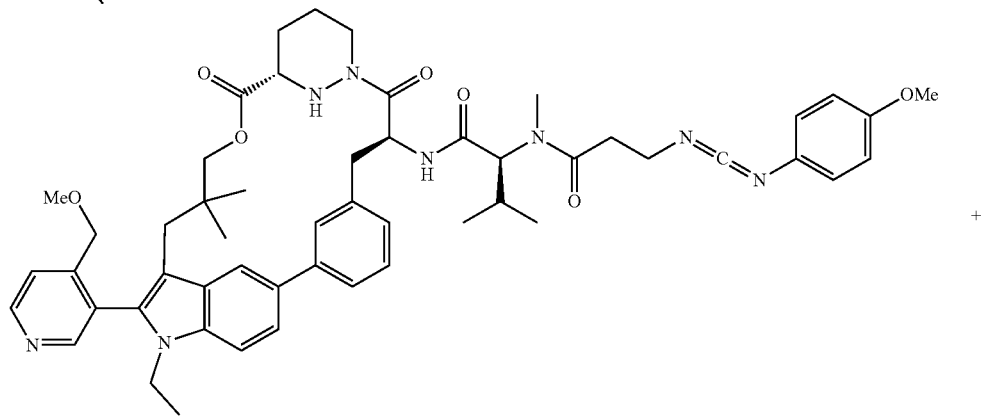

Isomer A

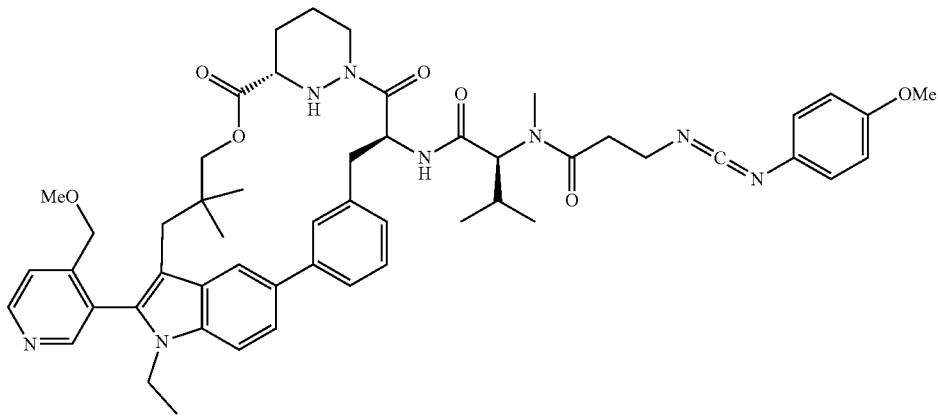

Isomer B

Step 1: Synthesis of (2S)—N-((6³S,4S)-1¹-ethyl-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(3-(3-(4-methoxyphenyl)thioureido)-N-methylpropanamido)-3-methylbutanamide To a solution of (6³S,4S)-4-amino-1¹-ethyl-1²-(4-(methoxymethyl)pyridin-3-yl)-10,10-dimethyl-6¹,6²,6³,6⁴,6⁵,6⁶-hexahydro-1¹H-8-oxa-1(5,3)-indola-6(1,3)- pyridazina-2(1,3)-benzenacycloundecaphane-5,7-dione (108 mg, 168 μmol) and N-(3-(3-(4-methoxyphenyl)thioureido)propanoyl)-N-methyl-L-valine (61.9 mg, 168 μmol) in MeCN (2 mL) at 0° C. was added 2,6-lutidine (97.8 μL, 840 μmol) followed by COMU (78.8 mg, 184 μmol). After 1 h at 0° C. the reaction was diluted with EtOAc and the organic portion washed with H₂O (15 mL) and brine (15 mL), dried over Na₂SO₄, and concentrated under reduced pressure. Purification by silica gel chromatography (20→100% EtOAc/Hex then 0→5% MeOH/EtOAc) afforded the desired product (117.0 mg 72.6% yield). LCMS (ESI) m/z: [M+H] calcd for $C_{53}H_{66}N_8O_7S$: 959.49; found 959.5.

Step 2: Synthesis of two isomers of (2S)—N-((6³S, 4S)-1¹-ethyl-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(3-((((4-methoxyphenyl)imino)methylene)amino)-N-methylpropanamido)-3-methylbutanamide To a solution of (2S)—N-((6³S,4S)-1¹-ethyl-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(3-(3-(4-methoxyphenyl)thioureido)-N-methylpropanamido)-3-methylbutanamide (117.0 mg, 121 μmol) in DCM (1 mL) was added DIPEA (63.2 μL, 363 μmol) followed by 2-chloro-1-methylpyridin-1-ium iodide (42.6 mg, 181 μmol). The reaction mixture was stirred overnight, at which point the solid was filtered and the crude solution was purified by reverse phase chromatography (40→100 MeCN/H₂O+0.4% NH₄OH) to afford two separated isomers as the desired earlier eluting isomer 15A (6.9 mg, 6.2% yield) and later eluting isomer 15B (2.5 mg, 2.2% yield). LCMS (ESI) m/z: [M+H] calcd for $C_{53}H_{64}N_8O_7$: 925.50; found 925.5 and LCMS (ESI) m/z: [M+H] calcd for $C_{53}H_{64}N_8O_7$: 925.50; found 925.6.

Example 25. Synthesis of (2S)-2-(3-(3-(2-chloroethyl)ureido)-N-methylpropanamido)-N-((6³S,4S)-1¹-ethyl-2⁵-hydroxy-1²-(2-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide

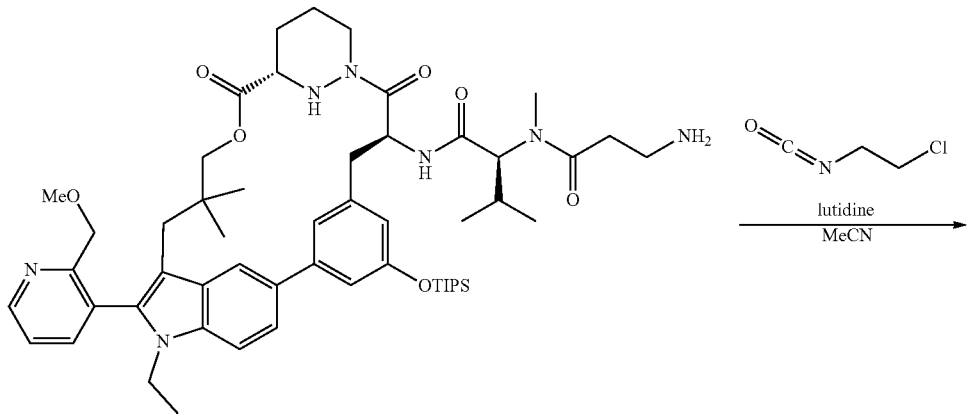

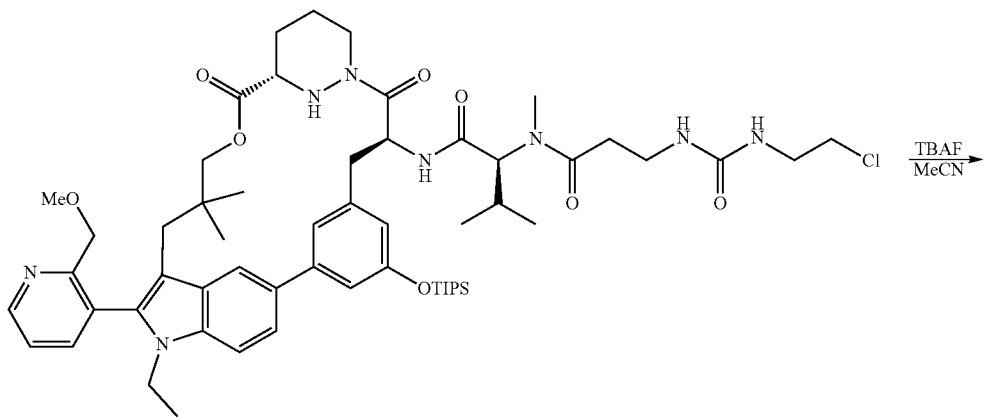

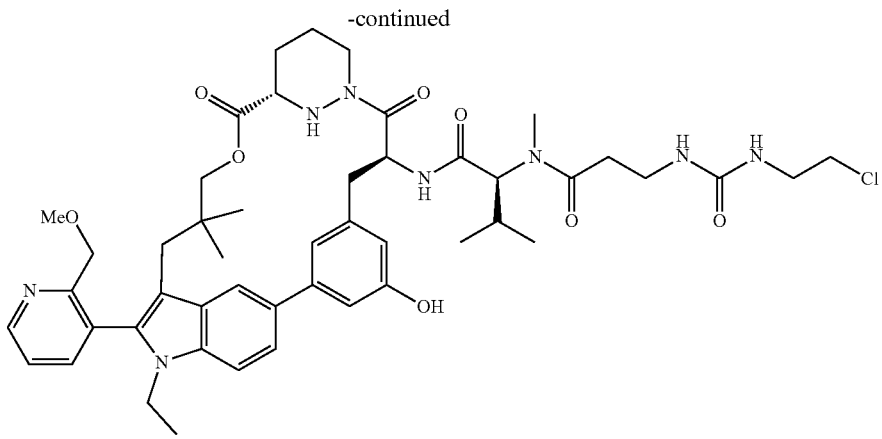

Step 1: Synthesis of (2S)-2-(3-(3-(2-chloroethyl)ureido)-N-methylpropanamido)-N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of (2S)-2-(3-amino-N-methylpropanamido)-N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide (106 mg, 109 µmol) in MeCN (544 µL) at 0° C. was added 1-chloro-2-isocyanatoethane (9.29 µL, 109 µmol) followed by Et₃N (15.1 µL, 109 µmol). After 12 min, the reaction was diluted with DCM (10 mL) and a solution of 1% formic acid in H₂O (10 mL). The aqueous layer was extracted with DCM (10 mL) and the combined organic layers were dried over Na₂SO₄, filtered, and then concentrated under reduced pressure to afford the desired product (117 mg, 100% yield), which was used in the next step without purification. LCMS (ESI) m/z: [M+H] calcd for C₅₇H₈₃ClN₈O₈Si: 1071.59; found 1071.5.

Step 2: Synthesis of (2S)-2-(3-(3-(2-chloroethyl)ureido)-N-methylpropanamido)-N-((6³S,4S)-1¹-ethyl-2⁵-hydroxy-1²-(2-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of (2S)-2-(3-(3-(2-chloroethyl)ureido)-N-methylpropanamido)-N-((6³S,4S)-1¹-ethyl-1²-(2-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide (117 mg, 109 µmol) in MeCN (1.1 mL) at 0° C. was added TBAF (1M in dioxane, 109 µL, 109 µmol). After 5 min, the reaction was concentrated under reduced pressure and the crude residue was purified by normal phase chromatography (20→100% B/A, B=10% MeOH/EtOAc, A=hexanes) followed by reverse phase chromatography (20→60% MeCN/H₂O) to afford the final product (82.2 mg, 82% yield). LCMS (ESI) m/z: [M+H] calcd for C₄₈H₆₃ClN₈O₈: 915.45; found 915.7.

Example 30. Synthesis of (2S)-2-(3-((4,5-dihydrooxazol-2-yl)amino)-N-methylpropanamido)-N-((6³S,4S)-1¹-ethyl-2⁵-hydroxy-1²-(2-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide

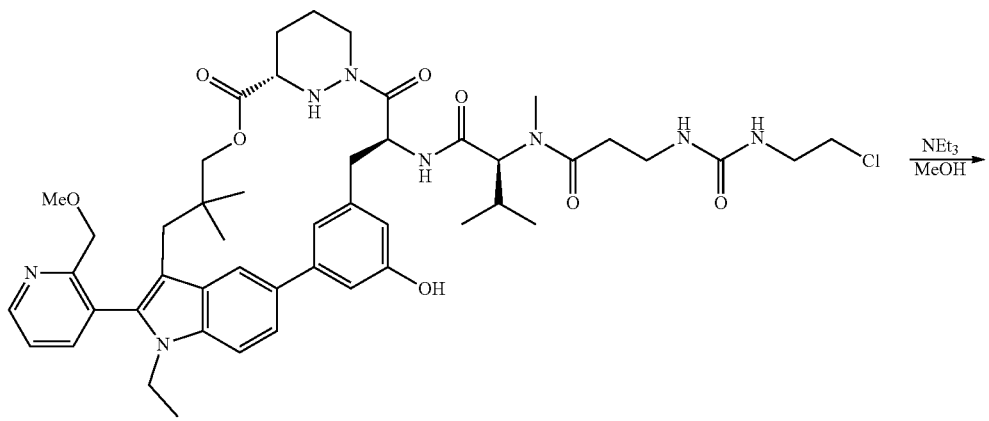

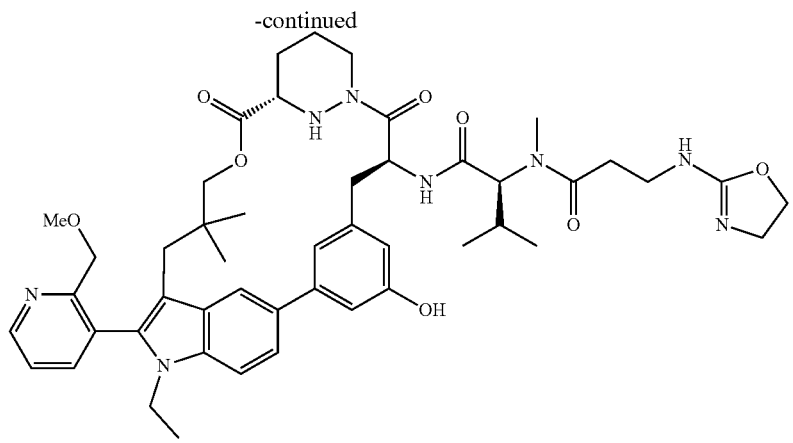

A solution of (2S)-2-(3-(3-(2-chloroethyl)ureido)-N-methylpropanamido)-N-(($6^3$S,4S)-$1^1$-ethyl-$2^5$-hydroxy-$1^2$-(2-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-3-methylbutanamide (55.0 mg, 60.0 μmol) and Et$_3$N (25.1 μL, 180 μmol) in MeOH (1.2 mL) was heated in the microwave at 150° C. for 1 min. The reaction mixture was cooled to room temperature and concentrated under reduced pressure. The crude residue was then purified by reverse phase chromatography (30→100% MeCN/H$_2$O+0.4% NH$_4$OH) to afford the final product (21.1 mg, 40% yield). LCMS (ESI) m/z: [M+H] calcd for C$_{48}$H$_{62}$N$_8$O$_8$: 879.48; found 879.4.

Example 31. Synthesis of (3S)—N-((2S)-1-((($6^3$S,4S)-$1^1$-ethyl-$2^5$-hydroxy-$1^2$-(4-(methoxymethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-pyridazina-2(1,3)-benzenacycloundecaphane-4-yl)amino)-3-methyl-1-oxobutan-2-yl)-N-methyl-1-((S)-oxirane-2-carbonyl)pyrrolidine-3-carboxamide

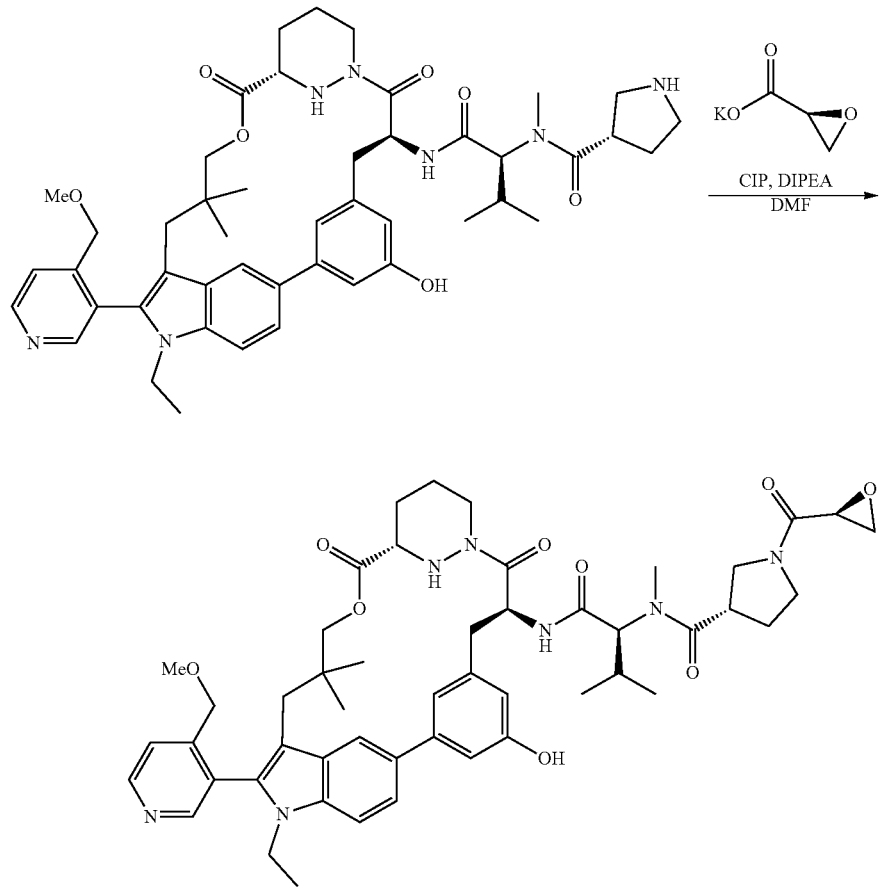

To a solution of potassium (S)-oxirane-2-carboxylate (16.98 mg, 0.135 mmol), 2-chloro-1,3-dimethylimidazolidinium hexafluorophosphate (87.46 mg, 0.314 mmol), and DIPEA (0.156 mL, 0.897 mmol) in DMF (1.5 mL) at 0° C. was added (3S)—N-((2S)-1-(((6$^3$S,4S)-1$^1$-ethyl-2$^5$-hydroxy-1$^2$-(4-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)-N-methylpyrrolidine-3-carboxamide (75.0 mg, 0.09 mmol). The resulting mixture was stirred overnight at room temperature, at which point it was diluted with EtOAc (100 mL). The organic layer was washed with brine (3×5 mL), dried over Na$_2$SO$_4$, filtered, and concentrated under reduced pressure. Purification by reverse phase chromatography (25→55% MeCN/H$_2$O) afforded the desired product (6.3 mg, 7.8% yield) as a solid. LCMS (ESI) m/z: [M+H] calcd for C$_{50}$H$_{63}$N$_7$O$_9$: 906.48; found 906.7.

Example 34. Synthesis of (2R)-1-acetyl-N-(2-(((2S)-1-(((6$^3$S,4S)-1$^1$-ethyl-2$^5$-hydroxy-1$^2$-(4-(methoxymethyl)pyridin-3-yl)-10,10-dimethyl-5,7-dioxo-6$^1$,6$^2$,6$^3$,6$^4$,6$^5$,6$^6$-hexahydro-1$^1$H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide

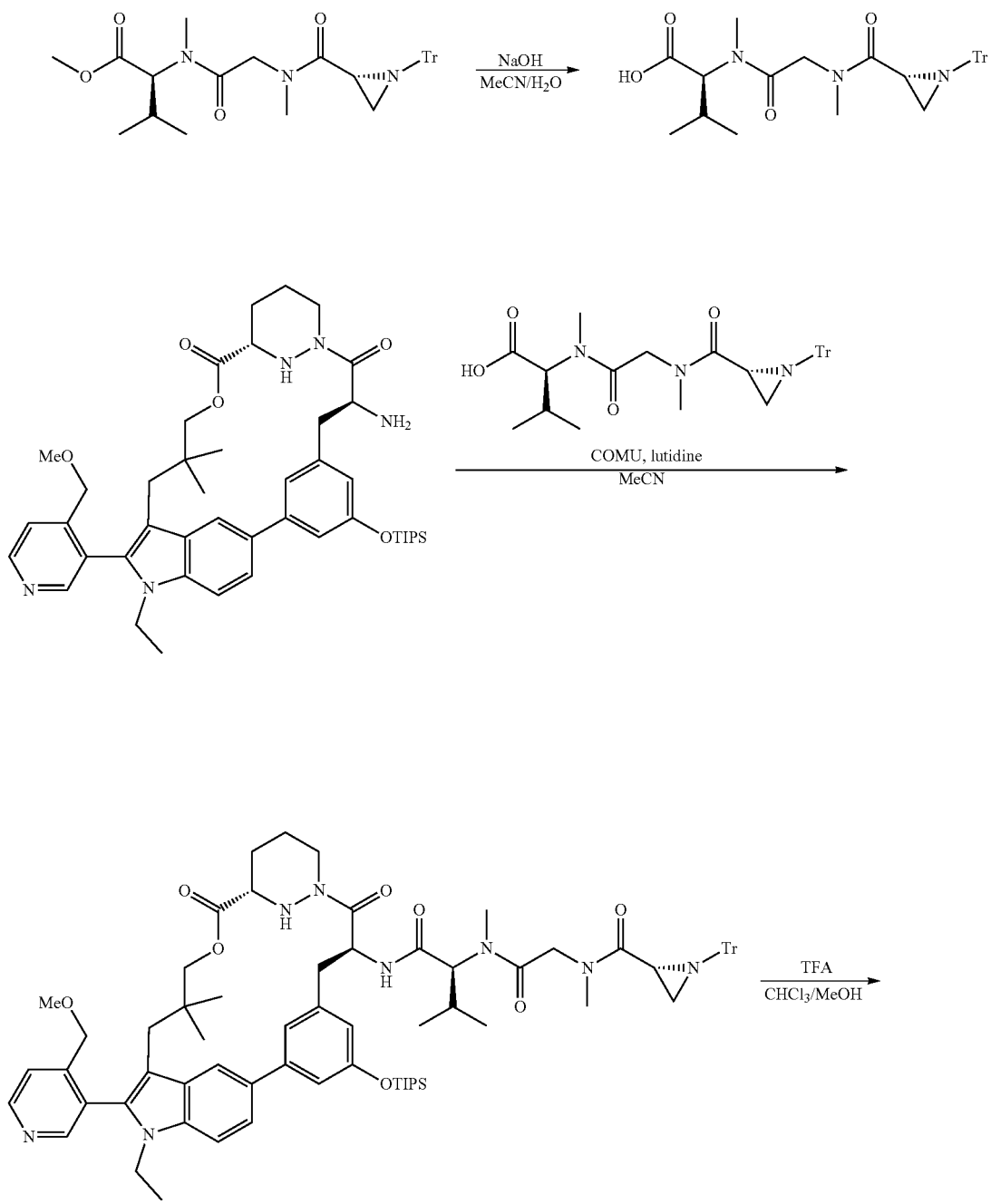

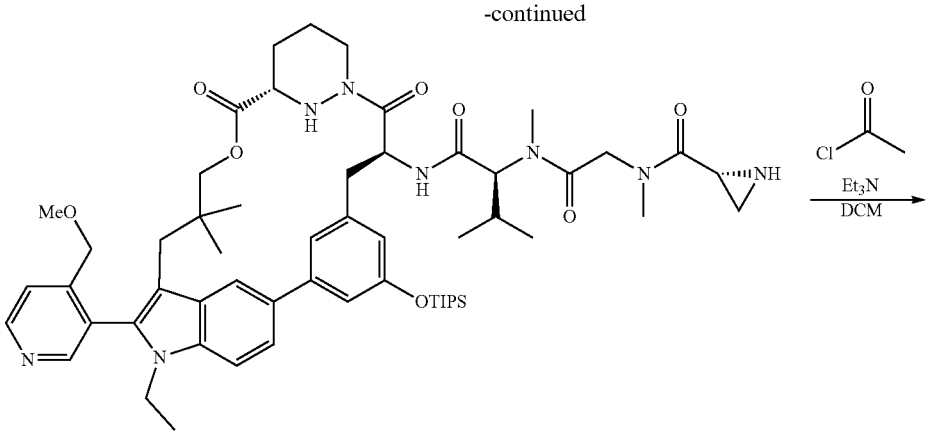

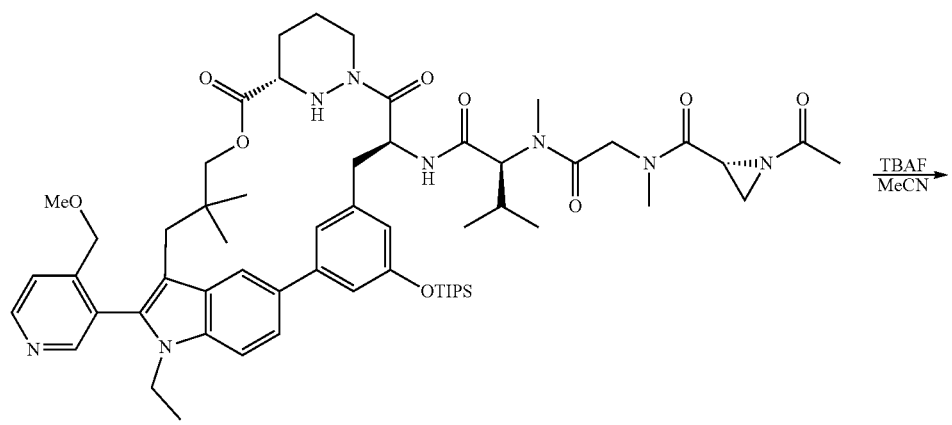

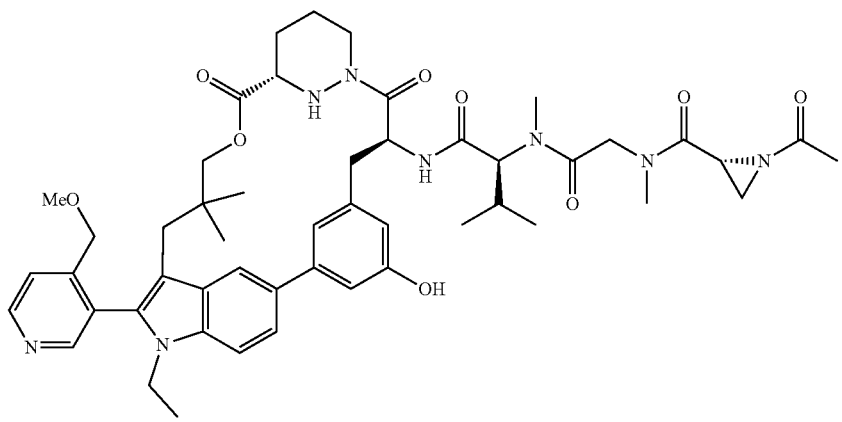 [SMILES: CCn1c(-c2cnccc2COC)c2c3cc(ccc31)-c1cc(O)cc(c1)C[C@H](NC(=O)[C@H](C(C)C)N(C)C(=O)CN(C)C(=O)[C@H]1CN1C(C)=O)C(=O)N1CCC[C@H](N1)C(=O)OCC(C)(C)C2]

Step 1: Synthesis of (2R)—N-(2-(((2S)-1-((($6^3$S, 4S)-$1^1$-ethyl-$1^2$-(4-(methoxymethyl)pyridin-3-yl)-10,10-dimethyl-5,7-dioxo-$2^5$-((triisopropylsilyl)oxy)-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-tritylaziridine-2-carboxamide To a solution of ($6^3$S,4S)-4-amino-$1^1$-ethyl-$1^2$-(4-(methoxymethyl)pyridin-3-yl)-10,10-dimethyl-$2^5$-((triisopropylsilyl)oxy)-$6^1$,$6^2$,$6^3$,$6^4$,$6^5$,$6^6$-hexahydro-$1^1$H-8-oxa-1 (5,3)-indola-6(1,3)-pyridazina-2(1,3)-benzenacycloundecaphane-5,7-dione (260 mg, 0.332 mmol) and N-methyl-N—(N-methyl-N—((R)-1-tritylaziridine-2-carbonyl)glycyl)-L-valine (204 mg, 0.399 mmol) in MeCN (3.3 mL) at 0° C. was added lutidine (192 μL, 1.66 mmol) followed by COMU (156 mg, 0.366 mmol). The reaction stirred at 0° C. for 1 h and was then diluted with EtOAc. The mixture was washed with H$_2$O/brine (1:1), dried over Na$_2$SO$_4$, filtered, and concentrated under reduced pressure. Purification by normal phase chromatography (0→100% EtOAc/hexanes) afforded the desired product (116 mg, 27% yield). LCMS (ESI) m/z: [M+H] calcd for C$_{76}$H$_{96}$N$_8$O$_8$Si: 1277.72; found 1277.7.

Step 2: Synthesis of (2R)—N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide To a solution of (2R)—N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-tritylaziridine-2-carboxamide (400 mg, 0.313 mmol) in MeOH (1.56 mL) and chloroform (1.56 mL) at 0° C. was added TFA (191 µL, 2.50 mmol). The reaction stirred at 0° C. for 2 h and was then quenched with lutidine (364 µL, 3.13 mmol). The reaction mixture was diluted with DCM, washed with H$_2$O, and concentrated under reduced pressure. Purification by reverse phase chromatography (10→100% MeCN/H$_2$O) afforded the desired product (100 mg, 31% yield). LCMS (ESI) m/z: [M+H] calcd for C$_{57}$H$_{82}$N$_8$O$_8$Si: 1035.61; found 1035.6.

Step 3: Synthesis of (2R)-1-acetyl-N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide To a solution of (2R)—N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide (33 mg, 0.032 mmol) in DCM (637 µL) at 0° C. was added Et$_3$N (22.1 µL, 0.159 mmol) followed by acetyl chloride (4.54 µL, 0.064 mmol). The reaction stirred at 0° C. for 1 h. The reaction was then diluted with DCM, washed with NaHCO$_3$, dried over Na$_2$SO$_4$, filtered, and concentrated under reduced pressure to afford the desired crude product (37 mg, 100% yield). LCMS (ESI) m/z: [M+H] calcd for C$_{59}$H$_{84}$N$_8$O$_9$Si: 1077.62; found 1077.6.

Step 4: Synthesis of (2R)-1-acetyl-N-(2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide To a solution of (2R)-1-acetyl-N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide (34 mg, 0.032 mmol) in MeCN (631 µL) at 0° C. was added TBAF (1M in THF, 31.5 µL, 0.032 mmol). The reaction stirred for 10 min and was then diluted with DCM, washed with brine, dried over Na$_2$SO$_4$, filtered, and concentrated under reduced pressure. Purification by reverse phase chromatography (10→100% MeCN/H$_2$O) afforded the desired product (8.5 mg, 29% yield). LCMS (ESI) m/z: [M+H] calcd for C$_{50}$H$_{64}$N$_8$O$_9$: 921.49; found 921.5.

Example 36. Synthesis of (2R)—N-(2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(methylsulfonyl)aziridine-2-carboxamide

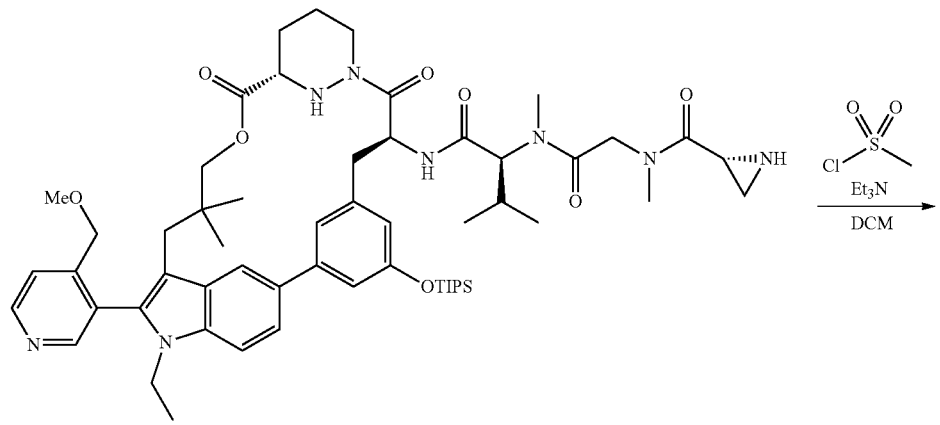

-continued

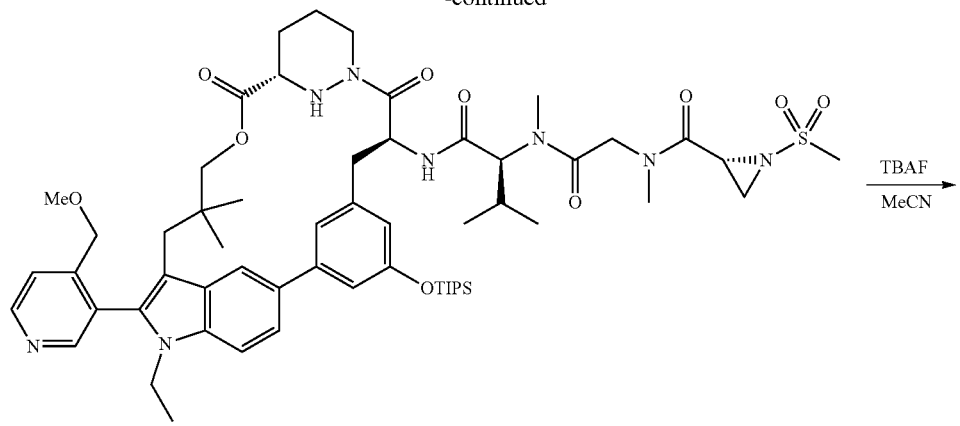

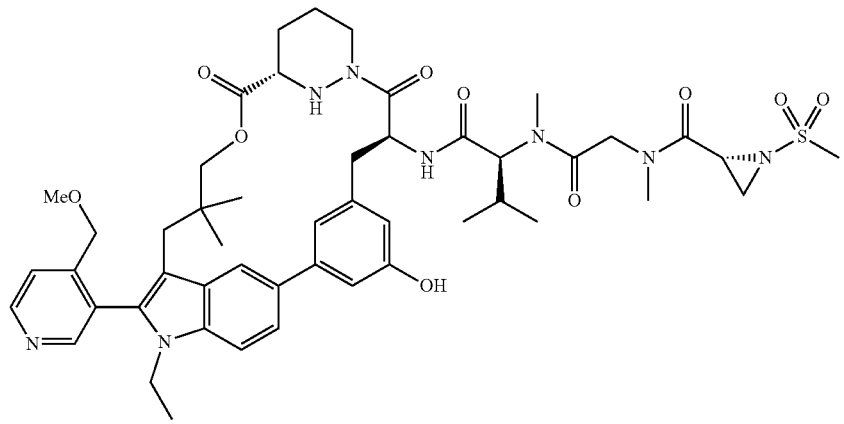

Step 1: Synthesis of (2R)—N-(2-(((2S)-1-(((6³S, 4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(methylsulfonyl)aziridine-2-carboxamide To a solution of (2R)—N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide (33 mg, 0.032 mmol) in DCM (637 µL) at 0° C. was added Et₃N (22.1 µL, 0.159 mmol) followed by methanesulfonyl chloride (4.93 µL, 0.064 mmol). The reaction was cooled to 0° C. for 1 h and was then diluted with DCM, washed with NaHCO₃, dried over Na₂SO₄, filtered, and concentrated under reduced pressure to afford the desired crude product (35 mg, 100% yield). LCMS (ESI) m/z: [M+H] calcd for C₅₈H₈₄N₈O₁₀SSi: 1113.59; found 1113.6.

Step 2: Synthesis of (2R)—N-(2-(((2S)-1-(((6³S, 4S)-1¹-ethyl-2⁵-hydroxy-1²-(4-(methoxymethyl) pyridin-3-yl)-10,10-dimethyl-5,7-dioxo-6¹,6²,6³,6⁴, 6⁵,6⁶-hexahydro-1¹H-8-oxa-1(5,3)-indola-6(1,3)-pyridazina-2(1,3)-benzenacycloundecaphane-4-yl) amino)-3-methyl-1-oxobutan-2-yl)(methyl)amino)-2-oxoethyl)-N-methyl-1-(methylsulfonyl)aziridine-2-carboxamide To a solution of (2R)—N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(methylsulfonyl)aziridine-2-carboxamide (35 mg, 0.032 mmol) in MeCN (646 µL) at 0° C. was added TBAF (1M in THF, 32.3 µL, 0.032 mmol). The reaction stirred for 10 min and was then diluted with DCM, washed with brine, dried over Na₂SO₄, filtered, and concentrated under reduced pressure. Purification by reverse phase chromatography (10→100% MeCN/H₂O) afforded the desired product (20 mg, 65% yield). LCMS (ESI) m/z: [M+H] calcd for C₄₉H₆₄N₈O₁₀S: 957.45; found 957.5.

Example 38. Synthesis of methyl (2R)-2-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6², 6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-1-carboxylate
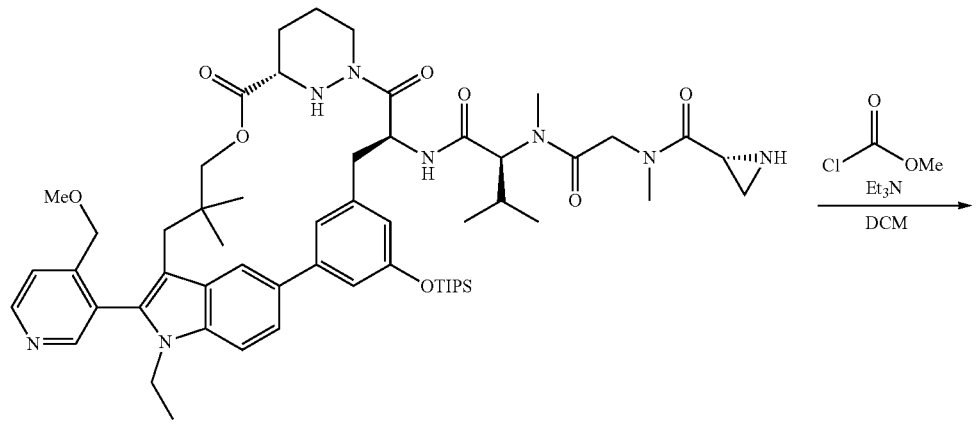
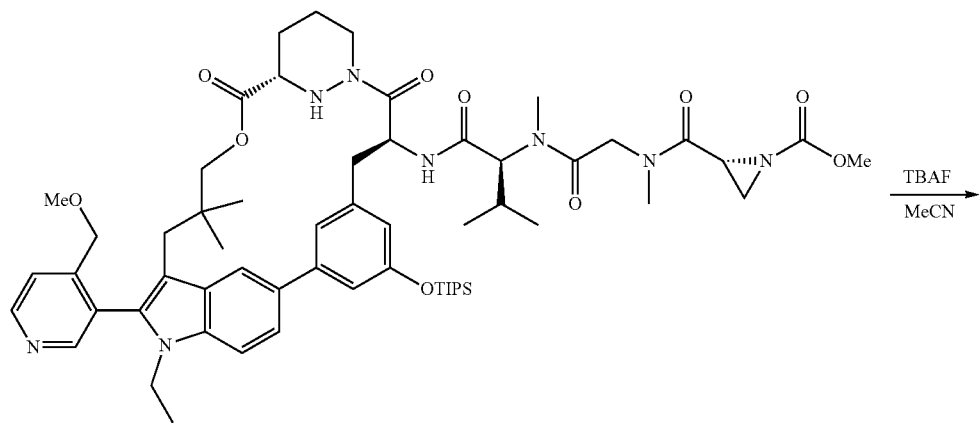
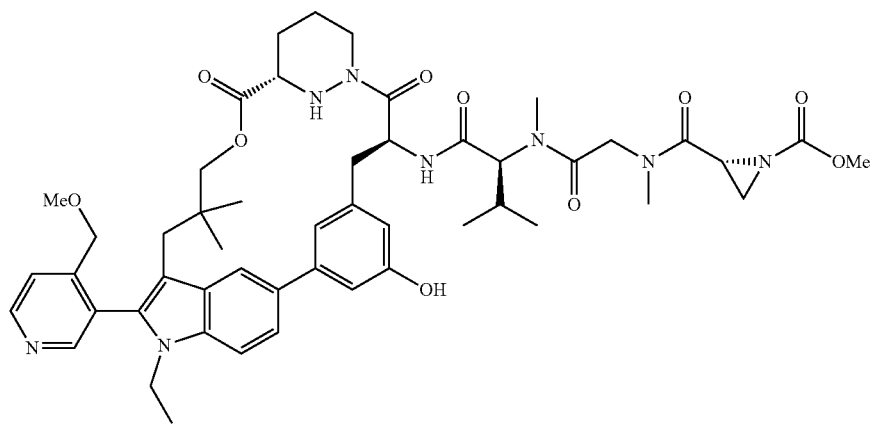

Step 1: Synthesis of methyl (2R)-2-((2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-1-carboxylate To a solution of (2R)—N-(2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide (46 mg, 0.044 mmol) in DCM (888 µL) at 0° C. was added E3N (30.8 µL, 0.22 mmol) followed by methyl chloroformate (4.46 µL, 0.058 mmol). The reaction stirred at 0° C. for 1 h and then the reaction was diluted with DCM, washed with NaHCO₃, dried over Na₂SO₄, filtered, and concentrated under reduced pressure to afford the desired crude product (56 mg, 100% yield). LCMS (ESI) m/z: [M+H] calcd for $C_{59}H_{84}N_8O_{10}Si$: 1093.62; found 1093.7.

Step 2: Synthesis of methyl (2R)-2-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-1-carboxylate To a solution of methyl (2R)-2-((2-(((2S)-1-(((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-1-carboxylate (56 mg, 0.051 mmol) in MeCN (1.0 mL) at 0° C. was added TBAF (1M in THF, 51.2 µL, 0.051 mmol). The reaction stirred for 15 min and was then diluted with DCM, washed with brine, dried over Na₂SO₄, filtered, and concentrated under reduced pressure. Purification by reverse phase chromatography (10→100% MeCN/H₂O) afforded the desired product (17 mg, 36% yield). LCMS (ESI) m/z: [M+H] calcd for $C_{50}H_{64}N_8O_{10}$: 937.48; found 937.6.

Example 48 and 49. Synthesis of methyl (2S,3R)-1-((R)-tert-butylsulfinyl)-3-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-2-carboxylate and methyl (2S,3R)-3-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-2-carboxylate

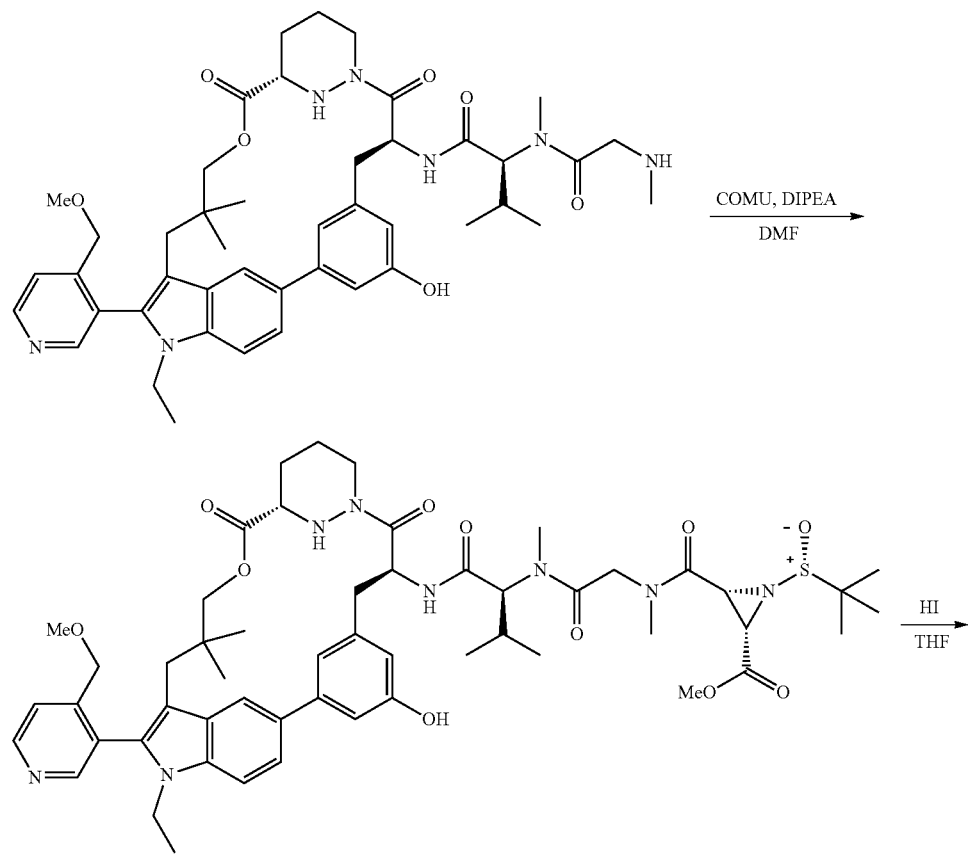

-continued

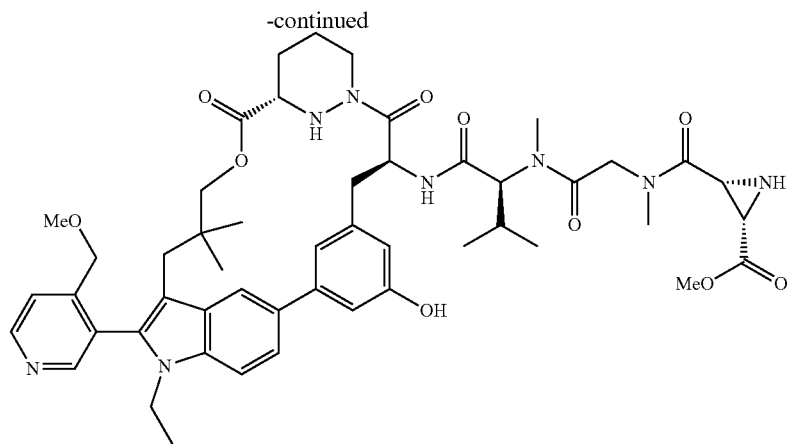

Step 1: Synthesis of methyl (2S,3R)-1-((R)-tert-butylsulfinyl)-3-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)aziridine-2-carboxylate To a solution of (2S)—N-((63S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(N-methyl-2-(methylamino)acetamido)butanamide (267.0 mg, 0.33 mmol) and (2R,3S)-1-((R)-tert-butylsulfinyl)-3-(methoxycarbonyl)aziridine-2-carboxylic acid (246.5 mg, 0.99 mmol) in DMF (4.5 mL) at 0° C. was added DIPEA (0.574 mL, 3.3 mmol) followed by a solution of COMU (211.8 mg, 0.49 mmol) in DMF (0.5 mL). The resulting mixture was stirred for 1 h at 0° C. and was then quenched with sat. NH₄Cl. The aqueous layer was extracted with EtOAc (3×20 mL) and the combined organic layers were washed with brine (2×50 mL), dried over Na₂SO₄, filtered, concentrated under reduced pressure. The crude product was purified by reverse phase chromatography (35→65% MeCN/H₂O) to afford the desired product (253 mg, 73.7% yield). LCMS (ESI) m/z: [M+H] calcd for $C_{54}H_{72}N_8O_{11}S$: 1041.51; found 1041.8.

Step 2: Synthesis of methyl (2S,3R)-3-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-2-carboxylate To a solution of methyl (2S,3R)-1-((R)-tert-butylsulfinyl)-3-((2-(((2S)-1-(((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)(methyl)carbamoyl)aziridine-2-carboxylate (200.0 mg, 0.19 mmol) in THF (4.0 mL) at 0° C. was added HI (1.0 mL), dropwise. The resulting mixture was stirred for 10 min at 0° C. and was then basified to pH 7 with DIPEA. The mixture was extracted with EtOAc (3×30 mL) and the combined organic layers were washed with brine (50 mL), dried over Na₂SO₄, filtered, and concentrated under reduced pressure. The residue was purified by reverse phase chromatography (35→65% MeCN/H₂O) to afford the desired product (13.2 mg, 7.3% yield). LCMS (ESI) m/z: [M+H] calcd for $C_{50}H_{64}N_8O_{10}$: 937.48; found 938.6.

Example 55. Synthesis of (2S)-2-(2-((1R,5S)-6-benzyl-2,4-dioxo-3,6-diazabicyclo[3.1.0]hexan-3-yl)-N-methylacetamido)-N-((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide

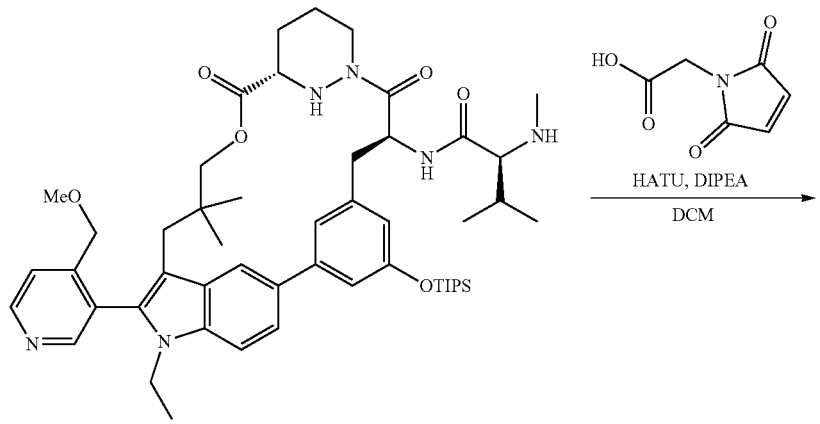

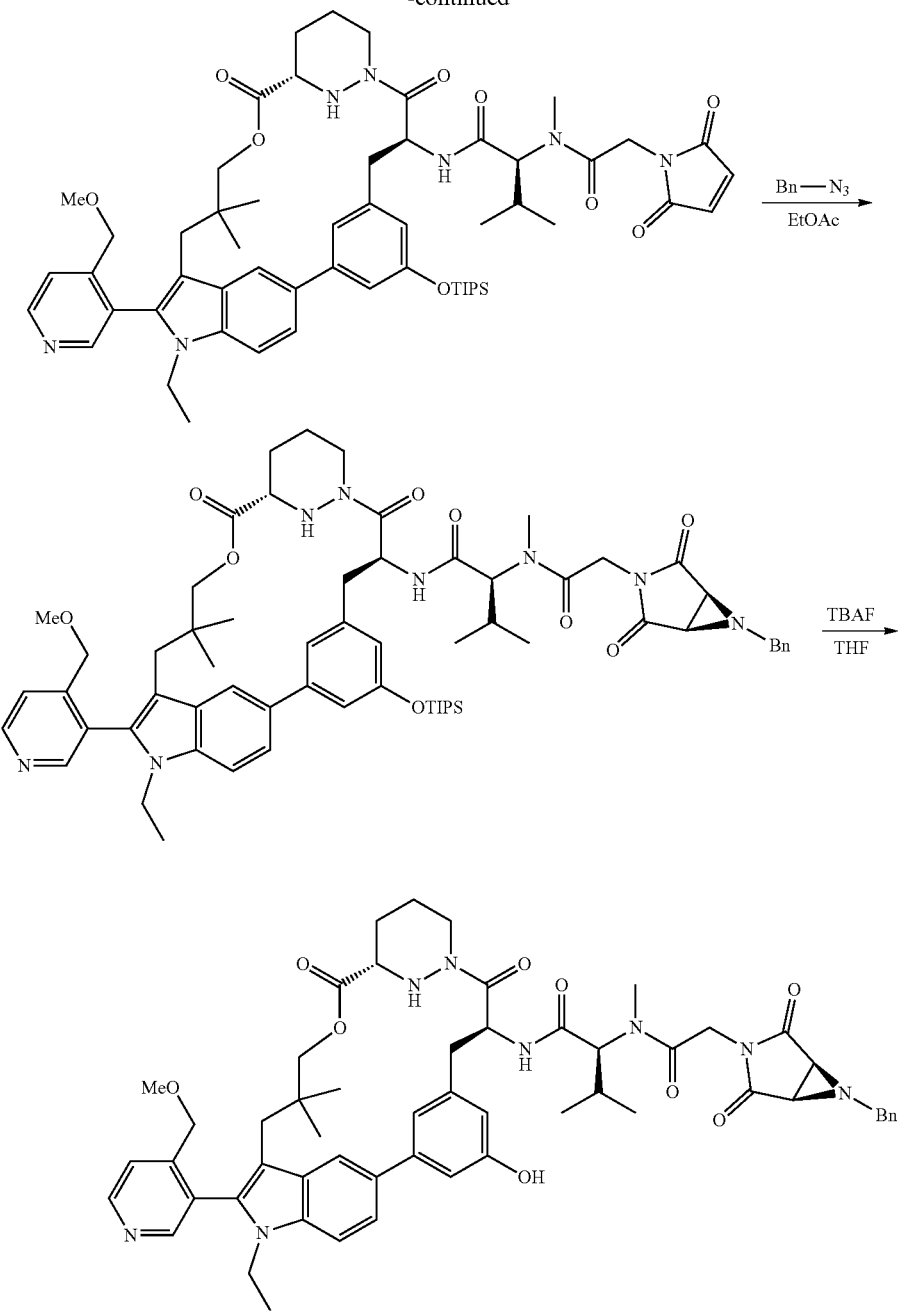

Step 1: Synthesis of (2S)-2-(2-(2,5-dioxo-2,5-dihydro-1H-pyrrol-1-yl)-N-methylacetamido)-N-((6³S, 4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of (2S)—N-((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino) butanamide (600.0 mg, 0.67 mmol) and 2-(2,5-dioxo-2,5-dihydro-1H-pyrrol-1-yl)acetic acid (124.7 mg, 0.80 mmol) in DCM (6.0 mL) at 0° C. was added DIPEA (0.934 mL, 5.36 mmol) followed by HATU (382.2 mg, 1.01 mmol). The reaction mixture was warmed to room temperature and stirred for 3 h. The reaction was then quenched by the addition of H₂O (20 mL). The aqueous layer was extracted with DCM (2×50 mL) and the combined organic layers were washed with brine (2×50 mL), dried over Na₂SO₄, and concentrated under reduced pressure. The residue was purified by normal phase chromatography (10→20% EtOAc/ pet. ether) to afford the desired product (260 mg, 33.8% yield). LCMS (ESI) m/z: [M+H] calcd for $C_{57}H_{77}N_7O_9Si$: 1032.56; found 1032.8.

Step 2: Synthesis of (2S)-2-(2-((1R,5S)-6-benzyl-2, 4-dioxo-3,6-diazabicyclo[3.1.0]hexan-3-yl)-N-methylacetamido)-N-((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of (2S)-2-(2-(2,5-dioxo-2,5-dihydro-1H-pyrrol-1-yl)-N-methylacetamido)-N-((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide (250.0 mg, 0.24 mmol) in EtOAc (2.0 mL) was added (azidomethyl)benzene (80.6 mg, 0.61 mmol). The reaction mixture was heated to 80° C. and stirred for 2 h. The reaction mixture was then heated to 120° C. and stirred for 2 days. The reaction mixture was then cooled to room temperature and quenched with H₂O. The aqueous layer was extracted with EtOAc and the combined organic layers were washed with brine, dried with Na₂SO₄, filtered, and concentrated under reduced pressure. The residue was purified by normal phase chromatography to afford the desired product (50 mg, 18.1% yield). LCMS (ESI) m/z: [M+H] calcd for C₆₄H₈₄N₈O₉Si: 1137.62; found 1138.3.

Step 3: Synthesis of (2S)-2-(2-((1R,5S)-6-benzyl-2, 4-dioxo-3,6-diazabicyclo[3.1.0]hexan-3-yl)-N-methylacetamido)-N-((6³S,4S)-1¹-ethyl-2⁵-hydroxy-1²-(4-(methoxymethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of (2S)-2-(2-((1R,5S)-6-benzyl-2,4-dioxo-3,6-diazabicyclo[3.1.0]hexan-3-yl)-N-methylacetamido)-N-((6³S,4S)-1¹-ethyl-1²-(4-(methoxymethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide (50.0 mg, 0.04 mmol) in THF (0.5 mL) at 0° C. was added 1M TBAF (0.07 mL, 0.07 mmol). The reaction mixture was stirred for 1 h. The reaction mixture was then diluted with H₂O and extracted with EtOAc. The combined organic layers were washed with brine, dried over Na₂SO₄, filtered, and concentrated under reduced pressure. The residue was purified by prep-TLC followed by reverse phase chromatography (45→72% MeCN/H₂O) to afford the desired product (20 mg, 46.4% yield). LCMS (ESI) m/z: [M+Na] calcd for C₅₅H₆₄N₈O₉: 1003.47; found 1003.8.

Example 95. Synthesis of (2R)—N-(2-(((1S)-1-cyclopentyl-2-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methylaziridine-2-carboxamide

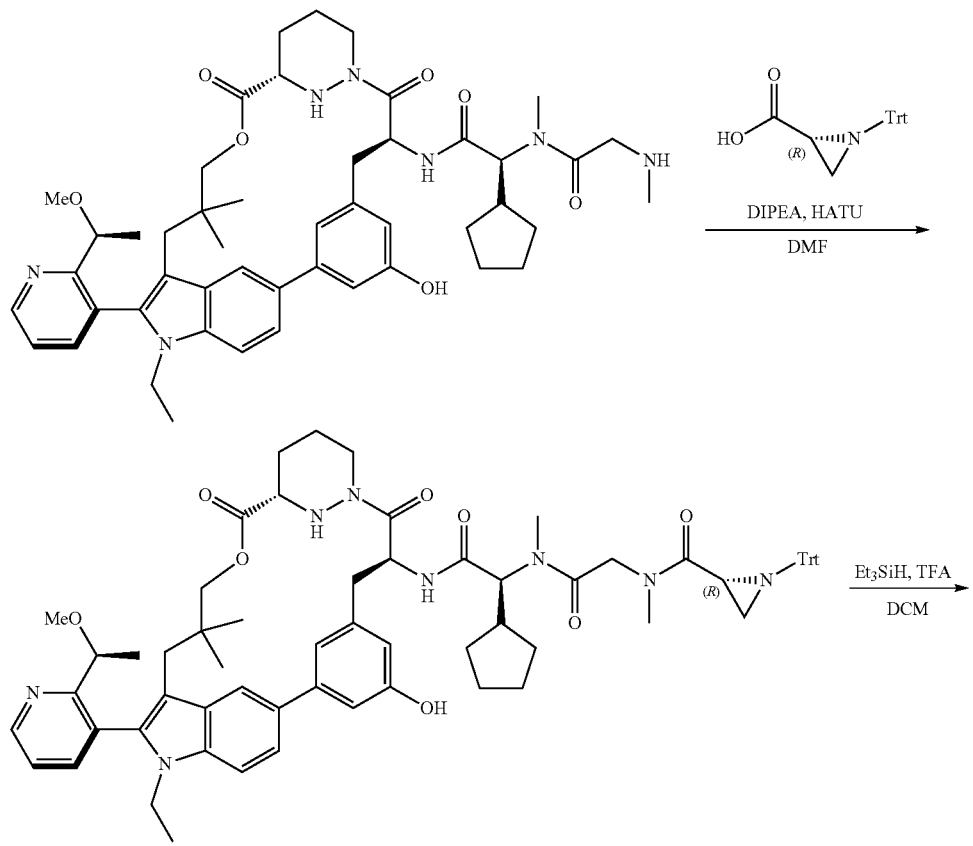

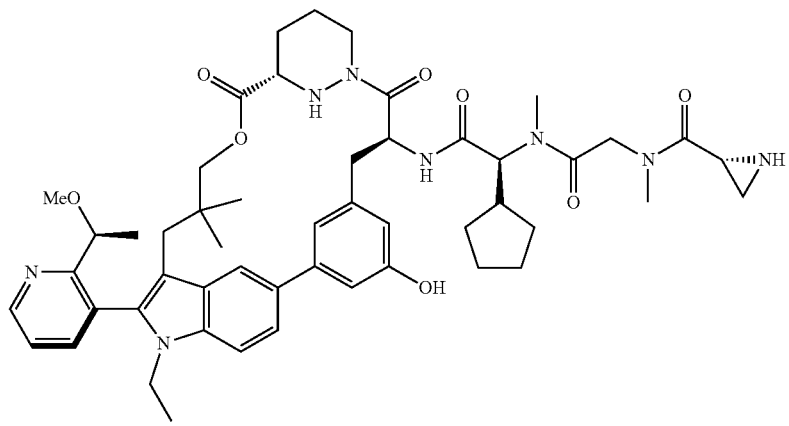

Step 1: Synthesis of (2R)—N-(2-(((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methyl-1-tritylaziridine-2-carboxamide To a mixture of (2S)-2-cyclopentyl-N-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)-2-(N-methyl-2-(methylamino)acetamido)acetamide (321.2 mg, 0.276 mmol), DIPEA (0.472 mL, 2.764 mmol), and (R)-1-tritylaziridine-2-carboxylic acid (136.59 mg, 0.415 mmol) in DMF (3.0 mL) at 0° C. was added HATU (126.14 mg, 0.332 mmol). The resulting mixture was stirred at 0° C. for 30 min, then diluted with $H_2O$ (30 mL) and extracted with EtOAc (3×30 mL). The combined organic layers were washed with brine (3×10 mL), dried with $Na_2SO_4$, filtered, and concentrated under reduced pressure. Purification by prep-TLC (50% EtOAc/pet. ether) afforded the desired product (200 mg, 62.3% yield). LCMS (ESI) m/z: [M+H] calcd for $C_{70}H_{80}N_8O_8$: 1161.62; found 1161.5.

Step 2: Synthesis of (2R)—N-(2-(((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methylaziridine-2-carboxamide To a mixture of (2R)—N-(2-(((1S)-1-cyclopentyl-2-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1$,$6^2$,$6^3$,$6^4$,$6^5$,$6^6$-hexahydro-$1^1$H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methyl-1-tritylaziridine-2-carboxamide (195.0 mg, 0.168 mmol) in DCM (2.0 mL) at 0° C. was added $Et_3SiH$ (78.09 mg, 0.672 mmol) and TFA (76.57 mg, 0.672 mmol). The resulting mixture was stirred at 0° C. for 30 min then basified to pH 8 with DIPEA and concentrated under reduced pressure. Purification by reverse phase chromatography (25→55% MeCN/$H_2O$) to afford the desired product (60 mg, 38.9% yield). LCMS (ESI) m/z: [M+H] calcd for $C_{51}H_{66}N_8O_8$: 919.51; found 919.5.

Example 87. Synthesis of 6-((S)-aziridin-2-yl)-N-((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylnicotinamide
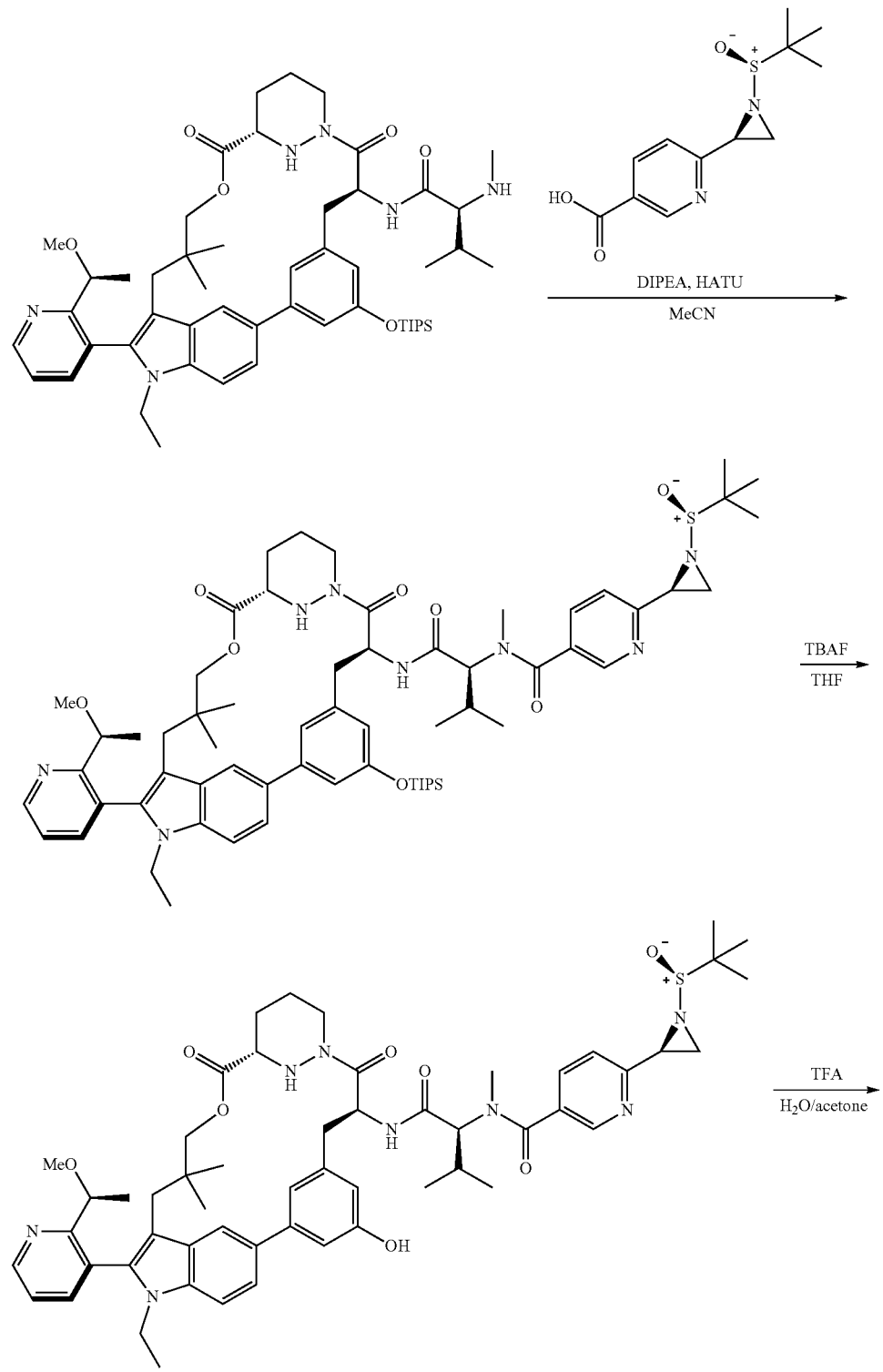

-continued

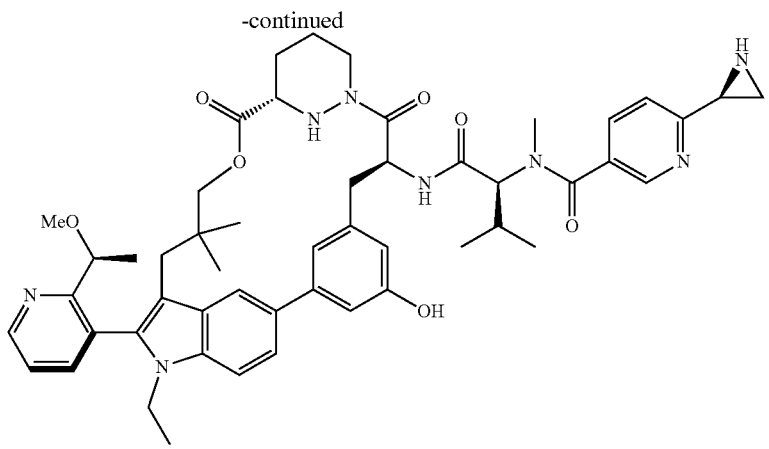

Step 1: Synthesis of 6-((2S)-1-(tert-butylsulfinyl) aziridin-2-yl)-N-((2S)-1-(((6³S,4S)-1¹-ethyl-1²-(2-((S)-1-methoxyethyl)pyridin-3-yl)-10,10-dimethyl-5, 7-dioxo-25-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) amino)-3-methyl-1-oxobutan-2-yl)-N-methylnicotinamide To a mixture of (2S)—N-((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-(methylamino) butanamide (198.24 mg, 0.218 mmol) and DIPEA (0.074 mL, 0.436 mmol) in MeCN (10 mL) at 0° C. was added HATU (200 mg, 0.526 mmol) and the resulting mixture was stirred for 3 min. To the mixture was then added a solution of 6-((2S)-1-(tert-butylsulfinyl)aziridin-2-yl)nicotinic acid (117.0 mg, 0.436 mmol) in MeCN (10 mL) in portions. The resulting mixture was stirred overnight at 0° C. and then was then quenched with H₂O extracted with EtOAc (3×20 mL). The combined organic layers were washed with brine (20 mL), dried with Na₂SO₄, filtered, and concentrated under reduced pressure to afford the desired product (430 mg, 85.0% yield). LCMS (ESI) m/z: [M+H] calcd for C₆₄H₉₀N₈O₈SSi: 1159.65; found 1159.8.

Step 2: Synthesis of 6-((2S)-1-(tert-butylsulfinyl) aziridin-2-yl)-N-((2S)-1-(((6³S,4S)-1¹-ethyl-2⁵-hydroxy-1²-(2-((S)-1-methoxyethyl)pyridin-3-yl)-10, 10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylnicotinamide To a solution of 6-((2S)-1-(tert-butylsulfinyl)aziridin-2-yl)-N-((2S)-1-(((6³S,4S)-1¹-ethyl-1²-(2-((S)-1-methoxyethyl)pyridin-3-yl)-10,10-dimethyl-5,7-dioxo-25-((triisopropylsilyl)oxy)-6¹,6²,6³,6⁴,6⁵,6⁶-hexahydro-1¹H-8-oxa-1 (5,3)-indola-6(1,3)-pyridazina-2(1,3)-benzenacycloundecaphane-4-yl)amino)-3-methyl-1-oxobutan-2-yl)-N-methylnicotinamide (430.0 mg, 0.371 mmol) in THF (50.0 mL) at 0° C. was added TBAF (1 M in THF, 1.1 mL, 1.11 mmol) in portions. The resulting mixture was stirred at 0° C. for 2 h and was then concentrated under reduced pressure. The residue was purified by prep-TLC (5% MeOH/DCM) to afford the desired product (290 mg, 78% yield). LCMS (ESI) m/z: [M+H] calcd for C₅₅H₇₀N₈O₈S: 1003.51; found 1003.8.

Step 3: Synthesis of 6-((S)-aziridin-2-yl)-N-((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5, 3)-indola-6(1,3)-pyridazina-2(1,3)-benzenacycloundecaphane-4-yl)amino)-3-methyl-1-oxobutan-2-yl)-N-methylnicotinamide To a solution of 6-((2S)-1-(tert-butylsulfinyl)aziridin-2-yl)-N-((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹, 6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylnicotinamide (150.0 mg, 0.150 mmol) in H₂O (15.0 mL) and acetone (15.0 mL) at 0° C. was added TFA (7.50 mL, 100.97 mmol) in portions. The resulting mixture was warmed to room temperature and stirred for 48 h and then was neutralized to pH 8 with sat. NaHCO₃. The aqueous layer was extracted with EtOAc, dried with Na₂SO₄, filtered, and concentrated under reduced pressure. Purification by reverse phase chromatography (38→58% MeCN/H₂O) afforded the desired product (10.0 mg, 7.4% yield). LCMS (ESI) m/z: [M+H] calcd for C₅₁H₆₂N₈O₇: 899.48; found 899.5.

Example 139. Synthesis of (2S)-2-((S)-7-(((R)-aziridin-2-yl)methyl)-1-oxo-2,7-diazaspiro[4.4]nonan-2-yl)-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide
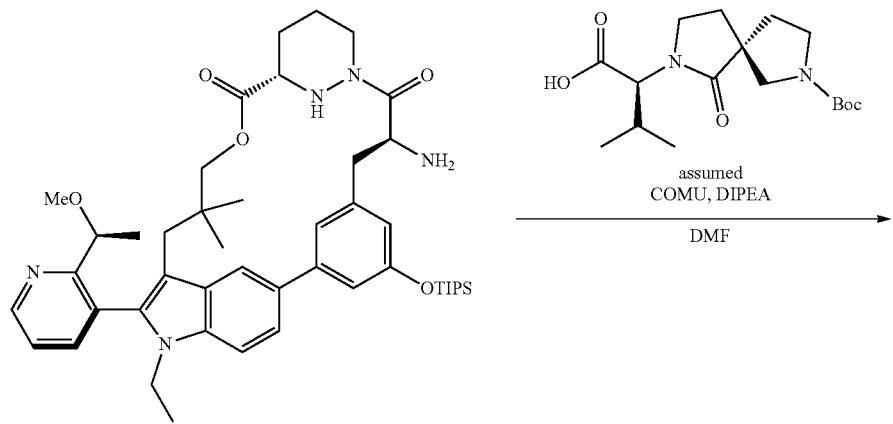
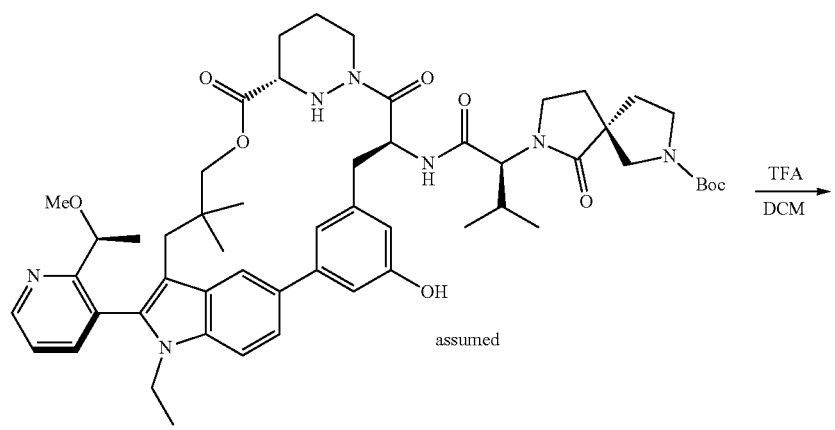
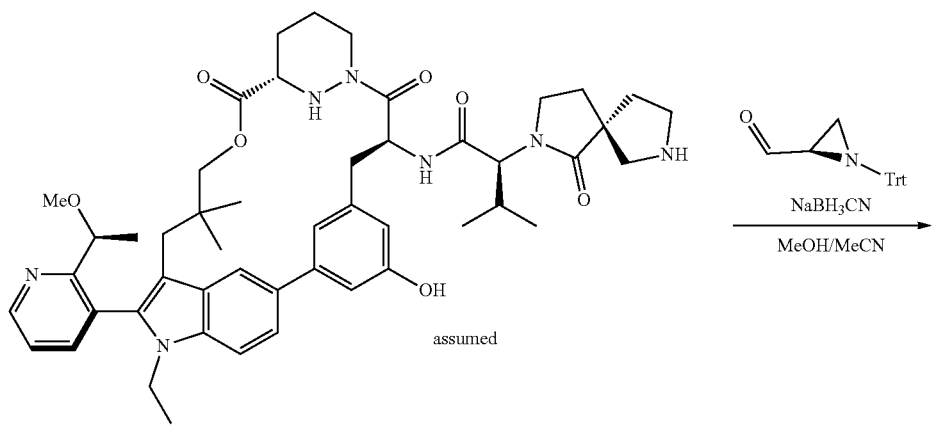

-continued

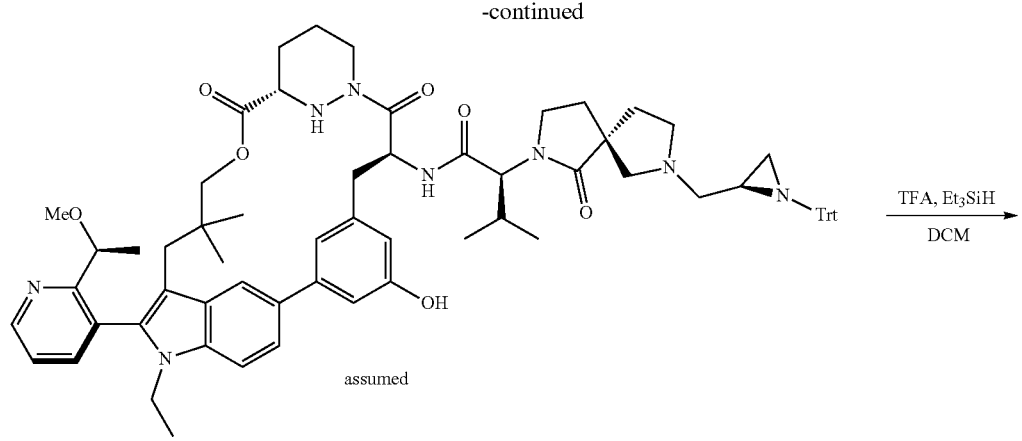

assumed

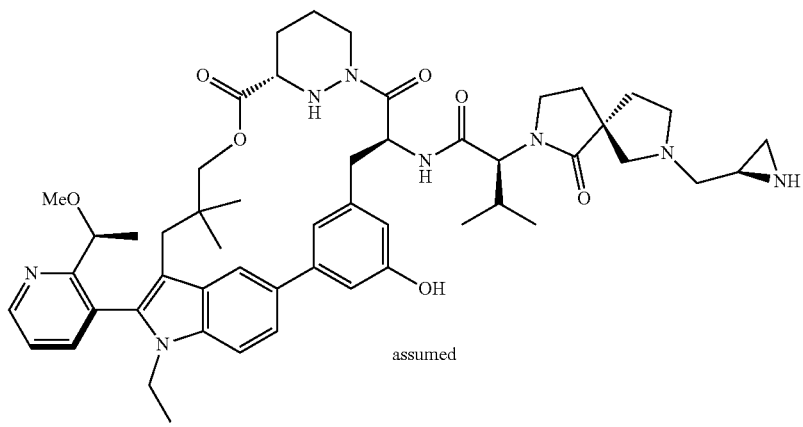

assumed

Step 1: Synthesis of tert-butyl (5R)-7-((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-6-oxo-2,7-diazaspiro[4.4]nonane-2-carboxylate To a solution of (6³S,4S)-4-amino-1¹-ethyl-2⁵-hydroxy-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (600 mg, 0.94 mmol) and DIPEA (820 µL, 4.7 mmol) in DMF (8 mL) at 0° C. was added (S)-2-((R)-7-(tert-butoxycarbonyl)-1-oxo-2,7-diazaspiro[4.4]nonan-2-yl)-3-methylbutanoic acid (380 mg, 1.13 mmol) and COMU (440 mg, 1.03 mmol). The reaction mixture was stirred for 1 h then was diluted with H₂O (100 mL) and extracted with EtOAc (3×50 mL). The combined organic layers were washed with brine (30 mL), dried with Na₂SO₄, filtered, and the filtrate was concentrated under reduced pressure. Purification by Prep-TLC (EtOAc) afforded the desired product (600 mg, 66% yield). LCMS (ESI) m/z: [M+H] calcd for $C_{54}H_{71}N_7O_9$: 962.54; found 962.5.

Step 2: Synthesis of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-1-oxo-2,7-diazaspiro[4.4]nonan-2-yl)butanamide To a solution of tert-butyl (5R)-7-((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-6-oxo-2,7-diazaspiro[4.4]nonane-2-carboxylate (600 mg, 0.62 mmol) in DCM (6 mL) at 0° C. was added TFA (3.0 mL, 40 mmol). The reaction mixture was stirred for 2 h and then was concentrated under reduced pressure. The residue was diluted with H₂O (100 mL), basified to pH 8 with sat. aq. NaHCO₃, and extracted with EtOAc (3×60 mL). The combined organic layers were washed with brine (30 mL), dried with Na₂SO₄, filtered, and concentrated under reduced pressure to afford the desired product (430 mg, 79% yield). LCMS (ESI) m/z: [M+H] calcd for $C_{49}H_{63}N_7O_7$: 862.49; found 862.5.

Step 3: Synthesis of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-1-oxo-7-(((S)-1-tritylaziridin-2-yl)methyl)-2,7-diazaspiro[4.4]nonan-2-yl)butanamide To a solution of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-1-oxo-2,7-diazaspiro[4.4]nonan-2-yl)butanamide (200 mg, 0.23 mmol) and (R)-1-tritylaziridine-2-carbaldehyde (110 mg, 0.35 mmol) in MeOH (0.50 mL) and MeCN (4.0 mL) was added NaBH₃CN (29 mg, 0.46 mmol). The reaction mixture was stirred for 2 h then was quenched with sat. aq. NH₄Cl and was extracted with EtOAc (3×50 mL). The combined organic layers were washed with brine (30 mL), dried with Na₂SO₄, filtered, and concentrated under reduced pressure. Purification by Prep-TLC (EtOAc) afforded desired product (145 mg, 53% yield). LCMS (ESI) m/z: [M+H] calcd for C₇₁H₈₂N₈O₇: 1159.64; found 1159.6.

Step 4: Synthesis of (2S)-2-((S)-7-(((R)-aziridin-2-yl)methyl)-1-oxo-2,7-diazaspiro[4.4]nonan-2-yl)-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methylbutanamide To a solution of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-3-methyl-2-((S)-1-oxo-7-(((S)-1-tritylaziridin-2-yl)methyl)-2,7-diazaspiro[4.4]nonan-2-yl)butanamide (140 mg, 0.12 mmol) in DCM (2.0 mL) 0° C. was added TFA (74 μL, 0.97 mmol) and Et₃SiH (150 μL, 0.97 mmol). The reaction mixture was stirred for 30 min then was basified to pH 8 with DIPEA. The resulting mixture was concentrated under reduced pressure. Purification by reverse phase chromatography (30→60% MeCN/H₂O) afforded the desired product (37.5 mg, 31% yield). LCMS (ESI) m/z: [M+H] calcd for C₅₂H₆₈N₈O₇: 917.53; found 917.4.

Example 133. Synthesis of (2R,3R)-3-cyclopropyl-N-(2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide

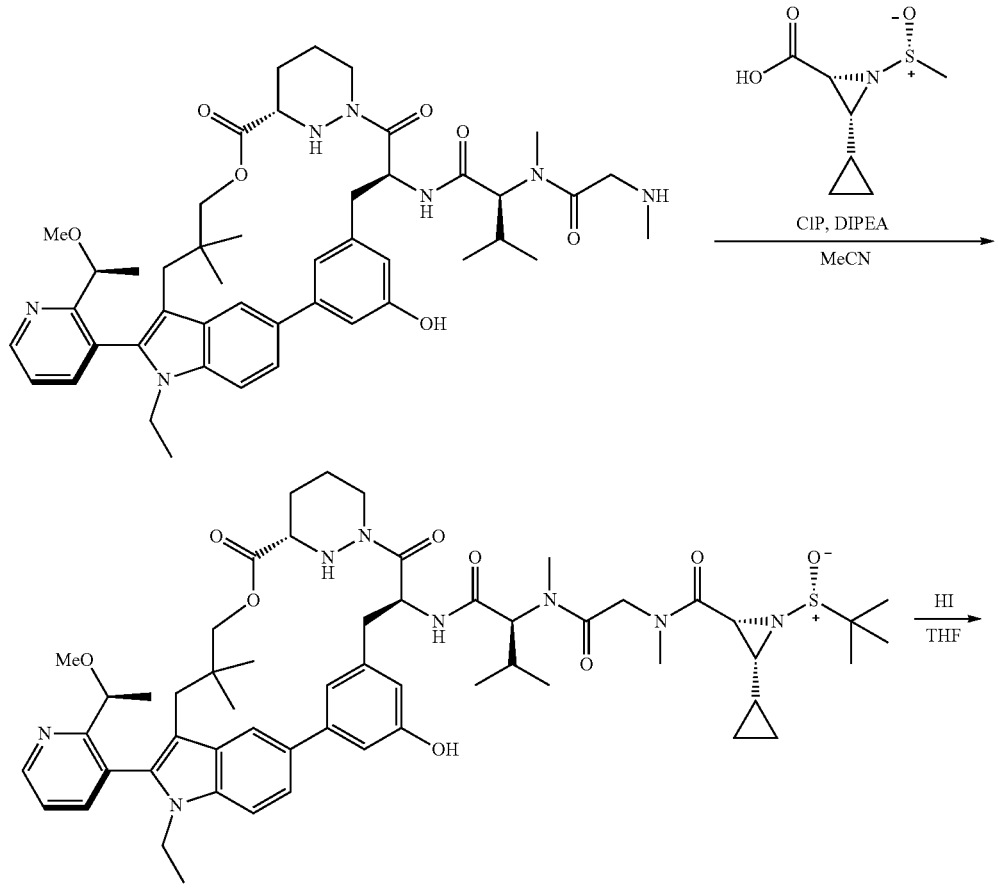

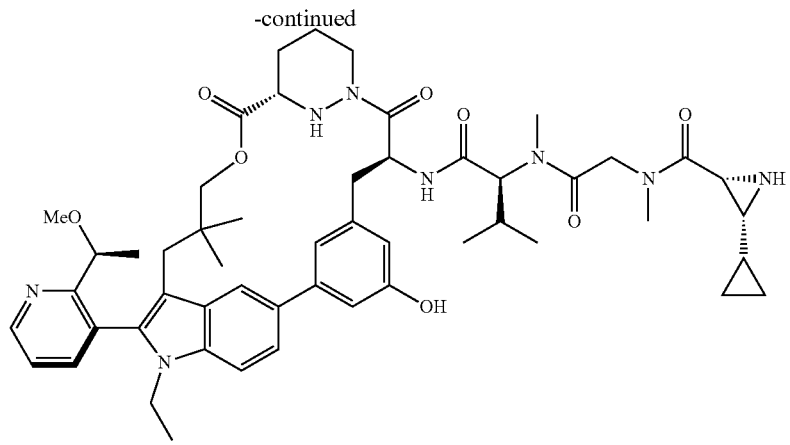

Step 1: Synthesis of (2R,3R)-1-(tert-butylsulfinyl)-3-cyclopropyl-N-(2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide To a solution of (2S)—N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)- benzenacycloundecaphane-4-yl)-3-methyl-2-(N-methyl-2-(methylamino)acetamido)butanamide (50 mg, 61 μmol) and (2R,3R)-1-(tert-butylsulfinyl)-3-cyclopropylaziridine-2-carboxylic acid (21 mg, 91 μmol) in MeCN at 0° C. was added DIPEA (210 μL, 1.2 mmol) and CIP (25 mg, 91 μmol). The resulting mixture was stirred for 2 h and was then concentrated under reduced pressure. Purification by Prep-TLC (9% EtOAc/pet. ether) afforded the desired product (270 mg, 54% yield). LCMS (ESI) m/z: [M+H] calcd for $C_{56}H_{76}N_8O_{9}S$: 1037.56; found 1037.4.

Step 2: Synthesis of (2R,3R)-3-cyclopropyl-N-(2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide To a mixture of (2R,3R)-1-(tert-butylsulfinyl)-3-cyclopropyl-N-(2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide (230 mg, 0.22 mmol) in THF at 0° C. was added HI (0.50 mL, 3.8 mmol, 57% wt in H₂O). The reaction mixture was stirred for 10 min and then neutralized to pH 8 with DIPEA and concentrated under reduced pressure. Purification by reverse phase chromatography (40→60% MeCN/H₂O) afforded desired product (20 mg, 11% yield) as a white solid. LCMS (ESI) m/z: [M+H] calcd for $C_{52}H_{68}N_8O_8$: 933.53; found 933.6.

Example 177. Synthesis of 4-((R)-aziridine-2-carbonyl)-N-((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)-N-methylpiperazine-1-carboxamide

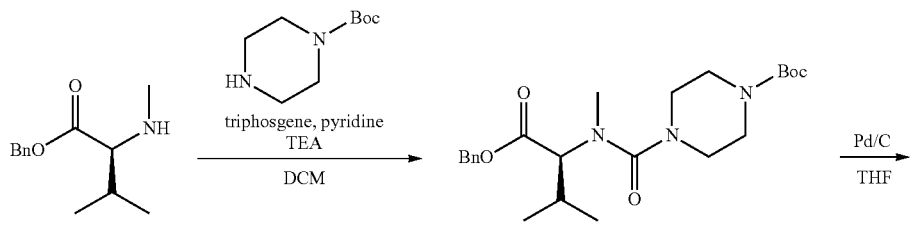

-continued
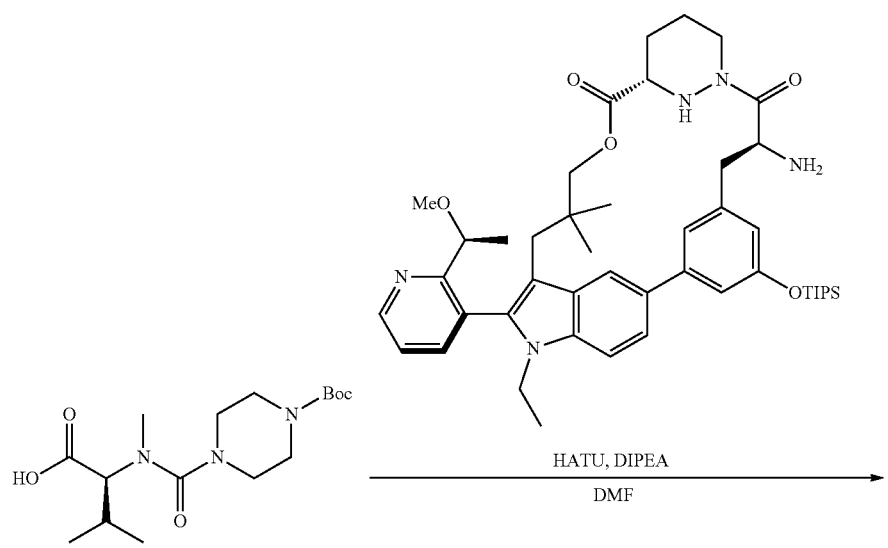
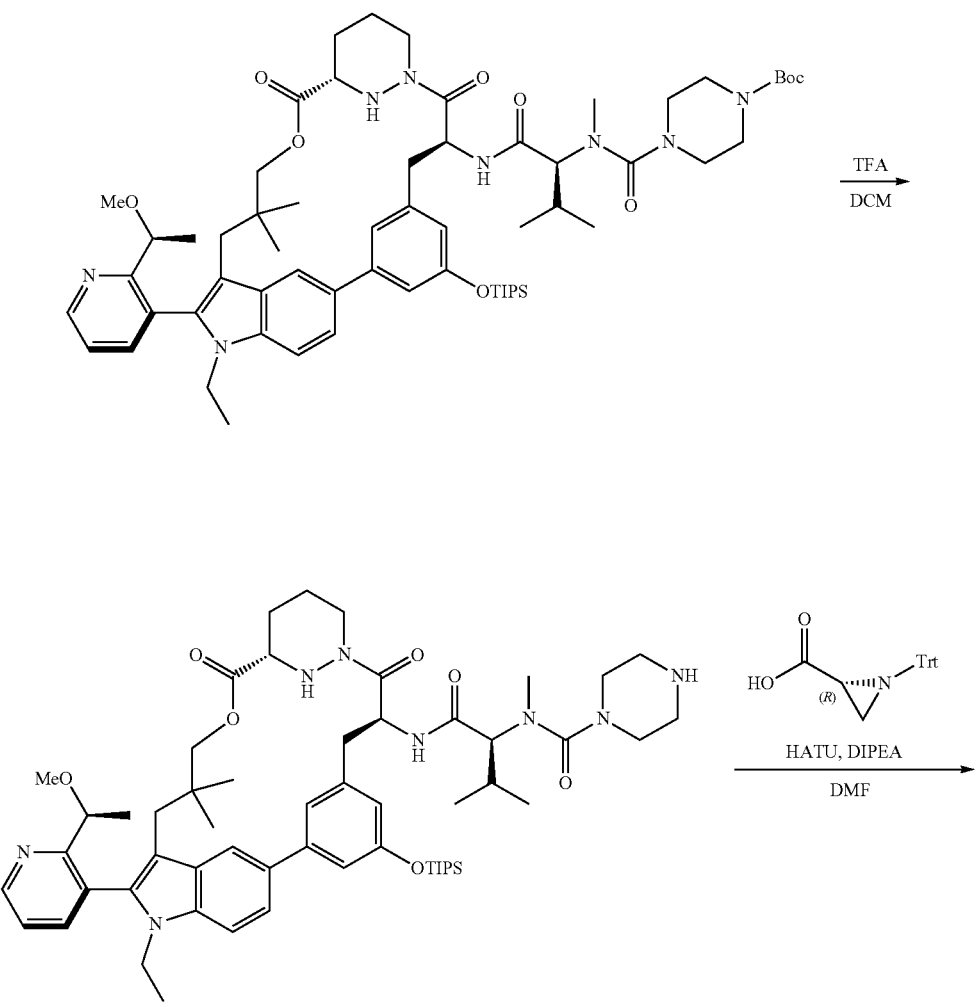

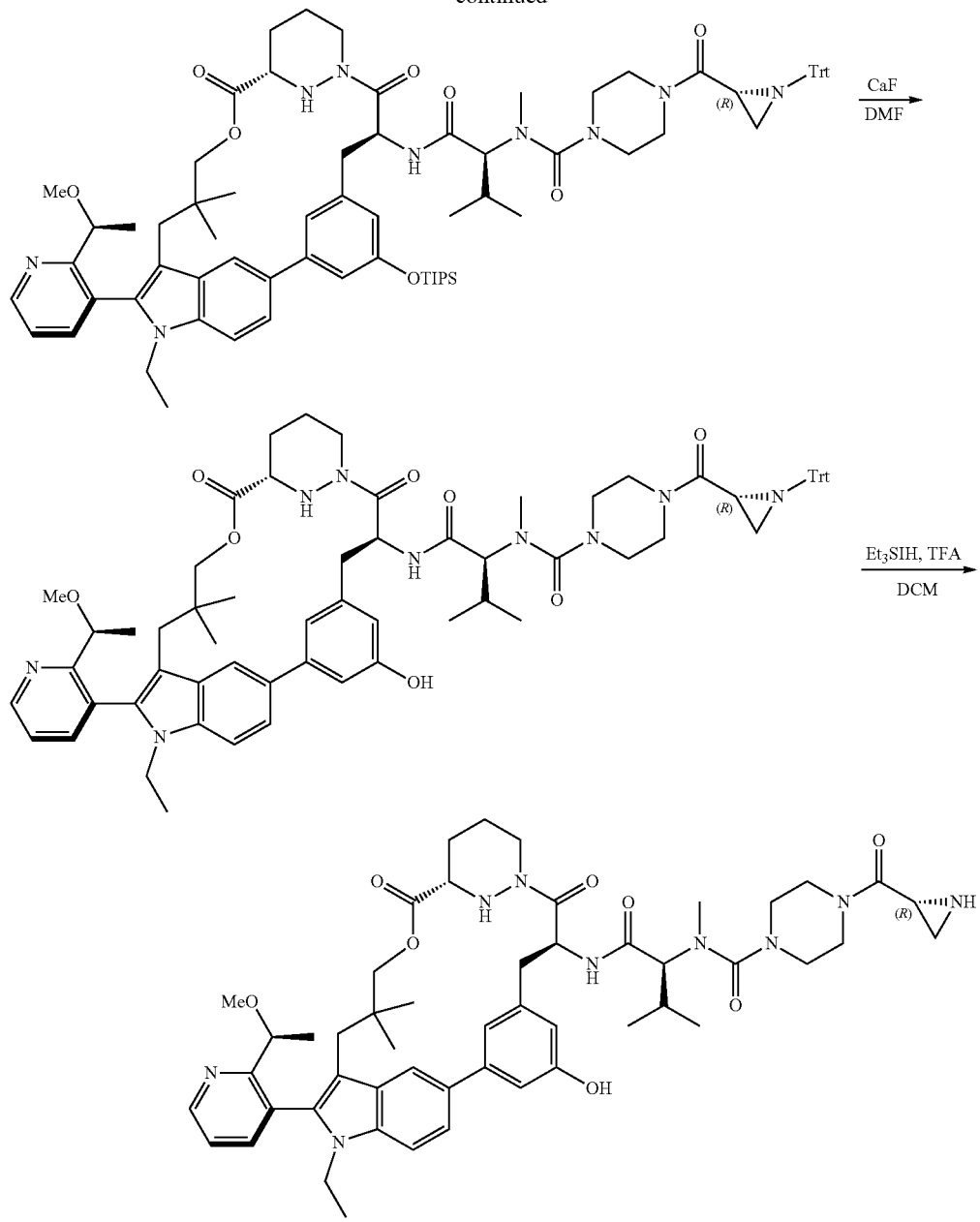

Step 1: Synthesis of tert-butyl (S)-4-((1-(benzyloxy)-3-methyl-1-oxobutan-2-yl)(methyl)carbamoyl) piperazine-1-carboxylate Into a 100-mL vial were added benzyl methyl-L-valinate (2.0 g, 9.038 mmol) and triphosgene (0.89 g, 2.982 mmol) in DCM (30 mL) followed by pyridine (2.14 g, 27.113 mmol) in portions at 0° C. under an $N_2$ atmosphere. The mixture was stirred for 2 h at room temperature. The crude product was used in the next step directly without further purification. Then, the resulting mixture was added to tert-butyl piperazine-1-carboxylate (2.22 g, 11.912 mmol) in DCM (25 mL) and $Et_3N$ (2.78 g, 27.489 mmol) in portions at room temperature under an $N_2$ atmosphere. The resulting mixture was concentrated under reduced pressure. The residue was purified by silica gel column chromatography, (30% EtOAc/pet. ether) to afford the desired product (3.6 g, 90.6% yield). LCMS (ESI) m/z: [M+H] calcd for $C_{23}H_{35}N_3O_5$: 434.26; found 434.2.

Step 2: Synthesis of N-(4-(tert-butoxycarbonyl) piperazine-1-carbonyl)-N-methyl-L-valine Into a 100-mL vial were added tert-butyl (S)-4-((1-(benzyloxy)-3-methyl-1-oxobutan-2-yl)(methyl)carbamoyl) piperazine-1-carboxylate (2.95 g, 6.804 mmol) and Pd/C (1.48 g) in THF (25 mL). the reaction was stirred for overnight at room temperature under a hydrogen atmosphere. The resulting mixture was filtered, the filter cake was washed with EtOAc (3×50 mL), and the combined organic layers were concentrated under reduced pressure to afford the desired product (2.4 g, crude). LCMS (ESI) m/z: [M+H] calcd for $C_{16}H_{29}N_3O_5$: 344.21; found 344.4.

Step 3: Synthesis of tert-butyl 4-(((2S)-1-((($6^3$S, 4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)piperazine-1-carboxylate Into a 50-mL vial was added ($6^3$S,4S)-4-amino-$1^1$-ethyl-$1^2$-(2-((S)-1-methoxyethyl)pyridin-3-yl)-10,10-dimethyl-$2^5$-((triisopropylsilyl)oxy)-$6^1,6^2,6^3,6^4,6^5,6^6$-hexahydro-$1^1$H-8-oxa-1(5,3)-indola-6(1,3)-pyridazina-2(1,3)-benzenacycloundecaphane-5,7-dione (1.0 g, 1.256 mmol) and N-(4-(tert-butoxycarbonyl) piperazine-1-carbonyl)-N-methyl-L-valine (647.04 mg, 1.884 mmol) in DMF (8 mL) followed by HATU (668.63 mg, 1.758 mmol) and DIPEA (811.69 mg, 6.280 mmol) in portions at room temperature. The resulting mixture was extracted with EtOAc (3×50 mL). The combined organic layers were washed with brine (2×20 mL), dried over $Na_2SO_4$, filtered, and concentrated under reduced pressure. The residue was purified by silica gel column chromatography (50% EtOAc/pet. ether) to afford the desired product (1.08 g, 76.7% yield). LCMS (ESI) m/z: [M+H] calcd for $C_{62}H_{92}N_8O_9Si$: 1121.68; found 1122.0.

Step 4: Synthesis of N-((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methylpiperazine-1-carboxamide Into a 100-mL vial was added tert-butyl 4-(((2S)-1-((($6^3$S, 4S)-$1^1$-ethyl-$1^2$-(2-((S)-1-methoxyethyl)pyridin-3-yl)-10, 10-dimethyl-5,7-dioxo-$2^5$-((triisopropylsilyl)oxy)-$6^1,6^2,6^3, 6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)(methyl)carbamoyl)piperazine-1-carboxylate (1.08 g, 0.963 mmol) and TFA (3.0 mL, 40.39 mmol) in DCM (12 mL). The reaction was stirred for 2 h at room temperature under an $N_2$ atmosphere. The resulting mixture was concentrated under reduced pressure to afford the desired product (907 mg, crude). LCMS (ESI) m/z: [M+Na] calcd for $C_{57}H_{83}N_8O_7Si$: 1042.61; found 1043.9.

Step 5: Synthesis of N-((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1,6^2,6^3, 6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methyl-4-((R)-1-tritylaziridine-2-carbonyl)piperazine-1-carboxamide Into a 40-mL vial was added N-((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1,6^2,6^3,6^4,6^5, 6^6$-hexahydro-$1^1$H-8-oxa-1(5,3)-indola-6(1,3)-pyridazina-2 (1,3)-benzenacycloundecaphane-4-yl)amino)-3-methyl-1-oxobutan-2-yl)-N-methylpiperazine-1-carboxamide (400.0 mg, 0.392 mmol) and (R)-1-tritylaziridine-2-carboxylic acid (193.49 mg, 0.587 mmol) in DMF (3.5 mL) followed by HATU (208.46 mg, 0.548 mmol) and DIPEA (253.06 mg, 1.958 mmol) in portions at room temperature under an $N_2$ atmosphere. The resulting mixture was extracted with EtOAc (3×60 mL) and the combined organic layers were washed with brine (2×10 mL), dried over $Na_2SO_4$, filtered, and concentrated under reduced pressure. The residue was purified by silica gel column chromatography, (50% EtOAc/ pet. ether) to afford the desired product (367 mg, 70.3% yield). LCMS (ESI) m/z: [M+H-TIPS] calcd for $C_{79}H_{101}N_9O_8Si$: 1176.63; found 1176.2.

Step 6: Synthesis of N-((2S)-1-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2 (1,3)- benzenacycloundecaphane-4-yl)amino)-3-methyl-1-oxobutan-2-yl)-N-methyl-4-((R)-1-tritylaziridine-2-carbonyl)piperazine-1-carboxamide Into a 100-mL vial was added N-((2S)-1-((($6^3$S,4S)-$1^1$-ethyl-$1^2$-(2-((S)-1-methoxyethyl)pyridin-3-yl)-10,10-dimethyl-5,7-dioxo-$2^5$-((triisopropylsilyl)oxy)-$6^1,6^2,6^3,6^4,6^5, 6^6$-hexahydro-$1^1$H-8-oxa-1(5,3)-indola-6(1,3)-pyridazina-2 (1,3)-benzenacycloundecaphane-4-yl)amino)-3-methyl-1-oxobutan-2-yl)-N-methyl-4-((R)-1-tritylaziridine-2-carbonyl)piperazine-1-carboxamide (161.0 mg, 0.121 mmol) and CsF (91.75 mg, 0.604 mmol) in DMF (1.5 mL). The reaction was stirred for 2 h at room temperature and was then extracted with EtOAc (3×20 mL). The combined organic layers were washed with brine (2×10 mL), dried over $Na_2SO_4$, filtered, and concentrated under reduced pressure. The residue was purified by Prep-TLC (50% EtOAc/ pet. ether) to afford the desired product (101 mg, 71.1% yield). LCMS (ESI) m/z: [M+H] calcd for $C_{70}H_{81}N_9O_8$: 1176.62; found 1176.9.

Step 7: Synthesis of 4-((R)-aziridine-2-carbonyl)-N-((2S)-1-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5, 3)-indola-6(1,3)-pyridazina-2(1,3)-benzenacycloundecaphane-4-yl)amino)-3-methyl-1-oxobutan-2-yl)-N-methylpiperazine-1-carboxamide Into a 40-mL vial was added N-((2S)-1-((($6^3$S,4S)-$1^1$-ethyl-$2^5$-hydroxy-$1^2$-(2-((S)-1-methoxyethyl)pyridin-3-yl)-10,10-dimethyl-5,7-dioxo-$6^1,6^2,6^3,6^4,6^5,6^6$-hexahydro-$1^1$H-8-oxa-1(5,3)-indola-6(1,3)-pyridazina-2(1,3)-benzenacycloundecaphane-4-yl)amino)-3-methyl-1-oxobutan-2-yl)-N-methyl-4-((R)-1-tritylaziridine-2-carbonyl) piperazine-1-carboxamide (101.0 mg, 0.086 mmol) and $Et_3SiH$ (49.91 mg, 0.429 mmol) in DCM (2.0 mL) was added TFA (48.94 mg, 0.429 mmol) in portions at room temperature under an $N_2$ atmosphere. The mixture was basified to pH 8 with DIPEA. The crude product was purified by Prep-HPLC to afford the desired product (29.6 mg, 36.9% yield). LCMS (ESI) m/z: [M+H] calcd for $C_{51}H_{67}N_9O_8$: 934.51; found 934.3.

Example 175. Synthesis of (2S)-2-((S)-7-((R)-aziridine-2-carbonyl)-1-oxo-2,7-diazaspiro[4.4]nonan-2-yl)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)acetamide
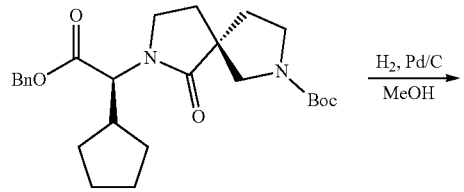
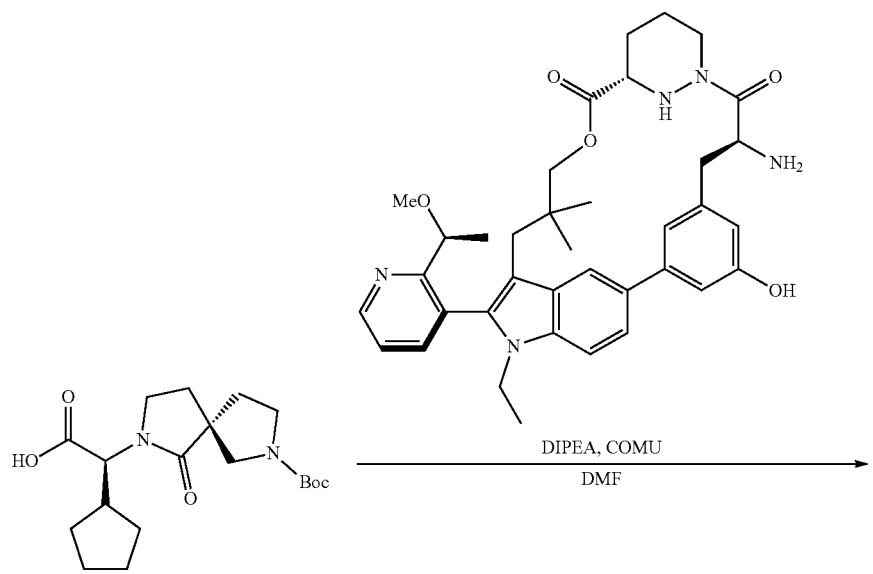
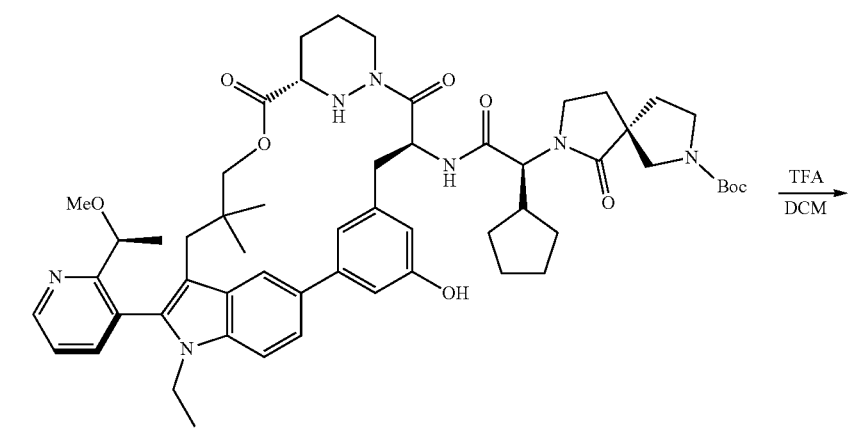

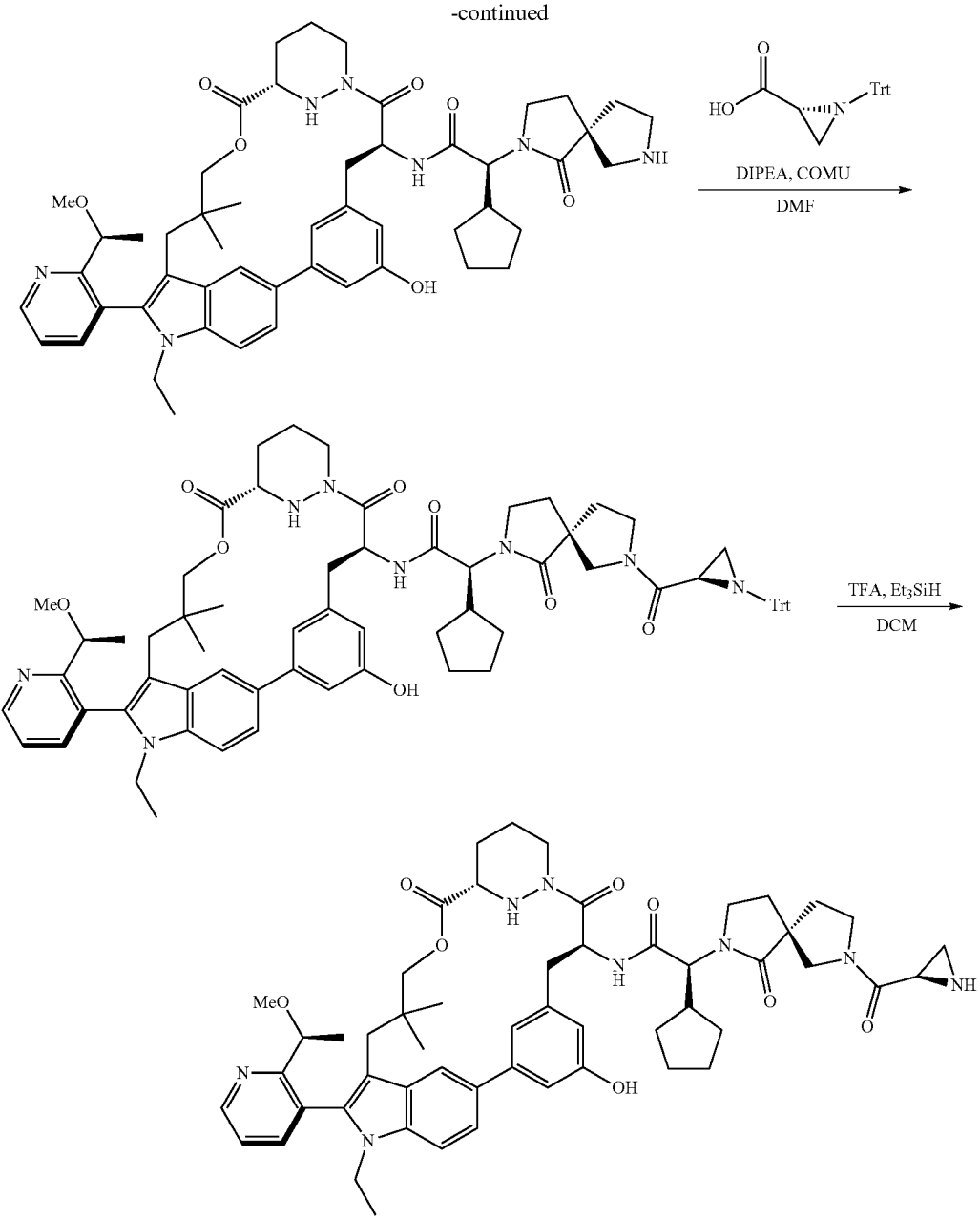

Step 1: Synthesis of (S)-2-((R)-7-(tert-butoxycarbonyl)-1-oxo-2,7-diazaspiro[4.4]nonan-2-yl)-2-cyclopentylacetic Acid To a solution stirred solution of tert-butyl (R)-7-((S)-2-(benzyloxy)-1-cyclopentyl-2-oxoethyl)-6-oxo-2,7-diazaspiro[4.4]nonane-2-carboxylate (1.0 g, 2.19 mmol) in MeOH (10 mL) at 0° C. was added Pd/C (200 mg). The resulting mixture was stirred for 1 h at room temperature under a hydrogen atmosphere, filtered, and the filter cake washed with MeOH (5×10 mL). The filtrate was concentrated under reduced pressure to afford the desired product (895 mg, crude) which was used without further purification. LCMS (ESI) m/z: [M+H] calcd for $C_{19}H_{30}N_2O_5$: 376.23; found 367.1.

Step 2: Synthesis of tert-butyl (5R)-7-((1S)-1-cyclopentyl-2-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)-6-oxo-2,7-diazaspiro[4.4]nonane-2-carboxylate To a stirred solution of (6³S,4S)-4-amino-1¹-ethyl-2⁵-hydroxy-1²-(2-((S)-1-methoxyethyl)pyridin-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (702 mg, 1.10 mmol) and DIPEA (1.91 mL, 1.10 mmol) in DMF (500 mL) at 0° C. was added (S)-2-((R)-7-(tert-butoxycarbonyl)-1-oxo-2,7-diazaspiro[4.4]nonan-2-yl)-2-cyclopentylacetic acid (523 mg, 1.43 mmol) and COMU (517 mg, 1.21 mmol). After 1 h at room temperature the reaction mixture was diluted with H₂O (150 mL). The aqueous layer was extracted with EtOAc (3×50 mL) and the combined organic layers were washed with brine, dried with Na₂SO₄, filtered, and concentrated under reduced pressure. Purification by normal phase chromatography (40% EtOAc/pet. ether) afforded the desired product (978 mg, 90.2% yield). LCMS (ESI) m/z: [M+H] calcd for $C_{56}H_{73}N_7O_9$: 988.56; found 988.7.

Step 3: Synthesis of (2S)-2-cyclopentyl-N-((6³S, 4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-1-oxo-2,7-diazaspiro[4.4]nonan-2-yl) acetamide To a stirred solution of tert-butyl (5R)-7-((1S)-1-cyclopentyl-2-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)-6-oxo-2,7-diazaspiro[4.4]nonane-2-carboxylate (300 mg, 0.304 mmol) in DCM (3.0 mL) at 0° C. was added TFA (1.5 mL). The resulting mixture was stirred for 30 min at room temperature. The reaction mixture was then diluted with toluene (2 mL) and concentrated under reduced pressure three times to afford the desired product (270 mg, crude) which was used without further purification. LCMS (ESI) m/z: [M+H] calcd for $C_{51}H_{65}N_7O_7$: 888.50; found 888.5.

Step 4: Synthesis of (2S)-2-cyclopentyl-N-((6³S, 4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-1-oxo-7-((R)-1-tritylaziridine-2-carbonyl)-2,7-diazaspiro[4.4]nonan-2-yl)acetamide To a stirred solution of (2S)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-1-oxo-2,7-diazaspiro[4.4]nonan-2-yl)acetamide (270 mg, 0.304 mmol) and DIPEA (0.53 mL, 3.0 mmol) in DMF (3.0 mL) at 0° C. was added (R)-1-tritylaziridine-2-carboxylic acid (130 mg, 0.395 mmol) and COMU (143 mg, 0.334 mmol). After 1 h at room temperature the reaction mixture was diluted with H₂O (30 mL). The aqueous layer was extracted with EtOAc (3×3 mL) and the combined organic layers were washed with brine, dried with Na₂SO₄, filtered, and concentrated under reduced pressure. Purification by prep-TLC (5% MeOH/DCM) afforded the desired product (332 mg, 91.1% yield). LCMS (ESI) m/z: [M+H] calcd for $C_{73}H_{82}N_8O_8$: 1199.64; found 1199.7.

Step 5: Synthesis of (2S)-2-((S)-7-((R)-aziridine-2-carbonyl)-1-oxo-2,7-diazaspiro[4.4]nonan-2-yl)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)acetamide To a stirred solution of (2S)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-1-oxo-7-((R)-1-tritylaziridine-2-carbonyl)-2,7-diazaspiro[4.4]nonan-2-yl)acetamide (309 mg, 0.258 mmol) in DCM (3.0 mL) at 0° C. was added Et₃SiH (164 mL, 1.03 mmol) and TFA (79 mL, 1.03 mmol). After 30 min the reaction mixture was basified to pH 8 with DIPEA and concentrated under reduced pressure. Purification by reverse phase chromatography (30→60% MeCN/H₂O) afforded the desired product (36 mg, 14.2% yield). LCMS (ESI) m/z: [M+H] calcd for $C_{54}H_{68}N_8O_8$: 957.53; found 957.3.

Example 214. Synthesis of (2S)-2-cyclopentyl-2-((S)-7-((2R,3R)-3-cyclopropylaziridine-2-carbonyl)-1-oxo-2,7-diazaspiro[4.4]nonan-2-yl)-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl) acetamide

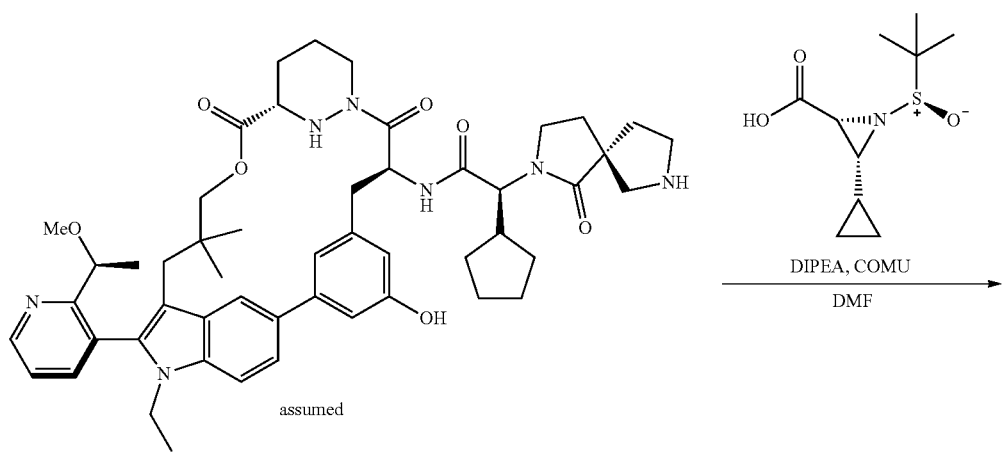

723

-continued

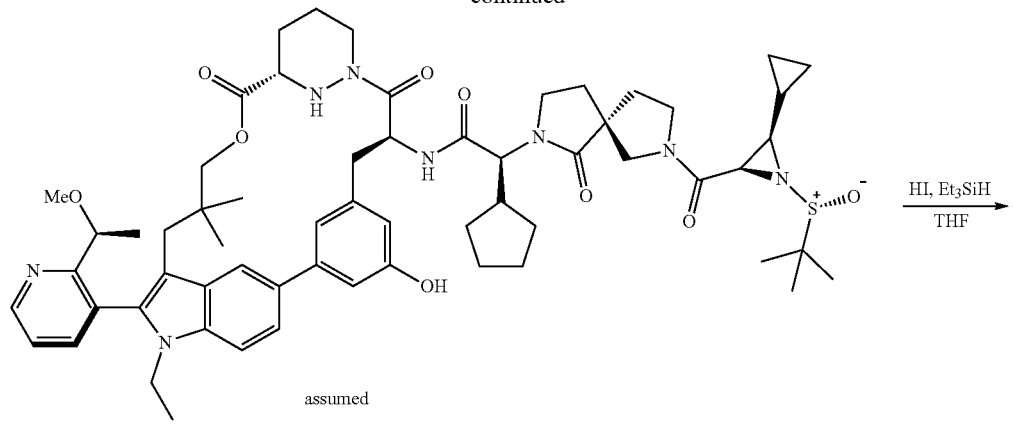

assumed

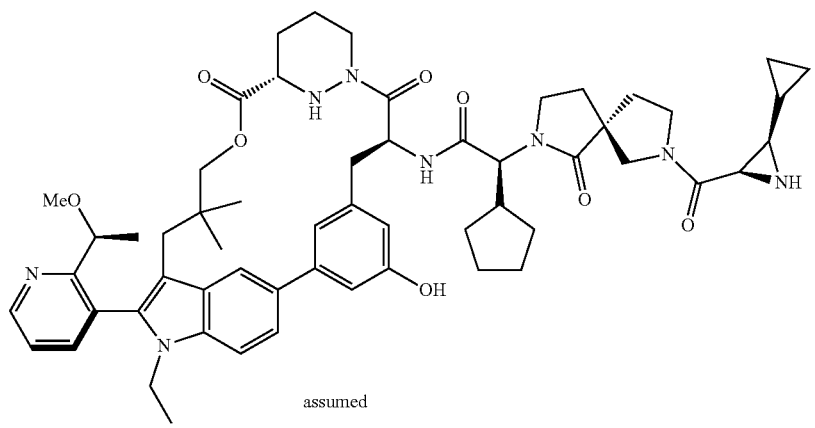

assumed

Step 1: Synthesis of (2S)-2-((5S)-7-((2R,3R)-1-(tert-butylsulfinyl)-3-cyclopropylaziridine-2-carbonyl)-1-oxo-2,7-diazaspiro[4.4]nonan-2-yl)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)acetamide To a stirred solution of (2S)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-((S)-1-oxo-2,7-diazaspiro[4.4]nonan-2-yl)acetamide (270 mg, 0.30 mmol) in DMF (3.0 mL) at 0° C. was added DIPEA (530 μL, 3.0 mmol) and (2R,3R)-1-(tert-butylsulfinyl)-3-cyclopropylaziridine-2-carboxylic acid (105 mg, 0.46 mmol) followed by COMU (140 mg, 0.33 mmol). The resulting mixture was stirred for 1 h at room temperature and was then diluted with H₂O (30 mL). The reaction mixture was extracted into EtOAc (3×7 mL). The combined organic layers were washed with brine (3×10 mL), dried over Na₂SO₄, filtered, and concentrated under reduced pressure. Purification by Prep-TLC (6% MeOH/DCM) afforded the desired product (237 mg, 71% yield). LCMS (ESI) m/z: [M+H] calcd for C₆₁H₈₀N₈O₉S: 1101.58; found 1101.3.

Step 2: Synthesis of (2S)-2-cyclopentyl-2-((S)-7-((2R,3R)-3-cyclopropylaziridine-2-carbonyl)-1-oxo-2,7-diazaspiro[4.4]nonan-2-yl)-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)- benzenacycloundecaphane-4-yl) acetamide To a stirred solution of (2S)-2-((5S)-7-((2R,3R)-1-(tert-butylsulfinyl)-3-cyclopropylaziridine-2-carbonyl)-1-oxo-2,7-diazaspiro[4.4]nonan-2-yl)-2-cyclopentyl-N-((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)acetamide (230 mg, 0.21 mmol) in THF (2.5 mL) at 0° C. was added Et₃SiH (130 μL, 0.83 mmol) and HI (125 μL, 0.41 mmol, 57% in H₂O). The resulting mixture was stirred for 30 min at room temperature then cooled to 0° C. and neutralized to pH 8. The mixture was concentrated under reduced pressure. Purification by Prep-TLC (8.3% MeOH/DCM) afforded the desired product (46 mg, 21% yield). LCMS (ESI) m/z: [M+H] calcd for C₅₇H₇₂N₈O₈: 997.55; found 997.2.

Example 209. Synthesis of (2R)—N-(2-(((1S)-1-cyclopentyl-2-(((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methylaziridine-2-carboxamide
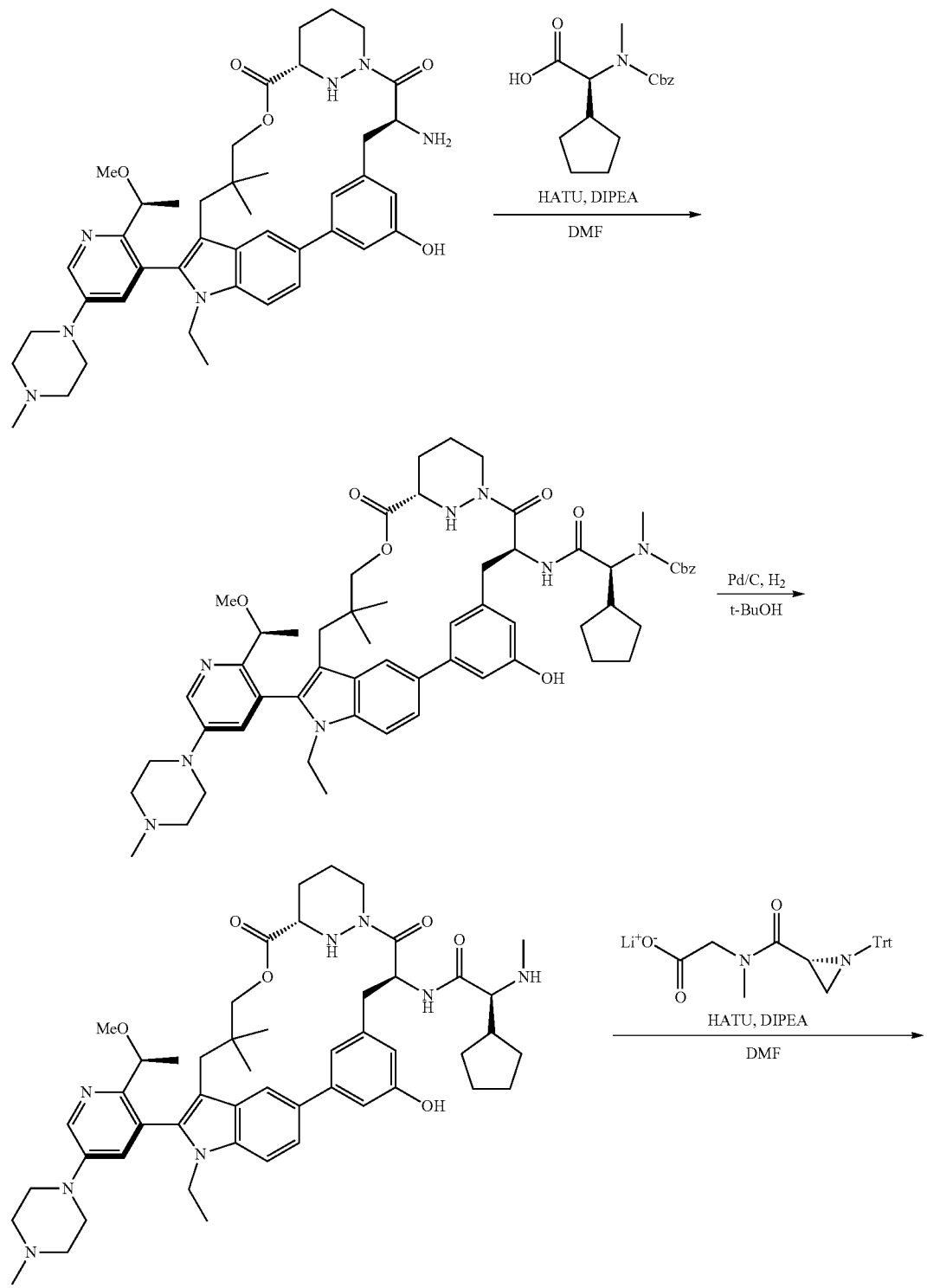

-continued

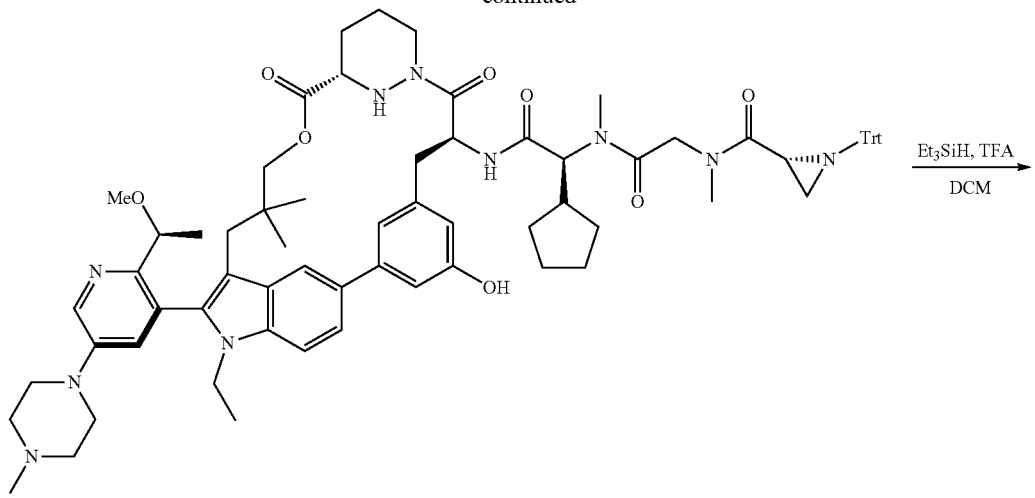

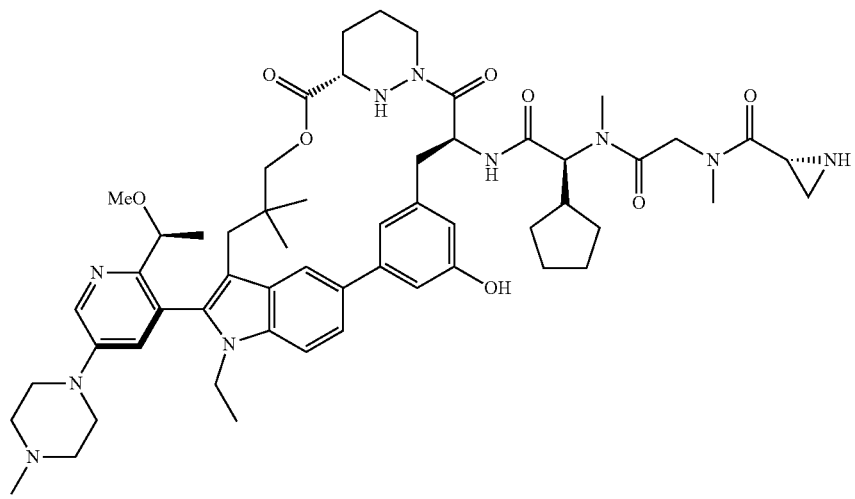

Step 1: Synthesis of benzyl (((1S)-1-cyclopentyl-2-(((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)carbamate To a stirred solution of (6³S, 4S)-4-amino-1¹-ethyl-2⁵-hydroxy-1²-(2-((S)-1-methoxyethyl)-5-(4-methylpiperazin-1-yl)pyridine-3-yl)-10,10-dimethyl-6¹,6²,6³,6⁴,6⁵,6⁶-hexahydro-1¹H-8-oxa-1(5,3)-indola-6(1,3)-pyridazina-2(1,3)-benzenacycloundecaphane-5,7-dione (490 mg, 0.664 mmol) and (S)-2-(((benzyloxy)carbonyl)(methyl)amino)-2-cyclopentylacetic acid (232 mg, 0.797 mmol) in DMF (5 mL) at 0° C. was added DIPEA (1.19 mL, 6.64 mmol) and HATU (303 mg, 0.797 mmol). The resulting mixture was stirred for 1 h at room temperature and then diluted with H₂O (20 mL). The aqueous phase was extracted with EtOAc (3×20 mL) and the combined organic layers were washed with brine, dried over Na₂SO₄, filtered, and concentrated under reduced pressure. Purification by reverse phase chromatography (0→100% MeCN/H₂O, 0.1% NH₄HCO₃) afforded the desired product (420 mg, 59.4% yield). LCMS (ESI) m/z: [M+H] calcd for $C_{58}H_{74}N_8O_8$: 1011.57; found 1011.6.

Step 2: Synthesis of (2S)-2-cyclopentyl-N-((6³S, 4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(methylamino)acetamide To a stirred solution of benzyl ((1S)-1-cyclopentyl-2-(((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)carbamate (450 mg, 0.445 mmol) in t-BuOH (10 mL) was added Pd/C (90 mg). The resulting mixture was warmed to 40° C. overnight under a hydrogen atmosphere, then filtered and the filter cake washed with MeOH. The filtrate was concentrated under reduced pressure to afford the desired product (420 mg, crude) which was used without further purification. LCMS (ESI) m/z: [M+H] calcd for $C_{50}H_{68}H_8O_6$: 877.54; found 877.5.

Step 3: Synthesis of (2R)—N-(2-(((1S)-1-cyclopentyl-2-(((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methyl-1-tritylaziridine-2-carboxamide To a stirred solution of (2S)-2-cyclopentyl-N-((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)-2-(methylamino)acetamide (130 mg, 0.148 mmol) and lithium (R)—N-methyl-N-(1-tritylaziridine-2-carbonyl)glycinate (78.3 mg, 0.193 mmol) in DMF (2 mL) at 0° C. was added DIPEA (264 mL, 1.48 mmol) and HATU (68 mg, 0.178 mmol). The resulting mixture was stirred for 1 h at room temperature and then diluted with H₂O (20 mL). The aqueous phase was extracted with EtOAc (3×10 mL) and the combined organic layers were washed with H₂O, dried with Na₂SO₄, filtered, and concentrated under reduced pressure. Purification by prep-TLC (10% MeOH/DCM) afforded the desired product (100 mg, 50.9% yield). LCMS (ESI) m/z: [M+Na] calcd for C₇₅H₉₀N₁₀O₈: 1281.69; found 1281.9.

Step 4: Synthesis of (2R)—N-(2-(((1S)-1-cyclopentyl-2-(((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methylaziridine-2-carboxamide To a stirred solution of (2R)—N-(2-(((1S)-1-cyclopentyl-2-(((6³S,4S)-1¹-ethyl-2⁵-hydroxy-1²-(2-((S)-1-methoxyethyl)-5-(4-methylpiperazin-1-yl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-2-oxoethyl)(methyl)amino)-2-oxoethyl)-N-methyl-1-tritylaziridine-2-carboxamide (100 mg, 0.079 mmol) in DCM (1.0 mL) at 0° C. was added Et₃SiH (51 mL, 0.318 mmol) and TFA (24 mL, 0.318 mmol). After 30 min the reaction mixture was basified to pH 8 with DIPEA and concentrated under reduced pressure. Purification by reverse phase chromatography (30→55% MeCN/H₂O) afforded the desired product (14 mg, 16.5% yield). LCMS (ESI) m/z: [M+H] calcd for C₅₆H₇₆N₁₀O₈: 1017.59; found 1017.6.

Example 268. Synthesis of (2R)—N-(2-(((2S)-1-(((6³S,4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(3-(2-oxopyrrolidin-1-yl)propyl)aziridine-2-carboxamide

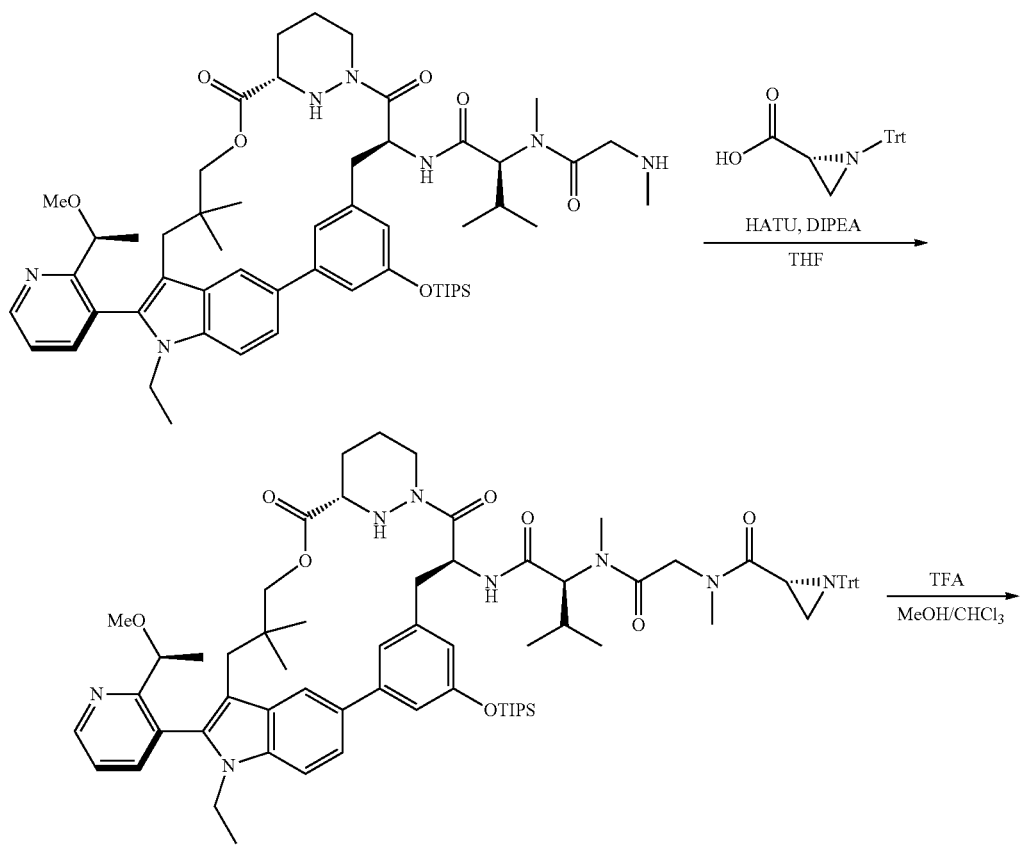

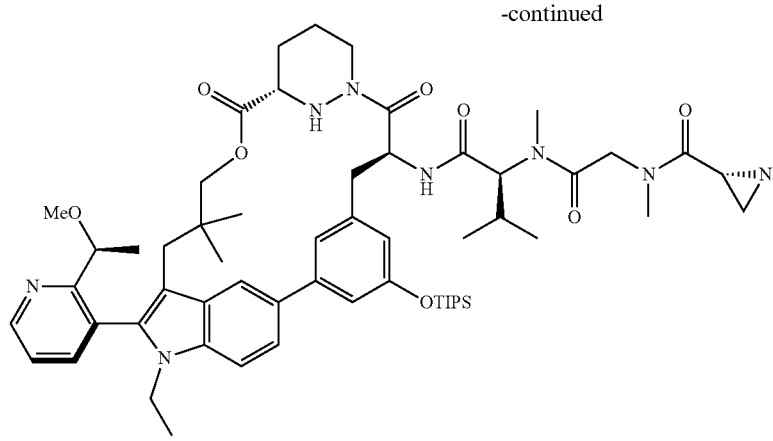
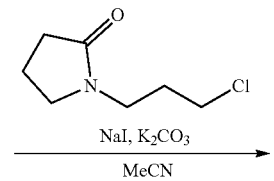
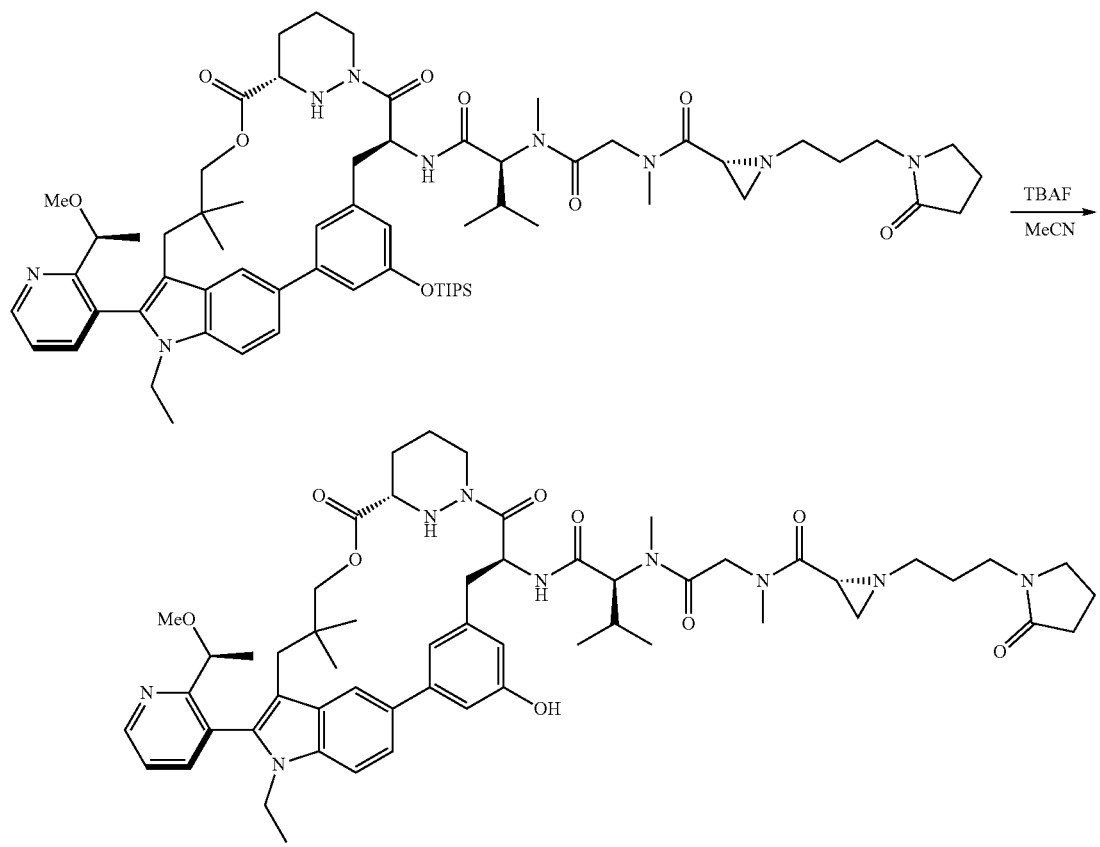

Step 1: Synthesis of (2R)—N-(2-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-tritylaziridine-2-carboxamide To a solution of (1S)-1-tritylaziridine-2-carboxylic acid (537.6 mg, 1.63 mmol), (2S)—N-((6³S,4S)-1¹-ethyl-1²-(2-((S)-1-methoxyethyl)pyridin-3-yl)-10,10-dimethyl-5,7-di-oxo-2⁵-((triisopropylsilyl)oxy)-6¹,6²,6³,6⁴,6⁵,6⁶-hexa- hydro-1¹H-8-oxa-1(5,3)-indola-6(1,3)-pyridazina-2(1,3)-benzenacycloundecaphane-4-yl)-3-methyl-2-(N-methyl-2-(methylamino)acetamido)butanamide (800 mg, 0.816 mmol) in THF (8 mL) was added DIPEA (0.711 mL, 4.08 mmol), HATU (465.4 mg, 1.22 mmol) at 0° C., the reaction was warmed to room temperature and stirred for 2 h. To the reaction was added H₂O (20 mL), the aqueous phase was extracted with DCM (3×30 mL) and the combined organic phases were washed with brine (20 mL), dried over Na₂SO₄, filtered, and concentrated under reduced pressure. The residue was purified by silica gel column chromatography (0→100% EtOAc/pet. ether) to afford the desired product (1 g, 94.9% yield).

Step 2: Synthesis of (2R)—N-(2-(((2S)-1-(((6³S, 4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide To a solution of (2R)—N-(2-(((2S)-1-(((6³S,4S)-1¹-ethyl-1²-(2-((S)-1-methoxyethyl)pyridine-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-tritylaziridine-2-carboxamide (1 g, 0.774 mmol) in MeOH (5 mL) and CHCl₃ (5 mL) was added TFA (1.15 mL, 15.48 mmol) at 0° C. The reaction was warmed to room temperature and stirred for 2 h. The reaction mixture was added dropwise to aq. NaHCO₃(30 mL) at 0° C. Then the pH was adjusted to pH 7-8 with using aq. NaHCO₃ at 0° C. The mixture was extracted with DCM (3×20 mL), dried over Na₂SO₄, filtered, and concentrated under reduced pressure to afford the desired product product (960 mg, crude), which was used directly in the next step without further purification.

Step 3: Synthesis of (2R)—N-(2-(((2S)-1-(((6³S, 4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(3-(2-oxopyrrolidin-1-yl)propyl)aziridine-2-carboxamide To a solution of (2R)—N-(2-(((2S)-1-(((6³S,4S)-1¹-ethyl-1²-(2-((S)-1-methoxyethyl)pyridine-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methylaziridine-2-carboxamide (960 mg, 0.915 mmol) in MeCN (10 mL) was added 1-(3-chloropropyl)pyrrolidin-2-one (887.1 mg, 5.49 mmol), K₂CO₃ (1.14 g, 8.23 mmol), NaI (411.4 mg, 2.74 mmol), the reaction was stirred at 80° C. for 24 h. To the reaction was added H₂O (20 mL), the aqueous phase was extracted with EtOAc (3×20 mL). The combined organic phase was dried over Na₂SO₄, filtered, and concentrated under reduced pressure. The residue was purified by reverse phase chromatography (73→93% MeCN/H₂O, 10 mM NH₄HCO₃) to afford product (80 mg, 7.5% yield). LCMS (ESI) m/z: [M+H] calcd for C₆₅H₉₆N₉O₉Si: 1174.7; found 1174.7.

Step 4: Synthesis of (2R)—N-(2-(((2S)-1-(((6³S, 4S)-1¹-ethyl-2⁵-hydroxy-1²-(2-((S)-1-methoxyethyl)pyridin-3-yl)-10,10-dimethyl-5,7-dioxo-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(3-(2-oxopyrrolidin-1-yl)propyl)aziridine-2-carboxamide To a solution of (2R)—N-(2-(((2S)-1-(((6³S,4S)-1¹-ethyl-1²-(2-((S)-1-methoxyethyl)pyridin-3-yl)-10,10-dimethyl-5,7-dioxo-2⁵-((triisopropylsilyl)oxy)-6¹,6²,6³,6⁴,6⁵,6⁶-hexahydro-1¹H-8-oxa-1(5,3)-indola-6(1,3)-pyridazina-2(1,3)-benzenacycloundecaphane-4-yl)amino)-3-methyl-1-oxobutan-2-yl)(methyl)amino)-2-oxoethyl)-N-methyl-1-(3-(2-oxopyrrolidin-1-yl)propyl)aziridine-2-carboxamide (80 mg, 0.068 mmol) in THF (1 mL) was added TBAF (1 M, 0.082 mL). The reaction was stirred for 1 h and then was added to H₂O (10 mL), the aqueous phase was extracted with EtOAc (3×10 mL). The combined organic phase was dried over Na₂SO₄, filtered, and concentrated under reduced pressure. The resulting residue was purified by reverse phase chromatography (25-65% MeCN/H₂O, 10 mM NH₄HCO₃ to afford the desired product (42 mg, 60.4% yield). LCMS (ESI) m/z: [M+H] calcd for C₅₆H₇₆N₉O₉: 1018.6; found 1018.5.

The following table of compounds (Table 4) were prepared using the aforementioned methods or variations thereof, as is known to those of skill in the art.

TABLE 4

Exemplary Compounds Prepared by Methods of the Present Invention

| Ex# | Molecular Formula | Calculated MW | Observed MW LCMS (ESI) m/z |
|---|---|---|---|
| 1 | $C_{50}H_{64}N_8O_8$ | [M + H] = 905.49 | [M + H] = 905.7 |
| 2 | $C_{50}H_{64}N_8O_8$ | [M + H] = 905.49 | [M + H] = 905.7 |
| 3 | $C_{51}H_{66}N_8O_8$ | [M + H] = 919.51 | [M + H] = 919.7 |
| 4 | $C_{51}H_{66}N_8O_8$ | [M + H] = 919.51 | [M + H] = 919.7 |
| 5 | $C_{49}H_{62}N_8O_8$ | [M + H] = 891.48 | [M + H] = 891.7 |
| 6 | $C_{49}H_{62}N_8O_8$ | [M + H] = 891.48 | [M + H] = 891.7 |
| 7 | $C_{48}H_{62}N_8O_8$ | [M + H] = 879.48 | [M + H] = 879.7 |
| 8 | $C_{48}H_{62}N_8O_8$ | [M + H] = 879.48 | [M + H] = 879.7 |
| 9 | $C_{56}H_{68}N_8O_8$ | [M + H] = 969.52 | [M + H] = 969.5 |
| 10 | $C_{56}H_{68}N_8O_8$ | [M + H] = 969.52 | [M + H] = 969.5 |
| 11 | $C_{54}H_{66}N_8O_8$ | [M + H] = 955.51 | [M + H] = 955.7 |
| 12 | $C_{54}H_{66}N_8O_8$ | [M + H] = 955.51 | [M + H] = 955.7 |
| 13 | $C_{49}H_{64}N_8O_{10}S$ | [M + H] = 957.45 | [M + H] = 957.5 |
| 14 | $C_{50}H_{64}N_8O_9$ | [M + H] = 921.49 | [M + H] = 921.5 |
| 15A | $C_{53}H_{64}N_8O_7$ | [M + H] = 925.50 | [M + H] = 925.5 |
| 15B | $C_{53}H_{64}N_8O_7$ | [M + H] = 925.50 | [M + H] = 925.5 |
| 16A | $C_{50}H_{66}N_8O_6S$ | [M + H] = 907.49 | [M + H] = 907.5 |
| 16B | $C_{50}H_{66}N_8O_6S$ | [M + H] = 907.49 | [M + H] = 907.5 |
| 17A | $C_{53}H_{71}N_9O_7$ | [M + H] = 946.56 | [M + H] = 946.6 |
| 17B | $C_{53}H_{71}N_9O_7$ | [M + H] = 946.56 | [M + H] = 946.6 |
| 18A | $C_{54}H_{66}N_8O_7$ | [M + H] = 940.52 | [M + H] = 939.6 |
| 18B | $C_{54}H_{66}N_8O_7$ | [M + H] = 940.52 | [M + H] = 939.6 |
| 19A | $C_{53}H_{64}N_8O_6$ | [M + H] = 909.50 | [M + H] = 909.6 |
| 19B | $C_{53}H_{64}N_8O_6$ | [M + H] = 909.50 | [M + H] = 909.5 |
| 20A | $C_{53}H_{64}N_8O_7$ | [M + H] = 925.50 | [M + H] = 925.5 |
| 20B | $C_{53}H_{64}N_8O_7$ | [M + H] = 925.50 | [M + H] = 925.5 |
| 21A | $C_{49}H_{64}N_8O_6$ | [M + H] = 861.50 | [M + H] = 861.5 |
| 21B | $C_{49}H_{64}N_8O_6$ | [M + H] = 861.50 | [M + H] = 861.5 |
| 22A | $C_{49}H_{64}N_8O_6$ | [M + H] = 861.50 | [M + H] = 861.6 |
| 22B | $C_{49}H_{64}N_8O_6$ | [M + H] = 861.50 | [M + H] = 861.5 |
| 23A | $C_{49}H_{64}N_8O_7$ | [M + H] = 877.50 | [M + H] = 877.6 |
| 23B | $C_{49}H_{64}N_8O_7$ | [M + H] = 877.50 | [M + H] = 877.6 |
| 24A | $C_{54}H_{66}N_8O_8$ | [M + H] = 955.51 | [M + H] = 955.6 |
| 24B | $C_{54}H_{66}N_8O_8$ | [M + H] = 955.51 | [M + H] = 955.6 |
| 25 | $C_{48}H_{63}ClN_8O_8$ | [M + H] = 915.45 | [M + H] = 915.7 |
| 26 | $C_{46}H_{60}ClN_7O_7$ | [M + H] = 858.43 | [M + H] = 858.7 |
| 27 | $C_{48}H_{62}N_8O_8$ | [M + H] = 879.48 | [M + H] = 879.4 |
| 28 | $C_{47}H_{60}N_8O_8$ | [M + H] = 865.46 | [M + H] = 865.7 |
| 29 | $C_{45}H_{57}N_7O_7$ | [M + H] = 808.44 | [M + H] = 808.8 |
| 30 | $C_{46}H_{59}N_7O_7$ | [M + H] = 822.46 | [M + H] = 822.4 |
| 31 | $C_{50}H_{63}N_7O_9$ | [M + H] = 906.46 | [M + H] = 906.7 |
| 32A | $C_{54}H_{66}N_8O_7$ | [M + H] = 940.18 | [M + H] = 939.6 |
| 32B | $C_{54}H_{66}N_8O_7$ | [M + H] = 940.18 | [M + H] = 939.6 |
| 33 | $C_{48}H_{62}N_8O_8$ | [M + H] = 879.48 | [M + H] = 878.5 |
| 34 | $C_{50}H_{64}N_8O_9$ | [M + H] = 921.49 | [M + H] = 921.5 |
| 35 | $C_{50}H_{64}N_8O_9$ | [M + H] = 921.49 | [M + H] = 921.6 |
| 36 | $C_{49}H_{64}N_8O_{10}S$ | [M + H] = 957.45 | [M + H] = 957.5 |
| 37 | $C_{49}H_{64}N_8O_{10}S$ | [M + H] = 957.45 | [M + H] = 957.5 |
| 38 | $C_{50}H_{64}N_8O_{10}$ | [M + H] = 937.48 | [M + H] = 937.6 |
| 39 | $C_{50}H_{64}N_8O_{10}$ | [M + H] = 937.48 | [M + H] = 937.5 |

TABLE 4-continued

Exemplary Compounds Prepared by Methods of the Present Invention

| Ex# | Molecular Formula | Calculated MW | Observed MW LCMS (ESI) m/z |
|---|---|---|---|
| 40 | $C_{49}H_{64}N_8O_8$ | [M + H] = 893.49 | [M + H] = 893.7 |
| 41 | $C_{49}H_{64}N_8O_8$ | [M + H] = 893.49 | [M + H] = 893.8 |
| 42A | $C_{49}H_{64}N_8O_8$ | [M + H] = 893.49 | [M + H] = 893.7 |
| 42B | $C_{49}H_{64}N_8O_8$ | [M + H] = 893.49 | [M + H] = 893.7 |
| 43A | $C_{51}H_{66}N_8O_8$ | [M + H] = 919.51 | [M + H] = 919.8 |
| 43B | $C_{51}H_{66}N_8O_8$ | [M + H] = 919.51 | [M + H] = 919.7 |
| 44 | $C_{51}H_{67}N_9O_8$ | [M + H] = 934.52 | [M + H] = 934.8 |
| 45 | $C_{51}H_{67}N_9O_8$ | [M + H] = 934.52 | [M + H] = 934.7 |
| 46 | $C_{51}H_{61}N_9O_8$ | [M + H] = 928.47 | [M + H] = 928.7 |
| 47A | $C_{51}H_{61}N_9O_8$ | [M + H] = 928.47 | [M + H] = 928.7 |
| 47B | $C_{51}H_{61}N_9O_8$ | [M + H] = 928.47 | [M + H] = 928.7 |
| 48 | $C_{54}H_{72}N_8O_{11}S$ | [M + H] = 1041.51 | [M + H] = 1041.8 |
| 49 | $C_{50}H_{64}N_8O_{10}$ | [M + H] = 937.48 | [M + H] = 938.6 |
| 50 | $C_{54}H_{72}N_8O_{11}S$ | [M + H] = 1041.51 | [M + H] = 1041.6 |
| 51 | $C_{50}H_{64}N_8O_{10}$ | [M + H] = 937.48 | [M + H] = 937.8 |
| 52 | $C_{55}H_{74}N_8O_9S$ | [M + H] = 1023.54 | [M + H] = 1023.8 |
| 53 | $C_{53}H_{72}N_8O_9S$ | [M + Na] = 1019.50 | [M + Na] = 1019.8 |
| 54 | $C_{53}H_{72}N_8O_9S$ | [M + H] = 997.52 | [M + H] = 997.7 |
| 55 | $C_{55}H_{64}N_8O_9$ | [M + H] = 1003.47 | [M + H] = 1003.8 |
| 56 | $C_{51}H_{68}N_8O_9S$ | [M + Na] = 991.47 | [M + Na] = 991.7 |
| 57 | $C_{51}H_{68}N_8O_9S$ | [M + H] = 969.49 | [M + H] = 969.8 |
| 58 | $C_{53}H_{68}N_8O_8$ | [M + H] = 945.52 | [M + H] = 945.8 |
| 59 | $C_{52}H_{66}N_8O_8$ | [M + H] = 931.51 | [M + H] = 931.8 |
| 60 | $C_{46}H_{59}N_7O_7$ | [M + H] = 822.46 | [M + H] = 822.7 |
| 61A | $C_{55}H_{68}N_8O_8$ | [M + H] = 969.52 | [M + H] = 969.6 |
| 61B | $C_{55}H_{68}N_8O_8$ | [M + H] = 969.52 | [M + H] = 969.6 |
| 62A | $C_{55}H_{68}N_8O_8$ | [M + H] = 955.51 | [M + H] = 955.5 |
| 62B | $C_{55}H_{68}N_8O_8$ | [M + H] = 955.51 | [M + H] = 955.5 |
| 63 | $C_{54}H_{66}N_8O_7$ | [M + H] = 939.51 | [M + H] = 939.6 |
| 64A | $C_{55}H_{68}N_8O_7$ | [M + H] = 953.53 | [M + H] = 953.6 |
| 64B | $C_{55}H_{68}N_8O_7$ | [M + H] = 953.53 | [M + H] = 953.6 |
| 65A | $C_{55}H_{66}N_8O_7$ | [M + H] = 951.51 | [M + H] = 951.7 |
| 65B | $C_{55}H_{66}N_8O_7$ | [M + H] = 951.51 | [M + H] = 951.6 |
| 66 | $C_{54}H_{67}N_9O_6$ | [M + H] = 938.53 | [M + H] = 938.5 |
| 67 | $C_{56}H_{69}N_9O_7$ | [M + H] = 980.54 | [M + H] = 980.1 |
| 68A | $C_{52}H_{64}N_8O_6S$ | [M + H] = 929.47 | [M + H] = 929.5 |
| 68B | $C_{52}H_{64}N_8O_6S$ | [M + H] = 929.47 | [M + H] = 929.5 |
| 69A | $C_{51}H_{68}N_8O_7$ | [M + H] = 891.51 | [M + H] = 891.5 |
| 69B | $C_{51}H_{68}N_8O_7$ | [M + H] = 891.51 | [M + H] = 891.5 |
| 70A | $C_{56}H_{68}N_8O_7$ | [M + H] = 965.53 | [M + H] = 965.6 |
| 70B | $C_{56}H_{68}N_8O_7$ | [M + H] = 965.53 | [M + H] = 965.6 |
| 71A | $C_{56}H_{68}N_8O_7$ | [M + H] = 965.53 | [M + H] = 965.5 |
| 71B | $C_{56}H_{68}N_8O_7$ | [M + H] = 965.53 | [M + H] = 965.5 |
| 72A | $C_{51}H_{66}N_8O_7$ | [M + H] = 903.51 | [M + H] = 903.5 |
| 72B | $C_{51}H_{66}N_8O_7$ | [M + H] = 903.51 | [M + H] = 903.6 |
| 73 | $C_{55}H_{68}N_8O_7$ | [M + H] = 953.53 | [M + H] = 953.6 |
| 74 | $C_{50}H_{66}N_8O_7$ | [M + H] = 891.51 | [M + H] = 891.6 |
| 75 | $C_{55}H_{68}N_8O_8$ | [M + H] = 969.52 | [M + H] = 969.9 |
| 76 | $C_{58}H_{72}N_8O_7$ | [M + H] = 993.56 | [M + H] = 993.5 |
| 77 | $C_{57}H_{70}N_8O_7$ | [M + H] = 979.54 | [M + H] = 979.5 |
| 78 | $C_{52}H_{68}N_8O_7$ | [M + H] = 917.53 | [M + H] = 917.5 |
| 79A | $C_{50}H_{66}N_8O_6$ | [M + H] = 875.52 | [M + H] = 875.6 |
| 79B | $C_{50}H_{66}N_8O_6$ | [M + H] = 875.52 | [M + H] = 875.6 |
| 80 | $C_{50}H_{66}N_8O_6$ | [M + H] = 875.52 | [M + H] = 875.6 |
| 81 | $C_{54}H_{66}N_8O_6$ | [M + H] = 923.52 | [M + H] = 923.5 |
| 82A | $C_{54}H_{66}N_8O_6$ | [M + H] = 923.52 | [M + H] = 923.6 |
| 82B | $C_{54}H_{66}N_8O_6$ | [M + H] = 923.52 | [M + H] = 923.6 |
| 83 | $C_{51}H_{64}N_{10}O_8$ | [M + H] = 945.50 | [M + H] = 945.6 |
| 84 | $C_{51}H_{64}N_{10}O_8$ | [M + H] = 945.50 | [M + H] = 945.6 |
| 85 | $C_{51}H_{68}N_8O_9$ | [M + H] = 937.52 | [M + H] = 837.6 |
| 86 | $C_{52}H_{68}N_8O_8$ | [M + H] = 933.52 | [M + H] = 933.7 |
| 87 | $C_{51}H_{62}N_8O_7$ | [M + H] = 899.48 | [M + H] = 899.5 |
| 88 | $C_{52}H_{68}N_8O_8$ | [M + H] = 933.52 | [M + H] = 933.6 |
| 89 | $C_{52}H_{68}N_8O_8$ | [M + H] = 933.52 | [M + H] = 933.6 |
| 90 | $C_{52}H_{70}N_8O_9$ | [M + H] = 951.53 | [M + H] = 951.6 |
| 91 | $C_{49}H_{66}N_8O_9S$ | [M + H] = 943.48 | [M + H] = 943.6 |
| 92 | $C_{49}H_{66}N_8O_9S$ | [M + H] = 943.48 | [M + H] = 943.5 |
| 93 | $C_{55}H_{68}N_8O_9$ | [M + H] = 985.52 | [M + H] = 985.7 |
| 94 | $C_{52}H_{66}N_8O_{10}$ | [M + H] = 963.50 | [M + H] = 963.6 |
| 95 | $C_{51}H_{66}N_8O_8$ | [M + H] = 919.51 | [M + H] = 919.5 |
| 96 | $C_{55}H_{68}N_8O_9$ | [M + H] = 985.52 | [M + H] = 985.7 |
| 97 | $C_{55}H_{68}N_8O_9$ | [M + H] = 985.52 | [M + H] = 985.7 |
| 98 | $C_{48}H_{58}N_8O_9$ | [M + H] = 891.44 | [M + H] = 891.6 |
| 99 | $C_{46}H_{59}N_7O_7$ | [M + H] = 822.46 | [M + H] = 822.6 |
| 100 | $C_{46}H_{59}N_7O_7$ | [M + H] = 822.46 | [M + H] = 822.6 |
| 101 | $C_{55}H_{74}N_8O_9S$ | [M + Na] = 1045.52 | [M + Na] = 1045.7 |
| 102 | $C_{50}H_{66}N_8O_8$ | [M + H] = 907.51 | [M + H] = 907.7 |
| 103 | $C_{51}H_{66}N_8O_8$ | [M + H] = 919.51 | [M + H] = 919.5 |
| 104 | $C_{51}H_{66}N_8O_8$ | [M + H] = 919.51 | [M + H] = 919.7 |
| 105 | $C_{49}H_{64}N_8O_8$ | [M + H] = 893.49 | [M + H] = 893.7 |
| 106 | $C_{51}H_{66}N_8O_7$ | [M + H] = 903.51 | [M + H] = 930.7 |
| 107 | $C_{49}H_{64}N_8O_7$ | [M + H] = 877.50 | [M + H] = 877.7 |
| 108 | $C_{52}H_{70}N_8O_9S$ | [M + H] = 983.51 | [M + H] = 983.8 |
| 109 | $C_{51}H_{64}N_8O_8$ | [M + H] = 917.49 | [M + H] = 917.7 |
| 110 | $C_{54}H_{66}N_8O_8$ | [M + H] = 955.51 | [M + H] = 955.7 |
| 111 | $C_{52}H_{66}N_8O_{10}$ | [M + H] = 963.50 | [M + H] = 963.8 |
| 112 | $C_{46}H_{59}N_7O_7$ | [M + H] = 822.46 | [M + H] = 822.6 |
| 113 | $C_{52}H_{66}N_8O_8$ | [M + Na] = 953.49 | [M + Na] = 953.6 |
| 114 | $C_{50}H_{66}N_8O_8$ | [M + H] = 907.51 | [M + H] = 907.7 |
| 115 | $C_{51}H_{64}N_8O_8$ | [M + H] = 917.49 | [M + H] = 917.6 |
| 116 | $C_{54}H_{66}N_8O_8$ | [M + H] = 955.51 | [M + H] = 955.7 |
| 117 | $C_{50}H_{66}N_8O_9S$ | [M + H] = 955.48 | [M + H] = 955.6 |
| 118 | $C_{50}H_{66}N_8O_9S$ | [M + H] = 955.48 | [M + H] = 955.8 |
| 119 | $C_{52}H_{70}N_8O_9S$ | [M + H] = 983.51 | [M + H] = 983.7 |
| 120 | $C_{48}H_{62}N_8O_8$ | [M + H] = 879.48 | [M + H] = 880.2 |
| 121 | $C_{51}H_{68}N_8O_6$ | [M + H] = 889.53 | [M + H] = 889.6 |
| 122 | $C_{51}H_{68}N_8O_6$ | [M + H] = 889.53 | [M + H] = 889.6 |
| 123 | $C_{55}H_{70}N_8O_6$ | [M + H] = 939.55 | [M + H] = 939.6 |
| 124 | $C_{53}H_{70}N_8O_6$ | [M + H] = 915.55 | [M + H] = 915.6 |
| 125 | $C_{54}H_{72}N_8O_6$ | [M + H] = 929.57 | [M + H] = 929.6 |
| 126 | $C_{57}H_{70}N_8O_6$ | [M + H] = 963.55 | [M + H] = 963.6 |
| 127 | $C_{52}H_{63}N_9O_8$ | [M + H] = 942.49 | [M + H] = 942.4 |
| 128 | $C_{55}H_{70}N_8O_8$ | [M + H] = 971.54 | [M + H] = 971.5 |
| 129 | $C_{49}H_{62}N_8O_8$ | [M + H] = 891.48 | [M + H] = 891.4 |
| 130 | $C_{49}H_{62}N_8O_7$ | [M + H] = 891.48 | [M + H] = 891.5 |
| 131 | $C_{52}H_{63}N_7O_7$ | [M + H] = 898.49 | [M + H] = 898.4 |
| 132 | $C_{52}H_{63}N_7O_7$ | [M + H] = 910.46 | [M + H] = 910.4 |
| 133 | $C_{52}H_{68}N_8O_8$ | [M + H] = 933.52 | [M + H] = 933.6 |
| 134 | $C_{52}H_{68}N_8O_8$ | [M + H] = 919.51 | [M + H] = 919.5 |
| 135 | $C_{52}H_{68}N_8O_8$ | [M + H] = 933.52 | [M + H] = 933.5 |
| 136 | $C_{52}H_{68}N_8O_8$ | [M + H] = 933.52 | [M + H] = 933.6 |
| 137 | $C_{53}H_{72}N_8O_9$ | [M + H] = 965.55 | [M + H] = 966.2 |
| 138 | $C_{52}H_{68}N_8O_7$ | [M + H] = 917.53 | [M + H] = 918.2 |
| 139 | $C_{52}H_{68}N_8O_7$ | [M + H] = 917.53 | [M + H] = 917.4 |
| 140 | $C_{48}H_{62}N_8O_8$ | [M + H] = 879.48 | [M + H] = 879.4 |
| 141 | $C_{51}H_{66}N_8O_8$ | [M + H] = 919.51 | [M + H] = 919.1 |
| 142 | $C_{52}H_{70}N_8O_8$ | [M + H] = 935.54 | [M + H] = 936.3 |
| 143 | $C_{51}H_{65}N_9O_9$ | [M + H] = 965.52 | [M + H] = 966.3 |
| 144 | $C_{52}H_{69}N_9O_8$ | [M + H] = 948.53 | [M + H] = 948.5 |
| 145 | $C_{52}H_{63}N_7O_7$ | [M + H] = 898.49 | [M + H] = 898.5 |
| 146 | $C_{52}H_{66}N_8O_8$ | [M + H] = 931.51 | [M + H] = 931.5 |
| 147 | $C_{48}H_{62}N_8O_8$ | [M + H] = 879.48 | [M + H] = 879.5 |
| 148 | $C_{52}H_{70}N_8O_8$ | [M + H] = 934.53 | [M + H] = 936.3 |
| 149 | $C_{52}H_{66}N_8O_8$ | [M + H] = 931.51 | [M + H] = 931.5 |
| 150 | $C_{49}H_{64}N_8O_8$ | [M + H] = 893.49 | [M + H] = 893.5 |
| 151 | $C_{51}H_{66}N_8O_8$ | [M + H] = 919.51 | [M + H] = 919.5 |
| 152 | $C_{51}H_{66}N_8O_8$ | [M + H] = 919.51 | [M + H] = 919.5 |
| 153 | $C_{52}H_{68}N_8O_8$ | [M + H] = 933.52 | [M + H] = 934.5 |
| 154 | $C_{52}H_{68}N_8O_8$ | [M + H] = 933.52 | [M + H] = 934.5 |
| 155 | $C_{56}H_{69}FN_8O_8$ | [M + H] = 1001.53 | [M + H] = 1001.9 |
| 156 | $C_{57}H_{72}N_8O_9$ | [M + H] = 1013.55 | [M + H] = 1013.9 |
| 157 | $C_{50}H_{64}N_8O_8$ | [M + H] = 905.49 | [M + H] = 905.5 |
| 158 | $C_{50}H_{64}N_8O_8$ | [M + H] = 905.49 | [M + H] = 905.6 |
| 159 | $C_{52}H_{70}N_8O_9$ | [M + H] = 951.53 | [M + H] = 951.6 |
| 160 | $C_{52}H_{70}N_8O_9$ | [M + H] = 951.53 | [M + H] = 951.6 |
| 161 | $C_{51}H_{68}N_8O_9$ | [M + H] = 937.52 | [M + H] = 937.6 |
| 162 | $C_{51}H_{68}N_8O_9$ | [M + H] = 937.52 | [M + H] = 937.6 |
| 163 | $C_{52}H_{66}N_8O_8$ | [M + H] = 931.51 | [M + H] = 931.5 |
| 164 | $C_{52}H_{66}N_8O_8$ | [M + H] = 931.51 | [M + H] = 931.5 |
| 165 | $C_{52}H_{68}N_8O_8$ | [M + H] = 933.53 | [M + H] = 933.5 |
| 166 | $C_{52}H_{66}N_8O_8$ | [M + H] = 931.51 | [M + H] = 931.5 |
| 167 | $C_{51}H_{66}N_8O_8$ | [M + H] = 919.51 | [M + H] = 919.7 |
| 168 | $C_{48}H_{64}N_{10}O_7S$ | [M + H] = 925.48 | [M + H] = 925.30 |
| 169 | $C_{48}H_{64}N_{10}O_7S$ | [M + H] = 925.48 | [M + H] = 925.30 |
| 170 | $C_{54}H_{70}N_8O_8$ | [M + H] = 959.54 | [M + H] = 959.40 |
| 171 | $C_{51}H_{65}FN_8O_8$ | [M + H] = 937.50 | [M + H] = 937.3 |
| 172 | $C_{52}H_{66}N_8O_8$ | [M + H] = 919.51 | [M + H] = 919.3 |
| 173 | $C_{52}H_{69}N_9O_8$ | [M + H] = 948.54 | [M + H] = 948.5 |

TABLE 4-continued

Exemplary Compounds Prepared by Methods of the Present Invention

| Ex# | Molecular Formula | Calculated MW | Observed MW LCMS (ESI) m/z |
|---|---|---|---|
| 174 | $C_{54}H_{68}N_8O_8$ | [M + H] = 957.53 | [M + H] = 957.3 |
| 175 | $C_{54}H_{68}N_8O_8$ | [M + H] = 957.53 | [M + H] = 957.3 |
| 176 | $C_{52}H_{68}N_8O_7$ | [M + H] = 917.53 | [M + H] = 918.1 |
| 177 | $C_{51}H_{67}N_9O_8$ | [M + H] = 934.52 | [M + H] = 934.3 |
| 178 | $C_{51}H_{66}N_8O_8$ | [M − H] = 917.49 | [M − H] = 917.6 |
| 179 | $C_{51}H_{66}N_8O_8$ | [M − H] = 917.49 | [M − H] = 917.7 |
| 180 | $C_{53}H_{68}N_8O_8$ | [M + H] = 945.53 | [M + H] = 945.6 |
| 181 | $C_{53}H_{68}N_8O_8$ | [M + H] = 943.51 | [M + H] = 943.6 |
| 182 | $C_{51}H_{66}N_8O_8$ | [M + H] = 919.51 | [M + H] = 919.8 |
| 183 | $C_{51}H_{65}N_9O_9$ | [M + H] = 918.50 | [M + H] = 948.6 |
| 184 | $C_{51}H_{65}FN_8O_8$ | [M + H] = 937.50 | [M + H] = 937.3 |
| 185 | $C_{51}H_{65}FN_8O_8$ | [M + H] = 937.50 | [M + H] = 937.2 |
| 186 | $C_{51}H_{66}N_8O_8$ | [M + H] = 919.51 | [M + H] = 919.5 |
| 187 | $C_{52}H_{63}N_9O_8$ | [M + H] = 942.49 | [M + H] = 942.3 |
| 188 | $C_{50}H_{65}N_9O_8$ | [M + H] = 920.51 | [M + H] = 920.3 |
| 189 | $C_{50}H_{65}N_9O_8$ | [M + H] = 920.51 | [M + H] = 920.3 |
| 190 | $C_{52}H_{69}N_9O_8$ | [M + H] = 948.54 | [M + H] = 948.5 |
| 191 | $C_{53}H_{68}N_8O_8$ | [M + H] = 945.53 | [M + H] = 945.5 |
| 192 | $C_{53}H_{68}N_8O_8$ | [M + H] = 945.53 | [M + H] = 945.4 |
| 193 | $C_{52}H_{68}N_8O_7$ | [M + H] = 917.53 | [M + H] = 918.0 |
| 194 | $C_{51}H_{65}N_9O_9$ | [M + H$_2$O] = 965.50 | [M + H] = 966.4 |
| 195 | $C_{53}H_{68}N_8O_8$ | [M + H] = 945.53 | [M + H] = 945.5 |
| 196 | $C_{53}H_{68}N_8O_8$ | [M + H] = 945.53 | [M + H] = 945.4 |
| 197 | $C_{51}H_{67}N_9O_8$ | [M + H] = 934.52 | [M + H] = 934.5 |
| 198 | $C_{54}H_{70}N_8O_8$ | [M + H] = 959.54 | [M + H] = 959.3 |
| 199 | $C_{53}H_{68}N_8O_8$ | [M + H] = 945.53 | [M + H] = 945.4 |
| 200 | $C_{53}H_{68}N_8O_8$ | [M + H] = 945.53 | [M + H] = 945.5 |
| 201 | $C_{53}H_{72}N_8O_9$ | [M + H] = 965.55 | [M + H] = 965.4 |
| 202 | $C_{53}H_{68}N_8O_8$ | [M + H] = 945.53 | [M + H] = 945.8 |
| 203 | $C_{51}H_{67}N_9O_8$ | [M + H] = 934.52 | [M + H] = 934.8 |
| 204 | $C_{51}H_{69}N_9O_8$ | [M + H] = 936.54 | [M + H] = 936.8 |
| 205 | $C_{51}H_{65}N_9O_9$ | [M + H] = 948.50 | [M + H] = 948.5 |
| 206 | $C_{52}H_{68}N_8O_8$ | [M + H] = 933.53 | [M + H] = 933.7 |
| 207 | $C_{52}H_{68}N_8O_8$ | [M + H] = 933.53 | [M + H] = 933.5 |
| 208 | $C_{52}H_{68}N_8O_8$ | [M + H] = 933.53 | [M + H] = 933.7 |
| 209 | $C_{56}H_{76}N_{10}O_8$ | [M + H] = 1017.59 | [M + H] = 1017.6 |
| 210 | $C_{51}H_{67}N_9O_7S$ | [M + H] = 950.50 | [M + H] = 950.2 |
| 211 | $C_{51}H_{67}N_7O_8$ | [M + H] = 906.52 | [M + H] = 906.4 |
| 212 | $C_{50}H_{61}N_9O_8S$ | [M + H] = 948.45 | [M + H] = 948.1 |
| 213 | $C_{49}H_{62}N_8O_8$ | [M + H] = 891.48 | [M + H] = 891.4 |
| 214 | $C_{57}H_{72}N_8O_8$ | [M + H] = 997.56 | [M + H] = 997.2 |
| 215 | $C_{57}H_{72}N_8O_8$ | [M + H] = 997.56 | [M + H] = 997.2 |
| 216 | $C_{48}H_{66}N_{10}O_7S$ | [M + H] = 927.49 | [M + H] = 927.5 |
| 217 | $C_{48}H_{66}N_{10}O_7S$ | [M + H] = 927.49 | [M + H] = 927.4 |
| 218 | $C_{48}H_{64}N_{10}O_7S$ | [M + H] = 925.48 | [M + H] = 925.4 |
| 219 | $C_{48}H_{64}N_{10}O_7S$ | [M + H] = 925.48 | [M + H] = 925.1 |
| 220 | $C_{48}H_{64}N_{10}O_7S$ | [M + H] = 925.48 | [M + H] = 925.4 |
| 221 | $C_{48}H_{64}N_{10}O_7S$ | [M + H] = 925.48 | [M + H] = 925.4 |
| 222 | $C_{49}H_{66}N_{10}O_7S$ | [M + H] = 939.49 | [M + H] = 939.5 |
| 223 | $C_{49}H_{66}N_{10}O_7S$ | [M + H] = 939.49 | [M + H] = 939.5 |
| 224 | $C_{49}H_{66}N_{10}O_7S$ | [M + H] = 939.49 | [M + H] = 940.0 |
| 225 | $C_{49}H_{66}N_{10}O_7S$ | [M + H] = 939.49 | [M + H] = 939.2 |
| 226 | $C_{49}H_{66}N_{10}O_7S$ | [M + H] = 939.49 | [M + H] = 939.1 |
| 227 | $C_{49}H_{66}N_{10}O_7S$ | [M + H] = 939.49 | [M + H] = 939.9 |
| 228 | $C_{49}H_{66}N_{10}O_7S$ | [M + H] = 939.49 | [M + H] = 940.0 |
| 229 | $C_{49}H_{66}N_{10}O_7S$ | [M + H] = 939.49 | [M + H] = 939.1 |
| 230 | $C_{57}H_{77}N_9O_8$ | [M + H] = 1016.60 | [M + H] = 1016.6 |
| 231 | $C_{51}H_{64}N_8O_9$ | [M + H] = 933.49 | [M + H] = 933.1 |
| 232 | $C_{51}H_{64}N_8O_9$ | [M + H] = 933.49 | [M + H] = 933.2 |
| 233 | $C_{55}H_{68}F_2N_8O_7$ | [M + H] = 991.53 | [M + H] = 992.0 |
| 234 | $C_{54}H_{69}N_9O_7S$ | [M + H] = 988.51 | [M + H] = 988.1 |
| 235 | $C_{49}H_{66}N_{10}O_7S$ | [M + H] = 939.49 | [M + H] = 939.5 |
| 236 | $C_{52}H_{68}N_8O_8$ | [M + H] = 933.53 | [M + H] = 933.5 |
| 237 | $C_{52}H_{68}N_8O_8$ | [M + H] = 933.53 | [M + H] = 933.5 |
| 238 | $C_{52}H_{68}N_8O_8$ | [M + H] = 933.53 | [M + H] = 933.5 |
| 239 | $C_{52}H_{68}N_8O_8$ | [M + H] = 933.53 | [M + H] = 933.5 |
| 240 | $C_{52}H_{68}N_8O_8$ | [M + H] = 933.53 | [M + H] = 933.5 |
| 241 | $C_{52}H_{68}N_8O_8$ | [M + H] = 933.53 | [M + H] = 933.5 |
| 242 | $C_{52}H_{68}N_8O_8$ | [M + H] = 933.53 | [M + H] = 933.5 |
| 243 | $C_{52}H_{68}N_8O_8$ | [M + H] = 933.53 | [M + H] = 933.5 |
| 244 | $C_{52}H_{66}N_8O_8$ | [M + H] = 931.51 | [M + H] = 931.5 |
| 245 | $C_{54}H_{70}N_8O_8$ | [M + H] = 959.54 | [M + H] = 959.5 |
| 246 | $C_{54}H_{70}N_8O_8$ | [M + H] = 959.54 | [M + H] = 959.5 |
| 247 | $C_{53}H_{70}N_8O_8$ | [M + H] = 947.54 | [M + H] = 947.4 |
| 248 | $C_{52}H_{68}N_8O_9$ | [M + H] = 949.52 | [M + H] = 949.5 |
| 249 | $C_{52}H_{68}N_8O_9$ | [M + H] = 949.52 | [M + H] = 949.5 |
| 250 | $C_{52}H_{67}N_9O_8$ | [M + H] = 946.52 | [M + H] = 946.5 |
| 251 | $C_{52}H_{67}N_9O_8$ | [M + H] = 946.52 | [M + H] = 946.5 |
| 252 | $C_{52}H_{69}N_9O_8$ | [M + H] = 948.54 | [M + H] = 948.5 |
| 253 | $C_{52}H_{69}N_9O_8$ | [M + H] = 948.54 | [M + H] = 948.5 |
| 254 | $C_{52}H_{69}N_9O_8$ | [M + H] = 948.54 | [M + H] = 948.5 |
| 255 | $C_{52}H_{69}N_9O_8$ | [M + H] = 948.54 | [M + H] = 948.5 |
| 256 | $C_{50}H_{66}N_9O_8$ | [M + H] = 907.51 | [M + H] = 907.5 |
| 257 | $C_{50}H_{66}N_8O_8$ | [M + H] = 907.51 | [M + H] = 907.5 |
| 258 | $C_{50}H_{63}F_3N_8O_8$ | [M + H] = 961.48 | [M + H] = 961.5 |
| 259 | $C_{50}H_{63}F_3N_8O_8$ | [M + H] = 961.48 | [M + H] = 961.5 |
| 260 | $C_{50}H_{63}F_3N_8O_8$ | [M + H] = 961.48 | [M + H] = 961.5 |
| 261 | $C_{50}H_{63}F_3N_8O_8$ | [M + H] = 961.48 | [M + H] = 961.5 |
| 262 | $C_{51}H_{68}N_8O_8$ | [M + H] = 921.53 | [M + H] = 921.5 |
| 263 | $C_{51}H_{68}N_8O_8$ | [M + H] = 921.53 | [M + H] = 921.5 |
| 264 | $C_{52}H_{70}N_8O_8$ | [M + H] = 935.54 | [M + H] = 935.3 |
| 265 | $C_{52}H_{70}N_8O_8$ | [M + H] = 935.54 | [M + H] = 935.3 |
| 266 | $C_{54}H_{72}N_8O_{10}$ | [M + H] = 993.55 | [M + H] = 993.5 |
| 267 | $C_{54}H_{72}N_8O_{10}$ | [M + H] = 993.55 | [M + H] = 993.5 |
| 268 | $C_{56}H_{75}N_9O_9$ | [M + H] = 1018.58 | [M + H] = 1018.6 |
| 269 | $C_{56}H_{75}N_9O_9$ | [M + H] = 1018.58 | [M + H] = 1018.5 |
| 270 | $C_{53}H_{71}N_9O_9$ | [M + H] = 978.55 | [M + H] = 978.5 |
| 271 | $C_{53}H_{71}N_9O_9$ | [M + H] = 978.55 | [M + H] = 978.5 |
| 272 | $C_{55}H_{73}N_9O_{10}$ | [M + H] = 1020.56 | [M + H] = 1020.5 |
| 273 | $C_{53}H_{69}N_9O_8$ | [M + H] = 960.54 | [M + H] = 960.5 |
| 274 | $C_{53}H_{69}N_9O_8$ | [M + H] = 960.54 | [M + H] = 960.5 |
| 275 | $C_{52}H_{68}N_8O_9$ | [M + H] = 949.52 | [M + H] = 949.3 |
| 276 | $C_{52}H_{68}N_8O_9$ | [M + H] = 949.52 | [M + H] = 949.3 |
| 277 | $C_{53}H_{70}N_8O_9$ | [M + H] = 963.54 | [M + H] = 963.5 |
| 278 | $C_{53}H_{70}N_8O_9$ | [M + H] = 963.54 | [M + H] = 963.5 |
| 279 | $C_{54}H_{72}N_8O_9$ | [M + H] = 977.55 | [M + H] = 977.5 |
| 280 | $C_{54}H_{72}N_8O_9$ | [M + H] = 977.55 | [M + H] = 977.6 |
| 281 | $C_{52}H_{68}N_8O_9$ | [M + H] = 949.52 | [M + H] = 949.3 |
| 282 | $C_{52}H_{68}N_8O_9$ | [M + H] = 949.52 | [M + H] = 949.3 |
| 283 | $C_{52}H_{68}N_8O_9$ | [M + H] = 949.52 | [M + H] = 949.5 |
| 284 | $C_{52}H_{68}N_8O_9$ | [M + H] = 949.52 | [M + H] = 949.5 |
| 285 | $C_{52}H_{68}N_8O_8$ | [M + H] = 933.53 | [M + H] = 933.5 |
| 286 | $C_{49}H_{63}N_7O_7$ | [M + H] = 862.49 | [M + H] = 862.4 |
| 287 | $C_{53}H_{70}N_8O_8$ | [M + H] = 947.54 | [M + H] = 947.5 |
| 288 | $C_{53}H_{70}N_8O_8$ | [M + H] = 947.54 | [M + H] = 947.5 |
| 289 | $C_{50}H_{68}N_{10}O_7S$ | [M + H] = 953.51 | [M + H] = 953.5 |
| 290 | $C_{50}H_{68}N_{10}O_7S$ | [M + H] = 953.51 | [M + H] = 953.4 |
| 291 | $C_{50}H_{68}N_{10}O_7S$ | [M + H] = 953.51 | [M + H] = 953.5 |
| 292 | $C_{50}H_{68}N_{10}O_7S$ | [M + H] = 953.51 | [M + H] = 953.5 |
| 293 | $C_{49}H_{66}N_{10}O_7S$ | [M + H] = 939.49 | [M + H] = 939.5 |
| 294 | $C_{49}H_{66}N_{10}O_7S$ | [M + H] = 939.49 | [M + H] = 939.5 |
| 295 | $C_{50}H_{68}N_{10}O_7S$ | [M + H] = 953.51 | [M + H] = 953.5 |
| 296 | $C_{49}H_{66}N_{10}O_7S$ | [M + H] = 939.49 | [M + H] = 939.4 |
| 297 | $C_{49}H_{66}N_{10}O_7S$ | [M + H] = 939.49 | [M + H] = 939.5 |
| 298 | $C_{49}H_{66}N_{10}O_7S$ | [M + H] = 939.49 | [M + H] = 939.5 |
| 299 | $C_{49}H_{66}N_{10}O_7S$ | [M + H] = 939.49 | [M + H] = 939.5 |
| 300 | $C_{49}H_{66}N_{10}O_7S$ | [M + H] = 939.49 | [M + H] = 939.4 |
| 301 | $C_{49}H_{66}N_{10}O_7S$ | [M + H] = 939.49 | [M + H] = 939.4 |
| 302 | $C_{49}H_{66}N_{10}O_7S$ | [M + H] = 939.49 | [M + H] = 939.4 |
| 303 | $C_{50}H_{66}N_{10}O_7S$ | [M + H] = 951.49 | [M + H] = 951.5 |
| 304 | $C_{50}H_{66}N_{10}O_7S$ | [M + H] = 951.49 | [M + H] = 951.5 |
| 305 | $C_{55}H_{70}N_8O_8$ | [M + H] = 971.54 | [M + H] = 971.1 |
| 306 | $C_{52}H_{66}N_8O_8$ | [M + H] = 931.51 | [M + H] = 931.2 |
| 307 | $C_{52}H_{66}N_8O_8$ | [M + H] = 931.51 | [M + H] = 931.2 |
| 308 | $C_{55}H_{69}N_9O_8$ | [M + H] = 984.54 | [M + H] = 984.4 |
| 309 | $C_{53}H_{70}N_8O_8$ | [M + H] = 947.54 | [M + H] = 947.5 |
| 310 | $C_{49}H_{66}N_{10}O_7S$ | [M + H] = 939.49 | [M + H] = 939.5 |
| 311 | $C_{51}H_{65}FN_8O_8$ | [M + H] = 937.50 | [M + H] = 937.2 |
| 312 | $C_{49}H_{63}N_7O_8$ | [M + H] = 878.48 | [M + H] = 878.4 |
| 313 | $C_{57}H_{72}N_8O_7$ | [M + H] = 981.56 | [M + H] = 981.5 |
| 314 | $C_{54}H_{69}FN_8O_8$ | [M + H] = 977.53 | [M + H] = 977.5 |
| 315 | $C_{54}H_{69}FN_8O_8$ | [M + H] = 977.53 | [M + H] = 977.5 |
| 316 | $C_{55}H_{69}N_9O_8$ | [M + H] = 984.54 | [M + H] = 984.4 |
| 317 | $C_{58}H_{78}N_8O_9$ | [M + H] = 1031.60 | [M + H] = 1031.5 |
| 318 | $C_{58}H_{72}F_2N_8O_7$ | [M + H] = 1031.56 | [M + H] = 1031.5 |
| 319 | $C_{58}H_{72}F_2N_8O_7$ | [M + H] = 948.48 | [M + H] = 948.4 |
| 320 | $C_{51}H_{65}N_9O_7S$ | [M + H] = 993.54 | [M + H] = 993.5 |
| 321 | $C_{55}H_{70}F_2N_8O_7$ | [M + H] = 1013.57 | [M + H] = 1013.5 |

TABLE 4-continued

Exemplary Compounds Prepared by
Methods of the Present Invention

| Ex# | Molecular Formula | Calculated MW | Observed MW LCMS (ESI) m/z |
|---|---|---|---|
| 322 | $C_{55}H_{70}F_2N_8O_7$ | [M + H] = 989.55 | [M + H] = 989.5 |
| 323 | $C_{58}H_{73}FN_8O_7$ | [M + H] = 989.55 | [M + H] = 989.5 |
| 324 | $C_{58}H_{73}FN_8O_7$ | [M + H] = 1086.60 | [M + H] = 1086.6 |
| 325 | $C_{55}H_{72}N_8O_9$ | [M + H] = 1057.63 | [M + H] = 1057.4 |
| 326 | $C_{55}H_{72}N_8O_9$ | [M + H] = 967.52 | [M + H] = 967.5 |
| 327 | $C_{59}H_{79}N_{11}O_7S$ | [M + H] = 973.56 | [M + H] = 973.4 |
| 328 | $C_{59}H_{79}N_{11}O_7S$ | [M + H] = 973.56 | [M + H] = 973.5 |
| 329 | $C_{54}H_{69}N_7O_{11}$ | [M + H] = 992.52 | [M + H] = 992.5 |
| 330 | $C_{51}H_{65}N_7O_9$ | [M + H] = 920.49 | [M + H] = 920.6 |
| 331 | $C_{57}H_{69}N_7O_9$ | [M + H] = 996.53 | [M + H] = 996.6 |
| 332 | $C_{52}H_{67}N_7O_9$ | [M + H] = 934.51 | [M + H] = 934.6 |

Biological Assays

Compounds 1-2, 4-18A, 19A-19B, 21A-24A, 27-32A, 33-43A, 44-45, 47B-54, 56-59, 68A, 69A, 71B, 72A, 73-78, 79B-82A, 83-97, 100-110, 112-117, 119-234, 236-294, and 297-332 exhibited: a) a % cross-linking to KRAS$^{G12D}$ of greater than zero within a 24-hour incubation timeframe in the assay described below; and/or b) an IC50 of 2 µM or less in the KRAS$^{G12D}$-B-Raf (AsPC-1) disruption assay described below.

Potency Assay: pERK

The purpose of this assay is to measure the ability of test compounds to inhibit K-Ras in cells. Activated K-Ras induces increased phosphorylation of ERK at Threonine 202 and Tyrosine 204 (pERK). This procedure measures a decrease in cellular pERK in response to test compounds. The procedure described below in NCI-H358 cells is applicable to K-Ras G12C.

Note: This protocol may be executed substituting other cell lines to characterize inhibitors of other RAS variants, including, for example, AsPC-1 (K-Ras G12D), Capan-1 (K-Ras G12V), or NCI-H1355 (K-Ras G13C).

NCI-H358 cells were grown and maintained using media and procedures recommended by the ATCC. On the day prior to compound addition, cells were plated in 384-well cell culture plates (40 µl/well) and grown overnight in a 37° C., 5% CO2 incubator. Test compounds were prepared in 10, 3-fold dilutions in DMSO, with a high concentration of 10 mM. On the day of assay, 40 nL of test compound was added to each well of cell culture plate using an Echo550 liquid handler (LabCyte®). Concentrations of test compound were tested in duplicate. After compound addition, cells were incubated 4 hours at 37° C., 5% CO2. Following incubation, culture medium was removed and cells were washed once with phosphate buffered saline.

In some experiments, cellular pERK level was determined using the AlphaLISA SureFire Ultra p-ERK1/2 Assay Kit (PerkinElmer). Cells were lysed in 25 µL lysis buffer, with shaking at 600 RPM at room temperature. Lysate (10 µL) was transferred to a 384-well Opti-plate (PerkinElmer) and 5 µL acceptor mix was added. After a 2-hour incubation in the dark, 5 µL donor mix was added, plate was sealed, and incubated 2 hours at room temperature. Signal was read on an Envision plate reader (PerkinElmer) using standard AlphaLISA settings. Analysis of raw data was carried out in Excel (Microsoft) and Prism (GraphPad). Signal was plotted vs. the decadal logarithm of compound concentration, and IC$_{50}$ was determined by fitting a 4-parameter sigmoidal concentration response model.

In other experiments, cellular pERK was determined by In-Cell Western. Following compound treatment, cells were washed twice with 200 µL tris buffered saline (TBS) and fixed for 15 minutes with 150 µL 4% paraformaldehyde in TBS. Fixed cells were washed 4 times for 5 minutes with TBS containing 0.1% Triton X-100 (TBST) and then blocked with 100 µL Odyssey blocking buffer (LI-COR) for 60 minutes at room temperature. Primary antibody (pERK, CST-4370, Cell Signaling Technology) was diluted 1:200 in blocking buffer, and 50 µL was added to each well and incubated overnight at 4° C. Cells were washed 4 times for 5 minutes with TBST. Secondary antibody (IR-800CW rabbit, LI-COR, diluted 1:800) and DNA stain DRAQ5 (LI-COR, diluted 1:2000) were added and incubated 1-2 hours at room temperature. Cells were washed 4 times for 5 minutes with TBST. Plates were scanned on a Li—COR Odyssey CLx Imager. Analysis of raw data was carried out in Excel (Microsoft) and Prism (Graph Pad). Signal was plotted vs. the decadal logarithm of compound concentration, and IC$_{50}$ was determined by fitting a 4-parameter sigmoidal concentration response model.

The following compounds exhibited a pERK EC50 of under 5 uM (AsPC-1 KRAS G12D): 179, 157, 178, 327, 205, 106, 242, 121, 183, 36, 158, 196, 84, 17A and B, 87, 187, 114, 182, 255, 254, 185, 236, 124, 19 7, 1, 107, 192, 34, 118, 296, 78, 89, 104, 74, 306, 310, 105, 152, 269, 229, 221, 294, 117, 119, 240, 151, 193, 86, 245, 12 8, 163, 272, 270, 79A and B, 232, 140, 138, 293, 38, 94, 110, 172, 271, 246, 72A and B, 108, 35, 14, 127, 7, 153, 39, 190, 96, 227, 13, 77, 286, 215, 244, 184, 284, 275, 147, 295, 204, 50, 161, 129, 176, 51, 290, 226, 218, 164, 282, 167, 162, 1 31, 228, 292, 233, 308, 304, 48, 9, 113, 298, 277, 54, 57, 219, 173, 220, 268, 49, 149, 247, 120, 154, 307, 56, 166, 11, 53, 101, 10, 8, 238, 97, 303, 132, 186, 52, 297, 93, 85, 83, 280, 103, 200, 276, 278, 144, 165, 199, 33, 139, 112, 224, 177, 2 41, 273, 237, 274, 191, 243, 319, 320, 225, 59, 311, 207, 239, 279, 160, 289, 171, 156, 92, 202, 43A, 266, 208, 281, 15 9, 300, 210, 223, 217, 283, 216, 231, 299, 90, 91, 267, 155, 259, 291, 258, 257, 262, 222, 137, 100, 256, 88, 316, 142, 3 18, 146, 198, 288, 302, 174, 265, 322, 12, 168, 42A, 201, 301, 263, 248, 287, 58, 305, 260, 134, 169, 313, 314, 323, 23 4, 136, 148, 102, 315, 141, 150, 309, 326, 261, 321, 175, 230, 249, 264, 95, 285, 135, 133, 170, 317, 328, 214, 209, 324, 325.

Determination of Cell Viability in RAS Mutant Cancer Cell Lines

Protocol: CellTiter-Glo® Cell Viability Assay

Note—The following protocol describes a procedure for monitoring cell viability of K-Ras mutant cancer cell lines in response to a compound of the invention. Other RAS isoforms may be employed, though the number of cells to be seeded will vary based on cell line used.

The purpose of this cellular assay was to determine the effects of test compounds on the proliferation of three human cancer cell lines (NCI-H358 (K-Ras G12C), AsPC-1 (K-Ras G12D), and Capan-1 (K-Ras G12V)) over a 5-day treatment period by quantifying the amount of ATP present at endpoint using the CellTiter-Glo® 2.0 Reagent (Promega).

Cells were seeded at 250 cells/well in 40 µL of growth medium in 384-well assay plates and incubated overnight in a humidified atmosphere of 5% CO$_2$ at 37° C. On the day of the assay, 10 mM stock solutions of test compounds were first diluted into 3 mM solutions with 100% DMSO. Well-mixed compound solutions (15 µL) were transferred to the next wells containing 30 µL of 100% DMSO, and repeated until a 9-concentration 3-fold serial dilution was made (starting assay concentration of 10 µM). Test compounds (132.5 nL) were directly dispensed into the assay plates containing cells. The plates were shaken for 15 seconds at 300 rpm, centrifuged, and incubated in a humidified atmosphere of 5% $CO_2$ at 37° C. for 5 days. On day 5, assay plates and their contents were equilibrated to room temperature for approximately 30 minutes. CellTiter-Glo® 2.0 Reagent (25 μL) was added, and plate contents were mixed for 2 minutes on an orbital shaker before incubation at room temperature for 10 minutes. Luminescence was measured using the PerkinElmer Enspire. Data were normalized by the following: (Sample signal/Avg. DMSO)*100. The data were fit using a four-parameter logistic fit.

*Key:
+++++: IC50≥10 uM
++++: 10 uM>IC50≥1 uM
+++: 1 uM>IC50≥0.1 uM
++: 0.1 uM>IC50≥0.01 uM
+: IC50<0.01 uM

TABLE 5

H358 Cell Viability assay data (K-Ras G12C, IC50, uM):

| IC50* | Examples of A compounds |
|---|---|
| + | 1, 44, 58, 59, 90, 95, 106, 136, 137, 142, 146, 148, 150, 155, 156, 159, 160, 165, 171, 174, 175, 186, 201, 207, 209, 222, 231, 236, 241, 261, 266, 267, 273, 274, 279, 280, 299, 301, 307, 319, 324, 325, 328, 42A, 43A |
| ++ | 2, 5, 7, 8, 9, 10, 13, 33, 41, 83, 85, 100, 102, 132, 133, 135, 144, 168, 169, 170, 191, 208, 214, 216, 217, 223, 224, 225, 226, 227, 228, 230, 234, 239, 248, 249, 256, 257, 258, 259, 260, 262, 263, 264, 265, 270, 276, 277, 283, 287, 288, 289, 290, 291, 292, 293, 296, 297, 298, 300, 302, 303, 316, 317, 322, 323, 326, 42B, 43B |
| +++ | 3, 4, 6, 11, 12, 14, 40, 45, 46, 48, 50, 52, 56, 63, 77, 103, 107, 141, 202, 210, 243, 285, 294, 304, 313, 318, 320, 321 |
| ++++ | 26, 29, 30, 31, 49, 60, 66, 96, 15 A and B, 16 A and B, 16 A and B, 17 A and B, 17 A and B, 18 A and B, 18 A and B, 19 A and B, 19 A and B, 20 A and B, 20 A and B, 22 A and B, 23 A and B, 24 A and B, 24 A and B, 32 A and B, 32 A and B, 47 A and B, 62 A and B, 62 A and B, 68 A and B, 68 A and B, 69 A and B, 69 A and B |
| +++++ | 15 A and B, 25, 27, 28, 47 A and B, 67 |

TABLE 6

AsPC-1 Cell Viability assay data (K-Ras G12D, IC50, uM):

| IC50* | Examples of A compounds |
|---|---|
| + | 209, 325 |
| ++ | 95, 133, 170, 175, 214, 230, 249, 285, 309, 313, 317, 321, 324 |
| +++ | 7, 12, 58, 59, 77, 88, 90, 100, 102, 103, 135, 136, 137, 141, 142, 144, 146, 148, 150, 155, 156, 159, 160, 168, 169, 171, 174, 186, 198, 201, 207, 210, 216, 217, 222, 223, 224, 225, 228, 231, 234, 239, 241, 243, 248, 256, 257, 258, 259, 260, 261, 262, 263, 264, 265, 266, 267, 270, 273, 274, 277, 279, 281, 283, 287, 288, 289, 291, 297, 298, 299, 300, 301, 302, 303, 305, 307, 311, 314, 315, 318, 319, 320, 323, 326, 328, 19 A and B, 42A, 43A |
| ++++ | 1, 8, 9, 10, 11, 13, 14, 29, 34, 35, 38, 39, 44, 48, 49, 52, 53, 54, 56, 57, 60, 63, 73, 74, 75, 76, 78, 80, 81, 83, 84, 85, 86, 87, 91, 92, 96, 97, 101, 104, 105, 106, 107, 108, 110, 112, 113, 114, 117, 119, 120, 121, 122, 128, 129, 132, 134, 139, 140, 147, 149, 151, 152, 153, 154, 157, 158, 161, 162, 163, 164, 165, 166, 167, 172, 173, 176, 177, 184, 185, 187, 190, 191, 192, 193, 196, 197, 199, 200, 202, 204, 208, 215, 218, 219, 220, 221, 226, 227, 229, 232, 233, 236, 237, 238, 240, 242, 244, 245, 246, 247, 255, 268, 269, 272, 275, 276, 278, 280, 282, 284, 286, 290, 292, 293, 294, 295, 296, 304, 306, 308, 310, 316, 322, 327, 16 A and B, 17 A and B, 17 A and B, 18 A and B, 18 A and B, 22 A and B, 23 A and B, 32 A and B, 42B, 61 A and B, 61 A and B, 62 A and B, 62 A and B, 64 A and B, 65 A and B, 65 A and B, 68 A and B, 69 A and B, 69 A and B, 70 A and B, 71 A and B, |

TABLE 6-continued

AsPC-1 Cell Viability assay data (K-Ras G12D, IC50, uM):

| IC50* | Examples of A compounds |
|---|---|
|  | 72 A and B, 72 A and B, 79 A and B, 79 A and B, 82 A and B, 82 A and B |
| +++++ | 2, 3, 4, 5, 6, 28, 31, 36, 37, 40, 41, 45, 46, 50, 51, 55, 66, 67, 89, 93, 94, 98, 99, 109, 111, 115, 116, 118, 126, 127, 130, 131, 138, 143, 145, 178, 179, 180, 181, 182, 183, 188, 189, 194, 195, 203, 205, 206, 211, 212, 213, 235, 250, 251, 252, 253, 254, 271, 312, 15 A and B, 15 A and B, 20 A and B, 20 A and B, 24 A and B, 24 A and B, 32 A and B, 43B, 47 A and B, 47 A and B, 64 A and B, 70 A and B, 71 A and B |

Disruption of B-Raf Ras-Binding Domain ($BRAF^{RBD}$) Interaction with K-Ras by Compounds of the Invention (Also Called a FRET Assay or an MOA Assay)

Note—The following protocol describes a procedure for monitoring disruption of K-Ras G12C (GMP-PNP) binding to $BRAF^{RBD}$ by a compound of the invention. This protocol may also be executed substituting other Ras proteins or nucleotides, such as K-Ras G12D and K-Ras G13D.

The purpose of this biochemical assay was to measure the ability of test compounds to facilitate ternary complex formation between a nucleotide-loaded K-Ras isoform and Cyclophilin A; the resulting ternary complex disrupts binding to a $BRAF^{RBD}$ construct, inhibiting K-Ras signaling through a RAF effector. Data is reported as 1050 values.

In assay buffer containing 25 mM HEPES pH 7.3, 0.002% Tween20, 0.1% BSA, 100 mM NaCl and 5 mM $MgCl_2$, tagless Cyclophilin A, His6-K-Ras-GMPPNP, and GST-$BRAF^{RBD}$ were combined in a 384-well assay plate at final concentrations of 25 μM, 12.5 nM, and 50 nM, respectively. Compound was present in plate wells as a 10-point 3-fold dilution series starting at a final concentration of 30 μM. After incubation at 25° C. for 3 hours, a mixture of anti-His Eu-W1024 and anti-GST allophycocyanin was then added to assay sample wells at final concentrations of 10 nM and 50 nM, respectively, and the reaction incubated for an additional 1.5 hours. TR-FRET signal was read on a microplate reader (Ex 320 nm, Em 665/615 nm). Compounds that facilitate disruption of a K-Ras:RAF complex were identified as those eliciting a decrease in the TR-FRET ratio relative to DMSO control wells.

Ras-Raf Disruption/FRET/MOA Assay Data (IC50, uM):
*Key:
+++++: IC50≥10 uM
++++: 10 uM>IC50≥1 uM
+++: 1 uM>IC50≥0.1 uM
++: 0.1 uM>IC50≥0.01 uM
+: IC50<0.01 uM

TABLE 7

KRAS G13D FRET data

| IC50* | Examples of A compounds |
|---|---|
| + | None |
| ++ | 12, 58, 83, 85, 86, 88, 89, 95, 100, 109, 113, 115, 120, 129, 130, 133, 135, 136, 137, 138, 139, 140, 143, 148, 149, 150, 157, 158, 162, 167, 170, 171, 172, 173, 174, 175, 176, 177, 182, 186, 193, 194, 195, 196, 197, 198, 204, 209, 230, 231, 239, 241, 248, 249, 256, 257, 262, 263, 264, 265, 274, 276, 285, 286, 288, 306, 307, 309, 325, 329, 330, 332, 258*, 259*, 260*, 261*, 281*, 282*, 283*, 284*, 314*, 315*, 316*, 42A, 43A |
| +++ | 1, 2, 3, 4, 5, 7, 8, 9, 11, 13, 14, 33, 34, 35, 36, 37, 38, 39, 40, 41, 44, 45, 48, 49, 50, 51, 52, 53, 54, 56, 57, 59, |

TABLE 7-continued

KRAS G13D FRET data

| IC50* | Examples of A compounds |
|---|---|
| | 84, 87, 90, 91, 92, 93, 94, 96, 97, 101, 102, 103, 104, 105, 108, 110, 111, 112, 116, 117, 118, 119, 127, 128, 131, 134, 141, 142, 144, 145, 146, 147, 151, 152, 153, 155, 156, 159, 160, 161, 163, 164, 165, 166, 168, 169, 178, 179, 180, 181, 183, 184, 185, 187, 188, 189, 190, 191, 199, 200, 201, 202, 203, 205, 206, 207, 208, 212, 213, 214, 215, 216, 217, 218, 219, 220, 221, 222, 223, 224, 225, 226, 227, 228, 229, 232, 236, 237, 238, 242, 243, 244, 245, 246, 247, 252, 253, 254, 255, 266, 267, 268, 269, 270, 271, 272, 273, 275, 277, 278, 279, 280, 287, 289, 291, 293, 294, 297, 298, 299, 300, 301, 302, 303, 305, 308, 311, 317, 322, 323, 326, 328, 331, 47 A and B, 69 A and B |
| ++++ | 6, 10, 25, 26, 27, 28, 29, 30, 31, 46, 55, 66, 67, 73, 74, 98, 106, 107, 114, 126, 132, 154, 192, 210, 211, 233, 235, 240, 250, 251, 290, 292, 295, 296, 304, 310, 312, 313, 318, 319, 320, 321, 324, 15 A and B, 17 A and B, 18 A and B, 19 A and B, 24 A and B, 32 A and B, 32 A and B, 42B, 43B, 47 A and B, 62 A and B, 72 A and B |
| +++++ | 60, 63, 75, 76, 77, 78, 80, 81, 99, 121, 122, 123, 124, 125, 234, 327, 15 A and B, 16 A and B, 16 A and B, 17 A and B, 18 A and B, 19 A and B, 20 A and B, 20 A and B, 22 A and B, 23 A and B, 24 A and B, 61 A and B, 61 A and B, 62 A and B, 64 A and B, 64 A and B, 65 A and B, 65 A and B, 68 A and B, 68 A and B, 69 A and B, 70 A and B, 70 A and B, 71 A and B, 71 A and B, 72 A and B, 79 A and B, 79 A and B, 82 A and B, 82 A and B |

TABLE 8

KRAS G12S FRET data

| IC50* | Examples of A compounds |
|---|---|
| + | 325, 264, 281, 135 |
| ++ | 263, 258, 230, 249, 287, 282, 209, 139, 315, 170, 283, 267, 150, 260, 274, 284, 42A, 167, 276, 261, 133, 137, 12, 256, 136, 257, 285, 288, 265, 88, 85, 231, 316, 330, 269, 262, 280, 148, 186, 278, 248, 259, 309, 162, 197, 314, 332, 160, 140, 175, 305, 95, 308, 158, 113, 273, 323, 268, 173, 322, 306, 43A, 214, 177, 171, 161, 146, 272, 207, 329, 157, 197, 201, 147, 103, 208, 200, 328, 241, 172, 90, 89, 105, 149, 279, 100, 159, 238, 93, 271, 91, 48, 174, 7, 35, 155, 307, 53, 36, 52, 92, 190, 156, 237, 302, 326, 59, 8, 142, 37, 33, 11, 141, 97, 127, 10, 13, 277, 58, 104, 275, 222, 129, 266, 204, 39, 191, 110, 176, 301, 96, 331, 54, 198, 239, 130, 255, 134, 83, 50, 1, 34, 289, 86, 38, 47 A and B, 168, 143, 169, 270, 298 |
| +++ | 14, 115, 152, 109, 49, 102, 223, 189, 44, 291, 144, 297, 120, 202, 153, 187, 185, 188, 56, 138, 195, 224, 254, 51, 178, 244, 286, 194, 45, 225, 181, 246, 9, 205, 166, 101, 196, 252, 2, 116, 243, 193, 216, 253, 179, 293, 217, 192, 112, 245, 311, 199, 203, 94, 165, 3, 163, 232, 151, 5, 294, 108, 183, 46, 215, 299, 119, 117, 4, 300, 164, 303, 184, 213, 227, 145, 57, 128, 304, 6, 220, 229, 218, 226, 228, 87, 251, 131, 84, 219, 111, 221, 242, 154, 310, 247, 180, 40, 47 A and B, 41, 290, 118, 236, 292, 31, 324, 296, 321, 250, 212, 206, 55, 126 |
| ++++ | 210, 240, 77, 121, 211, 319, 42B, 313, 132, 114, 98, 320, 295, 318, 43B, 235, 122, 107, 62 A and B, 312, 24 A and B, 106, 74, 234, 78, 66, 15 A and B, 233, 73, 69 A and B, 63, 29, 67, 22 A and B, 80, 23 A and B |
| +++++ | 25, 124, 32 A and B, 327, 27, 28, 26, 62 A and B, 72 A and B, 20 A and B, 79 A and B, 19 A and B, 16 A and B, 123, 24 A and B, 30, 17 A and B, 15 A and B, 19 A and B, 32 A and B, 18 A and B, 18 A and B, 17 A and B, 16 A and B, 20 A and B, 69 A and B, 60, 68 A and B, 68 A and B, 65 A and B, 65 A and B, 64 A and B, 64 A and B, 70 A and B, 71 A and B, 70 A and B, 71 A and B, 72 A and B, 61 A and B, 61 A and B, 82 A and B, 82 A and B, 81, 79 A and B, 76, 75, 99, 125 |

TABLE 9

KRAS G13C FRET data

| IC50* | Examples of A compounds |
|---|---|
| + | 84, 85, 89, 129, 135, 136, 139, 140, 182, 195, 205, 209, 230, 231, 256, 257, 258, 260, 282, 283, 284, 285, 325, 329, 330, 42A |
| ++ | 3, 4, 7, 8, 11, 12, 13, 14, 34, 35, 36, 37, 38, 39, 41, 44, 45, 48, 49, 50, 51, 53, 54, 56, 57, 58, 59, 77, 78, 83, 86, 87, 88, 90, 91, 92, 93, 94, 95, 96, 97, 100, 102, 103, 104, 105, 108, 109, 112, 113, 115, 117, 118, 119, 120, 124, 127, 128, 130, 131, 133, 134, 137, 138, 141, 142, 143, 144, 145, 146, 147, 148, 149, 150, 152, 155, 156, 157, 158, 159, 160, 161, 162, 167, 169, 170, 171, 172, 173, 174, 175, 176, 177, 178, 179, 180, 181, 183, 184, 185, 186, 187, 188, 189, 190, 191, 193, 194, 196, 197, 198, 200, 201, 203, 204, 207, 208, 212, 213, 214, 215, 232, 237, 238, 239, 241, 245, 246, 248, 249, 251, 252, 253, 254, 255, 259, 261, 262, 263, 264, 265, 266, 267, 268, 269, 270, 271, 272, 273, 274, 275, 276, 277, 278, 279, 280, 281, 286, 287, 288, 297, 301, 305, 306, 307, 308, 309, 311, 314, 315, 316, 317, 322, 323, 326, 328, 331, 332, 43A, 47 A and B, 47 A and B, 69 A and B |
| +++ | 1, 2, 5, 6, 9, 10, 31, 33, 40, 46, 52, 55, 66, 74, 76, 98, 101, 106, 107, 110, 111, 114, 116, 121, 122, 123, 125, 126, 151, 153, 154, 163, 164, 165, 166, 168, 192, 199, 202, 206, 211, 216, 217, 218, 219, 220, 221, 222, 223, 224, 225, 226, 227, 228, 229, 233, 236, 243, 244, 247, 250, 289, 290, 291, 292, 293, 294, 296, 298, 299, 300, 302, 303, 310, 312, 313, 318, 319, 320, 321, 324, 22 A and B, 42B, 70 A and B |
| ++++ | 25, 27, 28, 29, 63, 67, 73, 80, 132, 210, 234, 235, 240, 242, 295, 304, 327, 15 A and B, 16 A and B, 17 A and B, 17 A and B, 18 A and B, 19 A and B, 20 A and B, 23 A and B, 24 A and B, 32 A and B, 43B, 62 A and B, 65 A and B, 68 A and B, 69 A and B, 72 A and B, 79 A and B |
| +++++ | 26, 30, 60, 75, 81, 99, 15 A and B, 16 A and B, 18 A and B, 19 A and B, 20 A and B, 24 A and B, 32 A and B, 61 A and B, 61 A and B, 62 A and B, 64 A and B, 64 A and B, 65 A and B, 68 A and B, 70 A and B, 71 A and B, 71 A and B, 72 A and B, 79 A and B, 82 A and B, 82 A and B |

TABLE 10

KRAS G12V FRET data

| IC50* | Examples of A compounds |
|---|---|
| + | 325 |
| ++ | 1, 11, 12, 13, 36, 44, 48, 50, 58, 59, 83, 85, 88, 90, 93, 95, 96, 97, 100, 103, 113, 133, 135, 136, 137, 139, 140, 141, 146, 147, 148, 149, 150, 151, 155, 156, 157, 158, 159, 160, 161, 162, 165, 167, 170, 171, 172, 173, 174, 175, 177, 182, 186, 189, 190, 192, 197, 200, 201, 204, 207, 208, 209, 214, 230, 231, 239, 241, 248, 249, 256, 257, 258, 259, 260, 261, 262, 263, 264, 265, 267, 268, 269, 272, 273, 274, 276, 278, 279, 280, 281, 282, 283, 284, 285, 287, 288, 302, 305, 306, 307, 309, 314, 315, 316, 317, 322, 323, 326, 328, 329, 330, 331, 332, 42A, 43A |
| +++ | 2, 3, 4, 5, 6, 7, 8, 9, 10, 14, 31, 33, 34, 35, 37, 38, 39, 40, 41, 45, 49, 51, 52, 53, 54, 55, 56, 57, 84, 86, 87, 89, 91, 92, 94, 101, 102, 104, 105, 108, 109, 110, 111, 112, 115, 116, 117, 118, 119, 120, 127, 128, 129, 130, 131, 134, 142, 143, 144, 145, 152, 153, 154, 163, 164, 166, 168, 169, 176, 178, 179, 180, 181, 183, 184, 185, 187, 188, 191, 194, 195, 196, 198, 199, 202, 203, 205, 206, 212, 213, 215, 216, 217, 218, 219, 220, 221, 222, 223, 224, 225, 226, 227, 228, 229, 232, 236, 237, 238, 243, 244, 245, 246, 247, 250, 251, 252, 253, 254, 255, 266, 270, 271, 275, 277, 286, 289, 290, 291, 292, 293, 294, 297, 298, 299, 300, 301, 303, 304, 308, 310, 311, 321, 324, 47 A and B |
| ++++ | 29, 46, 66, 67, 74, 77, 78, 80, 98, 106, 107, 114, 121, 122, 123, 124, 126, 132, 138, 193, 210, 211, 233, 234, 235, 240, 242, 295, 296, 312, 313, 318, 319, 320, 15 A and B, 16 A and B, 22 A and B, 24 A and B, 42B, 43B, 47 A and B, 62 A and B, 69 A and B, 72 A and B, 79 A and B |
| +++++ | 73, 25, 26, 27, 28, 30, 60, 63, 75, 76, 81, 99, 125, 327, 15 A and B, 16 A and B, 17 A and B, 17 A and B, 18 A and B, 18 A and B, 19 A and B, 19 A and B, 20 A and B, 20 A and B, |

TABLE 10-continued

KRAS G12V FRET data

| IC50* | Examples of A compounds |
|---|---|
| | 23 A and B, 24 A and B, 32 A and B, 32 A and B, 61 A and B, 61 A and B, 62 A and B, 64 A and B, 64 A and B, 65 A and B, 65 A and B, 68 A and B, 68 A and B, 69 A and B, 70 A and B, 70 A and B, 71 A and B, 71 A and B, 72 A and B, 79 A and B, 82 A and B, 82 A and B |

TABLE 11

KRAS G12D FRET data

| IC50* | Examples of A compounds |
|---|---|
| + | 214, 305, 325 |
| ++ | 59, 88, 95, 103, 113, 133, 135, 136, 137, 139, 140, 141, 146, 148, 150, 167, 170, 171, 173, 175, 186, 198, 209, 230, 231, 241, 248, 249, 256, 258, 260, 261, 263, 264, 265, 267, 269, 274, 276, 278, 280, 281, 282, 283, 284, 285, 287, 309, 315, 316, 330, 42A, 43A |
| +++ | 1, 2, 7, 8, 12, 13, 14, 33, 34, 35, 36, 37, 38, 39, 40, 41, 44, 45, 48, 49, 50, 51, 52, 53, 54, 56, 58, 73, 74, 83, 85, 86, 89, 90, 91, 92, 93, 96, 97, 100, 101, 102, 104, 105, 110, 112, 115, 120, 127, 128, 129, 130, 131, 134, 138, 142, 143, 144, 147, 149, 151, 152, 153, 155, 156, 157, 158, 159, 160, 161, 162, 163, 164, 165, 166, 168, 169, 172, 174, 176, 177, 178, 179, 181, 182, 184, 185, 187, 188, 189, 190, 191, 192, 193, 194, 196, 197, 199, 200, 201, 202, 203, 204, 207, 208, 215, 216, 217, 222, 223, 224, 225, 227, 236, 237, 238, 239, 242, 243, 244, 245, 252, 253, 254, 255, 257, 259, 262, 266, 268, 270, 271, 272, 273, 275, 277, 279, 286, 288, 289, 291, 293, 294, 297, 298, 299, 300, 301, 302, 303, 304, 306, 307, 308, 311, 313, 314, 317, 321, 322, 323, 324, 326, 328, 329, 331, 332, 70 A and B |
| ++++ | 16 A and B, 3, 4, 5, 6, 9, 10, 11, 29, 31, 46, 57, 63, 66, 67, 76, 77, 78, 80, 84, 87, 94, 98, 106, 107, 108, 109, 111, 114, 116, 117, 118, 119, 121, 122, 123, 124, 125, 126, 132, 145, 154, 180, 183, 195, 205, 206, 210, 211, 212, 213, 218, 219, 220, 221, 226, 228, 229, 232, 233, 234, 235, 240, 246, 247, 250, 251, 290, 292, 295, 296, 310, 312, 318, 319, 320, 327, 15 A and B, 17 A and B, 17 A and B, 18 A and B, 19 A and B, 22 A and B, 23 A and B, 24 A and B, 32 A and B, 42B, 43B, 47 A and B, 47 A and B, 62 A and B, 68 A and B, 69 A and B, 72 A and B, 82 A and B |
| +++++ | 25, 26, 27, 28, 30, 55, 60, 75, 81, 99, 15 A and B, 16 A and B, 18 A and B, 19 A and B, 20 A and B, 20 A and B, 24 A and B, 32 A and B, 61 A and B, 61 A and B, 62 A and B, 64 A and B, 64 A and B, 65 A and B, 65 A and B, 68 A and B, 69 A and B, 70 A and B, 71 A and B, 71 A and B, 72 A and B, 79 A and B, 79 A and B, 82 A and B |

TABLE 12

KRAS WT FRET data

| IC50* | Examples of A compounds |
|---|---|
| + | 264, 325 |
| ++ | 12, 13, 35, 36, 37, 44, 45, 52, 53, 54, 58, 59, 83, 85, 86, 88, 89, 90, 91, 92, 93, 95, 96, 97, 100, 102, 103, 105, 109, 110, 112, 113, 115, 116, 120, 129, 130, 133, 134, 135, 136, 137, 138, 139, 140, 141, 143, 146, 147, 148, 149, 150, 155, 156, 157, 158, 159, 160, 161, 162, 167, 168, 169, 170, 171, 172, 173, 174, 175, 176, 177, 182, 183, 186, 189, 190, 191, 193, 195, 196, 197, 198, 201, 204, 205, 207, 208, 209, 213, 214, 222, 223, 230, 231, 237, 238, 239, 241, 245, 246, 248, 249, 252, 253, 256, 257, 258, 259, 260, 261, 262, 263, 265, 267, 268, 269, 271, 272, 273, 274, 276, 278, 279, 280, 281, 282, 283, 284, 285, 287, 288, 289, 291, 297, 298, 301, 302, 305, 306, 307, 308, 309, 314, 315, 316, 317, 322, 323, 326, 328, 329, 330, 331, 332, 42A, 43A |
| +++ | 1, 2, 3, 4, 5, 6, 7, 8, 9, 10, 11, 14, 33, 34, 38, 39, 40, 41, 48, 49, 50, 51, 56, 57, 84, 87, 94, 98, 101, 104, 108, 111, |

TABLE 12-continued

KRAS WT FRET data

| IC50* | Examples of A compounds |
|---|---|
| | 117, 118, 119, 121, 127, 128, 131, 142, 144, 145, 151, 152, 153, 154, 163, 164, 165, 166, 178, 179, 180, 181, 184, 185, 187, 188, 192, 194, 199, 200, 202, 203, 206, 211, 212, 215, 216, 217, 218, 219, 220, 221, 224, 225, 226, 227, 228, 229, 232, 236, 240, 242, 243, 244, 247, 250, 251, 254, 255, 266, 270, 275, 277, 286, 290, 292, 293, 294, 295, 296, 299, 300, 303, 304, 310, 311, 312, 318, 321, 324, 47 A and B |
| ++++ | 25, 26, 27, 29, 30, 31, 46, 55, 63, 66, 67, 73, 74, 76, 77, 78, 80, 106, 107, 114, 122, 123, 124, 126, 132, 210, 233, 234, 235, 313, 319, 320, 327, 15 A and B, 16 A and B, 22 A and B, 23 A and B, 24 A and B, 42B, 43B, 47 A and B, 62 A and B, 69 A and B, 79 A and B |
| +++++ | 28, 60, 75, 81, 99, 125, 15 A and B, 16 A and B, 17 A and B, 17 A and B, 18 A and B, 18 A and B, 19 A and B, 19 A and B, 20 A and B, 20 A and B, 24 A and B, 32 A and B, 32 A and B, 61 A and B, 61 A and B, 62 A and B, 64 A and B, 64 A and B, 65 A and B, 65 A and B, 68 A and B, 68 A and B, 69 A and B, 70 A and B, 70 A and B, 71 A and B, 71 A and B, 72 A and B, 72 A and B, 79 A and B, 82 A and B, 82 A and B |

TABLE 13

KRAS G12C FRET data

| IC50* | Examples of A compounds |
|---|---|
| + | 1, 7, 41, 58, 88, 90, 95, 109, 113, 115, 135, 137, 139, 140, 142, 146, 148, 149, 150, 151, 156, 161, 162, 165, 167, 171, 174, 175, 183, 184, 186, 190, 192, 196, 198, 200, 201, 203, 204, 209, 230, 231, 241, 249, 252, 263, 264, 266, 267, 268, 269, 270, 271, 272, 273, 274, 280, 281, 306, 307, 309, 311, 312, 325, 329, 330, 331, 42A, 43A |
| ++ | 2, 3, 4, 5, 6, 8, 9, 10, 11, 12, 13, 14, 31, 33, 34, 35, 36, 37, 38, 39, 44, 45, 48, 49, 50, 51, 52, 53, 54, 56, 59, 73, 74, 77, 78, 83, 84, 85, 86, 87, 89, 91, 92, 93, 94, 96, 97, 100, 101, 102, 103, 104, 105, 106, 110, 114, 117, 119, 124, 125, 128, 129, 130, 131, 133, 134, 136, 138, 141, 143, 144, 147, 152, 153, 154, 155, 157, 158, 159, 160, 168, 169, 170, 172, 173, 176, 177, 178, 179, 181, 182, 185, 188, 189, 191, 193, 195, 197, 202, 205, 206, 207, 208, 211, 213, 214, 215, 216, 217, 220, 222, 223, 224, 225, 232, 236, 237, 238, 239, 243, 244, 245, 246, 247, 248, 250, 251, 253, 254, 255, 256, 257, 258, 259, 260, 262, 265, 275, 276, 277, 278, 279, 282, 283, 284, 285, 287, 288, 289, 291, 293, 294, 297, 298, 299, 301, 302, 305, 308, 314, 315, 316, 317, 319, 322, 323, 326, 328, 332, 16 A and B, 17 A and B, 18 A and B, 22 A and B, 23 A and B, 32 A and B, 43B, 68 A and B, 69 A and B, 82 A and B |
| +++ | 40, 46, 55, 57, 66, 67, 75, 76, 80, 81, 98, 107, 108, 111, 112, 116, 118, 120, 121, 122, 123, 126, 127, 132, 145, 163, 164, 166, 180, 187, 194, 199, 210, 212, 218, 219, 221, 226, 227, 228, 229, 233, 234, 235, 240, 242, 286, 290, 292, 295, 296, 300, 303, 304, 310, 313, 318, 320, 321, 324, 15 A and B, 16 A and B, 17 A and B, 19 A and B, 20 A and B, 24 A and B, 42B, 47 A and B, 61 A and B, 62 A and B, 70 A and B, 72 A and B, 79 A and B |
| ++++ | 25, 26, 27, 28, 29, 63, 327, 18 A and B, 32 A and B, 47 A and B, 62 A and B, 65 A and B, 68 A and B, 69 A and B, 71 A and B, 72 A and B, 82 A and B |
| +++++ | 30, 60, 99, 15 A and B, 19 A and B, 20 A and B, 24 A and B, 61 A and B, 64 A and B, 64 A and B, 65 A and B, 70 A and B, 71 A and B, 79 A and B |

TABLE 14

KRAS Q61H FRET data

| IC50* | Examples of A compounds |
|---|---|
| + | 209, 230, 231, 246, 249, 258, 264, 281, 325 |
| ++ | 36, 37, 91, 92, 108, 117, 119, 141, 144, 163, 164, 166, 167, |

TABLE 14-continued

KRAS Q61H FRET data

| IC50* | Examples of A compounds |
|---|---|
| | 170, 186, 202, 203, 204, 205, 207, 208, 212, 213, 214, 215, 216, 217, 218, 220, 222, 223, 224, 225, 227, 228, 229, 232, 237, 238, 239, 241, 244, 245, 248, 252, 253, 254, 255, 256, 257, 259, 260, 261, 262, 263, 265, 266, 267, 268, 269, 271, 272, 273, 274, 275, 276, 277, 278, 279, 280, 282, 283, 284, 285, 286, 287, 288, 289, 291, 293, 294, 297, 298, 299, 300, 301, 302, 303, 304, 305, 306, 307, 308, 309, 311, 314, 315, 316, 317, 322, 323, 326, 328, 329, 330, 331, 332 |
| +++ | 165, 206, 210, 211, 219, 221, 226, 233, 235, 236, 240, 242, 243, 247, 250, 251, 270, 290, 292, 295, 296, 310, 312, 313, 318, 319, 320, 321, 324 |
| ++++ | 234, 327 |
| +++++ | None |

TABLE 15

NRAS G12C FRET data

| IC50* | Examples of A compounds |
|---|---|
| + | 1, 5, 7, 41, 58, 59, 86, 88, 90, 95, 109, 113, 115, 135, 136, 137, 138, 139, 140, 142, 146, 148, 149, 150, 151, 155, 156, 159, 160, 161, 162, 165, 167, 171, 174, 175, 184, 186, 192, 196, 198, 200, 201, 203, 204, 209, 230, 231, 241, 249, 252, 263, 264, 266, 267, 268, 269, 270, 271, 272, 273, 274, 276, 278, 280, 281, 284, 306, 307, 309, 311, 312, 325, 329, 330, 42A, 43A |
| ++ | 2, 3, 6, 8, 9, 10, 11, 12, 13, 14, 33, 34, 35, 36, 37, 38, 39, 44, 45, 48, 49, 50, 52, 53, 54, 73, 74, 77, 78, 83, 84, 85, 87, 89, 91, 92, 93, 96, 97, 100, 101, 102, 103, 104, 105, 106, 110, 114, 124, 125, 128, 129, 130, 131, 133, 134, 141, 143, 144, 147, 152, 153, 154, 157, 158, 168, 169, 170, 172, 173, 176, 177, 178, 179, 181, 182, 183, 185, 188, 189, 190, 191, 193, 195, 197, 202, 205, 206, 207, 208, 211, 213, 214, 215, 216, 217, 218, 222, 223, 224, 225, 227, 228, 232, 236, 237, 238, 239, 243, 244, 245, 246, 247, 248, 251, 253, 254, 255, 256, 257, 258, 259, 260, 261, 262, 265, 275, 277, 279, 282, 283, 285, 287, 288, 289, 291, 293, 294, 297, 298, 299, 300, 301, 302, 305, 308, 314, 315, 316, 317, 319, 322, 323, 326, 328, 331, 332, 16 A and B, 17 A and B, 18 A and B, 22 A and B, 23 A and B, 43B, 68 A and B, 69 A and B |
| +++ | 219, 4, 31, 40, 46, 51, 55, 56, 57, 66, 67, 75, 76, 80, 94, 107, 108, 111, 112, 116, 117, 118, 119, 120, 121, 122, 123, 126, 127, 132, 145, 163, 164, 166, 180, 187, 194, 199, 210, 212, 220, 221, 226, 229, 233, 235, 240, 242, 250, 286, 290, 292, 295, 296, 303, 304, 310, 313, 320, 321, 324, 15 A and B, 16 A and B, 17 A and B, 19 A and B, 20 A and B, 32 A and B, 42B, 47 A and B, 61 A and B, 62 A and B, 70 A and B, 71 A and B, 72 A and B, 72 A and B, 79 A and B, 82 A and B |
| ++++ | 318, 26, 28, 29, 63, 81, 98, 234, 327, 18 A and B, 24 A and B, 47 A and B, 62 A and B, 68 A and B, 69 A and B, 82 A and B |
| +++++ | 25, 27, 30, 60, 99, 15 A and B, 19 A and B, 20 A and B, 24 A and B, 32 A and B, 61 A and B, 64 A and B, 64 A and B, 65 A and B, 65 A and B, 70 A and B, 71 A and B, 79 A and B |

TABLE 16

NRAS WT FRET data

| IC50* | Examples of A compounds |
|---|---|
| + | 258, 264, 315, 325 |
| ++ | 37, 91, 92, 117, 141, 167, 170, 186, 204, 205, 207, 208, 209, 213, 214, 217, 222, 223, 224, 225, 230, 231, 237, 238, 239, 241, 245, 246, 248, 249, 252, 253, 255, 256, 257, 259, 260, 261, 262, 263, 265, 267, 268, 269, 272, 273, 274, 276, 278, 279, 280, 281, 282, 283, 284, 285, 287, 288, 289, 291, 297, 298, 301, 302, 305, 306, 307, 308, 309, 311, 314, 316, 317, 322, 323, 326, 328, 329, 330, 331, 332 |
| +++ | 36, 108, 119, 144, 163, 164, 165, 166, 202, 203, 206, 211, 212, 215, 216, 218, 219, 220, 221, 226, 227, 228, 229, 232, 236, 242, 243, 244, 247, 250, 251, 254, 266, 270, 271, 275, 277, 286, 290, 292, 293, 294, 295, 296, 299, 300, 303, 304, 310, 312, 321, 324 |
| ++++ | 210, 233, 234, 235, 240, 313, 318, 319, 320 |
| +++++ | 327 |

TABLE 17

NRAS Q61K FRET data

| IC50* | Examples of A compounds |
|---|---|
| + | None |
| ++ | 167, 170, 216, 217, 218, 219, 220, 222, 223, 224, 225, 227, 228, 229, 231, 246, 249, 258, 260, 264, 281, 289, 291, 293, 294, 297, 298, 299, 300, 301, 302, 315, 325, 326, 329 |
| +++ | 36, 37, 91, 92, 108, 117, 119, 141, 163, 186, 202, 203, 204, 205, 207, 208, 209, 212, 213, 214, 221, 226, 230, 232, 235, 237, 238, 239, 241, 245, 248, 252, 253, 254, 255, 256, 257, 259, 261, 262, 263, 265, 266, 267, 268, 269, 271, 272, 273, 274, 275, 276, 277, 278, 279, 280, 282, 283, 284, 285, 286, 287, 288, 290, 292, 295, 296, 303, 304, 305, 306, 307, 308, 309, 310, 311, 314, 316, 317, 319, 322, 323, 324, 328, 330, 331, 332 |
| ++++ | 144, 164, 165, 166, 206, 210, 211, 215, 233, 234, 236, 242, 243, 244, 247, 250, 251, 270, 312, 313, 318, 320, 321 |
| +++++ | 240, 327 |

TABLE 18

NRAS Q61R FRET data

| IC50* | Examples of A compounds |
|---|---|
| + | None |
| ++ | 170, 209, 222, 223, 224, 230, 249, 258, 264, 289, 297, 298, 301, 302, 325, 326, 329 |
| +++ | 36, 37, 91, 92, 108, 117, 141, 163, 167, 186, 202, 203, 204, 205, 207, 208, 212, 213, 214, 216, 217, 218, 219, 220, 221, 225, 226, 227, 228, 229, 231, 232, 237, 238, 239, 241, 244, 245, 246, 248, 252, 253, 254, 255, 256, 257, 259, 260, 261, 262, 263, 265, 266, 267, 268, 269, 271, 272, 273, 274, 275, 276, 278, 279, 280, 281, 282, 283, 284, 285, 286, 287, 288, 290, 291, 292, 293, 294, 296, 299, 300, 303, 304, 305, 306, 307, 308, 309, 310, 311, 314, 315, 316, 317, 322, 323, 324, 328, 330, 331, 332 |
| ++++ | 119, 144, 164, 165, 166, 206, 210, 211, 215, 234, 235, 236, 240, 242, 243, 247, 250, 251, 270, 277, 295, 312, 313, 318, 319, 320, 321 |
| +++++ | 233, 327 |

Cross-Linking of Ras Proteins with Compounds of the Invention to Form Conjugates Note—The following protocol describes a procedure for monitoring cross-linking of K-Ras G12C (GMP-PNP) to a compound of the invention. This protocol may also be executed substituting other Ras proteins or nucleotides, such as such as K-Ras G12D and K-Ras G13D.

The purpose of this biochemical assay was to measure the ability of test compounds to covalently label nucleotide-loaded K-Ras isoforms. In assay buffer containing 12.5 mM HEPES pH 7.4, 75 mM NaCl, 1 mM $MgCl_2$, 1 mM BME, 5 µM Cyclophilin A, and 2 µM test compound, a 5 µM stock of GMP-PNP-loaded K-Ras (1-169) G12C was diluted 10-fold to yield a final concentration of 0.5 µM; with final sample volume being 100 µL.

The sample was incubated at 25° C. for a time period of up to 24 hours prior to quenching by the addition of 10 µL of 5% Formic Acid. Quenched samples were centrifuged at 15000 rpm for 15 minutes in a benchtop centrifuge before injecting a 10 µL aliquot onto a reverse phase C4 column and eluting into the mass spectrometer with an increasing acetonitrile gradient in the mobile phase. Analysis of raw data was carried out using Waters MassLynx MS software, with % bound calculated from the deconvoluted protein peaks for labeled and unlabeled K-Ras.

In Vitro Cell Proliferation Panels

Potency for inhibition of cell growth was assessed at CrownBio using standard methods. Briefly, cell lines were cultured in appropriate medium, and then plated in 3D methylcellulose. Inhibition of cell growth was determined by CellTiter-Glo® after 5 days of culture with increasing concentrations of compounds. Compound potency was reported as the 50% inhibition concentration (absolute IC50). The assay took place over 7 days. On day 1, cells in 2D culture were harvested during logarithmic growth and suspended in culture medium at 1×105 cells/ml. Higher or lower cell densities were used for some cell lines based on prior optimization. 3.5 ml of cell suspension was mixed with 6.5% growth medium with 1% methylcellulose, resulting in a cell suspension in 0.65% methylcellulose. 90 µl of this suspension was distributed in the wells of 2 96-well plates. One plate was used for day 0 reading and 1 plate was used for the end-point experiment. Plates were incubated overnight at 37 C with 5% CO2. On day 2, one plate (for t0 reading) was removed and 10 µl growth medium plus 100 µl CellTiter-Glo® Reagent was added to each well. After mixing and a 10 minute incubation, luminescence was recorded on an EnVision Multi-Label Reader (Perkin Elmer). Compounds in DMSO were diluted in growth medium such that the final, maximum concentration of compound was 10 µM, and serial 4-fold dilutions were performed to generate a 9-point concentration series. 10 µl of compound solution at 10 times final concentration was added to wells of the second plate. Plate was then incubated for 120 hours at 37 C and 5% CO2. On day 7 the plates were removed, 100 µl CellTiter-Glo® Reagent was added to each well, and after mixing and a 10 minute incubation, luminescence was recorded on an EnVision Multi-Label Reader (Perkin Elmer). Data was exported to GeneData Screener and modeled with a sigmoidal concentration response model in order to determine the IC50 for compound response.

Not all cell lines with a given RAS mutation may be equally sensitive to a RAS inhibitor targeting that mutation, due to differential expression of efflux transporters, varying dependencies on RAS pathway activation for growth, or other reasons. This has been exemplified by the cell line KYSE-410 which, despite having a KRAS G12C mutation, is insensitive to the KRAS G12C (OFF) inhibitor MRTX-849 (Hallin et al., Cancer Discovery 10:54-71 (2020)), and the cell line SW1573, which is insensitive to the KRAS G12C (OFF) inhibitor AMG510 (Canon et al., Nature 575: 217-223 (2019)).

TABLE 19

IC50 values for various cancer cell lines with Compound B

| Cell Line | Histotype | Cancer Driver/Mutant | IC50* |
|---|---|---|---|
| A-375 | Skin | BRAF V600E | low sensitivity |
| KYSE-410 | HN/Esophagus | KRAS G12C | moderately sensitive |
| MIA PaCa-2 | Pancreas | KRAS G12C | very sensitive |
| NCI-H358 | Lung | KRAS G12C | very sensitive |
| SW1573 | Lung | KRAS G12C | low sensitivity |
| SW837 | Intestine/Large/Colorectum | KRAS G12C | very sensitive |
| LS513 | Intestine/Large/Colorectum | KRAS G12D | moderately sensitive |
| HuCCT1 | Liver/Bile duct | KRAS G12D | very sensitive |
| HCC1588 | Lung | KRAS G12D | low sensitivity |
| HPAC | Pancreas | KRAS G12D | very sensitive |
| AsPC-1 | Pancreas | KRAS G12D | moderately sensitive |
| AGS | Stomach | KRAS G12D | very sensitive |
| HEC-1-A | Uterus | KRAS G12D | very sensitive |
| SW403 | Intestine/Large/Colorectum | KRAS G12V | moderately sensitive |
| NOZ | Liver/Bile duct | KRAS G12V | low sensitivity |
| NCI-H441 | Lung | KRAS G12V | moderately sensitive |
| NCI-H727 | Lung | KRAS G12V | moderately sensitive |
| OVCAR-5 | Ovary | KRAS G12V | moderately sensitive |
| Capan-2 | Pancreas | KRAS G12V | moderately sensitive |
| SW48 | Intestine/Large/Colorectum | not MAPK (PIK3CAG914R, EGFR G719S) | |
| NCI-H2009 | Lung | other KRAS (G12A) | moderately sensitive |
| CAL-62 | HN/Thyroid | other KRAS (G12R) | low sensitivity |
| A549 | Lung | other KRAS (G12S) | low sensitivity |
| TOV-21G | Ovary | other KRAS (G13C) | low sensitivity |
| DV-90 | Lung | other KRAS (G13D) | low sensitivity |
| HCT116 | Intestine/Large/Colorectum | other KRAS (G13D) | moderately sensitive |
| NCI-H747 | Intestine/Large/Colorectum | other KRAS (G13D) | moderately sensitive |
| NCI-H460 | Lung | other KRAS (Q61H) | moderately sensitive |
| Calu-6 | Lung | other KRAS (Q61K) | moderately sensitive |
| SNU-668 | Stomach | other KRAS (Q61K) | moderately sensitive |
| OZ | Liver/Bile duct | other KRAS (Q61L) | moderately sensitive |
| SW948 | Intestine/Large/Colorectum | other KRAS (Q61L) | low sensitivity |
| BxPC-3 | Pancreas | other MAPK (BRAF V487_P492delinsA) | low sensitivity |
| NCI-H1975 | Lung | other MAPK (EGFR T790M, L858R) | moderately sensitive |
| NCI-H3122 | Lung | other MAPK (EML4-ALK(E13, A20)) | moderately sensitive |

TABLE 19-continued

IC50 values for various cancer cell lines with Compound B

| Cell Line | Histotype | Cancer Driver/Mutant | IC50* |
|---|---|---|---|
| YCC-1 | Stomach | other MAPK (KRAS Amp) | |
| MeWo | Skin | other MAPK (NF1 mut) | low sensitivity |
| NCI-H1838 | Lung | other MAPK (NF1 mut) | moderately sensitive |

*Key:
low sensitivity: IC50 ≥ 1 uM
moderately sensitive: 1 uM > IC50 ≥ 0.1 uM
very sensitive: IC50 < 0.1 uM
blank = not measured In Vivo PD and Efficacy Data with Compound a, a Compound of the Present Invention

FIG. 1A:

Methods: The human pancreatic adenocarcinoma HPAC KRAS G12D/wt xenograft model was used for a single-dose PD study. Compound A (AsPC-1 pERK K-Ras G12D EC50: 0.036 uM) was administered at 30 and 60 mg/kg by intraperitoneal injection (ip injection). The treatment groups with sample collections at various time points were summarized in Table 20 below. Tumor samples were collected to assess RAS/ERK signaling pathway modulation by measuring the mRNA level of human DUSP6 in qPCR assay.

TABLE 20

Summary of treatment groups, doses, and time points for single-dose PD study using HPAC tumors.

| Compound/group | Dose/Regimen | PD, n = 3/time point |
|---|---|---|
| Vehicle control | 10 ml/kg ip | 1 h, 24 h |
| Compound A | 30 mg/kg ip | 1 h, 4 h, 8 h, 24 h |
| Compound A | 60 mg/kg ip | 1 h, 4 h, 6 h, 24 h |

Results: In FIG. 1A, Compound A at either 30 mg/kg or 60 mg/kg led to inhibition of DUSP6 mRNA levels in tumors at all time points tested, indicating strong MAPK pathway modulation. The inhibitory effects of Compound A on DUSP6 mRNA levels are durable even 24 hours after drug administration.

FIG. 1B:

Methods: Effects of Compound A on tumor cell growth in vivo were evaluated in the human pancreatic adenocarcinoma HPAC KRAS G12D/wt xenograft model using female BALB/c nude mice (6-8 weeks old). Mice were implanted with HPAC tumor cells in PBS (3×106 cells/mouse) subcutaneously in the flank. Once tumors reached an average size of ~150 mm3, mice were randomized to treatment groups to start the administration of test articles or vehicle. Compound A was administered by intraperitoneal injection once daily. Body weight and tumor volume (using calipers) was measured twice weekly until study endpoints.

Results: Single-agent Compound A administered at 10 mg/kg ip daily led to a TGI of 89.9% at Day 28, while both 30 mg/kg and 60 mg/kg Compound A dosed ip daily resulted in complete regression of all tumors in the group (complete regression defined as >85% tumor regression from baseline) at the end of treatment (Day 35 after treatment started) in HPAC CDX model with heterozygous KRAS G12D. The anti-tumor activity of all 3 tested doses of Compound A was statistically significant compared with control group (***p<0.001, ordinary One-way ANOVA with multiple comparisons via a post-hoc Tukey's test).

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features set forth herein.

All publications, patents and patent applications are herein incorporated by reference in their entirety to the same extent as if each individual publication, patent or patent application was specifically and individually indicated to be incorporated by reference in its entirety.

The invention claimed is:

1. A compound, or a pharmaceutically acceptable salt thereof, selected from the group consisting of

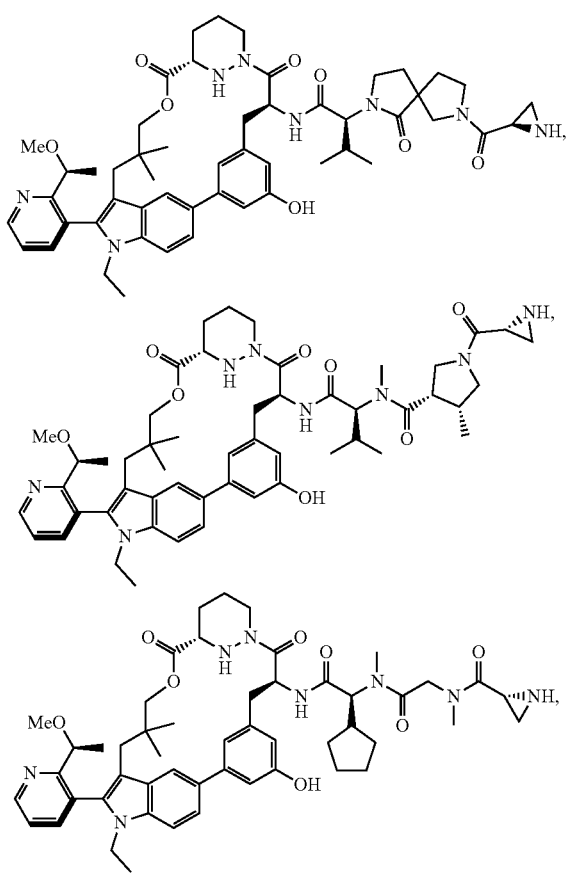

753
-continued
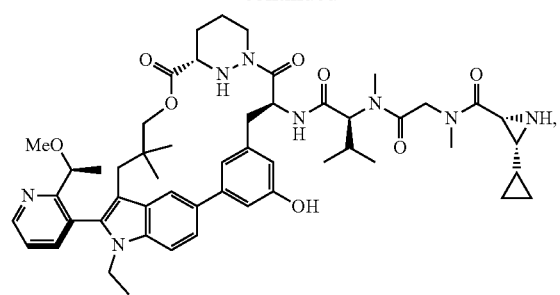
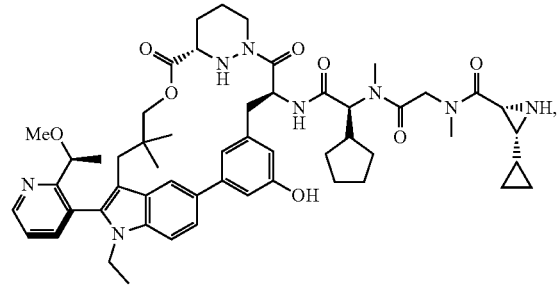
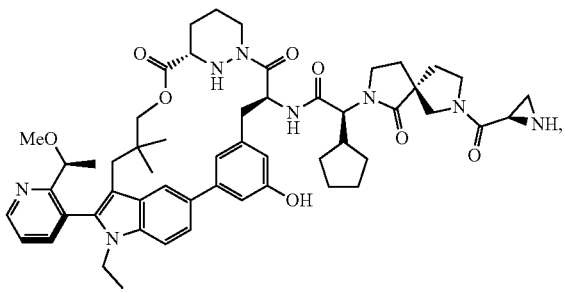
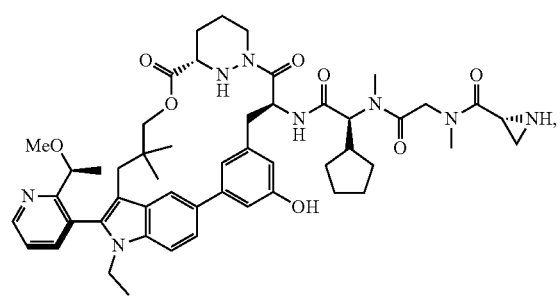
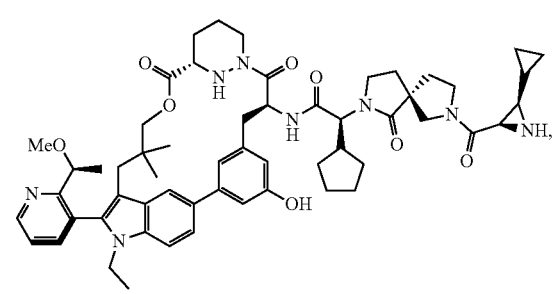
754
-continued
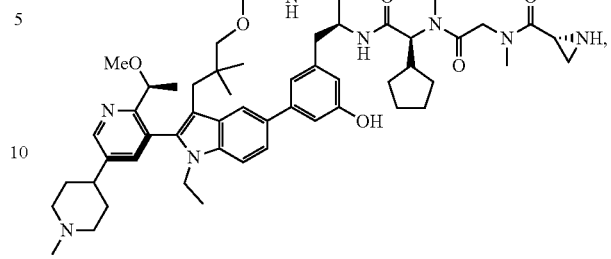
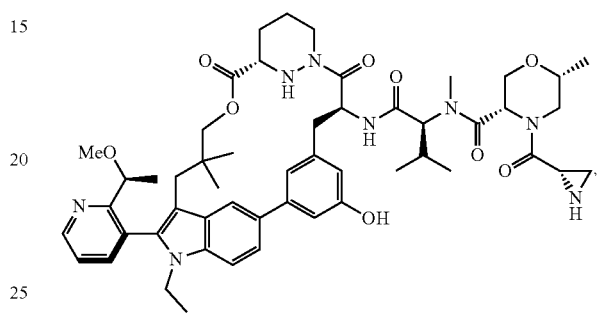
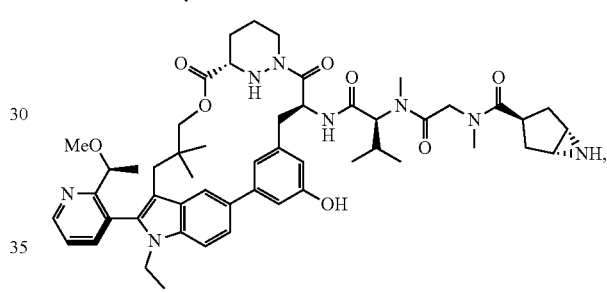
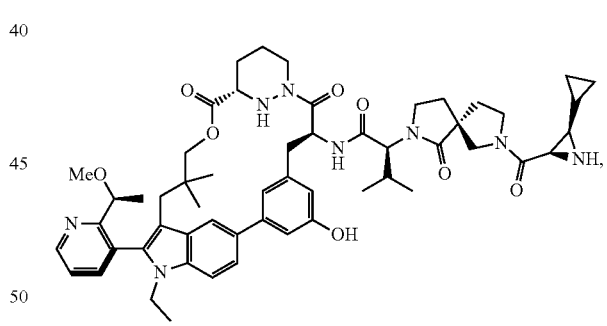
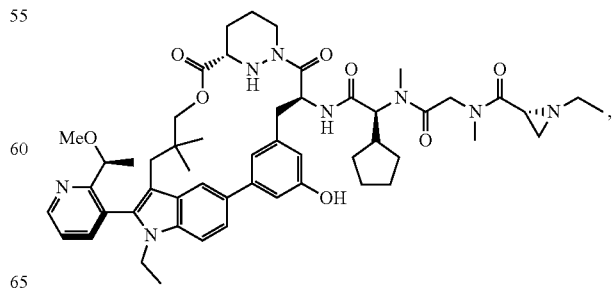

755
-continued
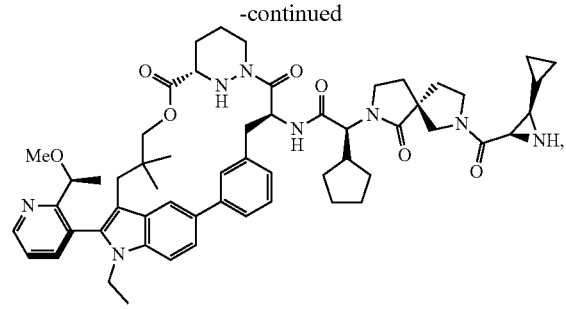
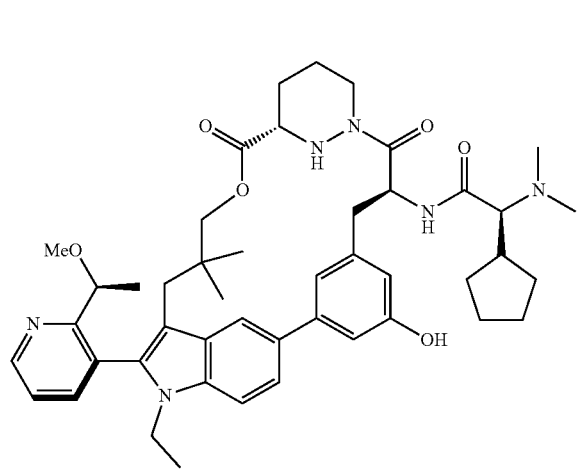
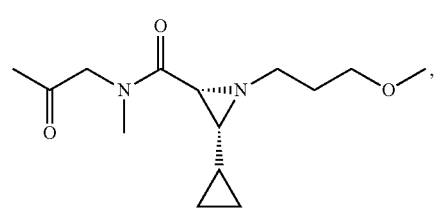
756
-continued
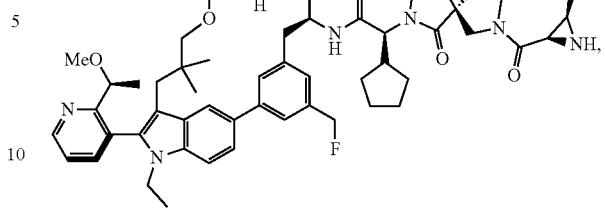
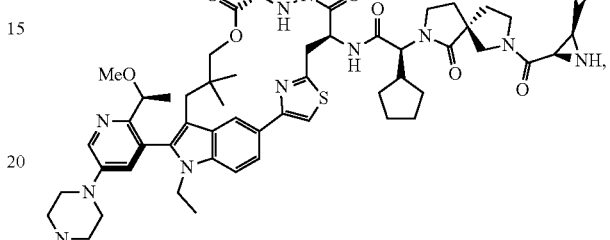
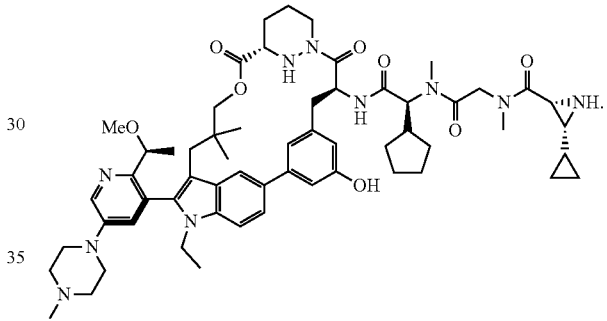
and
2. A pharmaceutical composition comprising a compound, or a pharmaceutically acceptable salt thereof, of claim 1 and a pharmaceutically acceptable excipient.
* * * * *